US012612412B2

(12) United States Patent
Szymaniak et al.

(10) Patent No.: US 12,612,412 B2
(45) Date of Patent: Apr. 28, 2026

(54) ANTIVIRAL HETEROCYCLIC COMPOUNDS

(71) Applicant: Enanta Pharmaceuticals, Inc., Watertown, MA (US)

(72) Inventors: Adam Szymaniak, Boston, MA (US); Jianming Yu, Plainsboro, NJ (US); Kevin McGrath, Brighton, MA (US); Xiben Li, Lexington, MA (US); Tyler J. Mann, Brighton, MA (US); Robert Leon, Sharon, MA (US); In Jong Kim, Lexington, MA (US); Yat Sun Or, Waltham, MA (US); Long Nguyen, Boston, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 1039 days.

(21) Appl. No.: 17/720,079

(22) Filed: Apr. 13, 2022

(65) Prior Publication Data

US 2023/0115580 A1 Apr. 13, 2023

Related U.S. Application Data

(63) Continuation-in-part of application No. 17/679,746, filed on Feb. 24, 2022, now Pat. No. 11,945,830.

(60) Provisional application No. 63/293,339, filed on Dec. 23, 2021, provisional application No. 63/171,895, filed on Apr. 7, 2021, provisional application No. 63/168,705, filed on Mar. 31, 2021, provisional application No. 63/154,318, filed on Feb. 26, 2021.

(51) Int. Cl.

| | |
|---|---|
| ***C07D 491/048*** | (2006.01) |
| ***A61K 45/06*** | (2006.01) |
| ***C07D 519/00*** | (2006.01) |

(52) U.S. Cl.

CPC .......... *C07D 491/048* (2013.01); *A61K 45/06* (2013.01); *C07D 519/00* (2013.01)

(58) Field of Classification Search

CPC ... C07D 491/048; C07D 519/00; A61K 45/06

See application file for complete search history.

(56) References Cited

U.S. PATENT DOCUMENTS

| | | | |
|---|---|---|---|
| 4,010,153 | A | 3/1977 | Kajfez et al. |
| 4,511,510 | A | 4/1985 | Mauri |
| 4,835,168 | A | 5/1989 | Paget et al. |
| 4,988,692 | A | 1/1991 | Gasc et al. |
| 5,571,809 | A | 11/1996 | Hargrave et al. |
| 5,637,697 | A | 6/1997 | Finch et al. |
| 5,646,140 | A | 7/1997 | Sugg et al. |
| 5,681,833 | A | 10/1997 | Castro et al. |
| 7,041,662 | B2 | 5/2006 | Sattlegger et al. |
| 7,582,624 | B2 | 9/2009 | Carter et al. |
| 8,999,969 | B2 | 4/2015 | Mackman et al. |
| 9,617,289 | B2 | 4/2017 | Tahri et al. |
| 9,732,098 | B2 | 8/2017 | Hunt et al. |
| 9,957,281 | B2 | 5/2018 | Shook et al. |
| 10,358,441 | B2 | 7/2019 | Kim et al. |
| 10,398,706 | B2 | 9/2019 | Shook et al. |
| 10,865,215 | B2 | 12/2020 | Shook et al. |
| 11,254,664 | B2 | 2/2022 | Zhu et al. |
| 11,420,976 | B2 | 8/2022 | He et al. |
| 11,505,558 | B1 | 11/2022 | Szymaniak et al. |
| 11,572,367 | B2 | 2/2023 | Szymaniak et al. |
| 11,945,830 | B2 | 4/2024 | Szymaniak et al. |
| 12,006,326 | B2 | 6/2024 | Szymaniak et al. |
| 12,162,857 | B2 | 12/2024 | Yu et al. |

(Continued)

FOREIGN PATENT DOCUMENTS

| | | | |
|---|---|---|---|
| CN | 109966244 | A | 7/2019 |
| EP | 0167919 | A2 | 1/1986 |

(Continued)

OTHER PUBLICATIONS

Pubchem, SID 471385789, Modify Date: Sep. 27, 2022 [retrieved on Jun. 15, 2024]., Retrieved from the Internet <URL: https://pubchem.ncbi.nlm.nih.gov/substance/471385789> entire document.

Pubchem, SID 311324621, Available Date: Feb. 23, 2016 [retrieved on Jul. 14, 2023]. Retrieved from the Internet: < URL: https://pubchem.ncbi.nlm.nih.gov/substance/311324621.

Pubchem, SID 74832 [retrieved on Jun. 12, 2023] Retrieved from the Internet <URL: https://pubchem.ncbi.nlm.nih.gov/substance/74832>.

(Continued)

*Primary Examiner* — Rebecca L Anderson

(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

(I)

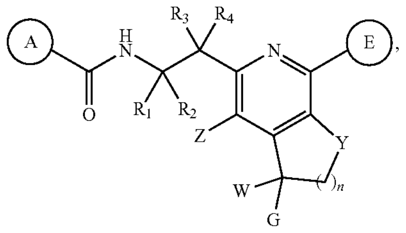

which inhibit Human Respiratory Syncytial Virus (HRSV) or Human Metapneumovirus (HMPV) inhibitors. The present invention further relates to pharmaceutical compositions comprising the aforementioned compounds for administration to a subject suffering from HRSV or HMPV infection. The invention also relates to methods of treating an HRSV or HMPV infection in a subject by administering a pharmaceutical composition comprising the compounds of the present invention.

22 Claims, No Drawings

(56) References Cited

U.S. PATENT DOCUMENTS

| | | | |
|---|---|---|---|
| 2005/0261339 | A1 | 11/2005 | Ohi et al. |
| 2006/0040923 | A1 | 2/2006 | Carter et al. |
| 2006/0083741 | A1 | 4/2006 | Hoffman et al. |
| 2007/0142403 | A1 | 6/2007 | Powell et al. |
| 2007/0185094 | A1 | 8/2007 | Lattmann et al. |
| 2007/0185096 | A1 | 8/2007 | Powell et al. |
| 2007/0293482 | A1 | 12/2007 | Dowdell et al. |
| 2008/0139536 | A1 | 6/2008 | Dowdell et al. |
| 2009/0274655 | A1 | 11/2009 | Grimes et al. |
| 2010/0015063 | A1 | 1/2010 | Carter et al. |
| 2010/0168384 | A1 | 7/2010 | Mdcaniel et al. |
| 2011/0274654 | A1 | 11/2011 | Bahadoor et al. |
| 2012/0196846 | A1 | 8/2012 | Mackman et al. |
| 2012/0245151 | A1 | 9/2012 | Gavai et al. |
| 2014/0038947 | A1 | 2/2014 | Glick et al. |
| 2014/0100365 | A1 | 4/2014 | Gavai et al. |
| 2014/0148573 | A1 | 5/2014 | Ku et al. |
| 2014/0328796 | A1 | 11/2014 | Phadke et al. |
| 2015/0038514 | A1 | 2/2015 | Grunenberg et al. |
| 2015/0065504 | A1 | 3/2015 | Wang et al. |
| 2015/0218111 | A1 | 8/2015 | Gavai et al. |
| 2015/0231152 | A1 | 8/2015 | Zhao et al. |
| 2015/0299210 | A1 | 10/2015 | Bailey et al. |
| 2016/0244460 | A1 | 8/2016 | Wang et al. |
| 2017/0022221 | A1 | 1/2017 | Blaisdell et al. |
| 2017/0226127 | A1 | 8/2017 | Estrada et al. |
| 2017/0226129 | A1 | 8/2017 | Yu et al. |
| 2017/0305935 | A1 | 10/2017 | Hunt et al. |
| 2017/0355717 | A1 | 12/2017 | Hunt et al. |
| 2018/0065932 | A1 | 3/2018 | Wang et al. |
| 2018/0193352 | A1 | 7/2018 | Shook et al. |
| 2018/0237425 | A1 | 8/2018 | Kim et al. |
| 2018/0258102 | A1 | 9/2018 | Shook et al. |
| 2018/0354912 | A1 | 12/2018 | Or et al. |
| 2019/0002478 | A1 | 1/2019 | Kim et al. |
| 2019/0002479 | A1 | 1/2019 | Kim et al. |
| 2019/0023692 | A1 | 1/2019 | Tahri et al. |
| 2019/0040084 | A1 | 2/2019 | Yu et al. |
| 2019/0092791 | A1 | 3/2019 | Hunt et al. |
| 2019/0152968 | A1 | 5/2019 | Blaisdell et al. |
| 2019/0177283 | A1 | 6/2019 | Hague |
| 2019/0192535 | A1 | 6/2019 | Shook et al. |
| 2019/0202841 | A1 | 7/2019 | Hunt et al. |
| 2019/0315766 | A1 | 10/2019 | Yu et al. |
| 2020/0377519 | A1 | 12/2020 | Qiu et al. |
| 2021/0238188 | A1 | 8/2021 | He et al. |
| 2022/0119398 | A1 | 4/2022 | Or et al. |
| 2022/0356189 | A1 | 11/2022 | Szymaniak et al. |
| 2023/0108803 | A1 | 4/2023 | Szymaniak et al. |
| 2023/0125803 | A1 | 4/2023 | Szymaniak et al. |
| 2023/0357258 | A1 | 11/2023 | Szymaniak et al. |
| 2023/0365525 | A1 | 11/2023 | Yu et al. |
| 2024/0368174 | A1 | 11/2024 | Szymaniak et al. |
| 2024/0368176 | A1 | 11/2024 | Szymaniak et al. |

FOREIGN PATENT DOCUMENTS

| | | | |
|---|---|---|---|
| JP | 2004043456 | A | 2/2004 |
| WO | 9308175 | A1 | 4/1993 |
| WO | 9426718 | A1 | 11/1994 |
| WO | 2004026843 | A1 | 4/2004 |
| WO | 2004052348 | A2 | 6/2004 |
| WO | 2004106310 | A1 | 12/2004 |
| WO | 2005042530 | A1 | 5/2005 |
| WO | 2005089769 | A1 | 9/2005 |
| WO | 2005090319 | A1 | 9/2005 |
| WO | 2006081389 | A1 | 8/2006 |
| WO | 2010103306 | A1 | 9/2010 |
| WO | 2011005842 | A1 | 1/2011 |
| WO | 2011112186 | A1 | 9/2011 |
| WO | 2011151651 | A1 | 12/2011 |
| WO | 2012012776 | A1 | 1/2012 |
| WO | 2012068622 | A1 | 5/2012 |
| WO | 2012080446 | A1 | 6/2012 |
| WO | 2012080447 | A1 | 6/2012 |
| WO | 2012080449 | A1 | 6/2012 |
| WO | 2012080450 | A1 | 6/2012 |
| WO | 2012080451 | A1 | 6/2012 |
| WO | 2013096681 | A1 | 6/2013 |
| WO | 2013186332 | A1 | 12/2013 |
| WO | 2013186334 | A1 | 12/2013 |
| WO | 2014031784 | A1 | 2/2014 |
| WO | 2014047369 | A1 | 3/2014 |
| WO | 2014047397 | A1 | 3/2014 |
| WO | 2014060411 | A1 | 4/2014 |
| WO | 2014125444 | A1 | 8/2014 |
| WO | 2014184350 | A1 | 11/2014 |
| WO | 2014186035 | A1 | 11/2014 |
| WO | 2014209983 | A1 | 12/2014 |
| WO | 2015026792 | A1 | 2/2015 |
| WO | 2015110446 | A1 | 7/2015 |
| WO | 2016018697 | A1 | 2/2016 |
| WO | 2016022464 | A1 | 2/2016 |
| WO | 2016055791 | A1 | 4/2016 |
| WO | 2016055792 | A1 | 4/2016 |
| WO | 2016097761 | A1 | 6/2016 |
| WO | 2016138158 | A1 | 9/2016 |
| WO | 2016166546 | A1 | 10/2016 |
| WO | 2017015449 | A1 | 1/2017 |
| WO | 2017123864 | A1 | 7/2017 |
| WO | 2017123884 | A1 | 7/2017 |
| WO | 2017175000 | A1 | 10/2017 |
| WO | 2018226801 | A1 | 12/2018 |
| WO | 2019067864 | A1 | 4/2019 |
| WO | 2021066922 | A1 | 4/2021 |
| WO | 2021198981 | A1 | 10/2021 |
| WO | 2021214136 | A1 | 10/2021 |
| WO | 2022182861 | A1 | 9/2022 |
| WO | 2022211812 | A1 | 10/2022 |

OTHER PUBLICATIONS

STN Registry database entry: CAS RN 1348594-72-8 (Entered STN: Dec. 4, 2011).

STN Registry database entry: CAS RN 1348849-53-5 (Entered STN: Dec. 5, 2011).

STN Registry database entry: CAS RN 1348924-24-2 (Entered STN: Dec. 5, 2011).

STN Registry database entry: CAS RN 1349463-13-3 (Entered STN: Dec. 6, 2011).

STN Registry database entry: CAS RN 1349533-81-8 (Entered STN: Dec. 6, 2011).

STN Registry database entry: CAS RN 1349749-23-0 (Entered STN: Dec. 6, 2011).

STN Registry database entry: CAS RN 1350148-32-1 (Entered STN: Dec. 7, 2011).

Pubchem-CID: 10595203, p. 3, Fig, Oct. 25, 2006.

"4-(2-Hydroxyethoxy)-3-methoxy-N-[3,3,Mar. 1, 22 trifluoro-2-[7-(4-fluorophenyl)-3-[2-(methylamino)ethyl]-2,3-dihydrofuro[2,3-c]pyridin-5-yl]-2-methylpropyl]benzamide", Pubmed Compound Record for CID 139332032, U.S. National Library of Medicine, Nov. 2, 2019, https://pubchem.ncbi.nlm.nih.gov/compound/139332032).

"N-[(2R)-2-[(3S)-3-Amino-7-(3-chloro-4-A fluorophenyl)-3-methyl-2H-furo[2,3-c]pyridin-5-yl]-3,3,3-trifluoro-2-hydroxypropyl]-4-ethoxy-3-methoxybenzamide", Pubchem Compound Record for CID 117923975, U.S. National Library of Medicine, Feb. 23, 2016 (Feb. 23, 2016), 1 pg -9 (https://pubchem.ncbi.nlm.nih.gov/compound/117923975); p. 2.

"N-[(2R)-2-[3-(Aminomethyl)-7-(4-fluorophenyl)-1-22 3-methyl-2H-furo[2,3-c]pyridin-5-yl]-3,3,3-trifluoro-2-hydroxypropyl]-4-(2-hydroxyethoxy)-3-methoxybenzamide", Pubmed Compound Record for CID 117924934, U.S. National Library of Medicine, Feb. 23, 2016, https://pubchem.ncbi.nlm.nih.gov/compound/117924934.

"N-[2-[8-[4-Fluoro-3-(1-fluoroethyl)phenyl]-4-iodo-4-methyl-2,3-dihydropyrano[2,3-]pyridin-6-yl]-2-oxoethyl]-3-methoxy-4-[2-[(4-methoxyphenyl)methoxy]ethoxy]benzamide", Pubchem Compound Record for CID 117924454, U.S. National library of Medicine, Feb. 23, 2016 (Feb. 23, 2016), pp. 1-8 (https://pubchem.ncbi.nlm.nih.gov/compound/117924454); p. 2.

(56) References Cited

OTHER PUBLICATIONS

Albright (Document No. 129:54301) retrieved from STN; entered in STN on Jun. 17, 1998.
Albright (Document No. 130:153583) retrieved from STN; entered in STN on Feb. 16, 1999.
Andrzej , (Document No. 144:274313) retrieved from STN; entered in STN on Mar. 3, 2006.
Aquino, C. J., "Discovery of 1,5-Benzodiazepines with Peripheral Cholecystokinin (CCK-A) Receptor Agonist Activity. 1. Optimization of the Agonist "Trigger"", J. Med. Chem., 39, 1996, 562-569.
Armstrong , "An Efficient Asymmetric Synthesis of (R)-3-Amino-2,3,4,5-tetrahydro-1H-[1]benzazepine-2-one", Tetrahedron Letters, 35(20), 1994, 3239-3242.
Bond, S. , "1,2, 3, 9b-Tetrahydro-5H-imidazo[2,1-a]isoindol-5-ones as a new class of respiratory syncytial virus (RSV) fusion inhibitors. Part 2: Identification of BTA9881 as a preclinical candidate", Bioorg & Med Chem Lett, 25, 2015, 976-981.
Carter, M. C, "1,4-Benzodiazepines as Inhibitors of Respiratory Syncytial Virus", J. Med. Chem., 49, DOI: http://dx.doi.org/10.1021/jm051185t, Mar. 9, 2006, 2311-2319.
Chapman, J. , "RSV604, a Novel Inhibitor of Respiratory Syncytial Virus Replication", Antimicrobial Agents and Chemotherapy, 51(9), 2007, 3346-3353.
Contreras-Romo, M. , "Exploring the Ligand Recognition Properties of the Human Vasopressin V1a Receptor Using QSAR and Molecular Modeling Studies", Chem. Biol. Drug. Des., 83, 2014, 207-223.
Fearns, R. , "New antiviral approaches for respiratory syncytial virus and other mononegaviruses: Inhibiting the RNA polymerase", Antiviral Research, 134, , http://dx.doi.org/10.1016/j.antiviral.2016.08.006, 2016, 63-76.
Fernandez, H. , "Ribavirin: A Clinical Overview", Euro J. Epidemiology, 2(1), Mar. 1, 1986, 1-14.
Fordyce , "Discovery of novel benzothienoazepine derivatives as potent inhibitors of respiratory syncytial virus", Bioorganic & Medicinal Chemistry Letters, 27, 2017, 2201-2206.
Heeney (Document No. 153:359062) retrieved from STN; entered in STN on Sep. 2, 2010.
Henderson, E. A, "1,4-Benzodiazepines as Inhibitors of Respiratory Syncytial Virus. The Identification of a Clinical Candidate", Journal of Medicinal Chemistry, 50(7), DOI: http://dx.doi.org/10.1021/jm0607471, Apr. 2007, 1685-1692.
Karmakar , "Crystallization-Induced Dynamic Resolution toward the Synthesis of (S)-7-Amino-5H,7H-dibenzo[b,d]-azepin-6-one: An Important Scaffold for γ-Secretase Inhibitors", Organic Process Research & Development, 20, 2016, 1717-1720.
Kozlova, A. , "Current State on Tryptophan 2,3-Dioxygenase Inhibitors: a Patent Review", Expert Opinion on Therapeutic Patents, 29(1), 2019, 1-32.
Lattmann, E. , "In vivo Evaluation of Substituted 3-Amino-1,4-benzodiazepines as Anti-depressant, Anxiolytic and Antinociceptive Agents", Arzneimittelforschung, 59(2), , doi: 10.1055/s-0031-1296366, 2009, 61-71.
Lee (Document No. 140:69941) retrieved from STN; entered in STN on Jul. 8, 2003.
Mackman, R. L., "Discovery of an Oral Respiratory Syncytial Virus (RSV) Fusion Inhibitor (GS-5806) and Clinical Proof of Concept in a Human RSV Challenge Study", J. Med. Chem., 58, 2015, 1630-1643.
Mayo Clinic Staff , "", Respiratory syncytial virus (RSV) [online], retrieved from from internet on Jun. 25, 2017 .; URL http://www.mayoclinic.org/diseases-condiitons/respiratory-syncytial-virus/basics/prevention.
Offel, M. , "Synthesis of Substituted 3-Anilino-5-phenyl-I,3-dihydro-2H-I, 4-benzodiazepine-2-ones and their Evaluation as Cholecystokinin-Ligands", Archiv Der Pharmazie, 339(4), , DOI: 10.1002/ardp.200500217, Apr. 1, 2006, 163-173.
Olszewska, W. , "Emerging drugs for respiratory syncytial virus infection", Expert Opin. Emerg. Drugs, 14(2), 2009, 207-217.
Peesapati (Document No. 120:244848) retreved from STN; entered in STN on May 14, 1994.
Perron, M. , "GS-5806 Inhibits a Broad Range of Respiratory Syncytial Virus Clinical Isolates by Blocking the Virus-Cell Fusion Process", Antimicrobial Agents and Chemotherapy, 60(3), https://www.ncbi.nlm.nih.gov/pmc/articles/PMC4776015/, 2016, 1264-1273.
Reider , "Metalated Allylaminosilane: A New, Practical Reagent for Stereoselective a-Hydroxyallylation of Aldehydes to Erythro-1,2-diol Skeletons", J. Org. Chem, 52, 1987, 955-957.
Setoi, H. , "Preparation of heterocyclylbenzamide derivatives as vasopressin antagonists", Document No. 131:116236, retrieved from STN; entered in STN on Aug. 6, 1999, Aug. 6, 1999.
Stein, D. S, "Oral ribavirin treatment of influenza A and B", Antimicrobial Agents and Chemotherapy, 31(8), , URL:http://dx.doi.org/I0.II28/AAC.31.8.I285>, Aug. 1987, 1285-1287.
Sudo, K. , "YM-53403, a unique anti-respiratory syncytial virus agent with a novel mechanism of action", Antiviral Research, 65, 2005, 125-131.
Wang (Document No. 160:385666) retreved from STN; entered in STN on Feb. 27, 2014.
Wang, G. , "Discovery of 4'-Chloromethyl-2'-deoxy-3',5'-di-O-isobutyryl-2'-fluorocytidine (ALS-8176), A First-in-Class RSV Polymerase Inhibitor for Treatment of Human Respiratory Syncytial Virus Infection", J. Med. Chem., 58, 2015, 1862-1878.
Xiong (Document No. 160:101182) retreved from STN; entered in STN on Nov. 12, 2013.
Xiong, H. , "Discovery of a Potent Respiratory Syncytial Virus RNA Polymerase Inhibitor", Bioorganic & Medicinal Chemistry Letters, 23, 2013, 6789-6793.
Zheng (Document No. 161 :399872) retrieved from STN; entered in STN on Jul. 23, 2014.

ANTIVIRAL HETEROCYCLIC COMPOUNDS

RELATED APPLICATIONS

This application is a continuation-in-part of U.S. application Ser. No. 17/679,746, filed Feb. 24, 2022, which claims the benefit of U.S. Provisional Application No. 63/154,318, filed Feb. 26, 2021, U.S. Provisional Application No. 63/168,705, filed Mar. 31, 2021, U.S. Provisional Application No. 63/171,895, filed Apr. 7, 2021, and U.S. Provisional Application No. 63/293,339, filed Dec. 23, 2021. The entire teachings of the above applications are incorporated herein by reference.

TECHNICAL FIELD

The present invention relates generally to compounds and pharmaceutical compositions useful as Respiratory Syncytial Virus (RSV) inhibitors and Human Metapneumovirus (HMPV) inhibitors.

BACKGROUND OF THE INVENTION

Human respiratory syncytial virus (HRSV) is a negative sense virus, containing a non-segmented, single-stranded linear RNA genome. As a Paramyxovirus of two serotypes in the genus Pneumoviridae, HRSV contains 10 genes that encode for 11 proteins. The nucleocapsid protein (N), the RNA polymerase protein (L), the phosphoprotein (P) and the transcription anti-termination factor (M2-1) along with the RNA genome make up the ribonucleoprotein (RNP) complex. Several small-molecule compounds have been shown to target the RNP complex. Additionally, the fusion protein (F), paramount for viral attachment to the host, has been extensively studied. High resolution structures of the F protein interacting with inhibitors have been attained, while structural studies with the N protein are earlier in development. A direct result of the HRSV protein studies and research, the F protein, L protein and N protein have been the major focus of drug discovery efforts.

The increased effort in HRSV drug discovery is a result of HRSV being the leading cause of acute lower respiratory infections (ALRI) in patients of all ages. In addition to respiratory infections, patient populations at high risk during HRSV infections include the elderly, immunocompromised, children up to the age of two and patients with chronic obstructive pulmonary disorder (COPD) or chronic heart failure (CHF). HRSV was found over four years to cause 177,500 hospital admissions and 14,000 deaths in the U.S. elderly population. It is well-known that almost all children will be infected with HRSV in the first 3 years after birth and HRSV infection is more severe in premature infants. In fact, HRSV is the most common cause of bronchiolitis and pneumonia in infants under the age of one in the U.S. It is estimated that approximately 3.2 million hospitalizations and 66,000 deaths worldwide in children less than 5 years old are due to HRSV. HRSV has been associated with more deaths of infants below one year old and more infant hospitalizations than influenza.

HRSV infection can also affect healthy individuals and repeated HRSV infections even over the course of two months can occur. Symptoms are similar to colds in healthy individuals, however fever, wheezing, rapid and difficult breathing, and cyanosis occur in more severe cases. Currently, the treatment options for HRSV infection are quite limited and there is no vaccine due to unsuccessful attempts to date. Palivizumab is a monoclonal antibody that is approved for prophylactic use, but its use is limited due to its high price. Palivizumab is generally only used for high risk infants, such as premature infants or those with cardiac/lung disease, but has been only 60% effective in reducing hospitalizations. Ribavirin is approved as an inhalation treatment option, but its effectiveness is limited and there are safety concerns associated with it. Taking into account the treatment options, and the consistent seasonality of the HRSV epidemic, the development of new therapeutic agents for the treatment of HRSV is desirable.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2015/110446, WO 2017/009316, *J. Med Chem.* 2015, 58, 1630-1643, *Bioorg. Med Chem. Lett.,* 2015, 25, 976-981 and *Nat. Commun.,* 2017, 8, 167. Examples of other N-protein inhibitors for treatment of HRSV have been disclosed in the following publications: WO 2004/026843, *J. Med Chem.* 2006, 49, 2311-2319, and *J. Med Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO 2011/005842, WO 2013/242525, WO 2014/031784, WO 2015/026792, WO 2016/0055791, WO 2016/138158 and J. Med. Chem. 2015, 58, 1862-1878.

Likewise, human metapneumovirus (HMPV), a negative-sense, single-stranded RNA enveloped virus, that belongs to the Pneumoviridae family and Metapneumovirus genus discovered by van Den Hoogen in 2001, is also a common cause of acute lower respiratory tract infections (ALRTIs). Although often mild, this virus can be serious and life-threatening in high-risk groups, such as children under the age of 5 years, elderly adults over the age of 65 years, and adults with underlying disease (e.g., Chronic Obstructive Pulmonary Disease (COPD), asthma, congestive heart failure, or diabetes). In healthy adults over the age of 65 years, the annual incidence rate of HMPV infection is 1.2/1,000, and 38% of disease (e.g., COPD), and individuals are twice as likely to have symptomatic disease and requirement for medical care. In immunocompromised individuals, HMPV is responsible for 6% of total respiratory infections in lung transplants and 3% of lower respiratory infections associated with stem cell transplant. HMPV infection is also thought to be associated with acute graft rejection.

Like HRSV, infection is thought to attach to the target cell via the glycoprotein (G) protein interactions and followed by fusion via the F protein. HMPV L protein sequence is homologous to HRSV L protein.

HMPV infection is the second most common cause of lower respiratory tract infection in children (behind HRSV) and also problematic for the elderly population. There are 4 subtypes of HMPV found in clinical isolates (A1, A2, B1 and B2). Reinfection occurs throughout childhood following initial infection. No therapeutics are currently available for HMPV infection.

Taking into account the seasonality and predictability of the HRSV and HMPV epidemics, HRSV epidemics in elderly institutions, and the severity of infection in high risk infants, the need for a potent and effective treatment for HRSV and HMPV is clear. The present invention has identified compounds that are heterocyclic molecules that are potent against HRSV-A/B and HMPV. The invention includes methods to prepare these molecules, methods for the RSV cell-based assay, the HMPV-GFP cell-based assay, the HMPV-TN/1501/A1 cell-based assay, and small-molecules that have potential to treat HRSV/HMPV infection.

SUMMARY OF THE INVENTION

The present invention provides compounds represented by Formula (I), and pharmaceutically acceptable salts, esters and prodrugs thereof that can be used to treat or prevent viral (particularly HRSV or HMPV) infection:

(I)

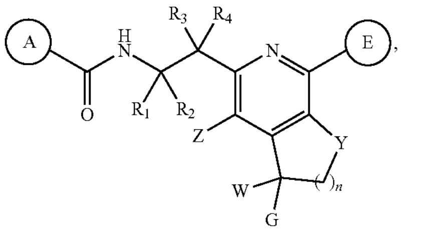

wherein:

A is selected from the group consisting of:
1) optionally substituted aryl; and
2) optionally substituted heteroaryl;

$R_1$ and $R_2$ are each independently selected from the group consisting of:
1) hydrogen;
2) fluorine; and
3) optionally substituted —$C_1$-$C_6$ alkyl;

alternatively, $R_1$ and $R_2$ are taken together with the carbon atom to which they are attached to form an optionally substituted 3- to 6-membered ring;

Z is selected from the group consisting of:
1) hydrogen;
2) halogen; and
3) optionally substituted —$C_1$-$C_6$ alkyl;

W is selected from the group consisting of:
1) hydrogen;
2) optionally substituted —$C_1$-$C_6$ alkoxy;
3) optionally substituted —$C_1$-$C_6$ alkyl; and
4) optionally substituted —$C_3$-$C_6$ cycloalkyl;

G is selected from the group consisting of:
1) —C(O)O$R_{12}$;
2) —C(O)N$R_{11}R_{12}$;
3) optionally substituted —$C_1$-$C_6$ alkyl-CN;
4) optionally substituted —$C_1$-$C_6$ alkyl-C(O)N$R_{11}R_{12}$;
5) optionally substituted —$C_1$-$C_6$ alkyl-C(O)N$R_{11}$S(O)$_2R_{12}$;
6) optionally substituted —$C_1$-$C_6$ alkyl-OC(O)N$R_{11}R_{12}$;
7) optionally substituted —$C_1$-$C_6$ alkyl-NH$R_{13}$;
8) optionally substituted —$C_1$-$C_6$ alkyl-NHC(O)$R_{13}$;

n is 1, 2 or 3; preferably n is 1 or 2;

Y is O, S(O)$_2$, or N$R_{14}$;

E is selected from the group consisting of:
1) optionally substituted aryl;
2) optionally substituted heteroaryl;
3) optionally substituted 3- to 8-membered heterocyclic, and
4) optionally substituted alkynyl;

$R_3$ is hydroxy or fluorine;

$R_4$ is selected from the group consisting of:
1) hydrogen;
2) optionally substituted —$C_1$-$C_6$ alkyl;
3) optionally substituted —$C_3$-$C_8$ cycloalkyl; and
4) optionally substituted 3- to 8-membered heterocyclic;

$R_{11}$ at each occurrence is independently selected from the group consisting of:
1) hydrogen;
2) optionally substituted —$C_1$-$C_8$-alkyl;
3) optionally substituted —$C_3$-$C_8$-cycloalkyl;
4) optionally substituted 4- to 8-membered heterocyclic;
5) optionally substituted aryl;
6) optionally substituted arylalkyl;
7) optionally substituted heteroaryl; and
8) optionally substituted heteroarylalkyl;

$R_{12}$ at each occurrence is independently selected from the group consisting of:
1) hydrogen;
2) optionally substituted —$C_1$-$C_8$-alkyl;
3) optionally substituted —$C_3$-$C_8$-cycloalkyl;
4) optionally substituted 4- to 8-membered heterocyclic;
5) optionally substituted aryl;
6) optionally substituted arylalkyl;
7) optionally substituted heteroaryl; and
8) optionally substituted heteroarylalkyl;

alternatively, $R_{11}$ and $R_{12}$ are taken together with the nitrogen atom to which they are attached to form a 3- to 12-membered heterocyclic ring, preferably the said 3- to 12-membered heterocyclic ring is, but not limited to morpholinyl, piperidinyl, piperazinyl, pyrrolidinyl, and, azetidine;

$R_{13}$ at each occurrence is independently selected from the group consisting of:
1) Optionally substituted —$C_1$-$C_8$ alkyl;
2) Optionally substituted —$C_3$-$C_8$ cycloalkyl;
3) Optionally substituted 4- to 8-membered heterocyclic;
4) Optionally substituted aryl;
5) Optionally substituted arylalkyl;
6) Optionally substituted heteroaryl; and
7) Optionally substituted heteroarylalkyl; and $R_{14}$ is selected from:
1) hydrogen;
2) optionally substituted —$C_1$-$C_8$-alkyl; and
3) optionally substituted —$C_3$-$C_8$-cycloalkyl;

Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), Y is O.

In certain embodiments of the compounds of Formula (I), Y is O, and n is 1 or 2.

In certain embodiments of the compounds of Formula (I), $R_1$ is hydrogen or F.

In certain embodiments of the compounds of Formula (I), $R_2$ is hydrogen or F.

In certain embodiments of the compounds of Formula (I), Z is hydrogen, Cl or F.

In certain embodiments of the compounds of Formula (I), $R_1$ is hydrogen, $R_2$ is hydrogen, and Z is hydrogen.

In certain embodiments of the compounds of Formula (I), W is optionally substituted methyl, optionally substituted ethyl, or optionally substituted cyclopropyl.

In certain embodiments of the compounds of Formula (I), W is cyclopropyl, ethyl, $—CH_3$, $—CH_2F$, $—CHF_2$, or $—CF_3$.

In certain embodiments of the compounds of Formula (I), $R_3$ is —OH.

In certain embodiments of the compounds of Formula (I), $R_4$ is optionally substituted methyl or optionally substituted cyclopropyl.

In certain embodiments of the compounds of Formula (I), $R_3$ is OH, and $R_4$ is $CF_3$ or cyclopropyl.

In certain embodiments of the compounds of Formula (I), $R_1$ is hydrogen, $R_2$ is hydrogen, $R_3$ is OH, and $R_4$ is $CF_3$.

In certain embodiments of the compounds of Formula (I), G is $—C(O)NR_{11}R_{12}$. In certain embodiments, G is $—C(O)NH_2$.

In certain embodiments of the compounds of Formula (I), G is $—CH_2NHR_{13}$, $—CH_2C(O)NR_{11}R_{12}$, $—CH_2NHC(O)R_{13}$, $—CH_2OC(O)NR_{11}R_{12}$, $—CH_2CN$, or $—CH_2C(O)NR_{11}S(O)_2R_{12}$. In certain embodiments, G is $—CH_2C(O)NH_2$.

In certain embodiments of the compounds of Formula (I), A is selected from one of the following by removal of a hydrogen atom:

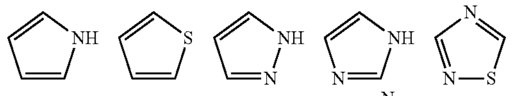
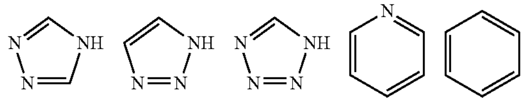
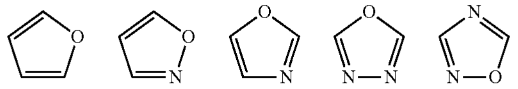
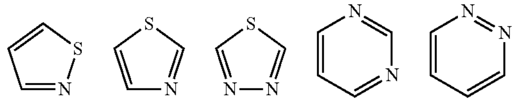
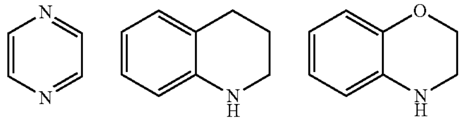
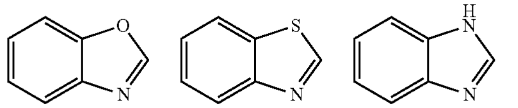
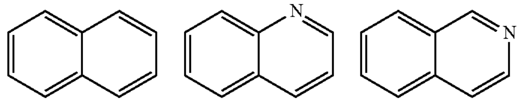
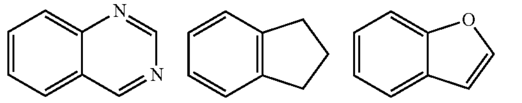
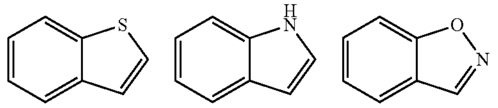

-continued

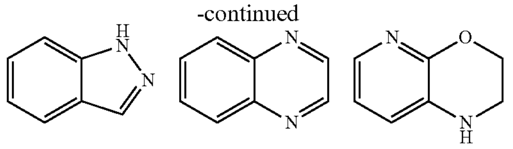
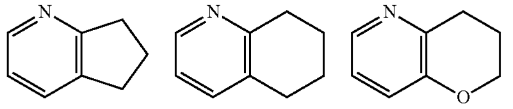
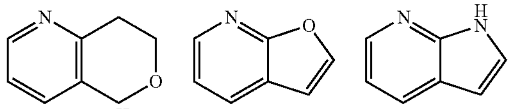
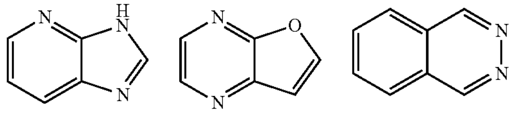
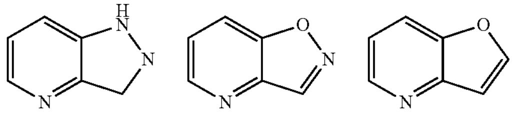
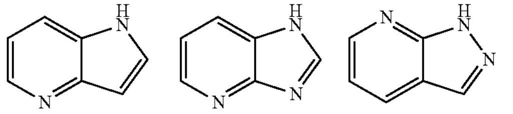
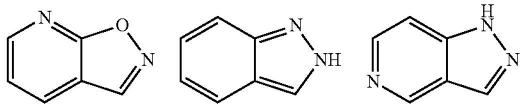
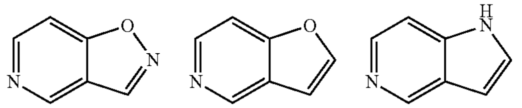
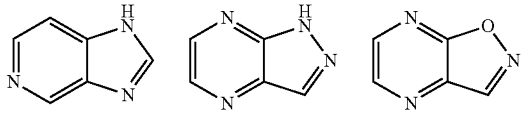
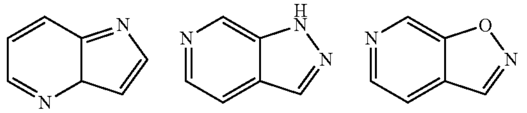
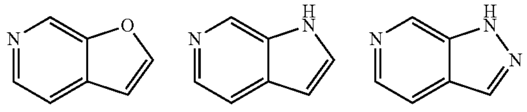
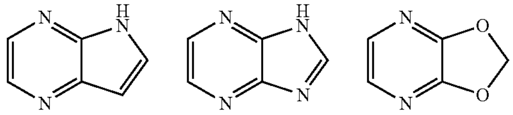
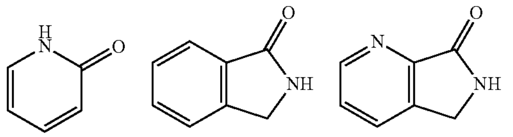
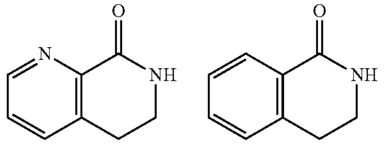
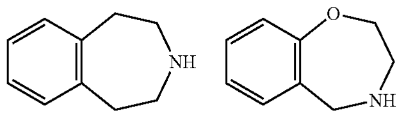

-continued
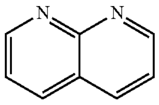
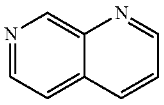
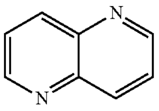
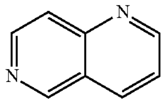
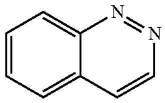
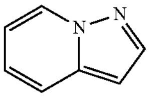
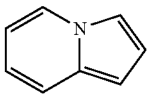,
wherein each of these groups is optionally substituted.
In certain embodiments of the compounds of Formula (I), A is selected from the groups set forth below,
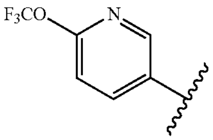
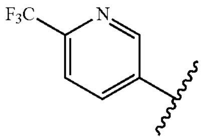
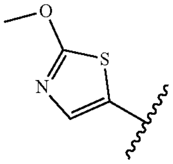
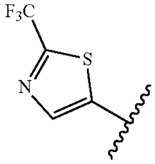
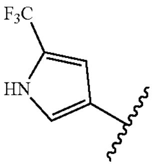
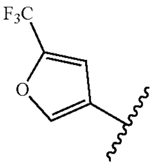
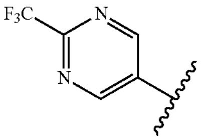
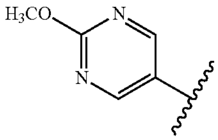
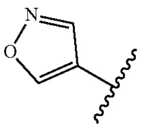
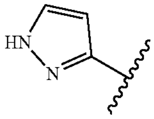
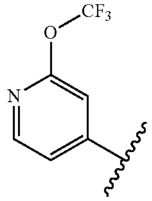
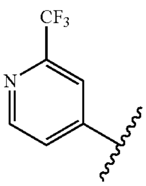
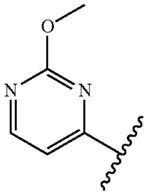
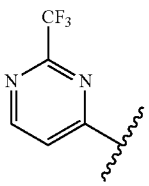
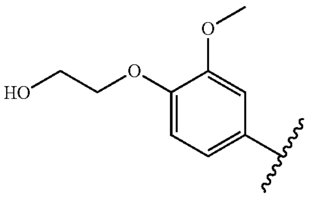
-continued
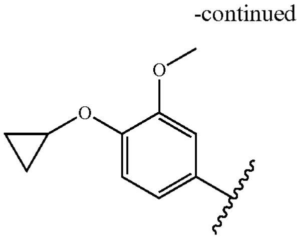
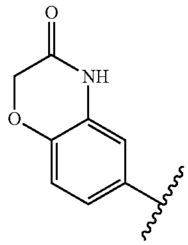
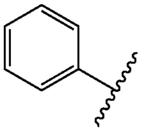
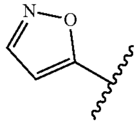
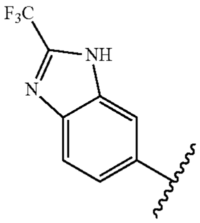
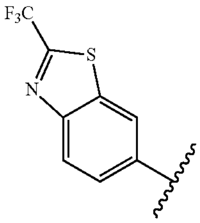
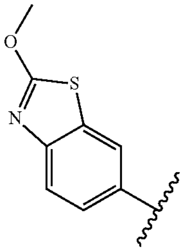
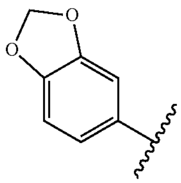
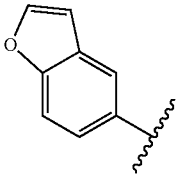
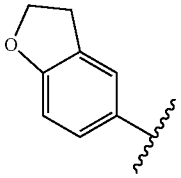
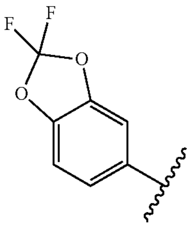
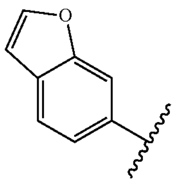
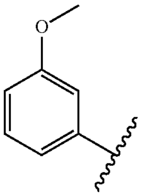
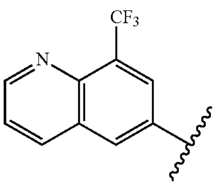
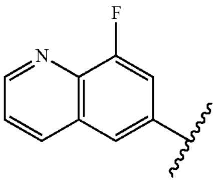
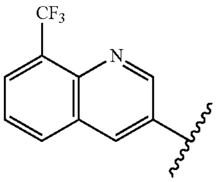

-continued
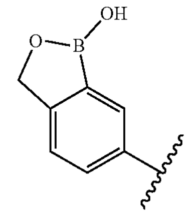
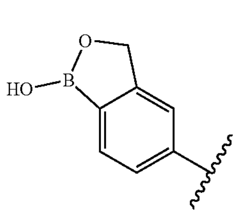
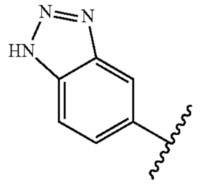
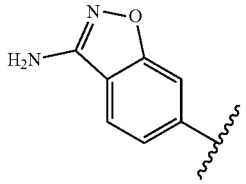
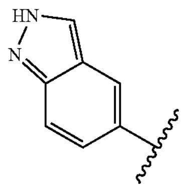
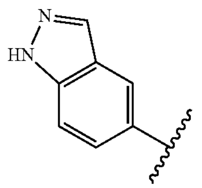
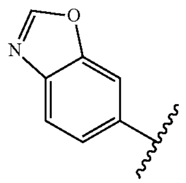
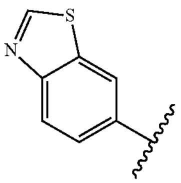
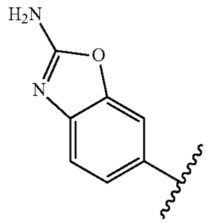
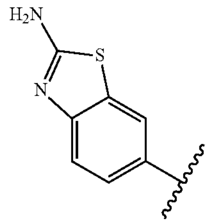
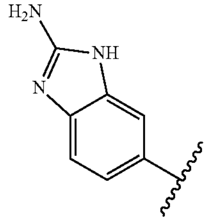
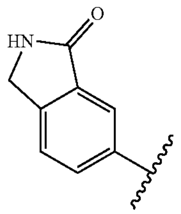
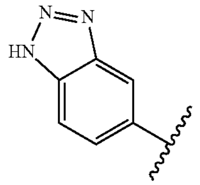
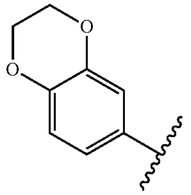
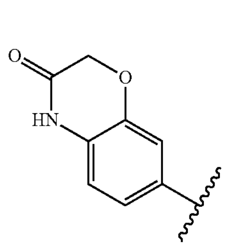
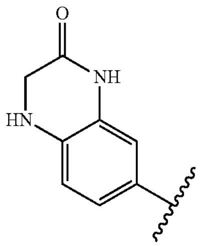
-continued
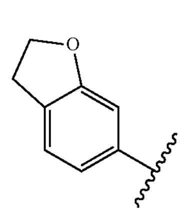
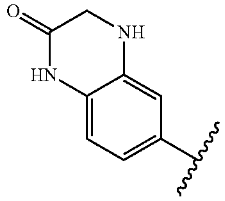
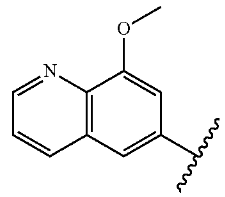
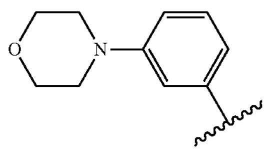
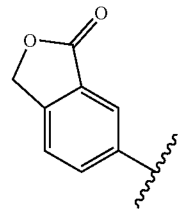
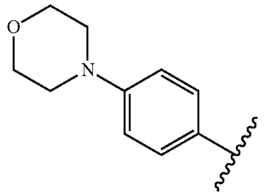
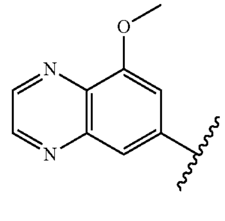
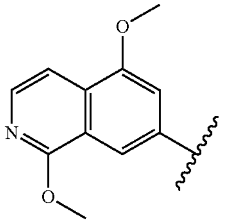
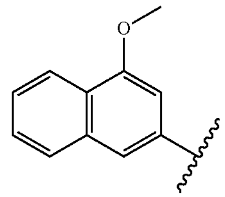
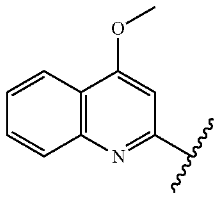
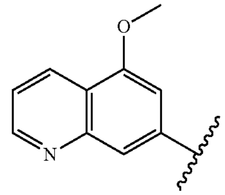
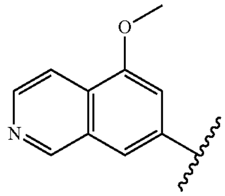
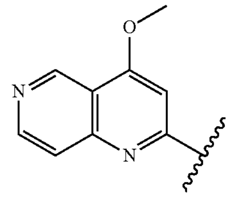
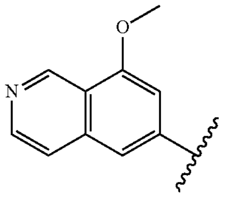
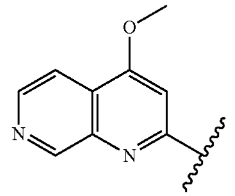
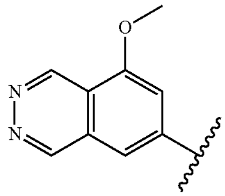

-continued
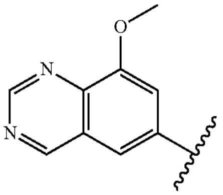
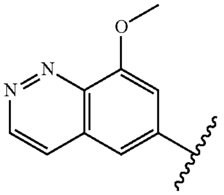
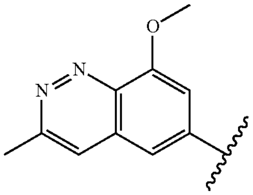
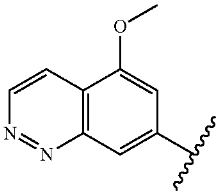
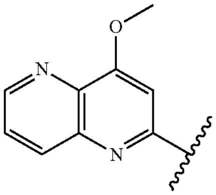
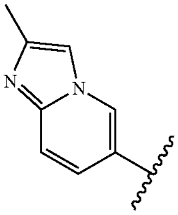
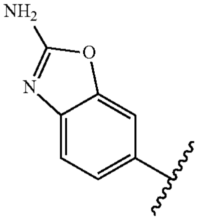
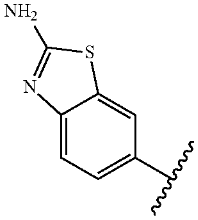
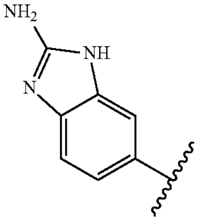
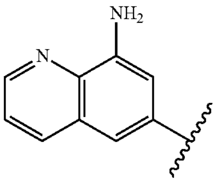
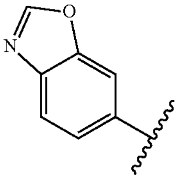
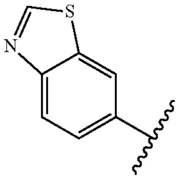
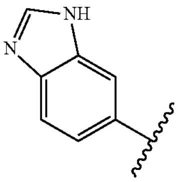
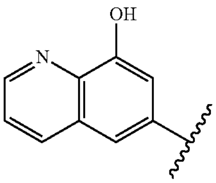
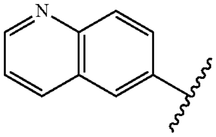
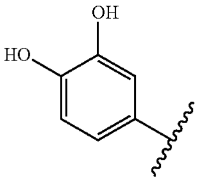
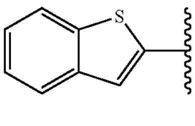
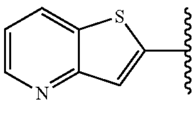
-continued
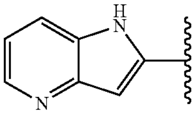
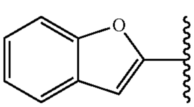
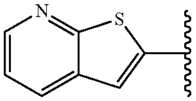
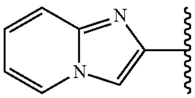
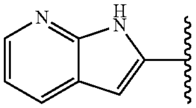
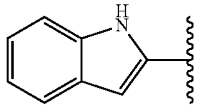
wherein each of these groups is optionally substituted.
In certain embodiments of the compounds of Formula (I), A is selected from the groups set forth below,
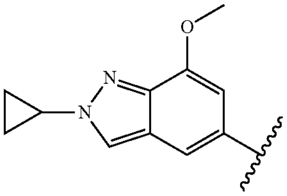
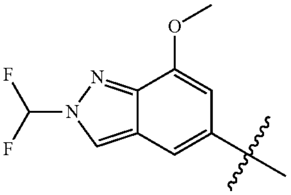
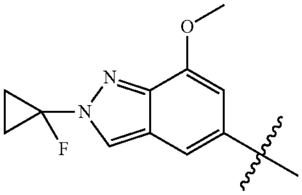
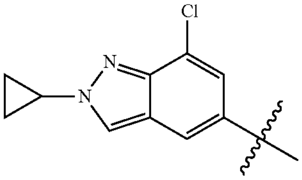
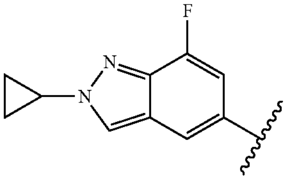
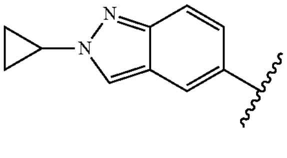

-continued

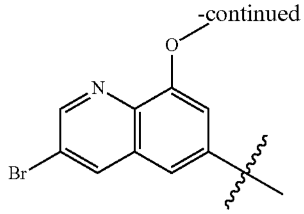

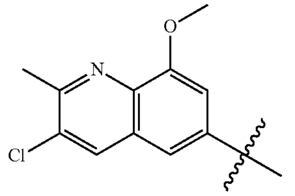

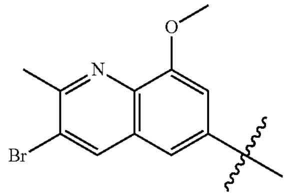

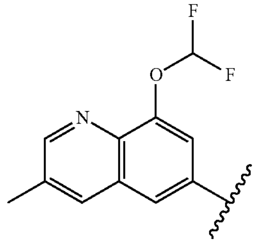

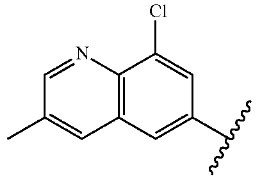

.

In certain embodiments of the compounds of Formula (I), A is

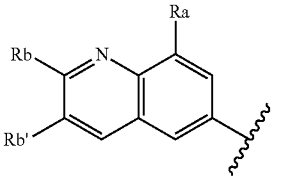

or

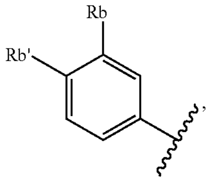

, wherein Ra is hydrogen, halogen, —CN, —$NO_2$, —$OR_{11}$, —$NR_{11}R_{12}$, —$NR_{11}C(O)R_{12}$, —$NR_{11}S(O)_2R_{12}$, —$S(O)_2R_{12}$, —$S(O)_2NR_{11}R_{12}$, —$NR_{11}C(O)NR_{11}R_{12}$, —$C(O)R_{11}$, —$C(O)OR_{11}$, —$C(O)NR_{11}R_{12}$, optionally substituted —$C_1$-$C_6$ alkyl, optionally substituted —$C_3$-$C_8$-cycloalkyl, optionally substituted 3- to 8-membered heterocyclic, optionally substituted aryl, or optionally substituted heteroaryl; Rb and Rb' are each independently selected from hydrogen, halogen, —$OR_{11}$, —$NR_{11}R_{12}$, optionally substituted —$C_1$-$C_6$-alkyl, optionally substituted —$C_3$-$C_8$-cycloalkyl, optionally substituted 3- to 8-membered heterocyclic, optionally substituted aryl, and optionally substituted heteroaryl. Alternatively, Rb and Rb' are taken together with the carbon atoms to which they are attached to form a 4- to 7-membered ring fused with the phenyl ring.

In certain embodiments of the compounds of Formula (I), E is optionally substituted aryl, preferably optionally substituted phenyl.

In certain embodiments of the compounds of Formula (I), E is selected from one of the following by removal of a hydrogen atom:

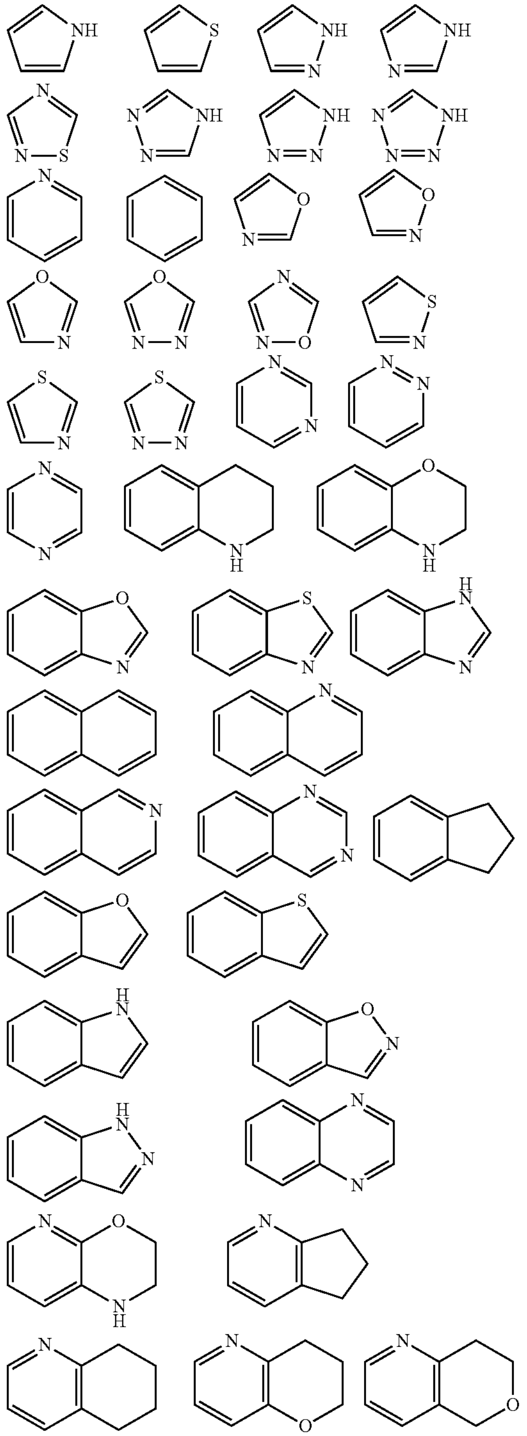

-continued
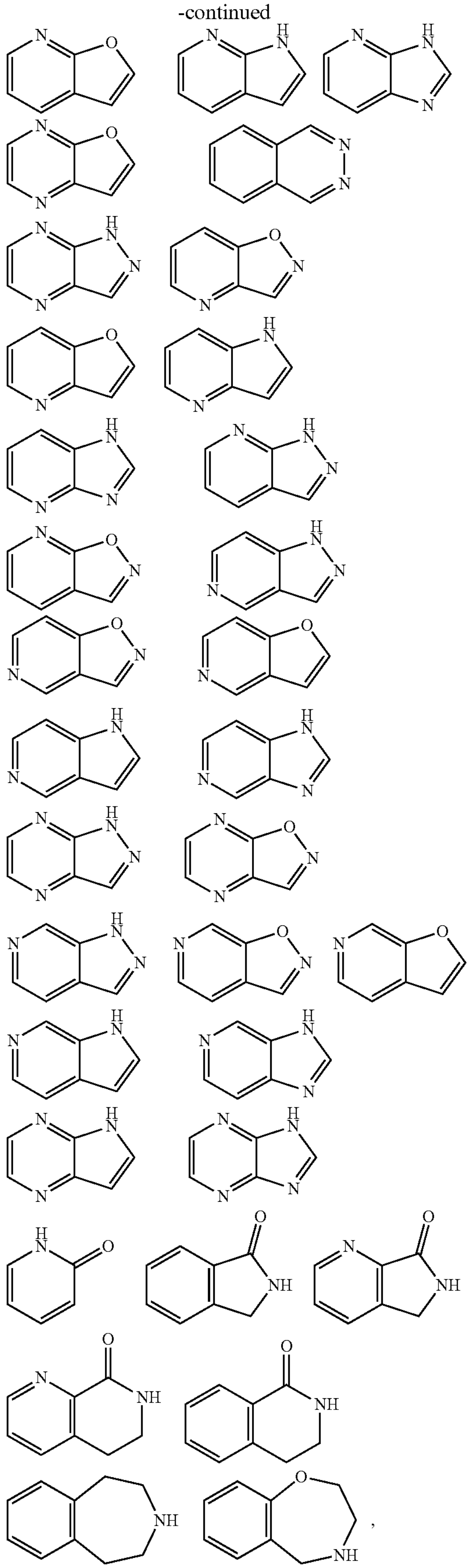
,
wherein each of these groups is optionally substituted.
In certain embodiments of the compounds of Formula (I), E is selected from the groups set forth below,
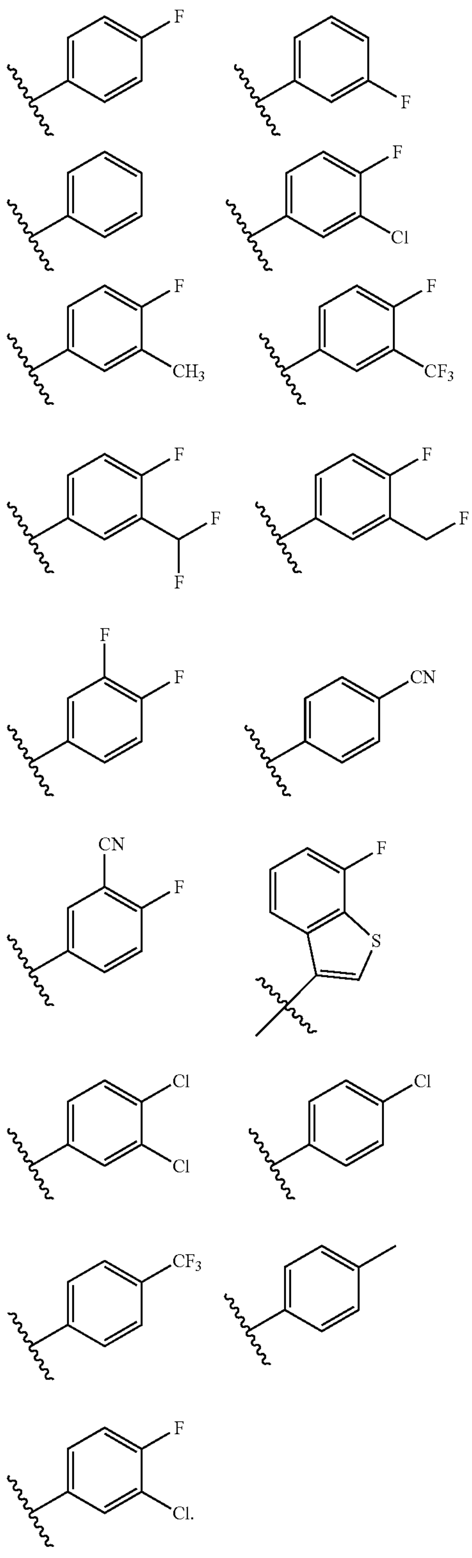
In certain embodiments of the compounds of Formula (I), E is selected from the groups set forth below,

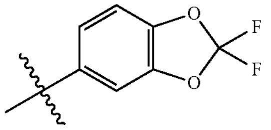

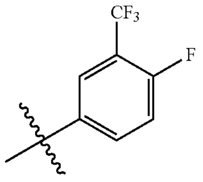

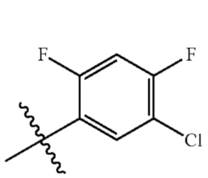

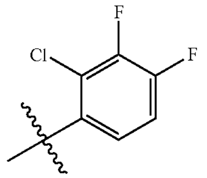

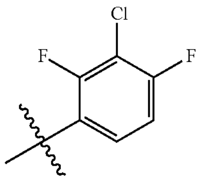

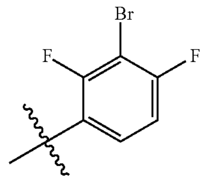

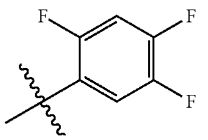

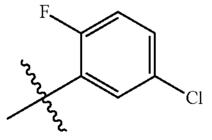

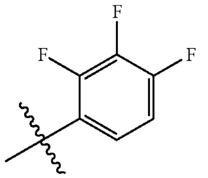

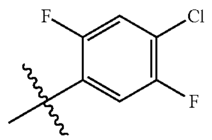

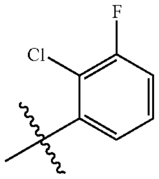

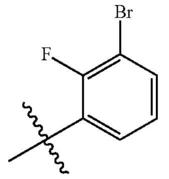

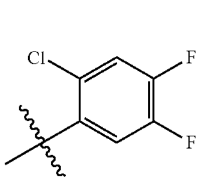

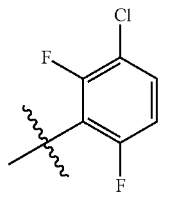

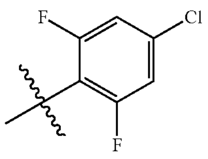

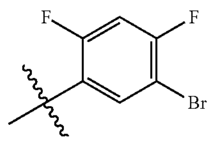

In one embodiment of the present invention, the compound of Formula (I) is represented by Formula (Ia) or Formula (Ib), or a pharmaceutically acceptable salt, ester or prodrug thereof:

(Ia)

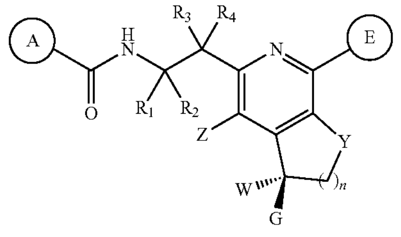

(Ib)

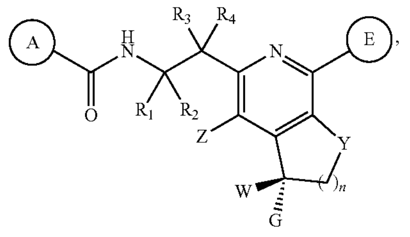

wherein A, $R_1$, $R_2$, Z, W, G, n, Y, E, $R_3$, and $R_4$ are as previously defined.

In a preferred embodiment, the compound of Formula (I) has the stereochemistry shown in Formula (Ib).

In one embodiment of the present invention, the compound of Formula (I) is represented by Formula (II), or a pharmaceutically acceptable salt, ester, or prodrug thereof:

(II)

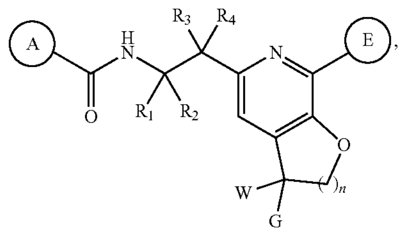

wherein A, $R_1$, $R_2$, W, G, n, E, $R_3$, and $R_4$ are as previously defined.

In one embodiment of the present invention, the compound of Formula (I) is represented by Formula (III) or a pharmaceutically acceptable salt, ester, or prodrug thereof:

(III)

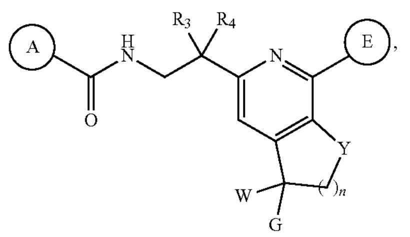

wherein A, W, G, n, Y, E, $R_3$, and $R_4$ are as previously defined.

In one embodiment of the present invention, the compound of Formula (I) is represented by one of Formulae (IV-1)~(IV-2), or a pharmaceutically acceptable salt, ester, or prodrug thereof:

(IV-1)

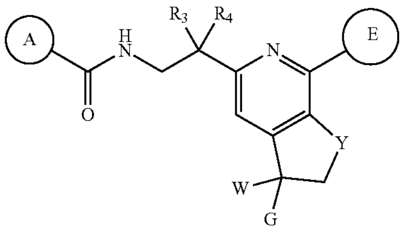

(IV-2)

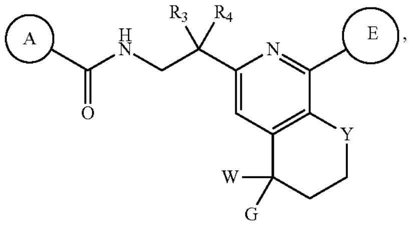

, wherein A, W, G, Y, E, $R_3$, and $R_4$ are as previously defined.

In one embodiment of the present invention, the compound of Formula (I) is represented by one of Formulae (V-1)~(V-4), or a pharmaceutically acceptable salt, ester, or prodrug thereof:

(V-1)

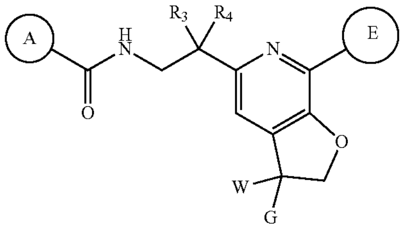

(V-2)

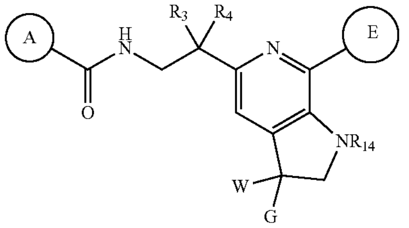

(V-3)

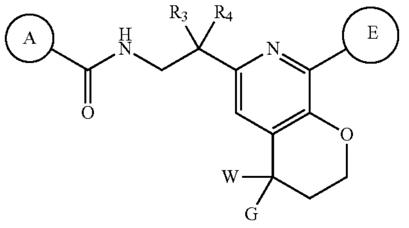

(V-4)

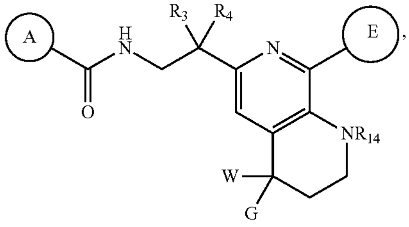

, wherein A, W, G, E, $R_{14}$, $R_3$, and $R_4$ are as previously defined.

In one embodiment of the present invention, the compound of Formula (I) is represented by one of Formulae (VI-1)~(VI-4), or a pharmaceutically acceptable salt, ester, or prodrug thereof:

(VI-1)

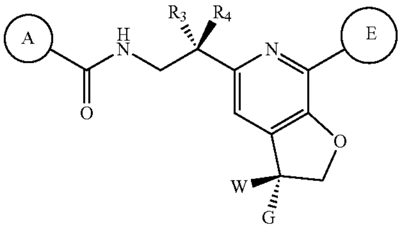

(VI-2)

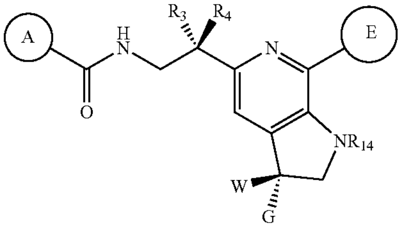

(VI-3)

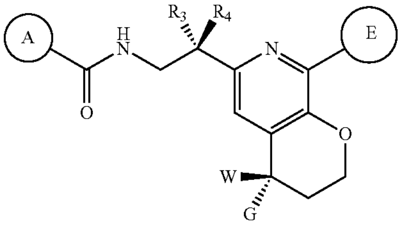

(VI-4)

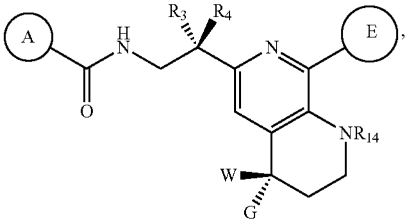

, wherein A, W, G, E, $R_{14}$, $R_3$, and $R_4$ are as previously defined. Preferably, W is optionally substituted methyl; more preferably, W is —$CH_3$ or —$CF_3$.

In one embodiment of the present invention, the compound of Formula (I) is represented by one of Formulae (VII-1)~(VII-12), or a pharmaceutically acceptable salt, ester, or prodrug thereof:

(VII-1)

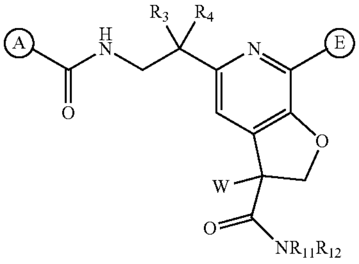

-continued
(VII-2)
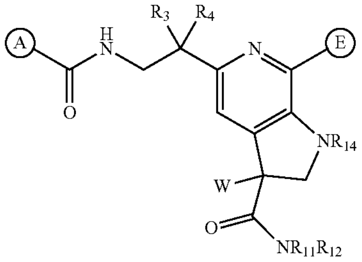
(VII-3)
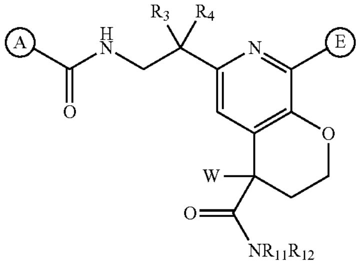
(VII-4)
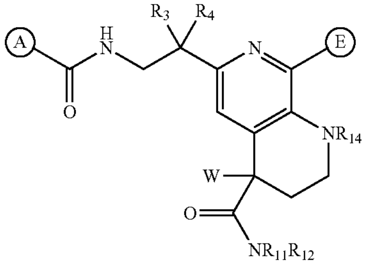
(VII-5)
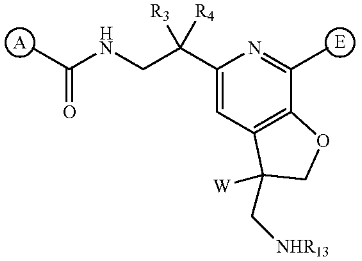
(VII-6)
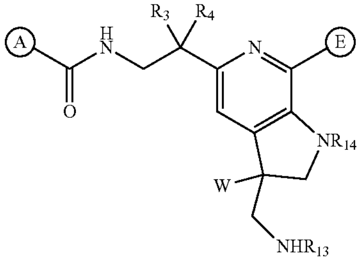
(VII-7)
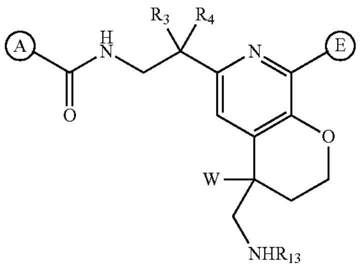
-continued
(VII-8)
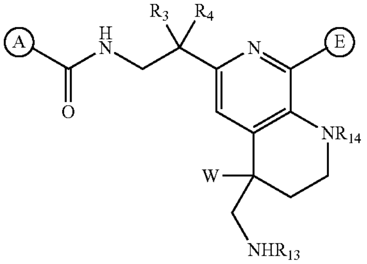
(VII-9)
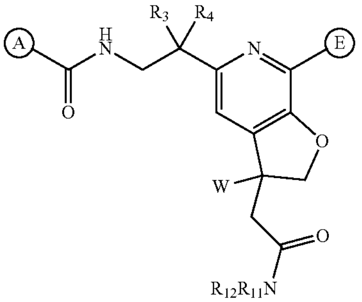
(VII-10)
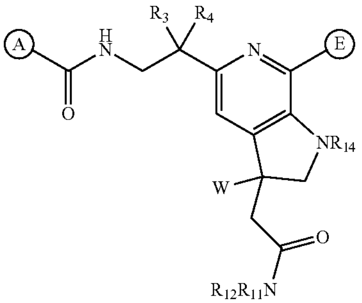
(VII-11)
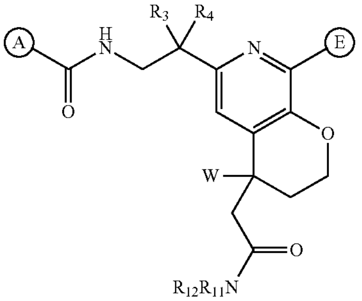
(VII-12)
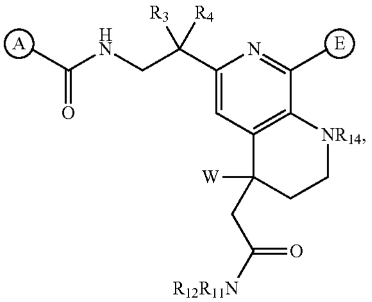
wherein A, W, E, $R_{11}$, $R_{12}$, $R_{13}$, $R_{14}$, $R_3$, and $R_4$ are as previously defined. Preferably, W is cyclopropyl, ethyl, —$CH_3$, —$CH_2F$, —$CHF_2$, or —$CF_3$; more preferably, W is —$CH_3$ or —$CF_3$.

In one embodiment of the present invention, the compound of Formula (I) is represented by one of Formulae (VIII-1)~(VIII-12), or a pharmaceutically acceptable salt, ester, or prodrug thereof:
(VIII-1)
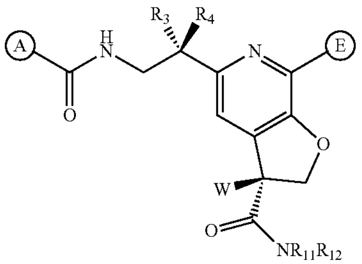
(VIII-2)
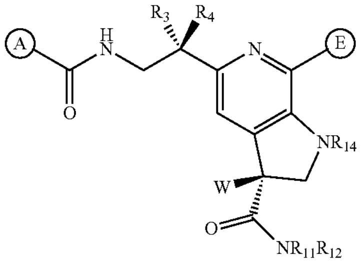
(VIII-3)
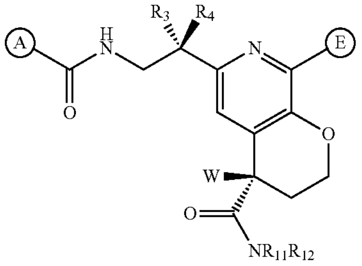
(VIII-4)
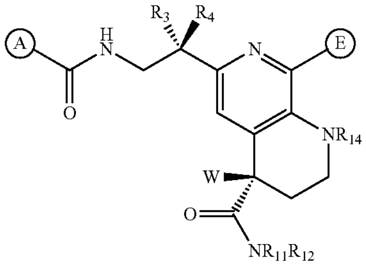
(VIII-5)
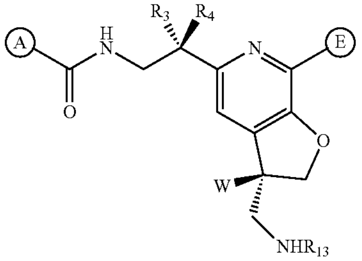
-continued
(VIII-6)
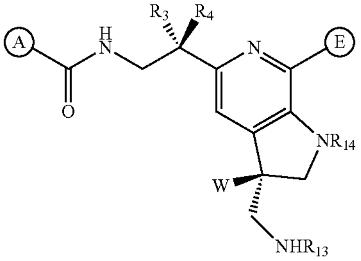
(VIII-7)
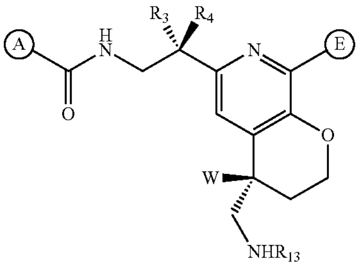
(VIII-8)
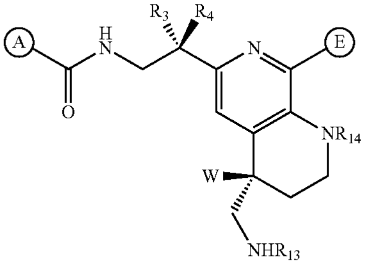
(VIII-9)
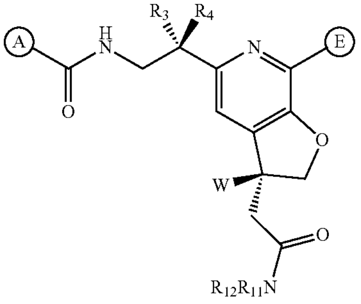
(VIII-10)
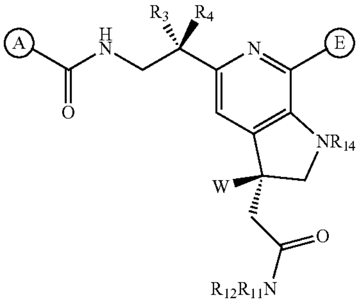

-continued (VIII-11)

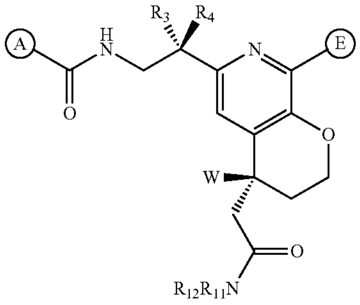

(VIII-12)

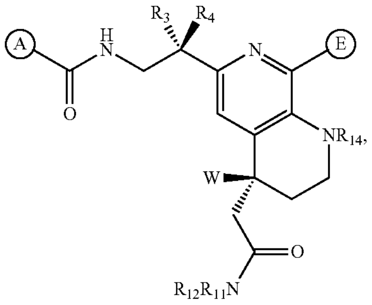

wherein A, W, E, $R_{11}$, $R_{12}$, $R_{13}$, $R_{14}$, $R_3$, and $R_4$ are as previously defined. Preferably, W is cyclopropyl, ethyl, $—CH_3$, $—CH_2F$, $—CHF_2$, or $—CF_3$; more preferably, W is $—CH_3$ or $—CF_3$.

In one embodiment of the present invention, the compound of Formula (I) is represented by one of Formulae (IX-1)~(IX-4), or a pharmaceutically acceptable salt, ester, or prodrug thereof:

(IX-1)

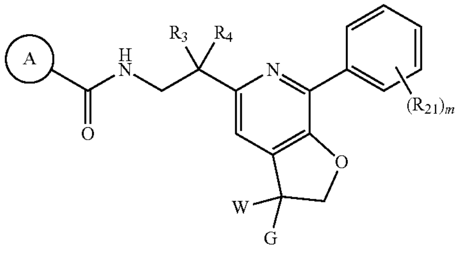

(IX-2)

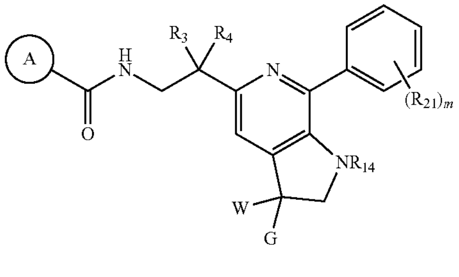

-continued (IX-3)

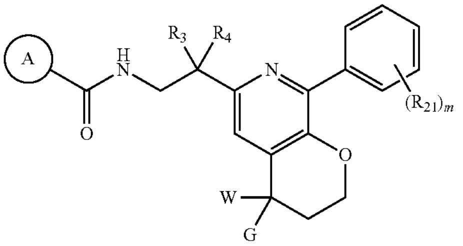

(IX-4)

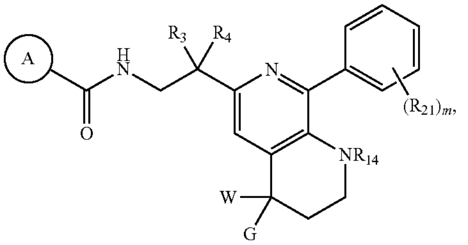

wherein each $R_{21}$ is independently optionally substituted methyl, halo, —CN, $—OR_{11}$, or $—NR_{11}R_{12}$; m is 0, 1, 2, 3, 4 or 5; A, W, G, Ru, $R_{12}$, $R_{14}$, $R_3$, and $R_4$ are as previously defined. Preferably, each $R_{21}$ is independently halo or optionally substituted methyl, and m is 1 or 2. More preferably, each $R_{21}$ is independently —F, —Cl, —CN, $—CF_3$, $—CH_2F$ or $—CHF_2$, and m is 1 or 2.

In one embodiment of the present invention, the compound of Formula (I) is represented by one of Formulae (X-1)~(X-4), or a pharmaceutically acceptable salt, ester, or prodrug thereof:

(X-1)

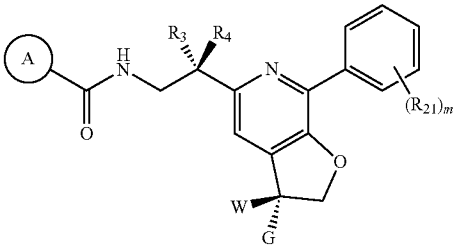

(X-2)

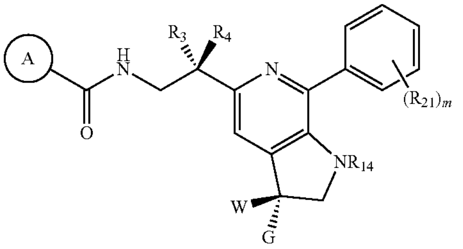

(X-3)

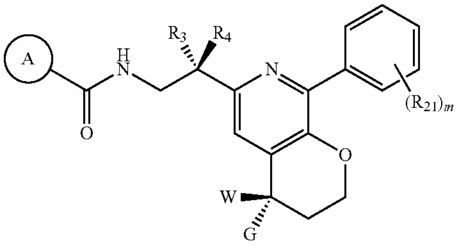

-continued (X-4)

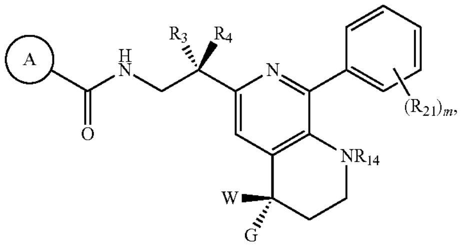

wherein $R_{21}$, m, A, W, G, $R_{14}$, $R_3$, and $R_4$ are as previously defined. Preferably, each $R_{21}$ is independently halo or optionally substituted methyl, and m is 1 or 2.

In one embodiment of the present invention, the compound of Formula (I) is represented by one of Formulae (XII-1)~(XII-12), or a pharmaceutically acceptable salt, ester, or prodrug thereof:

(XII-1)

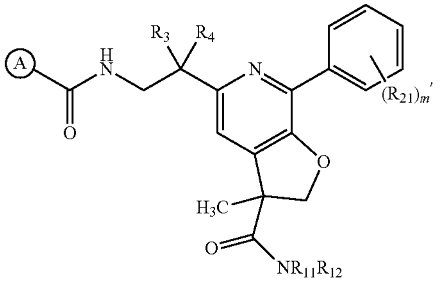

(XII-2)

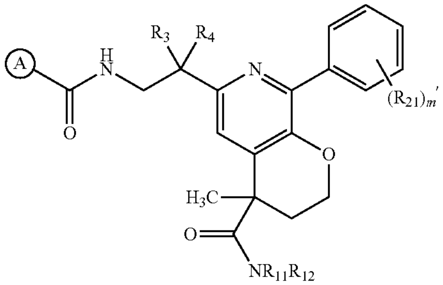

(XII-3)

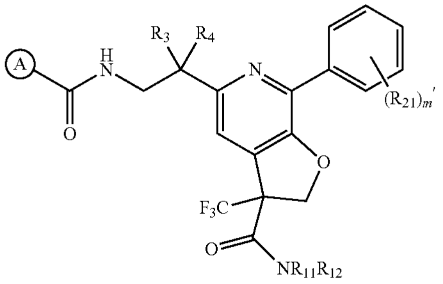

-continued (XII-4)

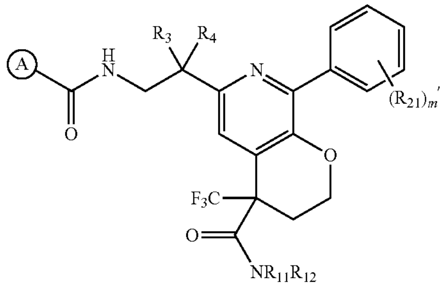

(XII-5)

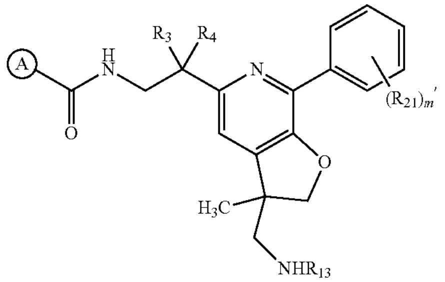

(XII-6)

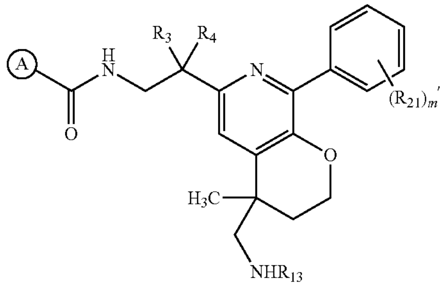

(XII-7)

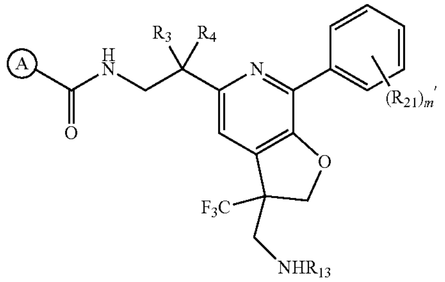

(XII-8)

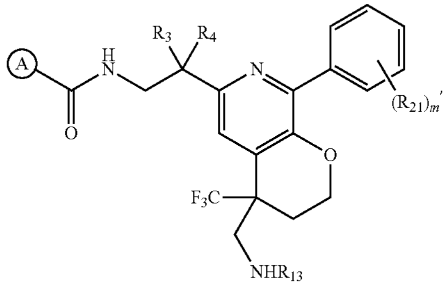

-continued
(XII-9)
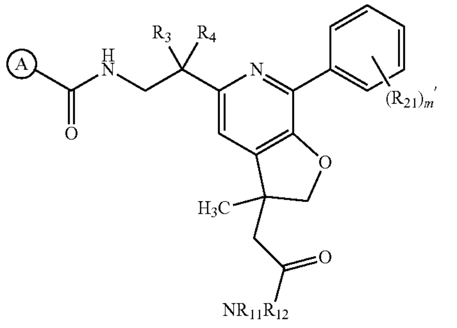
(XII-10)
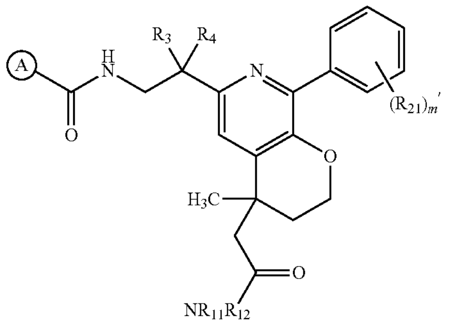
(XII-11)
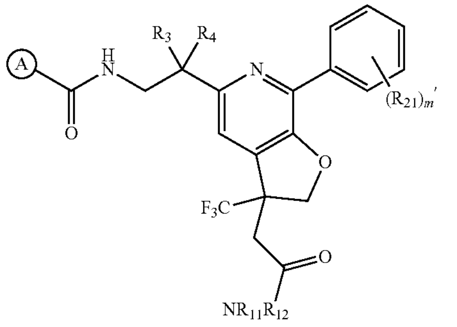
(XII-12)
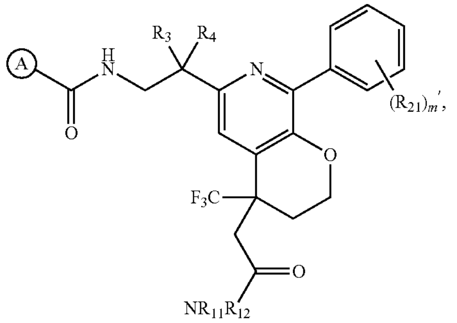
wherein m' is 0, 1, or 2. A, $R_3$, $R_4$, $R_{21}$, $R_{11}$, $R_{12}$ and $R_{13}$ are as previously defined. Preferably m' is 2.
In one embodiment of the present invention, the compound of Formula (I) is represented by one of Formulae (XIII-1)~(XIII-12), or a pharmaceutically acceptable salt, ester, or prodrug thereof:
(XIII-1)
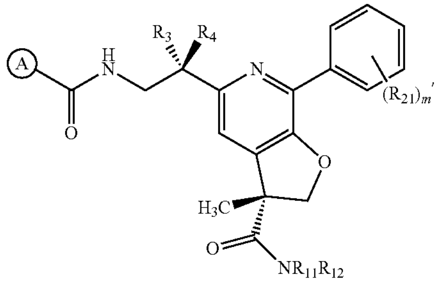
(XIII-2)
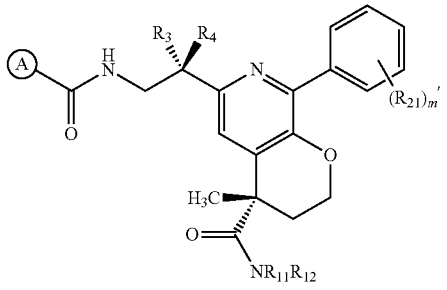
(XIII-3)
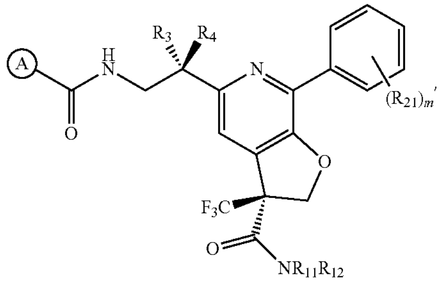
(XIII-4)
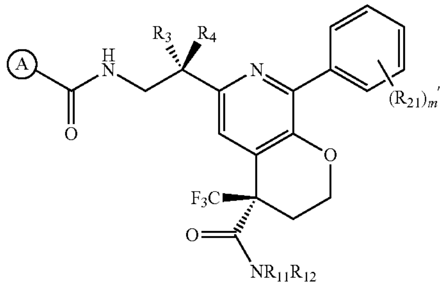
(XIII-5)
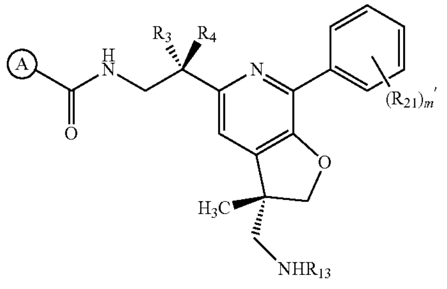

-continued
(XIII-6)
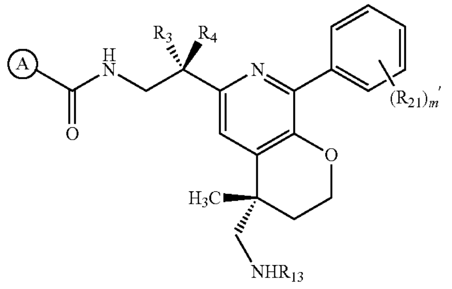
(XIII-7)
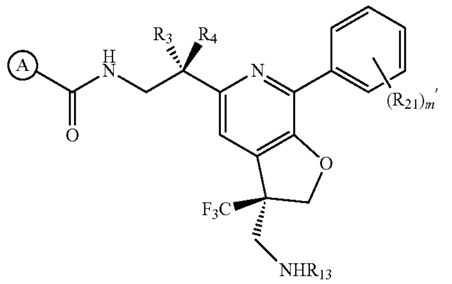
(XIII-8)
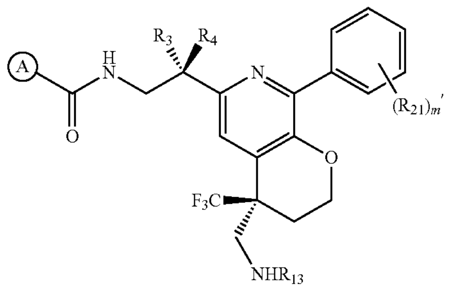
(XIII-9)
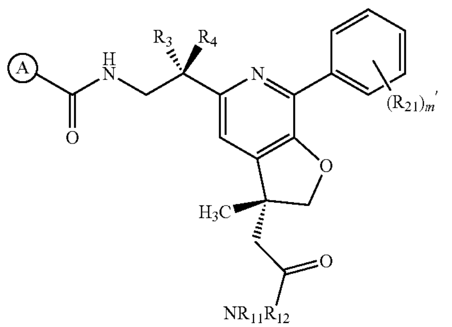
(XIII-10)
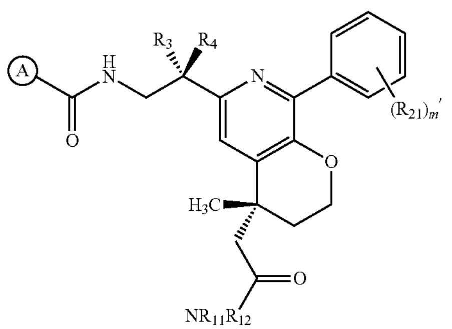
-continued
(XIII-11)
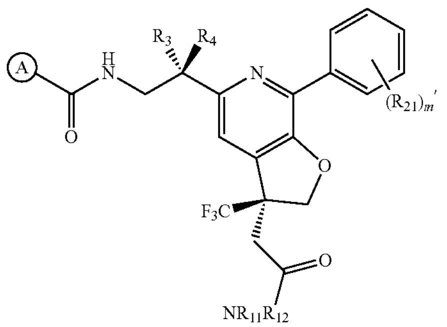
(XIII-12)
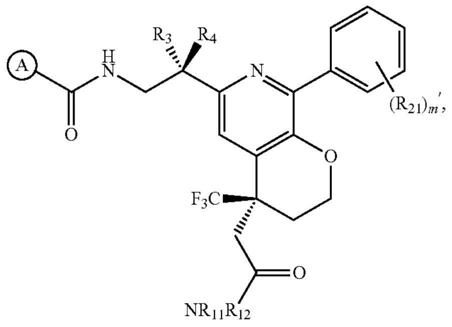
wherein $R_{21}$, m', A, $R_3$, $R_4$, Rn, $R_{12}$, and $R_{13}$ are as previously defined. Preferably m' is 2.
In one embodiment of the present invention, the compound of Formula (I) is represented by one of Formulae (XIV-1)~(XIV-6), or a pharmaceutically acceptable salt, ester or prodrug thereof:
(XIV-1)
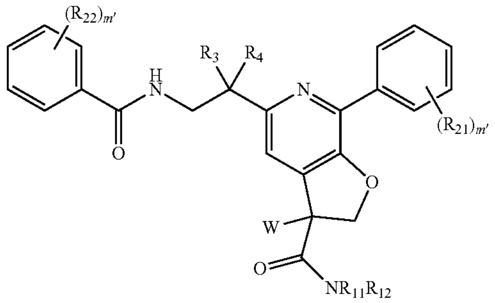
(XIV-2)
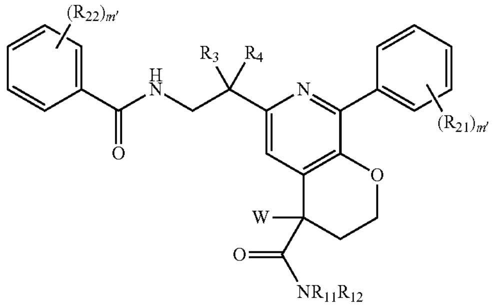

-continued (XIV-3)

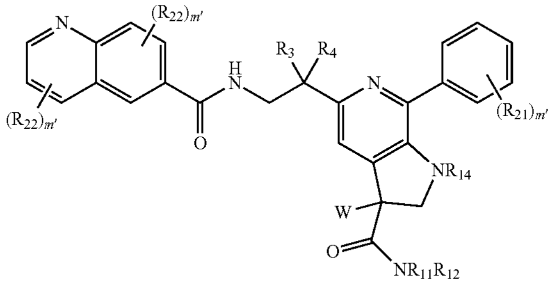

(XIV-4)

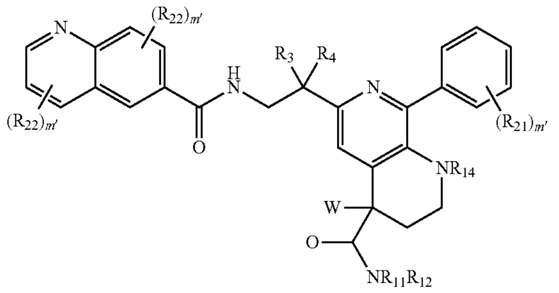

(XIV-5)

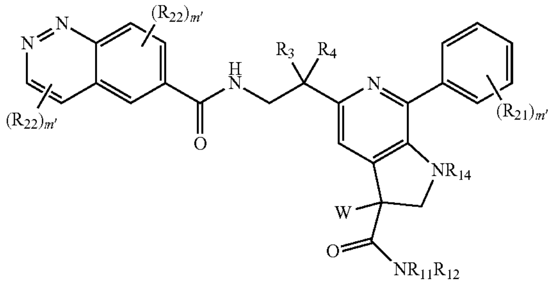

(XIV-6)

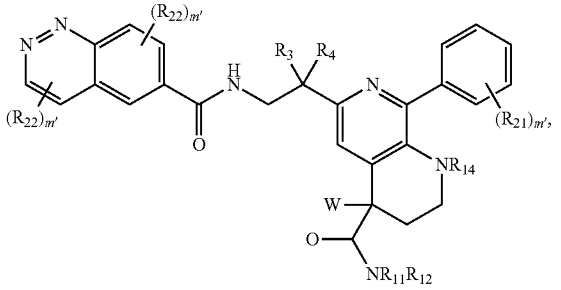

, wherein each $R_{22}$ is independently halo; —CN; —$NO_2$, —$OR_{11}$; —$NR_{11}R_{12}$; —$NR_{11}C(O)R_{12}$; —$NR_{11}S(O)_2R_{12}$; —$S(O)_2R_{12}$; —$S(O)_2NR_{11}R_{12}$, —$NR_{11}C(O)NR_{11}R_{12}$; —$C(O)R_{11}$, —$C(O)OR_{11}$; —$C(O)NR_{11}R_{12}$; optionally substituted —$C_1$-$C_6$ alkyl; optionally substituted —$C_3$-$C_8$-cycloalkyl; optionally substituted 3- to 8-membered heterocyclic; optionally substituted aryl; or optionally substituted heteroaryl, and W, m', $R_3$, $R_4$, $R_{21}$, $R_1$, and $R_{12}$ are as previously defined. Preferably, $R_{21}$ is halogen, $R_3$ is —OH, $R_4$ is —$CH_3$, —$CF_3$, or cyclopropyl, and W is cyclopropyl, ethyl, —$CH_3$, —$CH_2F$, —$CHF_2$, or —$CF_3$. In certain embodiments, two adjacent $R_{22}$ groups are taken together with the carbon atoms to which they are attached to form a 4- to 12-membered carbocyclic or heterocyclic, and which said 4- to 12-membered carbocyclic or heterocyclic is fused with the phenyl or quinolinyl.

In one embodiment of the present invention, the compound of Formula (I) is represented by one of Formulae (XV-1)~(XV-6), or a pharmaceutically acceptable salt, ester or prodrug thereof:

(XV-1)

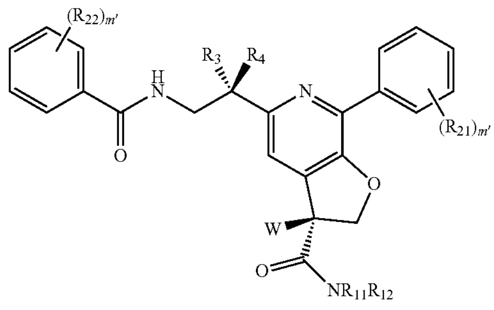

(XV-2)

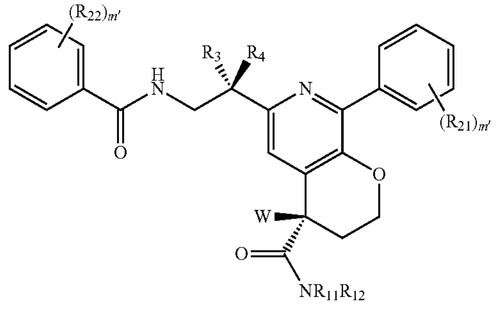

(XV-3)

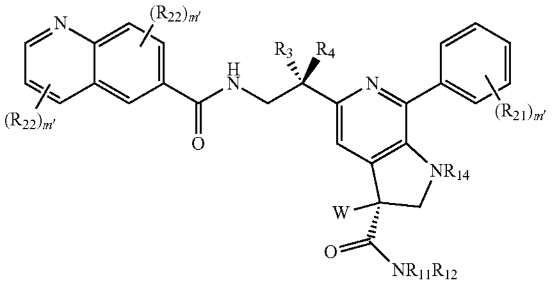

(XV-4)

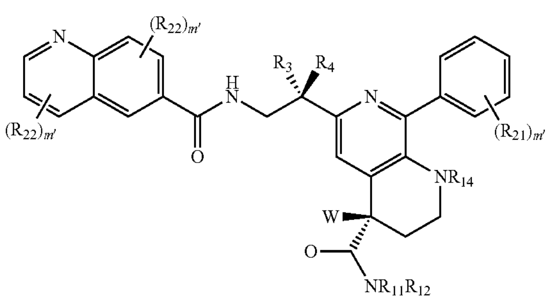

-continued (XV-5)

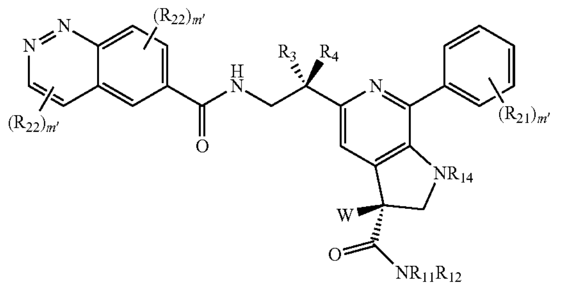

(XV-6)

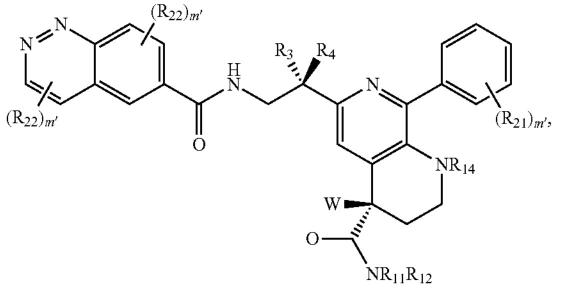

wherein W, m', $R_3$, $R_4$, $R_{21}$, $R_{22}$, $R_{11}$, and $R_{12}$ are as previously defined. Preferably, $R_{21}$ is halogen, $R_3$ is —OH, $R_4$ is —$CH_3$, —$CF_3$, or cyclopropyl, and W is cyclopropyl, ethyl, —$CH_3$, —$CH_2F$, —$CHF_2$, or —$CF_3$. In certain embodiment, two adjacent $R_{22}$ groups are taken together with the carbon atoms to which they are attached to form a 4- to 12-membered carbocyclic or heterocyclic ring, and which said 4- to 12-membered carbocyclic or heterocyclic is fused with the phenyl or quinolinyl.

In one embodiment of the present invention, the compound of Formula (I) is represented by one of Formulae (XVI-1)~(XVI-12), or a pharmaceutically acceptable salt, ester or prodrug thereof:

(XVI-1)

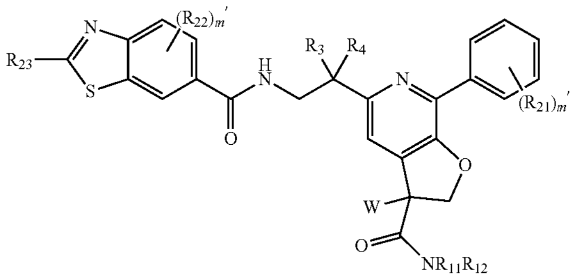

(XVI-2)

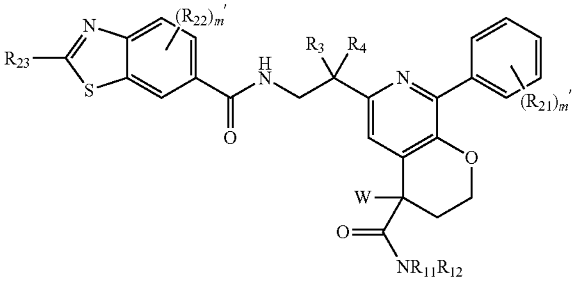

-continued (XVI-3)

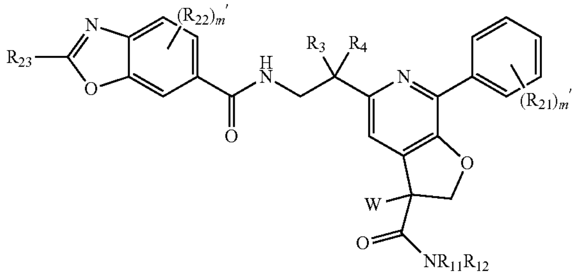

(XVI-4)

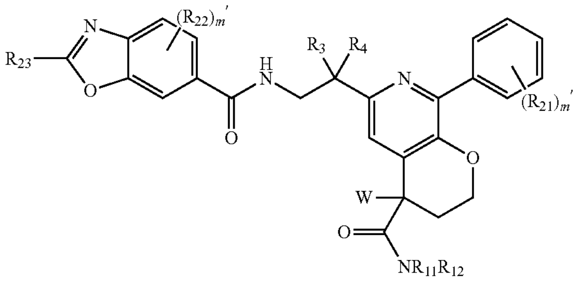

(XVI-5)

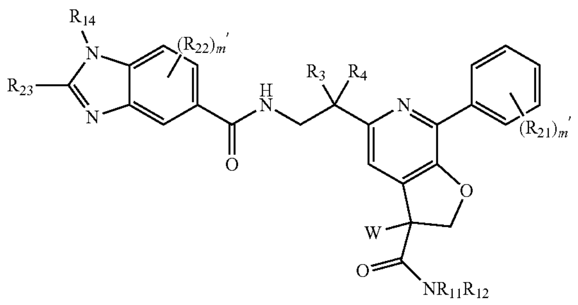

(XVI-6)

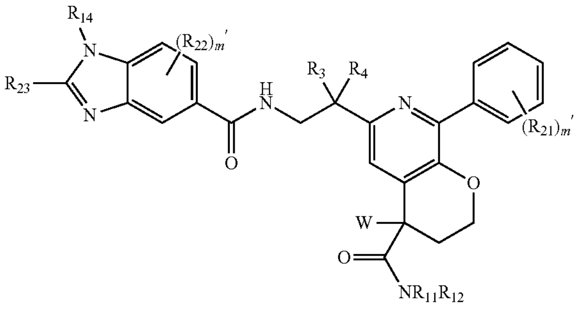

(XVI-7)

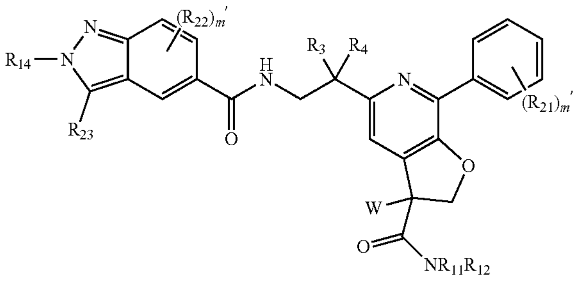

-continued (XVI-8)

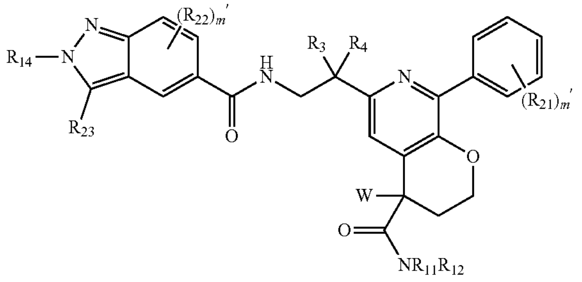

(XVI-9)

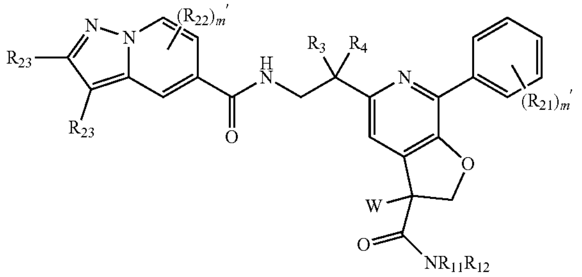

(XVI-10)

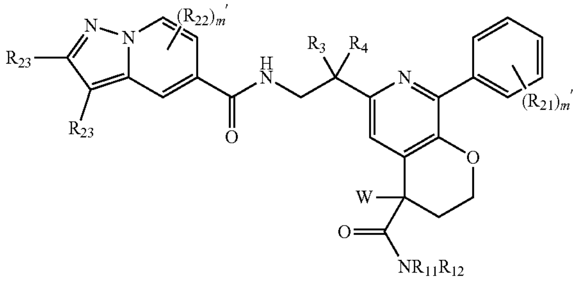

(XVI-11)

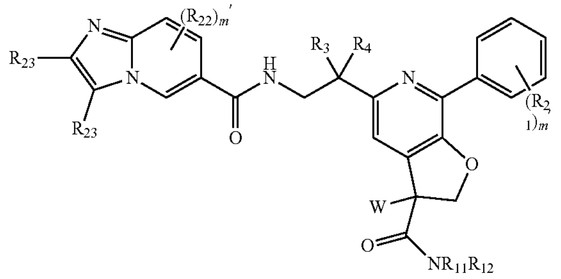

(XVI-12)

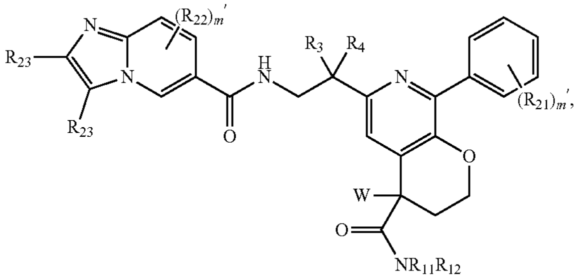

wherein $R_{23}$ is hydrogen; halo; —CN; —$NO_2$, —$OR_{11}$; —$NR_{11}R_{12}$; —$NR_{11}C(O)R_{12}$; —$NR_{11}S(O)_2R_{12}$; —$S(O)_2R_{12}$; —$S(O)_2NR_{11}R_{12}$, —$NR_{11}C(O)NR_{11}R_{12}$; —$C(O)R_{11}$, —$C(O)OR_{11}$; —$C(O)NR_{11}R_{12}$; optionally substituted —$C_1$-$C_6$ alkyl; optionally substituted —$C_3$-$C_8$-cycloalkyl; optionally substituted 3- to 8-membered heterocyclic; optionally substituted aryl; or optionally substituted heteroaryl; and W, $R_{21}$, $R_{22}$, m', $R_3$, $R_4$, $R_{11}$, and $R_{12}$ are as previously defined. Preferably, $R_{21}$ is halogen, $R_3$ is —OH, $R_4$ is —$CH_3$, —$CF_3$, or cyclopropyl, and W is cyclopropyl, ethyl, —$CH_3$, —$CH_2F$, —$CHF_2$, or —$CF_3$.

In one embodiment of the present invention, the compound of Formula (I) is represented by one of Formulae (XVII-1)~(XVII-12), or a pharmaceutically acceptable salt, ester or prodrug thereof:

(XVII-1)

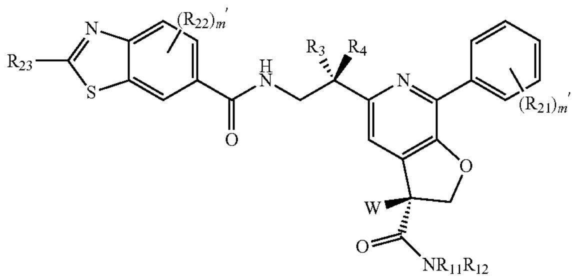

(XVII-2)

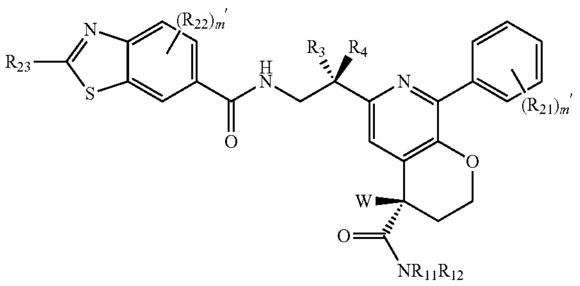

(XVII-3)

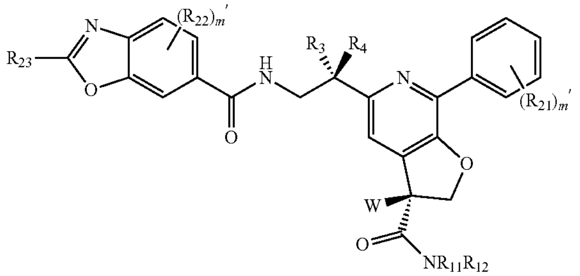

(XVII-4)

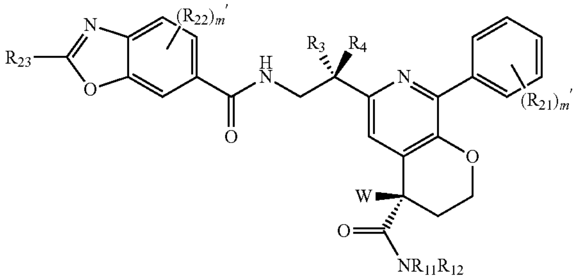

-continued (XVII-5)

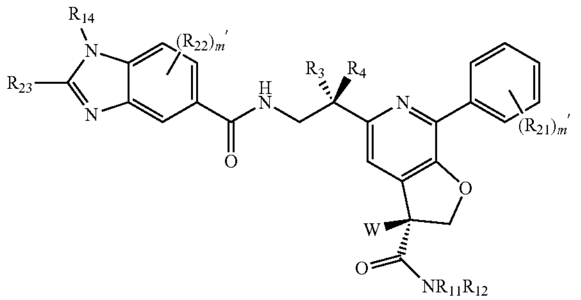

(XVII-6)

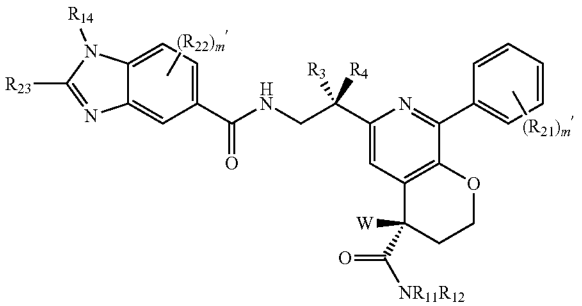

(XVII-7)

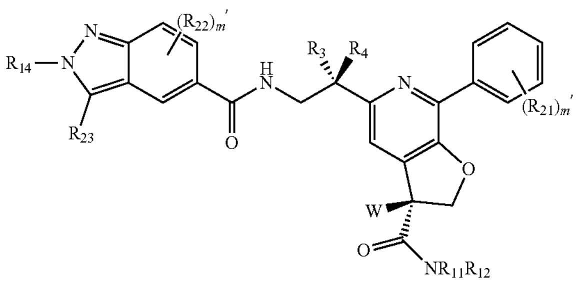

(XVII-8)

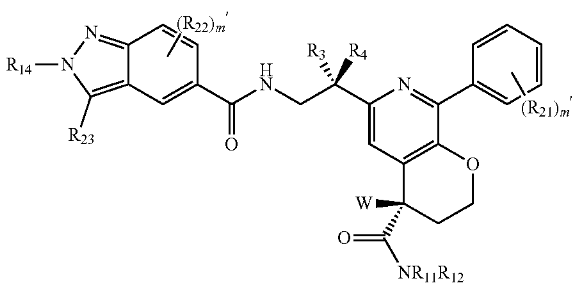

(XVII-9)

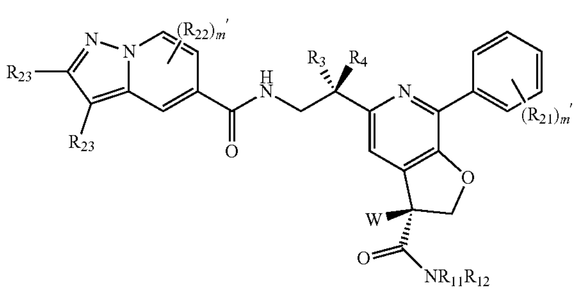

-continued (XVII-10)

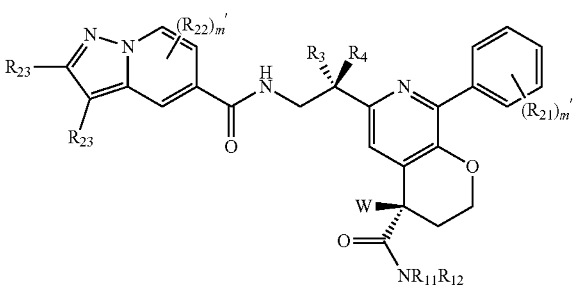

(XVII-11)

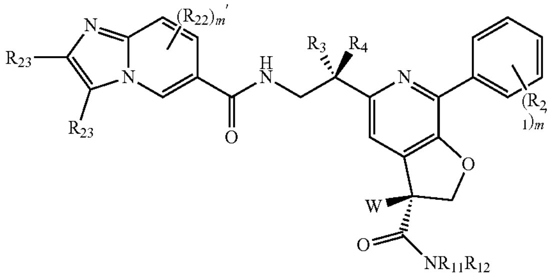

(XVII-12)

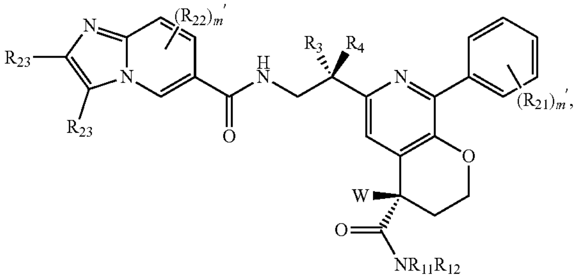

wherein W, $R_{21}$, $R_{22}$, $R_{23}$, m', $R_3$, $R_4$, $R_{11}$, and $R_{12}$ are as previously defined. Preferably, $R_{21}$ is halogen, $R_3$ is —OH, $R_4$ is —$CH_3$, —$CF_3$, or cyclopropyl, and W is cyclopropyl, ethyl, —$CH_3$, —$CH_2F$, —$CHF_2$, or —$CF_3$.

In one embodiment of the present invention, the compound of Formula (I) is represented by one of Formulae (XVIII-1)~(XVIII-14), or a pharmaceutically acceptable salt, ester or prodrug thereof:

(XVIII-1)

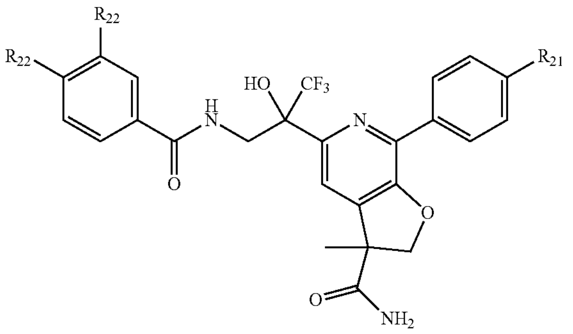

-continued
(XVIII-2)
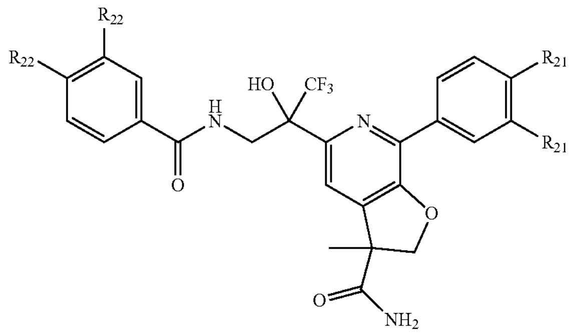
(XVIII-3)
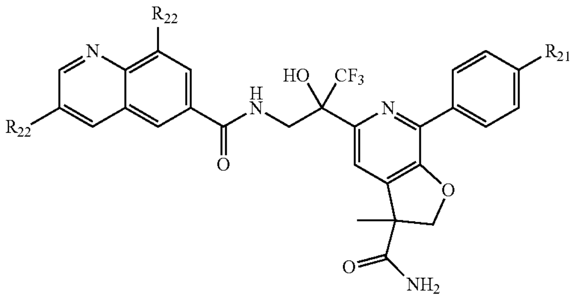
(XVIII-4)
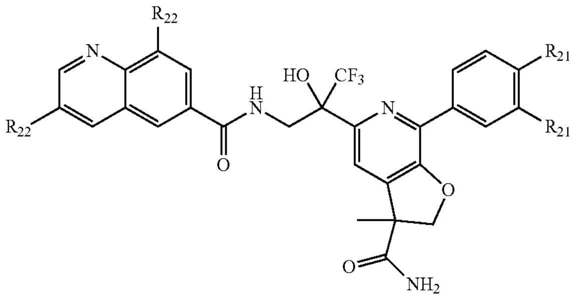
(XVIII-5)
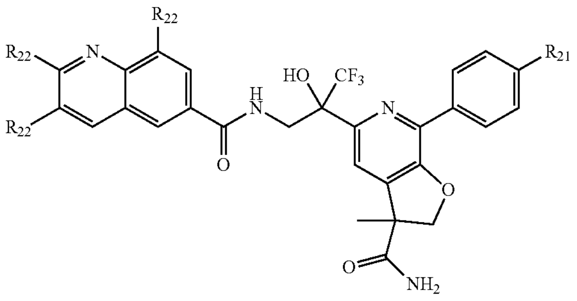
(XVIII-6)
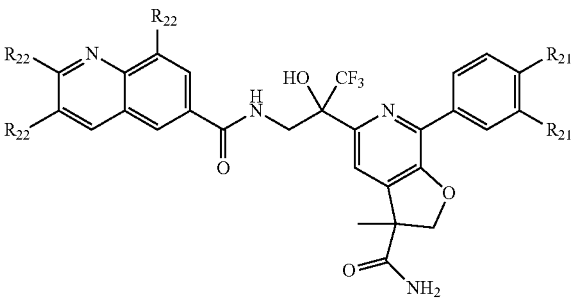
-continued
(XVIII-7)
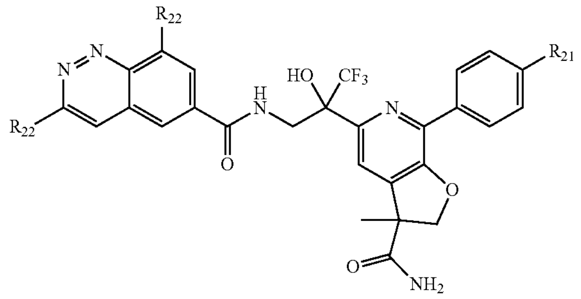
(XVIII-8)
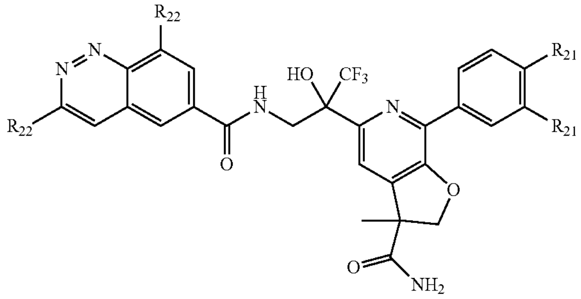
(XVIII-9)
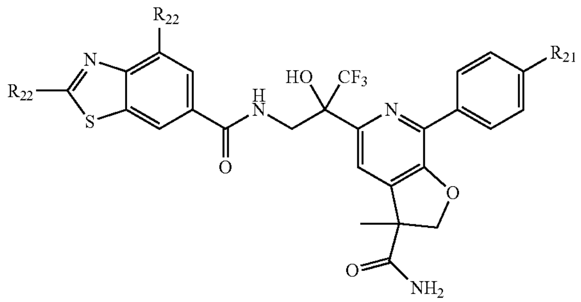
(XVIII-10)
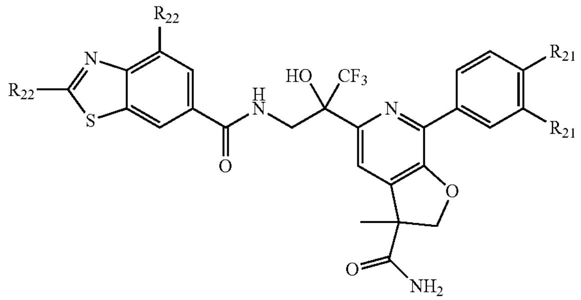
(XVIII-11)
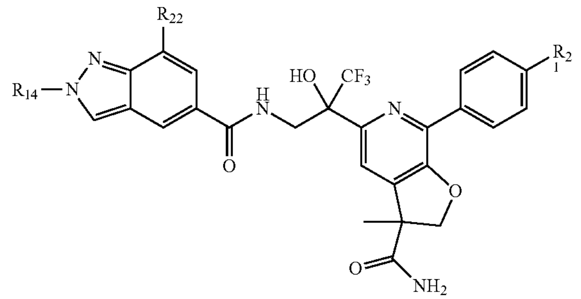

-continued
(XVIII-12)
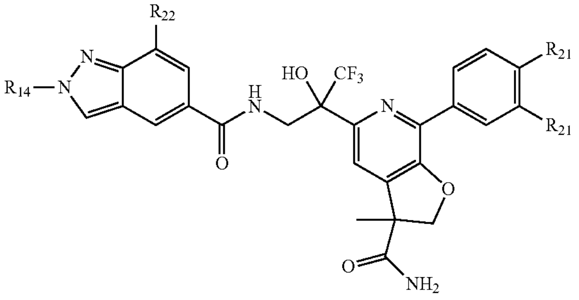
(XVIII-13)
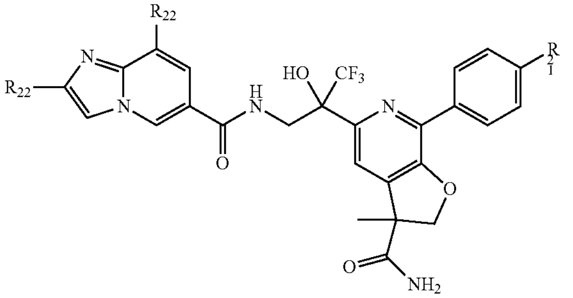
(XVIII-14)
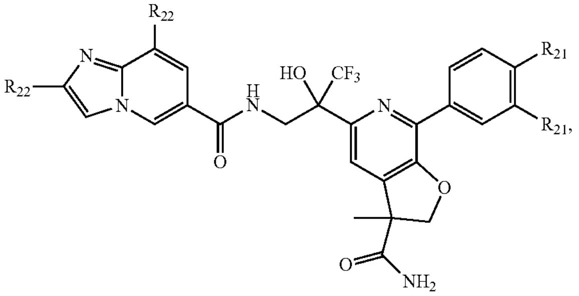
wherein $R_{14}$, $R_{21}$, and $R_{22}$ are as previously defined.
In one embodiment of the present invention, the compound of Formula (I) is represented by one of Formulae (XIX-1)~(XIX-14), or a pharmaceutically acceptable salt, ester, or prodrug thereof:
(XIX-1)
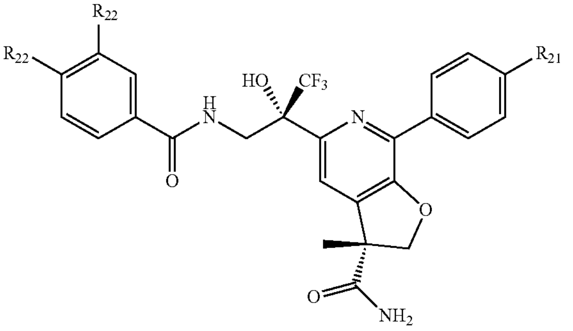
-continued
(XIX-2)
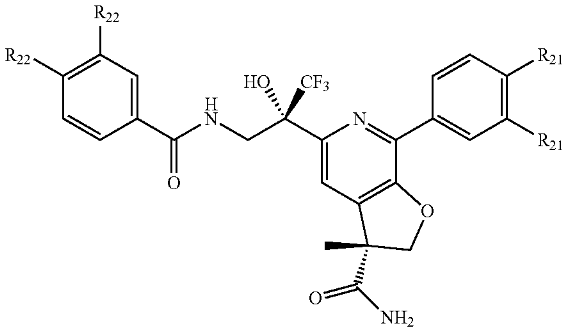
(XIX-3)
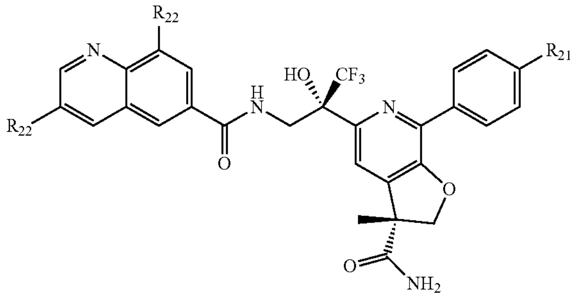
(XIX-4)
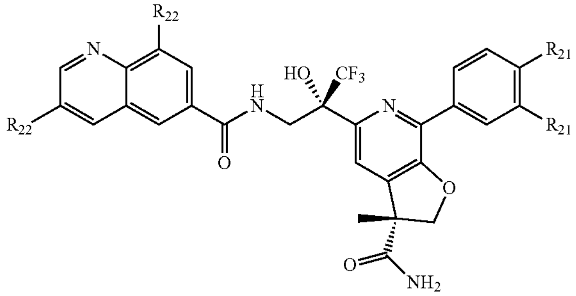
(XIX-5)
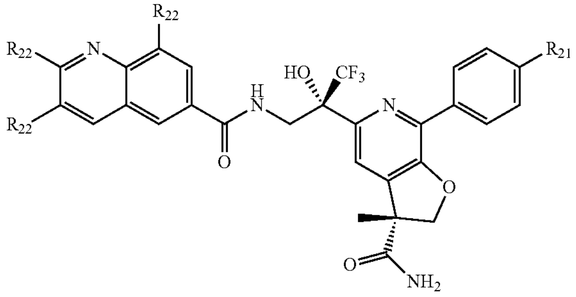
(XIX-6)
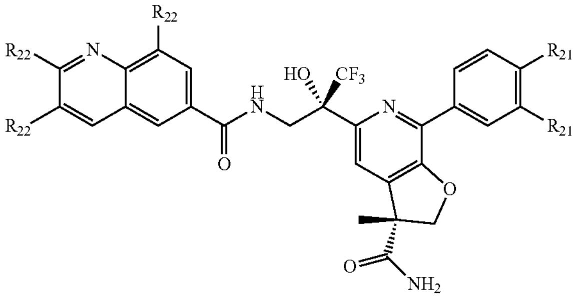

-continued
(XIX-7)
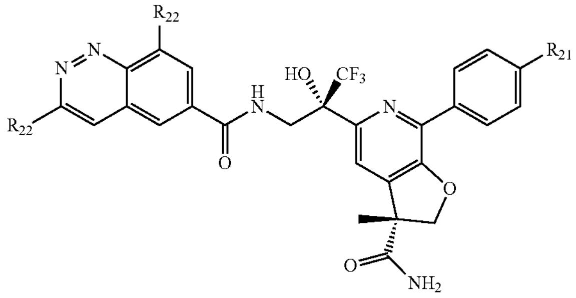
(XIX-8)
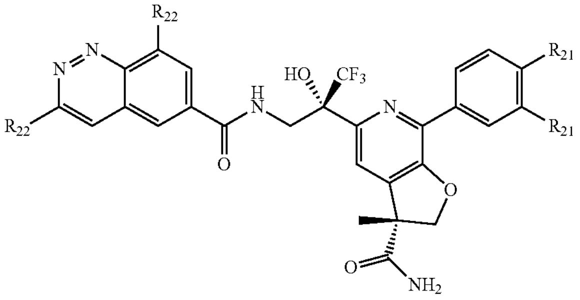
(XIX-9)
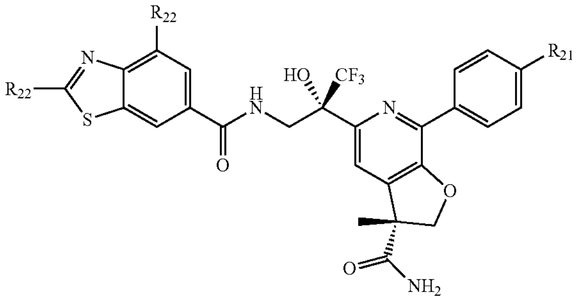
(XIX-10)
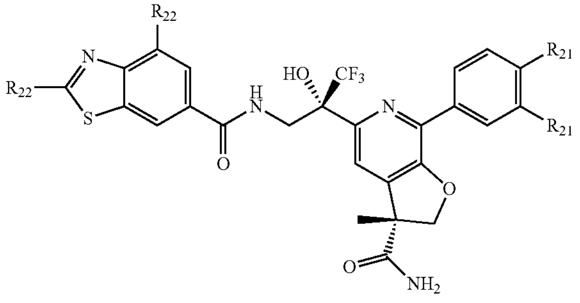
(XIX-11)
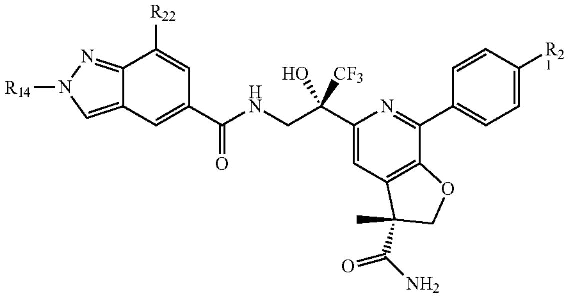
-continued
(XIX-12)
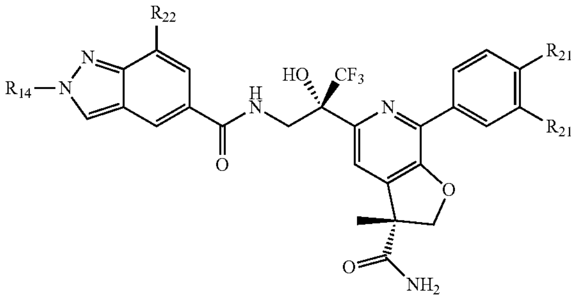
(XIX-13)
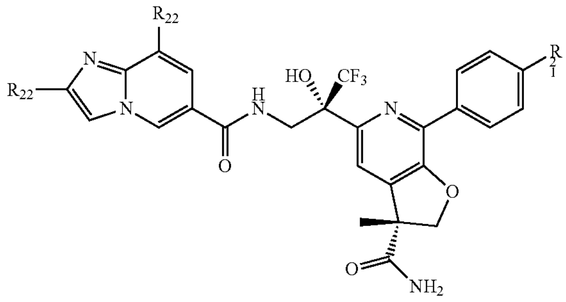
(XIX-14)
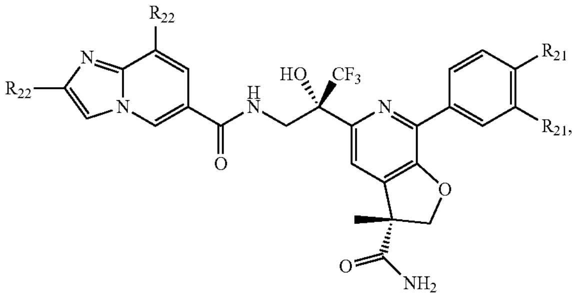
wherein $R_{14}$, $R_{21}$, and $R_{22}$ are as previously defined.
In one embodiment of the present invention, the compound of Formula (I) is represented by one of Formulae (XX-1)~(XX-20), or a pharmaceutically acceptable salt, ester or prodrug thereof:
(XX-1)
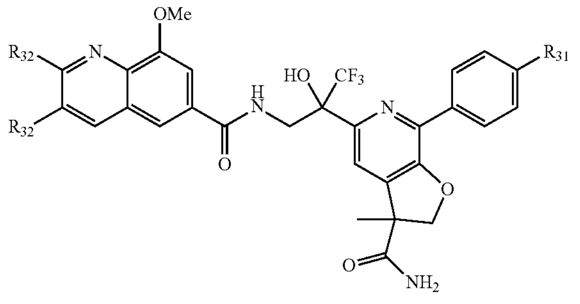

-continued
(XX-2)
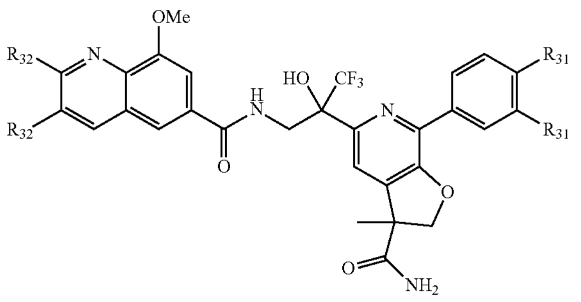
(XX-3)
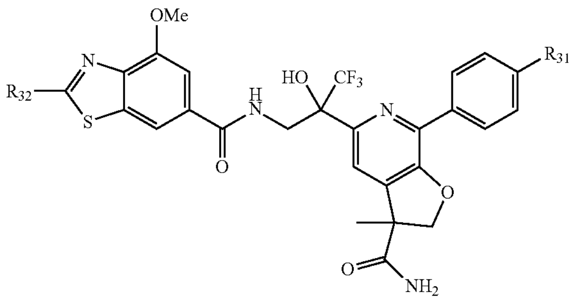
(XX-4)
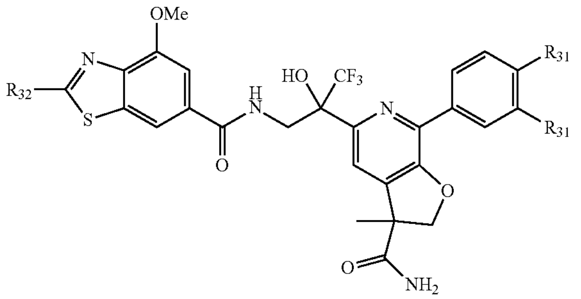
(XX-5)
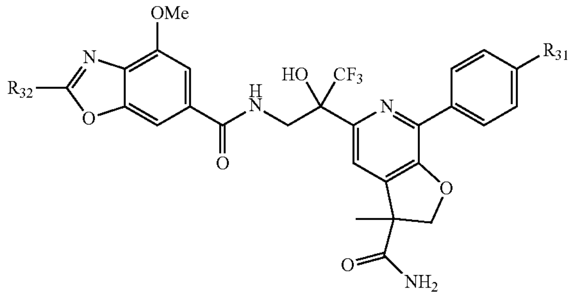
(XX-6)
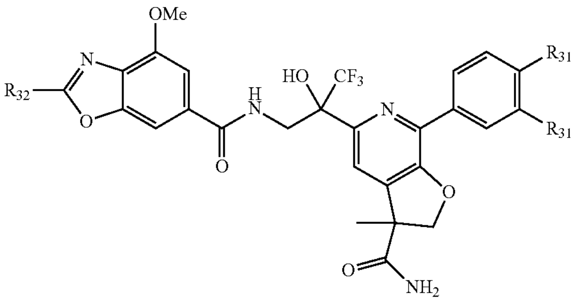
-continued
(XX-7)
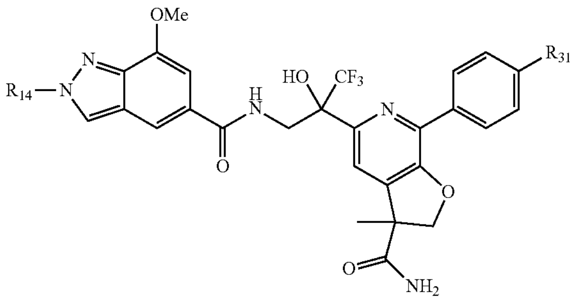
(XX-8)
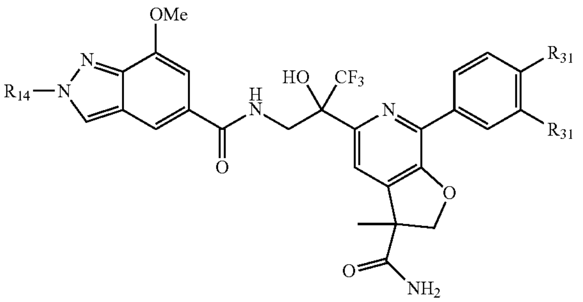
(XX-9)
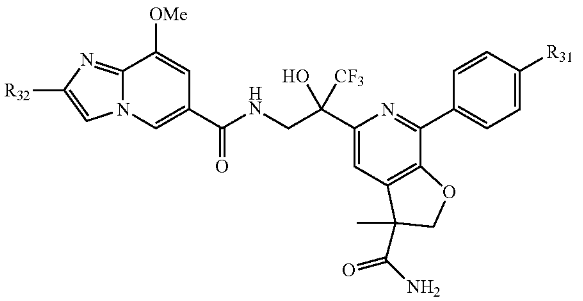
(XX-10)
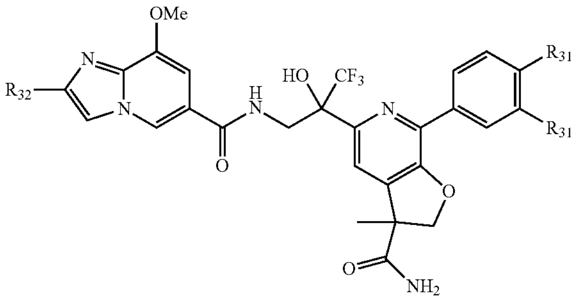
(XX-11)
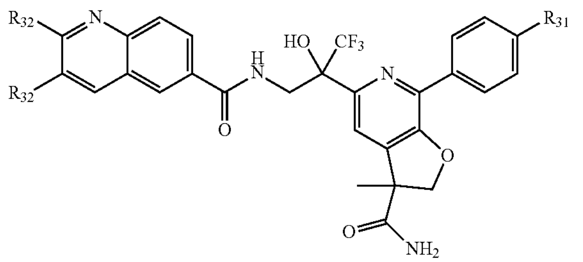

-continued (XX-12)

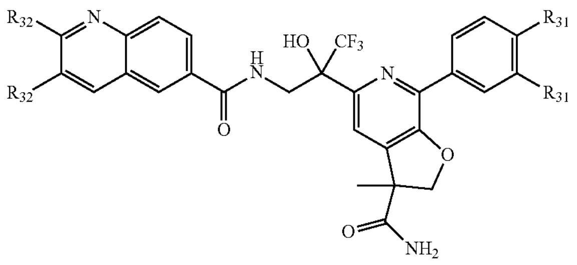

(XX-13)

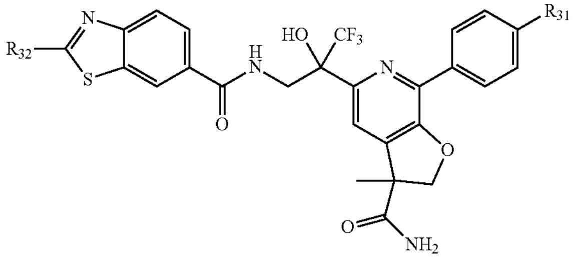

(XX-14)

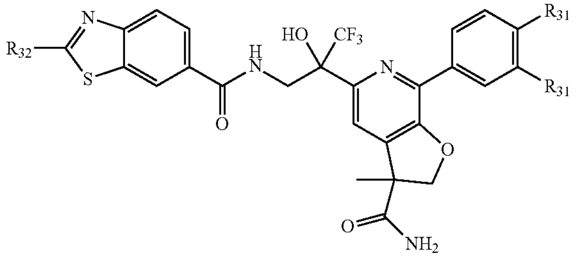

(XX-15)

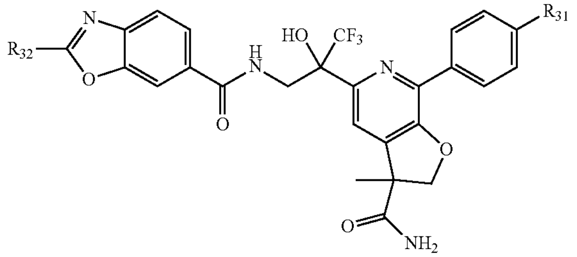

(XX-16)

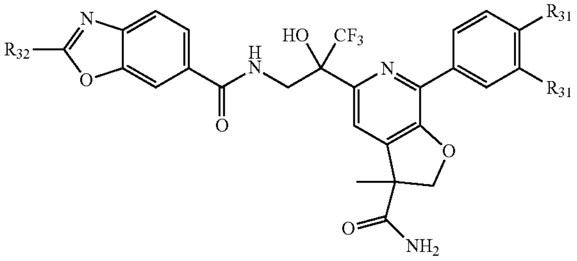

-continued (XX-17)

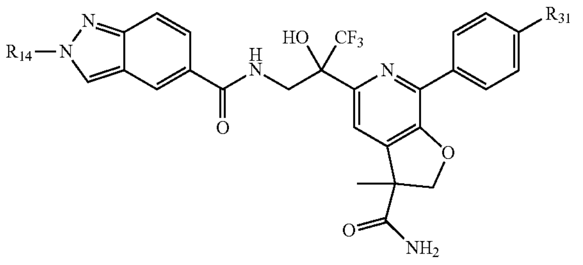

(XX-18)

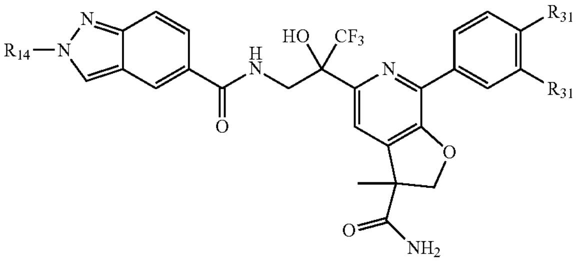

(XX-19)

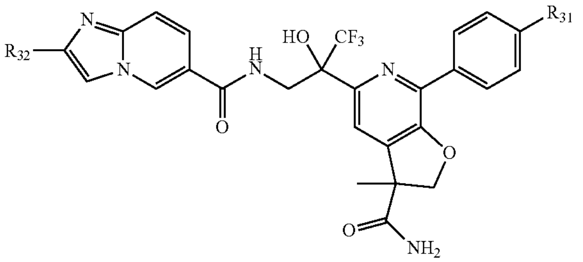

(XX-20)

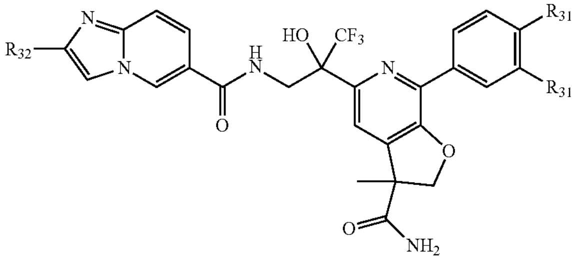

wherein each $R_{31}$ is independently optionally substituted —$C_1$-$C_3$ alkyl or halo; $R_{32}$ is independently halo, —$OR_{11}$, —$NR_{11}R_{12}$, —$NR_{11}C(O)R_{12}$, —$C(O)NR_{11}R_{12}$, —$C(O)R_{11}$, optionally substituted —$C_1$-$C_6$ alkyl, or optionally substituted —$C_3$-$C_8$-cycloalkyl; and $R_{11}$, $R_{12}$, and $R_{14}$ are as previously defined. Preferably, $R_{31}$ is halo, $R_{32}$ is halo, —$NH_2$, optionally substituted methyl, optionally substituted cyclopropyl, and $R_{14}$ is optionally substituted cyclopropyl.

In one embodiment of the present invention, the compound of Formula (I) is represented by one of Formulae (XXI-1)~(XXI-20), or a pharmaceutically acceptable salt, ester or prodrug thereof:

(XXI-1)
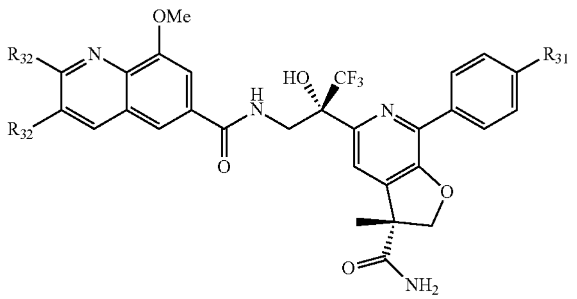
(XXI-2)
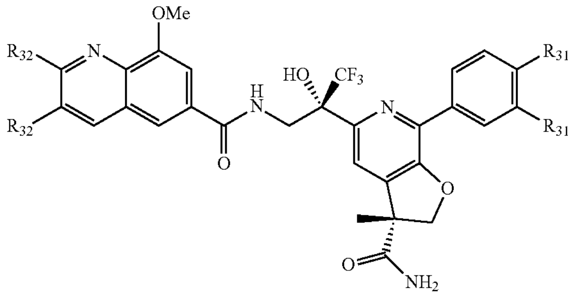
(XXI-3)
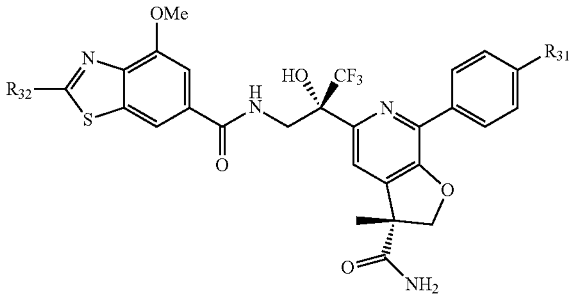
(XXI-4)
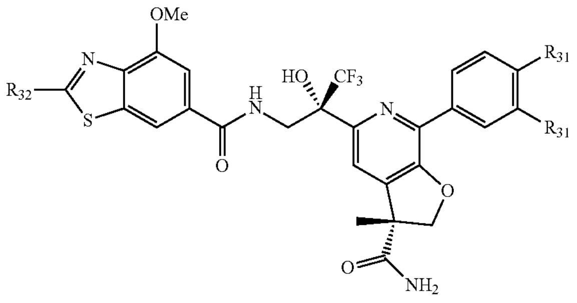
(XXI-5)
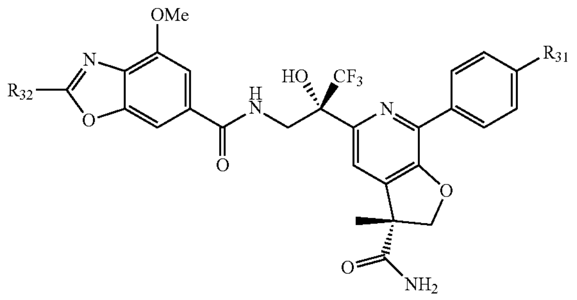
-continued
(XXI-6)
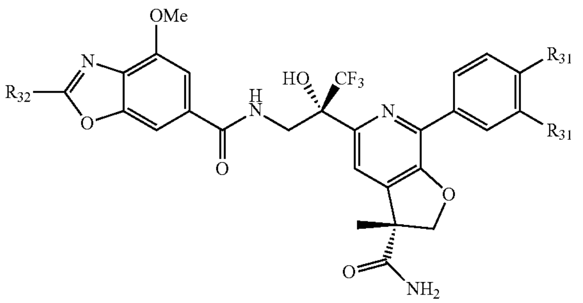
(XXI-7)
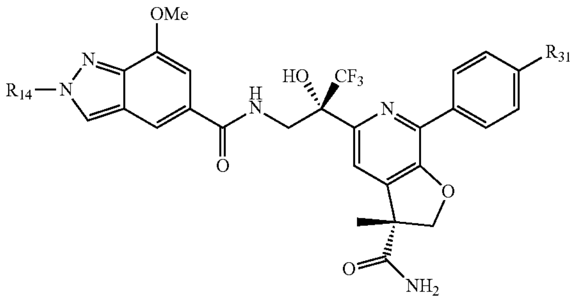
(XXI-8)
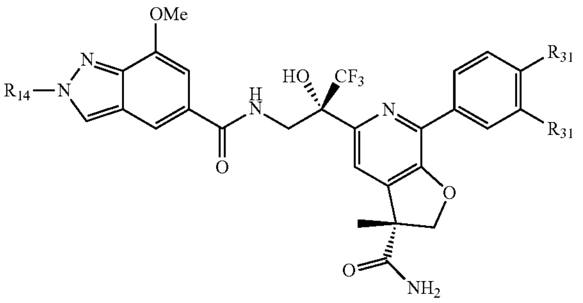
(XXI-9)
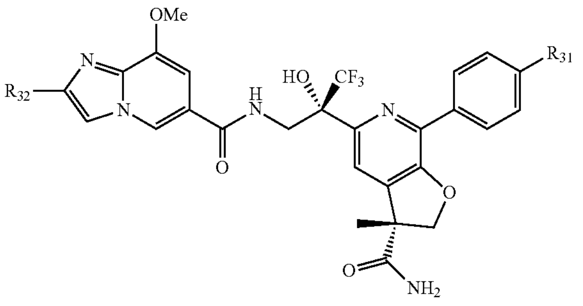
(XXI-10)
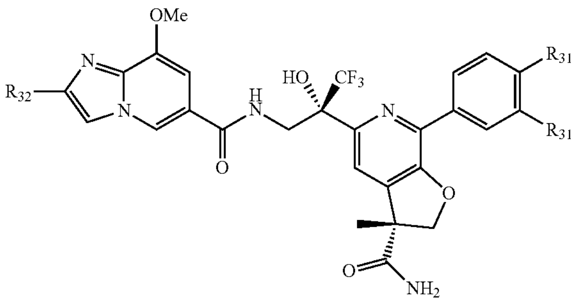

-continued (XXI-11)

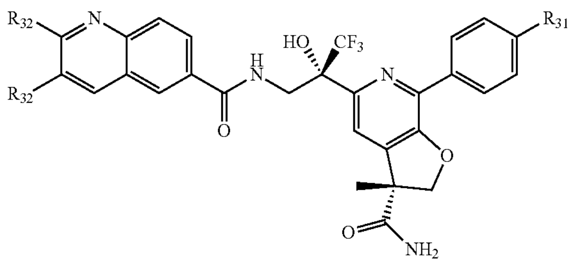

(XXI-12)

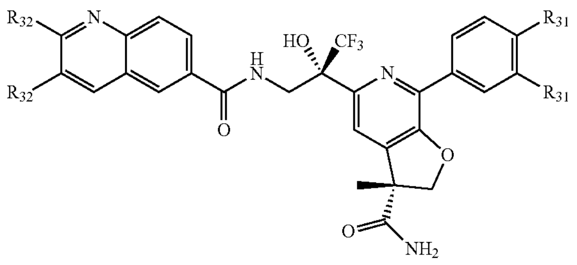

(XXI-13)

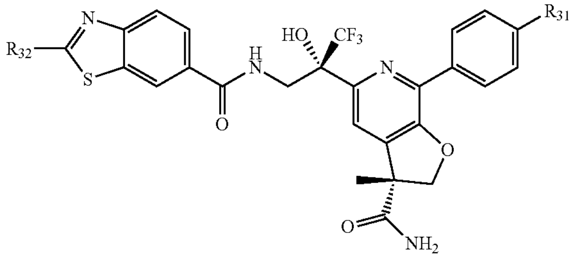

(XXI-14)

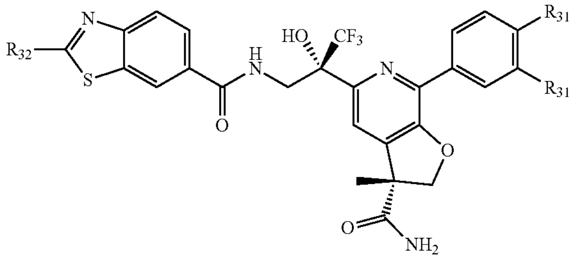

(XXI-15)

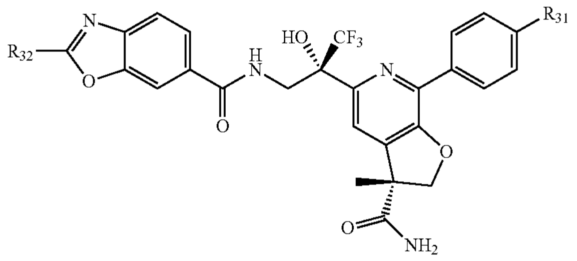

-continued (XXI-16)

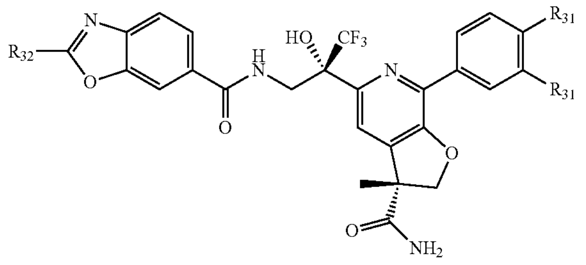

(XXI-17)

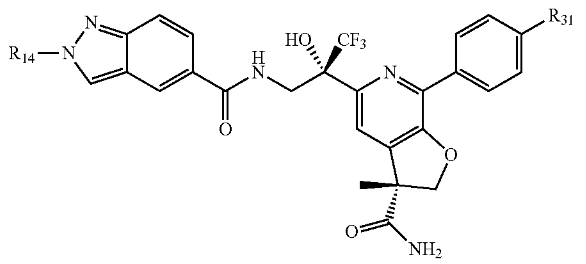

(XXI-18)

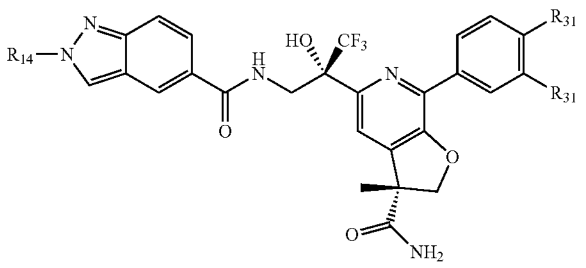

(XXI-19)

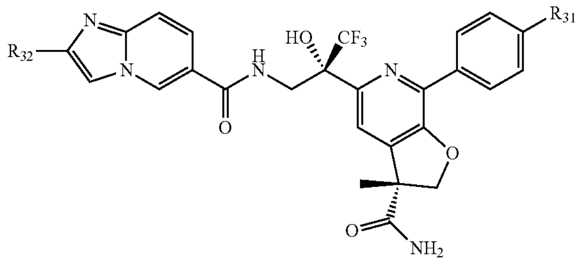

(XXI-20)

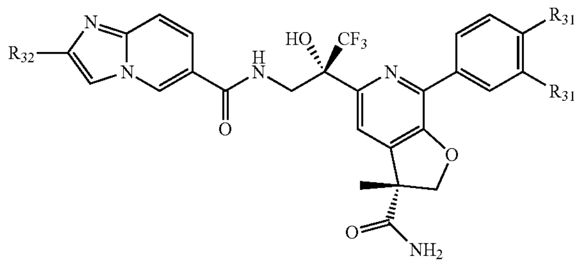

wherein $R_{31}$, $R_{32}$, $R_{11}$, $R_{12}$, and $R_{14}$ is as previously defined. Preferably, $R_{31}$ is halo, $R_{32}$ is halo, —$NH_2$, optionally substituted methyl, optionally substituted cyclopropyl, and $R_{14}$ is optionally substituted cyclopropyl.

In one embodiment of the present invention, the compound of Formula (I) is represented by one of Formulae (XXII-1)~(XXII-14), or a pharmaceutically acceptable salt, ester or prodrug thereof:

(XXII-1)
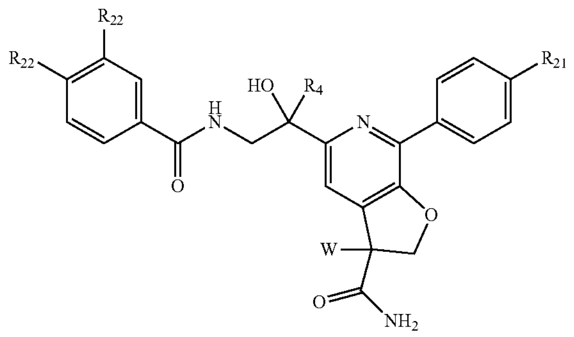
(XXII-2)
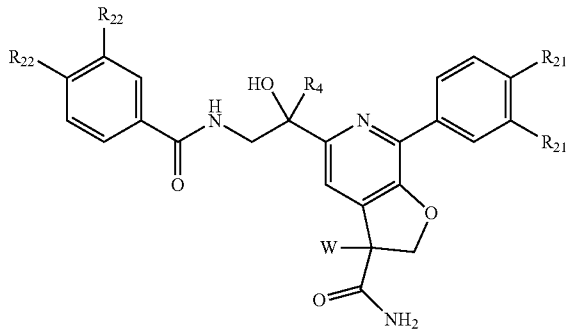
(XXII-3)
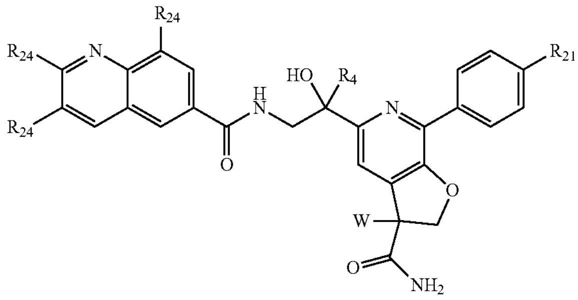
(XXII-4)
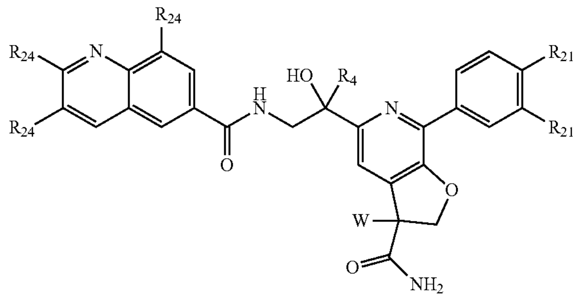
-continued
(XXII-5)
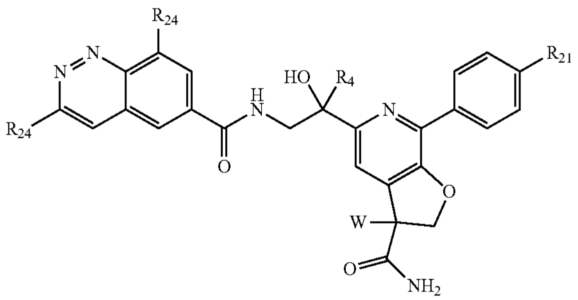
(XXII-6)
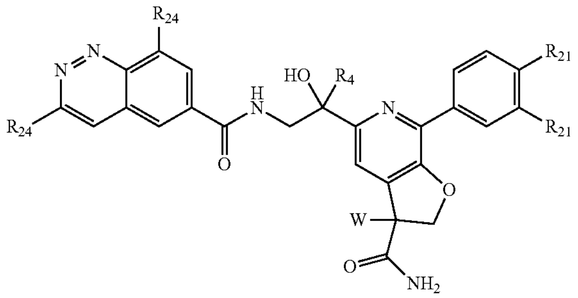
(XXII-7)
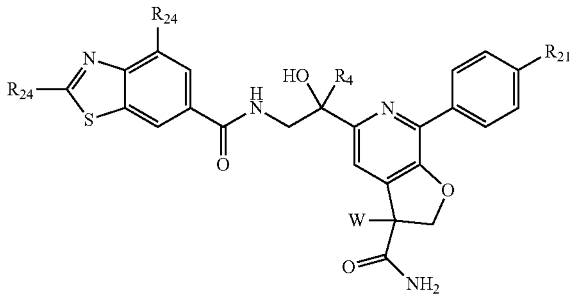
(XXII-8)
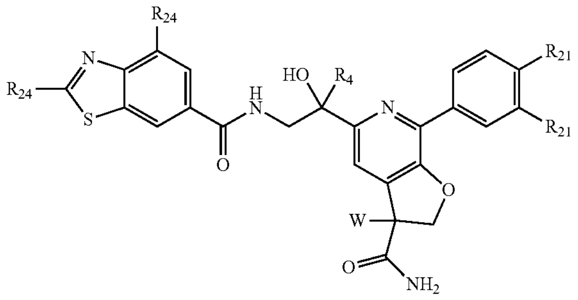
(XXII-9)
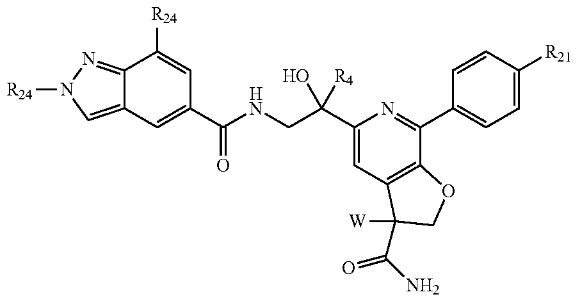

-continued (XXII-10)

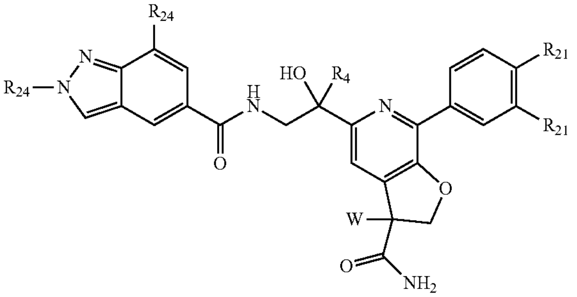

(XXII-11)

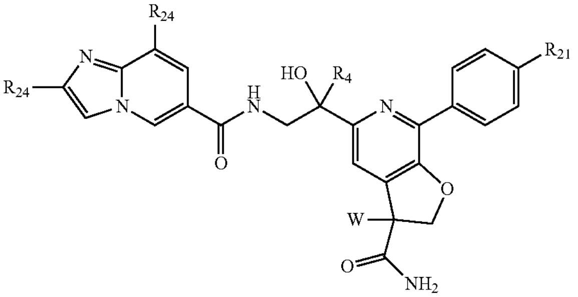

(XXII-12)

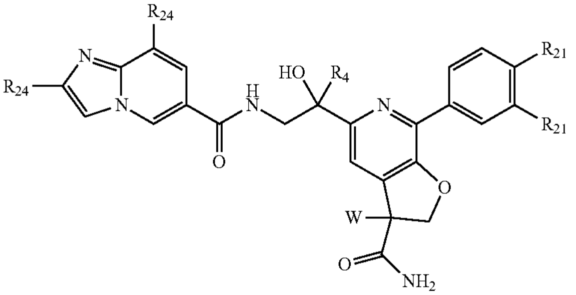

(XXII-13)

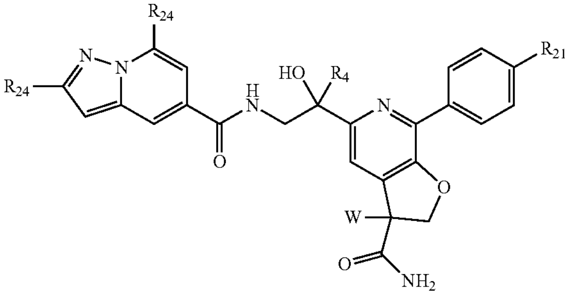

(XXII-14)

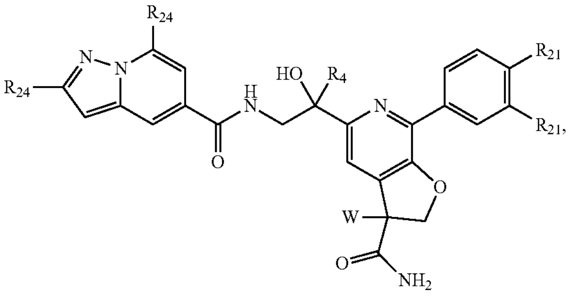

wherein $R_{24}$ is hydrogen or $R_{22}$; and W, $R_4$, $R_{14}$, $R_{21}$, and $R_{22}$ are as previously defined. Preferably, $R_4$ is optionally substituted —$C_3$-$C_6$ cycloalkyl. More preferably, $R_4$ is optionally substituted cyclopropyl or optionally substituted cyclobutyl.

In one embodiment of the present invention, the compound of Formula (I) is represented by one of Formulae (XXIII-1)~(XXIII-14), or a pharmaceutically acceptable salt, ester or prodrug thereof:

(XXIII-1)

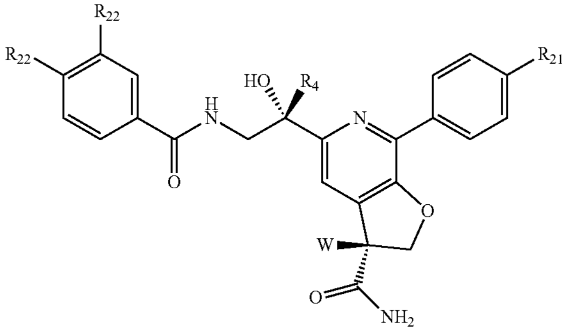

(XXIII-2)

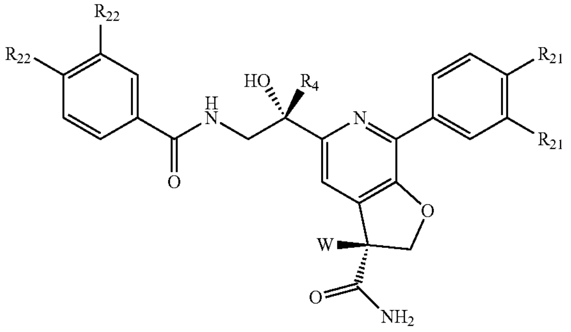

(XXIII-3)

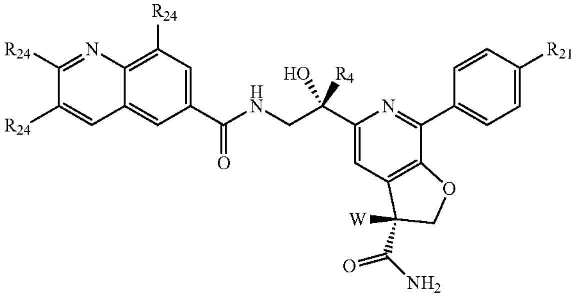

(XXIII-4)

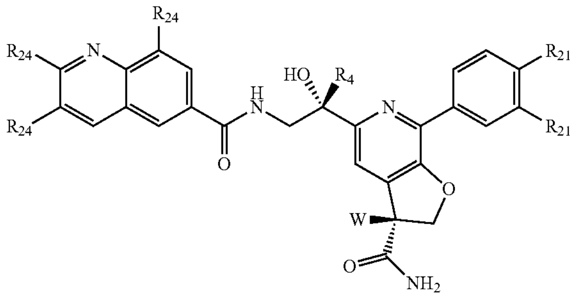

-continued
(XXIII-5)
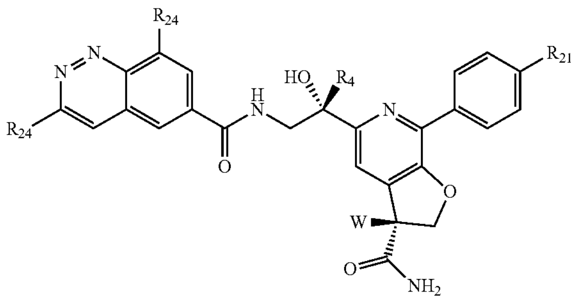
(XXIII-6)
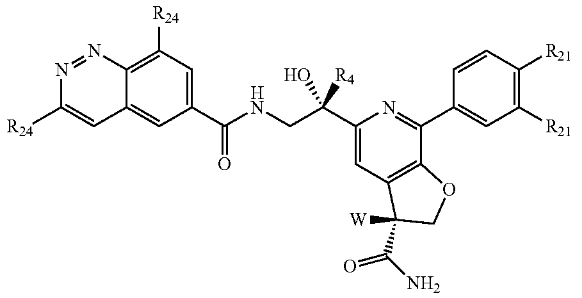
(XXIII-7)
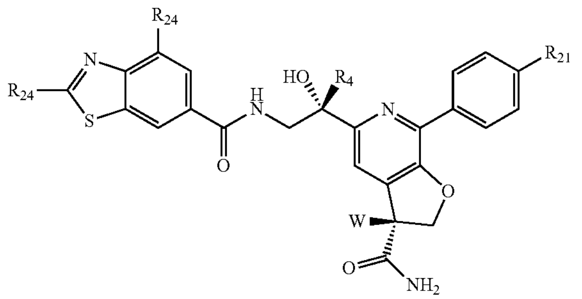
(XXIII-8)
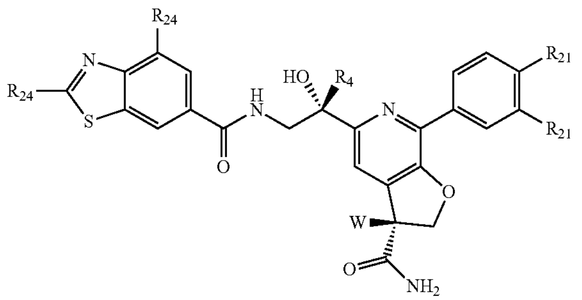
(XXIII-9)
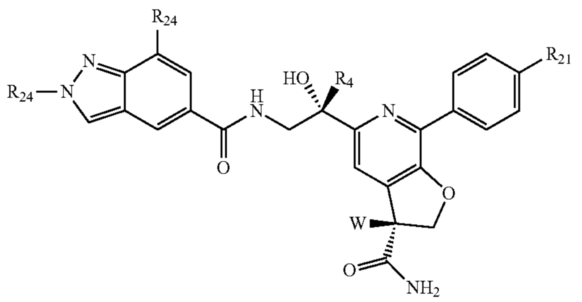
-continued
(XXIII-10)
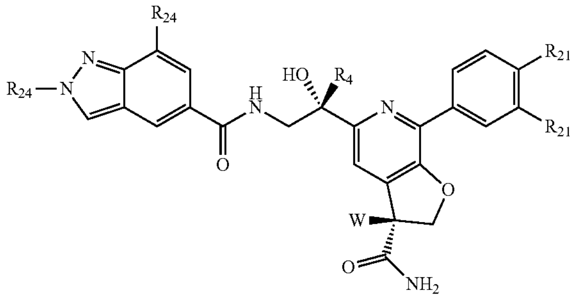
(XXIII-11)
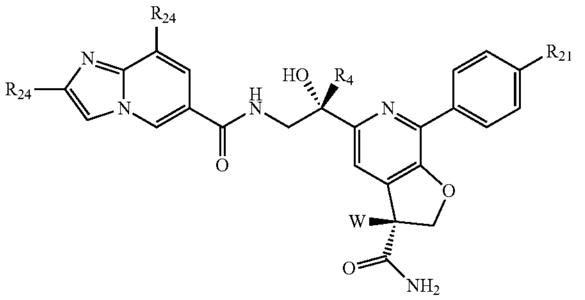
(XXIII-12)
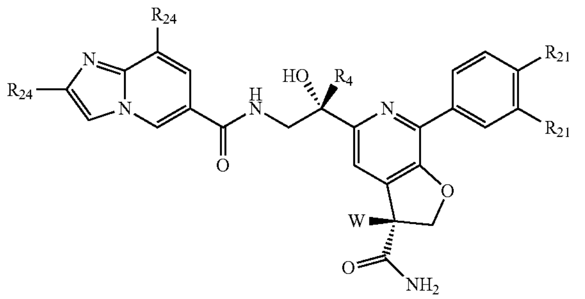
(XXIII-13)
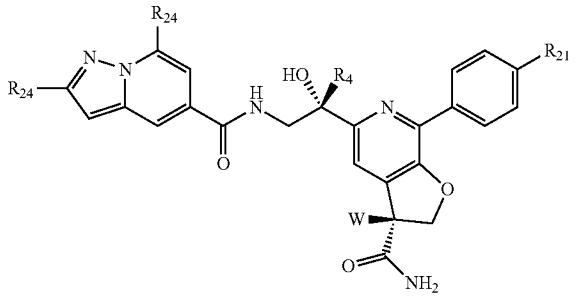
(XXIII-14)
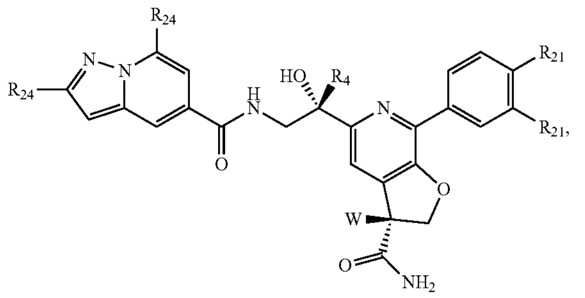

wherein W, $R_4$, $R_{14}$, $R_{21}$, $R_{22}$, and $R_{24}$ are as previously defined. Preferably, $R_4$ is optionally substituted —$C_3$-$C_6$ cycloalkyl. More preferably, $R_4$ is optionally substituted cyclopropyl or optionally substituted cyclobutyl, and W is optionally substituted methyl.

In one embodiment of the present invention, the compound of Formula (I) is represented by Formula (XXIV), or a pharmaceutically acceptable salt, ester, or prodrug thereof:

(XXIV)

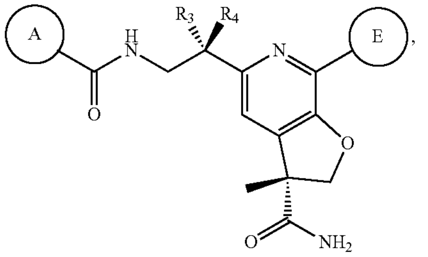

wherein A, E, $R_3$, and $R_4$ are each as previously defined.

In one embodiment of the present invention, the compound of Formula (I) is represented by Formula (XXIV), or a pharmaceutically acceptable salt, ester, or prodrug thereof, wherein $R_3$ is —OH; $R_4$ is optionally substituted methyl or optionally substituted —$C_3$-$C_6$ cycloalkyl; A is selected from:

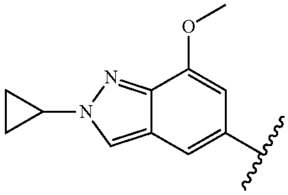

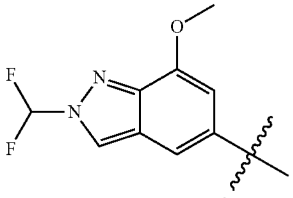

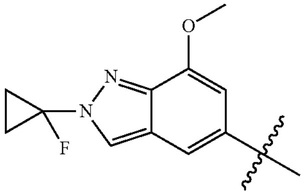

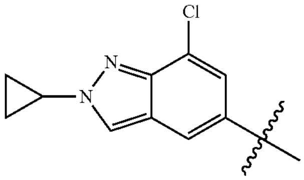

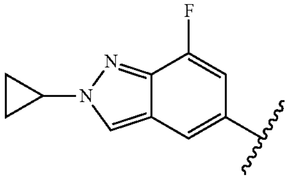

-continued

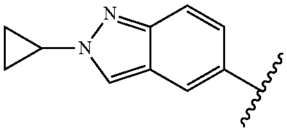

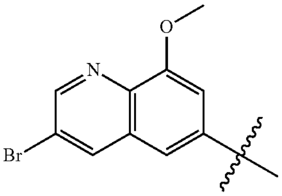

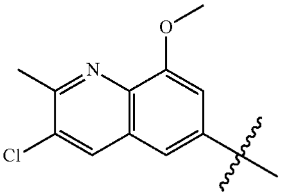

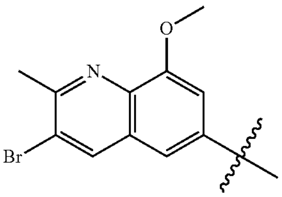

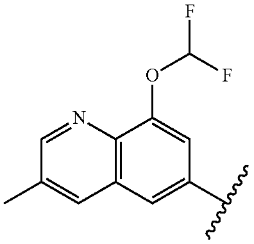

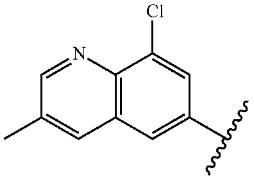

;

and E is selected from:

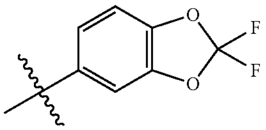

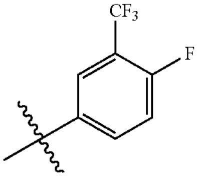

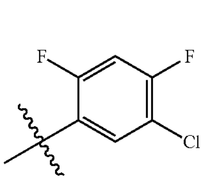

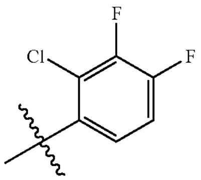

-continued

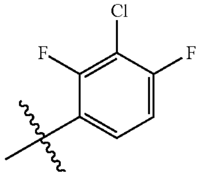

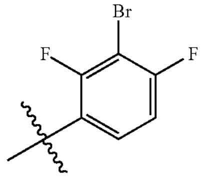

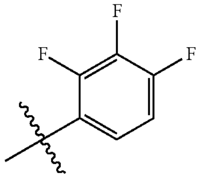

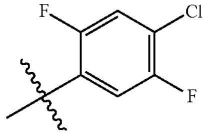

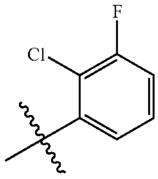

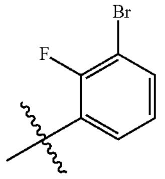

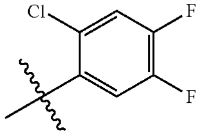

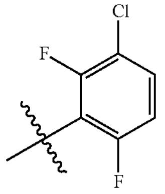

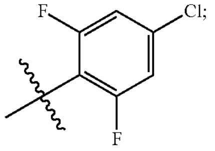 [SMILES: *c1c(F)cc(Cl)cc1F]

or E is selected from

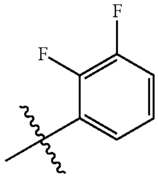

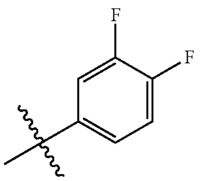

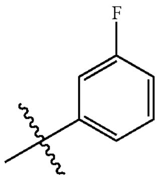

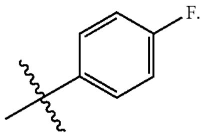

In one embodiment of the present invention, the compound of Formula (I) is represented by Formula (XXV), or a pharmaceutically acceptable salt, ester, or prodrug thereof:

(XXV)

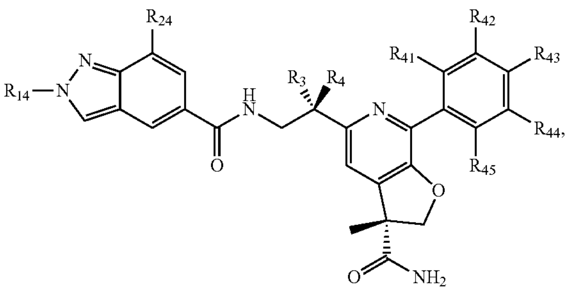

wherein each $R_{41}$, $R_{42}$, $R_{43}$, $R_{44}$, and $R_{45}$ are each independently selected form hydrogen, halogen, optionally substituted methyl, optionally substituted methoxyl or —CN. $R_3$, $R_4$, $R_{14}$, and $R_{24}$ are as previously defined. Preferably, $R_3$ is —OH; $R_4$ is optionally substituted methyl or optionally substituted —$C_3$-$C_6$ cycloalkyl; $R_{14}$ is optionally substituted —$C_3$-$C_6$ cycloalkyl or optionally substituted methyl; and $R_{24}$ is optionally substituted methoxyl or halogen.

In one embodiment of the present invention, the compound of Formula (XXV), or a pharmaceutically acceptable salt, ester or prodrug thereof, wherein $R_{42}$ and $R_{43}$ are taken together with the carbon atoms to which they are attached to form a fused 4- to 7-membered carbocyclic ring or heterocyclic ring.

In one embodiment of the present invention, the compound of Formula (XXV), or a pharmaceutically acceptable salt, ester or prodrug thereof, wherein $R_{41}$ and $R_{42}$ are taken together with the carbon atoms to which they are attached to form a fused 4- to 7-membered carbocyclic ring or heterocyclic ring.

In one embodiment of the present invention, the compound of Formula (I) is represented by one Formulae (XXVI-1)~(XXVI-3), or a pharmaceutically acceptable salt, ester, or prodrug thereof:

(XXVI-1)

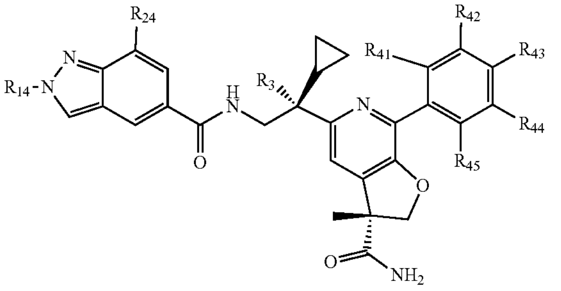

(XXVI-2)

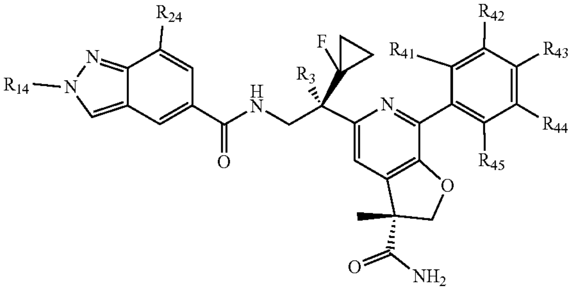

-continued (XXVI-3)

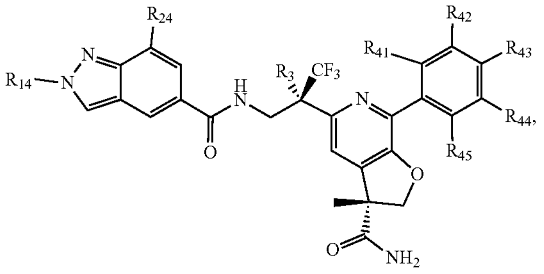

wherein $R_3$, $R_{14}$, $R_{24}$, $R_{41}$, $R_{42}$, $R_{43}$, $R_{44}$, and $R_{45}$ are as previously defined.

In one embodiment of the present invention, the compound of Formula (I) is represented by Formula (XXVII), or a pharmaceutically acceptable salt, ester, or prodrug thereof:

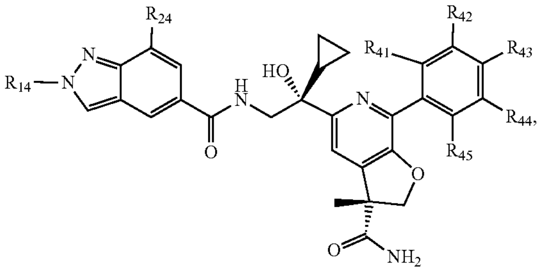

wherein $R_{14}$, $R_{24}$, $R_{41}$, $R_{42}$, $R_{43}$, $R_{44}$, and $R_{45}$ are as previously defined.

In one embodiment of the present invention, the compound of Formula (I) is represented by Formula (XXVIII), or a pharmaceutically acceptable salt, ester, or prodrug thereof.

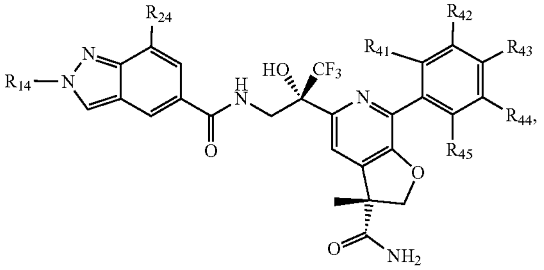

wherein $R_{14}$, $R_{24}$, $R_{41}$, $R_{42}$, $R_{43}$, $R_{44}$, and $R_{45}$ are as previously defined.

In one embodiment of the present invention, the compound of Formula (XXVII), or Formula (XXVIII), or a pharmaceutically acceptable salt, ester or prodrug thereof, wherein $R_{42}$ and $R_{43}$ are taken together with the carbon atoms to which they are attached to form a fused 4- to 7-membered carbocyclic ring or heterocyclic ring.

In one embodiment of the present invention, the compound of Formula (XXVII), or Formula (XXVIII), or a pharmaceutically acceptable salt, ester or prodrug thereof, wherein $R_{43}$ and $R_{44}$ are taken together with the carbon atoms to which they are attached to form a fused 4- to 7-membered carbocyclic ring or heterocyclic ring.

In one embodiment of the present invention, the compound of Formula (I) is represented by one of Formula (XXIV), Formula (XXV), Formulae (XXVI-1)~(XXVI-3), Formula (XXVII), or Formula (XXVIII), or a pharmaceutically acceptable salt, ester or prodrug, wherein $R_{14}$ is optionally substituted —$C_3$-$C_6$ cycloalkyl or optionally substituted methyl; $R_{24}$ is optionally substituted methoxyl or halogen; and each $R_{41}$, $R_{42}$, $R_{43}$, $R_{44}$, and $R_{45}$ are each independently selected from hydrogen, —F, —Cl, —$CH_3$, —$CF_3$, —$OCH_3$, or —$OCF_3$.

In one embodiment of the present invention, the compound of Formula (I) is represented by Formula (XXIV), Formula (XXV), Formulae (XXVI-1)~(XXVI-3), Formula (XXVII), or Formula (XXVIII), or a pharmaceutically acceptable salt, ester or prodrug, wherein $R_{14}$ is —$CHF_2$,

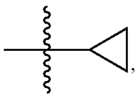, or 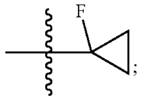;

$R_{24}$ is —F, —C, or —$OCH_3$; and

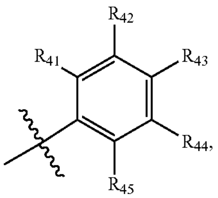

is selected from:

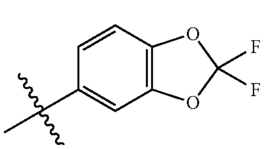
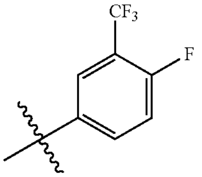
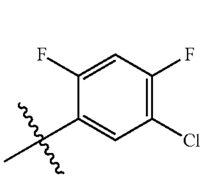
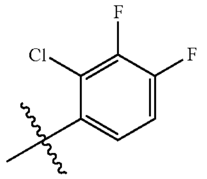
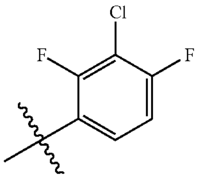
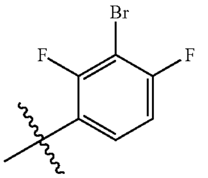
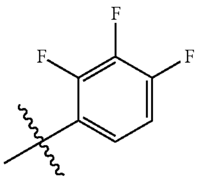
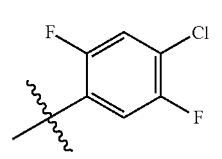

-continued

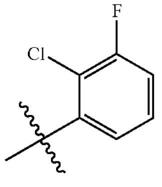

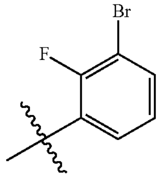

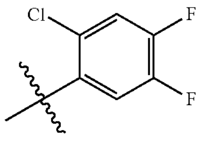

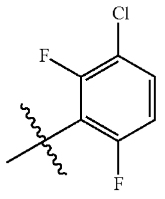

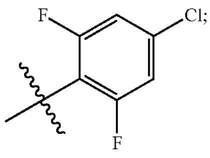

; or

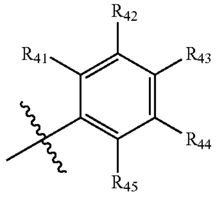

is selected from

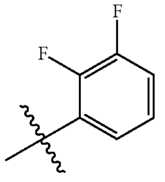

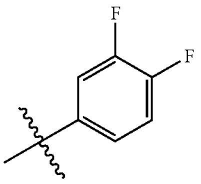

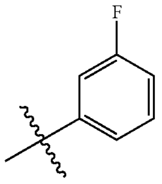

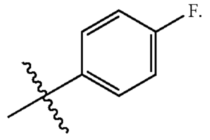

In one embodiment of the present invention, the compound of Formula (I) is represented by Formulae (XXIX-1)~(XXIX-3), or a pharmaceutically acceptable salt, ester, or prodrug thereof:

(XXIX-1)

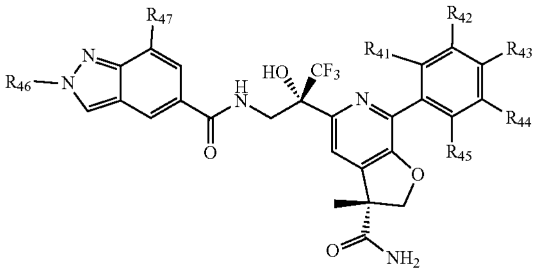

-continued (XXIX-2)

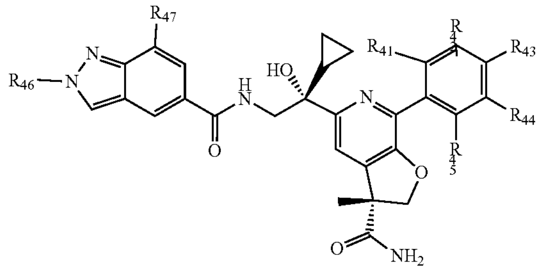

(XXIX-3)

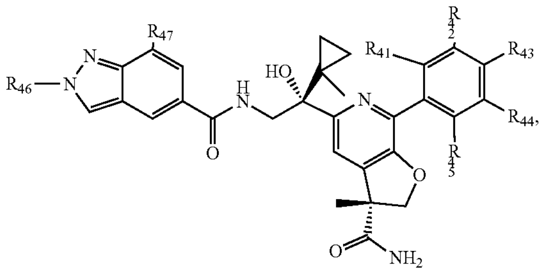

wherein $R_{46}$ is substituted methyl or optionally substituted cyclopropyl; $R_{47}$ is hydrogen, Cl, F, or optionally substituted methoxyl, $R_{41}$, $R_{42}$, $R_{43}$, $R_{44}$, and $R_{45}$ are as previously defined. In certain embodiments of the compounds of Formulas (XXIX-1), (XXIX-2) and (XXIX-3), $R_{46}$ is cyclopropyl, 1-fluorocyclopropyl or difluoromethyl.

In one embodiment of the present invention, the compound of one of Formulae (XXIX-1)~(XXIX-3), or a pharmaceutically acceptable salt, ester or prodrug thereof, wherein $R_{42}$ and $R_{43}$ are taken together with the carbon atoms to which they are attached to form a fused 4- to 7-membered carbocyclic ring or heterocyclic ring.

In one embodiment of the present invention, the compound of one of Formulae (XXIX-1)~(XXIX-3), or a pharmaceutically acceptable salt, ester or prodrug thereof, wherein $R_{43}$ and $R_{44}$ are taken together with the carbon atoms to which they are attached to form a fused 4- to 7-membered carbocyclic ring or heterocyclic ring.

It will be appreciated that the description of the present invention herein should be construed in congruity with the laws and principles of chemical bonding. In some instances, it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebulizer containing a medicament which comprises (a) a derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents; e.g., starches, arabic gums, gelatin, methylcellulose, carboxymethylcellulose or polyvinyl pyrrolidone; disaggregating agents, e.g., starch, alginic acid, alginates or sodium starch glycolate; effervescing mixtures; dyestuffs; sweeteners; wetting agents, such as lecithin, polysorbates, laurylsulphates; and, in general, nontoxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluant or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral center include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono-, bi-, or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl"$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "carbocycle" or "carbocyclic" refers to a saturated, partially unsaturated or aromatic cyclic group in which each atom within the ring is carbon. Examples of cabocyclics include cycloalkyl, cycloalkenyl and aryl groups.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, —$C_1$-$C_{12}$-alkyl; —$C_2$-$C_{12}$-alkenyl, —$C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$— $C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$— $C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably $C_1$ and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted when possible with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$.

In certain embodiments, a substituted alkyl, alkenyl or alkoxy group is substituted with one or more halogen atoms, preferably fluorine or chlorine atoms. Such substituted alkyl groups include fluoromethyl, difluoromethyl and trifluoromethyl. Such substituted alkoxy groups include fluoromethoxy, difluoromethoxy and trifluoromethoxy.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but are not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure (s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part*-2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2nd Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews,* 8:1-38(1992); Bundgaard, J. of *Pharmaceutical Sciences,* 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound.

The term "treating", as used herein, means relieving, lessening, reducing, eliminating, modulating, or ameliorating, i.e., causing regression of the disease state or condition. Treating can also include inhibiting, i.e., arresting the development, of an existing disease state or condition, and relieving or ameliorating, i.e., causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or nonstoichiometric amounts of solvent. Some compounds have a tendency to trap a fixed molar ratio of solvent molecules in the crystalline solid state, thus forming a solvate. If the solvent is water, the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:

ACN for acetonitrile;

AD-mix-β for (9S)-(9''S)-9,9''-[1,4-Phthalazinediylbis(oxy)]bis[10,11-dihydro-6'-methoxycinchonan];

Bn for benzyl;

BOP for (Benzotriazol-1-yloxy)tris(dimethylamino)phosphonium hexafluorophosphate;

BzCl for benzoyl chloride;

mCPBA for meta-chloroperbenzoic acid;

Cbz for benzyloxycarbonyl;

CDI for carbonyldiimidazole;

DAST for diethylaminosulfur trifluoride;

DBU for 1,8-Diazabicycloundec-7-ene;

DCE for dichloroethane;

DCM for dichloromethane;

Dess-Martin periodinane for 1,1,1-tris(acetyloxy)-1,1-dihydro-1,2-benziodoxol-3-(1H)-one;

DIAD for diisopropyl azodicarboxylate;

DIBAL-H for diisobutylaluminum hydride;

DMAP for N,N-dimethylaminopyridine;

DME for 1,2-dimethoxyethane;

DMF for N,N-dimethyl formamide;

DMSO for dimethylsulfoxide;

DPPA for diphenylphosphoryl azide or diphenyl phosphorylazidate;

dppf for 1,1'-Bis(diphenylphosphino)ferrocene;

EDCI or EDC for 1-(3-diethylaminopropyl)-3-ethylcarbodiimide hydrochloride;

EA or EtOAc for ethyl acetate;

Ghosez's reagent for 1-Chloro-N,N,2-trimethyl-1-propenylamine;

HATU for O (7-Azabenzotriazole-1-yl)-N,N,N',N'-tetramethyluronium hexafluorophosphate;

HCl for hydrochloric acid;

Hunig's base for diisopropylethylamine;

PyBOP for (Benzotriazol-1-yloxy)tripyrrolidinophosphonium hexafluorophosphate;

LDA for Lithium diisopropylamine;

Pd—C for palladium carbon;

PE for petroleum ether;

Ph for phenyl;

RT for reverse transcription;

RT-PCR for reverse transcription-polymerase chain reaction;

TBME for tert-butyl methyl ether;

TEA for triethylamine;

$Tf_2O$ for trifluoromethanesulfonic anhydride;

TFA for trifluoroacetic acid;

THE for tetrahydrofuran;

$(TMS)_2NH$ for hexamethyldisilazane;

TBS for tert-Butyldimethylsilyl;

TBDPS for tert-Butyldiphenylsilyl;

TMS for trimethylsilyl;

TPAP tetrapropylammonium perruthenate;

TPP or $PPh_3$ for triphenylphosphine;

Ts or tosyl for p-$CH_3C_6H_4SO_2$—;

tBOC or Boc for tert-butyloxy carbonyl; and

Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1 illustrates methods to prepare a compound of formula 11 from compounds 1 and 2, wherein n=1, 2 or 3; P is hydroxy protecting group; Ar is E; and E is as previously defined. Alkylation of the hydroxy pyridine 1 with hydroxy epoxide using Mitsunobu reaction conditions affords epoxide 4. Alternatively, hydroxy epoxide is converted to 3 which has a leaving group such as but not limited to, tosyl and methanlsulfonyl followed by alkylation in the presence of base such as but not limited to, $K_2CO_3$ and $Cs_2CO_3$, provides 4. Intramolecular epoxide opening mediated by base such as but not limited to, LDA, produces compound 5. Hydroxy group compound 5 is protected with proper protecting group such as but not limited to, TBDPS and TBS, affords compound 6. Trifluomethyl ketone 7 is obtained from iodine-magnesium exchange of compound 6 followed by addition of ester such as but not limited to, ethyl 2,2,2-trifluoroacetate. Trifluoromethyl ketone 7 in cross-coupled with various metal coupling partners 8, but not limited to, boronic acids, boronic esters, organotin reagents, organozinc reagents, organomagnesium reagents, organo silicon reagents or the like catalyzed by appropriate Pd, Ni, Cu or the like catalyst to afford compound 9. Nitromethane addition in the presence of base such as but not limited to, $K_2CO_3$ and $Cs_2CO_3$, to compound 9 affords compound 10. Reduction of nitro group with reducing reagents such as but not limited to, zinc and acetic acid, produces key intermediate 11.

Scheme 1

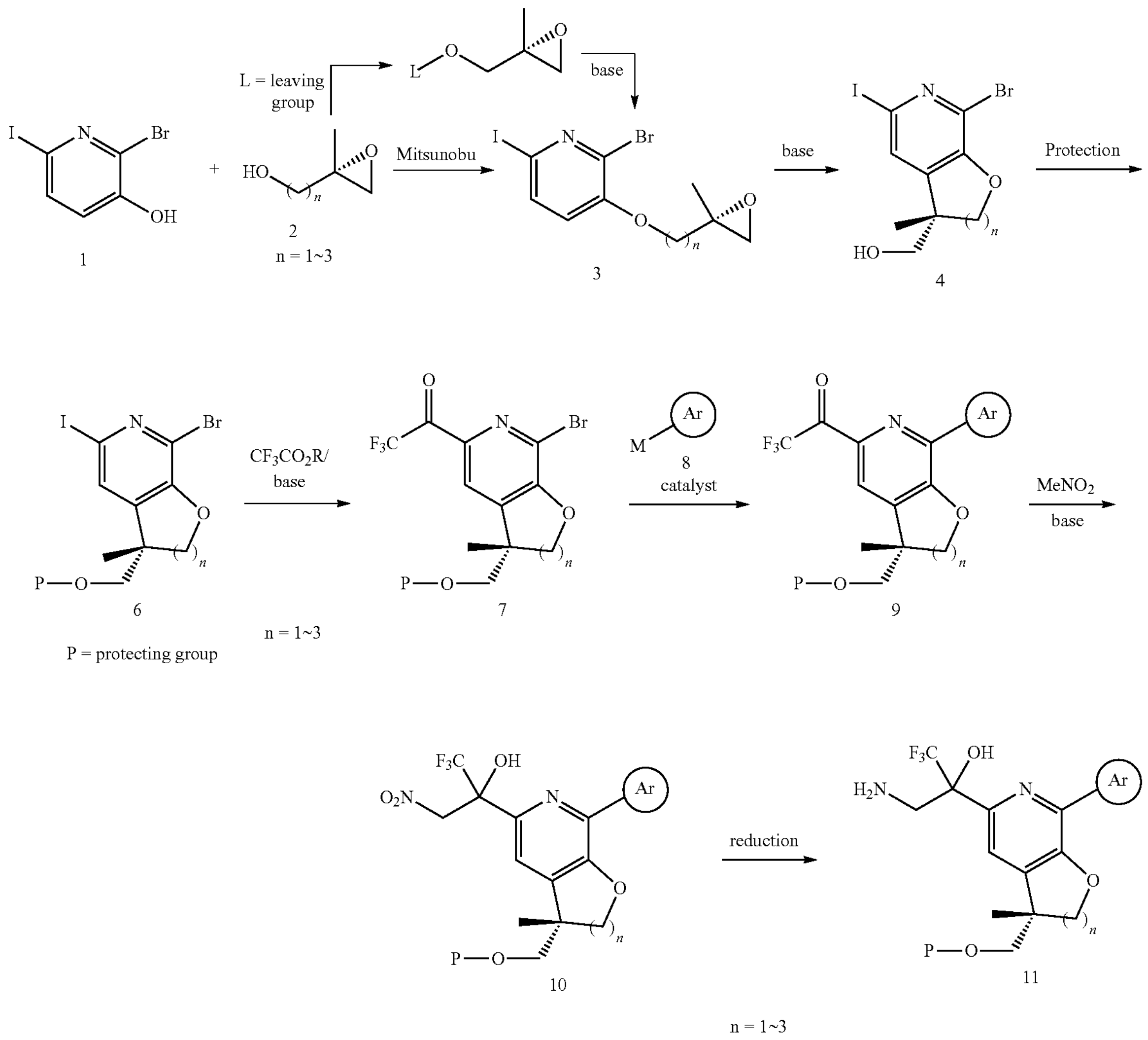

1, 2, 3, 4, 6, 7, 8, 9, 10, 11

As seen in scheme 2, wherein $Ar_1$ is A; Ar is E; R is $R_{11}$; n is 1, 2 or 3; and A, E, $R_{11}$ are as previously defined. Key intermediate 11 is coupled with various carboxylic acids to afford amide 14. Amide 14 is then reacted with a variety of electrophiles to produce various ethers, esters and carbamates of formula 15. Amide 14 is also oxidized to an aldehyde 16, and then reductive amination provides a variety of amines 17. The hydroxyl of —$CH_2OH$ in amide 14 is converted to cyanomethyl 18 via activation followed by cyanation. Compound 14-1 is further transformed to acetamide 19 in the presence of a catalyst such as, but not limited to, Parkin's catalyst.

Scheme 2

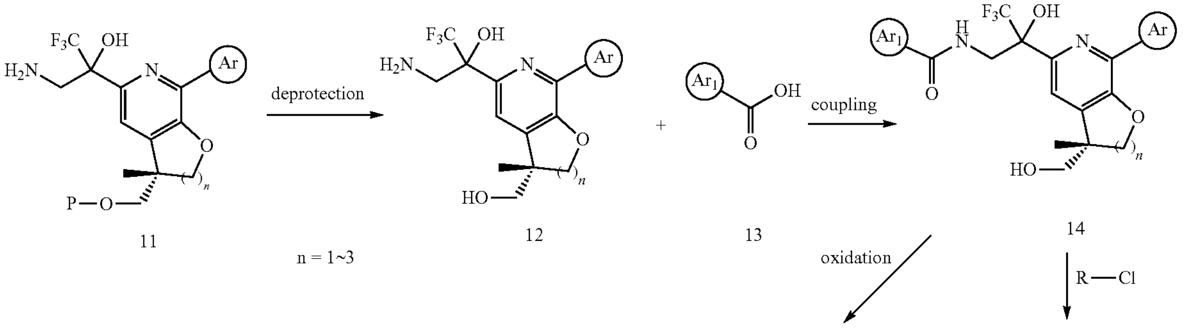

11, 12, 13, 14

-continued

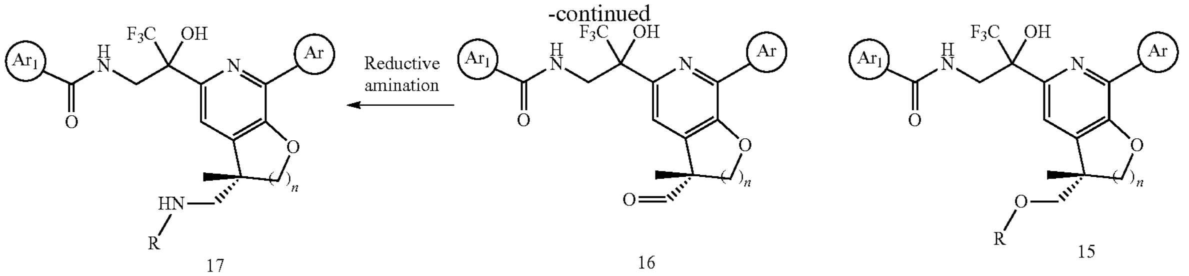

17 16 15 n =1~3

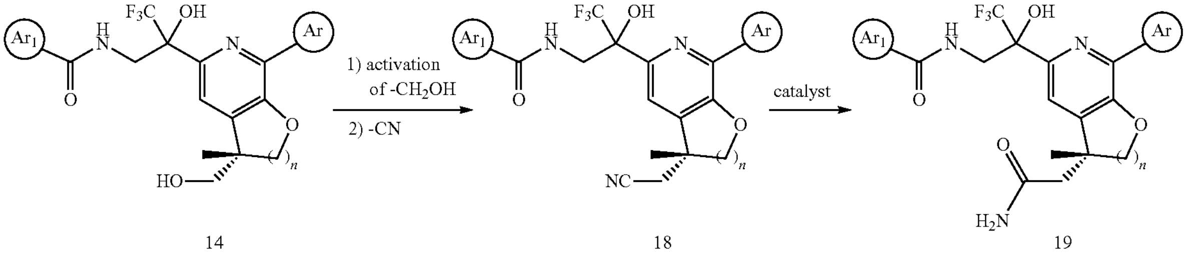

14 18 19

As seen in scheme 3, wherein $Ar_1$ is A; Ar is E; R is $R_{11}$; and A, E, $R_{11}$ are as previously defined. An aldehyde 16 is converted to the benzyl protected amine through reductive amination. Hydrogenolysis affords the free amine 20. Lastly, displacement with a variety of electrophiles gives N-substituted compounds 21.

Scheme 3

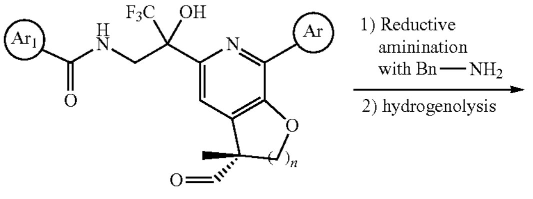

16

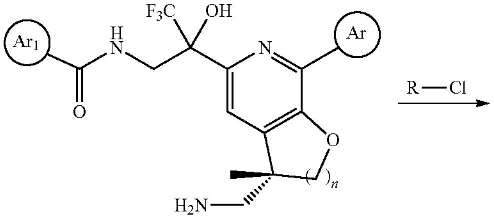

20

-continued

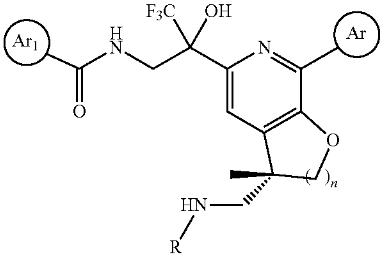

21

As seen in Scheme 4, wherein $Ar_1$ is A; Ar is E; R' is —$C_1$-$C_6$ alkyl, —$C_3$-$C_6$ cycloalkyl, aryl, or heteroaryl; n is 1, 2 or 3; and A and E are as previously defined. After oxidation of aldehyde 16 to acid 22, which is further converted to amides 23 and sulfonamides 24 using common methods such as but not limited to, HATU and DIPEA. From there diversification to a variety of esters and amides is conducted.

Scheme 4

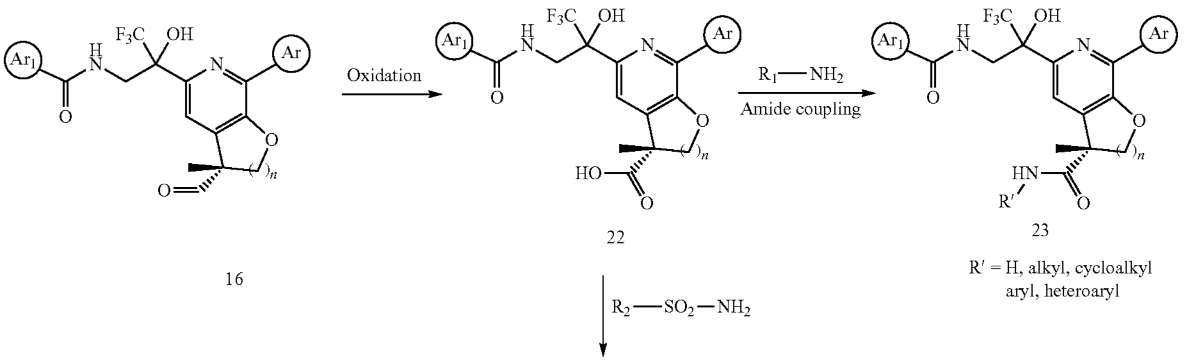

16

22

23

R′ = H, alkyl, cycloalkyl aryl, heteroaryl

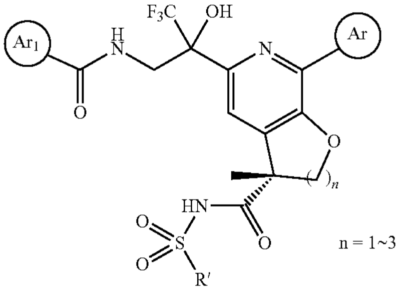

n = 1~3

24

R″ = alkyl, cycloalkyl, aryl, heteroaryl

Scheme 5 illustrates another method to prepare a compound of formula 11, wherein Ar is E; P is a hydroxy protecting group; n is 1, 2 or 3; and E is as previously defined. Ketone 9 is converted to compound of formula 26 via olefination. Alternatively, 26 is obtained from; 1) 6 via cross-coupling with metal coupling partner 6-1, which can be, but is not limited to, a boronic acid, a boronic ester, an organotin reagent, an organozinc reagent, an organomagnesium reagent, an organosilicon reagent or the like catalyzed by appropriate Pd, Ni, Cu or the like catalyst to afford compound 25; 2) compound 25 is converted to compound 26 as previously described method in scheme 1. With 26 in hand, Compounds of formula 27 are prepared by dihydroxylation followed by epoxide formation. Epoxide opening of compound 27 with amine equivalent such as but not limited to, $NH_4OH$ and $NH_3$, provides compounds of formula 11.

Scheme 5

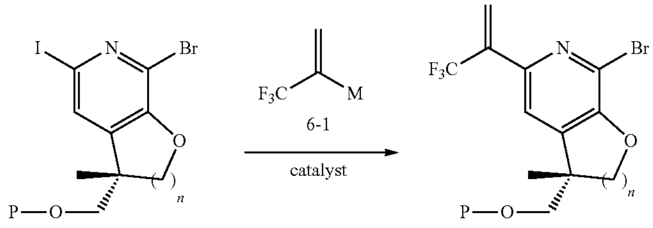

6

6-1

25

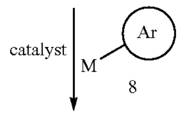

8

-continued

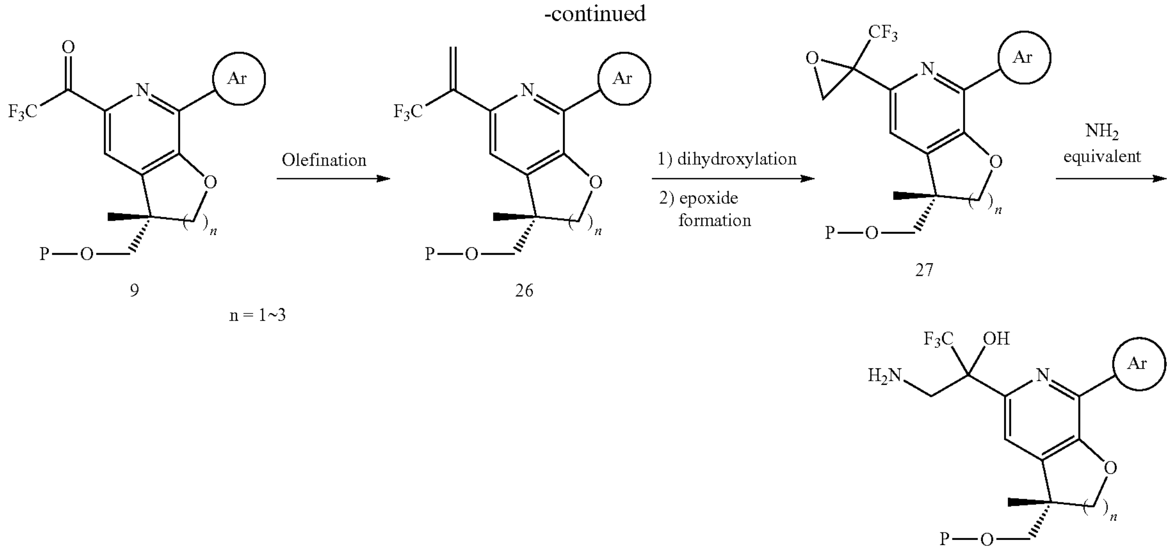

9 n = 1~3

26

27

11 n = 1~3

Scheme 6 illustrates another method to prepare a compound of formula 23, wherein $Ar_1$ is A; Ar is E; R' is $-C_1$-$C_6$ alkyl, $-C_3$-$C_6$ cycloalkyl, aryl, or heteroaryl; n is 1, 2 or 3; and A and E are as previously defined. Amine 11 is protected with a protecting group such as but not limited to, Boc and Cbz. After deprotection of hydroxy protecting group, subsequent oxidations provide acid 30. Compound 30 is coupled with various amines to provide amide 31. Deprotection of amine protecting group followed by subsequent amide formation affords compounds of formula 23.

Scheme 6

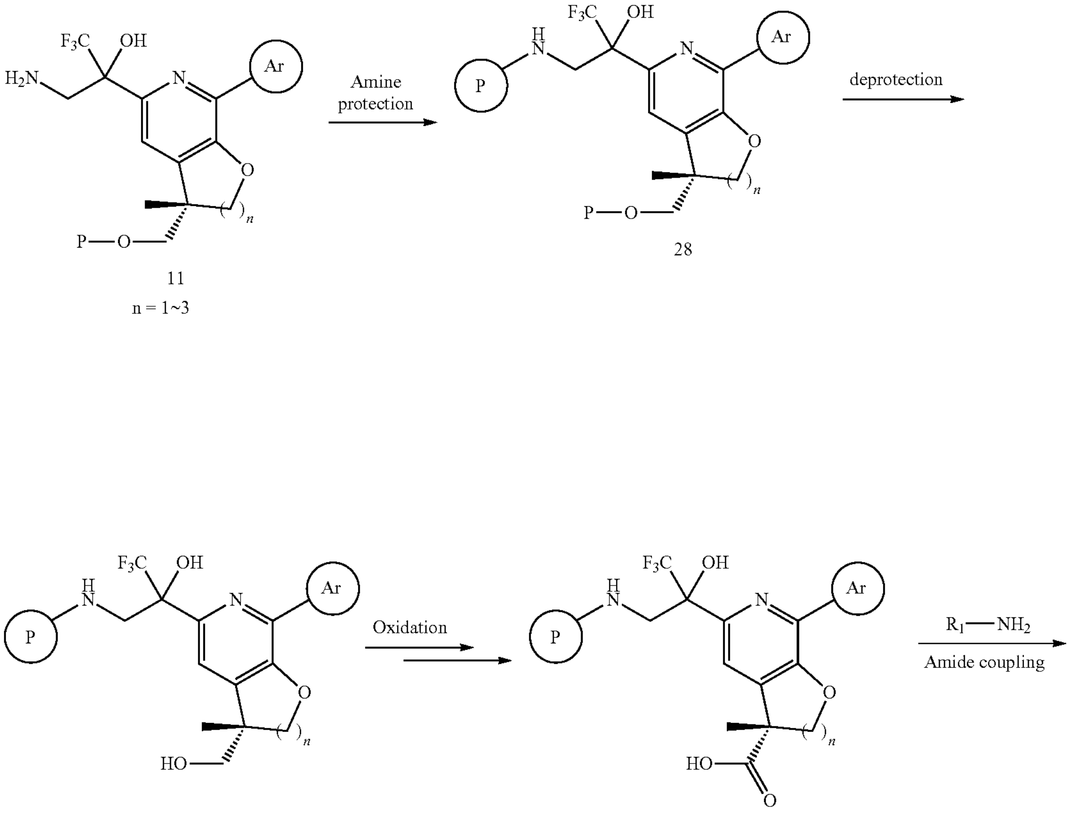

11 n = 1~3

28

29

30

-continued

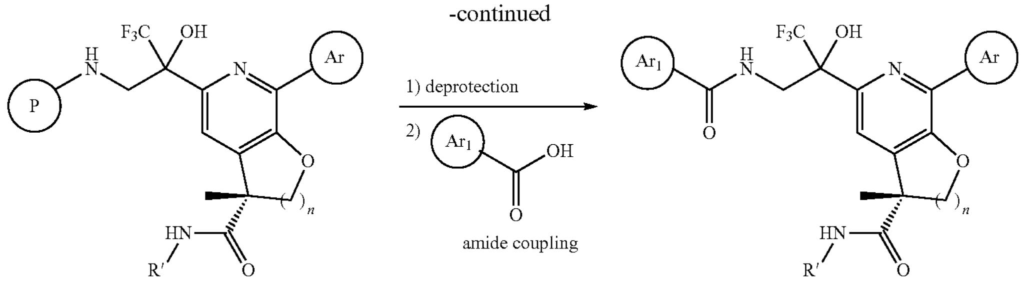

31 n = 1~3

23 n = 1~3

R′ = H, alkyl, cycloalkyl, aryl, heteroaryl

Scheme 7 illustrates an additional route for the synthesis of the desired compounds. The difference for this route is that it starts with oxidation and amide coupling to install the amide 33 at the beginning of the synthesis. Sequential vinylation and arylation afford the bis-coupled product 34. Asymmetric dihydroxylation followed by activation and substitution affords the amino alcohol precursor. Lastly, amide coupling with the respective aryl acid produces the desired compounds depicted by compound 36.

Scheme 7

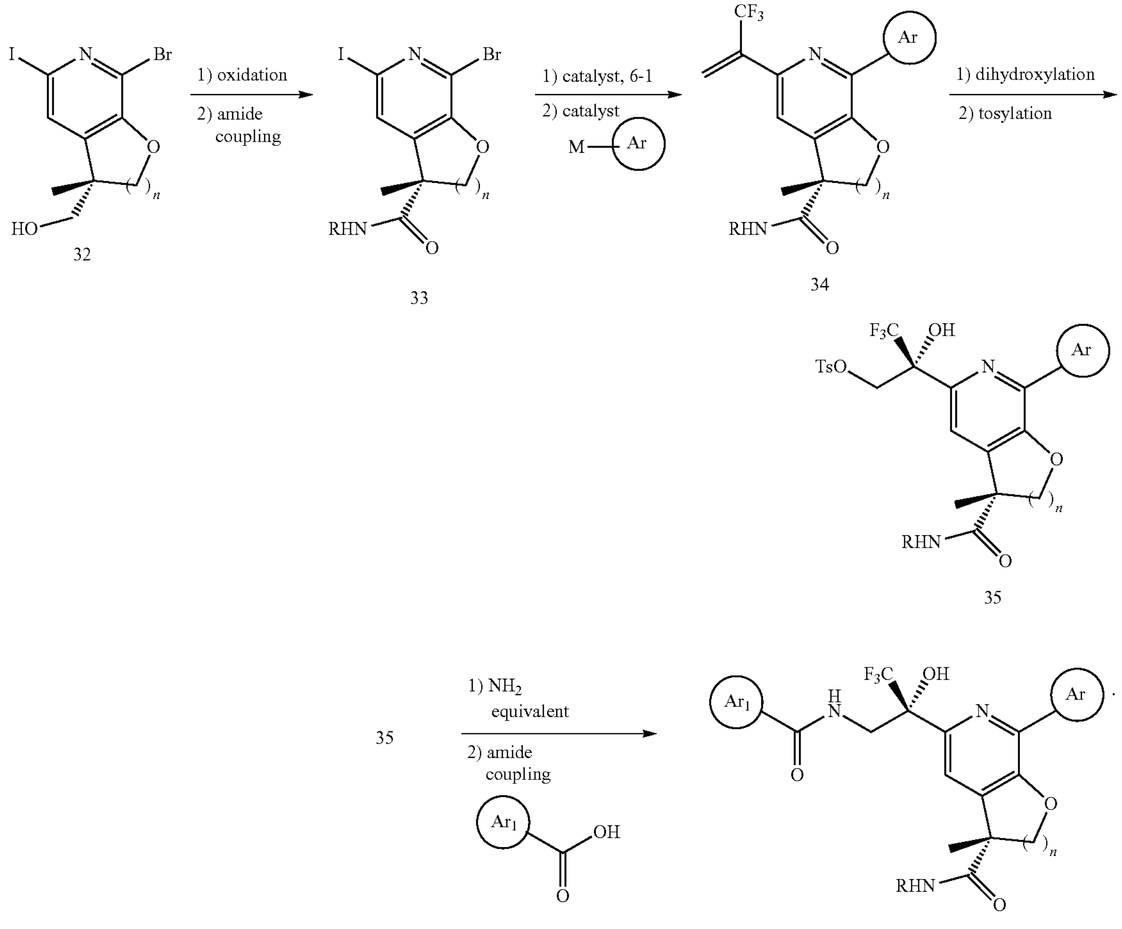

32

33

34

35

35

36

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art, and such changes and modifications including, without limitation, those relating to the chemical structures, substituents, derivatives, formulations and/or methods of the invention may be made without departing from the spirit of the invention and the scope of the appended claims.

Certain synthetic procedures useful in the preparation of compounds of the invention are disclosed in U.S. patent application Ser. No. 16/930,622, the contents of which are incorporated by reference herein in their entirety.

Example 1

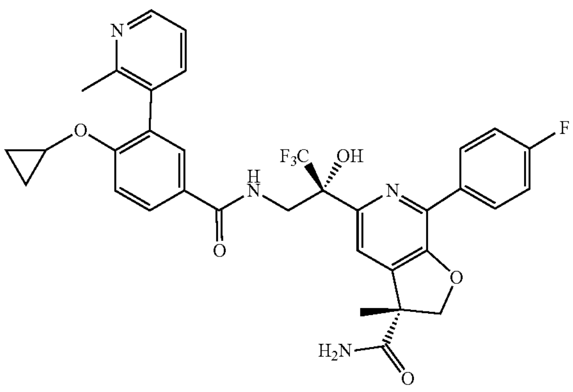 [SMILES: Cc1ncccc1-c1cc(C(=O)NC[C@](O)(c2cc3c(c(-c4ccc(F)cc4)n2)OC[C@]3(C)C(N)=O)C(F)(F)F)ccc1OC1CC1]

Example 1 Step a

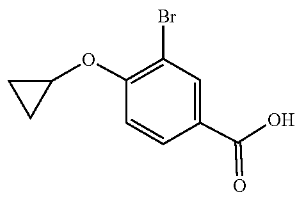 [SMILES: O=C(O)c1ccc(OC2CC2)c(Br)c1]

A solution of 3-bromo-4-hydroxybenzoate (16 g, 69.25 mmol), $Cs_2CO_3$ (68 g, 207.75 mmol), KI (46 g, 277.00 mmol) and bromocyclopropane (21 g, 173.12 mmol) in NMP (30 mL) was stirred for 16 hours at 180° C. in a Parr reactor. The resulting solution was diluted with water and extracted with EtOAC. The combined organics were dried and concentrated. The resulting solution was purified by reverse phase C18 column chromatography ($CH_3CN/H_2O$) to afford desired product as a yellow solid (3 g, 22%). ESI-MS m/z: 257.05 $[M+H]^+$. (Methyl ester product was also isolated and used).

Example 1 Step b

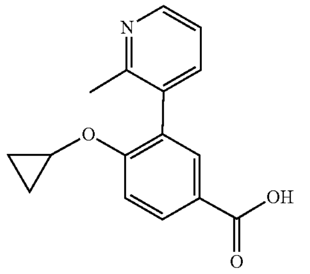 [SMILES: Cc1ncccc1-c1cc(C(=O)O)ccc1OC1CC1]

A solution of the compound from step a (250 mg, 0.98 mmol), $Pd(dppf)Cl_2$ (142 mg, 0.19 mmol), 2-methyl-3-(4,4,5,5-tetramethyl-1,3,2-dioxaborolan-2-yl)pyridine (425 mg, 1.94 mmol), $H_2O$ (0.1 mL) and $Cs_2CO_3$ (950 mg, 2.91 mmol) in dioxane (3 mL) was stirred for 2 hours at 90° C. under $N_2$ atmosphere. The resulting solution was purified by reverse phase C18 column chromatography (MeOH/0.1% FA in $H_2O$) to afford the desired product as a white solid (180 mg, 68%). ESI-MS m/z: 270.15 $[M+H]^+$.

Example 1 Step c

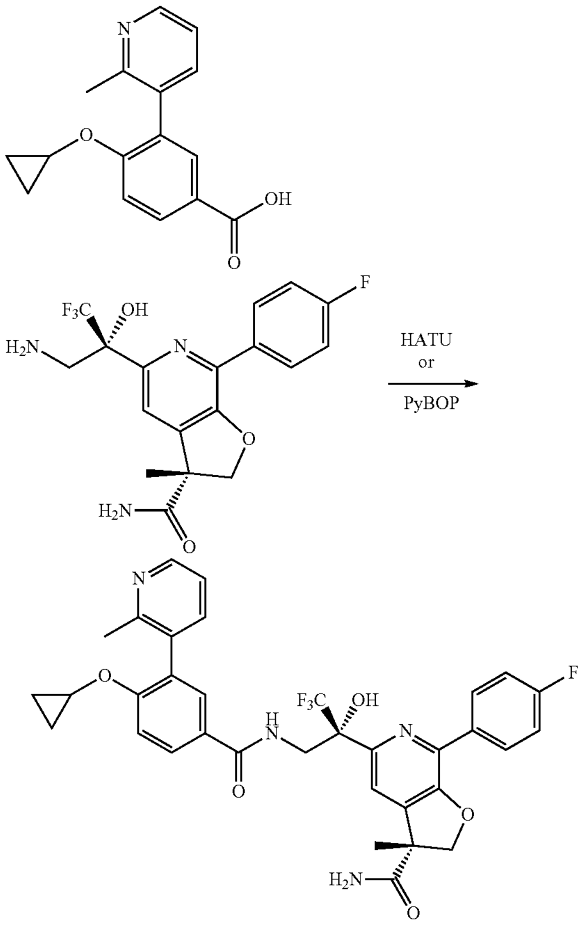

To a 2-dram vial equipped with a stir bar was added amine (30 mg, 0.075 mmol), acid (19.18 mg, 0.075 mmol), and the material was dissolved in DMF (0.2 M). Hunig's base (0.053 mL, 0.30 mmol) was added and the vial was cooled to 0° C. HATU (43 mg, 0.113 mmol) was added, the reaction stirred for 10 minutes, warmed to room temperature and monitored by LCMS (1 hr). The reaction was diluted with EtOAc and quenched with water. The aqueous was extracted with EtOAc and DCM/MeOH with a phase separator cartridge and concentrated. The material was purified by prep-HPLC 20-90%, MeCN/Water, 25 min to afford the title compound as a white solid (23.6 mg, 48%). ESI-MS m/z: 651.25 [M+H]$^+$.

Example 2

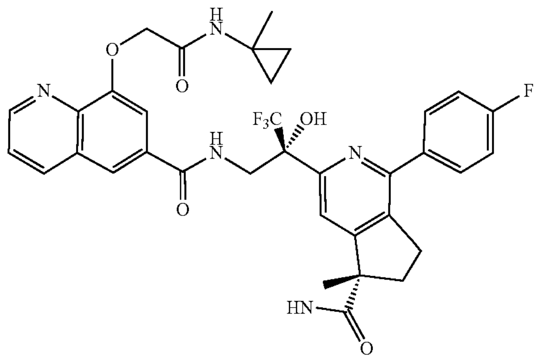

Example 2 Step a

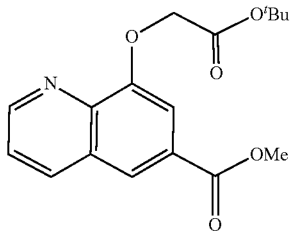 [SMILES: COC(=O)c1cc(OCC(=O)OC(C)(C)C)c2ncccc2c1]

To a 50 mL round-bottom flask equipped with a stir bar was added methyl 8-hydroxyquinoline-6-carboxylate (1.500 g, 7.38 mmol) and potassium carbonate (2.040 g, 14.76 mmol), and the solids were dissolved in DMF (0.5 M). tert-Butyl 2-bromoacetate (1.308 ml, 8.86 mmol) was then added, the reaction stirred at 40° C. and monitored by LCMS (2 hr). The reaction was cooled to r.t., diluted with EtOAc and quenched with water. Aqueous was extracted with EtOAc, and the combined organics dried, filtered, and concentrated. The residue was purified by automated column chromatography (silica gel, $R_f$=0.27 in 50% ethyl acetate in hexanes) to afford a white, solid (1.93 g, 82%). ESI-MS m/z: 262.0 [M+H]$^+$.

Example 2 Step b

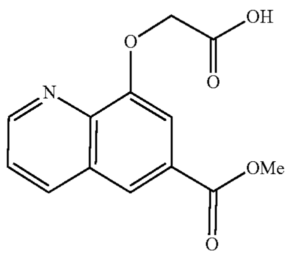 [SMILES: COC(=O)c1cc(OCC(=O)O)c2ncccc2c1]

To a 100 mL round-bottom flask containing step a (1.93 g, 6.08 mmol) was added a stir bar, and the solid dissolved in DCM (0.5 M). The flask was cooled to 0° C., and TFA (4.69 ml, 60.8 mmol) was added. The reaction was stirred for 10 minutes, warmed to room temperature and monitored by LCMS (added 5.0 eq. more TFA after 3 hr, 5.5 hr total). The mixture was quenched with water and diluted with DCM. Solid precipitates. Further diluted with DCM and stirred vigorously for 10 minutes. The solid was collected by filtration and washed multiple times with DCM and dried under high vacuum to afford a light brown, fluffy solid (2.21 g, 97%). ESI-MS m/z: 262.0 [M+H]$^+$.

Example 2 Step c

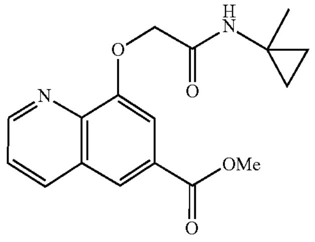 [SMILES: COC(=O)c1cc(OCC(=O)NC2(C)CC2)c2ncccc2c1]

To a 40 mL vial equipped with a stir bar was added step b (125 mg, 0.333 mmol). The solid was dissolved in DMF and cooled to 0° C. DIPEA (407 µl, 2.332 mmol) was added followed by 1-methylcyclopropan-1-amine hydrochloride (124 mg, 1.148 mmol). PyBOP (260 mg, 0.500 mmol) was then added in one portion, the reaction stirred for 10 minutes, warmed to room temperature and monitored by LCMS (1.5 hr). The reaction diluted was with EtOAc and quenched with water. The aqueous layer was extracted with EtOAc, with a phase separator cartridge, and the combined organics were concentrated. The residue was purified by automated column chromatography (silica gel, 0-20% methanol in dichloromethane) the title compound (98 mg, 82%). ESI-MS m/z: 216.0 [M+H]$^+$.

Example 2 Step d

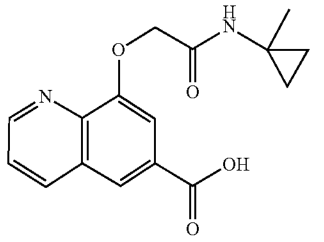 [SMILES: CC1(NC(=O)COc2cc(C(=O)O)cc3cccnc23)CC1]

General hydrolysis notes: In some cases, the reaction was heated to 45° C. to force material into solution and accelerate hydrolysis. After hydrolysis, the product was isolated by precipitation. If no precipitate, the product was either extracted, or the aqueous solution was concentrated (material dried and used crude). The major MS' m/z for all these compounds is C—C cleavage: ESI-MS m/z: 202.0 $[M+H]^+$.

To a 20 mL vial containing Example 2 Step c (9 mg, 0.312 mmol) was added a stir bar. The compound was dissolved in MeOH, THE and Water (0.2 M, 2:1:1). Lithium hydroxide hydrate (62 mg, 1.56 mmol) was added, the reaction stirred at room temperature and monitored by LCMS. The stir bar was removed, and the vial cooled to 0° C. The reaction was acidified with 2 M HCl, and the pH brought to around 4-5 (used 1M NaOH if too acidic). The product was extracted 3× with 10% MeOH/DCM with a phase separator and concentrated. Dried on high vacuum to afford the title compound (45 mg, 50%). ESI-MS m/z: 202.0 $[M+H]^+$.

Example 2 Step e

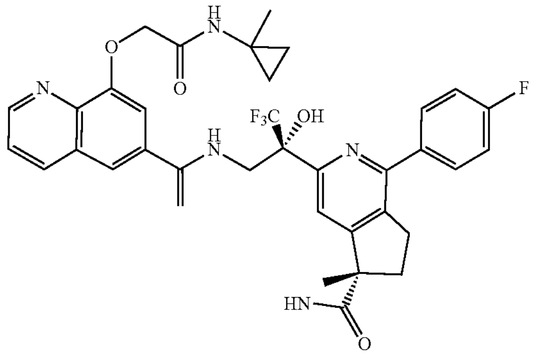 [SMILES: C=C(NC[C@](O)(c1cc2c(c(-c3ccc(F)cc3)n1)CC[C@]2(C)C(N)=O)C(F)(F)F)c1cc(OCC(=O)NC2(C)CC2)c2ncccc2c1]

The following example was prepared using the same procedures as Example 1 Step c, with the corresponding acid from step d and amine HCl salt (25 mg) coupling partners. The residue was purified by Gilson prep-HPLC (20-90%, MeCN/Water, 25 min) to afford the title compound (8 mg, 20%) ESI-MS m/z: 682.2.

Intermediate 1

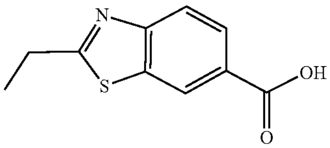

Intermediate 1 Step a

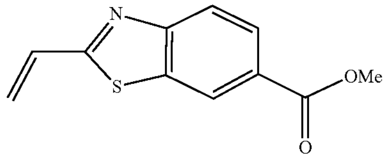

In a vial, 4,4,5,5-tetramethyl-2-vinyl-1,3,2-dioxaborolane (566 mg, 3.67 mmol), methyl 2-bromobenzo[d]thiazole-6-carboxylate (500 mg, 1.837 mmol), $PdCl_2$(dppf) DCM (75 mg, 0.092 mmol), and $Na_2CO_3$ (302 mg, 2.85 mmol) were dissolved in dioxane (6.9 ml), and water (2.3 ml). The reaction was heated to 100° C. for 3h. The reaction was cooled to room temperature and diluted with water. The aqueous layer was washed with EtOAc. The combined organic layer was dried over $MgSO_4$ and concentrated. The crude reaction mixture was purified by silica gel chromatography eluting with 0-50% EtOAc/Hexanes to give the title compound (180 mg, 0.821 mmol, 45%).

Intermediate 1 Steps b and c

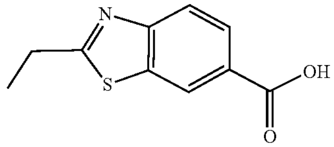

In a vial, the compound from step a (120 mg, 0.547 mmol) was dissolved in MeOH (5.47 ml). Pd/C (5.82 mg, 0.055 mmol) was added and the vial was purged with $H_2$. Reaction allowed to stir at room temperature under $H_2$ for 1 hr. Reaction purged with $N_2$ and reaction filtered through celite. Crude reaction mixture concentrated and purified by silica gel chromatography eluting with 0-50% EtOAc/Hexanes to give the title compound (80 mg, 0.362 mmol, 66%) The ester hydrolysis was carried out in a similar manner to Example 2 Step d. The title compound was isolated by precipitation to afford the desired product (50 mg, 0.241 mmol, 67%).

Intermediate 2

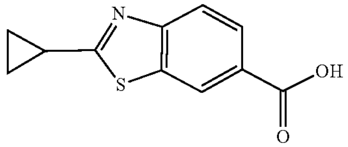 [SMILES: O=C(O)c1ccc2nc(C3CC3)sc2c1]

In a vial, cyclopropyltrifluoro-14-borane, potassium salt (326 mg, 2.205 mmol), methyl 2-bromobenzo[d]thiazole-6-carboxylate (200 mg, 0.735 mmol), palladiumtetrakis (42.5 mg, 0.037 mmol) and potassium phosphate (468 mg, 2.205 mmol) were dissolved in Toluene (2.76 ml) and Water (0.919 ml). The reaction was heated to 100° C. and allowed to stir overnight. The reaction was cooled to room temperature and water was added. Aqueous layer washed with EtOAc. Combined organic layer dried over $MgSO_4$ and concentrated. Crude reaction mixture purified by silica gel chromatography eluting with 0-50% EtOAc/Hexanes to give the title compound (80 mg, 0.343 mmol, 47%).

The ester hydrolysis was carried out in a similar manner to Example 2 Step d. The title compound was isolated by precipitation to afford the desired product (50 mg, 0.228 mmol, 67%).

Intermediate 3

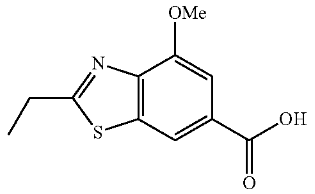 [SMILES: CCc1nc2c(OC)cc(C(=O)O)cc2s1]

Intermediate 3 Step a

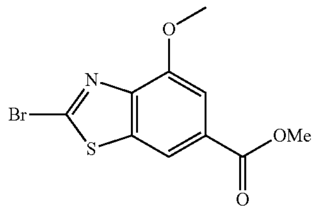 [SMILES: COC(=O)c1cc(OC)c2nc(Br)sc2c1]

A solution methyl 2-amino-4-methoxybenzo[d]thiazole-6-carboxylate (2 g), $CuBr_2$ (3.7 g, 16.78 mmol) and t-$BuNO_2$ (1.7 g, 16.77 mmol) in $CH_3CN$ was stirred for 16 hours at room temperature under $N_2$ atmosphere. The resulting solution was diluted with water, extracted with EtOAc and the organic layer was dried, concentrated. The resulting solution was purified by silica gel column chromatography (EtOAc in hexanes) to afford desired product (1.6 g, 63%) as orange solid. ESI-MS m/z: 301.90 $[M+H]^+$.

Intermediate 3 Step b

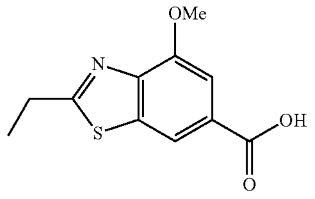 [SMILES: CCc1nc2c(OC)cc(C(=O)O)cc2s1]

The title compound was synthesized in a similar manner to Intermediate 1 using the compound from Intermediate 3 Step a. The ester hydrolysis was carried out in a similar manner to Example 2 Step d. The title compound was isolated by precipitation to afford the desired product (30 mg, 79%).

Intermediate 4

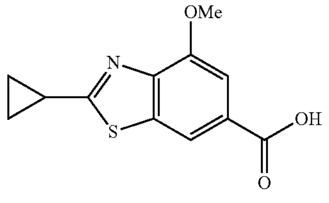 [SMILES: COc1cc(C(=O)O)cc2sc(C3CC3)nc12]

The title compound was synthesized in a similar manner to Intermediate 2 using the compound from Intermediate 3 Step a. The ester hydrolysis was carried out in a similar manner to Example 2 Step d. The title compound was isolated by precipitation to afford the desired product (57 mg, 75%).

Intermediate 5

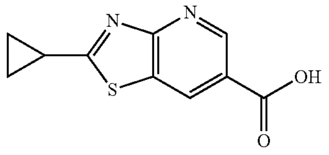 [SMILES: O=C(O)c1cnc2nc(C3CC3)sc2c1]

Intermediate 5 Step a

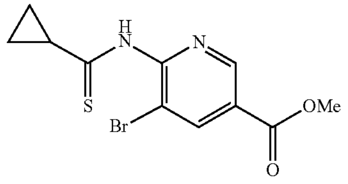 [SMILES: COC(=O)c1cnc(NC(=S)C2CC2)c(Br)c1]

In a vial, methyl 6-amino-5-bromonicotinate (500 mg, 2.164 mmol) was slurried in DCM (3.4 ml) and Pyridine (2.0 ml). The solution was cooled to 0° C. Cyclopropanecarbonyl chloride (590 μl, 6.49 mmol) was added dropwise and the solution became homogenous. Reaction allowed to stir for 2 hr. Reaction quenched upon addition of MeOH then concentrated. MeCN added and reaction evaporated to remove pyridine.

Dissolve in 1:1 THF/MeOH (5 mL) and cooled to 0° C. Added NaOMe in MeOH (620 μL, 2.7 mmol) slowly and allowed to stir 30 min. AcOH (250 uL) added which caused reaction to solidify. Solid broken up and water added. Solution allowed to stir a further 10 min before filtering and washing solid with water to obtain title compound (546 mg, 1.825 mmol, 84%).

Intermediate 5 Step b

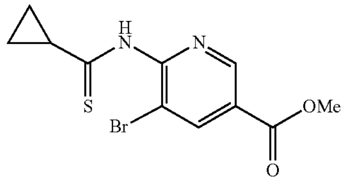 [SMILES: COC(=O)c1cnc(NC(=S)C2CC2)c(Br)c1]

In a vial, the compound from step a (400 mg, 1.337 mmol) was suspended in THE (5.35 ml) and Lawesson's reagent (595 mg, 1.471 mmol) was added. The reaction was heated to 65° C. overnight. The reaction was allowed to cool to room temperature and stand before concentrating. Crude reaction mixture purified by silica gel chromatography eluting with 0-50% EtOAc/Hexanes to give the title compound (400 mg, 1.27 mmol, 95%).

Intermediate 5 Steps c and d

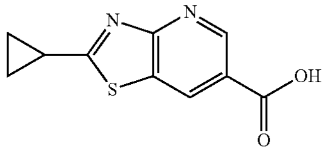 [SMILES: O=C(O)c1cnc2nc(C3CC3)sc2c1]

In a vial, the compound from step b (434 mg, 1.377 mmol) was dissolved in DMSO (3.44 ml). Sodium hydride (60.6 mg, 1.515 mmol) was added and the reaction was allowed to stir 5 min before sealing vial and heating to 70° C. for 5 h. Upon cooling, the reaction mixture was diluted with water and extracted with EtOAc. The aqueous phase was washed with EtOAc. The combined organic phase was washed with brine, dried over $MgSO_4$, filtered, and concentrated. Crude reaction mixture purified by silica gel chromatography eluting with 0-50% EtOAc/Hexanes to give the title compound (130 mg, 0.555 mmol, 40%).

The ester hydrolysis was carried out in a similar manner to Example 2 Step d. The title compound was isolated by precipitation to afford the desired product (50 mg, 0.232 mmol, 77%).

Intermediate 6

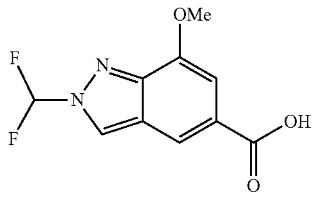 [SMILES: COc1cc(C(=O)O)cc2cn(C(F)F)nc12]

Intermediate 6 Step a

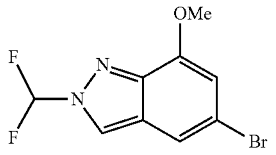 [SMILES: COc1cc(Br)cc2cn(C(F)F)nc12]

A solution of 5-bromo-1H-indazole (500 mg, 2.54 mmol) in EtOAc (5 mL) were added 2,2-difluoro-2-(fluorosulfonyl) acetic acid (542 mg, 3.05 mmol) and $K_2CO_3$ (701 mg, 5.08 mmol). The resulting mixture was stirred at rt for 2 hrs and then evaporated. The residue was purified by Combiflash eluting with 0-30% EtOAc/hexanes to obtain the desired product (380 mg, 60.6%) as a white foam. ESI-MS m/z: 248.9 $[M+H]^+$.

Intermediate 6 Steps b and c

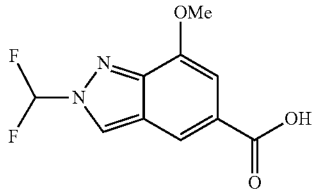 [SMILES: COc1cc(C(=O)O)cc2cn(C(F)F)nc12]

To a solution of DMF/EtOH (6 mL, 2:1) were added compound from step a (240 mg, 0.866 mmol), $Pd(OAc)_2$ (23.34 mg, 0.104 mmol), 1,3-Bis(diphenylphosphino)propane (86 mg, 0.208 mmol) and triethylamine (362 μl, 2.60 mmol). After degassed, CO balloon was subjected. The reaction mixture was heated at 80° C. for 12 hrs, cooled down to rt and diluted with EtOAc (150 mL). The solution was washed with brine, dried and purified by Combiflash eluting with 0-50% EtOAc/hexanes to obtain the desired product (130 mg, 55.5%) was a white solid. ESI-MS m/z: 271.2 $[M+H]^+$.

To a solution of compound from step b (120 mg, 0.468 mmol) in THF/water (5:1, 6 mL) was added LiOH (112 mg, 4.68 mmol). The resulting mixture was stirred at 45° C. for 20 hrs and then evaporated most of THF. The remaining mixture was neutralized to pH ~3 by adding aq. 1M HCl. The precipitated solid was filtered, washed with water, and dried to obtain the desired product (105 mg, 93.0%) as a white solid. ESI-MS m/z: 243.21 $[M+H]^+$.

Intermediate 7 Steps a and b

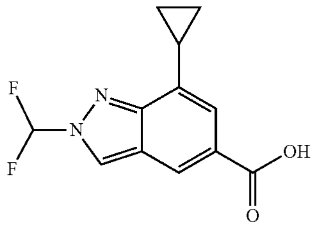 [SMILES: O=C(O)c1cc(C2CC2)c2nn(C(F)F)cc2c1]

To a solution of ethyl 7-chloro-2-(difluoromethyl)-2H-indazole-5-carboxylate (200 mg, 0.728 mmol) in 1,4-dioxane/water (2.1 mL, 20:1) were added cyclopropylboronic acid (125 mg, 1.456 mmol), XPhos Pd G2 (28.6 mg, 0.036 mmol) and $K_3PO_4$ (773 mg, 3.64 mmol). After degassed, the mixture was heated at 80° C. for 2 hrs and the reaction was completed. The reaction mixture was diluted with EtOAc (100 mL), washed with brine, dried and purified by combiflash eluting with 0-30% EtOAc/hexanes to obtain the desired product (93 mg, 45.6%) as a brown solid. ESI-MS m/z: 281.10 $[M+H]^+$.

To a solution of compound from step a (90 mg, 0.321 mmol) in THF/water (5:1, 6 mL) was added LiOH (77 mg, 3.21 mmol). The resulting mixture was stirred at 45° C. for 20 hrs and then evaporated most of THF. The remaining mixture was neutralized to pH ~3 by adding aq. 1M HCl. The precipitated solid was filtered, washed with water, and dried to obtain the desired product (60 mg, 74.1%) as a brown solid. ESI-MS m/z: 253.20 $[M+H]^+$.

Intermediate 8

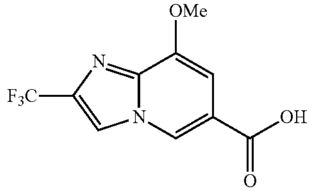 [SMILES: COc1cc(C(=O)O)cn2cc(C(F)(F)F)nc12]

Intermediate 8 Step a

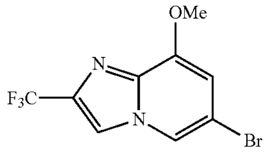 [SMILES: COc1cc(Br)cn2cc(C(F)(F)F)nc12]

To a solution of 5-bromo-3-methoxypyridin-2-amine (400 mg, 1.970 mmol) in EtOH (6 mL) was added 3-bromo-1,1,1-trifluoropropan-2-one (752 mg, 3.94 mmol). The resulting mixture was heated at 80° C. overnight. After evaporated the solvent, the residue was purified by Combiflash eluting with 0-40% EtOAc/hexanes to obtain the title compound (300 mg, 51.6%) as a colorless oil. ESI-MS m/z: 296.20 $[M+H]^+$.

Intermediate 8 Steps b and c

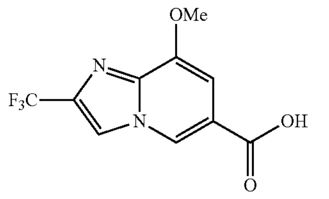

The title compound was made according to Intermediate 6 step. The crude material was purified by Combiflash eluting with 0-50% EtOAc/hexanes to obtain the desired product (200 mg, 68.2%) was a white solid. ESI-MS m/z: 289.17 $[M+H]^+$.

To a solution of compound from step b (200 mg, 0.694 mmol) in THF/water (5:1, 6 mL) was added LiOH (166 mg, 6.94 mmol). The resulting mixture was stirred at rt for 4 hrs and then evaporated most of THF. The remaining mixture was neutralized to pH ~3 by adding aq. 1M HCl. The precipitated solid was filtered, washed with water, and dried to obtain the desired product (120 mg, 66.5%) as a white solid. ESI-MS m/z: 261.20 $[M+H]^+$.

Intermediate 9

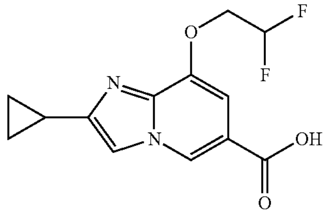 [SMILES: O=C(O)c1cc(OCC(F)F)c2nc(C3CC3)cn2c1]

Intermediate 9 Step a

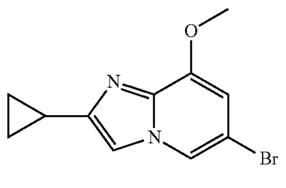

To a solution of 5-bromo-3-methoxypyridin-2-amine (2.0 g, 8.75 mmol) in EtOH (30 mL) was added 2-bromo-1-cyclopropylethan-1-one (1.99 g, 11.82 mmol). The resulting mixture was heated at 80° C. for 3 days. After evaporated the solvent, the residue was purified by Combiflash eluting with 0-100% EtOAc/hexanes and then 0-5% MeOH/DCM to obtain the title compound (1.88 g, 85%) as a brown foam. ESI-MS m/z: 268.20 $[M+H]^+$.

Example 671 Steps b and c

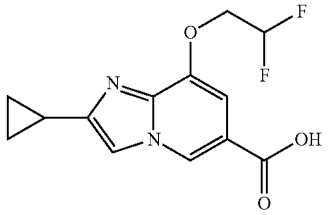 [SMILES: O=C(O)c1cc(OCC(F)F)c2nc(C3CC3)cn2c1]

To a solution of step a (500 mg, 1.872 mol) from step a in DCM (10 mL) was slowly added $BBr_3$ (3.74 mL, 3.74 mmol). The resulting mixture was stirred at rt for 20 hrs and then quenched with water (2 mL). After diluted with DCM (50 mL), the organic layer was separated, dried and evaporated. The residue was purified by Gilson prep-HPLC (20-90%, MeCN/Water, 25 min) to afford the desired product (40 mg, 8.44%) as a brown foam. ESI-MS m/z: 254.10 $[M+H]^+$.

To a solution of step b (40 mg, 0.158 mmol) from step b in DMF (2 mL) were added $K_2CO_3$ (43.7 mg, 0.316 mmol) and 2,2-difluoroethyl 4-methylbenzenesulfonate (187 mg, 0.79 mmol). The resulting mixture was heated at 60° C. in a sealed vessel for 20 hrs. After evaporated the solvent, the residue was purified by Combiflash eluting with 0-30% EtOAc/hexanes to obtain the desired product (35 mg, 85%) as a pale-yellow foam. ESI-MS m/z: 318.99 $[M+H]^+$.

Intermediate 9 steps d and e

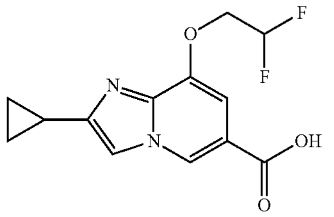 [SMILES: O=C(O)c1cc(OCC(F)F)c2nc(C3CC3)cn2c1]

To a solution of DMF/EtOH (6 mL, 2:1) were added compound from step c (35 mg, 0.11 mmol), $Pd(OAc)_2$ (2.97 mg, 0.013 mmol), 1,3-Bis(diphenylphosphino)propane (10.92 mg, 0.026 mmol) and triethylamine (46 μl, 0.33 mmol). After degassed, CO balloon was subjected. The reaction mixture was heated at 80° C. for 20 hrs, cooled down to rt and diluted with EtOAc (50 mL). The solution was washed with brine, dried and purified by Combiflash eluting with 0-50% EtOAc/hexanes to obtain the desired product (17 mg, 49.6%) was a white solid. ESI-MS m/z: 311.10 $[M+H]^+$.

To a solution of compound from step d (17 mg, 0.055 mmol) in THF/water (5:1, 1 mL) was added 2 N NaOH (0.2 mL). The resulting mixture was stirred at rt for 40 hrs and then evaporated most of THF. The remaining mixture was neutralized to pH ~3 by adding aq. 1M HCl. After extracted the mixture with 10% MeOH/DCM (50 mL×3), the combined organic layers were combined, dried and evaporated to obtain the desired product (7 mg, 45.3%) as a white solid. ESI-MS m/z: 283.07 $[M+H]^+$.

Intermediate 10

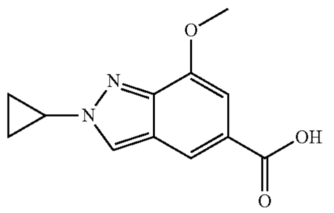 [SMILES: COc1cc(C(=O)O)cc2cn(C3CC3)nc12]

Intermediate 10 Step a

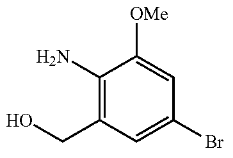

To a solution of 2-amino-5-bromo-3-methoxybenzoic acid (4.00 g, 16.25 mmol) in THE (60 mL) were added $BH_3$-THF (325 mL, 325.10 mmol) dropwise under ice/water bath and the reaction mixture was stirred at 50° C. overnight. The mixture was allowed to cool down to 0° C., quenched with MeOH and concentrated. The residue was diluted with aqueous $Na_2CO_3$ and extracted with EA. The combined organic layers were dried over anhydrous $Na_2SO_4$. After filtration, the filtrate was concentrated under reduced pressure to afford the crude product (4.4 g) as a yellow oil. ESI-MS m/z: 231.95 $[M+H]^+$.

Intermediate 10 Steps b and c

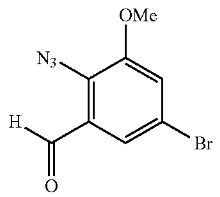 [SMILES: COc1cc(Br)cc(C=O)c1N=[N+]=[N-]]

A mixture of the compound from step a (4.40 g, 18.96 mmol) and $MnO_2$ (8.24 g, 94.80 mmol) in DCM (50 mL) was stirred for overnight at room temperature. The resulting mixture was filtered, the filter cake was washed with DCM. The filtrate was concentrated under reduced pressure. The residue was purified by silica gel column chromatography, eluted with PE/EA (10:1) to afford the desired product (2.9 g, 66%) as a red solid. ESI-MS m/z: 229.95 $[M+H]^+$.

To a solution of the compound from step b (2.90 g, 12.60 mmol) in HCl (6M) (30 mL) at 0° C. was added $NaNO_2$ (1.09 g, 15.80 mmol) in water (5 mL). After 30 min, the ice bath was removed and the reaction stirred at room temperature for 30 min. The solid was removed by filtration, the mother liquor was cooled to 0° C. and treated with $NaN_3$ (0.82 g, 12.60 mmol) in water (5 mL). The ice bath was removed and stirring was continued for 30 min. The resulting solid (3.8 g) was collected by filtration.

Intermediate 10 Step d

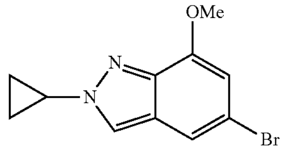 [SMILES: COc1cc(Br)cc2cn(C3CC3)nc12]

The compound from step c (3.80 g, 14.84 mmol) and aminocyclopropane (1.27 g, 22.26 mmol) in toluene (50 mL) were treated with molecular sieves. The reaction was stirred at room temperature for 2 hours, then heated at reflux for overnight. After cooling to room temperature, the mixture was filtered over celite and the solution was concentrated under reduced pressure. The residue was purified by silica gel column chromatography, eluted with PE/EA (1:1) to afford the desired product (2.4 g, 60%) as a brown oil. ESI-MS m/z: 267.05 $[M+H]^+$.

Intermediate 10 steps e and f

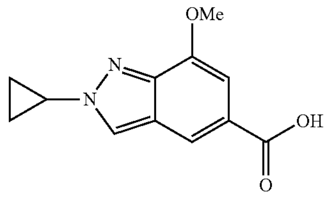 [SMILES: COc1cc(C(=O)O)cc2cn(C3CC3)nc12]

To a solution of the compound from step d (2.40 g, 8.98 mmol) in EtOH (10 mL) was added DMF (10 mL), TEA (2.5 mL), $Pd(OAc)_2$ (0.40 g, 1.78 mmol), dppp (1.48 g, 3.59 mmol) in a pressure tank. The mixture was pressurized to 15 atm with carbon monoxide at 100° C. for overnight. The reaction mixture was cooled to room temperature, concentrated under vacuum. The residue was purified by silica gel column chromatography, eluted with PE/EA (2:1) to afford the desired product (2.2 g, 94%) as a yellow oil. ESI-MS m/z: 261.10 $[M+H]^+$.

Into a 100 mL round-bottom flask were added the compound from step e (2.10 g, 8.07 mmol) and MeOH (30 mL) at room temperature. A solution of LiOH (1.93 g, 80.59 mmol) in $H_2O$ (10 mL) was added and stirred for 2 hours at room temperature. The resulting mixture was concentrated under reduced pressure. The mixture was acidified to pH 5 with HCl (2 M aq.). The product was collected by filtration and washed with water (1.28 g) ESI-MS m/z: 233.05 $[M+H]^+$.

Intermediate 11 Step a, b, and c

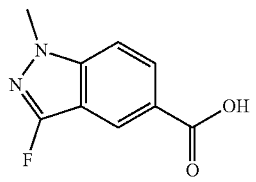

A solution of methyl 1H-indazole-5-carboxylate (3 g, 17.03 mmol) and F-TEDA-$BF_4$ (12 g, 34.06 mmol) in DMF was stirred for 16 hours at 80° C. under nitrogen atmosphere. The resulting solution was purified by reverse phase C18 column chromatography ($CH_3CN/H_2O$) to afford desired product (1.5 g, 45%) as a yellow solid. ESI-MS m/z: 194.95$[M+H]^+$.

A solution of the compound from step a (1.5 g, 7.72 mmol), $CH_3I$ (2.2 g, 15.45 mmol) and $Cs_2CO_3$ (7.6 g, 23.17 mmol) in DMF was stirred for 4 hours at room temperature. The resulting solution was diluted with water, extracted with EA, the organic layer was dried, concentrated. The resulting solution was purified by reverse phase C18 column chromatography ($CH_3CN/H_2O$) to afford desired product (600 mg, 37%) as a yellow solid. ESI-MS m/z: 209.00 $[M+H]^+$.

A solution of the compound from step b (600 mg, 2.88 mmol), LiOH (690 mg, 28.82 mmol) in THF/$H_2O$=10:1 (11 mL) was stirred for 16 hours at room temperature. The resulting mixture was concentrated under vacuum. The resulting solution was purified by reverse phase C18 column chromatography ($CH_3CN/H_2O$) to afford desired product (211.9 mg, 38%) as a light-yellow solid. ESI-MS m/z: 195.05 $[M+H]^+$.

Intermediate 12

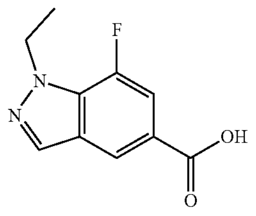

Intermediate 12 Step a

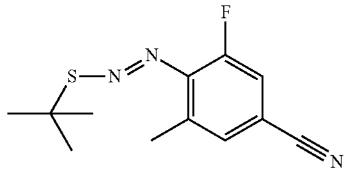 [SMILES: Cc1cc(C#N)cc(F)c1/N=N/SC(C)(C)C]

To a mixture of 4-amino-3-fluoro-5-methylbenzonitrile (1.60 g, 10.65 mmol) in HCl (8M) (15 mL) was added $NaNO_2$ (0.77 g, 11.19 mmol) in $H_2O$ (2 mL) dropwise at −5° C. The reaction was stirred for 30 min, 2-methyl-2-propanethiol (0.96 g, 10.64 mmol) in EtOH (5 mL) was added at 0° C. and stirred for 1 h. The reaction was quenched with Water/Ice, extracted with EA. The combined organic layers were concentrated under reduced pressure. The residue was purified by silica gel column chromatography, eluted with PE/EA (20:1) to afford the desired product (2.7 g, 99%) as an orange oil. ESI-MS m/z: 252.00 $[M+H]^+$.

Intermediate 12 Step b

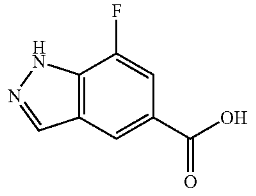 [SMILES: O=C(O)c1cc(F)c2[nH]ncc2c1]

A mixture of the compound from step a (2.70 g, 10.74 mmol) and t-BuOK (9.64 g, 85.91 mmol) in DMSO (25 mL) was stirred for 30 min at room temperature. The resulting mixture was diluted with water, extracted with EA. The combined organic layers were concentrated under reduced pressure. The residue was purified by reverse flash chromatography to afford the desired product (940 mg, 54%) as a yellow solid.

Intermediate 12 Steps c and d

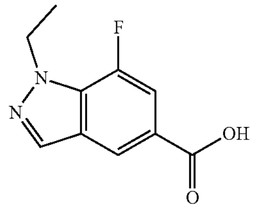

A mixture of the compound from step b (900 mg, 5.58 mmol), iodoethane (1.05 g, 6.7 mmol) and $K_2CO_3$ (1.54 g, 11.17 mmol) in DMF (8 mL) was stirred for overnight at room temperature. The resulting mixture was poured into water, extracted with EA. The combined organic layers were concentrated under reduced pressure. The residue was purified by reverse flash chromatography to afford the desired product (510 mg, 48%) as an off-white solid.

Into a 100 mL round-bottom flask were added the compound from step c (510 mg, 2.69 mmol), KOH (2.27 g, 40.46 mmol), EtOH (21 mL) and $H_2O$ (7 mL) at room temperature. The resulting mixture was stirred for overnight at 80° C. The resulting mixture was concentrated under reduced pressure. The residue was acidified to pH 5 with HCl (2 M aq.). The product was collected by filtration and washed with water to afford the title compound (545 mg). ESI-MS m/z: 209.15 $[M+H]^+$.

Intermediate 13 Steps a and b

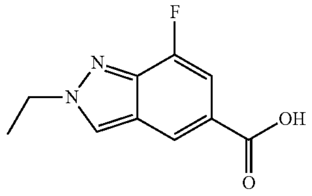

A mixture of the compound from Intermediate 12 step b (900 mg, 5.58 mmol), $K_2CO_3$ (1.54 g, 11.14 mmol) and iodoethane (1.05 g, 6.70 mmol,) in DMF (8 mL) was stirred for overnight at room temperature. The resulting mixture was poured into water, extracted with EA. The combined organic layers were concentrated under reduced pressure. The residue was purified by reverse flash chromatography to afford the desired product (280 mg, 26%) as an off-white solid.

Into a 100 mL round-bottom flask were added the compound from step a (280 mg, 1.48 mmol), KOH (1.25 g, 22.28 mmol), EtOH (21 mL) and $H_2O$ (7 mL) at room temperature. The resulting mixture was stirred for overnight at 80° C. The resulting mixture was concentrated under reduced pressure. The residue was acidified to pH 5 with HCl (2 M aq.). The product was collected by filtration and washed with water to afford the title compound (263 mg) ESI-MS m/z: 209.15 $[M+H]^+$.

Intermediate 14

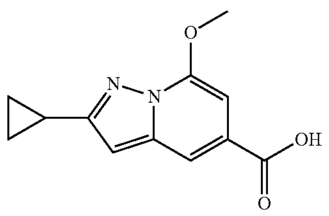 [SMILES: COc1cc(C(=O)O)cc2cc(C3CC3)nn12]

Intermediate 14 Step a

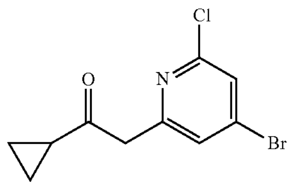 [SMILES: O=C(Cc1cc(Br)cc(Cl)n1)C1CC1]

Into a 250 mL 3-necked round-bottom flask were added 4-bromo-2-chloro-6-methylpyridine (4.5 g, 22 mmol) and THE (100 mL). The flask as cooled to −60° C. and LDA (4.43 mL, 33 mmol) was added dropwise and stirred for 30 minutes. N-methoxy-N-methylcyclopropanecarboxamide (4.2 g, 33 mmol) was then added. The resulting mixture was stirred for 1h at −60° C. under nitrogen atmosphere. The reaction was monitored by TLC. The reaction was quenched with sat. $NH_4Cl$ (aq.) and the aqueous layer was extracted with EtOAc. The resulting mixture was concentrated under reduced pressure. The residue was purified by reverse flash chromatography with the following conditions: column, C18 silica gel; mobile phase, MeCN in water, 10% to 50% gradient in 25 min; detector, UV 254 nm to afford the desired compound (2.8 g, 47%) as N off-white solid. ESI-MS m/z: 273.95 $[M+H]^+$.

Intermediate 14 Step b

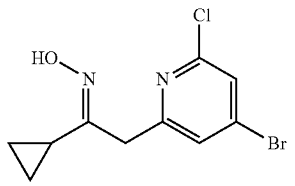 [SMILES: O/N=C(/Cc1cc(Br)cc(Cl)n1)C1CC1]

Into a 100 mL round-bottom flask were added the compound from step a (2.8 g, 10 mmol), $NH_2OH$ HCl (3.5 g, 51 mmol), NaOH (2 g, 51 mmol) and MeOH (30 mL) at room temperature. The resulting mixture was stirred for overnight at 60° C. under nitrogen atmosphere. The reaction was monitored by LCMS. The aqueous layer was extracted with EtOAc. The resulting mixture was concentrated under reduced pressure. The residue was purified by silica gel column chromatography, eluted with PE/EtOAc (1:1) to afford the desired compound (2.2 g, 75%) as an off-white solid. ESI-MS m/z: 288.95 $[M+H]^+$.

Intermediate 14 Steps c and d

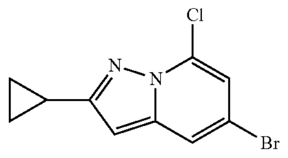 [SMILES: Clc1cc(Br)cc2cc(C3CC3)nn12]

Into a 100 mL round-bottom flask were added the compound from step b (2.2 g, 8 mmol), TFAA (1.8 g, 8 mmol), TEA (3.8 g, 38 mmol) and DME (15 mL) at room temperature. The resulting mixture was stirred for 2h at room temperature under nitrogen atmosphere. The reaction was monitored by LCMS. Desired product could be detected by LCMS. The resulting mixture was concentrated under reduced pressure. The residue was purified by reverse flash chromatography with the following conditions: column, C18 silica gel; mobile phase, MeCN in water, 10% to 50% gradient in 25 min; detector, UV 254 nm to afford the desired compound (1.8 g, 87%) as off-white solid. ESI-MS m/z: 270.95 $[M+H]^+$.

Into a 40 mL vial were added the compound from step c (1.8 g, 7 mmol), ferrous chloride (84 mg, 0.7 mmol) and DME (10 mL) at room temperature. The resulting mixture was stirred for 2h at 80° C. under nitrogen atmosphere. The reaction was monitored by TLC. The aqueous layer was extracted with EtOAc. The resulting mixture was concentrated under reduced pressure. The residue was purified by silica gel column chromatography, eluted with PE/EtOAc (1:1) to afford the desired compound (1.2 g, 67%) as an off-white solid. ESI-MS m/z: 270.95 $[M+H]^+$.

Intermediate 14 Step e

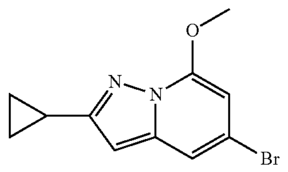

Into a 40 mL vial were added the compound form step d (1.2 g, 4.4 mmol), MeONa (716 mg, 13 mmol) and THE (10 mL) at room temperature. The resulting mixture was stirred for 2h at room temperature under nitrogen atmosphere. The reaction was monitored by LCMS. Desired product could be detected by LCMS. The resulting mixture was concentrated under reduced pressure. The residue was purified by reverse flash chromatography with the following conditions: column, C18 silica gel; mobile phase, MeCN in water, 10% to 50% gradient in 25 min; detector, UV 254 nm to afford the desired compound (800 mg, 68%) as off-white solid. ESI-MS m/z: 267.00 $[M+H]^+$.

Intermediate 14 Steps f and g

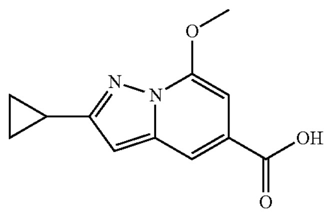 [SMILES: COc1cc(C(=O)O)cc2cc(C3CC3)nn12]

Into a 30 mL pressure tank reactor were added the compound form step e (400 mg, 1.5 mmol), $Pd(AcO)_2$ (101 mg, 0.45 mmol), DPPP (371 mg, 0.9 mmol), EtOH (4 mL), $Et_3N$ (1 mL) and DMF (4 mL) at room temperature. The resulting mixture was stirred for overnight at 100° C. under CO atmosphere at 10 atm. The reaction was monitored by TLC. The resulting mixture was filtered, the filter cake was washed with EtOH. The filtrate was concentrated under reduced pressure. The residue was purified by reverse flash chromatography with the following conditions: column, C18 silica gel; mobile phase, MeCN in water, 10% to 70% gradient in 25 min; detector, UV 254 nm to afford the desired compound (360 mg, 92%) as white solid. ESI-MS m/z: 261.10 $[M+H]^+$.

Into a 50 mL round-bottom flask were added the compound form step f (360 mg, 1.4 mmol), LiOH (166 mg, 7 mmol), MeOH (5 mL) and $H_2O$ (1 mL) at room temperature. The resulting mixture was stirred for 2h at room temperature under nitrogen atmosphere. The reaction was monitored by LCMS. The mixture was acidified to pH 6 with HCl (aq). The resulting mixture was concentrated under reduced pressure. The precipitated solids were collected by filtration and washed with water (3×3 mL) to afford the desired compound (280 mg, 87%) as off-white solid. ESI-MS m/z: 233.00 $[M+H]^+$.

Intermediate 15

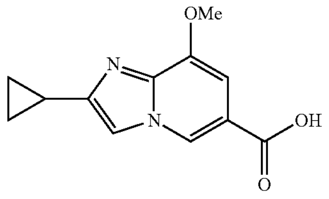 [SMILES: COc1cc(C(=O)O)cn2cc(C3CC3)nc12]

Intermediate 15 Step a

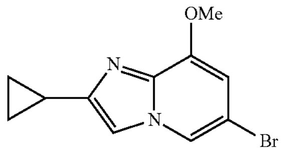 [SMILES: COc1cc(Br)cn2cc(C3CC3)nc12]

A solution of 5-bromo-3-methoxypyridin-2-amine (5 g, 24.63 mmol) and 2-bromo-1-cyclopropylethanone (8.03 g, 49.26 mmol) in EtOH (20 mL) was stirred for overnight at 80° C. The residue was purified by reverse phase flash to afford the desired product (4.4 g, 67%) as a yellow solid. ESI-MS m/z: 267.00 $[M+H]^+$.

Intermediate 15 steps b and c

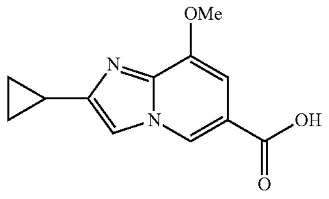 [SMILES: COc1cc(C(=O)O)cn2cc(C3CC3)nc12]

A solution of the compound from step a (4.4 g, 16.47 mmol), $Pd(OAc)_2$ (740 mg, 3.29 mmol) and dppp (2.7 g, 6.59 mmol) in DMF (12 mL), EtOH (12 mL) and TEA (3 mL) was stirred overnight at 100° C. under CO atmosphere. The residue was purified by silica gel column chromatography, eluted with PE/EA to afford the desired product (3 g, 70%) as a yellow solid. ESI-MS m/z: 261.00 $[M+H]^+$.

A solution of the compound from step b (3 g, 11.53 mmol) and LiOH (2.76 g, 115.25 mmol) in EtOH (10 mL) and $H_2O$ (10 mL) was stirred for 2 hrs at room temperature. The residue product was purified by reverse phase flash to afford the desired product 1.3 g as a yellow solid. ESI-MS m/z: 233.00 $[M+H]^+$.

Intermediate 16

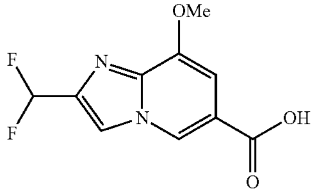 [SMILES: COc1cc(C(=O)O)cn2cc(C(F)F)nc12]

Intermediate 16 Step a

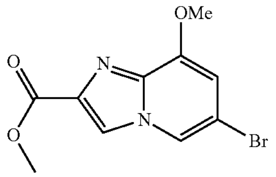 [SMILES: COC(=O)c1cn2cc(Br)cc(OC)c2n1]

A solution of 5-bromo-3-methoxypyridin-2-amine (4 g, 19.7 mmol) and methyl 3-bromo-2-oxopropanoate (7 g, 39.4 mmol) in EtOH (10 mL) was stirred for 16 hrs at 80° C. The residue product was purified by reverse phase flash to afford the desired product (4.6 g, 82%) as a yellow solid. ESI-MS m/z: 285.00 $[M+H]^+$.

Intermediate 16 steps b and c

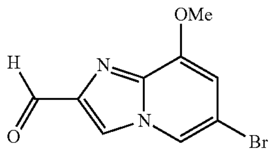 [SMILES: COc1cc(Br)cn2cc(C(F)F)nc12]

A solution of the compound from step a (3 g, 10.5 mmol) and DIBAL-H (30 mL) in THE (30 mL) was stirred for 1 hr at 0° C. The residue was purified by silica gel column chromatography, eluted with DCM/MeOH (10/1) to afford the desired product (1.6 g, 59%) as a yellow solid. ESI-MS m/z: 257.00 $[M+H]^+$.

A solution of the compound from step b (1 g, 3.9 mmol) and $MnO_2$ (3.4 g, 38.9 mmol) in DCM (20 mL) was stirred overnight at room temperature. The resulting mixture was filtered, and the filtrate was concentrated under reduced pressure. The crude 600 mg was used directly for next step. ESI-MS m/z: 255.00 $[M+H]^+$.

Intermediate 16 Step d

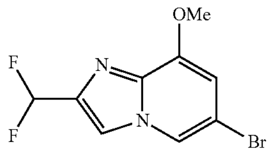

A solution of the compound from step c (600 mg, 2.4 mmol) and DAST (1 mL) in DCM (10 mL) was stirred for 2 hr at 0° C. The aqueous layer was extracted with EA. The residue was purified by silica gel column chromatography, eluted with PE/EA to afford the desired product (400 mg, 61%) as a yellow solid. ESI-MS m/z: 277.00 $[M+H]^+$.

Intermediate 16 Step e

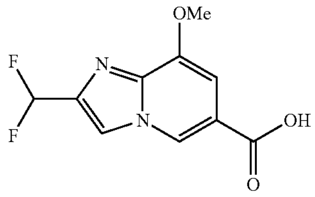 [SMILES: COc1cc(C(=O)O)cn2cc(C(F)F)nc12]

A solution of the compound from step d (400 mg, 1.4 mmol) and $Pd(dppf)Cl_2$ (211 mg, 0.29 mmol) in DMF (10 mL), $H_2O$ (10 mL) and TEA (2 mL) was stirred for 8 hrs at 100° C. under CO (15 atm). The residue product was purified by reverse phase flash to afford the desired product (188 mg, 54%) as a yellow solid. ESI-MS m/z: 243.00 $[M+H]^+$.

Intermediate 17

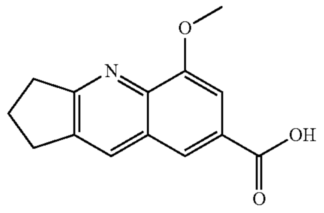 [SMILES: COc1cc(C(=O)O)cc2cc3c(nc12)CCC3]

Intermediate 17 Step a

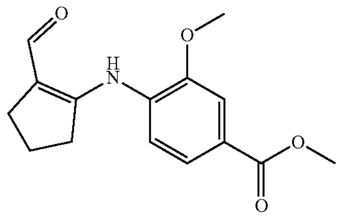 [SMILES: COC(=O)c1ccc(NC2=C(C=O)CCC2)c(OC)c1]

To a stirred solution of methyl 4-amino-3-methoxyphenyl carboxylate (500 mg, 2.76 mmol) and 2-bromocyclopent-1-ene-1-carbaldehyde (1.45 g) in toluene were added BINAP (687 mg, 1.10 mmol) and $Pd(OAc)_2$ (124 mg, 0.55 mmol). The reaction was heated to 90° C. under nitrogen atmosphere for 3 h. The resulting mixture was extracted with EtOAc (3×0 mL). The combined organic layers were washed with EtOAc (3×10 mL), dried over anhydrous $Na_2SO_4$. After filtration, the filtrate was concentrated under reduced pressure. The residue was purified by silica gel column chromatography, eluted with PE/EtOAc (1:1) to afford the desired product (600 mg, 79%) as a yellow oil. ESI-MS m/z: 276.00 $[M+H]^+$.

Intermediate 17 Steps b and c

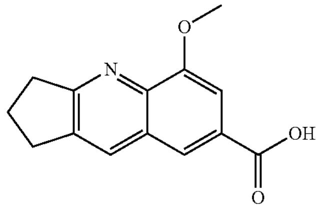 [SMILES: COc1cc(C(=O)O)cc2cc3c(nc12)CCC3]

A solution of the compound from step a (500 mg) and $In(TfO)_2$ (3 g) in xylene (5 mL) was stirred for 12 hr at 130° C. under $N_2$ atmosphere. The resulting mixture was concentrated under reduced pressure for next step directly. ESI-MS m/z: 258.00 $[M+H]^+$.

A solution of the compound from step c (1 g, 3.89 mmol) and LiOH (93 mg, 3.89 mmol) in $H_2O$ (10 mL) and MeOH (10 mL) was stirred for 12 hr at room temperature. The crude product was purified by reverse phase flash to afford the desired product (184.7 mg) as a white solid. ESI-MS m/z: 244.00 $[M+H]^+$.

Intermediate 18

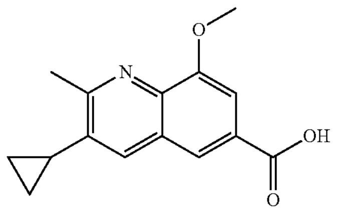 [SMILES: COc1cc(C(=O)O)cc2cc(C3CC3)c(C)nc12]

Intermediate 18 Steps a and b

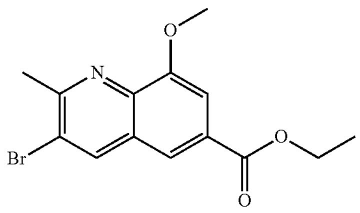 [SMILES: CCOC(=O)c1cc(OC)c2nc(C)c(Br)cc2c1]

A solution of (E)-2-bromocrotonaldehyde (10 g crude) and methyl 4-amino-3-methoxybenzoate (34 g, 134.24 mmol) in AcOH:HCl (2:3, 50 mL) was stirred for 1 h at 100° C. under nitrogen atmosphere. The resulting solution was concentrated to afford desired product (crude) as a yellow solid. ESI-MS m/z: 295.90 $[M+H]^+$.

A solution of the compound from step a, ethyl iodide (21 g, 135.08 mmol) and $Cs_2CO_3$ (66 g, 202.62 mmol) in DMF was stirred for overnight at room temperature. The resulting solution was diluted with water, extracted with EA(×3), the organic layer was dried, concentrated. The resulting solution was purified by silica gel column chromatography (PE:EA) to afford desired product (1 g) as a yellow solid. ESI-MS m/z: 323.90 $[M+H]^+$.

Intermediate 18 Steps c and d

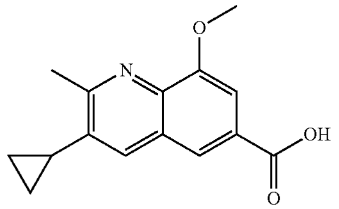 [SMILES: COc1cc(C(=O)O)cc2cc(C3CC3)c(C)nc12]

A solution of the compound from step b (1 g, 3.08 mmol), tricyclohexylphosphine (0.9 g, 3.08 mmol), cyclopropylboronic acid (0.8 g, 9.25 mmol), $Pd(OAc)_2$ (140 mg, 0.62 mmol) and $K_3PO_4$ (2 g, 9.25 mmol) in toluene and $H_2O$ was stirred for overnight at 110° C. under nitrogen atmosphere. The resulting mixture was concentrated under vacuum. The resulting solution was purified by silica gel column chromatography (PE:EA) to afford desired product as a yellow solid. ESI-MS m/z: 286.05 $[M+H]^+$.

A solution of the compound from step c and LiOH (441 mg, 18.43 mmol) in MeOH (10 mL) and $H_2O$ (10 mL) was stirred for 1 h at room temperature. The resulting mixture was concentrated under vacuum. The resulting solution was purified by reverse phase C18 column chromatography (CH3CN/H2O) to afford desired product (428 mg) as a yellow solid. ESI-MS m/z: 258.10 $[M+H]^+$.

Intermediate 19 Steps a and b

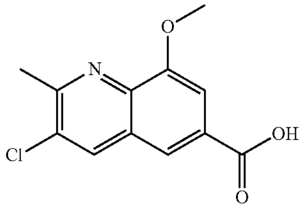 [SMILES: COc1cc(C(=O)O)cc2cc(Cl)c(C)nc12]

A solution of Intermediate 18 Step b (200 mg, 0.62 mmol), L-proline (142 mg, 1.23 mmol), chlorotrimethylaminyl (117 mg, 1.23 mmol) and $Cu_2O$ (176 mg, 1.23 mmol) in EtOH was stirred for 16 hours at 80° C. The resulting solution was diluted with water, extracted with EA (×3), the organic layer was dried, concentrated. The resulting solution was purified by silica gel column chromatography (PE:EA) to afford desired product (70 mg, 41%) as a yellow solid. ESI-MS m/z: 279.95 $[M+H]^+$.

A solution of the compound from step a (70 mg, 0.25 mmol) and LiOH (60 mg, 2.50 mmol) in THE (10 mL) and $H_2O$ (1 mL) was stirred for 1 h at room temperature. The resulting mixture was concentrated under vacuum. The resulting solution was purified by reverse phase C18 column chromatography ($MeCN/H_2O$) to afford desired product (50 mg, 79%) as a yellow solid. ESI-MS m/z: 251.95 $[M+H]^+$.

Intermediate 20 Steps a and b

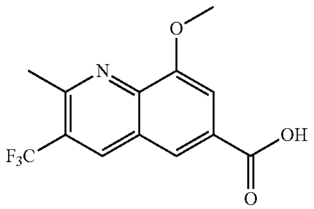 [SMILES: COc1cc(C(=O)O)cc2cc(C(F)(F)F)c(C)nc12]

A solution of Intermediate 18 Step b (200 mg, 0.62 mmol), methyl 2,2-difluoro-2-sulfoacetate (237 mg, 1.23 mmol), KF (72 mg, 1.23 mmol) and CuI (235 mg, 1.23 mmol) in NMP was stirred for 4 hours at 120° C. The resulting solution was diluted with water, extracted with EA (×3), the organic layer was dried, concentrated. The resulting solution was purified by silica gel column chromatography (PE:EA) to afford desired product (140 mg, 72%) as a yellow solid. ESI-MS m/z: 313.95 $[M+H]^+$.

A solution of the compound from step a (140 mg, 0.45 mmol) and LiOH (107 mg, 4.47 mmol) in MeOH (10 mL) and $H_2O$ (1 mL) was stirred for 1 h at room temperature. The resulting mixture was concentrated under vacuum. The resulting solution was purified by reverse phase C18 column chromatography ($CH_3CN/H_2O$) to afford desired product (70 mg, 55%) as a white solid. ESI-MS m/z: 285.90 $[M+H]^+$.

Intermediate 21

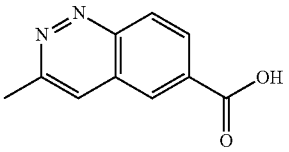

Intermediate 21 Step a

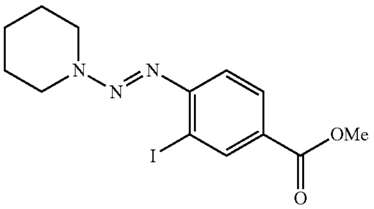 [SMILES: COC(=O)c1ccc(/N=N/N2CCCCC2)c(I)c1]

To a stirred solution of methyl 4-amino-3-iodobenzoate (2.7 g, 10 mmol) in HCl (6 mL) were added $NaNO_2$ (0.7 g in 5 mL water) dropwise at 5° C. for 1 hr. To the above mixture was added piperidine (1 mL) dropwise at 5° C. The resulting mixture was stirred for additional 1 hr at room temperature. The resulting mixture was extracted with EA and the combined organic layers were washed with water, dried over anhydrous $Na_2SO_4$. The residue purified by silica gel column chromatography (EtOAc in hexanes) to afford the desired product (2.7 g) as a yellow solid. ESI-MS m/z: 374.00 $[M+H]^+$.

Intermediate 21 Step b

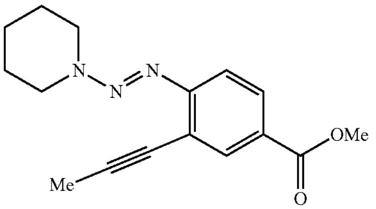 [SMILES: CC#Cc1cc(C(=O)OC)ccc1/N=N/N1CCCCC1]

To a dry and $N_2$-flushed 50 mL Schlenk tube, equipped with a magnetic stirrer and a septum, was added bromo (prop-1-yn-1-yl)magnesium (4.3 g, 29.94 mmol). The solution was cooled to −30° C. and $ZnBr_2$ (5.08 g, 22.56 mmol)

was added dropwise to the reaction mixture. The reaction mixture was warmed to room temperature for 30 minutes. The compound from step a (2 g, 5.36 mmol) was added followed by $(PPh_3)_4$ (309 mg, 0.27 mmol). The reaction mixture was stirred at room temperature for 2 hr and quenched by saturated aqueous $NH_4Cl$. The aqueous was extracted with EtOAc, dried, and concentrated under reduced pressure. The residue was purified by silica gel column chromatography (EtOAc in hexanes) to afford the desired product (2 g, 97%) as a yellow solid. ESI-MS m/z: 286.00 $[M+H]^+$.

Intermediate 21 Step c

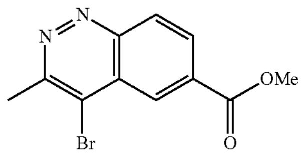 [SMILES: COC(=O)c1ccc2nnc(C)c(Br)c2c1]

A solution of the compound from step b (1.5 g, 5.26 mmol,) and HBr in water (850 mg, 10.51 mmol) in acetone (10 mL) was stirred for 2 hr at room temperature. The resulting mixture was extracted with EtOAc and the combined organic layers were washed with water and dried over anhydrous $Na_2SO_4$. The residue was purified by silica gel column chromatography (EtOAc in hexanes) to afford the desired product (900 mg, 61%) as a yellow solid. ESI-MS m/z: 281.00 $[M+H]^+$.

Intermediate 21 Step d

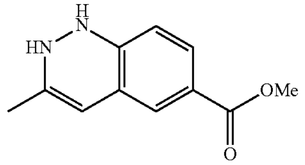

A solution of the compound from step c (900 mg, 3.2 mmol) and Pd/C (681 mg, 6.40 mmol) in MeOH (20 mL) was stirred for 2 hr at room temperature under $H_2$ atmosphere. The resulting mixture was filtered and the solution was concentrated to use directly for next step. ESI-MS m/z: 205.00 $[M+H]^+$.

Intermediate 21 Steps e and f

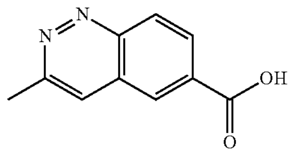

A solution of compound from step d and $MnO_2$ (1.5 g, 17.67 mmol) in THE (20 mL) was stirred for 2 hr at room temperature. The crude product was purified by reverse phase flash to afford the desired product (253 mg, 51%) as a yellow solid. ESI-MS m/z: 203.00 $[M+H]^+$. In a vial, compound from step e (100 mg, 0.495 mmol) and lithium hydroxide (118 mg, 4.95 mmol) were dissolved in THF (2.2 ml), MeOH (2.2 ml), and Water (0.55 ml). The reaction was allowed to stir at room temperature for 4 hours. Reaction diluted with water and the pH adjusted to 3-4 with 1M aq. HCl. Aqueous layer washed with DCM and 9:1 DCM/MeOH. Combined organic layer dried over $MgSO_4$ and concentrated under reduced pressure to furnish the title compound (45 mg, 48%). ESI-MS m/z: 188.68 $[M+H]^+$.

Intermediate 21a

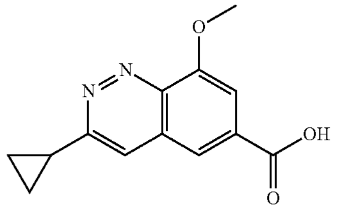 [SMILES: COc1cc(C(=O)O)cc2cc(C3CC3)nnc12]

Intermediate 21a Step a

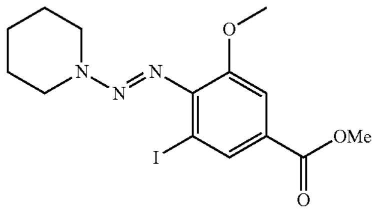 [SMILES: COC(=O)c1cc(I)c(/N=N/N2CCCCC2)c(OC)c1]

The following example was prepared in an analogous procedure to Intermediate 21 Step a with methyl 4-amino-3-iodo-5-methoxybenzoate (4 g, 13.03) to afford the title compound. (3.5 g) ESI-MS m/z: 404.00 $[M+H]^+$.

Intermediate 21a Step b

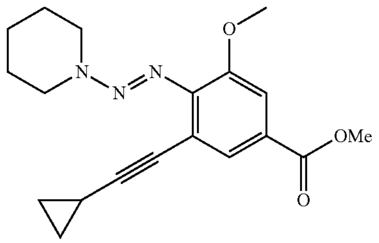 [SMILES: COC(=O)c1cc(C#CC2CC2)c(/N=N/N2CCCCC2)c(OC)c1]

The following example was prepared in an analogous procedure to Intermediate 21 Step b using cyclopropyl acetylene. The title compound was purified by silica gel chromatography to afford the title compound as a brown oil (3.6 g). ESI-MS m/z: 342.00 $[M+H]^+$.

Intermediate 21a Step c

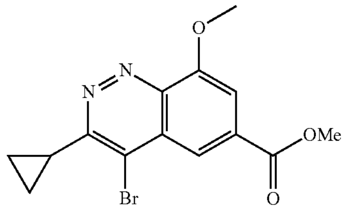 [SMILES: COC(=O)c1cc(OC)c2nnc(C3CC3)c(Br)c2c1]

The following example was prepared in an analogous procedure to Intermediate 21 Step c to afford the title compound (600 mg). ESI-MS m/z: 336.00 $[M+H]^+$.

Intermediate 21a Step d

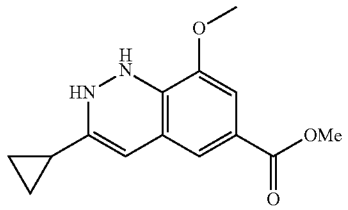 [SMILES: COC(=O)c1cc2c(c(OC)c1)NNC(C1CC1)=C2]

The following example was prepared in an analogous procedure to Intermediate 21 Step d to afford the title compound (500 mg). ESI-MS m/z: 261.00 $[M+H]^+$.

Intermediate 21a Steps e and f

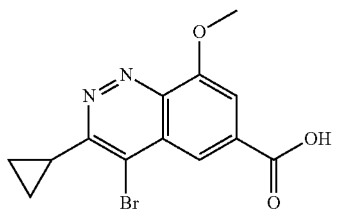 [SMILES: COc1cc(C(=O)O)cc2c(Br)c(C3CC3)nnc12]

The following example was prepared in an analogous procedure to Intermediate 21 steps e and f to afford the title compound (200 mg, 60%). ESI-MS m/z: 245.00 $[M+H]^+$.

Intermediate 22

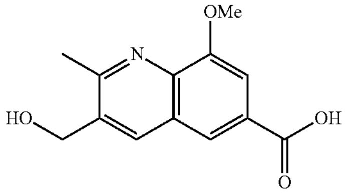 [SMILES: COc1cc(C(=O)O)cc2cc(CO)c(C)nc12]

Intermediate 22 Step a

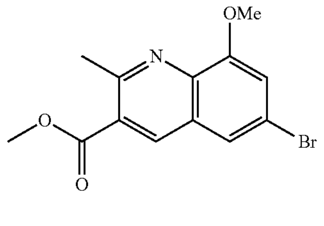 [SMILES: COC(=O)c1cc2cc(Br)cc(OC)c2nc1C]

To a stirred solution of 2-amino-5-bromo-3-methoxybenzaldehyde (2.2 g, 9.56 mmol), piperazine (2.5 g, 28.69 mmol) and methyl acetoacetate (2.2 g, 19.13 mmol) in MeOH was stirred for 1 h at room temperature. The resulting solution was diluted with water, extracted with EA(×3), the organic layer was dried and concentrated. The resulting solution was purified by silica gel column chromatography (PE:EA) to afford desired product (2.5 g, 84%) as a yellow solid. ESI-MS m/z: 309.85 $[M+H]^+$.

Intermediate 22 Steps b, c and d

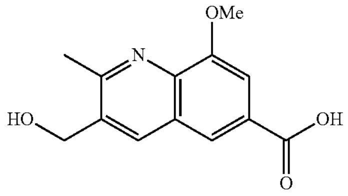 [SMILES: COc1cc(C(=O)O)cc2cc(CO)c(C)nc12]

A solution of the compound from step a (1 g, 28.69 mmol) in THE was treated with DIBAL-H (20 mL) for 1 h at room temperature under nitrogen atmosphere. The resulting solution was diluted with water, extracted with EA (×3), the organic layer was dried, concentrated. The resulting solution was purified by silica gel column chromatography (PE:EA) to afford desired product (1 g crude) as a yellow solid. ESI-MS m/z: 281.90 $[M+H]^+$.

A solution of the compound from step b (1 g crude), $Pd(OAc)_2$ (159 mg, 0.71 mmol), DPPP (585 mg, 1.42 mmol) and TEA (2.00 mL) in EtOH and DMF was stirred for 16 hours at 100° C. under CO atmosphere (15 atm). The resulting mixture was concentrated under vacuum. The resulting solution was purified by silica gel column chromatography (PE:EA) to afford desired product (600 mg crude) as a yellow solid. ESI-MS m/z: 276.10 $[M+H]^+$.

A solution of the compound from step c (600 mg crude) and LiOH (522 mg, 21.79 mmol) in $MeOH/H_2O$=10:1 (11 mL) was stirred for 1 hour at room temperature. The resulting mixture was concentrated under vacuum. The resulting solution was purified by reverse phase C18 column chromatography ($MeCN/H_2O$) to afford desired product (504.7 mg) as a light-yellow solid. ESI-MS m/z: 247.95 $[M+H]^+$.

Intermediate 23

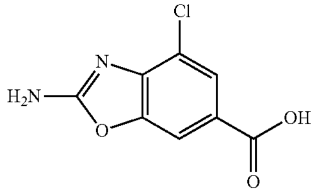 [SMILES: Nc1nc2c(Cl)cc(C(=O)O)cc2o1]

Intermediate 23 Step a

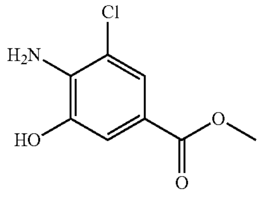

A solution of methyl 4-amino-3-hydroxybenzoate (5 g, 29.91 mmol) and NCS (4.8 g, 35.89 mmol) in CAN (20 mL) was stirred for 5 hr at 80° C. The residue was purified by silica gel column chromatography, eluted with PE/EA (10%) to afford the desired product (1.2 g) as a yellow solid. ESI-MS m/z: 202.00 $[M+H]^+$.

Intermediate 23 Step b and c

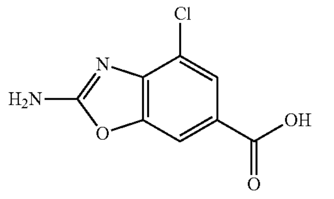 [SMILES: Nc1nc2c(Cl)cc(C(=O)O)cc2o1]

A solution of the compound from step a (1.2 g, 5.95 mmol) and BrCN (3.2 g, 29.74 mmol) in MeOH (42 mL) and $H_2O$ (18 mL) was stirred for 48 hr at 50° C. The resulting mixture was filtered, the filter cake was washed with EA and water to get the desired product (700 mg, 52%). ESI-MS m/z: 227.00 $[M+H]^+$.

A solution of the compound from step b (500 mg, 2.21 mmol) and LiOH (264 mg, 11.03 mmol) in THE (10 mL) and $H_2O$ (10 mL) was stirred for 1 hr at room temperature. The mixture was acidified to pH 7 with HCl (1M). The crude product was re-crystallized from the solution to afford the desired product (231 mg, 49%) as a brown solid. ESI-MS m/z: 213.00 $[M+H]^+$.

Intermediate 24

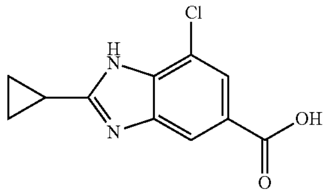 [SMILES: O=C(O)c1cc(Cl)c2[nH]c(C3CC3)nc2c1]

Intermediate 24 Step a

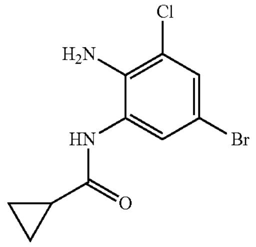 [SMILES: Nc1c(Cl)cc(Br)cc1NC(=O)C1CC1]

A mixture of 5-bromo-3-chlorobenzene-1,2-diamine (2.5 g, 11.29 mmol), cyclopropanecarboxylic acid (1.26 g, 14.64 mmol), HATU (4.29 g, 11.29 mmol), DIEA (2.9 g, 22.58 mmol) and DMF (50 mL) was stirred for overnight at room temperature. The reaction was monitored by LCMS. The resulting mixture was poured into water, extracted with EtOAc. The combined organic layers were washed with brine, dried over anhydrous $Na_2SO_4$. After filtration, the filtrate was concentrated under reduced pressure to afford the desired product (6.7 g, crude) as a brown oil. ESI-MS m/z: 289.00 $[M+H]^+$.

Intermediate 24 Steps b and c

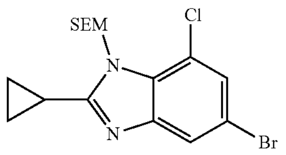 [SMILES: C[Si](C)(C)CCOCn1c(C2CC2)nc2cc(Br)cc(Cl)c21]

A solution of the compound from step a (6.7 g, 23.14 mmol) and acetic acid (60 mL) was stirred overnight at 100° C. The resulting mixture was concentrated under vacuum. The residue was purified by reverse flash chromatography with the following conditions: column, C18 silica gel; mobile phase, MeCN in water, 0% to 100% gradient in 30 min; detector, UV 254 nm. to afford the desired product (2 g, 32%) as a yellow solid. ESI-MS m/z: 271.00 $[M+H]^+$.

To a stirred solution of the compound from step b (2 g, 7.37 mmol) in DMF (20 mL) was added NaH (0.35 g, 14.73 mmol) in portions at 0° C. under nitrogen atmosphere. The resulting mixture was stirred for 30 min at the same temperature under nitrogen atmosphere. SEM-Cl (2.46 g, 14.76 mmol) was added dropwise and stirred for 2 hr at room temperature. The reaction was quenched with Water/Ice at room temperature. The resulting mixture was extracted with EtOAc. The combined organic layers were washed with brine, dried over anhydrous $Na_2SO_4$. After filtration, the filtrate was concentrated under reduced pressure to afford the desired product (2.6 g, 88%) as a yellow oil. ESI-MS m/z: 401.00 $[M+H]^+$.

Intermediate 24 Steps d and e

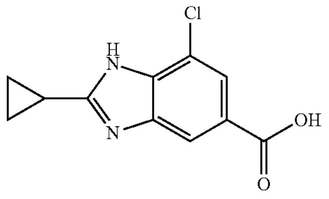 [SMILES: O=C(O)c1cc(Cl)c2[nH]c(C3CC3)nc2c1]

To a solution of the compound from step c (2.6 g, 6.47 mmol) in DMF (10 mL), $H_2O$ (10 mL) and TEA (2.5 mL) was added DPPP (1 g, 2.59 mmol) and $Pd(OAc)_2$ (0.29 g, 1.29 mmol) in a pressure tank. The mixture was pressurized to 15 atm with carbon monoxide and stirred at 100° C. for 2 days. The reaction mixture was cooled to room temperature and filtered to remove insoluble solids. The resulting mixture was concentrated under reduced pressure. The residue was purified by reverse flash chromatography with the following conditions: column, C18 silica gel; mobile phase, MeCN in water (0.05% FA), 10% to 80% gradient in 25 min; detector, UV 254 nm. to afford crude desired product (1.6 g, 67%) as a yellow solid. ESI-MS m/z: 367.10 $[M+H]^+$.

A solution of the compound from step d (1.6 g, 4.4 mmol) and HCl (6M, 5 mL) in EtOH (6 mL) and $H_2O$ (6 mL) was stirred for 16 hr at 80° C. The crude product was purified by reverse phase flash to afford the desired product (300 mg, 29%) as a white solid. ESI-MS m/z: 237.00 $[M+H]^+$.

Intermediate 25 Steps a and b

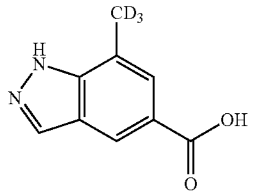 [SMILES: [2H]C([2H])([2H])c1cc(C(=O)O)cc2cn[nH]c12]

A solution of lithium chloride (0.5 M solution in THF) (10.00 ml, 5.00 mmol) and methyl-d3-magnesium iodide (1.0 M in diethyl ether) (5.00 ml, 5.00 mmol) was treated with zinc chloride (1.9 M in 2-MeTHF) (1.316 ml, 2.500 mmol) at room temperature. A solution of IPr PEPPSI (0.017 g, 0.025 mmol) and methyl 7-bromo-1H-indazole-5-carboxylate (0.128 g, 0.500 mmol) dissolved in 1.5 mL NMP was added dropwise and the resulting reaction mixture was stirred at room temperature overnight. Upon completion, the reaction was poured into 5% aq. citric acid and extracted with EtOAc. The organic extract was washed with brine, dried over anhydrous sodium sulfate, filtered, and concentrated. Purification by flash column chromatography on silica gel afforded the title compound (84 mg, 0.435 mmol, 87% yield) as an off-white solid. ESI-MS m/z: 193.7 $[M+H]^+$.

A solution of step a (0.083 g, 0.430 mmol) in THF (5 ml) was treated with potassium trimethylsilanolate (0.276 g, 2.148 mmol) and stirred at room temperature. Upon completion, the reaction was quenched with MeOH and silica gel, concentrated, and the resulting free-flowing admixture was directly purified by flash column chromatography on silica gel to afford the title compound as a white solid (0.075 g, 97% yield). ESI-MS m/z: 179.6 $[M+H]^+$.

Intermediate 26

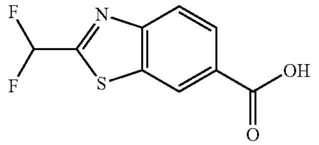 [SMILES: O=C(O)c1ccc2nc(C(F)F)sc2c1]

Intermediate 26 Step a

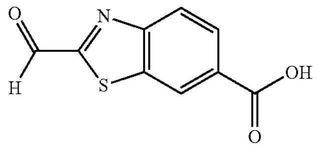 [SMILES: O=Cc1nc2ccc(C(=O)O)cc2s1]

Selenium dioxide (183 mg, 1.654 mmol) and 2-methylbenzo[d]thiazole-6-carboxylic acid (213 mg, 1.102 mmol) were dissolved in 1,4-Dioxane (2.205 ml) at rt. The reaction mixture was heated at 90° C. for 16h. The mixture was diluted with ethyl acetate and passed through a short silica gel plug. The plug was washed with ethyl acetate and the resulting solution was concentrated and used as crude. ESI-MS m/z: 207.61 $[M+H]^+$.

Intermediate 26 Step b

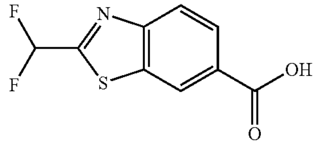 [SMILES: O=C(O)c1ccc2nc(C(F)F)sc2c1]

Step a (37 mg, 0.179 mmol) was dissolved in DCM (1 ml) and DAST (83 μl, 0.625 mmol) was added at 0° C. The reaction mixture was allowed to stir at 0° C. for 2 h. The reaction mixture was diluted with ethyl acetate and poured into 1N HCl solution. The aqueous layer was extracted with ethyl acetate for 3 times. The combined organic layers were dried and purified by flash chromatography to give the title compound. (15 mg, 36.6% yield). ESI-MS m/z: 230.00 $[M+H]^+$.

Intermediate 27 Steps a and b

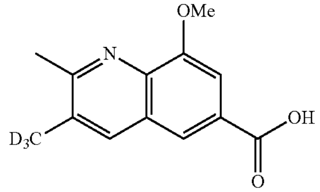 [SMILES: [2H]C([2H])([2H])c1cc2cc(C(=O)O)cc(OC)c2nc1C]

A solution of lithium chloride (0.5 M solution in THF) (6.17 ml, 3.08 mmol) and methyl-d3-magnesium iodide (1.0 M in diethyl ether) (3.08 ml, 3.08 mmol) was treated with zinc chloride (1.9 M in 2-MeTHF) (0.812 ml, 1.542 mmol) at room temperature. A solution of IPr PEPPSI (10.51 mg, 0.015 mmol) and ethyl 3-bromo-8-methoxy-2-methylquinoline-6-carboxylate (0.1 g, 0.308 mmol) dissolved in 1.5 mL NMP was added dropwise and the resulting reaction mixture was stirred at room temperature overnight. Upon completion, the reaction was poured into 5% aq. citric acid and extracted with EtOAc. The organic extract was washed with brine, dried over anhydrous sodium sulfate, filtered, and concentrated. Purification by flash chromatography afforded the desired product (50 mg, 61.8% yield) as a yellow solid. ESI-MS m/z: 263.02 $[M+H]^+$.

The ester hydrolysis was carried out according to Example 2 Step d to afford the desired compound.

Example 3

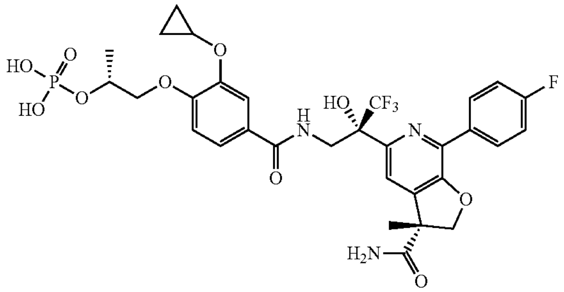 [SMILES: C[C@H](COc1ccc(C(=O)NC[C@](O)(c2cc3c(c(-c4ccc(F)cc4)n2)OC[C@]3(C)C(N)=O)C(F)(F)F)cc1OC1CC1)OP(=O)(O)O]

Example 3 Step a

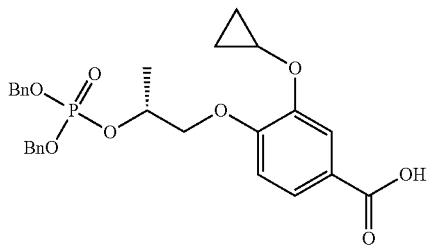 [SMILES: C[C@H](COc1ccc(C(=O)O)cc1OC1CC1)OP(=O)(OCc1ccccc1)OCc1ccccc1]

To a solution of (R)-3-cyclopropoxy-4-(2-hydroxypropoxy)benzoic acid (100 mg, 0.396 mmol) in THE (1.982 ml) was added 4-methylmorpholine (47.9 μl, 0.436 mmol) and tert-butylchlorodimethylsilane (65.7 mg, 0.436 mmol). After stirring the reaction mixture for 30 min, 1H-tetrazole (4405 μl, 1.982 mmol) and dibenzyl diisopropylphosphoramidite (400 μl, 1.189 mmol) were added. The reaction mixture was allowed to stir at room temperature for 5 h. The reaction mixture was cooled to 0° C., and then hydrogen peroxide (121 μl, 1.189 mmol) was added. The reaction mixture was slowly warmed to room temperature over 30 min. Saturated sodium sulfite was then added. After stirring vigorously for 30 min, the mixture was partitioned between ethyl acetate and saturated sodium sulfite. The pH value of the combined aqueous layers was adjusted to 3 with 1N HCl, and the resulting suspension was extracted with ethyl acetate. The combined organic layers were dried over $MgSO_4$. The solvent was removed, and the residue was purified by flash chromatography to yield the title compound (183 mg, 90% yield).

Example 3 Steps b and c

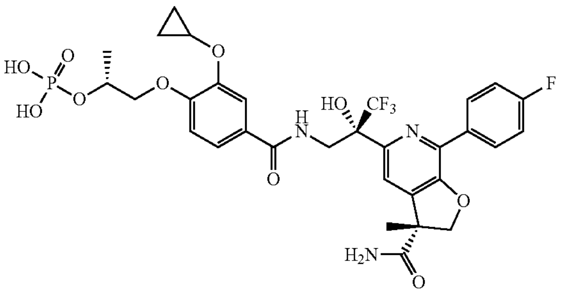 [SMILES: C[C@H](COc1ccc(C(=O)NC[C@](O)(c2cc3c(c(-c4ccc(F)cc4)n2)OC[C@]3(C)C(N)=O)C(F)(F)F)cc1OC1CC1)OP(=O)(O)O]

The amide coupling was carried out according to Example 1 Step c to afford the desired compound.

Step b (193 mg, 0.216 mmol) was dissolved in Ethyl acetate (2.159 ml) in a 40 mL vial. The vial was flushed with nitrogen gas three times. palladium on carbon (22.98 mg, 0.022 mmol) was added in one portion. The vial was flushed with hydrogen balloon and the reaction mixture was allowed to stir at 25° C. for 2h. The hydrogen gas was removed and flushed with nitrogen. The solution was filtered through celite and the residue was concentrated and purified by HPLC. ESI-MS m/z: 714.13 $[M+H]^+$.

Example 4

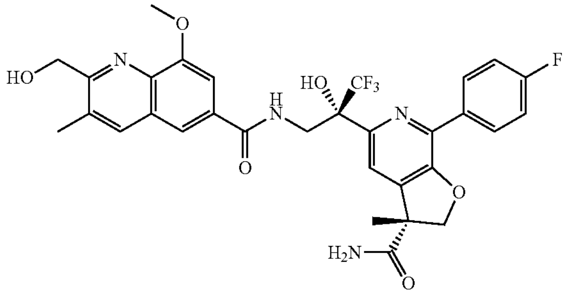 [SMILES: COc1cc(C(=O)NC[C@](O)(c2cc3c(c(-c4ccc(F)cc4)n2)OC[C@]3(C)C(N)=O)C(F)(F)F)cc2cc(C)c(CO)nc12]

Example 4 Step a

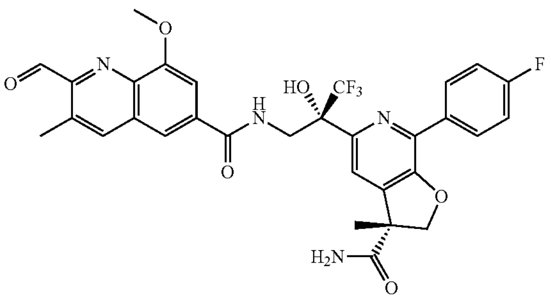 [SMILES: COc1cc(C(=O)NC[C@](O)(c2cc3c(c(-c4ccc(F)cc4)n2)OC[C@]3(C)C(N)=O)C(F)(F)F)cc2cc(C)c(C=O)nc12]

The following example was prepared according to Example 1 Step c with acid coupling partner 2-formyl-8-methoxy-3-methylquinoline-6-carboxylic acid (55 mg).

Example 4 Step b

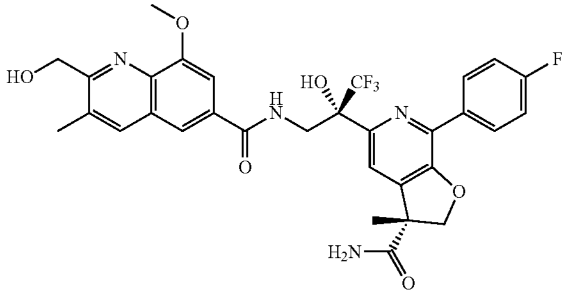 [SMILES: COc1cc(C(=O)NC[C@](O)(c2cc3c(c(-c4ccc(F)cc4)n2)OC[C@]3(C)C(N)=O)C(F)(F)F)cc2cc(C)c(CO)nc12]

The product from Step a (36 mg, 0.057 mmol) was dissolved in EtOH and sodium borohydride (4.35 mg, 0.115 mmol) was added at 0° C. The reaction mixture was allowed to stir at rt for 30 min. The reaction mixture was quenched by adding saturated $NH_4Cl$ carefully. The aqueous layer was extracted with ethyl acetate and the combined organic layers were dried and purified by HPLC to afford the title compound (14.5 mg, 40.1% yield). ESI-MS m/z: 629.27 $[M+H]^+$.

Example 5

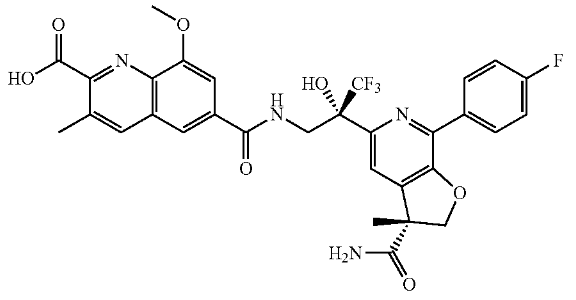 [SMILES: COc1cc(C(=O)NC[C@](O)(c2cc3c(c(-c4ccc(F)cc4)n2)OC[C@]3(C)C(N)=O)C(F)(F)F)cc2cc(C)c(C(=O)O)nc12]

Then Example 4 Step a (38 mg, 0.061 mmol) was dissolved in tBuOH and water. 2-methyl-2-butene (129 μl, 1.213 mmol) and sodium dihydrogen phosphate (72.8 mg, 0.606 mmol) were added at rt. Then sodium chlorite (68.6 mg, 0.606 mmol) was added. The reaction mixture was allowed to stir at rt for 30 min. The reaction was quenched by adding 15% $Na_2S_2O_3$ solution and the aqueous layer was extracted with ethyl acetate. The combined organic layers were dried and purified by HPLC to give the title compound (14 mg, 0.022 mmol, 35.9% yield). ESI-MS m/z: 643.15 $[M+H]^+$.

Intermediate 28 Steps a and b

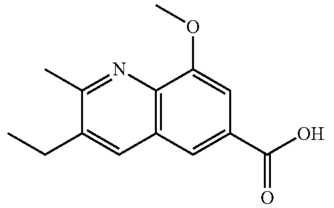 [SMILES: CCc1cc2cc(C(=O)O)cc(OC)c2nc1C]

A 100 mL rbf with stirbar was charged with methyl 4-amino-3-methoxybenzoate (2.86 g, 15.79 mmol) and (E)-2-ethylbut-2-enal (5.468 g, 18.94 mmol) then AcOH (23.68 ml) and HCl (15.79 ml). The mixture was then heated to 100° C. for 2 h. The mixture was then cooled to room temperature and partially concentrated at 60° C. under vacuum to afford a thick black oil. This oil was treated with 40 mL of EtOH and 250 μL of sulfuric acid then heated to 80° C. for 2 h. The mixture was cooled to room temperature then neutralized by the addition of 2 mL $NEt_3$, and concentrated. The resulting residue was purified by purified by automated silica gel column chromatography (0 to 45% ethyl acetate in hexanes) and dried under high vacuum to give the title compound as a colorless oil (49.8 mg, 1%). ESI-MS m/z: 274.2 $[M+H]^+$.

The ester hydrolysis was carried out in a similar manner to Example 2 Step d. The crude product was carried forward without further purification as a white solid. ESI-MS m/z: 246.0 $[M+H]^+$.

Intermediate 29

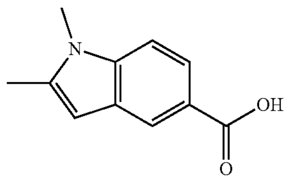

A 4 mL vial was charged with 2-methyl-1H-indole-5-carboxylic acid (125 mg, 0.714 mmol) then DMF (1.427 ml), the mixture was cooled to 0° C. then NaH (86 mg, 2.141 mmol) was added slowly. The mixture was stirred for 15 min then methyiodide (134 μL, 2.141 mmol) was added. After 2 h, the mixture was neutralized by addition of 1 M HCl (aq) then diluted with 2 mL dichloromethane. The layers were separated and the aqueous layer was washed with dichloromethane 5×1 mL. The combined organics were washed with water, then dried over $Na_2SO_4$ filtered and concentrated then purified by automated silica gel column chromatography and dried under high vacuum to give the title compound as a white solid (65 mg, 38%). ESI-MS m/z: 189.7 $[M+H]^+$.

Intermediate 30

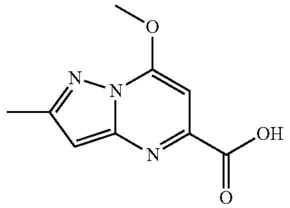

Intermediate 30 Step a

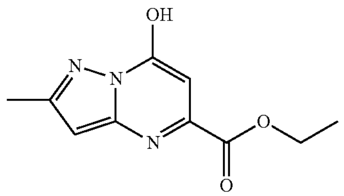 [SMILES: CCOC(=O)c1cc(O)n2nc(C)cc2n1]

A 20 mL vial was charged with 3-methyl-1H-pyrazol-5-amine (1.00 g, 10.3 mmol) AcOH (20.6 ml) and diethyl but-2-ynedioate (1.65 ml, 10.3 mmol). The mixture was stirred at 23° C. for 48 h, then poured into hexanes:EtOAc (1:1, 100 mL) and stirred for 1 h. The solids were collected by filtration to afford the title compound as a yellow solid (1.78 g, 78%) ESI-MS m/z: 221.9 $[M+H]^+$.

Intermediate 30 Steps b and c

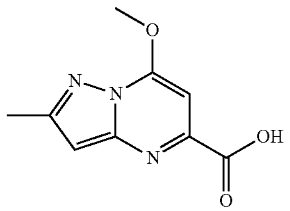

A 20 mL vial was charged with a 20 mL vial was charged with step a (250 mg, 1.13 mmol) cesium carbonate (736 mg, 2.26 mmol) DMF (2.3 ml) then MeI (212 μl, 3.39 mmol) was added. The mixture was stirred for 16 h. The mixture was then diluted with 5 mL water, and 5 mL dichloromethane. The layers were separated, and the aqueous layer was washed 5×5 mL with dichloromethane. The combined organics were washed with water 2×1 mL, then brine 1 mL, dried over $Na_2SO_4$, concentrated and purified by automated silica gel chromatography to afford the title compound as a yellow oil (205 mg, 77%) ESI-MS m/z: 235.9 $[M+H]^+$. The ester hydrolysis was carried out in a similar manner to Example 2 Step d. After acidification the product was collected by filtration and carried forward without further purification as a yellow solid. ESI-MS m/z: 207.7 $[M+H]^+$.

Intermediate 31

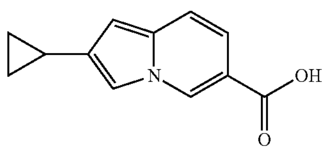 [SMILES: O=C(O)c1ccc2cc(C3CC3)cn2c1]

A 20 mL vial was charged with 6-methylnicotinic acid (333 mg, 2.43 mmol) and 2-bromo-1-cyclopropylethan-1-one (396 mg, 2.43 mmol) then acetonitrile (12.0 ml) and heated to 70° C. for 16 h, then triethylamine (1.35 mL, 9.71 mmol) was added and the mixture stirred an additional 3 h. The mixture was then diluted with 5 mL water and 5 mL EtOAc. The layers were separated and the aqueous layer was washed with EtOAc 4×5 mL. The combined organics were washed with 2 mL brine, dried over $Na_2SO_4$, filtered, concentrated and purifed by automated silica gel chromatography to afford the title compound (78 mg, 16%) ESI-MS m/z: 201.8 $[M+H]^+$.

Intermediate 32 steps a and b

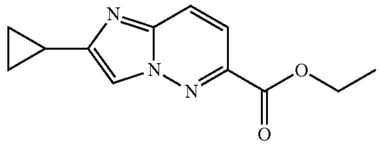 [SMILES: CCOC(=O)c1ccc2nc(C3CC3)cn2n1]

An 8 mL vial was charged with 6-bromo-2-cyclopropylimidazo[1,2-b]pyridazine (128 mg, 0.538 mmol) palladium (II) acetate (12 mg, 0.054 mmol) 1,3-bis(diphenylphosphino)propane (44.3 mg, 0.108 mmol), and the headspace of the vial was purged with $N_2$ for 30 min. A mixture of DMF (1.434 ml) ethanol (0.717 ml) and triethylamine (225 μl, 1.613 mmol) was degassed by sparging with $N_2$ for 30 min, then added to the mixture of solids. The vial was placed under a balloon of CO, and the mixture was heated to 80° C. for 16 h. Additional palladium(II) acetate (12 mg, 0.054 mmol) was added and the mixture heated to 100° C. for 4 h. The reaction vessel was degassed by sparging with $N_2$, then the mixture was concentrated and purified by automated silica gel chromatography to afford the title compound as a yellow oil (35 mg, 28%). ESI-MS m/z: 232.0 $[M+H]^+$.

The ester hydrolysis was carried out in a similar manner to Example 2 Step d. The product could not be extracted from the aqueous layer. The aqueous layer was concentrated to afford the title compound as a mixture with lithium chloride. ESI-MS m/z: 204.1 $[M+H]^+$.

Intermediate 33

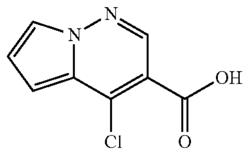 [SMILES: O=C(O)c1cnn2cccc2c1Cl]

Intermediate 33 Step a

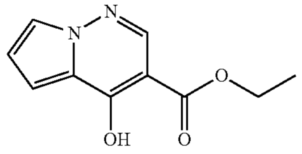

A 20 mL vial was charged with 1H-pyrrol-1-amine (1 ml, 13.15 mmol) and diethyl 2-(ethoxymethylene)malonate (3.11 ml, 15.39 mmol) they were, heated to 125° C. for 1 h. The mixture was diluted with a mixture of biphenyl (1 g) and diphenylether (3 ml) then heated to 200° C. for 2 h. The mixture was cooled to room temperature then purified by automated silica gel chromatography (0 to 10% ethyl acetate in cyclohexane) to afford the title compound as a yellow solid (1.43 g, 53%) ESI-MS m/z: 207.1 $[M+H]^+$.

Intermediate 33 Step b

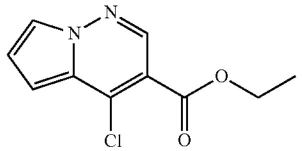

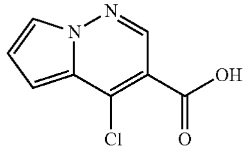

An 8 mL vial was charged with the compound from step a (300 mg, 1.46 mmol) $CCl_4$ (1.5 ml) celite (150 mg) and triphenylphosphine (1.13 g, 4.36 mmol). The mixture was heated to 75° C. for 16 h. The reaction was diluted with EtOAc and filtered through celite. The filtrate was concentrated and purified by automated silica gel chromatography to afford the expected ester (243 mg, 74%) as well as the hydrolysis product as a fluorescent yellow solid (19 mg, 7%) which was carried forward directly. ESI-MS m/z: 197.0/199.0 $[M+H]^+$.

Intermediate 34

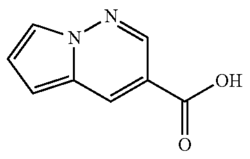 [SMILES: O=C(O)c1cnn2cccc2c1]

An 8 mL vial was charged with the ester from Intermediate 33 step b (131 mg, 0.583 mmol) and ammonium formate (184 mg, 2.92 mmol). A mixture of dioxane (2.92 ml) and ethanol (2.92 ml) was degassed by sparging with N2 for 30 min, then added to the mixture. Palladium on carbon (62.1 mg, 0.583 mmol, 10 wt %) was added and the mixture allowed to stir for 1 h then filtered through celite. The filtrate was concentrated and purified by automated silica gel chromatography to afford the product as a fluorescent yellow solid (77 mg, 70%) ESI-MS m/z: 191.1 $[M+H]^+$.

The ester hydrolysis was carried out in a similar manner to Example 2 Step d. After acidification the title compound was collected by filtration as a fluorescent yellow solid (19 mg, 32%) ESI-MS m/z: 163.0 $[M+H]^+$.

Intermediate 35 Steps a and b

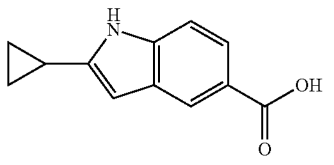 [SMILES: O=C(O)c1ccc2[nH]c(C3CC3)cc2c1]

An 8 mL vial was charged with methyl 4-amino-3-bromobenzoate (345 mg, 1.500 mmol) $Pd(PPh_3)_2Cl_2$ (211 mg, 0.300 mmol), copper(I) iodide (28.6 mg, 0.150 mmol), the reaction vessel was evacuated and backfilled with $N_2$ three times. Toluene (2 mL) and water (1 mL) were degassed by sparging with $N_2$ for 15 min, then added to the vial with the solids. Ethynylcyclopropane (508 μL, 6.00 mmol) and triethylamine (627 μL, 4.50 mmol) were added and the mixture stirred for 16 h at 70° C. The mixture was then diluted with water and EtOAc, the phases were separated, the organic layer was concentrated and purified by automated silica gel chromatography (0 to 10% ethyl acetate in cyclohexane). To afford the title compound as a colorless oil (298 mg, 92%) ESI-MS m/z: 216.1 $[M+H]^+$.

An 8 mL vial containing the compound from step a (99 mg, 0.46 mmol) was charged with dimethylsulfoxide (1 ml), and KOtBu (155 mg, 1.38 mmol) then heated to 100° C. for 30 min. The mixture was cooled to room temperature and diluted with water and EtOAc, then acidified to pH 3 with 1 M (aq) HCl. The layers were separated and the aqueous layer washed 4×3 mL with EtOAc. The combined organic layers were then washed twice with water, then with brine, dried over $Na_2SO_4$ and purified by automated silica gel chromatography (0 to 50% (1% AcOH in EtOAc) in cyclohexane) to afford the title compound as a white solid (45 mg, 49%). ESI-MS m/z: 202.1 $[M+H]^+$.

Intermediate 36

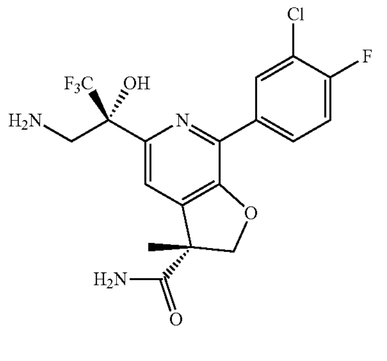

Intermediate 36 Step a

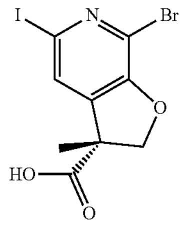

Into a 100 mL round-bottom flask were added Example 1, step b (3.80 g, 10.27 mmol), acetone (100 mL), the solution was cooled to 0° C., and then Jones reagent (1.9-2.2 M, 10 mL) was added dropwise (with internal temperature monitoring). The reaction was warmed to room temperature and monitored by LCMS (3 hr). The reaction was cooled to 0° C., quenched with $^i$PrOH and stirred for 15 minutes. The reaction was diluted with EtOAc and water. The aqueous was extracted, the combined organics were dried and concentrated under reduced pressure to get the crude product as a yellow solid (3.95 g, 99%). ESI-MS m/z: 383.80 $[M+H]^+$.

Intermediate 36 Step b

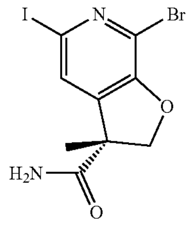

Into a 100 mL round-bottom flask were added the compound from step a (3.95 g, 10.28 mmol), $NH_4C_1$ (1.10 g, 20.57 mmol) and the solids dissolved in DMF (20 mL). Hunig's base (5.27 mL, 30.84 mmol) was added, the reaction was cooled to 0° C., and HATU (7.82 g, 20.56 mmol) was added. The reaction was warmed to room temperature and monitored by LCMS (1 hr). The reaction was diluted with EtOAc and water. The aqueous was extracted, the combined organics were dried and concentrated. The material was purified by automated column chromatography (silica gel, 0-100% EtOAc in hexanes) to afford the title compound (3 g, 76%). ESI-MS m/z: 382.95 $[M+H]^+$.

Intermediate 36 Step c

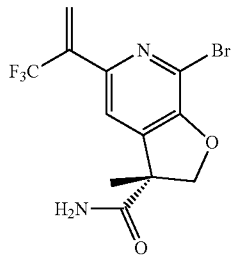 [SMILES: C=C(c1cc2c(c(Br)n1)OC[C@]2(C)C(N)=O)C(F)(F)F]

Into a 100 mL round-bottom flask were added the compound from step b (3.00 g, 7.83 mmol), 3,3,3-trifluoroprop-1-en-2-ylboronic acid (2.19 g, 15.65 mmol), $Pd(dppf)Cl_2$ (1.15 g, 1.56 mmol), and the material dissolved in dioxane (40 mL) and $H_2O$ (5 mL). $K_2CO_3$ (3.25 g, 23.50 mmol) was then added and the resulting mixture was stirred for 1 h at 90° C. under nitrogen atmosphere. The mixture was cooled to room temperature, poured into water, extracted with EtOAc and the combined organics were concentrated under reduced pressure. The residue was purified by column chromatography (silica gel, 0-100% EtOAc in hexanes) to afford desired product as a brown oil (2.3 g, 83%). ESI-MS m/z: 350.90 $[M+H]^+$.

Intermediate 36 Step d

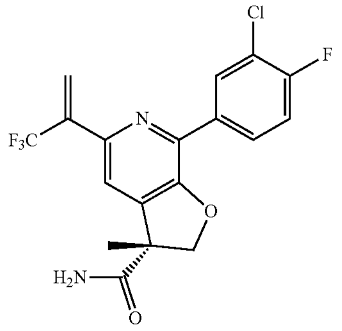 [SMILES: C=C(c1cc2c(c(-c3ccc(F)c(Cl)c3)n1)OC[C@]2(C)C(N)=O)C(F)(F)F]

To a stirred solution of step c (5.00 g, 14.24 mmol) and 3-chloro-4-fluorophenylboronic acid (3.72 g, 21.33 mmol) in THE (80 mL) were added $Na_2CO_3$ (3.32 g, 31.33 mmol), $H_2O$ (20 mL) and $Pd(PPh_3)_2C_{12}$ (1.00 g, 1.42 mmol). The resulting mixture was stirred for 1 h at 70° C. under nitrogen atmosphere. The reaction was monitored by TLC and LCMS. The resulting mixture was extracted with EtOAc, and the combined organic layers were washed with brine, dried, and concentrated under reduced pressure. The residue was purified by automated column chromatography (silica gel, 0-75% EtOAc in hexanes) to afford the title compound as a yellow solid (5.8 g, 99%). ESI-MS m/z: 401.05 $[M+H]^+$.

Intermediate 36 Step e

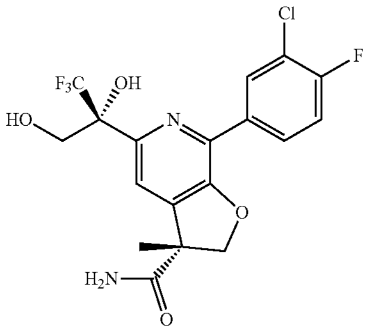 [SMILES: C[C@]1(C(N)=O)COc2c1cc([C@@](O)(CO)C(F)(F)F)nc2-c1ccc(F)c(Cl)c1]

To a 500 mL round-bottom flask equipped with a stir bar was added AD-mix-β (33.82 g, 43.41 mmol) and methanesulfonamide (1.38 g, 14.47 mmol). The solids were dissolved in tBuOH (60 mL) and $H_2O$ (100 mL), and the flask cooled to 0° C. and the compound from step d (5.80 g, 14.47 mmol) was added slowly as a solution of tBuOH (40 mL). The reaction was allowed to warm to room temperature naturally and stirred for 16 hrs. The reaction was quenched with the addition of sodium sulfite (0.25 g per g AD-mix), diluted with water and EtOAc. The layers were separated, and the aqueous layer was extracted with EtOAc. The combined organics were washed with brine, dried over $Na_2SO_4$, filtered concentrated and purified by automated column chromatography (silica gel, 0-100% EtOAc in hexanes) to afford the title compound as a white solid (5.48 g, 87%). ESI-MS m/z: 435. $[M+H]^+$.

Intermediate 36 Step f

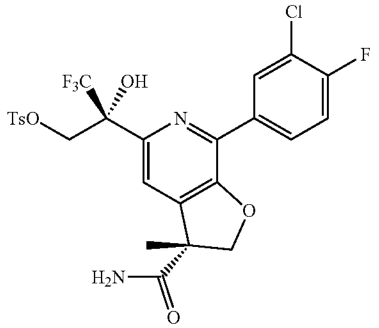 [SMILES: Cc1ccc(S(=O)(=O)OC[C@](O)(c2cc3c(c(-c4ccc(F)c(Cl)c4)n2)OC[C@]3(C)C(N)=O)C(F)(F)F)cc1]

Into a 250 mL round-bottom flask were added the compound from step e (4.70 g, 10.81 mmol) and DCM (80 mL) at room temperature. The solution was cooled to 0° C., and DMAP (264 mg, 2.16 mmol), TEA (3.28 g, 32.43 mmol and TsCl (2.47 g, 12.97 mmol) were then sequentially added. The resulting mixture was stirred for 1 h at 0° C. The mixture was acidified to pH 4 with 2 M HCl, and the aqueous extracted with DCM. The combined organic layers were dried over anhydrous $Na_2SO_4$ and concentrated under reduced pressure to afford the crude product as a light-yellow solid (6.2 g, 97%). ESI-MS m/z: 589.15 $[M+H]^+$.

Intermediate 36 Step g

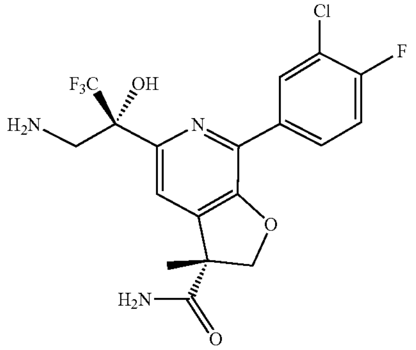 [SMILES: C[C@]1(C(N)=O)COc2c1cc([C@@](O)(CN)C(F)(F)F)nc2-c1ccc(F)c(Cl)c1]

Into a 100 mL round-bottom flask was added $NH_3$ in MeOH (35 mL) at room temperature, and the compound from step g (6.20 g, 10.52 mmol) was slowly added. The resulting mixture was stirred at room temperature and monitored by LCMS (5 hr). The mixture was dissolved in EtOAc, washed with sat. sodium bicarbonate 3x, brine, dried, and concentrated to afford the title compound (2.93 g, 64%). ESI-MS m/z: 434.05 $[M+H]^+$.

Intermediate 37

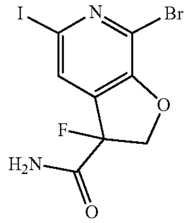 [SMILES: NC(=O)C1(F)COc2c1cc(I)nc2Br]

Intermediate 37 Step a

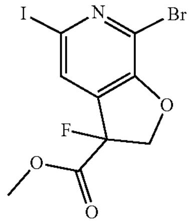 [SMILES: COC(=O)C1(F)COc2c1cc(I)nc2Br]

To a 20 mL vial equipped with a stir bar was added N-fluoro-N-(phenylsulfonyl)benzenesulfonamide (963 mg, 3.05 mmol) and methyl 7-bromo-5-iodo-2,3-dihydrofuro[2,3-c]pyridine-3-carboxylate (586 mg, 1.526 mmol), and the solids were dissolved in THE (0.25M). The vial was cooled to −78° C., and LDA (916 μl, 1.831 mmol) was slowly added. The reaction was stirred at −78 C for 1 hr. After 1 hr at −78° C., reaction gelled up. The reaction was warmed to rt and stirred and monitored by LCMS. The reaction was diluted with EtOAc and quenched with water and sat. ammonium chloride. EtOAc and DCM/MeOH 1× each extraction with a phase separator cartridge. Concentrated. The material was purified by automated column chromatography (0-100% EtOAc/cHex) to afford the title compound (483 mg, 71%). ESI-MS m/z: 401.86/403.86 $[M+H]^+$.

Intermediate 37 Step b

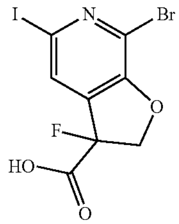 [SMILES: O=C(O)C1(F)COc2c1cc(I)nc2Br]

To a 20 mL vial containing step a (483 mg, 1.081 mmol) was added and stir bar, and the material was dissolved in THF/MeOH, and Water (1:1:1, 0.25 M). Lithium hydroxide hydrate (113 mg, 2.70 mmol) was added, the reaction stirred at room temperature and monitored by LCMS. The reaction was diluted with EtOAc and acidified to pH=2 with 2M HCl. EtOAc and DCM/MeOH extraction with a phase separator cartridge. The material was tritterated with DCM/hexanes to afford an orange solid. (455 mg, 92%) ESI-MS m/z: 387.82/387.82 $[M+H]^+$.

Intermediate 37 Step c

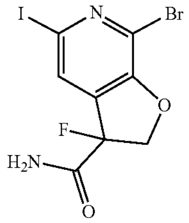 [SMILES: NC(=O)C1(F)COc2c1cc(I)nc2Br]

The above compound was prepared in an analogous fashion to Intermediate 36 Step b. The crude material was purified by automated column chromatography (silica gel, 0-100% EtOAc/cHex) to afford the title compound as an orange oil (243 mg, 43%) ESI-MS m/z: 386.33 $[M+H]^+$.

Intermediate 38

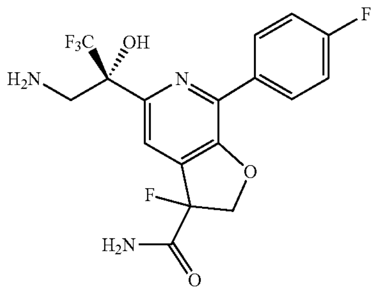 [SMILES: NC[C@](O)(c1cc2c(c(-c3ccc(F)cc3)n1)OCC2(F)C(N)=O)C(F)(F)F]

The above example was prepared in an analogous sequence to Intermediate 36 as a mixture of diastereomers to afford the desired amino alcohol (42 mg). ESI-MS m/z: 404.09 $[M+H]^+$.

The compounds in Table 1 were prepared by a method similar to that of Example 1 step c (PyBOP or HATU). The majority of compounds were purified by Gilson prep-HPLC, and some were purified by automated column chromatography (silica gel). Many of the aryl acid coupling partners were prepared according to Intermediates 1-38, or analogous procedures. In certain cases the aryl acid coupling partners were commercially available or prepared by previously described methods.

TABLE 1
| Example | Structure | MS+ m/z |
|---|---|---|
| 6 | 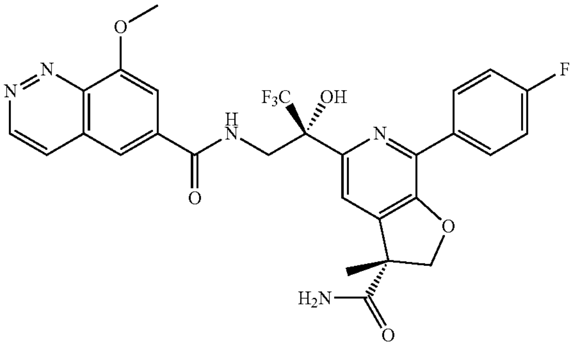 [SMILES: COc1cc(C(=O)NC[C@](O)(c2cc3c(c(-c4ccc(F)cc4)n2)OC[C@]3(C)C(N)=O)C(F)(F)F)cc2ccnnc12] | 586.21 |
| 7 | 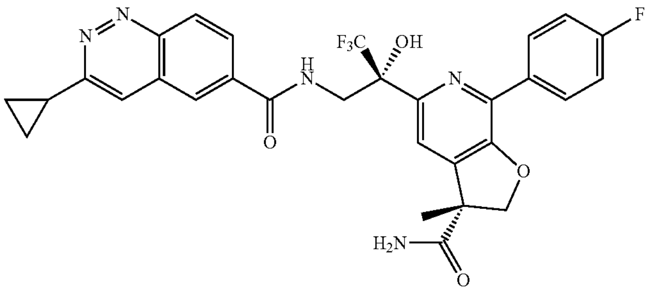 [SMILES: C[C@]1(C(N)=O)COc2c1cc([C@@](O)(CNC(=O)c1ccc3nnc(C4CC4)cc3c1)C(F)(F)F)nc2-c1ccc(F)cc1] | 596.19 |
| 8 | 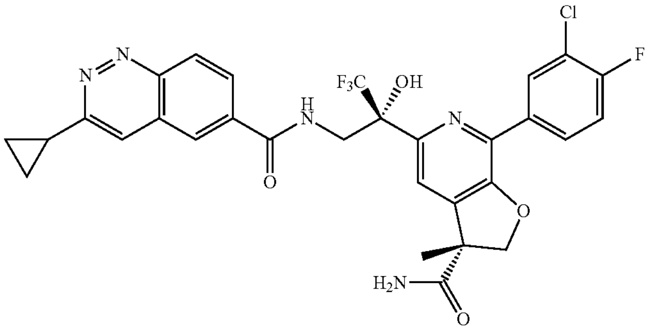 [SMILES: C[C@]1(C(N)=O)COc2c1cc([C@@](O)(CNC(=O)c1ccc3nnc(C4CC4)cc3c1)C(F)(F)F)nc2-c1ccc(F)c(Cl)c1] | 603.96 |
| 9 | 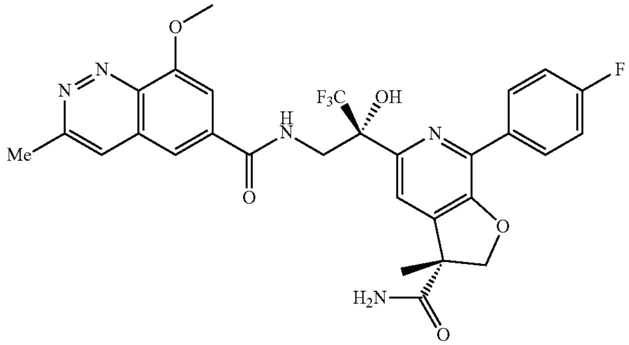 [SMILES: COc1cc(C(=O)NC[C@](O)(c2cc3c(c(-c4ccc(F)cc4)n2)OC[C@]3(C)C(N)=O)C(F)(F)F)cc2cc(C)nnc12] | 600.21 |

TABLE 1-continued
| Example | Structure | MS+ m/z |
|---|---|---|
| 10 | 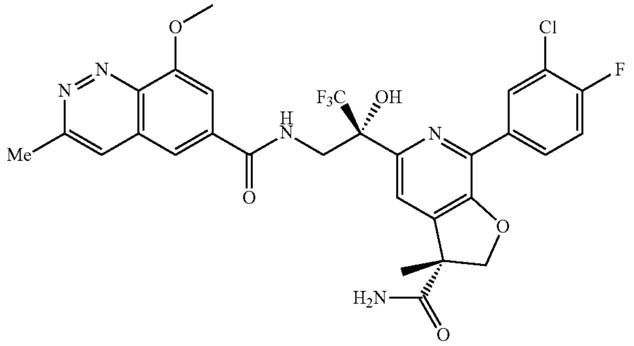 [SMILES: COc1cc(C(=O)NC[C@](O)(c2cc3c(c(-c4ccc(F)c(Cl)c4)n2)OC[C@]3(C)C(N)=O)C(F)(F)F)cc2cc(C)nnc12] | 634.19 |
| 11 | 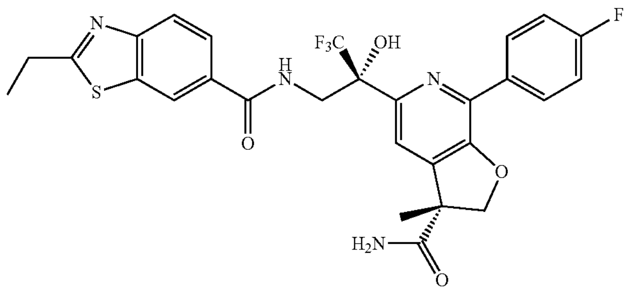 [SMILES: CCc1nc2ccc(C(=O)NC[C@](O)(c3cc4c(c(-c5ccc(F)cc5)n3)OC[C@]4(C)C(N)=O)C(F)(F)F)cc2s1] | 589.16 |
| 12 | 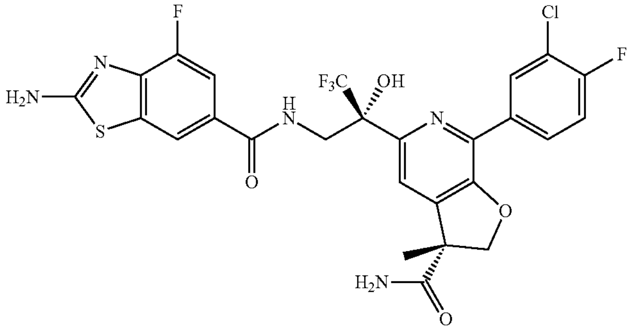 [SMILES: C[C@]1(C(N)=O)COc2c1cc([C@@](O)(CNC(=O)c1cc(F)c3nc(N)sc3c1)C(F)(F)F)nc2-c1ccc(F)c(Cl)c1] | 628.01 |
| 13 | 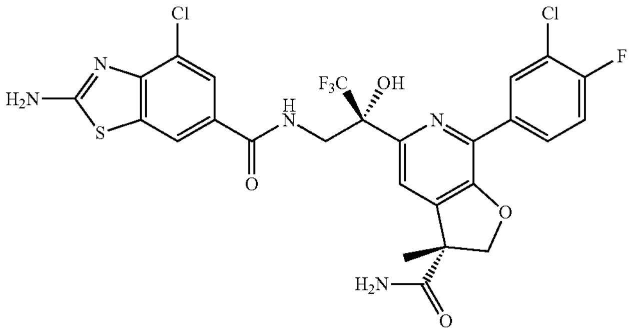 [SMILES: C[C@]1(C(N)=O)COc2c1cc([C@@](O)(CNC(=O)c1cc(Cl)c3nc(N)sc3c1)C(F)(F)F)nc2-c1ccc(F)c(Cl)c1] | 645.82 |

TABLE 1-continued
| Example | Structure | MS⁺ m/z |
| --- | --- | --- |
| 14 | 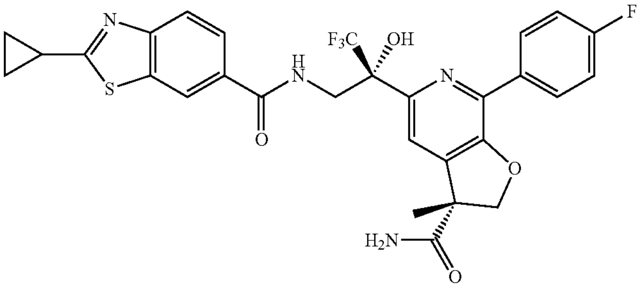 | 601.06 |
| 15 | 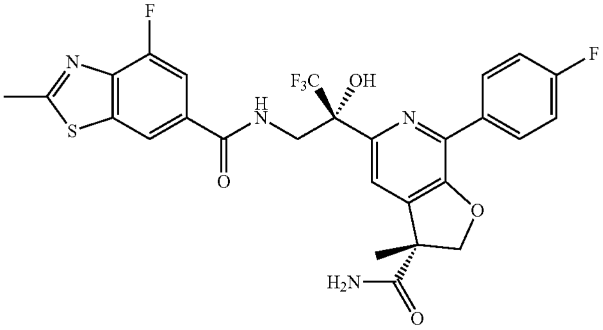 [SMILES: Cc1nc2c(F)cc(C(=O)NC[C@](O)(c3cc4c(c(-c5ccc(F)cc5)n3)OC[C@]4(C)C(N)=O)C(F)(F)F)cc2s1] | 593.05 |
| 16 | 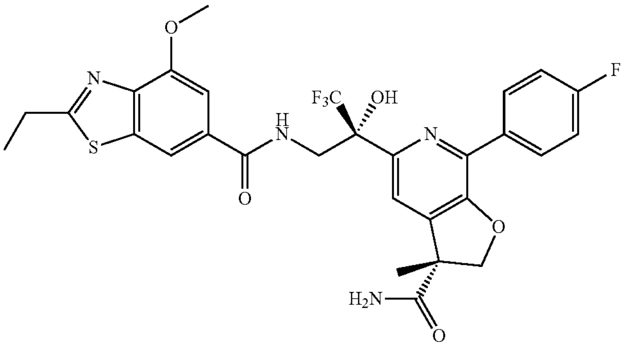 [SMILES: CCc1nc2c(OC)cc(C(=O)NC[C@](O)(c3cc4c(c(-c5ccc(F)cc5)n3)OC[C@]4(C)C(N)=O)C(F)(F)F)cc2s1] | 619.18 |
| 17 | 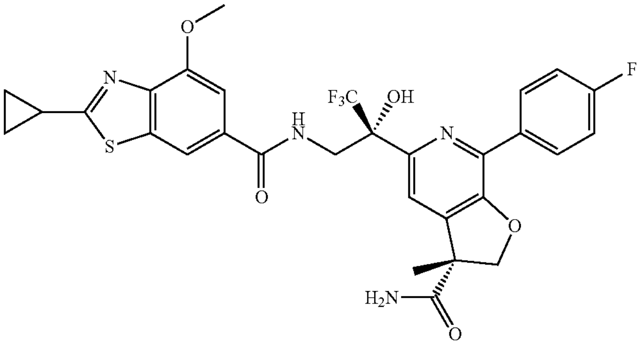 [SMILES: COc1cc(C(=O)NC[C@](O)(c2cc3c(c(-c4ccc(F)cc4)n2)OC[C@]3(C)C(N)=O)C(F)(F)F)cc2sc(C3CC3)nc12] | 631.12 |

TABLE 1-continued
| Example | Structure | MS⁺ m/z |
|---|---|---|
| 18 | 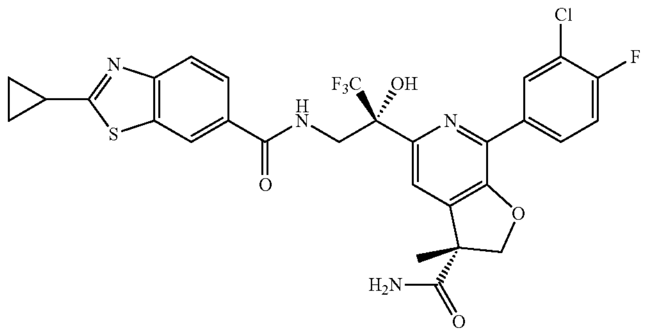 [SMILES: C[C@]1(C(N)=O)COc2c1cc([C@@](O)(CNC(=O)c1ccc3nc(C4CC4)sc3c1)C(F)(F)F)nc2-c1ccc(F)c(Cl)c1] | 634.99 |
| 19 | 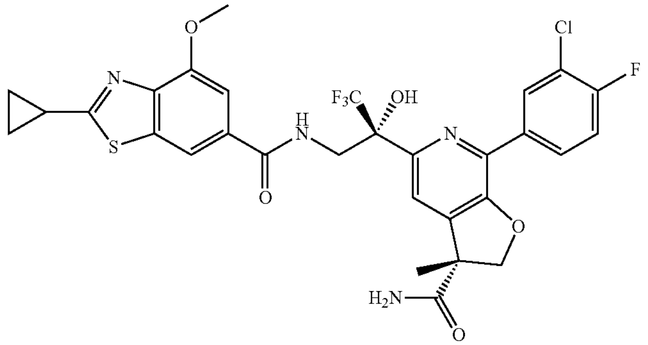 [SMILES: COc1cc(C(=O)NC[C@](O)(c2cc3c(c(-c4ccc(F)c(Cl)c4)n2)OC[C@]3(C)C(N)=O)C(F)(F)F)cc2sc(C3CC3)nc12] | 665.05 |
| 20 | 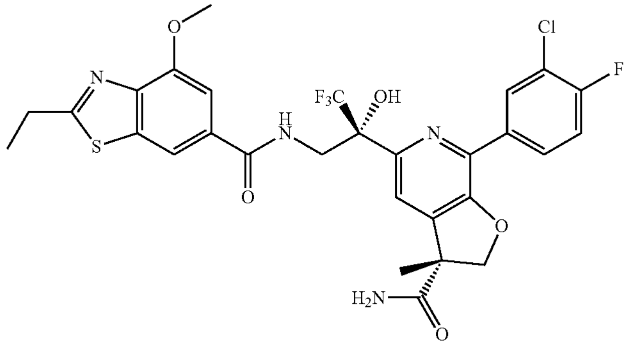 [SMILES: CCc1nc2c(OC)cc(C(=O)NC[C@](O)(c3cc4c(c(-c5ccc(F)c(Cl)c5)n3)OC[C@]4(C)C(N)=O)C(F)(F)F)cc2s1] | 652.99 |
| 21 | 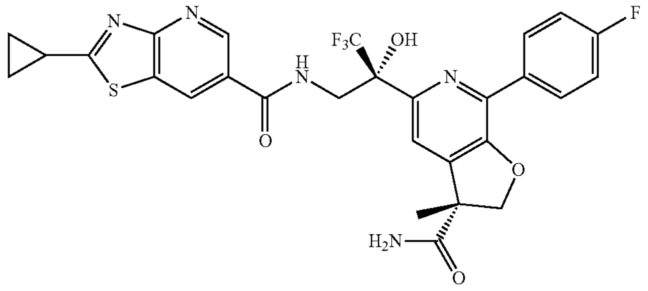 [SMILES: C[C@]1(C(N)=O)COc2c1cc([C@@](O)(CNC(=O)c1cnc3nc(C4CC4)sc3c1)C(F)(F)F)nc2-c1ccc(F)cc1] | 601.94 |

TABLE 1-continued
| Example | Structure | MS+ m/z |
| --- | --- | --- |
| 22 | 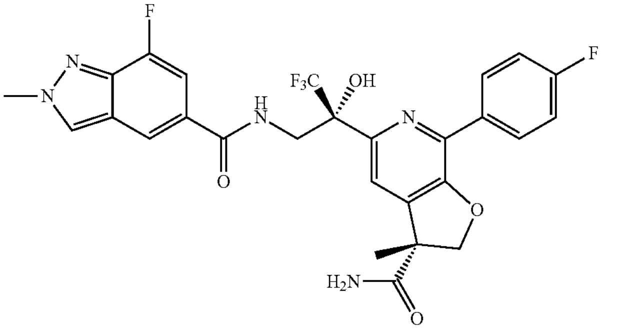 [SMILES: Cn1cc2cc(C(=O)NC[C@](O)(c3cc4c(c(-c5ccc(F)cc5)n3)OC[C@]4(C)C(N)=O)C(F)(F)F)cc(F)c2n1] | 576.17 |
| 23 | 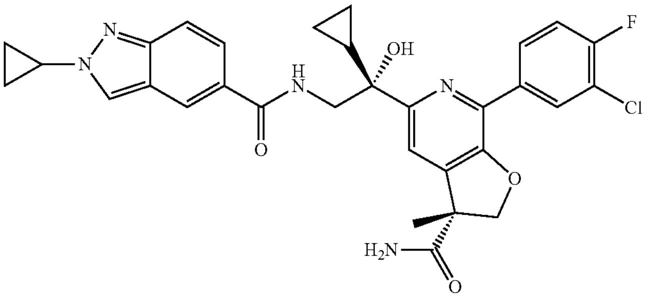 [SMILES: C[C@]1(C(N)=O)COc2c1cc([C@@](O)(CNC(=O)c1ccc3nn(C4CC4)cc3c1)C1CC1)nc2-c1ccc(F)c(Cl)c1] | 556.40 |
| 24 | 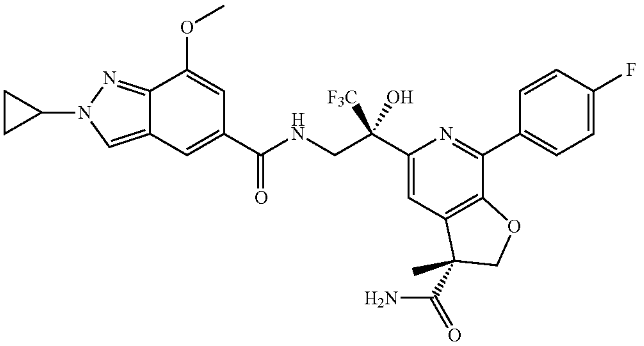 [SMILES: COc1cc(C(=O)NC[C@](O)(c2cc3c(c(-c4ccc(F)cc4)n2)OC[C@]3(C)C(N)=O)C(F)(F)F)cc2cn(C3CC3)nc12] | 614.19 |
| 25 | 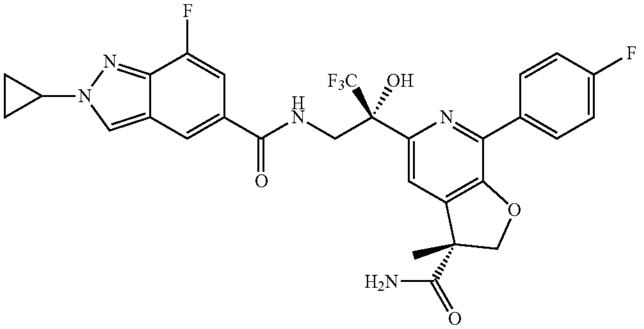 [SMILES: C[C@]1(C(N)=O)COc2c1cc([C@@](O)(CNC(=O)c1cc(F)c3nn(C4CC4)cc3c1)C(F)(F)F)nc2-c1ccc(F)cc1] | 602.17 |

TABLE 1-continued
| Example | Structure | MS+ m/z |
|---|---|---|
| 26 | 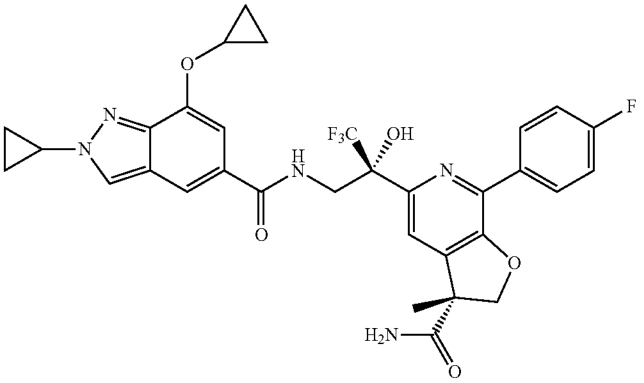 [SMILES: C[C@]1(C(N)=O)COc2c1cc([C@@](O)(CNC(=O)c1cc(OC3CC3)c3nn(C4CC4)cc3c1)C(F)(F)F)nc2-c1ccc(F)cc1] | 640.20 |
| 27 | 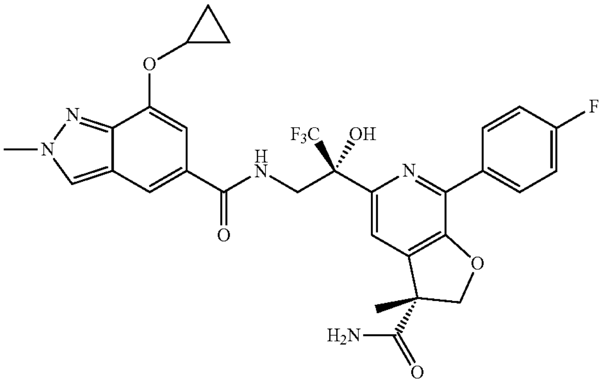 [SMILES: Cn1cc2cc(C(=O)NC[C@](O)(c3cc4c(c(-c5ccc(F)cc5)n3)OC[C@]4(C)C(N)=O)C(F)(F)F)cc(OC3CC3)c2n1] | 614.18 |
| 28 | 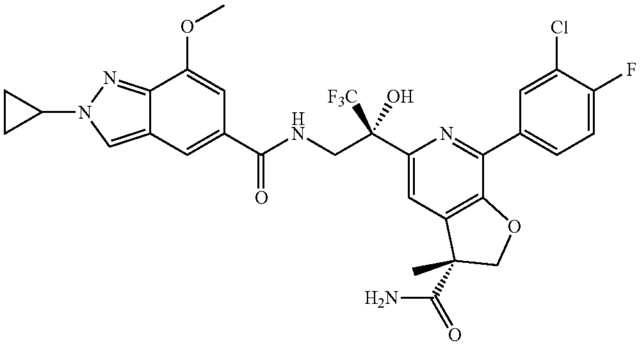 [SMILES: COc1cc(C(=O)NC[C@](O)(c2cc3c(c(-c4ccc(F)c(Cl)c4)n2)OC[C@]3(C)C(N)=O)C(F)(F)F)cc2cn(C3CC3)nc12] | 648.14 |
| 29 | 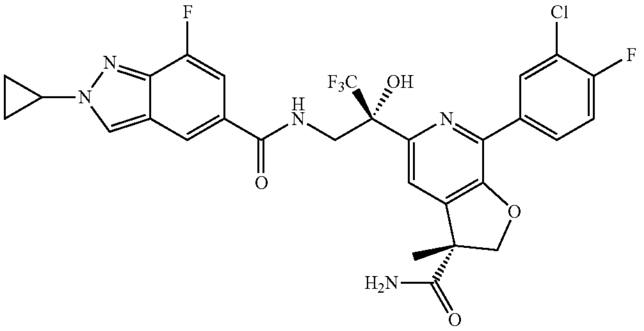 [SMILES: C[C@]1(C(N)=O)COc2c1cc([C@@](O)(CNC(=O)c1cc(F)c3nn(C4CC4)cc3c1)C(F)(F)F)nc2-c1ccc(F)c(Cl)c1] | 636.13 |

TABLE 1-continued
| Example | Structure | MS+ m/z |
|---|---|---|
| 30 | 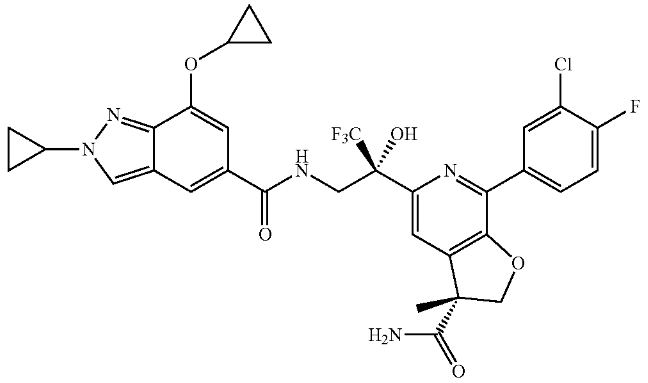 [SMILES: C[C@]1(C(N)=O)COc2c1cc([C@@](O)(CNC(=O)c1cc(OC3CC3)c3nn(C4CC4)cc3c1)C(F)(F)F)nc2-c1ccc(F)c(Cl)c1] | 674.16 |
| 31 | 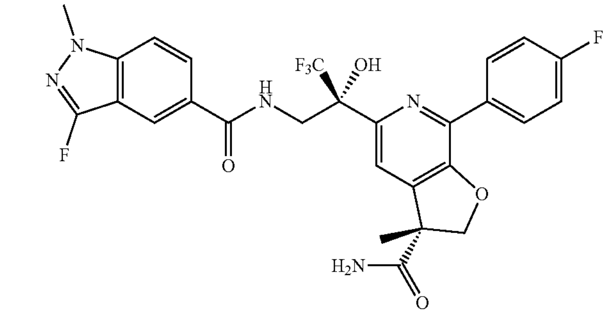 [SMILES: Cn1nc(F)c2cc(C(=O)NC[C@](O)(c3cc4c(c(-c5ccc(F)cc5)n3)OC[C@]4(C)C(N)=O)C(F)(F)F)ccc21] | 576.14 |
| 32 | 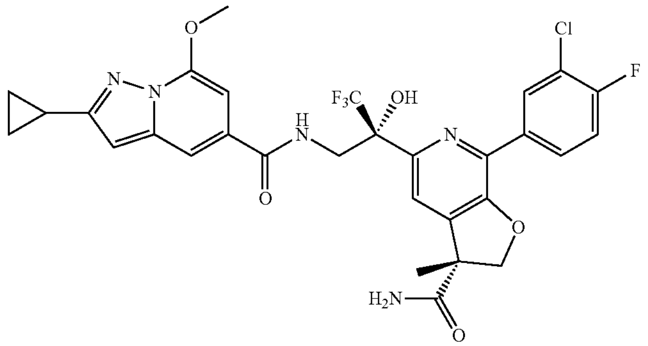 [SMILES: COc1cc(C(=O)NC[C@](O)(c2cc3c(c(-c4ccc(F)c(Cl)c4)n2)OC[C@]3(C)C(N)=O)C(F)(F)F)cc2cc(C3CC3)nn12] | 648.14 |
| 33 | 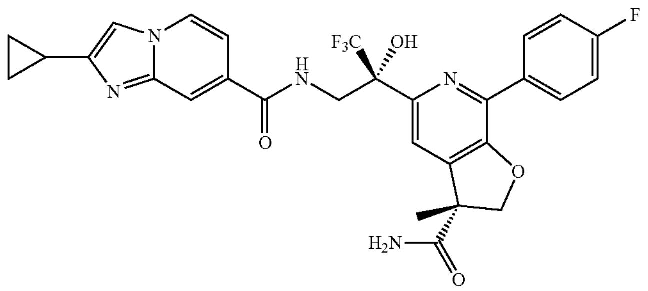 [SMILES: C[C@]1(C(N)=O)COc2c1cc([C@@](O)(CNC(=O)c1ccn3cc(C4CC4)nc3c1)C(F)(F)F)nc2-c1ccc(F)cc1] | 584.17 |

TABLE 1-continued
| Example | Structure | MS+ m/z |
|---|---|---|
| 34 | 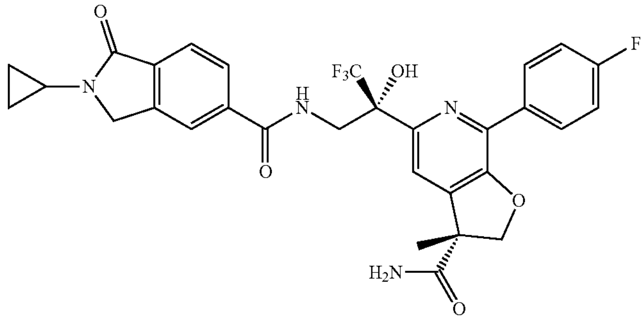 [SMILES: C[C@]1(C(N)=O)COc2c1cc([C@@](O)(CNC(=O)c1ccc3c(c1)CN(C1CC1)C3=O)C(F)(F)F)nc2-c1ccc(F)cc1] | 599.19 |
| 35 | 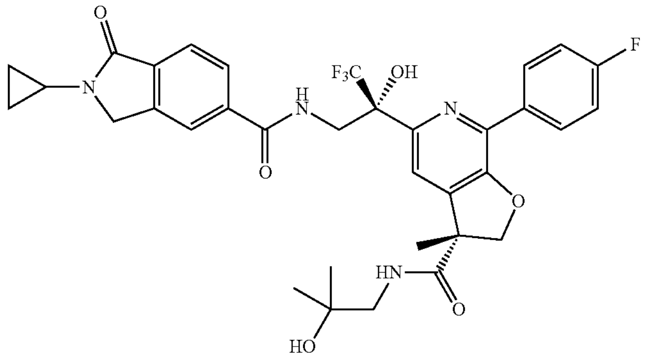 [SMILES: CC(C)(O)CNC(=O)[C@@]1(C)COc2c1cc([C@@](O)(CNC(=O)c1ccc3c(c1)CN(C1CC1)C3=O)C(F)(F)F)nc2-c1ccc(F)cc1] | 671.25 |
| 36 | 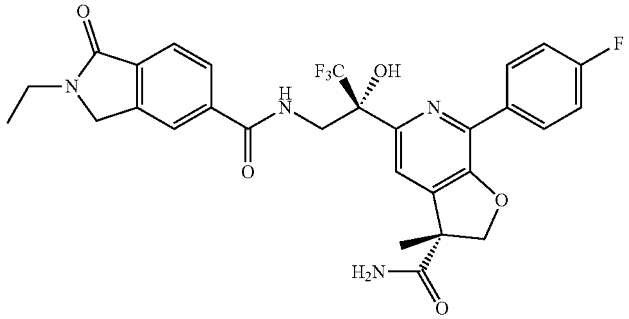 [SMILES: CCN1Cc2cc(C(=O)NC[C@](O)(c3cc4c(c(-c5ccc(F)cc5)n3)OC[C@]4(C)C(N)=O)C(F)(F)F)ccc2C1=O] | 587.19 |
| 37 | 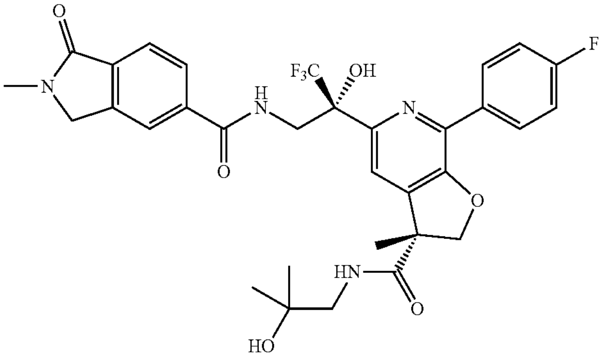 [SMILES: CN1Cc2cc(C(=O)NC[C@](O)(c3cc4c(c(-c5ccc(F)cc5)n3)OC[C@]4(C)C(=O)NCC(C)(C)O)C(F)(F)F)ccc2C1=O] | 659.25 |

TABLE 1-continued
| Example | Structure | MS+ m/z |
|---|---|---|
| 38 | 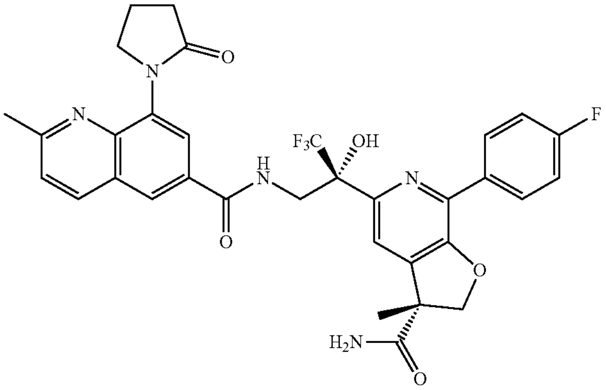 [SMILES: Cc1ccc2cc(C(=O)NC[C@](O)(c3cc4c(c(-c5ccc(F)cc5)n3)OC[C@]4(C)C(N)=O)C(F)(F)F)cc(N3CCCC3=O)c2n1] | 652.22 |
| 39 | 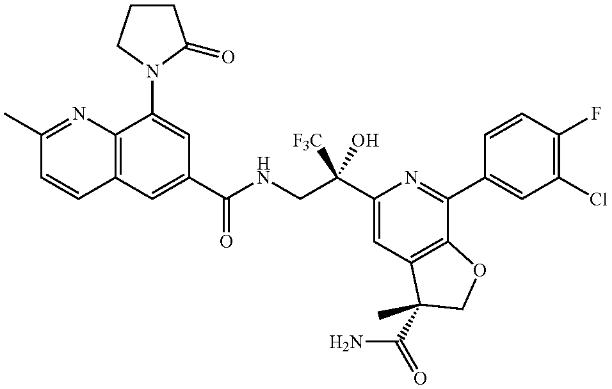 [SMILES: Cc1ccc2cc(C(=O)NC[C@](O)(c3cc4c(c(-c5ccc(F)c(Cl)c5)n3)OC[C@]4(C)C(N)=O)C(F)(F)F)cc(N3CCCC3=O)c2n1] | 686.18 |
| 40 | 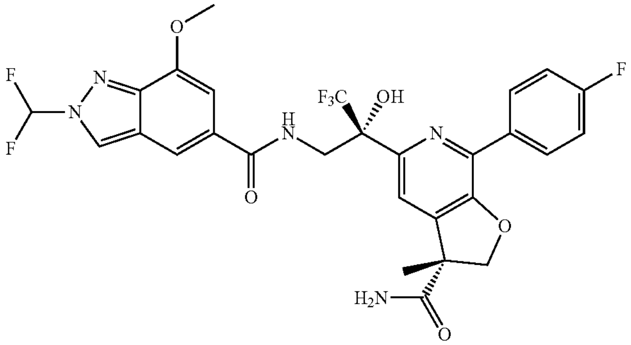 [SMILES: COc1cc(C(=O)NC[C@](O)(c2cc3c(c(-c4ccc(F)cc4)n2)OC[C@]3(C)C(N)=O)C(F)(F)F)cc2cn(C(F)F)nc12] | 624.10 |
| 41 | 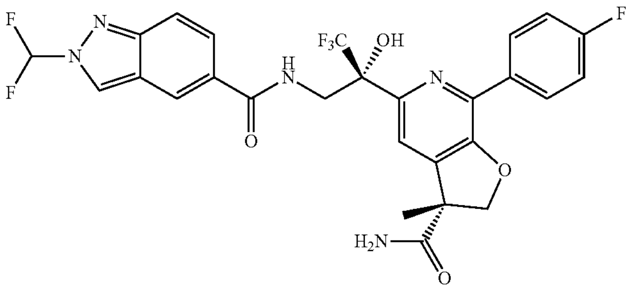 [SMILES: C[C@]1(C(N)=O)COc2c1cc([C@@](O)(CNC(=O)c1ccc3nn(C(F)F)cc3c1)C(F)(F)F)nc2-c1ccc(F)cc1] | 594.16 |

TABLE 1-continued
| Example | Structure | MS+ m/z |
|---|---|---|
| 42 | 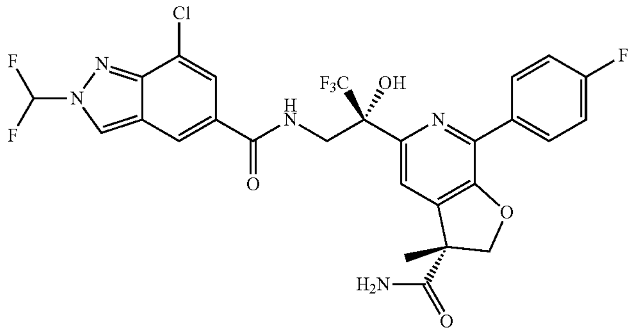 | 628.09 |
| 43 | 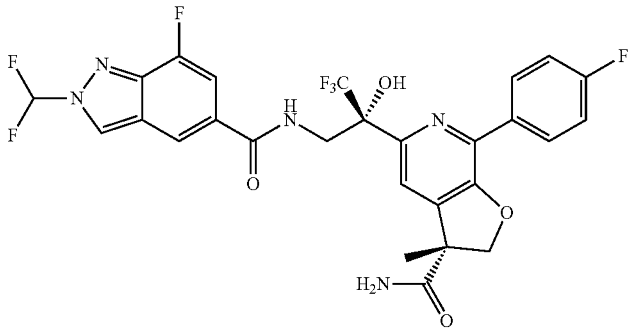 [SMILES: C[C@]1(C(N)=O)COc2c1cc([C@@](O)(CNC(=O)c1cc(Cl)c3nn(C(F)F)cc3c1)C(F)(F)F)nc2-c1ccc(F)cc1] | 612.13 |
| 44 | 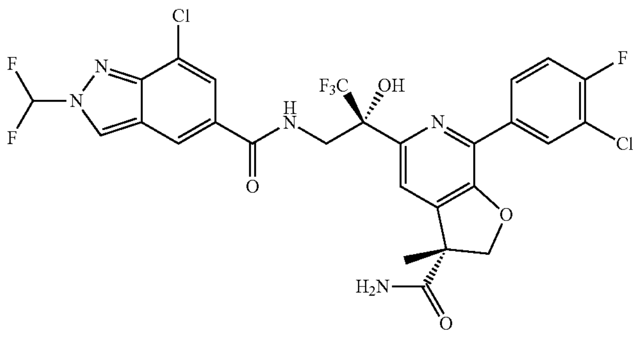 [SMILES: C[C@]1(C(N)=O)COc2c1cc([C@@](O)(CNC(=O)c1cc(F)c3nn(C(F)F)cc3c1)C(F)(F)F)nc2-c1ccc(F)c(Cl)c1] | 662.06 |
| 45 | 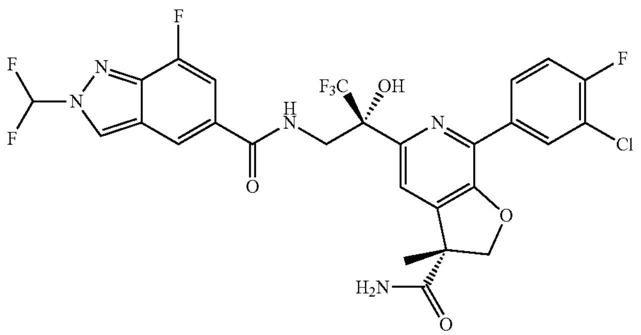 | 646.09 |

TABLE 1-continued
| Example | Structure | MS+ m/z |
|---|---|---|
| 46 | 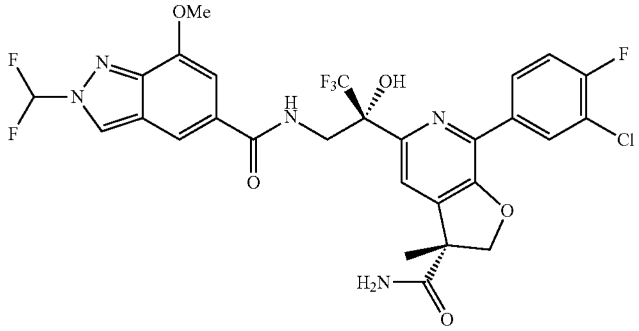 [SMILES: COc1cc(C(=O)NC[C@](O)(c2cc3c(c(-c4ccc(F)c(Cl)c4)n2)OC[C@]3(C)C(N)=O)C(F)(F)F)cc2cn(C(F)F)nc12] | 658.11 |
| 47 | 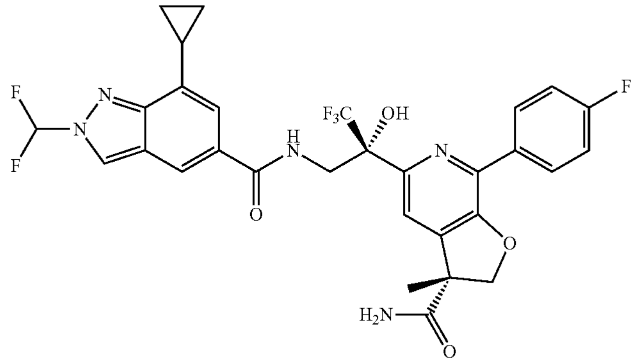 [SMILES: C[C@]1(C(N)=O)COc2c1cc([C@@](O)(CNC(=O)c1cc(C3CC3)c3nn(C(F)F)cc3c1)C(F)(F)F)nc2-c1ccc(F)cc1] | 634.16 |
| 48 | 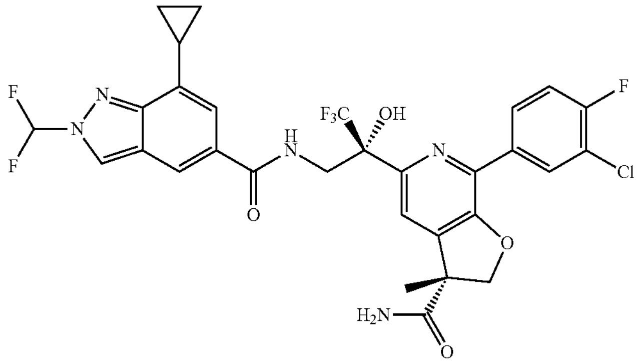 [SMILES: C[C@]1(C(N)=O)COc2c1cc([C@@](O)(CNC(=O)c1cc(C3CC3)c3nn(C(F)F)cc3c1)C(F)(F)F)nc2-c1ccc(F)c(Cl)c1] | 668.12 |
| 49 | 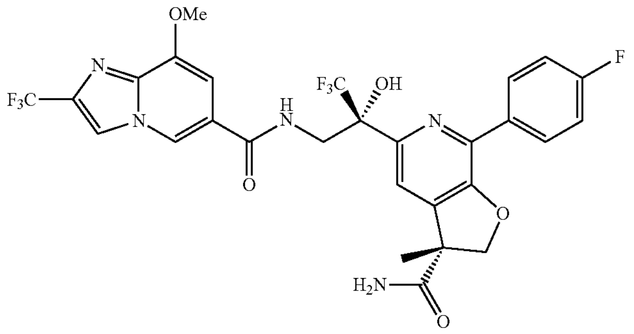 [SMILES: COc1cc(C(=O)NC[C@](O)(c2cc3c(c(-c4ccc(F)cc4)n2)OC[C@]3(C)C(N)=O)C(F)(F)F)cn2cc(C(F)(F)F)nc12] | 642.14 |

TABLE 1-continued
| Example | Structure | MS⁺ m/z |
| --- | --- | --- |
| 50 | 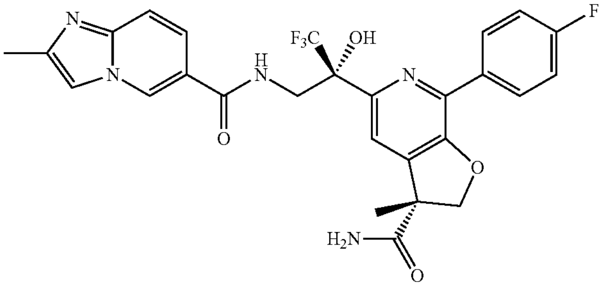 [SMILES: Cc1cn2cc(C(=O)NC[C@](O)(c3cc4c(c(-c5ccc(F)cc5)n3)OC[C@]4(C)C(N)=O)C(F)(F)F)ccc2n1] | 558.18 |
| 51 | 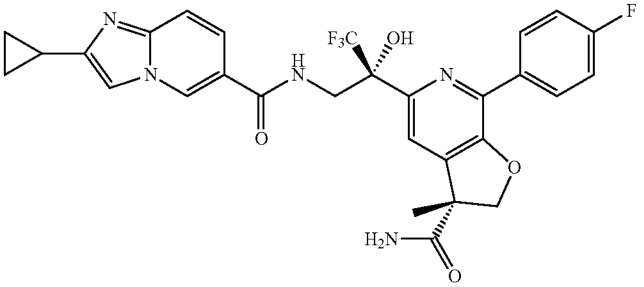 [SMILES: C[C@]1(C(N)=O)COc2c1cc([C@@](O)(CNC(=O)c1ccc3nc(C4CC4)cn3c1)C(F)(F)F)nc2-c1ccc(F)cc1] | 584.19 |
| 52 | 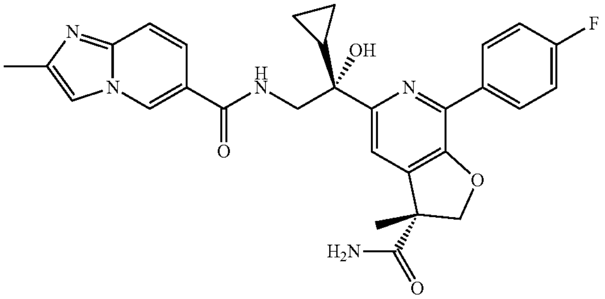 [SMILES: Cc1cn2cc(C(=O)NC[C@](O)(c3cc4c(c(-c5ccc(F)cc5)n3)OC[C@]4(C)C(N)=O)C3CC3)ccc2n1] | 530.22 |
| 53 | 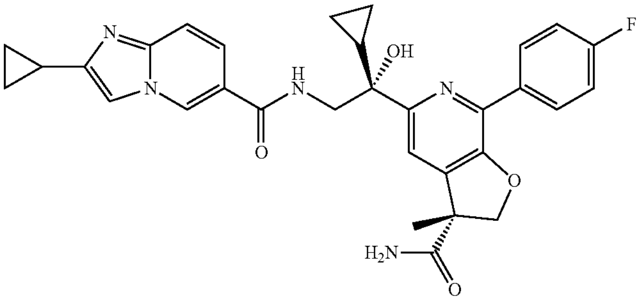 [SMILES: C[C@]1(C(N)=O)COc2c1cc([C@@](O)(CNC(=O)c1ccc3nc(C4CC4)cn3c1)C1CC1)nc2-c1ccc(F)cc1] | 556.24 |
| 54 | 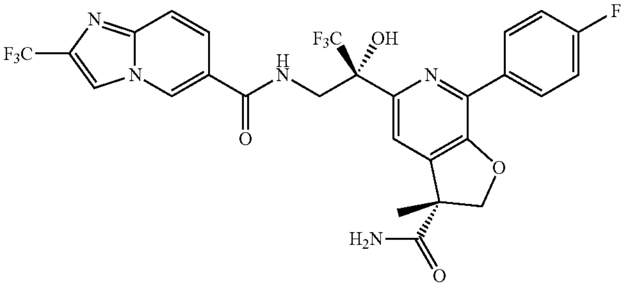 [SMILES: C[C@]1(C(N)=O)COc2c1cc([C@@](O)(CNC(=O)c1ccc3nc(C(F)(F)F)cn3c1)C(F)(F)F)nc2-c1ccc(F)cc1] | 612.30 |

TABLE 1-continued
| Example | Structure | MS+ m/z |
|---|---|---|
| 55 | 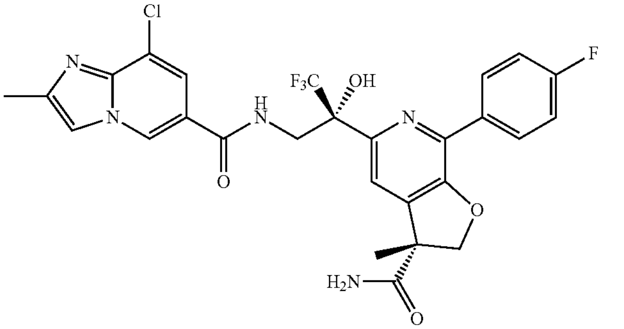 [SMILES: Cc1cn2cc(C(=O)NC[C@](O)(c3cc4c(c(-c5ccc(F)cc5)n3)OC[C@]4(C)C(N)=O)C(F)(F)F)cc(Cl)c2n1] | 592.12 |
| 56 | 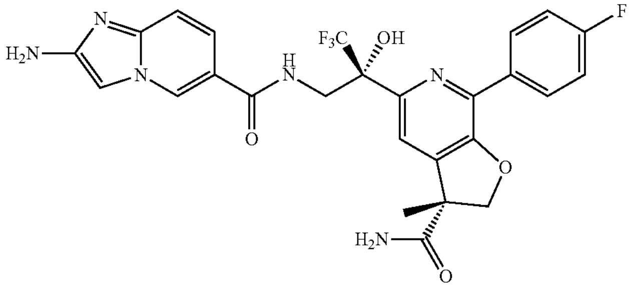 [SMILES: C[C@]1(C(N)=O)COc2c1cc([C@@](O)(CNC(=O)c1ccc3nc(N)cn3c1)C(F)(F)F)nc2-c1ccc(F)cc1] | 559.17 |
| 57 | 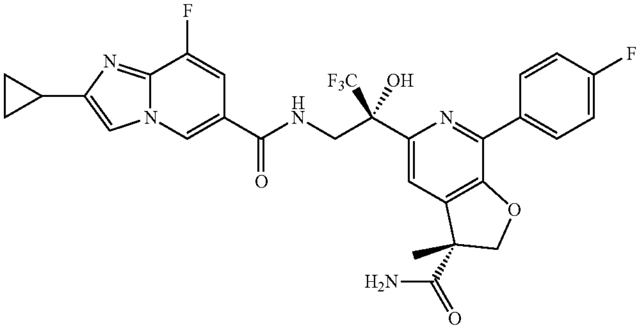 [SMILES: C[C@]1(C(N)=O)COc2c1cc([C@@](O)(CNC(=O)c1cc(F)c3nc(C4CC4)cn3c1)C(F)(F)F)nc2-c1ccc(F)cc1] | 602.17 |
| 58 | 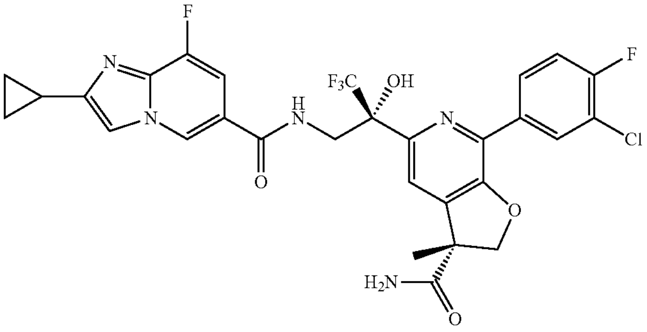 [SMILES: C[C@]1(C(N)=O)COc2c1cc([C@@](O)(CNC(=O)c1cc(F)c3nc(C4CC4)cn3c1)C(F)(F)F)nc2-c1ccc(F)c(Cl)c1] | 636.13 |

TABLE 1-continued
| Example | Structure | MS+ m/z |
|---|---|---|
| 59 | 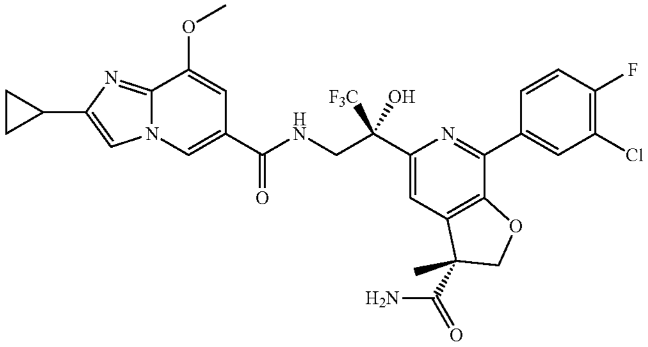 [SMILES: COc1cc(C(=O)NC[C@](O)(c2cc3c(c(-c4ccc(F)c(Cl)c4)n2)OC[C@]3(C)C(N)=O)C(F)(F)F)cn2cc(C3CC3)nc12] | 648.14 |
| 60 | 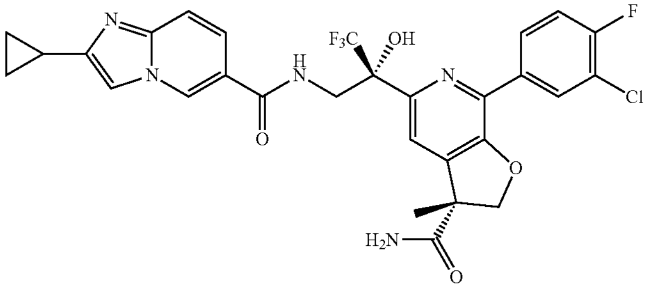 [SMILES: C[C@]1(C(N)=O)COc2c1cc([C@@](O)(CNC(=O)c1ccc3nc(C4CC4)cn3c1)C(F)(F)F)nc2-c1ccc(F)c(Cl)c1] | 618.14 |
| 61 | 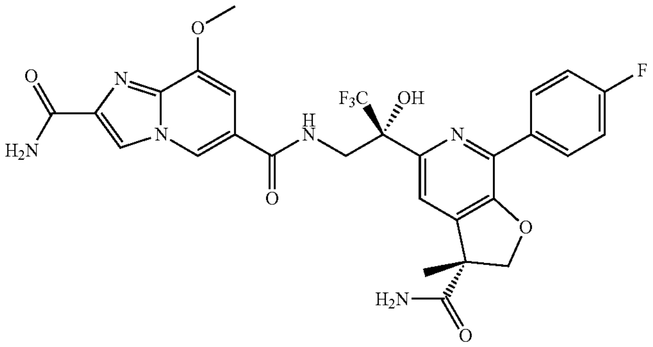 [SMILES: COc1cc(C(=O)NC[C@](O)(c2cc3c(c(-c4ccc(F)cc4)n2)OC[C@]3(C)C(N)=O)C(F)(F)F)cn2cc(C(N)=O)nc12] | 617.15 |
| 62 | 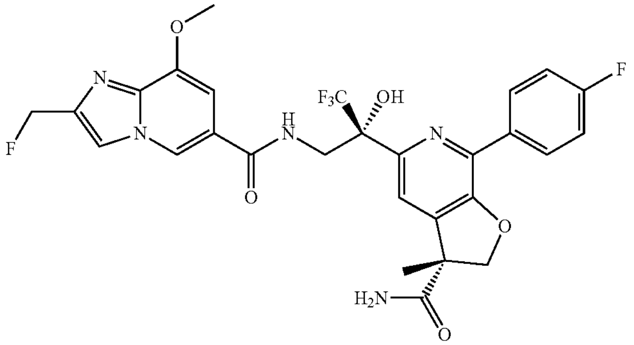 [SMILES: COc1cc(C(=O)NC[C@](O)(c2cc3c(c(-c4ccc(F)cc4)n2)OC[C@]3(C)C(N)=O)C(F)(F)F)cn2cc(CF)nc12] | 606.16 |

TABLE 1-continued
| Example | Structure | MS⁺ m/z |
|---|---|---|
| 63 | 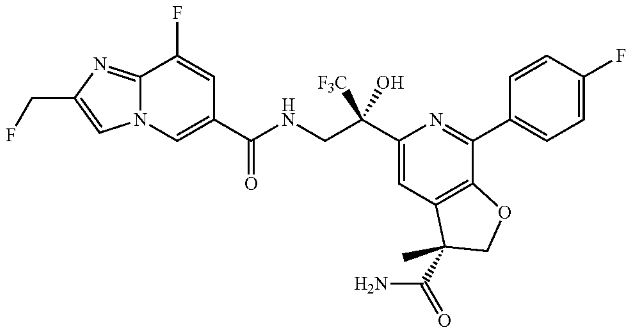 [SMILES: C[C@]1(C(N)=O)COc2c1cc([C@@](O)(CNC(=O)c1cc(F)c3nc(CF)cn3c1)C(F)(F)F)nc2-c1ccc(F)cc1] | 594.13 |
| 64 | 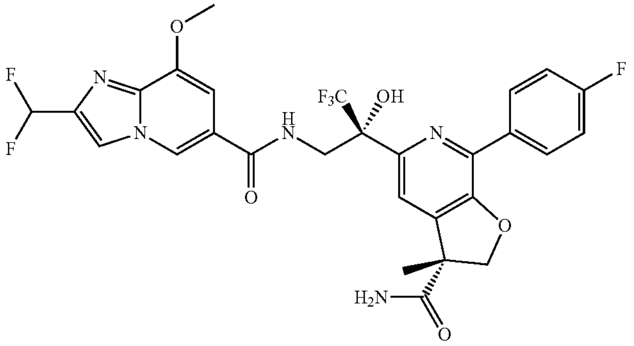 [SMILES: COc1cc(C(=O)NC[C@](O)(c2cc3c(c(-c4ccc(F)cc4)n2)OC[C@]3(C)C(N)=O)C(F)(F)F)cn2cc(C(F)F)nc12] | 624.14 |
| 65 | 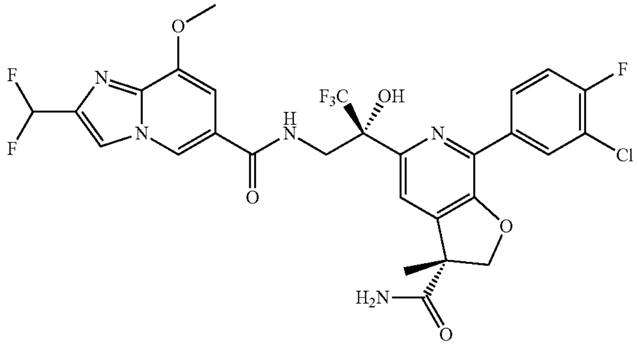 [SMILES: COc1cc(C(=O)NC[C@](O)(c2cc3c(c(-c4ccc(F)c(Cl)c4)n2)OC[C@]3(C)C(N)=O)C(F)(F)F)cn2cc(C(F)F)nc12] | 658.10 |
| 66 | 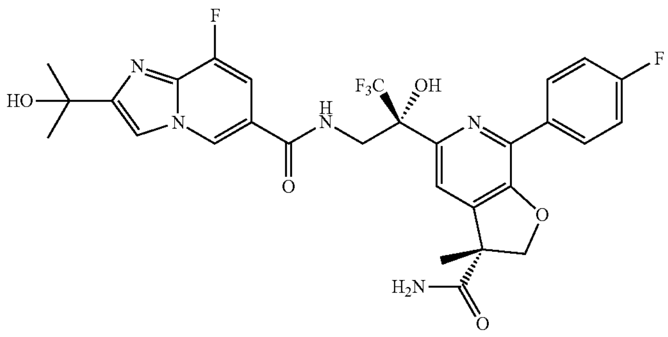 [SMILES: CC(C)(O)c1cn2cc(C(=O)NC[C@](O)(c3cc4c(c(-c5ccc(F)cc5)n3)OC[C@]4(C)C(N)=O)C(F)(F)F)cc(F)c2n1] | 620.17 |

TABLE 1-continued
| Example | Structure | MS+ m/z |
| --- | --- | --- |
| 67 | 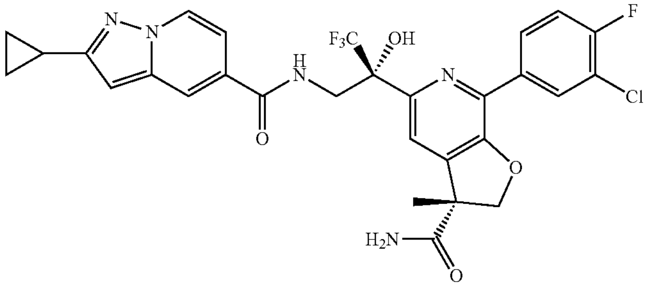 [SMILES: C[C@]1(C(N)=O)COc2c1cc([C@@](O)(CNC(=O)c1ccn3nc(C4CC4)cc3c1)C(F)(F)F)nc2-c1ccc(F)c(Cl)c1] | 618.15 |
| 68 | 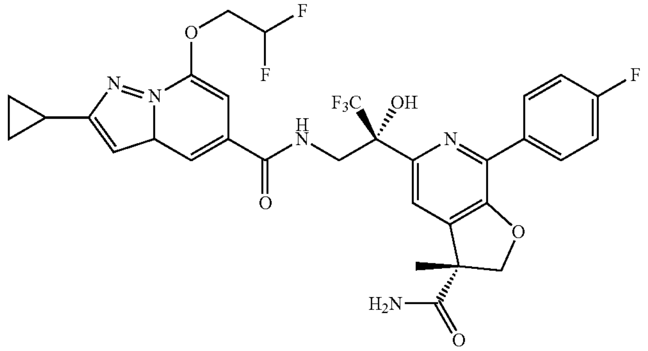 | 664.17 |
| 69 | 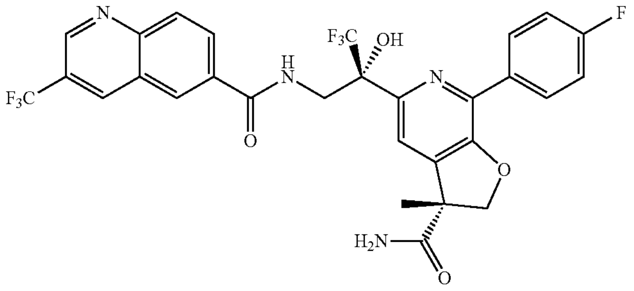 [SMILES: C[C@]1(C(N)=O)COc2c1cc([C@@](O)(CNC(=O)c1ccc3ncc(C(F)(F)F)cc3c1)C(F)(F)F)nc2-c1ccc(F)cc1] | 623.05 |
| 70 | 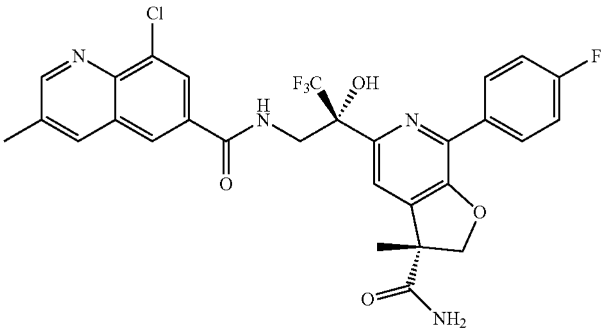 [SMILES: Cc1cnc2c(Cl)cc(C(=O)NC[C@](O)(c3cc4c(c(-c5ccc(F)cc5)n3)OC[C@]4(C)C(N)=O)C(F)(F)F)cc2c1] | 603.05 |

TABLE 1-continued
| Example | Structure | MS⁺ m/z |
|---|---|---|
| 71 | 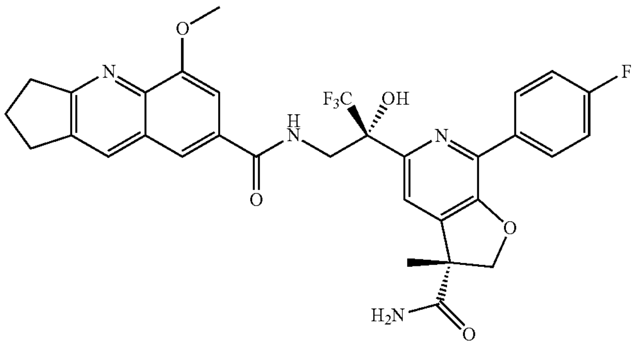 [SMILES: COc1cc(C(=O)NC[C@](O)(c2cc3c(c(-c4ccc(F)cc4)n2)OC[C@]3(C)C(N)=O)C(F)(F)F)cc2cc3c(nc12)CCC3] | 625.00 |
| 72 | 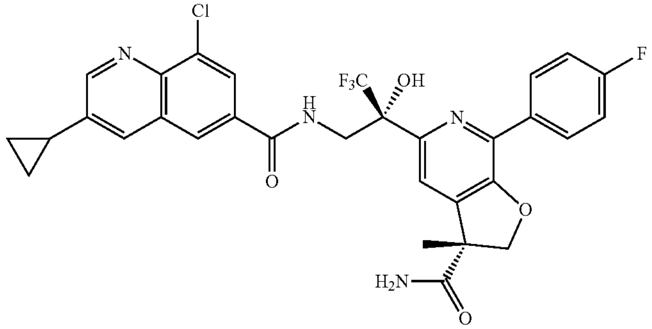 [SMILES: C[C@]1(C(N)=O)COc2c1cc([C@@](O)(CNC(=O)c1cc(Cl)c3ncc(C4CC4)cc3c1)C(F)(F)F)nc2-c1ccc(F)cc1] | 629.15 |
| 73 | 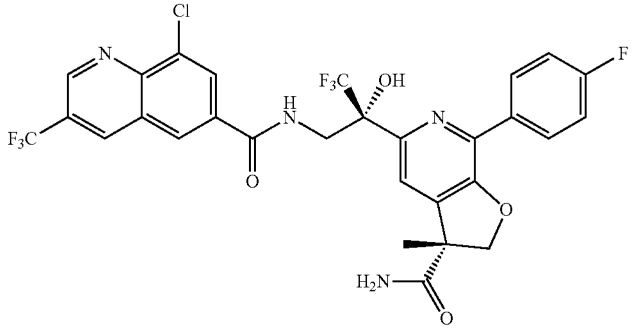 [SMILES: C[C@]1(C(N)=O)COc2c1cc([C@@](O)(CNC(=O)c1cc(Cl)c3ncc(C(F)(F)F)cc3c1)C(F)(F)F)nc2-c1ccc(F)cc1] | 657.15 |
| 74 | 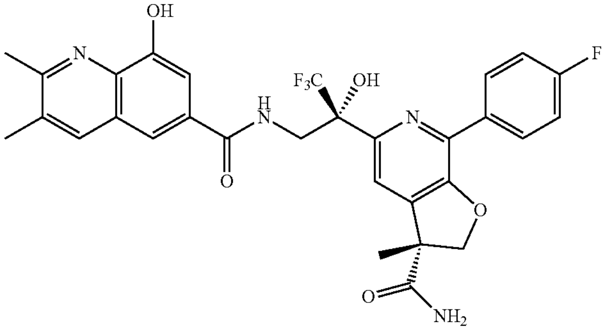 [SMILES: Cc1cc2cc(C(=O)NC[C@](O)(c3cc4c(c(-c5ccc(F)cc5)n3)OC[C@]4(C)C(N)=O)C(F)(F)F)cc(O)c2nc1C] | 599.40 |

TABLE 1-continued
| Example | Structure | MS+ m/z |
|---|---|---|
| 75 | 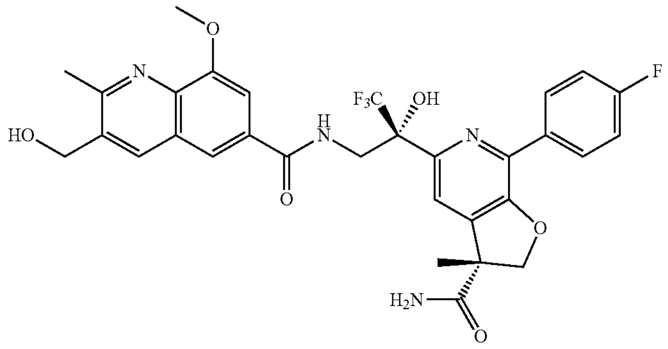 [SMILES: COc1cc(C(=O)NC[C@](O)(c2cc3c(c(-c4ccc(F)cc4)n2)OC[C@]3(C)C(N)=O)C(F)(F)F)cc2cc(CO)c(C)nc12] | 629.15 |
| 76 | 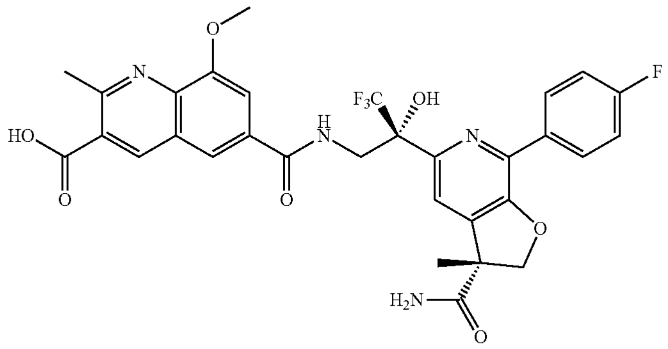 [SMILES: COc1cc(C(=O)NC[C@](O)(c2cc3c(c(-c4ccc(F)cc4)n2)OC[C@]3(C)C(N)=O)C(F)(F)F)cc2cc(C(=O)O)c(C)nc12] | 643.05 |
| 77 | 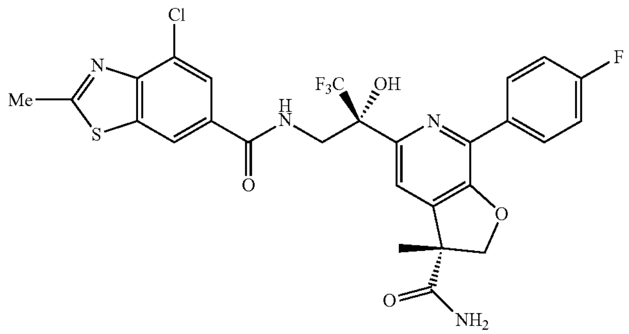 [SMILES: Cc1nc2c(Cl)cc(C(=O)NC[C@](O)(c3cc4c(c(-c5ccc(F)cc5)n3)OC[C@]4(C)C(N)=O)C(F)(F)F)cc2s1] | 609.16 |
| 78 | 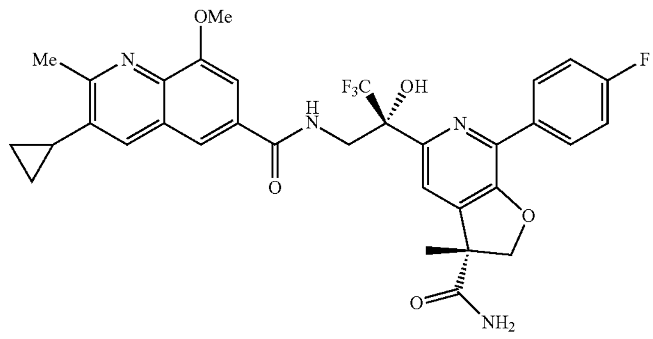 [SMILES: COc1cc(C(=O)NC[C@](O)(c2cc3c(c(-c4ccc(F)cc4)n2)OC[C@]3(C)C(N)=O)C(F)(F)F)cc2cc(C3CC3)c(C)nc12] | 639.10 |

TABLE 1-continued
| Example | Structure | MS+ m/z |
|---|---|---|
| 79 | 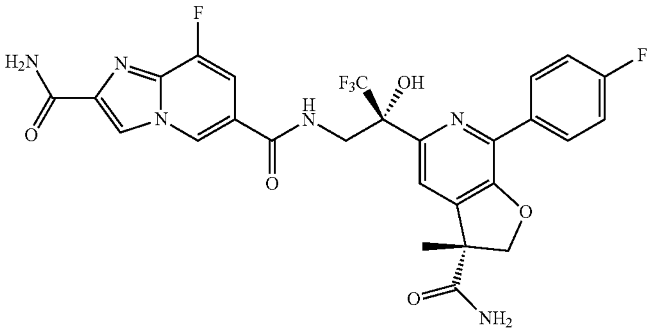 [SMILES: C[C@]1(C(N)=O)COc2c1cc([C@@](O)(CNC(=O)c1cc(F)c3nc(C(N)=O)cn3c1)C(F)(F)F)nc2-c1ccc(F)cc1] | 605.15 |
| 80 | 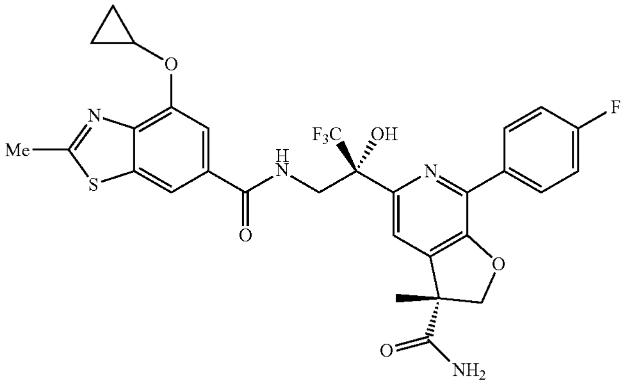 [SMILES: Cc1nc2c(OC3CC3)cc(C(=O)NC[C@](O)(c3cc4c(c(-c5ccc(F)cc5)n3)OC[C@]4(C)C(N)=O)C(F)(F)F)cc2s1] | 631.05 |
| 81 | 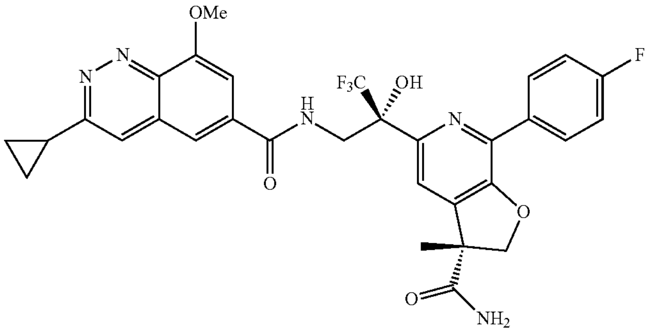 [SMILES: COc1cc(C(=O)NC[C@](O)(c2cc3c(c(-c4ccc(F)cc4)n2)OC[C@]3(C)C(N)=O)C(F)(F)F)cc2cc(C3CC3)nnc12] | 626.00 |
| 82 | 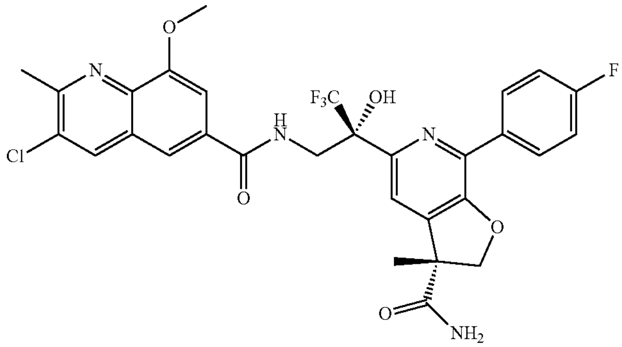 [SMILES: COc1cc(C(=O)NC[C@](O)(c2cc3c(c(-c4ccc(F)cc4)n2)OC[C@]3(C)C(N)=O)C(F)(F)F)cc2cc(Cl)c(C)nc12] | 633.00 |

TABLE 1-continued
| Example | Structure | MS+ m/z |
| --- | --- | --- |
| 83 | 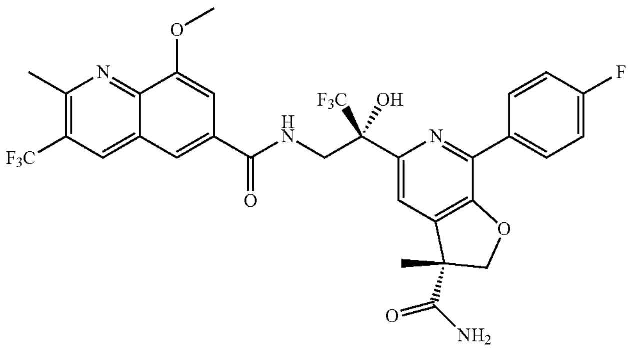 [SMILES: COc1cc(C(=O)NC[C@](O)(c2cc3c(c(-c4ccc(F)cc4)n2)OC[C@]3(C)C(N)=O)C(F)(F)F)cc2cc(C(F)(F)F)c(C)nc12] | 667.07 |
| 84 | 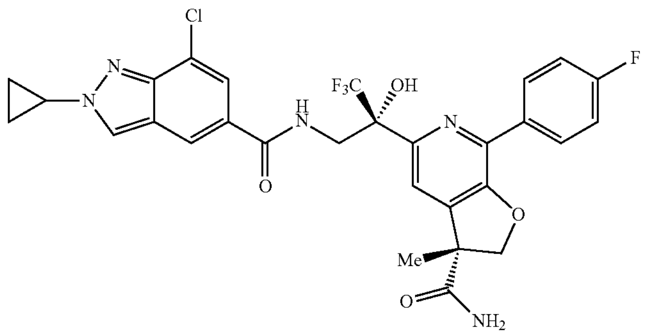 [SMILES: C[C@]1(C(N)=O)COc2c1cc([C@@](O)(CNC(=O)c1cc(Cl)c3nn(C4CC4)cc3c1)C(F)(F)F)nc2-c1ccc(F)cc1] | 618.20 |
| 85 | 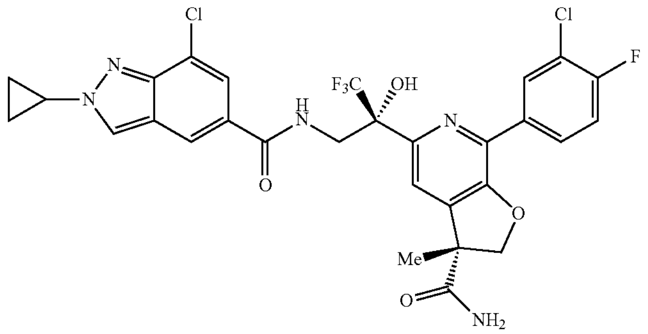 [SMILES: C[C@]1(C(N)=O)COc2c1cc([C@@](O)(CNC(=O)c1cc(Cl)c3nn(C4CC4)cc3c1)C(F)(F)F)nc2-c1ccc(F)c(Cl)c1] | 652.15 |
| 86 | 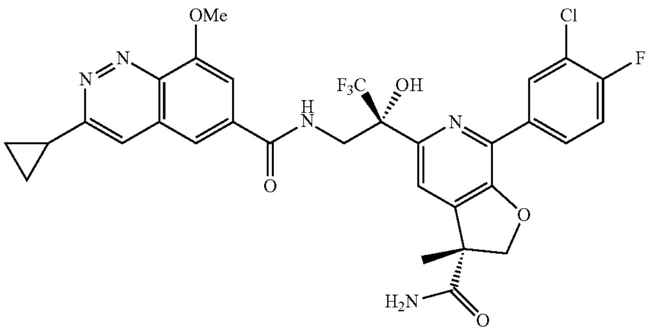 [SMILES: COc1cc(C(=O)NC[C@](O)(c2cc3c(c(-c4ccc(F)c(Cl)c4)n2)OC[C@]3(C)C(N)=O)C(F)(F)F)cc2cc(C3CC3)nnc12] | 660.20 |

TABLE 1-continued
| Example | Structure | MS+ m/z |
| --- | --- | --- |
| 87 | 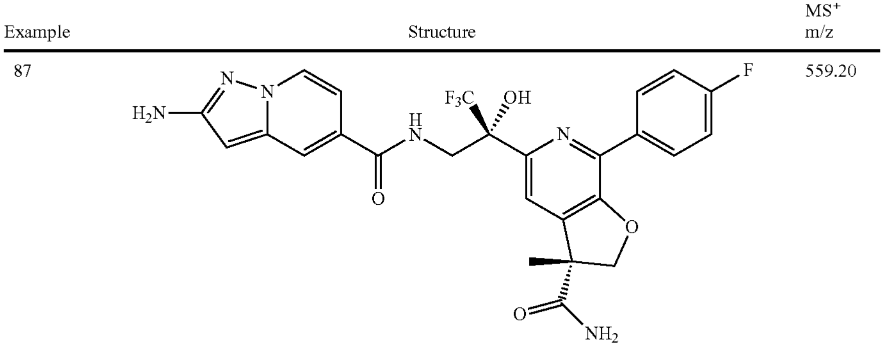 | 559.20 |
| 88 | 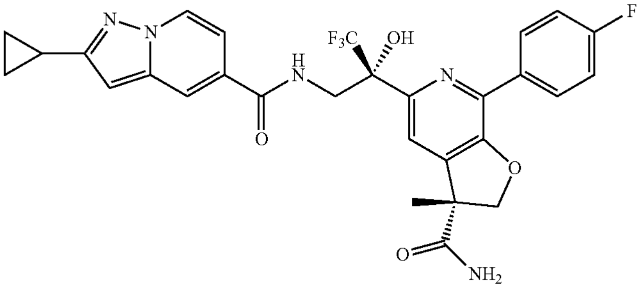 [SMILES: C[C@]1(C(N)=O)COc2c1cc([C@@](O)(CNC(=O)c1ccn3nc(C4CC4)cc3c1)C(F)(F)F)nc2-c1ccc(F)cc1] | 584.20 |
| 89 | 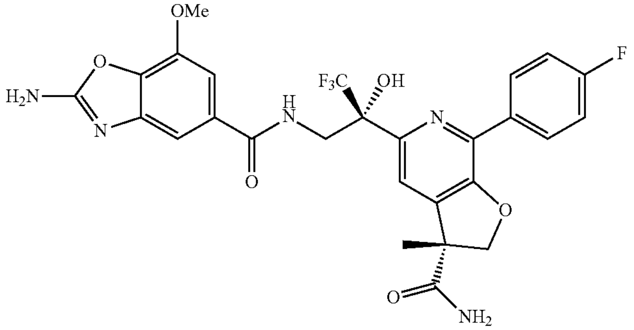 [SMILES: COc1cc(C(=O)NC[C@](O)(c2cc3c(c(-c4ccc(F)cc4)n2)OC[C@]3(C)C(N)=O)C(F)(F)F)cc2nc(N)oc12] | 590.15 |
| 90 | 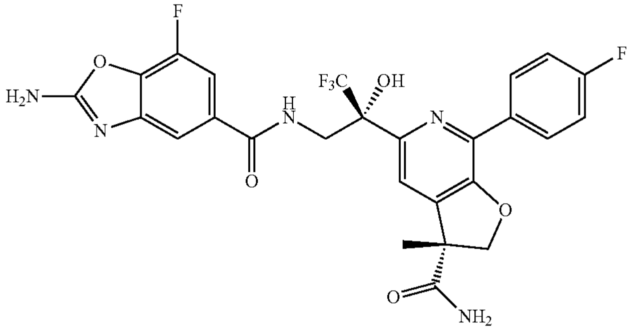 [SMILES: C[C@]1(C(N)=O)COc2c1cc([C@@](O)(CNC(=O)c1cc(F)c3oc(N)nc3c1)C(F)(F)F)nc2-c1ccc(F)cc1] | 578.15 |
| 91 | 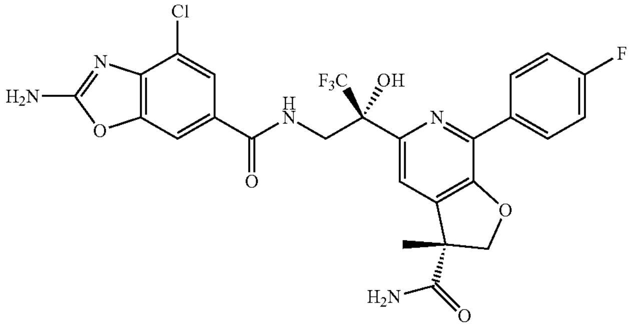 [SMILES: C[C@]1(C(N)=O)COc2c1cc([C@@](O)(CNC(=O)c1cc(Cl)c3nc(N)oc3c1)C(F)(F)F)nc2-c1ccc(F)cc1] | 594.10 |

TABLE 1-continued
| Example | Structure | MS+ m/z |
|---|---|---|
| 92 | 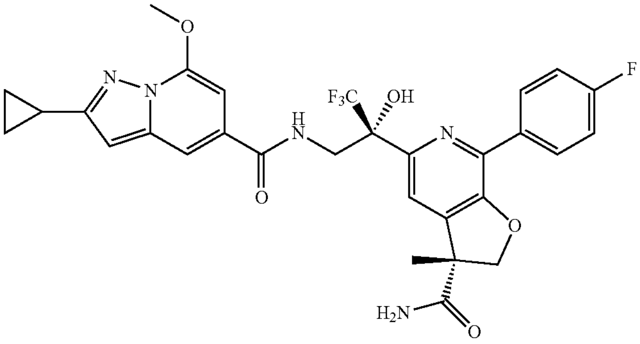 [SMILES: COc1cc(C(=O)NC[C@](O)(c2cc3c(c(-c4ccc(F)cc4)n2)OC[C@]3(C)C(N)=O)C(F)(F)F)cc2cc(C3CC3)nn12] | 614.15 |
| 93 | 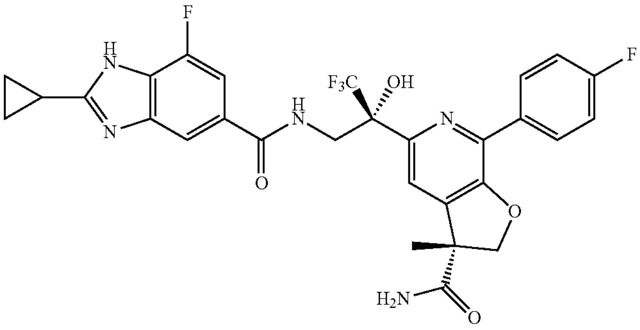 | 602.15 |
| 94 | 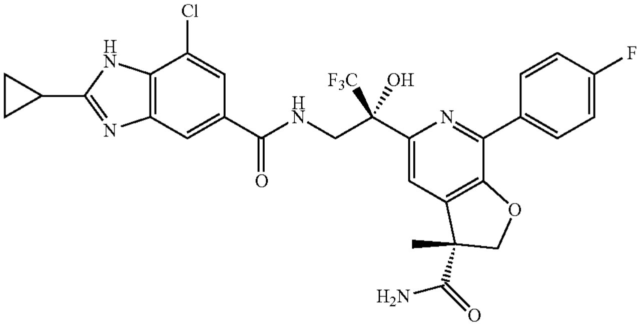 [SMILES: C[C@]1(C(N)=O)COc2c1cc([C@@](O)(CNC(=O)c1cc(F)c3[nH]c(C4CC4)nc3c1)C(F)(F)F)nc2-c1ccc(F)cc1] | 618.15 |
| 95 | 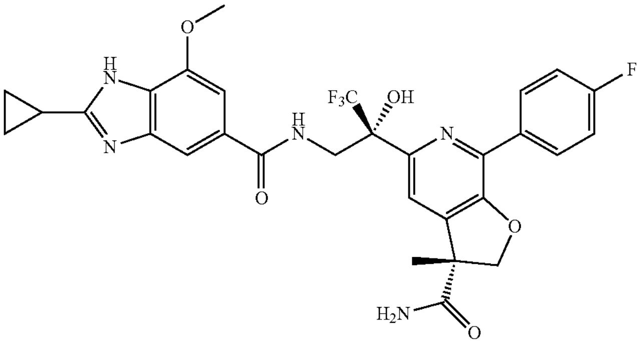 [SMILES: COc1cc(C(=O)NC[C@](O)(c2cc3c(c(-c4ccc(F)cc4)n2)OC[C@]3(C)C(N)=O)C(F)(F)F)cc2nc(C3CC3)[nH]c12] | 614.15 |

TABLE 1-continued
| Example | Structure | MS+ m/z |
| --- | --- | --- |
| 96 | 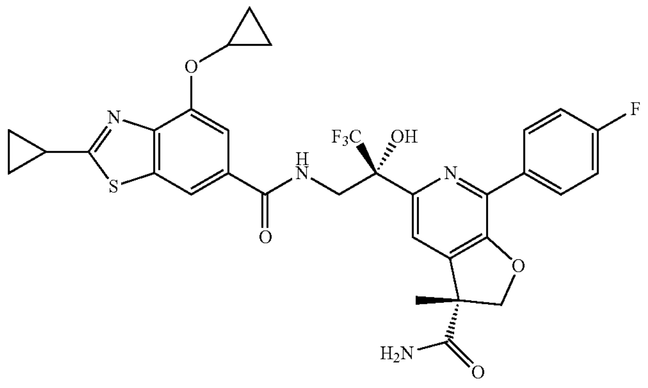 [SMILES: C[C@]1(C(N)=O)COc2c1cc([C@@](O)(CNC(=O)c1cc(OC3CC3)c3nc(C4CC4)sc3c1)C(F)(F)F)nc2-c1ccc(F)cc1] | 657.20 |
| 97 | 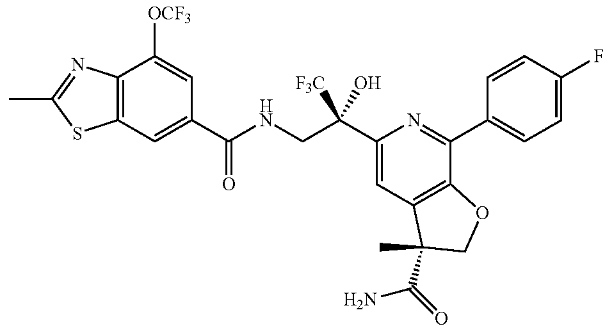 [SMILES: Cc1nc2c(OC(F)(F)F)cc(C(=O)NC[C@](O)(c3cc4c(c(-c5ccc(F)cc5)n3)OC[C@]4(C)C(N)=O)C(F)(F)F)cc2s1] | 659.05 |
| 98 | 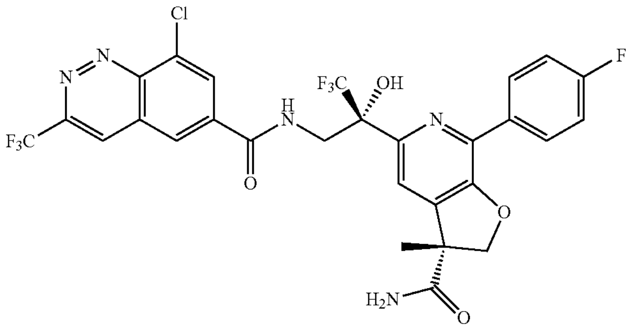 [SMILES: C[C@]1(C(N)=O)COc2c1cc([C@@](O)(CNC(=O)c1cc(Cl)c3nnc(C(F)(F)F)cc3c1)C(F)(F)F)nc2-c1ccc(F)cc1] | 658.10 |
| 99 | 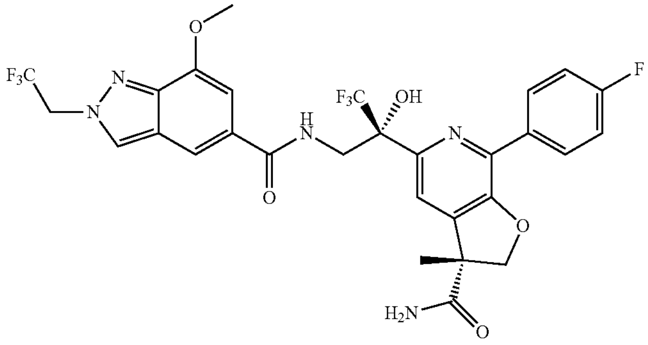 [SMILES: COc1cc(C(=O)NC[C@](O)(c2cc3c(c(-c4ccc(F)cc4)n2)OC[C@]3(C)C(N)=O)C(F)(F)F)cc2cn(CC(F)(F)F)nc12] | 656.15 |

TABLE 1-continued
| Example | Structure | MS+ m/z |
|---|---|---|
| 100 | 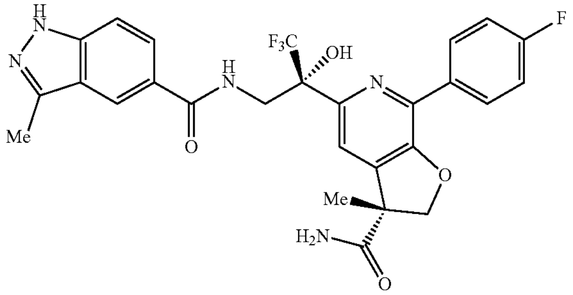 [SMILES: Cc1n[nH]c2ccc(C(=O)NC[C@](O)(c3cc4c(c(-c5ccc(F)cc5)n3)OC[C@]4(C)C(N)=O)C(F)(F)F)cc12] | 558.2 |
| 101 | 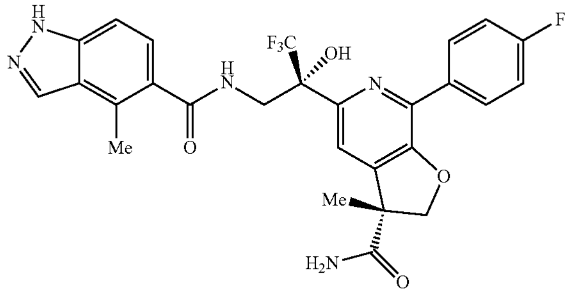 [SMILES: Cc1c(C(=O)NC[C@](O)(c2cc3c(c(-c4ccc(F)cc4)n2)OC[C@]3(C)C(N)=O)C(F)(F)F)ccc2[nH]ncc12] | 558.1 |
| 102 | 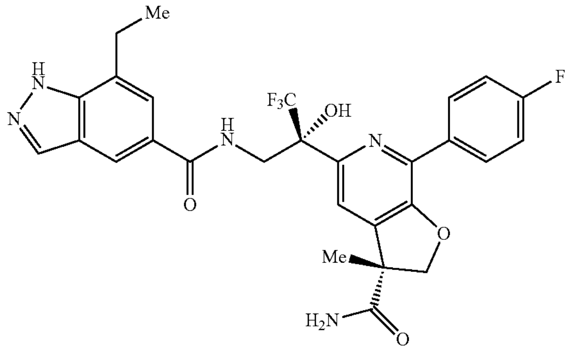 [SMILES: CCc1cc(C(=O)NC[C@](O)(c2cc3c(c(-c4ccc(F)cc4)n2)OC[C@]3(C)C(N)=O)C(F)(F)F)cc2cn[nH]c12] | 572.2 |
| 103 | 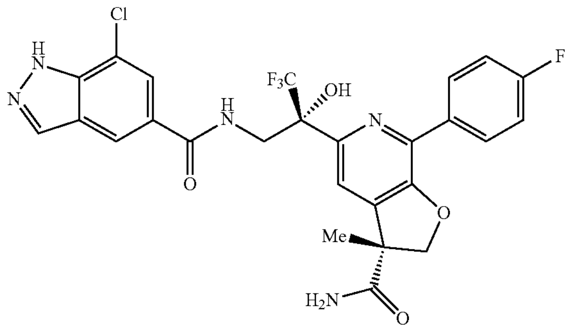 [SMILES: C[C@]1(C(N)=O)COc2c1cc([C@@](O)(CNC(=O)c1cc(Cl)c3[nH]ncc3c1)C(F)(F)F)nc2-c1ccc(F)cc1] | 578.0 |

TABLE 1-continued
| Example | Structure | MS⁺ m/z |
| --- | --- | --- |
| 104 | 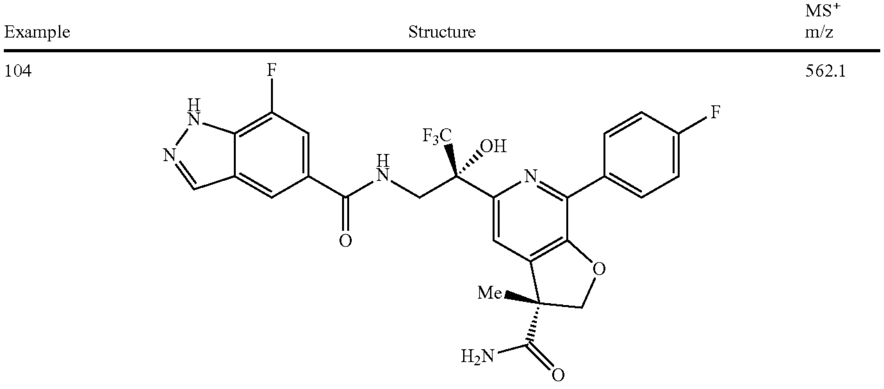 | 562.1 |
| 105 | 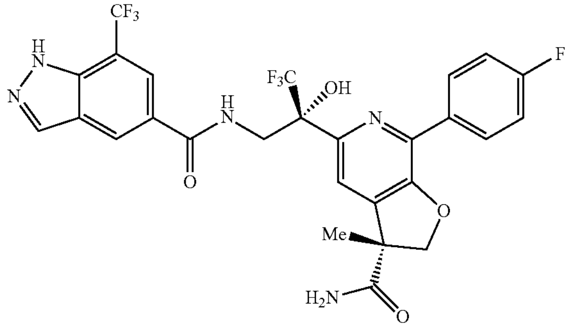 | 612.1 |
| 106 | 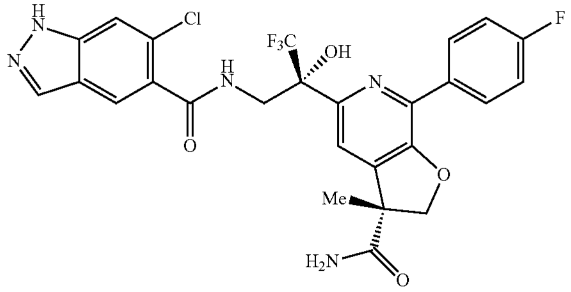 [SMILES: C[C@]1(C(N)=O)COc2c1cc([C@@](O)(CNC(=O)c1cc3cn[nH]c3cc1Cl)C(F)(F)F)nc2-c1ccc(F)cc1] | 578.0 |
| 107 | 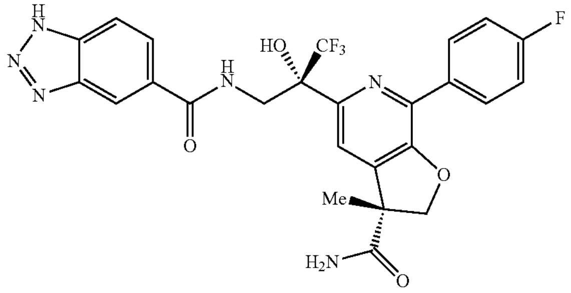 [SMILES: C[C@]1(C(N)=O)COc2c1cc([C@@](O)(CNC(=O)c1ccc3[nH]nnc3c1)C(F)(F)F)nc2-c1ccc(F)cc1] | 545.1 |
| 108 | 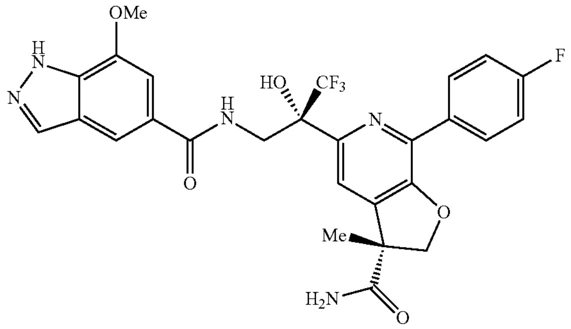 [SMILES: COc1cc(C(=O)NC[C@](O)(c2cc3c(c(-c4ccc(F)cc4)n2)OC[C@]3(C)C(N)=O)C(F)(F)F)cc2cn[nH]c12] | 574.0 |

TABLE 1-continued
| Example | Structure | MS+ m/z |
|---|---|---|
| 109 | 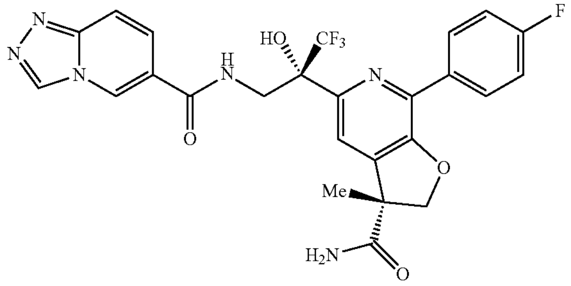 [SMILES: C[C@]1(C(N)=O)COc2c1cc([C@@](O)(CNC(=O)c1ccc3nncn3c1)C(F)(F)F)nc2-c1ccc(F)cc1] | 545.1 |
| 110 | 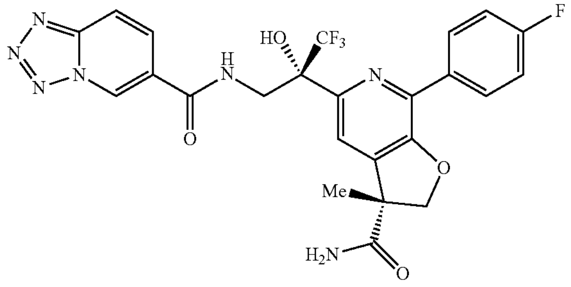 [SMILES: C[C@]1(C(N)=O)COc2c1cc([C@@](O)(CNC(=O)c1ccc3nnnn3c1)C(F)(F)F)nc2-c1ccc(F)cc1] | 546.1 |
| 111 | 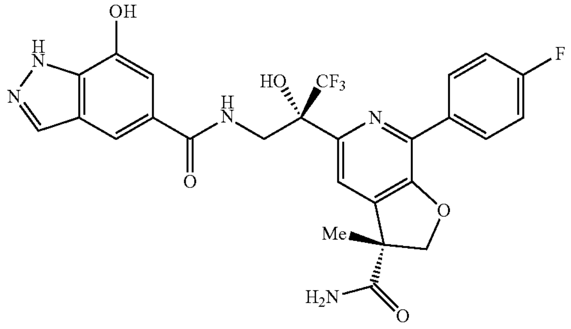 [SMILES: C[C@]1(C(N)=O)COc2c1cc([C@@](O)(CNC(=O)c1cc(O)c3[nH]ncc3c1)C(F)(F)F)nc2-c1ccc(F)cc1] | 560.00 |
| 112 | 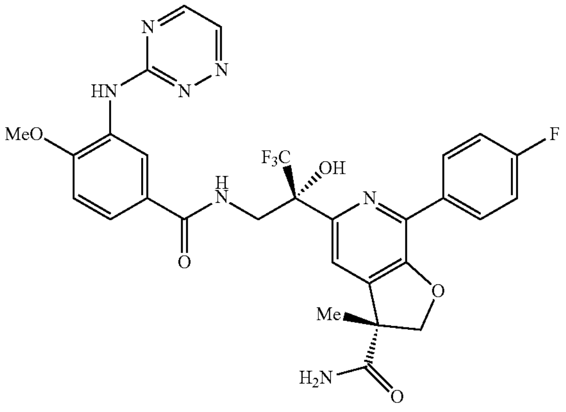 [SMILES: COc1ccc(C(=O)NC[C@](O)(c2cc3c(c(-c4ccc(F)cc4)n2)OC[C@]3(C)C(N)=O)C(F)(F)F)cc1Nc1nccnn1] | 628.30 |

TABLE 1-continued
| Example | Structure | MS+ m/z |
|---|---|---|
| 113 | 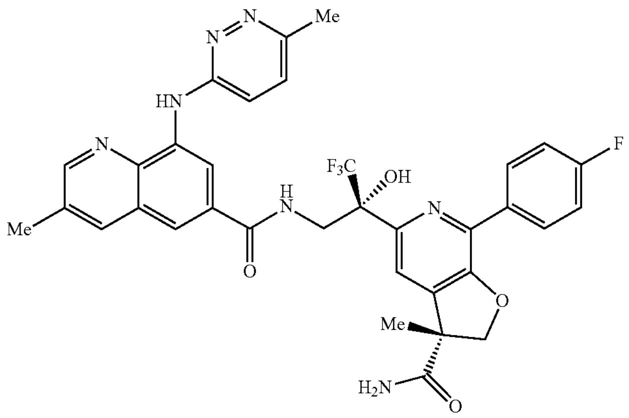 [SMILES: Cc1cnc2c(Nc3ccc(C)nn3)cc(C(=O)NC[C@](O)(c3cc4c(c(-c5ccc(F)cc5)n3)OC[C@]4(C)C(N)=O)C(F)(F)F)cc2c1] | 676.20 |
| 114 | 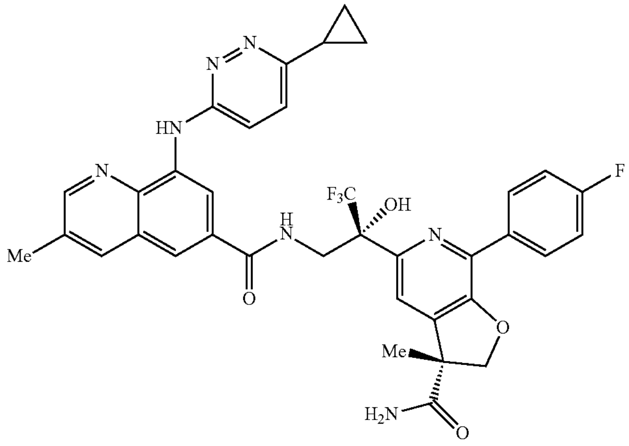 [SMILES: Cc1cnc2c(Nc3ccc(C4CC4)nn3)cc(C(=O)NC[C@](O)(c3cc4c(c(-c5ccc(F)cc5)n3)OC[C@]4(C)C(N)=O)C(F)(F)F)cc2c1] | 702.50 |
| 115 | 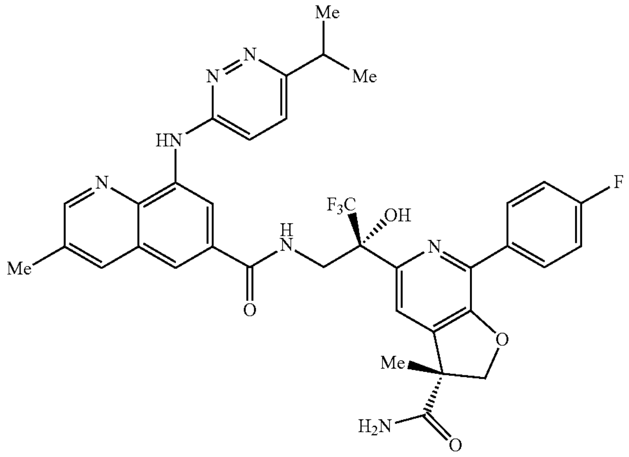 [SMILES: Cc1cnc2c(Nc3ccc(C(C)C)nn3)cc(C(=O)NC[C@](O)(c3cc4c(c(-c5ccc(F)cc5)n3)OC[C@]4(C)C(N)=O)C(F)(F)F)cc2c1] | 704.50 |

TABLE 1-continued
| Example | Structure | MS+ m/z |
| --- | --- | --- |
| 116 | 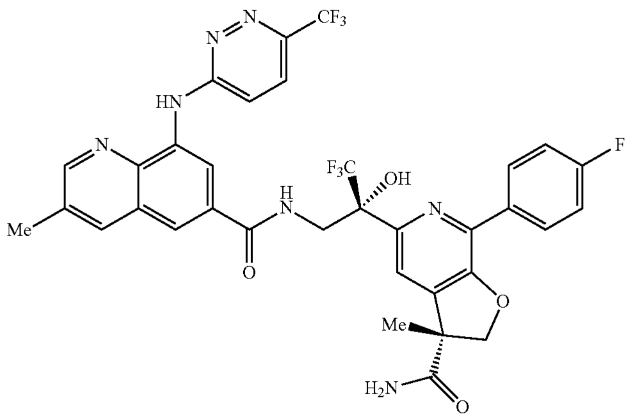 [SMILES: Cc1cnc2c(Nc3ccc(C(F)(F)F)nn3)cc(C(=O)NC[C@](O)(c3cc4c(c(-c5ccc(F)cc5)n3)OC[C@]4(C)C(N)=O)C(F)(F)F)cc2c1] | 730.30 |
| 117 | 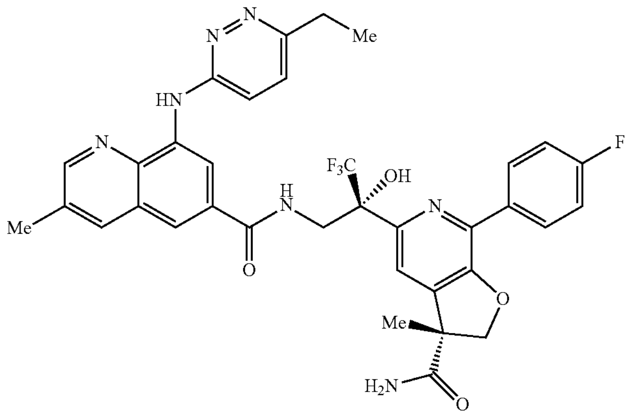 [SMILES: CCc1ccc(Nc2cc(C(=O)NC[C@](O)(c3cc4c(c(-c5ccc(F)cc5)n3)OC[C@]4(C)C(N)=O)C(F)(F)F)cc3cc(C)cnc23)nn1] | 690.50 |
| 118 | 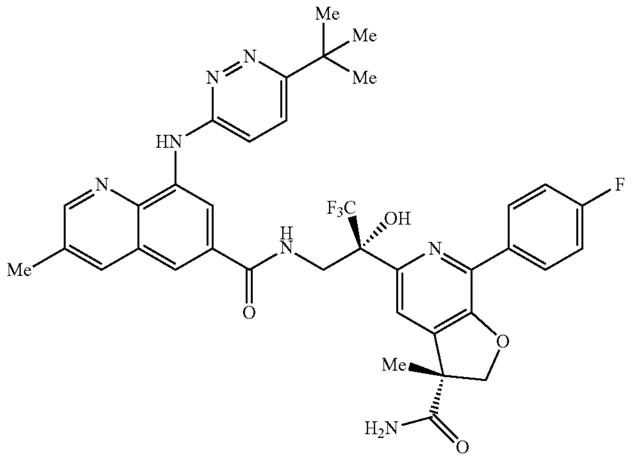 [SMILES: Cc1cnc2c(Nc3ccc(C(C)(C)C)nn3)cc(C(=O)NC[C@](O)(c3cc4c(c(-c5ccc(F)cc5)n3)OC[C@]4(C)C(N)=O)C(F)(F)F)cc2c1] | 718.50 |

TABLE 1-continued
| Example | Structure | MS+ m/z |
|---|---|---|
| 119 | 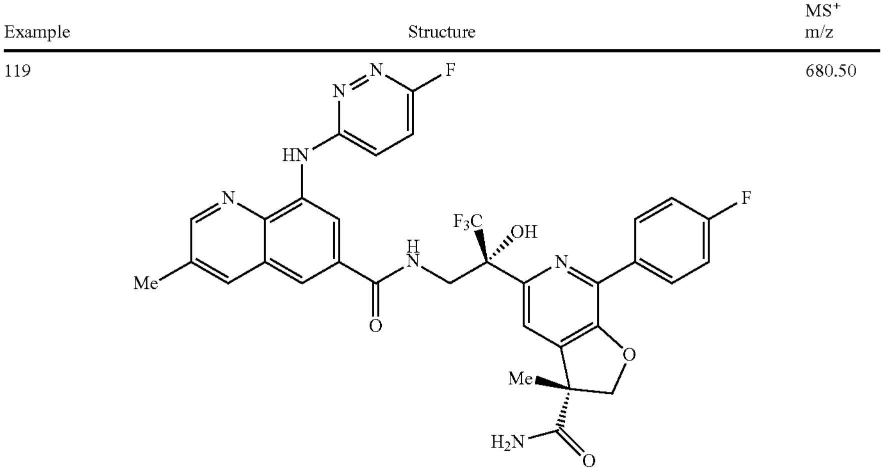 | 680.50 |
| 120 | 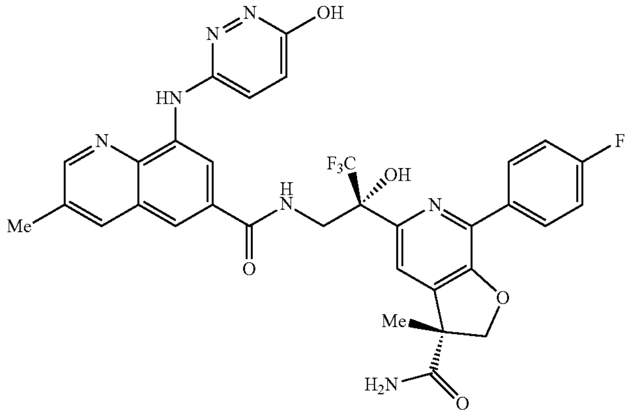 [SMILES: Cc1cnc2c(Nc3ccc(O)nn3)cc(C(=O)NC[C@](O)(c3cc4c(c(-c5ccc(F)cc5)n3)OC[C@]4(C)C(N)=O)C(F)(F)F)cc2c1] | 678.10 |
| 121 | 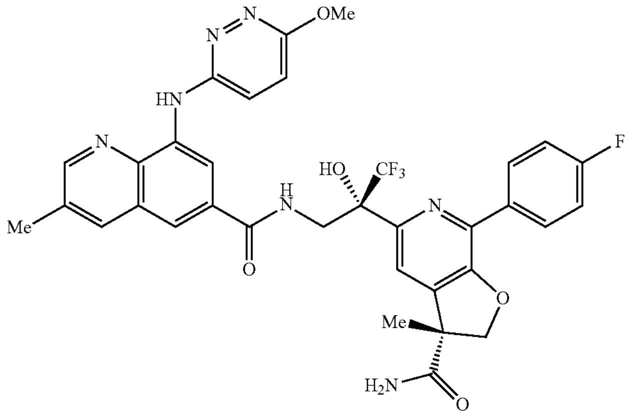 [SMILES: COc1ccc(Nc2cc(C(=O)NC[C@](O)(c3cc4c(c(-c5ccc(F)cc5)n3)OC[C@]4(C)C(N)=O)C(F)(F)F)cc3cc(C)cnc23)nn1] | 692.20 |
| 122 | 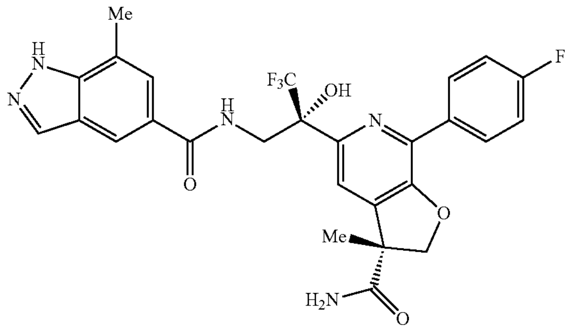 | 558.00 |

TABLE 1-continued
| Example | Structure | MS+ m/z |
|---|---|---|
| 123 | 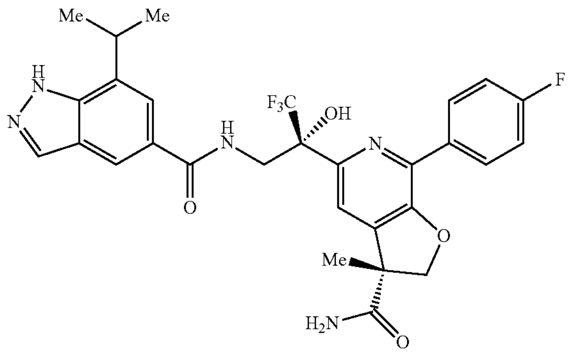 [SMILES: CC(C)c1cc(C(=O)NC[C@](O)(c2cc3c(c(-c4ccc(F)cc4)n2)OC[C@]3(C)C(N)=O)C(F)(F)F)cc2cn[nH]c12] | 586.20 |
| 124 | 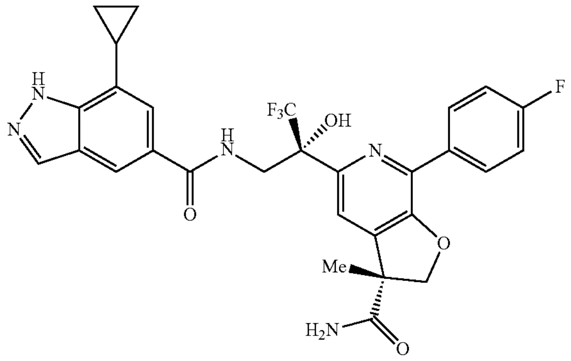 [SMILES: C[C@]1(C(N)=O)COc2c1cc([C@@](O)(CNC(=O)c1cc(C3CC3)c3[nH]ncc3c1)C(F)(F)F)nc2-c1ccc(F)cc1] | 548.20 |
| 125 | 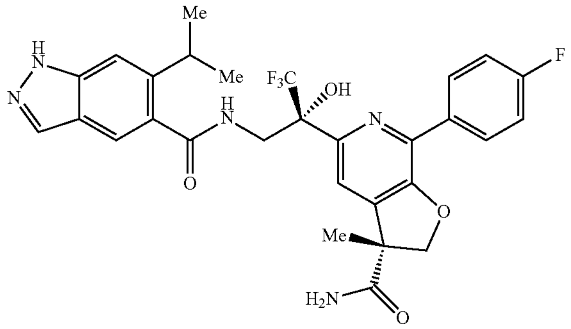 [SMILES: CC(C)c1cc2[nH]ncc2cc1C(=O)NC[C@](O)(c1cc2c(c(-c3ccc(F)cc3)n1)OC[C@]2(C)C(N)=O)C(F)(F)F] | 586.20 |
| 126 | 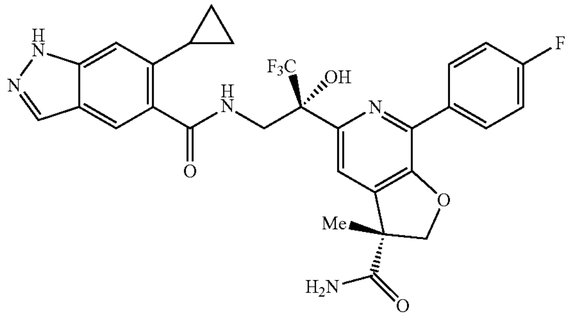 [SMILES: C[C@]1(C(N)=O)COc2c1cc([C@@](O)(CNC(=O)c1cc3cn[nH]c3cc1C1CC1)C(F)(F)F)nc2-c1ccc(F)cc1] | 584.10 |

TABLE 1-continued
| Example | Structure | MS+ m/z |
|---|---|---|
| 127 | 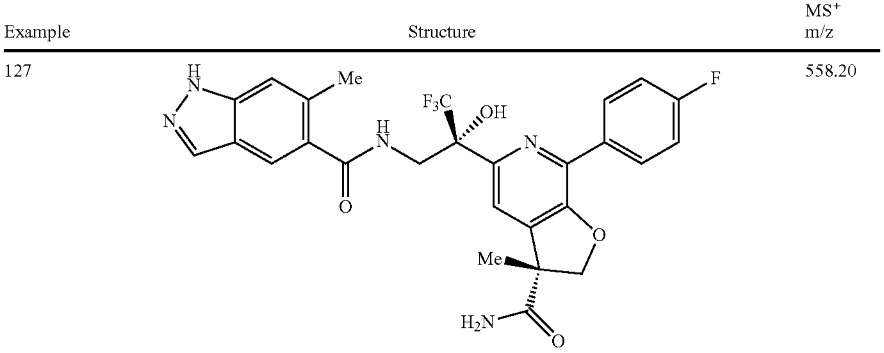 | 558.20 |
| 128 | 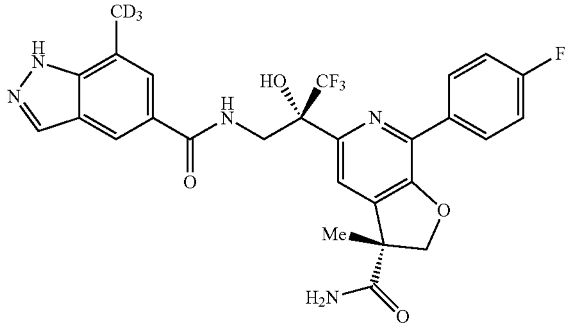 [SMILES: [2H]C([2H])([2H])c1cc(C(=O)NC[C@](O)(c2cc3c(c(-c4ccc(F)cc4)n2)OC[C@]3(C)C(N)=O)C(F)(F)F)cc2cn[nH]c12] | 561.10 |
| 129 | 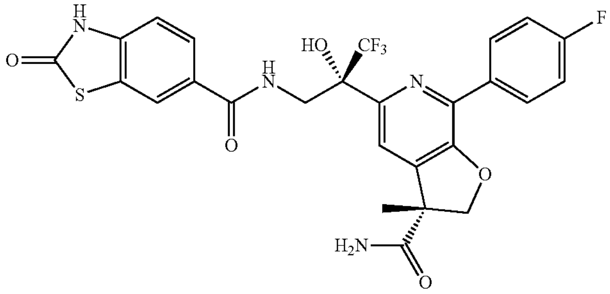 [SMILES: C[C@]1(C(N)=O)COc2c1cc([C@@](O)(CNC(=O)c1ccc3[nH]c(=O)sc3c1)C(F)(F)F)nc2-c1ccc(F)cc1] | 576.50 |
| 130 | 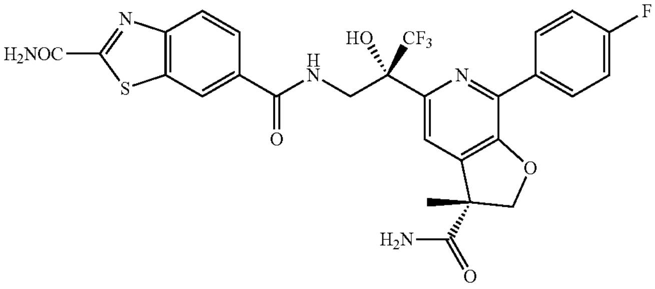 [SMILES: C[C@]1(C(N)=O)COc2c1cc([C@@](O)(CNC(=O)c1ccc3nc(C(N)=O)sc3c1)C(F)(F)F)nc2-c1ccc(F)cc1] | 604.12 |
| 131 | 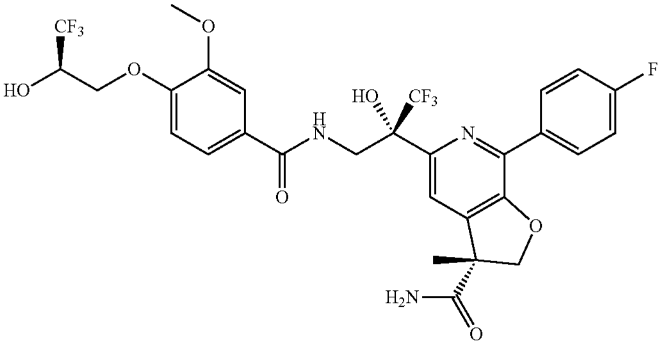 [SMILES: COc1cc(C(=O)NC[C@](O)(c2cc3c(c(-c4ccc(F)cc4)n2)OC[C@]3(C)C(N)=O)C(F)(F)F)ccc1OC[C@@H](O)C(F)(F)F] | 661.50 |

TABLE 1-continued
| Example | Structure | MS+ m/z |
|---|---|---|
| 132 | 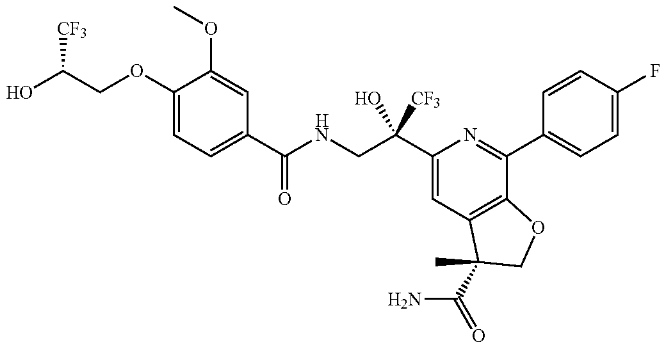 [SMILES: COc1cc(C(=O)NC[C@](O)(c2cc3c(c(-c4ccc(F)cc4)n2)OC[C@]3(C)C(N)=O)C(F)(F)F)ccc1OC[C@H](O)C(F)(F)F] | 661.50 |
| 133 | 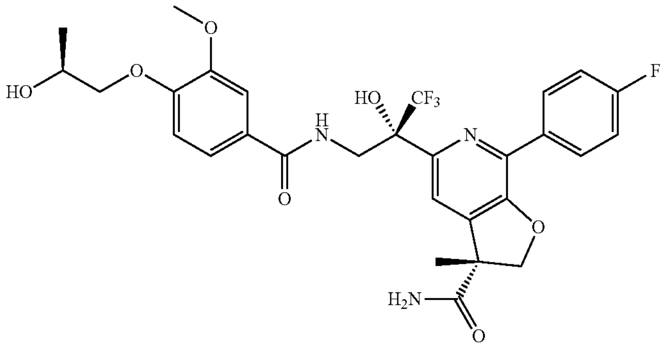 [SMILES: COc1cc(C(=O)NC[C@](O)(c2cc3c(c(-c4ccc(F)cc4)n2)OC[C@]3(C)C(N)=O)C(F)(F)F)ccc1OC[C@H](C)O] | 607.60 |
| 134 | 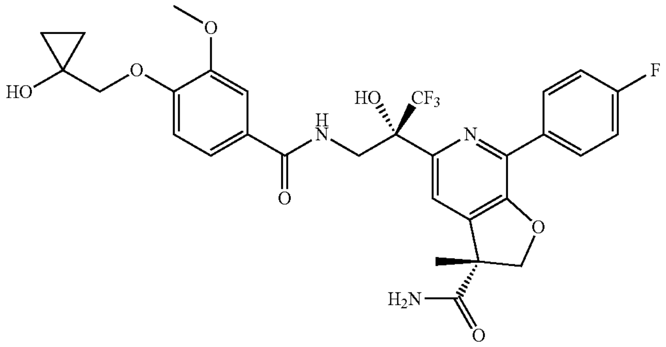 [SMILES: COc1cc(C(=O)NC[C@](O)(c2cc3c(c(-c4ccc(F)cc4)n2)OC[C@]3(C)C(N)=O)C(F)(F)F)ccc1OCC1(O)CC1] | 619.6 |
| 135 | 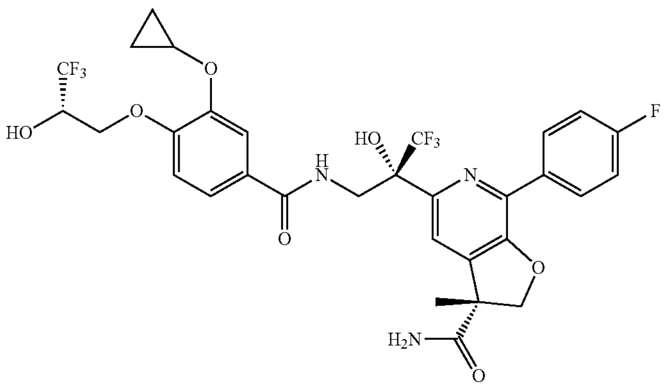 [SMILES: C[C@]1(C(N)=O)COc2c1cc([C@@](O)(CNC(=O)c1ccc(OC[C@H](O)C(F)(F)F)c(OC3CC3)c1)C(F)(F)F)nc2-c1ccc(F)cc1] | 687.60 |

TABLE 1-continued
| Example | Structure | MS+ m/z |
|---|---|---|
| 136 | 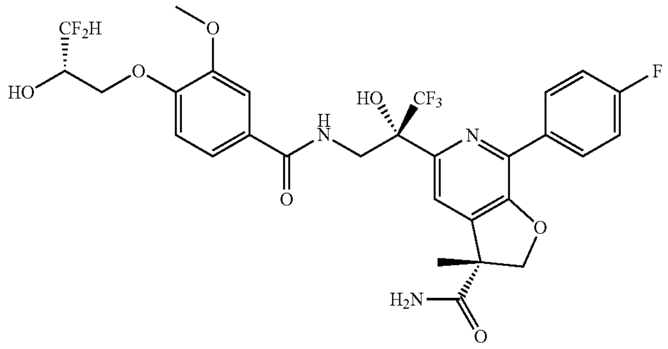 | 643.50 |
| 137 | 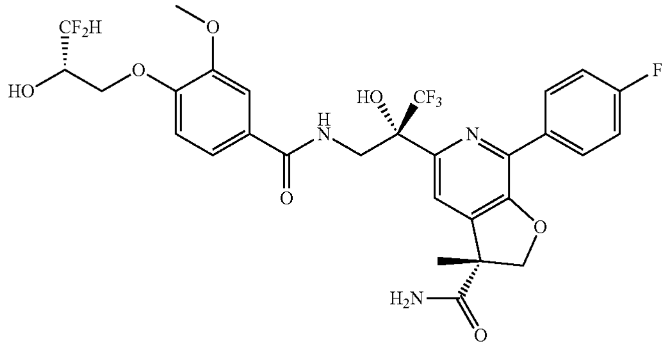 [SMILES: COc1cc(C(=O)NC[C@](O)(c2cc3c(c(-c4ccc(F)cc4)n2)OC[C@]3(C)C(N)=O)C(F)(F)F)ccc1OC[C@H](O)C(F)F] | 625.5 |
| 138 | 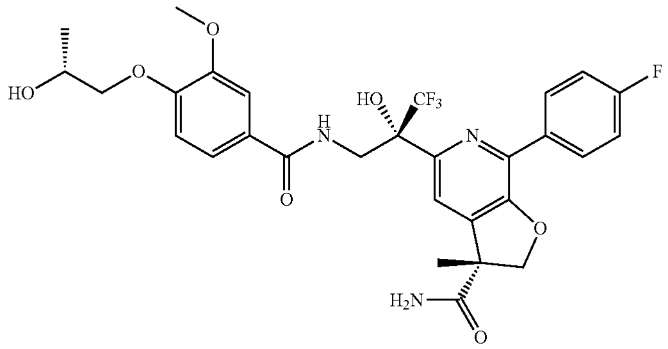 [SMILES: COc1cc(C(=O)NC[C@](O)(c2cc3c(c(-c4ccc(F)cc4)n2)OC[C@]3(C)C(N)=O)C(F)(F)F)ccc1OC[C@@H](C)O] | 606.60 |
| 139 | 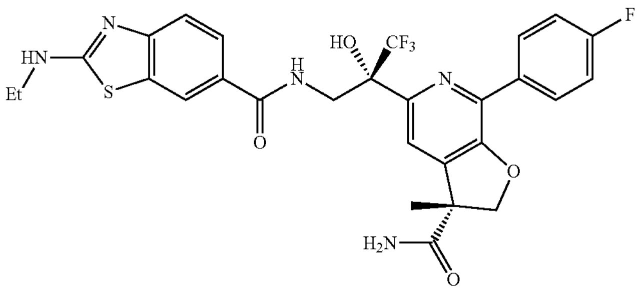 [SMILES: CCNc1nc2ccc(C(=O)NC[C@](O)(c3cc4c(c(-c5ccc(F)cc5)n3)OC[C@]4(C)C(N)=O)C(F)(F)F)cc2s1] | 603.60 |

TABLE 1-continued
| Example | Structure | MS+ m/z |
|---|---|---|
| 140 | 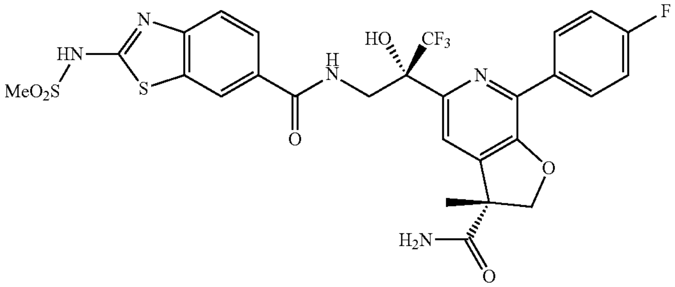 [SMILES: C[C@]1(C(N)=O)COc2c1cc([C@@](O)(CNC(=O)c1ccc3nc(NS(C)(=O)=O)sc3c1)C(F)(F)F)nc2-c1ccc(F)cc1] | 653.60 |
| 141 | 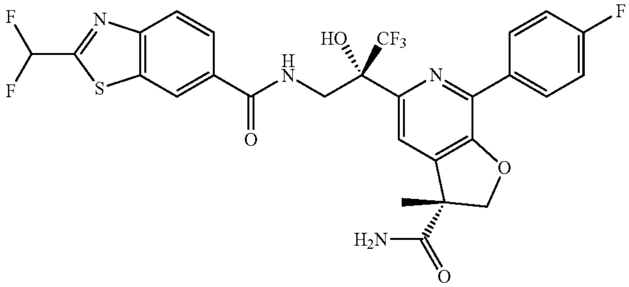 [SMILES: C[C@]1(C(N)=O)COc2c1cc([C@@](O)(CNC(=O)c1ccc3nc(C(F)F)sc3c1)C(F)(F)F)nc2-c1ccc(F)cc1] | 610.50 |
| 142 | 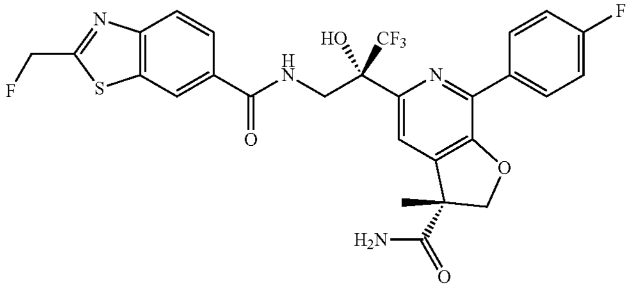 [SMILES: C[C@]1(C(N)=O)COc2c1cc([C@@](O)(CNC(=O)c1ccc3nc(CF)sc3c1)C(F)(F)F)nc2-c1ccc(F)cc1] | 592.50 |
| 143 | 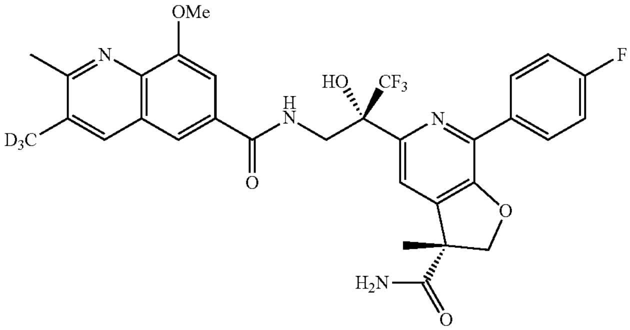 [SMILES: [2H]C([2H])([2H])c1cc2cc(C(=O)NC[C@](O)(c3cc4c(c(-c5ccc(F)cc5)n3)OC[C@]4(C)C(N)=O)C(F)(F)F)cc(OC)c2nc1C] | 615.60 |
| 144 | 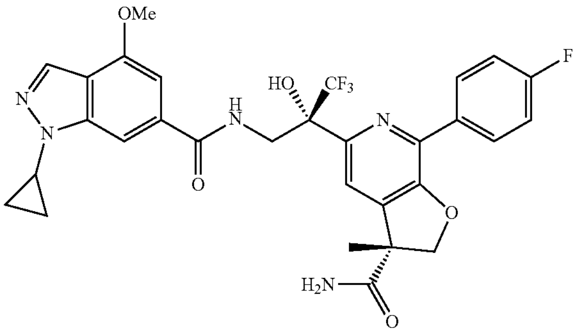 [SMILES: COc1cc(C(=O)NC[C@](O)(c2cc3c(c(-c4ccc(F)cc4)n2)OC[C@]3(C)C(N)=O)C(F)(F)F)cc2c1cnn2C1CC1] | 613.60 |

TABLE 1-continued
| Example | Structure | MS+ m/z |
|---|---|---|
| 145 | 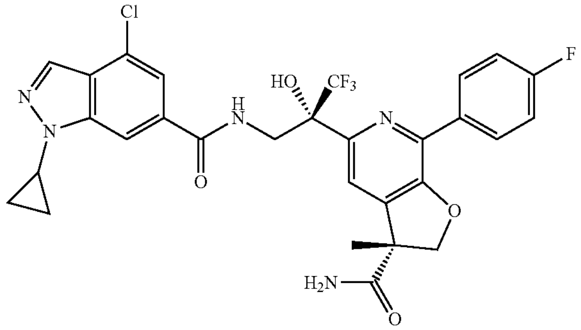 | 618.00 |
| 146 | 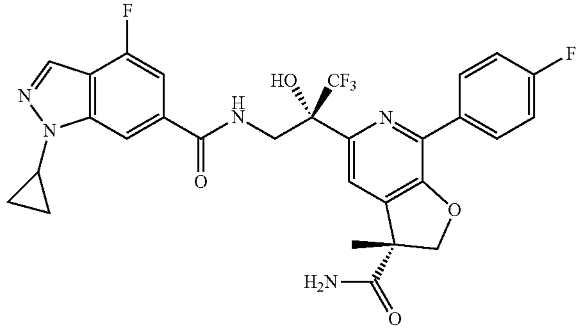 [SMILES: C[C@]1(C(N)=O)COc2c1cc([C@@](O)(CNC(=O)c1cc(F)c3cnn(C4CC4)c3c1)C(F)(F)F)nc2-c1ccc(F)cc1] | 601.50 |
| 147 | 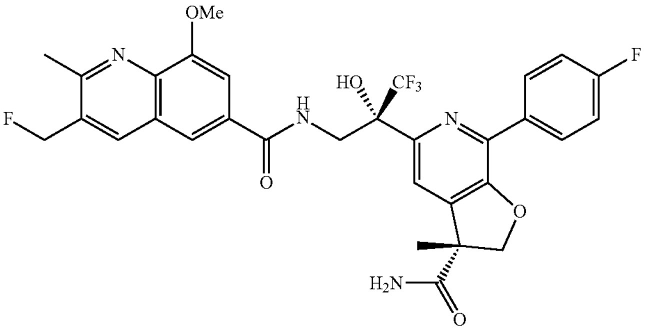 [SMILES: COc1cc(C(=O)NC[C@](O)(c2cc3c(c(-c4ccc(F)cc4)n2)OC[C@]3(C)C(N)=O)C(F)(F)F)cc2cc(CF)c(C)nc12] | 630.60 |
| 148 | 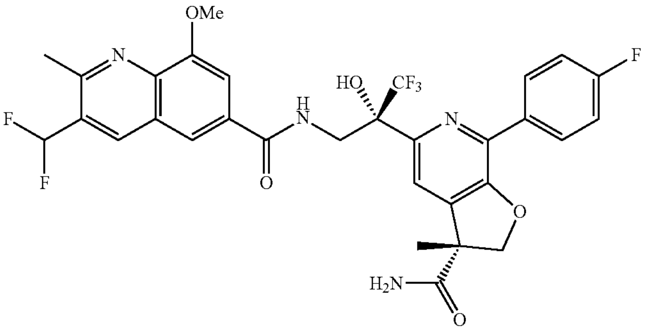 [SMILES: COc1cc(C(=O)NC[C@](O)(c2cc3c(c(-c4ccc(F)cc4)n2)OC[C@]3(C)C(N)=O)C(F)(F)F)cc2cc(C(F)F)c(C)nc12] | 648.60 |

TABLE 1-continued
| Example | Structure | MS⁺ m/z |
|---|---|---|
| 149 | 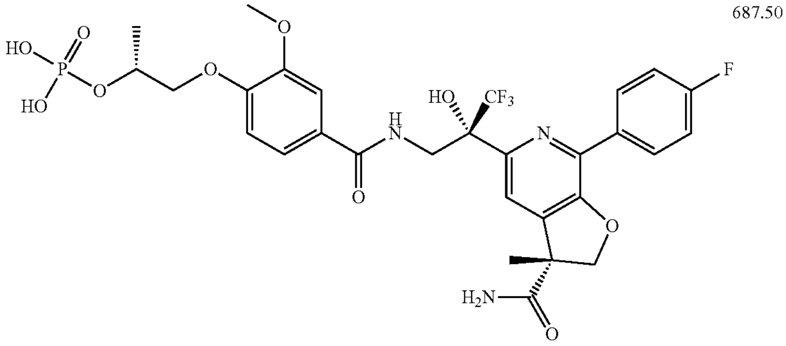 | 687.50 |
| 150 | 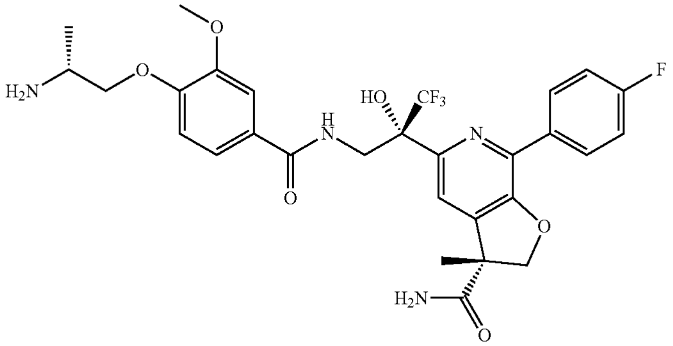 [SMILES: COc1cc(C(=O)NC[C@](O)(c2cc3c(c(-c4ccc(F)cc4)n2)OC[C@]3(C)C(N)=O)C(F)(F)F)ccc1OC[C@@H](C)N] | 606.60 |
| 151 | 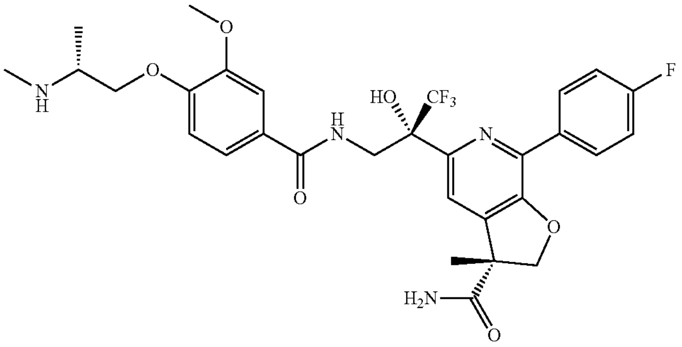 [SMILES: CN[C@H](C)COc1ccc(C(=O)NC[C@](O)(c2cc3c(c(-c4ccc(F)cc4)n2)OC[C@]3(C)C(N)=O)C(F)(F)F)cc1OC] | 620.60 |
| 152 | 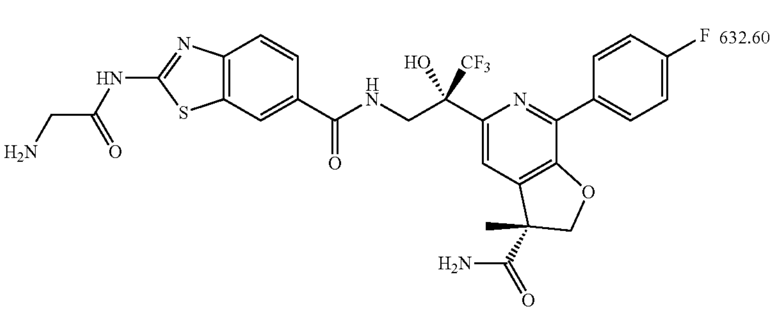 | 632.60 |

TABLE 1-continued
| Example | Structure | MS⁺ m/z |
|---|---|---|
| 153 | 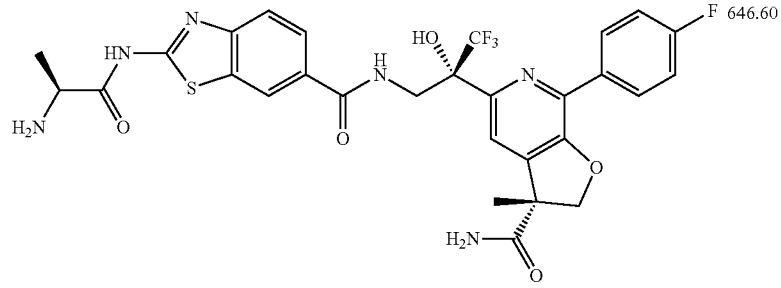 | 646.60 |
| 154 | 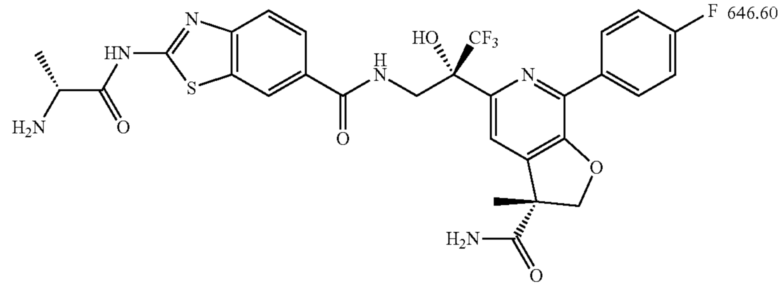 | 646.60 |
| 155 | 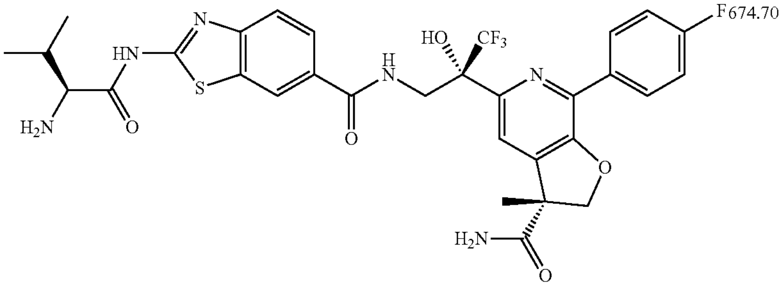 | 674.70 |
| 156 | 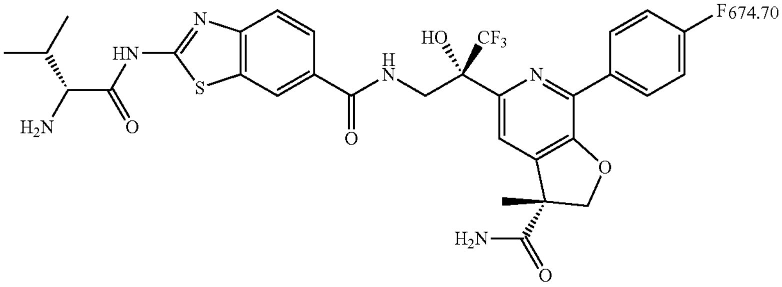 | 674.70 |
| 157 | 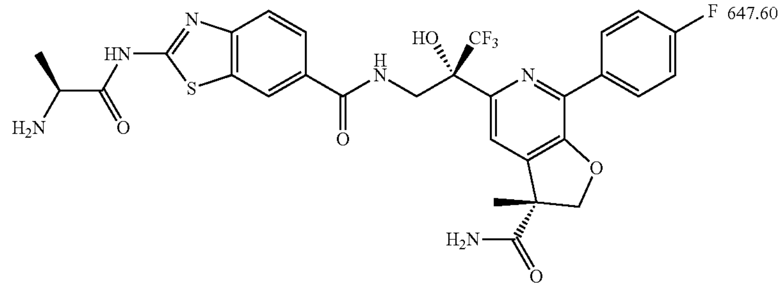 | 647.60 |

TABLE 1-continued
| Example | Structure | MS⁺ m/z |
|---|---|---|
| 158 | 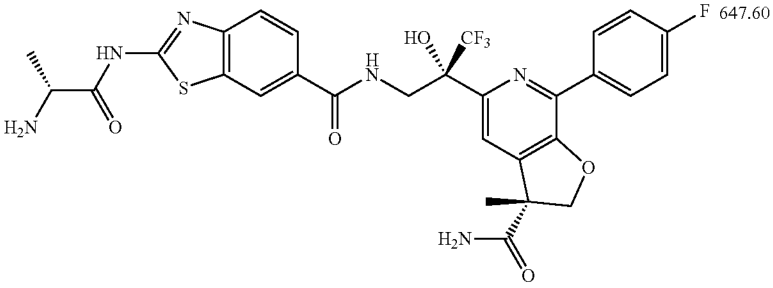 | 647.60 |
| 159 | 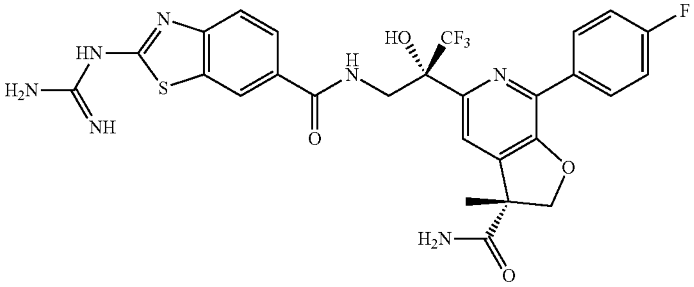 [SMILES: C[C@]1(C(N)=O)COc2c1cc([C@@](O)(CNC(=O)c1ccc3nc(NC(=N)N)sc3c1)C(F)(F)F)nc2-c1ccc(F)cc1] | 617.60 |
| 160 | 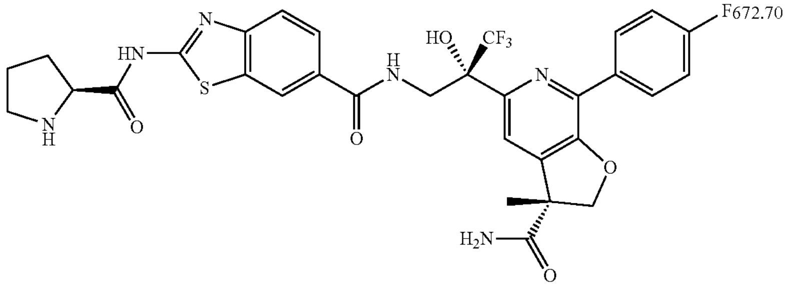 | 672.70 |
| 161 | 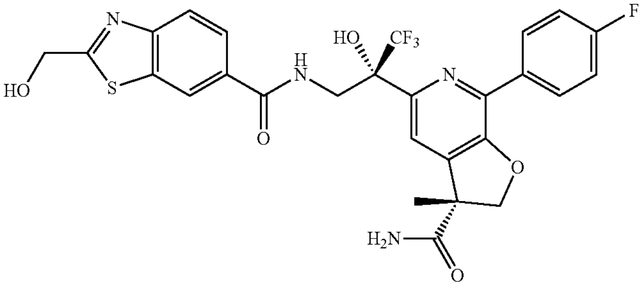 [SMILES: C[C@]1(C(N)=O)COc2c1cc([C@@](O)(CNC(=O)c1ccc3nc(CO)sc3c1)C(F)(F)F)nc2-c1ccc(F)cc1] | 590.60 |
| 162 | 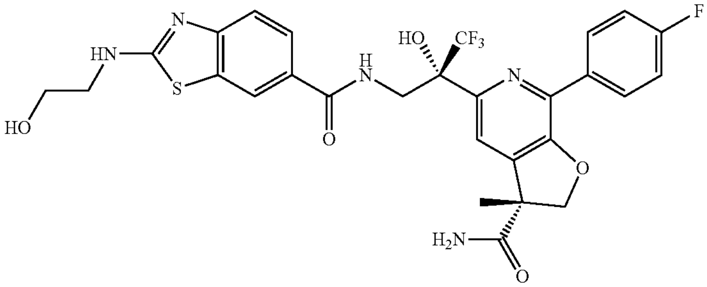 [SMILES: C[C@]1(C(N)=O)COc2c1cc([C@@](O)(CNC(=O)c1ccc3nc(NCCO)sc3c1)C(F)(F)F)nc2-c1ccc(F)cc1] | 619.60 |

TABLE 1-continued
| Example | Structure | MS+ m/z |
| --- | --- | --- |
| 163 | 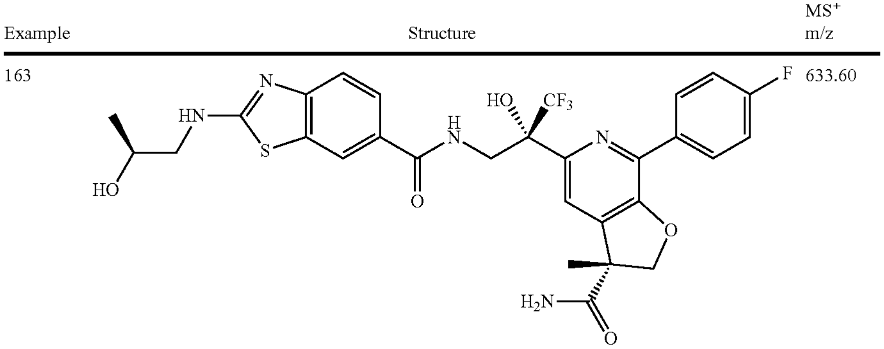 | 633.60 |
| 164 | 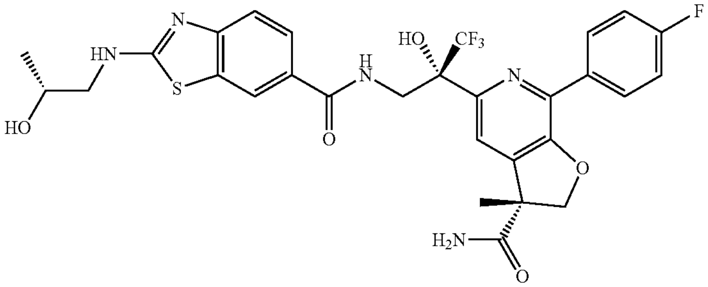 [SMILES: C[C@@H](O)CNc1nc2ccc(C(=O)NC[C@](O)(c3cc4c(c(-c5ccc(F)cc5)n3)OC[C@]4(C)C(N)=O)C(F)(F)F)cc2s1] | 633.60 |
| 165 | 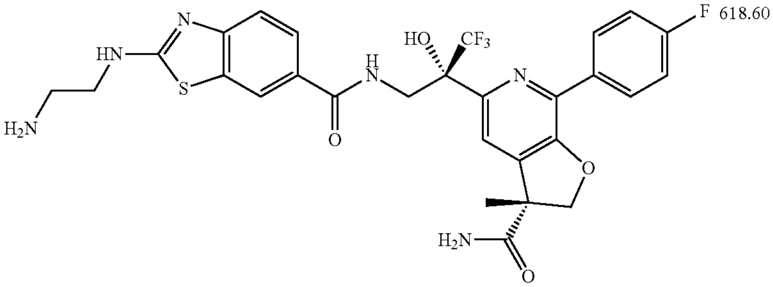 | 618.60 |
| 166 | 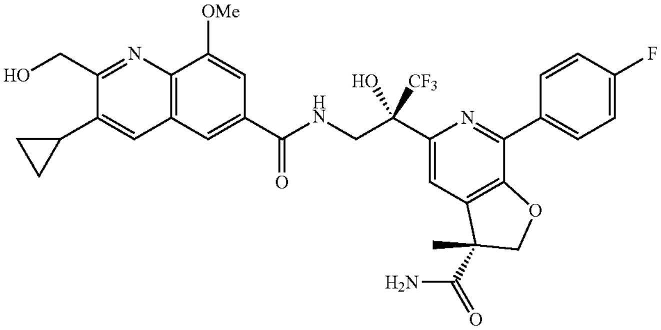 [SMILES: COc1cc(C(=O)NC[C@](O)(c2cc3c(c(-c4ccc(F)cc4)n2)OC[C@]3(C)C(N)=O)C(F)(F)F)cc2cc(C3CC3)c(CO)nc12] | 654.60 |
| 167 | 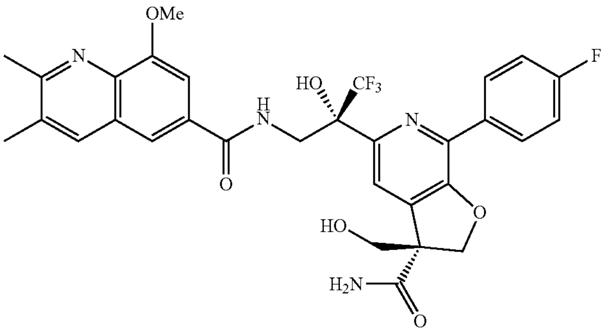 [SMILES: COc1cc(C(=O)NC[C@](O)(c2cc3c(c(-c4ccc(F)cc4)n2)OC[C@]3(CO)C(N)=O)C(F)(F)F)cc2cc(C)c(C)nc12] | 628.60 |

TABLE 1-continued
| Example | Structure | MS+ m/z |
|---|---|---|
| 168 | 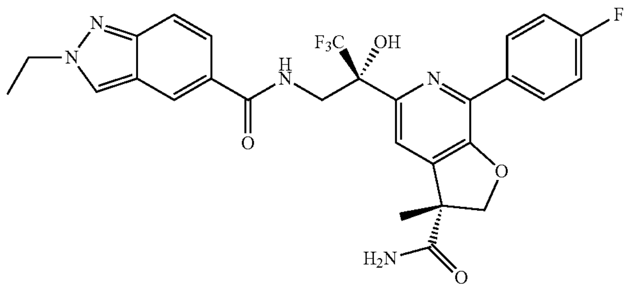 [SMILES: CCn1cc2cc(C(=O)NC[C@](O)(c3cc4c(c(-c5ccc(F)cc5)n3)OC[C@]4(C)C(N)=O)C(F)(F)F)ccc2n1] | 572.20 |
| 169 | 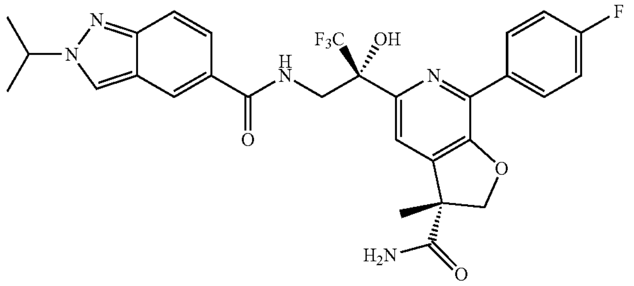 [SMILES: CC(C)n1cc2cc(C(=O)NC[C@](O)(c3cc4c(c(-c5ccc(F)cc5)n3)OC[C@]4(C)C(N)=O)C(F)(F)F)ccc2n1] | 586.20 |
| 170 | 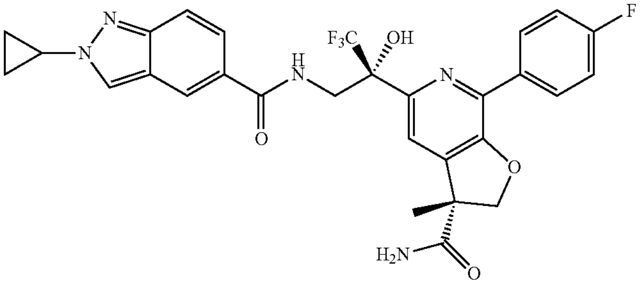 [SMILES: C[C@]1(C(N)=O)COc2c1cc([C@@](O)(CNC(=O)c1ccc3nn(C4CC4)cc3c1)C(F)(F)F)nc2-c1ccc(F)cc1] | 582.30 |
| 171 | 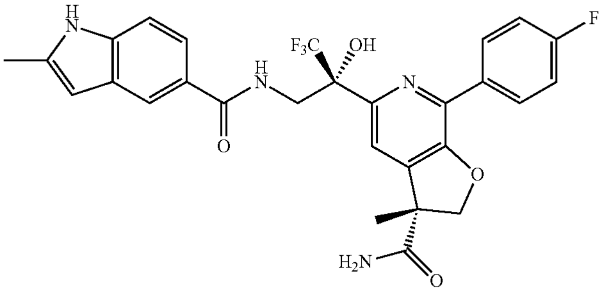 [SMILES: Cc1cc2cc(C(=O)NC[C@](O)(c3cc4c(c(-c5ccc(F)cc5)n3)OC[C@]4(C)C(N)=O)C(F)(F)F)ccc2[nH]1] | 557.10 |
| 172 | 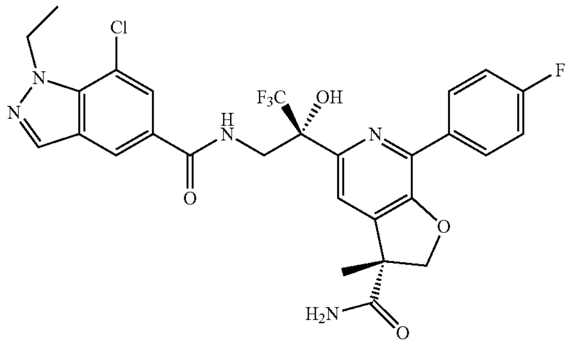 [SMILES: CCn1ncc2cc(C(=O)NC[C@](O)(c3cc4c(c(-c5ccc(F)cc5)n3)OC[C@]4(C)C(N)=O)C(F)(F)F)cc(Cl)c21] | 606.10 |

TABLE 1-continued
| Example | Structure | MS+ m/z |
|---|---|---|
| 173 | 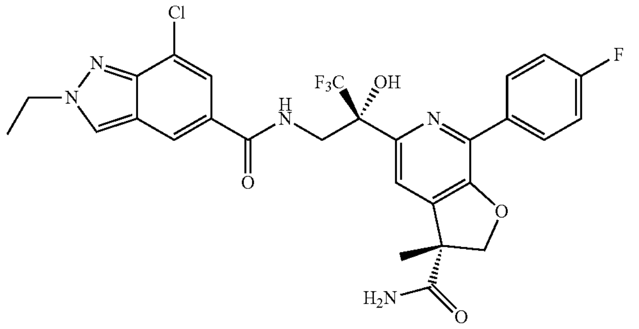 [SMILES: CCn1cc2cc(C(=O)NC[C@](O)(c3cc4c(c(-c5ccc(F)cc5)n3)OC[C@]4(C)C(N)=O)C(F)(F)F)cc(Cl)c2n1] | 606.10 |
| 174 | 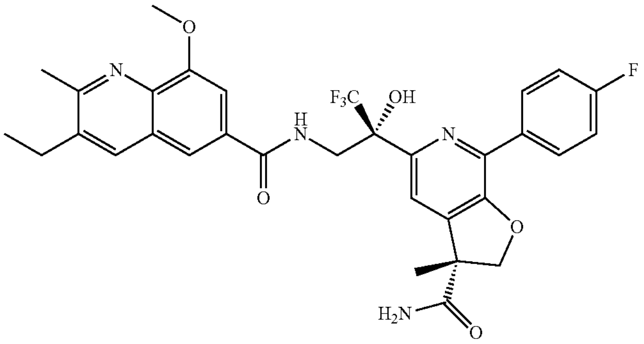 [SMILES: CCc1cc2cc(C(=O)NC[C@](O)(c3cc4c(c(-c5ccc(F)cc5)n3)OC[C@]4(C)C(N)=O)C(F)(F)F)cc(OC)c2nc1C] | 627.50 |
| 175 | 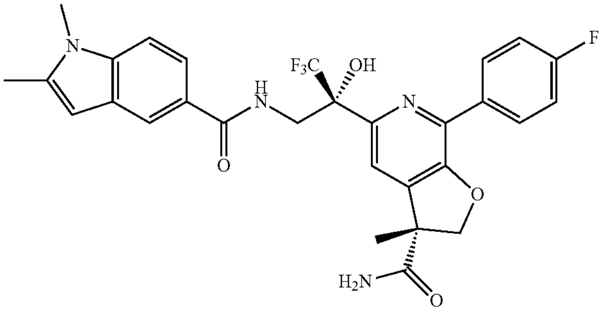 [SMILES: Cc1cc2cc(C(=O)NC[C@](O)(c3cc4c(c(-c5ccc(F)cc5)n3)OC[C@]4(C)C(N)=O)C(F)(F)F)ccc2n1C] | 571.20 |
| 176 | 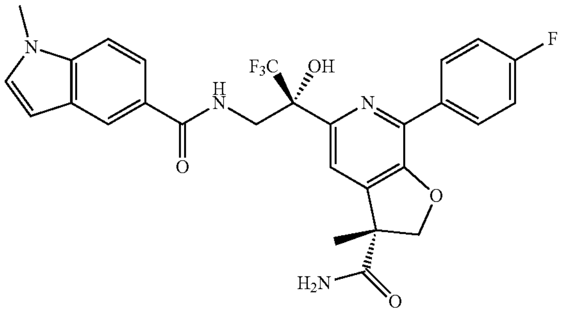 [SMILES: Cn1ccc2cc(C(=O)NC[C@](O)(c3cc4c(c(-c5ccc(F)cc5)n3)OC[C@]4(C)C(N)=O)C(F)(F)F)ccc21] | 557.10 |

TABLE 1-continued
| Example | Structure | MS+ m/z |
| --- | --- | --- |
| 177 | 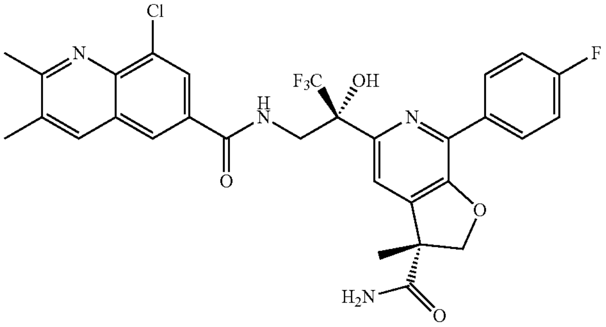 [SMILES: Cc1cc2cc(C(=O)NC[C@](O)(c3cc4c(c(-c5ccc(F)cc5)n3)OC[C@]4(C)C(N)=O)C(F)(F)F)cc(Cl)c2nc1C] | 617.20 |
| 178 | 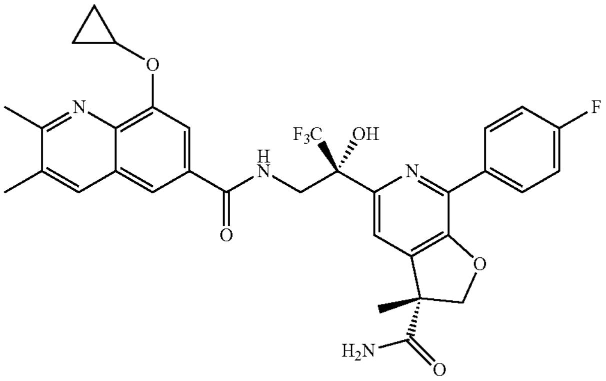 [SMILES: Cc1cc2cc(C(=O)NC[C@](O)(c3cc4c(c(-c5ccc(F)cc5)n3)OC[C@]4(C)C(N)=O)C(F)(F)F)cc(OC3CC3)c2nc1C] | 639.30 |
| 179 | 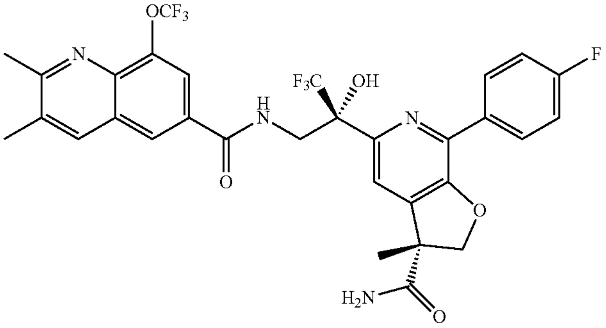 [SMILES: Cc1cc2cc(C(=O)NC[C@](O)(c3cc4c(c(-c5ccc(F)cc5)n3)OC[C@]4(C)C(N)=O)C(F)(F)F)cc(OC(F)(F)F)c2nc1C] | 667.30 |
| 180 | 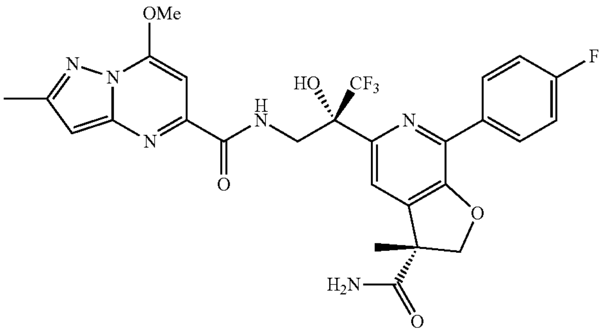 [SMILES: COc1cc(C(=O)NC[C@](O)(c2cc3c(c(-c4ccc(F)cc4)n2)OC[C@]3(C)C(N)=O)C(F)(F)F)nc2cc(C)nn12] | 589.10 |

TABLE 1-continued
| Example | Structure | MS+ m/z |
| --- | --- | --- |
| 181 | 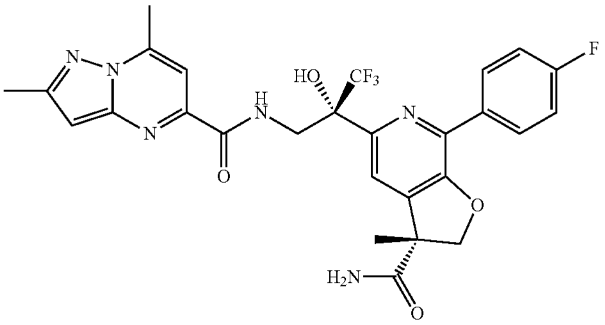 [SMILES: Cc1cc2nc(C(=O)NC[C@](O)(c3cc4c(c(-c5ccc(F)cc5)n3)OC[C@]4(C)C(N)=O)C(F)(F)F)cc(C)n2n1] | 573.10 |
| 182 | 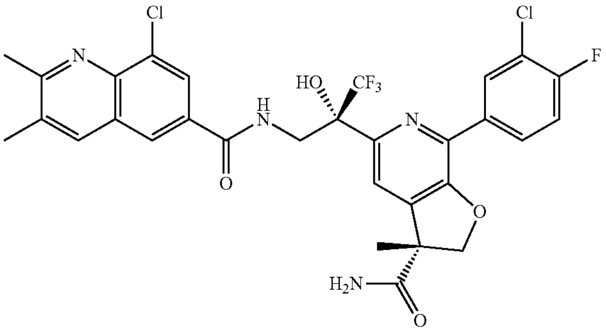 [SMILES: Cc1cc2cc(C(=O)NC[C@](O)(c3cc4c(c(-c5ccc(F)c(Cl)c5)n3)OC[C@]4(C)C(N)=O)C(F)(F)F)cc(Cl)c2nc1C] | 651.10 |
| 183 | 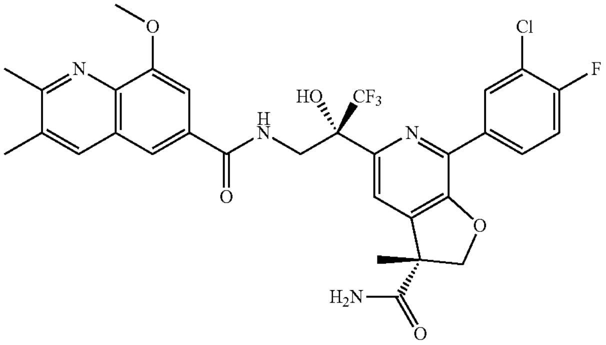 [SMILES: COc1cc(C(=O)NC[C@](O)(c2cc3c(c(-c4ccc(F)c(Cl)c4)n2)OC[C@]3(C)C(N)=O)C(F)(F)F)cc2cc(C)c(C)nc12] | 673.30 |
| 184 | 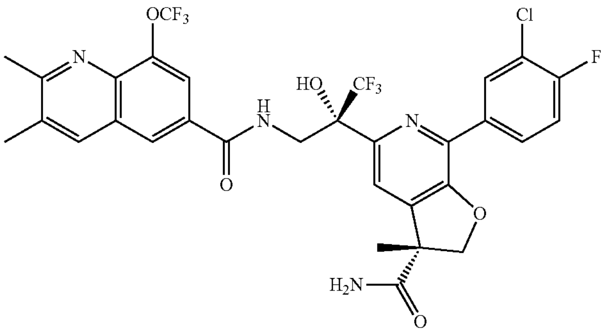 [SMILES: Cc1cc2cc(C(=O)NC[C@](O)(c3cc4c(c(-c5ccc(F)c(Cl)c5)n3)OC[C@]4(C)C(N)=O)C(F)(F)F)cc(OC(F)(F)F)c2nc1C] | 701.20 |

TABLE 1-continued
| Example | Structure | MS+ m/z |
|---|---|---|
| 185 | 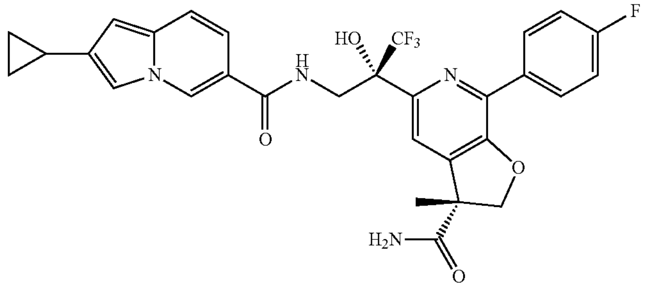 | 583.10 |
| 186 | 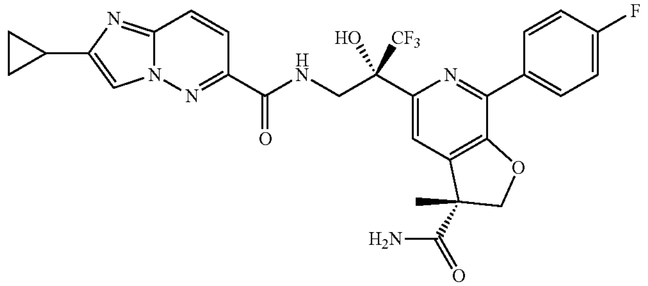 [SMILES: C[C@]1(C(N)=O)COc2c1cc([C@@](O)(CNC(=O)c1ccc3nc(C4CC4)cn3n1)C(F)(F)F)nc2-c1ccc(F)cc1] | 585.20 |
| 187 | 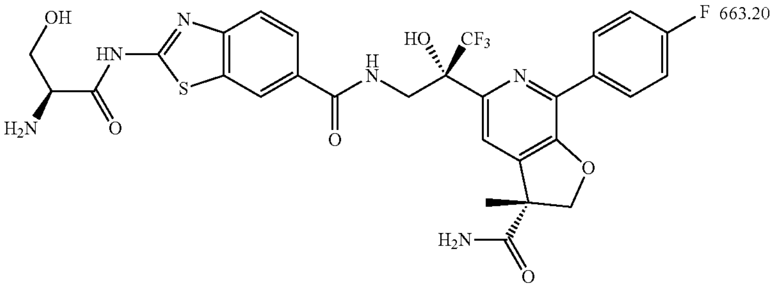 | 663.20 |
| 188 | 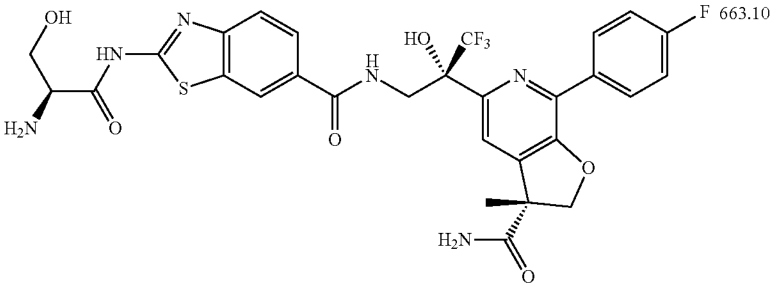 | 663.10 |
| 189 | 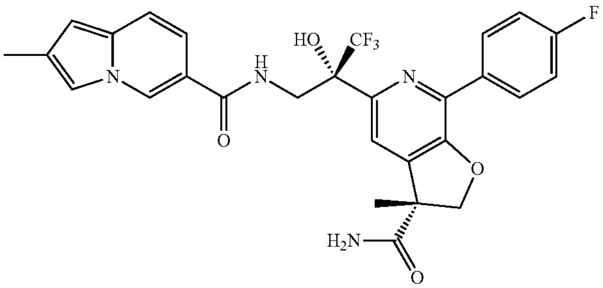 [SMILES: Cc1cc2ccc(C(=O)NC[C@](O)(c3cc4c(c(-c5ccc(F)cc5)n3)OC[C@]4(C)C(N)=O)C(F)(F)F)cn2c1] | 557.20 |

TABLE 1-continued
| Example | Structure | MS⁺ m/z |
|---|---|---|
| 190 | 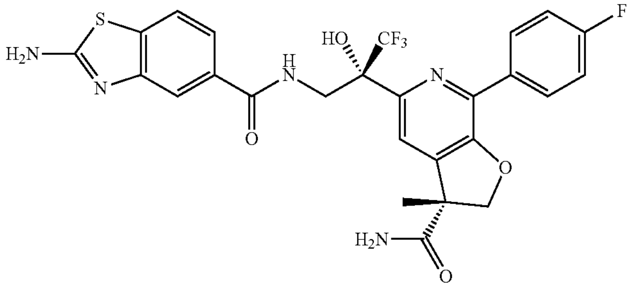 | 576.10 |
| 191 | 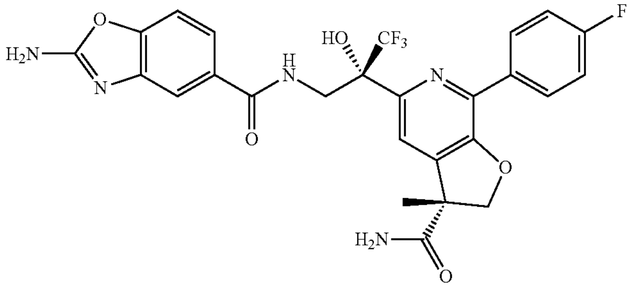 [SMILES: C[C@]1(C(N)=O)COc2c1cc([C@@](O)(CNC(=O)c1ccc3oc(N)nc3c1)C(F)(F)F)nc2-c1ccc(F)cc1] | 560.20 |
| 192 | 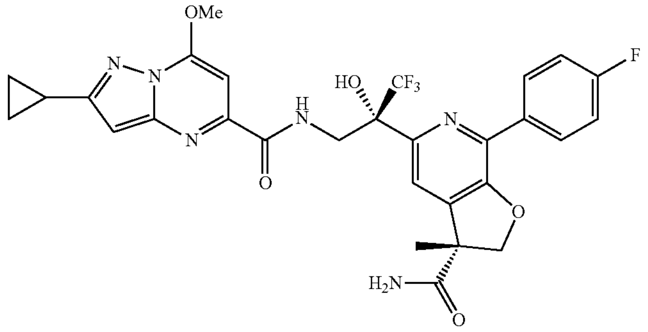 [SMILES: COc1cc(C(=O)NC[C@](O)(c2cc3c(c(-c4ccc(F)cc4)n2)OC[C@]3(C)C(N)=O)C(F)(F)F)nc2cc(C3CC3)nn12] | 615.10 |
| 193 | 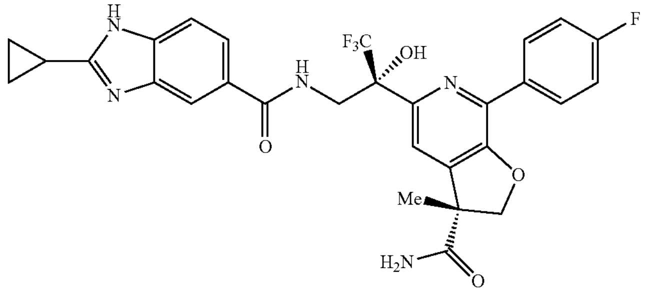 [SMILES: C[C@]1(C(N)=O)COc2c1cc([C@@](O)(CNC(=O)c1ccc3[nH]c(C4CC4)nc3c1)C(F)(F)F)nc2-c1ccc(F)cc1] | 584.20 |
| 194 | 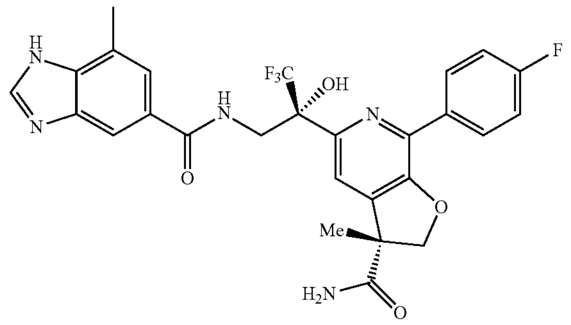 [SMILES: Cc1cc(C(=O)NC[C@](O)(c2cc3c(c(-c4ccc(F)cc4)n2)OC[C@]3(C)C(N)=O)C(F)(F)F)cc2nc[nH]c12] | 557.20 |

TABLE 1-continued
| Example | Structure | MS+ m/z |
|---|---|---|
| 195 | 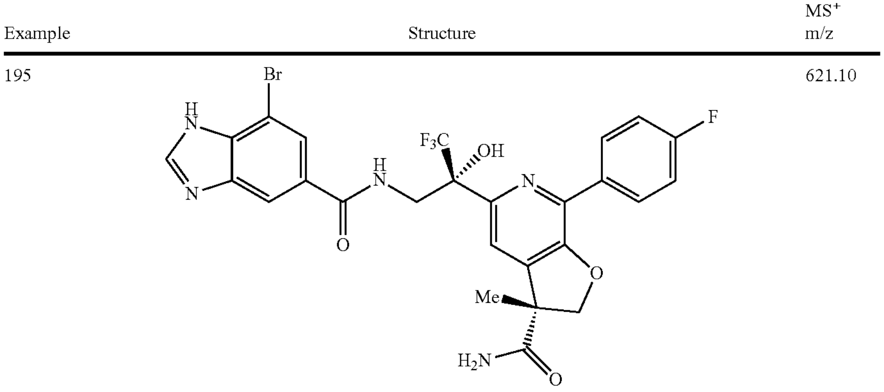 | 621.10 |
| 196 | 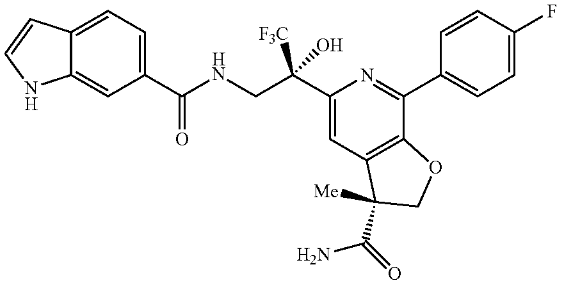 [SMILES: C[C@]1(C(N)=O)COc2c1cc([C@@](O)(CNC(=O)c1ccc3cc[nH]c3c1)C(F)(F)F)nc2-c1ccc(F)cc1] | 542.30 |
| 197 | 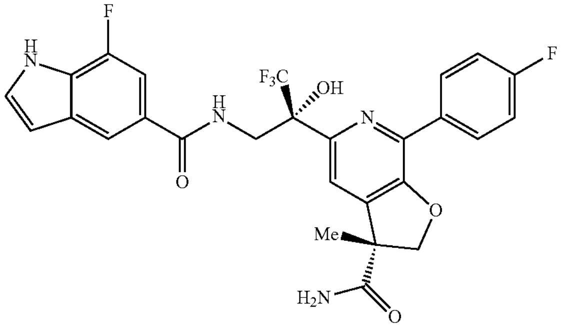 [SMILES: C[C@]1(C(N)=O)COc2c1cc([C@@](O)(CNC(=O)c1cc(F)c3[nH]ccc3c1)C(F)(F)F)nc2-c1ccc(F)cc1] | 561.10 |
| 198 | 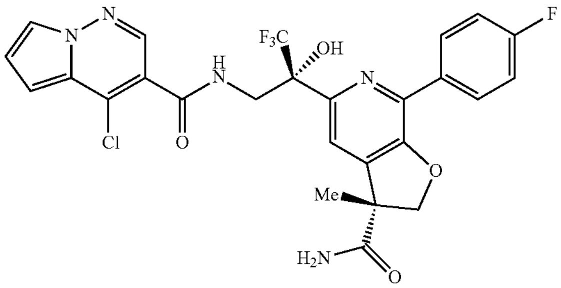 [SMILES: C[C@]1(C(N)=O)COc2c1cc([C@@](O)(CNC(=O)c1cnn3cccc3c1Cl)C(F)(F)F)nc2-c1ccc(F)cc1] | 578.10 |
| 199 | 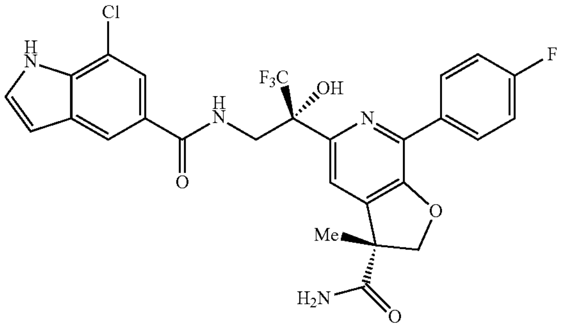 [SMILES: C[C@]1(C(N)=O)COc2c1cc([C@@](O)(CNC(=O)c1cc(Cl)c3[nH]ccc3c1)C(F)(F)F)nc2-c1ccc(F)cc1] | 577.10 |

TABLE 1-continued
| Example | Structure | MS⁺ m/z |
|---|---|---|
| 200 | 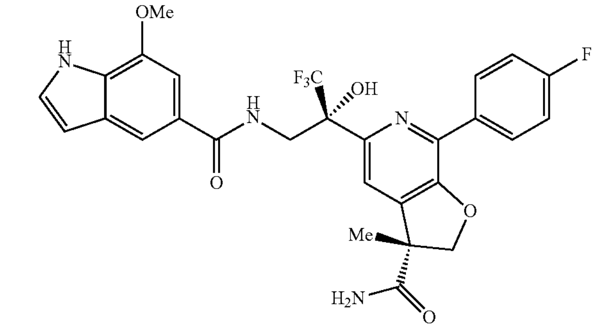 [SMILES: COc1cc(C(=O)NC[C@](O)(c2cc3c(c(-c4ccc(F)cc4)n2)OC[C@]3(C)C(N)=O)C(F)(F)F)cc2cc[nH]c12] | 572.30 |
| 201 | 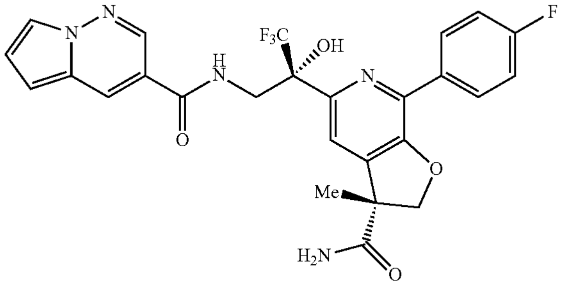 [SMILES: C[C@]1(C(N)=O)COc2c1cc([C@@](O)(CNC(=O)c1cnn3cccc3c1)C(F)(F)F)nc2-c1ccc(F)cc1] | 544.10 |
| 202 | 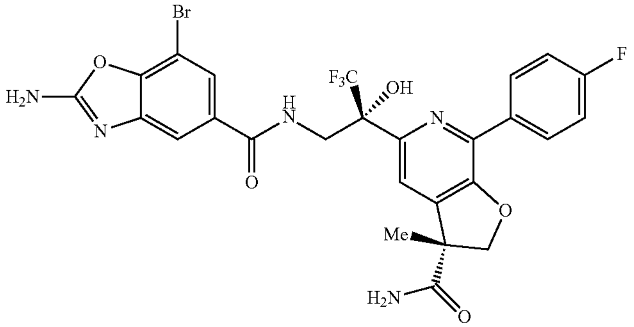 [SMILES: C[C@]1(C(N)=O)COc2c1cc([C@@](O)(CNC(=O)c1cc(Br)c3oc(N)nc3c1)C(F)(F)F)nc2-c1ccc(F)cc1] | 638.00 |
| 203 | 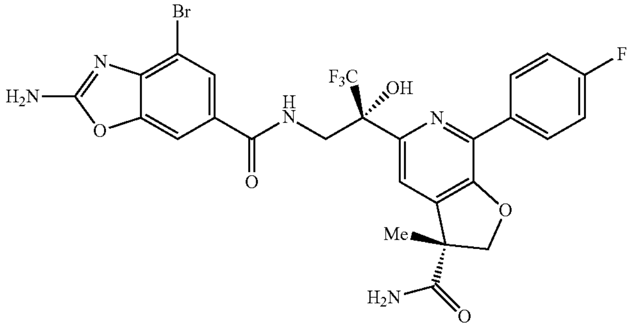 [SMILES: C[C@]1(C(N)=O)COc2c1cc([C@@](O)(CNC(=O)c1cc(Br)c3nc(N)oc3c1)C(F)(F)F)nc2-c1ccc(F)cc1] | 638.00 |

TABLE 1-continued
| Example | Structure | MS+ m/z |
|---|---|---|
| 204 | 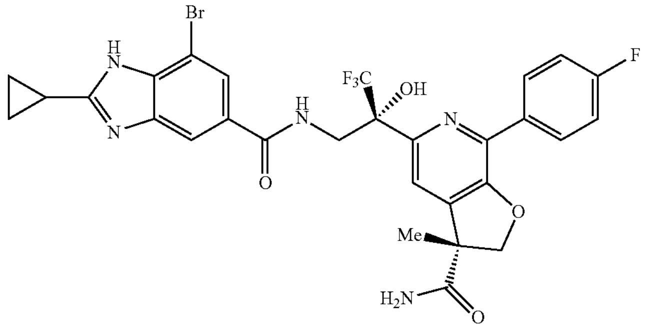 [SMILES: C[C@]1(C(N)=O)COc2c1cc([C@@](O)(CNC(=O)c1cc(Br)c3[nH]c(C4CC4)nc3c1)C(F)(F)F)nc2-c1ccc(F)cc1] | 662.20 |
| 205 | 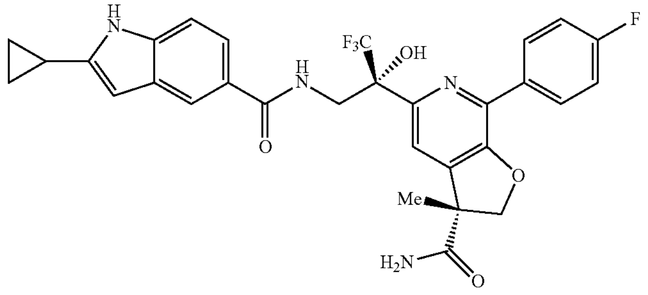 [SMILES: C[C@]1(C(N)=O)COc2c1cc([C@@](O)(CNC(=O)c1ccc3[nH]c(C4CC4)cc3c1)C(F)(F)F)nc2-c1ccc(F)cc1] | 583.20 |
| 206 | 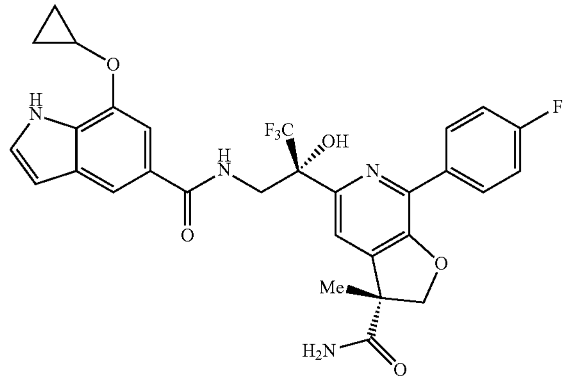 [SMILES: C[C@]1(C(N)=O)COc2c1cc([C@@](O)(CNC(=O)c1cc(OC3CC3)c3[nH]ccc3c1)C(F)(F)F)nc2-c1ccc(F)cc1] | 599.20 |
| 207 | 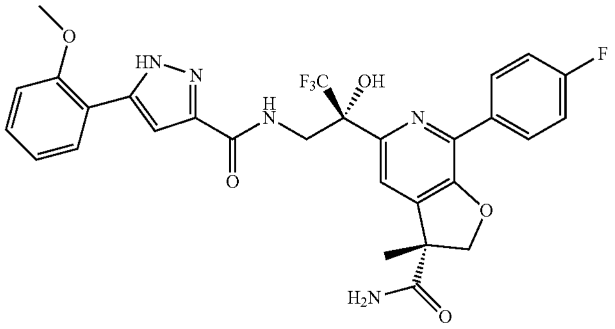 [SMILES: COc1ccccc1-c1cc(C(=O)NC[C@](O)(c2cc3c(c(-c4ccc(F)cc4)n2)OC[C@]3(C)C(N)=O)C(F)(F)F)n[nH]1] | 600.20 |

TABLE 1-continued
| Example | Structure | MS+ m/z |
|---|---|---|
| 208 | 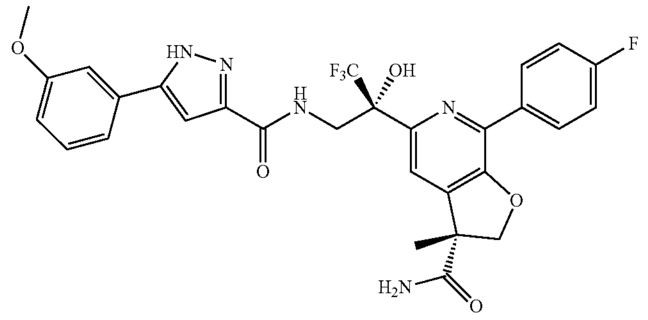 [SMILES: COc1cccc(-c2cc(C(=O)NC[C@](O)(c3cc4c(c(-c5ccc(F)cc5)n3)OC[C@]4(C)C(N)=O)C(F)(F)F)n[nH]2)c1] | 600.20 |
| 209 | 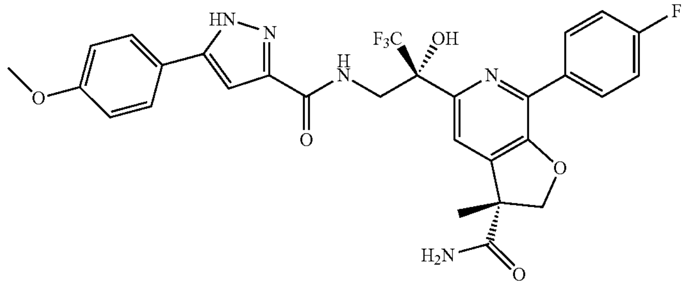 [SMILES: COc1ccc(-c2cc(C(=O)NC[C@](O)(c3cc4c(c(-c5ccc(F)cc5)n3)OC[C@]4(C)C(N)=O)C(F)(F)F)n[nH]2)cc1] | 600.20 |
| 210 | 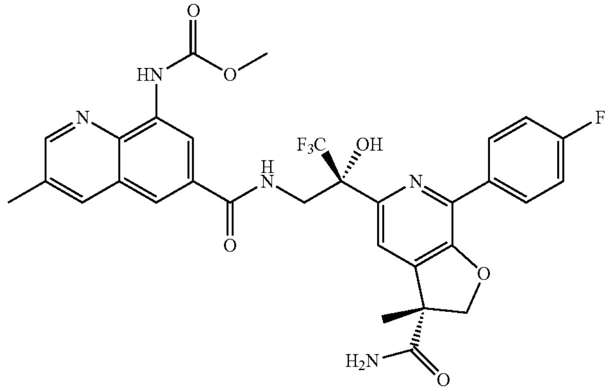 [SMILES: COC(=O)Nc1cc(C(=O)NC[C@](O)(c2cc3c(c(-c4ccc(F)cc4)n2)OC[C@]3(C)C(N)=O)C(F)(F)F)cc2cc(C)cnc12] | 642.23 |
| 211 | 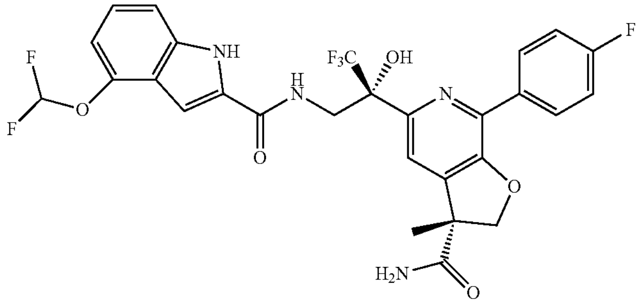 [SMILES: C[C@]1(C(N)=O)COc2c1cc([C@@](O)(CNC(=O)c1cc3c(OC(F)F)cccc3[nH]1)C(F)(F)F)nc2-c1ccc(F)cc1] | 609.17 |

TABLE 1-continued
| Example | Structure | MS+ m/z |
|---|---|---|
| 212 | 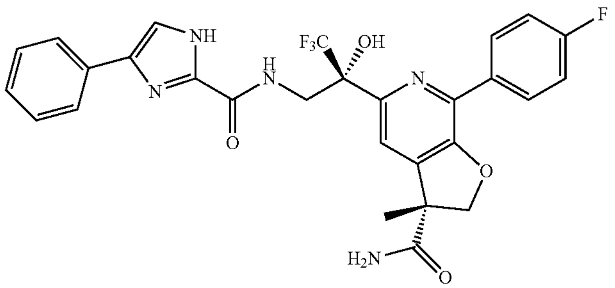 [SMILES: C[C@]1(C(N)=O)COc2c1cc([C@@](O)(CNC(=O)c1nc(-c3ccccc3)c[nH]1)C(F)(F)F)nc2-c1ccc(F)cc1] | 570.19 |
| 213 | 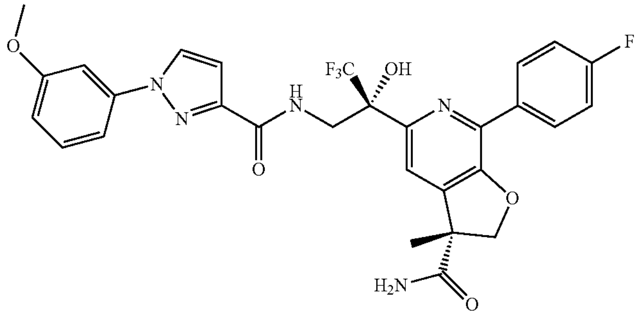 [SMILES: COc1cccc(-n2ccc(C(=O)NC[C@](O)(c3cc4c(c(-c5ccc(F)cc5)n3)OC[C@]4(C)C(N)=O)C(F)(F)F)n2)c1] | 600.22 |
| 214 | 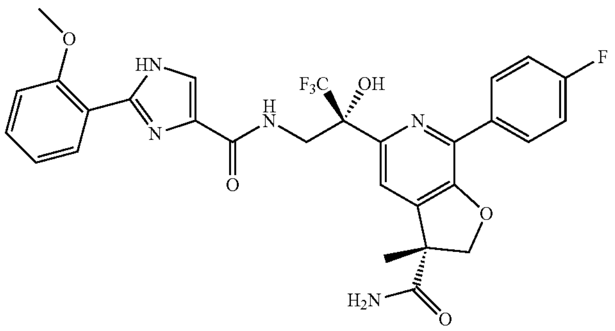 [SMILES: COc1ccccc1-c1nc(C(=O)NC[C@](O)(c2cc3c(c(-c4ccc(F)cc4)n2)OC[C@]3(C)C(N)=O)C(F)(F)F)c[nH]1] | 600.22 |
| 215 | 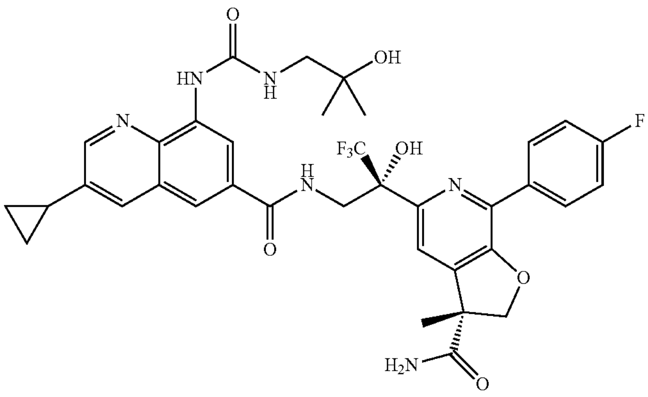 [SMILES: CC(C)(O)CNC(=O)Nc1cc(C(=O)NC[C@](O)(c2cc3c(c(-c4ccc(F)cc4)n2)OC[C@]3(C)C(N)=O)C(F)(F)F)cc2cc(C3CC3)cnc12] | 725.31 |

TABLE 1-continued
| Example | Structure | MS+ m/z |
| --- | --- | --- |
| 216 | 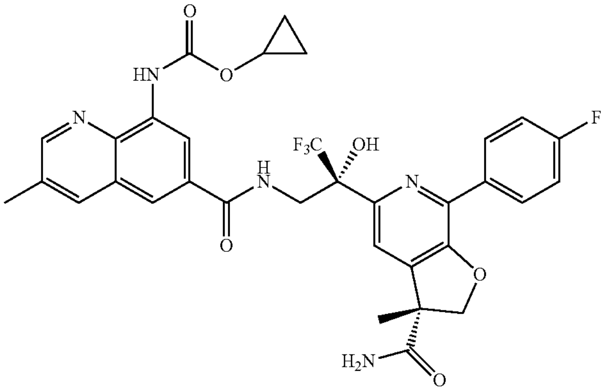 [SMILES: Cc1cnc2c(NC(=O)OC3CC3)cc(C(=O)NC[C@](O)(c3cc4c(c(-c5ccc(F)cc5)n3)OC[C@]4(C)C(N)=O)C(F)(F)F)cc2c1] | 668.25 |
| 217 | 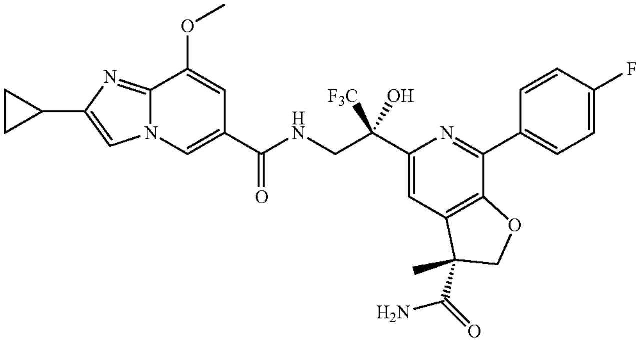 [SMILES: COc1cc(C(=O)NC[C@](O)(c2cc3c(c(-c4ccc(F)cc4)n2)OC[C@]3(C)C(N)=O)C(F)(F)F)cn2cc(C3CC3)nc12] | 614.24 |
| 218 | 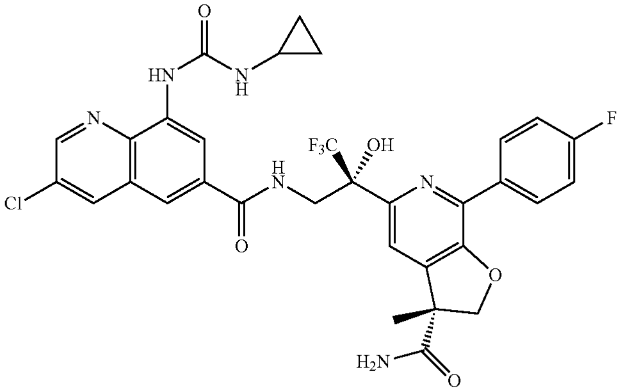 [SMILES: C[C@]1(C(N)=O)COc2c1cc([C@@](O)(CNC(=O)c1cc(NC(=O)NC3CC3)c3ncc(Cl)cc3c1)C(F)(F)F)nc2-c1ccc(F)cc1] | 687.14 |
| 219 | 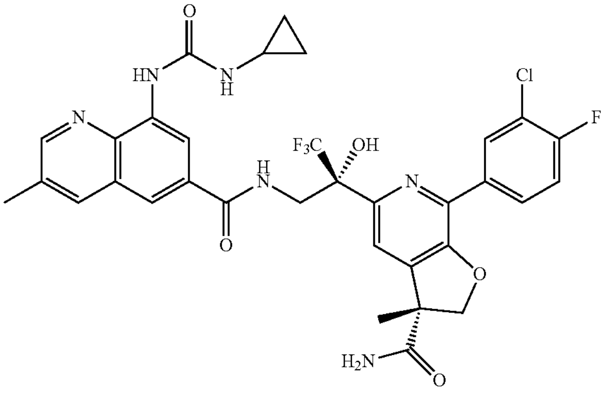 [SMILES: Cc1cnc2c(NC(=O)NC3CC3)cc(C(=O)NC[C@](O)(c3cc4c(c(-c5ccc(F)c(Cl)c5)n3)OC[C@]4(C)C(N)=O)C(F)(F)F)cc2c1] | 701.17 |

TABLE 1-continued
| Example | Structure | MS+ m/z |
|---|---|---|
| 220 | 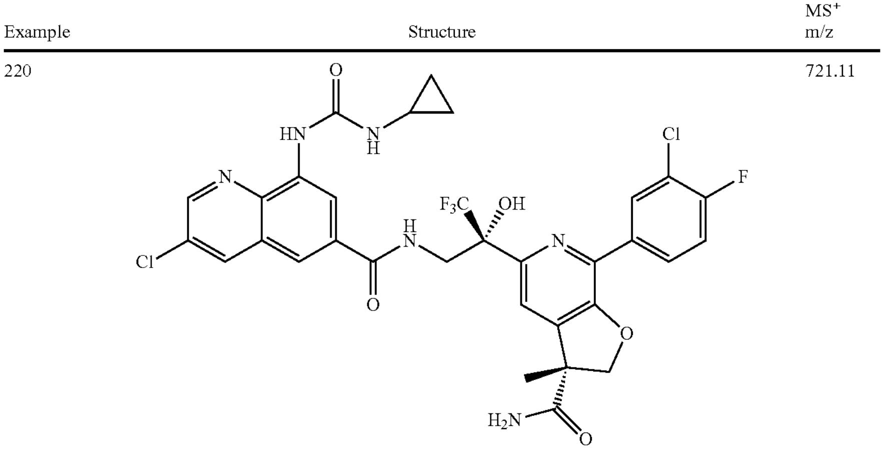 | 721.11 |
| 221 | 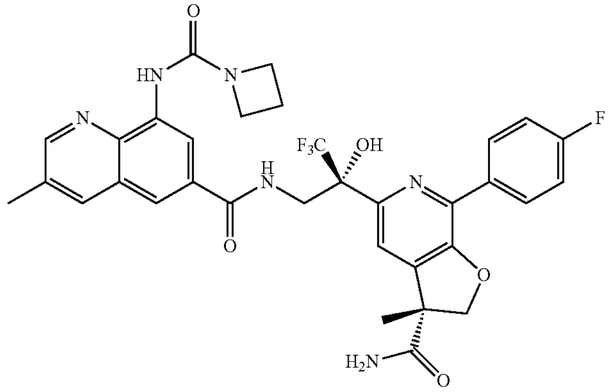 [SMILES: Cc1cnc2c(NC(=O)N3CCC3)cc(C(=O)NC[C@](O)(c3cc4c(c(-c5ccc(F)cc5)n3)OC[C@]4(C)C(N)=O)C(F)(F)F)cc2c1] | 667.21 |
| 222 | 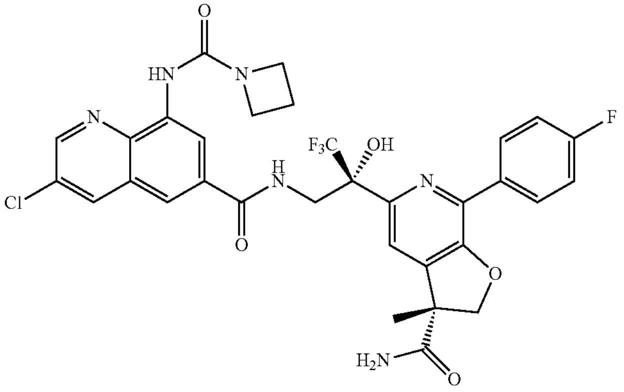 [SMILES: C[C@]1(C(N)=O)COc2c1cc([C@@](O)(CNC(=O)c1cc(NC(=O)N3CCC3)c3ncc(Cl)cc3c1)C(F)(F)F)nc2-c1ccc(F)cc1] | 687.15 |
| 223 | 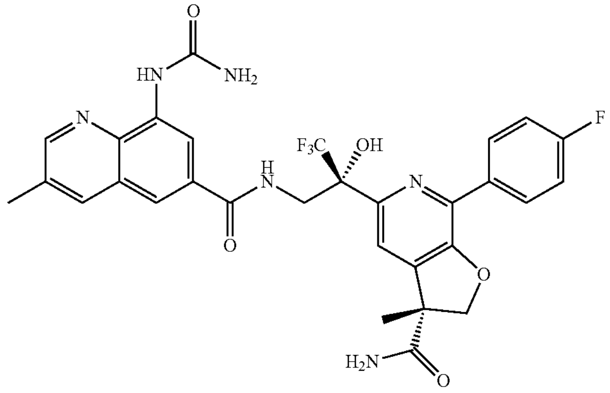 [SMILES: Cc1cnc2c(NC(N)=O)cc(C(=O)NC[C@](O)(c3cc4c(c(-c5ccc(F)cc5)n3)OC[C@]4(C)C(N)=O)C(F)(F)F)cc2c1] | 627.19 |

TABLE 1-continued
| Example | Structure | MS+ m/z |
|---|---|---|
| 224 | 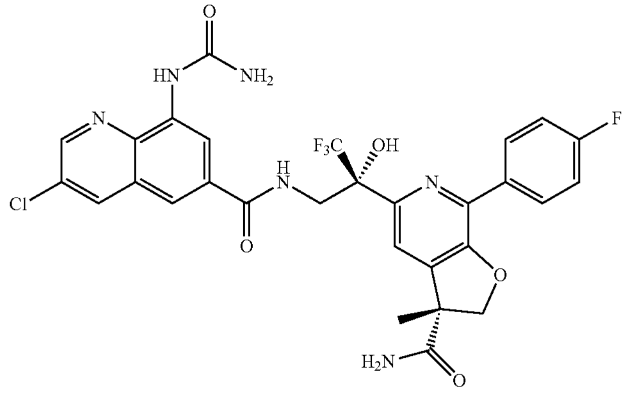 [SMILES: C[C@]1(C(N)=O)COc2c1cc([C@@](O)(CNC(=O)c1cc(NC(N)=O)c3ncc(Cl)cc3c1)C(F)(F)F)nc2-c1ccc(F)cc1] | 647.12 |
| 225 | 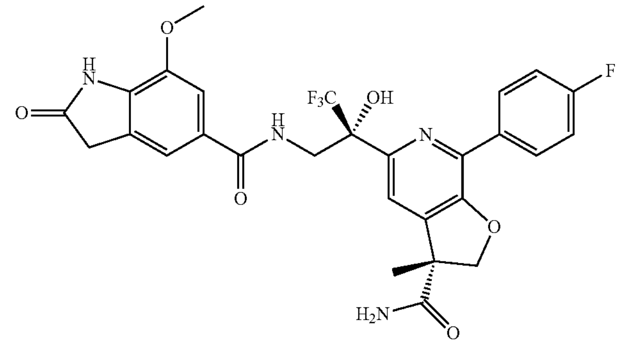 [SMILES: COc1cc(C(=O)NC[C@](O)(c2cc3c(c(-c4ccc(F)cc4)n2)OC[C@]3(C)C(N)=O)C(F)(F)F)cc2c1NC(=O)C2] | 589.15 |
| 226 | 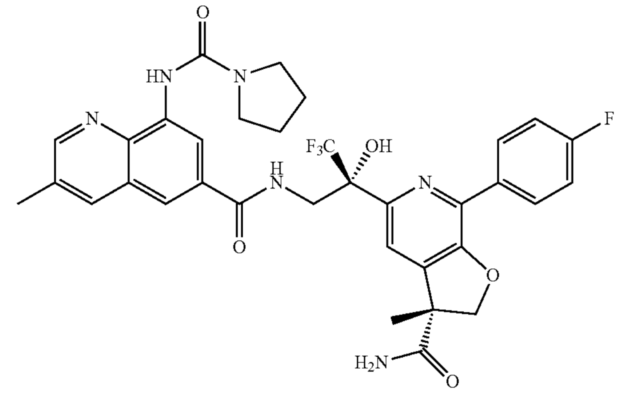 [SMILES: Cc1cnc2c(NC(=O)N3CCCC3)cc(C(=O)NC[C@](O)(c3cc4c(c(-c5ccc(F)cc5)n3)OC[C@]4(C)C(N)=O)C(F)(F)F)cc2c1] | 681.22 |
| 227 | 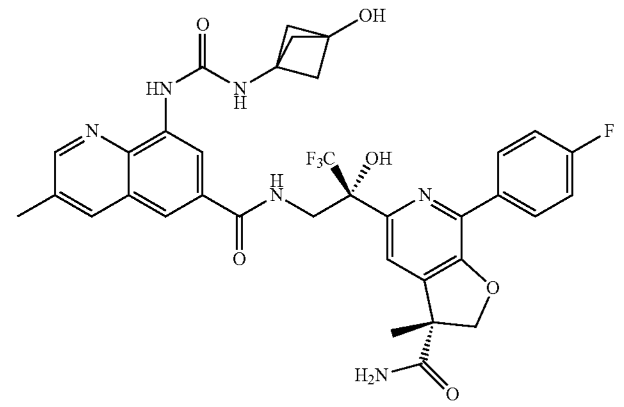 [SMILES: Cc1cnc2c(NC(=O)NC34CC(O)(C3)C4)cc(C(=O)NC[C@](O)(c3cc4c(c(-c5ccc(F)cc5)n3)OC[C@]4(C)C(N)=O)C(F)(F)F)cc2c1] | 709.21 |

TABLE 1-continued
| Example | Structure | MS+ m/z |
| --- | --- | --- |
| 228 | 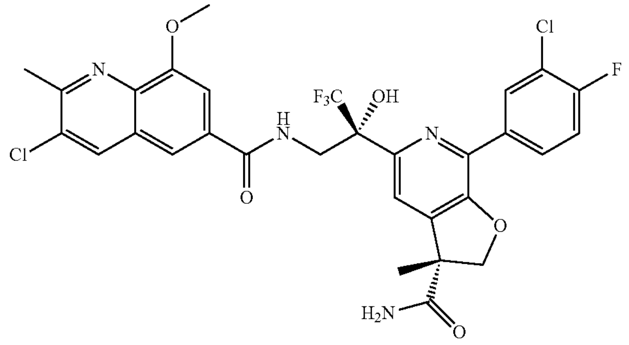 [SMILES: COc1cc(C(=O)NC[C@](O)(c2cc3c(c(-c4ccc(F)c(Cl)c4)n2)OC[C@]3(C)C(N)=O)C(F)(F)F)cc2cc(Cl)c(C)nc12] | 667.10 |
| 229 | 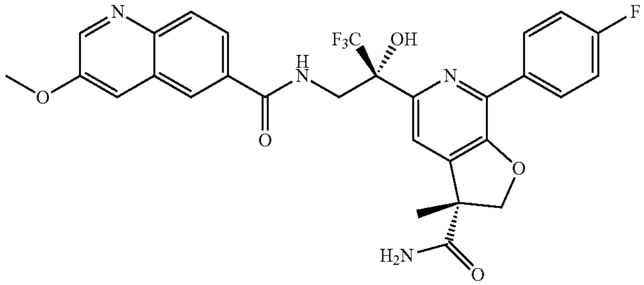 [SMILES: COc1cnc2ccc(C(=O)NC[C@](O)(c3cc4c(c(-c5ccc(F)cc5)n3)OC[C@]4(C)C(N)=O)C(F)(F)F)cc2c1] | 585.16 |
| 232 | 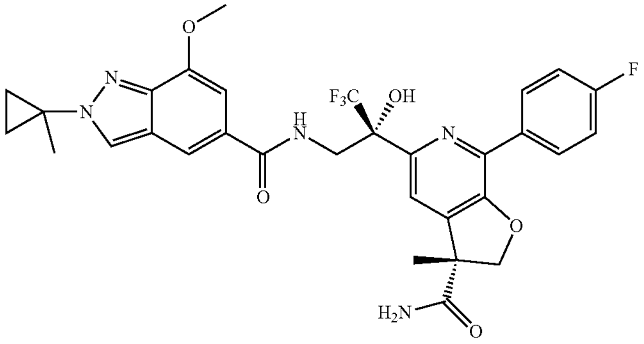 [SMILES: COc1cc(C(=O)NC[C@](O)(c2cc3c(c(-c4ccc(F)cc4)n2)OC[C@]3(C)C(N)=O)C(F)(F)F)cc2cn(C3(C)CC3)nc12] | 628.15 |

Intermediate 39

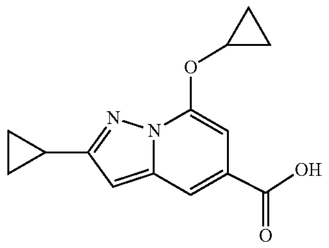 [SMILES: O=C(O)c1cc(OC2CC2)n2nc(C3CC3)cc2c1]

Intermediate 39 Step a

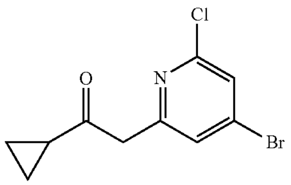 [SMILES: O=C(Cc1cc(Br)cc(Cl)n1)C1CC1]

Into a 250 mL 3-necked round-bottom flask was added 4-bromo-2-chloro-6-methylpyridine (3 g, 15 mmol), cyclopropanecarboxylic acid, methyl ester (22 mL, 22 mmol) and THF (50 mL) at 0° C. To the above mixture was added LiHMDS (3.7 g, 22 mmol) dropwise. The resulting mixture was stirred for additional 2 hr at 0° C. The reaction was monitored by TLC. The reaction was quenched by the addition of sat. $NH_4Cl$ (aq.). The aqueous layer was extracted with EtOAc. The resulting mixture was concentrated under reduced pressure. The residue was purified by silica gel column chromatography, eluted with PE/EA (7:1) to afford the desired compound (3.3 g, 83%) as a light yellow solid. ESI-MS m/z: 273.95 $[M+H]^+$.

Intermediate 39 Step b

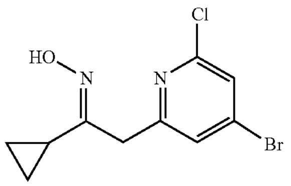 [SMILES: O/N=C(/Cc1cc(Br)cc(Cl)n1)C1CC1]

Into a 40 mL vial was added the compound from step a (3.3 g, 12 mmol), NaOAc (5 g, 60 mmol), hydroxylamine hydrochloride (4.2 g, 60 mmol) and MeOH (20 mL) at room temperature. The resulting mixture was stirred for overnight at 60° C. under nitrogen atmosphere. The reaction was monitored by LCMS. The aqueous layer was extracted with EtOAc. The resulting mixture was concentrated under reduced pressure. The residue was purified by silica gel column chromatography, eluted with PE/EA (5:1) to afford the desired compound (2.3 g, 66%) as a white solid. ESI-MS m/z: 288.95 $[M+H]^+$.

Intermediate 39 Steps c and d

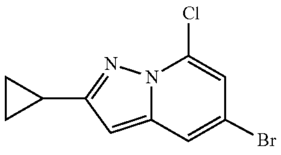 [SMILES: Clc1cc(Br)cc2cc(C3CC3)nn12]

Into a 20 mL vial was added the compound from step b (1.1 g, 3.8 mmol) and DME (10 mL) at 0° C. To the above mixture was added TFAA (0.9 g, 4 mmol) dropwise. The resulting mixture was stirred for additional 3 hr at room temperature. The reaction was monitored by TLC. The residue was purified by reverse flash chromatography with MeCN in water to give the desired compound (600 mg, 58%) as white solid. ESI-MS m/z: 270.95 $[M+H]^+$.

Into a 20 mL vial was added the compound from step c (600 mg, 2.2 mmol), ferrous chloride (56 mg, 0.44 mmol) and DME (10 mL) at room temperature. The resulting mixture was stirred for 2h at 80° C. under nitrogen atmosphere. The reaction was monitored by TLC. The aqueous layer was extracted with EtOAc. The resulting mixture was concentrated under reduced pressure. The residue was purified by silica gel column chromatography, eluted with PE/EA (5:1) to afford the desired compound (400 mg, 67%) as a white solid. ESI-MS m/z: 270.95 $[M+H]^+$.

Intermediate 39 Step e

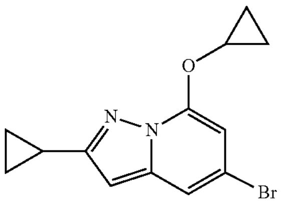 [SMILES: Brc1cc(OC2CC2)n2nc(C3CC3)cc2c1]

Into a 50 mL round-bottom flask was added the compound from step d (400 mg, 1.5 mmol), cyclopropanol (257 mg, 4.4 mmol), NaH (71 mg, 3 mmol) and DMF (10 mL) at 0° C. The resulting mixture was stirred for 2 hr at room temperature under nitrogen atmosphere. The reaction was quenched by the addition of sat. $NH_4Cl$ (aq.). The aqueous layer was extracted with EtOAc and concentrated under reduced pressure. The residue was purified by silica gel column chromatography, eluted with PE/EA (5:1) to afford the desired compound (360 mg, 83%) as a white solid. ESI-MS m/z: 293.00 $[M+H]^+$.

Intermediate 39 Step f

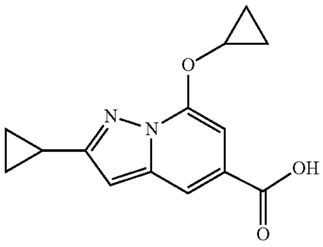 [SMILES: O=C(O)c1cc(OC2CC2)n2nc(C3CC3)cc2c1]

To a solution of the compound from step e (360 mg, 1.2 mmol) in EtOH (4 mL) and DMF (4 mL) was added $Pd(OAc)_2$ (83 mg, 0.4 mmol), DPPP (304 mg, 0.74 mmol) and TEA (1 mL) in a pressure tank. The mixture was pressurized to 10 atm with carbon monoxide at 100° C. overnight. The reaction mixture was cooled to room temperature and filtered to remove insoluble solids. The residue was purified by reverse flash chromatography to give the desired compound (300 mg, 85%) as white solid. ESI-MS m/z: 287.10 $[M+H]^+$.

Intermediate 39 Step g

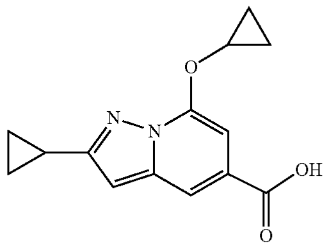 [SMILES: O=C(O)c1cc(OC2CC2)n2nc(C3CC3)cc2c1]

Into a 50 mL round-bottom flask were added the compound from step f (298 mg, 1 mmol), LiOH (125 mg, 5.2 mmol), MeOH (5 mL) and $H_2O$ (1 mL) at room temperature. The resulting mixture was stirred for 2h at room temperature under nitrogen atmosphere. The reaction was monitored by LCMS. The mixture was acidified to pH 6 with HCl (aq.). The resulting mixture was concentrated under reduced pressure. The residue was purified by reverse flash chromatography to give the desired compound (245 mg, 91%) as off-white solid. ESI-MS m/z: 259.10 $[M+H]^+$.

Intermediate 40

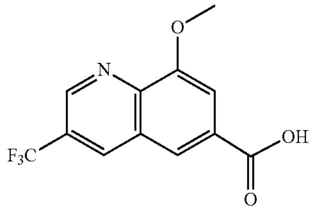 [SMILES: COc1cc(C(=O)O)cc2cc(C(F)(F)F)cnc12]

Intermediate 40 Steps a and b

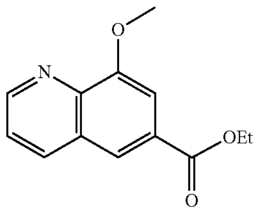 [SMILES: CCOC(=O)c1cc(OC)c2ncccc2c1]

A mixture of methyl 4-amino-3-methoxybenzoate (50.00 g, 275.95 mmol) and acrolein (30.94 g, 551.87 mmol) in HCl (100 mL) and AcOH (100 mL) was stirred for 1 h at 100° C. under nitrogen atmosphere. The resulting mixture was concentrated under vacuum used in next step directly. ESI-MS m/z: 204.10 $[M+H]^+$.

A mixture of the compound from step a, ethyl iodide (76.76 g, 492.16 mmol) and $Cs_2CO_3$ (240.52 g, 738.20 mmol) in DMF was stirred overnight at room temperature. The resulting mixture was filtered, the filter cake was washed with ethyl acetate (3×300 mL). The filtrate was concentrated under reduced pressure. The residue was purified by silica gel column chromatography, eluted with hexane/EA (1:1) to afford the crude product (25 g) as a yellow solid. ESI-MS m/z: 232.05 $[M+H]^+$.

Intermediate 40 Step c

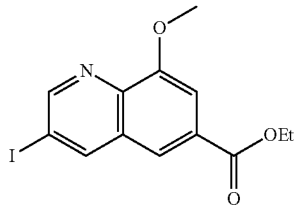 [SMILES: CCOC(=O)c1cc(OC)c2ncc(I)cc2c1]

A mixture of ethyl 8-methoxyquinoline-6-carboxylate (14.00 g, 60.54 mmol) and NIS (54.48 g, 242.16 mmol) in AcOH (300 mL) was stirred for 16 h at 100° C. under nitrogen atmosphere. The aqueous layer was extracted with EA. The resulting mixture was concentrated under vacuum. The residue was purified by silica gel column chromatography and reverse flash chromatography to afford the desired product (5.5 g, 14%) as a yellow solid. ESI-MS m/z: 358.00 $[M+H]^+$.

Intermediate 40 Step d

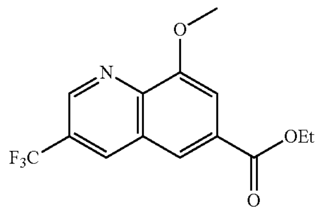 [SMILES: CCOC(=O)c1cc(OC)c2ncc(C(F)(F)F)cc2c1]

A mixture of the compound from step c (4.30 g, 12.04 mmol) and (1,10-Phenanthroline)(trifluoromethyl)copper(I) (5.65 g, 18.06 mmol) in DMF (70 mL) was stirred for 4 hours at 110° C. under nitrogen atmosphere. The mixture was allowed to cool down to room temperature. The resulting mixture was poured into water, extracted with EA. The combined organic layers were washed with brine and concentrated under reduced pressure. The residue was purified by silica gel column chromatography, eluted with PE/EA (4:1) to afford the desired product (2.6 g, 72%) as a light yellow solid. ESI-MS m/z: 300.15 $[M+H]^+$.

Intermediate 40 Step e

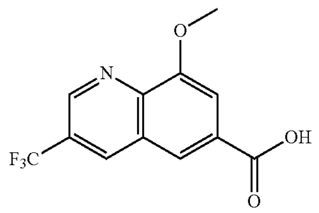 [SMILES: COc1cc(C(=O)O)cc2cc(C(F)(F)F)cnc12]

A mixture of the compound from step d (2.60 g, 8.69 mmol) and LiOH (2.08 g, 86.85 mmol) in MeOH (30 mL) and $H_2O$ (10 mL) was stirred for 2 hours at room temperature. The mixture was acidified to pH 4 with HCl (2 M aq.). The precipitated solids were collected by filtration and washed with water to afford the desired product (2.29 g, 97%) as a white solid. ESI-MS m/z: 271.95 $[M+H]^+$.

Intermediate 41

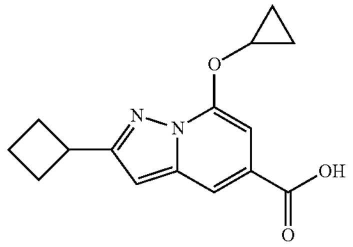 [SMILES: O=C(O)c1cc(OC2CC2)n2nc(C3CCC3)cc2c1]

The following compound was prepared in an analogous fashion to Intermediate 39. The residue was purified by reverse flash chromatography to afford the desired product (40 mg, 89%) as a light yellow solid. ESI-MS m/z: 247.10 $[M+H]^+$.

Intermediate 42

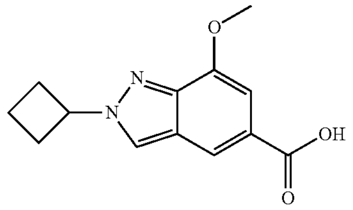 [SMILES: COc1cc(C(=O)O)cc2cn(C3CCC3)nc12]

The following compound was prepared in an analogous fashion to Intermediate 10. The crude residue was purified by reverse flash chromatography to afford the desired product (130 mg, 72%) as a white solid. ESI-MS m/z: 247.10 $[M+H]^+$.

Intermediate 43

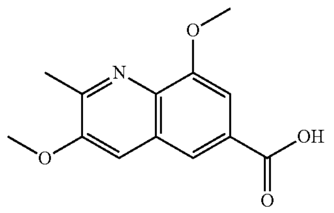 [SMILES: COc1cc2cc(C(=O)O)cc(OC)c2nc1C]

Intermediate 43 Steps a and b

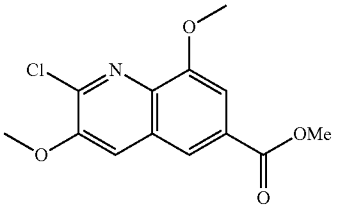 [SMILES: COC(=O)c1cc(OC)c2nc(Cl)c(OC)cc2c1]

To a 40 mL vial equipped with a stir bar was added methyl 3-methoxyquinoline-6-carboxylate (400 mg, 1.841 mmol) and the material was dissolved in DCM. mCPBA (883 mg, 3.68 mmol) was added, and the reaction was stirred overnight for 20 hr. The reaction was diluted with DCM and quenched with sodium thiosulfate. DCM/MeOH extraction with a phase separator cartridge, and the organics were concentrated. The reside was purified by automated column chromatography (silica gel, 0-20% methanol in DCM) to afford the desired compound (361 mg, 84%). ESI-MS m/z: 234.08 $[M+H]^+$.

To a 50 mL rbf containing a stir bar was step a (143 mg, 0.613 mmol), and the solid was dissolved in DCM. $POCl_3$ (114 μl, 1.226 mmol) was added, the flask equipped with a condenser, and the reaction heated to 45° C. for 2 hr. The reaction was diluted with DCM and quenched with water and saturated sodium bicarbonate. DCM and DCM/MeOH extraction with a phase separator cartridge, and the organics were concentrated. The reside was purified by automated column chromatography (silica gel, 0-90% EtOAc in hexanes) to afford the desired compound (102 mg, 66%). ESI-MS m/z: 252.04 $[M+H]^+$.

Intermediate 43 Step c

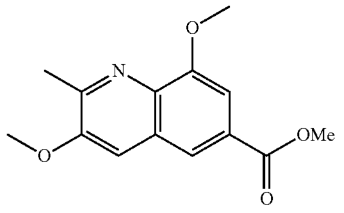 [SMILES: COC(=O)c1cc(OC)c2nc(C)c(OC)cc2c1]

To a 20 mL vial equipped with a stir bar was added $Pd(PPh_3)_4$ (4.59 mg, 3.97 μmol), step b (40 mg, 0.159 mmol), potassium carbonate (65.9 mg, 0.477 mmol) and methylboronic acid (47.6 mg, 0.795 mmol). The vial was purged with $N_2$ for 10 minutes. 1,4-Dioxane (1.060 ml) was added and the reaction was heated to 100° C. for 18 hrs. The reaction was diluted with EtOAc and quenched with water. EtOAc and DCM/MeOH extraction with a phase separator cartridge, and the organics were concentrated. The reside was purified by automated column chromatography (silica gel, 0-80% EtOAc in hexanes) to afford the desired compound (36 mg, 98%). ESI-MS m/z: 232.10 $[M+H]^+$.

Intermediate 43 Step d

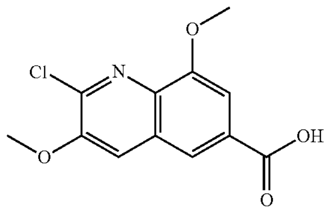 [SMILES: COc1cc2cc(C(=O)O)cc(OC)c2nc1Cl]

To a 20 mL vial equipped with a stir bar was added step c (36 mg, 0.156 mmol), and the material was dissolved in THF:MeOH:Water (1:1:1, 0.2 M). Lithium hydroxide hydrate (32.7 mg, 0.778 mmol) was added, and the reaction was warmed to 45° C. and monitored by LCMS. The vial was cooled to 0° C. and acidified to pH=4 with 2 M HCl. No precipitate, concentrated organics in vacuo. Solid precipitated. Cooled to 0° C., further precipitation. Solid collected via vacuum filtration and dried on high vacuum to afford the desired pdt as a white solid (18 mg, 53%). ESI-MS m/z: 217.82 $[M+H]^+$.

Example 233

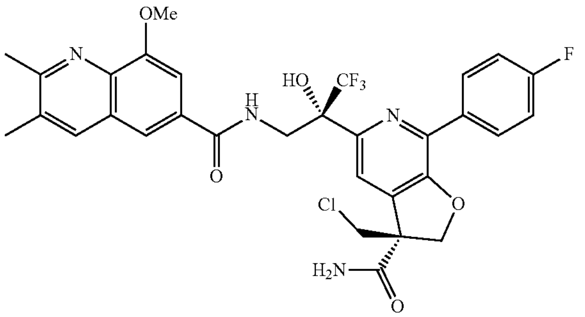 [SMILES: COc1cc(C(=O)NC[C@](O)(c2cc3c(c(-c4ccc(F)cc4)n2)OC[C@]3(CCl)C(N)=O)C(F)(F)F)cc2cc(C)c(C)nc12]

(S)-7-(4-fluorophenyl)-3-(hydroxymethyl)-5-((S)-1,1,1-trifluoro-2-hydroxy-3-(8-methoxy-2,3-dimethylquinoline-6-carboxamido)propan-2-yl)-2,3-dihydrofuro[2,3-c]pyridine-3-carboxamide, hydrochloride salt (20 mg, 0.032 mmol) was dissolved in DCM (1 ml) and DAST (1 eq, 4.2 μl, 0.032 mmol) was added at 0° C. The reaction mixture was allowed to stir at 0° C. for 2 h. The reaction mixture was quenched by adding MeOH and the solution was concentrated and purified by HPLC to give (S)-3-(chloromethyl)-7-(4-fluorophenyl)-5-((S)-1,1,1-trifluoro-2-hydroxy-3-(8-methoxy-2,3-dimethylquinoline-6-carboxamido)propan-2-yl)-2,3-dihydrofuro[2,3-c]pyridine-3-carboxamide (3.68 mg, 5.69 μmol, 17.88% yield). ESI-MS m/z: 647.074 $[M+H]^+$.

Intermediate 44

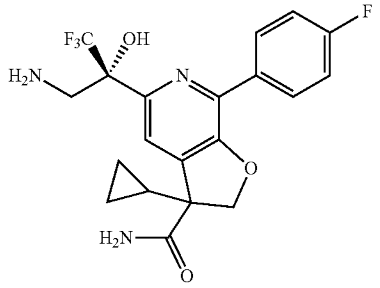 [SMILES: NC[C@](O)(c1cc2c(c(-c3ccc(F)cc3)n1)OCC2(C(N)=O)C1CC1)C(F)(F)F]

The above example was prepared in an analogous sequence to Intermediate 36 as a mixture of diastereomers to afford the desired amino alcohol (320 mg). ESI-MS m/z: 426.04 $[M+H]^+$.

Intermediate 45

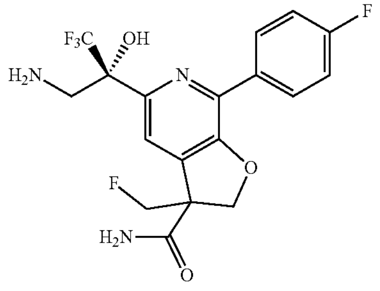 [SMILES: NC[C@](O)(c1cc2c(c(-c3ccc(F)cc3)n1)OCC2(CF)C(N)=O)C(F)(F)F]

Intermediate 45 Step a

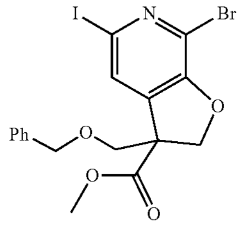 [SMILES: COC(=O)C1(COCc2ccccc2)COc2c1cc(I)nc2Br]

Into a 250 mL round-bottom flask were added methyl 7-bromo-5-iodo-2,3-dihydrofuro[2,3-c]pyridine-3-carboxylate (586 mg, 1.526 mmol), tetrahydrofuran (85 mL) and ((chloromethoxy)methyl)benzene (6.94 ml, 50.6 mmol). The mixture was cooled to −78° C. and lithium diisopropylamide (2 M solution in tetrahydrofuran/heptane/ethylbenzene, 9.27 mL, 18.54 mmol) was added dropwise over 15 min. The mixture was allowed to stir at −78° C. for 1 h, and was then warmed to 23° C. for 30 min. The reaction was diluted with EtOAc (100 mL) and water (50 mL). The layers were separated and the aqueous layer was extracted with EtOAc (3×50 mL), the combined organics were dried over $Na_2SO_4$, filtered and concentrated. The crude material was purified by automated column chromatography (silica gel, 0-10% EtOAc in hexanes) to afford the title compound (4.69 g, 55%). ESI-MS m/z: 503.55/505.47 $[M+H]^+$.

Intermediate 45 Step b

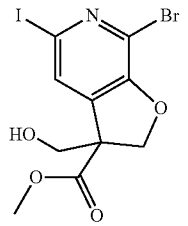 [SMILES: COC(=O)C1(CO)COc2c1cc(I)nc2Br]

Into a 100 mL round-bottom flask were added the compound from step a (4.69 g, 9.30 mmol), and chloroform (47 mL). The mixture was cooled to 0° C. and methanesulfonic acid was added. The mixture was allowed to warm to room temperature with stirring for 2 h and monitored by LCMS. The reaction was diluted with EtOAc and water. The aqueous was extracted, the combined organics were washed with $NaHCO_3$ dried over $Na_2SO_4$, filtered and concentrated. The material was purified by automated column chromatography (silica gel, 0-20% EtOAc in hexanes) to afford the title compound (2.25 g, 58%). ESI-MS m/z: 413.46/415.42 $[M+H]^+$.

Intermediate 45 Step c

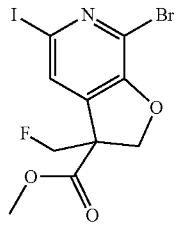 [SMILES: COC(=O)C1(CF)COc2c1cc(I)nc2Br]

Into a 50 mL round-bottom flask were added the compound from step b (2.12 g, 5.12 mmol), followed by dichloromethane (21 mL) then 2,6-lutidine (890 μL, 7.68 mmol). The mixture was cooled to −78° C., then triflic anhydride (1 M solution in dichloromethane, 5.63 mL 5.63 mmoL) was added dropwise over 10 min. The mixture was allowed to stir at −78° C. for 30 min and monitored by LCMS. The mixture was warmed to 0° C. and was then diluted with water and dichloromethane. The layers were separated and the aqueous layer was washed with dichloromethane (3×25 mL), the combined organics were washed with $NaHCO_3$ (sat. aq.) (2×mL) then concentrated. The resulting oil was dissolved in tetrahydrofuran (2 mL), and cooled to 0° C. To this mixture tetrabutylammonium fluoride (1 M in tetrahydrofuran, 5.37 mL, 5.37 mmol) was added, and the mixture allowed to warm to room temperature for 19 h. The reaction was diluted with EtOAc and water. The aqueous was extracted with EtOAc (3×20 mL), the combined organics were dried over $Na_2SO_4$ and concentrated. The material was purified by automated column chromatography (silica gel, 0-10% EtOAc in hexanes) to afford the title compound (2.00 g, 94%). ESI-MS m/z: 415.47/417.40 $[M+H]^+$.

Intermediate 45 Step d

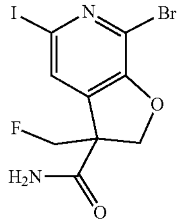

Into a 100 mL round-bottom flask containing the compound from step c (2.00 g, 4.81 mmol), was added ammonia (7 M solution in MeOH, 20.6 mL, 144 mmol). The mixture was heated to 45° C. for 1.5 h and monitored by LCMS. The mixture was cooled to room temperature, concentrated and the yellow solids were carried forward to the next step without further purification (1.93 g, >99%). ESI-MS m/z: 400.46/402.41 $[M+H]^+$.

Intermediate 45

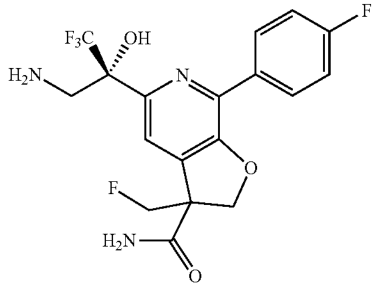 [SMILES: NC[C@](O)(c1cc2c(c(-c3ccc(F)cc3)n1)OCC2(CF)C(N)=O)C(F)(F)F]

The above compound was prepared in an analogous sequence to Intermediate 36 as a mixture of diastereomers to afford the desired amino alcohol (1.056 g, 85%). ESI-MS m/z: 417.97 $[M+H]^+$.

Intermediate 46

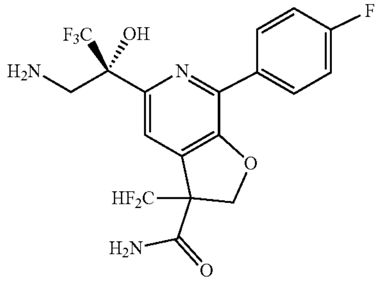

Intermediate 46 Step a

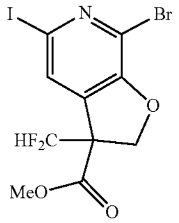

To a 250 mL round bottom flask equipped with a stir bar was added methyl 7-bromo-5-iodo-2,3-dihydrofuro[2,3-c]pyridine-3-carboxylate (2.044 g, 5.32 mmol) and the material was dissolved in THE (21.29 ml). The flask was cooled it −78° C., and (bromodifluoromethyl)trimethylsilane (1.656 ml, 10.65 mmol) followed by dropwise addition of lithium diisopropylamide (2.93 ml, 5.86 mmol). The reaction was stirred for 1 hr and −78° C., and then allowed to warm to room temperature. After 1.5 hr the reaction was diluted with EtOAc and quenched with sat. ammonium chloride. The aqueous was extracted with EtOAc, and the organics dried, filtered and concentrated. The crude material was purified by automated column chromatography (silica gel, 0-30% EtOAc in hexanes, large column volume) to afford the desired product (295.6 mg, 13%). ESI-MS m/z: 433.87/435.86 $[M+H]^+$.

Intermediate 46 Step b

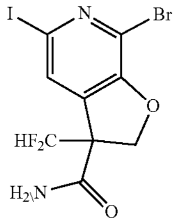

To a 40 mL vial containing step a (393.9 mg, 0.908 mmol) was added a stir bar and ammonia (3890 μl, 27.2 mmol) was added. The reaction was heated to 45° C. and monitored by LCMS (1.5 hr complete). The stir bar was removed, and the reaction concentrated. The material was trittered with DCM to afford a light brown solid as the desired product (360 mg, 96%). ESI-MS m/z: 418.87/420.87 $[M+H]^+$.

Intermediate 46

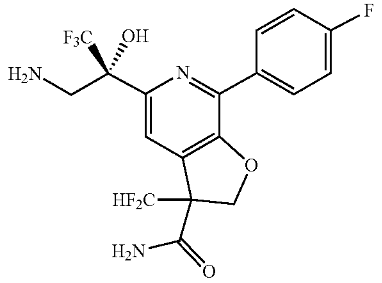

The following compound was prepared in an analgous fashion to Intermediate 36 to afford the desired amino alcohol as a mixture of diastereomers (105 mg, 92%). ESI-MS m/z: 436.11 $[M+H]^+$.

The following Table 2 contains examples that were prepared with the similar method to Example 1 Step c (PyBOP or HATU). The amine coupling partners were prepared according to Intermediates 44-46 or by analogous procedures as a mixture of diastereomers. The majority of compounds were purified by Gilson prep-HPLC. If depicted as a single diasteromer, the diastereomers were separated on Gilson prep-HPLC. The aryl acid coupling partners were prepared according to Intermediates 1-46 or by analogous procedures with slight modifications, and also prepared according to procedures found in U.S. patent application Ser. No. 16/930,622.

TABLE 2

| Example | Structure | $MS^+$ m/z |
|---|---|---|
| 234 | 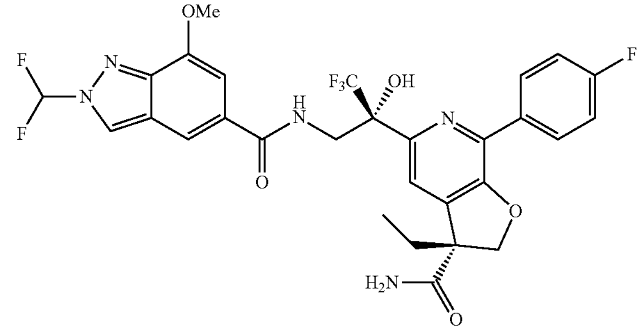 [SMILES: CC[C@]1(C(N)=O)COc2c1cc([C@@](O)(CNC(=O)c1cc(OC)c3nn(C(F)F)cc3c1)C(F)(F)F)nc2-c1ccc(F)cc1] | 638.21 |
| 235 | 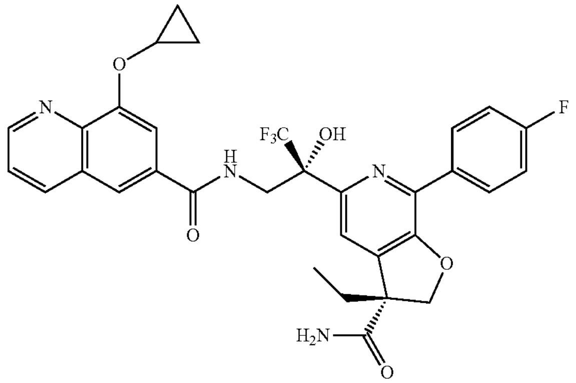 [SMILES: CC[C@]1(C(N)=O)COc2c1cc([C@@](O)(CNC(=O)c1cc(OC3CC3)c3ncccc3c1)C(F)(F)F)nc2-c1ccc(F)cc1] | 625.21 |
| 236 | 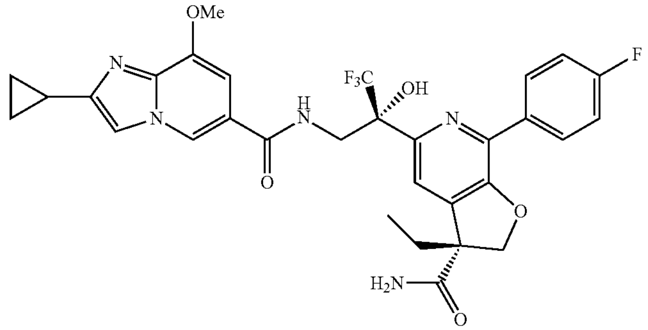 [SMILES: CC[C@]1(C(N)=O)COc2c1cc([C@@](O)(CNC(=O)c1cc(OC)c3nc(C4CC4)cn3c1)C(F)(F)F)nc2-c1ccc(F)cc1] | 628.22 |

TABLE 2-continued
| Example | Structure | MS⁺ m/z |
| --- | --- | --- |
| 237 | 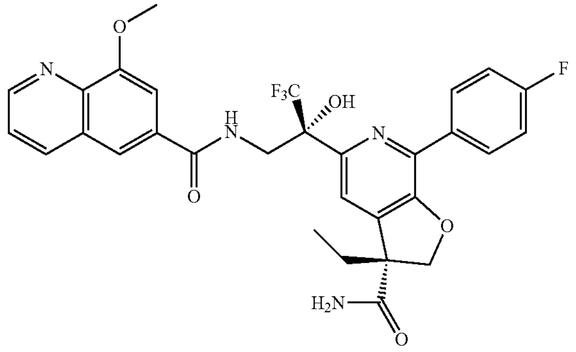 [SMILES: CC[C@]1(C(N)=O)COc2c1cc([C@@](O)(CNC(=O)c1cc(OC)c3ncccc3c1)C(F)(F)F)nc2-c1ccc(F)cc1] | 599.30 |
| 238 | 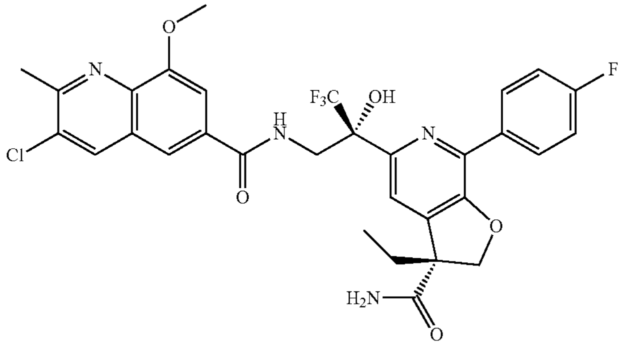 [SMILES: CC[C@]1(C(N)=O)COc2c1cc([C@@](O)(CNC(=O)c1cc(OC)c3nc(C)c(Cl)cc3c1)C(F)(F)F)nc2-c1ccc(F)cc1] | 647.36 |
| 239 | 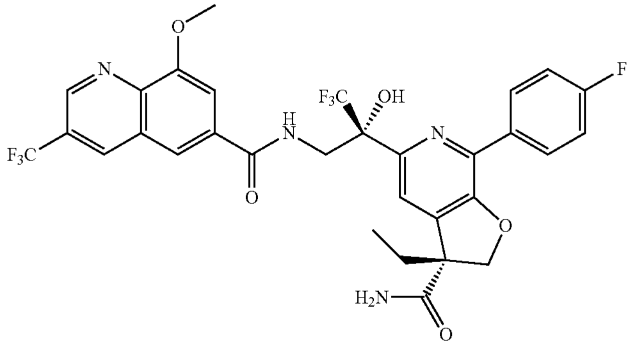 [SMILES: CC[C@]1(C(N)=O)COc2c1cc([C@@](O)(CNC(=O)c1cc(OC)c3ncc(C(F)(F)F)cc3c1)C(F)(F)F)nc2-c1ccc(F)cc1] | 667.37 |
| 240 | 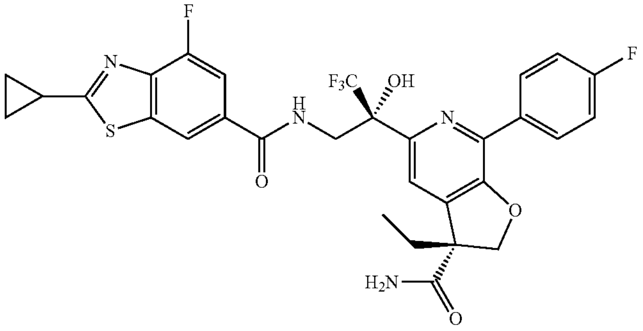 [SMILES: CC[C@]1(C(N)=O)COc2c1cc([C@@](O)(CNC(=O)c1cc(F)c3nc(C4CC4)sc3c1)C(F)(F)F)nc2-c1ccc(F)cc1] | 608.13 |

TABLE 2-continued
| Example | Structure | MS+ m/z |
| --- | --- | --- |
| 241 | 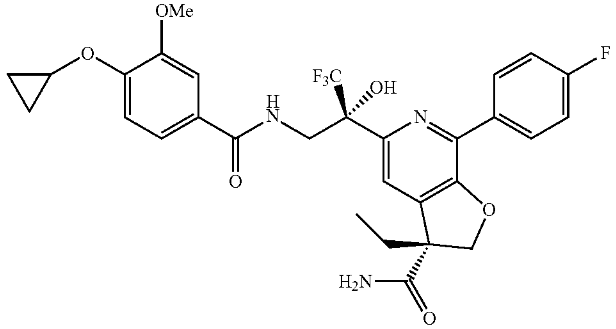 [SMILES: CC[C@]1(C(N)=O)COc2c1cc([C@@](O)(CNC(=O)c1ccc(OC3CC3)c(OC)c1)C(F)(F)F)nc2-c1ccc(F)cc1] | 604.31 |
| 242 | 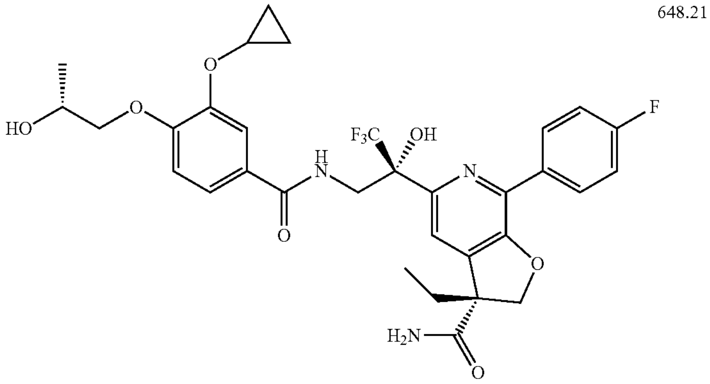 | 648.21 |
| 243 | 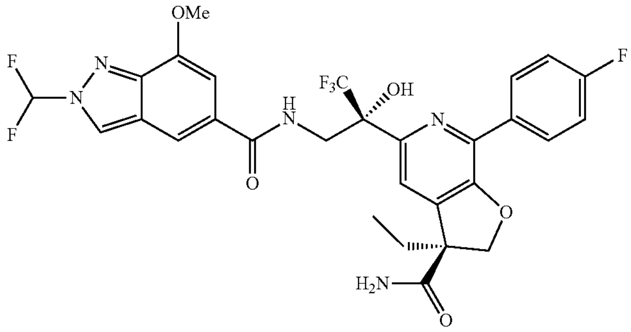 [SMILES: CC[C@@]1(C(N)=O)COc2c1cc([C@@](O)(CNC(=O)c1cc(OC)c3nn(C(F)F)cc3c1)C(F)(F)F)nc2-c1ccc(F)cc1] | 638.21 |
| 244 | 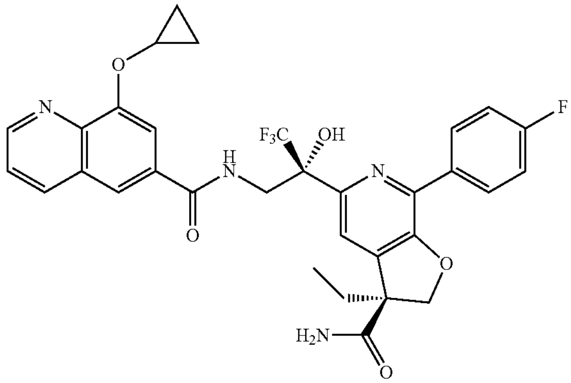 [SMILES: CC[C@@]1(C(N)=O)COc2c1cc([C@@](O)(CNC(=O)c1cc(OC3CC3)c3ncccc3c1)C(F)(F)F)nc2-c1ccc(F)cc1] | 625.19 |

TABLE 2-continued
| Example | Structure | MS⁺ m/z |
|---|---|---|
| 245 | 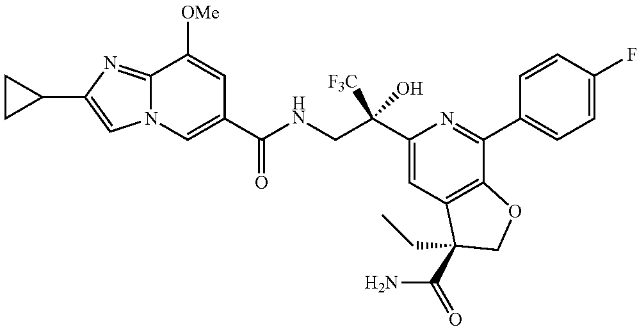 [SMILES: CC[C@@]1(C(N)=O)COc2c1cc([C@@](O)(CNC(=O)c1cc(OC)c3nc(C4CC4)cn3c1)C(F)(F)F)nc2-c1ccc(F)cc1] | 628.22 |
| 246 | 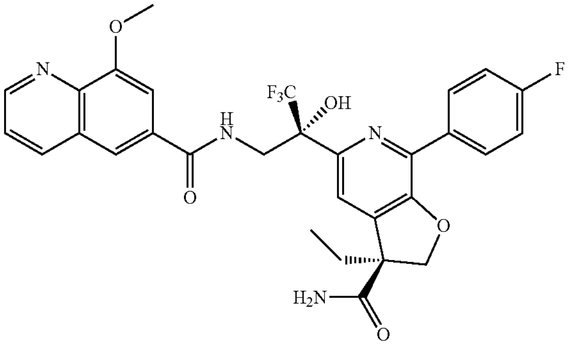 [SMILES: CC[C@@]1(C(N)=O)COc2c1cc([C@@](O)(CNC(=O)c1cc(OC)c3ncccc3c1)C(F)(F)F)nc2-c1ccc(F)cc1] | 599.29 |
| 247 | 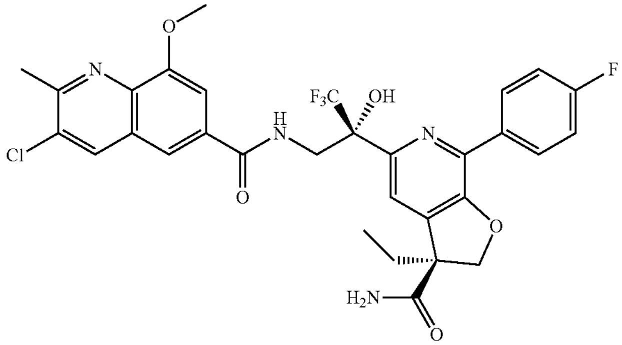 [SMILES: CC[C@@]1(C(N)=O)COc2c1cc([C@@](O)(CNC(=O)c1cc(OC)c3nc(C)c(Cl)cc3c1)C(F)(F)F)nc2-c1ccc(F)cc1] | 647.36 |
| 248 | 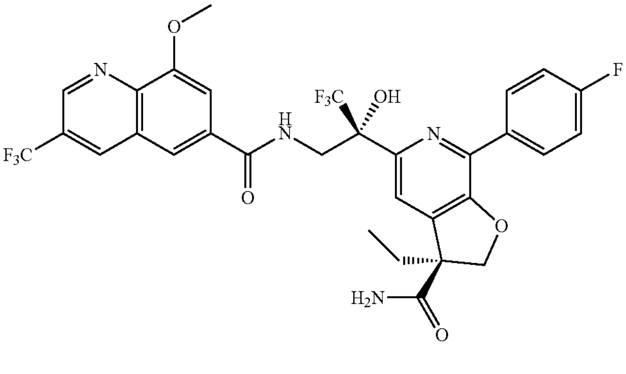 [SMILES: CC[C@@]1(C(N)=O)COc2c1cc([C@@](O)(CNC(=O)c1cc(OC)c3ncc(C(F)(F)F)cc3c1)C(F)(F)F)nc2-c1ccc(F)cc1] | 667.37 |

TABLE 2-continued
| Example | Structure | MS+ m/z |
|---|---|---|
| 249 | 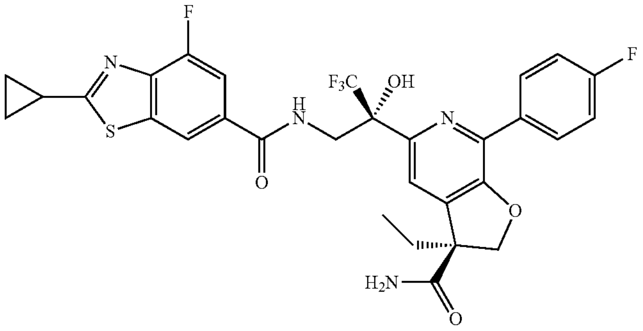 [SMILES: CC[C@@]1(C(N)=O)COc2c1cc([C@@](O)(CNC(=O)c1cc(F)c3nc(C4CC4)sc3c1)C(F)(F)F)nc2-c1ccc(F)cc1] | 608.12 |
| 250 | 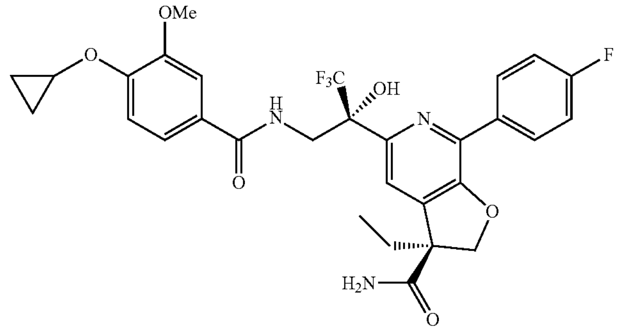 [SMILES: CC[C@@]1(C(N)=O)COc2c1cc([C@@](O)(CNC(=O)c1ccc(OC3CC3)c(OC)c1)C(F)(F)F)nc2-c1ccc(F)cc1] | 604.30 |
| 251 | 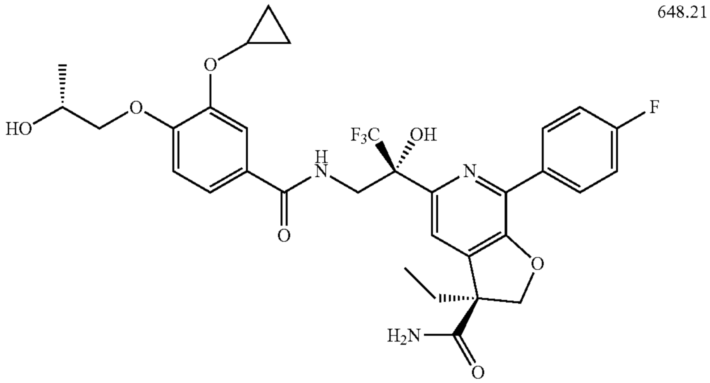 | 648.21 |
| 252 | 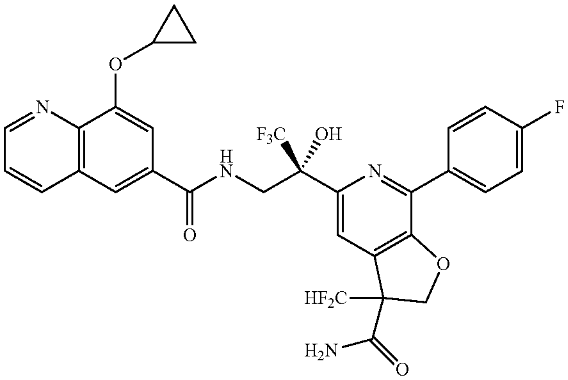 | 657.19 |

TABLE 2-continued
| Example | Structure | MS+ m/z |
|---|---|---|
| 253 | 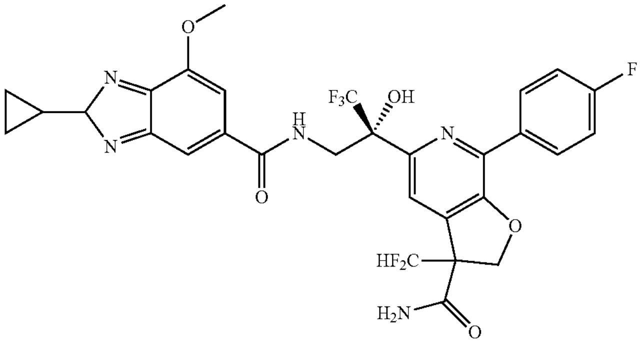 | 650.18 |
| 254 | 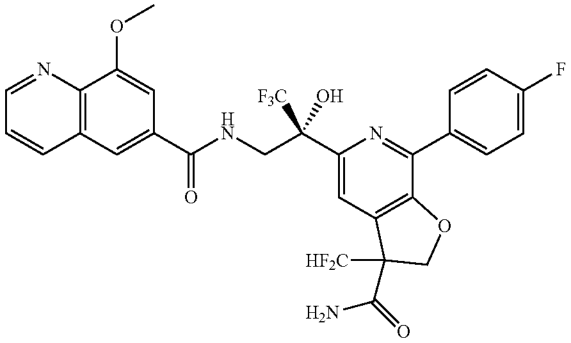 | 621.16 |
| 255 | 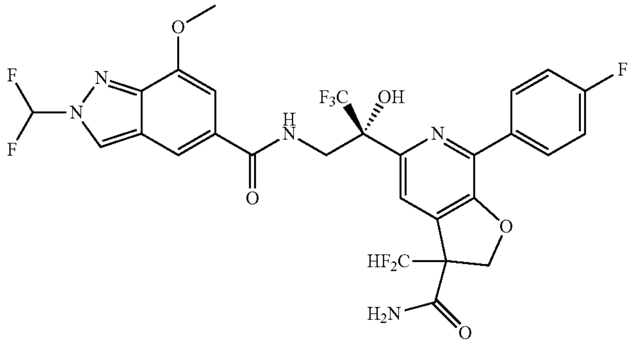 | 660.15 |
| 256 | 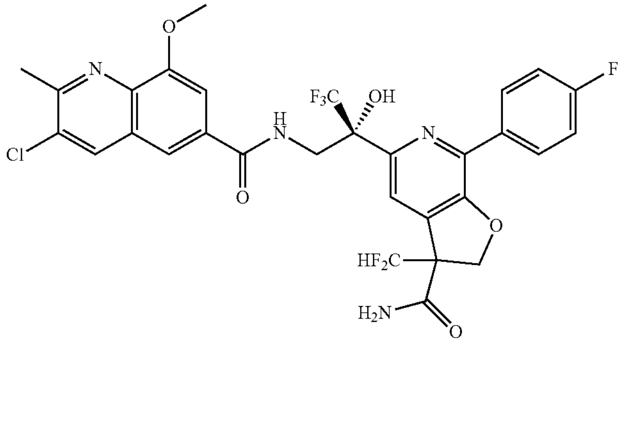 | 669.13 |

TABLE 2-continued
| Example | Structure | MS⁺ m/z |
|---|---|---|
| 257 | 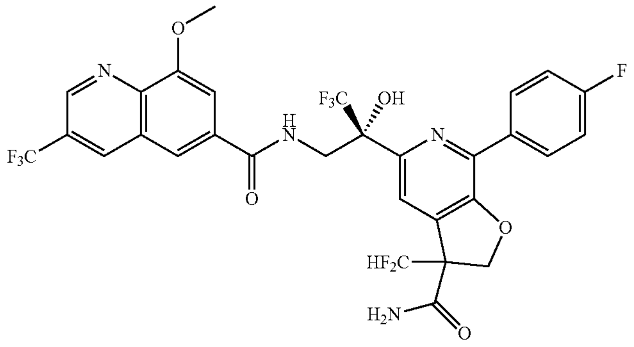 | 689.14 |
| 258 | 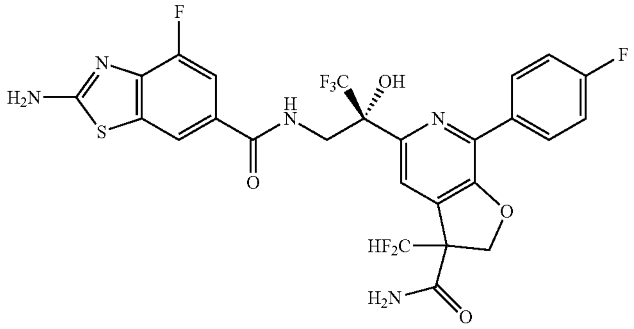 | 630.10 |
| 259 | 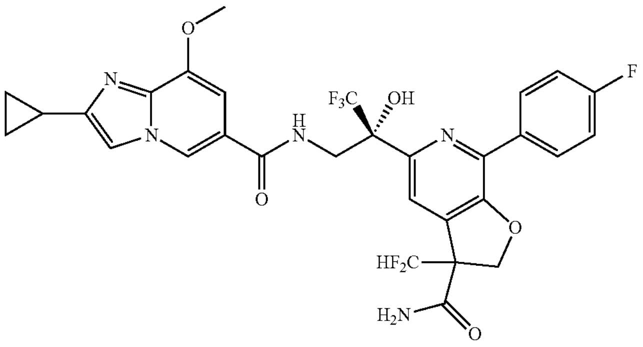 | 650.13 |
| 260 | 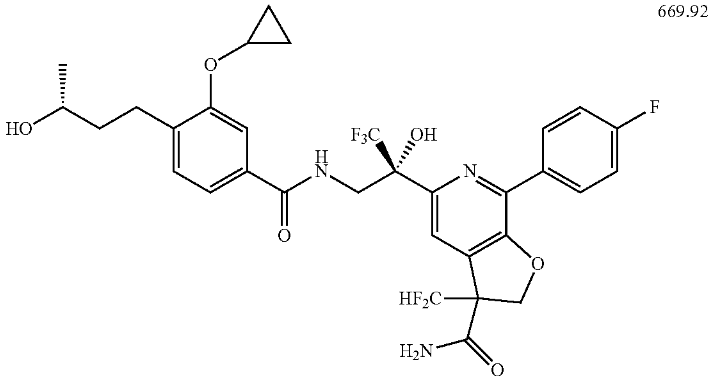 | 669.92 |

TABLE 2-continued
| Example | Structure | MS+ m/z |
| --- | --- | --- |
| 261 | 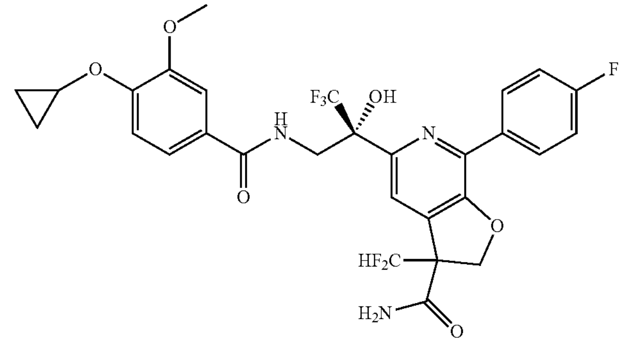 | 625.85 |
| 262 | 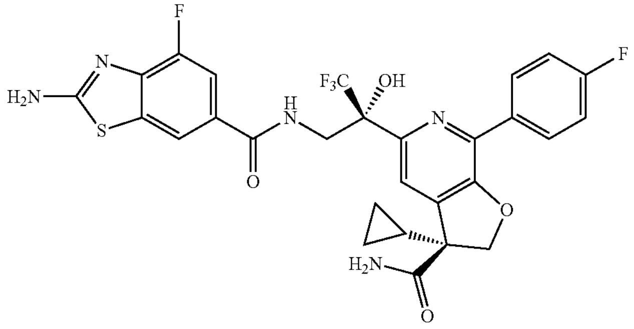 [SMILES: NC(=O)[C@]1(C2CC2)COc2c1cc([C@@](O)(CNC(=O)c1cc(F)c3nc(N)sc3c1)C(F)(F)F)nc2-c1ccc(F)cc1] | 619.97 |
| 263 | 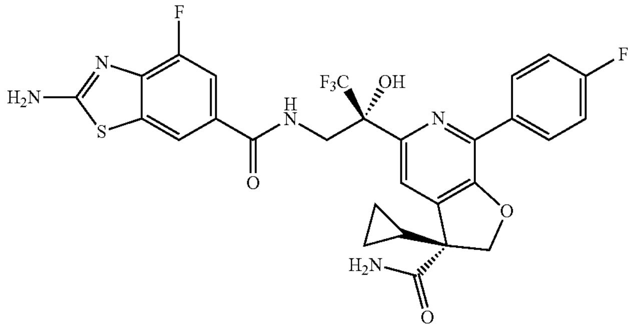 [SMILES: NC(=O)[C@@]1(C2CC2)COc2c1cc([C@@](O)(CNC(=O)c1cc(F)c3nc(N)sc3c1)C(F)(F)F)nc2-c1ccc(F)cc1] | 619.97 |
| 264 | 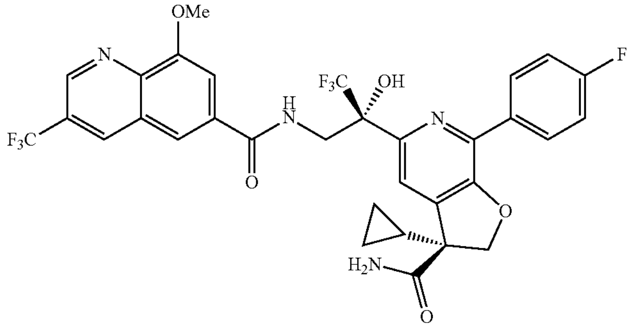 [SMILES: COc1cc(C(=O)NC[C@](O)(c2cc3c(c(-c4ccc(F)cc4)n2)OC[C@]3(C(N)=O)C2CC2)C(F)(F)F)cc2cc(C(F)(F)F)cnc12] | 679.07 |

TABLE 2-continued
| Example | Structure | MS+ m/z |
|---|---|---|
| 265 | 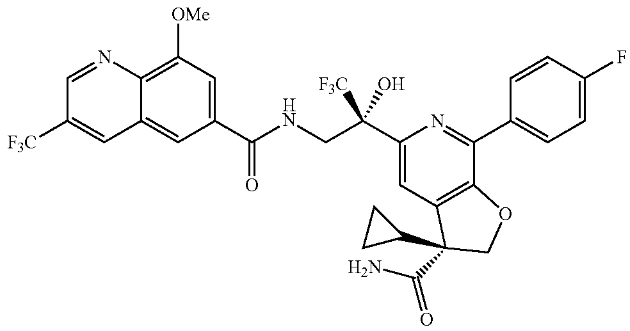 [SMILES: COc1cc(C(=O)NC[C@](O)(c2cc3c(c(-c4ccc(F)cc4)n2)OC[C@@]3(C(N)=O)C2CC2)C(F)(F)F)cc2cc(C(F)(F)F)cnc12] | 679.07 |
| 266 | 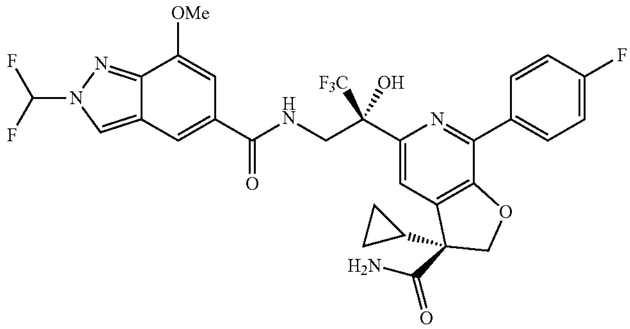 [SMILES: COc1cc(C(=O)NC[C@](O)(c2cc3c(c(-c4ccc(F)cc4)n2)OC[C@]3(C(N)=O)C2CC2)C(F)(F)F)cc2cn(C(F)F)nc12] | 650.01 |
| 267 | 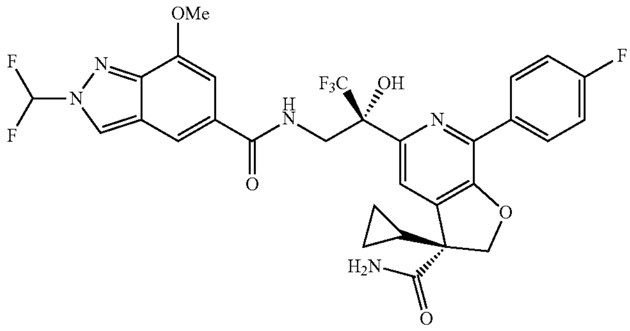 [SMILES: COc1cc(C(=O)NC[C@](O)(c2cc3c(c(-c4ccc(F)cc4)n2)OC[C@@]3(C(N)=O)C2CC2)C(F)(F)F)cc2cn(C(F)F)nc12] | 650.01 |
| 268 | 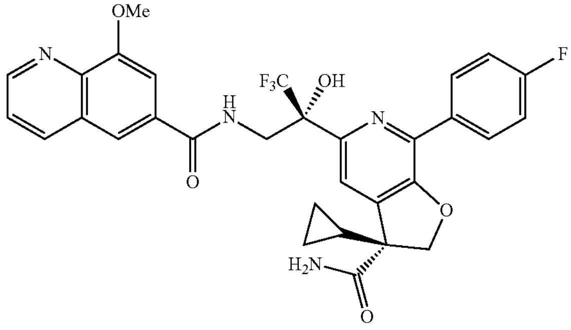 [SMILES: COc1cc(C(=O)NC[C@](O)(c2cc3c(c(-c4ccc(F)cc4)n2)OC[C@@]3(C(N)=O)C2CC2)C(F)(F)F)cc2cccnc12] | 611.06 |

TABLE 2-continued
| Example | Structure | MS+ m/z |
|---|---|---|
| 269 | 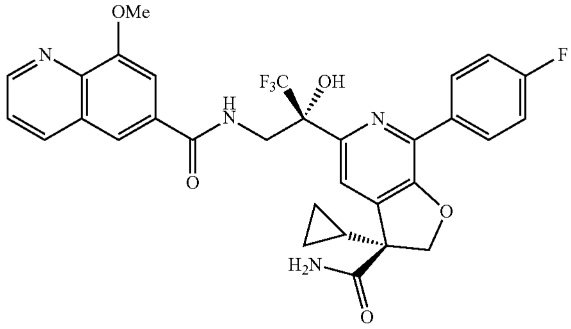 [SMILES: COc1cc(C(=O)NC[C@](O)(c2cc3c(c(-c4ccc(F)cc4)n2)OC[C@]3(C(N)=O)C2CC2)C(F)(F)F)cc2cccnc12] | 611.06 |
| 270 | 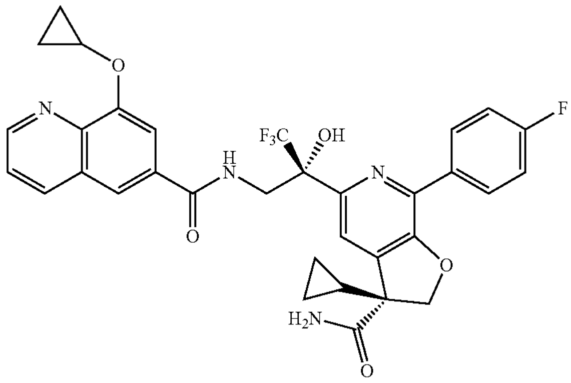 [SMILES: NC(=O)[C@@]1(C2CC2)COc2c1cc([C@@](O)(CNC(=O)c1cc(OC3CC3)c3ncccc3c1)C(F)(F)F)nc2-c1ccc(F)cc1] | 637.06 |
| 271 | 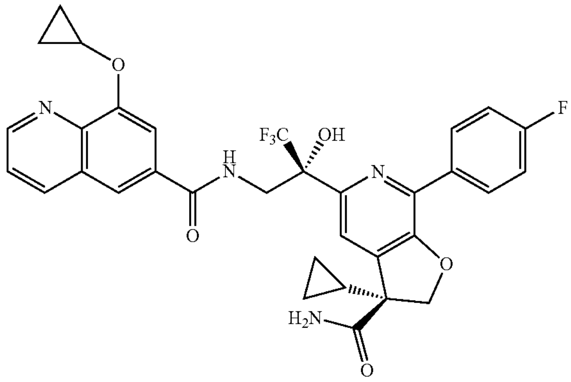 [SMILES: NC(=O)[C@]1(C2CC2)COc2c1cc([C@@](O)(CNC(=O)c1cc(OC3CC3)c3ncccc3c1)C(F)(F)F)nc2-c1ccc(F)cc1] | 637.06 |
| 272 | 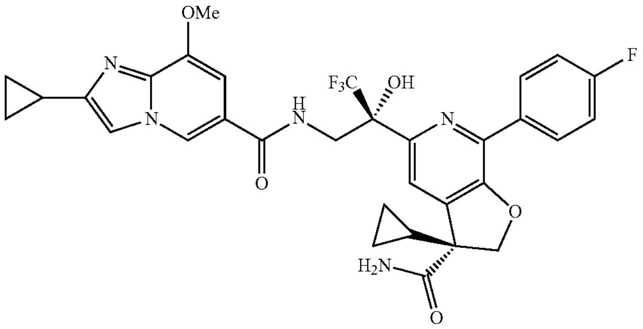 [SMILES: COc1cc(C(=O)NC[C@](O)(c2cc3c(c(-c4ccc(F)cc4)n2)OC[C@@]3(C(N)=O)C2CC2)C(F)(F)F)cn2cc(C3CC3)nc12] | 640.15 |

TABLE 2-continued
| Example | Structure | MS+ m/z |
|---|---|---|
| 273 | 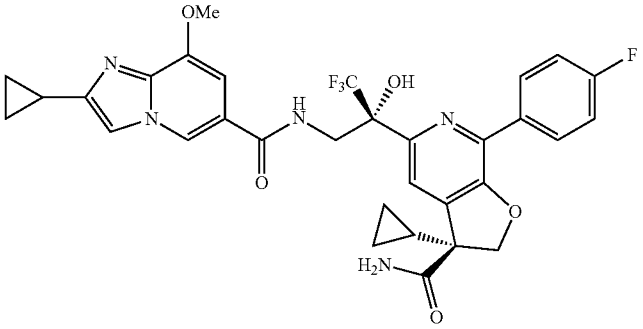 [SMILES: COc1cc(C(=O)NC[C@](O)(c2cc3c(c(-c4ccc(F)cc4)n2)OC[C@]3(C(N)=O)C2CC2)C(F)(F)F)cn2cc(C3CC3)nc12] | 640.15 |
| 274 | 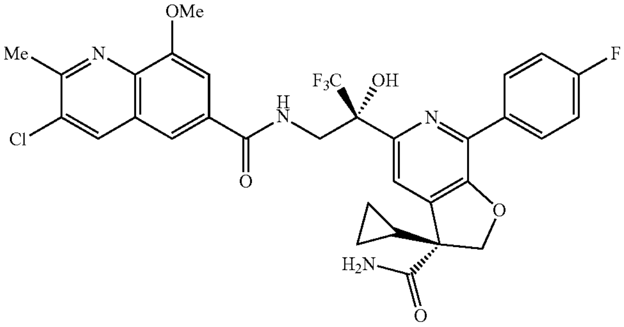 [SMILES: COc1cc(C(=O)NC[C@](O)(c2cc3c(c(-c4ccc(F)cc4)n2)OC[C@@]3(C(N)=O)C2CC2)C(F)(F)F)cc2cc(Cl)c(C)nc12] | 659.11 |
| 275 | 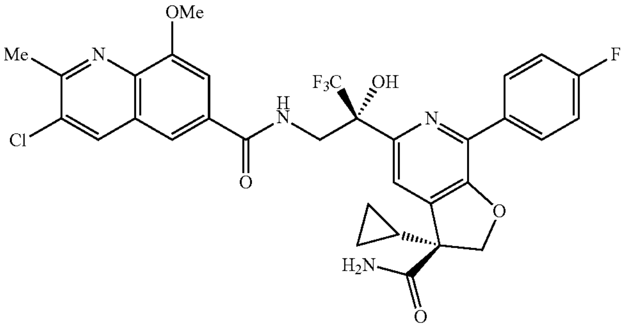 [SMILES: COc1cc(C(=O)NC[C@](O)(c2cc3c(c(-c4ccc(F)cc4)n2)OC[C@]3(C(N)=O)C2CC2)C(F)(F)F)cc2cc(Cl)c(C)nc12] | 659.11 |
| 276 | 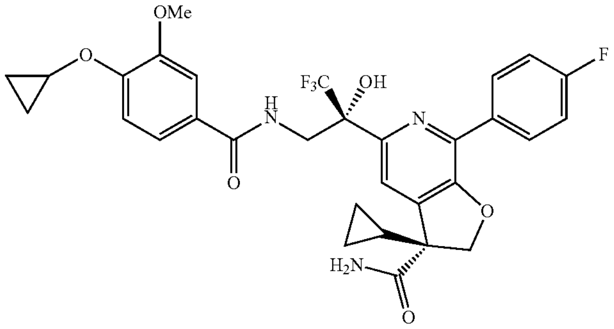 [SMILES: COc1cc(C(=O)NC[C@](O)(c2cc3c(c(-c4ccc(F)cc4)n2)OC[C@@]3(C(N)=O)C2CC2)C(F)(F)F)ccc1OC1CC1] | 616.02 |

TABLE 2-continued
| Example | Structure | MS+ m/z |
|---|---|---|
| 277 | 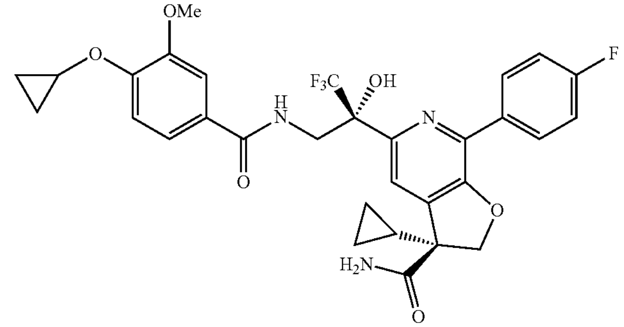 [SMILES: COc1cc(C(=O)NC[C@](O)(c2cc3c(c(-c4ccc(F)cc4)n2)OC[C@]3(C(N)=O)C2CC2)C(F)(F)F)ccc1OC1CC1] | 616.02 |
| 278 | 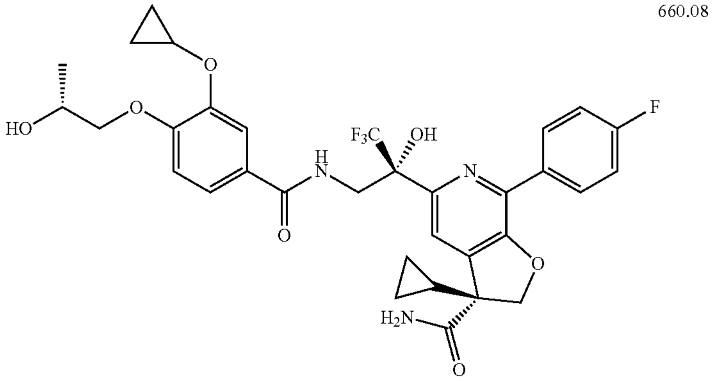 | 660.08 |
| 279 | 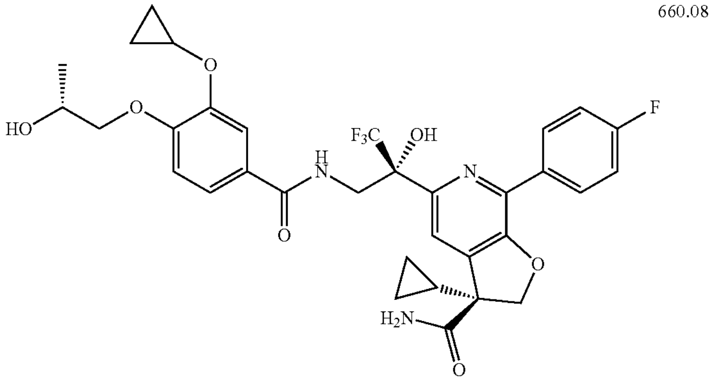 | 660.08 |
| 280 | 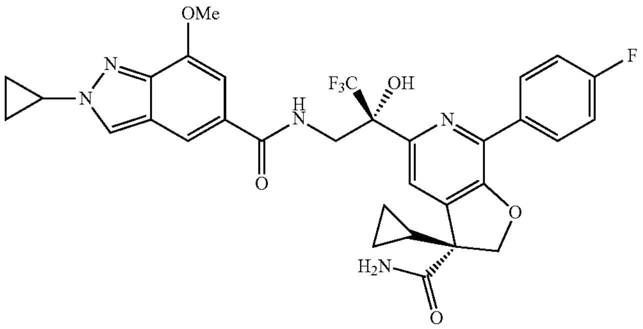 [SMILES: COc1cc(C(=O)NC[C@](O)(c2cc3c(c(-c4ccc(F)cc4)n2)OC[C@@]3(C(N)=O)C2CC2)C(F)(F)F)cc2cn(C3CC3)nc12] | 640.08 |

TABLE 2-continued
| Example | Structure | MS+ m/z |
|---|---|---|
| 281 | 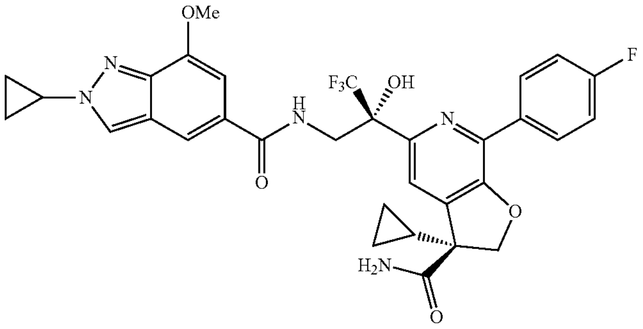 [SMILES: COc1cc(C(=O)NC[C@](O)(c2cc3c(c(-c4ccc(F)cc4)n2)OC[C@]3(C(N)=O)C2CC2)C(F)(F)F)cc2cn(C3CC3)nc12] | 640.08 |
| 282 | 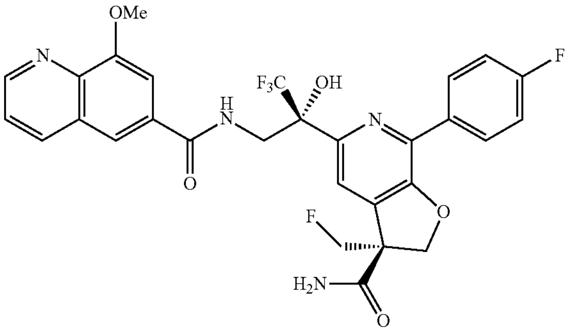 [SMILES: COc1cc(C(=O)NC[C@](O)(c2cc3c(c(-c4ccc(F)cc4)n2)OC[C@@]3(CF)C(N)=O)C(F)(F)F)cc2cccnc12] | 602.82 |
| 283 | 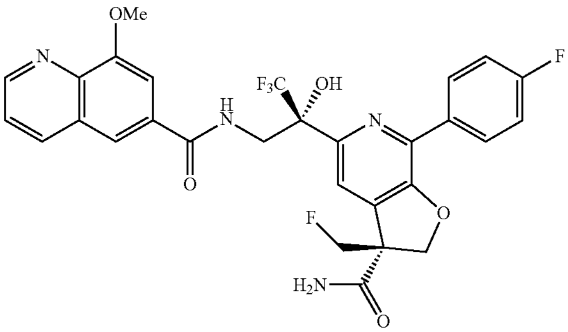 [SMILES: COc1cc(C(=O)NC[C@](O)(c2cc3c(c(-c4ccc(F)cc4)n2)OC[C@]3(CF)C(N)=O)C(F)(F)F)cc2cccnc12] | 603.11 |
| 284 | 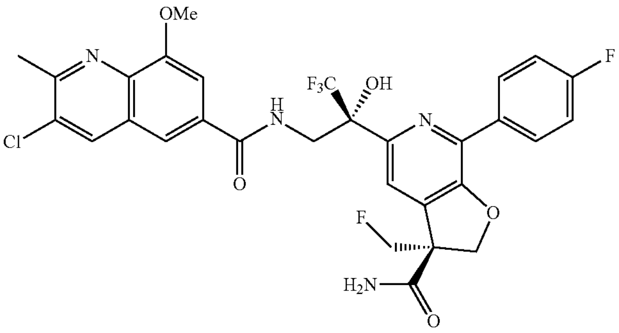 [SMILES: COc1cc(C(=O)NC[C@](O)(c2cc3c(c(-c4ccc(F)cc4)n2)OC[C@@]3(CF)C(N)=O)C(F)(F)F)cc2cc(Cl)c(C)nc12] | 650.96 |

TABLE 2-continued
| Example | Structure | MS+ m/z |
|---|---|---|
| 285 | 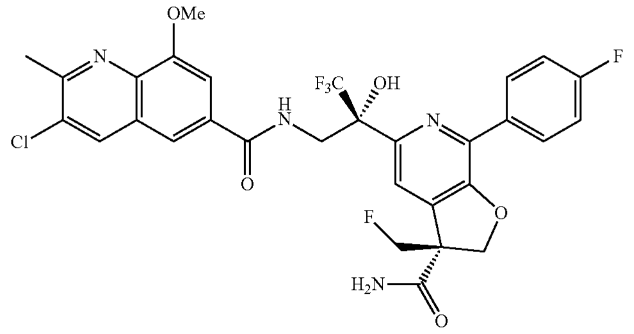 [SMILES: COc1cc(C(=O)NC[C@](O)(c2cc3c(c(-c4ccc(F)cc4)n2)OC[C@]3(CF)C(N)=O)C(F)(F)F)cc2cc(Cl)c(C)nc12] | 651.35 |
| 286 | 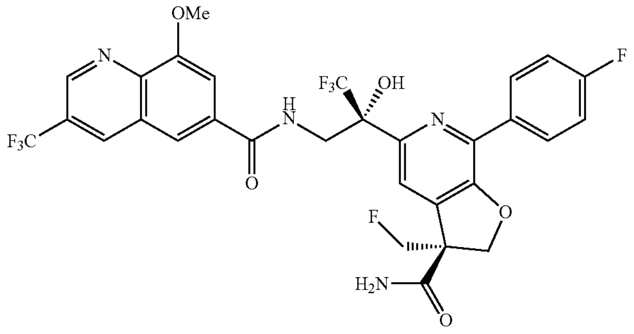 [SMILES: COc1cc(C(=O)NC[C@](O)(c2cc3c(c(-c4ccc(F)cc4)n2)OC[C@@]3(CF)C(N)=O)C(F)(F)F)cc2cc(C(F)(F)F)cnc12] | 670.94 |
| 287 | 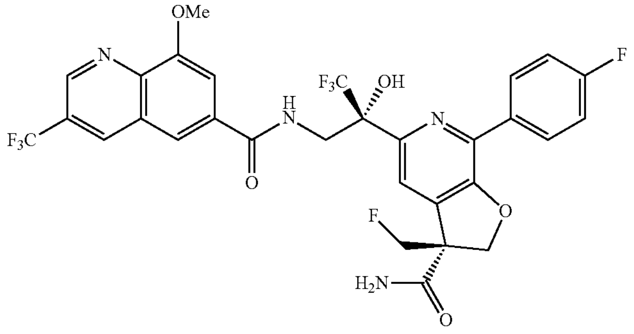 [SMILES: COc1cc(C(=O)NC[C@](O)(c2cc3c(c(-c4ccc(F)cc4)n2)OC[C@]3(CF)C(N)=O)C(F)(F)F)cc2cc(C(F)(F)F)cnc12] | 670.94 |
| 288 | 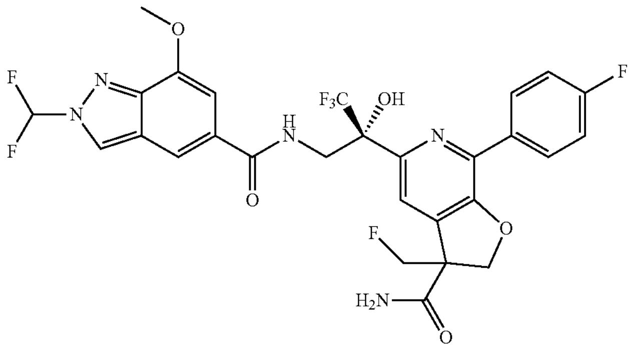 [SMILES: COc1cc(C(=O)NC[C@](O)(c2cc3c(c(-c4ccc(F)cc4)n2)OCC3(CF)C(N)=O)C(F)(F)F)cc2cn(C(F)F)nc12] | 641.82 |

TABLE 2-continued
| Example | Structure | MS+ m/z |
|---|---|---|
| 289 | 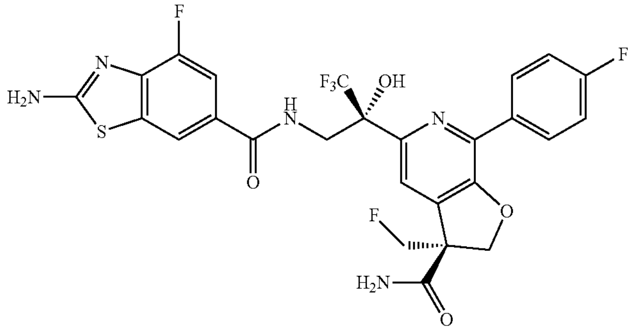 [SMILES: NC(=O)[C@]1(CF)COc2c1cc([C@@](O)(CNC(=O)c1cc(F)c3nc(N)sc3c1)C(F)(F)F)nc2-c1ccc(F)cc1] | 611.89 |
| 290 | 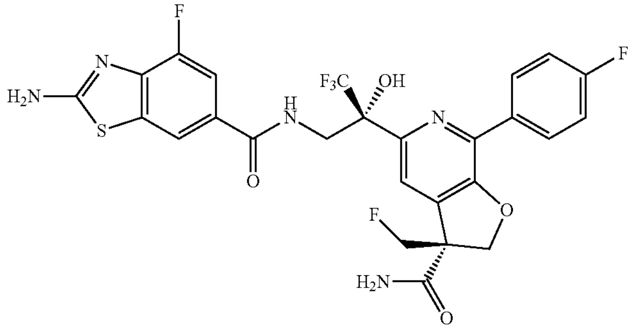 [SMILES: NC(=O)[C@@]1(CF)COc2c1cc([C@@](O)(CNC(=O)c1cc(F)c3nc(N)sc3c1)C(F)(F)F)nc2-c1ccc(F)cc1] | 612.04 |
| 291 | 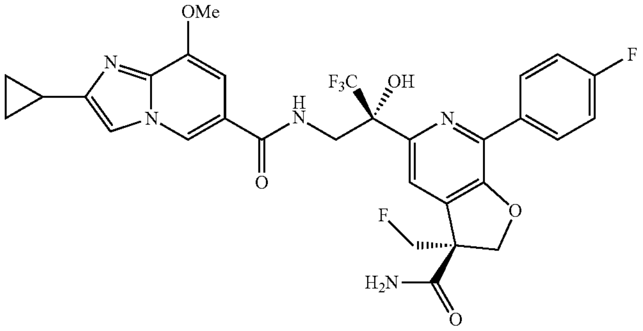 [SMILES: COc1cc(C(=O)NC[C@](O)(c2cc3c(c(-c4ccc(F)cc4)n2)OC[C@@]3(CF)C(N)=O)C(F)(F)F)cn2cc(C3CC3)nc12] | 632.15 |
| 292 | 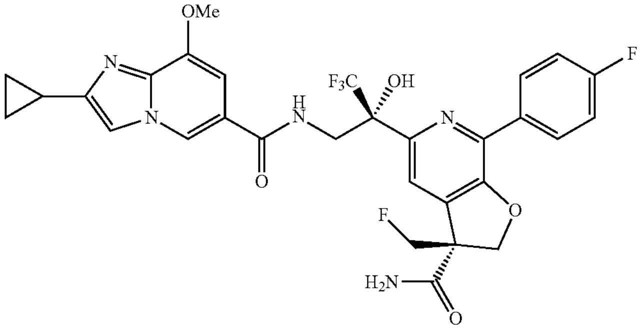 [SMILES: COc1cc(C(=O)NC[C@](O)(c2cc3c(c(-c4ccc(F)cc4)n2)OC[C@]3(CF)C(N)=O)C(F)(F)F)cn2cc(C3CC3)nc12] | 632.10 |

TABLE 2-continued
| Example | Structure | MS+ m/z |
|---|---|---|
| 293 | 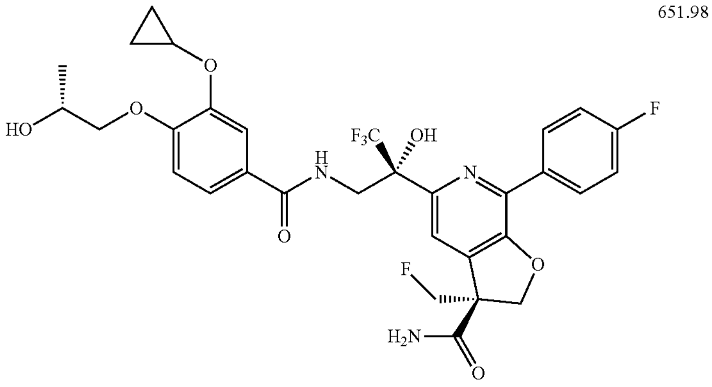 | 651.98 |
| 294 | 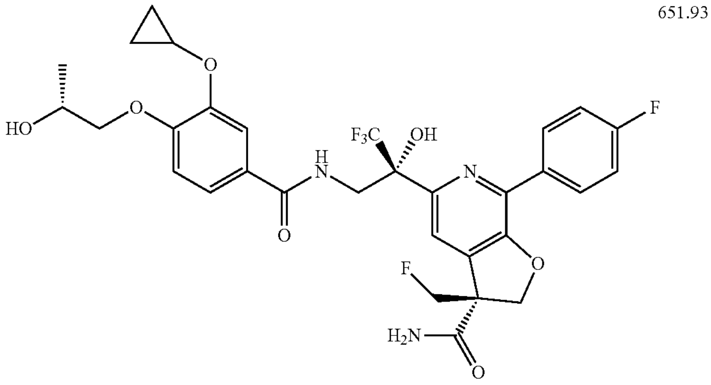 | 651.93 |
| 295 | 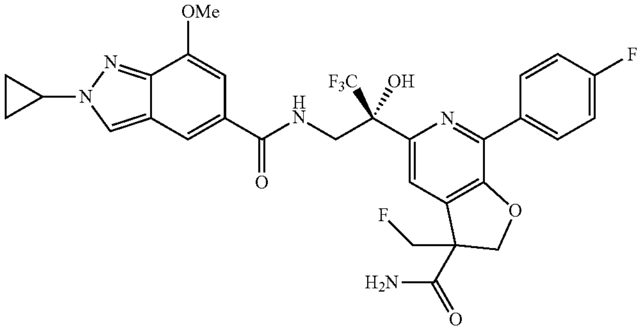 [SMILES: COc1cc(C(=O)NC[C@](O)(c2cc3c(c(-c4ccc(F)cc4)n2)OCC3(CF)C(N)=O)C(F)(F)F)cc2cn(C3CC3)nc12] | 631.91 |
| 296 | 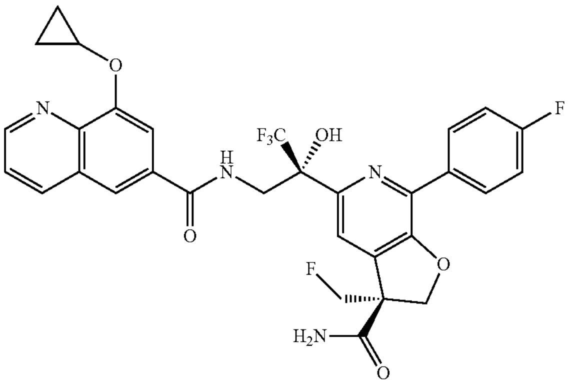 [SMILES: NC(=O)[C@]1(CF)COc2c1cc([C@@](O)(CNC(=O)c1cc(OC3CC3)c3ncccc3c1)C(F)(F)F)nc2-c1ccc(F)cc1] | 629.03 |

TABLE 2-continued
| Example | Structure | MS+ m/z |
|---|---|---|
| 297 | 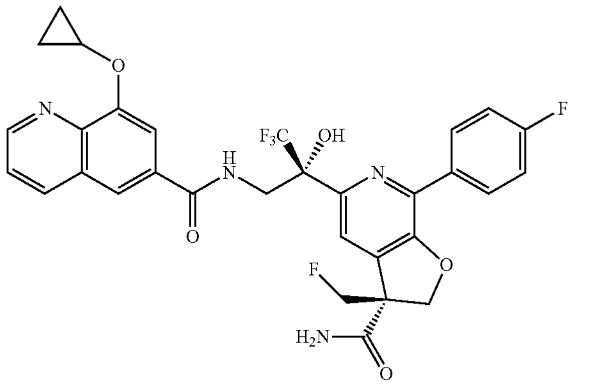 [SMILES: NC(=O)[C@@]1(CF)COc2c1cc([C@@](O)(CNC(=O)c1cc(OC3CC3)c3ncccc3c1)C(F)(F)F)nc2-c1ccc(F)cc1] | 629.13 |
| 298 | 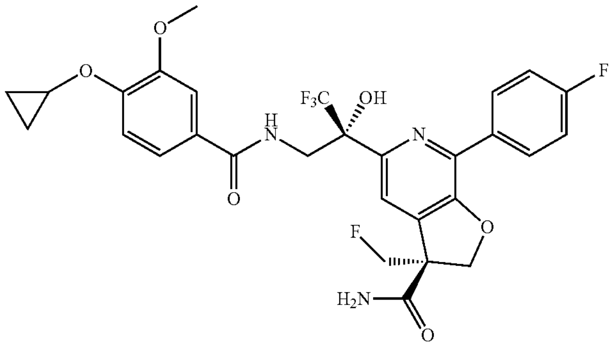 [SMILES: COc1cc(C(=O)NC[C@](O)(c2cc3c(c(-c4ccc(F)cc4)n2)OC[C@@]3(CF)C(N)=O)C(F)(F)F)ccc1OC1CC1] | 607.86 |
| 299 | 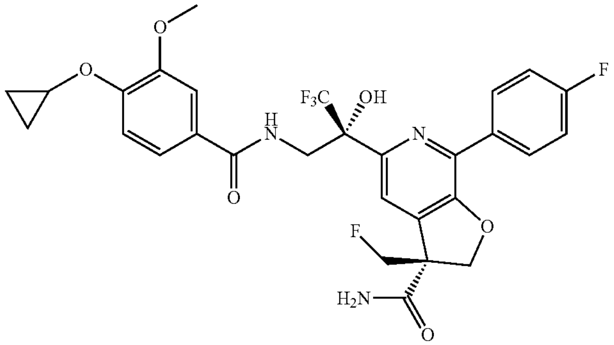 [SMILES: COc1cc(C(=O)NC[C@](O)(c2cc3c(c(-c4ccc(F)cc4)n2)OC[C@]3(CF)C(N)=O)C(F)(F)F)ccc1OC1CC1] | 607.91 |

The following Table 3 contains examples that were prepared with the similar method to Example 1 Step c (PyBOP or HATU). The majority of compounds were purified by Gilson prep-HPLC, and some were purified by automated column chromatography (silica gel). The aryl acid coupling partners were prepared according to Intermediates 1-43, or by analogous procedures with slight modifications and also prepared according to procedures found in U.S. patent application Ser. No. 16/930,622.

TABLE 3

| Example | Structure | MS+ m/z |
|---|---|---|
| 300 | 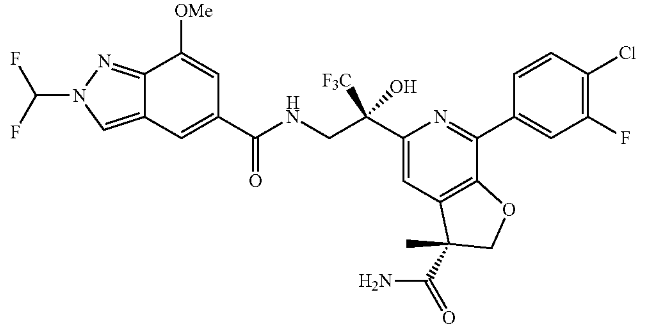 [SMILES: COc1cc(C(=O)NC[C@](O)(c2cc3c(c(-c4ccc(Cl)c(F)c4)n2)OC[C@]3(C)C(N)=O)C(F)(F)F)cc2cn(C(F)F)nc12] | 658.34 |
| 301 | 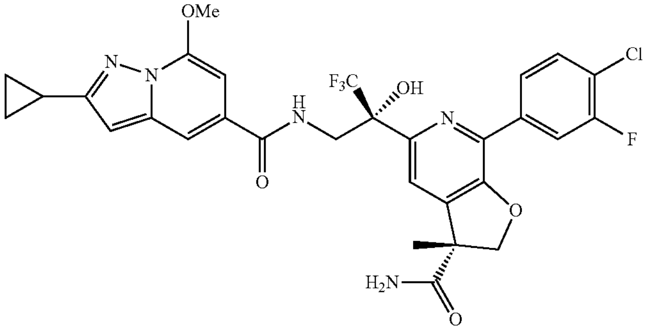 [SMILES: COc1cc(C(=O)NC[C@](O)(c2cc3c(c(-c4ccc(Cl)c(F)c4)n2)OC[C@]3(C)C(N)=O)C(F)(F)F)cc2cc(C3CC3)nn12] | 648.35 |
| 302 | 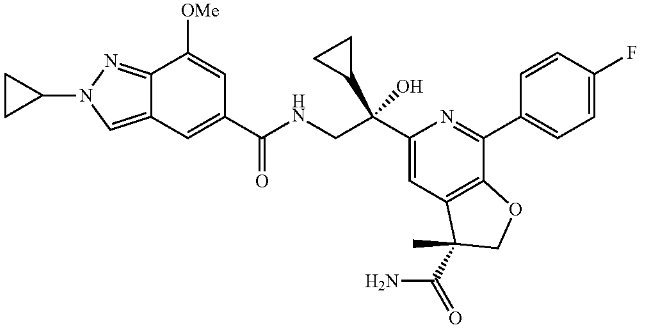 [SMILES: COc1cc(C(=O)NC[C@](O)(c2cc3c(c(-c4ccc(F)cc4)n2)OC[C@]3(C)C(N)=O)C2CC2)cc2cn(C3CC3)nc12] | 586.24 |
| 303 | 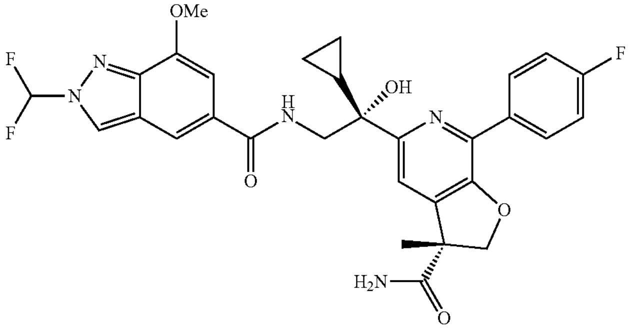 [SMILES: COc1cc(C(=O)NC[C@](O)(c2cc3c(c(-c4ccc(F)cc4)n2)OC[C@]3(C)C(N)=O)C2CC2)cc2cn(C(F)F)nc12] | 596.20 |

TABLE 3-continued
| Example | Structure | MS+ m/z |
|---|---|---|
| 304 | 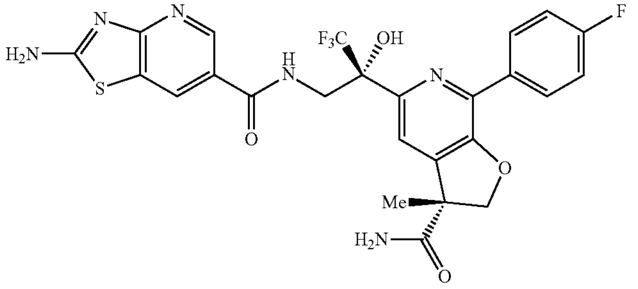 [SMILES: C[C@]1(C(N)=O)COc2c1cc([C@@](O)(CNC(=O)c1cnc3nc(N)sc3c1)C(F)(F)F)nc2-c1ccc(F)cc1] | 601.94 |
| 305 | 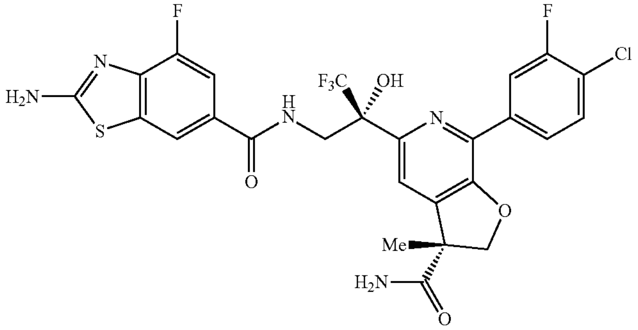 | 627.83 |
| 306 | 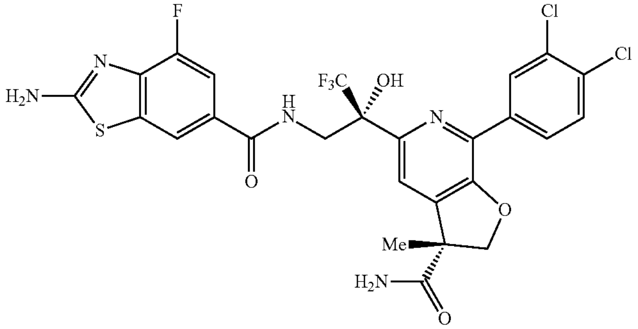 [SMILES: C[C@]1(C(N)=O)COc2c1cc([C@@](O)(CNC(=O)c1cc(F)c3nc(N)sc3c1)C(F)(F)F)nc2-c1ccc(Cl)c(F)c1] | 643.81 |
| 307 | 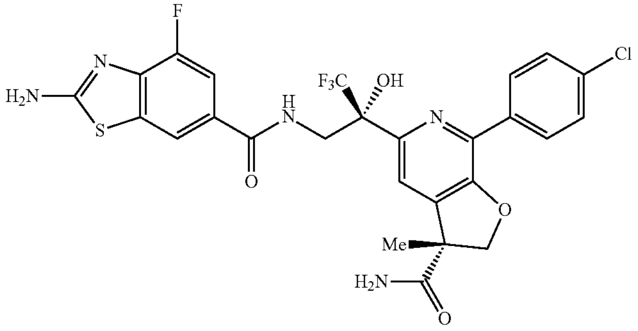 | 609.83 |

TABLE 3-continued
| Example | Structure | MS+ m/z |
|---|---|---|
| 308 | 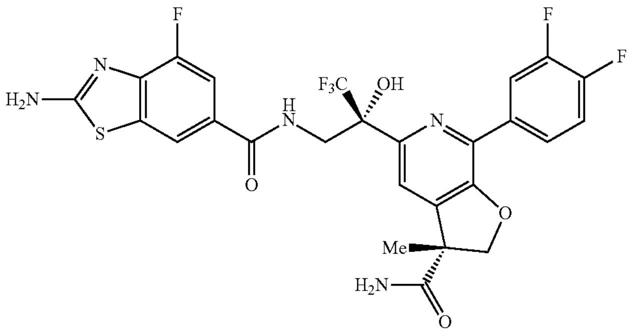 [SMILES: C[C@]1(C(N)=O)COc2c1cc([C@@](O)(CNC(=O)c1cc(F)c3nc(N)sc3c1)C(F)(F)F)nc2-c1ccc(F)c(F)c1] | 611.84 |
| 309 | 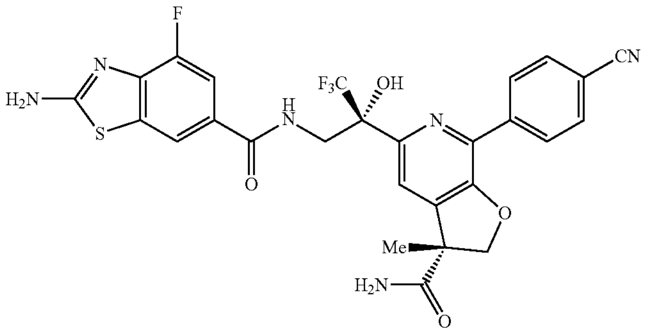 [SMILES: C[C@]1(C(N)=O)COc2c1cc([C@@](O)(CNC(=O)c1cc(F)c3nc(N)sc3c1)C(F)(F)F)nc2-c1ccc(C#N)cc1] | 600.89 |
| 310 | 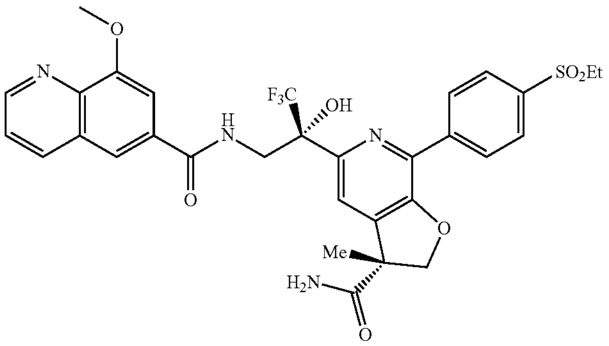 | 684.95 |
| 311 | 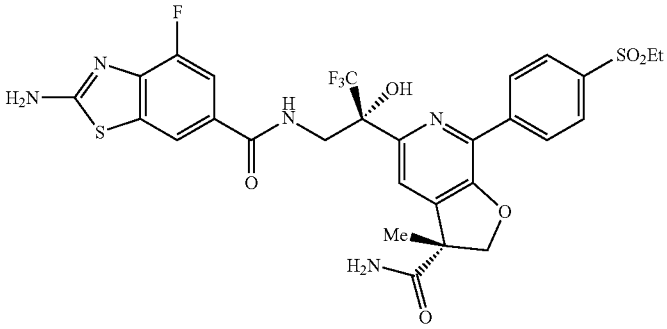 | 667.91 |

TABLE 3-continued
| Example | Structure | MS+ m/z |
|---|---|---|
| 312 | 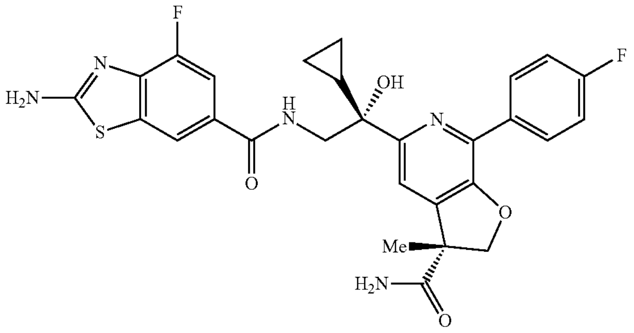 [SMILES: C[C@]1(C(N)=O)COc2c1cc([C@@](O)(CNC(=O)c1cc(F)c3nc(N)sc3c1)C1CC1)nc2-c1ccc(F)cc1] | 586.14 |
| 313 | 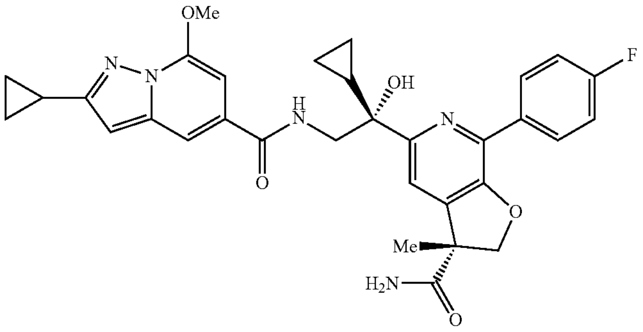 [SMILES: COc1cc(C(=O)NC[C@](O)(c2cc3c(c(-c4ccc(F)cc4)n2)OC[C@]3(C)C(N)=O)C2CC2)cc2cc(C3CC3)nn12] | 566.03 |
| 314 | 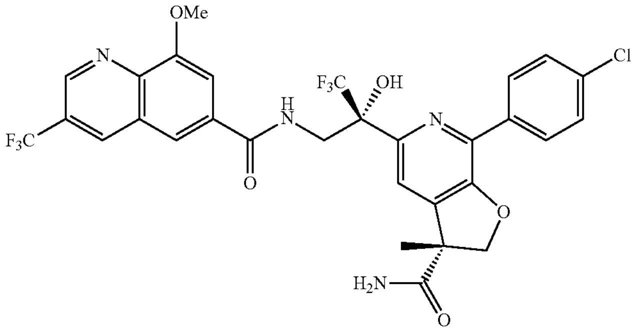 [SMILES: COc1cc(C(=O)NC[C@](O)(c2cc3c(c(-c4ccc(Cl)cc4)n2)OC[C@]3(C)C(N)=O)C(F)(F)F)cc2cc(C(F)(F)F)cnc12] | 669.14 |
| 315 | 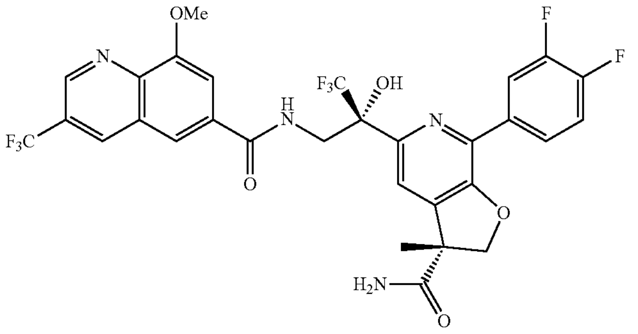 [SMILES: COc1cc(C(=O)NC[C@](O)(c2cc3c(c(-c4ccc(F)c(F)c4)n2)OC[C@]3(C)C(N)=O)C(F)(F)F)cc2cc(C(F)(F)F)cnc12] | 671.15 |

TABLE 3-continued
| Example | Structure | MS+ m/z |
|---|---|---|
| 316 | 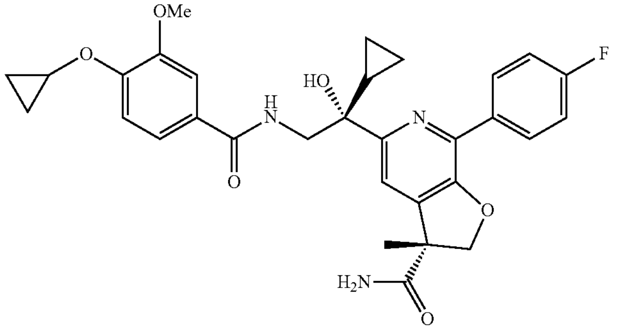 [SMILES: COc1cc(C(=O)NC[C@](O)(c2cc3c(c(-c4ccc(F)cc4)n2)OC[C@]3(C)C(N)=O)C2CC2)ccc1OC1CC1] | 561.2 |
| 317 | 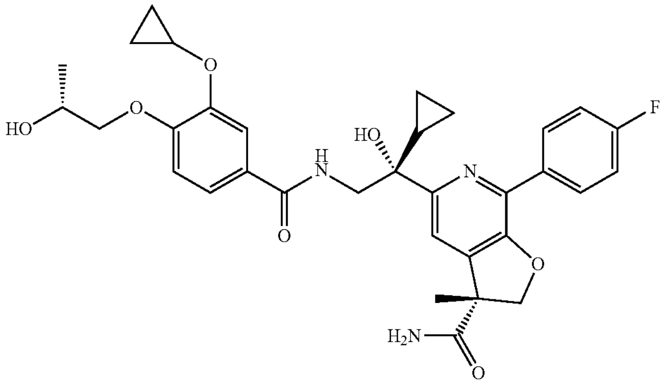 [SMILES: C[C@@H](O)COc1ccc(C(=O)NC[C@](O)(c2cc3c(c(-c4ccc(F)cc4)n2)OC[C@]3(C)C(N)=O)C2CC2)cc1OC1CC1] | 605.30 |
| 318 | 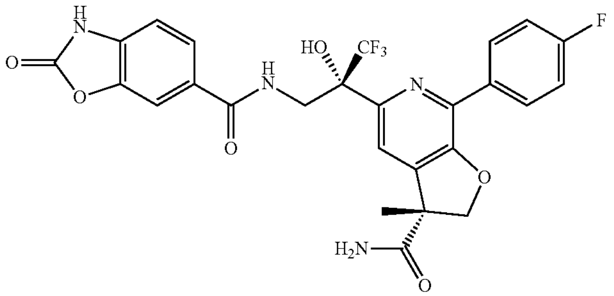 [SMILES: C[C@]1(C(N)=O)COc2c1cc([C@@](O)(CNC(=O)c1ccc3[nH]c(=O)oc3c1)C(F)(F)F)nc2-c1ccc(F)cc1] | 560.10 |
| 319 | 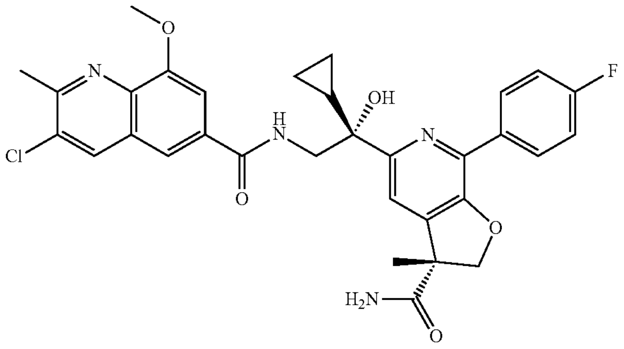 [SMILES: COc1cc(C(=O)NC[C@](O)(c2cc3c(c(-c4ccc(F)cc4)n2)OC[C@]3(C)C(N)=O)C2CC2)cc2cc(Cl)c(C)nc12] | 605.03 |

TABLE 3-continued
| Example | Structure | MS+ m/z |
|---|---|---|
| 320 | 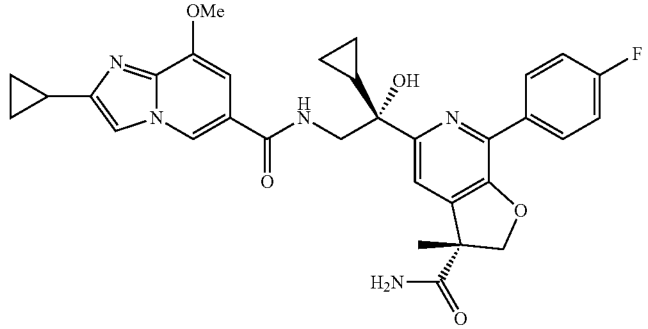 [SMILES: COc1cc(C(=O)NC[C@](O)(c2cc3c(c(-c4ccc(F)cc4)n2)OC[C@]3(C)C(N)=O)C2CC2)cn2cc(C3CC3)nc12] | 586.20 |
| 321 | 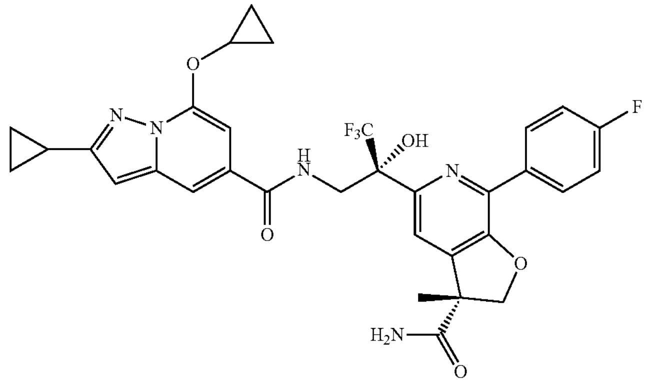 [SMILES: C[C@]1(C(N)=O)COc2c1cc([C@@](O)(CNC(=O)c1cc(OC3CC3)n3nc(C4CC4)cc3c1)C(F)(F)F)nc2-c1ccc(F)cc1] | 640.20 |
| 322 | 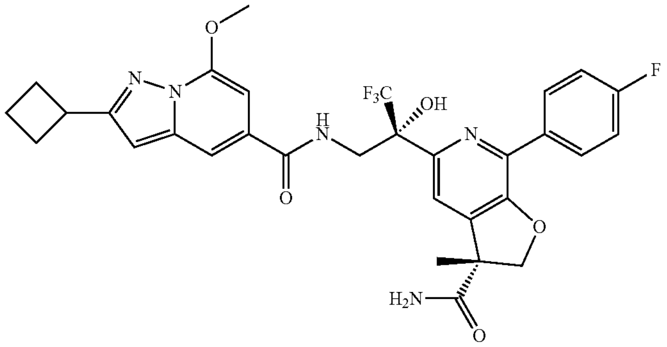 [SMILES: COc1cc(C(=O)NC[C@](O)(c2cc3c(c(-c4ccc(F)cc4)n2)OC[C@]3(C)C(N)=O)C(F)(F)F)cc2cc(C3CCC3)nn12] | 628.40 |
| 323 | 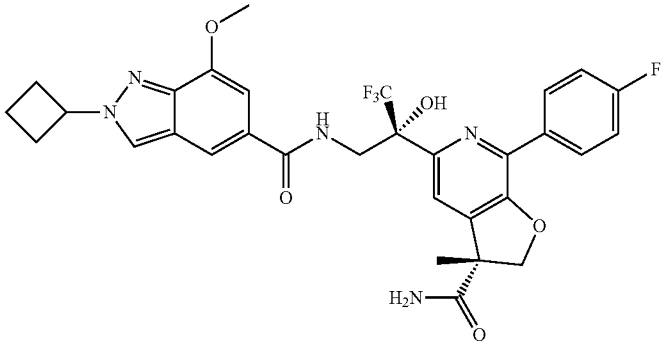 [SMILES: COc1cc(C(=O)NC[C@](O)(c2cc3c(c(-c4ccc(F)cc4)n2)OC[C@]3(C)C(N)=O)C(F)(F)F)cc2cn(C3CCC3)nc12] | 628.40 |

TABLE 3-continued
| Example | Structure | MS⁺ m/z |
|---|---|---|
| 324 | 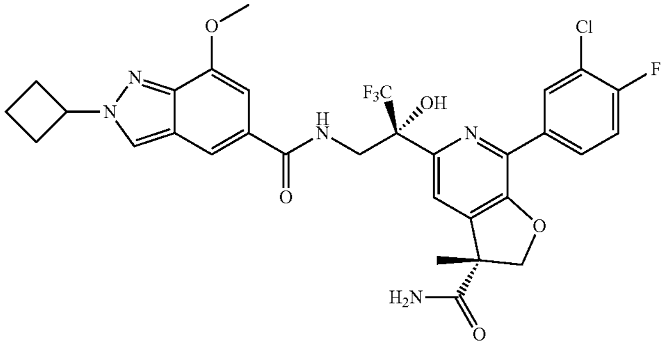 [SMILES: COc1cc(C(=O)NC[C@](O)(c2cc3c(c(-c4ccc(F)c(Cl)c4)n2)OC[C@]3(C)C(N)=O)C(F)(F)F)cc2cn(C3CCC3)nc12] | 662.40 |
| 325 | 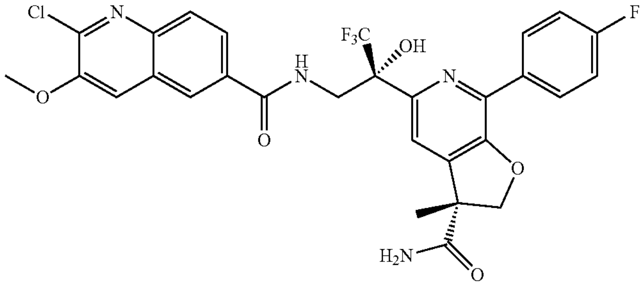 [SMILES: COc1cc2cc(C(=O)NC[C@](O)(c3cc4c(c(-c5ccc(F)cc5)n3)OC[C@]4(C)C(N)=O)C(F)(F)F)ccc2nc1Cl] | 619.15 |
| 326 | 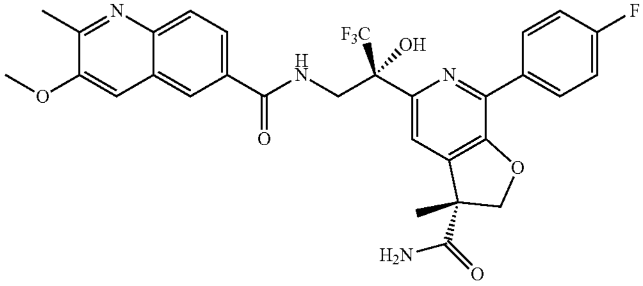 [SMILES: COc1cc2cc(C(=O)NC[C@](O)(c3cc4c(c(-c5ccc(F)cc5)n3)OC[C@]4(C)C(N)=O)C(F)(F)F)ccc2nc1C] | 599.22 |
| 327 | 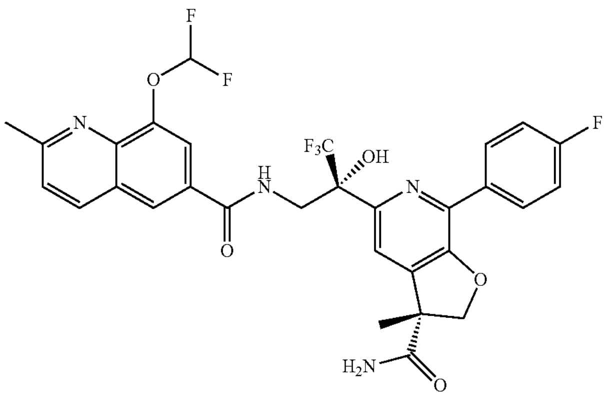 [SMILES: Cc1ccc2cc(C(=O)NC[C@](O)(c3cc4c(c(-c5ccc(F)cc5)n3)OC[C@]4(C)C(N)=O)C(F)(F)F)cc(OC(F)F)c2n1] | 635.17 |

TABLE 3-continued
| Example | Structure | MS⁺ m/z |
|---|---|---|
| 328 | 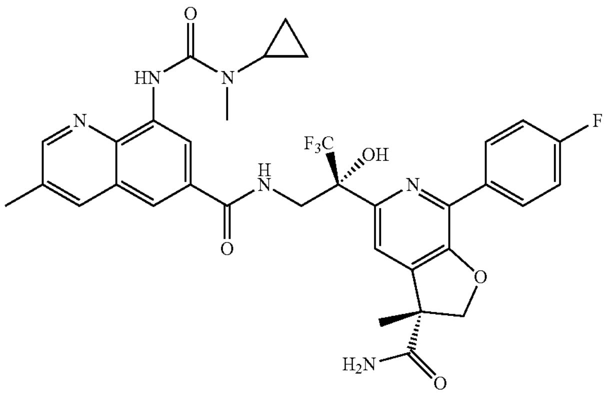 [SMILES: Cc1cnc2c(NC(=O)N(C)C3CC3)cc(C(=O)NC[C@](O)(c3cc4c(c(-c5ccc(F)cc5)n3)OC[C@]4(C)C(N)=O)C(F)(F)F)cc2c1] | 681.02 |
| 329 | 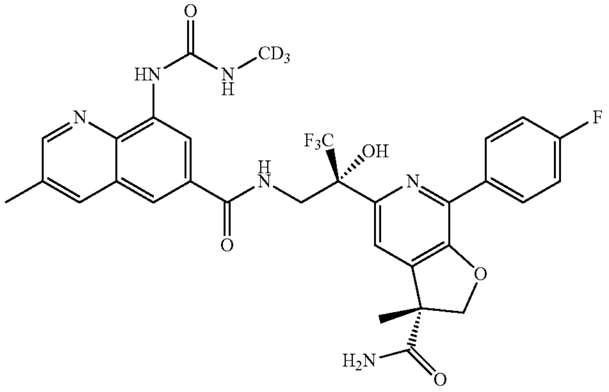 [SMILES: [2H]C([2H])([2H])NC(=O)Nc1cc(C(=O)NC[C@](O)(c2cc3c(c(-c4ccc(F)cc4)n2)OC[C@]3(C)C(N)=O)C(F)(F)F)cc2cc(C)cnc12] | 644.35 |
| 330 | 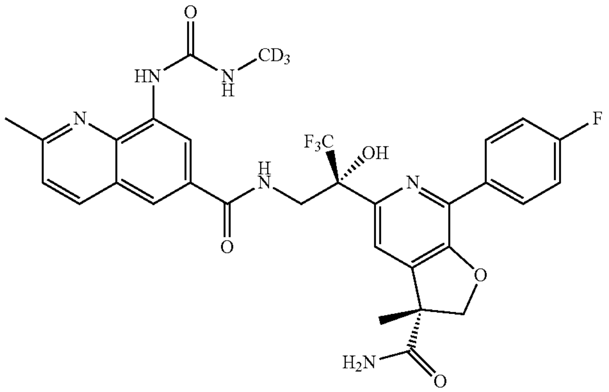 [SMILES: [2H]C([2H])([2H])NC(=O)Nc1cc(C(=O)NC[C@](O)(c2cc3c(c(-c4ccc(F)cc4)n2)OC[C@]3(C)C(N)=O)C(F)(F)F)cc2ccc(C)nc12] | 644 .34 |
| 331 | 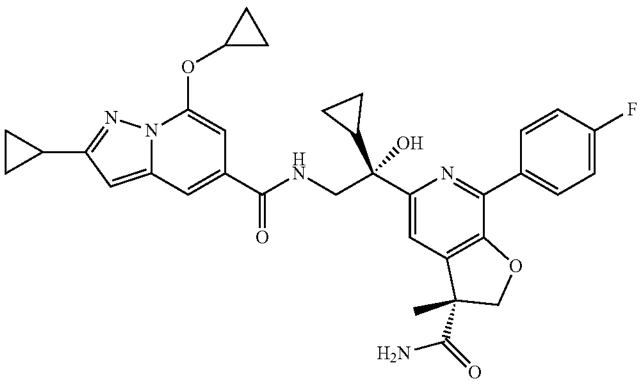 [SMILES: C[C@]1(C(N)=O)COc2c1cc([C@@](O)(CNC(=O)c1cc(OC3CC3)n3nc(C4CC4)cc3c1)C1CC1)nc2-c1ccc(F)cc1] | 612.26 |

TABLE 3-continued

| Example | Structure | MS+ m/z |
|---|---|---|
| 332 | 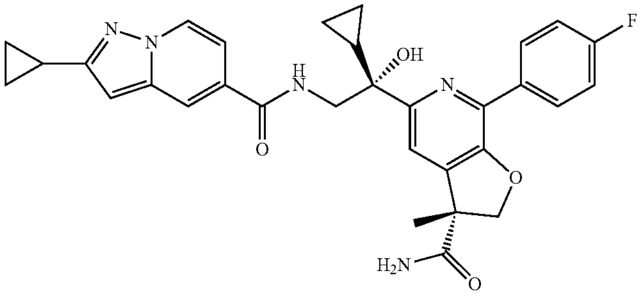 [SMILES: C[C@]1(C(N)=O)COc2c1cc([C@@](O)(CNC(=O)c1ccn3nc(C4CC4)cc3c1)C1CC1)nc2-c1ccc(F)cc1] | 556.23 |

The following Table 4 contains examples that were prepared with the similar method to Example 1 step c (PyBOP or HATU). The majority of compounds were purified by Gilson prep-HPLC, and some were purified by automated column chromatography (silica gel). The aryl acid coupling partners were commercially available.

TABLE 4

| Example | Structure | MS+ m/z |
|---|---|---|
| 333 | 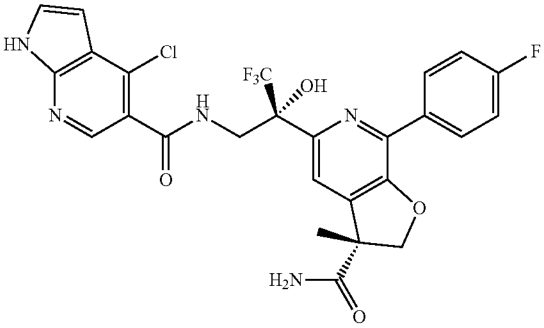 [SMILES: C[C@]1(C(N)=O)COc2c1cc([C@@](O)(CNC(=O)c1cnc3[nH]ccc3c1Cl)C(F)(F)F)nc2-c1ccc(F)cc1] | 578.00 |
| 334 | 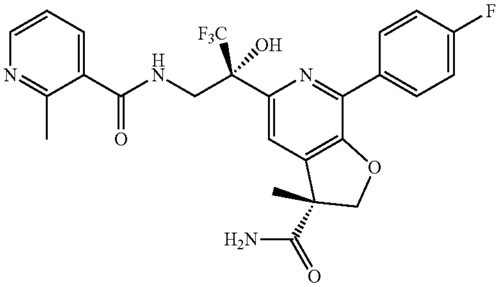 [SMILES: Cc1ncccc1C(=O)NC[C@](O)(c1cc2c(c(-c3ccc(F)cc3)n1)OC[C@]2(C)C(N)=O)C(F)(F)F] | 519.0 |
| 335 | 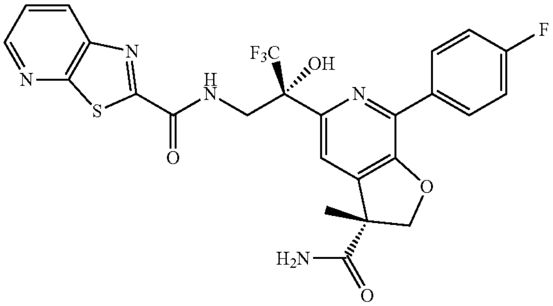 [SMILES: C[C@]1(C(N)=O)COc2c1cc([C@@](O)(CNC(=O)c1nc3cccnc3s1)C(F)(F)F)nc2-c1ccc(F)cc1] | 562.00 |

TABLE 4-continued
| Example | Structure | MS+ m/z |
|---|---|---|
| 336 | 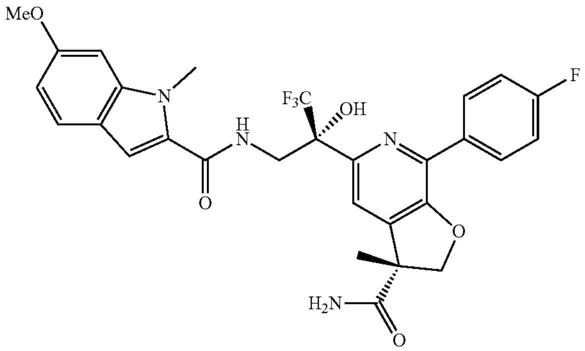 [SMILES: COc1ccc2cc(C(=O)NC[C@](O)(c3cc4c(c(-c5ccc(F)cc5)n3)OC[C@]4(C)C(N)=O)C(F)(F)F)n(C)c2c1] | 587.05 |
| 337 | 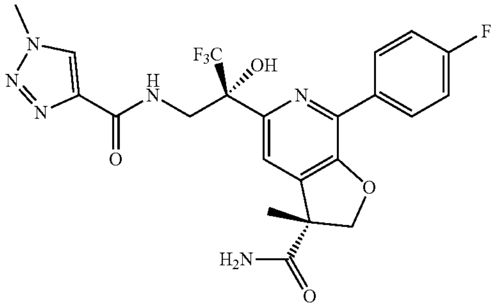 [SMILES: Cn1cc(C(=O)NC[C@](O)(c2cc3c(c(-c4ccc(F)cc4)n2)OC[C@]3(C)C(N)=O)C(F)(F)F)nn1] | 509.05 |
| 338 | 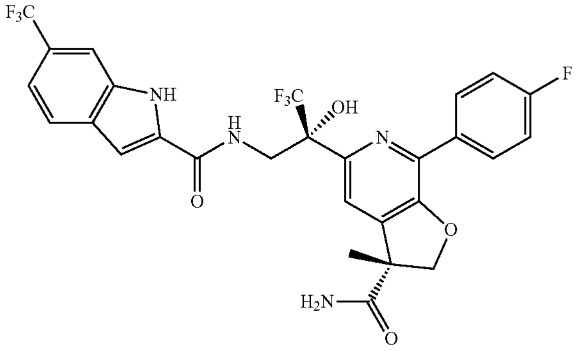 [SMILES: C[C@]1(C(N)=O)COc2c1cc([C@@](O)(CNC(=O)c1cc3ccc(C(F)(F)F)cc3[nH]1)C(F)(F)F)nc2-c1ccc(F)cc1] | 610.85 |
| 339 | 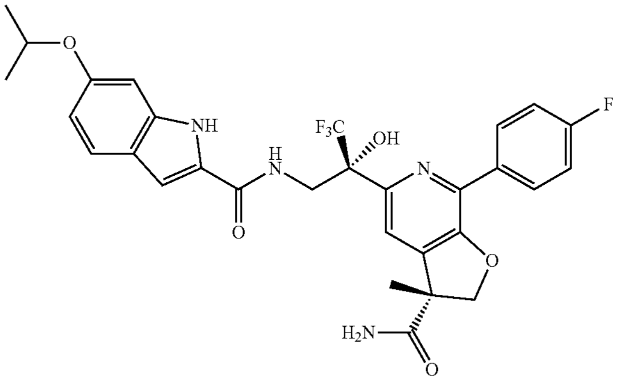 [SMILES: CC(C)Oc1ccc2cc(C(=O)NC[C@](O)(c3cc4c(c(-c5ccc(F)cc5)n3)OC[C@]4(C)C(N)=O)C(F)(F)F)[nH]c2c1] | 600.57 |

TABLE 4-continued
| Example | Structure | MS+ m/z |
|---|---|---|
| 340 | 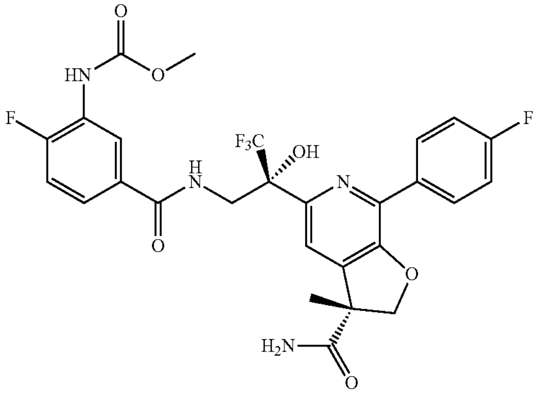 [SMILES: COC(=O)Nc1cc(C(=O)NC[C@](O)(c2cc3c(c(-c4ccc(F)cc4)n2)OC[C@]3(C)C(N)=O)C(F)(F)F)ccc1F] | 594.05 |
| 341 | 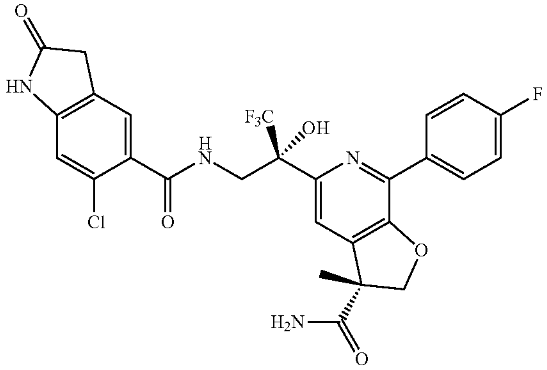 [SMILES: C[C@]1(C(N)=O)COc2c1cc([C@@](O)(CNC(=O)c1cc3c(cc1Cl)NC(=O)C3)C(F)(F)F)nc2-c1ccc(F)cc1] | 592.90 |
| 342 | 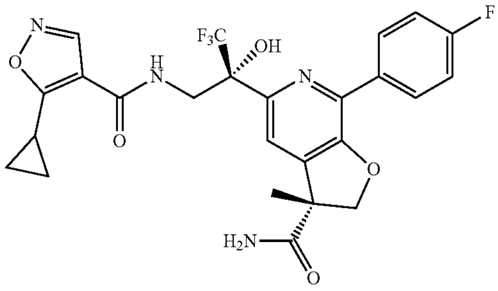 [SMILES: C[C@]1(C(N)=O)COc2c1cc([C@@](O)(CNC(=O)c1cnoc1C1CC1)C(F)(F)F)nc2-c1ccc(F)cc1] | 535.05 |
| 343 | 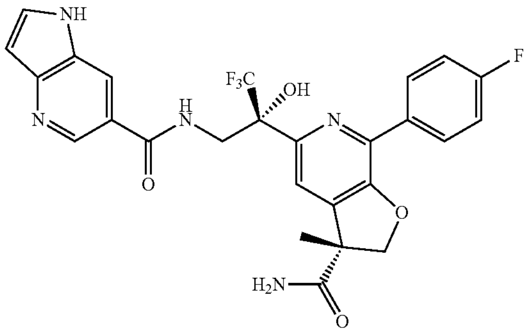 [SMILES: C[C@]1(C(N)=O)COc2c1cc([C@@](O)(CNC(=O)c1cnc3cc[nH]c3c1)C(F)(F)F)nc2-c1ccc(F)cc1] | 543.85 |

TABLE 4-continued
| Example | Structure | MS⁺ m/z |
|---|---|---|
| 344 | 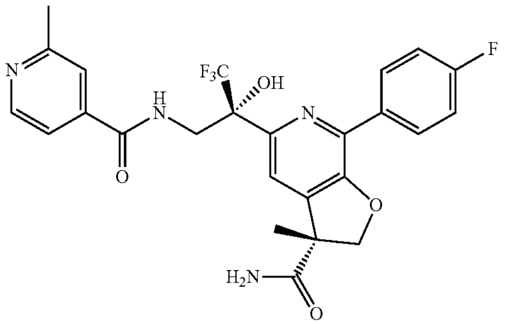 [SMILES: Cc1cc(C(=O)NC[C@](O)(c2cc3c(c(-c4ccc(F)cc4)n2)OC[C@]3(C)C(N)=O)C(F)(F)F)ccn1] | 519.00 |
| 345 | 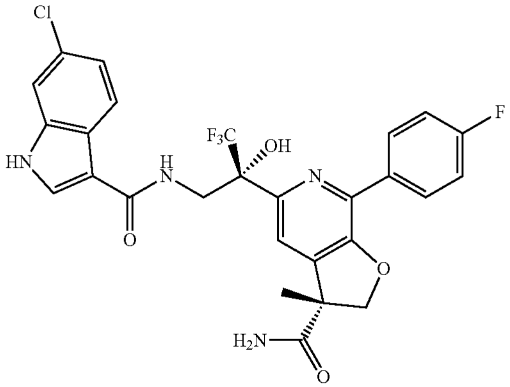 [SMILES: C[C@]1(C(N)=O)COc2c1cc([C@@](O)(CNC(=O)c1c[nH]c3cc(Cl)ccc13)C(F)(F)F)nc2-c1ccc(F)cc1] | 576.85 |
| 346 | 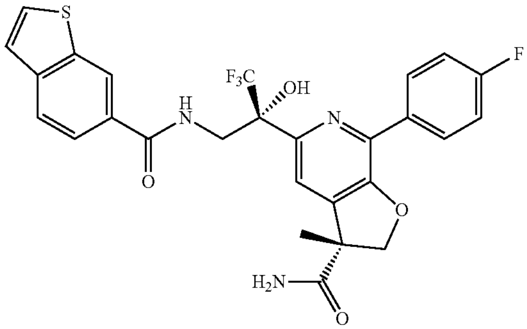 [SMILES: C[C@]1(C(N)=O)COc2c1cc([C@@](O)(CNC(=O)c1ccc3ccsc3c1)C(F)(F)F)nc2-c1ccc(F)cc1] | 559.80 |
| 347 | 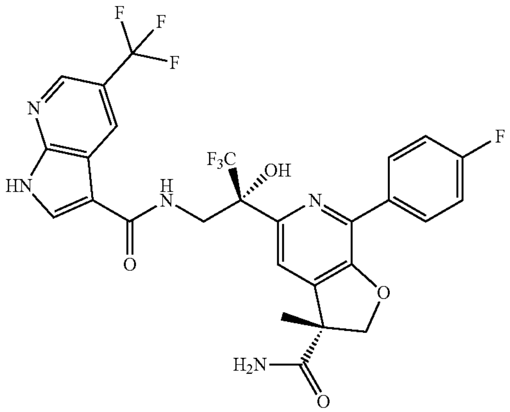 [SMILES: C[C@]1(C(N)=O)COc2c1cc([C@@](O)(CNC(=O)c1c[nH]c3ncc(C(F)(F)F)cc13)C(F)(F)F)nc2-c1ccc(F)cc1] | 611.85 |

TABLE 4-continued
| Example | Structure | MS+ m/z |
|---|---|---|
| 348 | 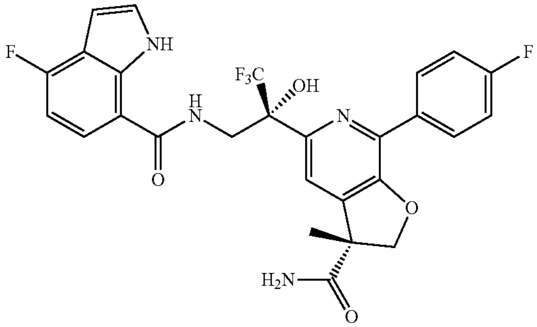 [SMILES: C[C@]1(C(N)=O)COc2c1cc([C@@](O)(CNC(=O)c1ccc(F)c3cc[nH]c13)C(F)(F)F)nc2-c1ccc(F)cc1] | 560.85 |
| 349 | 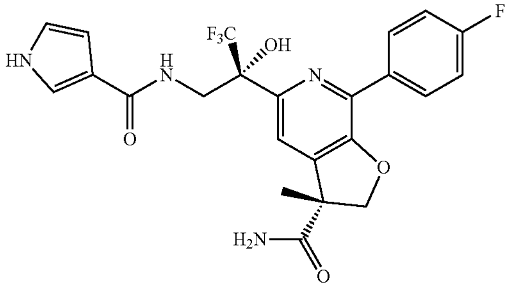 [SMILES: C[C@]1(C(N)=O)COc2c1cc([C@@](O)(CNC(=O)c1cc[nH]c1)C(F)(F)F)nc2-c1ccc(F)cc1] | 492.85 |
| 350 | 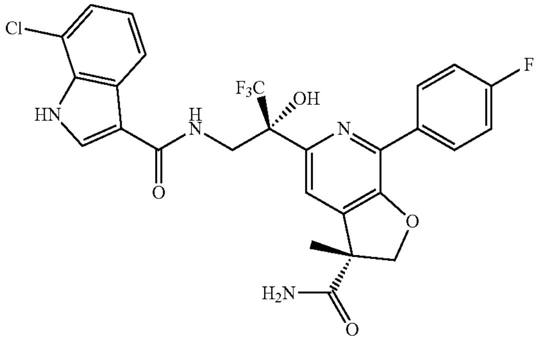 [SMILES: C[C@]1(C(N)=O)COc2c1cc([C@@](O)(CNC(=O)c1c[nH]c3c(Cl)cccc13)C(F)(F)F)nc2-c1ccc(F)cc1] | 576.80 |
| 351 | 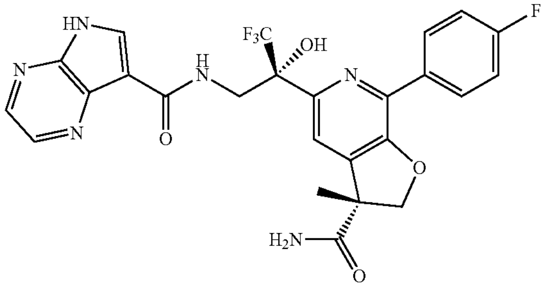 [SMILES: C[C@]1(C(N)=O)COc2c1cc([C@@](O)(CNC(=O)c1c[nH]c3nccnc13)C(F)(F)F)nc2-c1ccc(F)cc1] | 544.90 |

TABLE 4-continued
| Example | Structure | MS+ m/z |
|---|---|---|
| 352 | 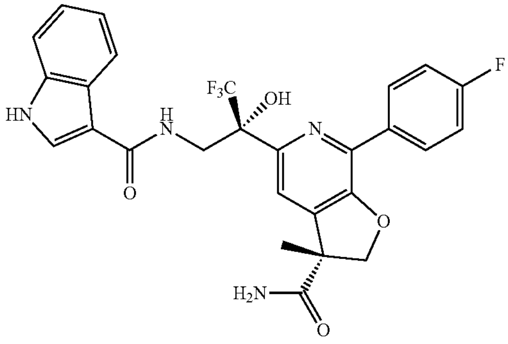 [SMILES: C[C@]1(C(N)=O)COc2c1cc([C@@](O)(CNC(=O)c1c[nH]c3ccccc13)C(F)(F)F)nc2-c1ccc(F)cc1] | 540.90 |
| 353 | 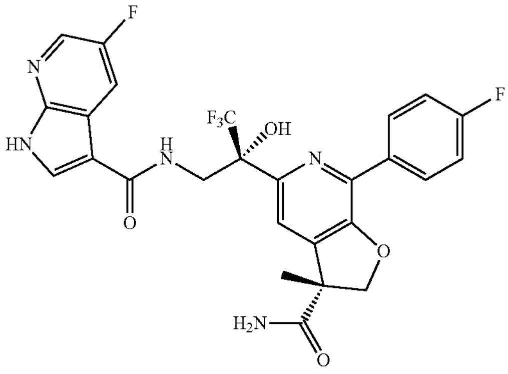 [SMILES: C[C@]1(C(N)=O)COc2c1cc([C@@](O)(CNC(=O)c1c[nH]c3ncc(F)cc13)C(F)(F)F)nc2-c1ccc(F)cc1] | 561.90 |
| 354 | 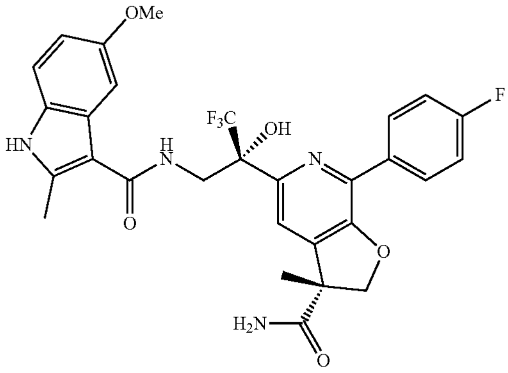 [SMILES: COc1ccc2[nH]c(C)c(C(=O)NC[C@](O)(c3cc4c(c(-c5ccc(F)cc5)n3)OC[C@]4(C)C(N)=O)C(F)(F)F)c2c1] | 586.90 |
| 355 | 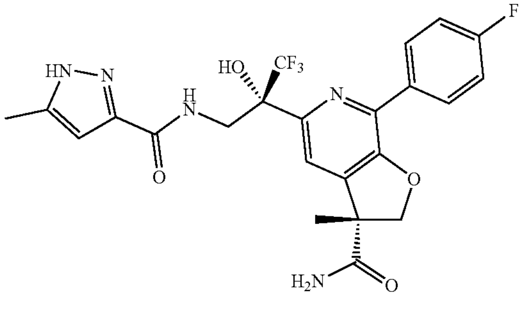 [SMILES: Cc1cc(C(=O)NC[C@](O)(c2cc3c(c(-c4ccc(F)cc4)n2)OC[C@]3(C)C(N)=O)C(F)(F)F)n[nH]1] | 507.15 |

TABLE 4-continued
| Example | Structure | MS+ m/z |
| --- | --- | --- |
| 356 | 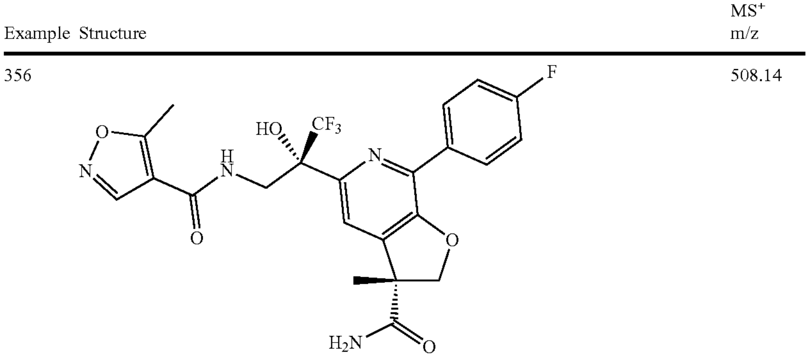 | 508.14 |
| 357 | 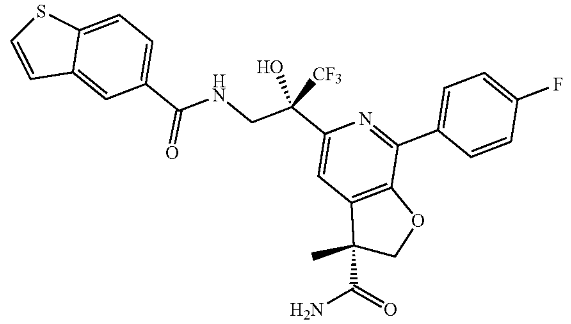 [SMILES: C[C@]1(C(N)=O)COc2c1cc([C@@](O)(CNC(=O)c1ccc3sccc3c1)C(F)(F)F)nc2-c1ccc(F)cc1] | 559.1 |
| 358 | 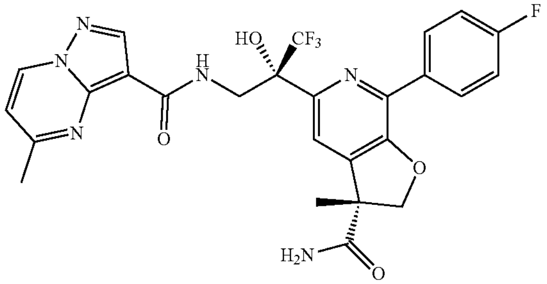 [SMILES: Cc1ccn2ncc(C(=O)NC[C@](O)(c3cc4c(c(-c5ccc(F)cc5)n3)OC[C@]4(C)C(N)=O)C(F)(F)F)c2n1] | 558.16 |
| 359 | 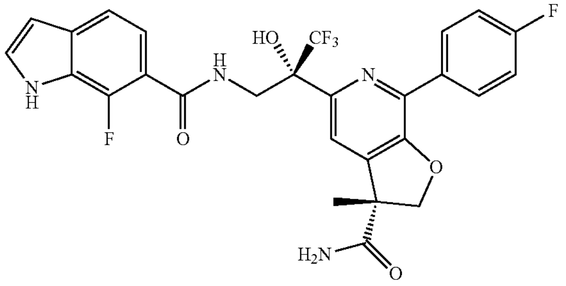 [SMILES: C[C@]1(C(N)=O)COc2c1cc([C@@](O)(CNC(=O)c1ccc3cc[nH]c3c1F)C(F)(F)F)nc2-c1ccc(F)cc1] | 561.05 |
| 360 | 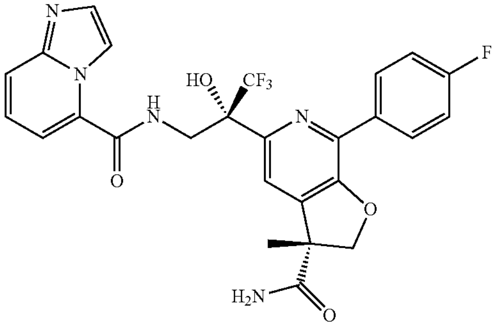 [SMILES: C[C@]1(C(N)=O)COc2c1cc([C@@](O)(CNC(=O)c1cccc3nccn13)C(F)(F)F)nc2-c1ccc(F)cc1] | 544.10 |

TABLE 4-continued
| Example | Structure | MS+ m/z |
|---|---|---|
| 361 | 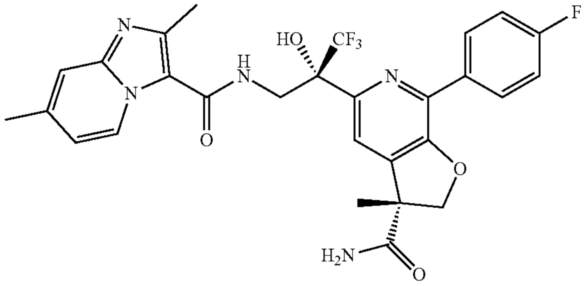 [SMILES: Cc1ccn2c(C(=O)NC[C@](O)(c3cc4c(c(-c5ccc(F)cc5)n3)OC[C@]4(C)C(N)=O)C(F)(F)F)c(C)nc2c1] | 572.15 |
| 362 | 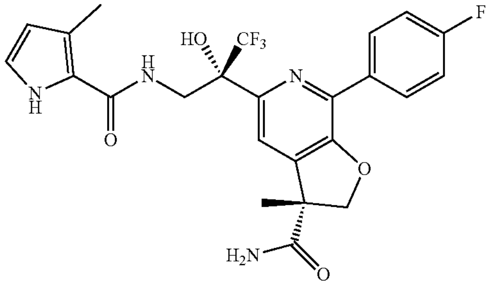 [SMILES: Cc1cc[nH]c1C(=O)NC[C@](O)(c1cc2c(c(-c3ccc(F)cc3)n1)OC[C@]2(C)C(N)=O)C(F)(F)F] | 507.05 |
| 363 | 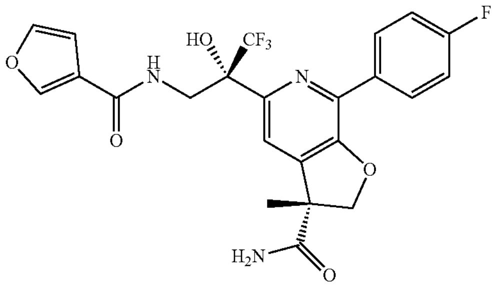 [SMILES: C[C@]1(C(N)=O)COc2c1cc([C@@](O)(CNC(=O)c1ccoc1)C(F)(F)F)nc2-c1ccc(F)cc1] | 494.00 |
| 364 | 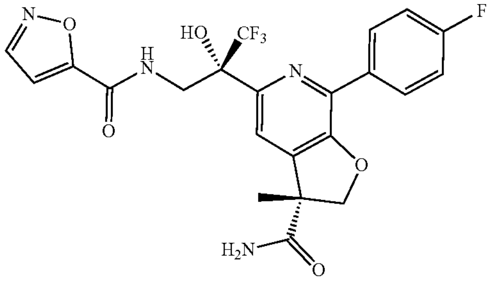 [SMILES: C[C@]1(C(N)=O)COc2c1cc([C@@](O)(CNC(=O)c1ccno1)C(F)(F)F)nc2-c1ccc(F)cc1] | 495.00 |
| 365 | 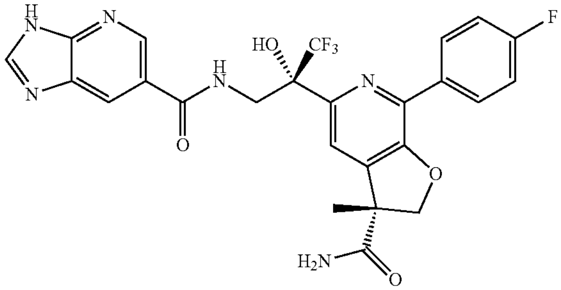 [SMILES: C[C@]1(C(N)=O)COc2c1cc([C@@](O)(CNC(=O)c1cnc3[nH]cnc3c1)C(F)(F)F)nc2-c1ccc(F)cc1] | 545.10 |

TABLE 4-continued
| Example | Structure | MS+ m/z |
|---|---|---|
| 366 | 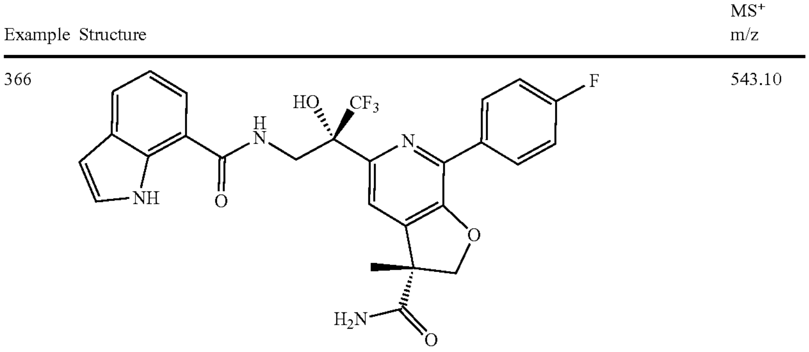 | 543.10 |
| 367 | 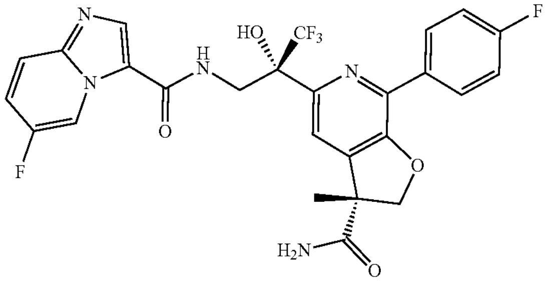 [SMILES: C[C@]1(C(N)=O)COc2c1cc([C@@](O)(CNC(=O)c1cnc3ccc(F)cn13)C(F)(F)F)nc2-c1ccc(F)cc1] | 562.10 |
| 368 | 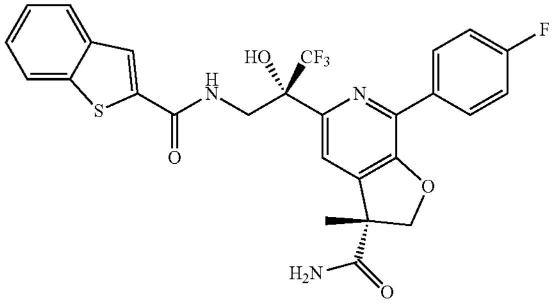 [SMILES: C[C@]1(C(N)=O)COc2c1cc([C@@](O)(CNC(=O)c1cc3ccccc3s1)C(F)(F)F)nc2-c1ccc(F)cc1] | 560.05 |
| 369 | 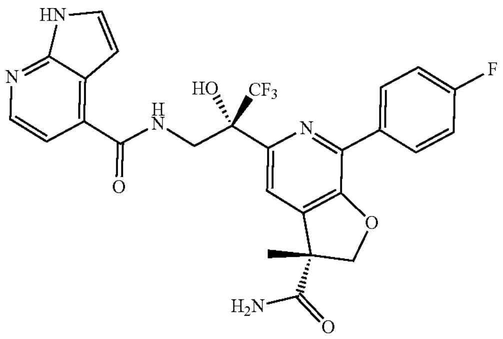 [SMILES: C[C@]1(C(N)=O)COc2c1cc([C@@](O)(CNC(=O)c1ccnc3[nH]ccc13)C(F)(F)F)nc2-c1ccc(F)cc1] | 544.05 |
| 370 | 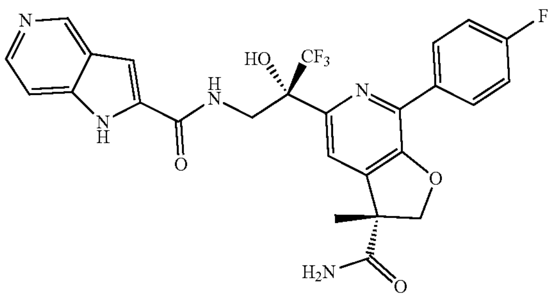 [SMILES: C[C@]1(C(N)=O)COc2c1cc([C@@](O)(CNC(=O)c1cc3cnccc3[nH]1)C(F)(F)F)nc2-c1ccc(F)cc1] | 544.05 |

TABLE 4-continued
| Example | Structure | MS+ m/z |
|---|---|---|
| 371 | 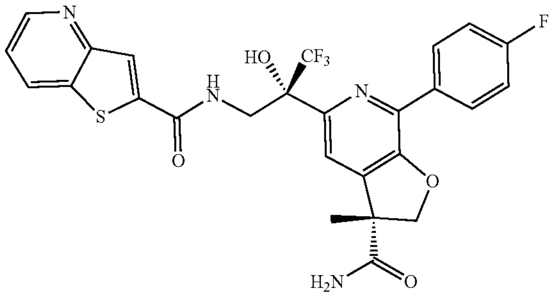 [SMILES: C[C@]1(C(N)=O)COc2c1cc([C@@](O)(CNC(=O)c1cc3ncccc3s1)C(F)(F)F)nc2-c1ccc(F)cc1] | 561.05 |
| 372 | 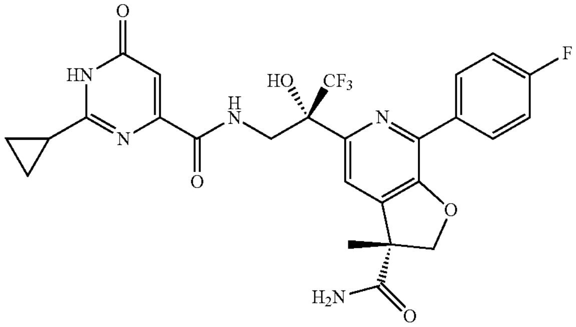 [SMILES: C[C@]1(C(N)=O)COc2c1cc([C@@](O)(CNC(=O)c1cc(=O)[nH]c(C3CC3)n1)C(F)(F)F)nc2-c1ccc(F)cc1] | 562.10 |
| 373 | 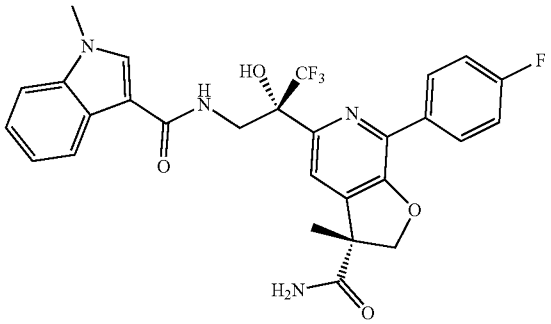 [SMILES: Cn1cc(C(=O)NC[C@](O)(c2cc3c(c(-c4ccc(F)cc4)n2)OC[C@]3(C)C(N)=O)C(F)(F)F)c2ccccc21] | 557.10 |
| 374 | 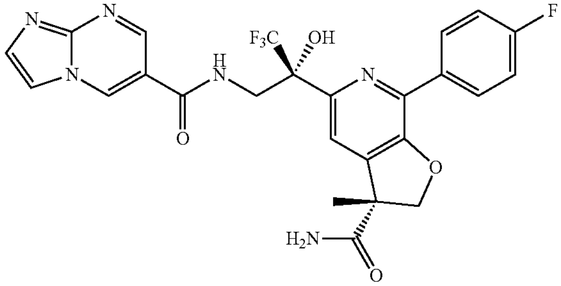 [SMILES: C[C@]1(C(N)=O)COc2c1cc([C@@](O)(CNC(=O)c1cnc3nccn3c1)C(F)(F)F)nc2-c1ccc(F)cc1] | 545.05 |
| 375 | 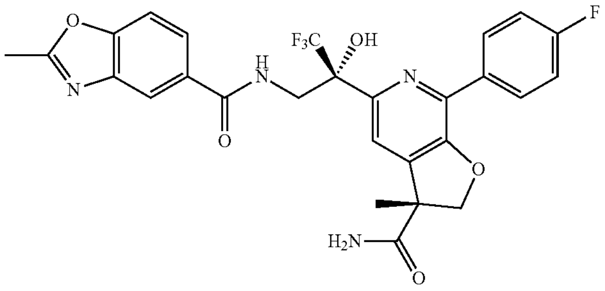 [SMILES: Cc1nc2cc(C(=O)NC[C@](O)(c3cc4c(c(-c5ccc(F)cc5)n3)OC[C@]4(C)C(N)=O)C(F)(F)F)ccc2o1] | 559.16 |

TABLE 4-continued
| Example | Structure | MS+ m/z |
|---|---|---|
| 376 | 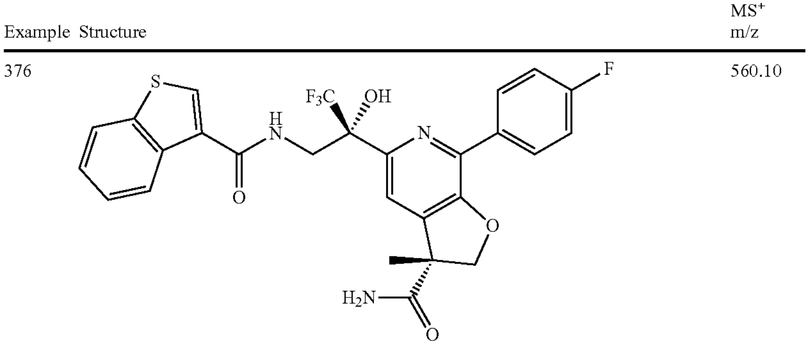 | 560.10 |
| 377 | 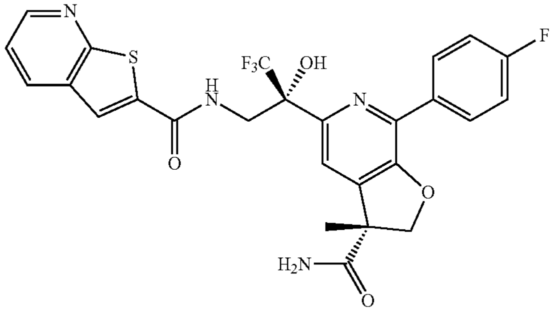 [SMILES: C[C@]1(C(N)=O)COc2c1cc([C@@](O)(CNC(=O)c1cc3cccnc3s1)C(F)(F)F)nc2-c1ccc(F)cc1] | 561.05 |
| 378 | 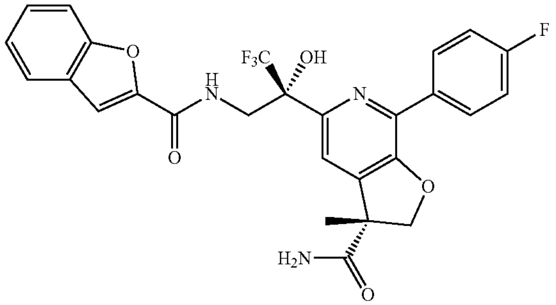 [SMILES: C[C@]1(C(N)=O)COc2c1cc([C@@](O)(CNC(=O)c1cc3ccccc3o1)C(F)(F)F)nc2-c1ccc(F)cc1] | 544.05 |
| 379 | 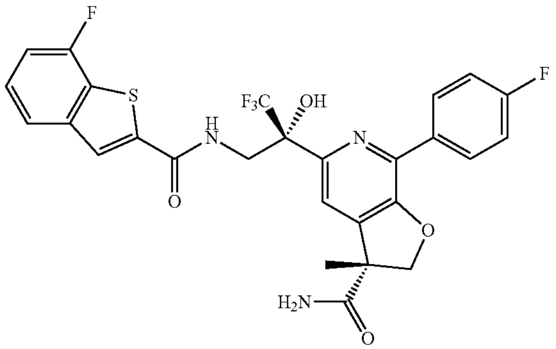 [SMILES: C[C@]1(C(N)=O)COc2c1cc([C@@](O)(CNC(=O)c1cc3cccc(F)c3s1)C(F)(F)F)nc2-c1ccc(F)cc1] | 577.05 |
| 380 | 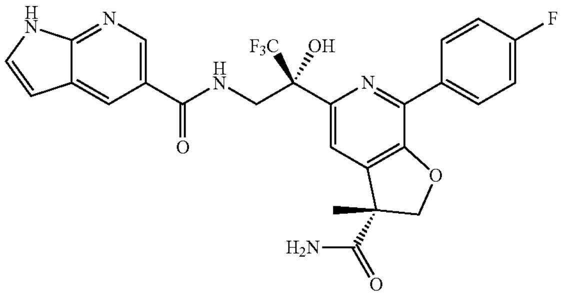 [SMILES: C[C@]1(C(N)=O)COc2c1cc([C@@](O)(CNC(=O)c1cnc3[nH]ccc3c1)C(F)(F)F)nc2-c1ccc(F)cc1] | 544.05 |

TABLE 4-continued
| Example | Structure | MS+ m/z |
|---|---|---|
| 381 | 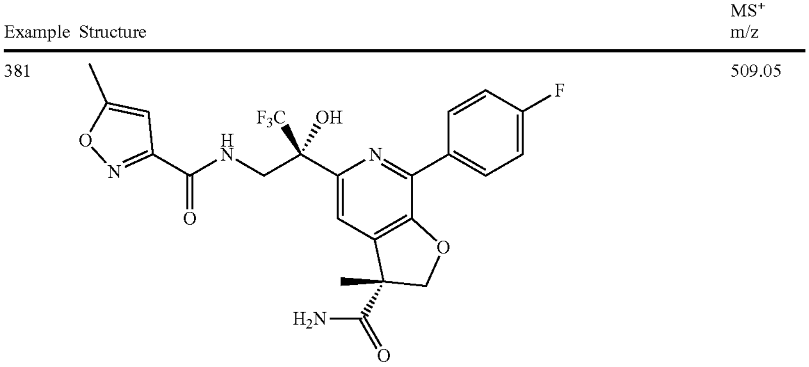 | 509.05 |
| 382 | 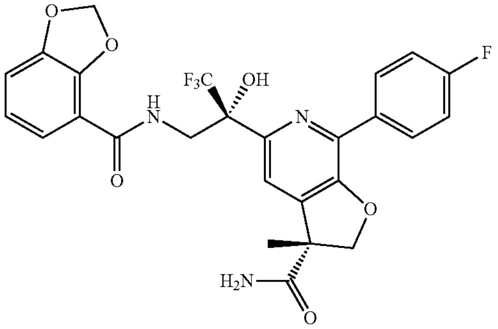 [SMILES: C[C@]1(C(N)=O)COc2c1cc([C@@](O)(CNC(=O)c1cccc3c1OCO3)C(F)(F)F)nc2-c1ccc(F)cc1] | 548.05 |
| 383 | 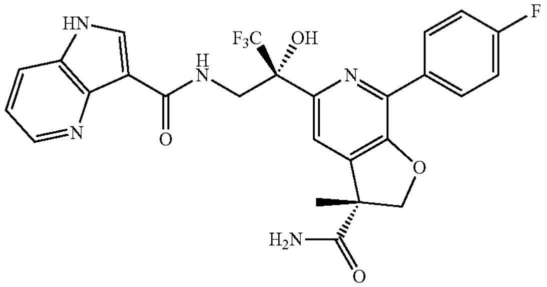 [SMILES: C[C@]1(C(N)=O)COc2c1cc([C@@](O)(CNC(=O)c1c[nH]c3cccnc13)C(F)(F)F)nc2-c1ccc(F)cc1] | 544.01 |
| 384 | 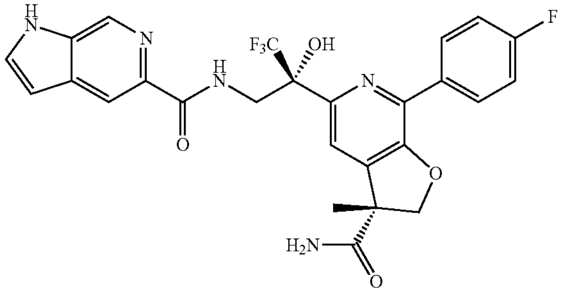 [SMILES: C[C@]1(C(N)=O)COc2c1cc([C@@](O)(CNC(=O)c1cc3cc[nH]c3cn1)C(F)(F)F)nc2-c1ccc(F)cc1] | 544.05 |
| 385 | 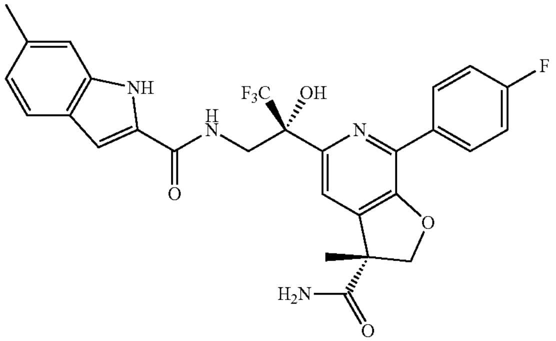 [SMILES: Cc1ccc2cc(C(=O)NC[C@](O)(c3cc4c(c(-c5ccc(F)cc5)n3)OC[C@]4(C)C(N)=O)C(F)(F)F)[nH]c2c1] | 557.10 |

TABLE 4-continued
| Example | Structure | MS+ m/z |
|---|---|---|
| 386 | 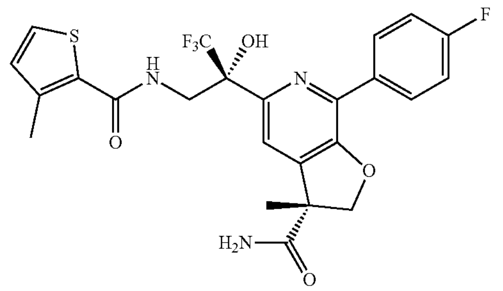 [SMILES: Cc1ccsc1C(=O)NC[C@](O)(c1cc2c(c(-c3ccc(F)cc3)n1)OC[C@]2(C)C(N)=O)C(F)(F)F] | 524.05 |
| 387 | 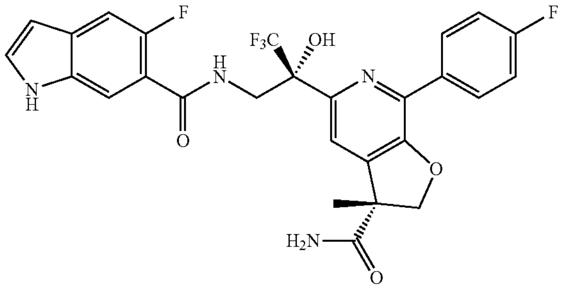 [SMILES: C[C@]1(C(N)=O)COc2c1cc([C@@](O)(CNC(=O)c1cc3[nH]ccc3cc1F)C(F)(F)F)nc2-c1ccc(F)cc1] | 561.15 |
| 388 | 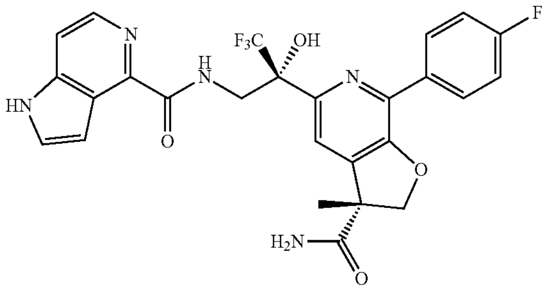 [SMILES: C[C@]1(C(N)=O)COc2c1cc([C@@](O)(CNC(=O)c1nccc3[nH]ccc13)C(F)(F)F)nc2-c1ccc(F)cc1] | 544.05 |
| 389 | 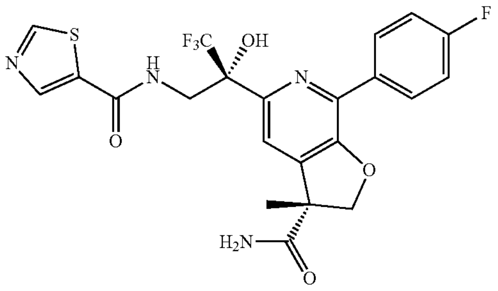 [SMILES: C[C@]1(C(N)=O)COc2c1cc([C@@](O)(CNC(=O)c1cncs1)C(F)(F)F)nc2-c1ccc(F)cc1] | 510.95 |
| 390 | 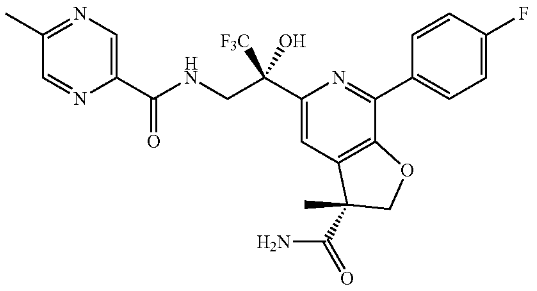 [SMILES: Cc1cnc(C(=O)NC[C@](O)(c2cc3c(c(-c4ccc(F)cc4)n2)OC[C@]3(C)C(N)=O)C(F)(F)F)cn1] | 520.05 |

TABLE 4-continued
| Example | Structure | MS+ m/z |
| --- | --- | --- |
| 391 | 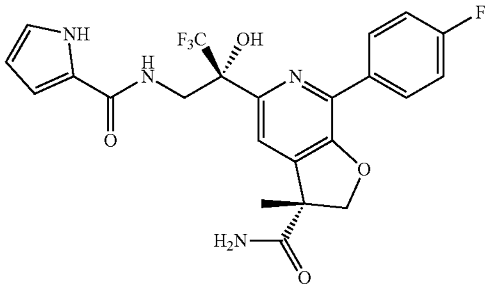 [SMILES: C[C@]1(C(N)=O)COc2c1cc([C@@](O)(CNC(=O)c1ccc[nH]1)C(F)(F)F)nc2-c1ccc(F)cc1] | 493.00 |
| 392 | 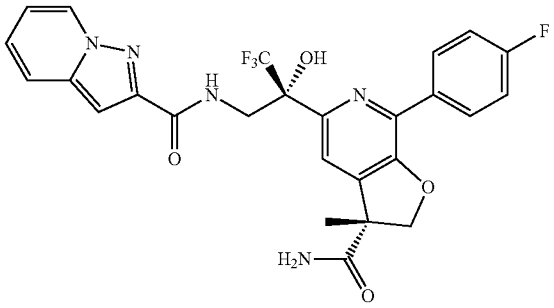 [SMILES: C[C@]1(C(N)=O)COc2c1cc([C@@](O)(CNC(=O)c1cc3ccccn3n1)C(F)(F)F)nc2-c1ccc(F)cc1] | 544.10 |
| 393 | 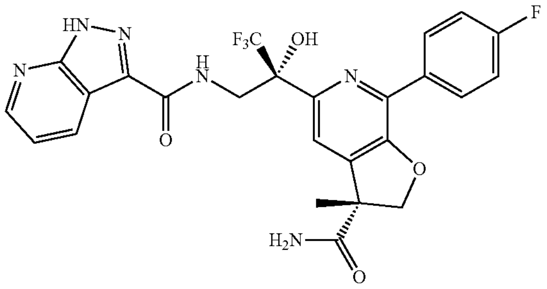 [SMILES: C[C@]1(C(N)=O)COc2c1cc([C@@](O)(CNC(=O)c1n[nH]c3ncccc13)C(F)(F)F)nc2-c1ccc(F)cc1] | 545.10 |
| 394 | 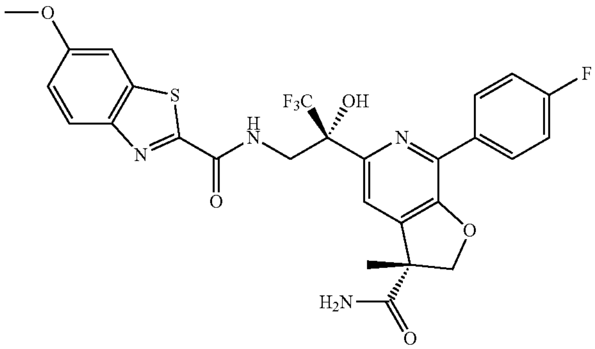 [SMILES: COc1ccc2nc(C(=O)NC[C@](O)(c3cc4c(c(-c5ccc(F)cc5)n3)OC[C@]4(C)C(N)=O)C(F)(F)F)sc2c1] | 591.05 |
| 395 | 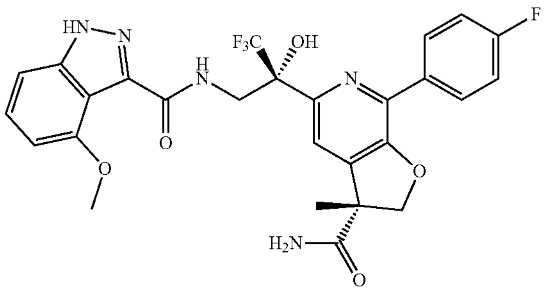 [SMILES: COc1cccc2[nH]nc(C(=O)NC[C@](O)(c3cc4c(c(-c5ccc(F)cc5)n3)OC[C@]4(C)C(N)=O)C(F)(F)F)c12] | 574.10 |

TABLE 4-continued
| Example | Structure | MS+ m/z |
|---|---|---|
| 396 | 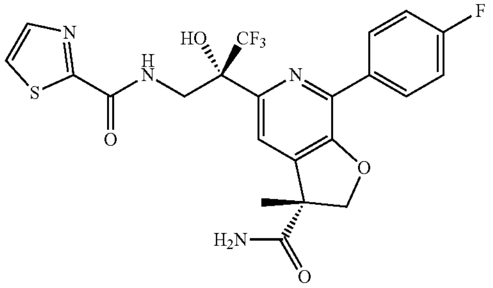 [SMILES: C[C@]1(C(N)=O)COc2c1cc([C@@](O)(CNC(=O)c1nccs1)C(F)(F)F)nc2-c1ccc(F)cc1] | 510.10 |
| 397 | 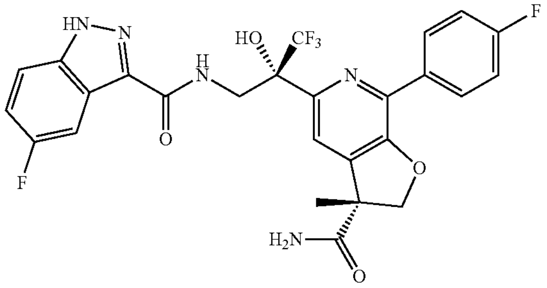 [SMILES: C[C@]1(C(N)=O)COc2c1cc([C@@](O)(CNC(=O)c1n[nH]c3ccc(F)cc13)C(F)(F)F)nc2-c1ccc(F)cc1] | 561.10 |
| 398 | 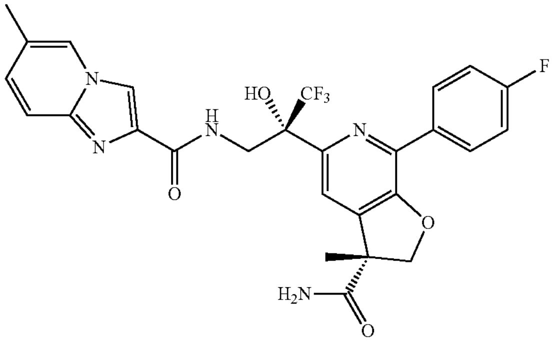 [SMILES: Cc1ccc2nc(C(=O)NC[C@](O)(c3cc4c(c(-c5ccc(F)cc5)n3)OC[C@]4(C)C(N)=O)C(F)(F)F)cn2c1] | 557.20 |
| 399 | 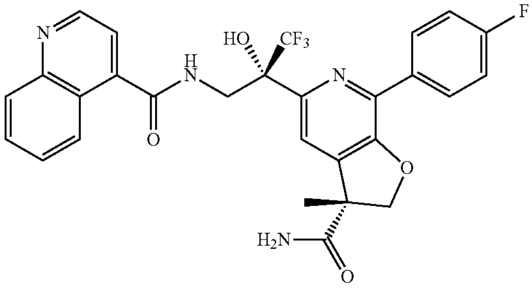 [SMILES: C[C@]1(C(N)=O)COc2c1cc([C@@](O)(CNC(=O)c1ccnc3ccccc13)C(F)(F)F)nc2-c1ccc(F)cc1] | 554.20 |
| 400 | 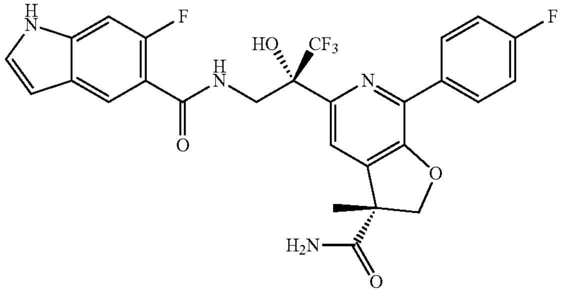 [SMILES: C[C@]1(C(N)=O)COc2c1cc([C@@](O)(CNC(=O)c1cc3cc[nH]c3cc1F)C(F)(F)F)nc2-c1ccc(F)cc1] | 560.10 |

TABLE 4-continued
| Example | Structure | MS+ m/z |
|---|---|---|
| 401 | 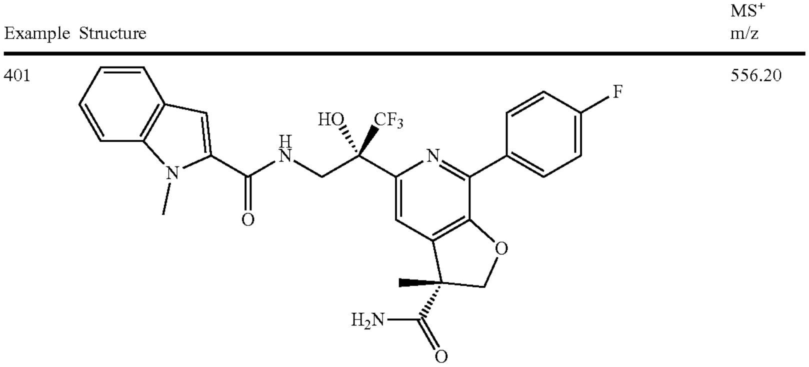 | 556.20 |
| 402 | 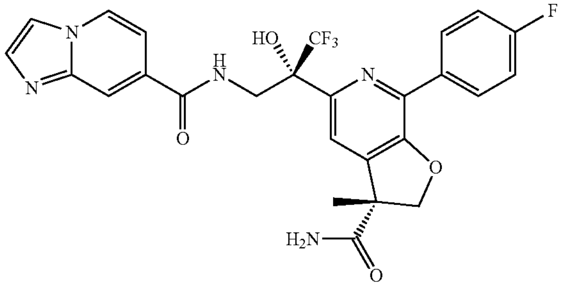 [SMILES: C[C@]1(C(N)=O)COc2c1cc([C@@](O)(CNC(=O)c1ccn3ccnc3c1)C(F)(F)F)nc2-c1ccc(F)cc1] | 543.20 |
| 403 | 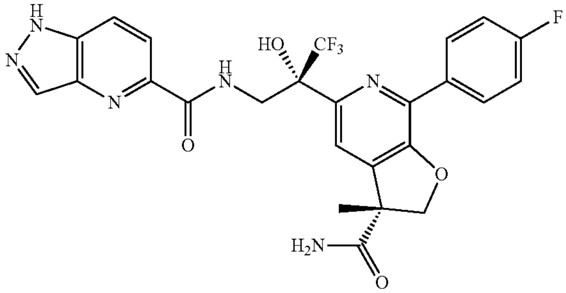 [SMILES: C[C@]1(C(N)=O)COc2c1cc([C@@](O)(CNC(=O)c1ccc3[nH]ncc3n1)C(F)(F)F)nc2-c1ccc(F)cc1] | 544.10 |
| 404 | 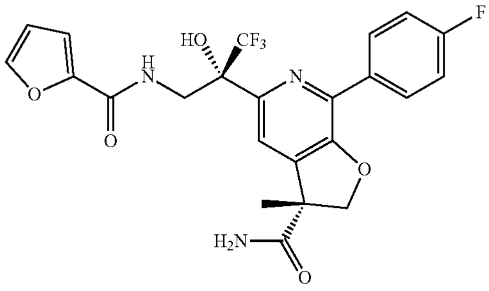 [SMILES: C[C@]1(C(N)=O)COc2c1cc([C@@](O)(CNC(=O)c1ccco1)C(F)(F)F)nc2-c1ccc(F)cc1] | 493.10 |
| 405 | 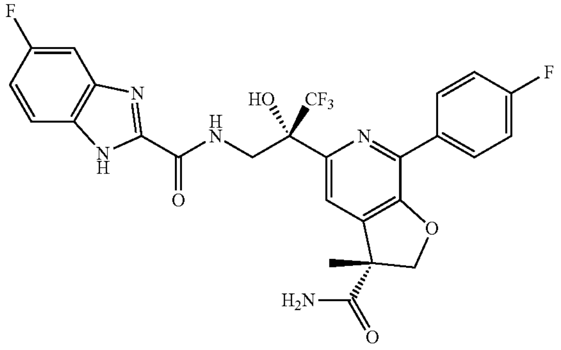 [SMILES: C[C@]1(C(N)=O)COc2c1cc([C@@](O)(CNC(=O)c1nc3cc(F)ccc3[nH]1)C(F)(F)F)nc2-c1ccc(F)cc1] | 561.10 |

TABLE 4-continued
| Example | Structure | MS+ m/z |
|---|---|---|
| 406 | 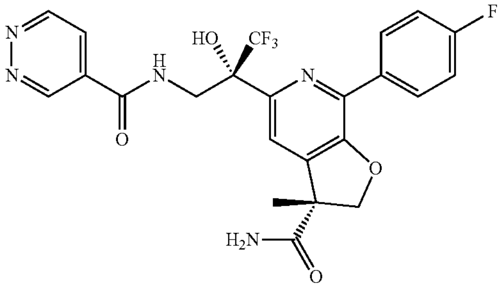 [SMILES: C[C@]1(C(N)=O)COc2c1cc([C@@](O)(CNC(=O)c1ccnnc1)C(F)(F)F)nc2-c1ccc(F)cc1] | 505.10 |
| 407 | 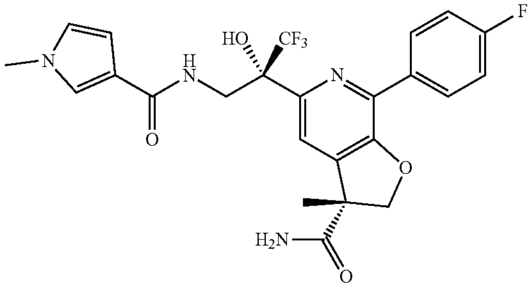 [SMILES: Cn1ccc(C(=O)NC[C@](O)(c2cc3c(c(-c4ccc(F)cc4)n2)OC[C@]3(C)C(N)=O)C(F)(F)F)c1] | 506.20 |
| 408 | 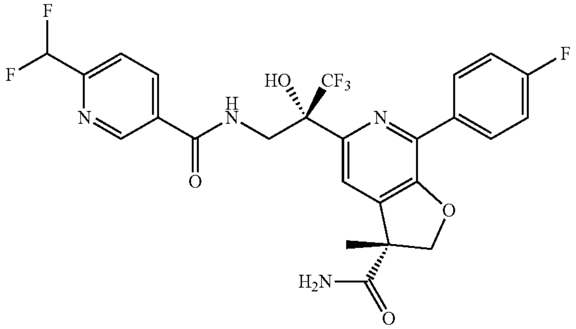 [SMILES: C[C@]1(C(N)=O)COc2c1cc([C@@](O)(CNC(=O)c1ccc(C(F)F)nc1)C(F)(F)F)nc2-c1ccc(F)cc1] | 554.10 |
| 409 | 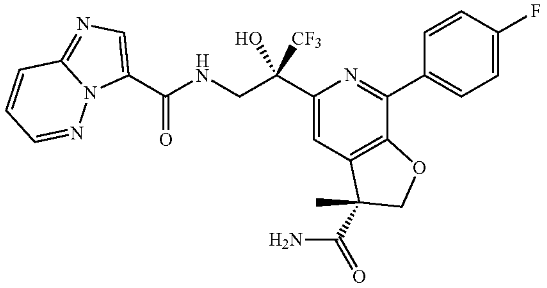 [SMILES: C[C@]1(C(N)=O)COc2c1cc([C@@](O)(CNC(=O)c1cnc3cccnn13)C(F)(F)F)nc2-c1ccc(F)cc1] | 544.10 |
| 410 | 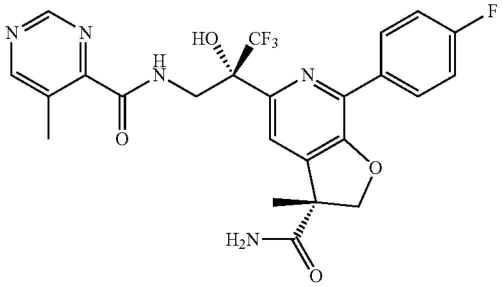 [SMILES: Cc1cncnc1C(=O)NC[C@](O)(c1cc2c(c(-c3ccc(F)cc3)n1)OC[C@]2(C)C(N)=O)C(F)(F)F] | 519.20 |

TABLE 4-continued
| Example | Structure | MS⁺ m/z |
| --- | --- | --- |
| 411 | 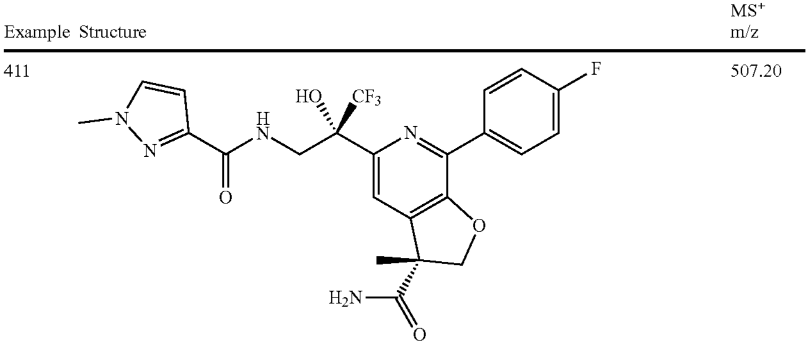 | 507.20 |
| 412 | 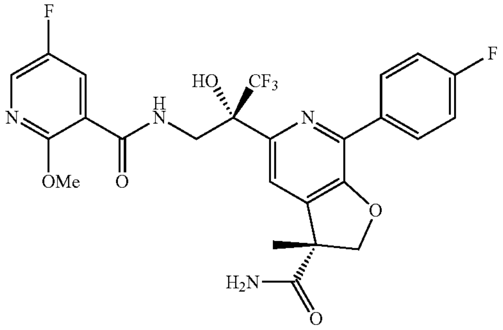 [SMILES: COc1ncc(F)cc1C(=O)NC[C@](O)(c1cc2c(c(-c3ccc(F)cc3)n1)OC[C@]2(C)C(N)=O)C(F)(F)F] | 552.10 |
| 413 | 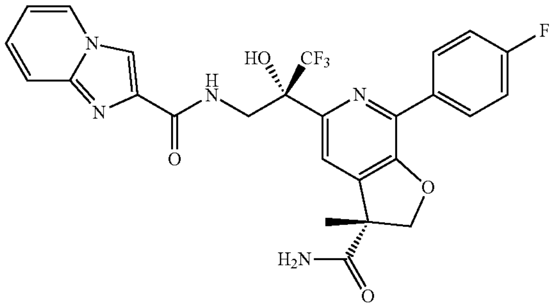 [SMILES: C[C@]1(C(N)=O)COc2c1cc([C@@](O)(CNC(=O)c1cn3ccccc3n1)C(F)(F)F)nc2-c1ccc(F)cc1] | 543.20 |
| 414 | 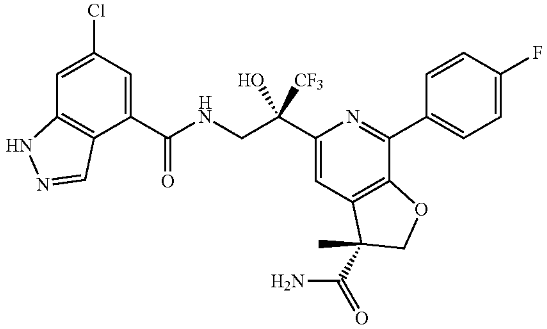 [SMILES: C[C@]1(C(N)=O)COc2c1cc([C@@](O)(CNC(=O)c1cc(Cl)cc3[nH]ncc13)C(F)(F)F)nc2-c1ccc(F)cc1] | 577.10 |
| 415 | 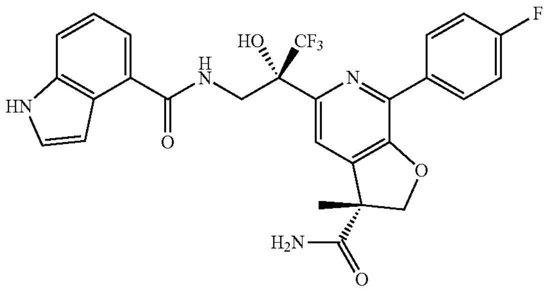 [SMILES: C[C@]1(C(N)=O)COc2c1cc([C@@](O)(CNC(=O)c1cccc3[nH]ccc13)C(F)(F)F)nc2-c1ccc(F)cc1] | 542.20 |

TABLE 4-continued
| Example | Structure | MS+ m/z |
|---|---|---|
| 416 | 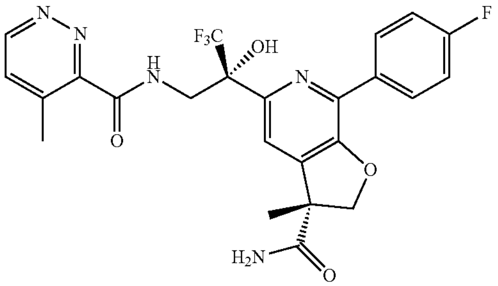 [SMILES: Cc1ccnnc1C(=O)NC[C@](O)(c1cc2c(c(-c3ccc(F)cc3)n1)OC[C@]2(C)C(N)=O)C(F)(F)F] | 520.05 |
| 417 | 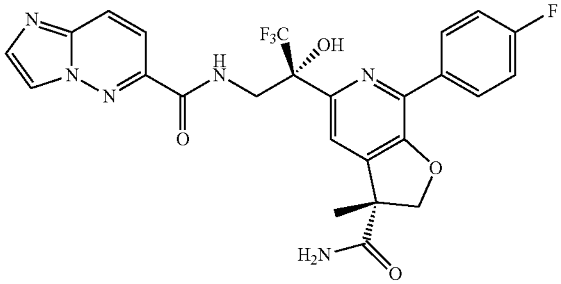 [SMILES: C[C@]1(C(N)=O)COc2c1cc([C@@](O)(CNC(=O)c1ccc3nccn3n1)C(F)(F)F)nc2-c1ccc(F)cc1] | 545.05 |
| 418 | 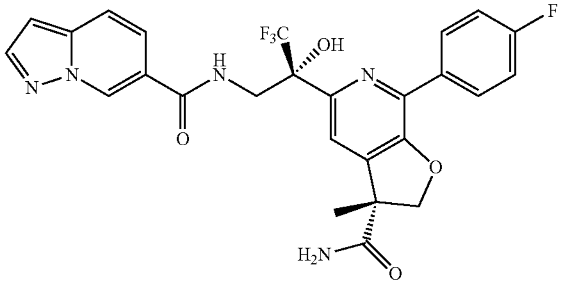 [SMILES: C[C@]1(C(N)=O)COc2c1cc([C@@](O)(CNC(=O)c1ccc3ccnn3c1)C(F)(F)F)nc2-c1ccc(F)cc1] | 544.05 |
| 419 | 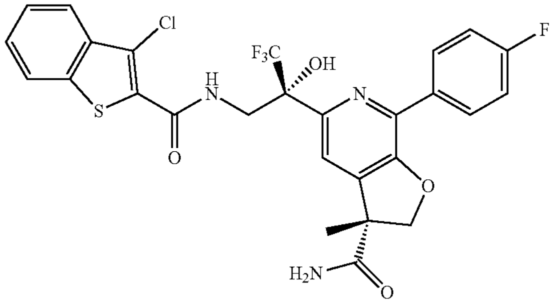 [SMILES: C[C@]1(C(N)=O)COc2c1cc([C@@](O)(CNC(=O)c1sc3ccccc3c1Cl)C(F)(F)F)nc2-c1ccc(F)cc1] | 594.00 |
| 420 | 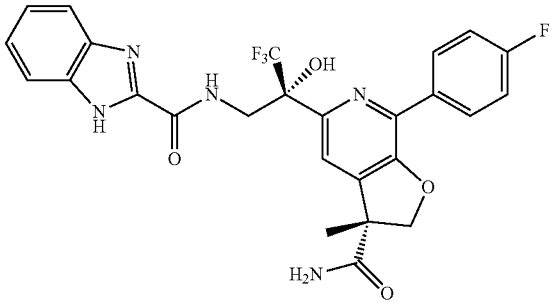 [SMILES: C[C@]1(C(N)=O)COc2c1cc([C@@](O)(CNC(=O)c1nc3ccccc3[nH]1)C(F)(F)F)nc2-c1ccc(F)cc1] | 544.05 |

TABLE 4-continued
| Example | Structure | MS+ m/z |
|---|---|---|
| 421 | 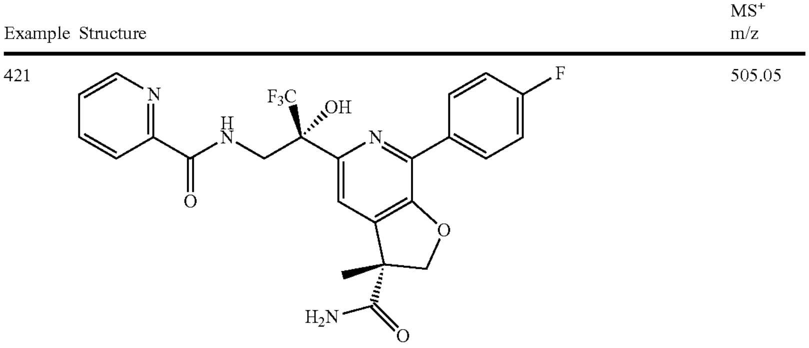 | 505.05 |
| 422 | 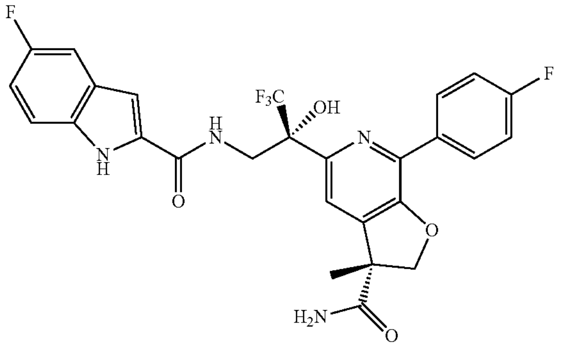 [SMILES: C[C@]1(C(N)=O)COc2c1cc([C@@](O)(CNC(=O)c1cc3cc(F)ccc3[nH]1)C(F)(F)F)nc2-c1ccc(F)cc1] | 561.05 |
| 423 | 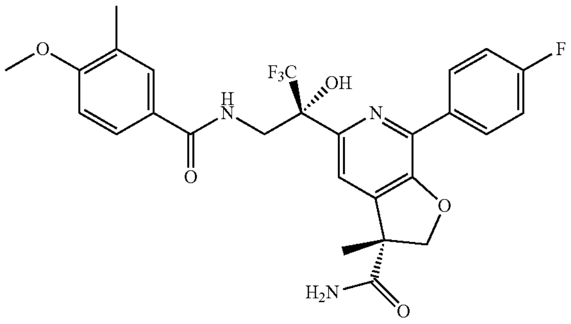 [SMILES: COc1ccc(C(=O)NC[C@](O)(c2cc3c(c(-c4ccc(F)cc4)n2)OC[C@]3(C)C(N)=O)C(F)(F)F)cc1C] | 548.05 |
| 424 | 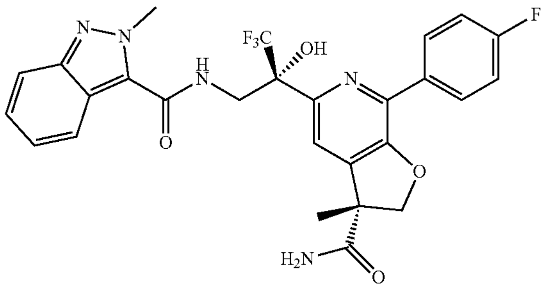 [SMILES: Cn1nc2ccccc2c1C(=O)NC[C@](O)(c1cc2c(c(-c3ccc(F)cc3)n1)OC[C@]2(C)C(N)=O)C(F)(F)F] | 558.15 |
| 425 | 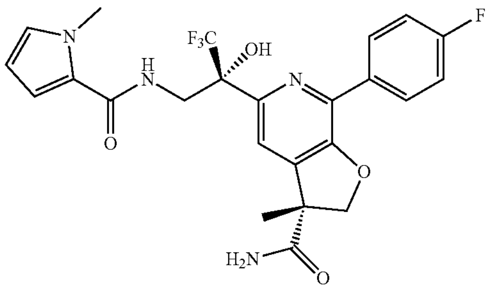 [SMILES: Cn1cccc1C(=O)NC[C@](O)(c1cc2c(c(-c3ccc(F)cc3)n1)OC[C@]2(C)C(N)=O)C(F)(F)F] | 507.05 |

TABLE 4-continued
| Example | Structure | MS⁺ m/z |
|---|---|---|
| 426 | 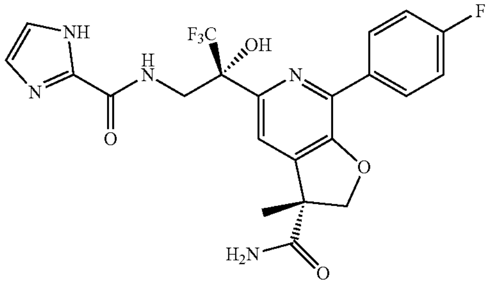 [SMILES: C[C@]1(C(N)=O)COc2c1cc([C@@](O)(CNC(=O)c1ncc[nH]1)C(F)(F)F)nc2-c1ccc(F)cc1] | 494.05 |
| 427 | 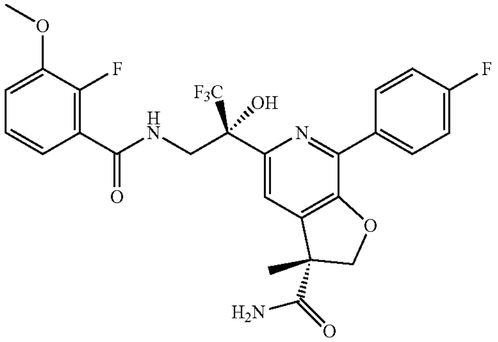 [SMILES: COc1cccc(C(=O)NC[C@](O)(c2cc3c(c(-c4ccc(F)cc4)n2)OC[C@]3(C)C(N)=O)C(F)(F)F)c1F] | 552.05 |
| 428 | 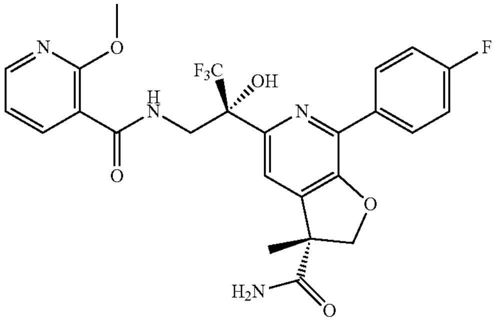 [SMILES: COc1ncccc1C(=O)NC[C@](O)(c1cc2c(c(-c3ccc(F)cc3)n1)OC[C@]2(C)C(N)=O)C(F)(F)F] | 535.05 |
| 429 | 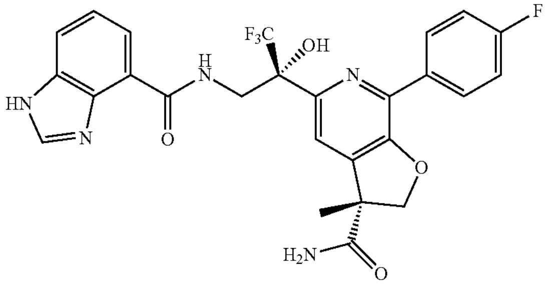 [SMILES: C[C@]1(C(N)=O)COc2c1cc([C@@](O)(CNC(=O)c1cccc3[nH]cnc13)C(F)(F)F)nc2-c1ccc(F)cc1] | 544.10 |

TABLE 4-continued
| Example | Structure | MS+ m/z |
|---|---|---|
| 430 | 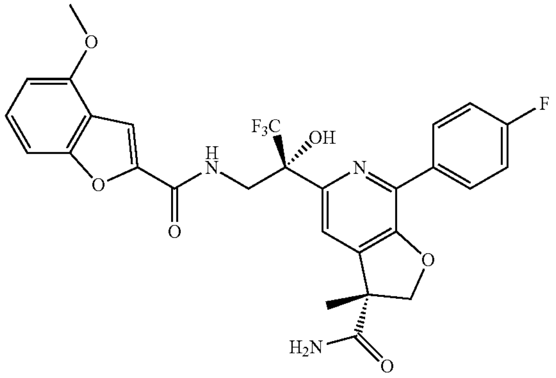 [SMILES: COc1cccc2oc(C(=O)NC[C@](O)(c3cc4c(c(-c5ccc(F)cc5)n3)OC[C@]4(C)C(N)=O)C(F)(F)F)cc12] | 574.10 |
| 431 | 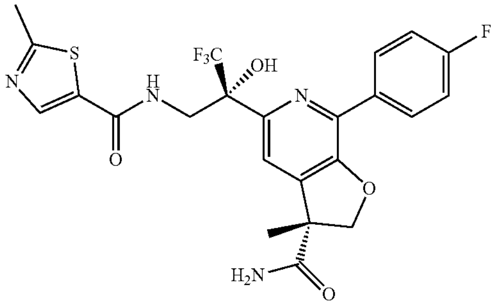 [SMILES: Cc1ncc(C(=O)NC[C@](O)(c2cc3c(c(-c4ccc(F)cc4)n2)OC[C@]3(C)C(N)=O)C(F)(F)F)s1] | 525.05 |
| 432 | 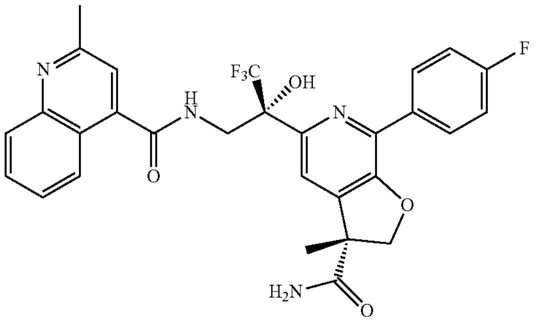 [SMILES: Cc1cc(C(=O)NC[C@](O)(c2cc3c(c(-c4ccc(F)cc4)n2)OC[C@]3(C)C(N)=O)C(F)(F)F)c2ccccc2n1] | 569.10 |
| 433 | 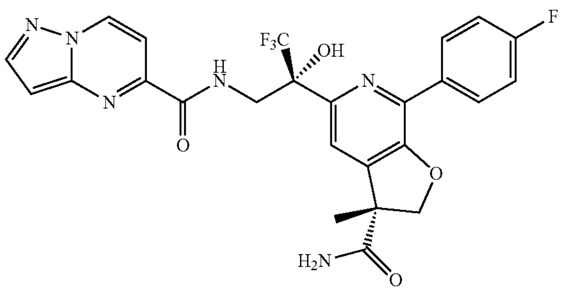 [SMILES: C[C@]1(C(N)=O)COc2c1cc([C@@](O)(CNC(=O)c1ccn3nccc3n1)C(F)(F)F)nc2-c1ccc(F)cc1] | 545.10 |

TABLE 4-continued
| Example | Structure | MS+ m/z |
|---|---|---|
| 434 | 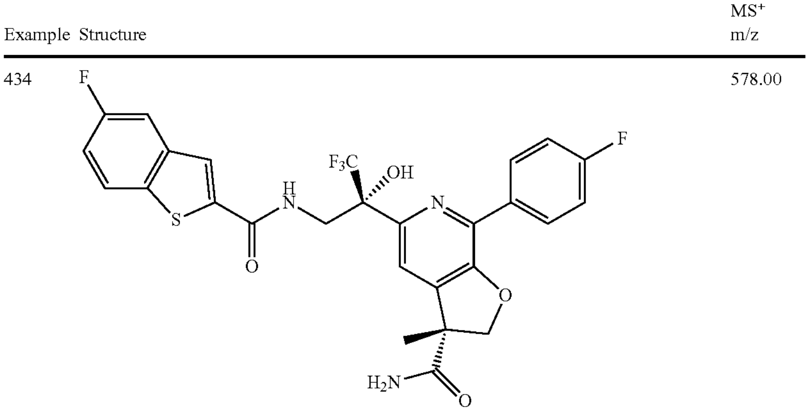 | 578.00 |
| 435 | 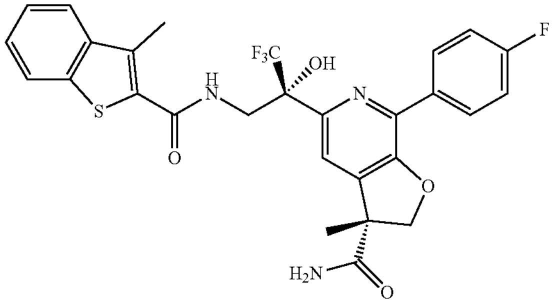 [SMILES: Cc1c(C(=O)NC[C@](O)(c2cc3c(c(-c4ccc(F)cc4)n2)OC[C@]3(C)C(N)=O)C(F)(F)F)sc2ccccc12] | 574.00 |
| 436 | 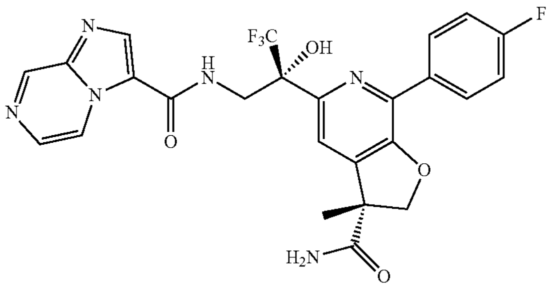 [SMILES: C[C@]1(C(N)=O)COc2c1cc([C@@](O)(CNC(=O)c1cnc3cnccn13)C(F)(F)F)nc2-c1ccc(F)cc1] | 545.00 |
| 437 | 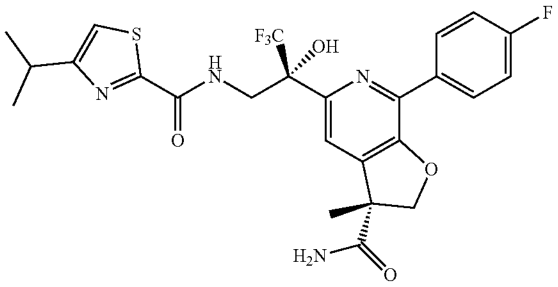 [SMILES: CC(C)c1csc(C(=O)NC[C@](O)(c2cc3c(c(-c4ccc(F)cc4)n2)OC[C@]3(C)C(N)=O)C(F)(F)F)n1] | 553.10 |
| 438 | 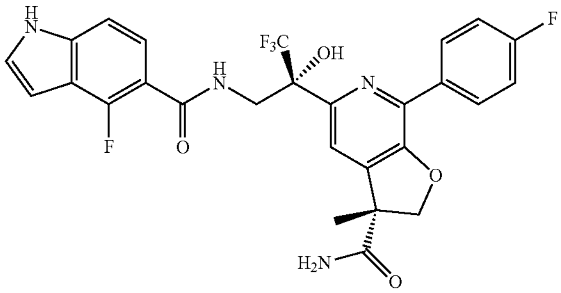 [SMILES: C[C@]1(C(N)=O)COc2c1cc([C@@](O)(CNC(=O)c1ccc3[nH]ccc3c1F)C(F)(F)F)nc2-c1ccc(F)cc1] | 561.05 |

TABLE 4-continued
| Example | Structure | MS+ m/z |
|---|---|---|
| 439 | 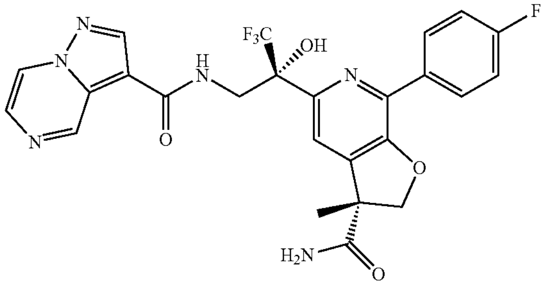 [SMILES: C[C@]1(C(N)=O)COc2c1cc([C@@](O)(CNC(=O)c1cnn3ccncc13)C(F)(F)F)nc2-c1ccc(F)cc1] | 545.05 |
| 440 | 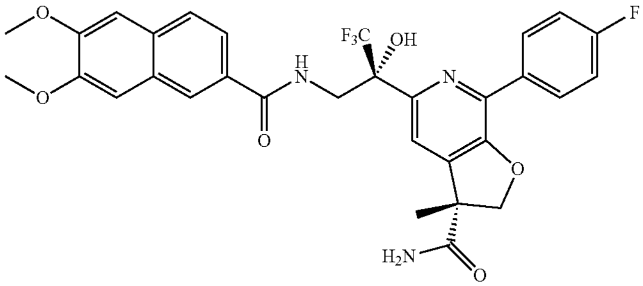 [SMILES: COc1cc2ccc(C(=O)NC[C@](O)(c3cc4c(c(-c5ccc(F)cc5)n3)OC[C@]4(C)C(N)=O)C(F)(F)F)cc2cc1OC] | 614.20 |
| 441 | 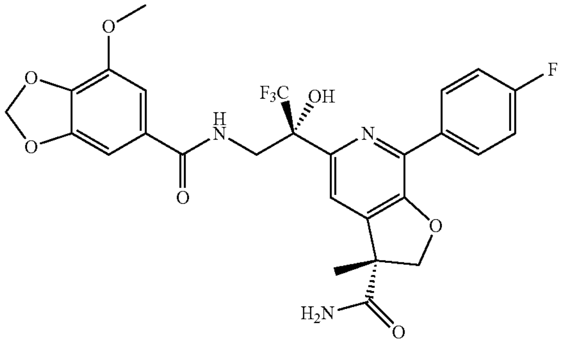 [SMILES: COc1cc(C(=O)NC[C@](O)(c2cc3c(c(-c4ccc(F)cc4)n2)OC[C@]3(C)C(N)=O)C(F)(F)F)cc2c1OCO2] | 578.18 |
| 442 | 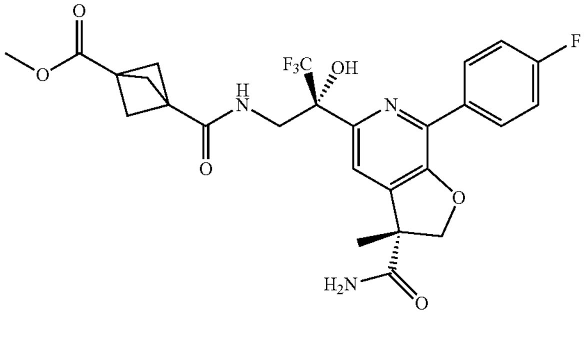 [SMILES: COC(=O)C12CC(C(=O)NC[C@](O)(c3cc4c(c(-c5ccc(F)cc5)n3)OC[C@]4(C)C(N)=O)C(F)(F)F)(C1)C2] | 552.17 |

TABLE 4-continued
| Example | Structure | MS+ m/z |
|---|---|---|
| 443 | 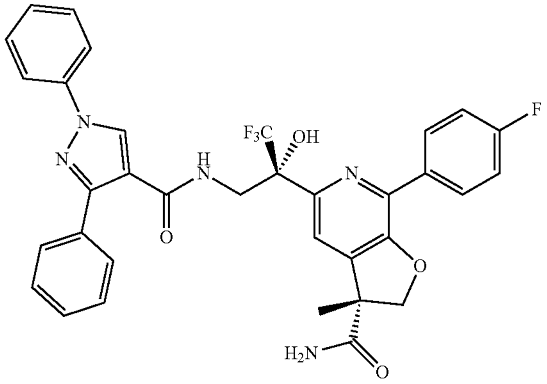 [SMILES: C[C@]1(C(N)=O)COc2c1cc([C@@](O)(CNC(=O)c1cn(-c3ccccc3)nc1-c1ccccc1)C(F)(F)F)nc2-c1ccc(F)cc1] | 646.38 |
| 444 | 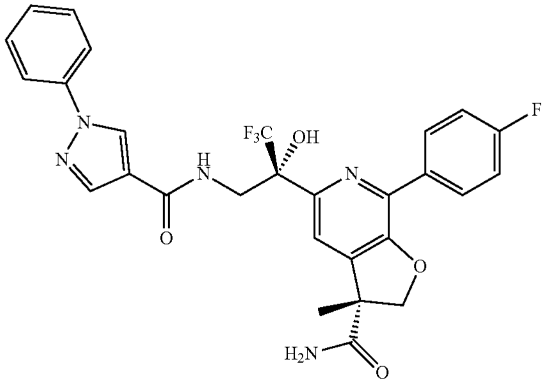 [SMILES: C[C@]1(C(N)=O)COc2c1cc([C@@](O)(CNC(=O)c1cnn(-c3ccccc3)c1)C(F)(F)F)nc2-c1ccc(F)cc1] | 570.29 |
| 445 | 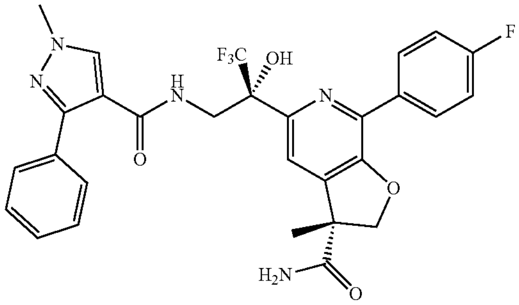 [SMILES: Cn1cc(C(=O)NC[C@](O)(c2cc3c(c(-c4ccc(F)cc4)n2)OC[C@]3(C)C(N)=O)C(F)(F)F)c(-c2ccccc2)n1] | 584.01 |
| 446 | 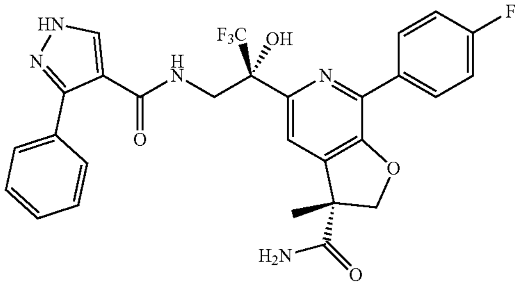 [SMILES: C[C@]1(C(N)=O)COc2c1cc([C@@](O)(CNC(=O)c1c[nH]nc1-c1ccccc1)C(F)(F)F)nc2-c1ccc(F)cc1] | 569.96 |

TABLE 4-continued
| Example | Structure | MS⁺ m/z |
|---|---|---|
| 447 | 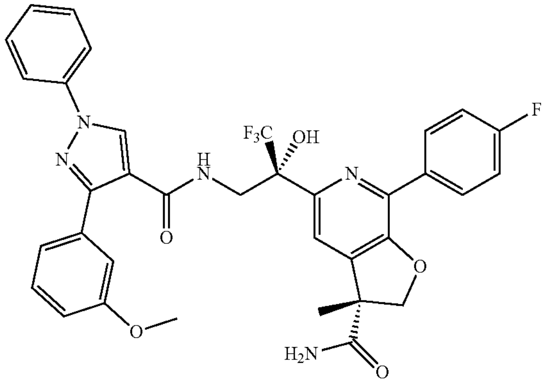 [SMILES: COc1cccc(-c2nn(-c3ccccc3)cc2C(=O)NC[C@](O)(c2cc3c(c(-c4ccc(F)cc4)n2)OC[C@]3(C)C(N)=O)C(F)(F)F)c1] | 675.98 |
| 448 | 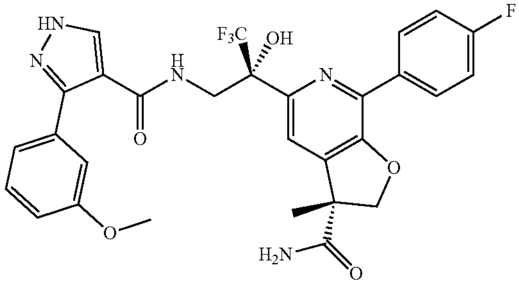 [SMILES: COc1cccc(-c2n[nH]cc2C(=O)NC[C@](O)(c2cc3c(c(-c4ccc(F)cc4)n2)OC[C@]3(C)C(N)=O)C(F)(F)F)c1] | 600.32 |
| 449 | 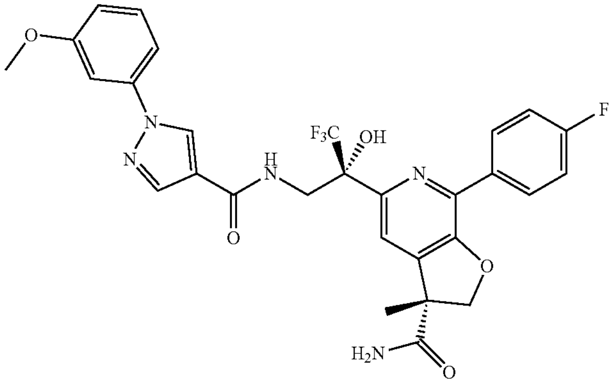 [SMILES: COc1cccc(-n2cc(C(=O)NC[C@](O)(c3cc4c(c(-c5ccc(F)cc5)n3)OC[C@]4(C)C(N)=O)C(F)(F)F)cn2)c1] | 600.31 |
| 450 | 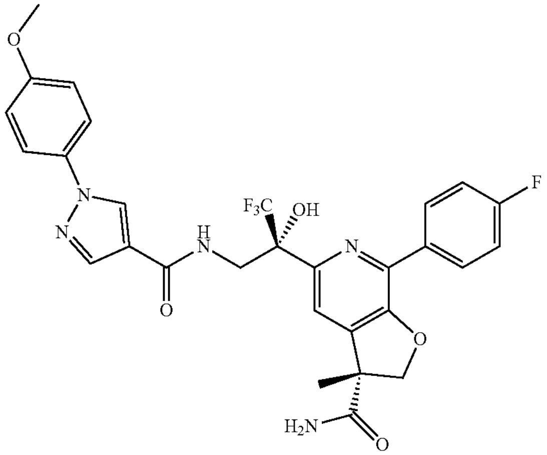 [SMILES: COc1ccc(-n2cc(C(=O)NC[C@](O)(c3cc4c(c(-c5ccc(F)cc5)n3)OC[C@]4(C)C(N)=O)C(F)(F)F)cn2)cc1] | 600.18 |

TABLE 4-continued
| Example | Structure | MS+ m/z |
|---|---|---|
| 451 | 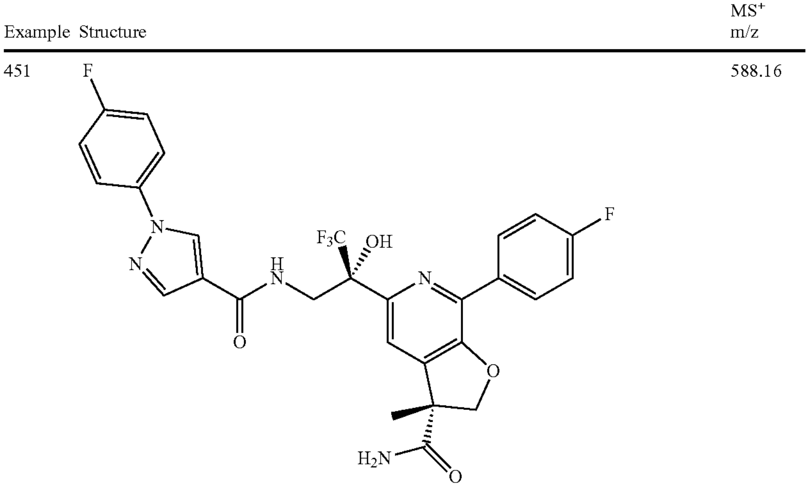 | 588.16 |
| 452 | 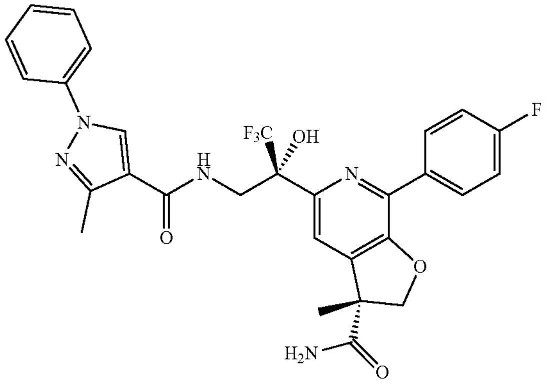 [SMILES: Cc1nn(-c2ccccc2)cc1C(=O)NC[C@](O)(c1cc2c(c(-c3ccc(F)cc3)n1)OC[C@]2(C)C(N)=O)C(F)(F)F] | 584.19 |
| 453 | 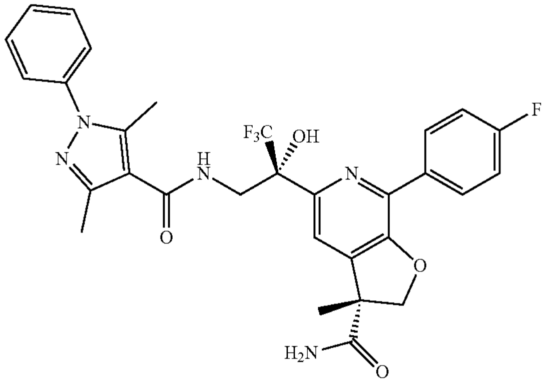 [SMILES: Cc1nn(-c2ccccc2)c(C)c1C(=O)NC[C@](O)(c1cc2c(c(-c3ccc(F)cc3)n1)OC[C@]2(C)C(N)=O)C(F)(F)F] | 598.20 |
| 454 | 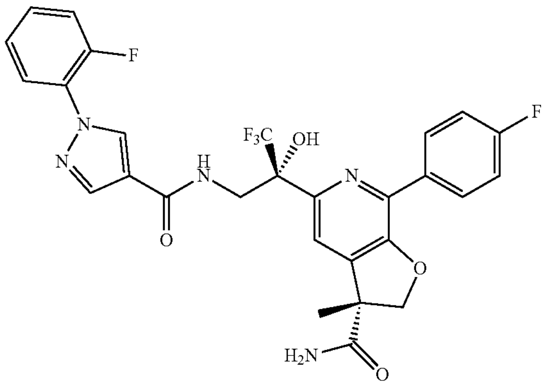 [SMILES: C[C@]1(C(N)=O)COc2c1cc([C@@](O)(CNC(=O)c1cnn(-c3ccccc3F)c1)C(F)(F)F)nc2-c1ccc(F)cc1] | 587.89 |

TABLE 4-continued
| Example | Structure | MS+ m/z |
|---|---|---|
| 455 | 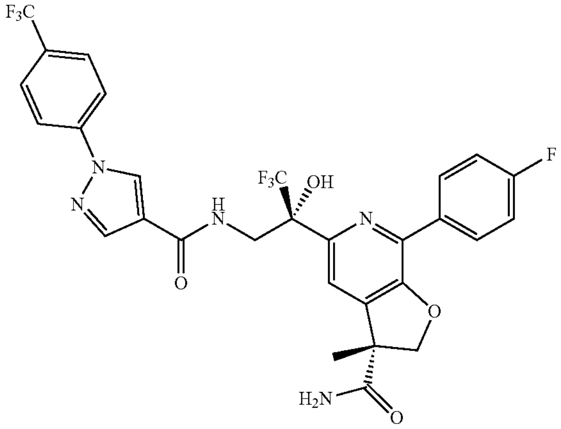 [SMILES: C[C@]1(C(N)=O)COc2c1cc([C@@](O)(CNC(=O)c1cnn(-c3ccc(C(F)(F)F)cc3)c1)C(F)(F)F)nc2-c1ccc(F)cc1] | 637.85 |
| 456 | 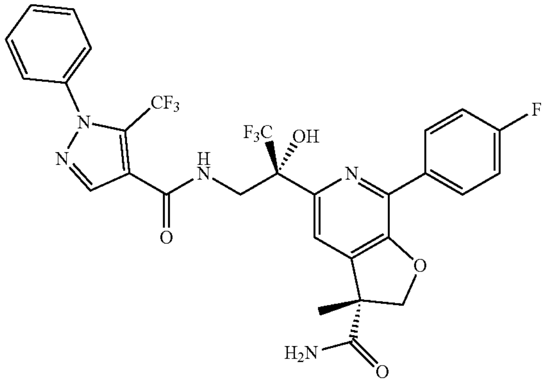 [SMILES: C[C@]1(C(N)=O)COc2c1cc([C@@](O)(CNC(=O)c1cnn(-c3ccccc3)c1C(F)(F)F)C(F)(F)F)nc2-c1ccc(F)cc1] | 637.92 |
| 457 | 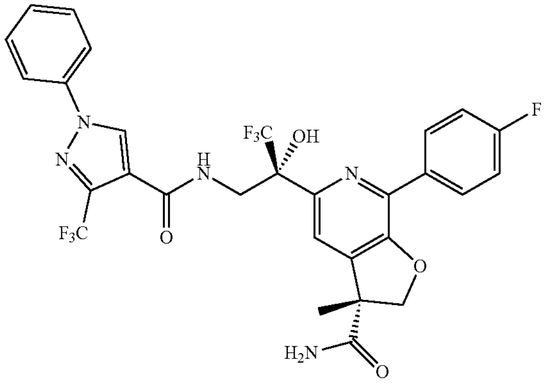 [SMILES: C[C@]1(C(N)=O)COc2c1cc([C@@](O)(CNC(=O)c1cn(-c3ccccc3)nc1C(F)(F)F)C(F)(F)F)nc2-c1ccc(F)cc1] | 637.85 |

TABLE 4-continued
| Example | Structure | MS+ m/z |
|---|---|---|
| 458 | 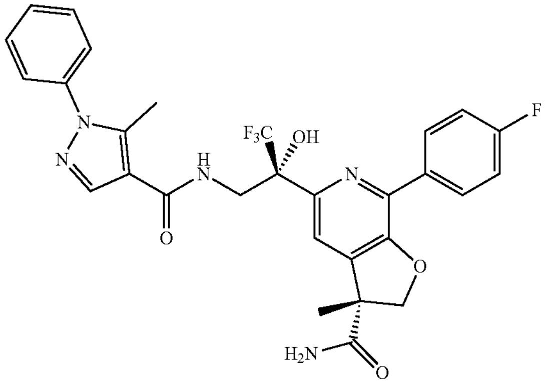 [SMILES: Cc1c(C(=O)NC[C@](O)(c2cc3c(c(-c4ccc(F)cc4)n2)OC[C@]3(C)C(N)=O)C(F)(F)F)cnn1-c1ccccc1] | 584.19 |
| 459 | 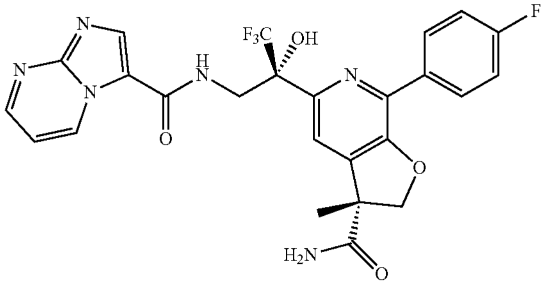 [SMILES: C[C@]1(C(N)=O)COc2c1cc([C@@](O)(CNC(=O)c1cnc3ncccn13)C(F)(F)F)nc2-c1ccc(F)cc1] | 535.05 |
| 460 | 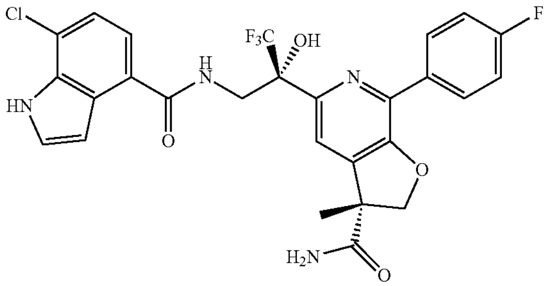 [SMILES: C[C@]1(C(N)=O)COc2c1cc([C@@](O)(CNC(=O)c1ccc(Cl)c3[nH]ccc13)C(F)(F)F)nc2-c1ccc(F)cc1] | 558.10 |
| 461 | 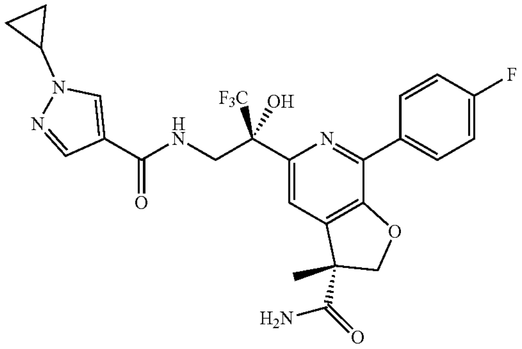 [SMILES: C[C@]1(C(N)=O)COc2c1cc([C@@](O)(CNC(=O)c1cnn(C3CC3)c1)C(F)(F)F)nc2-c1ccc(F)cc1] | 534.20 |

TABLE 4-continued
| Example | Structure | MS+ m/z |
|---|---|---|
| 462 | 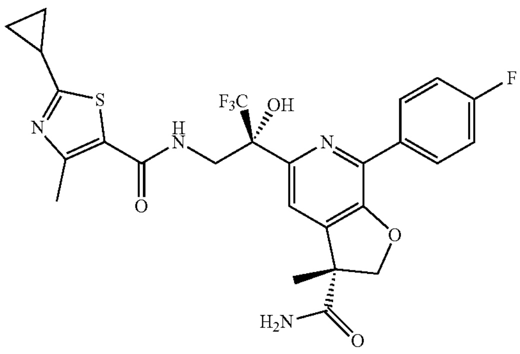 [SMILES: Cc1nc(C2CC2)sc1C(=O)NC[C@](O)(c1cc2c(c(-c3ccc(F)cc3)n1)OC[C@]2(C)C(N)=O)C(F)(F)F] | 565.17 |
| 463 | 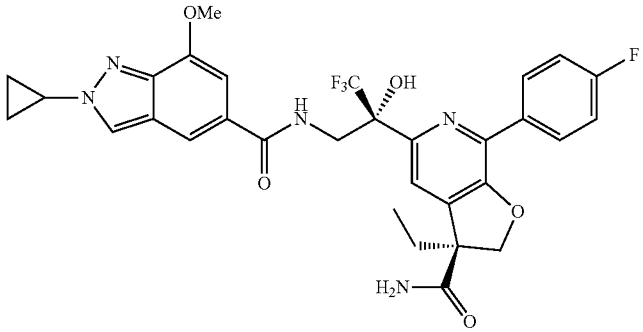 [SMILES: CC[C@@]1(C(N)=O)COc2c1cc([C@@](O)(CNC(=O)c1cc(OC)c3nn(C4CC4)cc3c1)C(F)(F)F)nc2-c1ccc(F)cc1] | 628.33 |
| 464 | 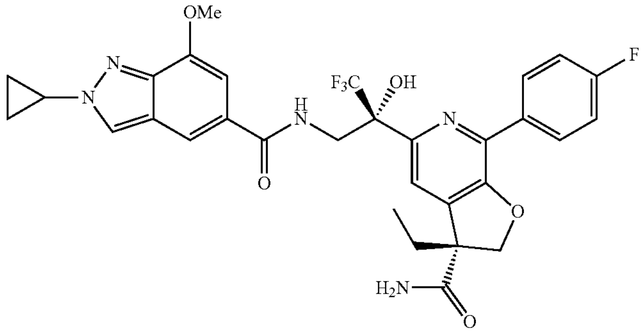 [SMILES: CC[C@]1(C(N)=O)COc2c1cc([C@@](O)(CNC(=O)c1cc(OC)c3nn(C4CC4)cc3c1)C(F)(F)F)nc2-c1ccc(F)cc1] | 628.34 |
| 465 | 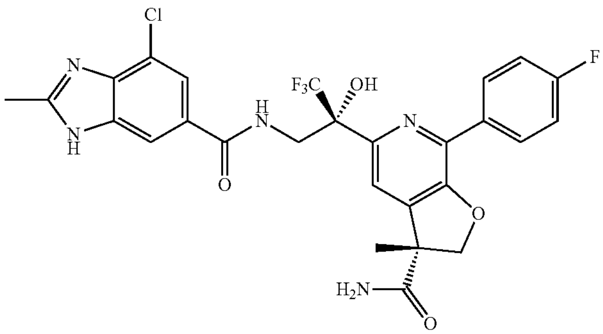 [SMILES: Cc1nc2c(Cl)cc(C(=O)NC[C@](O)(c3cc4c(c(-c5ccc(F)cc5)n3)OC[C@]4(C)C(N)=O)C(F)(F)F)cc2[nH]1] | 592.02 |

TABLE 4-continued
| Example | Structure | MS+ m/z |
| --- | --- | --- |
| 466 | 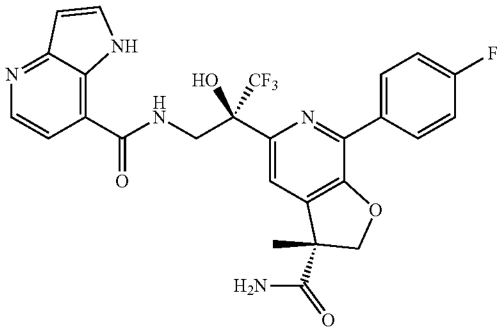 [SMILES: C[C@]1(C(N)=O)COc2c1cc([C@](O)(CNC(=O)c1ccnc3cc[nH]c13)C(F)(F)F)nc2-c1ccc(F)cc1] | 544.20 |
| 467 | 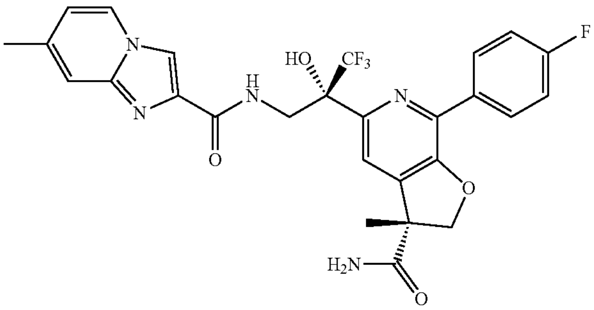 [SMILES: Cc1ccn2cc(C(=O)NC[C@](O)(c3cc4c(c(-c5ccc(F)cc5)n3)OC[C@]4(C)C(N)=O)C(F)(F)F)nc2c1] | 558.08 |
| 468 | 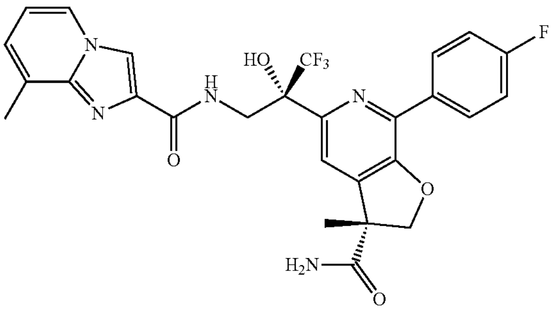 [SMILES: Cc1cccn2cc(C(=O)NC[C@](O)(c3cc4c(c(-c5ccc(F)cc5)n3)OC[C@]4(C)C(N)=O)C(F)(F)F)nc12] | 558.10 |
| 469 | 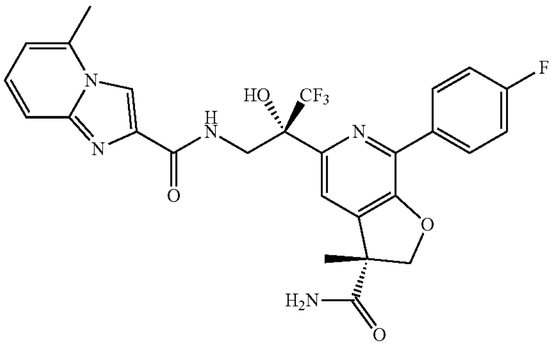 [SMILES: Cc1cccc2nc(C(=O)NC[C@](O)(c3cc4c(c(-c5ccc(F)cc5)n3)OC[C@]4(C)C(N)=O)C(F)(F)F)cn12] | 558.10 |

TABLE 4-continued
| Example | Structure | MS+ m/z |
| --- | --- | --- |
| 470 | 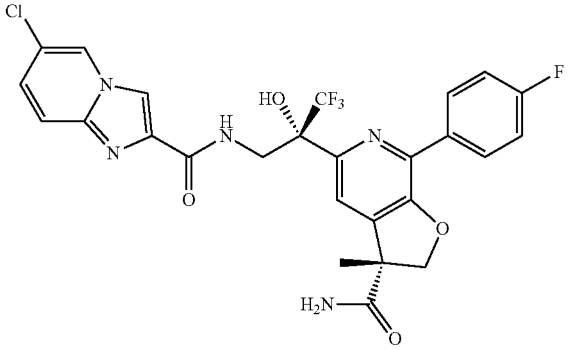 [SMILES: C[C@]1(C(N)=O)COc2c1cc([C@@](O)(CNC(=O)c1cn3cc(Cl)ccc3n1)C(F)(F)F)nc2-c1ccc(F)cc1] | 577.92 |
| 471 | 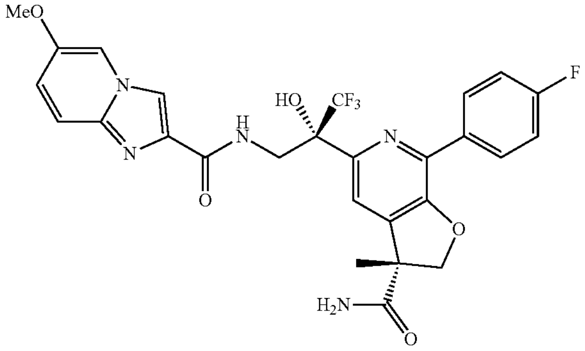 [SMILES: COc1ccc2nc(C(=O)NC[C@](O)(c3cc4c(c(-c5ccc(F)cc5)n3)OC[C@]4(C)C(N)=O)C(F)(F)F)cn2c1] | 574.03 |
| 472 | 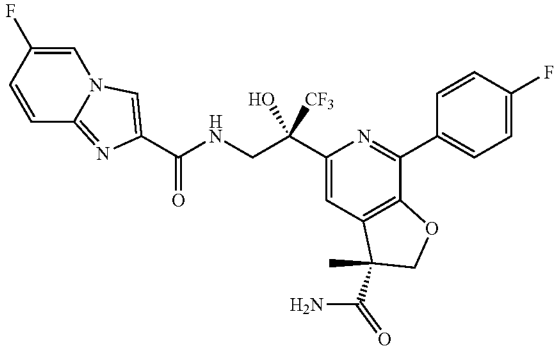 [SMILES: C[C@]1(C(N)=O)COc2c1cc([C@@](O)(CNC(=O)c1cn3cc(F)ccc3n1)C(F)(F)F)nc2-c1ccc(F)cc1] | 561.90 |
| 473 | 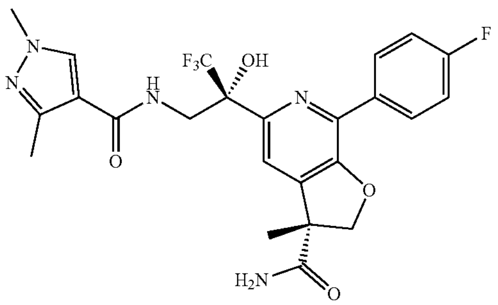 [SMILES: Cc1nn(C)cc1C(=O)NC[C@](O)(c1cc2c(c(-c3ccc(F)cc3)n1)OC[C@]2(C)C(N)=O)C(F)(F)F] | 522.20 |

TABLE 4-continued
| Example | Structure | MS+ m/z |
|---|---|---|
| 474 | 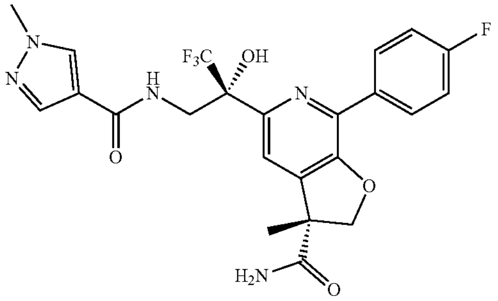 [SMILES: Cn1cc(C(=O)NC[C@](O)(c2cc3c(c(-c4ccc(F)cc4)n2)OC[C@]3(C)C(N)=O)C(F)(F)F)cn1] | 508.17 |
| 475 | 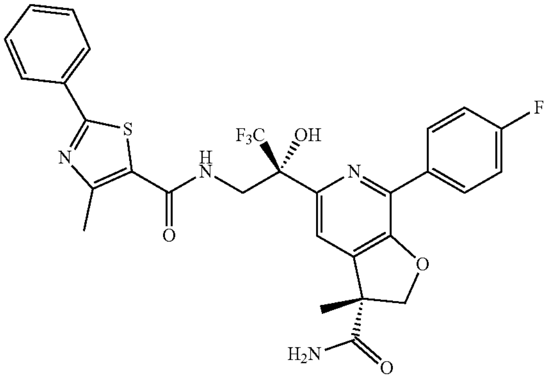 [SMILES: Cc1nc(-c2ccccc2)sc1C(=O)NC[C@](O)(c1cc2c(c(-c3ccc(F)cc3)n1)OC[C@]2(C)C(N)=O)C(F)(F)F] | 601.17 |
| 476 | 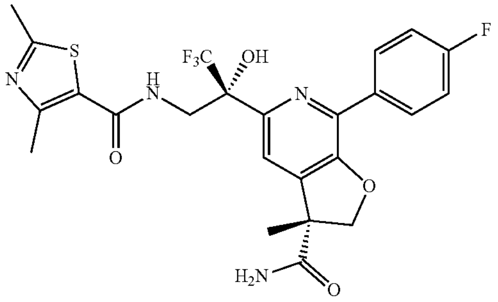 [SMILES: Cc1nc(C)c(C(=O)NC[C@](O)(c2cc3c(c(-c4ccc(F)cc4)n2)OC[C@]3(C)C(N)=O)C(F)(F)F)s1] | 539.15 |
| 477 | 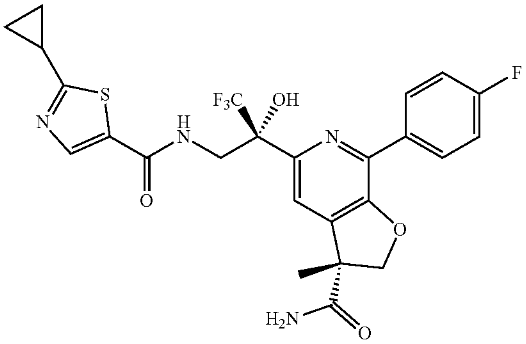 [SMILES: C[C@]1(C(N)=O)COc2c1cc([C@@](O)(CNC(=O)c1cnc(C3CC3)s1)C(F)(F)F)nc2-c1ccc(F)cc1] | 551.16 |

TABLE 4-continued
| Example | Structure | MS+ m/z |
|---|---|---|
| 478 | 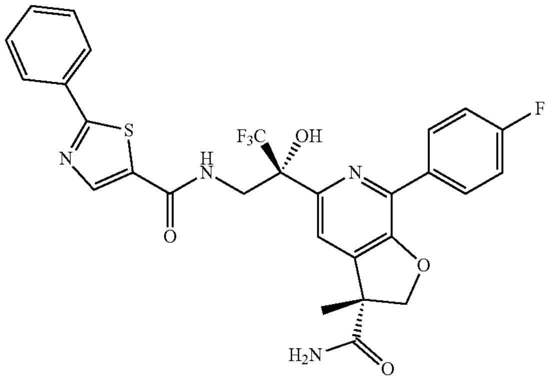 [SMILES: C[C@]1(C(N)=O)COc2c1cc([C@@](O)(CNC(=O)c1cnc(-c3ccccc3)s1)C(F)(F)F)nc2-c1ccc(F)cc1] | 587.15 |
| 479 | 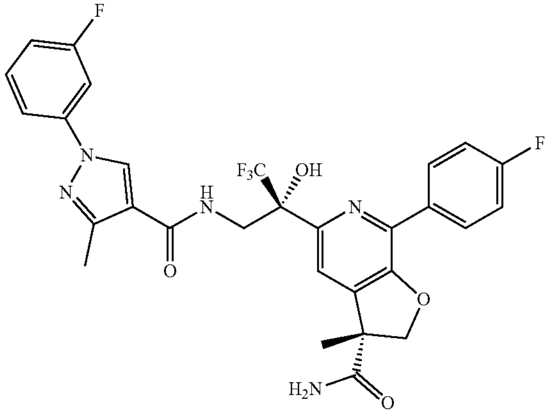 [SMILES: Cc1nn(-c2cccc(F)c2)cc1C(=O)NC[C@](O)(c1cc2c(c(-c3ccc(F)cc3)n1)OC[C@]2(C)C(N)=O)C(F)(F)F] | 601.92 |
| 480 | 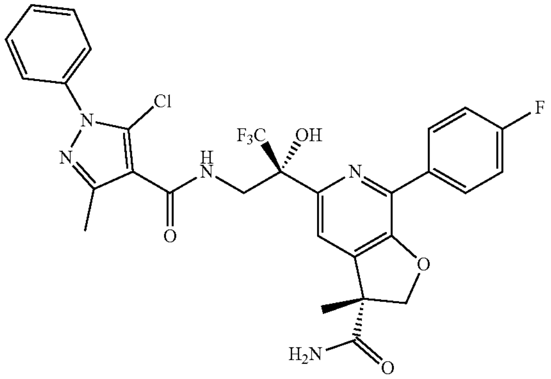 [SMILES: Cc1nn(-c2ccccc2)c(Cl)c1C(=O)NC[C@](O)(c1cc2c(c(-c3ccc(F)cc3)n1)OC[C@]2(C)C(N)=O)C(F)(F)F] | 617.90 |
| 481 | 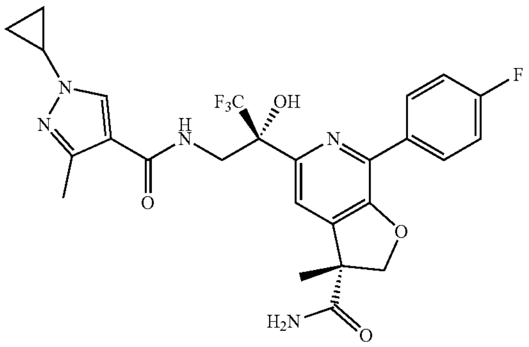 [SMILES: Cc1nn(C2CC2)cc1C(=O)NC[C@](O)(c1cc2c(c(-c3ccc(F)cc3)n1)OC[C@]2(C)C(N)=O)C(F)(F)F] | 548.08 |

TABLE 4-continued
| Example | Structure | MS+ m/z |
|---|---|---|
| 482 | 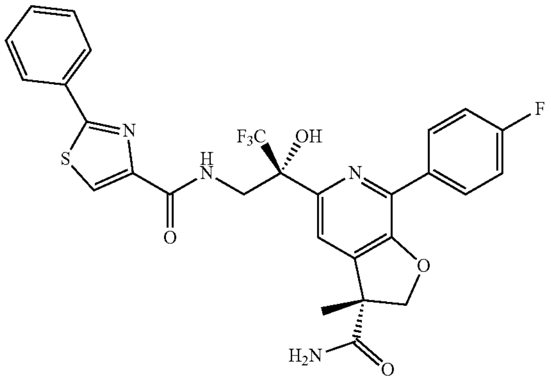 [SMILES: C[C@]1(C(N)=O)COc2c1cc([C@@](O)(CNC(=O)c1csc(-c3ccccc3)n1)C(F)(F)F)nc2-c1ccc(F)cc1] | 587.14 |
| 483 | 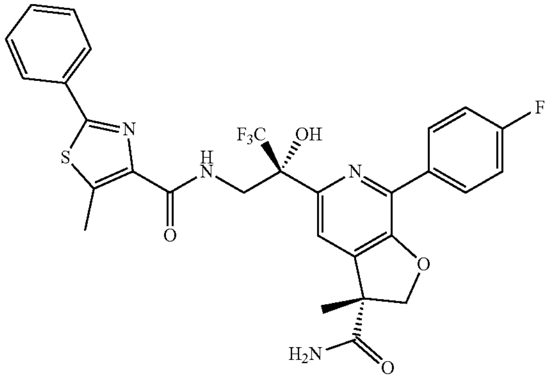 [SMILES: Cc1sc(-c2ccccc2)nc1C(=O)NC[C@](O)(c1cc2c(c(-c3ccc(F)cc3)n1)OC[C@]2(C)C(N)=O)C(F)(F)F] | 601.15 |
| 484 | 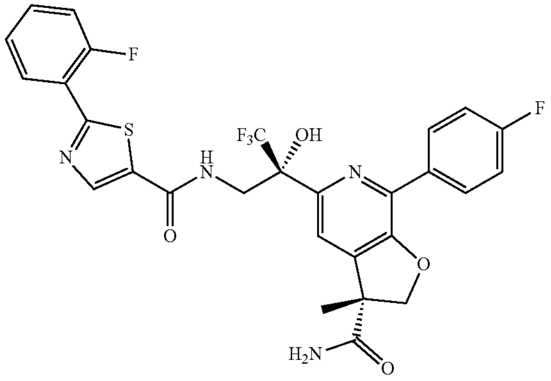 [SMILES: C[C@]1(C(N)=O)COc2c1cc([C@@](O)(CNC(=O)c1cnc(-c3ccccc3F)s1)C(F)(F)F)nc2-c1ccc(F)cc1] | 605.12 |
| 485 | 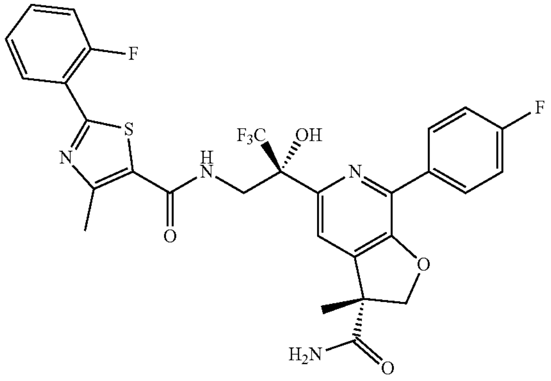 [SMILES: Cc1nc(-c2ccccc2F)sc1C(=O)NC[C@](O)(c1cc2c(c(-c3ccc(F)cc3)n1)OC[C@]2(C)C(N)=O)C(F)(F)F] | 619.14 |

TABLE 4-continued
| Example | Structure | MS+ m/z |
|---|---|---|
| 486 | 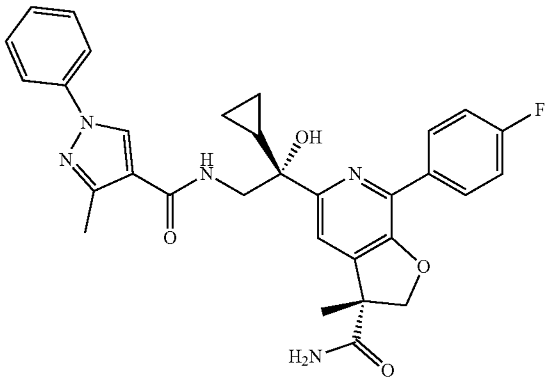 [SMILES: Cc1nn(-c2ccccc2)cc1C(=O)NC[C@](O)(c1cc2c(c(-c3ccc(F)cc3)n1)OC[C@]2(C)C(N)=O)C1CC1] | 556.49 |
| 487 | 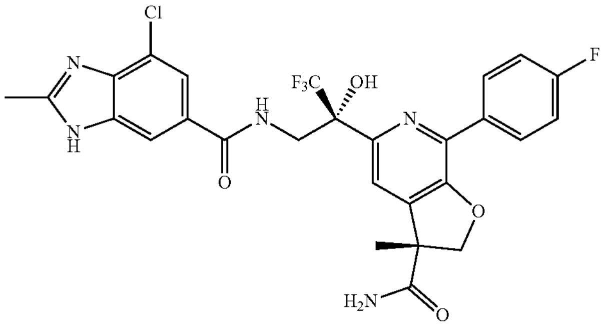 [SMILES: Cc1nc2c(Cl)cc(C(=O)NC[C@](O)(c3cc4c(c(-c5ccc(F)cc5)n3)OC[C@]4(C)C(N)=O)C(F)(F)F)cc2[nH]1] | 592.02 |
| 488 | 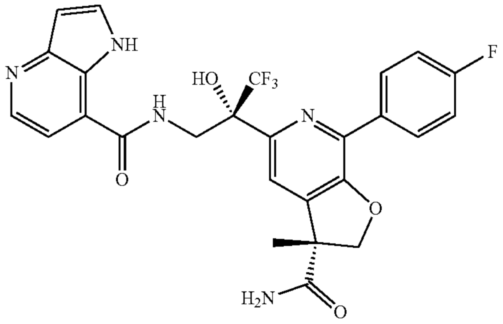 [SMILES: C[C@]1(C(N)=O)COc2c1cc([C@@](O)(CNC(=O)c1ccnc3cc[nH]c13)C(F)(F)F)nc2-c1ccc(F)cc1] | 544.20 |
| 489 | 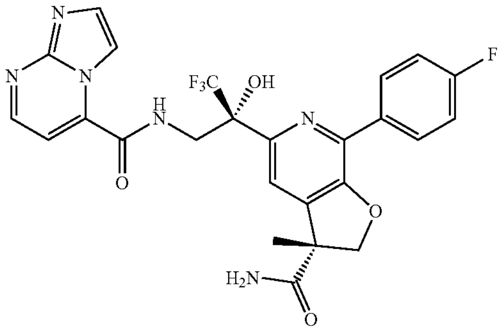 [SMILES: C[C@]1(C(N)=O)COc2c1cc([C@@](O)(CNC(=O)c1ccnc3nccn13)C(F)(F)F)nc2-c1ccc(F)cc1] | 545.37 |

TABLE 4-continued

| Example | Structure | MS+ m/z |
|---|---|---|
| 490 | 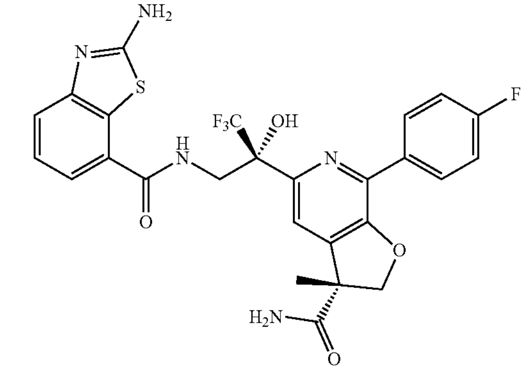 [SMILES: C[C@]1(C(N)=O)COc2c1cc([C@@](O)(CNC(=O)c1cccc3nc(N)sc13)C(F)(F)F)nc2-c1ccc(F)cc1] | 576.34 |

Intermediate 47

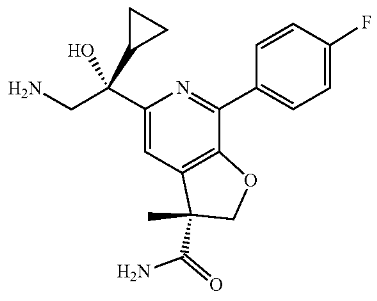 [SMILES: C[C@]1(C(N)=O)COc2c1cc([C@@](O)(CN)C1CC1)nc2-c1ccc(F)cc1]

Intermediate 47 Step a

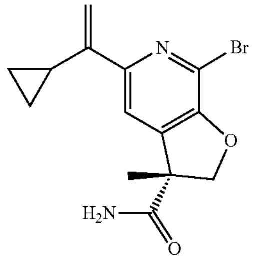 [SMILES: C=C(c1cc2c(c(Br)n1)OC[C@]2(C)C(N)=O)C1CC1]

A mixture of (R)-7-bromo-5-iodo-3-methyl-2,3-dihydrofuro[2,3-c]pyridine-3-carboxamide (3.5 g, 9.14 mmol), cyclopropyl vinyl boronic acid pinacol ester (2.13 g, 10.96 mmol), Pd(dppf)$Cl_2$ (1.34 g, 1.83 mmol), $K_2CO_3$ (3.16 g, 22.84 mmol) in dioxane (18 mL) and $H_2O$ (2 mL) was stirred for 2 hours at 90° C. under nitrogen atmosphere. The reaction was monitored by LCMS. The resulting mixture was filtered, the filter cake was washed with EA. The filtrate was concentrated under reduced pressure. The residue was purified by silica gel column chromatography (eluted 50% ethyl acetate in hexanes) to afford the desired product (2.2 g, 74%) as a brown oil. ESI-MS m/z: 322.90 $[M+H]^+$.

Intermediate 47 Step b

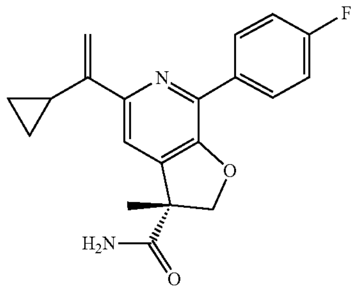 [SMILES: C=C(c1cc2c(c(-c3ccc(F)cc3)n1)OC[C@]2(C)C(N)=O)C1CC1]

A mixture of the compound from step a (1.5 g, 4.64 mmol), 4-fluorophenylboronic acid (0.97 g, 6.96 mmol), $Pd(PPh_3)_2Cl_2$ (0.33 g, 0.46 mmol), and $Na_2CO_3$ (1.23 g, 11.60 mmol) in THE (10 mL) and $H_2O$ (2.5 mL) was stirred for 1 h at 70° C. under nitrogen atmosphere. The reaction was monitored by TLC. The resulting mixture was filtered, the filter cake was washed with EA. The filtrate was concentrated under reduced pressure. The residue was purified by silica gel column chromatography (eluted with 33% ethyl acetate in hexanes) to afford the desired product (1.2 g, 76%) as a yellow oil. ESI-MS m/z: 339.05 $[M+H]^+$.

Intermediate 47 Step c

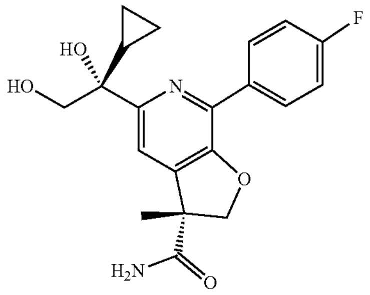 [SMILES: C[C@]1(C(N)=O)COc2c1cc([C@@](O)(CO)C1CC1)nc2-c1ccc(F)cc1]

A solution of the compound from step b (1.2 g, 3.54 mmol) in t-BuOH (40 mL) and $H_2O$ (40 mL) was cooled to 0° C. Methanesulfonamide (0.34 g, 3.54 mmol) and AD-mix-β (8.29 g, 10.64 mmol) were added and the reaction was stirred overnight at room temperature and monitored by LCMS. The resulting mixture was poured into water and extracted with ethyl acetate. The combined organic layers were concentrated under reduced pressure. The residue was purified by reverse flash chromatography (MeCN in water, 0.1% FA) to afford the desired product (1.1 g, 83%) as an off-white solid. ESI-MS m/z: 373.25[M+H]$^+$.

Intermediate 47 Step d

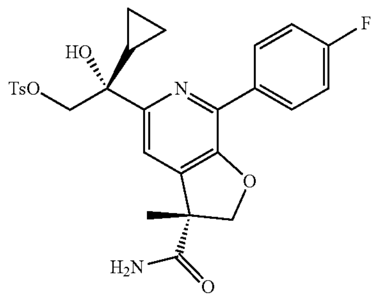 [SMILES: Cc1ccc(S(=O)(=O)OC[C@](O)(c2cc3c(c(-c4ccc(F)cc4)n2)OC[C@]3(C)C(N)=O)C2CC2)cc1]

A solution of the compound from step c (1.7 g, 4.56 mmol) in DCM (70 mL) was cooled to 0 C°. TsCl (1.31 g, 6.84 mmol), TEA (1.39 g, 13.69 mmol) and DMAP (0.22 g, 1.82 mmol) were added and the reaction stirred for 3 hours at room temperature. The reaction was monitored by LCMS. The mixture was acidified to pH 4 with HCl (2 M aq.). The resulting mixture was extracted with $CH_2C_{12}$. The combined organic layers were concentrated under reduced pressure. The residue was purified by silica gel column chromatography (eluted with 66% ethyl acetate in hexanes) to afford the desired product (1.6 g, 66%) as a yellow solid. ESI-MS m/z: 527.30 [M+H]$^+$.

Intermediate 47 Step e

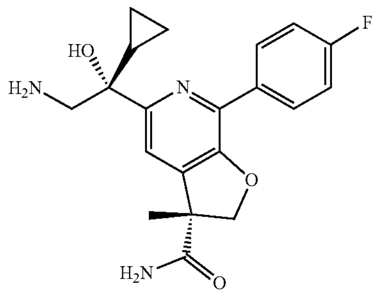 [SMILES: C[C@]1(C(N)=O)COc2c1cc([C@@](O)(CN)C1CC1)nc2-c1ccc(F)cc1]

Into a 250 mL round-bottom flask containing step d (1.6 g, 3.04 mmol) were added $NH_3$ (68 mL, 156 eq, 7N in MeOH) at room temperature. The resulting mixture was stirred for 20 hr at room temperature and monitored by LCMS. The solvent was removed, and the crude mixture was dissolved in EtOAc. The organics were washed 3× with sat. sodium bicarbonate, and the organics were concentrated. The crude material was triturated with DCM to afford the desired product (590.9 mg, 52%) as an off-white solid. ESI-MS m/z: 372.15 [M+H]$^+$.

Intermediate 48

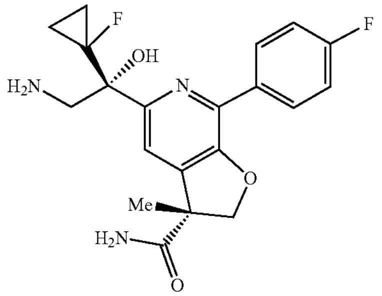 [SMILES: C[C@]1(C(N)=O)COc2c1cc([C@@](O)(CN)C1(F)CC1)nc2-c1ccc(F)cc1]

Intermediate 48 Step a

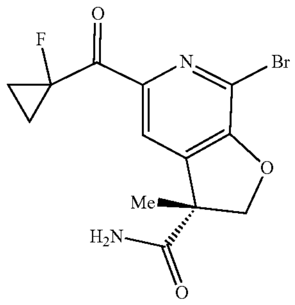 [SMILES: C[C@]1(C(N)=O)COc2c1cc(C(=O)C1(F)CC1)nc2Br]

In a vial, the compound from Intermediate 36 Step b (6.5 g, 17 mmol) and 1-fluoro-N-methoxy-N-methylcyclopropane-1-carboxamide (3 g, 20.39 mmol) were dissolved in THE (121 ml) and cooled to 0° C. Isopropylmagnesium chloride (16.99 ml, 34.0 mmol) was added slowly and the reaction was allowed to stir at 0° C. After stirring for 3 hours, water added at 0° C. and reaction allowed to warm to RT. The aqueous layer washed with EtOAc and combined organic layer dried over $MgSO_4$ and concentrated. The crude reaction mixture purified by silica gel column chromatography eluting with 0-50% EtOAc/Hexanes to give the title compound (2.8 g, 48%) as a foaming white solid. ESI-MS m/z: 343.17 [M+H]$^+$.

Intermediate 48 Step b

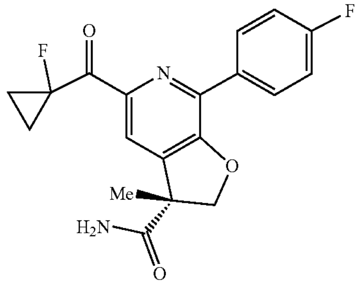 [SMILES: C[C@]1(C(N)=O)COc2c1cc(C(=O)C1(F)CC1)nc2-c1ccc(F)cc1]

In a vial, the compound from step a (1.4 g, 4.08 mmol), (4-fluorophenyl)boronic acid (0.685 g, 4.90 mmol), $PdCl_2$ (dppf) DCM (0.200 g, 0.245 mmol), and $K_2CO_3$ (1.692 g, 12.24 mmol) were dissolved in 1,4-Dioxane (16.32 ml) and Water (4.08 ml). The reaction was sparged with $N_2$ and sealed. The reaction was heated to 90° C. After 4 hours, the reaction was cooled to RT and water was added. The aqueous layer was washed with EtOAc. The combined organic layer was washed with water and brine before drying over $MgSO_4$ and concentrating. The crude reaction mixture purified by silica gel column chromatography eluting with 0-70% EtOAc/Hexanes to give the title compound (1.12 g, 77%). ESI-MS m/z: 359.06 $[M+H]^+$.

Intermediate 48 Step c

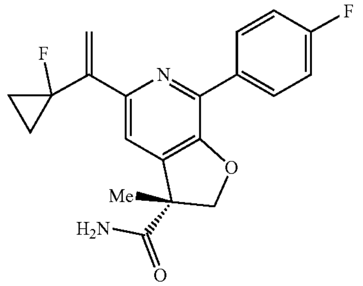 [SMILES: C=C(c1cc2c(c(-c3ccc(F)cc3)n1)OC[C@]2(C)C(N)=O)C1(F)CC1]

A vial was charged with methyltriphenylphosphonium bromide (3.00 g, 8.41 mmol), and THE (18.7 ml), then cooled to 0° C. in an ice bath. Potassium tert-butoxide (0.906 g, 8.07 mmol) was added slowly as a solution in THE (2 mL), and the now yellow suspension was stirred for 30 min at 0° C. The compound from step b (1.205 g, 3.36 mmol) was added as a solution in THE (15 ml). The reaction was allowed to stir at 0° C. for 2 hours before allowing to warm to room temperature and stir an additional 2 hours. The reaction was quenched upon addition of MeOH (5 mL) then Water (20 mL). The solution was diluted with diluted with EtOAc and the layers were separated. The aqueous layer washed with EtOAc and the combined organic layer was washed with brine, dried over $MgSO_4$, and concentrated. The crude reaction mixture purified by silica gel column chromatography eluting with 0-80% EtOAc/Hexanes to give the title compound (741 mg, 61.8%). ESI-MS m/z: 357.39 $[M+H]^+$.

Intermediate 48 Step d

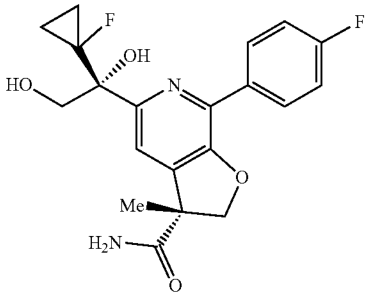 [SMILES: C[C@]1(C(N)=O)COc2c1cc([C@@](O)(CO)C1(F)CC1)nc2-c1ccc(F)cc1]

The above compound was prepared in an analogous fashion to Intermediate 36 Step e. The reaction mixture was purified by silica gel column chromatography eluting with 0-80% EtOAc/Hex to afford the title compound (480 mg, 59%). ESI-MS m/z: 391.33 $[M+H]^+$.

Intermediate 48 Step e

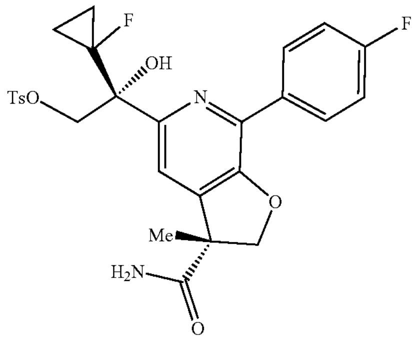 [SMILES: Cc1ccc(S(=O)(=O)OC[C@](O)(c2cc3c(c(-c4ccc(F)cc4)n2)OC[C@]3(C)C(N)=O)C2(F)CC2)cc1]

The above compound was prepared in an analogous fashion to Intermediate 36 Step f. After aqueous workup, the title compound (585 mg, 87%) was taken forward without further purification. ESI-MS m/z: 545.38 $[M+H]^+$.

Intermediate 48 Step f

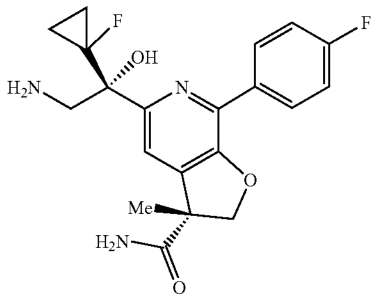 [SMILES: C[C@]1(C(N)=O)COc2c1cc([C@@](O)(CN)C1(F)CC1)nc2-c1ccc(F)cc1]

The above compound was prepared in an analogous fashion to Intermediate 36 Step g. After aqueous workup, the title compound (381 mg, 91%) was taken forward without further purification. ESI-MS m/z: 390.35 $[M+H]^+$.

Intermediate 49

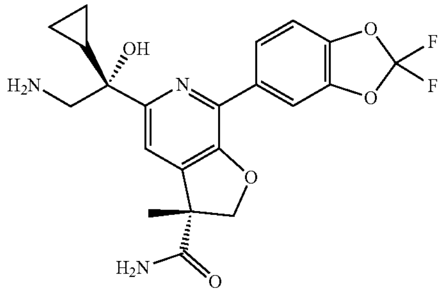 [SMILES: C[C@]1(C(N)=O)COc2c1cc([C@@](O)(CN)C1CC1)nc2-c1ccc2c(c1)OC(F)(F)O2]

The above compound was prepared in an analogous fashion to Intermediate 47 to afford the desired amino alcohol (473 mg, 64%). ESI-MS m/z: 434.40 $[M+H]^+$.

Intermediate 50

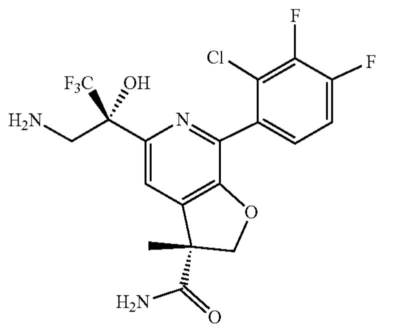 [SMILES: C[C@]1(C(N)=O)COc2c1cc([C@@](O)(CN)C(F)(F)F)nc2-c1ccc(F)c(F)c1Cl]

The above compound was prepared in an analogous fashion to Intermediate 36 to afford the desired amino alcohol (493 mg, 92%). ESI-MS m/z: 452.25 $[M+H]^+$.

Intermediate 51

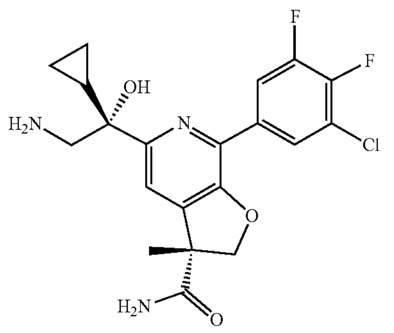 [SMILES: C[C@]1(C(N)=O)COc2c1cc([C@@](O)(CN)C1CC1)nc2-c1cc(F)c(F)c(Cl)c1]

The above compound was prepared in an analogous fashion to Intermediate 47 to afford the desired amino alcohol (246 mg, 83%). ESI-MS m/z: 424.31 $[M+H]^+$.

Intermediate 52

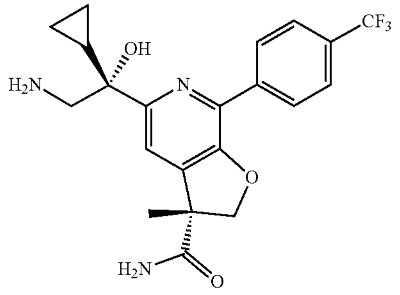 [SMILES: C[C@]1(C(N)=O)COc2c1cc([C@@](O)(CN)C1CC1)nc2-c1ccc(C(F)(F)F)cc1]

The above compound was prepared in an analogous fashion to Intermediate 47 to afford the desired amino alcohol (147 mg, 95%). ESI-MS m/z: 422.36 $[M+H]^+$.

Intermediate 53

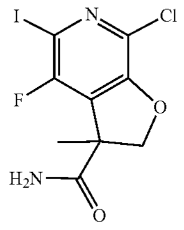 [SMILES: CC1(C(N)=O)COc2c(Cl)nc(I)c(F)c21]

Intermediate 53 Step a

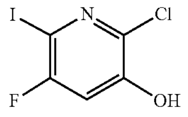

Into a 500 mL round-bottom flask were added 2-chloro-5-fluoropyridin-3-ol (10 g, 68 mmol), $K_2CO_3$ (19 g, 136 mmol), 12 (19 g, 75 mmol) and $H_2O$ (200 mL) at room temperature. The resulting mixture was stirred for overnight at room temperature under nitrogen atmosphere and monitored by LCMS. The reaction was quenched by the addition of sat. sodium hyposulfite (aq.) at room temperature and extracted with EtOAc. The residue was purified by silica gel column chromatography (eluted with 9% ethyl acetate in hexanes) to afford the desired compound (16.7 g, 90%) as a white solid. ESI-MS m/z: 273.90 $[M+H]^+$.

Intermediate 53 Step b

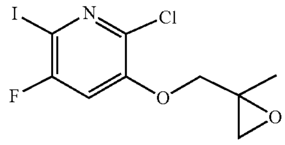

Into a 250 mL vial were added the compound from step a (12.4 g, 45 mmol), (2-methyloxiran-2-yl)methyl 4-methylbenzenesulfonate, $K_2CO_3$ (13 g, 91 mmol), KI (9 g, 54 mmol) and DMF (50 mL) at room temperature. The resulting mixture was stirred for overnight at 50° C. under nitrogen atmosphere. The reaction was monitored by LCMS. The reaction was quenched with water and the aqueous layer was extracted with EtOAc. The resulting mixture was concentrated under reduced pressure. The residue was purified by reverse flash to afford the desired compound (9.6 g, 63%) as white solid. ESI-MS m/z: 343.80 $[M+H]^+$.

Intermediate 53 Step c

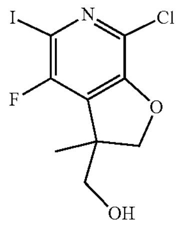

Into a 50 mL 3-necked round-bottom flask were added the compound from step b (1.5 g, 4 mmol), THE (15 mL) and LDA (2.4 mL, 5 mmol) at 0° C. The resulting mixture was stirred for 1h at room temperature under nitrogen atmosphere. The reaction was monitored by TLC. The reaction was quenched by the addition of sat. $NH_4Cl$ (aq.) at 0° C. The aqueous layer was extracted with EtOAc. The residue was purified by reverse flash afford the desired compound (430 mg, 29%) as white solid. ESI-MS m/z: 343.80 $[M+H]^+$.

Intermediate 53 Step d

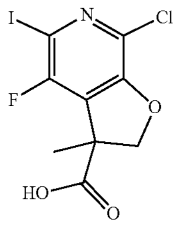 [SMILES: CC1(C(=O)O)COc2c(Cl)nc(I)c(F)c21]

Into a 100 mL round-bottom flask were added the compound from step c (400 mg, 1 mmol), acetone (10 mL) and Jones Reagent (1 mL) at 0° C. The resulting mixture was stirred for 3 hr at room temperature under nitrogen atmosphere. The reaction was monitored by LCMS. The aqueous layer was extracted with EtOAc and concentrated under reduced pressure. The crude product was used in the next step directly without further purification. ESI-MS m/z: 357.85 $[M+H]^+$.

Intermediate 53 Step e

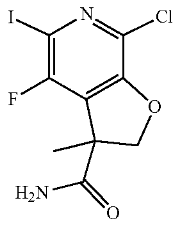 [SMILES: CC1(C(N)=O)COc2c(Cl)nc(I)c(F)c21]

Into a 50 mL round-bottom flask were added the crude compound from step d, CDI (726 mg, 4 mmol) and THE (5 mL) at room temperature. The resulting mixture was stirred for 2 hr at room temperature under nitrogen atmosphere. Then the resulting mixture was added to $NH_3 \cdot H_2O$ (50 mL) dropwise and stirred for 1 hr. The reaction was monitored by TLC. The aqueous layer was extracted with EtOAc and the residue was purified by reverse flash to afford the desired compound (218.8 mg, 69%) as white solid. ESI-MS m/z: 356.90 $[M+H]^+$.

Intermediate 54

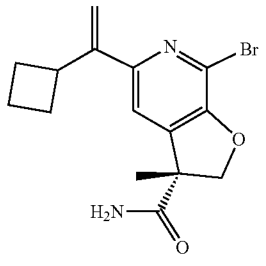 [SMILES: C=C(c1cc2c(c(Br)n1)OC[C@]2(C)C(N)=O)C1CCC1]

The following compound was prepared in an analogous sequence to Intermediate 48 steps a and b. ESI-MS m/z: 336.95 $[M+H]^+$.

Intermediate 55

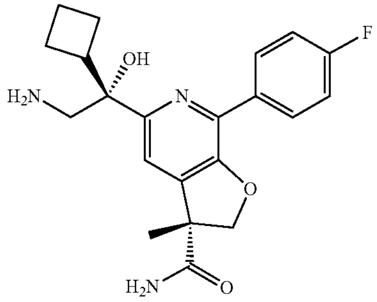 [SMILES: C[C@]1(C(N)=O)COc2c1cc([C@@](O)(CN)C1CCC1)nc2-c1ccc(F)cc1]

The above compound was prepared in an analogous fashion to Intermediate 36. After aqueous workup, the title compound (45 mg, 63%) was isolated as a white solid. ESI-MS m/z: 386.40 $[M+H]^+$.

Intermediate 56

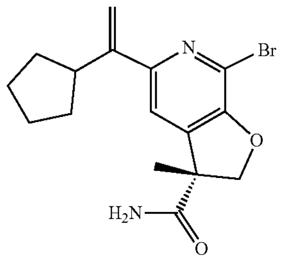 [SMILES: C=C(c1cc2c(c(Br)n1)OC[C@]2(C)C(N)=O)C1CCCC1]

The following compound was prepared in an analogous sequence to Intermediate 48 steps a and b steps a and b. ESI-MS m/z: 351.05 $[M+H]^+$.

Intermediate 57

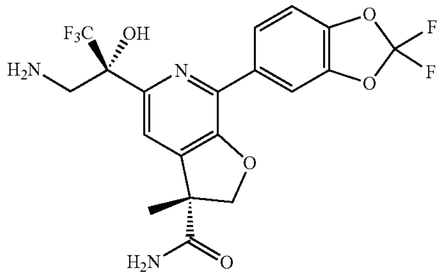 [SMILES: C[C@]1(C(N)=O)COc2c1cc([C@@](O)(CN)C(F)(F)F)nc2-c1ccc2c(c1)OC(F)(F)O2]

The above compound was prepared in an analogous fashion to Intermediate 36 with the corresponding aryl boronic acid. The crude material was purified by automated column chromatography (silica gel, 10% MeOH in DCM) to afford the desired product (1.80 g, 57%) as an off-white solid. ESI-MS m/z: 462.05 $[M+H]^+$.

Intermediate 58

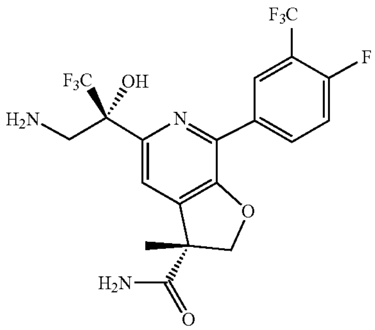 [SMILES: C[C@]1(C(N)=O)COc2c1cc([C@@](O)(CN)C(F)(F)F)nc2-c1ccc(F)c(C(F)(F)F)c1]

The above compound was prepared in an analogous fashion to Intermediate 36 with the corresponding aryl boronic acid. The crude material was purified by prep-TLC (silica gel, 10% MeOH in DCM with $NH_3$) to afford the desired product (508 mg, 74%) as a white solid. ESI-MS m/z: 468.05 $[M+H]^+$.

Intermediate 59

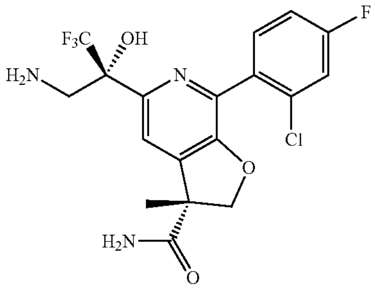 [SMILES: C[C@]1(C(N)=O)COc2c1cc([C@@](O)(CN)C(F)(F)F)nc2-c1ccc(F)cc1Cl]

The above compound was prepared in an analogous fashion to Intermediate 36 with the corresponding aryl boronic acid. The crude material was purified by prep-TLC (silica gel, 6% MeOH in DCM with $NH_3$) to afford the desired product (450 mg, 72%) as a white solid. ESI-MS m/z: 434.10 $[M+H]^+$.

Intermediate 60

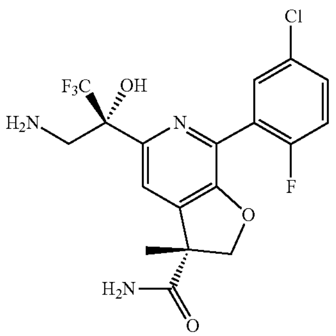 [SMILES: C[C@]1(C(N)=O)COc2c1cc([C@@](O)(CN)C(F)(F)F)nc2-c1cc(Cl)ccc1F]

The above compound was prepared in an analogous fashion to Intermediate 36 with the corresponding aryl boronic acid. The crude material was purified by prep-TLC (silica gel, 6% MeOH in DCM with $NH_3$) to afford the desired product (468.9 mg, 92%) as a white solid. ESI-MS m/z: 433.95 $[M+H]^+$.

Intermediate 61

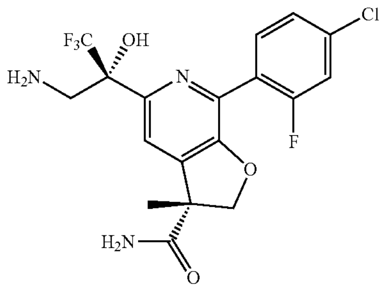 [SMILES: C[C@]1(C(N)=O)COc2c1cc([C@@](O)(CN)C(F)(F)F)nc2-c1ccc(Cl)cc1F]

The above compound was prepared in an analogous fashion to Intermediate 36 with the corresponding aryl boronic acid. The crude material was purified by prep-TLC (silica gel, 6% MeOH in DCM with $NH_3$) to afford the desired product as a white solid. ESI-MS m/z: 434.10 $[M+H]^+$.

Intermediate 62

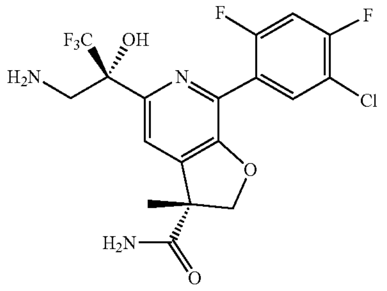 [SMILES: C[C@]1(C(N)=O)COc2c1cc([C@@](O)(CN)C(F)(F)F)nc2-c1cc(Cl)c(F)cc1F]

The above compound was prepared in an analogous fashion to Intermediate 36 with the corresponding aryl boronic acid. The crude material was purified by prep-TLC (silica gel, 6% MeOH in DCM with $NH_3$) to afford the desired product as a white solid. ESI-MS m/z: 452.00 $[M+H]^+$.

Intermediate 63

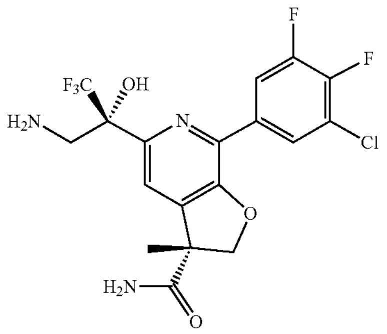 [SMILES: C[C@]1(C(N)=O)COc2c1cc([C@@](O)(CN)C(F)(F)F)nc2-c1cc(F)c(F)c(Cl)c1]

The above compound was prepared in an analogous fashion to Intermediate 36 with the corresponding aryl boronic acid pinacol ester. The aryl boronic acid pinacol ester was prepared from the corresponding bromide by Pd-catalyzed borylation. The crude material was purified by prep-TLC (silica gel, 6% MeOH in DCM with $NH_3$) to afford the desired product (355 mg, 67%) as a white solid. ESI-MS m/z: 452.10 $[M+H]^+$.

Intermediate 64

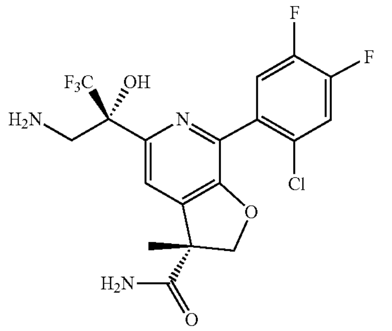 [SMILES: C[C@]1(C(N)=O)COc2c1cc([C@@](O)(CN)C(F)(F)F)nc2-c1cc(F)c(F)cc1Cl]

The above compound was prepared in an analogous fashion to Intermediate 36 with the corresponding aryl boronic acid. The crude material was purified by prep-TLC (silica gel, 6% MeOH in DCM with $NH_3$) to afford the desired product (570.3 mg, 87%) as a white solid. ESI-MS m/z: 452.10 $[M+H]^+$.

Intermediate 65

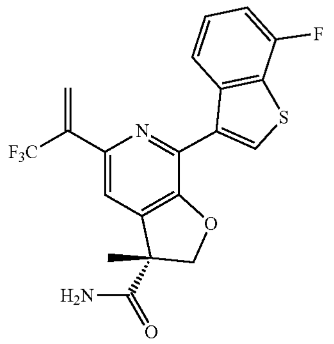 [SMILES: C=C(c1cc2c(c(-c3csc4c(F)cccc34)n1)OC[C@]2(C)C(N)=O)C(F)(F)F]

Into a 40 mL sealed tube were added 3-bromo-7-fluoro-1-benzothiophene (1.29 g, 5.60 mmol), bis(pinacolato)diboron (1.42 g, 5.59 mmol), KOAc (1.65 g, 16.81 mmol), $Pd(dppf)Cl_2 \cdot CH_2Cl_2$ (365 mg, 0.45 mmol) and dioxane (18 mL) at room temperature. The resulting mixture was stirred for 1 hr at 110° C. under nitrogen atmosphere. The reaction was monitored by LCMS. The mixture was allowed to cool down to room temperature. (R)-7-bromo-3-methyl-5-(3,3,3-trifluoroprop-1-en-2-yl)-2,3-dihydrofuro[2,3-c]pyridine-3-carboxamide (787 mg, 2.24 mmol), $K_2CO_3$ (0.93 g, 6.72 mmol), $Pd(dppf)Cl_2 \cdot CH_2Cl_2$ (365 mg, 0.45 mmol) and $H_2O$ (2 mL) was added and stirred for another 2 hr at 80° C. The resulting mixture was filtered, the filter cake was washed with EA. The filtrate was concentrated under reduced pressure. The residue was purified by reverse flash chromatography to afford the desired product (460 mg, 48%) as a brown oil. ESI-MS m/z: 422.95 $[M+H]^+$.

Intermediate 66

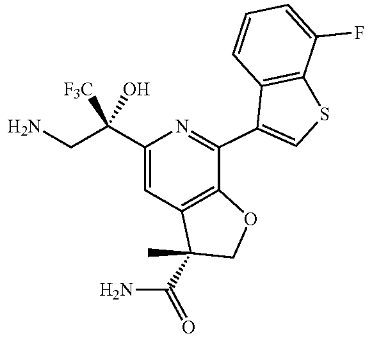 [SMILES: C[C@]1(C(N)=O)COc2c1cc([C@@](O)(CN)C(F)(F)F)nc2-c1csc2c(F)cccc12]

The above compound was prepared in an analogous fashion to Intermediate 36 with Intermediate 65. The crude material was purified by prep-TLC (silica gel, 8% MeOH in DCM with $NH_3$) to afford the desired product (251.3 mg, 73%) as a white solid. ESI-MS m/z: 456.00 $[M+H]^+$.

Intermediate 67

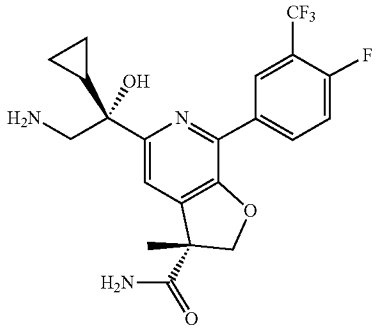 [SMILES: C[C@]1(C(N)=O)COc2c1cc([C@@](O)(CN)C1CC1)nc2-c1ccc(F)c(C(F)(F)F)c1]

The above compound was prepared in an analogous fashion to Intermediate 47 with the corresponding aryl boronic acid. The crude material was purified by prep-TLC (silica gel, 10% MeOH in DCM with $NH_3$) to afford the desired product (291.1 mg, 61%) as a white solid. ESI-MS m/z: 440.00 $[M+H]^+$.

Intermediate 68

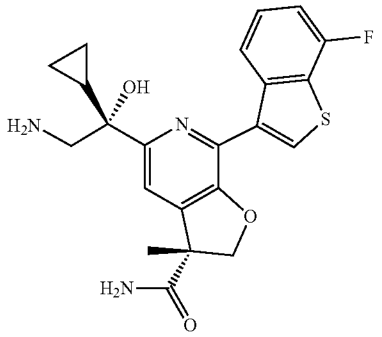 [SMILES: C[C@]1(C(N)=O)COc2c1cc([C@@](O)(CN)C1CC1)nc2-c1csc2c(F)cccc12]

The above compound was prepared in an analogous fashion to Intermediate 47 and Intermediate 65 with the corresponding aryl boronic acid. The crude material was purified by prep-TLC (silica gel, 6% MeOH in DCM with $NH_3$) to afford the desired product (114.2 mg, 49%) as a white solid. ESI-MS m/z: 428.05 $[M+H]^+$.

Intermediate 69

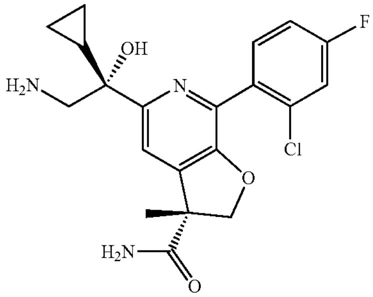 [SMILES: C[C@]1(C(N)=O)COc2c1cc([C@@](O)(CN)C1CC1)nc2-c1ccc(F)cc1Cl]

The above compound was prepared in an analogous fashion to Intermediate 47 with the corresponding aryl boronic acid. The crude material was purified by prep-TLC (silica gel, MeOH in DCM with $NH_3$) to afford the desired product (220 mg, 64%) as a white solid. ESI-MS m/z: 406.10 $[M+H]^+$.

Intermediate 70

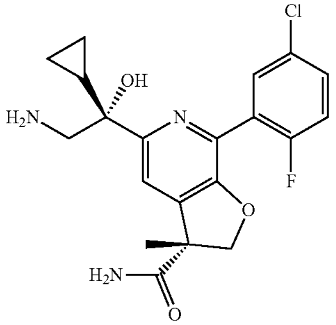 [SMILES: C[C@]1(C(N)=O)COc2c1cc([C@@](O)(CN)C1CC1)nc2-c1cc(Cl)ccc1F]

The above compound was prepared in an analogous fashion to Intermediate 47 with the corresponding aryl boronic acid. The crude material was purified by prep-TLC (silica gel, MeOH in DCM with $NH_3$) to afford the desired product (267.8 mg, 64%) as a white solid. ESI-MS m/z: 406.10 $[M+H]^+$.

Intermediate 71

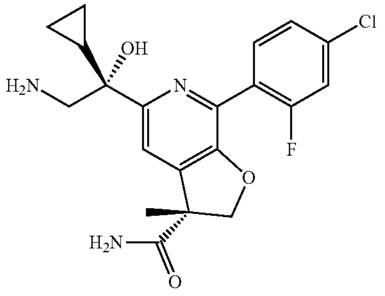 [SMILES: C[C@]1(C(N)=O)COc2c1cc([C@@](O)(CN)C1CC1)nc2-c1ccc(Cl)cc1F]

The above compound was prepared in an analogous fashion to Intermediate 47 with the corresponding aryl boronic acid. The crude material was purified by prep-TLC (silica gel, MeOH in DCM with $NH_3$) to afford the desired product (262.1 mg, 53%) as a white solid. ESI-MS m/z: 406.15 $[M+H]^+$.

Intermediate 72

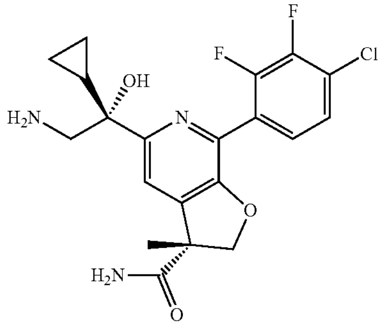 [SMILES: C[C@]1(C(N)=O)COc2c1cc([C@@](O)(CN)C1CC1)nc2-c1ccc(Cl)c(F)c1F]

The above compound was prepared in an analogous fashion to Intermediate 47 with the corresponding aryl boronic acid. The crude material was purified by prep-TLC (silica gel, 6% MeOH in DCM with $NH_3$) to afford the desired product (250 mg, 68%) as a white solid. ESI-MS m/z: 424.00 $[M+H]^+$.

Intermediate 73 Steps a and b

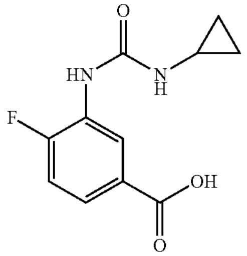 [SMILES: O=C(Nc1cc(C(=O)O)ccc1F)NC1CC1]

To a vial were added methyl 3-amino-4-fluorobenzoate (50 mg, 0.296 mmol), isocyanatocyclopropane (24.56 mg, 0.296 mmol) and EtOH (2 mL). The resulting mixture was stirred at rt for 20 hr. After removed the solvent, the residue was purified by automated column chromatography (silica gel 4 g column, eluting with 0-50% EtOAc/hexanes) to obtain the desired product (30 mg, 40.2%) as a pale-yellow foam. ESI-MS m/z: 253.10 $[M+H]^+$. To a vial with solvents of $THF/H_2O$ (2 mL, 9:1) were added step a (90 mg, 0.357 mmol) and 2N NaOH (1 mL). After stirred at rt overnight, the mixture was neutralized to pH~3 by adding 1N HCl. The solid was precipitated out. After filtered and dried in oven, the desired product (85 mg, 100%) was obtained. ESI-MS m/z: 239.20 $[M+H]^+$.

Intermediate 74

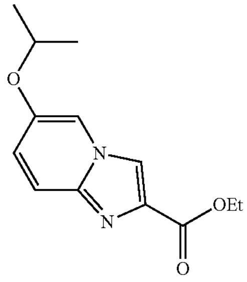 [SMILES: CCOC(=O)c1cn2cc(OC(C)C)ccc2n1]

A 2 mL MW vial was charged with ethyl 6-hydroxyimidazo[1,2-a]pyridine-2-carboxylate (60 mg, 0.291 mmol) and 2-bromopropane (165 μl, 1.164 mmol) and DMF (0.582 ml). Cesium carbonate (284 mg, 0.873 mmol) was added subsequently. The reaction vial was capped and heated at 140° C. for 2 h in a microwave reactor. The reaction mixture was diluted with ethyl acetate and water. The organic layer was washed with brine and dried and concentrated and used in the next step without further purification. ESI-MS m/z: 249.12 $[M+H]^+$.

Intermediate 75

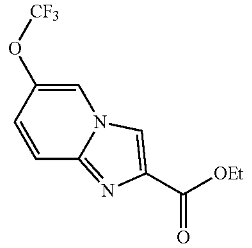 [SMILES: CCOC(=O)c1cn2cc(OC(F)(F)F)ccc2n1]

Ethyl 3-bromo-2-oxopropanoate (68.5 μl, 0.546 mmol) and 5-(trifluoromethoxy)pyridin-2-amine (81 mg, 0.455 mmol) were dissolved in DME (1.137 ml) and MeOH (1.137 ml). The reaction mixture was heated at 80° C. for 18h. The solvent was removed, and the residue was purified by flash chromatography to give the desired product (78 mg, 62.6%). ESI-MS m/z: 275.057 $[M+H]^+$.

Intermediate 76

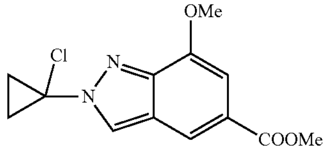 [SMILES: COC(=O)c1cc(OC)c2nn(C3(Cl)CC3)cc2c1]

Methyl 2-(1-hydroxycyclopropyl)-7-methoxy-2H-indazole-5-carboxylate (55 mg, 0.210 mmol) was dissolved in dichloromethane (1.049 ml) at 0° C. Thionyl chloride (61.2 μl, 0.839 mmol) was added and the mixture was allowed to stir at 50° C. for 18 h. The reaction mixture was purified by flash chromatography directly to give the desired product (34 mg, 57.8%). ESI-MS m/z: 281.061 $[M+H]^+$.

Intermediate 77

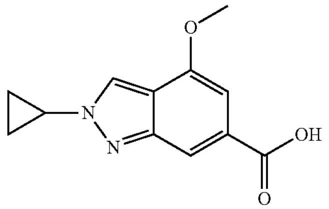 [SMILES: COc1cc(C(=O)O)cc2nn(C3CC3)cc12]

Intermediate 77 Step a

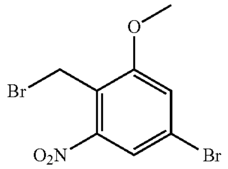

Into a 100 mL round-bottom flask were added 5-bromo-1-methoxy-2-methyl-3-nitrobenzene (1 g, 4 mmol), NBS (0.8 g, 4.5 mmol), AIBN (0.13 g, 0.8 mmol) and $CCl_4$ (20 mL) at room temperature. The resulting mixture was stirred for overnight at 80° C. under nitrogen atmosphere and monitored by LCMS. The reaction was quenched by the addition of water and the resulting mixture was extracted with EtOAc. The combined organics were dried over sodium sulfate, filtered and concentrated. The crude product was used in the next step directly without further purification. ESI-MS m/z: 325.90 $[M+H]^+$.

Intermediate 77 Step b

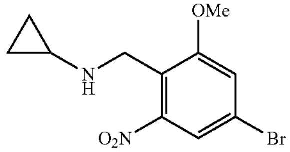

Into a 100 mL round-bottom flask were the compound from step a (1.33 g, 4 mmol,), aminocyclopropane (2.34 g, 41 mmol), $K_2CO_3$ (1.13 g, 8 mmol) and DMF (10 mL) at room temperature. The resulting mixture was stirred for 3h at room temperature under nitrogen atmosphere. The reaction was monitored by LCMS. The aqueous layer was extracted with EtOAc. The residue was purified by silica gel column chromatography (eluted with 16% ethyl acetate in hexanes) to afford the desired compound (1.07 g, 87%) as a white solid. ESI-MS m/z: 301.00 $[M+H]^+$.

Intermediate 77 Step c

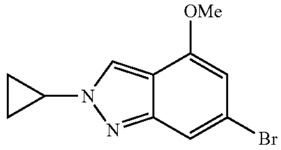 [SMILES: COc1cc(Br)cc2nn(C3CC3)cc12]

Into a 100 mL 3-necked round-bottom flask were added the compound from step b (500 mg, 1.7 mmol) and THE (6 mL) at 0° C. NaOH (664 mg, 17 mmol) in $H_2O$ (6 mL) was added over 2 min and then Zinc (326 mg, 5 mmol) was added in 6 portions during 3 hr and stirred for another 1 hr. The reaction was monitored by LCMS. The mixture was acidified to pH 3 with HCl (aq.). The aqueous layer was extracted with $CH_2Cl_2$, dried over anhydrous $Na_2SO_4$. After filtration, the filtrate was concentrated under reduced pressure and washed with hexane and resulted in the desired compound (310 mg, 70%) as white solid. ESI-MS m/z: 267.00 $[M+H]^+$.

Intermediate 77 Step d

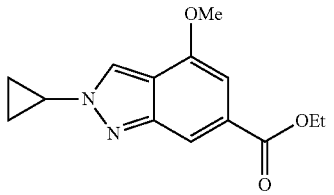 [SMILES: CCOC(=O)c1cc(OC)c2cn(C3CC3)nc2c1]

Into a 30 mL pressure tank reactor were added the compound from step c (240 mg, 0.9 mmol), dppp (222 mg, 0.5 mmol), $Pd(OAc)_2$ (60 mg, 0.3 mmol), DMF (4 mL), EtOH (4 mL) and TEA (1 mL) at room temperature. The resulting mixture was stirred for overnight at 100° C. under CO atmosphere at 15 atm. The reaction was monitored by LCMS. The resulting mixture was filtered, the filter cake was washed with EA. The filtrate was concentrated under reduced pressure. The residue was purified by reverse phase silica gel chromatography ($MeCN/H_2O$) to afford the desired compound (210 mg, 90%) as white solid. ESI-MS m/z: 261.10 $[M+H]^+$.

Intermediate 77 Step e

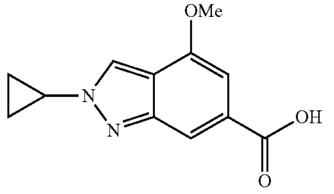 [SMILES: COc1cc(C(=O)O)cc2nn(C3CC3)cc12]

Into a 50 mL round-bottom flask were added the compound from step d (470 mg, 1.8 mmol), lithium hydroxide (216 mg, 9 mmol), methanol (10 mL) and $H_2O$ (3 mL) at room temperature. The resulting mixture was stirred for 1 hr at room temperature under nitrogen atmosphere. The reaction was monitored by LCMS. The mixture was acidified to pH 6 with HCl (aq.). The resulting mixture was washed with water and evaporated to give the desired compound (317.8 mg, 76%) as yellow solid. ESI-MS m/z: 233.10 $[M+H]^+$.

Intermediate 78

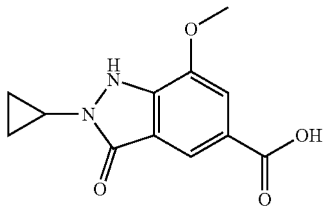 [SMILES: COc1cc(C(=O)O)cc2c(=O)n(C3CC3)[nH]c12]

Intermediate 78 Step a

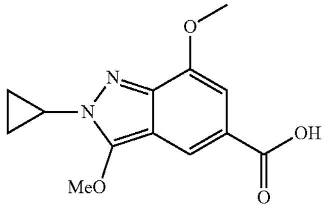 [SMILES: COc1cc(C(=O)O)cc2c(OC)n(C3CC3)nc12]

Into a 50 mL round-bottom flask were added methyl 3-[(cyclopropylamino)methyl]-5-methoxy-4-nitrobenzoate (3 g, 11 mmol), KOH (6 g, 107 mmol), MeOH (20 mL) and $H_2O$ (2 mL) at room temperature. The resulting mixture was stirred for 72 hr at 80° C. under nitrogen atmosphere. The reaction was monitored by TLC. The mixture was acidified to pH 6 with HCl (aq.). The residue was purified by reverse phase silica gel chromatography ($MeCN/H_2O$) to afford the desired compound (580 mg, 21%) as white solid. ESI-MS m/z: 263.10 $[M+H]^+$.

Intermediate 78 Step b

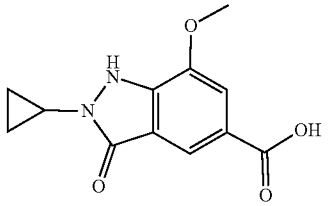 [SMILES: COc1cc(C(=O)O)cc2c(=O)n(C3CC3)[nH]c12]

Into a 40 mL vial were added the compound from step a (1.28 g, 5 mmol) and AcOH (6 mL) at room temperature. The resulting mixture was stirred for 3 days at 120° C. under nitrogen atmosphere. The reaction was monitored by LCMS. The resulting mixture was concentrated under reduced pressure. The residue was purified by reverse phase silica gel chromatography ($MeCN/H_2O$) to afford the desired compound (0.96 g, 79%) as brown solid. ESI-MS m/z: 249.05 $[M+H]^+$.

Intermediate 79

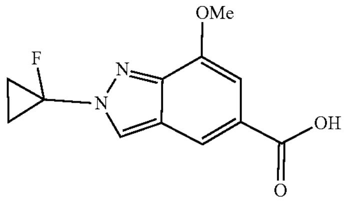 [SMILES: COc1cc(C(=O)O)cc2cn(C3(F)CC3)nc12]

Intermediate 79 Step a

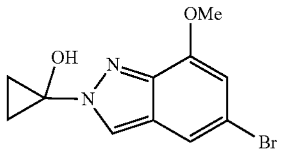 [SMILES: COc1cc(Br)cc2cn(C3(O)CC3)nc12]

A solution of 5-bromo-7-methoxy-1H-indazole (3.00 g, 13.21 mmol) in MeCN (50 mL) was treated with 1-(benzenesulfonyl) cyclopropan-1-ol (3.14 g, 15.85 mmol) and TEA (1.60 g, 15.85 mmol) for overnight at room temperature. The reaction was monitored by LCMS. The resulting mixture was extracted with EtOAc and concentrated. The residue was purified by silica gel column chromatography (eluted with 50% ethyl acetate in hexanes) to afford the desired compound (2.40 g, 64%) as a yellow solid. ESI-MS m/z: 283.00 [M+H]+.

Intermediate 79 Step b

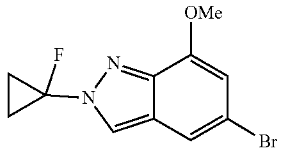 [SMILES: COc1cc(Br)cc2cn(C3(F)CC3)nc12]

A solution of the compound from step a (2.43 g, 8.58 mmol) in DCM (20 mL) was treated with BAST (5.69 g, 25.74 mmol) for 1.5 hours at 0° C. to r.t. The reaction was monitored by LCMS and quenched with water. The aqueous layer was extracted with EtOAc and concentrated. The residue was purified by silica gel column chromatography (eluted with 50% ethyl acetate in hexanes) to afford the desired compound (1.2 g, 49%) as a yellow solid. ESI-MS m/z: 285.00 [M+H]+.

Intermediate 79 Steps c and d

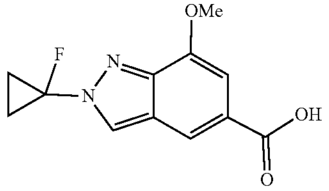 [SMILES: COc1cc(C(=O)O)cc2cn(C3(F)CC3)nc12]

The following compound was prepared according to the same procedures as Intermediate 77 steps d and e to afford the desired product (312.6 mg, 58%) as a white solid. ESI-MS m/z: 250.95 [M+H]+.

Intermediate 80

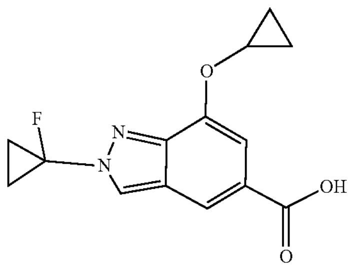 [SMILES: O=C(O)c1cc(OC2CC2)c2nn(C3(F)CC3)cc2c1]

The following compound was prepared according to the same procedures as Intermediate 79 to afford the desired product (170.3 mg, 76%) as a white solid. ESI-MS m/z: 276.95 [M+H]+.

Intermediate 81

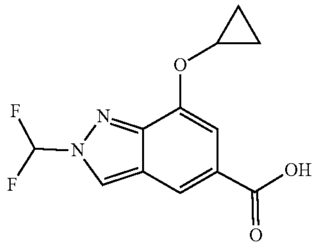 [SMILES: O=C(O)c1cc(OC2CC2)c2nn(C(F)F)cc2c1]

Intermediate 81 Steps a and b

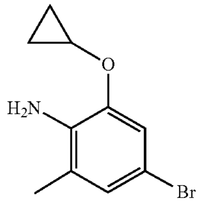

A mixture of 5-bromo-1-fluoro-3-methyl-2-nitrobenzene (5 g, 21.37 mmol), cyclopropanol (2.5 g, 42.73 mmol) and $Cs_2CO_3$ (21 g, 64 mmol) in DMF (20 mL) was stirred for 2 hr at 50° C. under $N_2$ atmosphere. The resulting mixture was extracted with EtOAc (3×200 mL). The combined organic layers were washed with water, concentrated under reduced pressure to afford the crude product without further purification.

A solution/mixture of the compound from step a (5 g, 18.38 mmol), Fe (10.3 g, 183.76 mmol) and $NH_4Cl$ (9.8 g, 183.76 mmol) in EtOH (40 mL) and $H_2O$ (20 mL) was stirred for 2 hr at 80° C. The residue was purified by silica gel column chromatography (ethyl acetate in hexanes) to afford the desired product (3.6 g, 81%) as a yellow solid. ESI-MS m/z: 242.00 [M+H]+.

Intermediate 81 Steps c and d

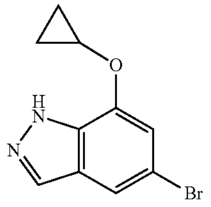 [SMILES: Brc1cc(OC2CC2)c2[nH]ncc2c1]

To the compound from step b (1.5 g, 6.2 mmol) was added to a 50% aqueous solution of fluoroboric acid (9.8 mL) at room temperature and stirred for 5 min. The mixture was cooled in an ice bath for 10 min and an aqueous solution of $NaNO_2$ (900 mg, 13.04 mmol) in 1.7 mL $H_2O$ was added to the mixture. The reaction mixture was stirred at 10° C. for 30 min, during which the product precipitated. The cooled reaction mixture was filtered through a Buchner funnel and the solid product washed with small amounts of $H_2O$, MeOH and $Et_2O$, and dried under high vacuum to obtain the crude product as a brown solid. ESI-MS m/z: 253.00 [M+H]+.

In a dry flask, 18-crown-6 (0.05 g, 0.2 mmol) and potassium acetate (2.9 g, 29.4 mmol) were dried under high vacuum for 1 hr. $CHCl_3$ (70 mL) was added and stirred at room temperature for 10 min. Then step c was added to the mixture in small portions under $N_2$ atmosphere. The reaction mixture was stirred at room temperature for 3 h, filtered and the residue washed with $CHCl_3$. The filtrate was washed with water (3×40 mL) and the organic layer was dried over $Na_2SO_4$, filtered and concentrated in vacuo to give the crude product. The crude product was purified by flash column chromatography (hexane/EtOAc) to afford the desired product (1.8 g, 82%) as a yellow solid. ESI-MS m/z: 253.00 $[M+H]^+$.

Intermediate 81 Steps e, f, g

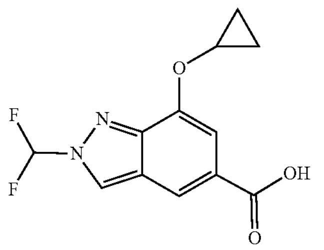 [SMILES: O=C(O)c1cc(OC2CC2)c2nn(C(F)F)cc2c1]

The following intermediate was prepared in an analogous fashion to Intermediate 6 steps a-c to afford the desired product (330 mg, 87%) as a yellow solid. ESI-MS m/z: 269.10 $[M+H]^+$.

Intermediate 82

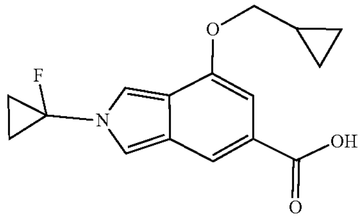 [SMILES: O=C(O)c1cc(OCC2CC2)c2cn(C3(F)CC3)cc2c1]

Intermediate 82 Steps a-d

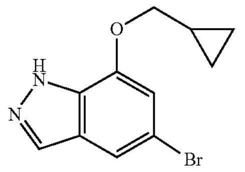 [SMILES: Brc1cc(OCC2CC2)c2[nH]ncc2c1]

The following intermediate was prepared in an analogous fashion to Intermediate 81 steps a-d using cyclopropanemethanol to afford the desired product (1.85 g, 66%) as a light-yellow solid. ESI-MS m/z: 266.90 $[M+H]^+$.

Intermediate 82 Step e-h

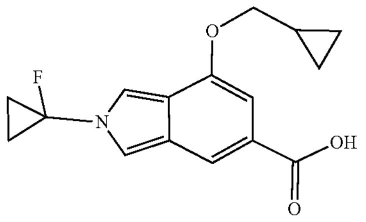 [SMILES: O=C(O)c1cc(OCC2CC2)c2cn(C3(F)CC3)cc2c1]

The following intermediate was prepared in an analogous fashion to Intermediate 79 steps a-d to afford the desired product (298 mg, 60%) as a white solid. ESI-MS m/z: 291.10 $[M+H]^+$.

Intermediate 83

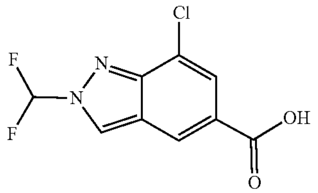 [SMILES: O=C(O)c1cc(Cl)c2nn(C(F)F)cc2c1]

The following intermediate was prepared in an analogous fashion to Intermediate 6 to afford the desired product (260 mg, 69%) as a white solid. ESI-MS m/z: 247.00 $[M+H]^+$.

Intermediate 84

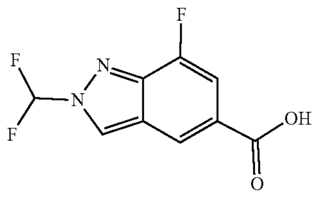 [SMILES: O=C(O)c1cc(F)c2nn(C(F)F)cc2c1]

The following intermediate was prepared in an analogous fashion to Intermediate 6 to afford the desired product. ESI-MS m/z: 231.00 $[M+H]^+$.

Intermediate 85

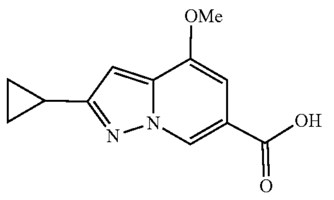 [SMILES: COc1cc(C(=O)O)cn2nc(C3CC3)cc12]

Intermediate 85 Step a

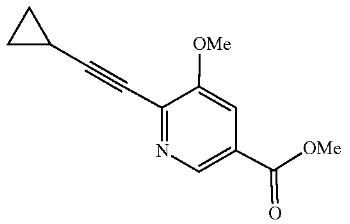 [SMILES: COC(=O)c1cnc(C#CC2CC2)c(OC)c1]

A solution/mixture of methyl 6-chloro-5-methoxypyridine-3-carboxylate (1 g, 4.96 mmol), ethynylcyclopropane (0.66 g, 9.92 mmol), $Pd(PPh_3)_4$ (1.15 g, 0.99 mmol), CuI (0.47 g, 2.48 mmol,) and $Et_3N$ (1.51 g, 14.88 mmol) in 1,4-dioxane (30 mL) was stirred for overnight at 90° C. under $N_2$ atmosphere. The residue was purified by silica gel column chromatography (eluted with 50% ethyl acetate in hexanes) to afford the desired product (1 g, 87%) as a yellow solid. ESI-MS m/z: 232.00 $[M+H]^+$.

Intermediate 85 Steps b-d

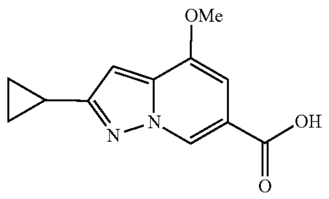 [SMILES: COc1cc(C(=O)O)cn2nc(C3CC3)cc12]

To a solution of the compound from step a (1 g, 4.32 mmol) in $CH_2Cl_2$ (100 mL) was added a solution of amino 2,4,6-trimethylbenzenesulfonate (1.21 g, 5.62 mmol) in $CH_2Cl_2$ (50 mL) under ice cooling, and the reaction mixture was stirred for another one hour. $Et_2O$ (12 mL) was added to the reaction mixture to precipitate crystals. The filtrate was filtered off and then dried under reduced pressure to afford a crude product as a pale-yellow solid. ESI-MS m/z: 247.00 $[M+H]^+$. A solution/mixture of the compound from step b (500 mg, 2.02 mmol) and $K_2CO_3$ (559 mg, 4.04 mmol) in MeOH (50 mL) was stirred for 2 hr at room temperature under $N_2$ atmosphere. The residue was purified by silica gel column chromatography (eluted with ethyl acetate in hexanes) to afford the desired product (220 mg, 44%) as a yellow solid. ESI-MS m/z: 247.00 $[M+H]^+$. A solution of the compound from step c (220 mg, 0.89 mmol) and LiOH (214 mg, 8.93 mmol) in MeOH (10 mL) and $H_2O$ (10 mL) was stirred for 2 hr at room temperature. The mixture was acidified to pH 5-6 with HCl. The resulting mixture was filtered, the filter cake was collected to afford the desired product (160 mg, 77%) as a white solid. ESI-MS m/z: 233.00 $[M+H]^+$.

Intermediate 86

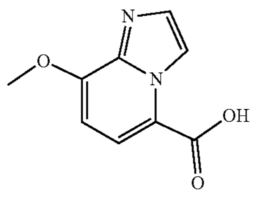

Intermediate 86 Step a

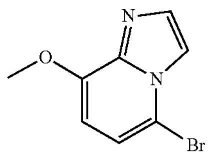

A mixture of 3-methoxy-6-bromopyridin 2-ylamine (1.0 g, 3.6 mmol) and chloroacetaldehyde (1.2 mL, 50% wt in water) in EtOH (12 mL) was stirred at reflux for 1 hour, then concentrated under reduced pressure. The residue was partitioned between an saturated solution of sodium bicarbonate and EtOAc. The organic layer was separated and washed with brine, dried over $Na_2SO_4$, filtered and concentrated. The residue was purified by flash chromatography (Si-PPC, $MeOH/Et_2O$, gradient 0:100 to 1:99) to give the desired product as a beige solid (960 mg, 88%). ESI-MS m/z: 227.00 $[M+H]^+$.

Intermediate 86 Steps b and c

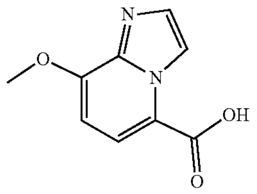

The following example was prepared in an analogous fashion to Intermediate 77 to afford the desired product (340 mg, 49%) as a yellow solid. ESI-MS m/z: 192.95 $[M+H]^+$.

Intermediate 87

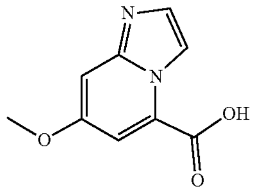

Intermediate 87 Steps a and b

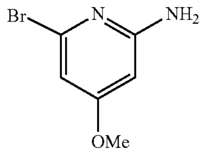

To a solution of 2,6-dibromo-4-methoxypyridine (5 g, 18.73 mmol), tert-butyl carbamate (2.19 g, 18.73 mmol) and $Cs_2CO_3$ (12.21 g, 37.46 mmol) in 1,4-dioxane (60 mL) was added $Pd(OAc)_2$ (0.42 g, 1.87 mmol) and Xantphos (1.08 g, 1.87 mmol). The reaction was heated to 100° C. for 16 hr under $N_2$ atmosphere. After cooling the reaction to room temperature, water was added and extracted with EA (50 mL×3). The combined organic layers were washed with water, dried over anhydrous $Na_2SO_4$. After filtration, the filtrate was concentrated under reduced pressure. The residue was purified by silica gel column chromatography, eluted with PE/EA to afford the desired product (2 g, 35%) as a yellow solid. ESI-MS m/z: 303.00 $[M+H]^+$.

A solution of the compound from step a (1.5 g) and TFA (8 mL) in DCM (20 mL) was stirred for 2 hr at room temperature. The residue product was purified by reverse phase flash with the following conditions (water (0.05% FA)/MeOH) to afford the desired product (520 mg) as a white solid. ESI-MS m/z: 203.00 $[M+H]^+$.

Intermediate 87 Steps c-e

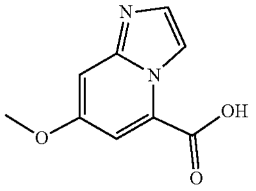

The following example was prepared in an analogous fashion to Intermediate 86 to afford the desired product (300 mg, 86%) as a yellow solid. ESI-MS m/z: 192.95 $[M+H]^+$.

Intermediate 88

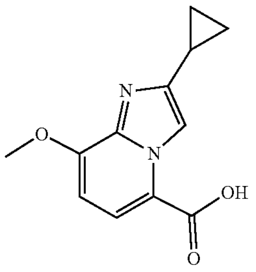 [SMILES: COc1ccc(C(=O)O)n2cc(C3CC3)nc12]

Intermediate 88 Step a

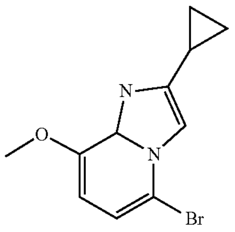

A solution of 6-bromo-3-methoxypyridin-2-amine (1 g, 4.93 mmol) and 2-bromo-1-cyclopropylethanone (963 mg, 5.91 mmol) in EtOH (10 mL) was stirred for overnight at 80° C. The reaction was quenched with water and the resulting mixture was extracted with EA (3×200 mL). The combined organic layers were washed with $NaHCO_3$ (3×200 mL), dried over anhydrous $NaSO_4$. After filtration, the filtrate was concentrated under reduced pressure. The residue was purified by silica gel column chromatography, eluted with PE/EA to afford the desired product (360 mg, 27%) as a yellow solid. ESI-MS m/z: 267.00 $[M+H]^+$.

Intermediate 88 Steps b and c

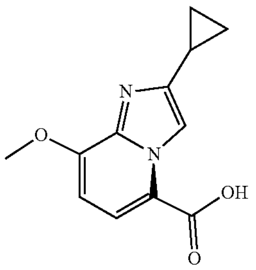

The following example was prepared in an analogous fashion to Intermediate 86 to afford the desired product (110 mg, 62%) as a yellow solid. ESI-MS m/z: 233.00 $[M+H]^+$.

Intermediate 89

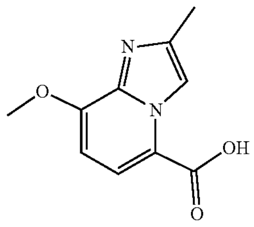

The following example was prepared in an analogous fashion to Intermediate 86 to afford the desired product. ESI-MS m/z: 206.95 $[M+H]^+$.

Intermediate 90

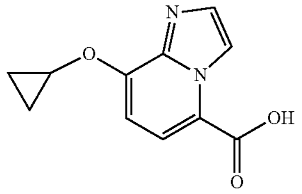 [SMILES: O=C(O)c1ccc(OC2CC2)c2nccn12]

Intermediate 90 Step a

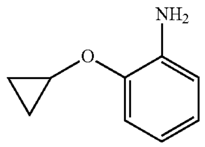 [SMILES: Nc1ccccc1OC1CC1]

A solution/mixture of 3-cyclopropoxy-2-nitropyridine (1.8 g, 1 mmol), Fe (5.58 g, 100 mmol) and $NH_4C_1$ (5.34 g, 100 mmol) in EtOH (60 mL) and $H_2O$ (30 mL) was stirred for 2 hr at 80° C. The residue was purified by silica gel column chromatography, eluted with PE/EA to afford the desired product (1.4 g, 93%) as a yellow solid. ESI-MS m/z: 151.00 $[M+H]^+$.

Intermediate 90 Step b

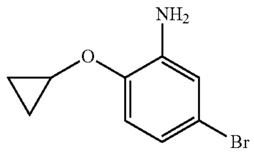 [SMILES: Nc1cc(Br)ccc1OC1CC1]

A solution/mixture of the compound from step a (1.4 g, 9.32 mmol) and $Br_2$ (2.98 g, 18.64 mmol) in AcOH (30 mL) was stirred for overnight at room temperature. The resulting mixture was quenched with sat. sodium thiosulfate and extracted with EA. The combined organic layers were washed with $NaHCO_3$ solution (3×200 mL), dried over anhydrous $Na_2SO_4$. After filtration, the filtrate was concentrated under reduced pressure to afford the desired product (1.4 g, 66%) as a yellow solid. ESI-MS m/z: 229.00 $[M+H]^+$.

Intermediate 90 Steps c-e

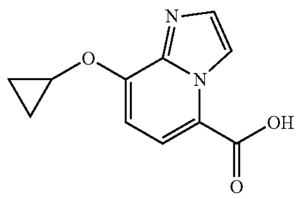 [SMILES: O=C(O)c1ccc(OC2CC2)c2nccn12]

The following example was prepared in an analogous fashion to Intermediate 86 to afford the desired product. ESI-MS m/z: 219.00 $[M+H]^+$.

Intermediate 91

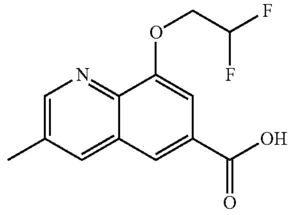 [SMILES: Cc1cnc2c(OCC(F)F)cc(C(=O)O)cc2c1]

Intermediate 91 Steps a and b

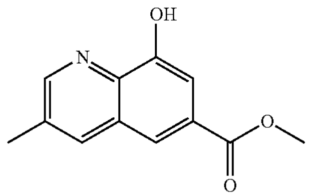

A solution of 3-hydroxy-4-aminobenzoic acid (10 g, 65.30 mmol) and methacrolein (9.15 g, 130.60 mmol) in HCl (40 mL) and AcOH (60 mL) was stirred for 1 hr at 100° C. under $N_2$ atmosphere. The combined layers were concentrated under reduced pressure to afford the desired product (5.6 g, 42%) as a brown solid. ESI-MS m/z: 204.00 $[M+H]^+$.

A solution/mixture of the compound from step a (5.6 g, 27.56 mmol) and $H_2SO_4$ (5 mL) in MeOH (50 mL,) was stirred for 1 hr at 80° C. under reflux. The mixture was neutralized to pH 7 with NaOH solution. The resulting mixture was extracted with EA (3×300 ml). The combined organic layers were concentrated under reduced pressure to afford the desired product (2.5 g, 42%) as yellow solid. ESI-MS m/z: 218.00 $[M+H]^+$.

Intermediate 91 Steps c and d

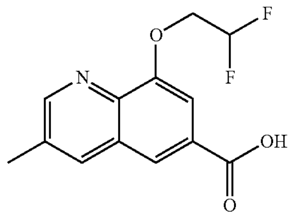 [SMILES: Cc1cnc2c(OCC(F)F)cc(C(=O)O)cc2c1]

A solution of the compound from step b (500 mg, 2.30 mmol), 2-bromo-1,1-difluoroethane (667 mg, 4.6 mmol) and $K_2CO_3$ (954 mg, 6.91 mmol) in DMF (20 mL) was stirred for overnight at 80° C. The residue was purified by silica gel column chromatography, eluted with PE/EA to afford the desired product (500 mg, 62%) as a yellow solid. ESI-MS m/z: 282.00 $[M+H]^+$.

A solution of the compound from step c (500 mg, 1.78 mmol) and LiOH (426 mg, 17.78 mmol) in MeOH (20 mL) and $H_2O$ (20 mL) was stirred for 30 min at room temperature. The mixture was acidified to pH 7 with HCl. The crude product was re-crystallized from the water to afford the desired product (270 mg, 57%) as a yellow solid. ESI-MS m/z: 267.95 $[M+H]^+$.

Intermediate 92 Steps a and b

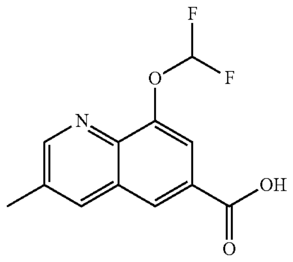 [SMILES: Cc1cnc2c(OC(F)F)cc(C(=O)O)cc2c1]

A solution of methyl 8-hydroxy-3-methylquinoline-6-carboxylate (3 g, 13.81 mmol), sodium 2-chloro-2,2-difluoroacetate (3.16 g, 20.72 mmol) and $Cs_2CO_3$ (9 g, 27.61 mmol) in DMF (30 mL) was stirred for 4 hr at 80° C. under $N_2$ atmosphere. The resulting mixture was extracted with EA (3×200 mL). The combined organic layers were washed with water (3×200 ml), dried over anhydrous $Na_2SO_4$. After filtration, the filtrate was concentrated under reduced pressure. The residue was purified by silica gel column chromatography, eluted with PE/EA to afford the desired product (2 g, 54%) as a yellow solid. ESI-MS m/z: 268.00 $[M+H]^+$.

A solution of the compound from step a (3 g, 11.23 mmol), LiOH (2.7 g, 112.26 mmol) in MeOH (30 mL) and $H_2O$ (30 mL) was stirred for 4 hours at room temperature. The mixture/residue was acidified to pH 7 with HCl, the resulting mixture was filtered, the filter cake was washed with water. The residue was purified by reverse flash chromatography with the following conditions (silica gel, MeCN in water, 10% to 50% gradient in 10 min) to afford the desired product (800 mg, 28%) as a yellow solid. ESI-MS m/z: 254.20 $[M+H]^+$.

Intermediate 93 Steps a and b

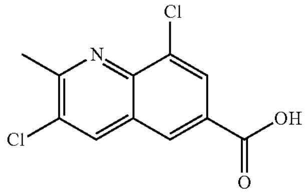 [SMILES: Cc1nc2c(Cl)cc(C(=O)O)cc2cc1Cl]

A mixture of methyl 4-amino-3-chlorobenzoate (1.5 g, 8.08 mmol) and (2Z)-2-chlorobut-2-enal (1.27 g, 12.12 mmol) in HCl (10 mL), AcOH (15 mL) was stirred for 20 min at 100° C. The reaction was monitored by LCMS. The mixture was allowed to cool down to room temperature, concentrated under vacuum. The residue dissolved in MeOH (20 mL) and $H_2SO_4$ (2 mL), stirred for another 1 h at 80° C. The resulting mixture was poured into water, extracted with EA. The combined organic layers were concentrated under reduced pressure. The residue was purified by reverse flash chromatography to afford the desired product (110 mg, 5%) as a yellow solid. ESI-MS m/z: 269.90 $[M+H]^+$.

Into a 100 mL round-bottom flask were added the compound from step a (110 mg, 0.40 mmol), THE (4 mL), MeOH (1 mL), LiOH (97 mg, 4.07 mmol) and $H_2O$ (1 mL) at room temperature. The resulting mixture was stirred for 3 hours at room temperature. The mixture was acidified to pH 5 with HCl (1 M aq.). The product was precipitated. The precipitated solids were collected by filtration and washed with water to afford the desired product (65 mg). ESI-MS m/z: 256.00 $[M+H]^+$.

Intermediate 94

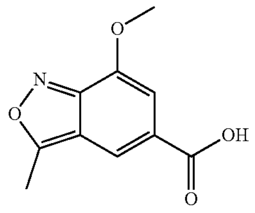

Intermediate 94 Step a

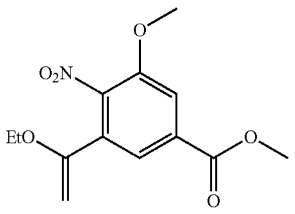 [SMILES: C=C(OCC)c1cc(C(=O)OC)cc(OC)c1[N+](=O)[O-]]

A solution of methyl 3-bromo-5-methoxy-4-nitrobenzoate (3.60 g, 12.43 mmol) in toluene (20 mL) was treated with tributyl(1-ethoxyethenyl)stannane (5.39 g, 14.91 mmol) and Pd(dppf)$Cl_2$ (1.82 g, 2.49 mmol) and stirred for 2 hours at 110° C. under nitrogen atmosphere. The reaction was monitored by LCMS. The resulting mixture was filtered, the filter cake was washed with EA. The filtrate was concentrated under reduced pressure. The residue was purified by silica gel column chromatography (eluted with 25% ethyl acetate in hexanes) to afford the compound (2.69 g, 77%) as a yellow oil. ESI-MS m/z: 282.20 $[M+H]^+$.

Intermediate 94 Step b

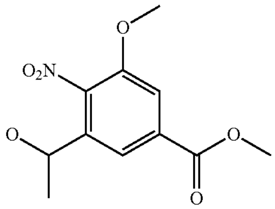 [SMILES: COC(=O)c1cc(OC)c([N+](=O)[O-])c(C(C)O)c1]

A solution of the compound from step a (2.69 g, 9.56 mmol) in DCM (30 mL) was treated with HCl (3 mL) for overnight at room temperature. The reaction was monitored by LCMS. The aqueous layer was extracted with $CH_2Cl_2$. The residue was purified by silica gel column chromatography (eluted with 50% ethyl acetate in hexanes) to afford the compound (1.82 g, 75%) as a white solid. ESI-MS m/z: 253.85 $[M+H]^+$.

Intermediate 94 Steps c and d

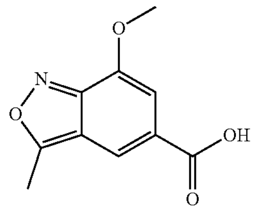

Into a 250 mL round-bottom flask were added the compound from step b (1.82 g, 7.18 mmol) and a solution of NaOAc (21.83 g, 266.09 mmol) in MeOH (90 mL) and THE (90 mL) was treated with $SnCl_2$ (18.19 g, 94.92 mmol) and stirred for 16 hrs at room temperature under nitrogen atmosphere. The reaction was monitored by LCMS. The resulting mixture was filtered, the filter cake was washed with ethyl acetate. The filtrate was concentrated under reduced pressure. The residue was purified by silica gel column chromatography, eluted with PE/EA (7:3) to afford the compound (851 mg, 54%) as a white solid. ESI-MS m/z: 222.10 $[M+H]^+$. Into a 250 mL round-bottom flask were added the compound from step c (840 mg, 3.80 mmol) and THE (40 mL) at room temperature. A solution of LiOH (909 mg, 37.97 mmol) in MeOH (10 mL) and $H_2O$ (10 mL) was added and stirred for 5 hours at room temperature. The reaction was monitored by LCMS. The mixture was acidified to pH 4 with HCl then the product was precipitated. The precipitated solids were collected by filtration and washed with $H_2O$ to afford the compound (646 mg, 81%) as an orange solid. ESI-MS m/z: 207.95 $[M+H]^+$.

Intermediate 95

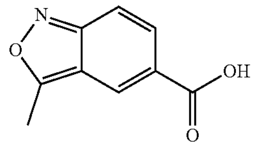

The following compounds was prepared in an analogous procedure to Intermediate 94 to afford the desired product (741 mg, 88%) as an orange solid. ESI-MS m/z: 178.10 $[M+H]^+$.

The following Table 5 contains examples that were prepared with the similar method to Example 1 Step c (PyBOP or HATU). The majority of compounds were purified by prep-HPLC (ACN/$H_2O$, 20-90%, 25 min), and some were purified by automated column chromatography (silica gel). The aryl acid coupling partners were prepared according to Intermediates 1-95, or by analogous procedures with slight modifications and also prepared according to procedures found in U.S. patent application Ser. No. 16/930,622.

TABLE 5
| Example | Structure | MS+ m/z |
|---|---|---|
| 491 | 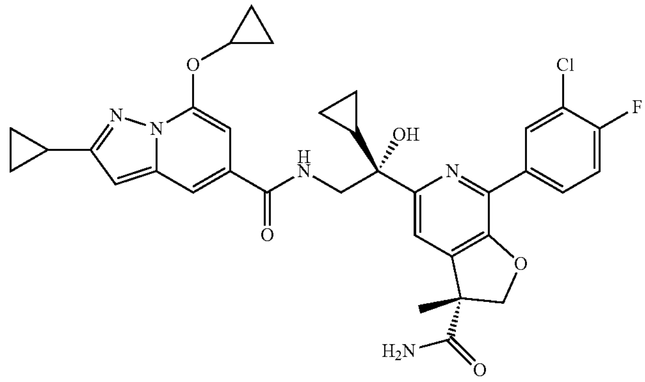 [SMILES: C[C@]1(C(N)=O)COc2c1cc([C@@](O)(CNC(=O)c1cc(OC3CC3)n3nc(C4CC4)cc3c1)C1CC1)nc2-c1ccc(F)c(Cl)c1] | 646.27 |
| 492 | 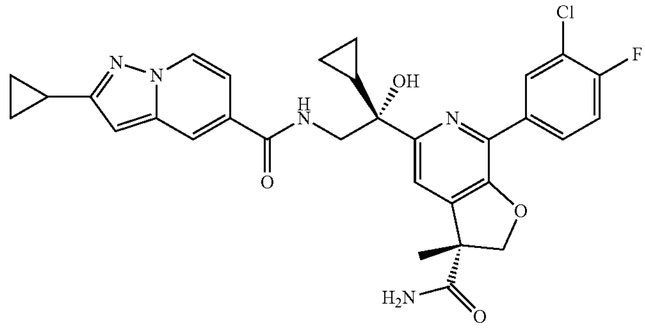 [SMILES: C[C@]1(C(N)=O)COc2c1cc([C@@](O)(CNC(=O)c1ccn3nc(C4CC4)cc3c1)C1CC1)nc2-c1ccc(F)c(Cl)c1] | 590.19 |
| 493 | 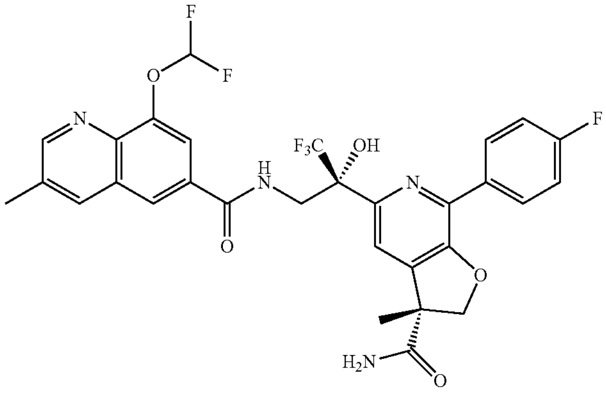 [SMILES: Cc1cnc2c(OC(F)F)cc(C(=O)NC[C@](O)(c3cc4c(c(-c5ccc(F)cc5)n3)OC[C@]4(C)C(N)=O)C(F)(F)F)cc2c1] | 635.34 |
| 494 | 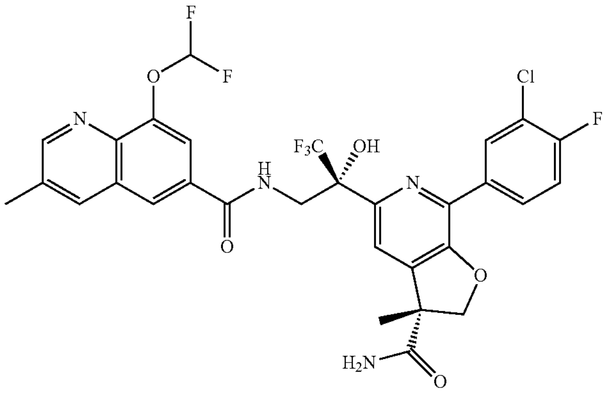 [SMILES: Cc1cnc2c(OC(F)F)cc(C(=O)NC[C@](O)(c3cc4c(c(-c5ccc(F)c(Cl)c5)n3)OC[C@]4(C)C(N)=O)C(F)(F)F)cc2c1] | 669.12 |

TABLE 5-continued
| Example | Structure | MS+ m/z |
|---|---|---|
| 495 | 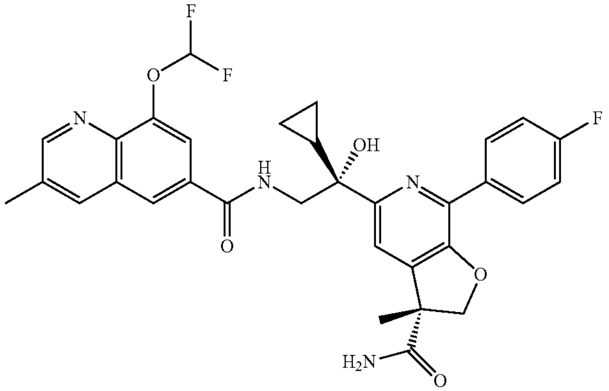 [SMILES: Cc1cnc2c(OC(F)F)cc(C(=O)NC[C@](O)(c3cc4c(c(-c5ccc(F)cc5)n3)OC[C@]4(C)C(N)=O)C3CC3)cc2c1] | 607.22 |
| 496 | 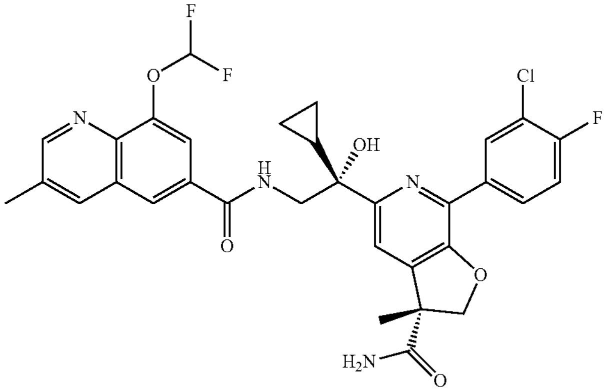 [SMILES: Cc1cnc2c(OC(F)F)cc(C(=O)NC[C@](O)(c3cc4c(c(-c5ccc(F)c(Cl)c5)n3)OC[C@]4(C)C(N)=O)C3CC3)cc2c1] | 641.17 |
| 497 | 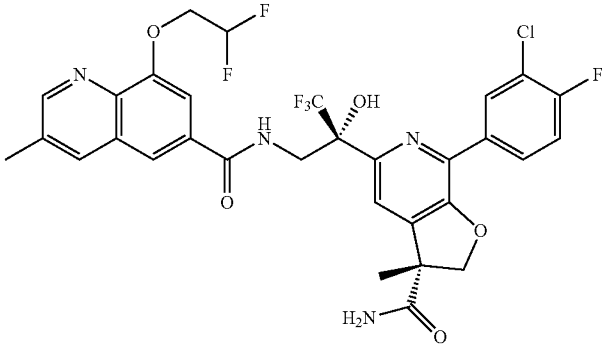 [SMILES: Cc1cnc2c(OCC(F)F)cc(C(=O)NC[C@](O)(c3cc4c(c(-c5ccc(F)c(Cl)c5)n3)OC[C@]4(C)C(N)=O)C(F)(F)F)cc2c1] | 683.19 |
| 498 | 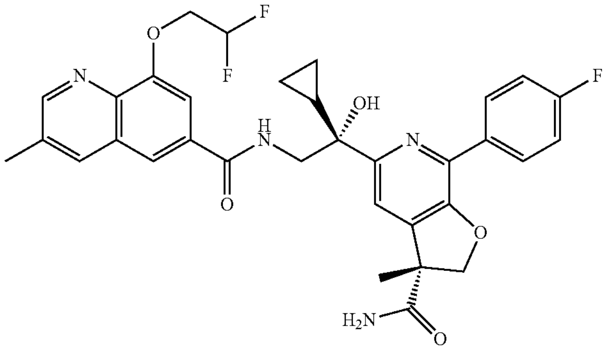 [SMILES: Cc1cnc2c(OCC(F)F)cc(C(=O)NC[C@](O)(c3cc4c(c(-c5ccc(F)cc5)n3)OC[C@]4(C)C(N)=O)C3CC3)cc2c1] | 621.25 |

TABLE 5-continued
| Example | Structure | MS+ m/z |
|---|---|---|
| 499 | 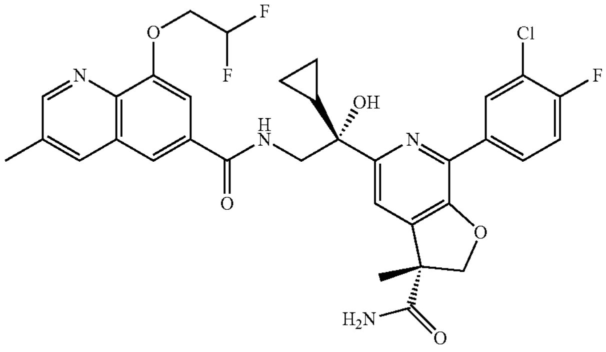 [SMILES: Cc1cnc2c(OCC(F)F)cc(C(=O)NC[C@](O)(c3cc4c(c(-c5ccc(F)c(Cl)c5)n3)OC[C@]4(C)C(N)=O)C3CC3)cc2c1] | 655.15 |
| 500 | 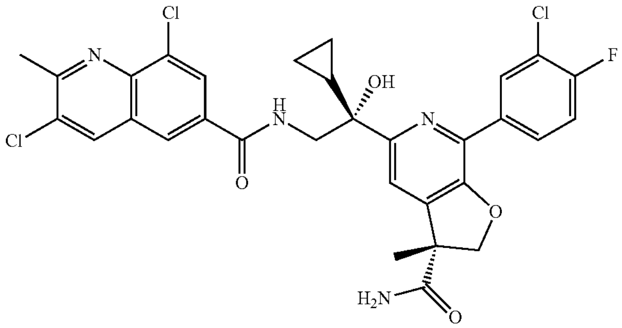 [SMILES: Cc1nc2c(Cl)cc(C(=O)NC[C@](O)(c3cc4c(c(-c5ccc(F)c(Cl)c5)n3)OC[C@]4(C)C(N)=O)C3CC3)cc2cc1Cl] | 642.95 |
| 501 | 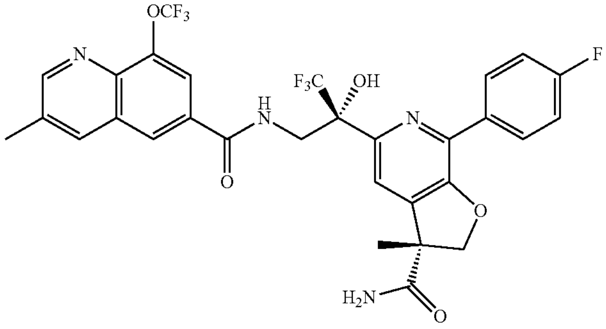 [SMILES: Cc1cnc2c(OC(F)(F)F)cc(C(=O)NC[C@](O)(c3cc4c(c(-c5ccc(F)cc5)n3)OC[C@]4(C)C(N)=O)C(F)(F)F)cc2c1] | 653.29 |
| 502 | 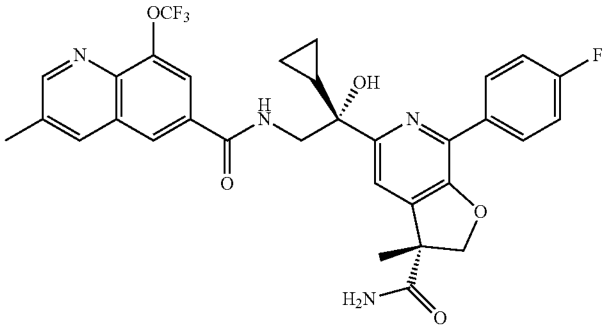 [SMILES: Cc1cnc2c(OC(F)(F)F)cc(C(=O)NC[C@](O)(c3cc4c(c(-c5ccc(F)cc5)n3)OC[C@]4(C)C(N)=O)C3CC3)cc2c1] | 625.39 |

TABLE 5-continued
| Example | Structure | MS+ m/z |
|---|---|---|
| 503 | 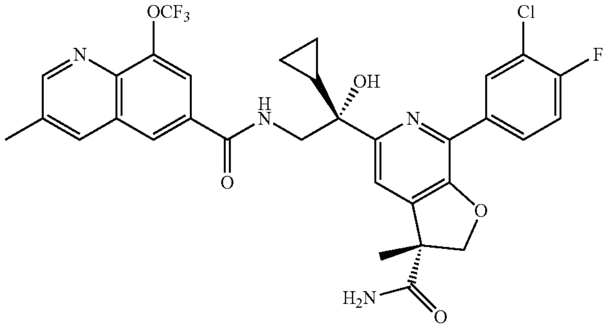 [SMILES: Cc1cnc2c(OC(F)(F)F)cc(C(=O)NC[C@](O)(c3cc4c(c(-c5ccc(F)c(Cl)c5)n3)OC[C@]4(C)C(N)=O)C3CC3)cc2c1] | 659.13 |
| 504 | 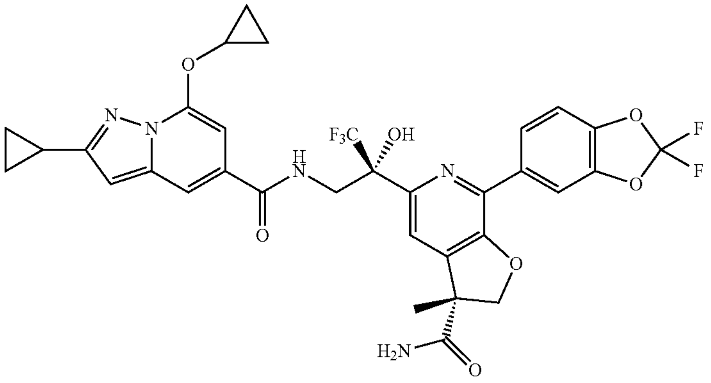 [SMILES: C[C@]1(C(N)=O)COc2c1cc([C@@](O)(CNC(=O)c1cc(OC3CC3)n3nc(C4CC4)cc3c1)C(F)(F)F)nc2-c1ccc2c(c1)OC(F)(F)O2] | 702.24 |
| 505 | 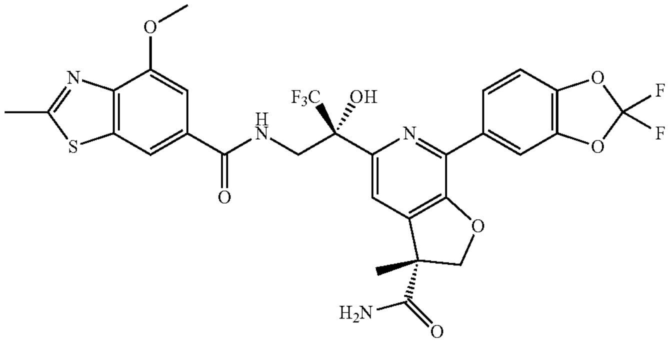 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2sc(C)nc12] | 667.32 |
| 506 | 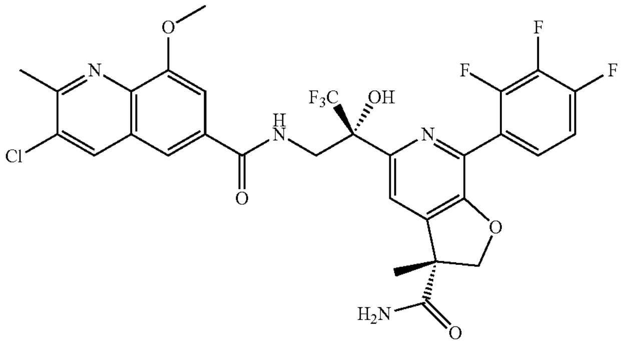 [SMILES: COc1cc(C(=O)NC[C@](O)(c2cc3c(c(-c4ccc(F)c(F)c4F)n2)OC[C@]3(C)C(N)=O)C(F)(F)F)cc2cc(Cl)c(C)nc12] | 669.43 |

TABLE 5-continued
| Example | Structure | MS+ m/z |
|---|---|---|
| 507 | 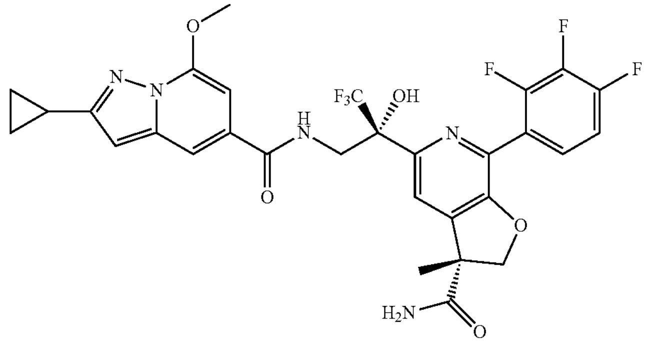 [SMILES: COc1cc(C(=O)NC[C@](O)(c2cc3c(c(-c4ccc(F)c(F)c4F)n2)OC[C@]3(C)C(N)=O)C(F)(F)F)cc2cc(C3CC3)nn12] | 650.42 |
| 508 | 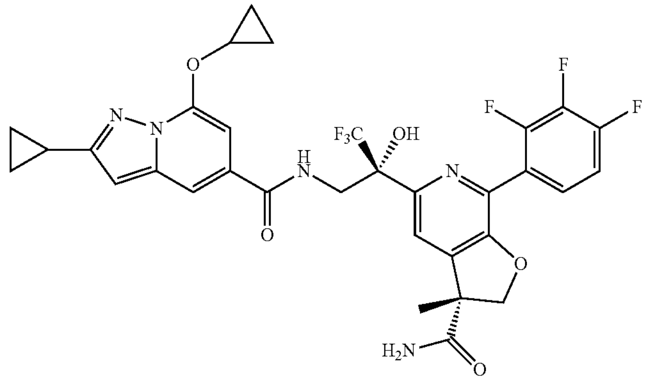 [SMILES: C[C@]1(C(N)=O)COc2c1cc([C@@](O)(CNC(=O)c1cc(OC3CC3)n3nc(C4CC4)cc3c1)C(F)(F)F)nc2-c1ccc(F)c(F)c1F] | 676.58 |
| 509 | 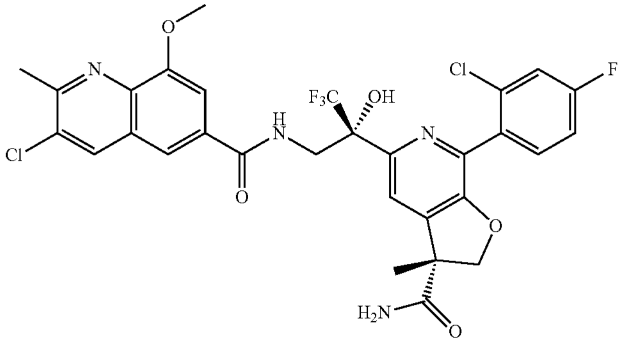 [SMILES: COc1cc(C(=O)NC[C@](O)(c2cc3c(c(-c4ccc(F)cc4Cl)n2)OC[C@]3(C)C(N)=O)C(F)(F)F)cc2cc(Cl)c(C)nc12] | 667.22 |
| 510 | 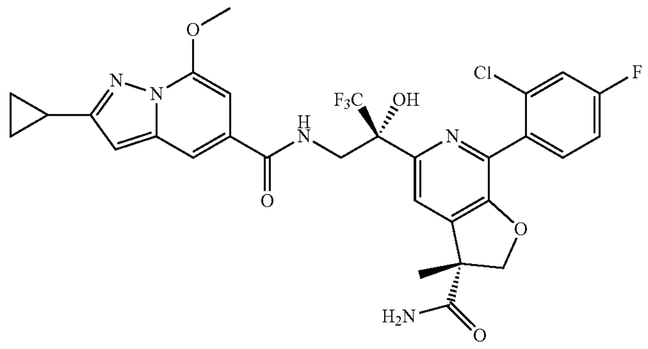 [SMILES: COc1cc(C(=O)NC[C@](O)(c2cc3c(c(-c4ccc(F)cc4Cl)n2)OC[C@]3(C)C(N)=O)C(F)(F)F)cc2cc(C3CC3)nn12] | 648.29 |

TABLE 5-continued
| Example | Structure | MS+ m/z |
|---|---|---|
| 511 | 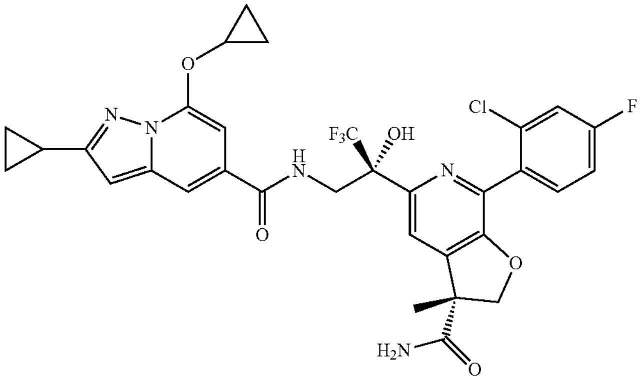 [SMILES: C[C@]1(C(N)=O)COc2c1cc([C@@](O)(CNC(=O)c1cc(OC3CC3)n3nc(C4CC4)cc3c1)C(F)(F)F)nc2-c1ccc(F)cc1Cl] | 667.22 |
| 512 | 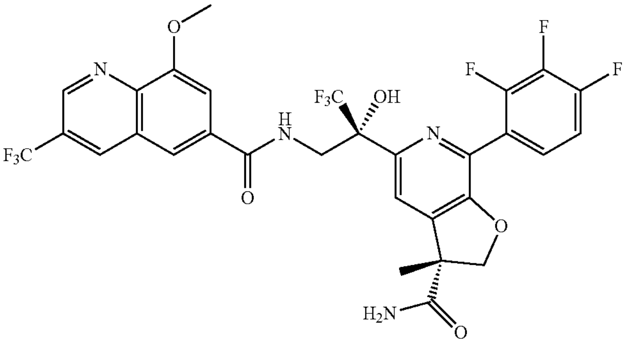 [SMILES: COc1cc(C(=O)NC[C@](O)(c2cc3c(c(-c4ccc(F)c(F)c4F)n2)OC[C@]3(C)C(N)=O)C(F)(F)F)cc2cc(C(F)(F)F)cnc12] | 689.42 |
| 513 | 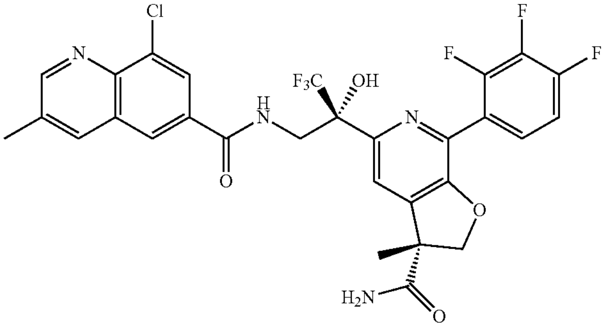 [SMILES: Cc1cnc2c(Cl)cc(C(=O)NC[C@](O)(c3cc4c(c(-c5ccc(F)c(F)c5F)n3)OC[C@]4(C)C(N)=O)C(F)(F)F)cc2c1] | 639.28 |
| 514 | 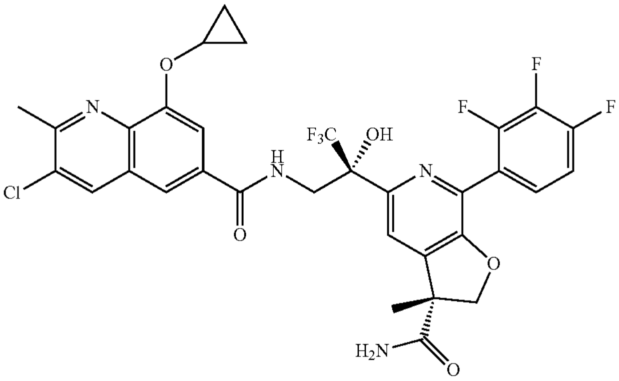 [SMILES: Cc1nc2c(OC3CC3)cc(C(=O)NC[C@](O)(c3cc4c(c(-c5ccc(F)c(F)c5F)n3)OC[C@]4(C)C(N)=O)C(F)(F)F)cc2cc1Cl] | 695.48 |

TABLE 5-continued
| Example | Structure | MS+ m/z |
|---|---|---|
| 515 | 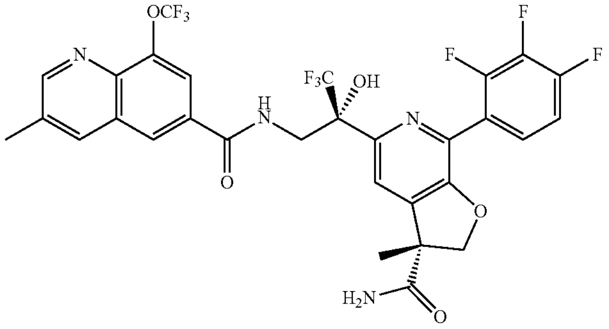 [SMILES: Cc1cnc2c(OC(F)(F)F)cc(C(=O)NC[C@](O)(c3cc4c(c(-c5ccc(F)c(F)c5F)n3)OC[C@]4(C)C(N)=O)C(F)(F)F)cc2c1] | 689.39 |
| 516 | 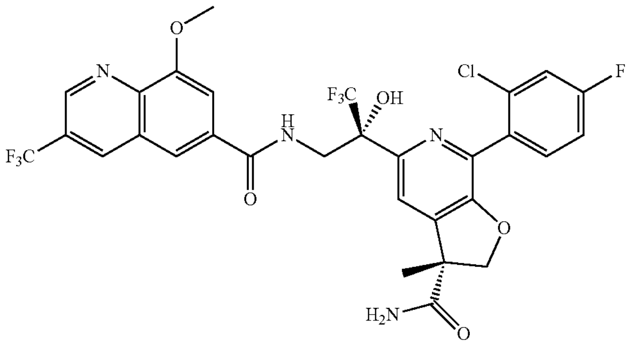 [SMILES: COc1cc(C(=O)NC[C@](O)(c2cc3c(c(-c4ccc(F)cc4Cl)n2)OC[C@]3(C)C(N)=O)C(F)(F)F)cc2cc(C(F)(F)F)cnc12] | 687.22 |
| 517 | 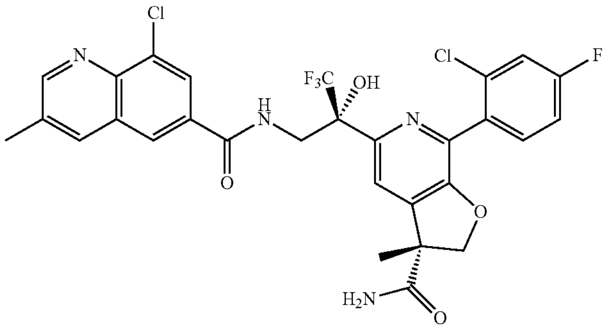 [SMILES: Cc1cnc2c(Cl)cc(C(=O)NC[C@](O)(c3cc4c(c(-c5ccc(F)cc5Cl)n3)OC[C@]4(C)C(N)=O)C(F)(F)F)cc2c1] | 637.18 |
| 518 | 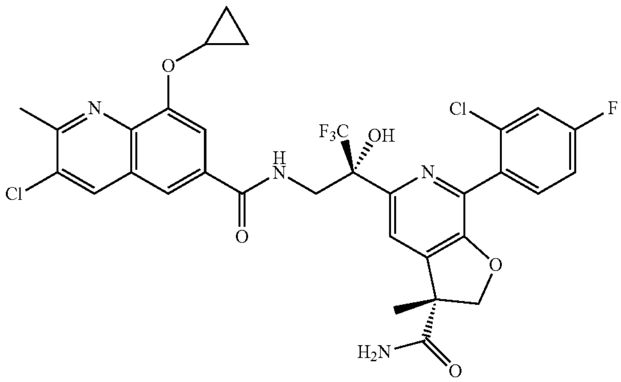 [SMILES: Cc1nc2c(OC3CC3)cc(C(=O)NC[C@](O)(c3cc4c(c(-c5ccc(F)cc5Cl)n3)OC[C@]4(C)C(N)=O)C(F)(F)F)cc2cc1Cl] | 693.20 |

TABLE 5-continued
| Example | Structure | MS+ m/z |
|---|---|---|
| 519 | 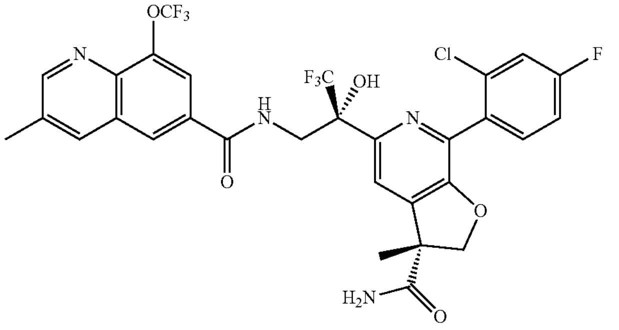 [SMILES: Cc1cnc2c(OC(F)(F)F)cc(C(=O)NC[C@](O)(c3cc4c(c(-c5ccc(F)cc5Cl)n3)OC[C@]4(C)C(N)=O)C(F)(F)F)cc2c1] | 687.42 |
| 520 | 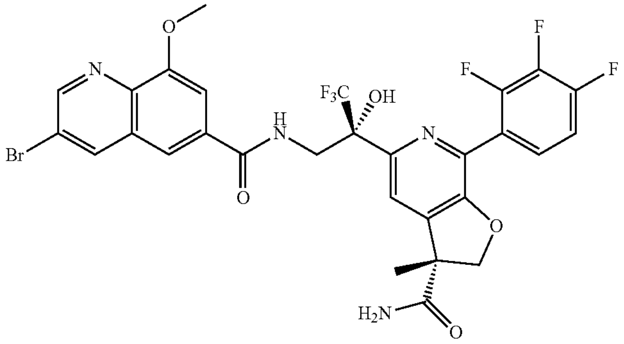 [SMILES: COc1cc(C(=O)NC[C@](O)(c2cc3c(c(-c4ccc(F)c(F)c4F)n2)OC[C@]3(C)C(N)=O)C(F)(F)F)cc2cc(Br)cnc12] | 699.18 |
| 521 | 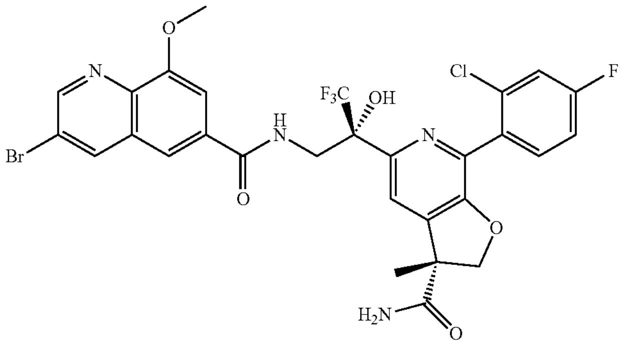 [SMILES: COc1cc(C(=O)NC[C@](O)(c2cc3c(c(-c4ccc(F)cc4Cl)n2)OC[C@]3(C)C(N)=O)C(F)(F)F)cc2cc(Br)cnc12] | 697.12 |
| 522 | 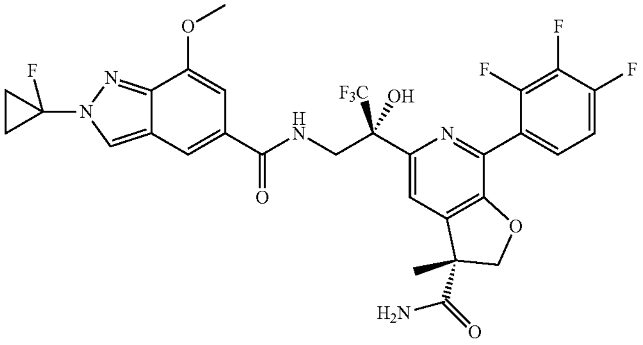 [SMILES: COc1cc(C(=O)NC[C@](O)(c2cc3c(c(-c4ccc(F)c(F)c4F)n2)OC[C@]3(C)C(N)=O)C(F)(F)F)cc2cn(C3(F)CC3)nc12] | 668.22 |

TABLE 5-continued
| Example | Structure | MS+ m/z |
|---|---|---|
| 523 | 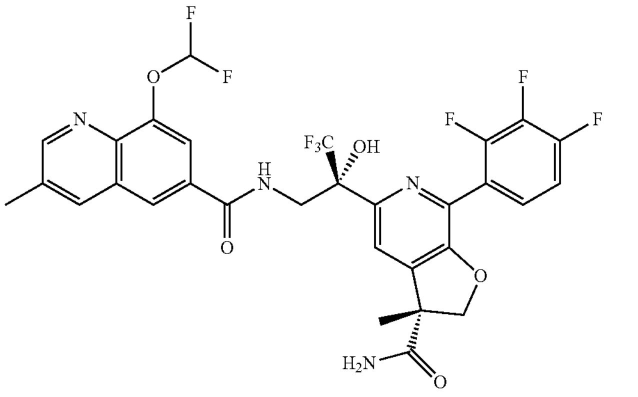 [SMILES: Cc1cnc2c(OC(F)F)cc(C(=O)NC[C@](O)(c3cc4c(c(-c5ccc(F)c(F)c5F)n3)OC[C@]4(C)C(N)=O)C(F)(F)F)cc2c1] | 671.41 |
| 524 | 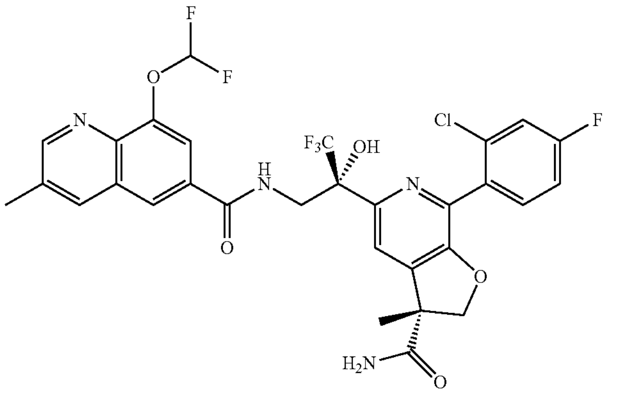 [SMILES: Cc1cnc2c(OC(F)F)cc(C(=O)NC[C@](O)(c3cc4c(c(-c5ccc(F)cc5Cl)n3)OC[C@]4(C)C(N)=O)C(F)(F)F)cc2c1] | 669.33 |
| 525 | 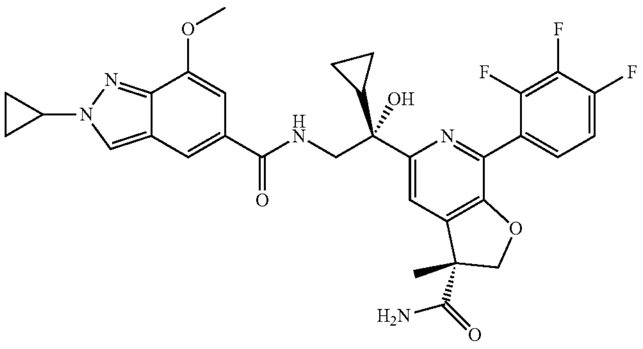 [SMILES: COc1cc(C(=O)NC[C@](O)(c2cc3c(c(-c4ccc(F)c(F)c4F)n2)OC[C@]3(C)C(N)=O)C2CC2)cc2cn(C3CC3)nc12] | 621.51 |
| 526 | 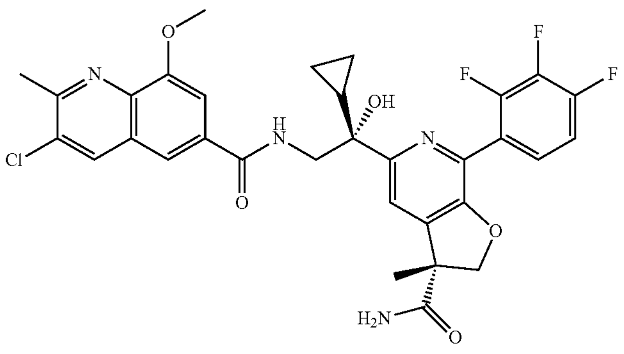 [SMILES: COc1cc(C(=O)NC[C@](O)(c2cc3c(c(-c4ccc(F)c(F)c4F)n2)OC[C@]3(C)C(N)=O)C2CC2)cc2cc(Cl)c(C)nc12] | 641.49 |

TABLE 5-continued
| Example | Structure | MS+ m/z |
|---|---|---|
| 527 | 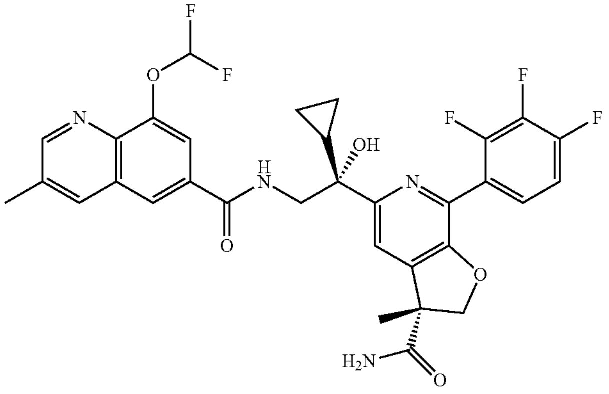 [SMILES: Cc1cnc2c(OC(F)F)cc(C(=O)NC[C@](O)(c3cc4c(c(-c5ccc(F)c(F)c5F)n3)OC[C@]4(C)C(N)=O)C3CC3)cc2c1] | 641.41 |
| 528 | 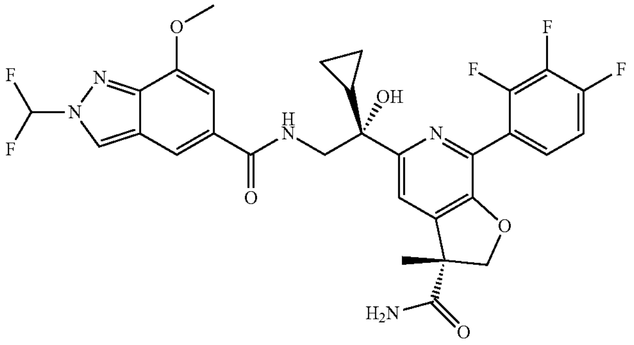 [SMILES: COc1cc(C(=O)NC[C@](O)(c2cc3c(c(-c4ccc(F)c(F)c4F)n2)OC[C@]3(C)C(N)=O)C2CC2)cc2cn(C(F)F)nc12] | 632.23 |
| 529 | 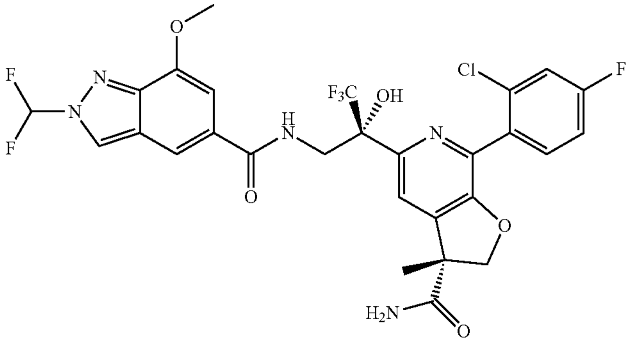 [SMILES: COc1cc(C(=O)NC[C@](O)(c2cc3c(c(-c4ccc(F)cc4Cl)n2)OC[C@]3(C)C(N)=O)C(F)(F)F)cc2cn(C(F)F)nc12] | 658.20 |
| 530 | 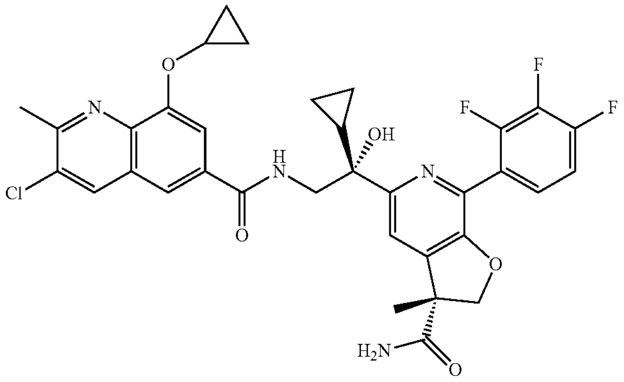 [SMILES: Cc1nc2c(OC3CC3)cc(C(=O)NC[C@](O)(c3cc4c(c(-c5ccc(F)c(F)c5F)n3)OC[C@]4(C)C(N)=O)C3CC3)cc2cc1Cl] | 667.49 |

TABLE 5-continued
| Example | Structure | MS+ m/z |
|---|---|---|
| 531 | 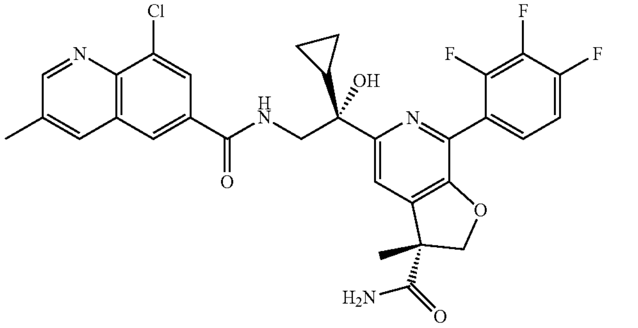 [SMILES: Cc1cnc2c(Cl)cc(C(=O)NC[C@](O)(c3cc4c(c(-c5ccc(F)c(F)c5F)n3)OC[C@]4(C)C(N)=O)C3CC3)cc2c1] | 611.43 |
| 532 | 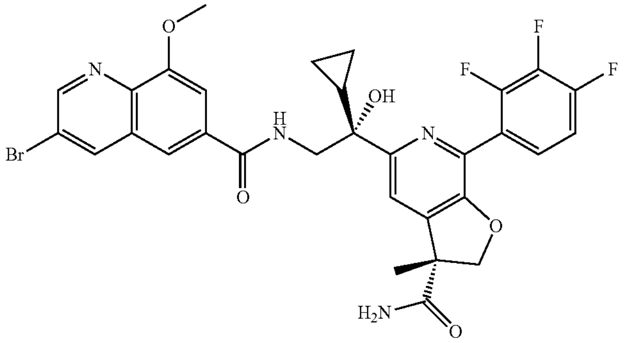 | 671.30 |
| 533 | 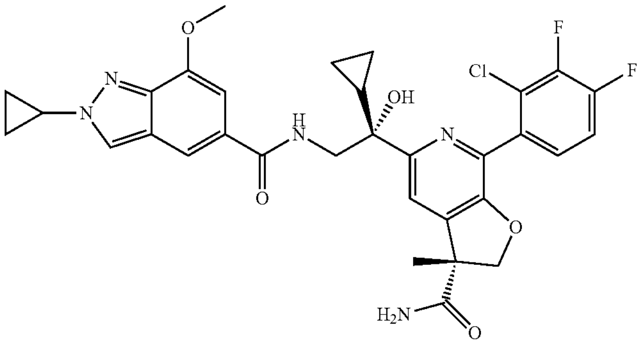 [SMILES: COc1cc(C(=O)NC[C@](O)(c2cc3c(c(-c4ccc(F)c(F)c4Cl)n2)OC[C@]3(C)C(N)=O)C2CC2)cc2cn(C3CC3)nc12] | 638.47 |
| 534 | 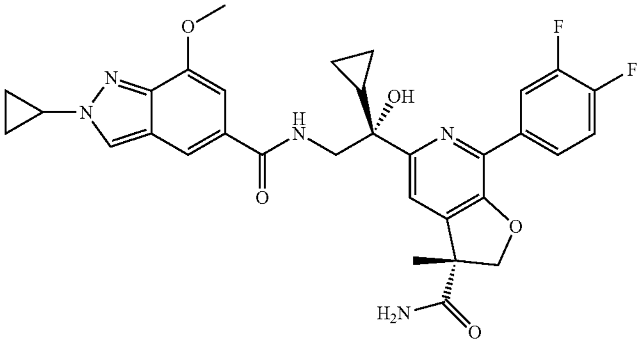 [SMILES: COc1cc(C(=O)NC[C@](O)(c2cc3c(c(-c4ccc(F)c(F)c4)n2)OC[C@]3(C)C(N)=O)C2CC2)cc2cn(C3CC3)nc12] | 604.51 |

TABLE 5-continued
| Example | Structure | MS+ m/z |
|---|---|---|
| 535 | 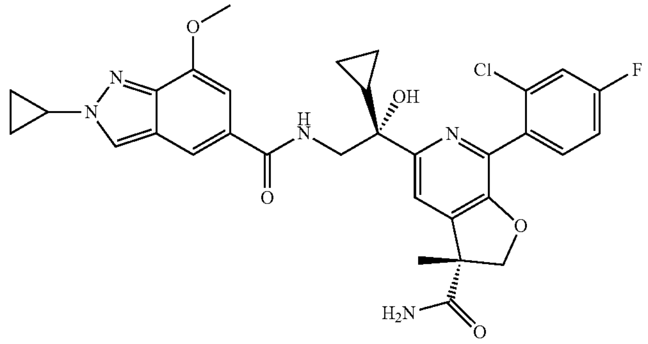 [SMILES: COc1cc(C(=O)NC[C@](O)(c2cc3c(c(-c4ccc(F)cc4Cl)n2)OC[C@]3(C)C(N)=O)C2CC2)cc2cn(C3CC3)nc12] | 620.47 |
| 536 | 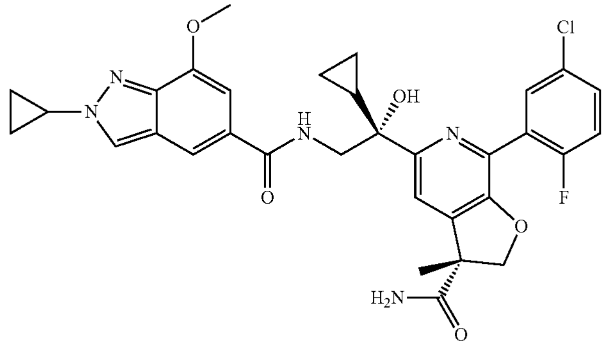 [SMILES: COc1cc(C(=O)NC[C@](O)(c2cc3c(c(-c4cc(Cl)ccc4F)n2)OC[C@]3(C)C(N)=O)C2CC2)cc2cn(C3CC3)nc12] | 620.48 |
| 537 | 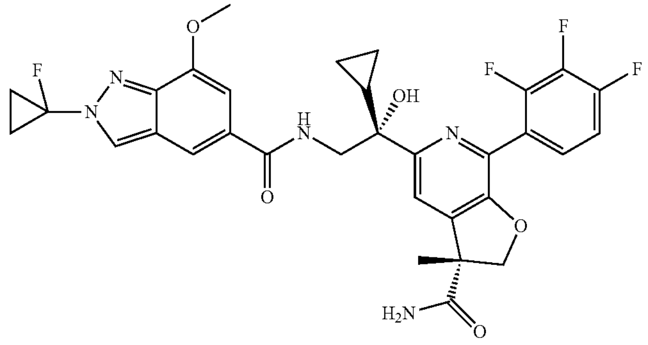 [SMILES: COc1cc(C(=O)NC[C@](O)(c2cc3c(c(-c4ccc(F)c(F)c4F)n2)OC[C@]3(C)C(N)=O)C2CC2)cc2cn(C3(F)CC3)nc12] | 640.48 |
| 538 | 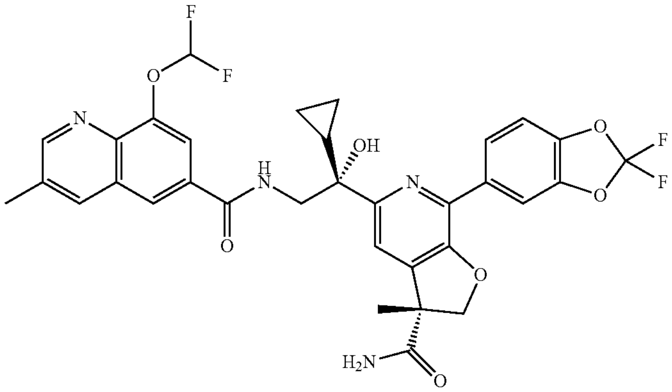 [SMILES: Cc1cnc2c(OC(F)F)cc(C(=O)NC[C@](O)(c3cc4c(c(-c5ccc6c(c5)OC(F)(F)O6)n3)OC[C@]4(C)C(N)=O)C3CC3)cc2c1] | 669.46 |

TABLE 5-continued
| Example | Structure | MS+ m/z |
|---|---|---|
| 539 | 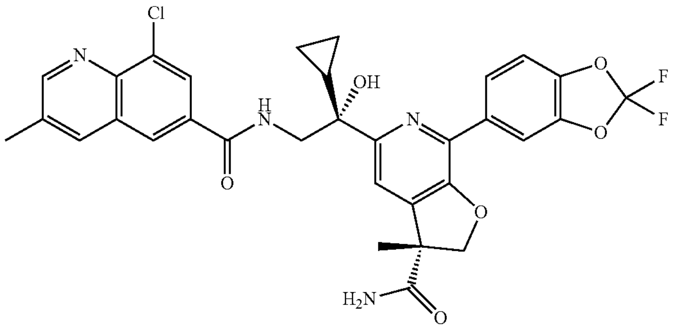 [SMILES: Cc1cnc2c(Cl)cc(C(=O)NC[C@](O)(c3cc4c(c(-c5ccc6c(c5)OC(F)(F)O6)n3)OC[C@]4(C)C(N)=O)C3CC3)cc2c1] | 637.45 |
| 540 | 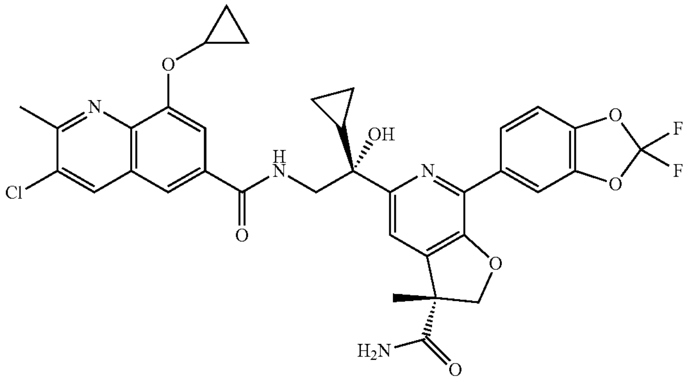 [SMILES: Cc1nc2c(OC3CC3)cc(C(=O)NC[C@](O)(c3cc4c(c(-c5ccc6c(c5)OC(F)(F)O6)n3)OC[C@]4(C)C(N)=O)C3CC3)cc2cc1Cl] | 693.51 |
| 541 | 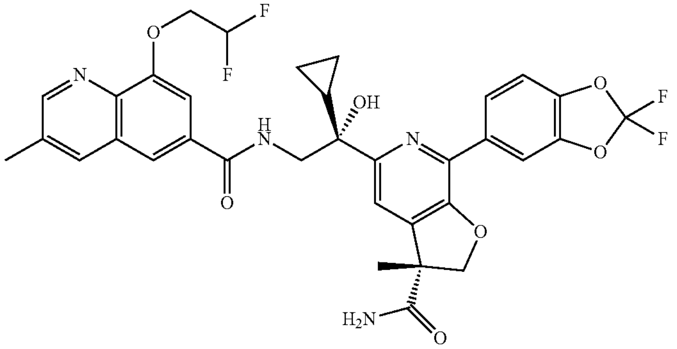 [SMILES: Cc1cnc2c(OCC(F)F)cc(C(=O)NC[C@](O)(c3cc4c(c(-c5ccc6c(c5)OC(F)(F)O6)n3)OC[C@]4(C)C(N)=O)C3CC3)cc2c1] | 683.49 |
| 542 | 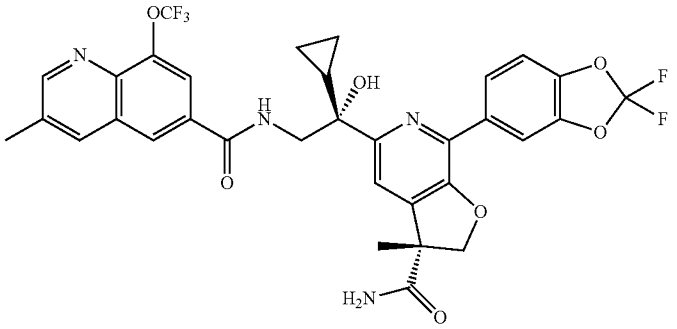 [SMILES: Cc1cnc2c(OC(F)(F)F)cc(C(=O)NC[C@](O)(c3cc4c(c(-c5ccc6c(c5)OC(F)(F)O6)n3)OC[C@]4(C)C(N)=O)C3CC3)cc2c1] | 687.45 |

TABLE 5-continued
| Example | Structure | MS+ m/z |
|---|---|---|
| 543 | 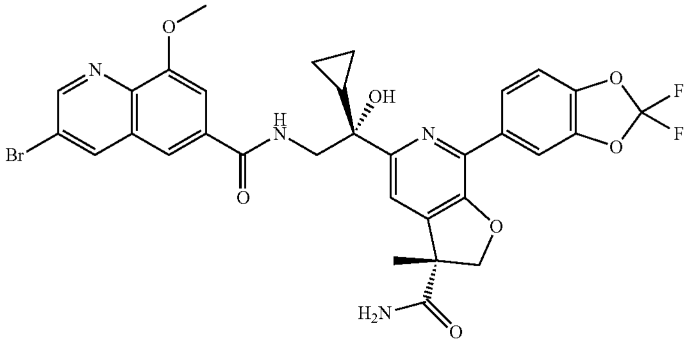 [SMILES: COc1cc(C(=O)NC[C@](O)(c2cc3c(c(-c4ccc5c(c4)OC(F)(F)O5)n2)OC[C@]3(C)C(N)=O)C2CC2)cc2cc(Br)cnc12] | 697.32 |
| 544 | 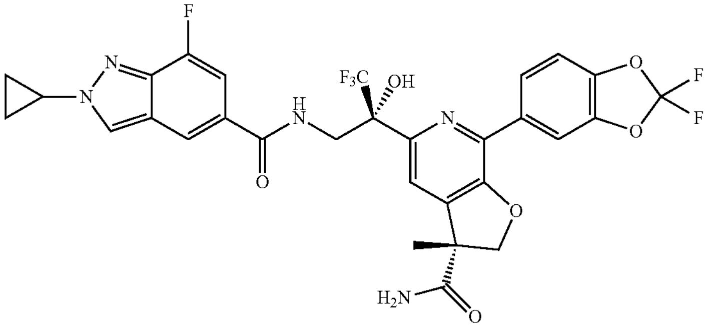 | 664.42 |
| 545 | 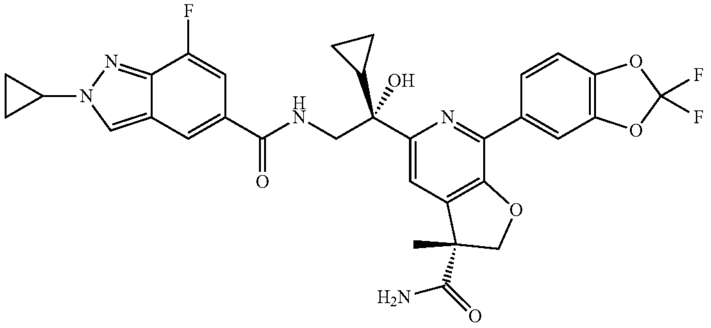 [SMILES: C[C@]1(C(N)=O)COc2c1cc([C@@](O)(CNC(=O)c1cc(F)c3nn(C4CC4)cc3c1)C1CC1)nc2-c1ccc2c(c1)OC(F)(F)O2] | 636.48 |
| 546 | 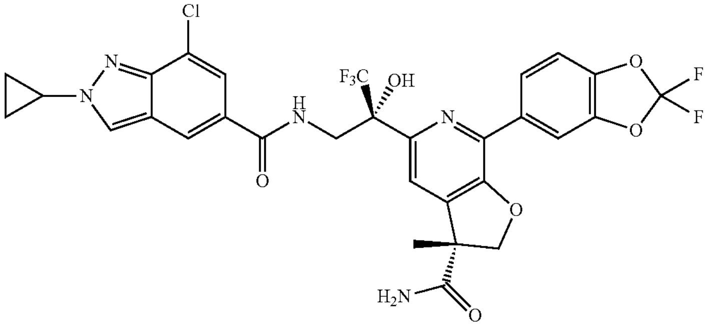 [SMILES: C[C@]1(C(N)=O)COc2c1cc([C@@](O)(CNC(=O)c1cc(Cl)c3nn(C4CC4)cc3c1)C(F)(F)F)nc2-c1ccc2c(c1)OC(F)(F)O2] | 680.40 |

TABLE 5-continued
| Example | Structure | MS+ m/z |
| --- | --- | --- |
| 547 | 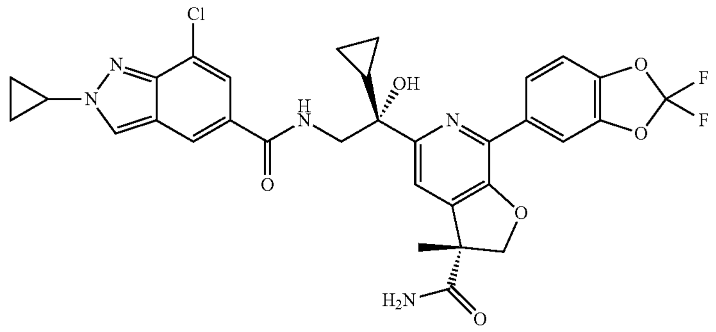 | 652.57 |
| 548 | 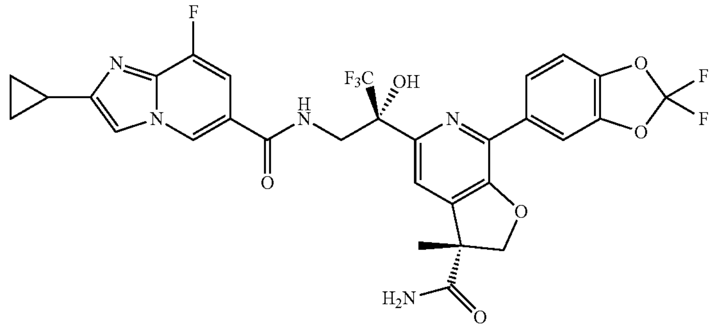 [SMILES: C[C@]1(C(N)=O)COc2c1cc([C@@](O)(CNC(=O)c1cc(F)c3nc(C4CC4)cn3c1)C(F)(F)F)nc2-c1ccc2c(c1)OC(F)(F)O2] | 664.40 |
| 549 | 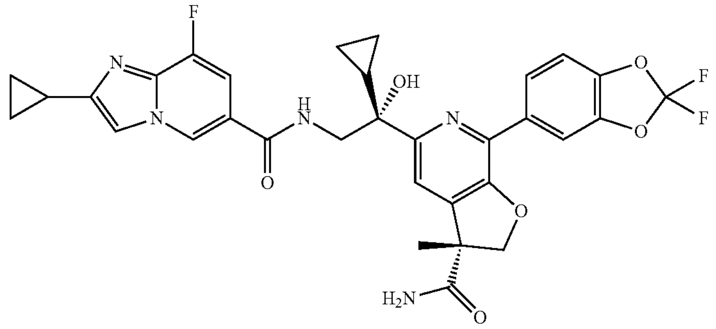 [SMILES: C[C@]1(C(N)=O)COc2c1cc([C@@](O)(CNC(=O)c1cc(F)c3nc(C4CC4)cn3c1)C1CC1)nc2-c1ccc2c(c1)OC(F)(F)O2] | 636.45 |
| 550 | 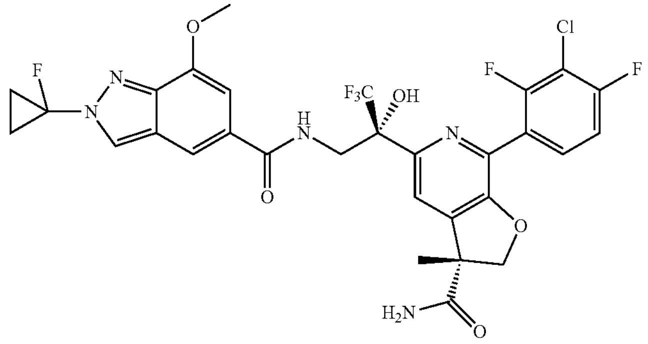 [SMILES: COc1cc(C(=O)NC[C@](O)(c2cc3c(c(-c4ccc(F)c(Cl)c4F)n2)OC[C@]3(C)C(N)=O)C(F)(F)F)cc2cn(C3(F)CC3)nc12] | 684.40 |

TABLE 5-continued
| Example | Structure | MS+ m/z |
|---|---|---|
| 551 | 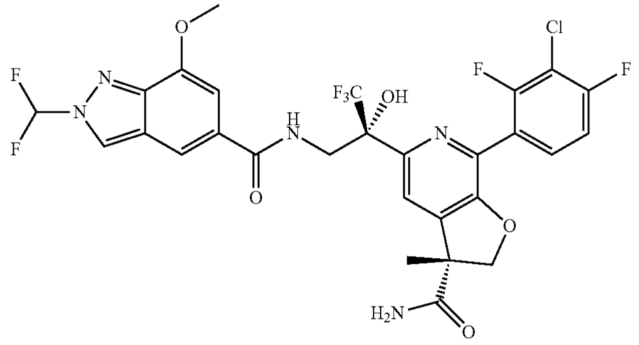 [SMILES: COc1cc(C(=O)NC[C@](O)(c2cc3c(c(-c4ccc(F)c(Cl)c4F)n2)OC[C@]3(C)C(N)=O)C(F)(F)F)cc2cn(C(F)F)nc12] | 676.38 |
| 552 | 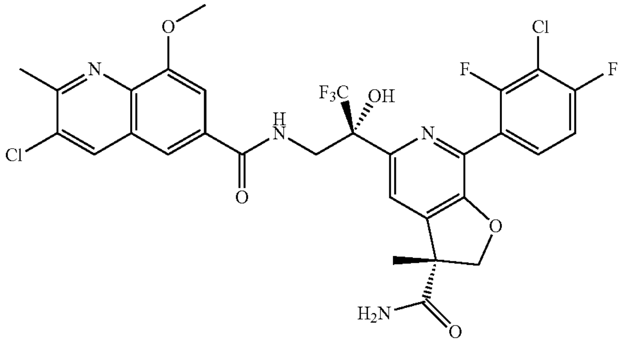 [SMILES: COc1cc(C(=O)NC[C@](O)(c2cc3c(c(-c4ccc(F)c(Cl)c4F)n2)OC[C@]3(C)C(N)=O)C(F)(F)F)cc2cc(Cl)c(C)nc12] | 685.35 |
| 553 | 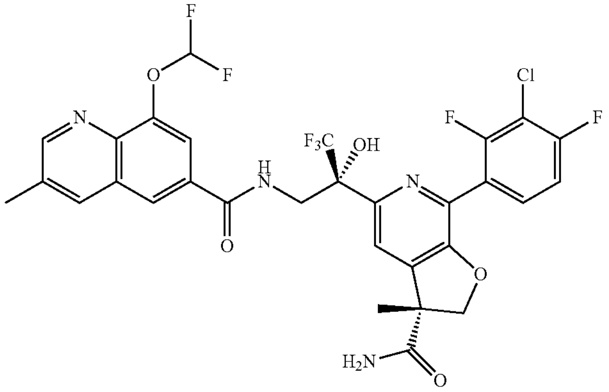 [SMILES: Cc1cnc2c(OC(F)F)cc(C(=O)NC[C@](O)(c3cc4c(c(-c5ccc(F)c(Cl)c5F)n3)OC[C@]4(C)C(N)=O)C(F)(F)F)cc2c1] | 687.36 |
| 554 | 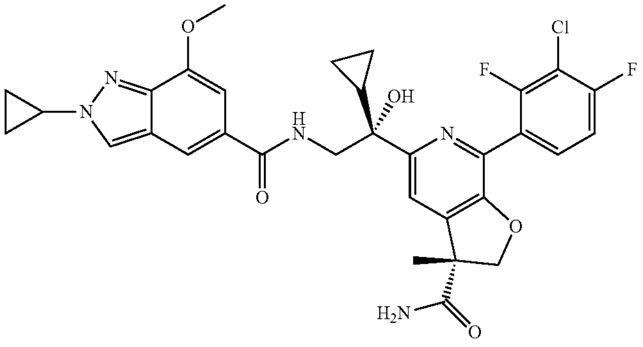 [SMILES: COc1cc(C(=O)NC[C@](O)(c2cc3c(c(-c4ccc(F)c(Cl)c4F)n2)OC[C@]3(C)C(N)=O)C2CC2)cc2cn(C3CC3)nc12] | 638.49 |

TABLE 5-continued
| Example | Structure | MS+ m/z |
|---|---|---|
| 555 | 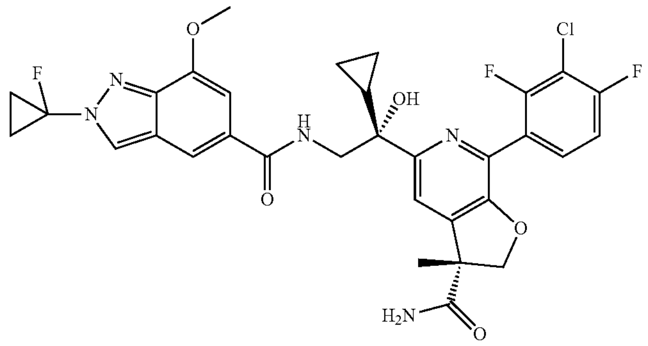 | 656.48 |
| 556 | 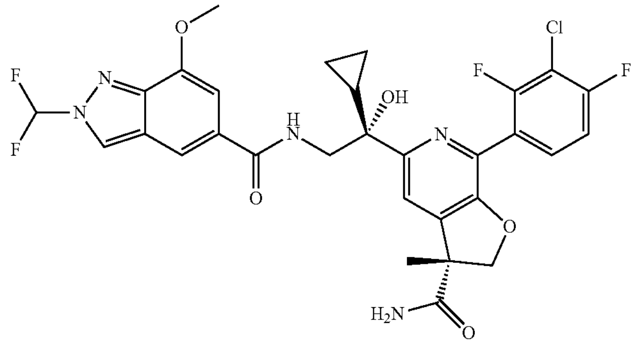 [SMILES: COc1cc(C(=O)NC[C@](O)(c2cc3c(c(-c4ccc(F)c(Cl)c4F)n2)OC[C@]3(C)C(N)=O)C2CC2)cc2cn(C(F)F)nc12] | 648.17 |
| 557 | 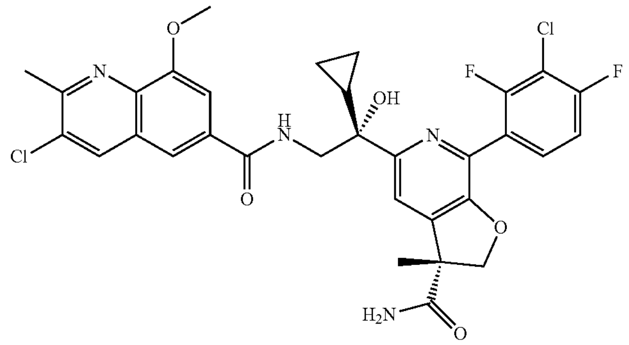 [SMILES: COc1cc(C(=O)NC[C@](O)(c2cc3c(c(-c4ccc(F)c(Cl)c4F)n2)OC[C@]3(C)C(N)=O)C2CC2)cc2cc(Cl)c(C)nc12] | 657.43 |
| 558 | 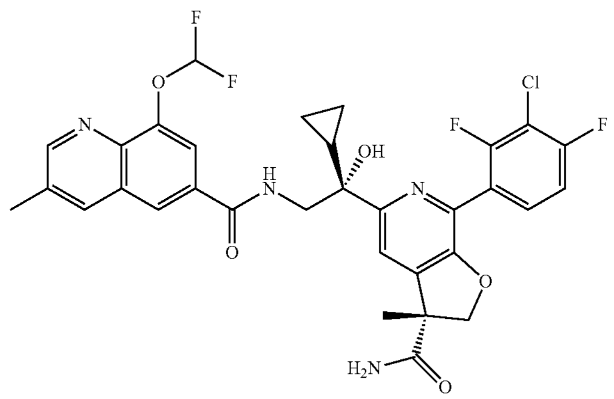 [SMILES: Cc1cnc2c(OC(F)F)cc(C(=O)NC[C@](O)(c3cc4c(c(-c5ccc(F)c(Cl)c5F)n3)OC[C@]4(C)C(N)=O)C3CC3)cc2c1] | 659.42 |

TABLE 5-continued
| Example | Structure | MS+ m/z |
| --- | --- | --- |
| 559 | 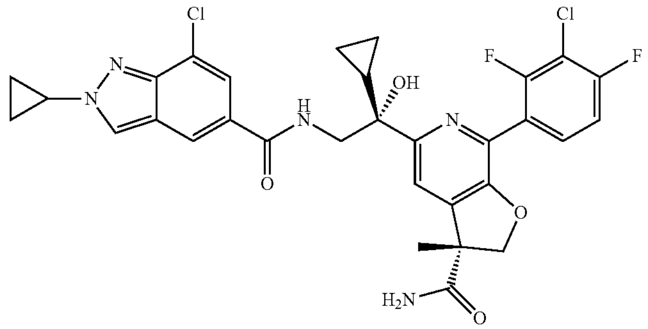 [SMILES: C[C@]1(C(N)=O)COc2c1cc([C@@](O)(CNC(=O)c1cc(Cl)c3nn(C4CC4)cc3c1)C1CC1)nc2-c1ccc(F)c(Cl)c1F] | 642.39 |
| 560 | 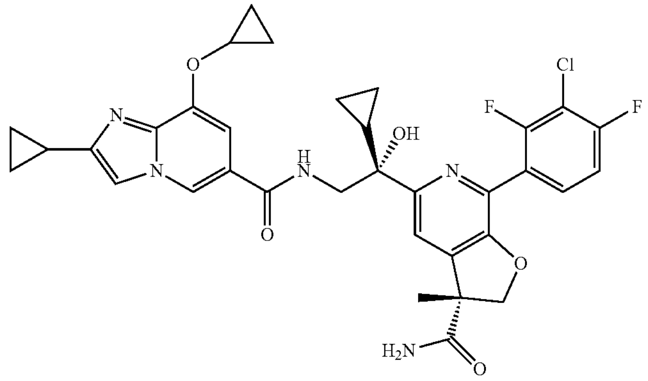 [SMILES: C[C@]1(C(N)=O)COc2c1cc([C@@](O)(CNC(=O)c1cc(OC3CC3)c3nc(C4CC4)cn3c1)C1CC1)nc2-c1ccc(F)c(Cl)c1F] | 664.49 |
| 561 | 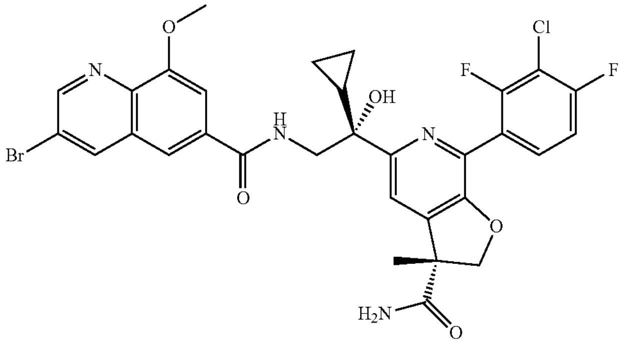 | 687.27 |
| 562 | 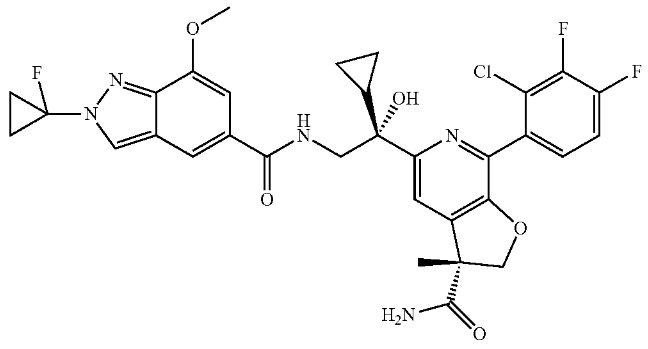 | 656.21 |

TABLE 5-continued
| Example | Structure | MS+ m/z |
|---|---|---|
| 563 | 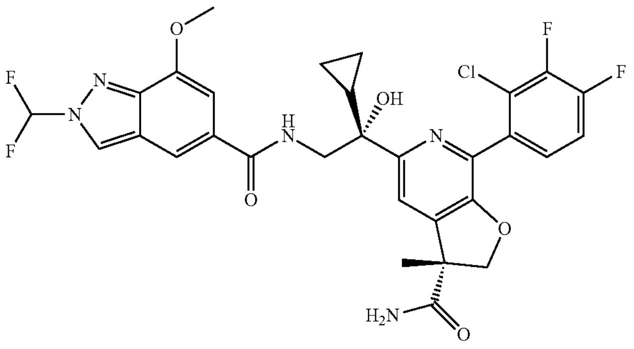 [SMILES: COc1cc(C(=O)NC[C@](O)(c2cc3c(c(-c4ccc(F)c(F)c4Cl)n2)OC[C@]3(C)C(N)=O)C2CC2)cc2cn(C(F)F)nc12] | 648.17 |
| 564 | 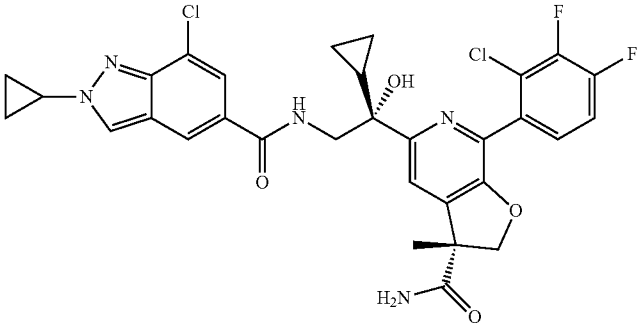 [SMILES: C[C@]1(C(N)=O)COc2c1cc([C@@](O)(CNC(=O)c1cc(Cl)c3nn(C4CC4)cc3c1)C1CC1)nc2-c1ccc(F)c(F)c1Cl] | 642.16 |
| 565 | 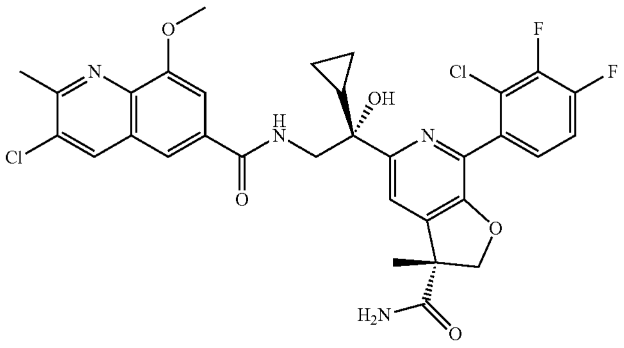 [SMILES: COc1cc(C(=O)NC[C@](O)(c2cc3c(c(-c4ccc(F)c(F)c4Cl)n2)OC[C@]3(C)C(N)=O)C2CC2)cc2cc(Cl)c(C)nc12] | 657.19 |
| 566 | 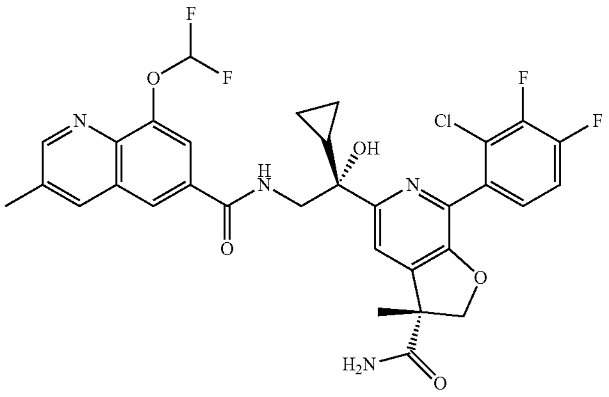 [SMILES: Cc1cnc2c(OC(F)F)cc(C(=O)NC[C@](O)(c3cc4c(c(-c5ccc(F)c(F)c5Cl)n3)OC[C@]4(C)C(N)=O)C3CC3)cc2c1] | 659.20 |

TABLE 5-continued
| Example | Structure | MS+ m/z |
|---|---|---|
| 567 | 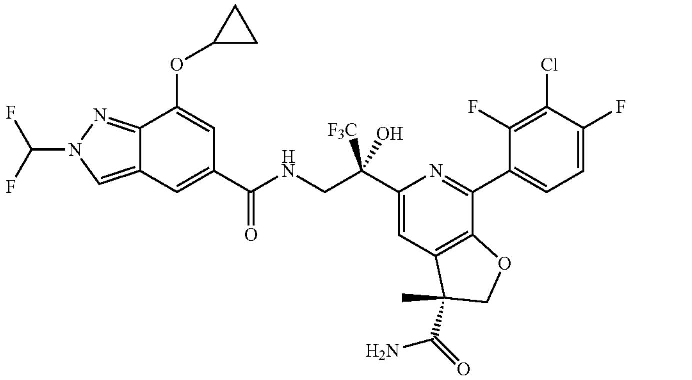 [SMILES: C[C@]1(C(N)=O)COc2c1cc([C@@](O)(CNC(=O)c1cc(OC3CC3)c3nn(C(F)F)cc3c1)C(F)(F)F)nc2-c1ccc(F)c(Cl)c1F] | 702.31 |
| 568 | 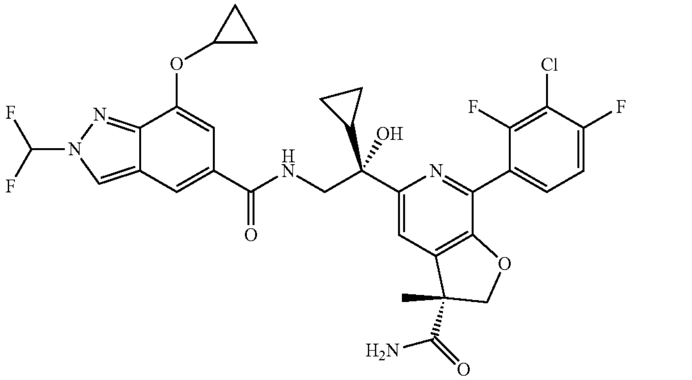 [SMILES: C[C@]1(C(N)=O)COc2c1cc([C@@](O)(CNC(=O)c1cc(OC3CC3)c3nn(C(F)F)cc3c1)C1CC1)nc2-c1ccc(F)c(Cl)c1F] | 674.46 |
| 569 | 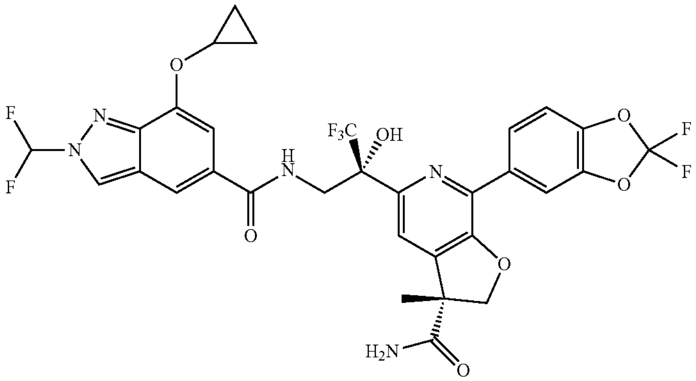 [SMILES: C[C@]1(C(N)=O)COc2c1cc([C@@](O)(CNC(=O)c1cc(OC3CC3)c3nn(C(F)F)cc3c1)C(F)(F)F)nc2-c1ccc2c(c1)OC(F)(F)O2] | 712.42 |
| 570 | 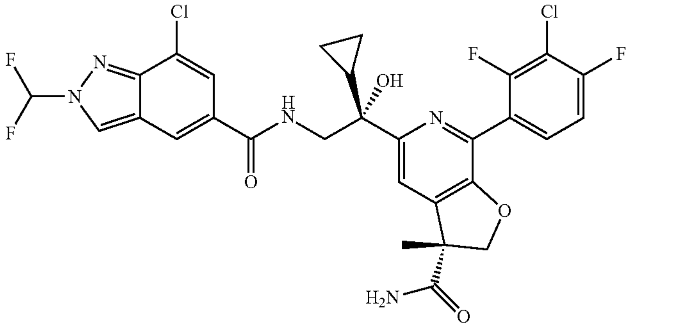 [SMILES: C[C@]1(C(N)=O)COc2c1cc([C@@](O)(CNC(=O)c1cc(Cl)c3nn(C(F)F)cc3c1)C1CC1)nc2-c1ccc(F)c(Cl)c1F] | 652.20 |

TABLE 5-continued
| Example | Structure | MS+ m/z |
|---|---|---|
| 571 | 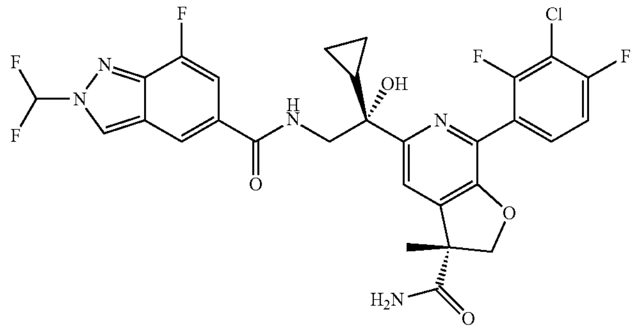 [SMILES: C[C@]1(C(N)=O)COc2c1cc([C@@](O)(CNC(=O)c1cc(F)c3nn(C(F)F)cc3c1)C1CC1)nc2-c1ccc(F)c(Cl)c1F] | 636.26 |
| 572 | 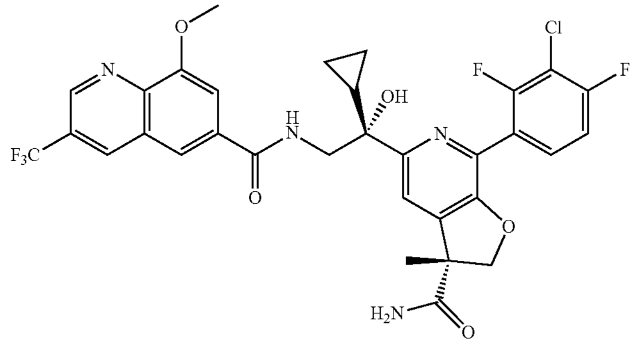 [SMILES: COc1cc(C(=O)NC[C@](O)(c2cc3c(c(-c4ccc(F)c(Cl)c4F)n2)OC[C@]3(C)C(N)=O)C2CC2)cc2cc(C(F)(F)F)cnc12] | 677.32 |
| 573 | 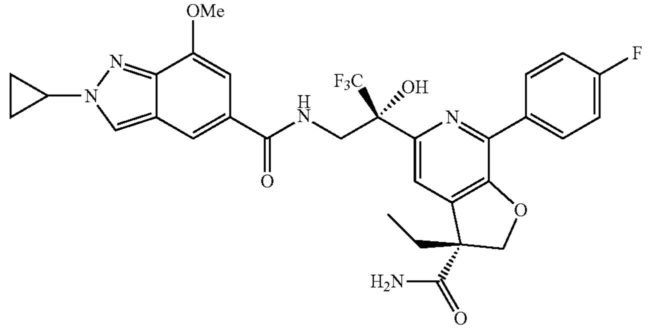 [SMILES: CC[C@]1(C(N)=O)COc2c1cc([C@@](O)(CNC(=O)c1cc(OC)c3nn(C4CC4)cc3c1)C(F)(F)F)nc2-c1ccc(F)cc1] | 627.60 |
| 574 | 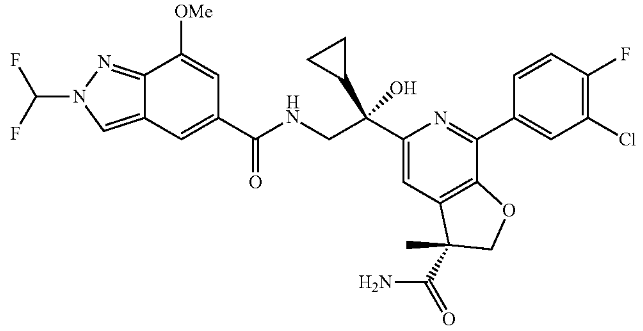 [SMILES: COc1cc(C(=O)NC[C@](O)(c2cc3c(c(-c4ccc(F)c(Cl)c4)n2)OC[C@]3(C)C(N)=O)C2CC2)cc2cn(C(F)F)nc12] | 630.02 |

TABLE 5-continued
| Example | Structure | MS+ m/z |
|---|---|---|
| 575 | 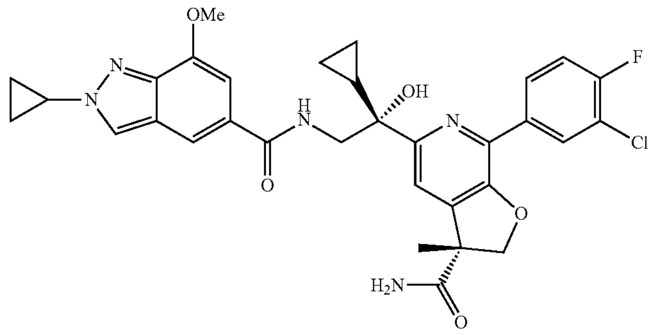 [SMILES: COc1cc(C(=O)NC[C@](O)(c2cc3c(c(-c4ccc(F)c(Cl)c4)n2)OC[C@]3(C)C(N)=O)C2CC2)cc2cn(C3CC3)nc12] | 620.08 |
| 576 | 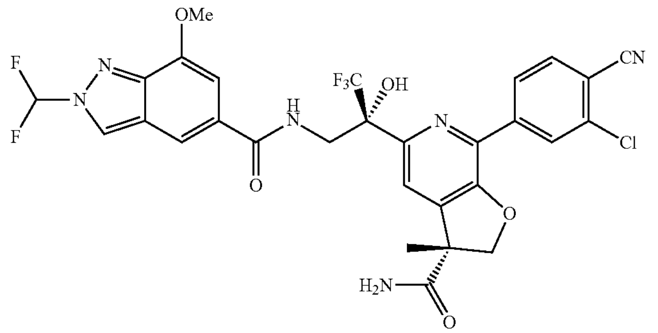 [SMILES: COc1cc(C(=O)NC[C@](O)(c2cc3c(c(-c4ccc(C#N)c(Cl)c4)n2)OC[C@]3(C)C(N)=O)C(F)(F)F)cc2cn(C(F)F)nc12] | 664.97 |
| 577 | 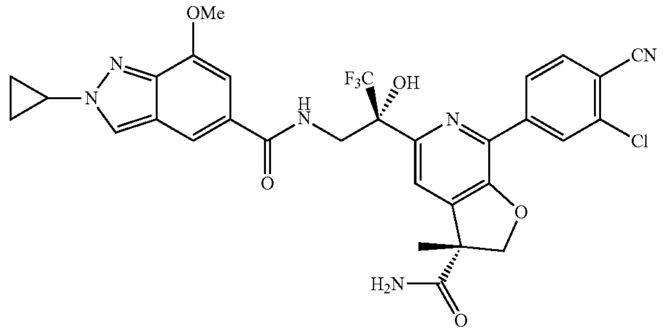 [SMILES: COc1cc(C(=O)NC[C@](O)(c2cc3c(c(-c4ccc(C#N)c(Cl)c4)n2)OC[C@]3(C)C(N)=O)C(F)(F)F)cc2cn(C3CC3)nc12] | 665.03 |
| 578 | 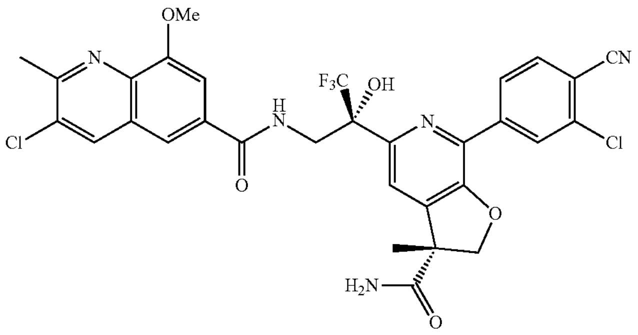 [SMILES: COc1cc(C(=O)NC[C@](O)(c2cc3c(c(-c4ccc(C#N)c(Cl)c4)n2)OC[C@]3(C)C(N)=O)C(F)(F)F)cc2cc(Cl)c(C)nc12] | 674.46 |

TABLE 5-continued
| Example | Structure | MS+ m/z |
|---|---|---|
| 579 | 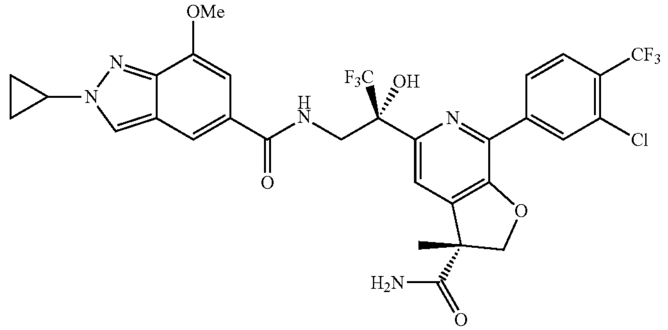 [SMILES: COc1cc(C(=O)NC[C@](O)(c2cc3c(c(-c4ccc(C(F)(F)F)c(Cl)c4)n2)OC[C@]3(C)C(N)=O)C(F)(F)F)cc2cn(C3CC3)nc12] | 698.02 |
| 580 | 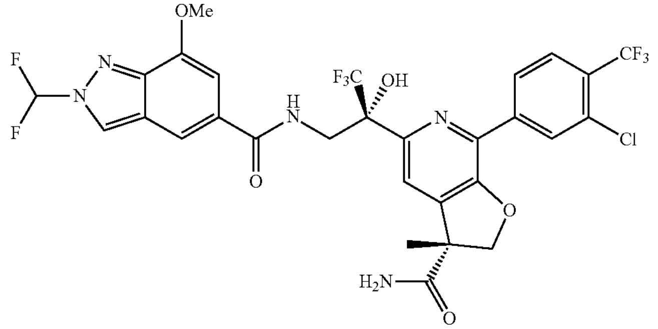 [SMILES: COc1cc(C(=O)NC[C@](O)(c2cc3c(c(-c4ccc(C(F)(F)F)c(Cl)c4)n2)OC[C@]3(C)C(N)=O)C(F)(F)F)cc2cn(C(F)F)nc12] | 707.96 |
| 581 | 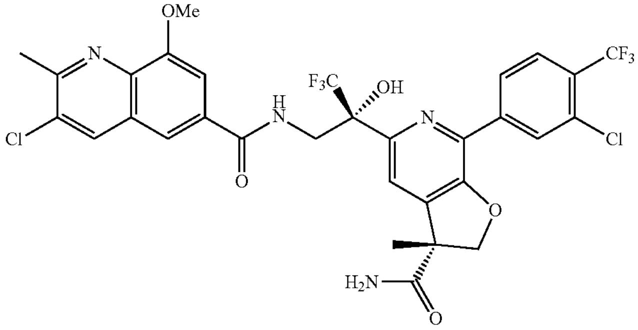 [SMILES: COc1cc(C(=O)NC[C@](O)(c2cc3c(c(-c4ccc(C(F)(F)F)c(Cl)c4)n2)OC[C@]3(C)C(N)=O)C(F)(F)F)cc2cc(Cl)c(C)nc12] | 717.45 |
| 582 | 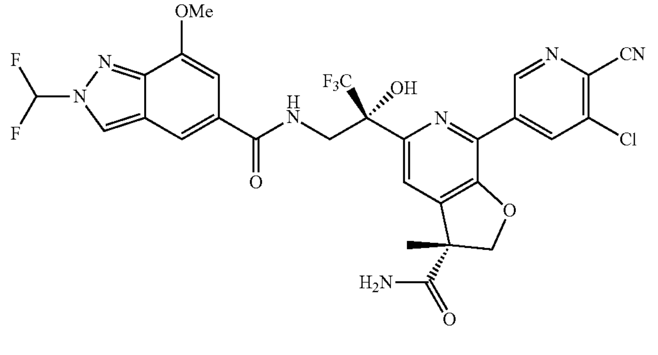 [SMILES: COc1cc(C(=O)NC[C@](O)(c2cc3c(c(-c4cnc(C#N)c(Cl)c4)n2)OC[C@]3(C)C(N)=O)C(F)(F)F)cc2cn(C(F)F)nc12] | 665.96 |

TABLE 5-continued
| Example | Structure | MS+ m/z |
|---|---|---|
| 583 | 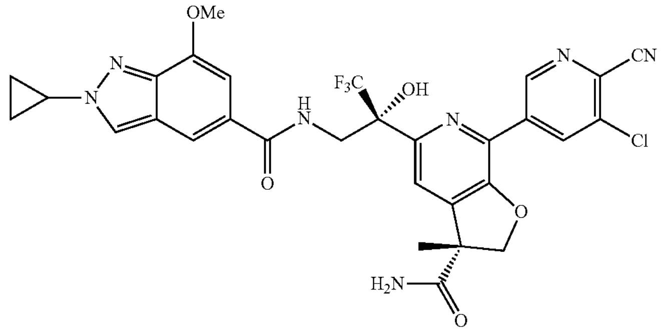 [SMILES: COc1cc(C(=O)NC[C@](O)(c2cc3c(c(-c4cnc(C#N)c(Cl)c4)n2)OC[C@]3(C)C(N)=O)C(F)(F)F)cc2cn(C3CC3)nc12] | 656.02 |
| 584 | 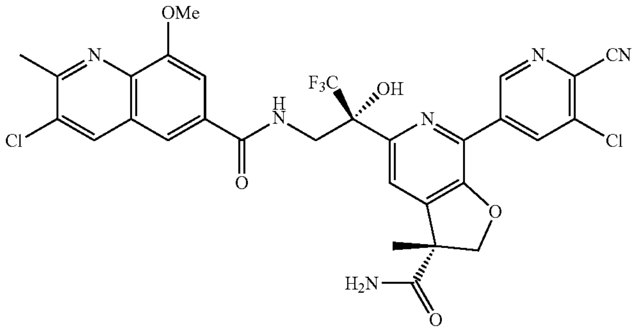 [SMILES: COc1cc(C(=O)NC[C@](O)(c2cc3c(c(-c4cnc(C#N)c(Cl)c4)n2)OC[C@]3(C)C(N)=O)C(F)(F)F)cc2cc(Cl)c(C)nc12] | 675.45 |
| 585 | 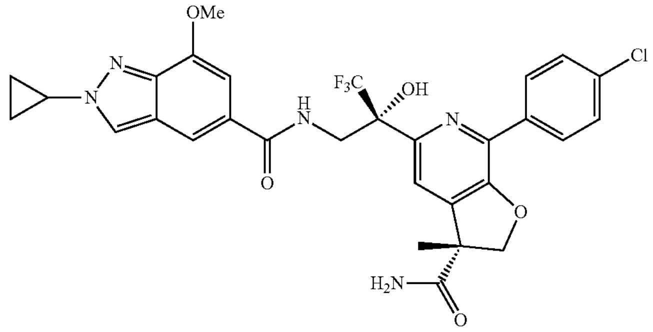 [SMILES: COc1cc(C(=O)NC[C@](O)(c2cc3c(c(-c4ccc(Cl)cc4)n2)OC[C@]3(C)C(N)=O)C(F)(F)F)cc2cn(C3CC3)nc12] | 630.02 |
| 586 | 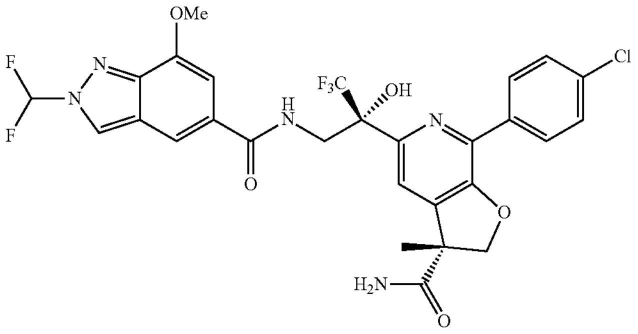 [SMILES: COc1cc(C(=O)NC[C@](O)(c2cc3c(c(-c4ccc(Cl)cc4)n2)OC[C@]3(C)C(N)=O)C(F)(F)F)cc2cn(C(F)F)nc12] | 639.96 |

TABLE 5-continued
| Example | Structure | MS⁺ m/z |
|---|---|---|
| 587 | 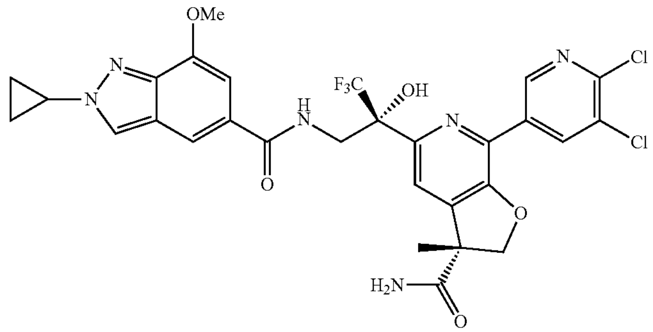 [SMILES: COc1cc(C(=O)NC[C@](O)(c2cc3c(c(-c4cnc(Cl)c(Cl)c4)n2)OC[C@]3(C)C(N)=O)C(F)(F)F)cc2cn(C3CC3)nc12] | 665.45 |
| 588 | 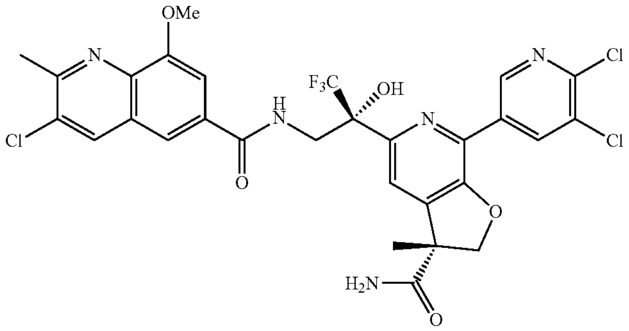 [SMILES: COc1cc(C(=O)NC[C@](O)(c2cc3c(c(-c4cnc(Cl)c(Cl)c4)n2)OC[C@]3(C)C(N)=O)C(F)(F)F)cc2cc(Cl)c(C)nc12] | 684.88 |
| 589 | 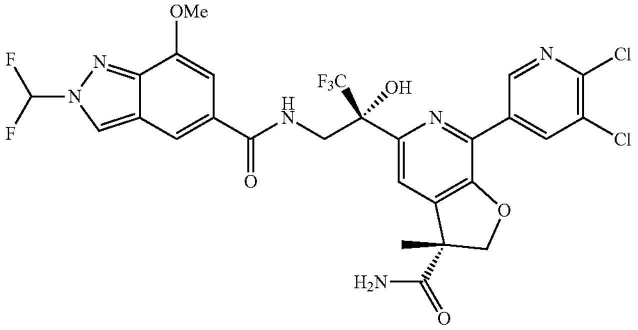 [SMILES: COc1cc(C(=O)NC[C@](O)(c2cc3c(c(-c4cnc(Cl)c(Cl)c4)n2)OC[C@]3(C)C(N)=O)C(F)(F)F)cc2cn(C(F)F)nc12] | 675.39 |
| 590 | 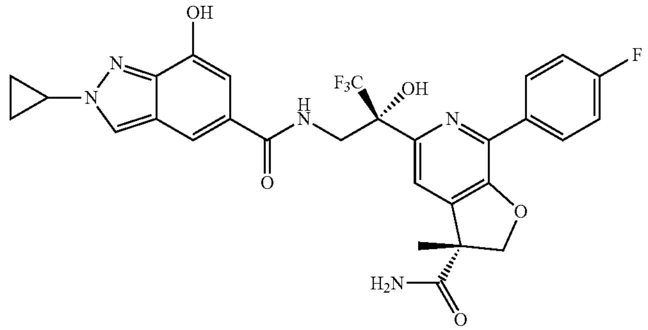 [SMILES: C[C@]1(C(N)=O)COc2c1cc([C@@](O)(CNC(=O)c1cc(O)c3nn(C4CC4)cc3c1)C(F)(F)F)nc2-c1ccc(F)cc1] | 599.54 |

TABLE 5-continued
| Example | Structure | MS+ m/z |
| --- | --- | --- |
| 591 | 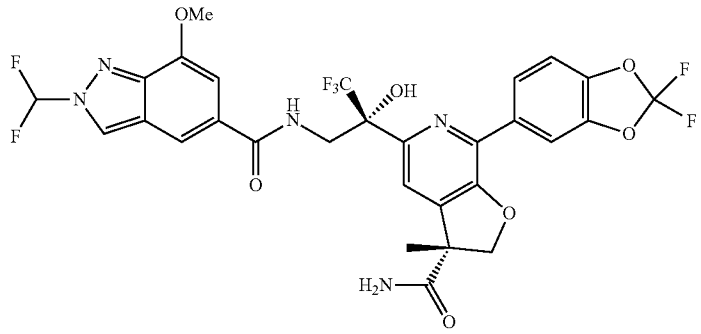 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cn(C(F)F)nc12] | 685.51 |
| 592 | 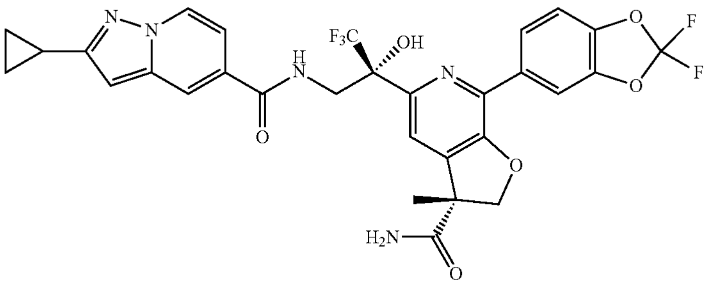 [SMILES: C[C@]1(C(N)=O)COc2c1cc([C@@](O)(CNC(=O)c1ccn3nc(C4CC4)cc3c1)C(F)(F)F)nc2-c1ccc2c(c1)OC(F)(F)O2] | 645.54 |
| 593 | 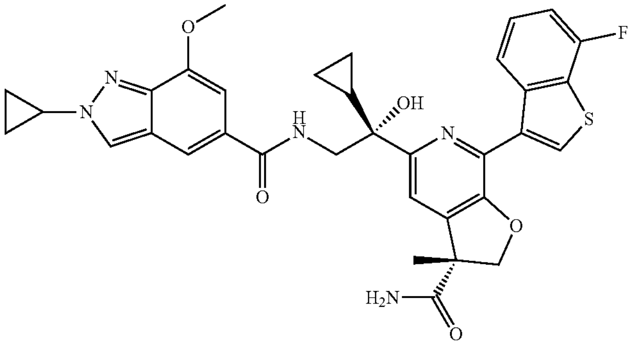 [SMILES: COc1cc(C(=O)NC[C@](O)(c2cc3c(c(-c4csc5c(F)cccc45)n2)OC[C@]3(C)C(N)=O)C2CC2)cc2cn(C3CC3)nc12] | 641.72 |
| 594 | 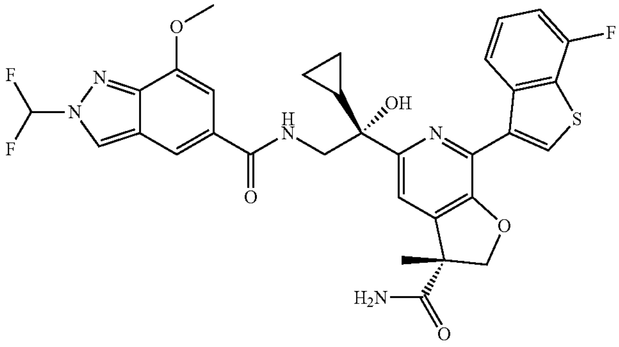 [SMILES: COc1cc(C(=O)NC[C@](O)(c2cc3c(c(-c4csc5c(F)cccc45)n2)OC[C@]3(C)C(N)=O)C2CC2)cc2cn(C(F)F)nc12] | 651.66 |

TABLE 5-continued
| Example | Structure | MS+ m/z |
|---|---|---|
| 595 | 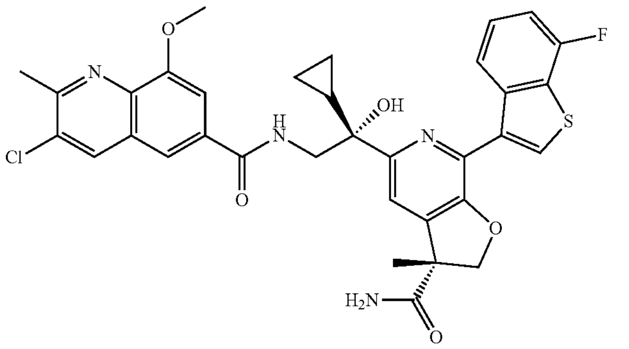 [SMILES: COc1cc(C(=O)NC[C@](O)(c2cc3c(c(-c4csc5c(F)cccc45)n2)OC[C@]3(C)C(N)=O)C2CC2)cc2cc(Cl)c(C)nc12] | 661.15 |
| 596 | 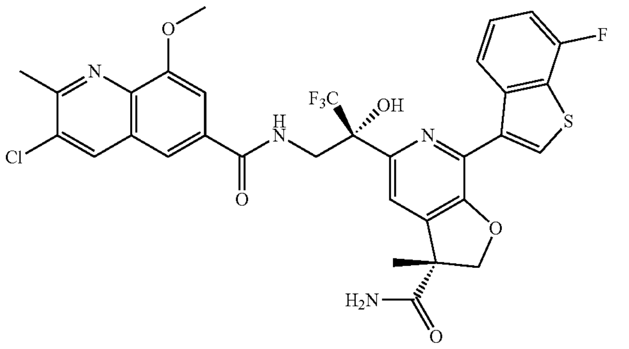 [SMILES: COc1cc(C(=O)NC[C@](O)(c2cc3c(c(-c4csc5c(F)cccc45)n2)OC[C@]3(C)C(N)=O)C(F)(F)F)cc2cc(Cl)c(C)nc12] | 689.08 |
| 597 | 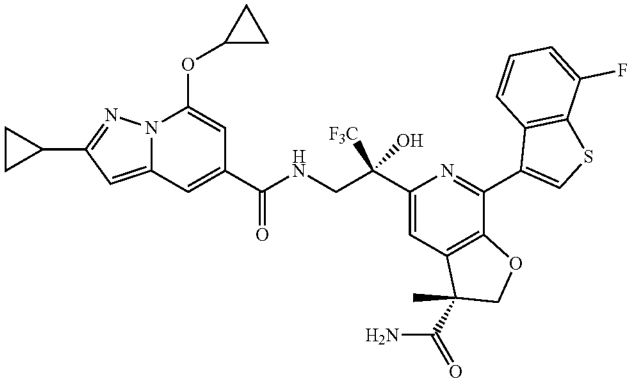 [SMILES: C[C@]1(C(N)=O)COc2c1cc([C@@](O)(CNC(=O)c1cc(OC3CC3)n3nc(C4CC4)cc3c1)C(F)(F)F)nc2-c1csc2c(F)cccc12] | 695.69 |
| 598 | 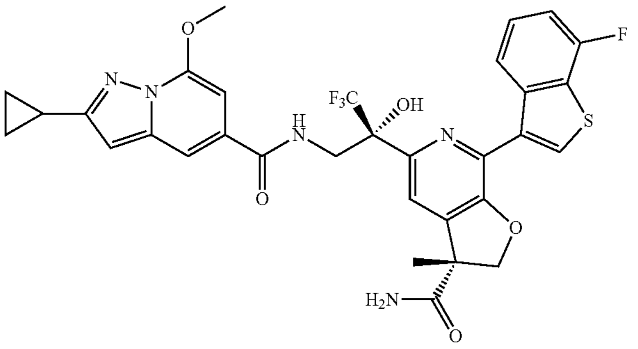 [SMILES: COc1cc(C(=O)NC[C@](O)(c2cc3c(c(-c4csc5c(F)cccc45)n2)OC[C@]3(C)C(N)=O)C(F)(F)F)cc2cc(C3CC3)nn12] | 669.65 |

TABLE 5-continued
| Example | Structure | MS+ m/z |
|---|---|---|
| 599 | 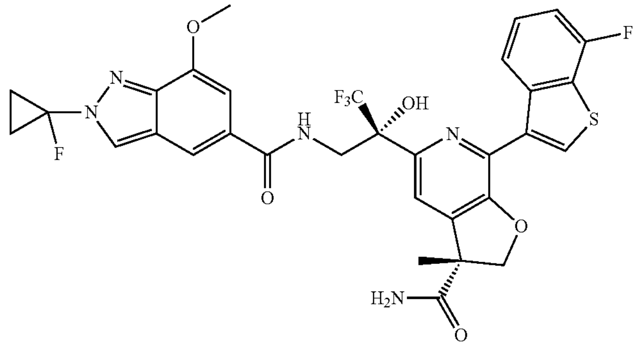 [SMILES: COc1cc(C(=O)NC[C@](O)(c2cc3c(c(-c4csc5c(F)cccc45)n2)OC[C@]3(C)C(N)=O)C(F)(F)F)cc2cn(C3(F)CC3)nc12] | 687.64 |
| 600 | 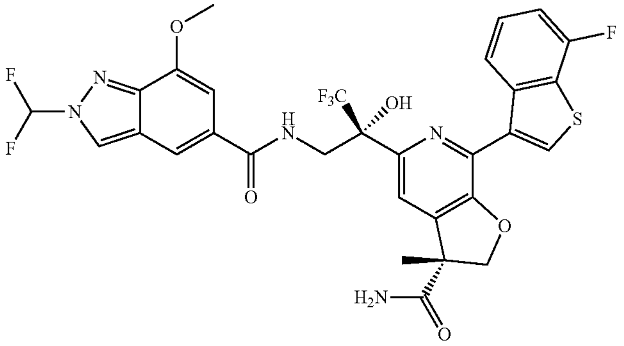 [SMILES: COc1cc(C(=O)NC[C@](O)(c2cc3c(c(-c4csc5c(F)cccc45)n2)OC[C@]3(C)C(N)=O)C(F)(F)F)cc2cn(C(F)F)nc12] | 679.59 |
| 601 | 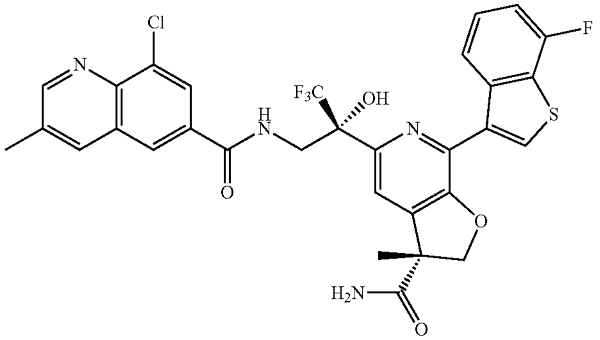 [SMILES: Cc1cnc2c(Cl)cc(C(=O)NC[C@](O)(c3cc4c(c(-c5csc6c(F)cccc56)n3)OC[C@]4(C)C(N)=O)C(F)(F)F)cc2c1] | 659.05 |
| 602 | 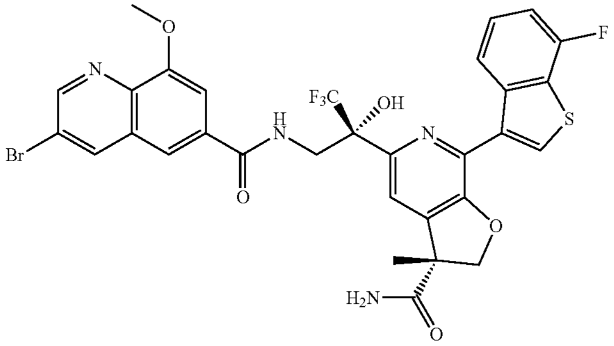 [SMILES: COc1cc(C(=O)NC[C@](O)(c2cc3c(c(-c4csc5c(F)cccc45)n2)OC[C@]3(C)C(N)=O)C(F)(F)F)cc2cc(Br)cnc12] | 719.51 |

TABLE 5-continued
| Example | Structure | MS+ m/z |
|---|---|---|
| 603 | 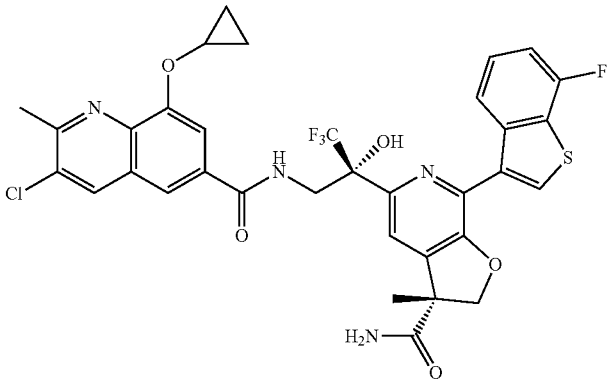 [SMILES: Cc1nc2c(OC3CC3)cc(C(=O)NC[C@](O)(c3cc4c(c(-c5csc6c(F)cccc56)n3)OC[C@]4(C)C(N)=O)C(F)(F)F)cc2cc1Cl] | 715.12 |
| 604 | 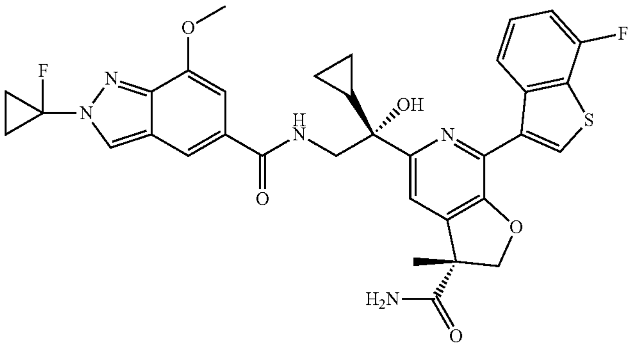 [SMILES: COc1cc(C(=O)NC[C@](O)(c2cc3c(c(-c4csc5c(F)cccc45)n2)OC[C@]3(C)C(N)=O)C2CC2)cc2cn(C3(F)CC3)nc12] | 659.71 |
| 605 | 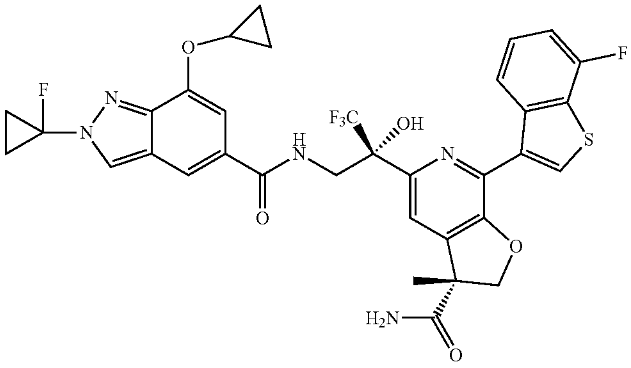 [SMILES: C[C@]1(C(N)=O)COc2c1cc([C@@](O)(CNC(=O)c1cc(OC3CC3)c3nn(C4(F)CC4)cc3c1)C(F)(F)F)nc2-c1csc2c(F)cccc12] | 713.68 |
| 606 | 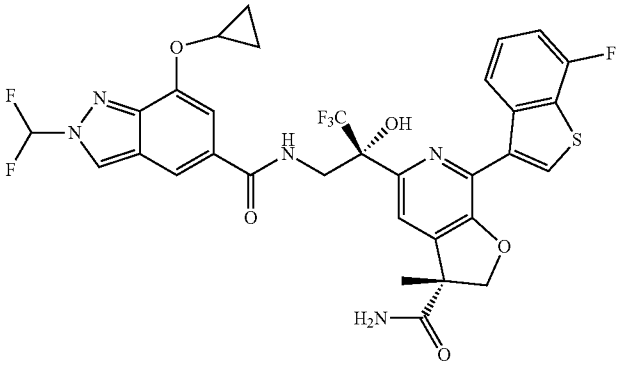 [SMILES: C[C@]1(C(N)=O)COc2c1cc([C@@](O)(CNC(=O)c1cc(OC3CC3)c3nn(C(F)F)cc3c1)C(F)(F)F)nc2-c1csc2c(F)cccc12] | 705.63 |

TABLE 5-continued
| Example | Structure | MS+ m/z |
|---|---|---|
| 607 | 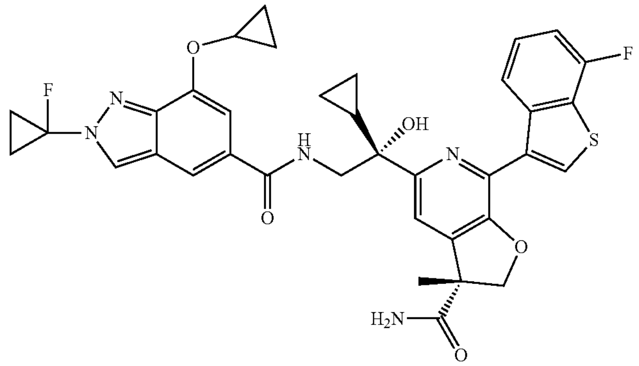 [SMILES: C[C@]1(C(N)=O)COc2c1cc([C@@](O)(CNC(=O)c1cc(OC3CC3)c3nn(C4(F)CC4)cc3c1)C1CC1)nc2-c1csc2c(F)cccc12] | 685.75 |
| 608 | 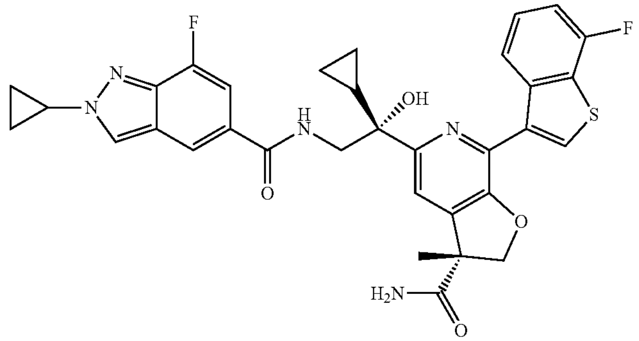 | 629.68 |
| 609 | 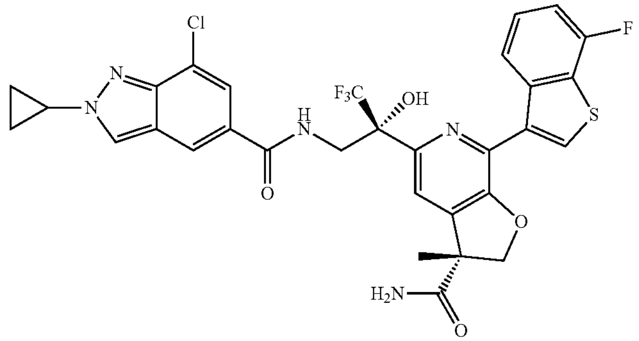 [SMILES: C[C@]1(C(N)=O)COc2c1cc([C@@](O)(CNC(=O)c1cc(Cl)c3nn(C4CC4)cc3c1)C(F)(F)F)nc2-c1csc2c(F)cccc12] | 674.07 |
| 610 | 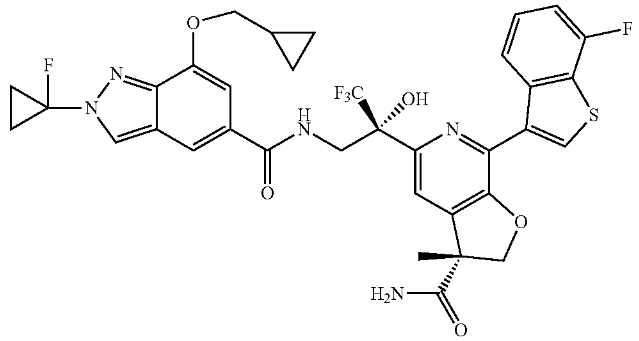 [SMILES: C[C@]1(C(N)=O)COc2c1cc([C@@](O)(CNC(=O)c1cc(OCC3CC3)c3nn(C4(F)CC4)cc3c1)C(F)(F)F)nc2-c1csc2c(F)cccc12] | 727.71 |

TABLE 5-continued
| Example | Structure | MS+ m/z |
|---|---|---|
| 611 | 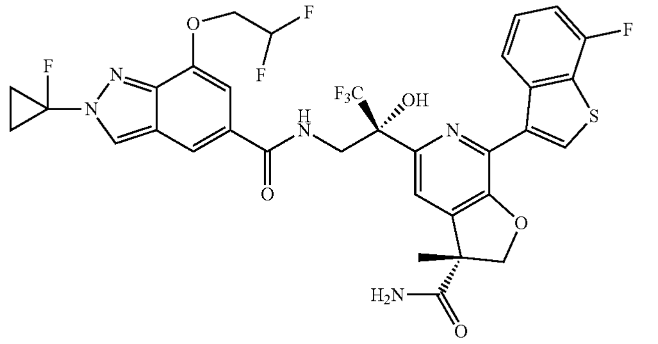 [SMILES: C[C@]1(C(N)=O)COc2c1cc([C@@](O)(CNC(=O)c1cc(OCC(F)F)c3nn(C4(F)CC4)cc3c1)C(F)(F)F)nc2-c1csc2c(F)cccc12] | 737.65 |
| 612 | 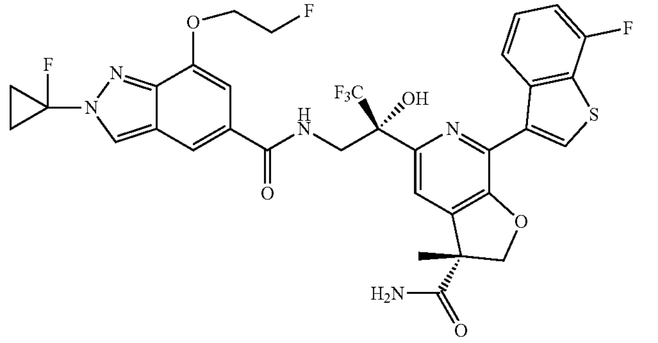 [SMILES: C[C@]1(C(N)=O)COc2c1cc([C@@](O)(CNC(=O)c1cc(OCCF)c3nn(C4(F)CC4)cc3c1)C(F)(F)F)nc2-c1csc2c(F)cccc12] | 719.66 |
| 613 | 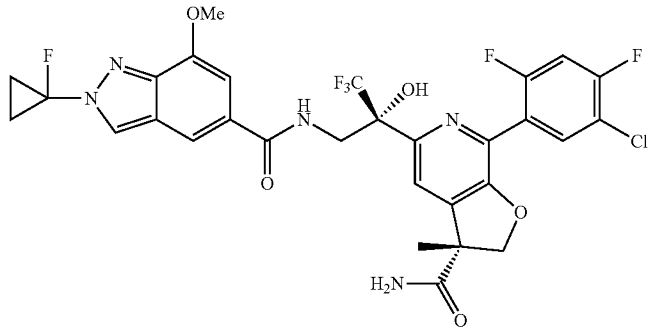 [SMILES: COc1cc(C(=O)NC[C@](O)(c2cc3c(c(-c4cc(Cl)c(F)cc4F)n2)OC[C@]3(C)C(N)=O)C(F)(F)F)cc2cn(C3(F)CC3)nc12] | 683.99 |
| 614 | 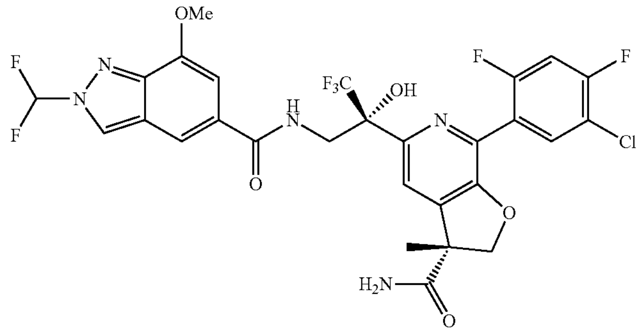 [SMILES: COc1cc(C(=O)NC[C@](O)(c2cc3c(c(-c4cc(Cl)c(F)cc4F)n2)OC[C@]3(C)C(N)=O)C(F)(F)F)cc2cn(C(F)F)nc12] | 675.94 |

TABLE 5-continued
| Example | Structure | MS+ m/z |
|---|---|---|
| 615 | 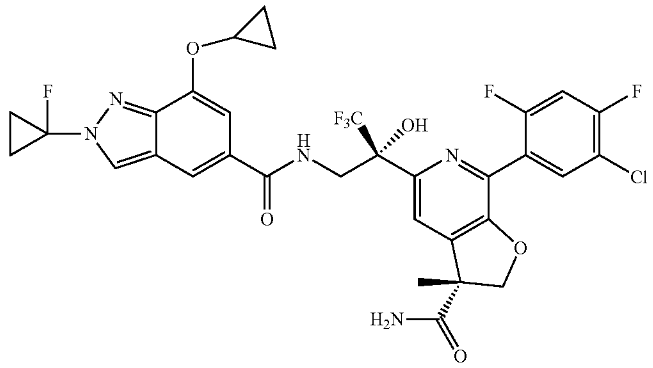 [SMILES: C[C@]1(C(N)=O)COc2c1cc([C@@](O)(CNC(=O)c1cc(OC3CC3)c3nn(C4(F)CC4)cc3c1)C(F)(F)F)nc2-c1cc(Cl)c(F)cc1F] | 710.03 |
| 616 | 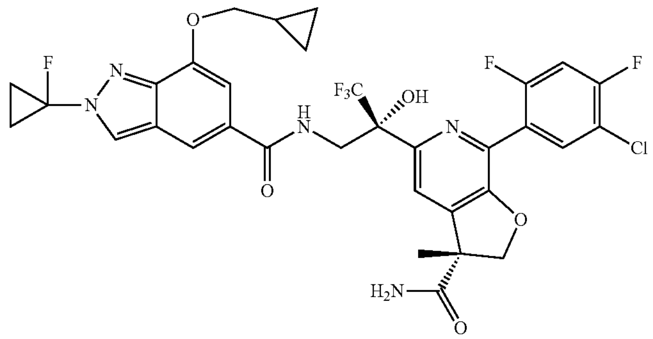 [SMILES: C[C@]1(C(N)=O)COc2c1cc([C@@](O)(CNC(=O)c1cc(OCC3CC3)c3nn(C4(F)CC4)cc3c1)C(F)(F)F)nc2-c1cc(Cl)c(F)cc1F] | 724.06 |
| 617 | 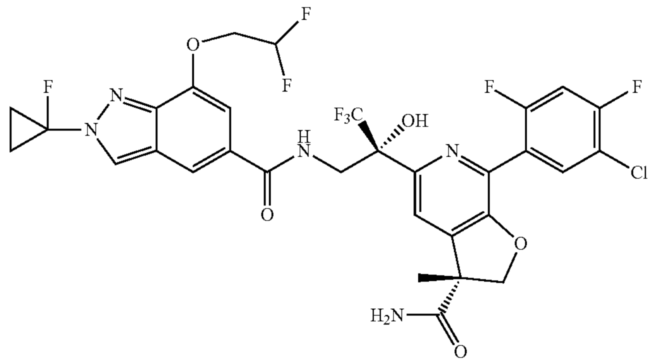 [SMILES: C[C@]1(C(N)=O)COc2c1cc([C@@](O)(CNC(=O)c1cc(OCC(F)F)c3nn(C4(F)CC4)cc3c1)C(F)(F)F)nc2-c1cc(Cl)c(F)cc1F] | 734.00 |
| 618 | 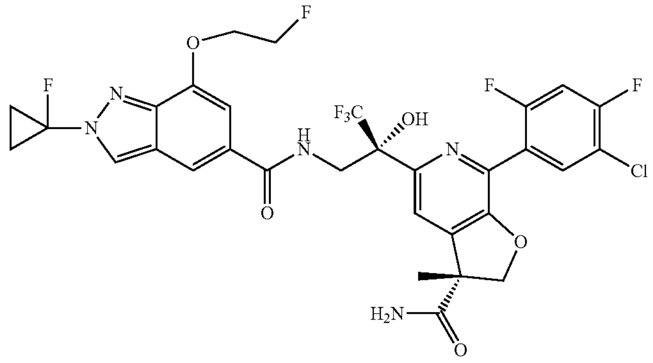 [SMILES: C[C@]1(C(N)=O)COc2c1cc([C@@](O)(CNC(=O)c1cc(OCCF)c3nn(C4(F)CC4)cc3c1)C(F)(F)F)nc2-c1cc(Cl)c(F)cc1F] | 716.01 |

TABLE 5-continued
| Example | Structure | MS+ m/z |
| --- | --- | --- |
| 619 | 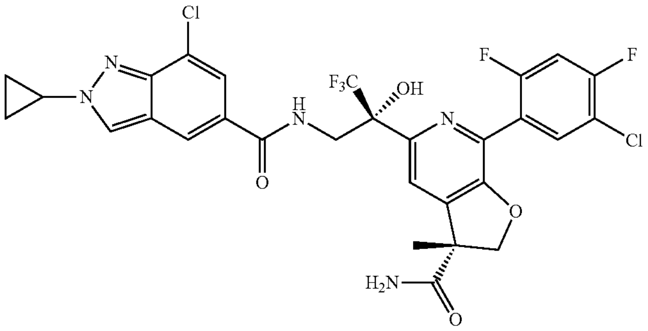 | 670.42 |
| 620 | 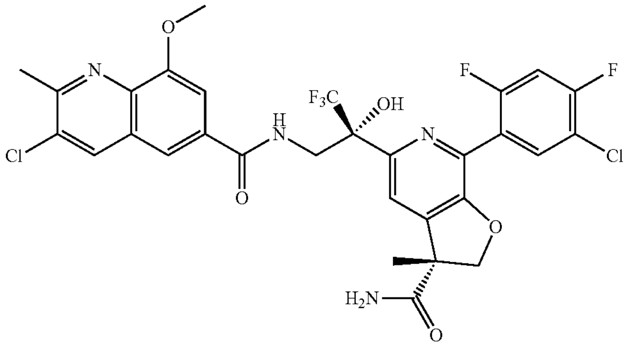 [SMILES: COc1cc(C(=O)NC[C@](O)(c2cc3c(c(-c4cc(Cl)c(F)cc4F)n2)OC[C@]3(C)C(N)=O)C(F)(F)F)cc2cc(Cl)c(C)nc12] | 685.43 |
| 621 | 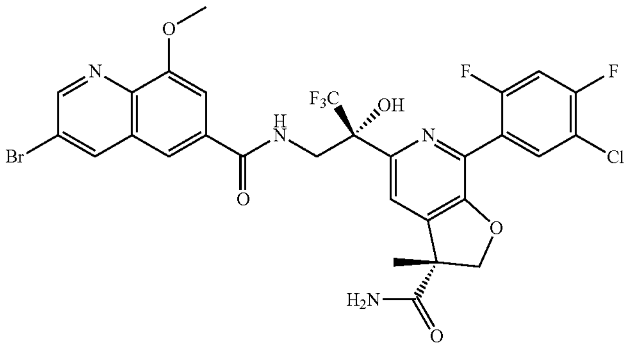 [SMILES: COc1cc(C(=O)NC[C@](O)(c2cc3c(c(-c4cc(Cl)c(F)cc4F)n2)OC[C@]3(C)C(N)=O)C(F)(F)F)cc2cc(Br)cnc12] | 715.86 |
| 622 | 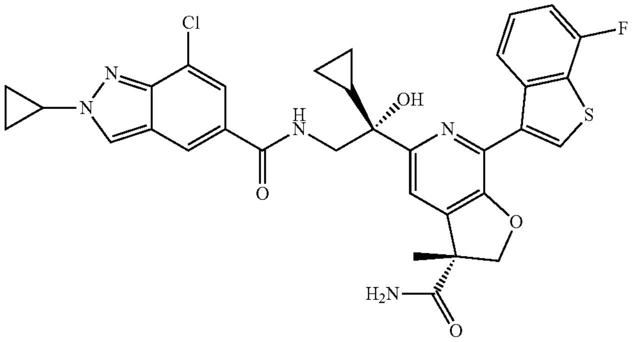 [SMILES: C[C@]1(C(N)=O)COc2c1cc([C@@](O)(CNC(=O)c1cc(Cl)c3nn(C4CC4)cc3c1)C1CC1)nc2-c1csc2c(F)cccc12] | 646.13 |

TABLE 5-continued
| Example | Structure | MS+ m/z |
|---|---|---|
| 623 | 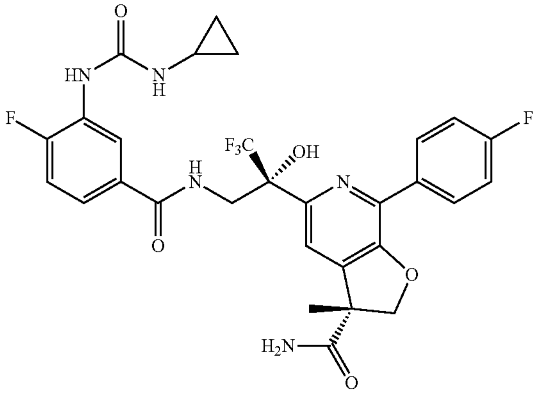 [SMILES: C[C@]1(C(N)=O)COc2c1cc([C@@](O)(CNC(=O)c1ccc(F)c(NC(=O)NC3CC3)c1)C(F)(F)F)nc2-c1ccc(F)cc1] | 620.16 |
| 624 | 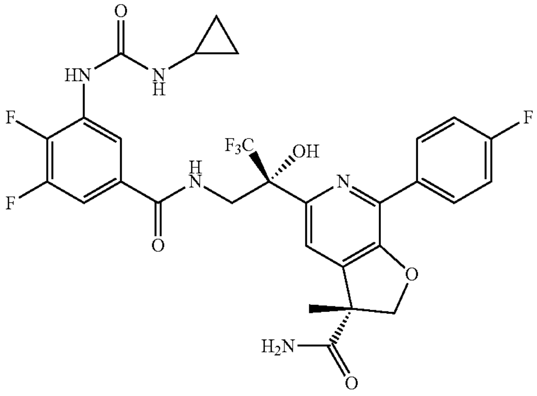 [SMILES: C[C@]1(C(N)=O)COc2c1cc([C@@](O)(CNC(=O)c1cc(F)c(F)c(NC(=O)NC3CC3)c1)C(F)(F)F)nc2-c1ccc(F)cc1] | 637.54 |
| 625 | 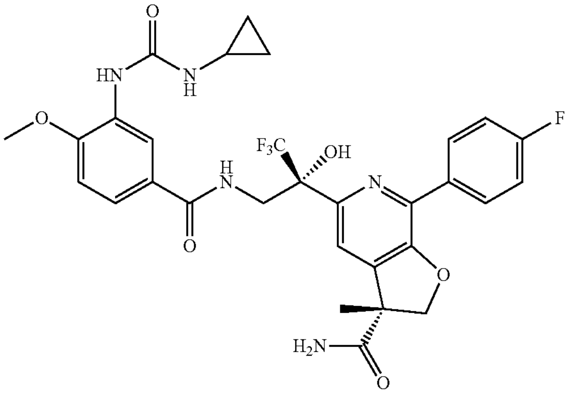 [SMILES: COc1ccc(C(=O)NC[C@](O)(c2cc3c(c(-c4ccc(F)cc4)n2)OC[C@]3(C)C(N)=O)C(F)(F)F)cc1NC(=O)NC1CC1] | 631.58 |
| 626 | 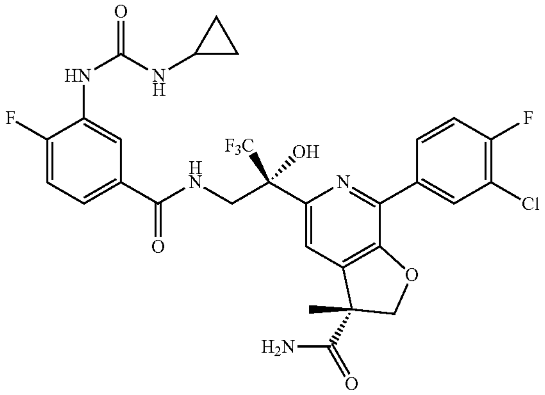 [SMILES: C[C@]1(C(N)=O)COc2c1cc([C@@](O)(CNC(=O)c1ccc(F)c(NC(=O)NC3CC3)c1)C(F)(F)F)nc2-c1ccc(F)c(Cl)c1] | 653.99 |

TABLE 5-continued
| Example | Structure | MS+ m/z |
| --- | --- | --- |
| 627 | 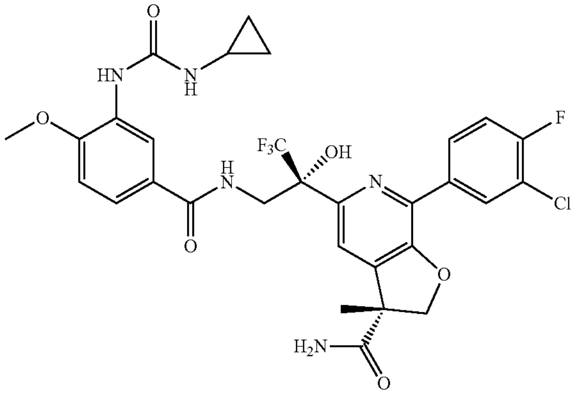 [SMILES: COc1ccc(C(=O)NC[C@](O)(c2cc3c(c(-c4ccc(F)c(Cl)c4)n2)OC[C@]3(C)C(N)=O)C(F)(F)F)cc1NC(=O)NC1CC1] | 666.03 |
| 628 | 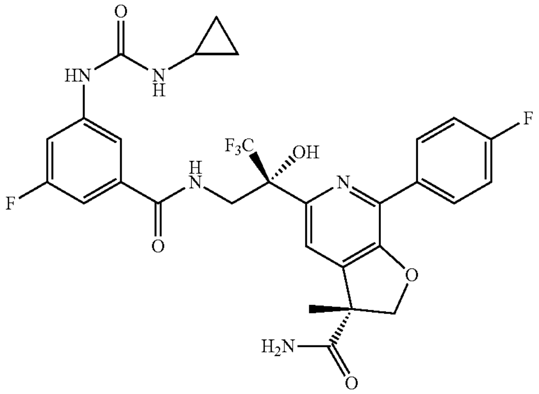 [SMILES: C[C@]1(C(N)=O)COc2c1cc([C@@](O)(CNC(=O)c1cc(F)cc(NC(=O)NC3CC3)c1)C(F)(F)F)nc2-c1ccc(F)cc1] | 619.55 |
| 629 | 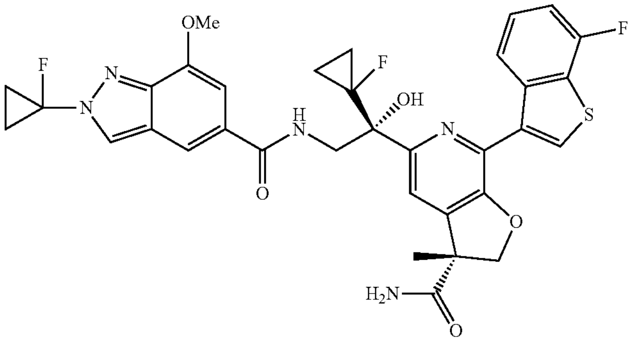 [SMILES: COc1cc(C(=O)NC[C@](O)(c2cc3c(c(-c4csc5c(F)cccc45)n2)OC[C@]3(C)C(N)=O)C2(F)CC2)cc2cn(C3(F)CC3)nc12] | 677.70 |
| 630 | 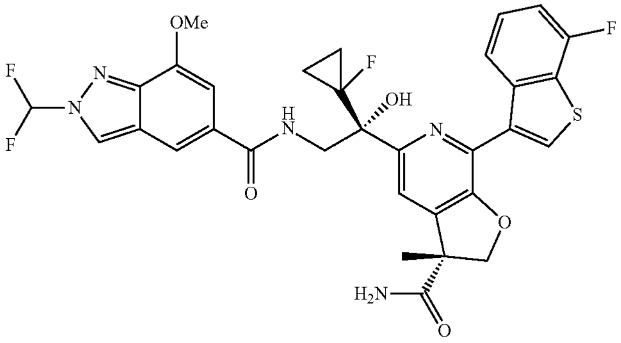 [SMILES: COc1cc(C(=O)NC[C@](O)(c2cc3c(c(-c4csc5c(F)cccc45)n2)OC[C@]3(C)C(N)=O)C2(F)CC2)cc2cn(C(F)F)nc12] | 669.65 |

TABLE 5-continued
| Example | Structure | MS+ m/z |
|---|---|---|
| 631 | 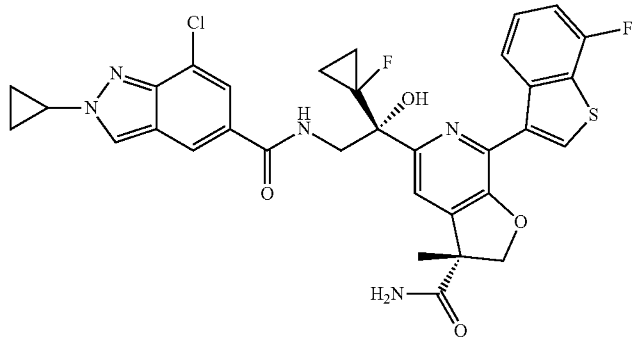 [SMILES: C[C@]1(C(N)=O)COc2c1cc([C@@](O)(CNC(=O)c1cc(Cl)c3nn(C4CC4)cc3c1)C1(F)CC1)nc2-c1csc2c(F)cccc12] | 664.12 |
| 632 | 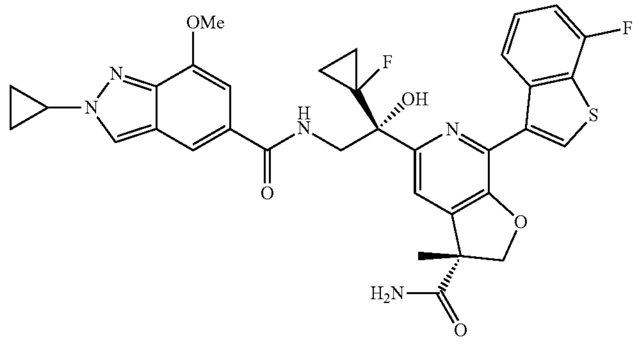 [SMILES: COc1cc(C(=O)NC[C@](O)(c2cc3c(c(-c4csc5c(F)cccc45)n2)OC[C@]3(C)C(N)=O)C2(F)CC2)cc2cn(C3CC3)nc12] | 659.71 |
| 633 | 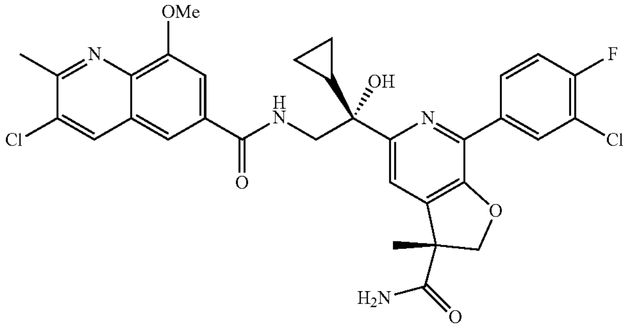 [SMILES: COc1cc(C(=O)NC[C@](O)(c2cc3c(c(-c4ccc(F)c(Cl)c4)n2)OC[C@]3(C)C(N)=O)C2CC2)cc2cc(Cl)c(C)nc12] | 638.90 |
| 634 | 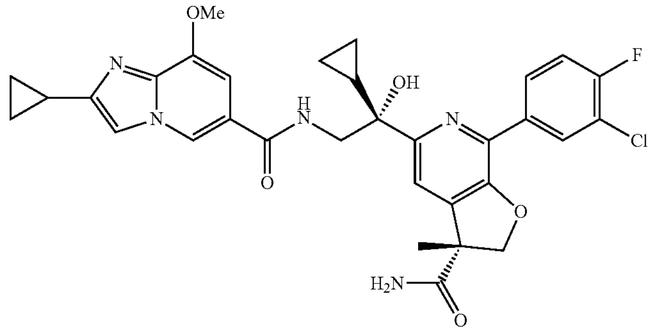 [SMILES: COc1cc(C(=O)NC[C@](O)(c2cc3c(c(-c4ccc(F)c(Cl)c4)n2)OC[C@]3(C)C(N)=O)C2CC2)cn2cc(C3CC3)nc12] | 620.83 |

TABLE 5-continued
| Example | Structure | MS+ m/z |
|---|---|---|
| 635 | 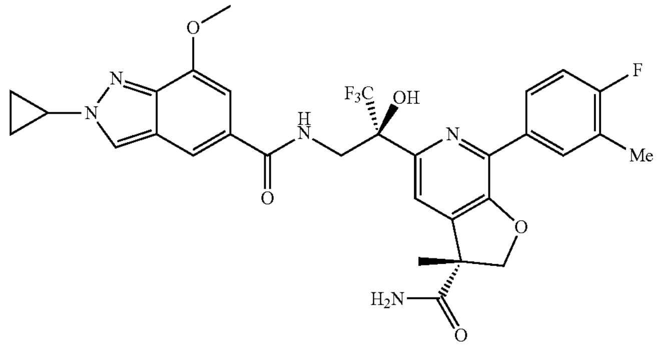 [SMILES: COc1cc(C(=O)NC[C@@](O)(c2cc3c(c(-c4ccc(F)c(C)c4)n2)OC[C@]3(C)C(N)=O)C(F)(F)F)cc2cn(C3CC3)nc12] | 627.96 |
| 636 | 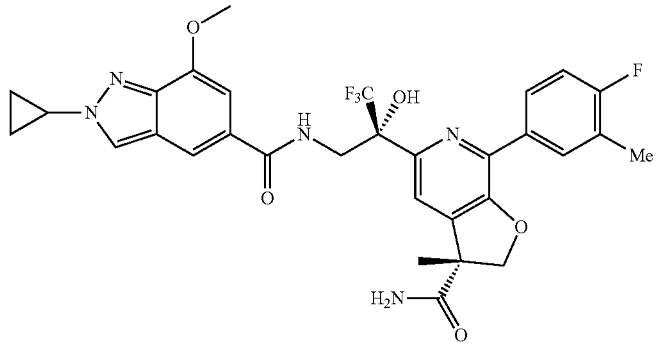 [SMILES: COc1cc(C(=O)NC[C@](O)(c2cc3c(c(-c4ccc(F)c(C)c4)n2)OC[C@]3(C)C(N)=O)C(F)(F)F)cc2cn(C3CC3)nc12] | 628.10 |
| 637 | 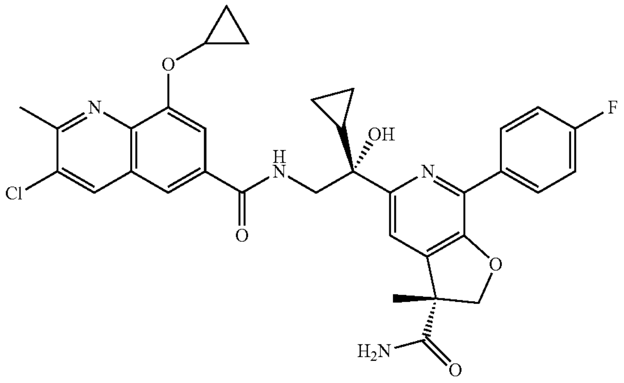 [SMILES: Cc1nc2c(OC3CC3)cc(C(=O)NC[C@](O)(c3cc4c(c(-c5ccc(F)cc5)n3)OC[C@]4(C)C(N)=O)C3CC3)cc2cc1Cl] | 631.25 |
| 638 | 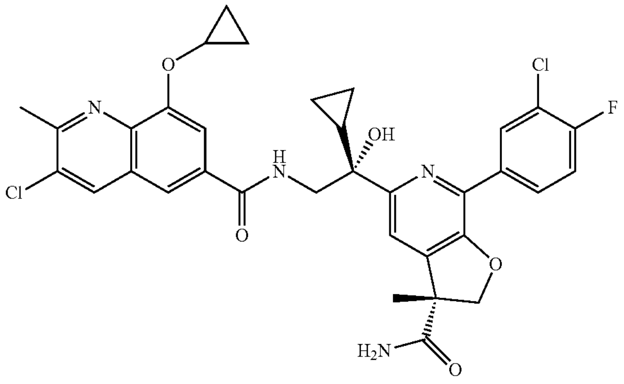 [SMILES: Cc1nc2c(OC3CC3)cc(C(=O)NC[C@](O)(c3cc4c(c(-c5ccc(F)c(Cl)c5)n3)OC[C@]4(C)C(N)=O)C3CC3)cc2cc1Cl] | 665.01 |

TABLE 5-continued
| Example | Structure | MS⁺ m/z |
|---|---|---|
| 639 | 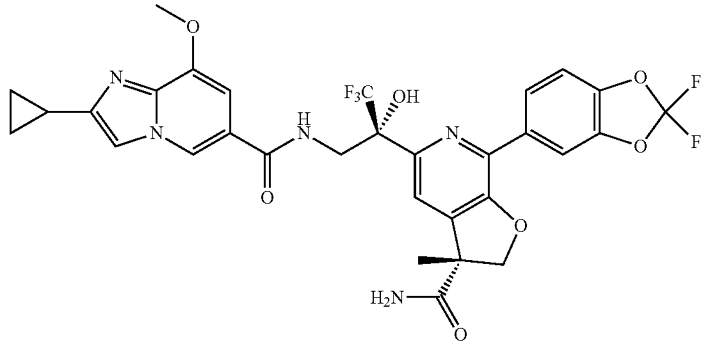 [SMILES: COc1cc(C(=O)NC[C@](O)(c2cc3c(c(-c4ccc5c(c4)OC(F)(F)O5)n2)OC[C@]3(C)C(N)=O)C(F)(F)F)cn2cc(C3CC3)nc12] | 676.38 |
| 640 | 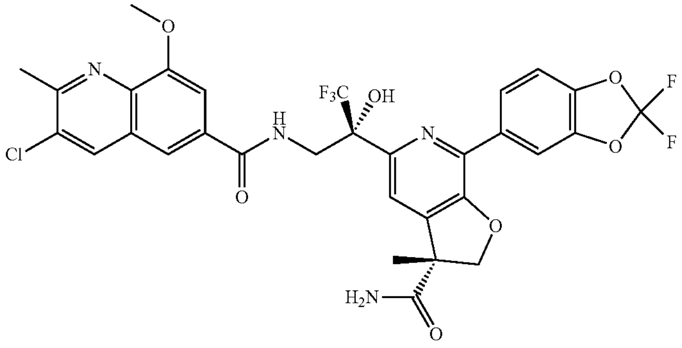 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(Cl)c(C)nc12] | 695.05 |
| 641 | 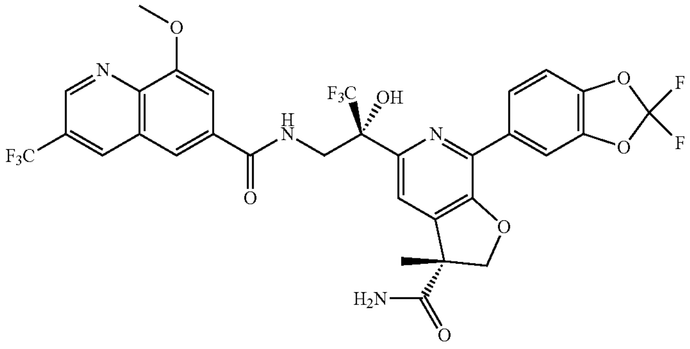 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(C(F)(F)F)cnc12] | 695.05 |
| 642 | 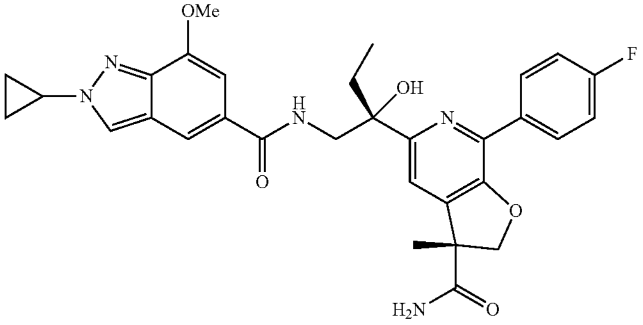 [SMILES: CC[C@](O)(CNC(=O)c1cc(OC)c2nn(C3CC3)cc2c1)c1cc2c(c(-c3ccc(F)cc3)n1)OC[C@]2(C)C(N)=O] | 574.48 |

TABLE 5-continued
| Example | Structure | MS+ m/z |
|---|---|---|
| 643 | 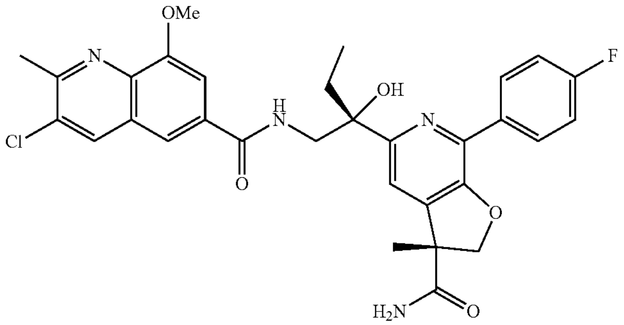 [SMILES: CC[C@](O)(CNC(=O)c1cc(OC)c2nc(C)c(Cl)cc2c1)c1cc2c(c(-c3ccc(F)cc3)n1)OC[C@]2(C)C(N)=O] | 593.48 |
| 644 | 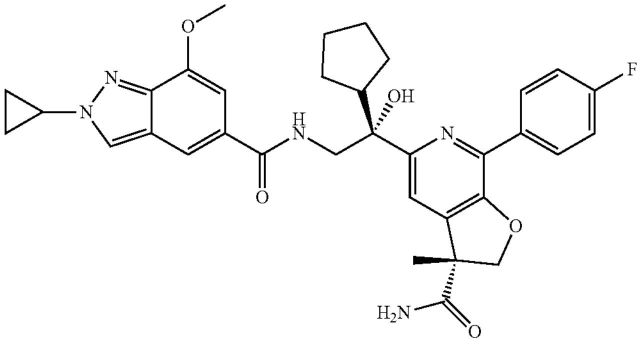 [SMILES: COc1cc(C(=O)NC[C@](O)(c2cc3c(c(-c4ccc(F)cc4)n2)OC[C@]3(C)C(N)=O)C2CCCC2)cc2cn(C3CC3)nc12] | 615.53 |
| 645 | 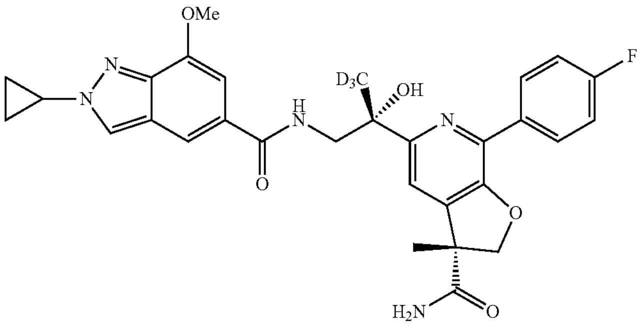 [SMILES: [2H]C([2H])([2H])[C@](O)(CNC(=O)c1cc(OC)c2nn(C3CC3)cc2c1)c1cc2c(c(-c3ccc(F)cc3)n1)OC[C@]2(C)C(N)=O] | 563.56 |
| 646 | 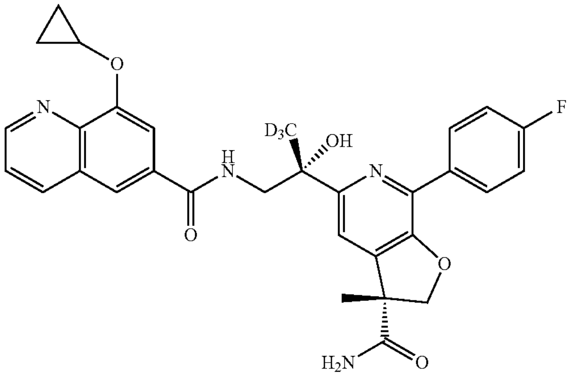 [SMILES: [2H]C([2H])([2H])[C@](O)(CNC(=O)c1cc(OC2CC2)c2ncccc2c1)c1cc2c(c(-c3ccc(F)cc3)n1)OC[C@]2(C)C(N)=O] | 560.52 |

TABLE 5-continued
| Example | Structure | MS+ m/z |
|---|---|---|
| 647 | 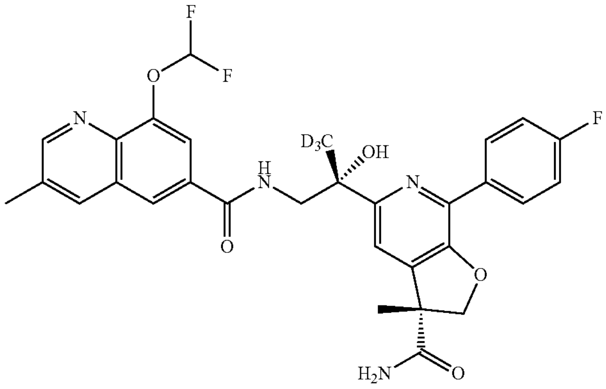 [SMILES: [2H]C([2H])([2H])[C@](O)(CNC(=O)c1cc(OC(F)F)c2ncc(C)cc2c1)c1cc2c(c(-c3ccc(F)cc3)n1)OC[C@]2(C)C(N)=O] | 582.55 |
| 648 | 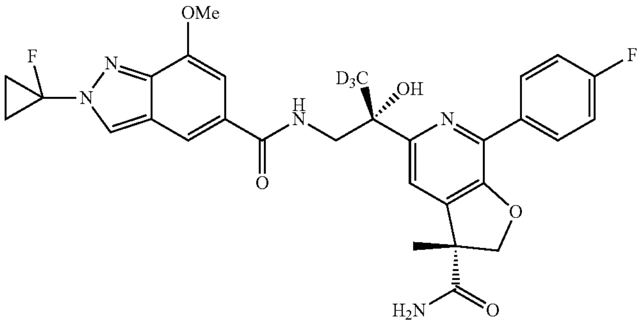 [SMILES: [2H]C([2H])([2H])[C@](O)(CNC(=O)c1cc(OC)c2nn(C3(F)CC3)cc2c1)c1cc2c(c(-c3ccc(F)cc3)n1)OC[C@]2(C)C(N)=O] | 584.51 |
| 649 | 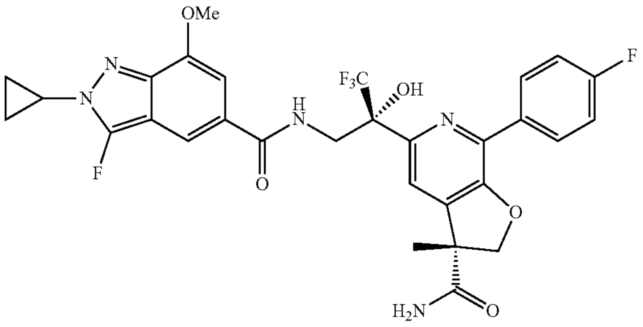 [SMILES: COc1cc(C(=O)NC[C@](O)(c2cc3c(c(-c4ccc(F)cc4)n2)OC[C@]3(C)C(N)=O)C(F)(F)F)cc2c(F)n(C3CC3)nc12] | 632.46 |
| 650 | 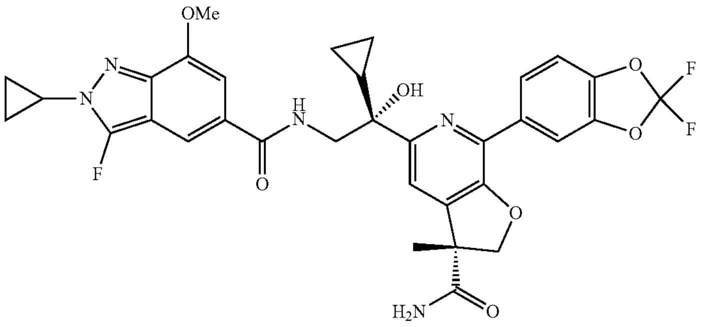 [SMILES: COc1cc(C(=O)NC[C@](O)(c2cc3c(c(-c4ccc5c(c4)OC(F)(F)O5)n2)OC[C@]3(C)C(N)=O)C2CC2)cc2c(F)n(C3CC3)nc12] | 666.52 |

TABLE 5-continued
| Example | Structure | MS⁺ m/z |
|---|---|---|
| 651 | 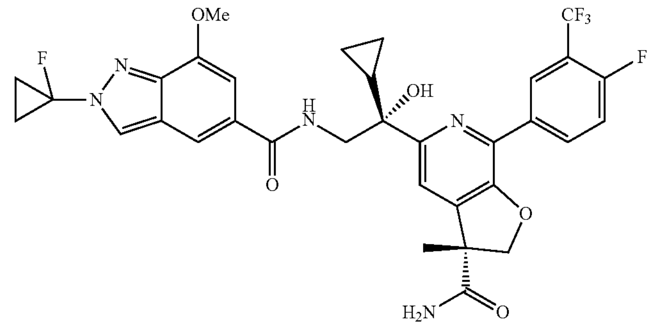 [SMILES: COc1cc(C(=O)NC[C@](O)(c2cc3c(c(-c4ccc(F)c(C(F)(F)F)c4)n2)OC[C@]3(C)C(N)=O)C2CC2)cc2cn(C3(F)CC3)nc12] | 672.51 |
| 652 | 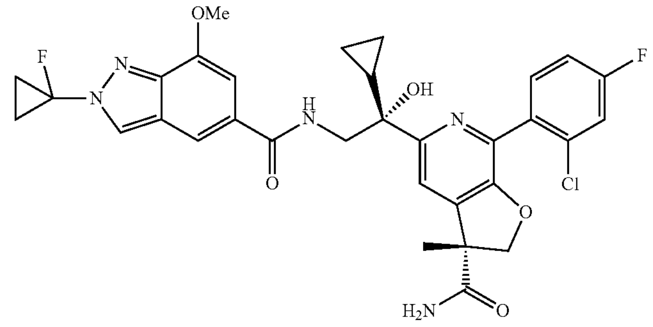 [SMILES: COc1cc(C(=O)NC[C@](O)(c2cc3c(c(-c4ccc(F)cc4Cl)n2)OC[C@]3(C)C(N)=O)C2CC2)cc2cn(C3(F)CC3)nc12] | 638.45 |
| 653 | 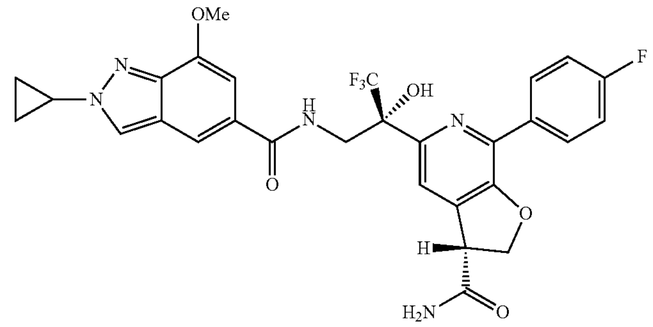 [SMILES: COc1cc(C(=O)NC[C@](O)(c2cc3c(c(-c4ccc(F)cc4)n2)OC[C@@H]3C(N)=O)C(F)(F)F)cc2cn(C3CC3)nc12] | 600.46 |
| 654 | 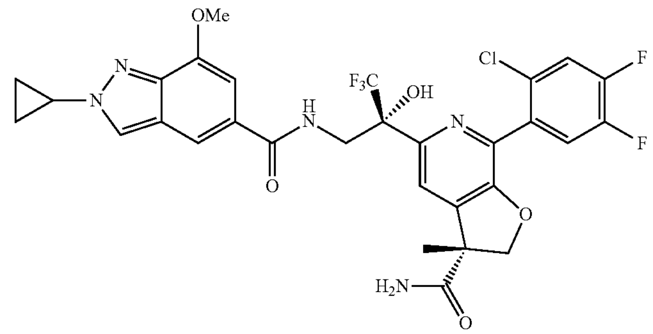 [SMILES: COc1cc(C(=O)NC[C@](O)(c2cc3c(c(-c4cc(F)c(F)cc4Cl)n2)OC[C@]3(C)C(N)=O)C(F)(F)F)cc2cn(C3CC3)nc12] | 666.42 |

TABLE 5-continued
| Example | Structure | MS+ m/z |
|---|---|---|
| 655 | 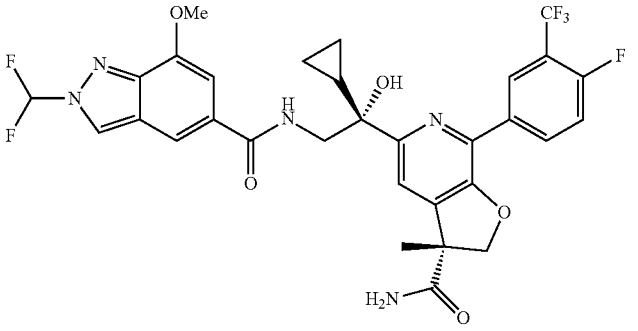 [SMILES: COc1cc(C(=O)NC[C@](O)(c2cc3c(c(-c4ccc(F)c(C(F)(F)F)c4)n2)OC[C@]3(C)C(N)=O)C2CC2)cc2cn(C(F)F)nc12] | 664.44 |
| 656 | 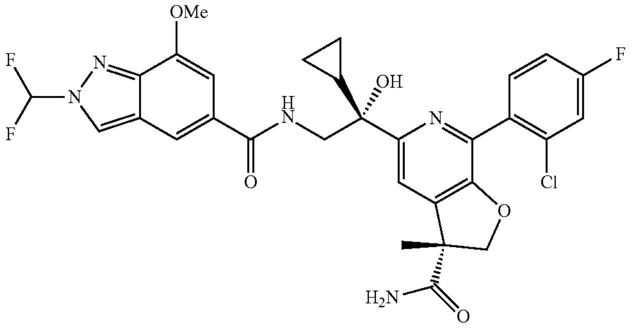 [SMILES: COc1cc(C(=O)NC[C@](O)(c2cc3c(c(-c4ccc(F)cc4Cl)n2)OC[C@]3(C)C(N)=O)C2CC2)cc2cn(C(F)F)nc12] | 630.40 |
| 657 | 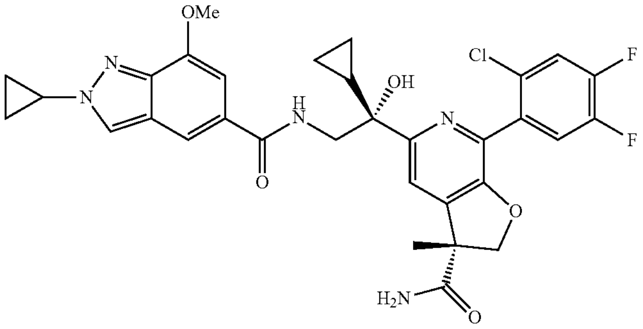 [SMILES: COc1cc(C(=O)NC[C@](O)(c2cc3c(c(-c4cc(F)c(F)cc4Cl)n2)OC[C@]3(C)C(N)=O)C2CC2)cc2cn(C3CC3)nc12] | 630.40 |
| 658 | 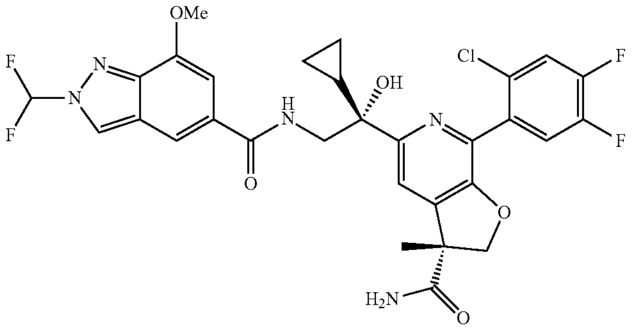 [SMILES: COc1cc(C(=O)NC[C@](O)(c2cc3c(c(-c4cc(F)c(F)cc4Cl)n2)OC[C@]3(C)C(N)=O)C2CC2)cc2cn(C(F)F)nc12] | 648.43 |

TABLE 5-continued
| Example | Structure | MS+ m/z |
|---|---|---|
| 659 | 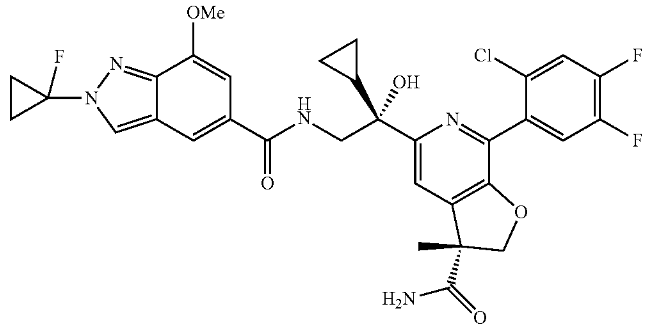 [SMILES: COc1cc(C(=O)NC[C@](O)(c2cc3c(c(-c4cc(F)c(F)cc4Cl)n2)OC[C@]3(C)C(N)=O)C2CC2)cc2cn(C3(F)CC3)nc12] | 656.47 |
| 660 | 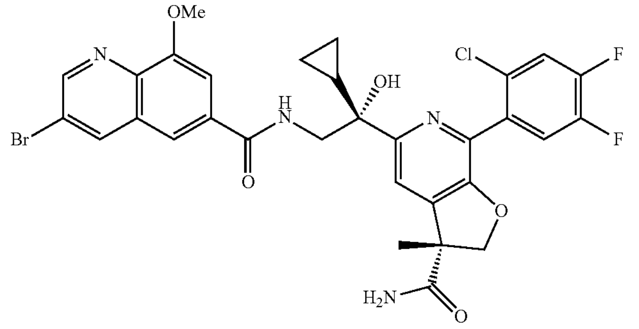 [SMILES: COc1cc(C(=O)NC[C@](O)(c2cc3c(c(-c4cc(F)c(F)cc4Cl)n2)OC[C@]3(C)C(N)=O)C2CC2)cc2cc(Br)cnc12] | 687.28 |
| 661 | 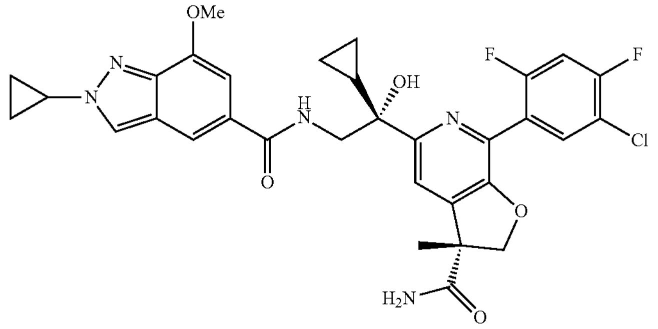 [SMILES: COc1cc(C(=O)NC[C@](O)(c2cc3c(c(-c4cc(Cl)c(F)cc4F)n2)OC[C@]3(C)C(N)=O)C2CC2)cc2cn(C3CC3)nc12] | 638.47 |
| 662 | 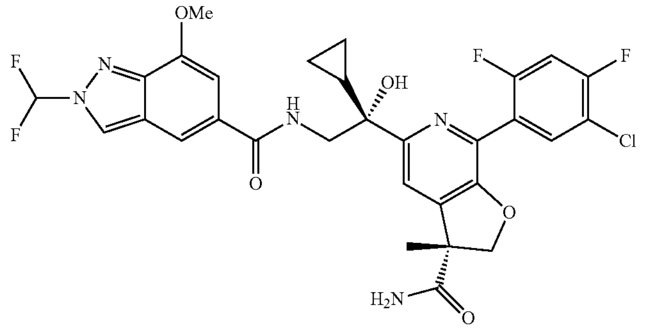 [SMILES: COc1cc(C(=O)NC[C@](O)(c2cc3c(c(-c4cc(Cl)c(F)cc4F)n2)OC[C@]3(C)C(N)=O)C2CC2)cc2cn(C(F)F)nc12] | 648.45 |

TABLE 5-continued
| Example | Structure | MS+ m/z |
|---|---|---|
| 663 | 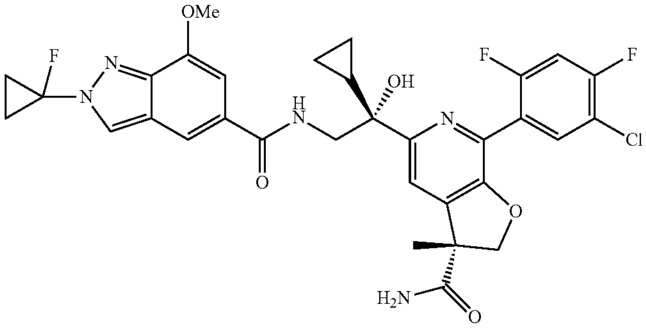 [SMILES: COc1cc(C(=O)NC[C@](O)(c2cc3c(c(-c4cc(Cl)c(F)cc4F)n2)OC[C@]3(C)C(N)=O)C2CC2)cc2cn(C3(F)CC3)nc12] | 656.46 |
| 664 | 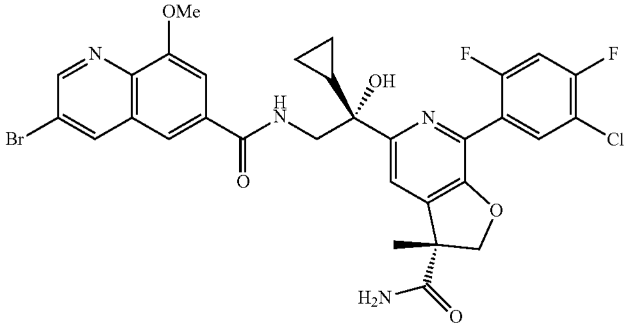 [SMILES: COc1cc(C(=O)NC[C@](O)(c2cc3c(c(-c4cc(Cl)c(F)cc4F)n2)OC[C@]3(C)C(N)=O)C2CC2)cc2cc(Br)cnc12] | 689.24 |
| 665 | 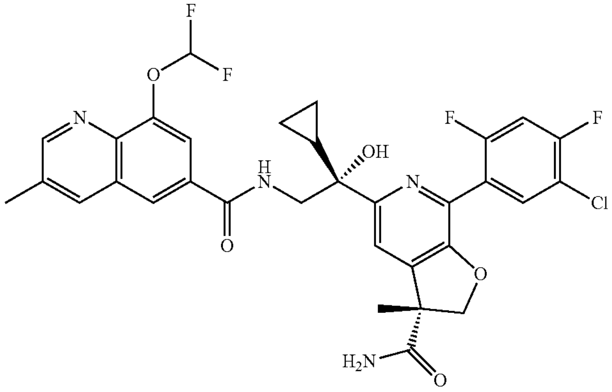 [SMILES: Cc1cnc2c(OC(F)F)cc(C(=O)NC[C@](O)(c3cc4c(c(-c5cc(Cl)c(F)cc5F)n3)OC[C@]4(C)C(N)=O)C3CC3)cc2c1] | 659.42 |
| 666 | 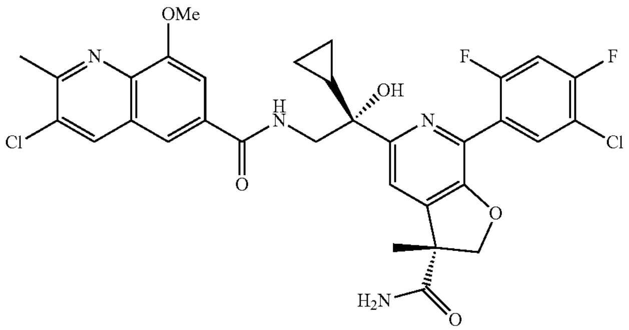 [SMILES: COc1cc(C(=O)NC[C@](O)(c2cc3c(c(-c4cc(Cl)c(F)cc4F)n2)OC[C@]3(C)C(N)=O)C2CC2)cc2cc(Cl)c(C)nc12] | 657.38 |

TABLE 5-continued
| Example | Structure | MS+ m/z |
|---|---|---|
| 667 | 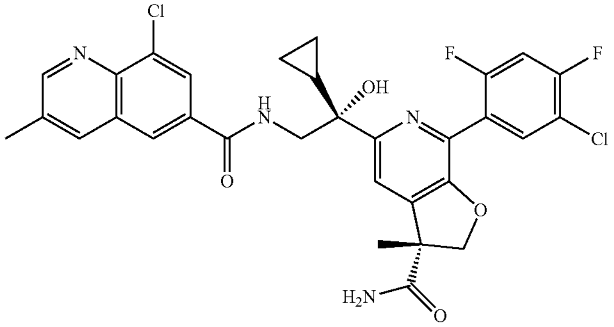 [SMILES: Cc1cnc2c(Cl)cc(C(=O)NC[C@](O)(c3cc4c(c(-c5cc(Cl)c(F)cc5F)n3)OC[C@]4(C)C(N)=O)C3CC3)cc2c1] | 630.40 |
| 668 | 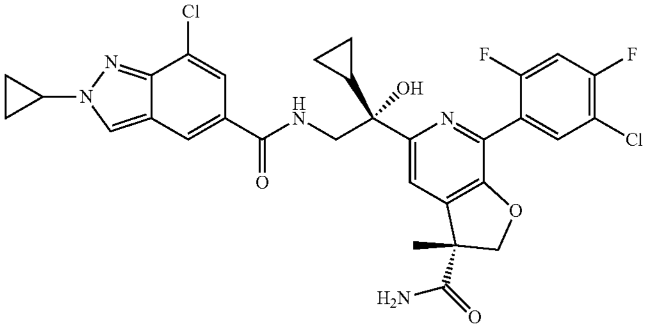 [SMILES: C[C@]1(C(N)=O)COc2c1cc([C@@](O)(CNC(=O)c1cc(Cl)c3nn(C4CC4)cc3c1)C1CC1)nc2-c1cc(Cl)c(F)cc1F] | 642.38 |
| 669 | 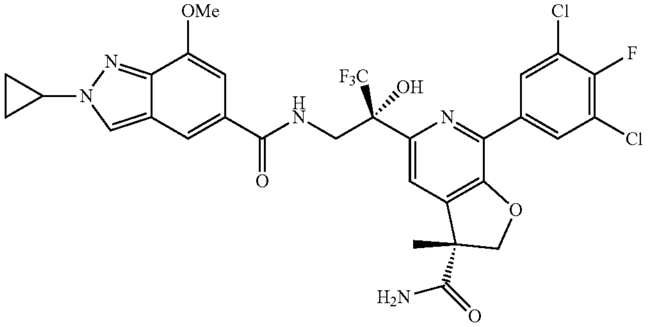 [SMILES: COc1cc(C(=O)NC[C@](O)(c2cc3c(c(-c4cc(Cl)c(F)c(Cl)c4)n2)OC[C@]3(C)C(N)=O)C(F)(F)F)cc2cn(C3CC3)nc12] | 682.35 |
| 670 | 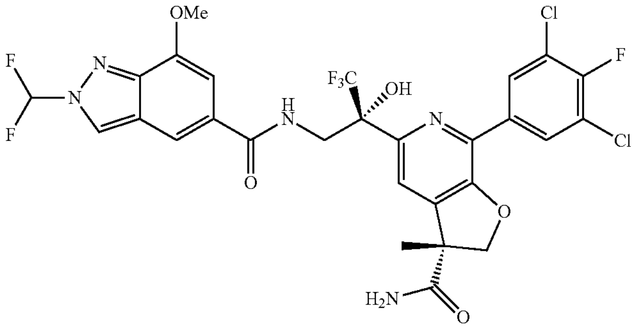 [SMILES: COc1cc(C(=O)NC[C@](O)(c2cc3c(c(-c4cc(Cl)c(F)c(Cl)c4)n2)OC[C@]3(C)C(N)=O)C(F)(F)F)cc2cn(C(F)F)nc12] | 692.32 |

TABLE 5-continued
| Example | Structure | MS+ m/z |
|---|---|---|
| 671 | 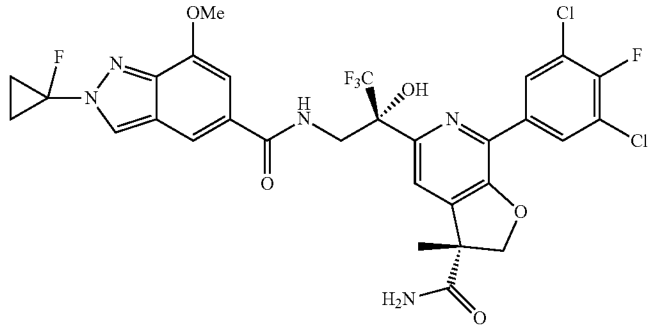 [SMILES: COc1cc(C(=O)NC[C@](O)(c2cc3c(c(-c4cc(Cl)c(F)c(Cl)c4)n2)OC[C@]3(C)C(N)=O)C(F)(F)F)cc2cn(C3(F)CC3)nc12] | 700.33 |
| 672 | 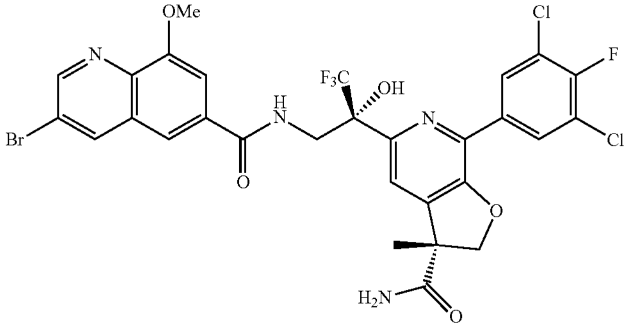 [SMILES: COc1cc(C(=O)NC[C@](O)(c2cc3c(c(-c4cc(Cl)c(F)c(Cl)c4)n2)OC[C@]3(C)C(N)=O)C(F)(F)F)cc2cc(Br)cnc12] | 731.15 |
| 673 | 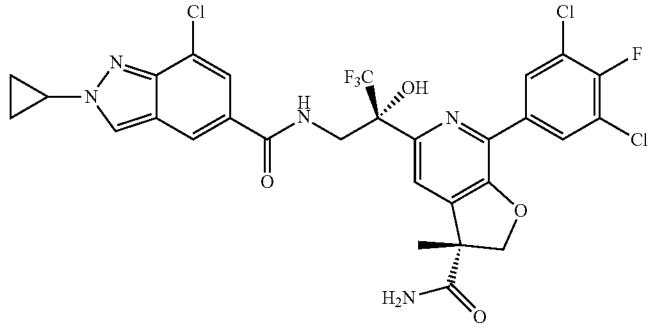 [SMILES: C[C@]1(C(N)=O)COc2c1cc([C@@](O)(CNC(=O)c1cc(Cl)c3nn(C4CC4)cc3c1)C(F)(F)F)nc2-c1cc(Cl)c(F)c(Cl)c1] | 686.24 |
| 674 | 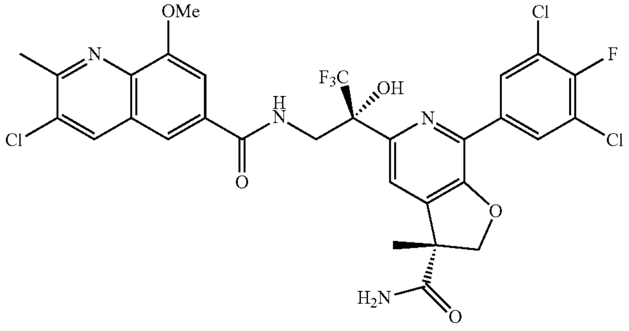 [SMILES: COc1cc(C(=O)NC[C@](O)(c2cc3c(c(-c4cc(Cl)c(F)c(Cl)c4)n2)OC[C@]3(C)C(N)=O)C(F)(F)F)cc2cc(Cl)c(C)nc12] | 701.30 |

TABLE 5-continued
| Example | Structure | MS+ m/z |
| --- | --- | --- |
| 675 | 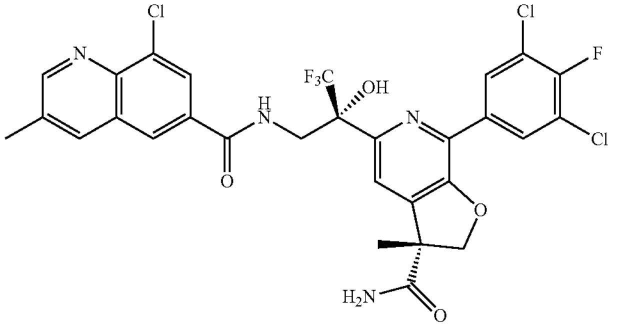 [SMILES: Cc1cnc2c(Cl)cc(C(=O)NC[C@](O)(c3cc4c(c(-c5cc(Cl)c(F)c(Cl)c5)n3)OC[C@]4(C)C(N)=O)C(F)(F)F)cc2c1] | 671.16 |
| 676 | 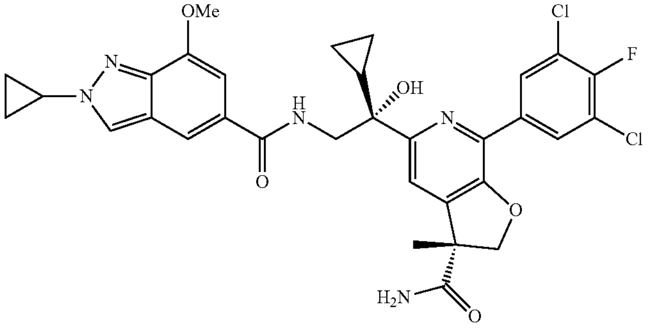 [SMILES: COc1cc(C(=O)NC[C@](O)(c2cc3c(c(-c4cc(Cl)c(F)c(Cl)c4)n2)OC[C@]3(C)C(N)=O)C2CC2)cc2cn(C3CC3)nc12] | 654.35 |
| 677 | 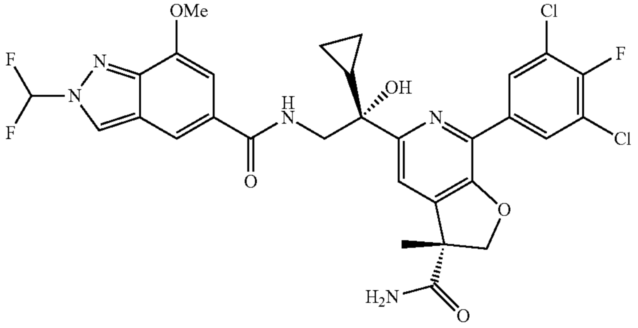 [SMILES: COc1cc(C(=O)NC[C@](O)(c2cc3c(c(-c4cc(Cl)c(F)c(Cl)c4)n2)OC[C@]3(C)C(N)=O)C2CC2)cc2cn(C(F)F)nc12] | 664.19 |
| 678 | 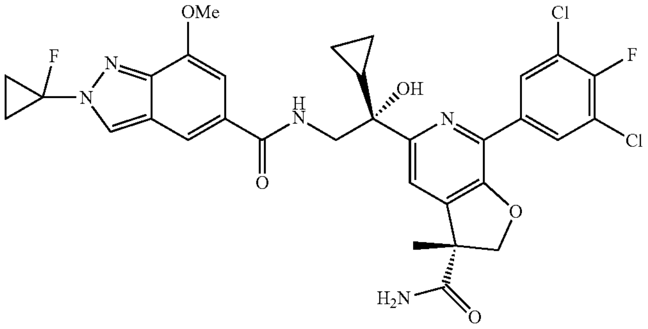 [SMILES: COc1cc(C(=O)NC[C@](O)(c2cc3c(c(-c4cc(Cl)c(F)c(Cl)c4)n2)OC[C@]3(C)C(N)=O)C2CC2)cc2cn(C3(F)CC3)nc12] | 672.31 |

TABLE 5-continued
| Example | Structure | MS⁺ m/z |
|---|---|---|
| 679 | 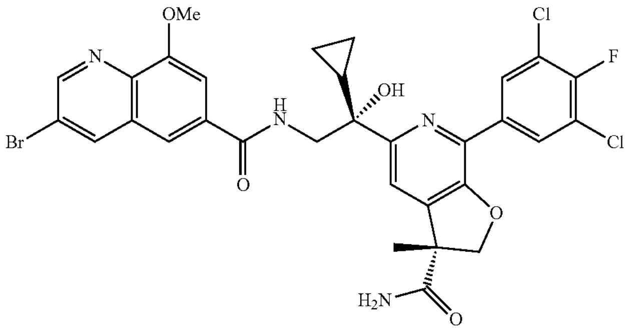 [SMILES: COc1cc(C(=O)NC[C@](O)(c2cc3c(c(-c4cc(Cl)c(F)c(Cl)c4)n2)OC[C@]3(C)C(N)=O)C2CC2)cc2cc(Br)cnc12] | 703.06 |
| 680 | 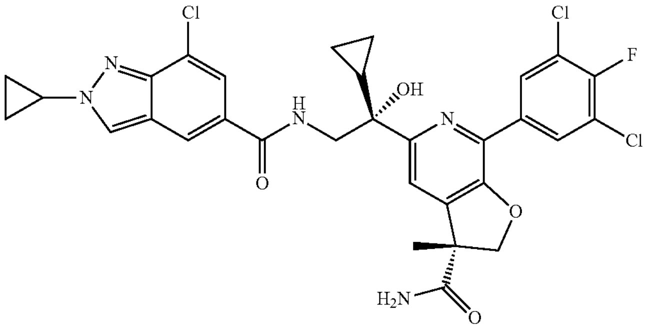 [SMILES: C[C@]1(C(N)=O)COc2c1cc([C@@](O)(CNC(=O)c1cc(Cl)c3nn(C4CC4)cc3c1)C1CC1)nc2-c1cc(Cl)c(F)c(Cl)c1] | 658.24 |
| 681 | 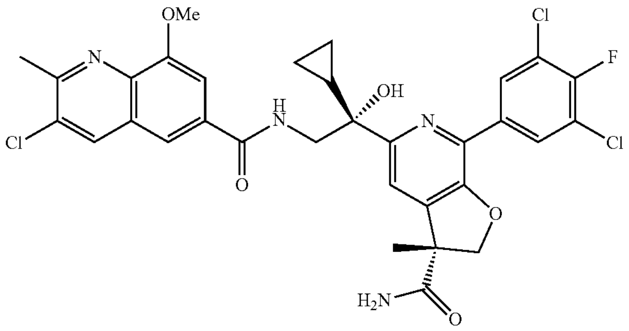 [SMILES: COc1cc(C(=O)NC[C@](O)(c2cc3c(c(-c4cc(Cl)c(F)c(Cl)c4)n2)OC[C@]3(C)C(N)=O)C2CC2)cc2cc(Cl)c(C)nc12] | 673.25 |
| 682 | 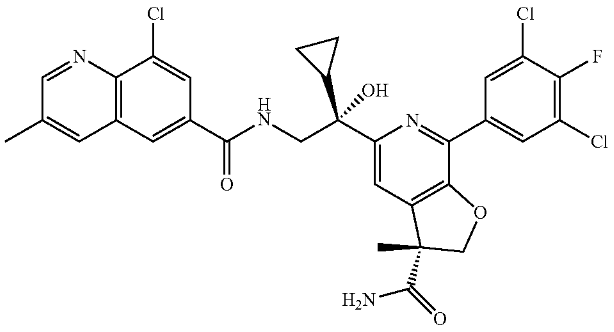 [SMILES: Cc1cnc2c(Cl)cc(C(=O)NC[C@](O)(c3cc4c(c(-c5cc(Cl)c(F)c(Cl)c5)n3)OC[C@]4(C)C(N)=O)C3CC3)cc2c1] | 643.26 |

TABLE 5-continued
| Example | Structure | MS+ m/z |
|---|---|---|
| 683 | 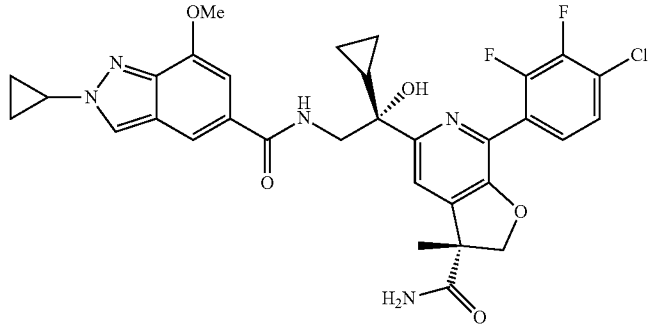 [SMILES: COc1cc(C(=O)NC[C@](O)(c2cc3c(c(-c4ccc(Cl)c(F)c4F)n2)OC[C@]3(C)C(N)=O)C2CC2)cc2cn(C3CC3)nc12] | 638.33 |
| 684 | 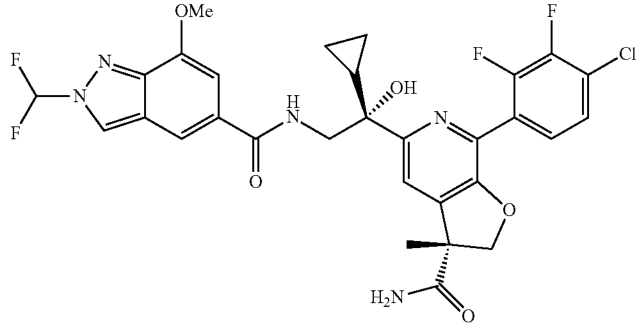 [SMILES: COc1cc(C(=O)NC[C@](O)(c2cc3c(c(-c4ccc(Cl)c(F)c4F)n2)OC[C@]3(C)C(N)=O)C2CC2)cc2cn(C(F)F)nc12] | 648.27 |
| 685 | 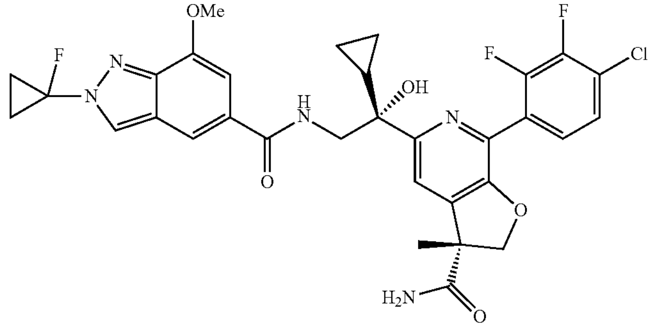 [SMILES: COc1cc(C(=O)NC[C@](O)(c2cc3c(c(-c4ccc(Cl)c(F)c4F)n2)OC[C@]3(C)C(N)=O)C2CC2)cc2cn(C3(F)CC3)nc12] | 656.33 |
| 686 | 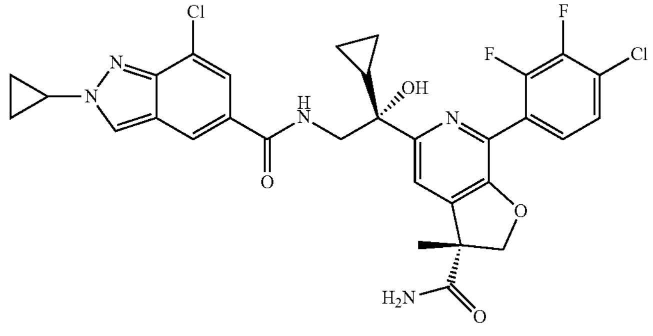 [SMILES: C[C@]1(C(N)=O)COc2c1cc([C@@](O)(CNC(=O)c1cc(Cl)c3nn(C4CC4)cc3c1)C1CC1)nc2-c1ccc(Cl)c(F)c1F] | 642.29 |

TABLE 5-continued
| Example | Structure | MS+ m/z |
|---|---|---|
| 687 | 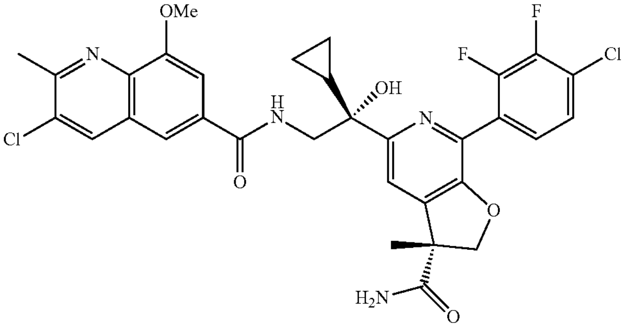 [SMILES: COc1cc(C(=O)NC[C@](O)(c2cc3c(c(-c4ccc(Cl)c(F)c4F)n2)OC[C@]3(C)C(N)=O)C2CC2)cc2cc(Cl)c(C)nc12] | 657.27 |
| 688 | 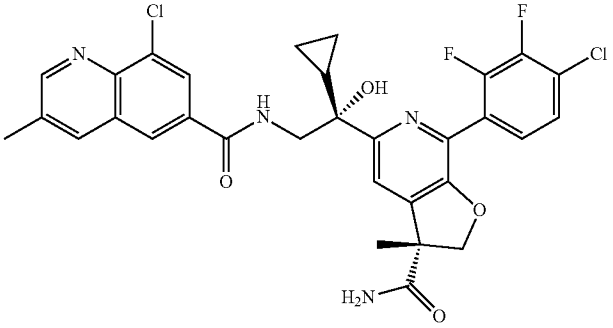 [SMILES: Cc1cnc2c(Cl)cc(C(=O)NC[C@](O)(c3cc4c(c(-c5ccc(Cl)c(F)c5F)n3)OC[C@]4(C)C(N)=O)C3CC3)cc2c1] | 627.26 |
| 689 | 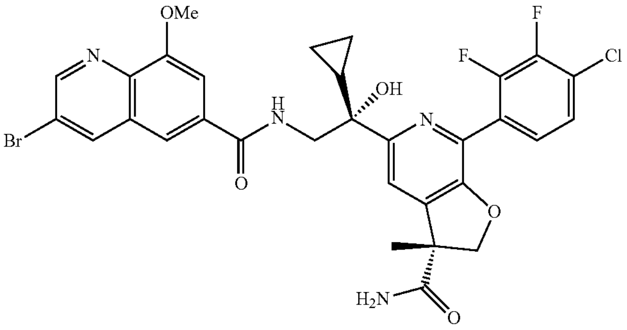 [SMILES: COc1cc(C(=O)NC[C@](O)(c2cc3c(c(-c4ccc(Cl)c(F)c4F)n2)OC[C@]3(C)C(N)=O)C2CC2)cc2cc(Br)cnc12] | 687.13 |
| 690 | 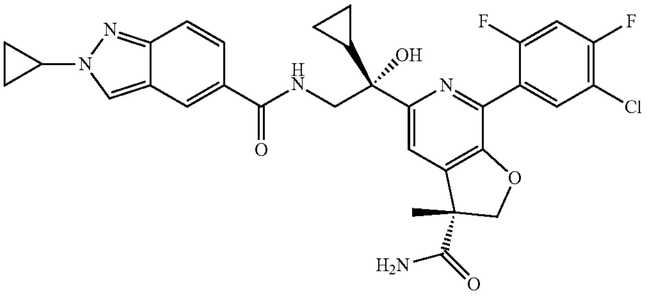 [SMILES: C[C@]1(C(N)=O)COc2c1cc([C@@](O)(CNC(=O)c1ccc3nn(C4CC4)cc3c1)C1CC1)nc2-c1cc(Cl)c(F)cc1F] | 608.32 |

TABLE 5-continued
| Example | Structure | MS+ m/z |
|---|---|---|
| 691 | 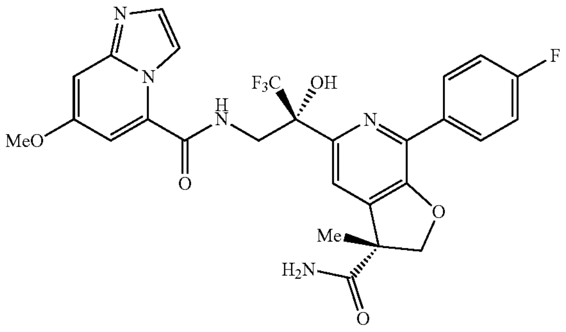 [SMILES: COc1cc(C(=O)NC[C@](O)(c2cc3c(c(-c4ccc(F)cc4)n2)OC[C@]3(C)C(N)=O)C(F)(F)F)n2ccnc2c1] | 574.17 |
| 692 | 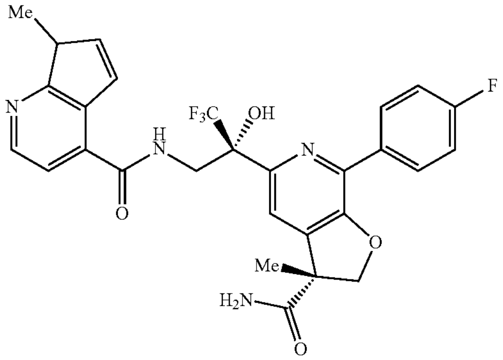 [SMILES: CC1C=Cc2c(C(=O)NC[C@](O)(c3cc4c(c(-c5ccc(F)cc5)n3)OC[C@]4(C)C(N)=O)C(F)(F)F)ccnc21] | 558.13 |
| 693 | 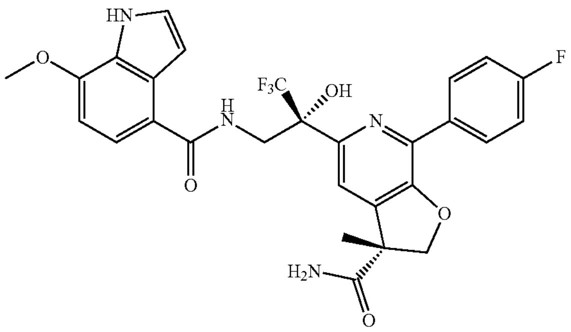 [SMILES: COc1ccc(C(=O)NC[C@](O)(c2cc3c(c(-c4ccc(F)cc4)n2)OC[C@]3(C)C(N)=O)C(F)(F)F)c2cc[nH]c12] | 573.01 |
| 694 | 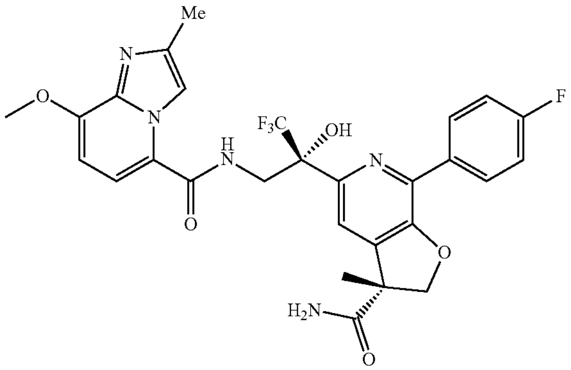 [SMILES: COc1ccc(C(=O)NC[C@](O)(c2cc3c(c(-c4ccc(F)cc4)n2)OC[C@]3(C)C(N)=O)C(F)(F)F)n2cc(C)nc12] | 588.16 |

TABLE 5-continued
| Example | Structure | MS+ m/z |
|---|---|---|
| 695 | 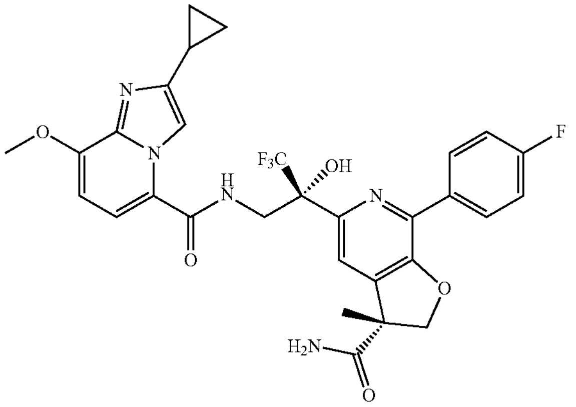 [SMILES: COc1ccc(C(=O)NC[C@](O)(c2cc3c(c(-c4ccc(F)cc4)n2)OC[C@]3(C)C(N)=O)C(F)(F)F)n2cc(C3CC3)nc12] | 614.17 |
| 696 | 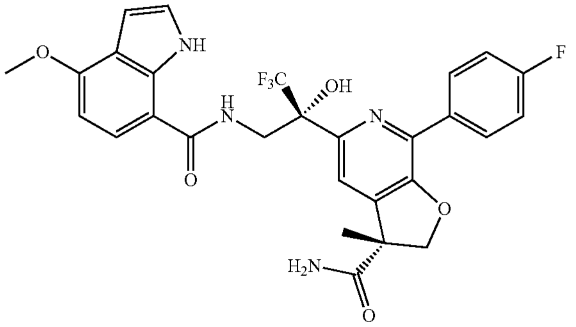 [SMILES: COc1ccc(C(=O)NC[C@](O)(c2cc3c(c(-c4ccc(F)cc4)n2)OC[C@]3(C)C(N)=O)C(F)(F)F)c2[nH]ccc12] | 572.99 |
| 697 | 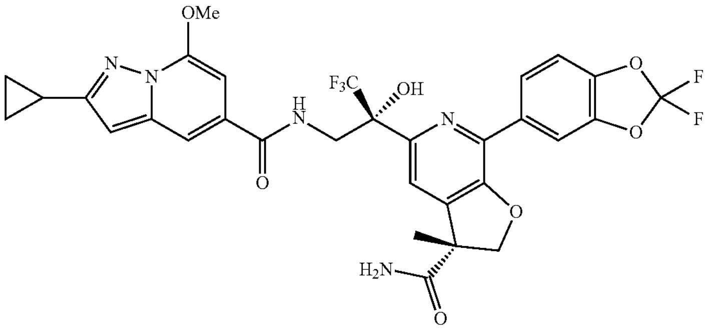 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(C3CC3)nn12] | 676.45 |
| 698 | 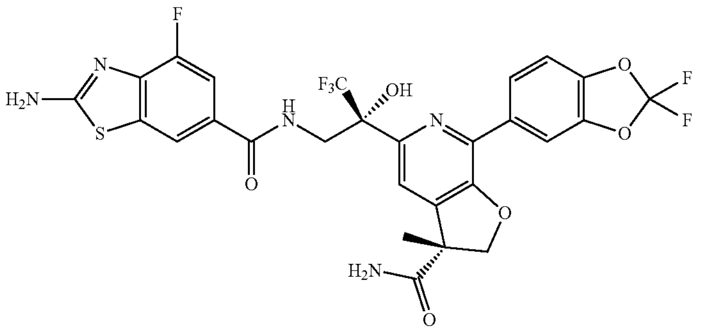 [SMILES: C[C@]1(C(N)=O)COc2c1cc([C@@](O)(CNC(=O)c1cc(F)c3nc(N)sc3c1)C(F)(F)F)nc2-c1ccc2c(c1)OC(F)(F)O2] | 656.31 |

TABLE 5-continued
| Example | Structure | MS+ m/z |
|---|---|---|
| 699 | 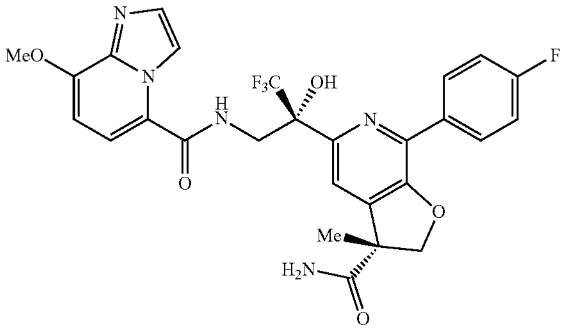 [SMILES: COc1ccc(C(=O)NC[C@](O)(c2cc3c(c(-c4ccc(F)cc4)n2)OC[C@]3(C)C(N)=O)C(F)(F)F)n2ccnc12] | 574.15 |
| 700 | 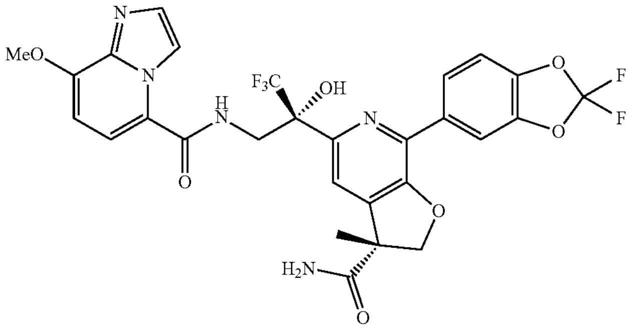 [SMILES: COc1ccc(C(=O)NC[C@](O)(c2cc3c(c(-c4ccc5c(c4)OC(F)(F)O5)n2)OC[C@]3(C)C(N)=O)C(F)(F)F)n2ccnc12] | 636.28 |
| 701 | 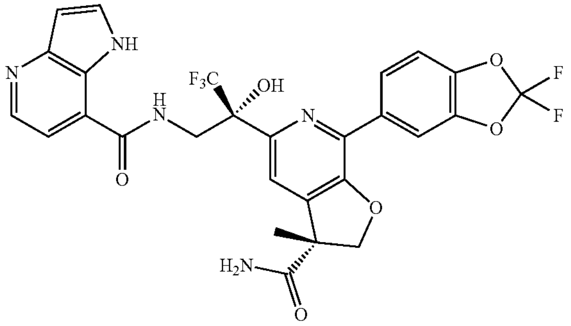 [SMILES: C[C@]1(C(N)=O)COc2c1cc([C@@](O)(CNC(=O)c1ccnc3cc[nH]c13)C(F)(F)F)nc2-c1ccc2c(c1)OC(F)(F)O2] | 606.28 |
| 702 | 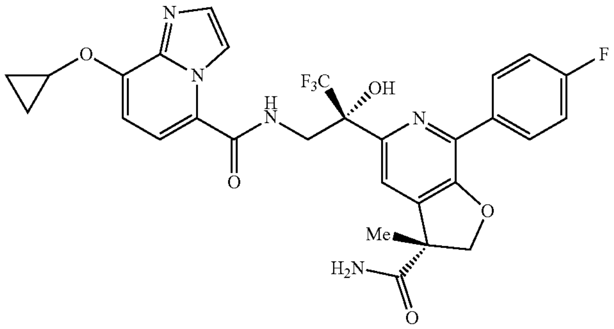 [SMILES: C[C@]1(C(N)=O)COc2c1cc([C@@](O)(CNC(=O)c1ccc(OC3CC3)c3nccn13)C(F)(F)F)nc2-c1ccc(F)cc1] | 600.47 |

TABLE 5-continued
| Example | Structure | MS⁺ m/z |
|---|---|---|
| 703 | 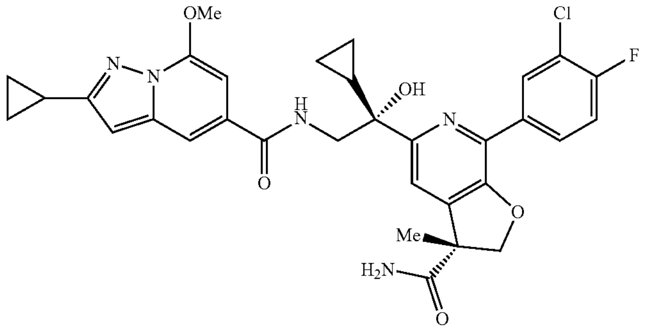 [SMILES: COc1cc(C(=O)NC[C@](O)(c2cc3c(c(-c4ccc(F)c(Cl)c4)n2)OC[C@]3(C)C(N)=O)C2CC2)cc2cc(C3CC3)nn12] | 620.08 |
| 704 | 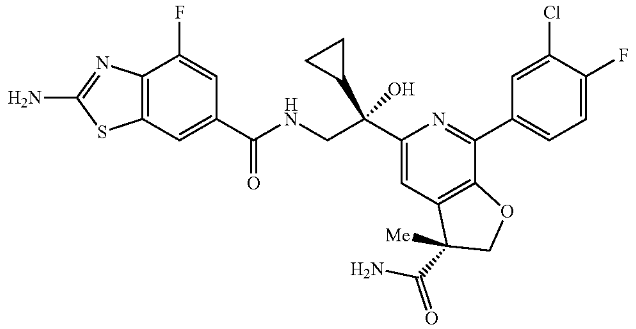 [SMILES: C[C@]1(C(N)=O)COc2c1cc([C@@](O)(CNC(=O)c1cc(F)c3nc(N)sc3c1)C1CC1)nc2-c1ccc(F)c(Cl)c1] | 599.95 |
| 705 | 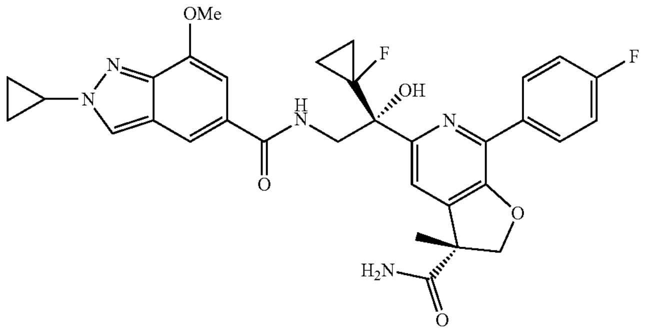 [SMILES: COc1cc(C(=O)NC[C@](O)(c2cc3c(c(-c4ccc(F)cc4)n2)OC[C@]3(C)C(N)=O)C2(F)CC2)cc2cn(C3CC3)nc12] | 604.46 |
| 706 | 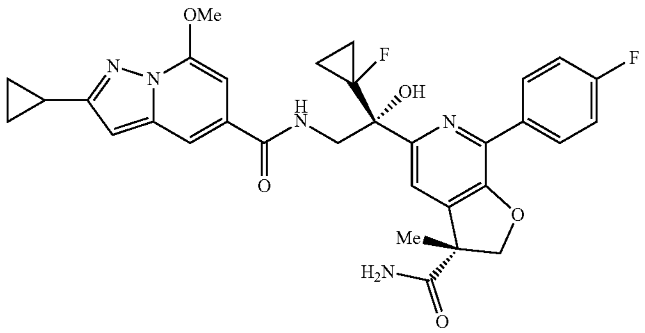 [SMILES: COc1cc(C(=O)NC[C@](O)(c2cc3c(c(-c4ccc(F)cc4)n2)OC[C@]3(C)C(N)=O)C2(F)CC2)cc2cc(C3CC3)nn12] | 604.47 |

TABLE 5-continued
| Example | Structure | MS+ m/z |
|---|---|---|
| 707 | 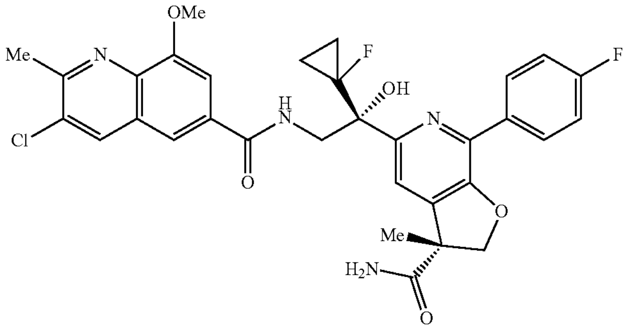 [SMILES: COc1cc(C(=O)NC[C@](O)(c2cc3c(c(-c4ccc(F)cc4)n2)OC[C@]3(C)C(N)=O)C2(F)CC2)cc2cc(Cl)c(C)nc12] | 623.47 |
| 708 | 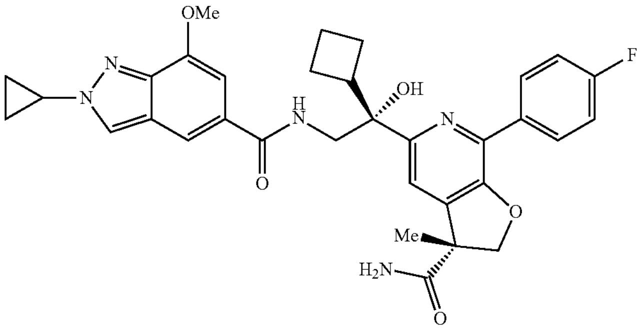 [SMILES: COc1cc(C(=O)NC[C@](O)(c2cc3c(c(-c4ccc(F)cc4)n2)OC[C@]3(C)C(N)=O)C2CCC2)cc2cn(C3CC3)nc12] | 600.53 |
| 709 | 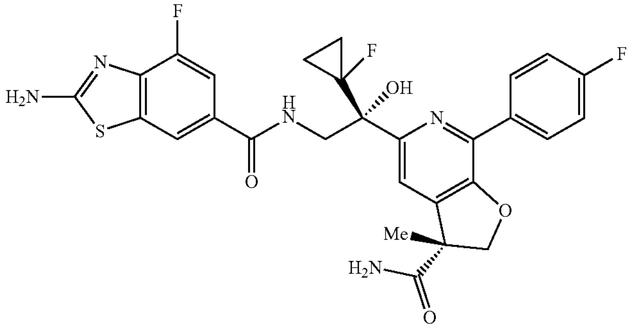 [SMILES: C[C@]1(C(N)=O)COc2c1cc([C@@](O)(CNC(=O)c1cc(F)c3nc(N)sc3c1)C1(F)CC1)nc2-c1ccc(F)cc1] | 584.40 |
| 710 | 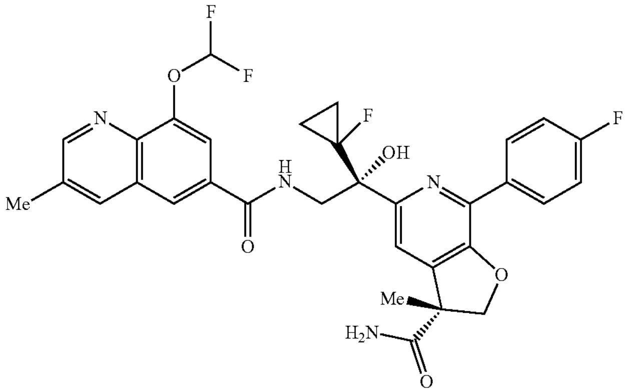 [SMILES: Cc1cnc2c(OC(F)F)cc(C(=O)NC[C@](O)(c3cc4c(c(-c5ccc(F)cc5)n3)OC[C@]4(C)C(N)=O)C3(F)CC3)cc2c1] | 625.41 |

TABLE 5-continued
| Example | Structure | MS⁺ m/z |
|---|---|---|
| 711 | 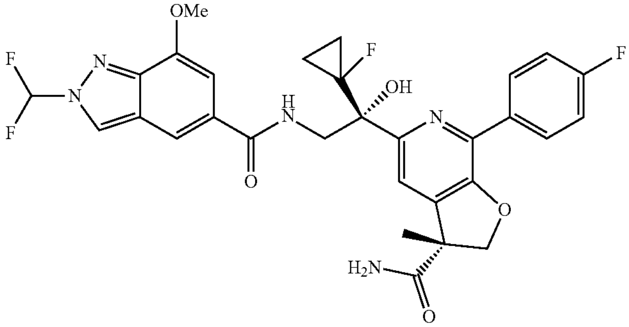 [SMILES: COc1cc(C(=O)NC[C@](O)(c2cc3c(c(-c4ccc(F)cc4)n2)OC[C@]3(C)C(N)=O)C2(F)CC2)cc2cn(C(F)F)nc12] | 614.51 |
| 712 | 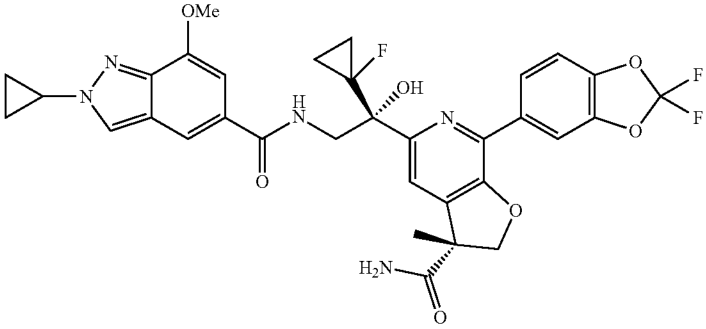 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2cn(C3CC3)nc12] | 666.53 |
| 713 | 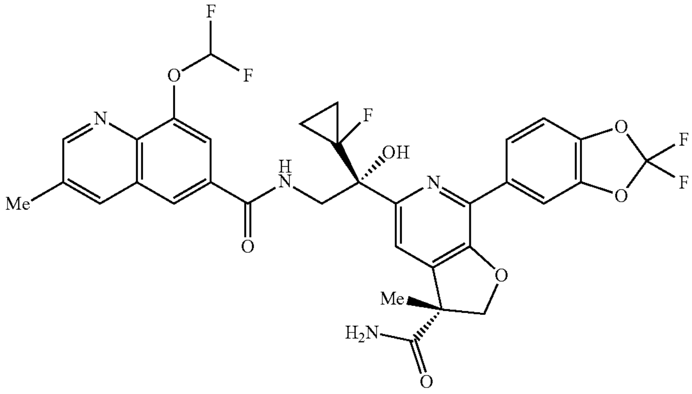 [SMILES: Cc1cnc2c(OC(F)F)cc(C(=O)NC[C@](O)(c3cc4c(c(-c5ccc6c(c5)OC(F)(F)O6)n3)OC[C@]4(C)C(N)=O)C3(F)CC3)cc2c1] | 687.48 |
| 714 | 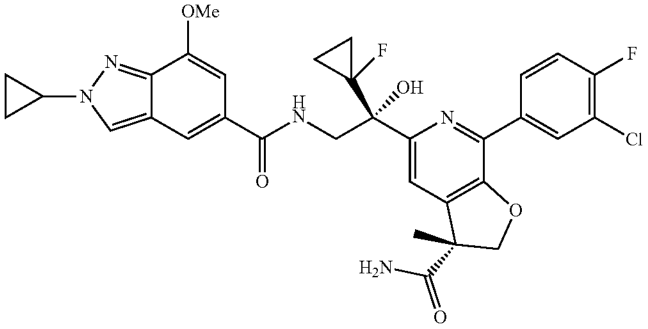 [SMILES: COc1cc(C(=O)NC[C@](O)(c2cc3c(c(-c4ccc(F)c(Cl)c4)n2)OC[C@]3(C)C(N)=O)C2(F)CC2)cc2cn(C3CC3)nc12] | 638.50 |

TABLE 5-continued
| Example | Structure | MS+ m/z |
|---|---|---|
| 715 | 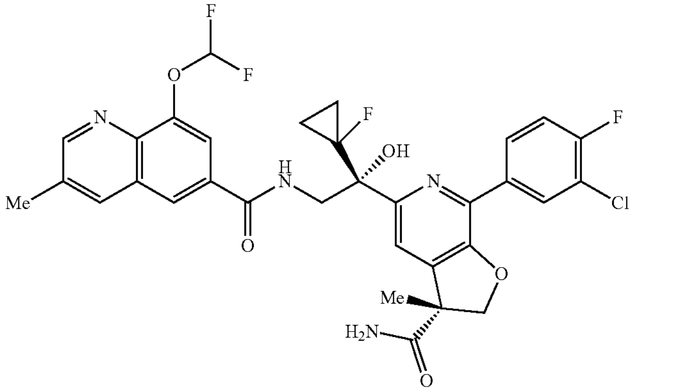 [SMILES: Cc1cnc2c(OC(F)F)cc(C(=O)NC[C@](O)(c3cc4c(c(-c5ccc(F)c(Cl)c5)n3)OC[C@]4(C)C(N)=O)C3(F)CC3)cc2c1] | 659.48 |
| 716 | 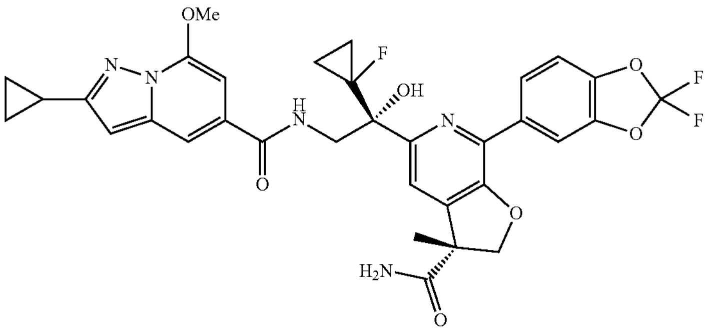 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2cc(C3CC3)nn12] | 666.57 |
| 717 | 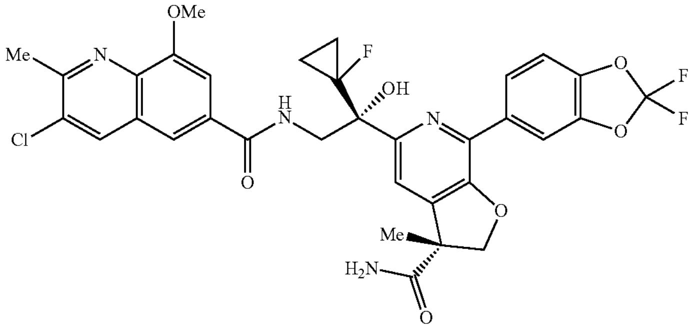 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2cc(Cl)c(C)nc12] | 685.46 |
| 718 | 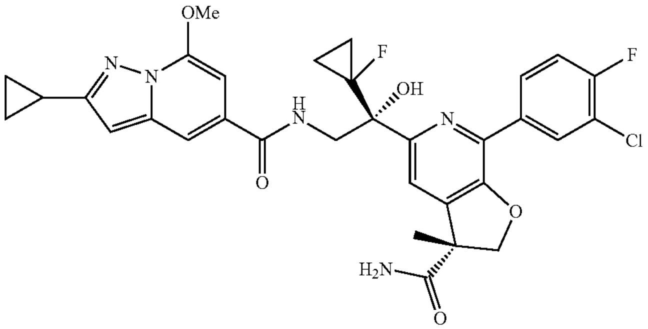 [SMILES: COc1cc(C(=O)NC[C@](O)(c2cc3c(c(-c4ccc(F)c(Cl)c4)n2)OC[C@]3(C)C(N)=O)C2(F)CC2)cc2cc(C3CC3)nn12] | 638.53 |

TABLE 5-continued
| Example | Structure | MS+ m/z |
| --- | --- | --- |
| 719 | 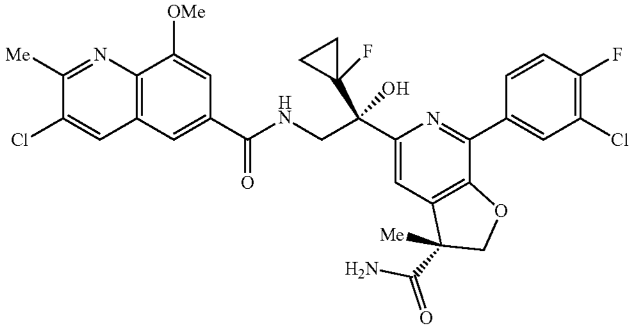 [SMILES: COc1cc(C(=O)NC[C@](O)(c2cc3c(c(-c4ccc(F)c(Cl)c4)n2)OC[C@]3(C)C(N)=O)C2(F)CC2)cc2cc(Cl)c(C)nc12] | 657.39 |
| 720 | 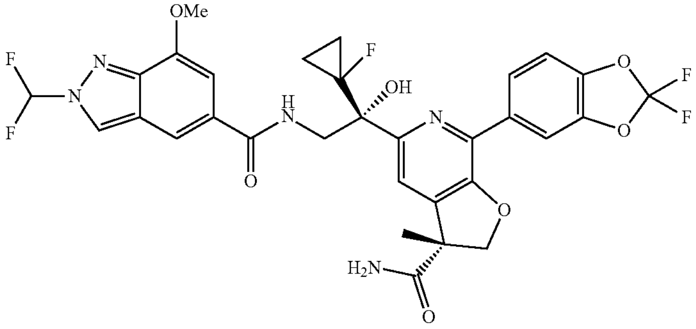 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2cn(C(F)F)nc12] | 676.50 |
| 721 | 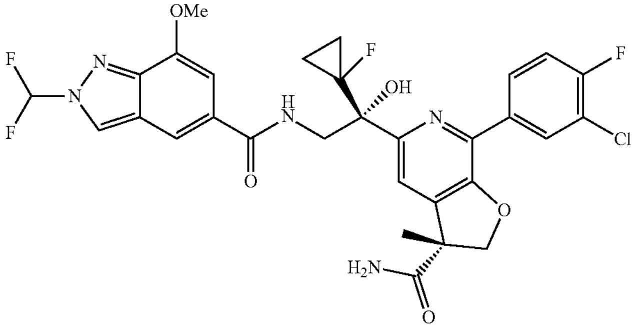 [SMILES: COc1cc(C(=O)NC[C@](O)(c2cc3c(c(-c4ccc(F)c(Cl)c4)n2)OC[C@]3(C)C(N)=O)C2(F)CC2)cc2cn(C(F)F)nc12] | 648.50 |
| 722 | 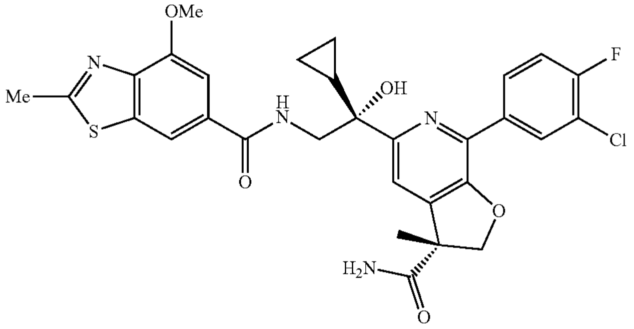 [SMILES: COc1cc(C(=O)NC[C@](O)(c2cc3c(c(-c4ccc(F)c(Cl)c4)n2)OC[C@]3(C)C(N)=O)C2CC2)cc2sc(C)nc12] | 611.46 |

TABLE 5-continued
| Example | Structure | MS+ m/z |
|---|---|---|
| 723 | 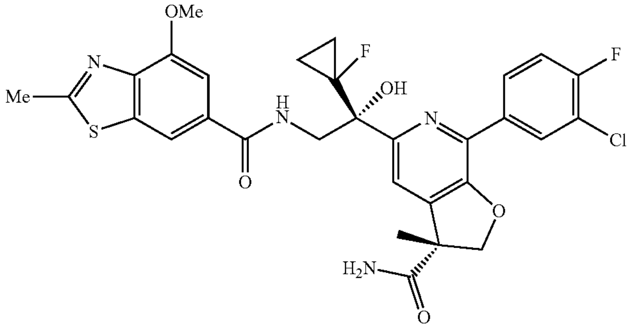 [SMILES: COc1cc(C(=O)NC[C@](O)(c2cc3c(c(-c4ccc(F)c(Cl)c4)n2)OC[C@]3(C)C(N)=O)C2(F)CC2)cc2sc(C)nc12] | 629.48 |
| 724 | 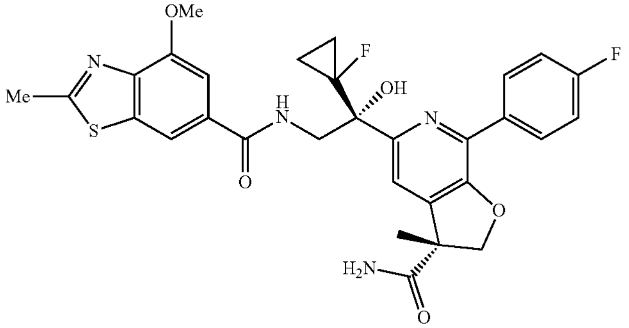 [SMILES: COc1cc(C(=O)NC[C@](O)(c2cc3c(c(-c4ccc(F)cc4)n2)OC[C@]3(C)C(N)=O)C2(F)CC2)cc2sc(C)nc12] | 595.44 |
| 725 | 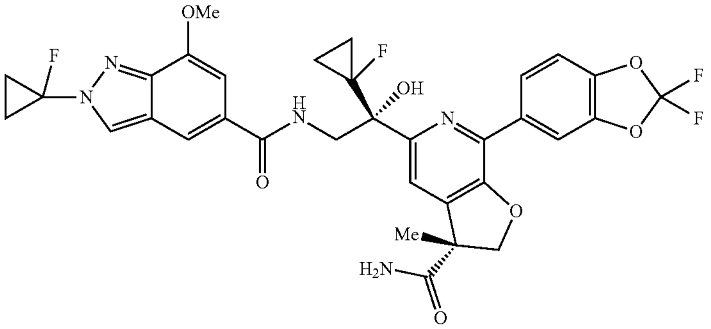 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2cn(C3(F)CC3)nc12] | 684.45 |
| 726 | 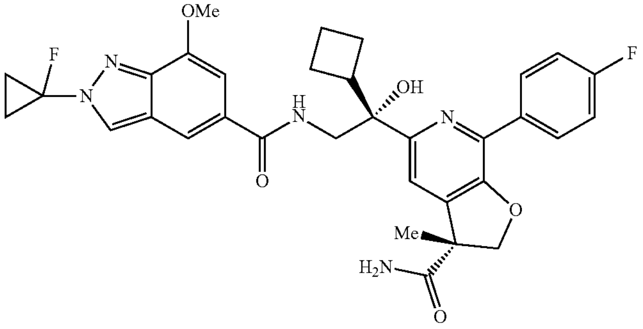 [SMILES: COc1cc(C(=O)NC[C@](O)(c2cc3c(c(-c4ccc(F)cc4)n2)OC[C@]3(C)C(N)=O)C2CCC2)cc2cn(C3(F)CC3)nc12] | 618.52 |

TABLE 5-continued
| Example | Structure | MS+ m/z |
|---|---|---|
| 727 | 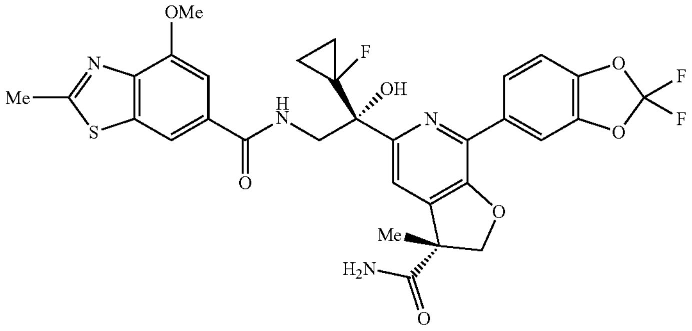 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2sc(C)nc12] | 657.40 |
| 728 | 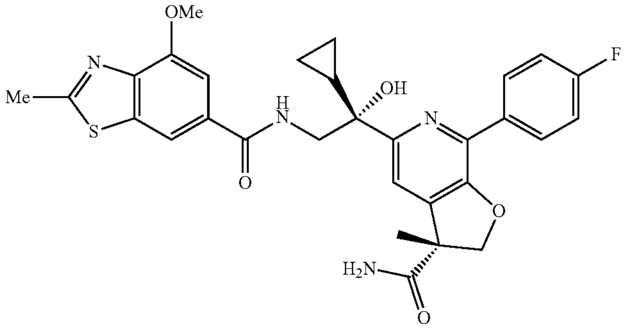 [SMILES: COc1cc(C(=O)NC[C@](O)(c2cc3c(c(-c4ccc(F)cc4)n2)OC[C@]3(C)C(N)=O)C2CC2)cc2sc(C)nc12] | 577.43 |
| 729 | 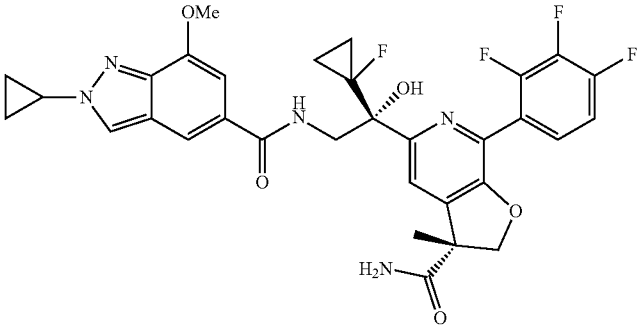 [SMILES: COc1cc(C(=O)NC[C@](O)(c2cc3c(c(-c4ccc(F)c(F)c4F)n2)OC[C@]3(C)C(N)=O)C2(F)CC2)cc2cn(C3CC3)nc12] | 640.49 |
| 730 | 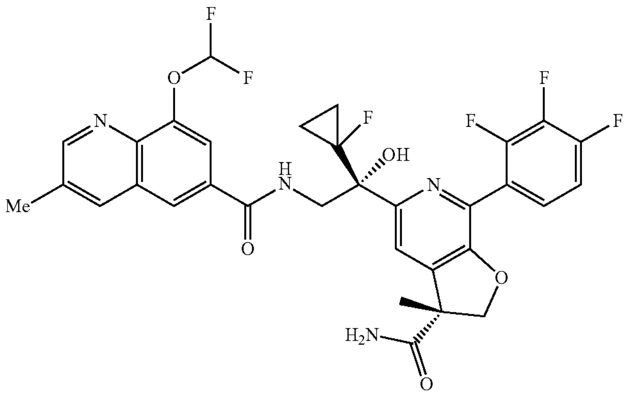 [SMILES: Cc1cnc2c(OC(F)F)cc(C(=O)NC[C@](O)(c3cc4c(c(-c5ccc(F)c(F)c5F)n3)OC[C@]4(C)C(N)=O)C3(F)CC3)cc2c1] | 661.43 |

TABLE 5-continued
| Example | Structure | MS+ m/z |
|---|---|---|
| 731 | 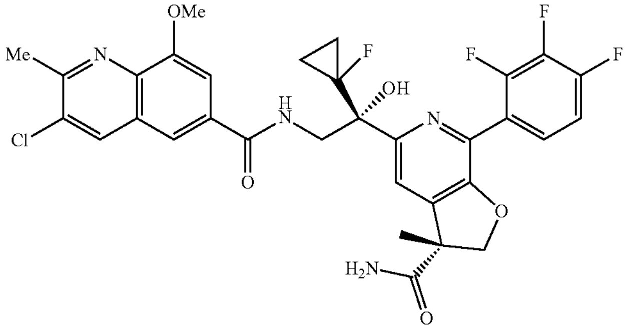 [SMILES: COc1cc(C(=O)NC[C@](O)(c2cc3c(c(-c4ccc(F)c(F)c4F)n2)OC[C@]3(C)C(N)=O)C2(F)CC2)cc2cc(Cl)c(C)nc12] | 659.47 |
| 732 | 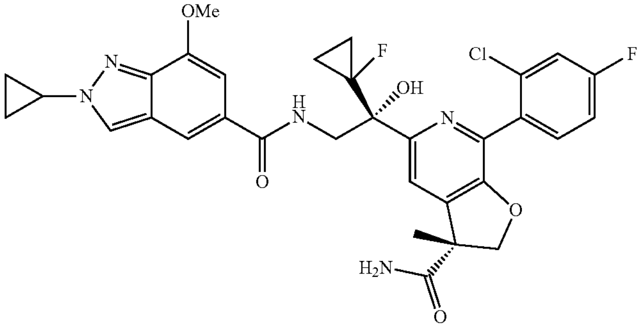 [SMILES: COc1cc(C(=O)NC[C@](O)(c2cc3c(c(-c4ccc(F)cc4Cl)n2)OC[C@]3(C)C(N)=O)C2(F)CC2)cc2cn(C3CC3)nc12] | 638.48 |
| 733 | 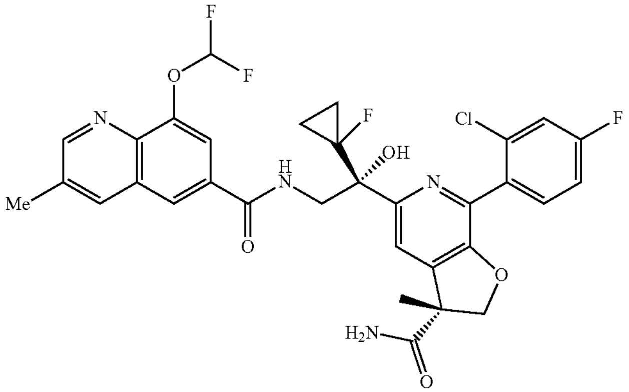 [SMILES: Cc1cnc2c(OC(F)F)cc(C(=O)NC[C@](O)(c3cc4c(c(-c5ccc(F)cc5Cl)n3)OC[C@]4(C)C(N)=O)C3(F)CC3)cc2c1] | 659.59 |
| 734 | 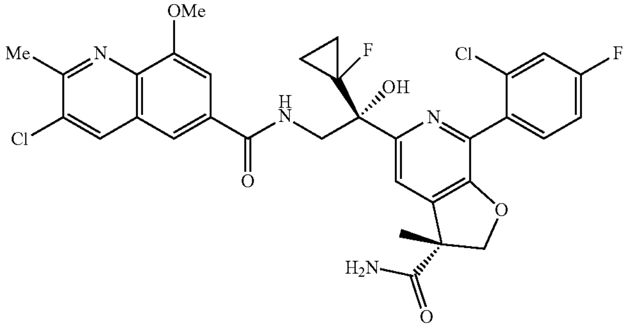 [SMILES: COc1cc(C(=O)NC[C@](O)(c2cc3c(c(-c4ccc(F)cc4Cl)n2)OC[C@]3(C)C(N)=O)C2(F)CC2)cc2cc(Cl)c(C)nc12] | 657.41 |

TABLE 5-continued
| Example | Structure | MS+ m/z |
|---|---|---|
| 735 | 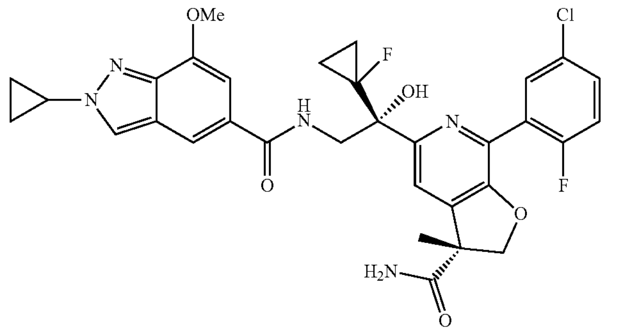 [SMILES: COc1cc(C(=O)NC[C@](O)(c2cc3c(c(-c4cc(Cl)ccc4F)n2)OC[C@]3(C)C(N)=O)C2(F)CC2)cc2cn(C3CC3)nc12] | 638.46 |
| 736 | 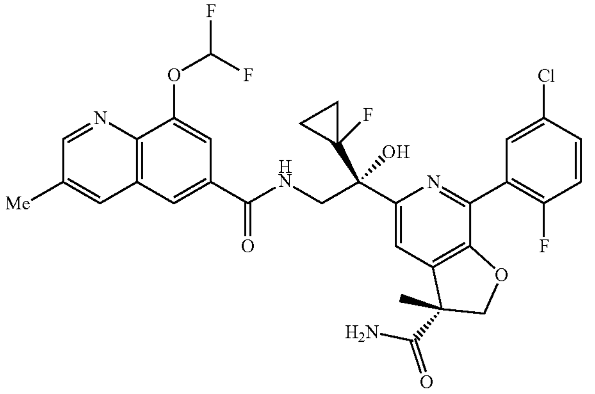 [SMILES: Cc1cnc2c(OC(F)F)cc(C(=O)NC[C@](O)(c3cc4c(c(-c5cc(Cl)ccc5F)n3)OC[C@]4(C)C(N)=O)C3(F)CC3)cc2c1] | 659.45 |
| 737 | 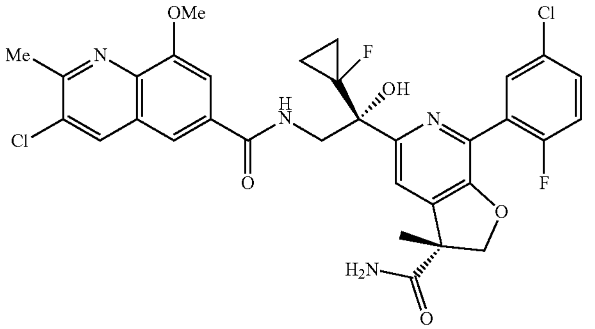 [SMILES: COc1cc(C(=O)NC[C@](O)(c2cc3c(c(-c4cc(Cl)ccc4F)n2)OC[C@]3(C)C(N)=O)C2(F)CC2)cc2cc(Cl)c(C)nc12] | 657.36 |
| 738 | 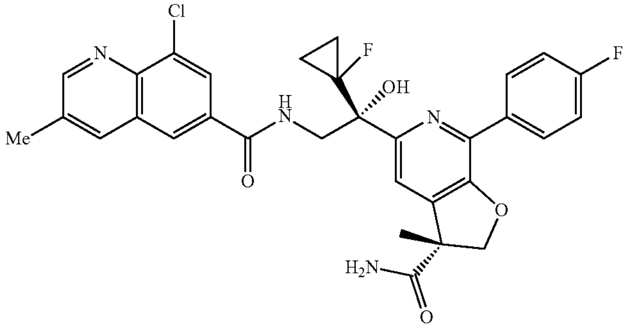 [SMILES: Cc1cnc2c(Cl)cc(C(=O)NC[C@](O)(c3cc4c(c(-c5ccc(F)cc5)n3)OC[C@]4(C)C(N)=O)C3(F)CC3)cc2c1] | 593.50 |

TABLE 5-continued
| Example | Structure | MS+ m/z |
|---|---|---|
| 739 | 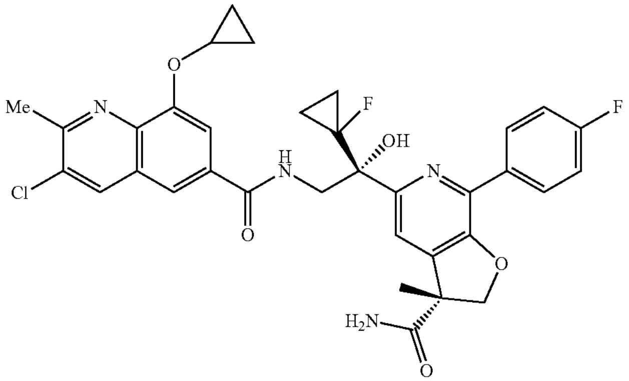 [SMILES: Cc1nc2c(OC3CC3)cc(C(=O)NC[C@](O)(c3cc4c(c(-c5ccc(F)cc5)n3)OC[C@]4(C)C(N)=O)C3(F)CC3)cc2cc1Cl] | 649.42 |
| 740 | 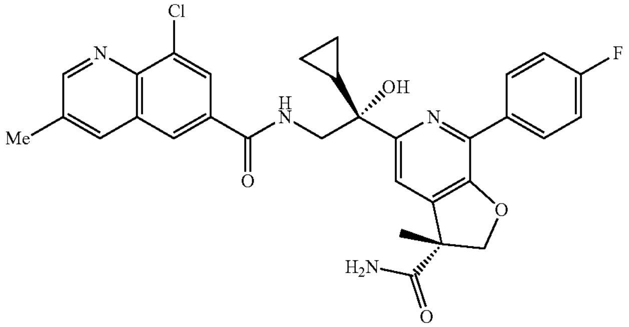 | 575.49 |
| 741 | 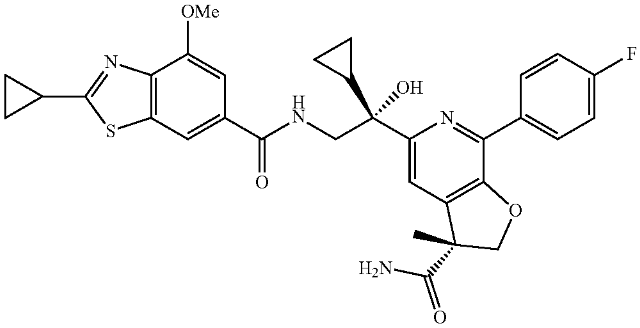 [SMILES: COc1cc(C(=O)NC[C@](O)(c2cc3c(c(-c4ccc(F)cc4)n2)OC[C@]3(C)C(N)=O)C2CC2)cc2sc(C3CC3)nc12] | 603.47 |
| 742 | 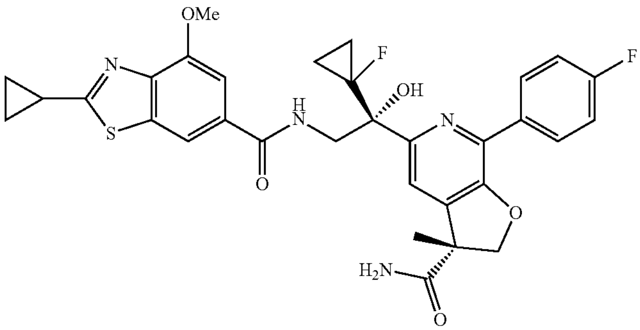 [SMILES: COc1cc(C(=O)NC[C@](O)(c2cc3c(c(-c4ccc(F)cc4)n2)OC[C@]3(C)C(N)=O)C2(F)CC2)cc2sc(C3CC3)nc12] | 621.47 |

TABLE 5-continued
| Example | Structure | MS+ m/z |
|---|---|---|
| 743 | 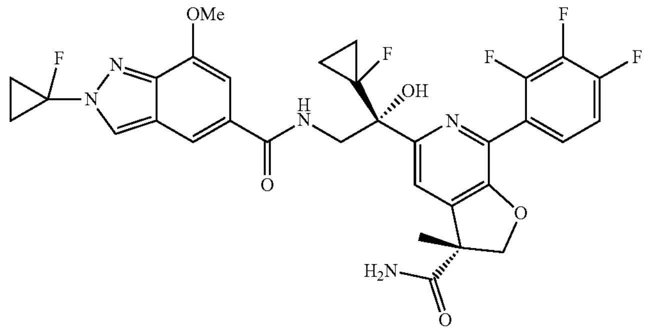 [SMILES: COc1cc(C(=O)NC[C@](O)(c2cc3c(c(-c4ccc(F)c(F)c4F)n2)OC[C@]3(C)C(N)=O)C2(F)CC2)cc2cn(C3(F)CC3)nc12] | 658.45 |
| 744 | 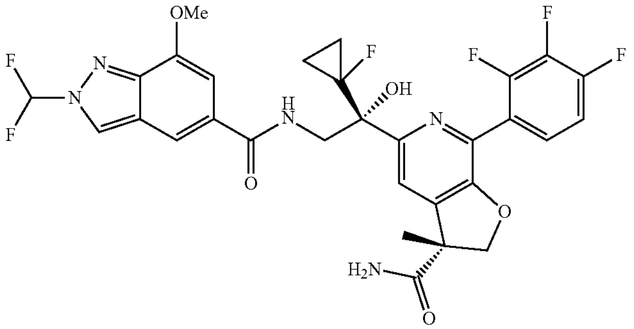 [SMILES: COc1cc(C(=O)NC[C@](O)(c2cc3c(c(-c4ccc(F)c(F)c4F)n2)OC[C@]3(C)C(N)=O)C2(F)CC2)cc2cn(C(F)F)nc12] | 650.40 |
| 745 | 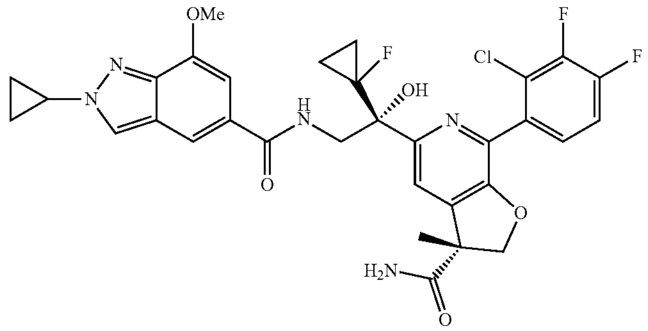 [SMILES: COc1cc(C(=O)NC[C@](O)(c2cc3c(c(-c4ccc(F)c(F)c4Cl)n2)OC[C@]3(C)C(N)=O)C2(F)CC2)cc2cn(C3CC3)nc12] | 656.44 |
| 746 | 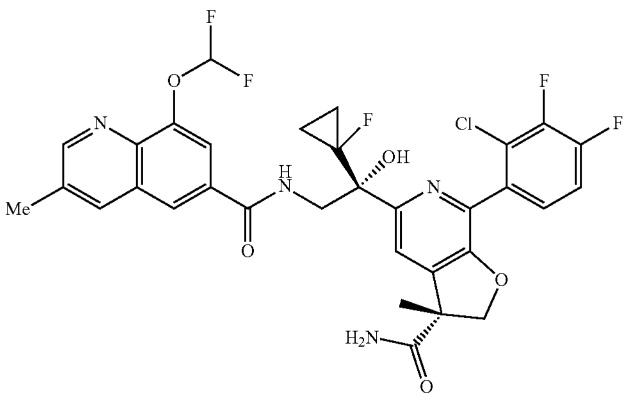 [SMILES: Cc1cnc2c(OC(F)F)cc(C(=O)NC[C@](O)(c3cc4c(c(-c5ccc(F)c(F)c5Cl)n3)OC[C@]4(C)C(N)=O)C3(F)CC3)cc2c1] | 677.40 |

TABLE 5-continued
| Example | Structure | MS+ m/z |
|---|---|---|
| 747 | 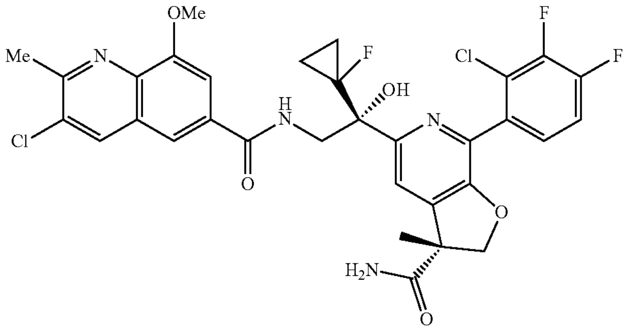 [SMILES: COc1cc(C(=O)NC[C@](O)(c2cc3c(c(-c4ccc(F)c(F)c4Cl)n2)OC[C@]3(C)C(N)=O)C2(F)CC2)cc2cc(Cl)c(C)nc12] | 675.37 |
| 748 | 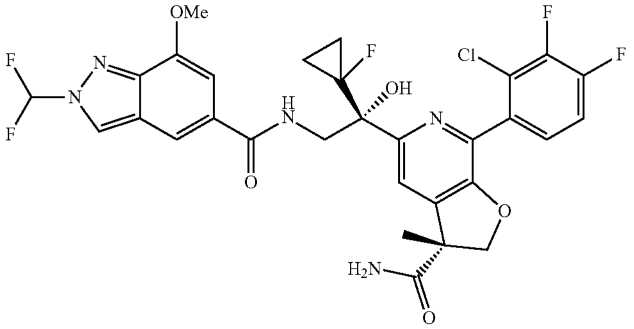 [SMILES: COc1cc(C(=O)NC[C@](O)(c2cc3c(c(-c4ccc(F)c(F)c4Cl)n2)OC[C@]3(C)C(N)=O)C2(F)CC2)cc2cn(C(F)F)nc12] | 666.40 |
| 749 | 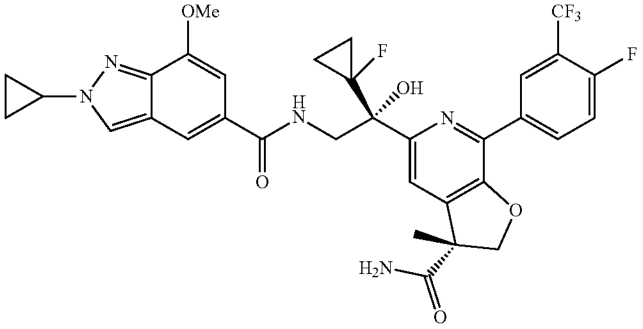 [SMILES: COc1cc(C(=O)NC[C@](O)(c2cc3c(c(-c4ccc(F)c(C(F)(F)F)c4)n2)OC[C@]3(C)C(N)=O)C2(F)CC2)cc2cn(C3CC3)nc12] | 672.43 |
| 750 | 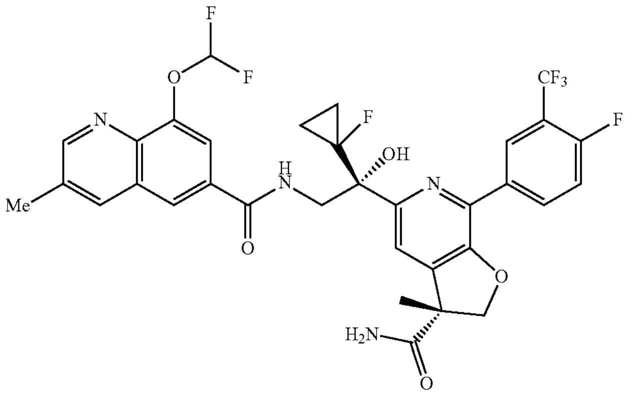 [SMILES: Cc1cnc2c(OC(F)F)cc(C(=O)NC[C@](O)(c3cc4c(c(-c5ccc(F)c(C(F)(F)F)c5)n3)OC[C@]4(C)C(N)=O)C3(F)CC3)cc2c1] | 693.39 |

TABLE 5-continued
| Example | Structure | MS+ m/z |
|---|---|---|
| 751 | 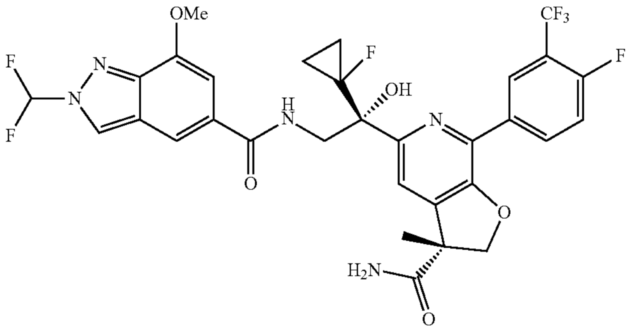 [SMILES: COc1cc(C(=O)NC[C@](O)(c2cc3c(c(-c4ccc(F)c(C(F)(F)F)c4)n2)OC[C@]3(C)C(N)=O)C2(F)CC2)cc2cn(C(F)F)nc12] | 682.39 |
| 752 | 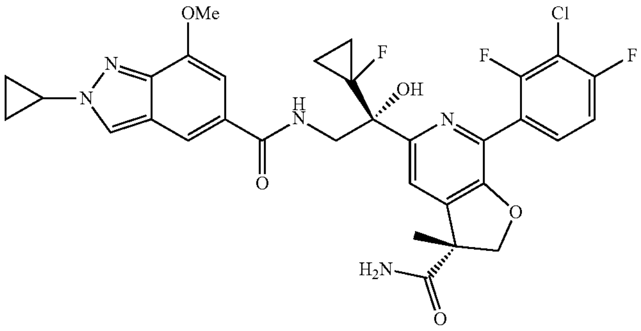 | 656.39 |
| 753 | 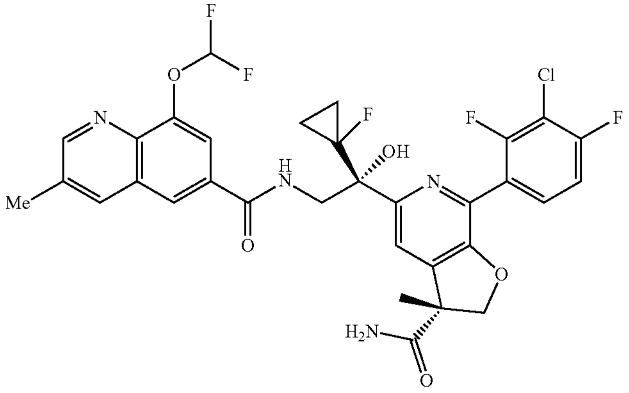 | 677.38 |
| 754 | 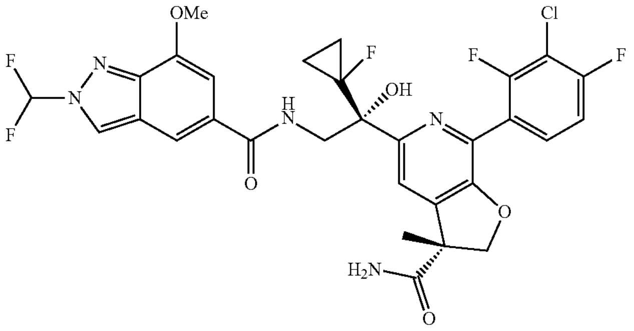 | 666.37 |

TABLE 5-continued
| Example | Structure | MS+ m/z |
|---|---|---|
| 755 | 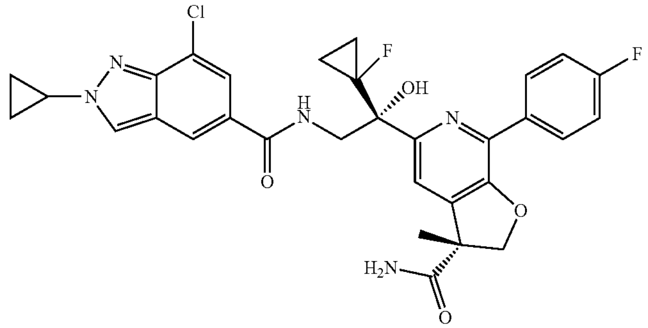 [SMILES: C[C@]1(C(N)=O)COc2c1cc([C@@](O)(CNC(=O)c1cc(Cl)c3nn(C4CC4)cc3c1)C1(F)CC1)nc2-c1ccc(F)cc1] | 608.38 |
| 756 | 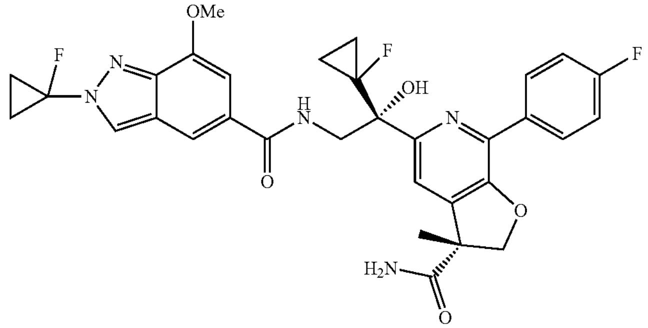 [SMILES: COc1cc(C(=O)NC[C@](O)(c2cc3c(c(-c4ccc(F)cc4)n2)OC[C@]3(C)C(N)=O)C2(F)CC2)cc2cn(C3(F)CC3)nc12] | 622.40 |
| 757 | 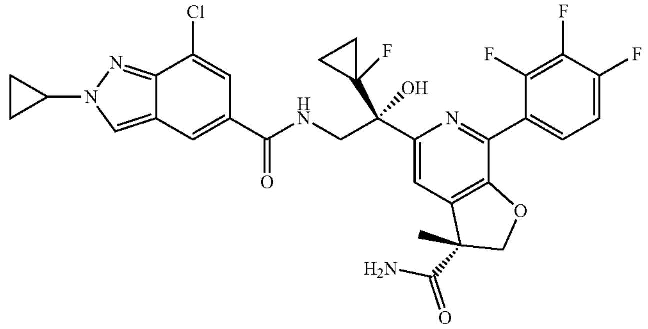 [SMILES: C[C@]1(C(N)=O)COc2c1cc([C@@](O)(CNC(=O)c1cc(Cl)c3nn(C4CC4)cc3c1)C1(F)CC1)nc2-c1ccc(F)c(F)c1F] | 644.36 |
| 758 | 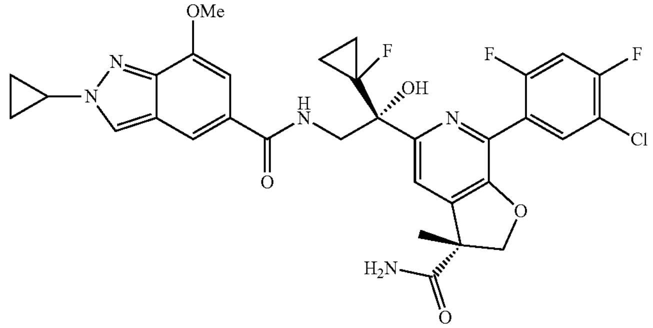 [SMILES: COc1cc(C(=O)NC[C@](O)(c2cc3c(c(-c4cc(Cl)c(F)cc4F)n2)OC[C@]3(C)C(N)=O)C2(F)CC2)cc2cn(C3CC3)nc12] | 656.36 |

TABLE 5-continued
| Example | Structure | MS+ m/z |
|---|---|---|
| 759 | 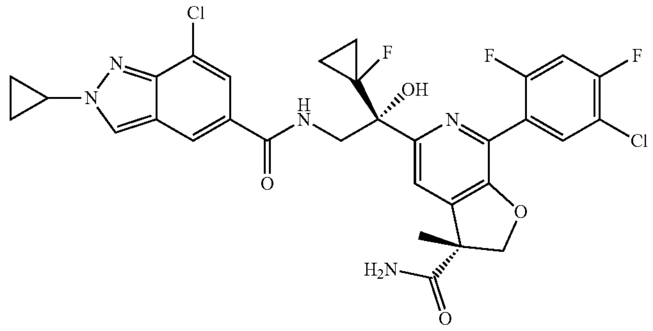 [SMILES: C[C@]1(C(N)=O)COc2c1cc([C@@](O)(CNC(=O)c1cc(Cl)c3nn(C4CC4)cc3c1)C1(F)CC1)nc2-c1cc(Cl)c(F)cc1F] | 660.29 |
| 760 | 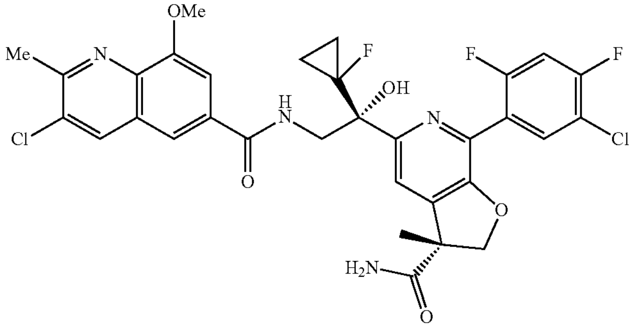 [SMILES: COc1cc(C(=O)NC[C@](O)(c2cc3c(c(-c4cc(Cl)c(F)cc4F)n2)OC[C@]3(C)C(N)=O)C2(F)CC2)cc2cc(Cl)c(C)nc12] | 675.25 |
| 761 | 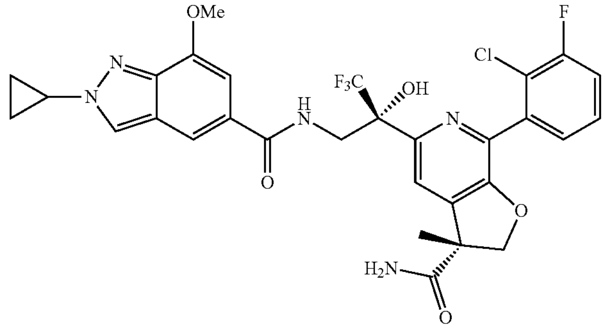 [SMILES: COc1cc(C(=O)NC[C@](O)(c2cc3c(c(-c4cccc(F)c4Cl)n2)OC[C@]3(C)C(N)=O)C(F)(F)F)cc2cn(C3CC3)nc12] | 648.34 |
| 762 | 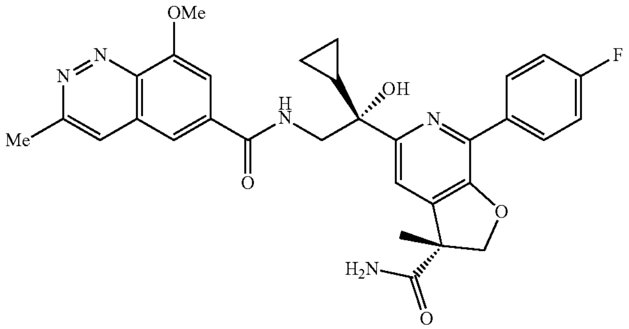 [SMILES: COc1cc(C(=O)NC[C@](O)(c2cc3c(c(-c4ccc(F)cc4)n2)OC[C@]3(C)C(N)=O)C2CC2)cc2cc(C)nnc12] | 572.38 |

TABLE 5-continued
| Example | Structure | MS+ m/z |
|---|---|---|
| 763 | 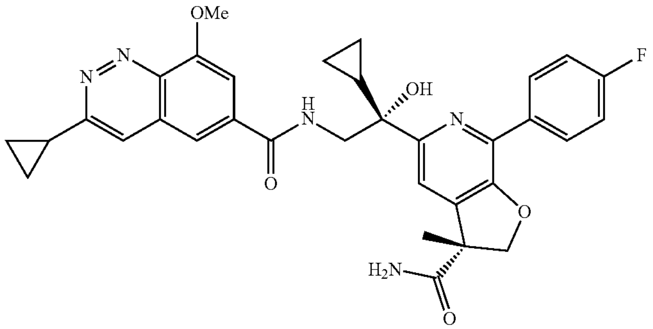 [SMILES: COc1cc(C(=O)NC[C@](O)(c2cc3c(c(-c4ccc(F)cc4)n2)OC[C@]3(C)C(N)=O)C2CC2)cc2cc(C3CC3)nnc12] | 598.38 |
| 764 | 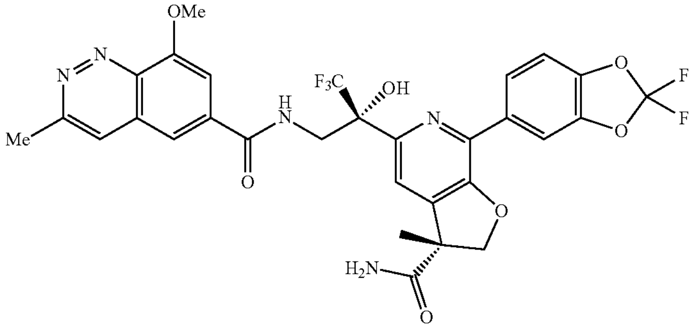 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(C)nnc12] | 662.31 |
| 765 | 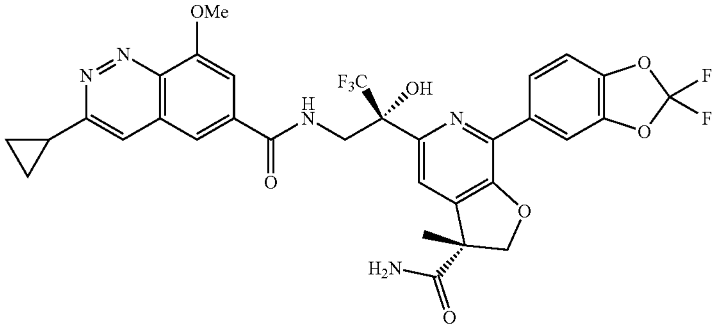 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(C3CC3)nnc12] | 688.32 |
| 766 | 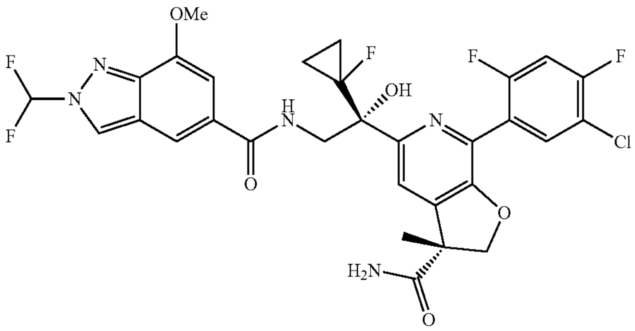 [SMILES: COc1cc(C(=O)NC[C@](O)(c2cc3c(c(-c4cc(Cl)c(F)cc4F)n2)OC[C@]3(C)C(N)=O)C2(F)CC2)cc2cn(C(F)F)nc12] | 666.28 |

TABLE 5-continued
| Example | Structure | MS+ m/z |
|---|---|---|
| 767 | 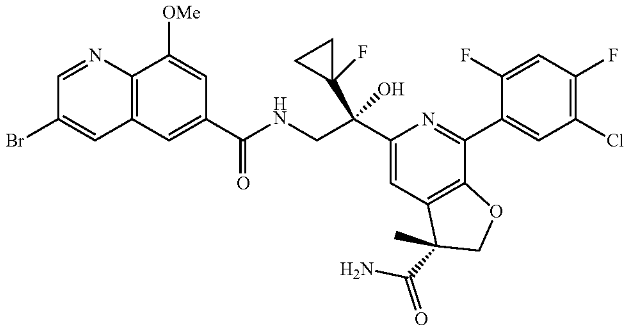 [SMILES: COc1cc(C(=O)NC[C@](O)(c2cc3c(c(-c4cc(Cl)c(F)cc4F)n2)OC[C@]3(C)C(N)=O)C2(F)CC2)cc2cc(Br)cnc12] | 707.08 |
| 768 | 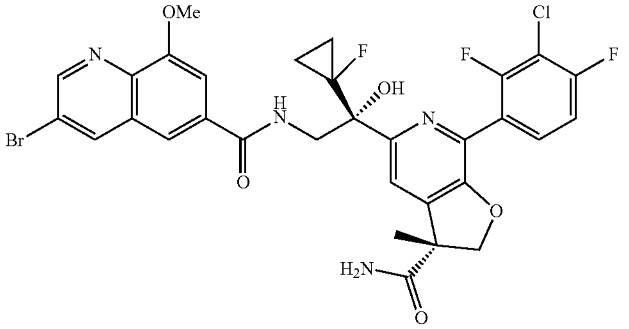 [SMILES: COc1cc(C(=O)NC[C@](O)(c2cc3c(c(-c4ccc(F)c(Cl)c4F)n2)OC[C@]3(C)C(N)=O)C2(F)CC2)cc2cc(Br)cnc12] | 707.08 |
| 769 | 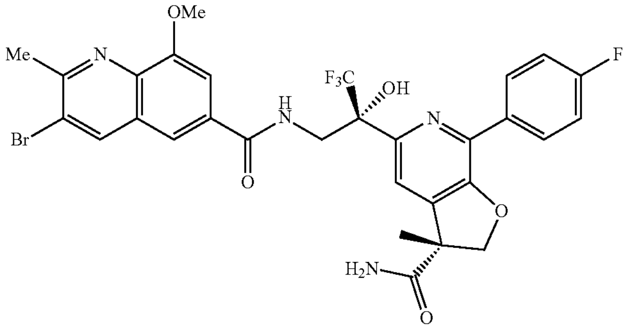 [SMILES: COc1cc(C(=O)NC[C@](O)(c2cc3c(c(-c4ccc(F)cc4)n2)OC[C@]3(C)C(N)=O)C(F)(F)F)cc2cc(Br)c(C)nc12] | 677.12 |
| 770 | 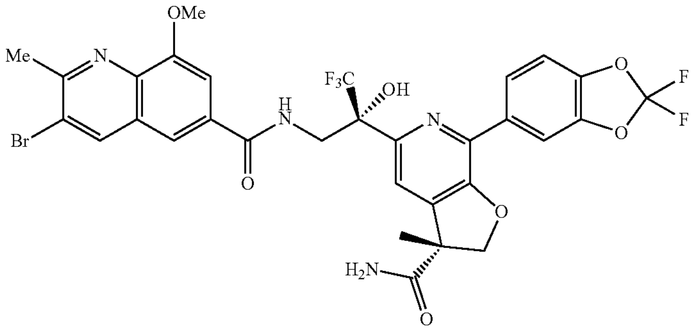 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(Br)c(C)nc12] | 739.09 |

TABLE 5-continued
| Example | Structure | MS+ m/z |
|---|---|---|
| 771 | 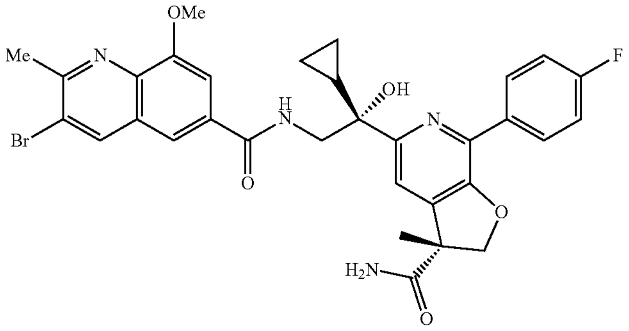 [SMILES: COc1cc(C(=O)NC[C@](O)(c2cc3c(c(-c4ccc(F)cc4)n2)OC[C@]3(C)C(N)=O)C2CC2)cc2cc(Br)c(C)nc12] | 649.18 |
| 772 | 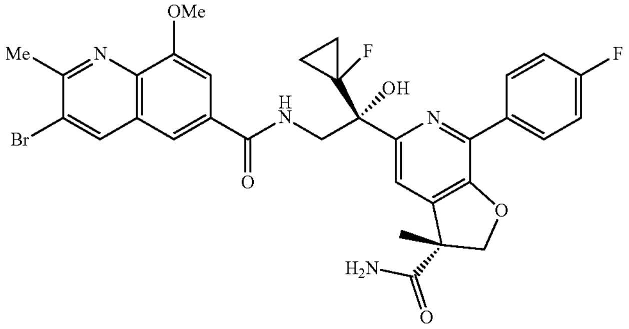 [SMILES: COc1cc(C(=O)NC[C@](O)(c2cc3c(c(-c4ccc(F)cc4)n2)OC[C@]3(C)C(N)=O)C2(F)CC2)cc2cc(Br)c(C)nc12] | 667.21 |
| 773 | 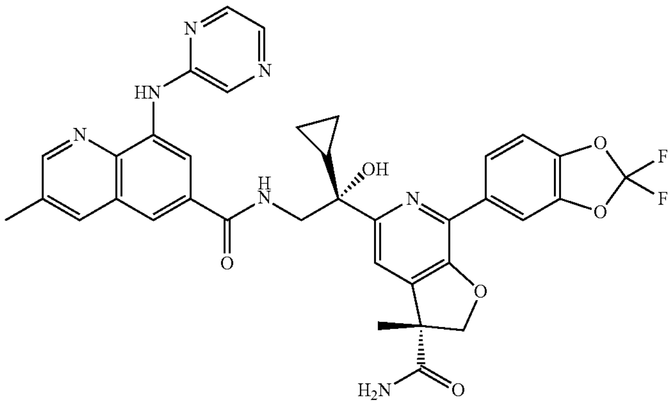 [SMILES: Cc1cnc2c(Nc3cnccn3)cc(C(=O)NC[C@](O)(c3cc4c(c(-c5ccc6c(c5)OC(F)(F)O6)n3)OC[C@]4(C)C(N)=O)C3CC3)cc2c1] | 696.53 |
| 774 | 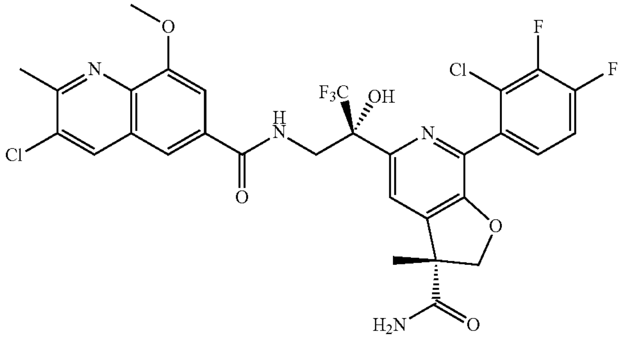 [SMILES: COc1cc(C(=O)NC[C@](O)(c2cc3c(c(-c4ccc(F)c(F)c4Cl)n2)OC[C@]3(C)C(N)=O)C(F)(F)F)cc2cc(Cl)c(C)nc12] | 685.27 |

TABLE 5-continued
| Example | Structure | MS+ m/z |
|---|---|---|
| 775 | 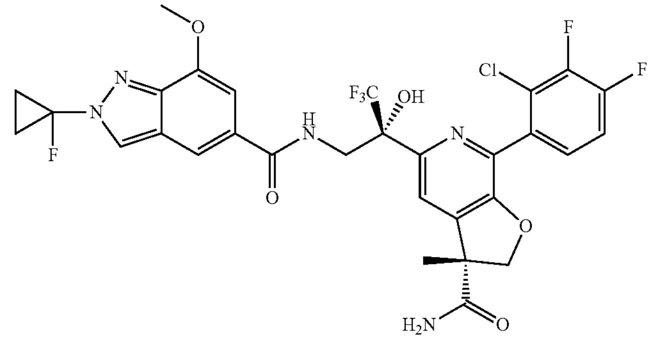 [SMILES: COc1cc(C(=O)NC[C@](O)(c2cc3c(c(-c4ccc(F)c(F)c4Cl)n2)OC[C@]3(C)C(N)=O)C(F)(F)F)cc2cn(C3(F)CC3)nc12] | 684.46 |
| 776 | 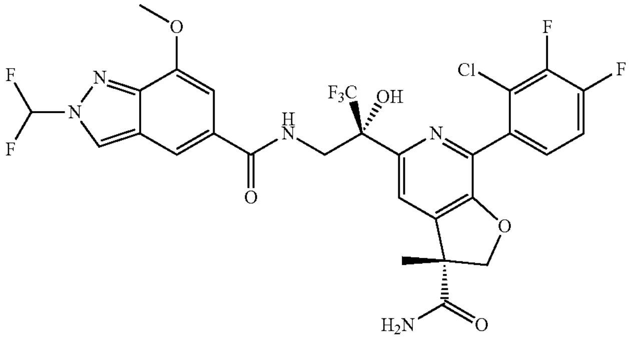 [SMILES: COc1cc(C(=O)NC[C@](O)(c2cc3c(c(-c4ccc(F)c(F)c4Cl)n2)OC[C@]3(C)C(N)=O)C(F)(F)F)cc2cn(C(F)F)nc12] | 676.49 |
| 777 | 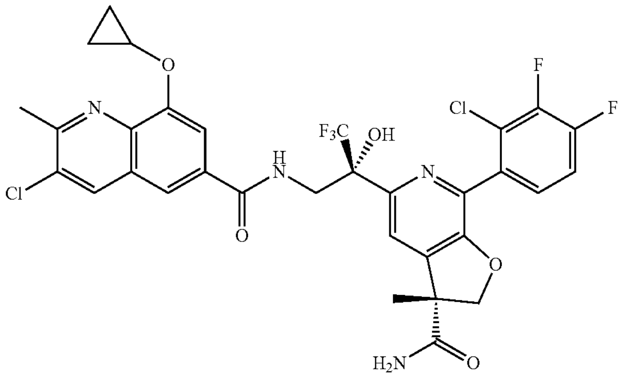 [SMILES: Cc1nc2c(OC3CC3)cc(C(=O)NC[C@](O)(c3cc4c(c(-c5ccc(F)c(F)c5Cl)n3)OC[C@]4(C)C(N)=O)C(F)(F)F)cc2cc1Cl] | 711.39 |
| 778 | 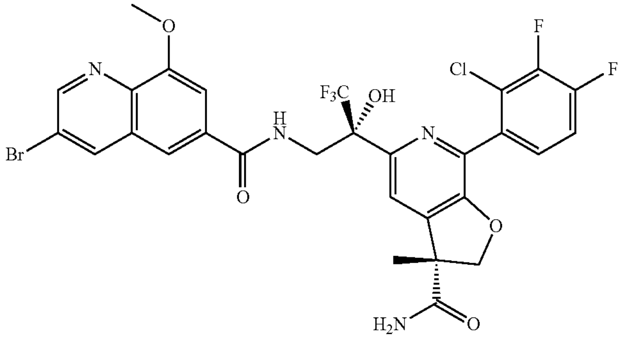 | 717.05 |

TABLE 5-continued
| Example | Structure | MS+ m/z |
|---|---|---|
| 779 | 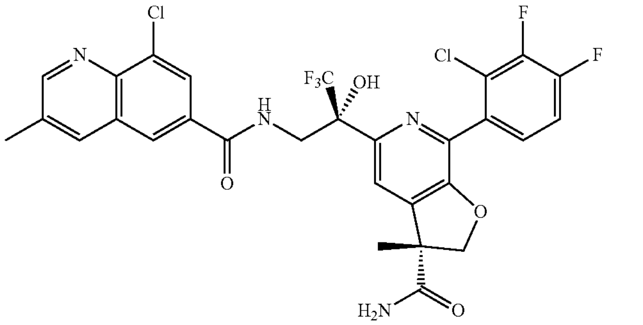 [SMILES: Cc1cnc2c(Cl)cc(C(=O)NC[C@](O)(c3cc4c(c(-c5ccc(F)c(F)c5Cl)n3)OC[C@]4(C)C(N)=O)C(F)(F)F)cc2c1] | 655.27 |
| 780 | 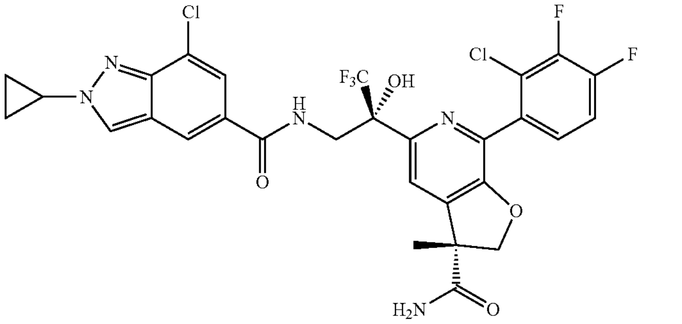 [SMILES: C[C@]1(C(N)=O)COc2c1cc([C@@](O)(CNC(=O)c1cc(Cl)c3nn(C4CC4)cc3c1)C(F)(F)F)nc2-c1ccc(F)c(F)c1Cl] | 670.30 |
| 781 | 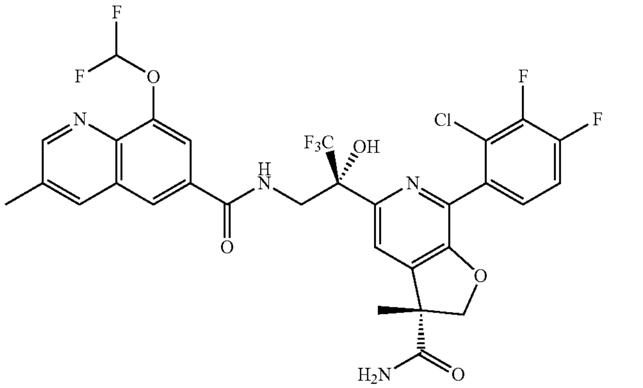 [SMILES: Cc1cnc2c(OC(F)F)cc(C(=O)NC[C@](O)(c3cc4c(c(-c5ccc(F)c(F)c5Cl)n3)OC[C@]4(C)C(N)=O)C(F)(F)F)cc2c1] | 687.41 |
| 782 | 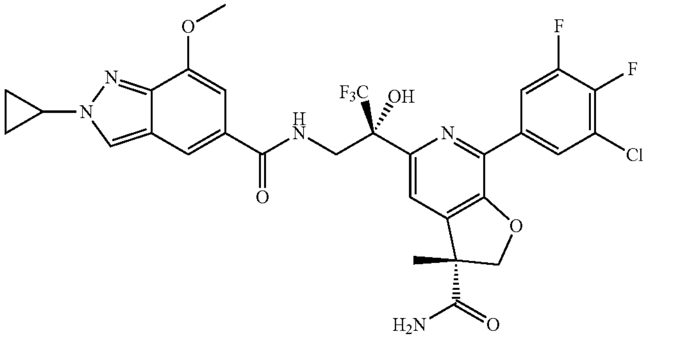 [SMILES: COc1cc(C(=O)NC[C@](O)(c2cc3c(c(-c4cc(F)c(F)c(Cl)c4)n2)OC[C@]3(C)C(N)=O)C(F)(F)F)cc2cn(C3CC3)nc12] | 666.33 |

TABLE 5-continued
| Example | Structure | MS+ m/z |
|---|---|---|
| 783 | 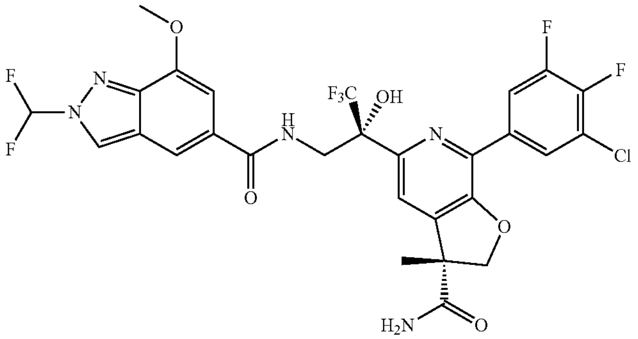 [SMILES: COc1cc(C(=O)NC[C@](O)(c2cc3c(c(-c4cc(F)c(F)c(Cl)c4)n2)OC[C@]3(C)C(N)=O)C(F)(F)F)cc2cn(C(F)F)nc12] | 676.35 |
| 784 | 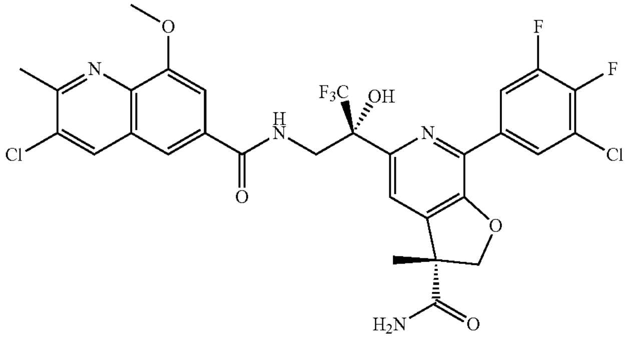 | 685.24 |
| 785 | 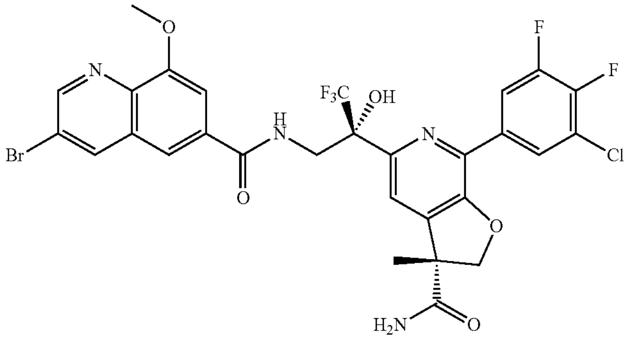 [SMILES: COc1cc(C(=O)NC[C@](O)(c2cc3c(c(-c4cc(F)c(F)c(Cl)c4)n2)OC[C@]3(C)C(N)=O)C(F)(F)F)cc2cc(Cl)c(C)nc12] | 717.22 |
| 786 | 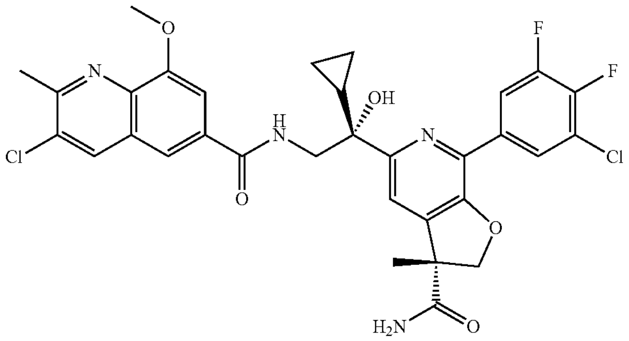 [SMILES: COc1cc(C(=O)NC[C@](O)(c2cc3c(c(-c4cc(F)c(F)c(Cl)c4)n2)OC[C@]3(C)C(N)=O)C2CC2)cc2cc(Cl)c(C)nc12] | 657.24 |

TABLE 5-continued
| Example | Structure | MS+ m/z |
|---|---|---|
| 787 | 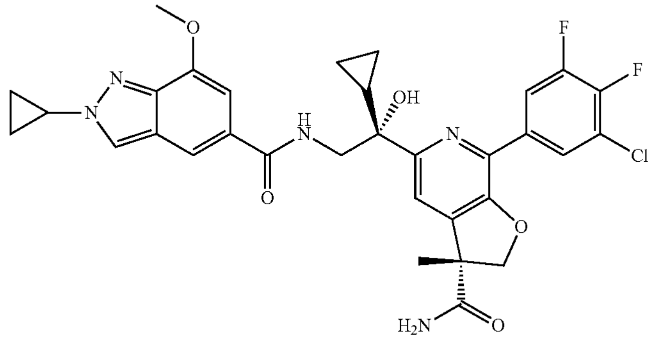 [SMILES: COc1cc(C(=O)NC[C@](O)(c2cc3c(c(-c4cc(F)c(F)c(Cl)c4)n2)OC[C@]3(C)C(N)=O)C2CC2)cc2cn(C3CC3)nc12] | 638.38 |
| 788 | 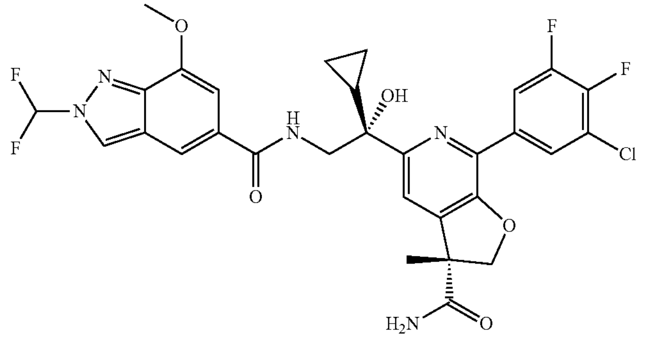 [SMILES: COc1cc(C(=O)NC[C@](O)(c2cc3c(c(-c4cc(F)c(F)c(Cl)c4)n2)OC[C@]3(C)C(N)=O)C2CC2)cc2cn(C(F)F)nc12] | 648.34 |
| 789 | 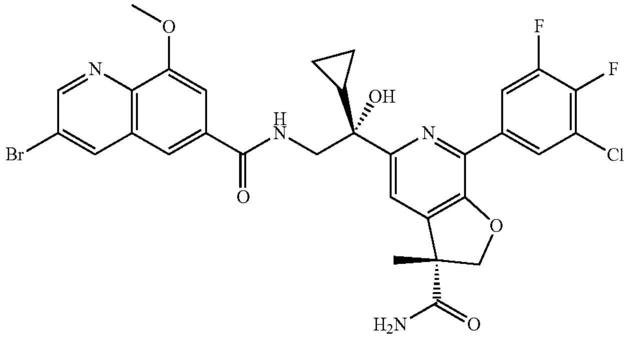 [SMILES: COc1cc(C(=O)NC[C@](O)(c2cc3c(c(-c4cc(F)c(F)c(Cl)c4)n2)OC[C@]3(C)C(N)=O)C2CC2)cc2cc(Br)cnc12] | 689.14 |
| 790 | 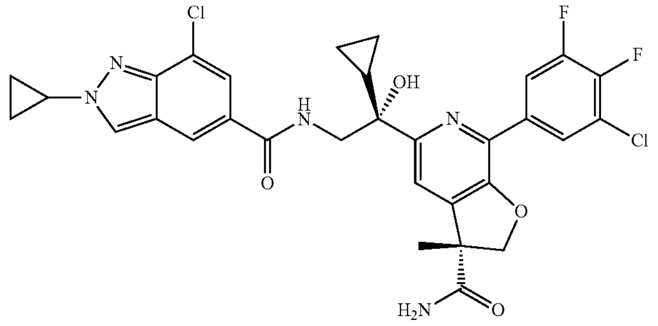 [SMILES: C[C@]1(C(N)=O)COc2c1cc([C@@](O)(CNC(=O)c1cc(Cl)c3nn(C4CC4)cc3c1)C1CC1)nc2-c1cc(F)c(F)c(Cl)c1] | 642.37 |

TABLE 5-continued
| Example | Structure | MS+ m/z |
|---|---|---|
| 791 | 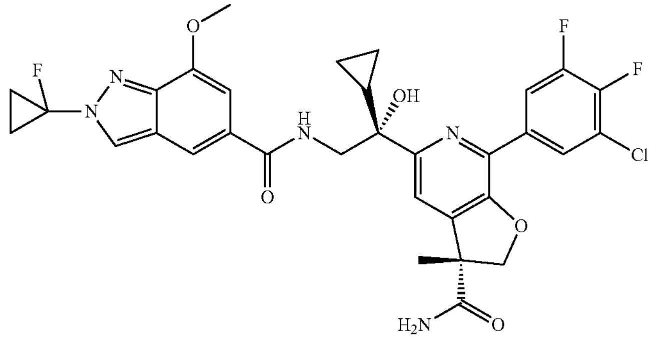 [SMILES: COc1cc(C(=O)NC[C@](O)(c2cc3c(c(-c4cc(F)c(F)c(Cl)c4)n2)OC[C@]3(C)C(N)=O)C2CC2)cc2cn(C3(F)CC3)nc12] | 656.39 |
| 792 | 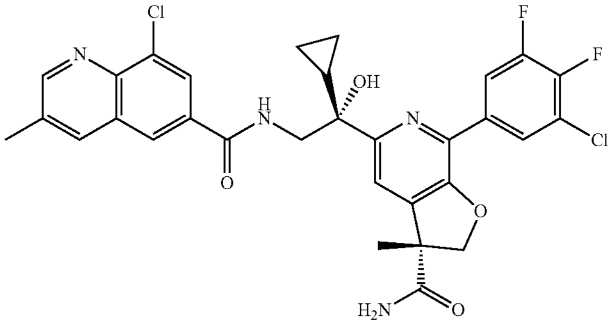 [SMILES: Cc1cnc2c(Cl)cc(C(=O)NC[C@](O)(c3cc4c(c(-c5cc(F)c(F)c(Cl)c5)n3)OC[C@]4(C)C(N)=O)C3CC3)cc2c1] | 627.36 |
| 793 | 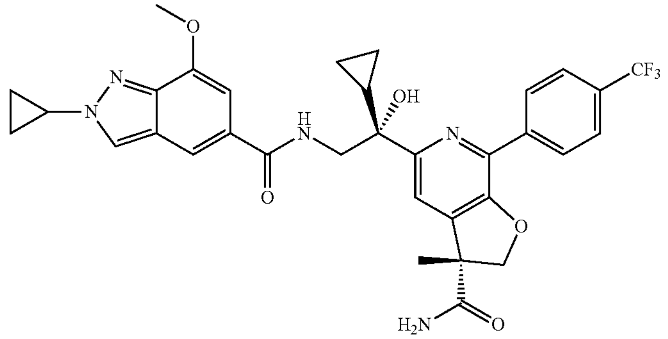 [SMILES: COc1cc(C(=O)NC[C@](O)(c2cc3c(c(-c4ccc(C(F)(F)F)cc4)n2)OC[C@]3(C)C(N)=O)C2CC2)cc2cn(C3CC3)nc12] | 636.50 |
| 794 | 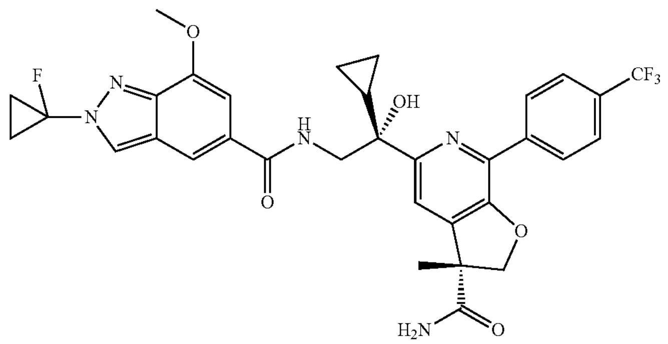 [SMILES: COc1cc(C(=O)NC[C@](O)(c2cc3c(c(-c4ccc(C(F)(F)F)cc4)n2)OC[C@]3(C)C(N)=O)C2CC2)cc2cn(C3(F)CC3)nc12] | 654.37 |

TABLE 5-continued
| Example | Structure | MS+ m/z |
|---|---|---|
| 795 | 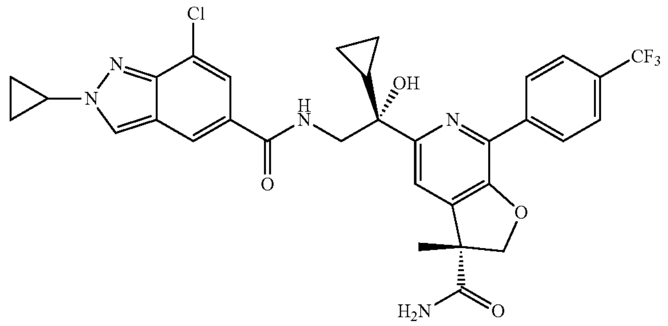 [SMILES: C[C@]1(C(N)=O)COc2c1cc([C@@](O)(CNC(=O)c1cc(Cl)c3nn(C4CC4)cc3c1)C1CC1)nc2-c1ccc(C(F)(F)F)cc1] | 640.46 |
| 796 | 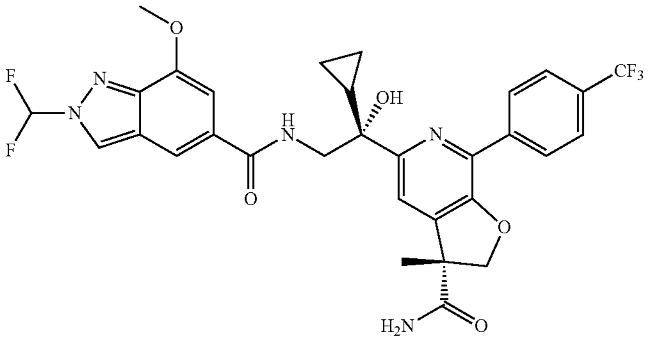 [SMILES: COc1cc(C(=O)NC[C@](O)(c2cc3c(c(-c4ccc(C(F)(F)F)cc4)n2)OC[C@]3(C)C(N)=O)C2CC2)cc2cn(C(F)F)nc12] | 646.56 |
| 797 | 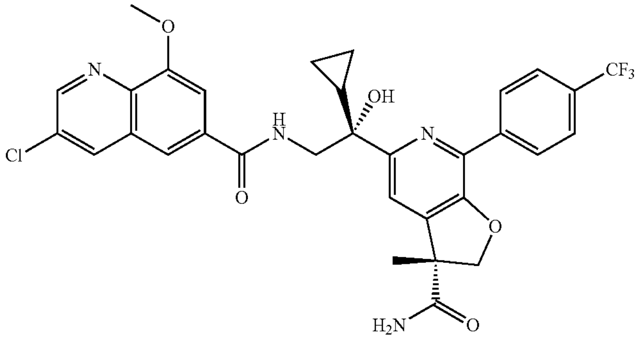 [SMILES: COc1cc(C(=O)NC[C@](O)(c2cc3c(c(-c4ccc(C(F)(F)F)cc4)n2)OC[C@]3(C)C(N)=O)C2CC2)cc2cc(Cl)cnc12] | 655.41 |
| 798 | 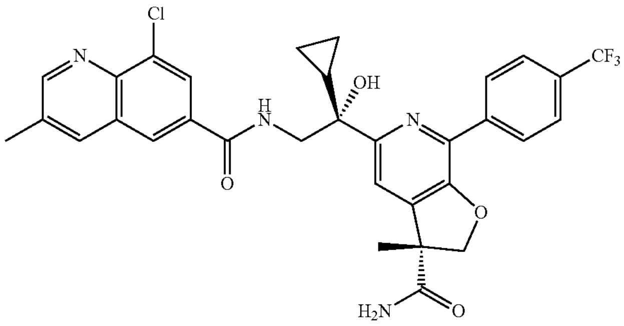 [SMILES: Cc1cnc2c(Cl)cc(C(=O)NC[C@](O)(c3cc4c(c(-c5ccc(C(F)(F)F)cc5)n3)OC[C@]4(C)C(N)=O)C3CC3)cc2c1] | 625.41 |

TABLE 5-continued
| Example | Structure | MS+ m/z |
|---|---|---|
| 799 | 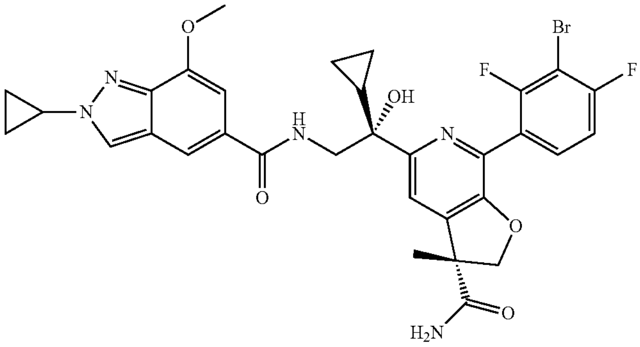 | 684.24 |
| 800 | 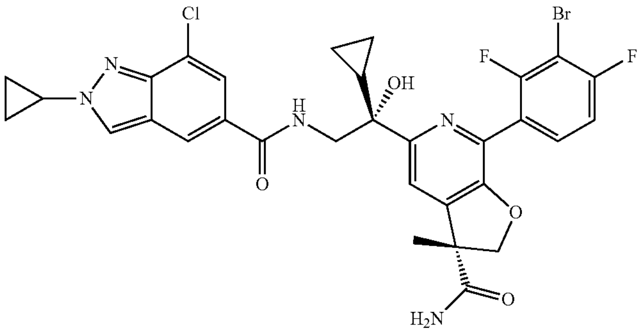 [SMILES: C[C@]1(C(N)=O)COc2c1cc([C@@](O)(CNC(=O)c1cc(Cl)c3nn(C4CC4)cc3c1)C1CC1)nc2-c1ccc(F)c(Br)c1F] | 688.11 |
| 801 | 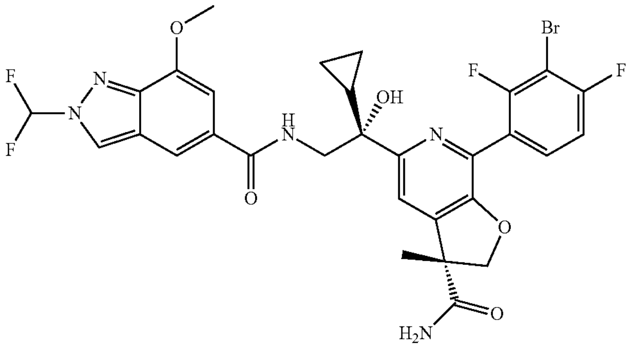 [SMILES: COc1cc(C(=O)NC[C@](O)(c2cc3c(c(-c4ccc(F)c(Br)c4F)n2)OC[C@]3(C)C(N)=O)C2CC2)cc2cn(C(F)F)nc12] | 694.11 |
| 802 | 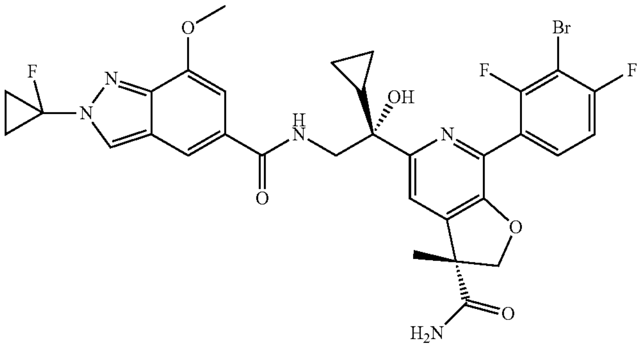 [SMILES: COc1cc(C(=O)NC[C@](O)(c2cc3c(c(-c4ccc(F)c(Br)c4F)n2)OC[C@]3(C)C(N)=O)C2CC2)cc2cn(C3(F)CC3)nc12] | 702.27 |

TABLE 5-continued
| Example | Structure | MS+ m/z |
|---|---|---|
| 803 | 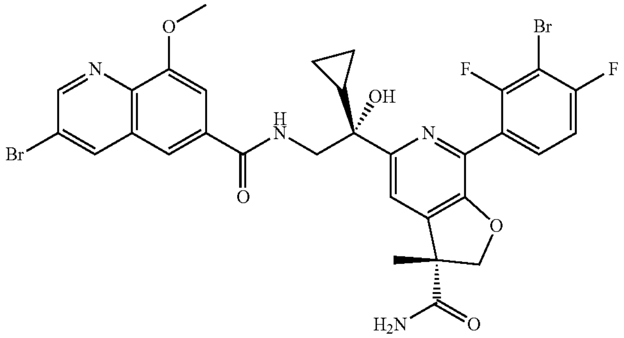 | 733.11 |
| 804 | 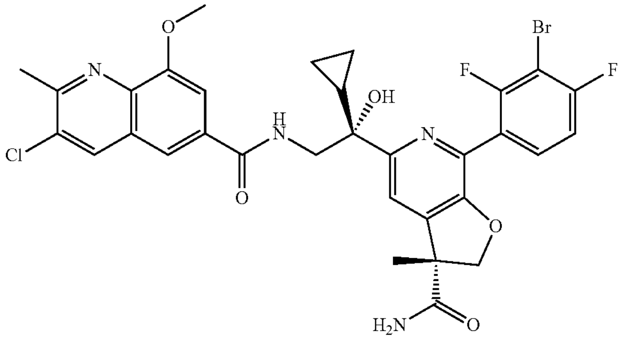 [SMILES: COc1cc(C(=O)NC[C@](O)(c2cc3c(c(-c4ccc(F)c(Br)c4F)n2)OC[C@]3(C)C(N)=O)C2CC2)cc2cc(Cl)c(C)nc12] | 703.18 |
| 805 | 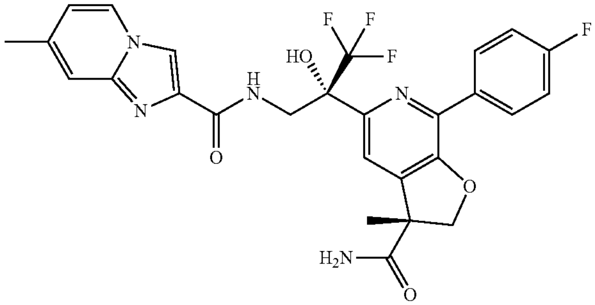 [SMILES: Cc1ccn2cc(C(=O)NC[C@](O)(c3cc4c(c(-c5ccc(F)cc5)n3)OC[C@]4(C)C(N)=O)C(F)(F)F)nc2c1] | 558.16 |
| 806 | 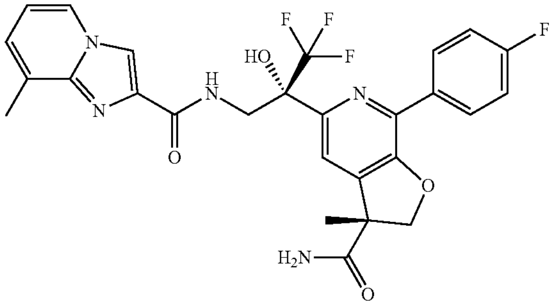 [SMILES: Cc1cccn2cc(C(=O)NC[C@](O)(c3cc4c(c(-c5ccc(F)cc5)n3)OC[C@]4(C)C(N)=O)C(F)(F)F)nc12] | 558.16 |

TABLE 5-continued
| Example | Structure | MS+ m/z |
|---|---|---|
| 807 | 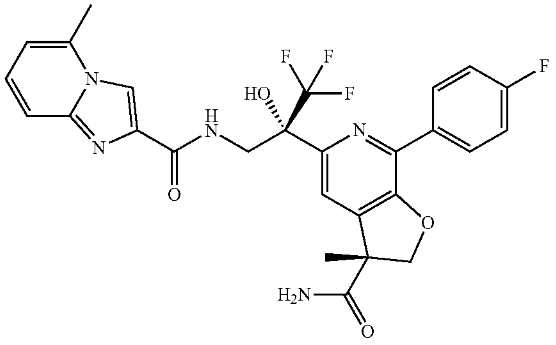 [SMILES: Cc1cccc2nc(C(=O)NC[C@](O)(c3cc4c(c(-c5ccc(F)cc5)n3)OC[C@]4(C)C(N)=O)C(F)(F)F)cn12] | 558.16 |
| 808 | 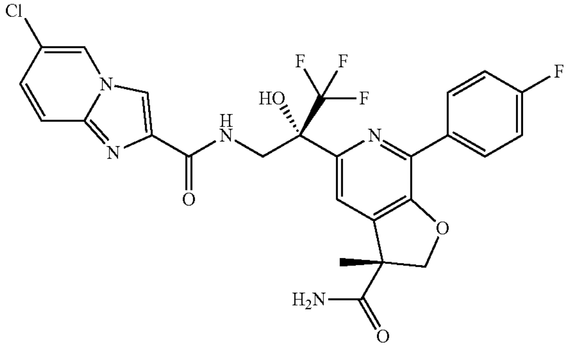 [SMILES: C[C@]1(C(N)=O)COc2c1cc([C@@](O)(CNC(=O)c1cn3cc(Cl)ccc3n1)C(F)(F)F)nc2-c1ccc(F)cc1] | 578.11 |
| 809 | 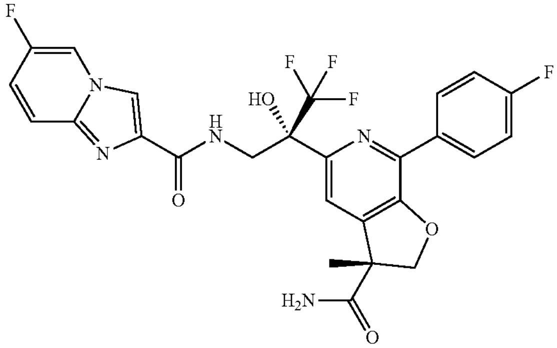 [SMILES: C[C@]1(C(N)=O)COc2c1cc([C@@](O)(CNC(=O)c1cn3cc(F)ccc3n1)C(F)(F)F)nc2-c1ccc(F)cc1] | 562.14 |
| 810 | 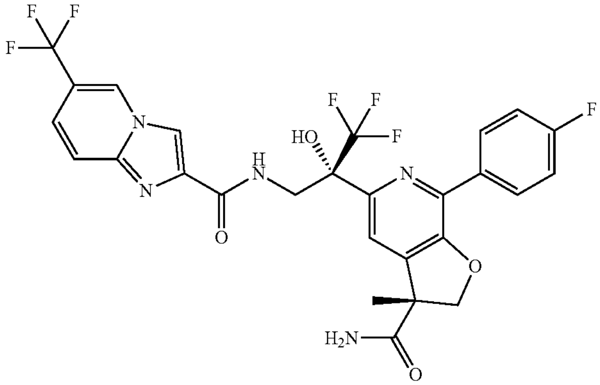 [SMILES: C[C@]1(C(N)=O)COc2c1cc([C@@](O)(CNC(=O)c1cn3cc(C(F)(F)F)ccc3n1)C(F)(F)F)nc2-c1ccc(F)cc1] | 612.14 |

TABLE 5-continued
| Example | Structure | MS⁺ m/z |
|---|---|---|
| 811 | 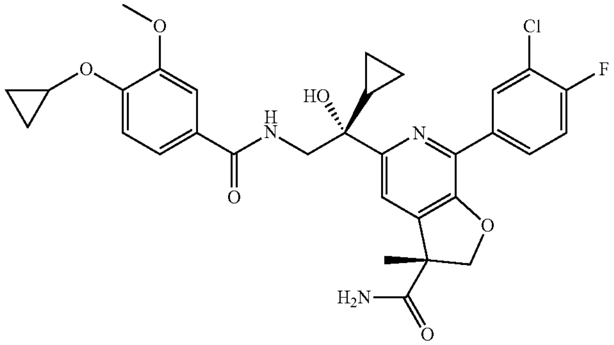 [SMILES: COc1cc(C(=O)NC[C@](O)(c2cc3c(c(-c4ccc(F)c(Cl)c4)n2)OC[C@]3(C)C(N)=O)C2CC2)ccc1OC1CC1] | 596.18 |
| 812 | 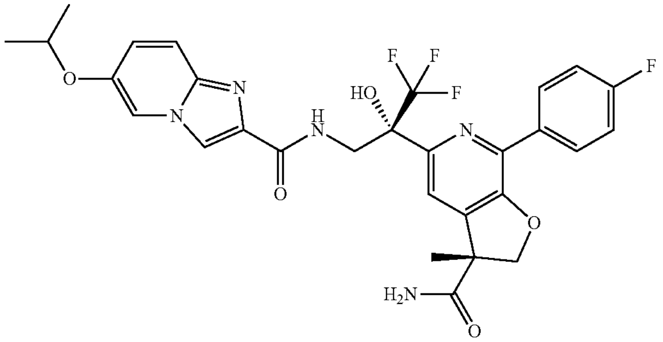 [SMILES: CC(C)Oc1ccc2nc(C(=O)NC[C@](O)(c3cc4c(c(-c5ccc(F)cc5)n3)OC[C@]4(C)C(N)=O)C(F)(F)F)cn2c1] | 602.19 |
| 813 | 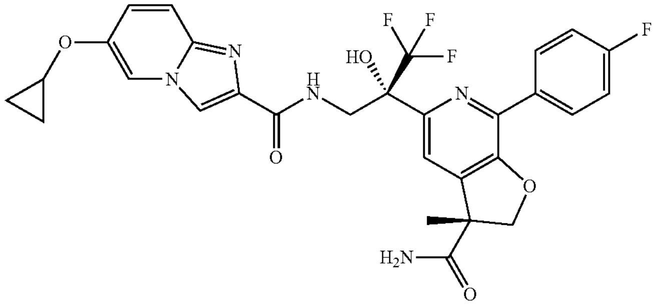 [SMILES: C[C@]1(C(N)=O)COc2c1cc([C@@](O)(CNC(=O)c1cn3cc(OC4CC4)ccc3n1)C(F)(F)F)nc2-c1ccc(F)cc1] | 600.17 |
| 814 | 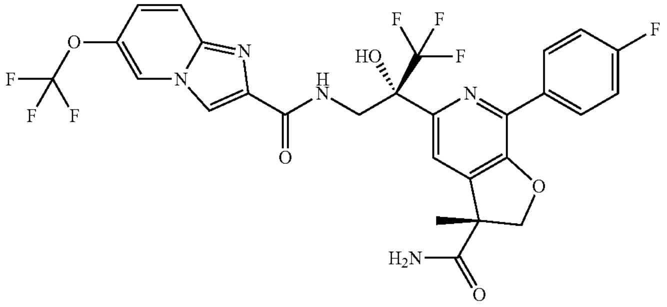 [SMILES: C[C@]1(C(N)=O)COc2c1cc([C@@](O)(CNC(=O)c1cn3cc(OC(F)(F)F)ccc3n1)C(F)(F)F)nc2-c1ccc(F)cc1] | 628.13 |

TABLE 5-continued
| Example | Structure | MS+ m/z |
|---|---|---|
| 815 | 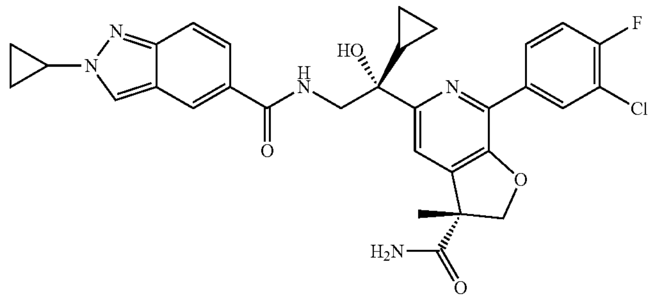 [SMILES: C[C@]1(C(N)=O)COc2c1cc([C@@](O)(CNC(=O)c1ccc3nn(C4CC4)cc3c1)C1CC1)nc2-c1ccc(F)c(Cl)c1] | 590.18 |
| 816 | 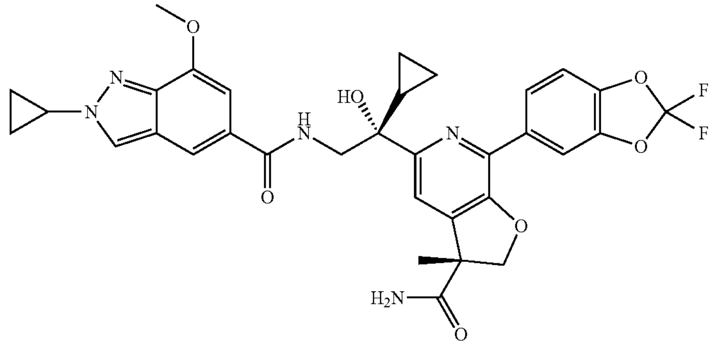 [SMILES: COc1cc(C(=O)NC[C@](O)(c2cc3c(c(-c4ccc5c(c4)OC(F)(F)O5)n2)OC[C@]3(C)C(N)=O)C2CC2)cc2cn(C3CC3)nc12] | 648.21 |
| 817 | 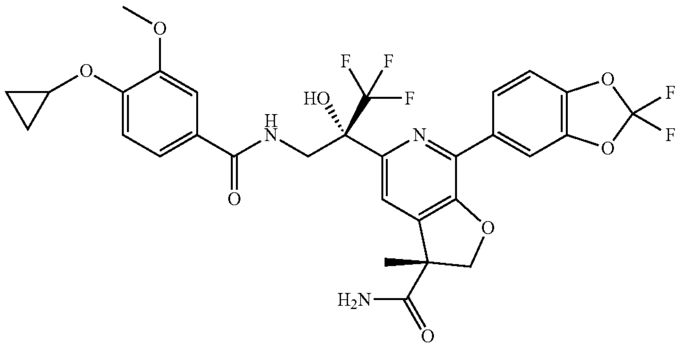 [SMILES: COc1cc(C(=O)NC[C@](O)(c2cc3c(c(-c4ccc5c(c4)OC(F)(F)O5)n2)OC[C@]3(C)C(N)=O)C(F)(F)F)ccc1OC1CC1] | 652.16 |
| 818 | 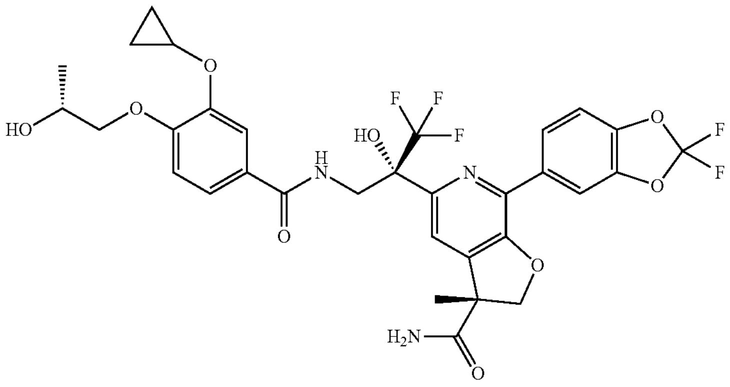 [SMILES: C[C@@H](O)COc1ccc(C(=O)NC[C@](O)(c2cc3c(c(-c4ccc5c(c4)OC(F)(F)O5)n2)OC[C@]3(C)C(N)=O)C(F)(F)F)cc1OC1CC1] | 696.19 |

TABLE 5-continued
| Example | Structure | MS+ m/z |
|---|---|---|
| 819 | 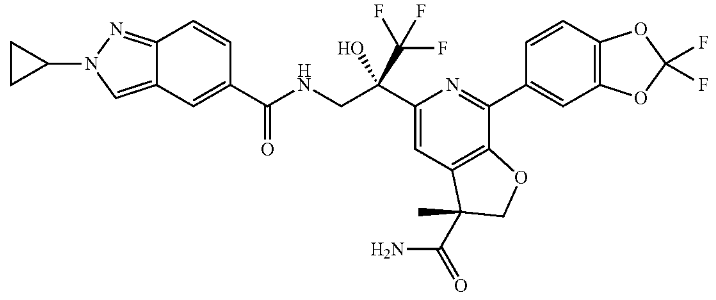 [SMILES: C[C@]1(C(N)=O)COc2c1cc([C@@](O)(CNC(=O)c1ccc3nn(C4CC4)cc3c1)C(F)(F)F)nc2-c1ccc2c(c1)OC(F)(F)O2] | 646.1 |
| 820 | 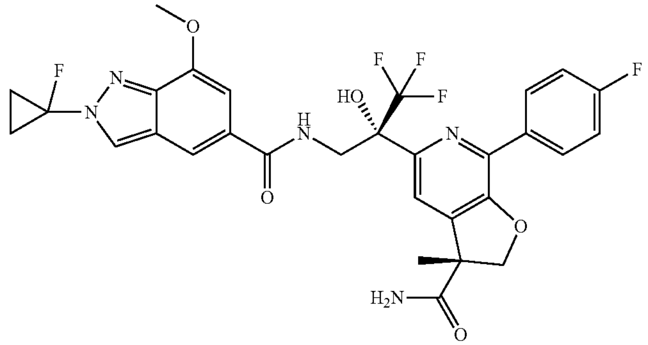 [SMILES: COc1cc(C(=O)NC[C@](O)(c2cc3c(c(-c4ccc(F)cc4)n2)OC[C@]3(C)C(N)=O)C(F)(F)F)cc2cn(C3(F)CC3)nc12] | 632.18 |
| 821 | 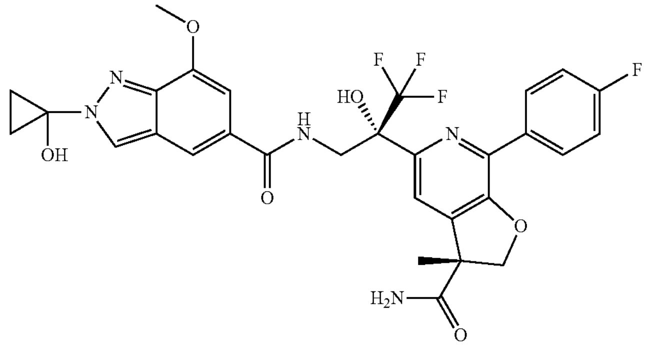 [SMILES: COc1cc(C(=O)NC[C@](O)(c2cc3c(c(-c4ccc(F)cc4)n2)OC[C@]3(C)C(N)=O)C(F)(F)F)cc2cn(C3(O)CC3)nc12] | 630.19 |
| 822 | 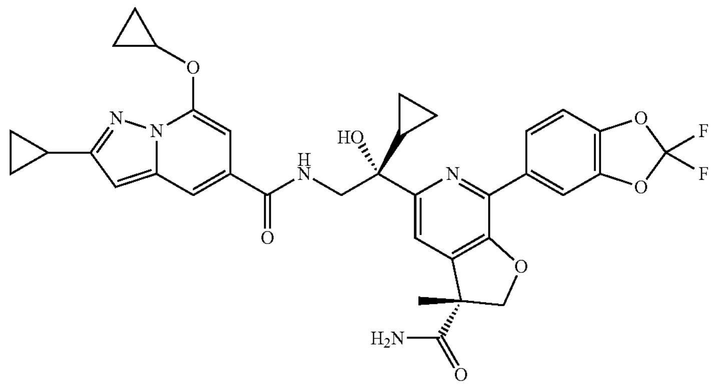 [SMILES: C[C@]1(C(N)=O)COc2c1cc([C@@](O)(CNC(=O)c1cc(OC3CC3)n3nc(C4CC4)cc3c1)C1CC1)nc2-c1ccc2c(c1)OC(F)(F)O2] | 674.23 |

TABLE 5-continued
| Example | Structure | MS+ m/z |
|---|---|---|
| 823 | 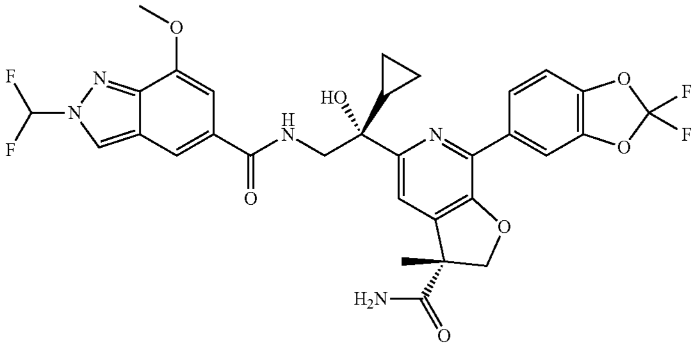 [SMILES: COc1cc(C(=O)NC[C@](O)(c2cc3c(c(-c4ccc5c(c4)OC(F)(F)O5)n2)OC[C@]3(C)C(N)=O)C2CC2)cc2cn(C(F)F)nc12] | 658.18 |
| 824 | 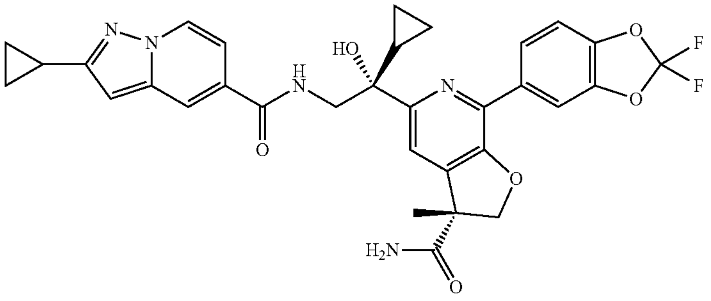 [SMILES: C[C@]1(C(N)=O)COc2c1cc([C@@](O)(CNC(=O)c1ccn3nc(C4CC4)cc3c1)C1CC1)nc2-c1ccc2c(c1)OC(F)(F)O2] | 618.20 |
| 825 | 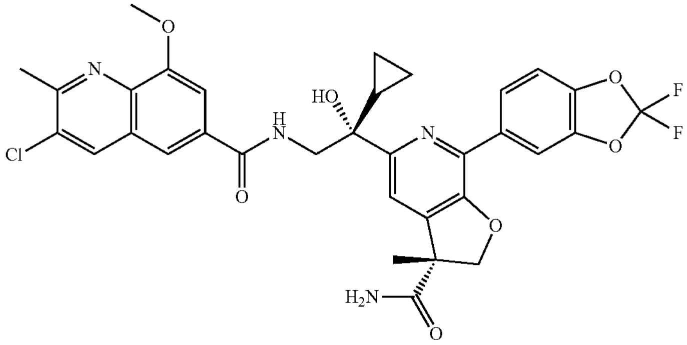 [SMILES: COc1cc(C(=O)NC[C@](O)(c2cc3c(c(-c4ccc5c(c4)OC(F)(F)O5)n2)OC[C@]3(C)C(N)=O)C2CC2)cc2cc(Cl)c(C)nc12] | 667.16 |
| 826 | 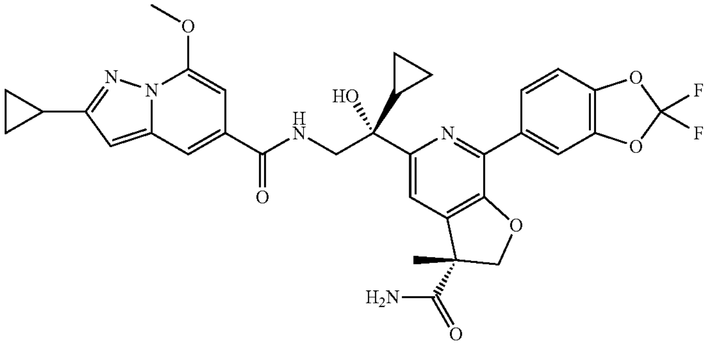 [SMILES: COc1cc(C(=O)NC[C@](O)(c2cc3c(c(-c4ccc5c(c4)OC(F)(F)O5)n2)OC[C@]3(C)C(N)=O)C2CC2)cc2cc(C3CC3)nn12] | 648.21 |

TABLE 5-continued
| Example | Structure | MS+ m/z |
|---|---|---|
| 827 | 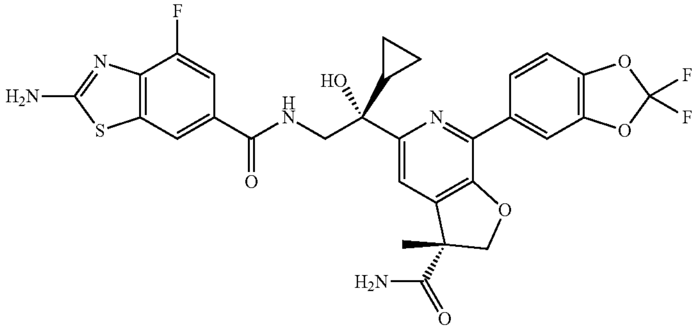 [SMILES: C[C@]1(C(N)=O)COc2c1cc([C@@](O)(CNC(=O)c1cc(F)c3nc(N)sc3c1)C1CC1)nc2-c1ccc2c(c1)OC(F)(F)O2] | 628.14 |
| 828 | 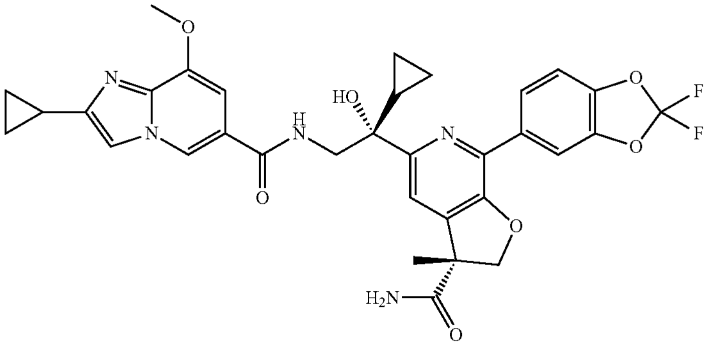 [SMILES: COc1cc(C(=O)NC[C@](O)(c2cc3c(c(-c4ccc5c(c4)OC(F)(F)O5)n2)OC[C@]3(C)C(N)=O)C2CC2)cn2cc(C3CC3)nc12] | 648.21 |
| 829 | 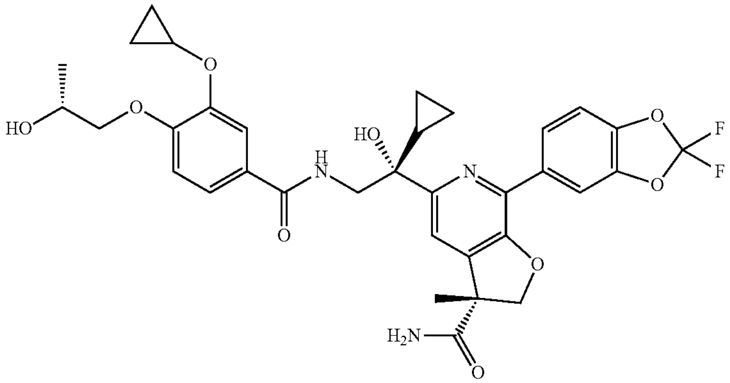 [SMILES: C[C@@H](O)COc1ccc(C(=O)NC[C@](O)(c2cc3c(c(-c4ccc5c(c4)OC(F)(F)O5)n2)OC[C@]3(C)C(N)=O)C2CC2)cc1OC1CC1] | 668.23 |
| 830 | 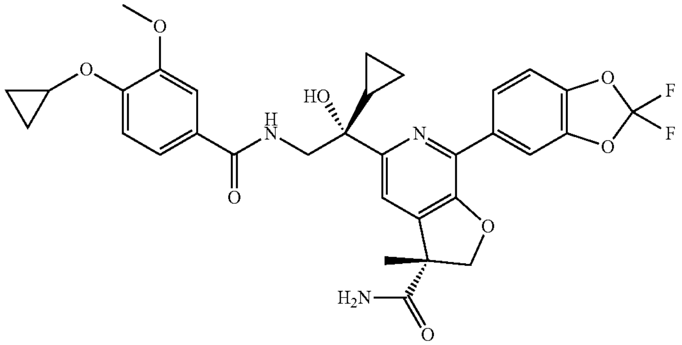 [SMILES: COc1cc(C(=O)NC[C@](O)(c2cc3c(c(-c4ccc5c(c4)OC(F)(F)O5)n2)OC[C@]3(C)C(N)=O)C2CC2)ccc1OC1CC1] | 624.20 |

TABLE 5-continued
| Example | Structure | MS⁺ m/z |
|---|---|---|
| 831 | 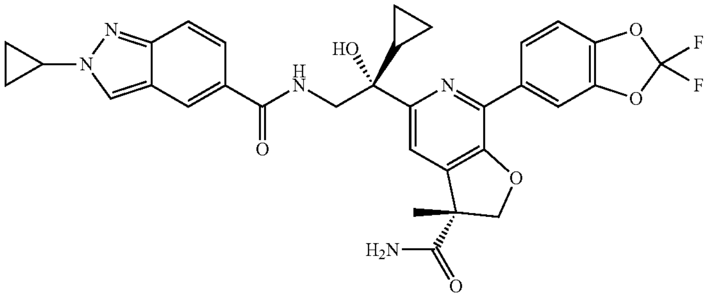 [SMILES: C[C@]1(C(N)=O)COc2c1cc([C@@](O)(CNC(=O)c1ccc3nn(C4CC4)cc3c1)C1CC1)nc2-c1ccc2c(c1)OC(F)(F)O2] | 618.20 |
| 832 | 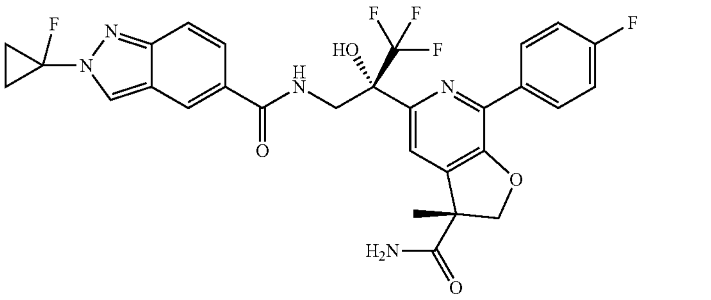 [SMILES: C[C@]1(C(N)=O)COc2c1cc([C@@](O)(CNC(=O)c1ccc3nn(C4(F)CC4)cc3c1)C(F)(F)F)nc2-c1ccc(F)cc1] | 602.17 |
| 833 | 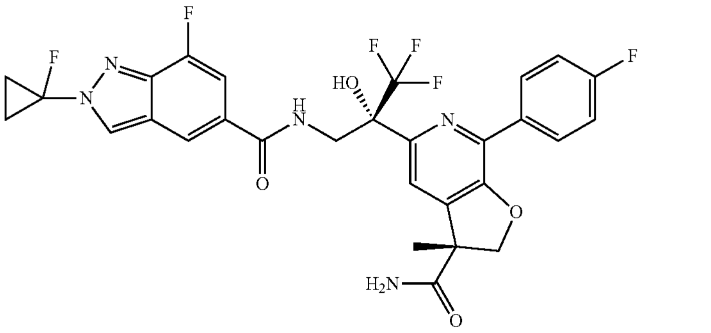 | 620.16 |
| 834 | 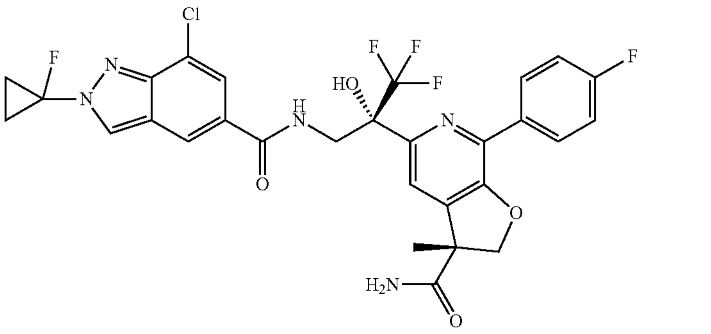 [SMILES: C[C@]1(C(N)=O)COc2c1cc([C@@](O)(CNC(=O)c1cc(F)c3nn(C4(F)CC4)cc3c1)C(F)(F)F)nc2-c1ccc(F)cc1] | 636.13 |

TABLE 5-continued
| Example | Structure | MS+ m/z |
| --- | --- | --- |
| 835 | 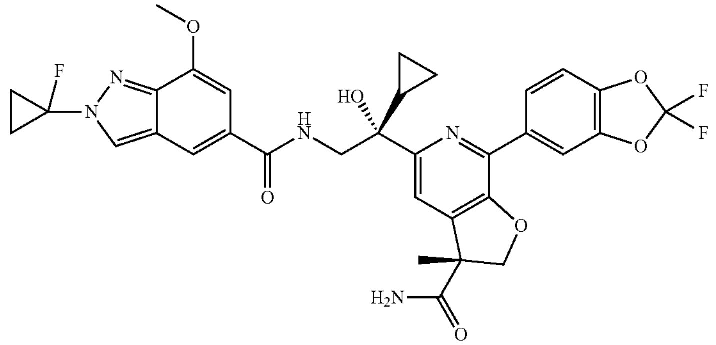 [SMILES: COc1cc(C(=O)NC[C@](O)(c2cc3c(c(-c4ccc5c(c4)OC(F)(F)O5)n2)OC[C@]3(C)C(N)=O)C2CC2)cc2cn(C3(F)CC3)nc12] | 666.21 |
| 836 | 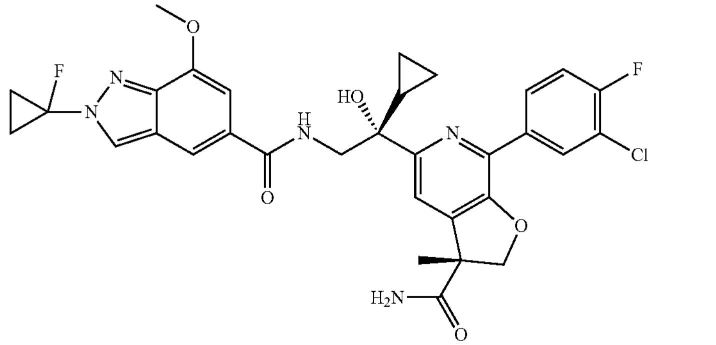 | 638.19 |
| 837 | 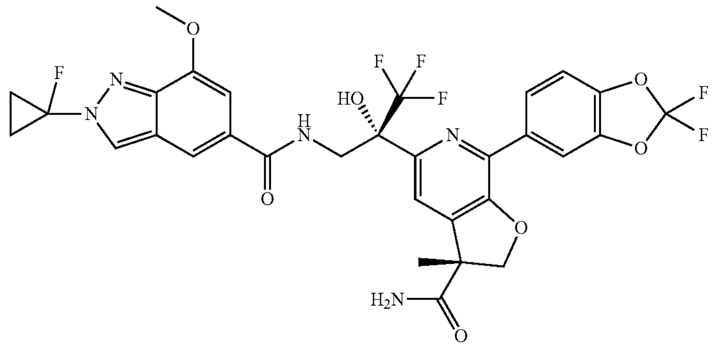 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cn(C3(F)CC3)nc12] | 694.16 |
| 838 | 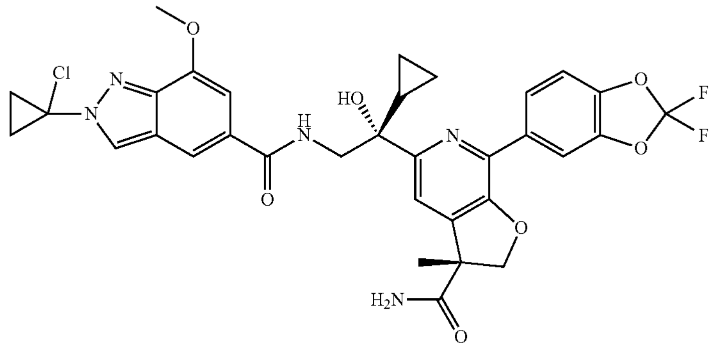 | 682.18 |

TABLE 5-continued
| Example | Structure | MS+ m/z |
|---|---|---|
| 839 | 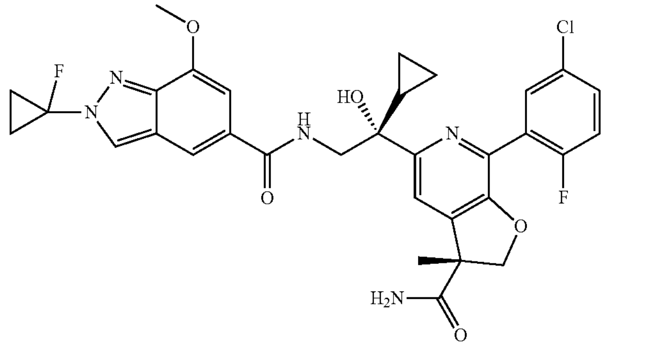 | 638.19 |
| 840 | 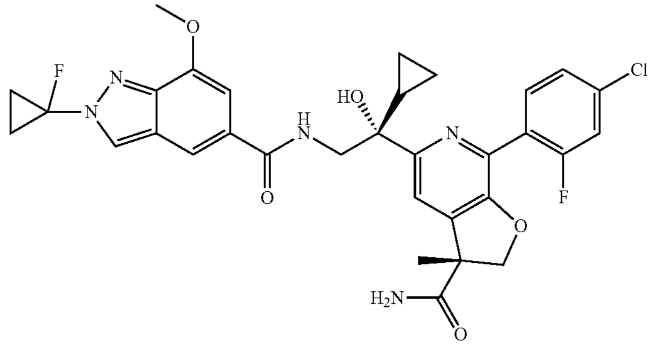 [SMILES: COc1cc(C(=O)NC[C@](O)(c2cc3c(c(-c4ccc(Cl)cc4F)n2)OC[C@]3(C)C(N)=O)C2CC2)cc2cn(C3(F)CC3)nc12] | 638.19 |
| 841 | 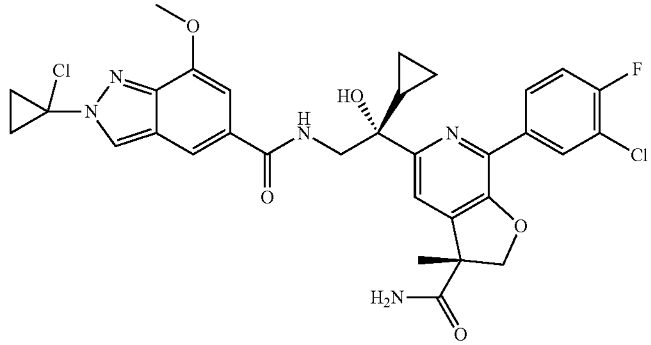 [SMILES: COc1cc(C(=O)NC[C@](O)(c2cc3c(c(-c4ccc(F)c(Cl)c4)n2)OC[C@]3(C)C(N)=O)C2CC2)cc2cn(C3(Cl)CC3)nc12] | 654.16 |
| 842 | 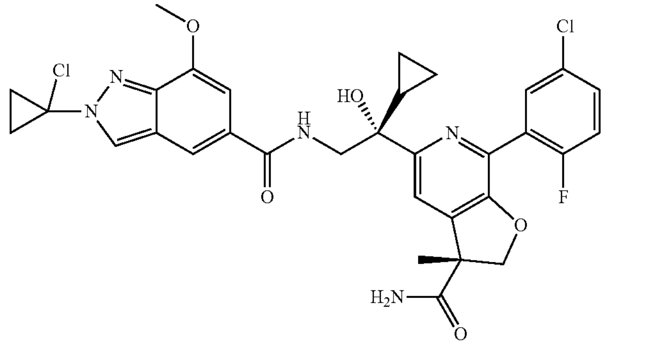 [SMILES: COc1cc(C(=O)NC[C@](O)(c2cc3c(c(-c4cc(Cl)ccc4F)n2)OC[C@]3(C)C(N)=O)C2CC2)cc2cn(C3(Cl)CC3)nc12] | 654.16 |

TABLE 5-continued
| Example | Structure | MS+ m/z |
|---|---|---|
| 843 | 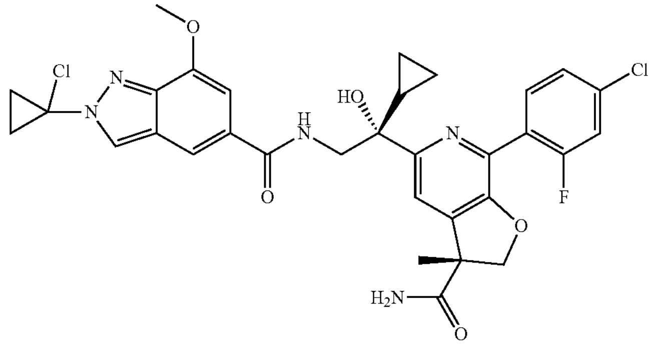 | 654.16 |
| 844 | 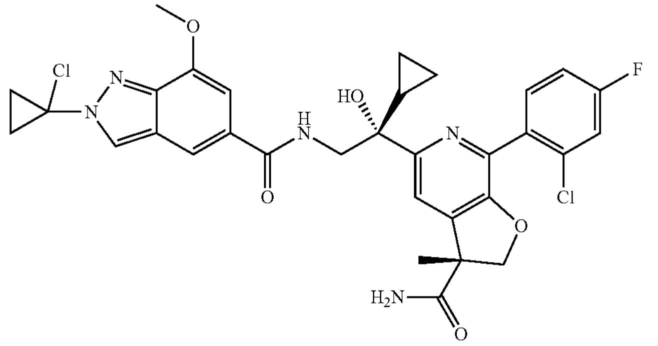 [SMILES: COc1cc(C(=O)NC[C@](O)(c2cc3c(c(-c4ccc(F)cc4Cl)n2)OC[C@]3(C)C(N)=O)C2CC2)cc2cn(C3(Cl)CC3)nc12] | 654.16 |
| 845 | 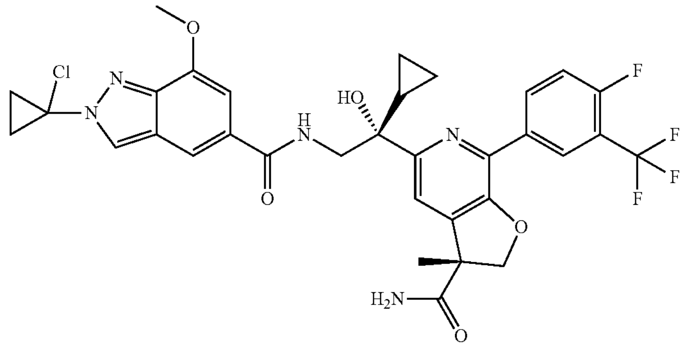 [SMILES: COc1cc(C(=O)NC[C@](O)(c2cc3c(c(-c4ccc(F)c(C(F)(F)F)c4)n2)OC[C@]3(C)C(N)=O)C2CC2)cc2cn(C3(Cl)CC3)nc12] | 688.18 |
| 846 | 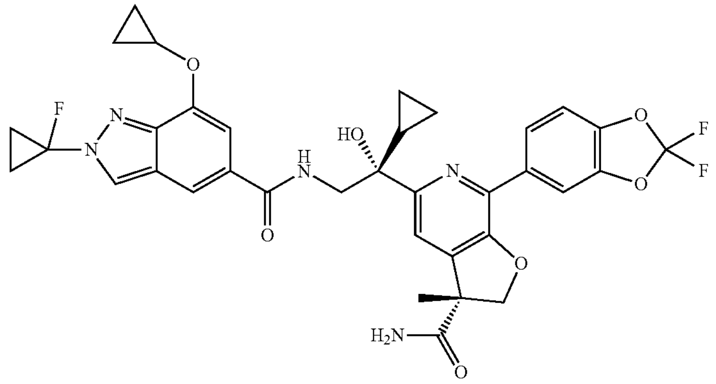 [SMILES: C[C@]1(C(N)=O)COc2c1cc([C@@](O)(CNC(=O)c1cc(OC3CC3)c3nn(C4(F)CC4)cc3c1)C1CC1)nc2-c1ccc2c(c1)OC(F)(F)O2] | 692.22 |

TABLE 5-continued
| Example | Structure | MS+ m/z |
|---|---|---|
| 847 | 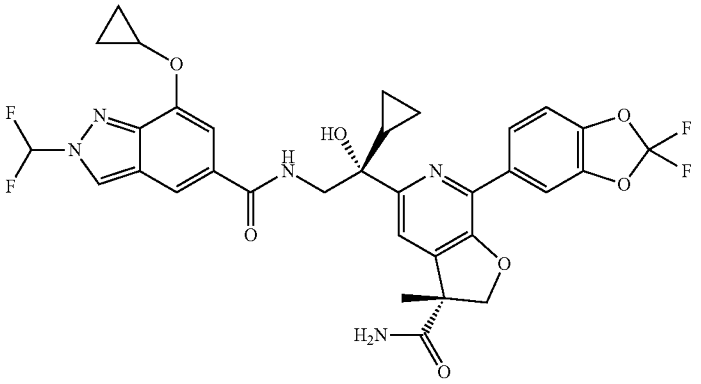 [SMILES: C[C@]1(C(N)=O)COc2c1cc([C@@](O)(CNC(=O)c1cc(OC3CC3)c3nn(C(F)F)cc3c1)C1CC1)nc2-c1ccc2c(c1)OC(F)(F)O2] | 684.20 |
| 848 | 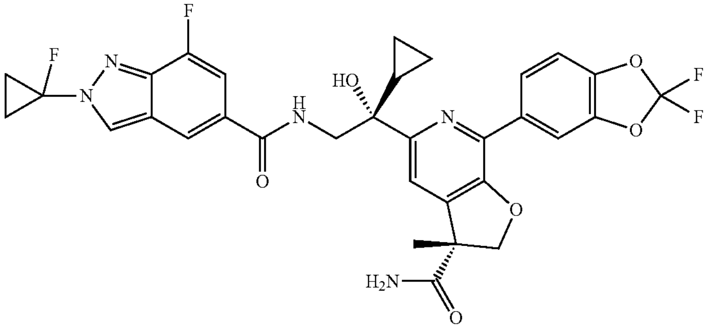 [SMILES: C[C@]1(C(N)=O)COc2c1cc([C@@](O)(CNC(=O)c1cc(F)c3nn(C4(F)CC4)cc3c1)C1CC1)nc2-c1ccc2c(c1)OC(F)(F)O2] | 654.19 |
| 849 | 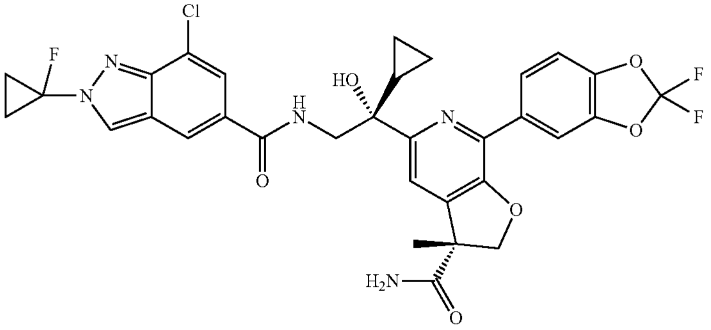 | 670.16 |
| 850 | 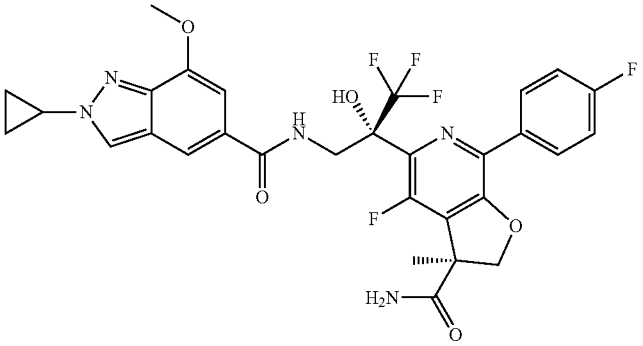 [SMILES: COc1cc(C(=O)NC[C@](O)(c2nc(-c3ccc(F)cc3)c3c(c2F)[C@](C)(C(N)=O)CO3)C(F)(F)F)cc2cn(C3CC3)nc12] | 632.18 |

TABLE 5-continued
| Example | Structure | MS+ m/z |
| --- | --- | --- |
| 851 | 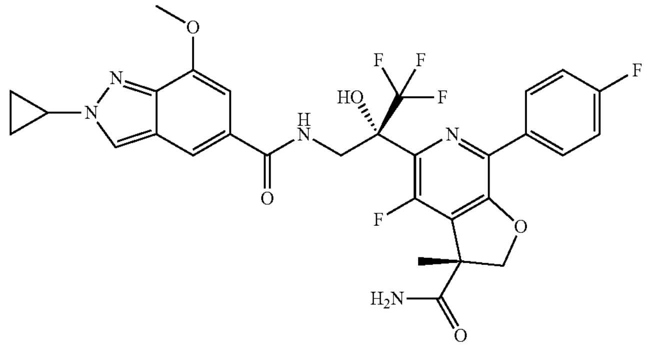 [SMILES: COc1cc(C(=O)NC[C@](O)(c2nc(-c3ccc(F)cc3)c3c(c2F)[C@@](C)(C(N)=O)CO3)C(F)(F)F)cc2cn(C3CC3)nc12] | 632.18 |
| 852 | 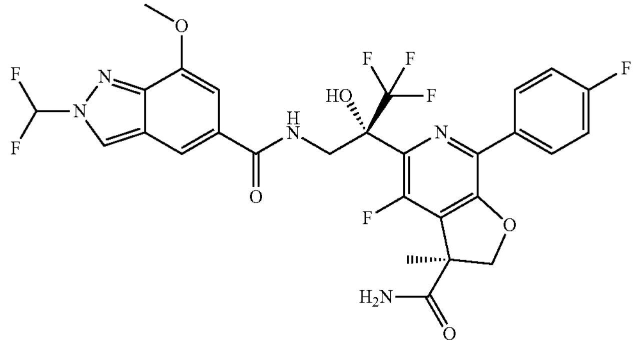 [SMILES: COc1cc(C(=O)NC[C@](O)(c2nc(-c3ccc(F)cc3)c3c(c2F)[C@](C)(C(N)=O)CO3)C(F)(F)F)cc2cn(C(F)F)nc12] | 642.15 |
| 853 | 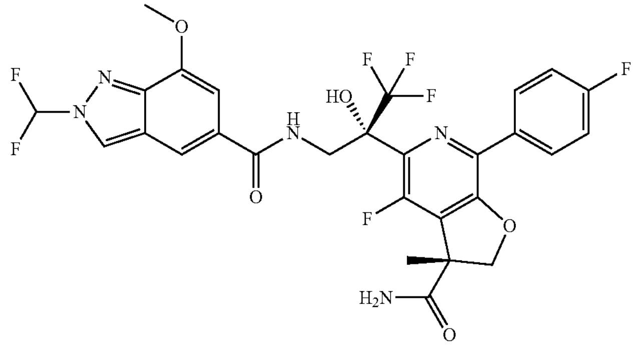 [SMILES: COc1cc(C(=O)NC[C@](O)(c2nc(-c3ccc(F)cc3)c3c(c2F)[C@@](C)(C(N)=O)CO3)C(F)(F)F)cc2cn(C(F)F)nc12] | 642.15 |
| 854 | 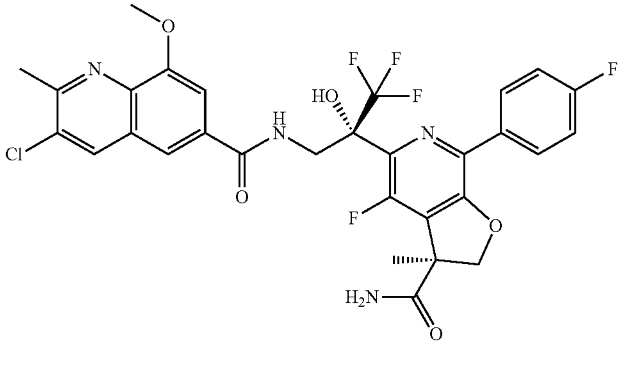 [SMILES: COc1cc(C(=O)NC[C@](O)(c2nc(-c3ccc(F)cc3)c3c(c2F)[C@](C)(C(N)=O)CO3)C(F)(F)F)cc2cc(Cl)c(C)nc12] | 651.13 |

TABLE 5-continued
| Example | Structure | MS+ m/z |
|---|---|---|
| 855 | 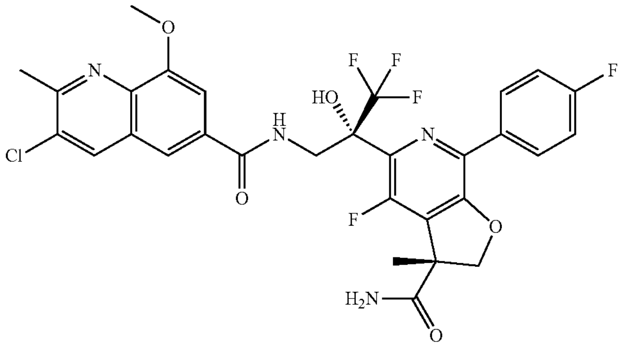 [SMILES: COc1cc(C(=O)NC[C@](O)(c2nc(-c3ccc(F)cc3)c3c(c2F)[C@@](C)(C(N)=O)CO3)C(F)(F)F)cc2cc(Cl)c(C)nc12] | 651.13 |
| 856 | 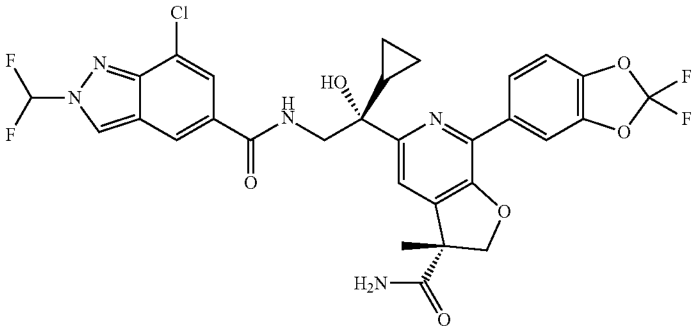 [SMILES: C[C@]1(C(N)=O)COc2c1cc([C@@](O)(CNC(=O)c1cc(Cl)c3nn(C(F)F)cc3c1)C1CC1)nc2-c1ccc2c(c1)OC(F)(F)O2] | 662.13 |
| 857 | 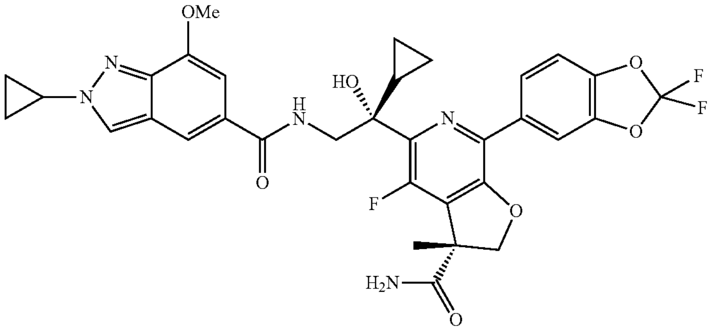 [SMILES: COc1cc(C(=O)NC[C@](O)(c2nc(-c3ccc4c(c3)OC(F)(F)O4)c3c(c2F)[C@@](C)(C(N)=O)CO3)C2CC2)cc2cn(C3CC3)nc12] | 666.21 |
| 858 | 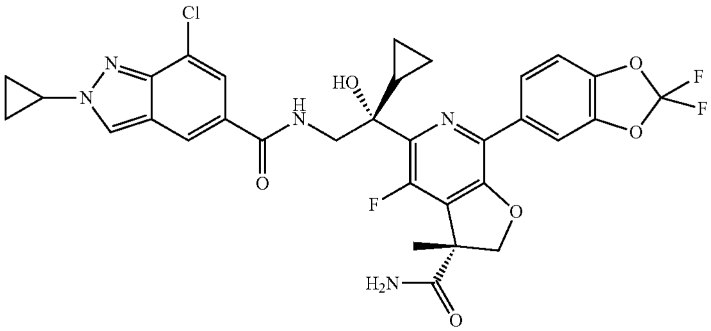 [SMILES: C[C@]1(C(N)=O)COc2c(-c3ccc4c(c3)OC(F)(F)O4)nc([C@@](O)(CNC(=O)c3cc(Cl)c4nn(C5CC5)cc4c3)C3CC3)c(F)c21] | 670.16 |

TABLE 5-continued
| Example | Structure | MS+ m/z |
|---|---|---|
| 859 | 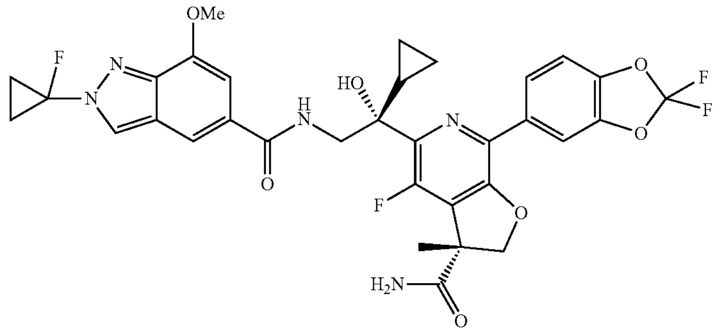 [SMILES: COc1cc(C(=O)NC[C@](O)(c2nc(-c3ccc4c(c3)OC(F)(F)O4)c3c(c2F)[C@@](C)(C(N)=O)CO3)C2CC2)cc2cn(C3(F)CC3)nc12] | 684.20 |
| 860 | 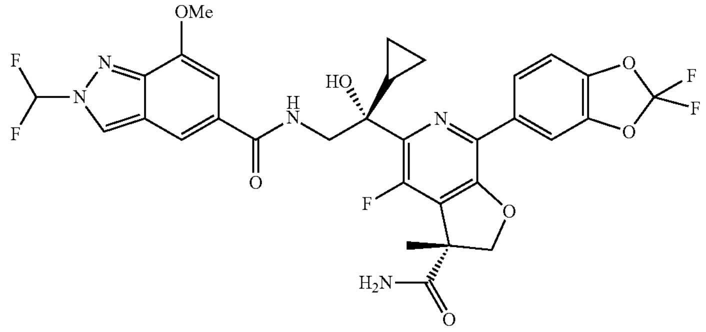 [SMILES: COc1cc(C(=O)NC[C@](O)(c2nc(-c3ccc4c(c3)OC(F)(F)O4)c3c(c2F)[C@@](C)(C(N)=O)CO3)C2CC2)cc2cn(C(F)F)nc12] | 676.17 |
| 861 | 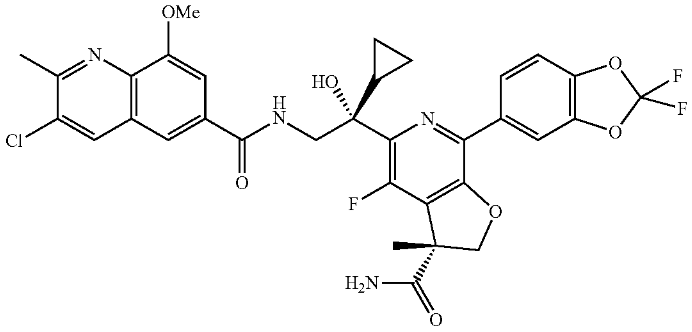 [SMILES: COc1cc(C(=O)NC[C@](O)(c2nc(-c3ccc4c(c3)OC(F)(F)O4)c3c(c2F)[C@@](C)(C(N)=O)CO3)C2CC2)cc2cc(Cl)c(C)nc12] | 685.16 |
| 862 | 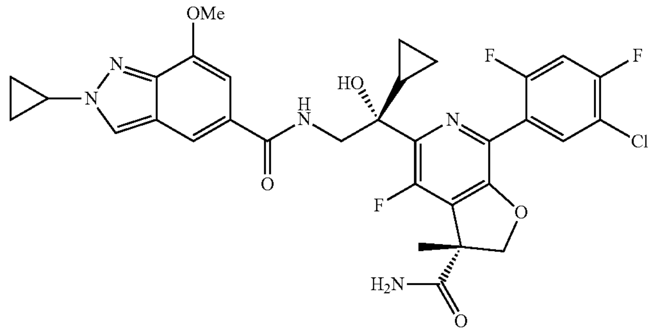 [SMILES: COc1cc(C(=O)NC[C@](O)(c2nc(-c3cc(Cl)c(F)cc3F)c3c(c2F)[C@@](C)(C(N)=O)CO3)C2CC2)cc2cn(C3CC3)nc12] | 656.18 |

TABLE 5-continued
| Example | Structure | MS⁺ m/z |
|---|---|---|
| 863 | 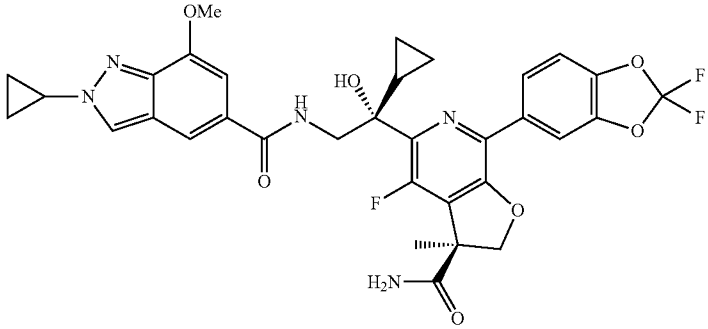 [SMILES: COc1cc(C(=O)NC[C@](O)(c2nc(-c3ccc4c(c3)OC(F)(F)O4)c3c(c2F)[C@](C)(C(N)=O)CO3)C2CC2)cc2cn(C3CC3)nc12] | 666.21 |
| 864 | 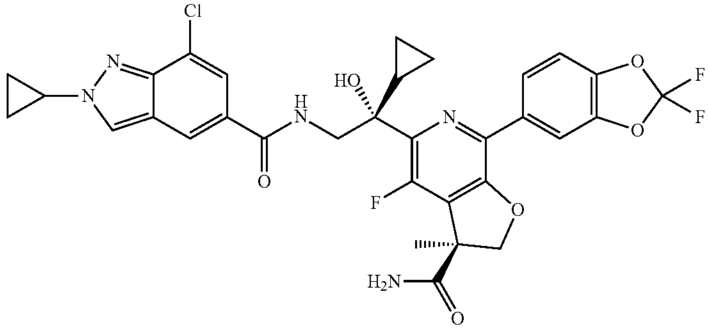 [SMILES: C[C@@]1(C(N)=O)COc2c(-c3ccc4c(c3)OC(F)(F)O4)nc([C@@](O)(CNC(=O)c3cc(Cl)c4nn(C5CC5)cc4c3)C3CC3)c(F)c21] | 670.16 |
| 865 | 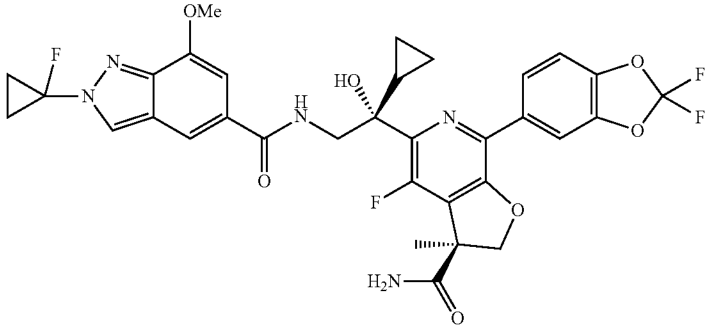 [SMILES: COc1cc(C(=O)NC[C@](O)(c2nc(-c3ccc4c(c3)OC(F)(F)O4)c3c(c2F)[C@](C)(C(N)=O)CO3)C2CC2)cc2cn(C3(F)CC3)nc12] | 684.20 |
| 866 | 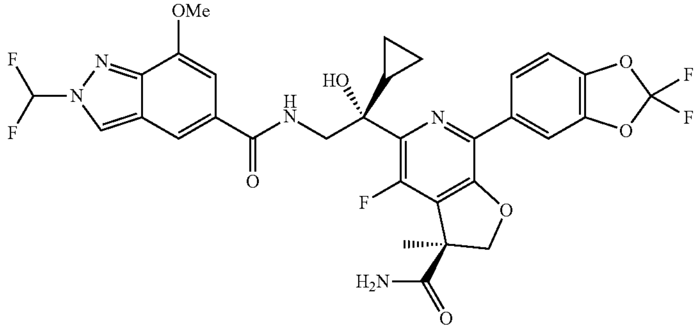 [SMILES: COc1cc(C(=O)NC[C@](O)(c2nc(-c3ccc4c(c3)OC(F)(F)O4)c3c(c2F)[C@](C)(C(N)=O)CO3)C2CC2)cc2cn(C(F)F)nc12] | 676.17 |

TABLE 5-continued
| Example | Structure | MS+ m/z |
|---|---|---|
| 867 | 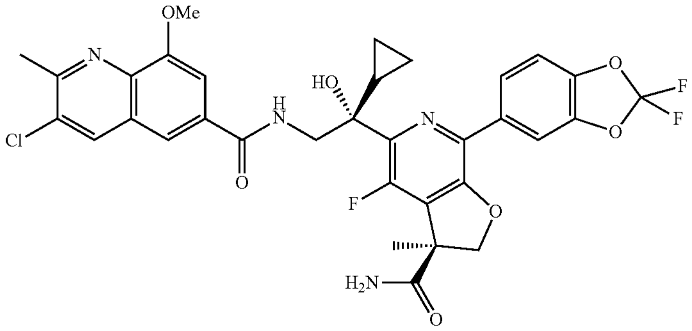 [SMILES: COc1cc(C(=O)NC[C@](O)(c2nc(-c3ccc4c(c3)OC(F)(F)O4)c3c(c2F)[C@](C)(C(N)=O)CO3)C2CC2)cc2cc(Cl)c(C)nc12] | 685.16 |
| 868 | 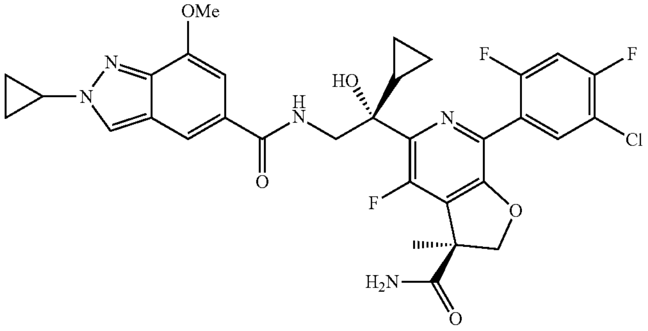 [SMILES: COc1cc(C(=O)NC[C@](O)(c2nc(-c3cc(Cl)c(F)cc3F)c3c(c2F)[C@](C)(C(N)=O)CO3)C2CC2)cc2cn(C3CC3)nc12] | 656.18 |
| 869 | 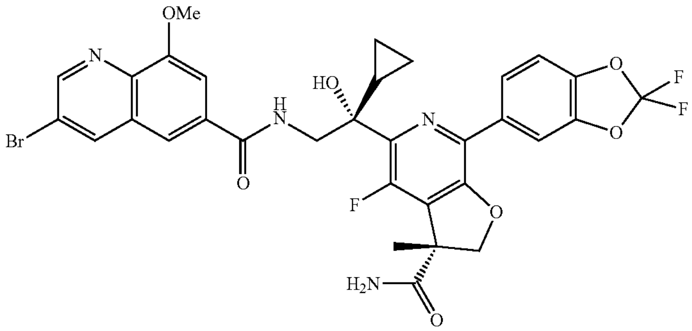 [SMILES: COc1cc(C(=O)NC[C@](O)(c2nc(-c3ccc4c(c3)OC(F)(F)O4)c3c(c2F)[C@@](C)(C(N)=O)CO3)C2CC2)cc2cc(Br)cnc12] | 715.09 |
| 870 | 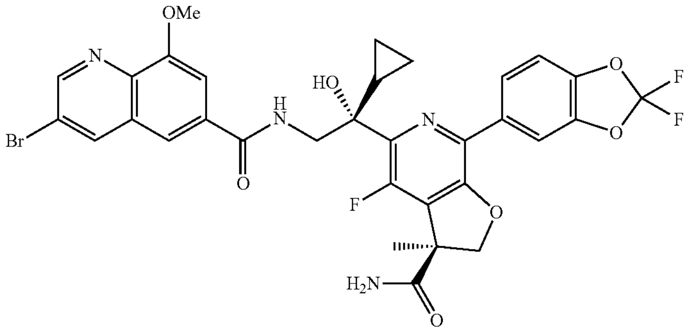 [SMILES: COc1cc(C(=O)NC[C@](O)(c2nc(-c3ccc4c(c3)OC(F)(F)O4)c3c(c2F)[C@](C)(C(N)=O)CO3)C2CC2)cc2cc(Br)cnc12] | 715.09 |

TABLE 5-continued
| Example | Structure | MS+ m/z |
|---|---|---|
| 871 | 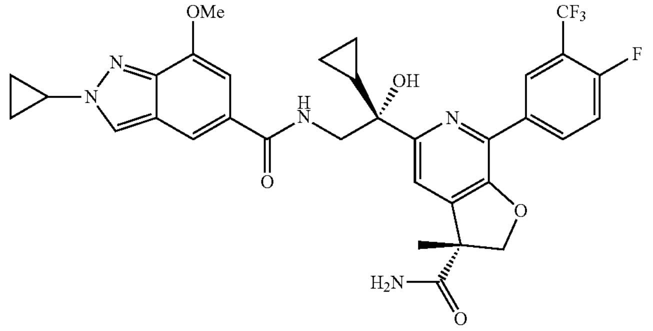 [SMILES: COc1cc(C(=O)NC[C@](O)(c2cc3c(c(-c4ccc(F)c(C(F)(F)F)c4)n2)OC[C@]3(C)C(N)=O)C2CC2)cc2cn(C3CC3)nc12] | 654.20 |
| 872 | 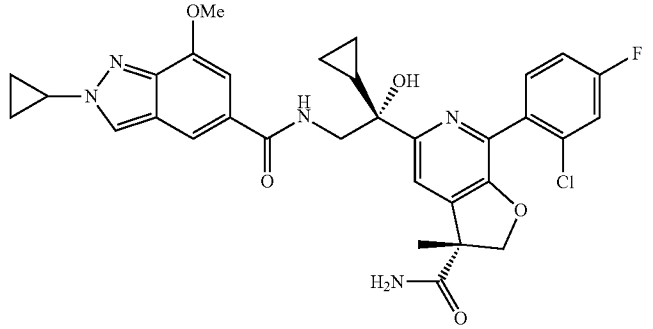 [SMILES: COc1cc(C(=O)NC[C@](O)(c2cc3c(c(-c4ccc(F)cc4Cl)n2)OC[C@]3(C)C(N)=O)C2CC2)cc2cn(C3CC3)nc12] | 620.40 |
| 873 | 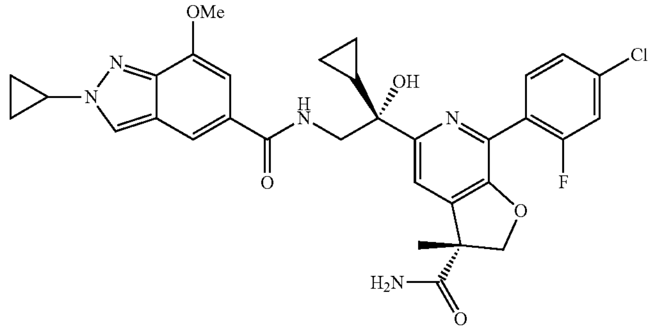 [SMILES: COc1cc(C(=O)NC[C@](O)(c2cc3c(c(-c4ccc(Cl)cc4F)n2)OC[C@]3(C)C(N)=O)C2CC2)cc2cn(C3CC3)nc12] | 620.15 |
| 874 | 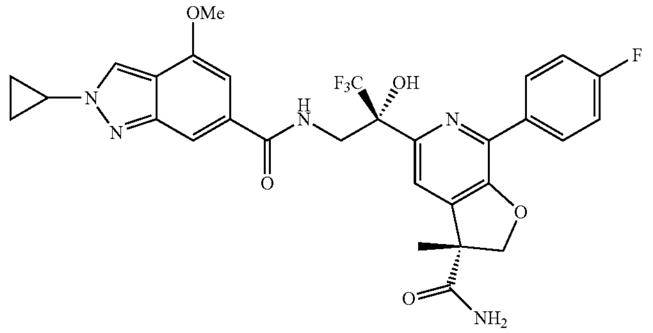 [SMILES: COc1cc(C(=O)NC[C@](O)(c2cc3c(c(-c4ccc(F)cc4)n2)OC[C@]3(C)C(N)=O)C(F)(F)F)cc2nn(C3CC3)cc12] | 614.20 |

TABLE 5-continued
| Example | Structure | MS+ m/z |
|---|---|---|
| 875 | 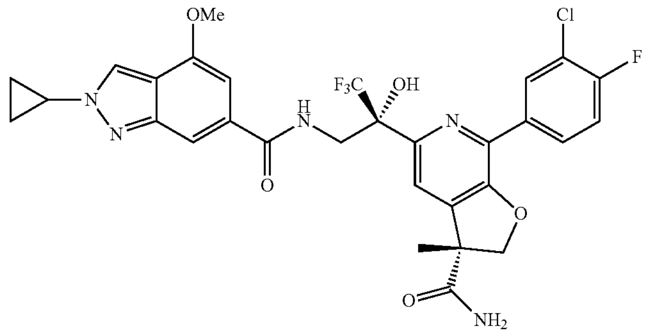 [SMILES: COc1cc(C(=O)NC[C@](O)(c2cc3c(c(-c4ccc(F)c(Cl)c4)n2)OC[C@]3(C)C(N)=O)C(F)(F)F)cc2nn(C3CC3)cc12] | 614.20 |
| 876 | 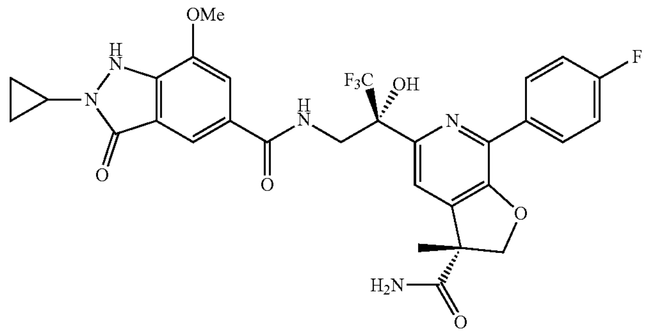 [SMILES: COc1cc(C(=O)NC[C@](O)(c2cc3c(c(-c4ccc(F)cc4)n2)OC[C@]3(C)C(N)=O)C(F)(F)F)cc2c(=O)n(C3CC3)[nH]c12] | 630.20 |
| 877 | 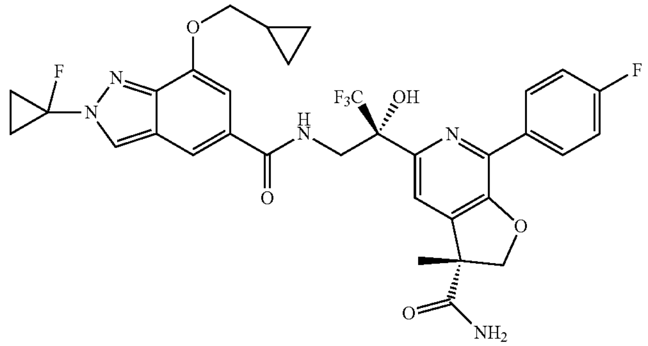 [SMILES: C[C@]1(C(N)=O)COc2c1cc([C@@](O)(CNC(=O)c1cc(OCC3CC3)c3nn(C4(F)CC4)cc3c1)C(F)(F)F)nc2-c1ccc(F)cc1] | 672.20 |
| 878 | 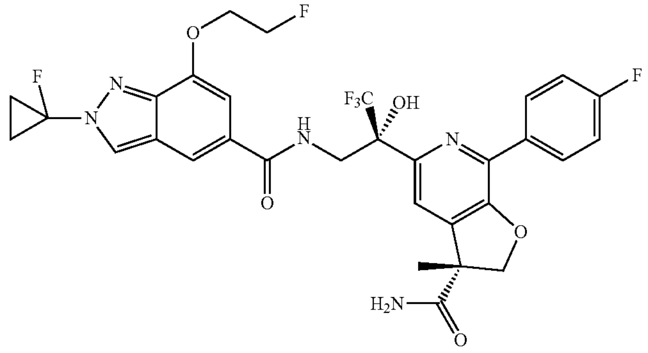 [SMILES: C[C@]1(C(N)=O)COc2c1cc([C@@](O)(CNC(=O)c1cc(OCCF)c3nn(C4(F)CC4)cc3c1)C(F)(F)F)nc2-c1ccc(F)cc1] | 664.10 |

TABLE 5-continued
| Example | Structure | MS+ m/z |
|---|---|---|
| 879 | 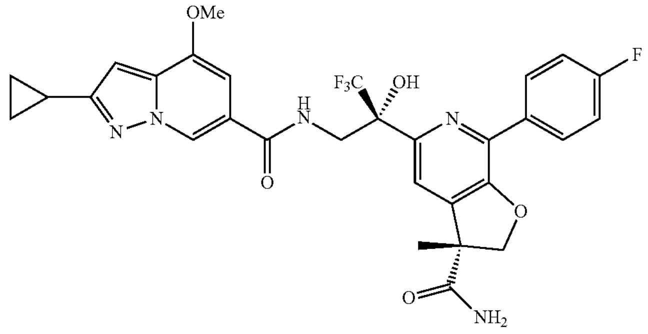 [SMILES: COc1cc(C(=O)NC[C@](O)(c2cc3c(c(-c4ccc(F)cc4)n2)OC[C@]3(C)C(N)=O)C(F)(F)F)cn2nc(C3CC3)cc12] | 614.25 |
| 880 | 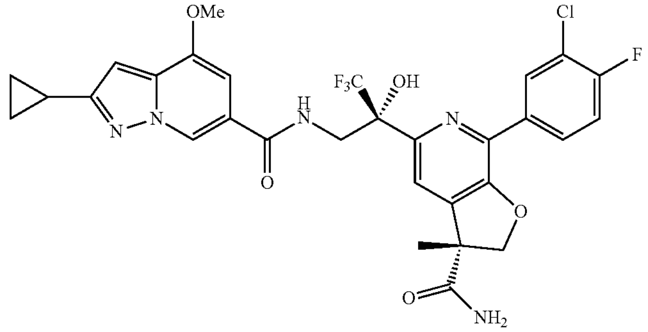 [SMILES: COc1cc(C(=O)NC[C@](O)(c2cc3c(c(-c4ccc(F)c(Cl)c4)n2)OC[C@]3(C)C(N)=O)C(F)(F)F)cn2nc(C3CC3)cc12] | 648.15 |
| 881 | 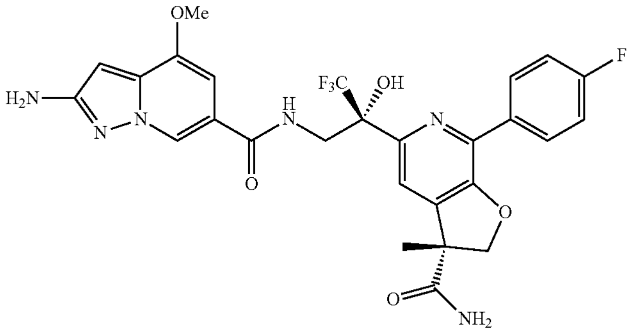 [SMILES: COc1cc(C(=O)NC[C@](O)(c2cc3c(c(-c4ccc(F)cc4)n2)OC[C@]3(C)C(N)=O)C(F)(F)F)cn2nc(N)cc12] | 589.15 |
| 882 | 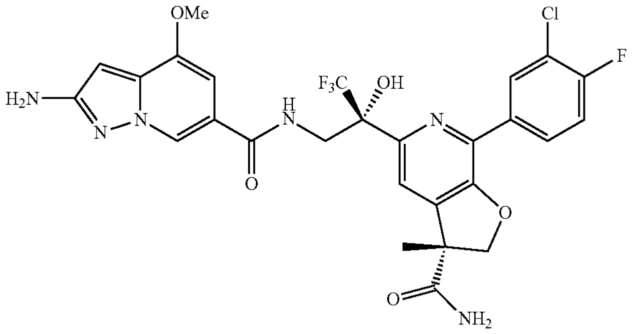 [SMILES: COc1cc(C(=O)NC[C@](O)(c2cc3c(c(-c4ccc(F)c(Cl)c4)n2)OC[C@]3(C)C(N)=O)C(F)(F)F)cn2nc(N)cc12] | 589.15 |

TABLE 5-continued
| Example | Structure | MS+ m/z |
|---|---|---|
| 883 | 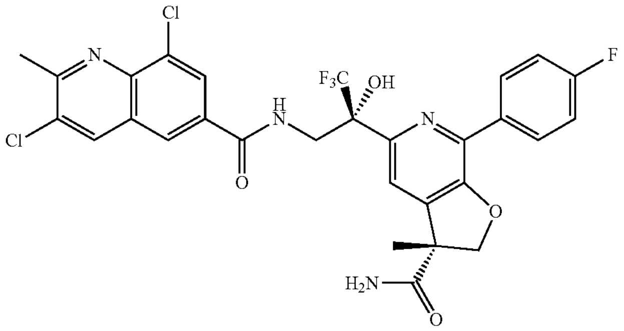 [SMILES: Cc1nc2c(Cl)cc(C(=O)NC[C@](O)(c3cc4c(c(-c5ccc(F)cc5)n3)OC[C@]4(C)C(N)=O)C(F)(F)F)cc2cc1Cl] | 637.15 |
| 884 | 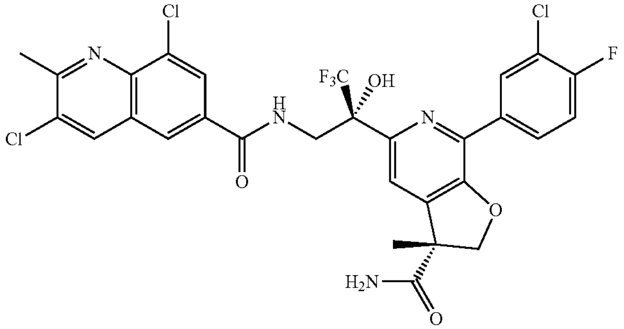 [SMILES: Cc1nc2c(Cl)cc(C(=O)NC[C@](O)(c3cc4c(c(-c5ccc(F)c(Cl)c5)n3)OC[C@]4(C)C(N)=O)C(F)(F)F)cc2cc1Cl] | 671.00 |
| 885 | 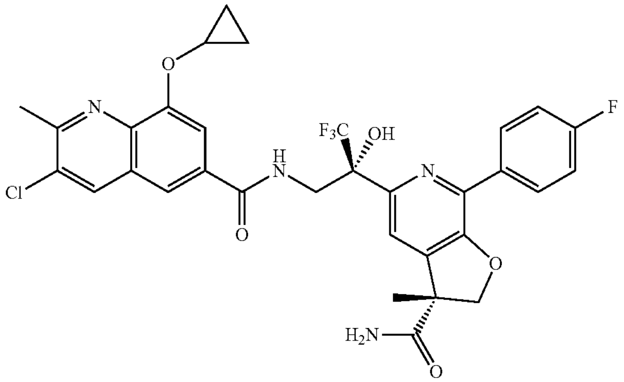 [SMILES: Cc1nc2c(OC3CC3)cc(C(=O)NC[C@](O)(c3cc4c(c(-c5ccc(F)cc5)n3)OC[C@]4(C)C(N)=O)C(F)(F)F)cc2cc1Cl] | 659.10 |
| 886 | 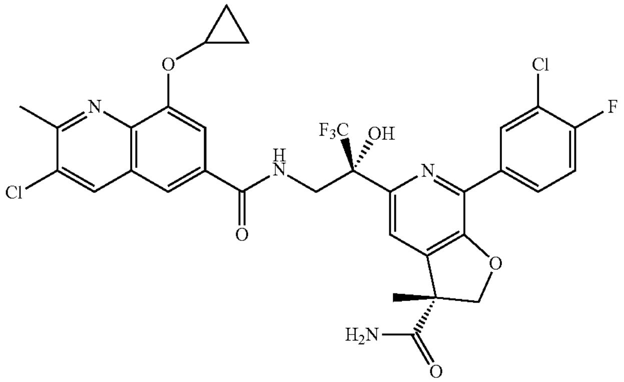 [SMILES: Cc1nc2c(OC3CC3)cc(C(=O)NC[C@](O)(c3cc4c(c(-c5ccc(F)c(Cl)c5)n3)OC[C@]4(C)C(N)=O)C(F)(F)F)cc2cc1Cl] | 693.05 |

TABLE 5-continued

| Example | Structure | MS+ m/z |
|---|---|---|
| 887 | 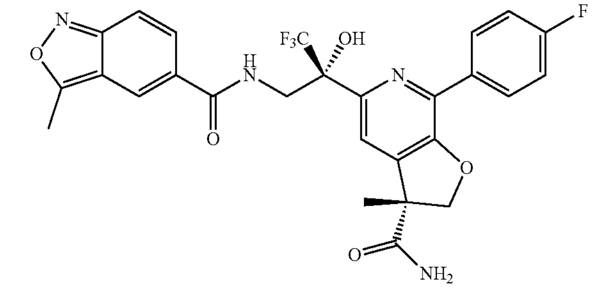 [SMILES: Cc1onc2ccc(C(=O)NC[C@](O)(c3cc4c(c(-c5ccc(F)cc5)n3)OC[C@]4(C)C(N)=O)C(F)(F)F)cc12] | 559.10 |
| 888 | 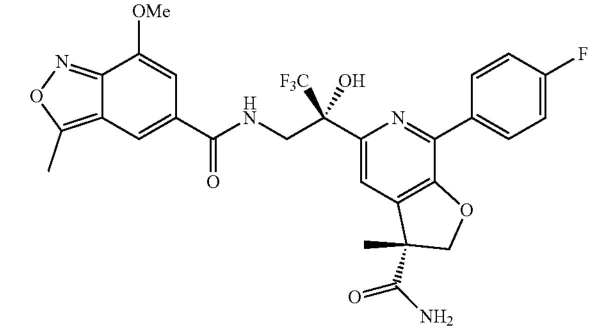 [SMILES: COc1cc(C(=O)NC[C@](O)(c2cc3c(c(-c4ccc(F)cc4)n2)OC[C@]3(C)C(N)=O)C(F)(F)F)cc2c(C)onc12] | 589.10 |
| 889 | 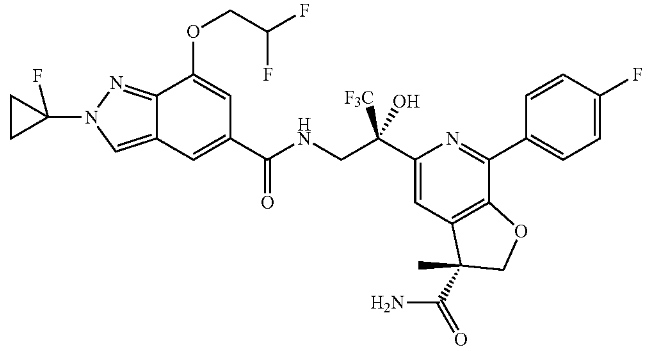 [SMILES: C[C@]1(C(N)=O)COc2c1cc([C@@](O)(CNC(=O)c1cc(OCC(F)F)c3nn(C4(F)CC4)cc3c1)C(F)(F)F)nc2-c1ccc(F)cc1] | 682.10 |

Intermediate 96

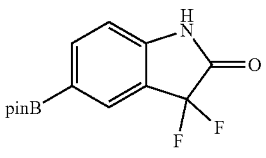

Intermediate 96 Step a

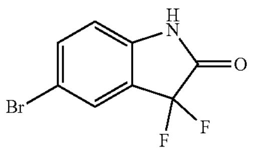 [SMILES: O=C1Nc2ccc(Br)cc2C1(F)F]

Into a 100 mL round-bottom flask were added 5-bromoisatin (1 g, 4 mmol), and DCM (5 mL) at room temperature. DAST (1.43 g, 9 mmol) was added dropwise. The resulting mixture was stirred for 1 hr at 0° C. under nitrogen atmosphere. The reaction was monitored by LCMS. The reaction was quenched with water and the aqueous layer was extracted with EA. The residue was purified by silica gel column chromatography (eluted with 25% ethyl acetate in hexanes) to afford the desired compound (900 mg, 82%) as a light-yellow solid.

Intermediate 96 Step b

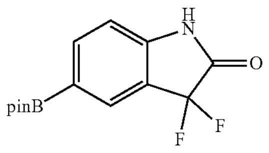

A solution of the compound from step a (300 mg, 1.2 mmol), bis(pinacolato)diboron (461 mg, 1.8 mmol), $Pd(dppf)Cl_2CH_2Cl_2$ (197 mg, 0.24 mmol), KOAc (356 mg, 4 mmol) in dioxane (5 mL) mixture was stirred for 2 hr at 90° C. under nitrogen atmosphere. The reaction was monitored by TLC. The aqueous layer was extracted with EtOAc.

The resulting mixture was concentrated under reduced pressure. The residue was purified by reverse flash to afford the desired compound (297 mg, 83%) as yellow solid.

Intermediate 97

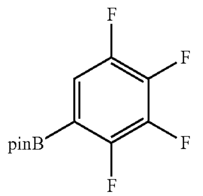

The following compound was prepared in an analogous fashion to Intermediate 96 Step b above to afford the desired product that was used directly in the next step crude.

Intermediate 98

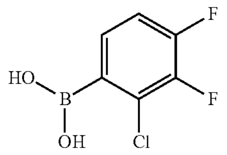 [SMILES: OB(O)c1ccc(F)c(F)c1Cl]

In a 50 mL round bottom flask, to a solution of 1-bromo-2-chloro-3,4-difluorobenzene (850 mg, 3.7 mmol) in THF (30 mL) was added n-BuLi (2.8 mL, 5.6 mmol) dropwise at −78° C. under $N_2$ atmosphere. The reaction mixture was stirred at −78° C. for 5 mins. Then $B(OMe)_3$ (583 mg, 5.6 mmol) was added dropwise and the mixture and stirred for another 30 mins at room temperature. The mixture was acidified to pH 5 with HCl (3 M aq.). The reaction was quenched with sat. $NH_4Cl$, and then the mixture was extracted with EtOAc. The combined organic extracts were washed with brine, dried over anhydrous $Na_2SO_4$, and concentrated under vacuum to afford the desired crude compound (790 mg, 109%) as a yellow oil. The crude product was used in the next step directly without further purification.

Example 890

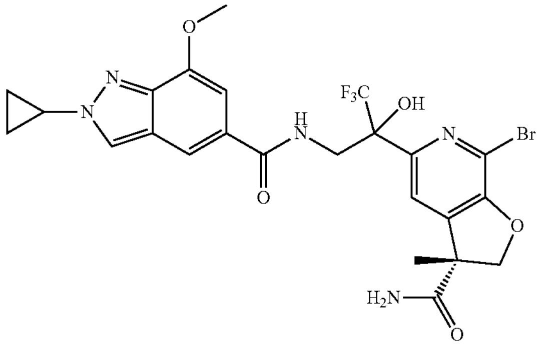 [SMILES: COc1cc(C(=O)NCC(O)(c2cc3c(c(Br)n2)OC[C@]3(C)C(N)=O)C(F)(F)F)cc2cn(C3CC3)nc12]

Example 890 Step a

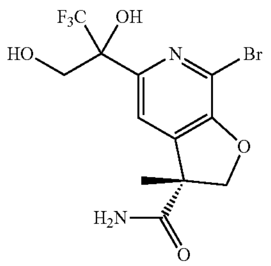 [SMILES: C[C@]1(C(N)=O)COc2c1cc(C(O)(CO)C(F)(F)F)nc2Br]

To a 250 mL round-bottom flask containing Intermediate 36 Step c (5.09 g, 14.50 mmol) was added THF (24.16 mL), Acetone (24.16 mL) and Water (24.16 mL). The flask was cooled to 0° C., and NMO (4.25 g, 36.2 mmol) was added followed by potassium osmate dihydrate (0.230 g, 0.623 mmol). The reaction was stirred for 10 minutes, warmed to room temperature and allowed to stir overnight for 20 hr. Sodium sulfite was added, the mixture diluted with water and the reaction stirred for 20 minutes. The mixture was diluted with EtOAc and the aqueous layer was extracted. The combined organics were dried with sodium sulfate, filtered, and concentrated. The crude mixture was purified by automated column chromatography (silica gel, 0-100% ethyl acetate in hexanes) to afford the desired product as a white solid (4.12 g, 74%) and mixture of diastereomers. ESI-MS m/z: 385.21 $[M+H]^+$.

Example 890 Step b

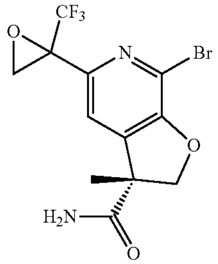 [SMILES: C[C@]1(C(N)=O)COc2c1cc(C1(C(F)(F)F)CO1)nc2Br]

To a 250 mL round-bottom flask containing step a (4.118 g, 10.69 mmol) was added DCM (36 mL, 0.3 M). DMAP (0.065 g, 0.535 mmol) was added followed by TEA (4.47 ml, 32.1 mmol). The flask was cooled to 0° C., and TsCl (2.242 g, 11.76 mmol) was added, stirred for 10 minutes, warmed to room temperature and monitored by LCMS (1 hr). The reaction was concentrated, and the crude residue was purified by automated column chromatography (silica gel, 0-100% ethyl acetate in hexanes) to afford the desired product as a white solid (3.92 g, 99%), a mixture of diastereomers, and a mixture of epoxide (major) and tosylate. ESI-MS m/z: 367.19 $[M+H]^+$.

Example 890 Step c

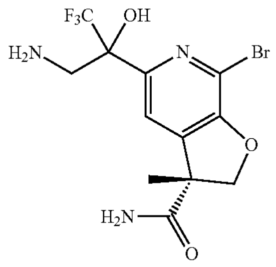 [SMILES: C[C@]1(C(N)=O)COc2c1cc(C(O)(CN)C(F)(F)F)nc2Br]

To a 500 mL round-bottom flask containing step b (3.92 g, 10.70 mmol) was added ammonia (239 mL, 1670 mmol, 7N in MeOH) at 0° C. The reaction was stirred for 10 minutes, warmed to room temperature and monitored by LCMS (3.5 hr). The stir was then removed and the reaction concentrated. The crude material was dissolved in EtOAc and the organics were washed 3× with saturated sodium bicarbonate. The organics were concentrated, and the crude material was triturated with DCM/hexanes to afford a white solid (2.41 g, 59%) as a mixture of diastereomers. ESI-MS m/z: 384.21 [M+H]+.

Example 890 Step d

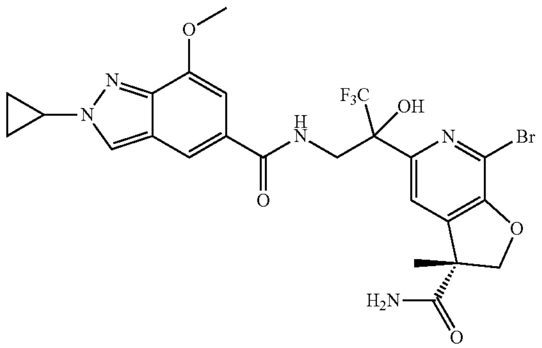 [SMILES: COc1cc(C(=O)NCC(O)(c2cc3c(c(Br)n2)OC[C@]3(C)C(N)=O)C(F)(F)F)cc2cn(C3CC3)nc12]

To a 100 mL round bottom flask equipped with a stir bar was added step c (1.000 g, 2.60 mmol) and 2-cyclopropyl-7-methoxy-2H-indazole-5-carboxylic acid (0.605 g, 2.60 mmol). The solids were dissolved in N,N-Dimethylformamide (13.02 mL, 0.2 M), and DIPEA (0.909 mL, 5.21 mmol) was added. The vial was cooled to 0° C., and PyBOP (1.626 g, 3.12 mmol) was added. The reaction was stirred for 10 minutes, warmed to room temperature and monitored by LCMS (1 hr). The reaction was quenched with sat. ammonium chloride and diluted with EtOAc. The aqueous was extracted with EtOAc, and the combined organics were dried with sodium sulfate, filtered, and concentrated. The crude mixture was purified by automated column chromatography (silica gel, 0-100% ethyl acetate in hexanes) to afford the desired product as an oil. The oil was dissolved in EtOAc and washed with water and brine to remove DMF and concentrated to afford the product as a white solid (597 mg, 38%) as a mixture of diastereomers. ESI-MS m/z: 598.12 [M+H]+.

Example 891

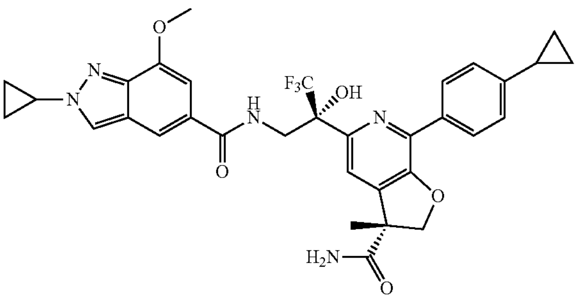 [SMILES: COc1cc(C(=O)NC[C@](O)(c2cc3c(c(-c4ccc(C5CC5)cc4)n2)OC[C@]3(C)C(N)=O)C(F)(F)F)cc2cn(C3CC3)nc12]

To a 2 dram vial equipped with a stir bar and septa cap was added $PdCl_2$(dppf) (6.11 mg, 8.36 μmol), potassium carbonate (26.0 mg, 0.188 mmol), (4-cyclopropylphenyl) boronic acid (16.24 mg, 0.100 mmol) and Example 890 (50 mg, 0.084 mmol). The material was dissolved in 1,4-dioxane (0.3 mL, 4:1, 0.2 M) and water (0.084 mL) and purged with nitrogen. The reaction was heated to 90° C. and monitored by LCMS (2 hr). The reaction was diluted with EtOAc, filtered through a short pad of silica gel, the pad was washed with EtOAc and the organics were concentrated. The crude material was purified and diastereomers were separated by prep-HPLC (ACN/$H_2O$, 20-90%, 25 min) to afford the desired product as a white solid (3 mg, 6%). ESI-MS m/z: 636.26 [M+H]+.

Example 892

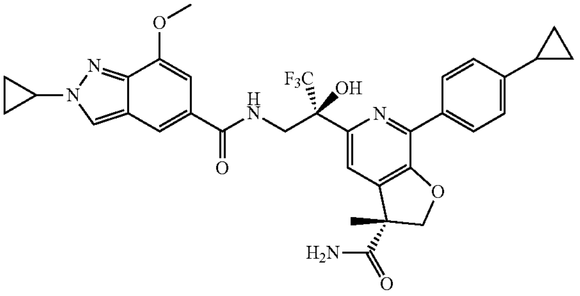 [SMILES: COc1cc(C(=O)NC[C@@](O)(c2cc3c(c(-c4ccc(C5CC5)cc4)n2)OC[C@]3(C)C(N)=O)C(F)(F)F)cc2cn(C3CC3)nc12]

The following example was purified by prep-HPLC (ACN/$H_2O$, 20-90%, 25 min) from Example 891 as a white solid (3 mg, 6%). ESI-MS m/z: 636.26 [M+H]+.

The following Table 6 contains examples that were prepared with a similar method to Example 891 using Example 890. If necessary to push conversion, more palladium and boronic acid were added. The majority of compounds were purified and the diastereomers were separated by prep-HPLC (ACN/$H_2O$, 20-90%, 25 min). If reported as a mixture of diastereomers, they were likely not separable by HPLC.

TABLE 6
| Example | Structure | MS⁺ m/z |
|---|---|---|
| 893 | 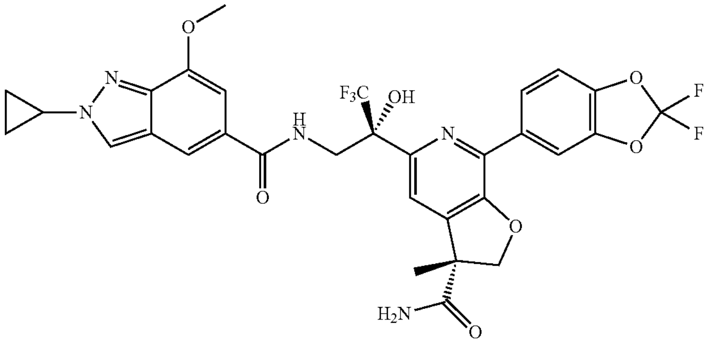 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cn(C3CC3)nc12] | 676.19 |
| 894 | 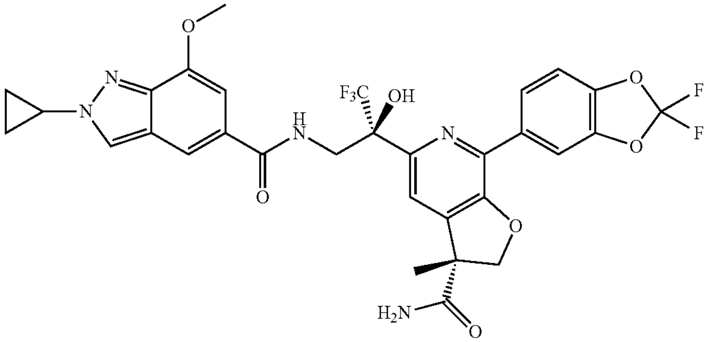 [SMILES: COc1cc(C(=O)NC[C@@](O)(c2cc3c(c(-c4ccc5c(c4)OC(F)(F)O5)n2)OC[C@]3(C)C(N)=O)C(F)(F)F)cc2cn(C3CC3)nc12] | 676.19 |
| 895 | 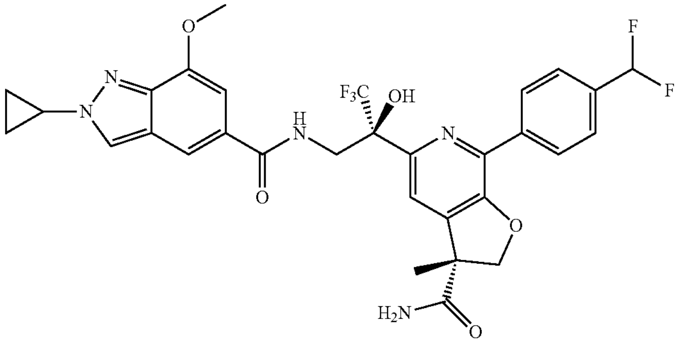 [SMILES: COc1cc(C(=O)NC[C@@](O)(c2cc3c(c(-c4ccc(C(F)F)cc4)n2)OC[C@]3(C)C(N)=O)C(F)(F)F)cc2cn(C3CC3)nc12] | 646.22 |
| 896 | 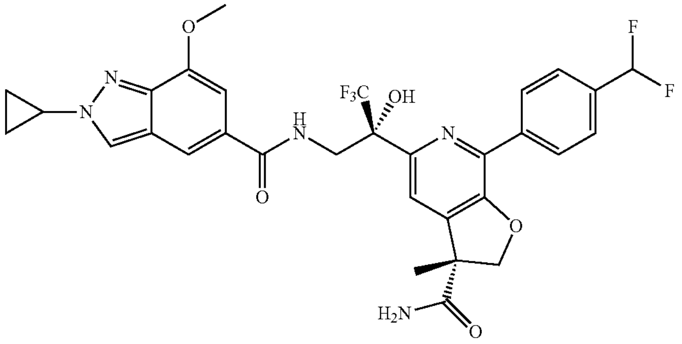 [SMILES: COc1cc(C(=O)NC[C@](O)(c2cc3c(c(-c4ccc(C(F)F)cc4)n2)OC[C@]3(C)C(N)=O)C(F)(F)F)cc2cn(C3CC3)nc12] | 646.22 |

TABLE 6-continued
| Example | Structure | MS+ m/z |
|---|---|---|
| 897 | 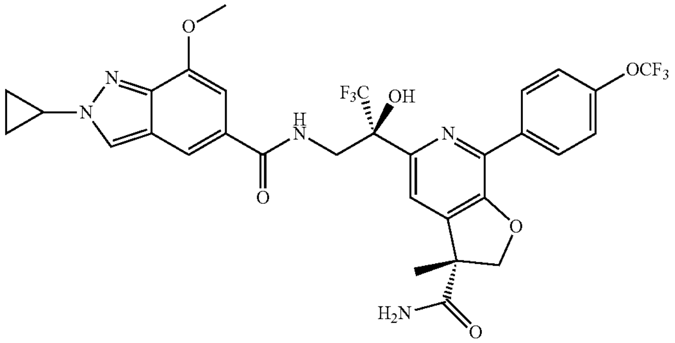 [SMILES: COc1cc(C(=O)NC[C@@](O)(c2cc3c(c(-c4ccc(OC(F)(F)F)cc4)n2)OC[C@]3(C)C(N)=O)C(F)(F)F)cc2cn(C3CC3)nc12] | 680.08 |
| 898 | 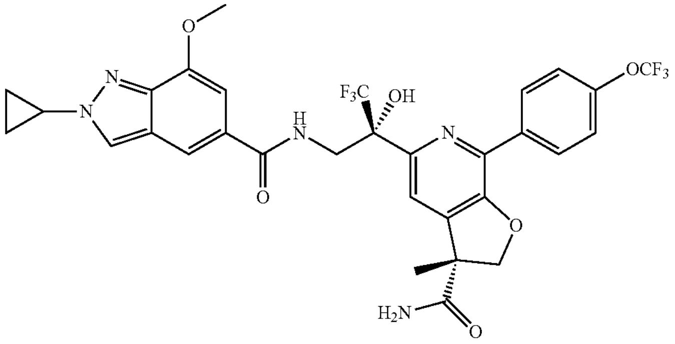 [SMILES: COc1cc(C(=O)NC[C@](O)(c2cc3c(c(-c4ccc(OC(F)(F)F)cc4)n2)OC[C@]3(C)C(N)=O)C(F)(F)F)cc2cn(C3CC3)nc12] | 680.08 |
| 899 | 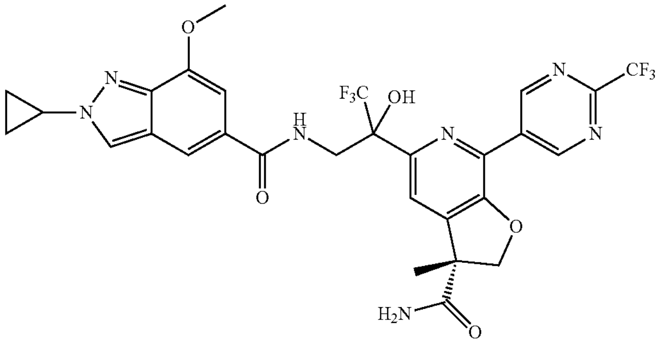 [SMILES: COc1cc(C(=O)NCC(O)(c2cc3c(c(-c4cnc(C(F)(F)F)nc4)n2)OC[C@]3(C)C(N)=O)C(F)(F)F)cc2cn(C3CC3)nc12] | 666.01 |
| 900 | 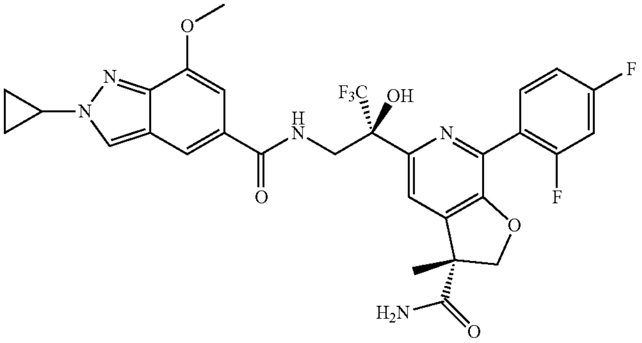 [SMILES: COc1cc(C(=O)NC[C@@](O)(c2cc3c(c(-c4ccc(F)cc4F)n2)OC[C@]3(C)C(N)=O)C(F)(F)F)cc2cn(C3CC3)nc12] | 632.08 |

TABLE 6-continued
| Example | Structure | MS+ m/z |
|---|---|---|
| 901 | 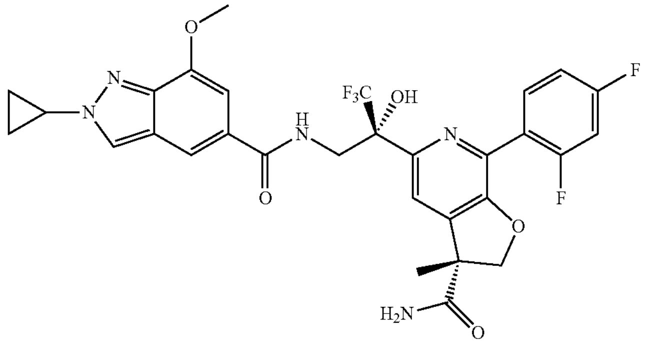 [SMILES: COc1cc(C(=O)NC[C@](O)(c2cc3c(c(-c4ccc(F)cc4F)n2)OC[C@]3(C)C(N)=O)C(F)(F)F)cc2cn(C3CC3)nc12] | 632.08 |
| 902 | 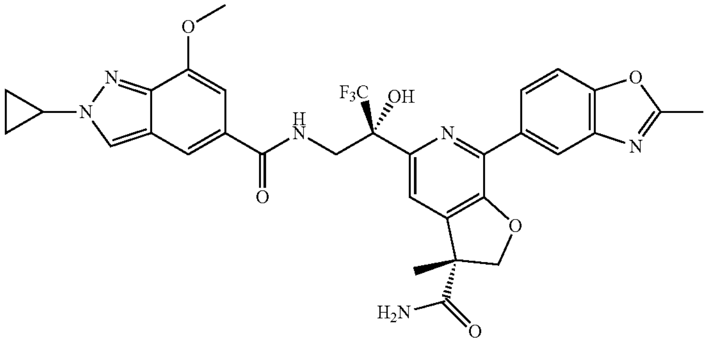 [SMILES: COc1cc(C(=O)NC[C@](O)(c2cc3c(c(-c4ccc5oc(C)nc5c4)n2)OC[C@]3(C)C(N)=O)C(F)(F)F)cc2cn(C3CC3)nc12] | 651.06 |
| 903 | 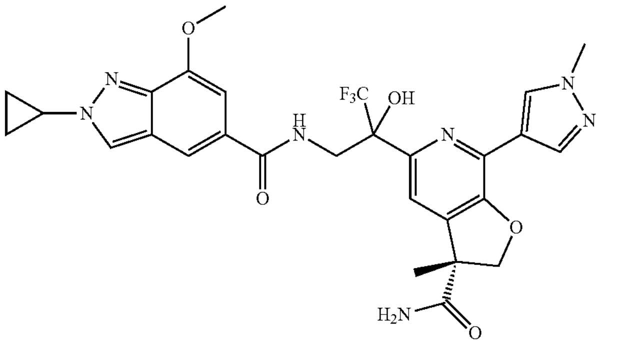 [SMILES: COc1cc(C(=O)NCC(O)(c2cc3c(c(-c4cnn(C)c4)n2)OC[C@]3(C)C(N)=O)C(F)(F)F)cc2cn(C3CC3)nc12] | 600.06 |
| 904 | 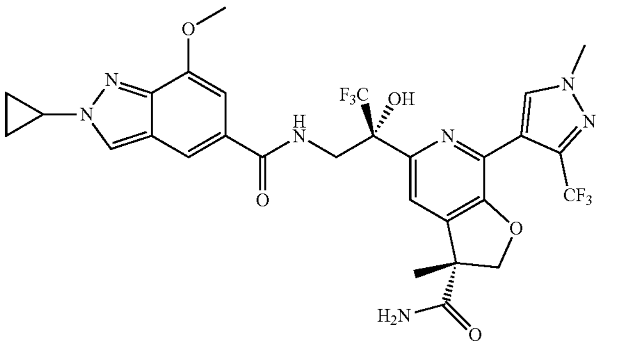 [SMILES: COc1cc(C(=O)NC[C@](O)(c2cc3c(c(-c4cn(C)nc4C(F)(F)F)n2)OC[C@]3(C)C(N)=O)C(F)(F)F)cc2cn(C3CC3)nc12] | 668.07 |

TABLE 6-continued
| Example | Structure | MS+ m/z |
|---|---|---|
| 905 | 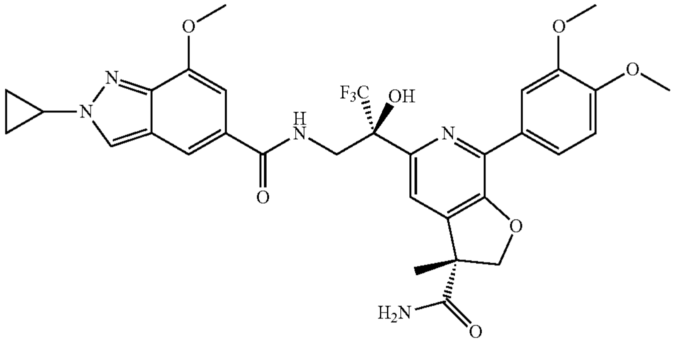 [SMILES: COc1ccc(-c2nc([C@](O)(CNC(=O)c3cc(OC)c4nn(C5CC5)cc4c3)C(F)(F)F)cc3c2OC[C@]3(C)C(N)=O)cc1OC] | 656.16 |
| 906 | 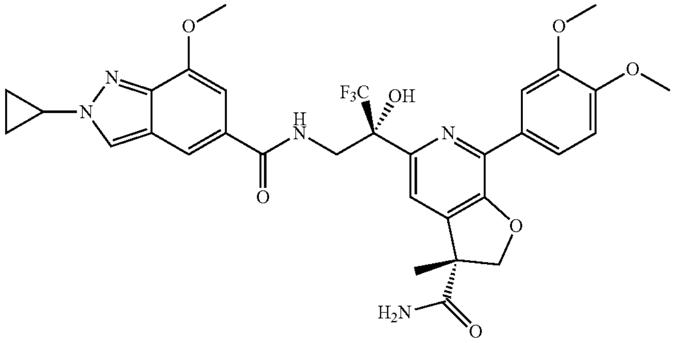 [SMILES: COc1ccc(-c2nc([C@@](O)(CNC(=O)c3cc(OC)c4nn(C5CC5)cc4c3)C(F)(F)F)cc3c2OC[C@]3(C)C(N)=O)cc1OC] | 656.16 |
| 907 | 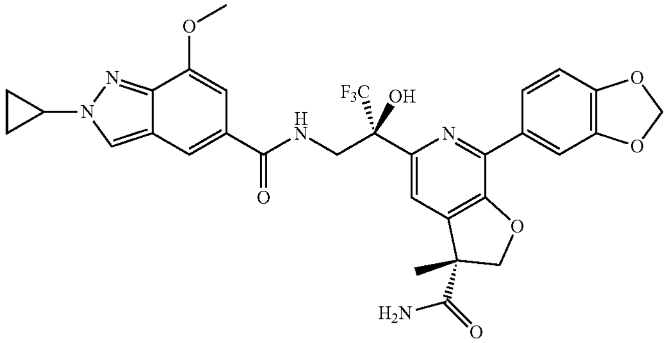 [SMILES: COc1cc(C(=O)NC[C@@](O)(c2cc3c(c(-c4ccc5c(c4)OCO5)n2)OC[C@]3(C)C(N)=O)C(F)(F)F)cc2cn(C3CC3)nc12] | 640.22 |
| 908 | 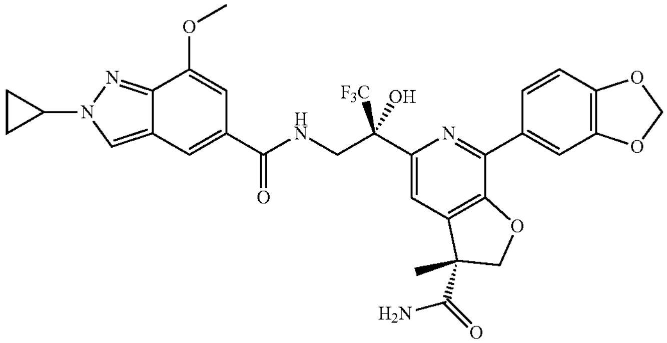 [SMILES: COc1cc(C(=O)NC[C@](O)(c2cc3c(c(-c4ccc5c(c4)OCO5)n2)OC[C@]3(C)C(N)=O)C(F)(F)F)cc2cn(C3CC3)nc12] | 640.22 |

TABLE 6-continued
| Example | Structure | MS+ m/z |
|---|---|---|
| 909 | 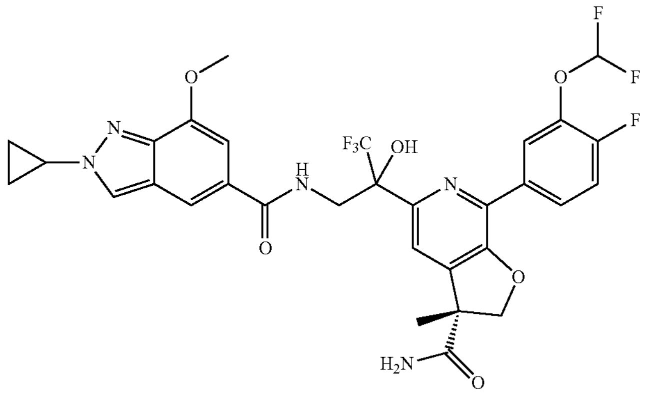 [SMILES: COc1cc(C(=O)NCC(O)(c2cc3c(c(-c4ccc(F)c(OC(F)F)c4)n2)OC[C@]3(C)C(N)=O)C(F)(F)F)cc2cn(C3CC3)nc12] | 680.21 |
| 910 | 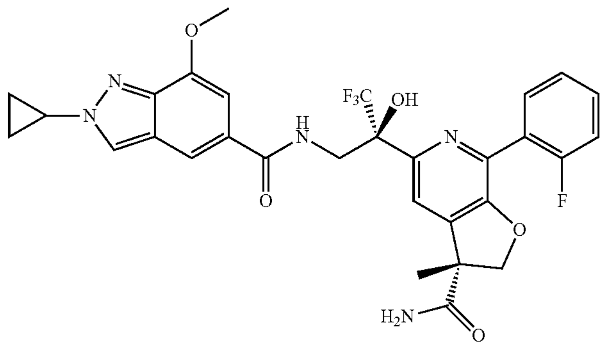 [SMILES: COc1cc(C(=O)NC[C@@](O)(c2cc3c(c(-c4ccccc4F)n2)OC[C@]3(C)C(N)=O)C(F)(F)F)cc2cn(C3CC3)nc12] | 614.15 |
| 911 | 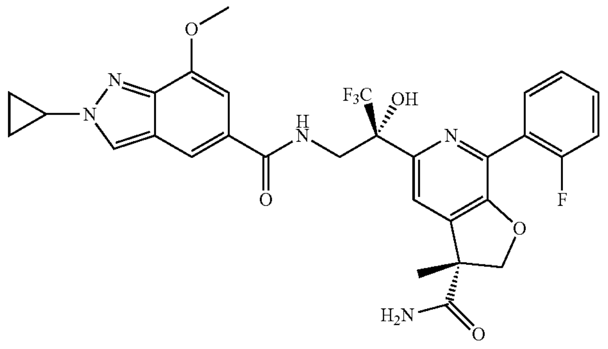 [SMILES: COc1cc(C(=O)NC[C@](O)(c2cc3c(c(-c4ccccc4F)n2)OC[C@]3(C)C(N)=O)C(F)(F)F)cc2cn(C3CC3)nc12] | 614.15 |
| 912 | 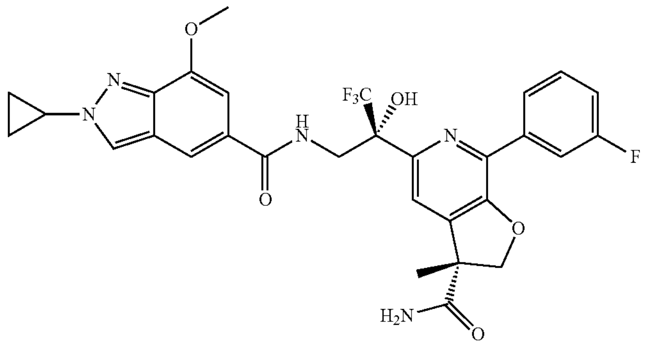 [SMILES: COc1cc(C(=O)NC[C@](O)(c2cc3c(c(-c4cccc(F)c4)n2)OC[C@]3(C)C(N)=O)C(F)(F)F)cc2cn(C3CC3)nc12] | 614.24 |

TABLE 6-continued
| Example | Structure | MS+ m/z |
|---|---|---|
| 913 | 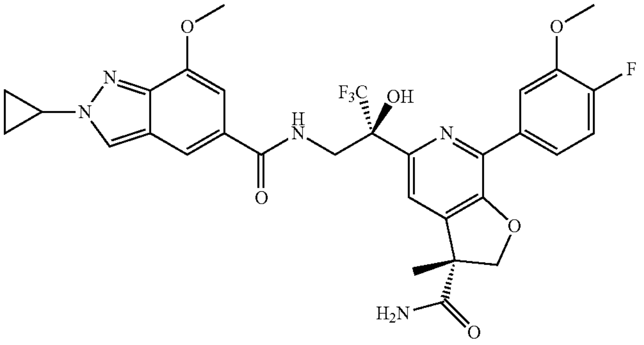 [SMILES: COc1cc(-c2nc([C@](O)(CNC(=O)c3cc(OC)c4nn(C5CC5)cc4c3)C(F)(F)F)cc3c2OC[C@]3(C)C(N)=O)ccc1F] | 644.40 |
| 914 | 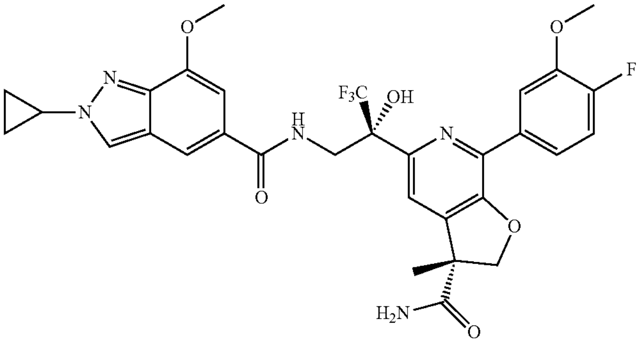 [SMILES: COc1cc(-c2nc([C@@](O)(CNC(=O)c3cc(OC)c4nn(C5CC5)cc4c3)C(F)(F)F)cc3c2OC[C@]3(C)C(N)=O)ccc1F] | 644.40 |
| 915 | 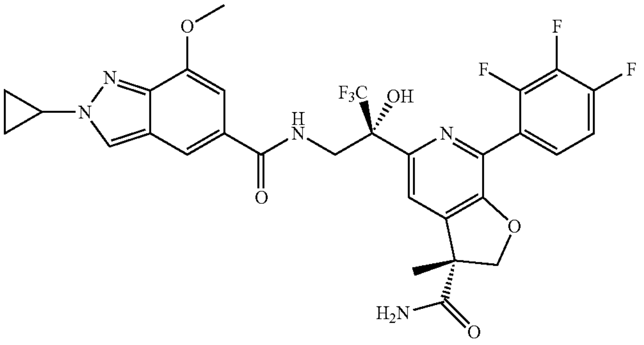 [SMILES: COc1cc(C(=O)NC[C@](O)(c2cc3c(c(-c4ccc(F)c(F)c4F)n2)OC[C@]3(C)C(N)=O)C(F)(F)F)cc2cn(C3CC3)nc12] | 650.21 |
| 916 | 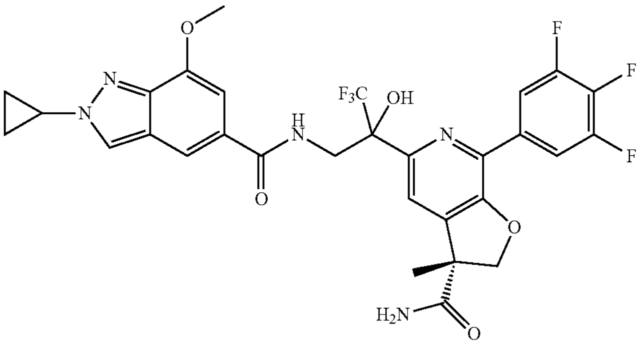 [SMILES: COc1cc(C(=O)NCC(O)(c2cc3c(c(-c4cc(F)c(F)c(F)c4)n2)OC[C@]3(C)C(N)=O)C(F)(F)F)cc2cn(C3CC3)nc12] | 650.16 |

TABLE 6-continued
| Example | Structure | MS+ m/z |
|---|---|---|
| 917 | 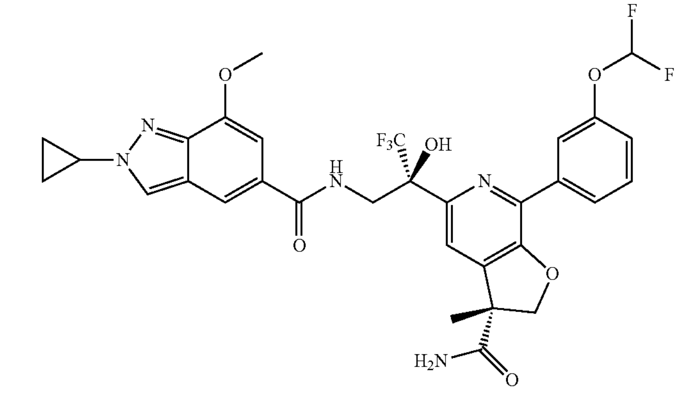 [SMILES: COc1cc(C(=O)NC[C@@](O)(c2cc3c(c(-c4cccc(OC(F)F)c4)n2)OC[C@]3(C)C(N)=O)C(F)(F)F)cc2cn(C3CC3)nc12] | 662.43 |
| 918 | 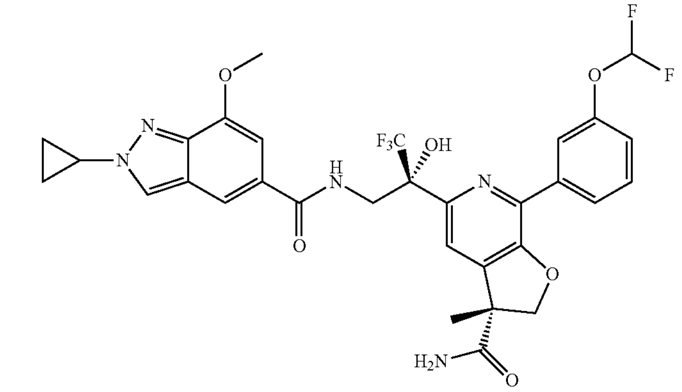 [SMILES: COc1cc(C(=O)NC[C@](O)(c2cc3c(c(-c4cccc(OC(F)F)c4)n2)OC[C@]3(C)C(N)=O)C(F)(F)F)cc2cn(C3CC3)nc12] | 662.43 |
| 919 | 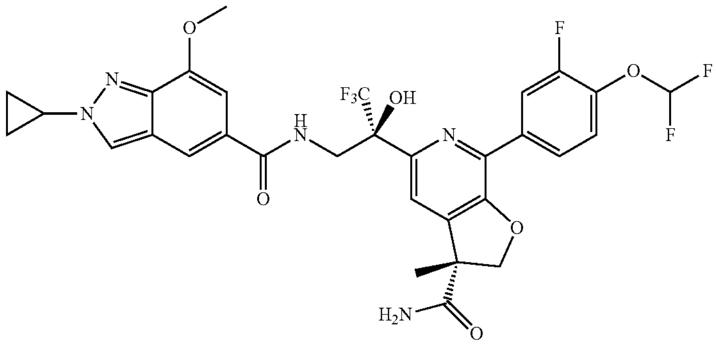 [SMILES: COc1cc(C(=O)NC[C@@](O)(c2cc3c(c(-c4ccc(OC(F)F)c(F)c4)n2)OC[C@]3(C)C(N)=O)C(F)(F)F)cc2cn(C3CC3)nc12] | 680.45 |
| 920 | 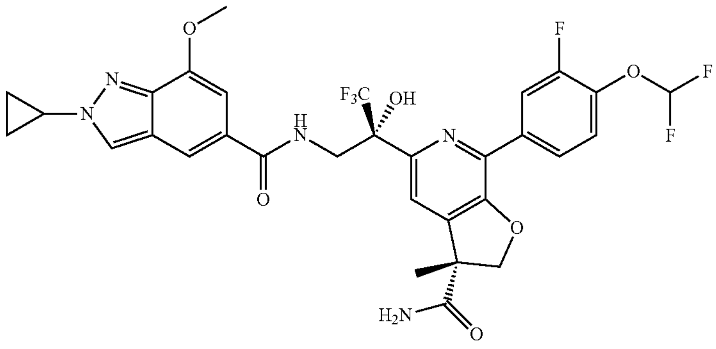 [SMILES: COc1cc(C(=O)NC[C@](O)(c2cc3c(c(-c4ccc(OC(F)F)c(F)c4)n2)OC[C@]3(C)C(N)=O)C(F)(F)F)cc2cn(C3CC3)nc12] | 680.45 |

TABLE 6-continued
| Example | Structure | MS⁺ m/z |
|---|---|---|
| 921 | 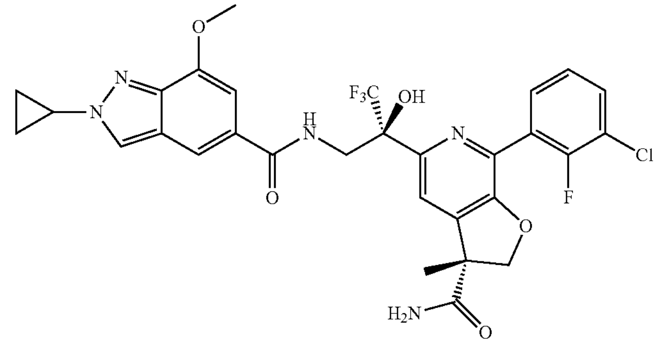 [SMILES: COc1cc(C(=O)NC[C@@](O)(c2cc3c(c(-c4cccc(Cl)c4F)n2)OC[C@]3(C)C(N)=O)C(F)(F)F)cc2cn(C3CC3)nc12] | 648.19 |
| 922 | 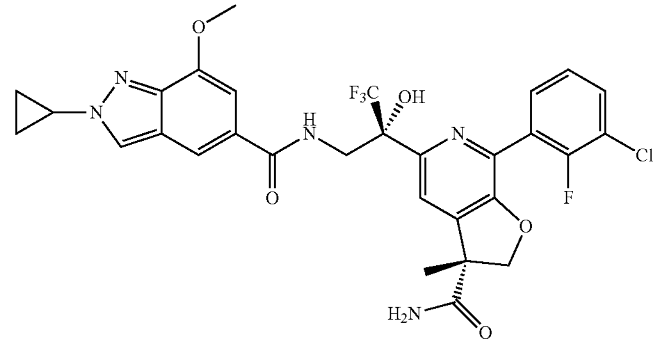 [SMILES: COc1cc(C(=O)NC[C@](O)(c2cc3c(c(-c4cccc(Cl)c4F)n2)OC[C@]3(C)C(N)=O)C(F)(F)F)cc2cn(C3CC3)nc12] | 648.19 |
| 923 | 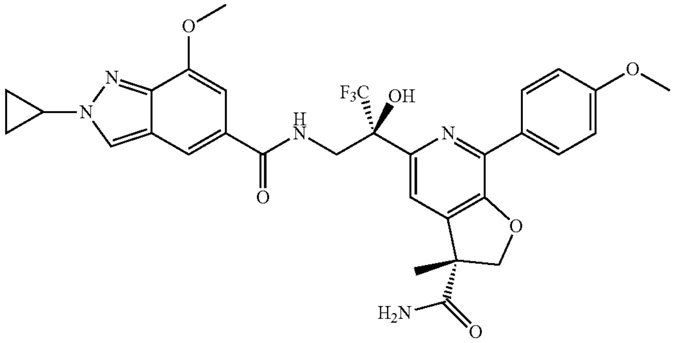 [SMILES: COc1ccc(-c2nc([C@](O)(CNC(=O)c3cc(OC)c4nn(C5CC5)cc4c3)C(F)(F)F)cc3c2OC[C@]3(C)C(N)=O)cc1] | 626.44 |
| 924 | 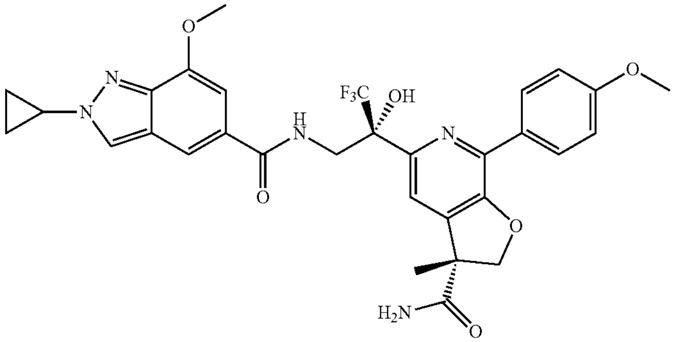 [SMILES: COc1ccc(-c2nc([C@@](O)(CNC(=O)c3cc(OC)c4nn(C5CC5)cc4c3)C(F)(F)F)cc3c2OC[C@]3(C)C(N)=O)cc1] | 626.44 |

TABLE 6-continued
| Example | Structure | MS+ m/z |
|---|---|---|
| 925 | 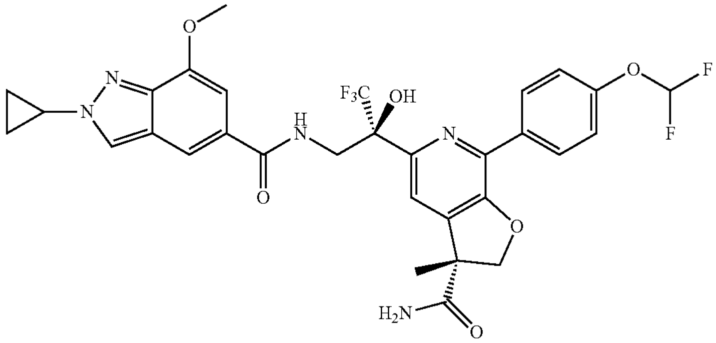 [SMILES: COc1cc(C(=O)NC[C@@](O)(c2cc3c(c(-c4ccc(OC(F)F)cc4)n2)OC[C@]3(C)C(N)=O)C(F)(F)F)cc2cn(C3CC3)nc12] | 662.44 |
| 926 | 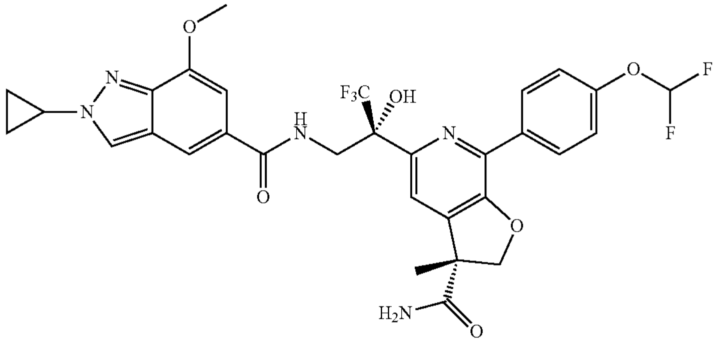 [SMILES: COc1cc(C(=O)NC[C@](O)(c2cc3c(c(-c4ccc(OC(F)F)cc4)n2)OC[C@]3(C)C(N)=O)C(F)(F)F)cc2cn(C3CC3)nc12] | 662.44 |
| 927 | 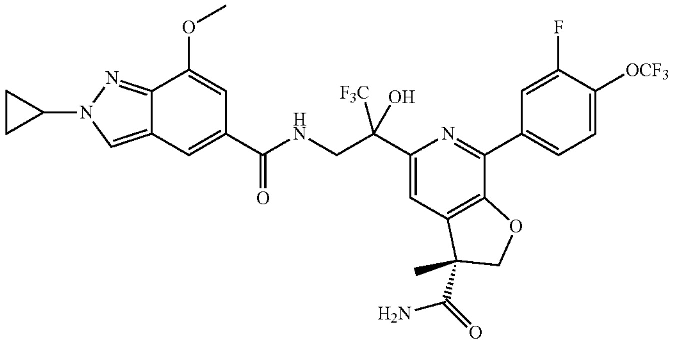 [SMILES: COc1cc(C(=O)NCC(O)(c2cc3c(c(-c4ccc(OC(F)(F)F)c(F)c4)n2)OC[C@]3(C)C(N)=O)C(F)(F)F)cc2cn(C3CC3)nc12] | 698.12 |
| 928 | 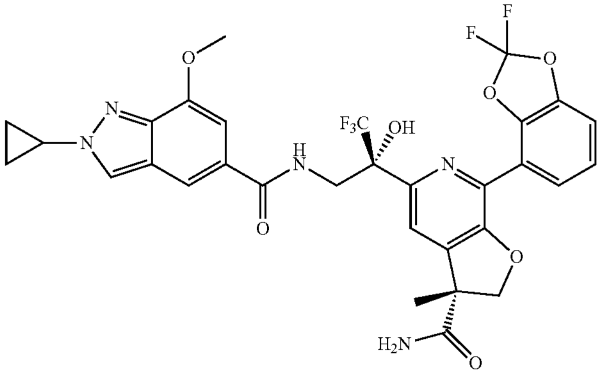 [SMILES: COc1cc(C(=O)NC[C@](O)(c2cc3c(c(-c4cccc5c4OC(F)(F)O5)n2)OC[C@]3(C)C(N)=O)C(F)(F)F)cc2cn(C3CC3)nc12] | 676.44 |

TABLE 6-continued
| Example | Structure | MS+ m/z |
|---|---|---|
| 929 | 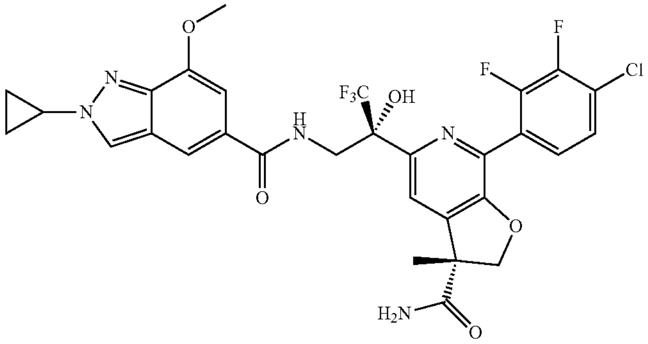 [SMILES: COc1cc(C(=O)NC[C@](O)(c2cc3c(c(-c4ccc(Cl)c(F)c4F)n2)OC[C@]3(C)C(N)=O)C(F)(F)F)cc2cn(C3CC3)nc12] | 666.41 |
| 930 | 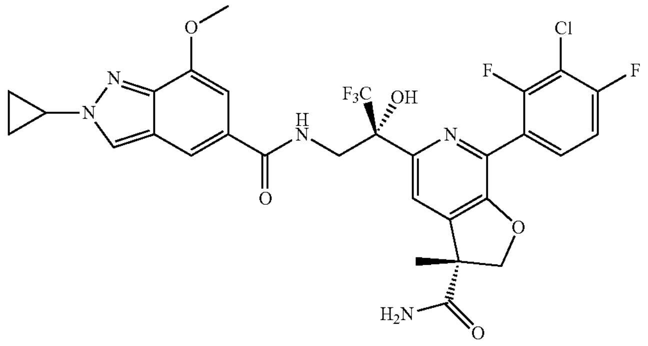 [SMILES: COc1cc(C(=O)NC[C@](O)(c2cc3c(c(-c4ccc(F)c(Cl)c4F)n2)OC[C@]3(C)C(N)=O)C(F)(F)F)cc2cn(C3CC3)nc12] | 666.47 |
| 931 | 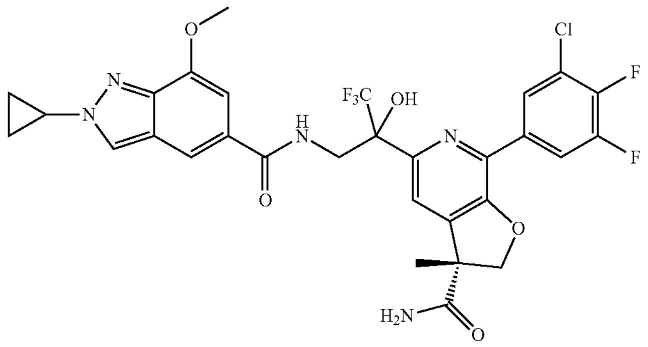 [SMILES: COc1cc(C(=O)NCC(O)(c2cc3c(c(-c4cc(F)c(F)c(Cl)c4)n2)OC[C@]3(C)C(N)=O)C(F)(F)F)cc2cn(C3CC3)nc12] | 666.42 |
| 932 | 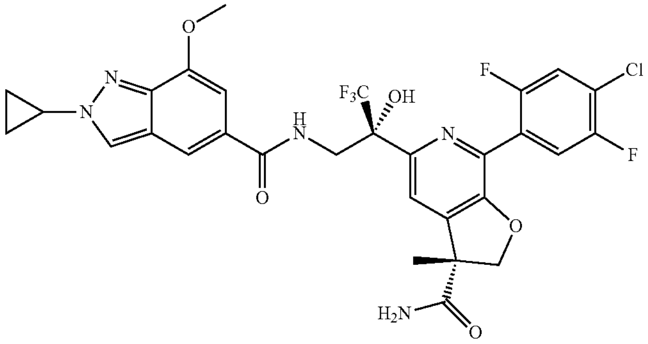 [SMILES: COc1cc(C(=O)NC[C@](O)(c2cc3c(c(-c4cc(F)c(Cl)cc4F)n2)OC[C@]3(C)C(N)=O)C(F)(F)F)cc2cn(C3CC3)nc12] | 666.09 |

TABLE 6-continued
| Example | Structure | MS+ m/z |
|---|---|---|
| 933 | 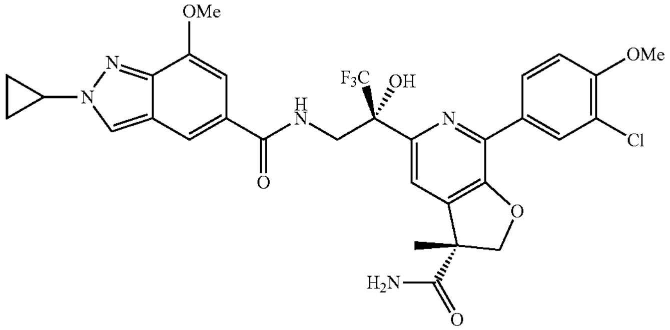 [SMILES: COc1ccc(-c2nc([C@@](O)(CNC(=O)c3cc(OC)c4nn(C5CC5)cc4c3)C(F)(F)F)cc3c2OC[C@]3(C)C(N)=O)cc1Cl] | 660.05 |
| 934 | 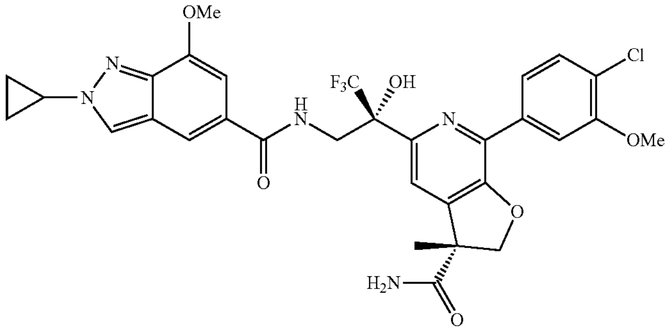 [SMILES: COc1cc(-c2nc([C@@](O)(CNC(=O)c3cc(OC)c4nn(C5CC5)cc4c3)C(F)(F)F)cc3c2OC[C@]3(C)C(N)=O)ccc1Cl] | 660.05 |
| 935 | 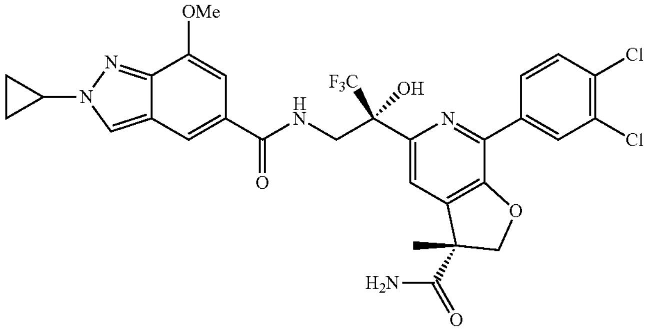 [SMILES: COc1cc(C(=O)NC[C@](O)(c2cc3c(c(-c4ccc(Cl)c(Cl)c4)n2)OC[C@]3(C)C(N)=O)C(F)(F)F)cc2cn(C3CC3)nc12] | 664.46 |
| 936 | 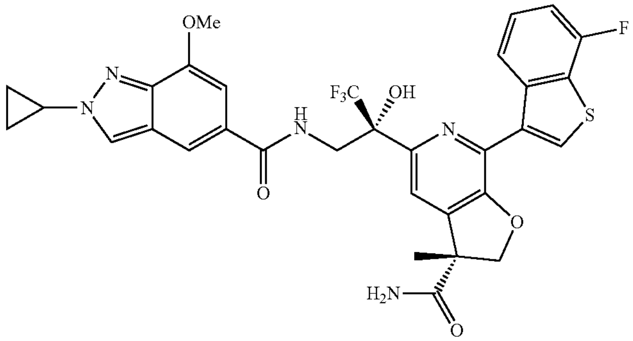 [SMILES: COc1cc(C(=O)NC[C@](O)(c2cc3c(c(-c4csc5c(F)cccc45)n2)OC[C@]3(C)C(N)=O)C(F)(F)F)cc2cn(C3CC3)nc12] | 669.65 |

TABLE 6-continued
| Example | Structure | MS+ m/z |
|---|---|---|
| 937 | 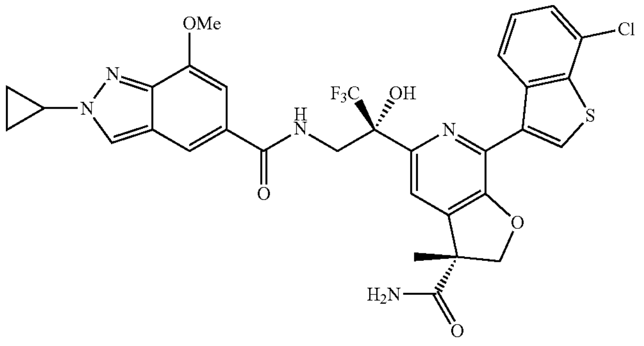 [SMILES: COc1cc(C(=O)NC[C@](O)(c2cc3c(c(-c4csc5c(Cl)cccc45)n2)OC[C@]3(C)C(N)=O)C(F)(F)F)cc2cn(C3CC3)nc12] | 686.10 |
| 938 | 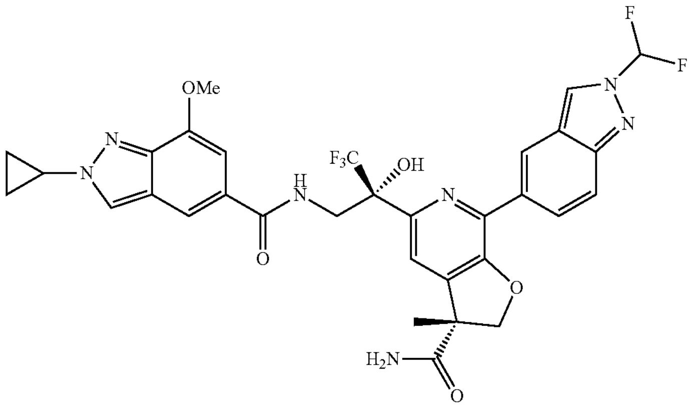 [SMILES: COc1cc(C(=O)NC[C@](O)(c2cc3c(c(-c4ccc5nn(C(F)F)cc5c4)n2)OC[C@]3(C)C(N)=O)C(F)(F)F)cc2cn(C3CC3)nc12] | 685.61 |
| 939 | 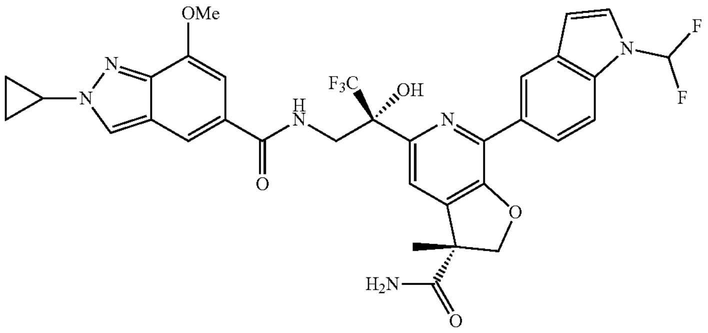 [SMILES: COc1cc(C(=O)NC[C@](O)(c2cc3c(c(-c4ccc5c(ccn5C(F)F)c4)n2)OC[C@]3(C)C(N)=O)C(F)(F)F)cc2cn(C3CC3)nc12] | 684.62 |
| 940 | 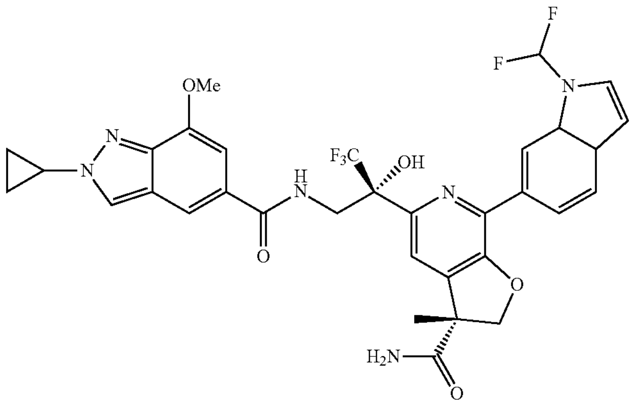 [SMILES: COc1cc(C(=O)NC[C@](O)(c2cc3c(c(C4=CC5C(C=C4)C=CN5C(F)F)n2)OC[C@]3(C)C(N)=O)C(F)(F)F)cc2cn(C3CC3)nc12] | 684.62 |

TABLE 6-continued
| Example | Structure | MS+ m/z |
|---|---|---|
| 941 | 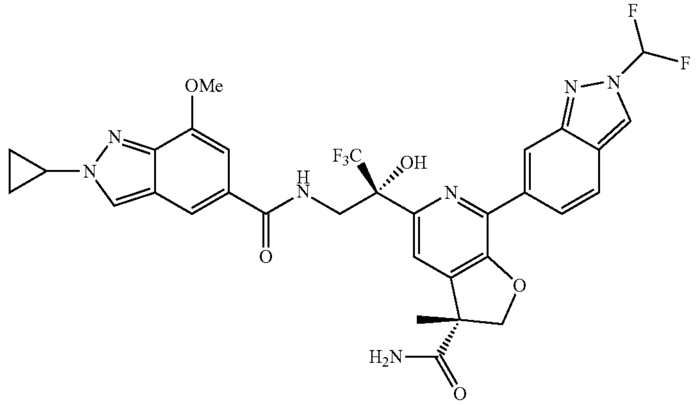 [SMILES: COc1cc(C(=O)NC[C@](O)(c2cc3c(c(-c4ccc5cn(C(F)F)nc5c4)n2)OC[C@]3(C)C(N)=O)C(F)(F)F)cc2cn(C3CC3)nc12] | 685.61 |
| 942 | 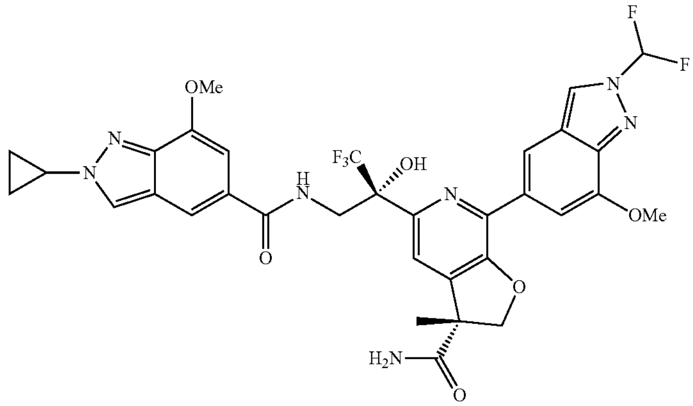 [SMILES: COc1cc(-c2nc([C@@](O)(CNC(=O)c3cc(OC)c4nn(C5CC5)cc4c3)C(F)(F)F)cc3c2OC[C@]3(C)C(N)=O)cc2cn(C(F)F)nc12] | 715.64 |
| 943 | 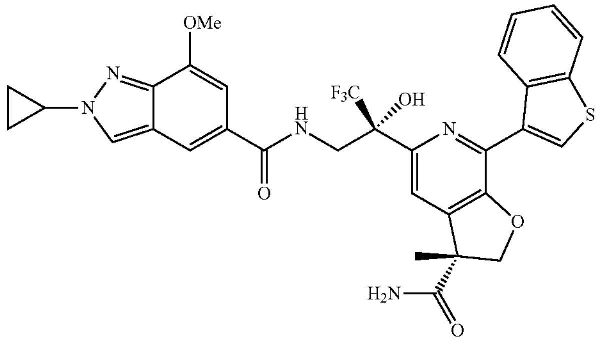 [SMILES: COc1cc(C(=O)NC[C@](O)(c2cc3c(c(-c4csc5ccccc45)n2)OC[C@]3(C)C(N)=O)C(F)(F)F)cc2cn(C3CC3)nc12] | 651.66 |
| 944 | 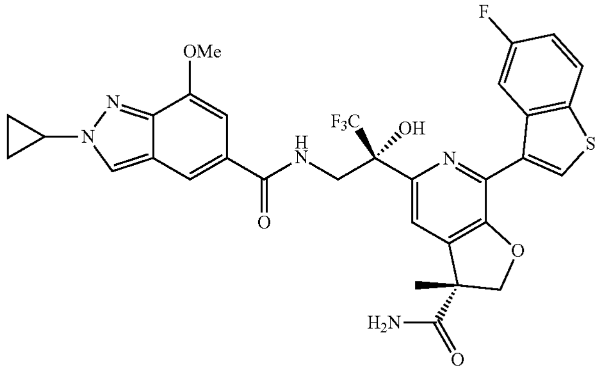 [SMILES: COc1cc(C(=O)NC[C@](O)(c2cc3c(c(-c4csc5ccc(F)cc45)n2)OC[C@]3(C)C(N)=O)C(F)(F)F)cc2cn(C3CC3)nc12] | 669.65 |

TABLE 6-continued
| Example | Structure | MS+ m/z |
|---|---|---|
| 945 | 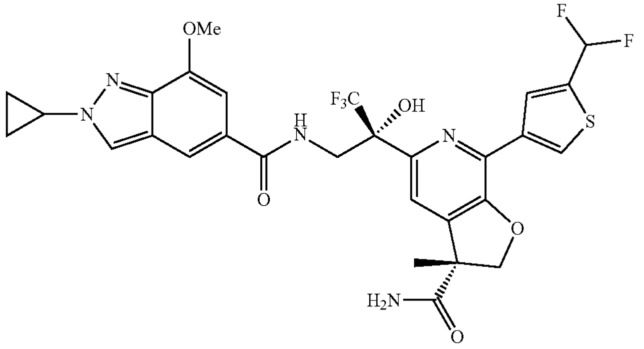 [SMILES: COc1cc(C(=O)NC[C@](O)(c2cc3c(c(-c4csc(C(F)F)c4)n2)OC[C@]3(C)C(N)=O)C(F)(F)F)cc2cn(C3CC3)nc12] | 651.61 |
| 946 | 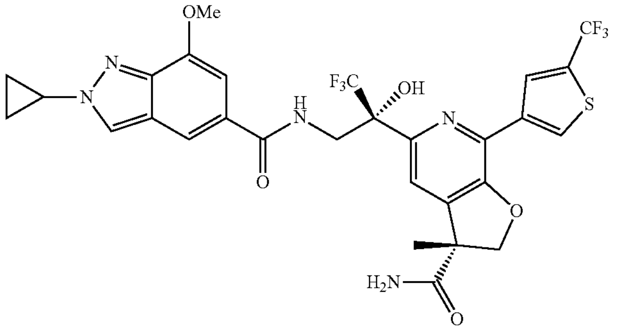 [SMILES: COc1cc(C(=O)NC[C@](O)(c2cc3c(c(-c4csc(C(F)(F)F)c4)n2)OC[C@]3(C)C(N)=O)C(F)(F)F)cc2cn(C3CC3)nc12] | 669.60 |
| 947 | 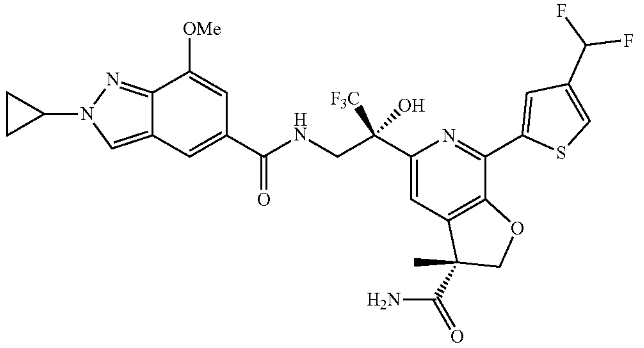 [SMILES: COc1cc(C(=O)NC[C@](O)(c2cc3c(c(-c4cc(C(F)F)cs4)n2)OC[C@]3(C)C(N)=O)C(F)(F)F)cc2cn(C3CC3)nc12] | 651.61 |
| 948 | 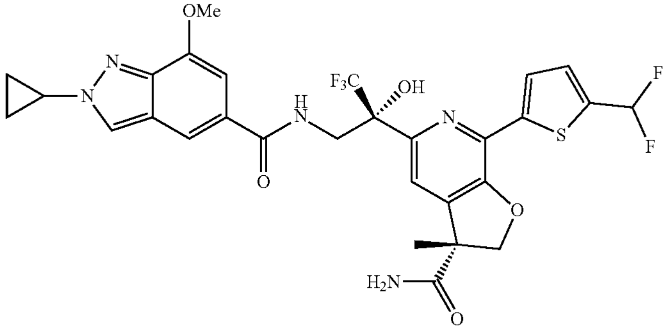 [SMILES: COc1cc(C(=O)NC[C@](O)(c2cc3c(c(-c4ccc(C(F)F)s4)n2)OC[C@]3(C)C(N)=O)C(F)(F)F)cc2cn(C3CC3)nc12] | 651.61 |

TABLE 6-continued
| Example | Structure | MS+ m/z |
|---|---|---|
| 949 | 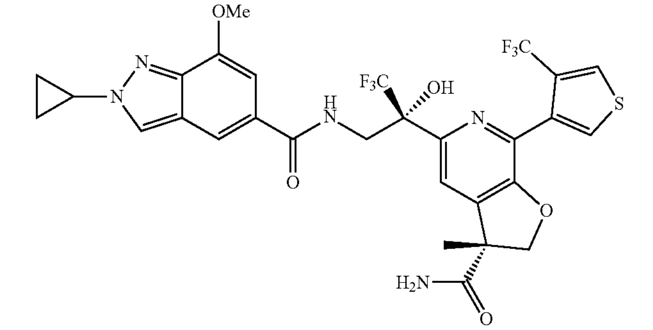 [SMILES: COc1cc(C(=O)NC[C@](O)(c2cc3c(c(-c4cscc4C(F)(F)F)n2)OC[C@]3(C)C(N)=O)C(F)(F)F)cc2cn(C3CC3)nc12] | 651.61 |
| 950 | 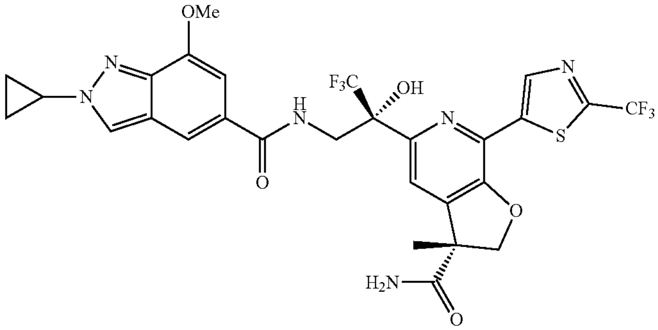 [SMILES: COc1cc(C(=O)NC[C@](O)(c2cc3c(c(-c4cnc(C(F)(F)F)s4)n2)OC[C@]3(C)C(N)=O)C(F)(F)F)cc2cn(C3CC3)nc12] | 670.59 |
| 951 | 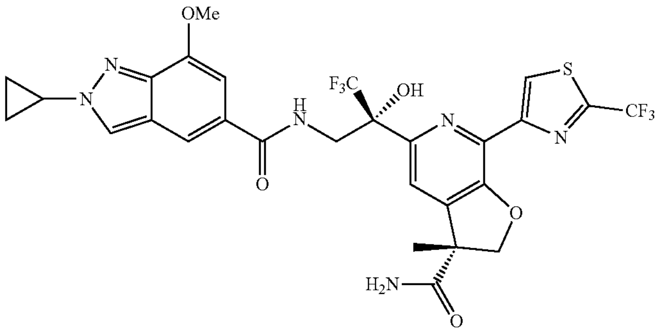 [SMILES: COc1cc(C(=O)NC[C@](O)(c2cc3c(c(-c4csc(C(F)(F)F)n4)n2)OC[C@]3(C)C(N)=O)C(F)(F)F)cc2cn(C3CC3)nc12] | 670.59 |
| 952 | 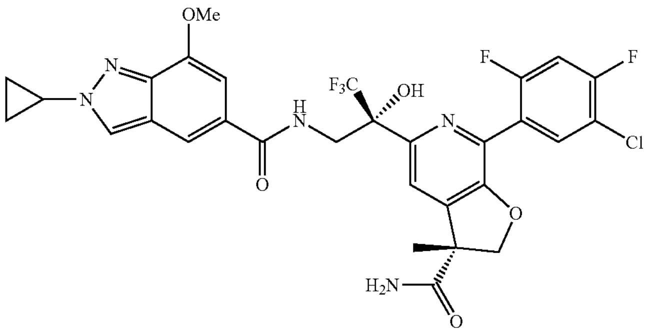 [SMILES: COc1cc(C(=O)NC[C@](O)(c2cc3c(c(-c4cc(Cl)c(F)cc4F)n2)OC[C@]3(C)C(N)=O)C(F)(F)F)cc2cn(C3CC3)nc12] | 666.00 |

TABLE 6-continued
| Example | Structure | MS+ m/z |
|---|---|---|
| 953 | 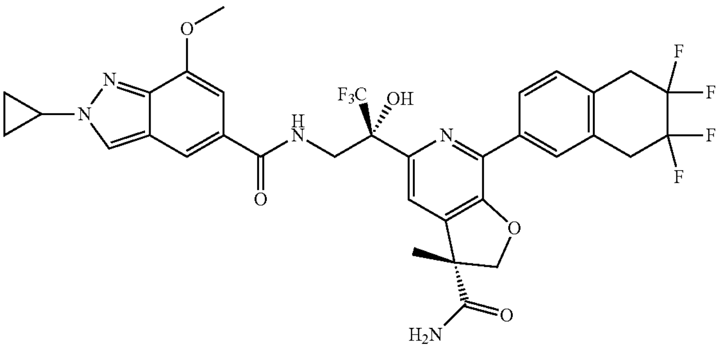 [SMILES: COc1cc(C(=O)NC[C@](O)(c2cc3c(c(-c4ccc5c(c4)CC(F)(F)C(F)(F)C5)n2)OC[C@]3(C)C(N)=O)C(F)(F)F)cc2cn(C3CC3)nc12] | 726.11 |
| 954 | 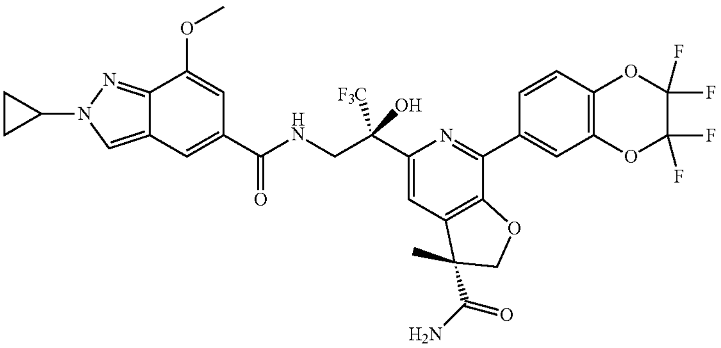 [SMILES: COc1cc(C(=O)NC[C@@](O)(c2cc3c(c(-c4ccc5c(c4)OC(F)(F)C(F)(F)O5)n2)OC[C@]3(C)C(N)=O)C(F)(F)F)cc2cn(C3CC3)nc12] | 726.11 |
| 955 | 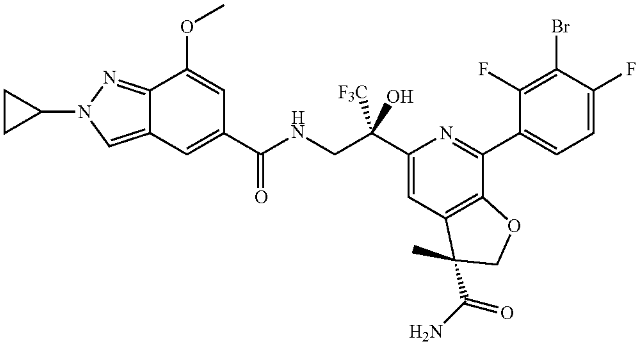 [SMILES: COc1cc(C(=O)NC[C@@](O)(c2cc3c(c(-c4ccc(F)c(Br)c4F)n2)OC[C@]3(C)C(N)=O)C(F)(F)F)cc2cn(C3CC3)nc12] | 712.18 |
| 956 | 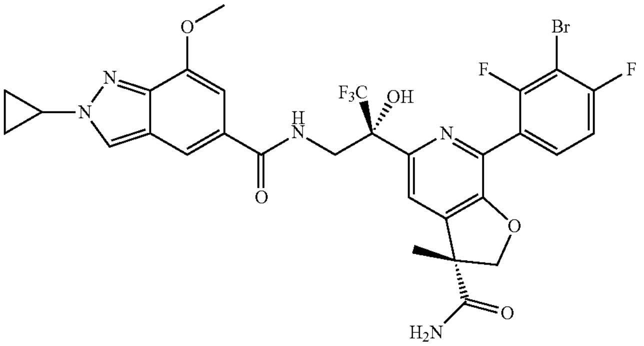 [SMILES: COc1cc(C(=O)NC[C@](O)(c2cc3c(c(-c4ccc(F)c(Br)c4F)n2)OC[C@]3(C)C(N)=O)C(F)(F)F)cc2cn(C3CC3)nc12] | 712.18 |

TABLE 6-continued
| Example | Structure | MS+ m/z |
|---|---|---|
| 957 | 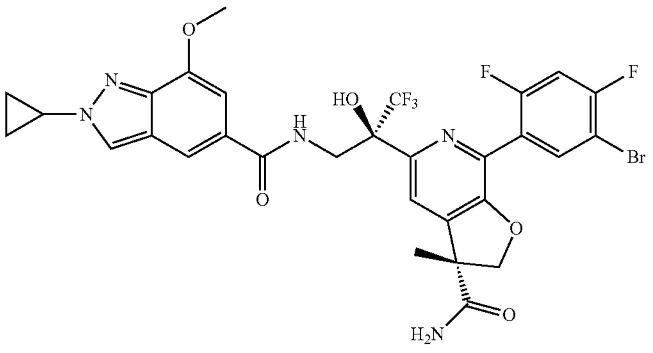 | 712.08 |
| 958 | 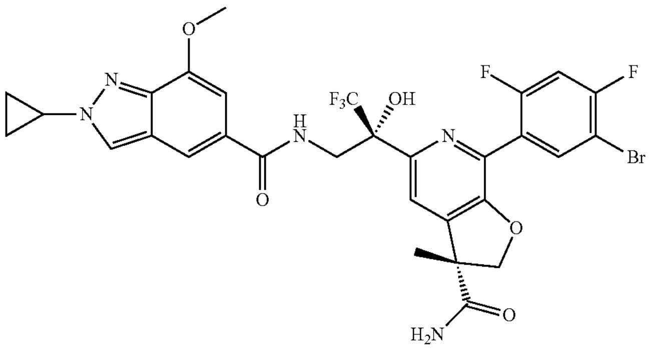 [SMILES: COc1cc(C(=O)NC[C@](O)(c2cc3c(c(-c4cc(Br)c(F)cc4F)n2)OC[C@]3(C)C(N)=O)C(F)(F)F)cc2cn(C3CC3)nc12] | 712.08 |
| 959 | 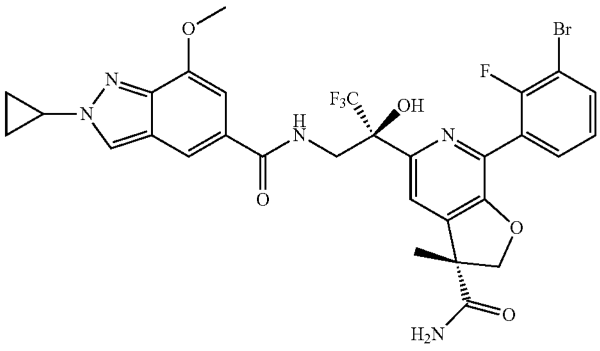 [SMILES: COc1cc(C(=O)NC[C@@](O)(c2cc3c(c(-c4cccc(Br)c4F)n2)OC[C@]3(C)C(N)=O)C(F)(F)F)cc2cn(C3CC3)nc12] | 694.06 |
| 960 | 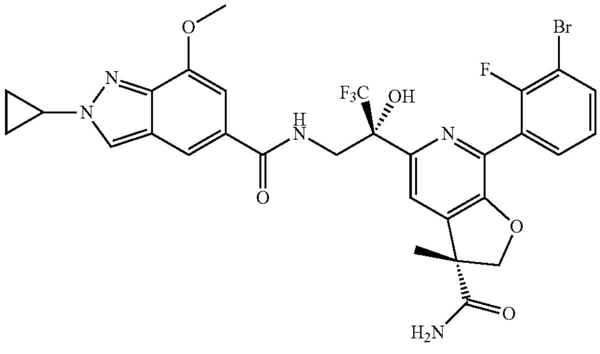 [SMILES: COc1cc(C(=O)NC[C@](O)(c2cc3c(c(-c4cccc(Br)c4F)n2)OC[C@]3(C)C(N)=O)C(F)(F)F)cc2cn(C3CC3)nc12] | 694.06 |

TABLE 6-continued
| Example | Structure | MS+ m/z |
|---|---|---|
| 961 | 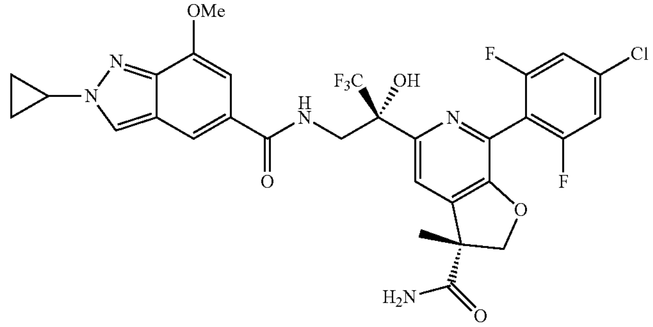 [SMILES: COc1cc(C(=O)NC[C@](O)(c2cc3c(c(-c4c(F)cc(Cl)cc4F)n2)OC[C@]3(C)C(N)=O)C(F)(F)F)cc2cn(C3CC3)nc12] | 666.14 |
| 962 | 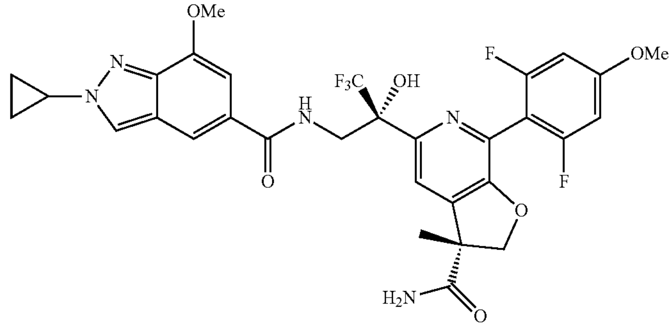 [SMILES: COc1cc(F)c(-c2nc([C@@](O)(CNC(=O)c3cc(OC)c4nn(C5CC5)cc4c3)C(F)(F)F)cc3c2OC[C@]3(C)C(N)=O)c(F)c1] | 662.19 |
| 963 | 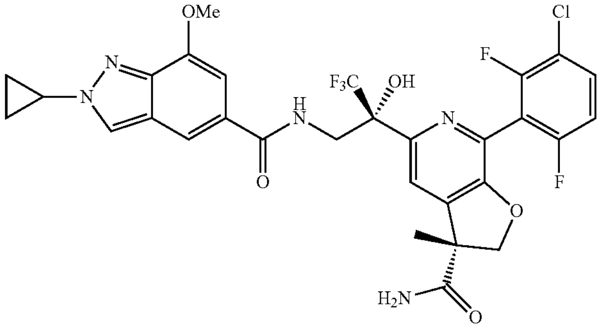 [SMILES: COc1cc(C(=O)NC[C@](O)(c2cc3c(c(-c4c(F)ccc(F)c4F)n2)OC[C@]3(C)C(N)=O)C(F)(F)F)cc2cn(C3CC3)nc12] | 666.14 |
| 964 | 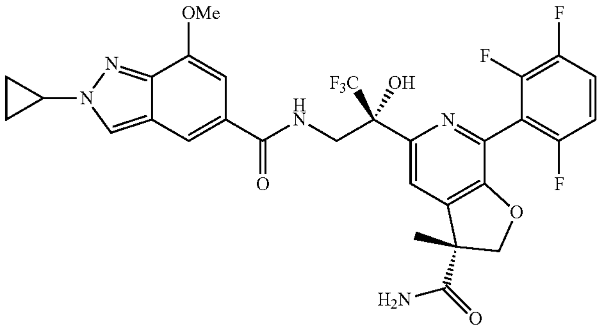 | 650.17 |

TABLE 6-continued
| Example | Structure | MS+ m/z |
| --- | --- | --- |
| 965 | 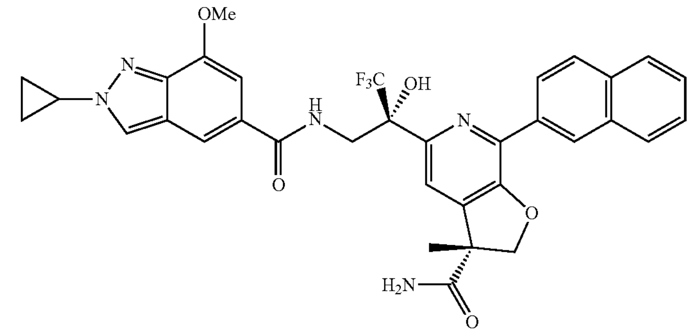 [SMILES: COc1cc(C(=O)NC[C@](O)(c2cc3c(c(-c4ccc5ccccc5c4)n2)OC[C@]3(C)C(N)=O)C(F)(F)F)cc2cn(C3CC3)nc12] | 646.20 |
| 966 | 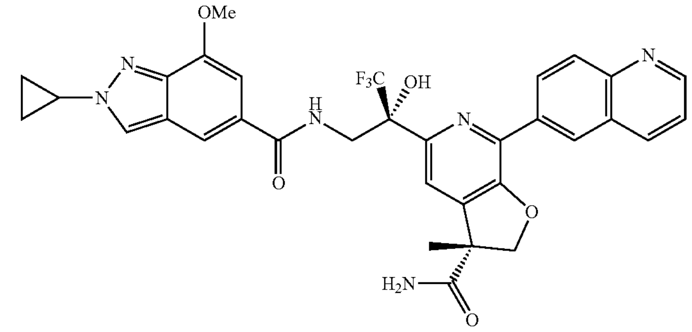 [SMILES: COc1cc(C(=O)NC[C@](O)(c2cc3c(c(-c4ccc5ncccc5c4)n2)OC[C@]3(C)C(N)=O)C(F)(F)F)cc2cn(C3CC3)nc12] | 647.25 |
| 967 | 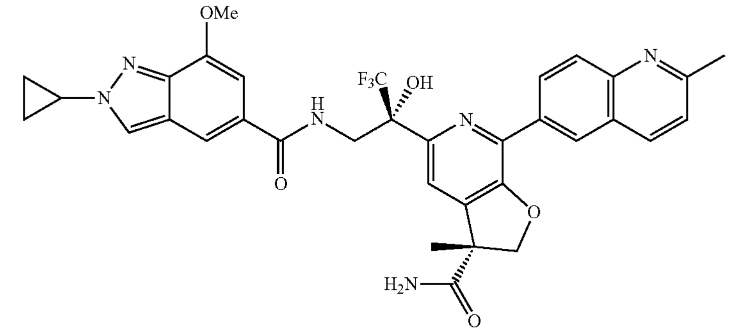 [SMILES: COc1cc(C(=O)NC[C@](O)(c2cc3c(c(-c4ccc5nc(C)ccc5c4)n2)OC[C@]3(C)C(N)=O)C(F)(F)F)cc2cn(C3CC3)nc12] | 661.20 |
| 968 | 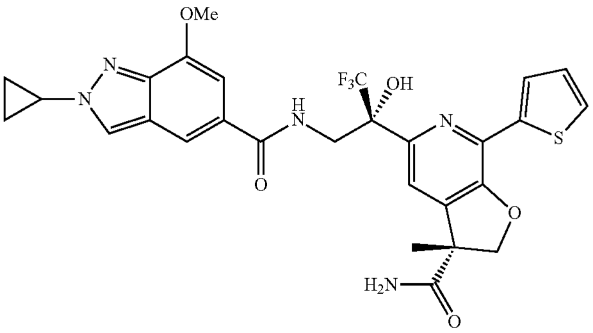 [SMILES: COc1cc(C(=O)NC[C@](O)(c2cc3c(c(-c4cccs4)n2)OC[C@]3(C)C(N)=O)C(F)(F)F)cc2cn(C3CC3)nc12] | 602.15 |

TABLE 6-continued
| Example | Structure | MS+ m/z |
|---|---|---|
| 969 | 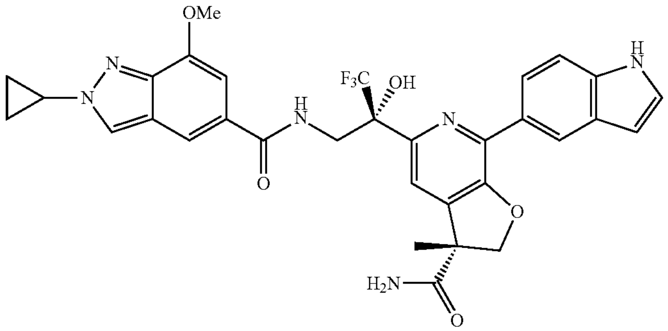 [SMILES: COc1cc(C(=O)NC[C@](O)(c2cc3c(c(-c4ccc5[nH]ccc5c4)n2)OC[C@]3(C)C(N)=O)C(F)(F)F)cc2cn(C3CC3)nc12] | 635.25 |
| 970 | 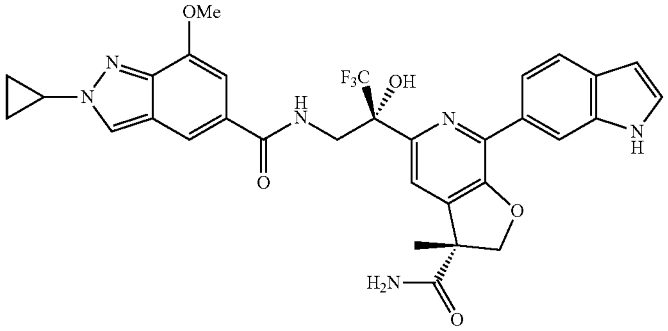 [SMILES: COc1cc(C(=O)NC[C@](O)(c2cc3c(c(-c4ccc5cc[nH]c5c4)n2)OC[C@]3(C)C(N)=O)C(F)(F)F)cc2cn(C3CC3)nc12] | 635.30 |
| 971 | 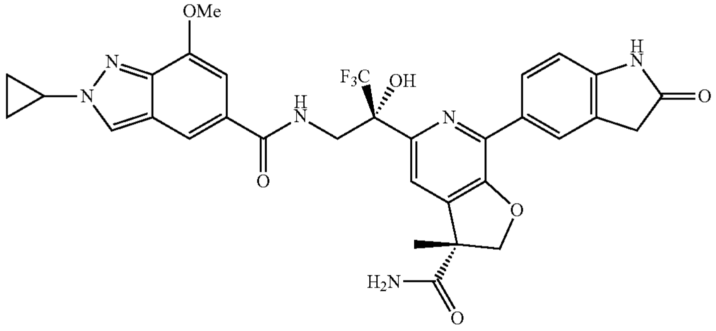 [SMILES: COc1cc(C(=O)NC[C@](O)(c2cc3c(c(-c4ccc5c(c4)CC(=O)N5)n2)OC[C@]3(C)C(N)=O)C(F)(F)F)cc2cn(C3CC3)nc12] | 651.25 |
| 972 | 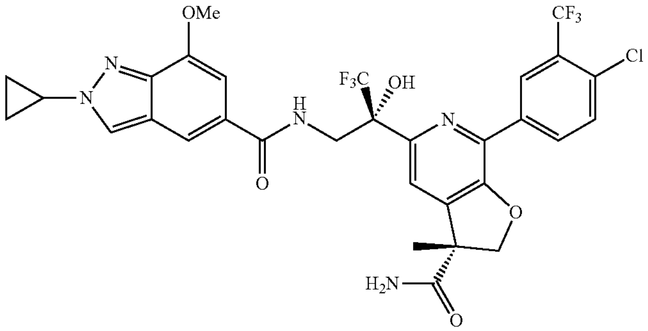 [SMILES: COc1cc(C(=O)NC[C@](O)(c2cc3c(c(-c4ccc(Cl)c(C(F)(F)F)c4)n2)OC[C@]3(C)C(N)=O)C(F)(F)F)cc2cn(C3CC3)nc12] | 698.15 |

TABLE 6-continued
| Example | Structure | MS+ m/z |
| --- | --- | --- |
| 973 | 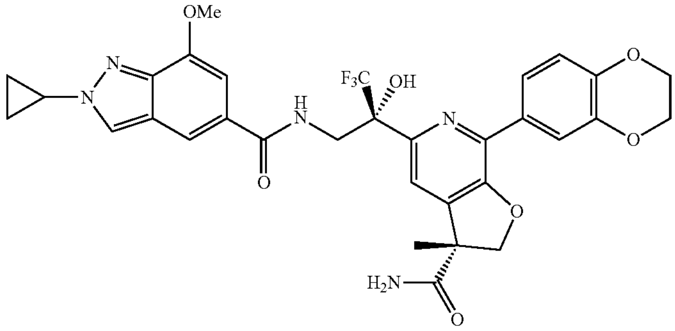 [SMILES: COc1cc(C(=O)NC[C@](O)(c2cc3c(c(-c4ccc5c(c4)OCCO5)n2)OC[C@]3(C)C(N)=O)C(F)(F)F)cc2cn(C3CC3)nc12] | 654.20 |
| 974 | 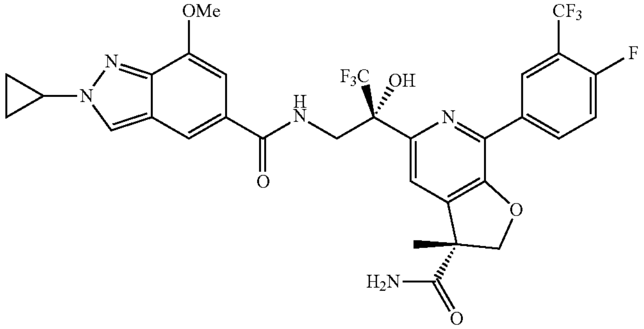 [SMILES: COc1cc(C(=O)NC[C@](O)(c2cc3c(c(-c4ccc(F)c(C(F)(F)F)c4)n2)OC[C@]3(C)C(N)=O)C(F)(F)F)cc2cn(C3CC3)nc12] | 682.20 |
| 975 | 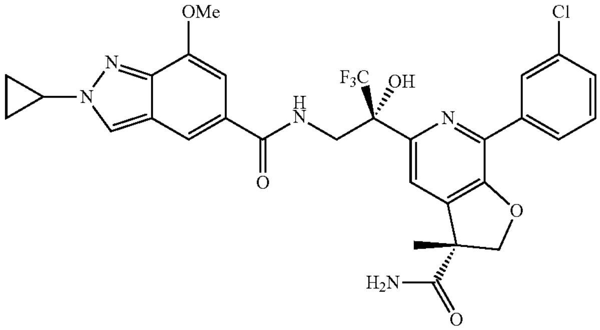 [SMILES: COc1cc(C(=O)NC[C@](O)(c2cc3c(c(-c4cccc(Cl)c4)n2)OC[C@]3(C)C(N)=O)C(F)(F)F)cc2cn(C3CC3)nc12] | 630.20 |
| 976 | 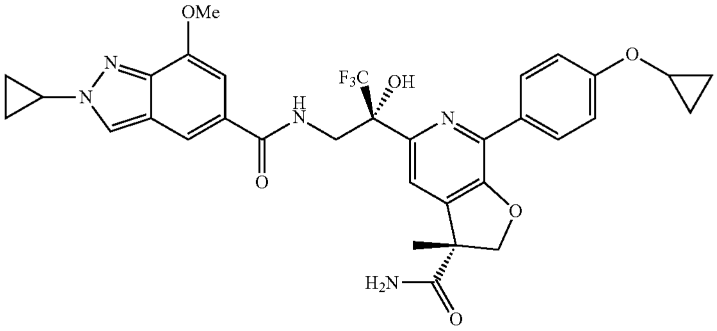 [SMILES: COc1cc(C(=O)NC[C@](O)(c2cc3c(c(-c4ccc(OC5CC5)cc4)n2)OC[C@]3(C)C(N)=O)C(F)(F)F)cc2cn(C3CC3)nc12] | 652.25 |

TABLE 6-continued
| Example | Structure | MS+ m/z |
|---|---|---|
| 977 | 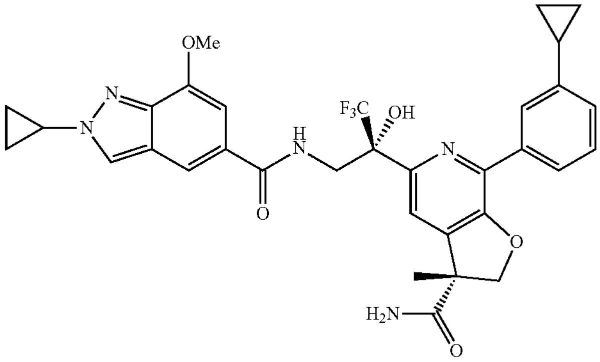 [SMILES: COc1cc(C(=O)NC[C@](O)(c2cc3c(c(-c4cccc(C5CC5)c4)n2)OC[C@]3(C)C(N)=O)C(F)(F)F)cc2cn(C3CC3)nc12] | 636.25 |
| 978 | 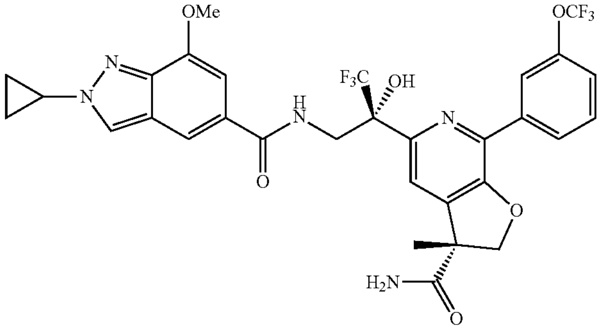 [SMILES: COc1cc(C(=O)NC[C@](O)(c2cc3c(c(-c4cccc(OC(F)(F)F)c4)n2)OC[C@]3(C)C(N)=O)C(F)(F)F)cc2cn(C3CC3)nc12] | 680.20 |
| 979 | 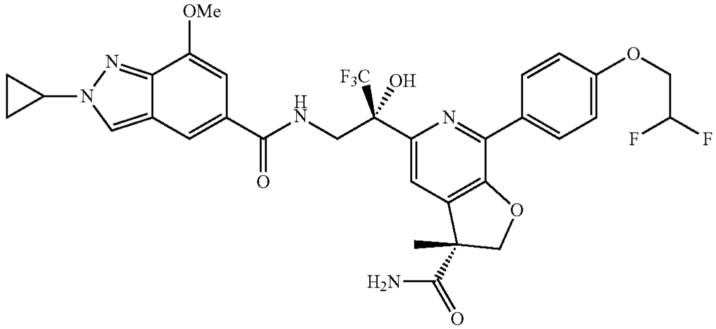 [SMILES: COc1cc(C(=O)NC[C@](O)(c2cc3c(c(-c4ccc(OCC(F)F)cc4)n2)OC[C@]3(C)C(N)=O)C(F)(F)F)cc2cn(C3CC3)nc12] | 676.25 |
| 980 | 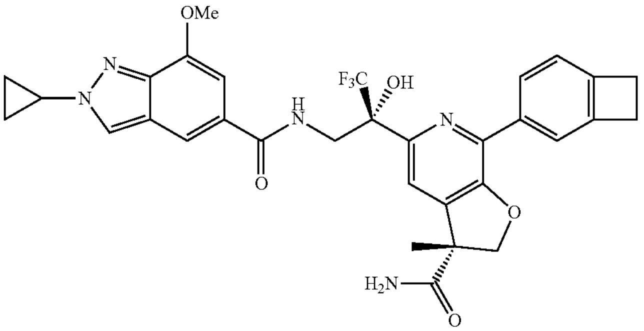 [SMILES: COc1cc(C(=O)NC[C@](O)(c2cc3c(c(-c4ccc5c(c4)CC5)n2)OC[C@]3(C)C(N)=O)C(F)(F)F)cc2cn(C3CC3)nc12] | 622.25 |

TABLE 6-continued
| Example | Structure | MS+ m/z |
|---|---|---|
| 981 | 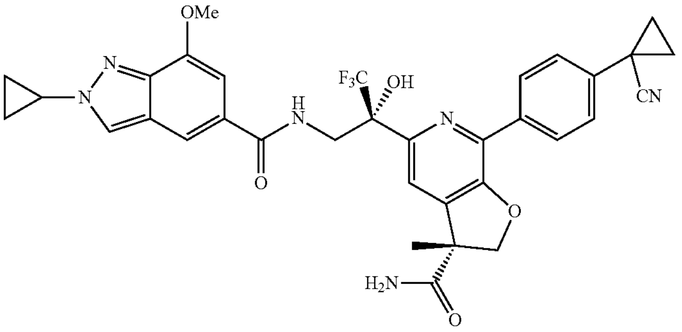 [SMILES: COc1cc(C(=O)NC[C@](O)(c2cc3c(c(-c4ccc(C5(C#N)CC5)cc4)n2)OC[C@]3(C)C(N)=O)C(F)(F)F)cc2cn(C3CC3)nc12] | 661.25 |
| 982 | 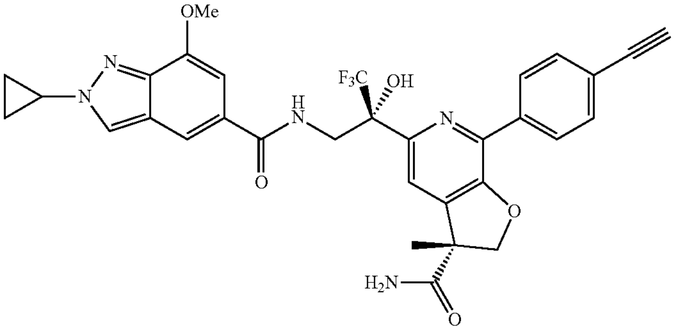 [SMILES: C#Cc1ccc(-c2nc([C@@](O)(CNC(=O)c3cc(OC)c4nn(C5CC5)cc4c3)C(F)(F)F)cc3c2OC[C@]3(C)C(N)=O)cc1] | 620.15 |
| 983 | 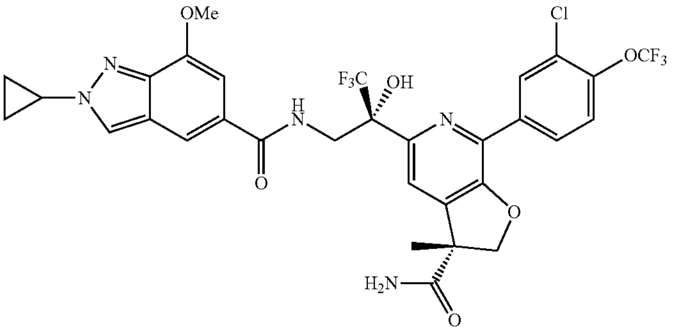 [SMILES: COc1cc(C(=O)NC[C@](O)(c2cc3c(c(-c4ccc(OC(F)(F)F)c(Cl)c4)n2)OC[C@]3(C)C(N)=O)C(F)(F)F)cc2cn(C3CC3)nc12] | 714.15 |
| 984 | 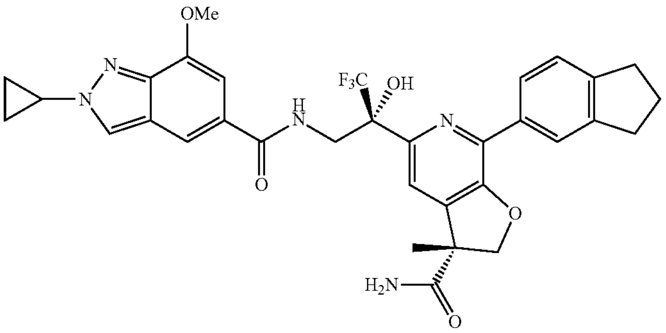 [SMILES: COc1cc(C(=O)NC[C@](O)(c2cc3c(c(-c4ccc5c(c4)CCC5)n2)OC[C@]3(C)C(N)=O)C(F)(F)F)cc2cn(C3CC3)nc12] | 636.25 |

TABLE 6-continued
| Example | Structure | MS⁺ m/z |
|---|---|---|
| 985 | 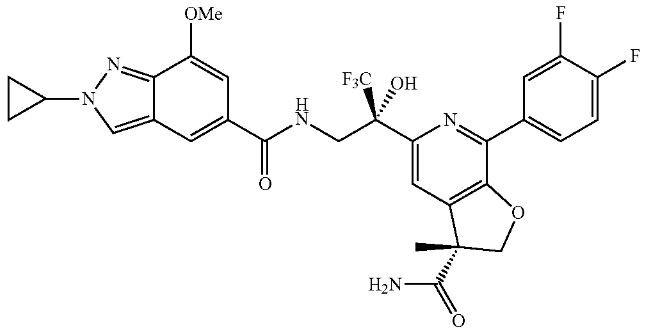 [SMILES: COc1cc(C(=O)NC[C@](O)(c2cc3c(c(-c4ccc(F)c(F)c4)n2)OC[C@]3(C)C(N)=O)C(F)(F)F)cc2cn(C3CC3)nc12] | 632.20 |
| 986 | 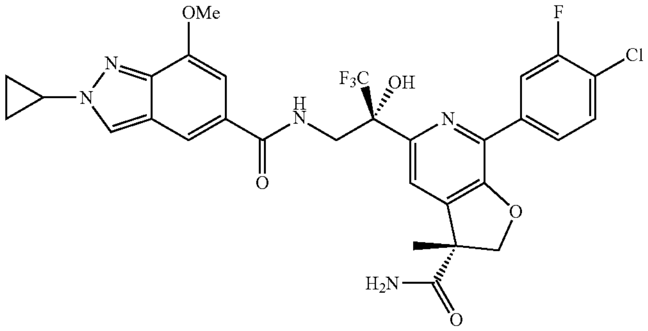 [SMILES: COc1cc(C(=O)NC[C@](O)(c2cc3c(c(-c4ccc(Cl)c(F)c4)n2)OC[C@]3(C)C(N)=O)C(F)(F)F)cc2cn(C3CC3)nc12] | 648.10 |
| 987 | 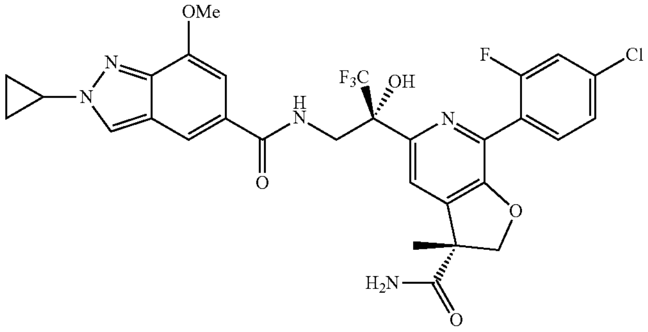 [SMILES: COc1cc(C(=O)NC[C@](O)(c2cc3c(c(-c4ccc(Cl)cc4F)n2)OC[C@]3(C)C(N)=O)C(F)(F)F)cc2cn(C3CC3)nc12] | 648.15 |
| 988 | 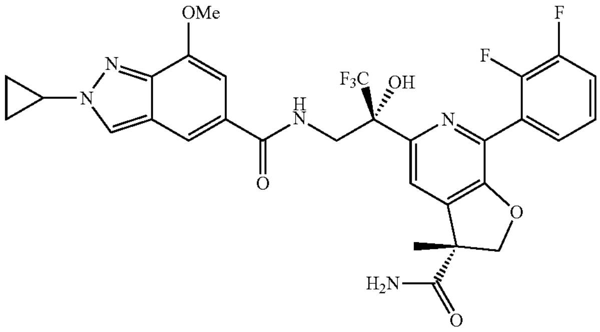 [SMILES: COc1cc(C(=O)NC[C@](O)(c2cc3c(c(-c4cccc(F)c4F)n2)OC[C@]3(C)C(N)=O)C(F)(F)F)cc2cn(C3CC3)nc12] | 632.15 |

TABLE 6-continued
| Example | Structure | MS⁺ m/z |
|---|---|---|
| 989 | 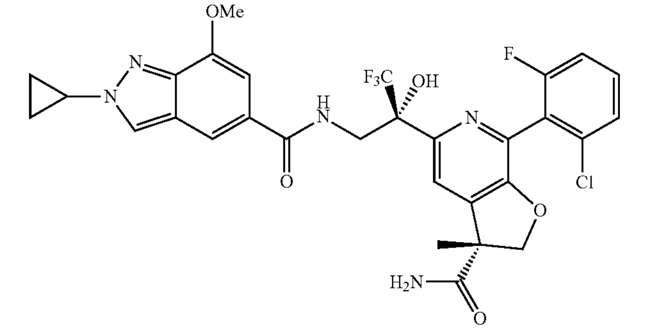 [SMILES: COc1cc(C(=O)NC[C@](O)(c2cc3c(c(-c4c(F)cccc4Cl)n2)OC[C@]3(C)C(N)=O)C(F)(F)F)cc2cn(C3CC3)nc12] | 648.15 |
| 990 | 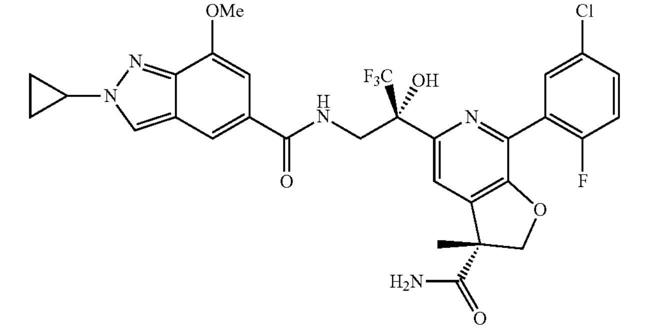 [SMILES: COc1cc(C(=O)NC[C@](O)(c2cc3c(c(-c4cc(Cl)ccc4F)n2)OC[C@]3(C)C(N)=O)C(F)(F)F)cc2cn(C3CC3)nc12] | 648.10 |
| 991 | 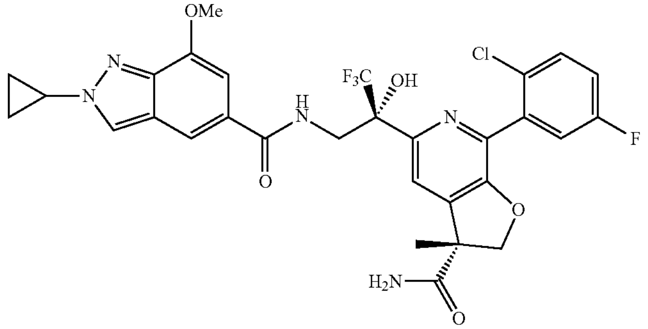 | 648.10 |
| 992 | 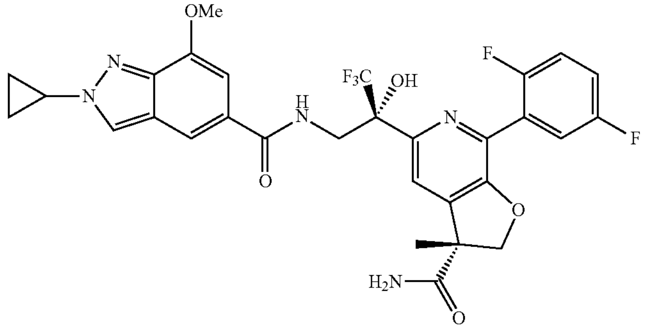 [SMILES: COc1cc(C(=O)NC[C@](O)(c2cc3c(c(-c4cc(F)ccc4F)n2)OC[C@]3(C)C(N)=O)C(F)(F)F)cc2cn(C3CC3)nc12] | 632.15 |

TABLE 6-continued
| Example | Structure | MS+ m/z |
|---|---|---|
| 993 | 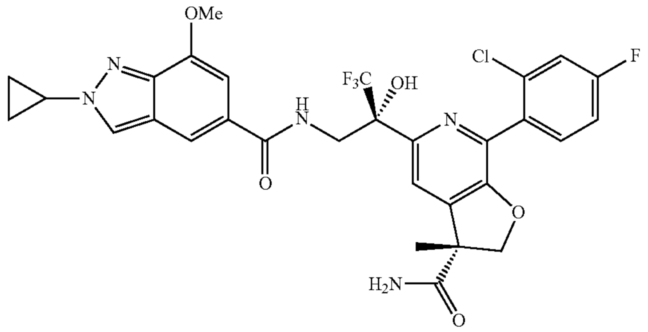 [SMILES: COc1cc(C(=O)NC[C@](O)(c2cc3c(c(-c4ccc(F)cc4Cl)n2)OC[C@]3(C)C(N)=O)C(F)(F)F)cc2cn(C3CC3)nc12] | 648.10 |
| 994 | 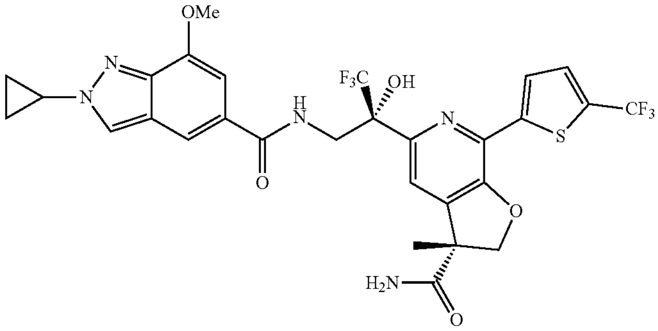 [SMILES: COc1cc(C(=O)NC[C@](O)(c2cc3c(c(-c4ccc(C(F)(F)F)s4)n2)OC[C@]3(C)C(N)=O)C(F)(F)F)cc2cn(C3CC3)nc12] | 670.20 |
| 995 | 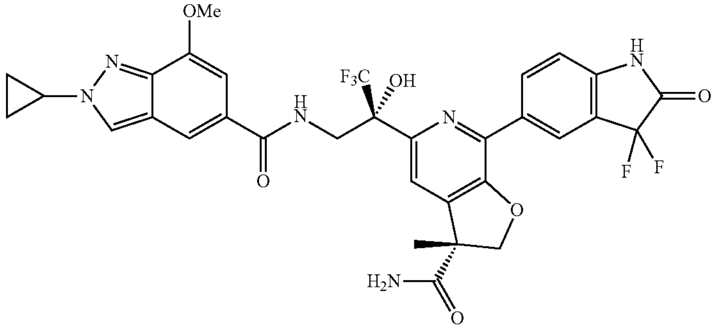 [SMILES: COc1cc(C(=O)NC[C@](O)(c2cc3c(c(-c4ccc5c(c4)C(F)(F)C(=O)N5)n2)OC[C@]3(C)C(N)=O)C(F)(F)F)cc2cn(C3CC3)nc12] | 687.25 |
| 996 | 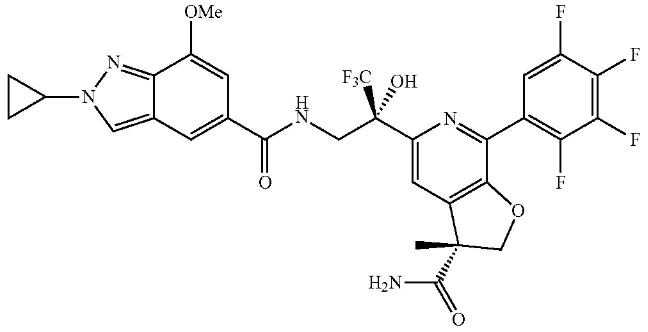 [SMILES: COc1cc(C(=O)NC[C@](O)(c2cc3c(c(-c4cc(F)c(F)c(F)c4F)n2)OC[C@]3(C)C(N)=O)C(F)(F)F)cc2cn(C3CC3)nc12] | 668.15 |

TABLE 6-continued

| Example | Structure | MS+ m/z |
|---|---|---|
| 997 | 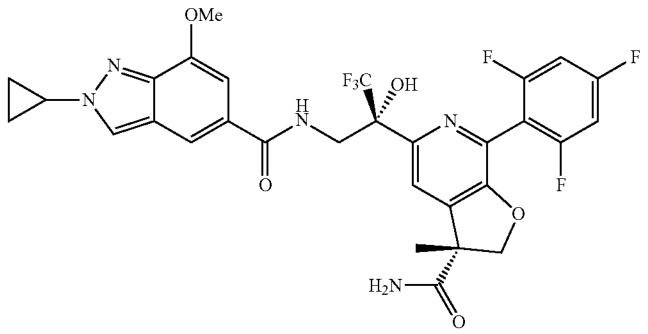 [SMILES: COc1cc(C(=O)NC[C@](O)(c2cc3c(c(-c4c(F)cc(F)cc4F)n2)OC[C@]3(C)C(N)=O)C(F)(F)F)cc2cn(C3CC3)nc12] | 650.15 |

The following Table 7 contains examples that were prepared with the similar method to Example 1 Step c (PyBOP or HATU). The majority of compounds were purified by prep-HPLC (ACN/$H_2O$, 20-90%, 25 min) If depicted as a single diastereomer, they were separated during prep-HPLC purification. The amine coupling partners were prepared in analogous fashion to Intermediates 45 & 46. The aryl acid coupling partners were prepared according to Intermediates 1-95, or by analogous procedures with slight modifications and also prepared according to procedures found in U.S. patent application Ser. No. 16/930,622.

TABLE 7

| Example | Structure | MS+ m/z |
|---|---|---|
| 998 | 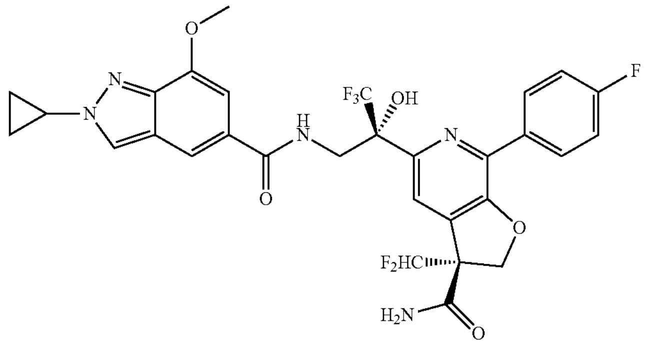 [SMILES: COc1cc(C(=O)NC[C@](O)(c2cc3c(c(-c4ccc(F)cc4)n2)OC[C@]3(C(N)=O)C(F)F)C(F)(F)F)cc2cn(C3CC3)nc12] | 650.16 |
| 999 | 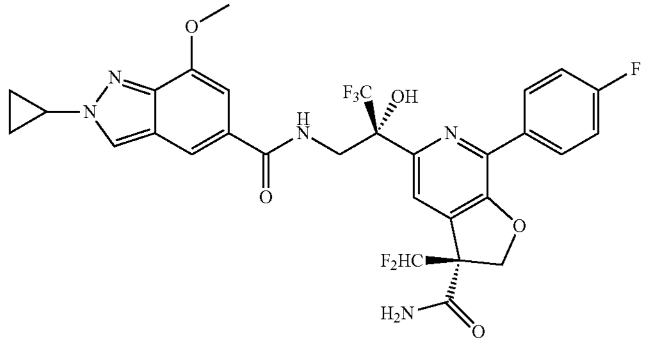 [SMILES: COc1cc(C(=O)NC[C@](O)(c2cc3c(c(-c4ccc(F)cc4)n2)OC[C@@]3(C(N)=O)C(F)F)C(F)(F)F)cc2cn(C3CC3)nc12] | 650.16 |

TABLE 7-continued
| Example | Structure | MS⁺ m/z |
|---|---|---|
| 1000 | 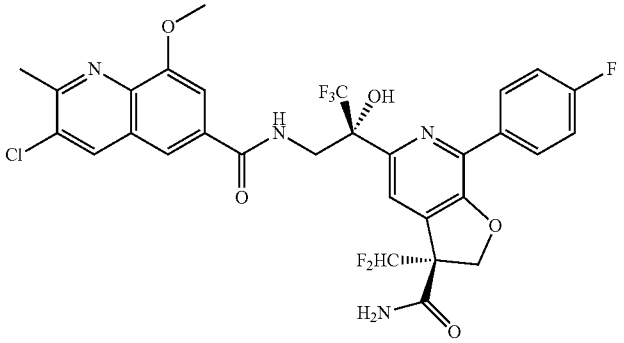 [SMILES: COc1cc(C(=O)NC[C@](O)(c2cc3c(c(-c4ccc(F)cc4)n2)OC[C@]3(C(N)=O)C(F)F)C(F)(F)F)cc2cc(Cl)c(C)nc12] | 669.12 |
| 1001 | 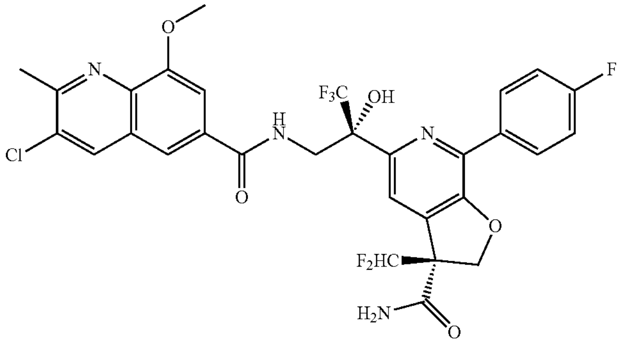 [SMILES: COc1cc(C(=O)NC[C@](O)(c2cc3c(c(-c4ccc(F)cc4)n2)OC[C@@]3(C(N)=O)C(F)F)C(F)(F)F)cc2cc(Cl)c(C)nc12] | 669.12 |
| 1002 | 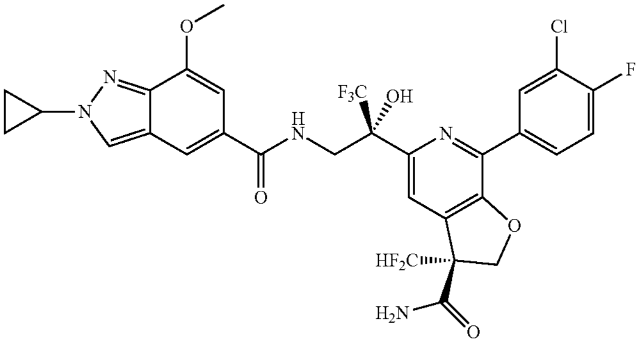 | 684.15 |
| 1003 | 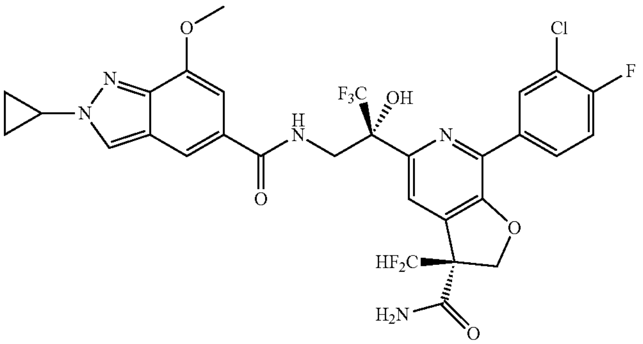 | 684.15 |

TABLE 7-continued
| Example | Structure | MS+ m/z |
|---|---|---|
| 1004 | 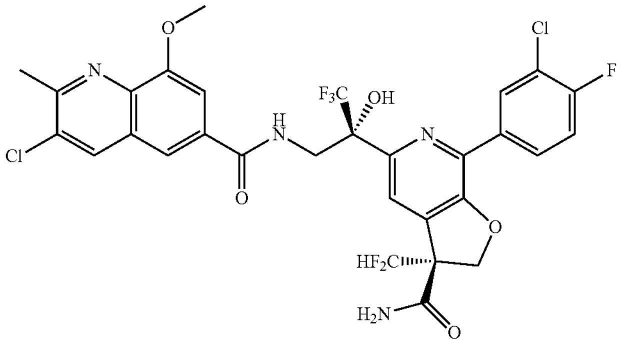 | 703.11 |
| 1005 | 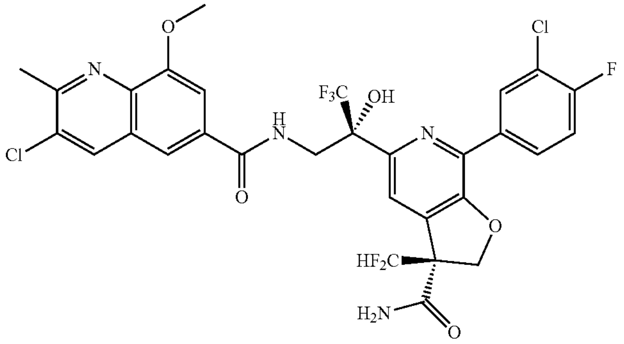 | 703.11 |
| 1006 | 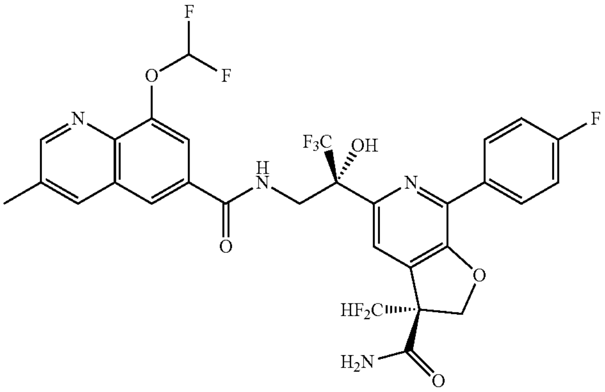 | 671.27 |
| 1007 | 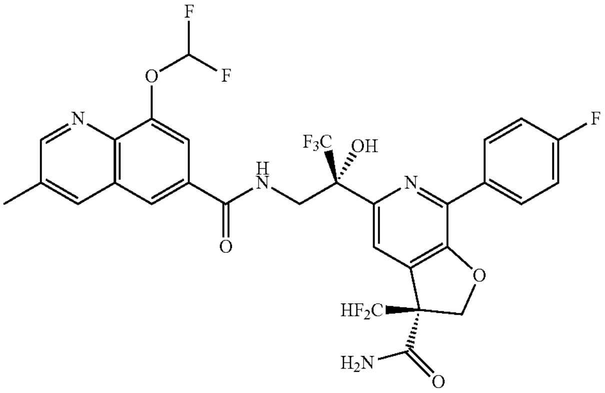 | 671.27 |

TABLE 7-continued
| Example | Structure | MS+ m/z |
|---|---|---|
| 1008 | 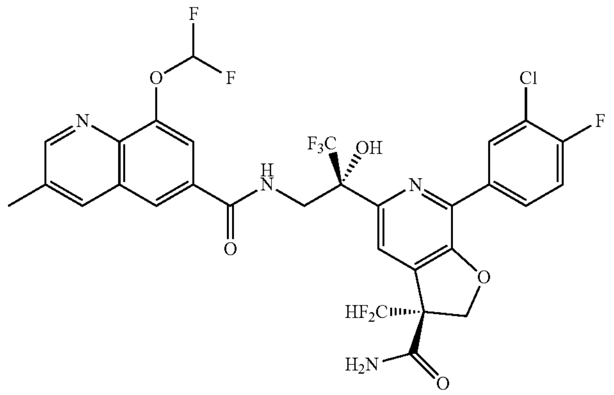 | 705.25 |
| 1009 | 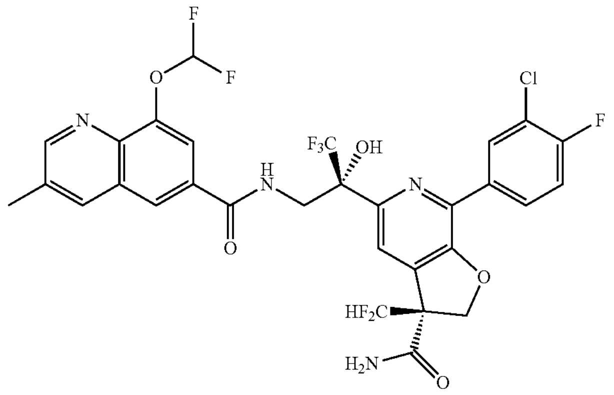 | 705.25 |
| 1010 | 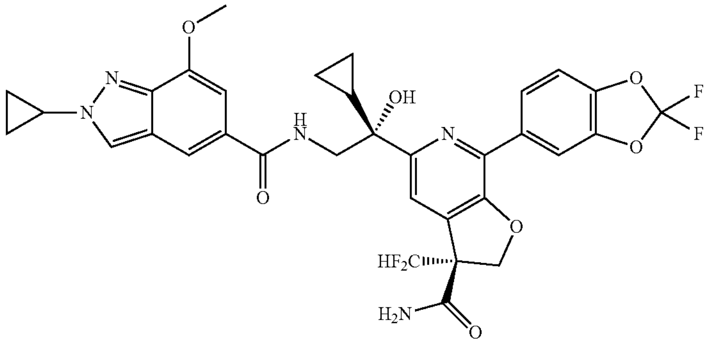 | 684.40 |
| 1011 | 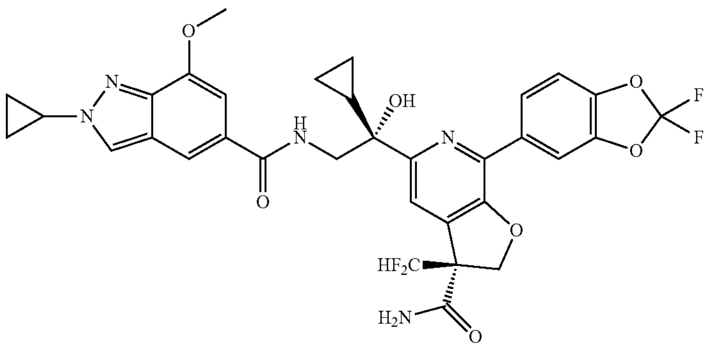 | 684.40 |

TABLE 7-continued
| Example | Structure | MS+ m/z |
| --- | --- | --- |
| 1012 | 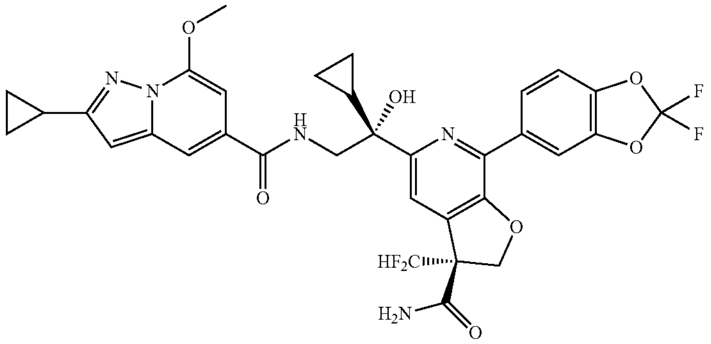 | 684.45 |
| 1013 | 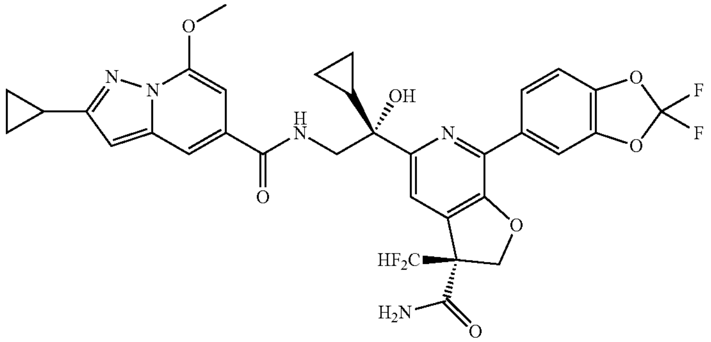 | 684.45 |
| 1014 | 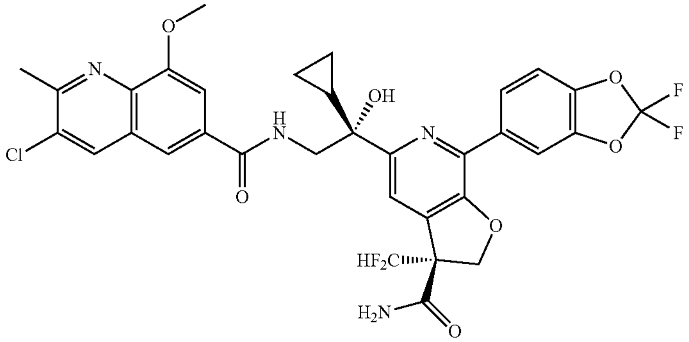 | 703.44 |
| 1015 | 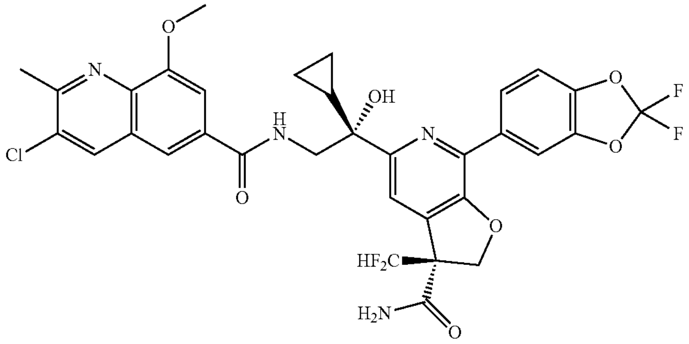 | 703.44 |

TABLE 7-continued
| Example | Structure | MS+ m/z |
| --- | --- | --- |
| 1016 | 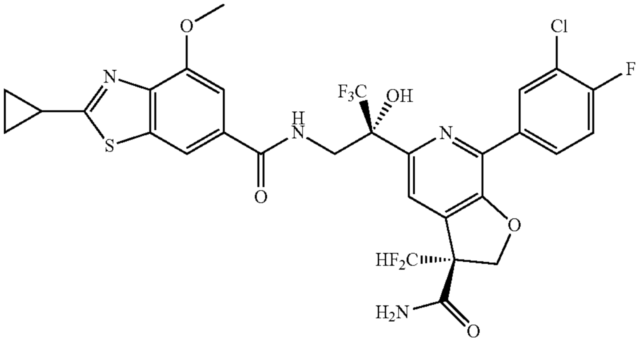 | 701.21 |
| 1017 | 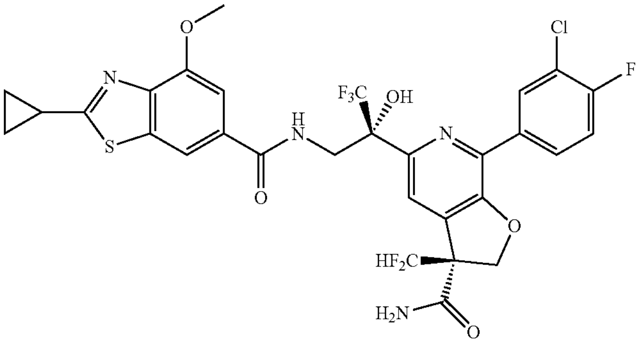 | 701.21 |
| 1018 | 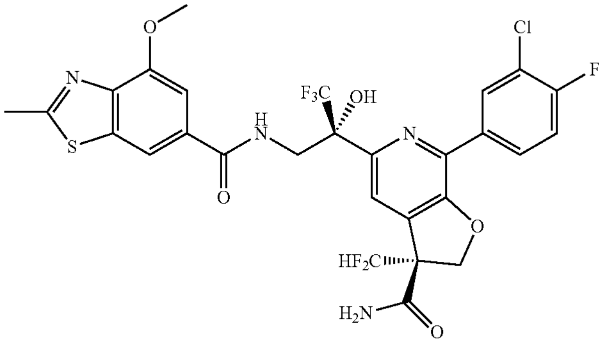 | 675.28 |
| 1019 | 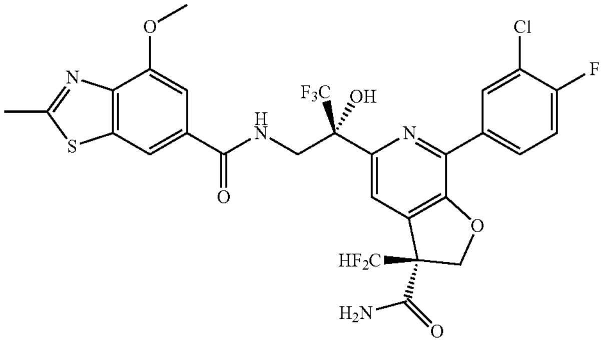 | 675.28 |

TABLE 7-continued
| Example | Structure | MS+ m/z |
|---|---|---|
| 1020 | 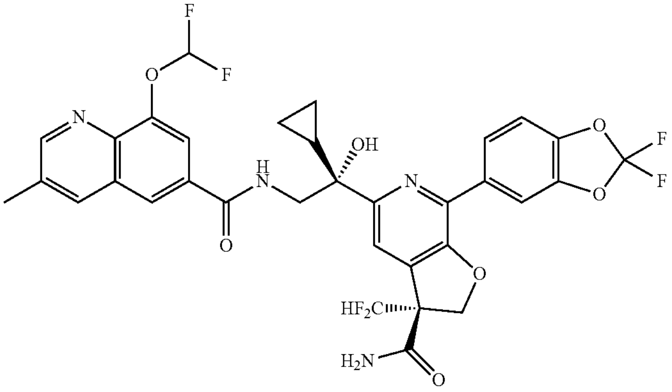 | 705.42 |
| 1021 | 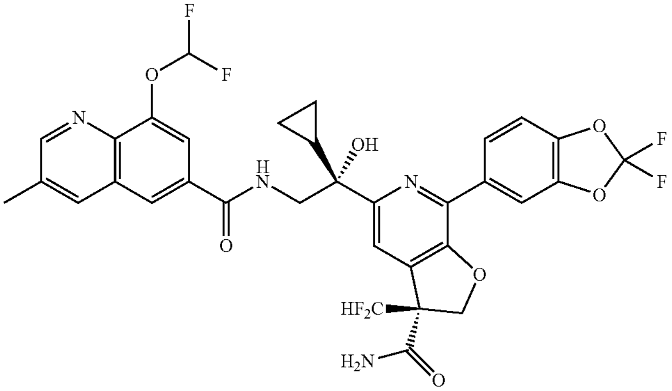 | 705.42 |
| 1022 | 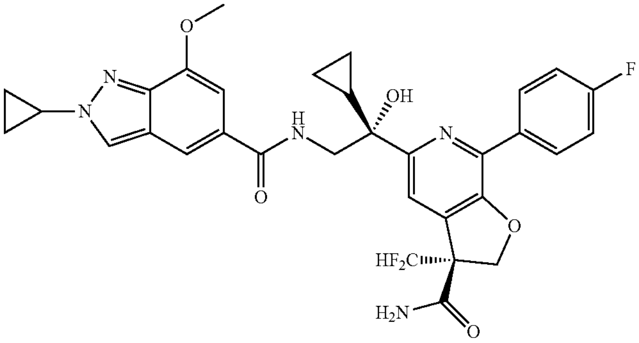 | 622.49 |
| 1023 | 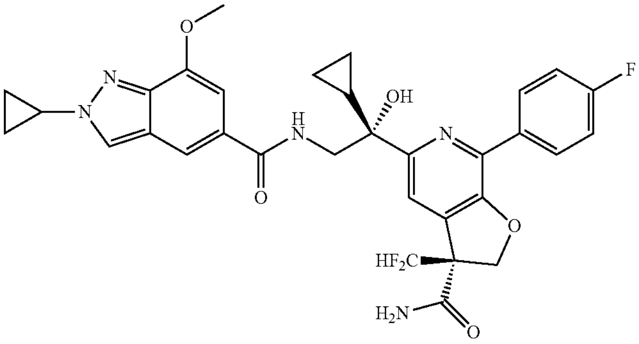 | 622.49 |

TABLE 7-continued
| Example | Structure | MS+ m/z |
| --- | --- | --- |
| 1024 | 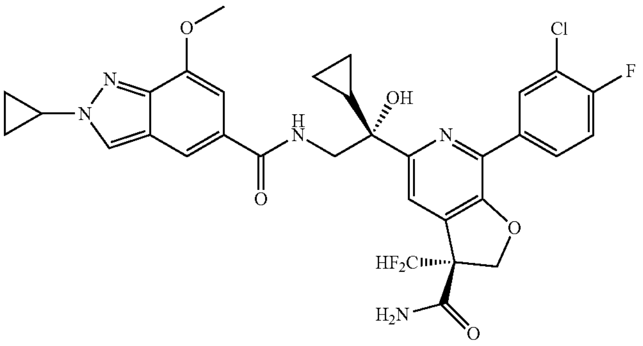 | 656.43 |
| 1025 | 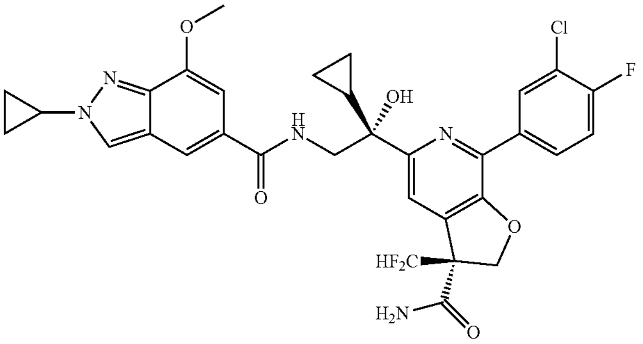 | 656.43 |
| 1026 | 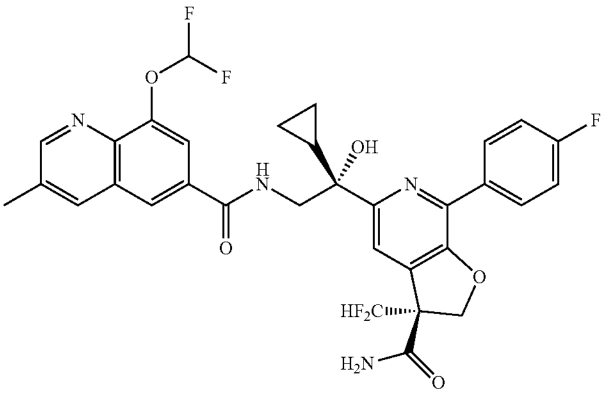 | 643.43 |
| 1027 | 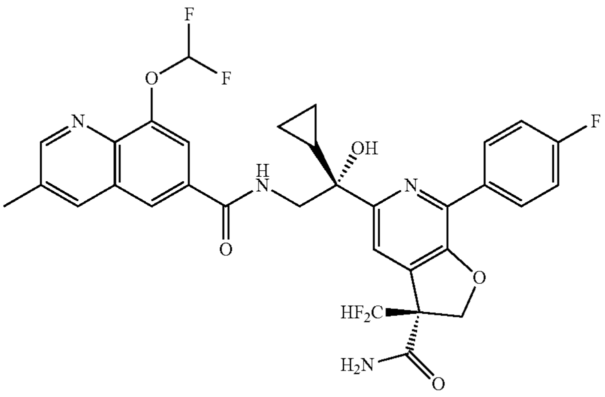 | 643.43 |

TABLE 7-continued
| Example | Structure | MS+ m/z |
|---|---|---|
| 1028 | 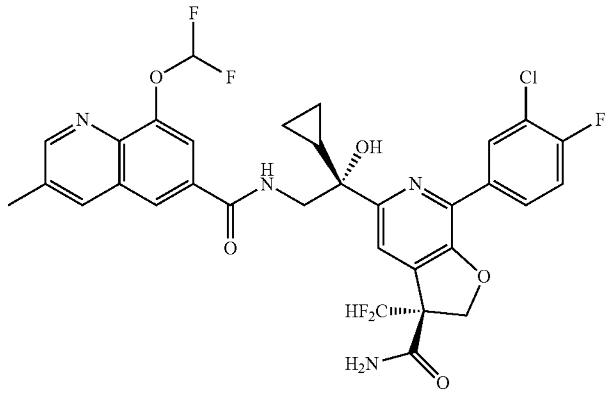 | 677.42 |
| 1029 | 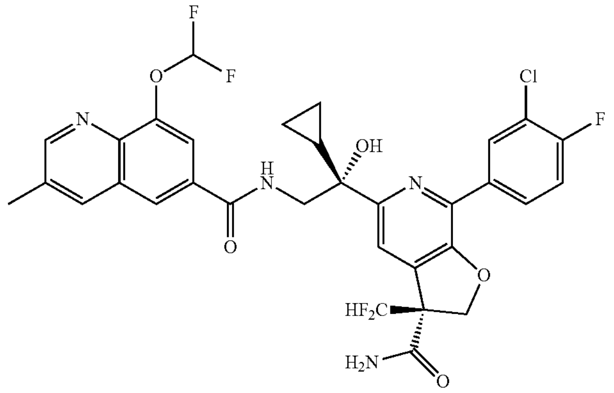 | 677.42 |
| 1030 | 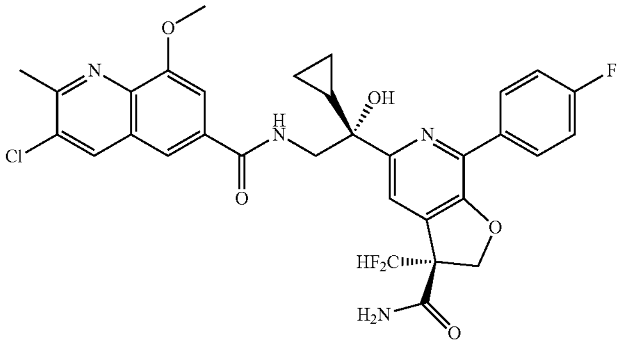 | 641.42 |
| 1031 | 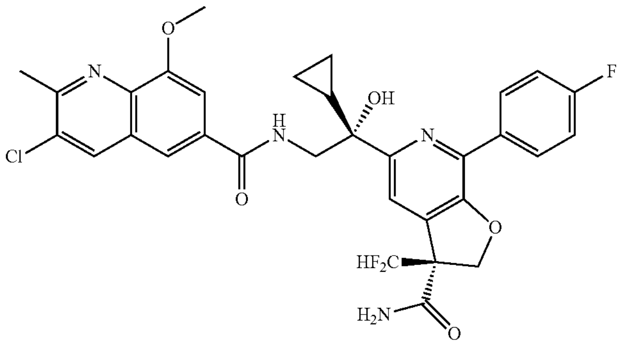 | 641.42 |

TABLE 7-continued
| Example | Structure | MS⁺ m/z |
| --- | --- | --- |
| 1032 | 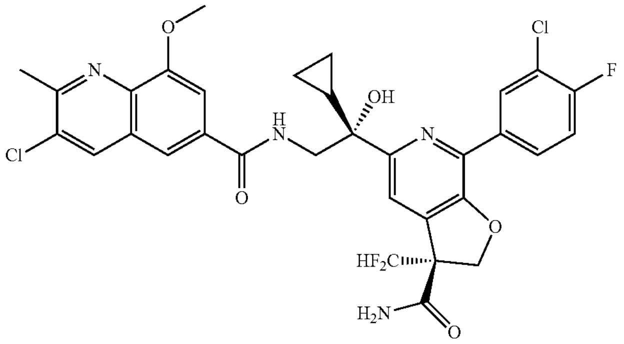 | 675.13 |
| 1033 | 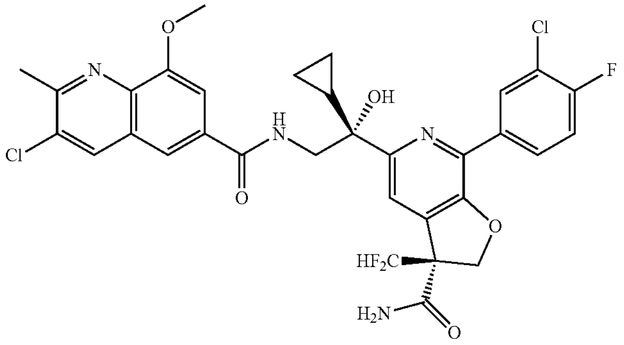 | 675.13 |
| 1034 | 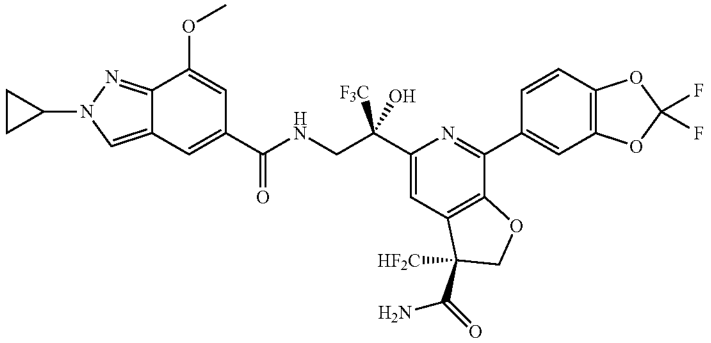 | 712.48 |
| 1035 | 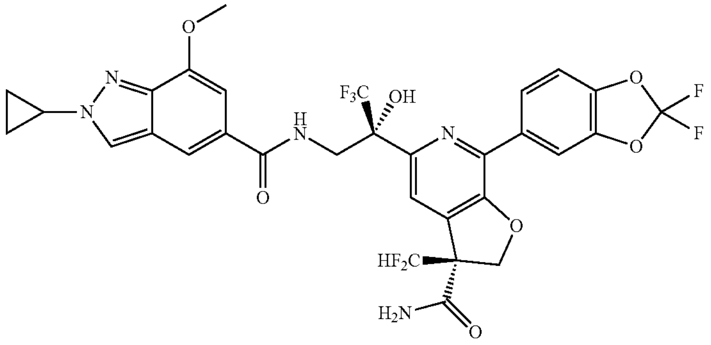 | 712.48 |

TABLE 7-continued
| Example | Structure | MS⁺ m/z |
|---|---|---|
| 1036 | 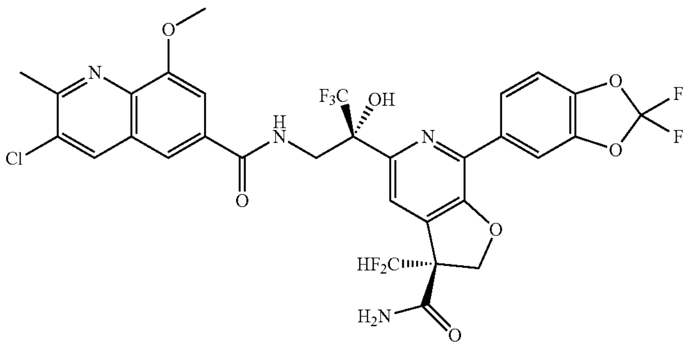 | 731.47 |
| 1037 | 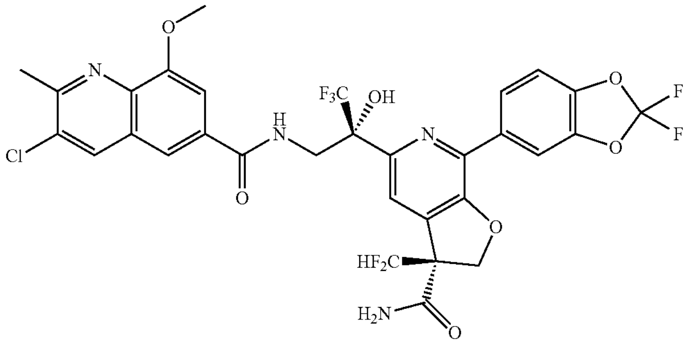 | 731.47 |
| 1038 | 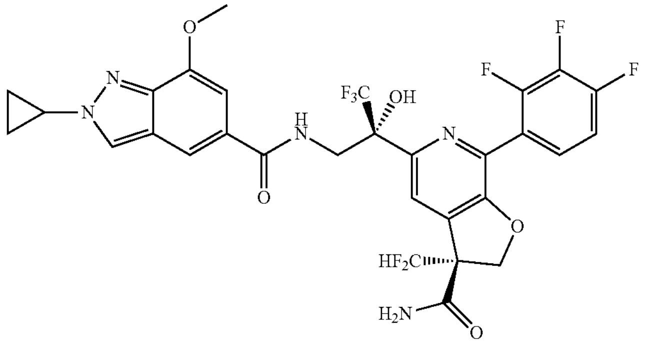 | 686.44 |
| 1039 | 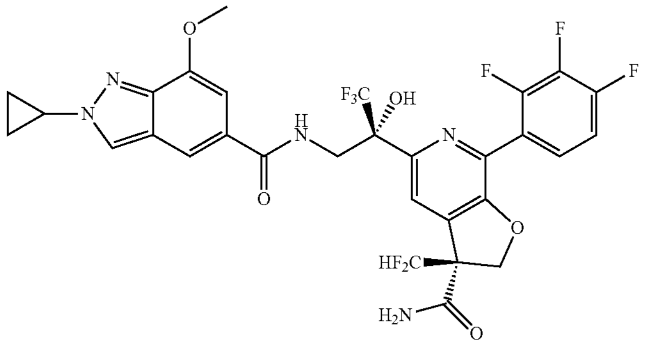 | 686.44 |

TABLE 7-continued
| Example | Structure | MS+ m/z |
| --- | --- | --- |
| 1040 | 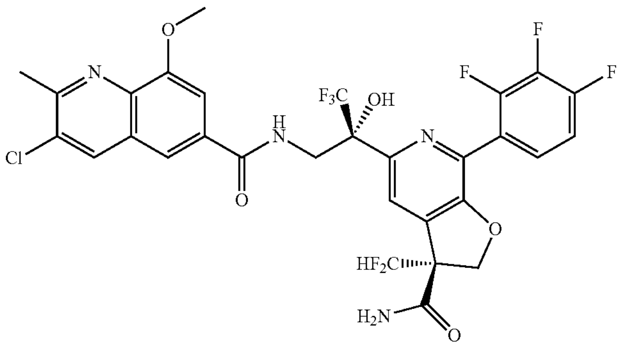 | 705.41 |
| 1041 | 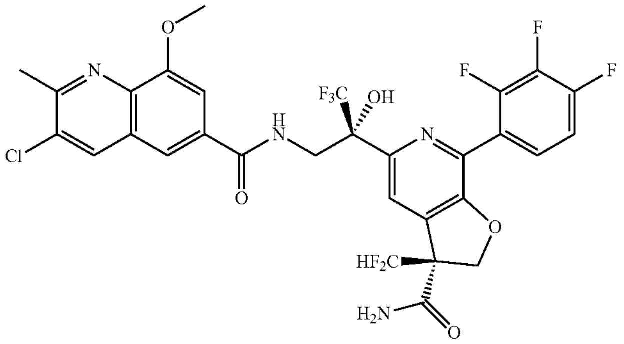 | 705.41 |
| 1042 | 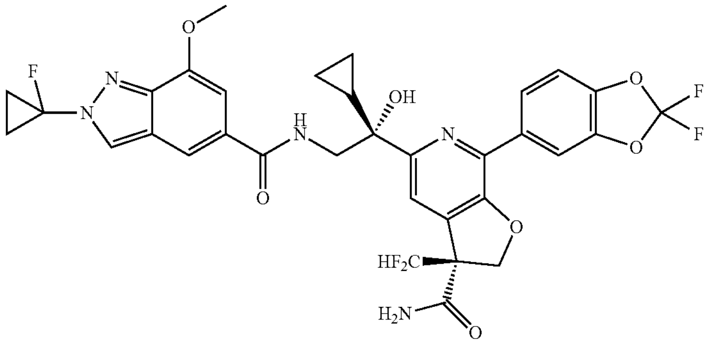 | 702.26 |
| 1043 | 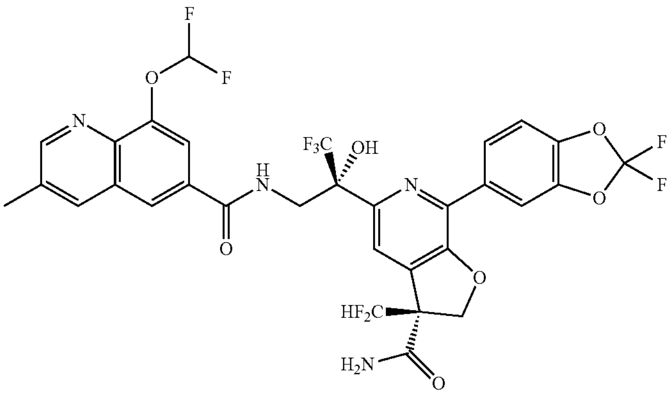 | 733.36 |

TABLE 7-continued
| Example | Structure | MS+ m/z |
|---|---|---|
| 1044 | 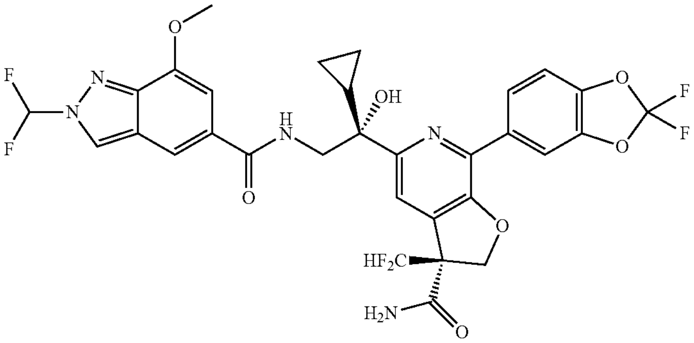 | 694.22 |
| 1045 | 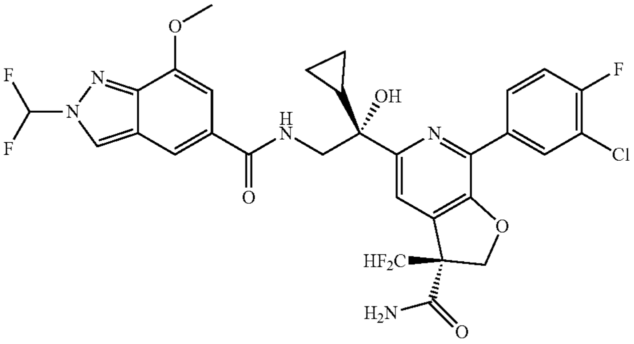 | 666.19 |
| 1046 | 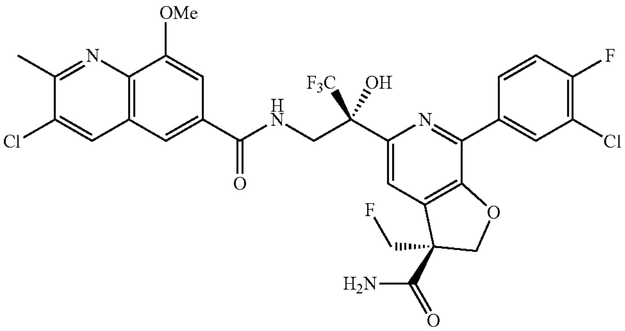 [SMILES: COc1cc(C(=O)NC[C@](O)(c2cc3c(c(-c4ccc(F)c(Cl)c4)n2)OC[C@@]3(CF)C(N)=O)C(F)(F)F)cc2cc(Cl)c(C)nc12] | 684.95 |
| 1047 | 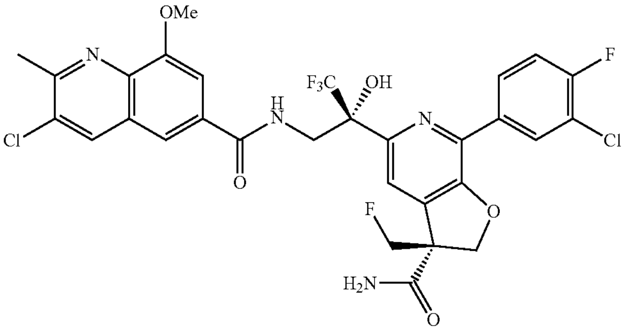 [SMILES: COc1cc(C(=O)NC[C@](O)(c2cc3c(c(-c4ccc(F)c(Cl)c4)n2)OC[C@]3(CF)C(N)=O)C(F)(F)F)cc2cc(Cl)c(C)nc12] | 684.90 |

TABLE 7-continued
| Example | Structure | MS+ m/z |
|---|---|---|
| 1048 | 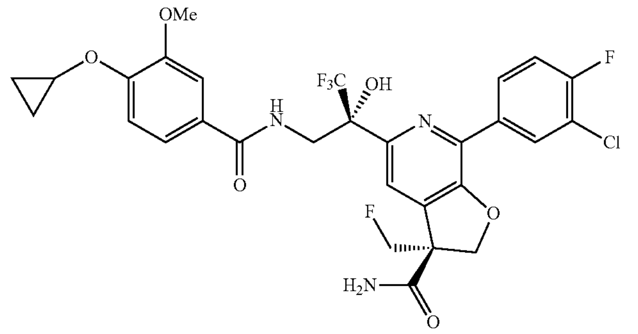 [SMILES: COc1cc(C(=O)NC[C@](O)(c2cc3c(c(-c4ccc(F)c(Cl)c4)n2)OC[C@@]3(CF)C(N)=O)C(F)(F)F)ccc1OC1CC1] | 641.99 |
| 1049 | 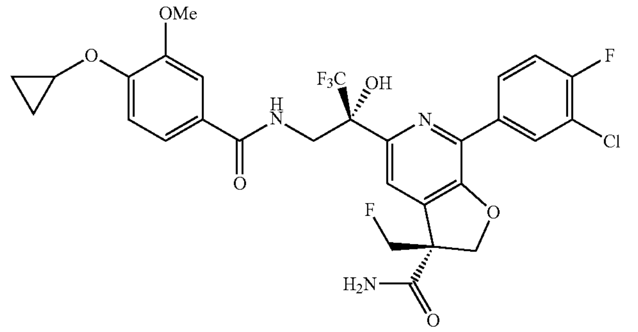 [SMILES: COc1cc(C(=O)NC[C@](O)(c2cc3c(c(-c4ccc(F)c(Cl)c4)n2)OC[C@]3(CF)C(N)=O)C(F)(F)F)ccc1OC1CC1] | 641.99 |
| 1050 | 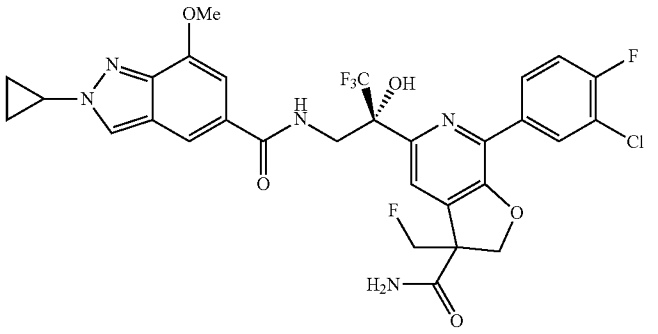 [SMILES: COc1cc(C(=O)NC[C@](O)(c2cc3c(c(-c4ccc(F)c(Cl)c4)n2)OCC3(CF)C(N)=O)C(F)(F)F)cc2cn(C3CC3)nc12] | 666.05 |
| 1051 | 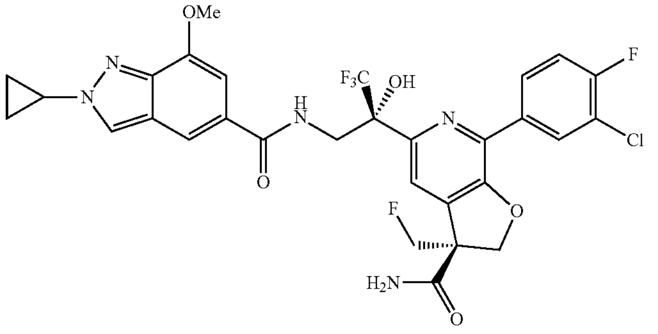 [SMILES: COc1cc(C(=O)NC[C@](O)(c2cc3c(c(-c4ccc(F)c(Cl)c4)n2)OC[C@@]3(CF)C(N)=O)C(F)(F)F)cc2cn(C3CC3)nc12] | 666.06 |

TABLE 7-continued
| Example | Structure | MS⁺ m/z |
|---|---|---|
| 1052 | 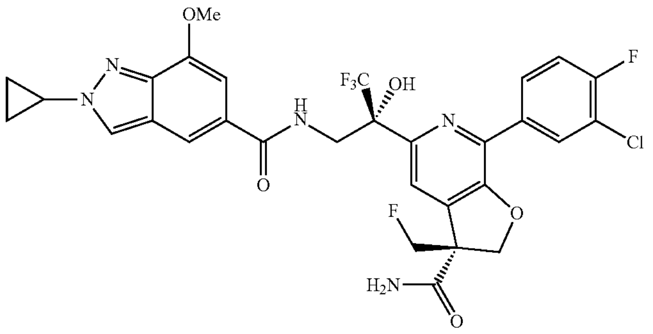 [SMILES: COc1cc(C(=O)NC[C@](O)(c2cc3c(c(-c4ccc(F)c(Cl)c4)n2)OC[C@]3(CF)C(N)=O)C(F)(F)F)cc2cn(C3CC3)nc12] | 666.08 |
| 1053 | 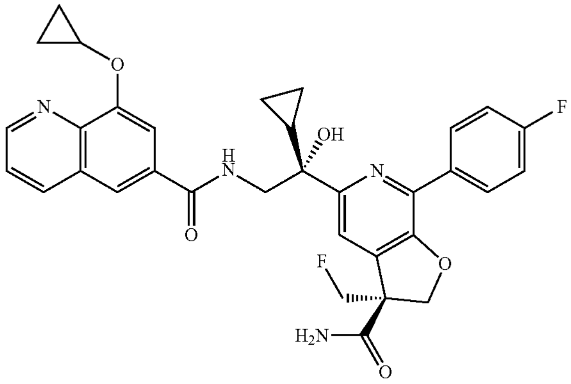 [SMILES: NC(=O)[C@]1(CF)COc2c1cc([C@@](O)(CNC(=O)c1cc(OC3CC3)c3ncccc3c1)C1CC1)nc2-c1ccc(F)cc1] | 601.52 |
| 1054 | 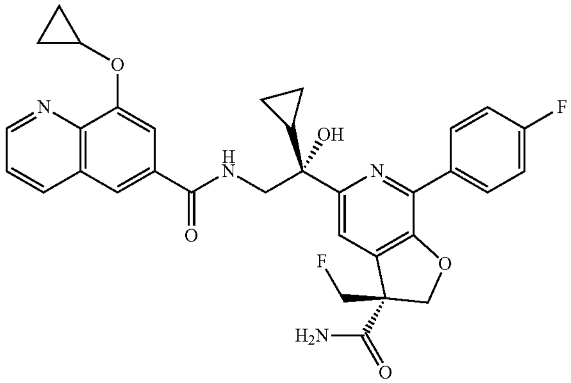 [SMILES: NC(=O)[C@@]1(CF)COc2c1cc([C@@](O)(CNC(=O)c1cc(OC3CC3)c3ncccc3c1)C1CC1)nc2-c1ccc(F)cc1] | 601.52 |
| 1055 | 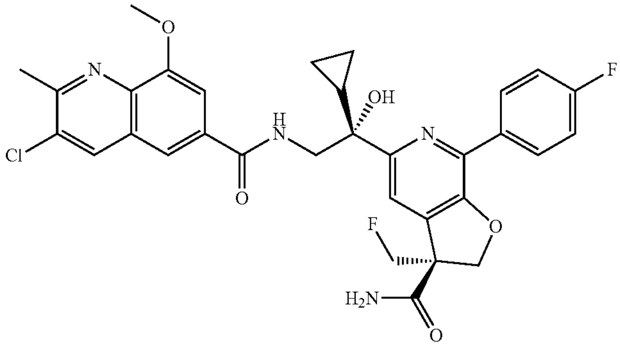 [SMILES: COc1cc(C(=O)NC[C@](O)(c2cc3c(c(-c4ccc(F)cc4)n2)OC[C@@]3(CF)C(N)=O)C2CC2)cc2cc(Cl)c(C)nc12] | 623.40 |

TABLE 7-continued
| Example | Structure | MS+ m/z |
|---|---|---|
| 1056 | 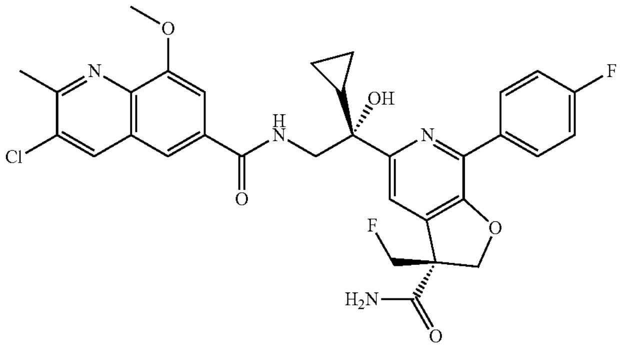 [SMILES: COc1cc(C(=O)NC[C@](O)(c2cc3c(c(-c4ccc(F)cc4)n2)OC[C@]3(CF)C(N)=O)C2CC2)cc2cc(Cl)c(C)nc12] | 623.51 |
| 1057 | 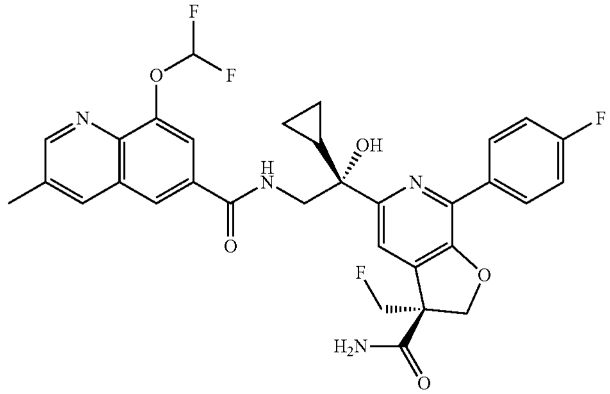 [SMILES: Cc1cnc2c(OC(F)F)cc(C(=O)NC[C@](O)(c3cc4c(c(-c5ccc(F)cc5)n3)OC[C@@]4(CF)C(N)=O)C3CC3)cc2c1] | 625.50 |
| 1058 | 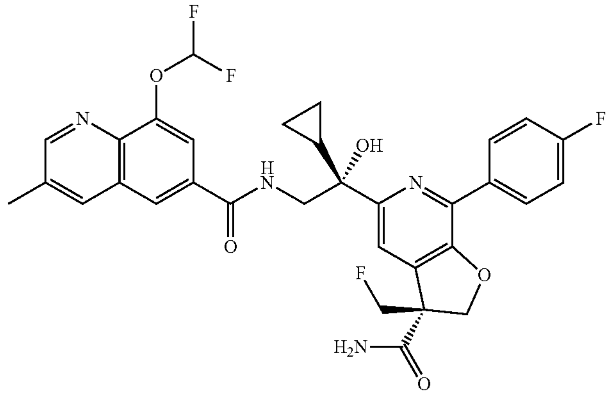 [SMILES: Cc1cnc2c(OC(F)F)cc(C(=O)NC[C@](O)(c3cc4c(c(-c5ccc(F)cc5)n3)OC[C@]4(CF)C(N)=O)C3CC3)cc2c1] | 625.48 |
| 1059 | 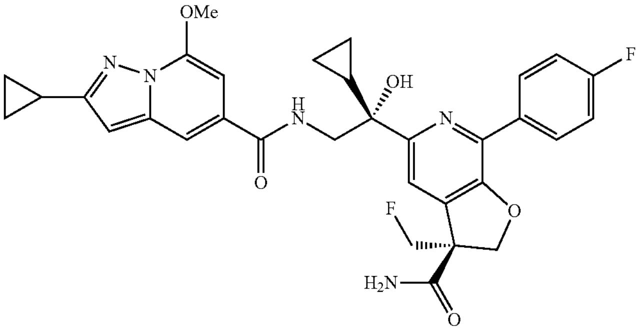 [SMILES: COc1cc(C(=O)NC[C@](O)(c2cc3c(c(-c4ccc(F)cc4)n2)OC[C@@]3(CF)C(N)=O)C2CC2)cc2cc(C3CC3)nn12] | 604.54 |

TABLE 7-continued
| Example | Structure | MS+ m/z |
| --- | --- | --- |
| 1060 | 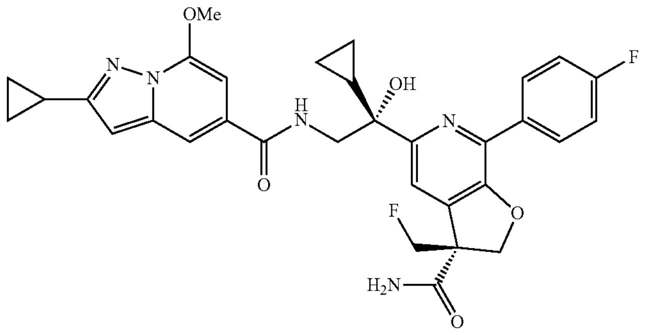 [SMILES: COc1cc(C(=O)NC[C@](O)(c2cc3c(c(-c4ccc(F)cc4)n2)OC[C@]3(CF)C(N)=O)C2CC2)cc2cc(C3CC3)nn12] | 604.57 |
| 1061 | 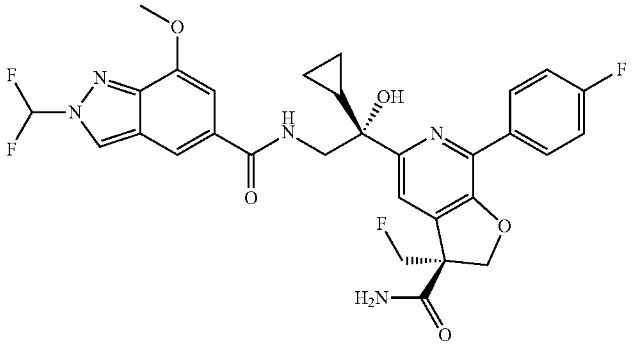 [SMILES: COc1cc(C(=O)NC[C@](O)(c2cc3c(c(-c4ccc(F)cc4)n2)OC[C@@]3(CF)C(N)=O)C2CC2)cc2cn(C(F)F)nc12] | 614.47 |
| 1062 | 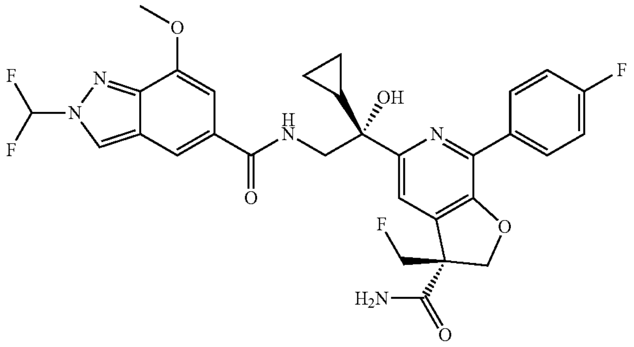 [SMILES: COc1cc(C(=O)NC[C@](O)(c2cc3c(c(-c4ccc(F)cc4)n2)OC[C@]3(CF)C(N)=O)C2CC2)cc2cn(C(F)F)nc12] | 614.88 |
| 1063 | 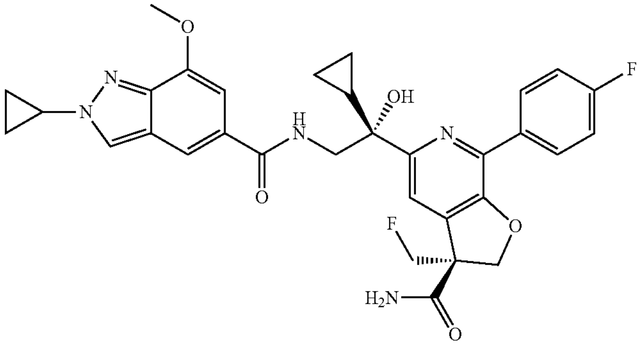 [SMILES: COc1cc(C(=O)NC[C@](O)(c2cc3c(c(-c4ccc(F)cc4)n2)OC[C@@]3(CF)C(N)=O)C2CC2)cc2cn(C3CC3)nc12] | 604.59 |

TABLE 7-continued

| Example | Structure | MS⁺ m/z |
|---|---|---|
| 1064 | 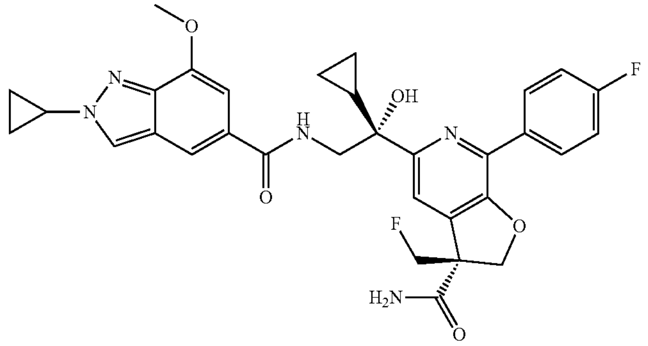 [SMILES: COc1cc(C(=O)NC[C@](O)(c2cc3c(c(-c4ccc(F)cc4)n2)OC[C@]3(CF)C(N)=O)C2CC2)cc2cn(C3CC3)nc12] | 604.53 |
| 1065 | 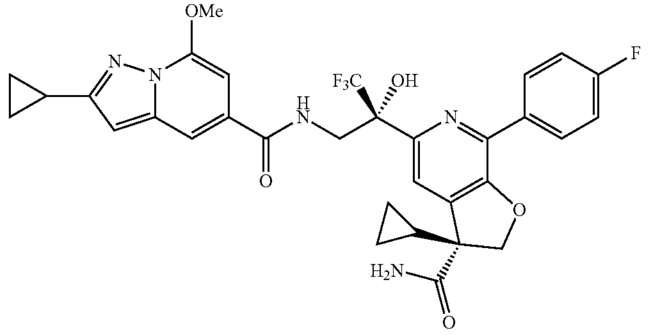 [SMILES: COc1cc(C(=O)NC[C@](O)(c2cc3c(c(-c4ccc(F)cc4)n2)OC[C@@]3(C(N)=O)C2CC2)C(F)(F)F)cc2cc(C3CC3)nn12] | 640.12 |
| 1066 | 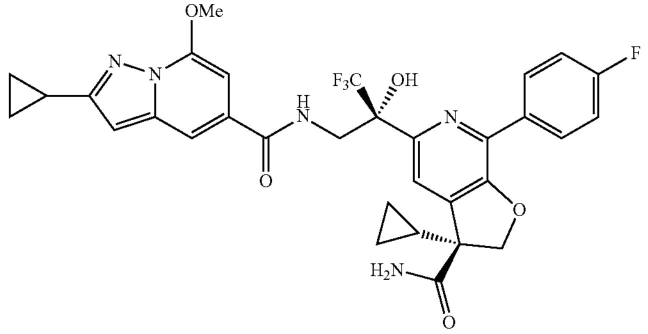 [SMILES: COc1cc(C(=O)NC[C@](O)(c2cc3c(c(-c4ccc(F)cc4)n2)OC[C@]3(C(N)=O)C2CC2)C(F)(F)F)cc2cc(C3CC3)nn12] | 640.02 |

Intermediate 99

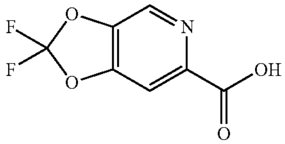 [SMILES: O=C(O)c1cc2c(cn1)OC(F)(F)O2]

Intermediate 99 Steps a and b

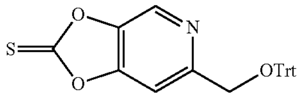

5-(benzyloxy)-2-(hydroxymethyl)-1H-pyridin-4-one (5 g, 21.62 mmol), Trt-Cl (6.63 g, 23.78 mmol) and DMAP (2.91 g, 23.78 mmol) was suspended in DMF (50 mL), and the mixture was stirred for overnight at 95° C. The reaction was monitored by LCMS. After cooling to room temperature, the mixture was treated with cold water and stirred for 30 min. The precipitated solids were collected by filtration and washed with water and MeOH, dried to give the desired product (8.8 g, 86%) as a light grey solid. ESI-MS m/z: 474.30 $[M+H]^+$.

To a solution of the compound from step a (4.4 g, 9.29 mmol) in THE (120 mL), $H_2O$ (12 mL) and aqueous NaOH 2 M (6 mL) was added Pd/C (2.2 g, 20.67 mmol) under nitrogen atmosphere. The resulting mixture was stirred for 2 hours at room temperature under hydrogen atmosphere. The reaction was monitored by TLC. The resulting mixture was filtered, the filter cake was washed with acetonitrile. The filtrate was concentrated under reduced pressure. To a suspension of the residue in DCM (100 mL) were added DMAP (2.27 g, 18.58 mmol) and thiophosgene (1.58 g, 13.75 mmol). After stirring for 1 hour at room temperature, the reaction was monitored by TLC. The reaction was quenched with water and extracted with $CH_2Cl_2$. The combined organic layers were washed with brine, dried over anhydrous $Na_2SO_4$. After filtration, the filtrate was concentrated under reduced pressure. The residue was purified by silica gel column chromatography, eluted with P/EA (10:1) to afford the desired product (3.3 g, 83%) as a yellow solid. ESI-MS m/z: 448.20 $[M+Na]^+$.

Intermediate 99 Steps c and d

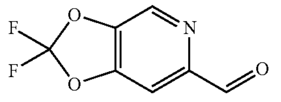 [SMILES: O=Cc1cc2c(cn1)OC(F)(F)O2]

To a solution of the compound from step b (3.3 g, 7.75 mmol) in DCM (100 mL) were added HF Pyridine (33 mL) and DBDMH (3.77 g, 13.18 mmol) keeping the temperature below −60° C. The reaction mixture was allowed to warm to 0° C. over 20 min. After stirring for 2 hours at the temperature, the reaction was quenched with 2 M aqueous NaOH, extracted with $CH_2Cl_2$. The combined organic layers were dried over anhydrous $Na_2SO_4$. After filtration, the filtrate was concentrated under reduced pressure. The residue was purified by silica gel column chromatography, eluted with PE/EA (1:1) to afford the desired product (740 mg, 50%) as a yellow oil. ESI-MS m/z: 190.05 $[M+H]^+$.

Intermediate 99 Step e

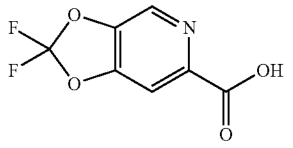 [SMILES: O=C(O)c1cc2c(cn1)OC(F)(F)O2]

To a solution of the compound from step d (550 mg, 2.94 mmol) in acetone (20 mL) and $H_2O$ (10 mL) were added 2-methyl-2-butene (2.06 g, 29.40 mmol), $NaH_2PO_4$ (529 mg, 4.41 mmol) and $NaClO_2$ (532 mg, 5.88 mmol). The resulting mixture was stirred for 2 hours at room temperature. The mixture was treated with $NaHSO_3$ (1.07 g, 10.28 mmol) and concentrated under reduce pressure to remove acetone. The mixture was treated with brine (10 mL) and extracted twice with EA/THF (1:1). The combined organic layers were dried over anhydrous $Na_2SO_4$. After filtration, the filtrate was concentrated under reduced pressure. The residue was purified by reverse flash chromatography to afford the desired product (151.8 mg, 25%) as a white solid. ESI-MS m/z: 203.90 $[M+H]^+$.

Intermediate 100

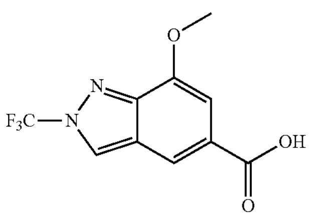 [SMILES: COc1cc(C(=O)O)cc2cn(C(F)(F)F)nc12]

Intermediate 100 Steps and b

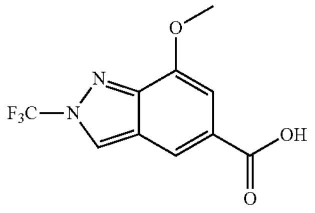 [SMILES: COc1cc(C(=O)O)cc2cn(C(F)(F)F)nc12]

A mixture of 5-bromo-7-methoxy-1H-indazole (500 mg, 2.2 mmol), $Cs_2CO_3$ (2.15 g, 6.6 mmol) and $CBr_2F_2$ (5 mL) in ACN (25 mL) was stirred for overnight at room temperature under $N_2$ atmosphere. The residue was purified by reverse flash chromatography to afford the desired product (200 mg, 26%) as a yellow oil. ESI-MS m/z: 355.00 $[M+H]^+$.

A solution of the compound from step a (400 mg, 1.12 mmol) and $AgBF_4$ (656 mg, 3.37 mmol) in DCM (20 mL) was stirred for 2 hours at room temperature. The resulting mixture was washed with 3×100 mL of $NaHCO_3$. The resulting mixture was extracted with EA (3×100 mL). The combined organic layers were washed with water (3×100 mL), dried over anhydrous $Na_2SO_4$. After filtration, the filtrate was concentrated under reduced pressure. The residue was purified by silica gel column chromatography, eluted with PE/EA to afford the desired product (300 mg, 90%) as a yellow solid. ESI-MS m/z: 295.00 $[M+H]^+$.

Intermediate 100 Steps c and d

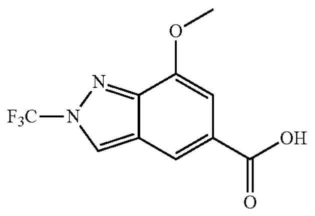 [SMILES: COc1cc(C(=O)O)cc2cn(C(F)(F)F)nc12]

The following compound was prepared according to the same procedures as Intermediate 77 steps d and e to afford the desired product (200 mg, 72%) as a white solid. ESI-MS m/z: 275.00 $[M+H]^+$.

Intermediate 101

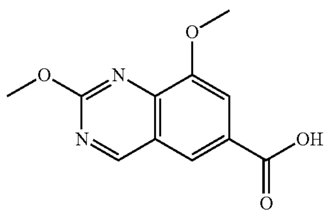 [SMILES: COc1ncc2cc(C(=O)O)cc(OC)c2n1]

Intermediate 101 Steps a, b and c

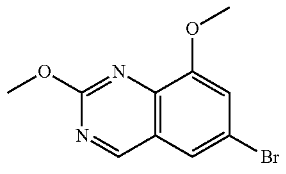

A mixture of 2-amino-5-bromo-3-methoxybenzaldehyde (9.6 g, 41.73 mmol) and urea (37.59 g, 625.92 mmol) was stirred for 2 hours at 180° C. The mixture was allowed to cool down to room temperature and poured into ice water. The precipitated solids were collected by filtration and washed with water and dried in vacuum to afford the crude product (11 g) as a grey solid. ESI-MS m/z: 254.85 $[M+H]^+$.

A solution of the compound from step a (11 g, 43.12 mmol) in phosphorus oxychloride (100 mL) was stirred for 5 hours at 110° C. The mixture was allowed to cool down to room temperature and concentrated under reduced pressure. The residue was dissolved in EA and poured into ice water with vigorous stirring. The resulting mixture was extracted with EA. The combined organic layers were washed with brine, dried over anhydrous $Na_2SO_4$. After filtration, the filtrate was concentrated under reduced pressure. The residue was purified by silica gel column chromatography, eluted with PE/EA (2:1) to afford the desired product (2.4 g, 20%) as a light-yellow solid. ESI-MS m/z: 272.95 $[M+H]^+$.

A mixture of the compound from step b (2.4 g, 8.77 mmol) and NaOMe (0.47 g, 8.77 mmol) in MeOH (30 mL) was stirred for 1 h at room temperature and heated to reflux for 1 hour. The reaction was monitored by LCMS. The resulting mixture was concentrated under reduced pressure. The residue was stirred with water. The precipitated solids were collected by filtration and washed with water and dried in vacuum to afford the desired product (2.2 g, 93%) as a light-yellow solid. ESI-MS m/z: 268.85 $[M+H]^+$.

Intermediate 101 Steps d and e

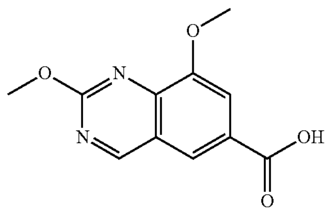 [SMILES: COc1ncc2cc(C(=O)O)cc(OC)c2n1]

The following compound was prepared according to the same procedures as Intermediate 77 steps d and e to afford the desired product (658.6 mg, 77%) as a white solid. ESI-MS m/z: 235.00 $[M+H]^+$.

Intermediate 102

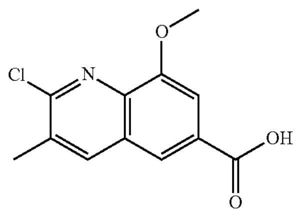 [SMILES: COc1cc(C(=O)O)cc2cc(C)c(Cl)nc12]

Intermediate 102 Steps a and b

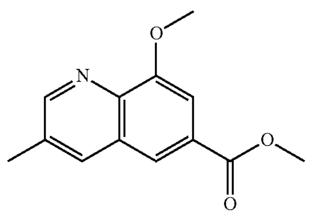

A solution of methyl 4-amino-3-methoxybenzoate (4 g, 22.07 mmol) in HCl (15 mL) were added methacrolein (3.87 g, 55.19 mmol). The resulting mixture was stirred for 5h at 100° C. The reaction was monitored by LCMS. The resulting mixture was concentrated under reduced pressure. The crude product was used in the next step directly without further purification. This resulted in 8-methoxy-3-methylquinoline-6-carboxylic acid (4 g, 83%) as a brown crude solid. ESI-MS m/z: 218.05 $[M+H]^+$.

A solution of the compound from step a (4 g, 18.41 mmol) in MeOH (120 mL) were added $SOCl_2$ (8.76 g, 73.65 mmol). The resulting mixture was stirred for 40 min at 80° C. The reaction was monitored by LCMS. The resulting mixture was concentrated under reduced pressure. The residue was dissolved in water (40 mL). The mixture was basified to pH 7 with 1M aq $NaHCO_3$, extracted and evaporated. The residue was purified by silica gel column chromatography, eluted with PE/EA (1:2) to afford the compound (1.8 g, 42%) as a brown solid. ESI-MS m/z: 232.00 $[M+H]^+$.

Intermediate 102 Steps c and d

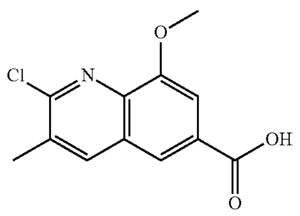 [SMILES: COc1cc(C(=O)O)cc2cc(C)c(Cl)nc12]

A solution of the compound from step b (1.8 g, 7.78 mmol) in DCM (20 mL) was added with m-CPBA (4.03 g, 23.35 mmol) in portions at 0° C. The resulting mixture was stirred for overnight at room temperature. The reaction was monitored by LCMS. The resulting mixture was washed with 1 M NaOH. The aqueous layer was basified to pH 2 with conc. HCl. The resulting mixture was filtered, the filter cake was washed with water. The filtrate was concentrated under reduced pressure. The crude product was used in the next step directly without further purification. ESI-MS m/z: 233.95 $[M+H]^+$.

A solution of the compound from step c (5 g crude) and $POCl_3$ (42.73 g, 278.707 mmol, 13 equiv) was stirred for 1 h at 95° C. The reaction mixture was slowly added to water (20 mL) and the reaction was monitored by LCMS. The resulting mixture was concentrated under reduced pressure. The residue was purified by reverse flash to afford the titled compound (100 mg, 1.85%) as a white solid. ESI-MS m/z: 251.95 $[M+H]^+$.

Intermediate 103

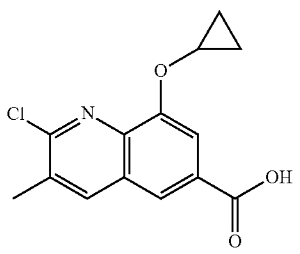 [SMILES: Cc1cc2cc(C(=O)O)cc(OC3CC3)c2nc1Cl]

This intermediate was prepared in an analogous fashion to Intermediate 102. (80 mg, 70%) ESI-MS m/z: 277.95 $[M+H]^+$.

Intermediate 104

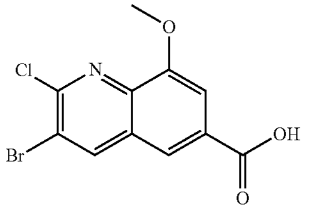 [SMILES: COc1cc(C(=O)O)cc2cc(Cl)c(Cl)nc12]

The following compound was prepared in an analogous fashion to Intermediate 102 above (64 mg, 74%) ESI-MS m/z: 318.10 $[M+H]^+$.

Intermediate 105

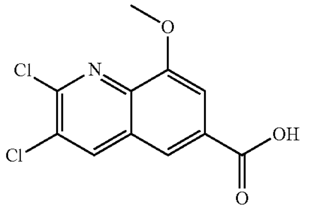

The above compound was prepared in an analogous fashion to Intermediate 102 above (32 mg, 46%) ESI-MS m/z: 268.15 $[M+H]^+$.

Intermediate 106

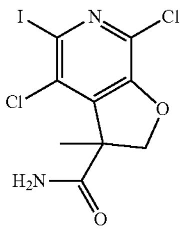 [SMILES: CC1(C(N)=O)COc2c(Cl)nc(I)c(Cl)c21]

Intermediate 106 Steps a, b and c

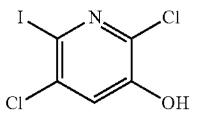

Into a 250 mL round-bottom flask were added 2,5-dichloro-3-fluoropyridine (10 g, 60.25 mmol), (4-methoxyphenyl)methanol (9.16 g, 66.27 mmol), $Cs_2CO_3$ (39.26 g, 121 mmol) and DMF (40 mL) at room temperature. The resulting mixture was stirred for 1h at 80° C. The reaction was monitored by LCMS. The aqueous layer was extracted with EtOAc. The resulting mixture was washed with brine. The resulting mixture was concentrated under vacuum. The residue was purified by silica gel column chromatography to afford the desired compound (14 g, 81%) as a white solid. ESI-MS m/z: 284.25 $[M+H]^+$.

Into a 100 mL round-bottom flask were added the compound from the step a (5 g, 18 mmol) and DCM (24 mL) at room temperature. To the above mixture was added $CF_3COOH$ (6 g, 52.62 mmol) dropwise. The resulting mixture was stirred for additional overnight at room temperature. The reaction was monitored by LCMS. The aqueous layer was extracted with $CH_2Cl_2$. The resulting mixture was concentrated under vacuum and the crude product was used in the next step directly without further purification. ESI-MS m/z: 165.10 $[M+H]^+$.

Into a 100 mL round-bottom flask were added the compound from the step c (6.2 g, 37.81 mmol), 12 (10.56 g, 41.59 mmol), $K_2CO_3$ (10.45 g, 75.61 mmol) and $H_2O$ (40 mL) at room temperature. The resulting mixture was stirred for 2h at room temperature. The reaction was monitored by LCMS. The reaction was quenched with sat. sodium hyposulfite (aq.) at 0° C. The mixture was acidified to pH 6 with conc. HCl. The aqueous layer was extracted with EtOAc. The residue was purified by silica gel column chromatography to afford the desired compound as a white solid. ESI-MS m/z: 290.15 $[M+H]^+$.

Intermediate 106 d and e

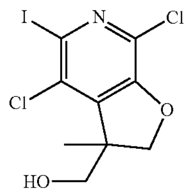

Into a 250 mL round-bottom flask were added the compound from the step c (3.9 g, 13.45 mmol), (2-methyloxiran-2-yl)methyl 4-methylbenzenesulfonate (3.91 g, 16.14 mmol), KI (2.2 g, 13.45 mmol), $K_2CO_3$ (3.7 g, 26.91 mmol) and DMF (20 mL) at room temperature. The resulting mixture was stirred overnight at 50° C. The reaction was monitored by LCMS. The reaction was quenched with sat. $NH_4Cl$ (aq.) at 0° C. The aqueous layer was extracted with EtOAc. The residue was purified by reverse flash chromatography to afford the desired compound (3.0 g, 65%) as a yellow oil. ESI-MS m/z: 359.95 $[M+H]^+$.

Into a 50 mL 3-necked round-bottom flask were added the compound from the step d (1.85 g, 5.13 mmol) and LDA (2M in THF) (3.9 mL) at 0° C. The resulting mixture was stirred for 1h at room temperature under nitrogen atmosphere. The reaction was monitored by LCMS. Desired product could be detected by LCMS. The reaction was quenched with sat. $NH_4Cl$ (aq.) and extracted with EA, The resulting mixture was concentrated under reduced pressure. The residue was purified by reverse flash chromatography to afford the desired compound as a yellow oil. ESI-MS m/z: 360.15 $[M+H]^+$.

Intermediate 106 Steps f and g

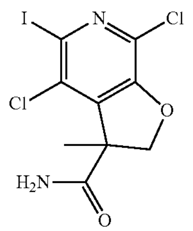 [SMILES: CC1(C(N)=O)COc2c(Cl)nc(I)c(Cl)c21]

Into a 250 mL round-bottom flask were added the compound from the step e (6.6 g, 18.33 mmol), acetone (20 mL) and Jones reagent (8 mL, 40.39 mmol) in portions at 0° C. under nitrogen atmosphere. The resulting mixture was stirred for 3 h at room temperature under nitrogen atmosphere. The reaction was monitored by LCMS. The aqueous layer was extracted with EtOAc. The resulting liquid was dried under vacuum. The crude product was used in the next step directly without further purification. ESI-MS m/z: 374.20 [M+H]+.

Into a 250 mL round-bottom flask were added the compound from the step f (3.5 g, 9.35 mmol), CDI and THE (50 mL) at room temperature. The resulting mixture was stirred for 2h at room temperature under nitrogen atmosphere. Then the resulting mixture was added to $NH_3H_2O$ (400 mL) dropwise and stirred for 2h. The reaction was monitored by LCMS. The aqueous layer was extracted with EtOAc, The residue was purified by reverse flash chromatography to afford the desired compound (1 g, 28.65%) as white solid. ESI-MS m/z: 372.90 [M+H]+.

Intermediate 107

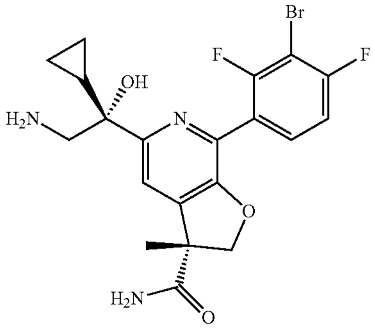 [SMILES: C[C@]1(C(N)=O)COc2c1cc([C@@](O)(CN)C1CC1)nc2-c1ccc(F)c(Br)c1F]

The above compound was prepared in an analogous fashion to Intermediate 47 with the corresponding aryl boronic acid. (95 mg, 91%) ESI-MS m/z: 470.16 [M+H]+.

Intermediate 108

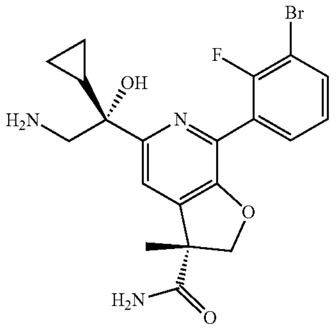 [SMILES: C[C@]1(C(N)=O)COc2c1cc([C@@](O)(CN)C1CC1)nc2-c1cccc(Br)c1F]

The above compound was prepared in an analogous fashion to Intermediate 47 with the corresponding aryl boronic acid. (476 mg, 86%) ESI-MS m/z: 452.13 [M+H]+.

Intermediate 109

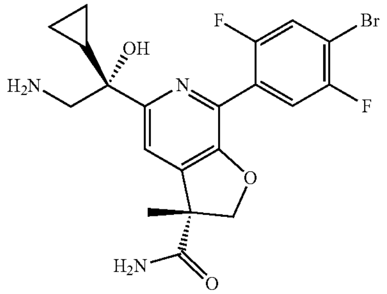 [SMILES: C[C@]1(C(N)=O)COc2c1cc([C@@](O)(CN)C1CC1)nc2-c1cc(F)c(Br)cc1F]

The above compound was prepared in an analogous fashion to Intermediate 47 with the corresponding aryl boronic acid. (382 mg, 68%) ESI-MS m/z: 470/10 [M+H]+.

Intermediate 110

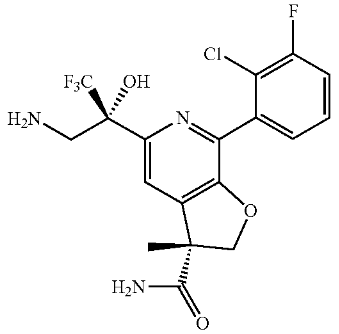 [SMILES: C[C@]1(C(N)=O)COc2c1cc([C@@](O)(CN)C(F)(F)F)nc2-c1cccc(F)c1Cl]

The above compound was prepared in an analogous fashion to Intermediate 47 with the corresponding aryl boronic acid. The crude material was purified by prep-TLC (silica gel, MeOH in DCM with $NH_3$) to afford the desired product (305 mg, 59%) as a white solid. ESI-MS m/z: 434.15 [M+H]+.

Intermediate 111

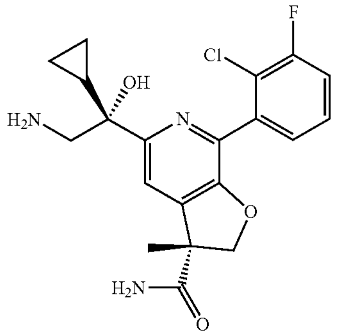 [SMILES: C[C@]1(C(N)=O)COc2c1cc([C@@](O)(CN)C1CC1)nc2-c1cccc(F)c1Cl]

The above compound was prepared in an analogous fashion to Intermediate 47 with the corresponding aryl boronic acid. The crude material was purified by prep-TLC (silica gel, MeOH in DCM with $NH_3$) to afford the desired product (170 mg, 72%) as a white solid. ESI-MS m/z: 406.16 [M+H]+.

Intermediate 112

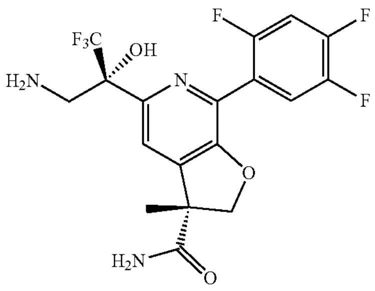 [SMILES: C[C@]1(C(N)=O)COc2c1cc([C@@](O)(CN)C(F)(F)F)nc2-c1cc(F)c(F)cc1F]

The above compound was prepared in an analogous fashion to Intermediate 47 with the corresponding aryl boronic acid. The crude material was concentrated to dryness, redissolved in EtOAc, washed with $NaHCO_3$ (sat. aq.) 5×1 mL. The organic layer was dried over $Na_2SO_4$ filtered and concentrated to afford the desired product (1.311 g, 80%) as a white powder. ESI-MS m/z: 436.23 $[M+H]^+$.

Intermediate 113

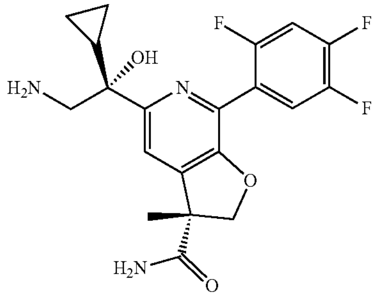 [SMILES: C[C@]1(C(N)=O)COc2c1cc([C@@](O)(CN)C1CC1)nc2-c1cc(F)c(F)cc1F]

The above compound was prepared in an analogous fashion to Intermediate 47 with the corresponding aryl boronic acid. The crude material was concentrated to dryness, redissolved in EtOAc, washed with $NaHCO_3$ (sat. aq.) 5×1 mL. The organic layer was dried over $Na_2SO_4$ filtered and concentrated to afford the desired product (589.7 mg, 82%) as a yellow powder. ESI-MS m/z: 408.29 $[M+H]^+$.

The following Table 8 contains examples that were prepared with the similar method to Example 1 Step c (PyBOP or HATU). The majority of compounds were purified by prep-HPLC (ACN/$H_2O$, 20-90%, 25 min), and some were purified by automated column chromatography (silica gel). The aryl acid and amine coupling partners were prepared according to Intermediates 1-113, or by analogous procedures with slight modifications, and also prepared according to procedures found in U.S. patent application Ser. No. 16/930,622.

TABLE 8

| Example | Structure | $MS^+$ m/z |
|---|---|---|
| 1067 | 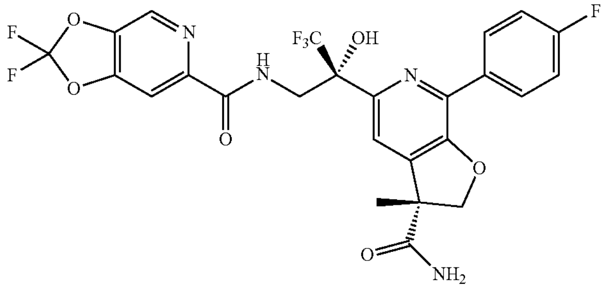 [SMILES: C[C@]1(C(N)=O)COc2c1cc([C@@](O)(CNC(=O)c1cc3c(cn1)OC(F)(F)O3)C(F)(F)F)nc2-c1ccc(F)cc1] | 585.20 |
| 1068 | 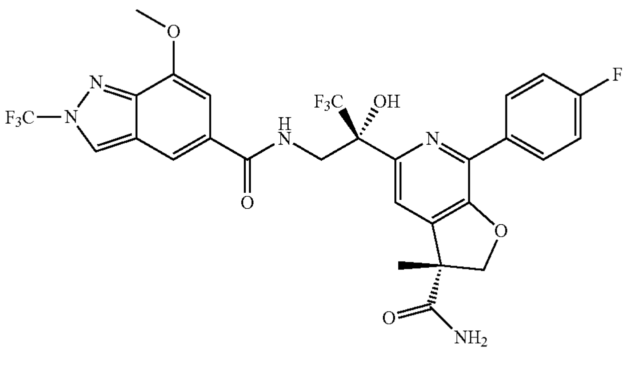 [SMILES: COc1cc(C(=O)NC[C@](O)(c2cc3c(c(-c4ccc(F)cc4)n2)OC[C@]3(C)C(N)=O)C(F)(F)F)cc2cn(C(F)(F)F)nc12] | 642.15 |

TABLE 8-continued
| Example | Structure | MS+ m/z |
|---|---|---|
| 1069 | 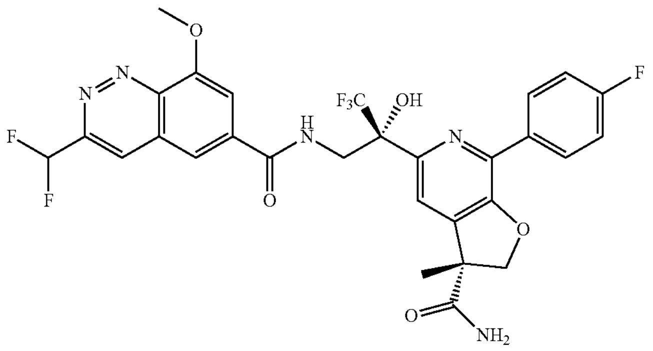 [SMILES: COc1cc(C(=O)NC[C@](O)(c2cc3c(c(-c4ccc(F)cc4)n2)OC[C@]3(C)C(N)=O)C(F)(F)F)cc2cc(C(F)F)nnc12] | 636.20 |
| 1070 | 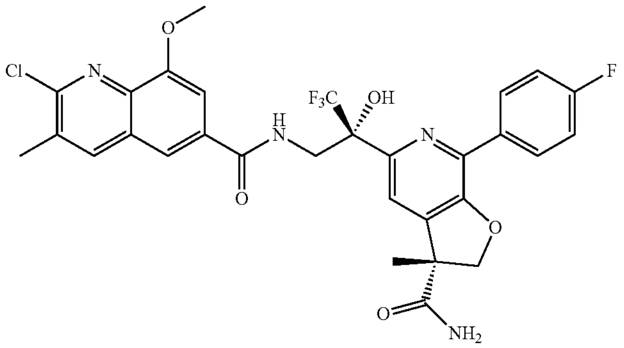 [SMILES: COc1cc(C(=O)NC[C@](O)(c2cc3c(c(-c4ccc(F)cc4)n2)OC[C@]3(C)C(N)=O)C(F)(F)F)cc2cc(C)c(Cl)nc12] | 633.25 |
| 1071 | 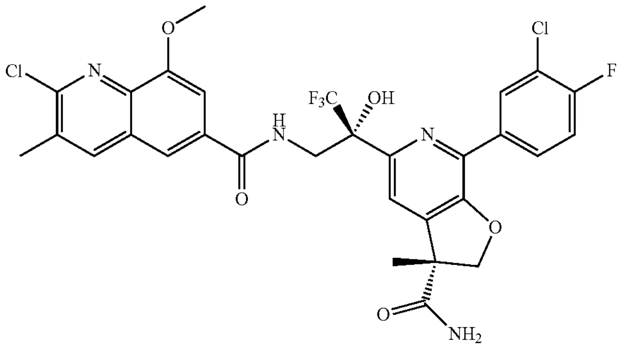 | 667.20 |
| 1072 | 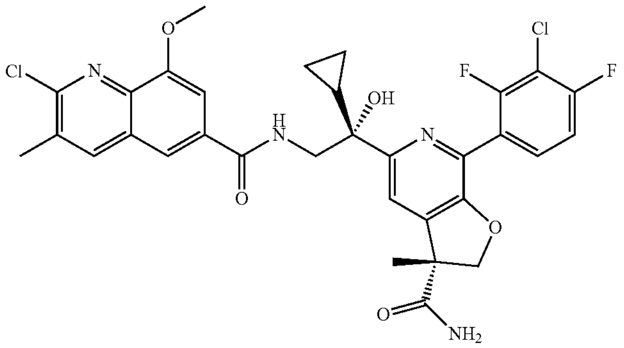 [SMILES: COc1cc(C(=O)NC[C@](O)(c2cc3c(c(-c4ccc(F)c(Cl)c4F)n2)OC[C@]3(C)C(N)=O)C2CC2)cc2cc(C)c(Cl)nc12] | 657.20 |

TABLE 8-continued
| Example | Structure | MS+ m/z |
|---|---|---|
| 1073 | 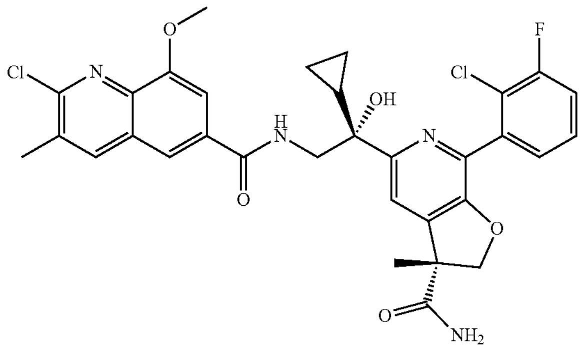 [SMILES: COc1cc(C(=O)NC[C@](O)(c2cc3c(c(-c4cccc(F)c4Cl)n2)OC[C@]3(C)C(N)=O)C2CC2)cc2cc(C)c(Cl)nc12] | 639.20 |
| 1074 | 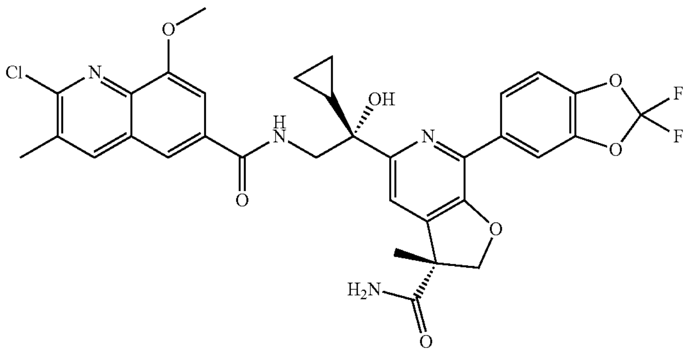 [SMILES: COc1cc(C(=O)NC[C@](O)(c2cc3c(c(-c4ccc5c(c4)OC(F)(F)O5)n2)OC[C@]3(C)C(N)=O)C2CC2)cc2cc(C)c(Cl)nc12] | 667.25 |
| 1075 | 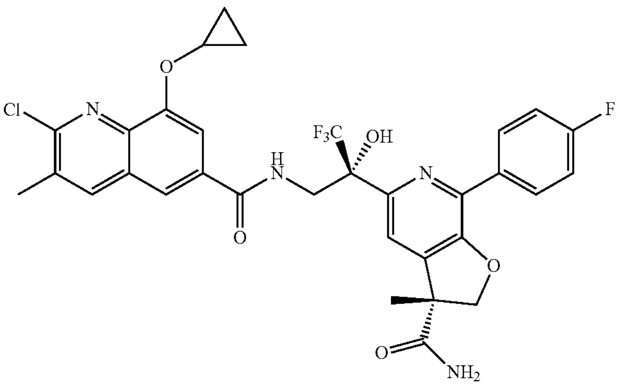 [SMILES: Cc1cc2cc(C(=O)NC[C@](O)(c3cc4c(c(-c5ccc(F)cc5)n3)OC[C@]4(C)C(N)=O)C(F)(F)F)cc(OC3CC3)c2nc1Cl] | 659.40 |
| 1076 | 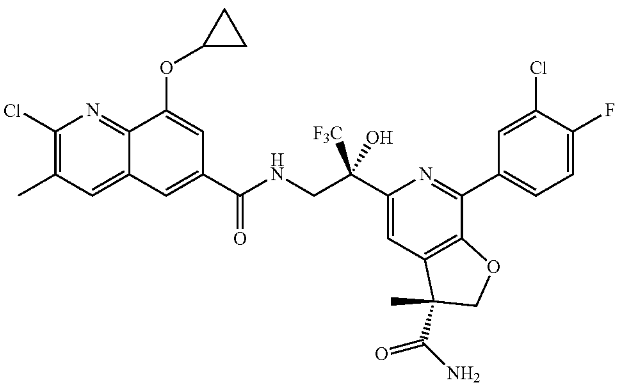 [SMILES: Cc1cc2cc(C(=O)NC[C@](O)(c3cc4c(c(-c5ccc(F)c(Cl)c5)n3)OC[C@]4(C)C(N)=O)C(F)(F)F)cc(OC3CC3)c2nc1Cl] | 693.35 |

TABLE 8-continued
| Example | Structure | MS+ m/z |
|---|---|---|
| 1077 | 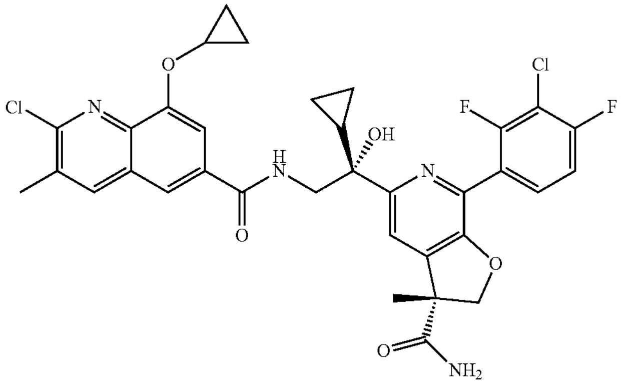 [SMILES: Cc1cc2cc(C(=O)NC[C@](O)(c3cc4c(c(-c5ccc(F)c(Cl)c5F)n3)OC[C@]4(C)C(N)=O)C3CC3)cc(OC3CC3)c2nc1Cl] | 683.40 |
| 1078 | 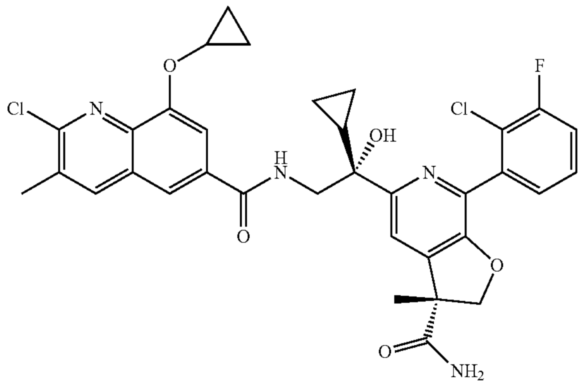 [SMILES: Cc1cc2cc(C(=O)NC[C@](O)(c3cc4c(c(-c5cccc(F)c5Cl)n3)OC[C@]4(C)C(N)=O)C3CC3)cc(OC3CC3)c2nc1Cl] | 665.40 |
| 1079 | 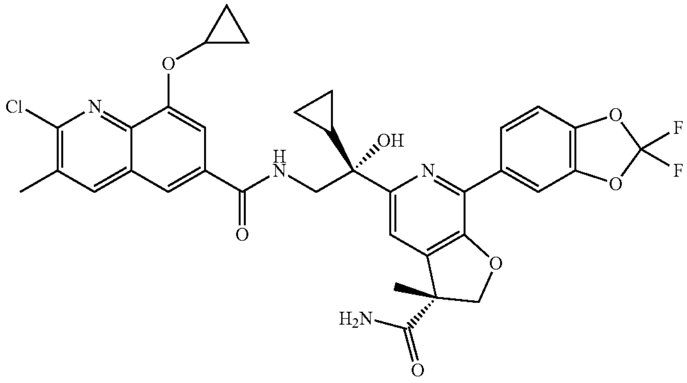 [SMILES: Cc1cc2cc(C(=O)NC[C@](O)(c3cc4c(c(-c5ccc6c(c5)OC(F)(F)O6)n3)OC[C@]4(C)C(N)=O)C3CC3)cc(OC3CC3)c2nc1Cl] | 694.45 |
| 1080 | 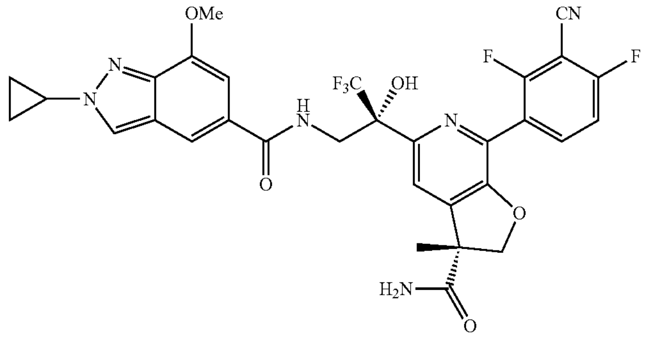 [SMILES: COc1cc(C(=O)NC[C@](O)(c2cc3c(c(-c4ccc(F)c(C#N)c4F)n2)OC[C@]3(C)C(N)=O)C(F)(F)F)cc2cn(C3CC3)nc12] | 657.19 |

TABLE 8-continued
| Example | Structure | MS⁺ m/z |
| --- | --- | --- |
| 1081 | 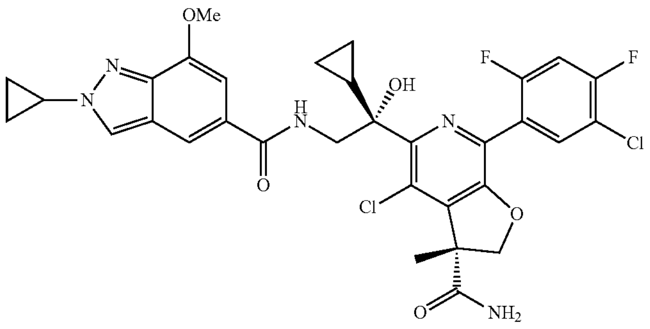 [SMILES: COc1cc(C(=O)NC[C@](O)(c2nc(-c3cc(Cl)c(F)cc3F)c3c(c2Cl)[C@@](C)(C(N)=O)CO3)C2CC2)cc2cn(C3CC3)nc12] | 673.20 |
| 1082 | 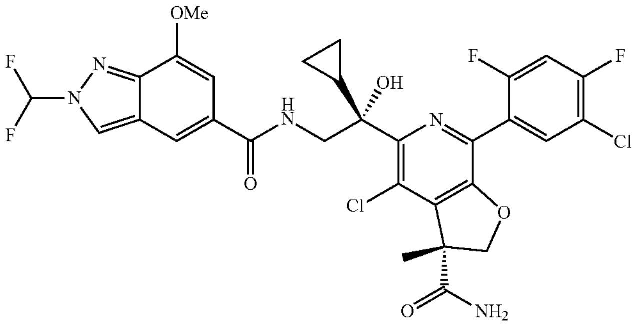 [SMILES: COc1cc(C(=O)NC[C@](O)(c2nc(-c3cc(Cl)c(F)cc3F)c3c(c2Cl)[C@@](C)(C(N)=O)CO3)C2CC2)cc2cn(C(F)F)nc12] | 685.13 |
| 1083 | 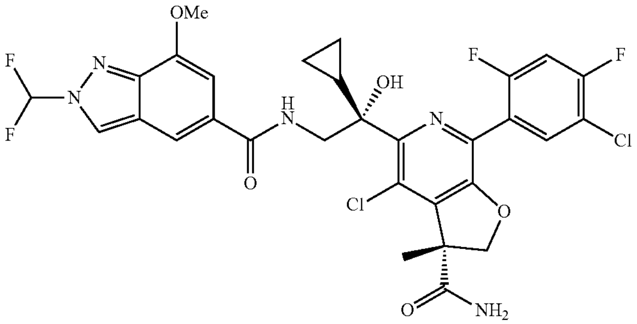 [SMILES: COc1cc(C(=O)NC[C@](O)(c2nc(-c3cc(Cl)c(F)cc3F)c3c(c2Cl)[C@@](C)(C(N)=O)CO3)C2CC2)cc2cn(C(F)F)nc12] | 685.13 |
| 1084 | 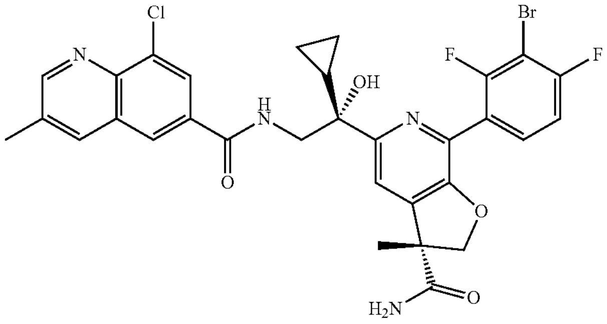 [SMILES: Cc1cnc2c(Cl)cc(C(=O)NC[C@](O)(c3cc4c(c(-c5ccc(F)c(Br)c5F)n3)OC[C@]4(C)C(N)=O)C3CC3)cc2c1] | 673.12 |

TABLE 8-continued
| Example | Structure | MS⁺ m/z |
|---|---|---|
| 1085 | 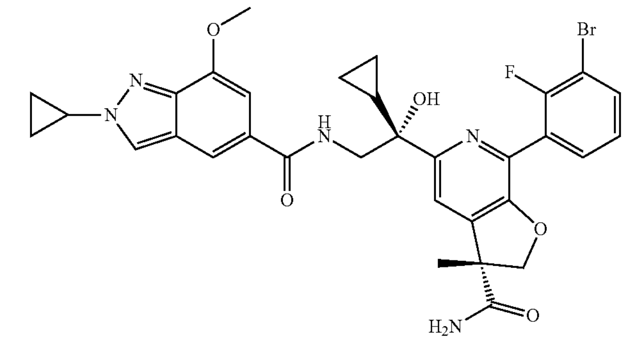 [SMILES: COc1cc(C(=O)NC[C@](O)(c2cc3c(c(-c4cccc(Br)c4F)n2)OC[C@]3(C)C(N)=O)C2CC2)cc2cn(C3CC3)nc12] | 666.17 |
| 1086 | 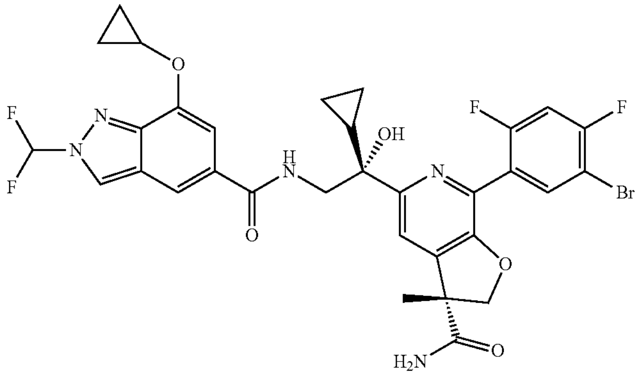 [SMILES: C[C@]1(C(N)=O)COc2c1cc([C@@](O)(CNC(=O)c1cc(OC3CC3)c3nn(C(F)F)cc3c1)C1CC1)nc2-c1cc(Br)c(F)cc1F] | 720.07 |
| 1087 | 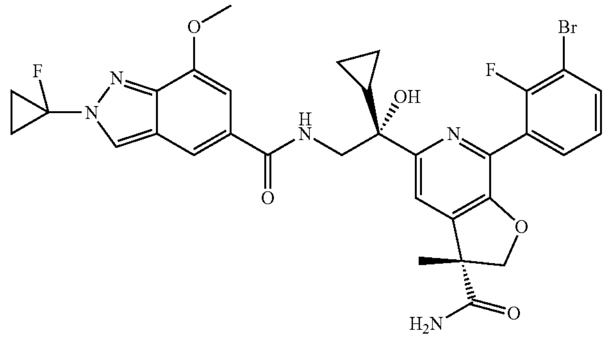 [SMILES: COc1cc(C(=O)NC[C@](O)(c2cc3c(c(-c4cccc(Br)c4F)n2)OC[C@]3(C)C(N)=O)C2CC2)cc2cn(C3(F)CC3)nc12] | 684.19 |
| 1088 | 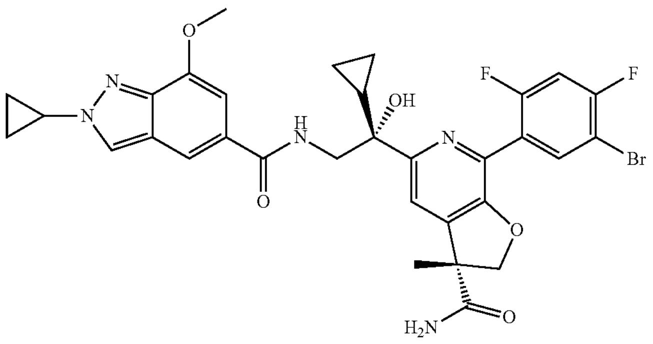 [SMILES: COc1cc(C(=O)NC[C@](O)(c2cc3c(c(-c4cc(Br)c(F)cc4F)n2)OC[C@]3(C)C(N)=O)C2CC2)cc2cn(C3CC3)nc12] | 684.17 |

TABLE 8-continued
| Example | Structure | MS+ m/z |
| --- | --- | --- |
| 1089 | 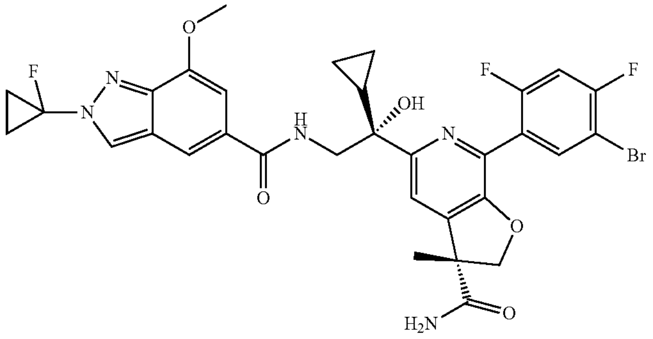 [SMILES: COc1cc(C(=O)NC[C@](O)(c2cc3c(c(-c4cc(Br)c(F)cc4F)n2)OC[C@]3(C)C(N)=O)C2CC2)cc2cn(C3(F)CC3)nc12] | 702.16 |
| 1090 | 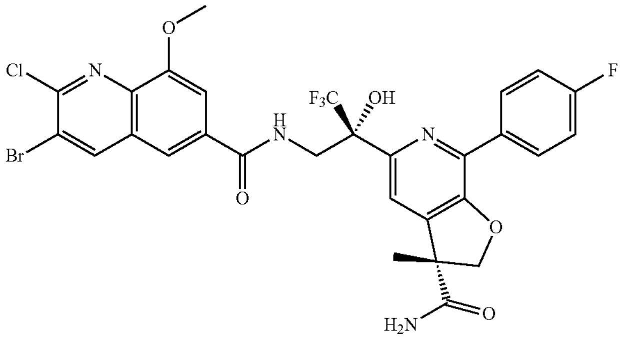 | 699.07 |
| 1091 | 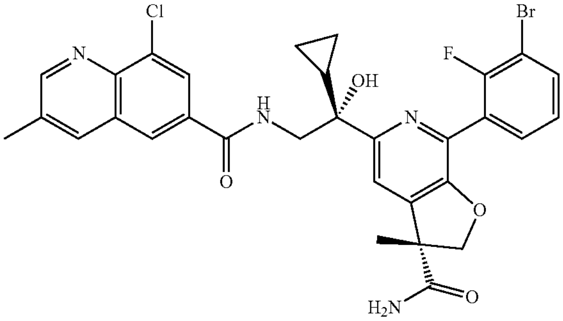 [SMILES: Cc1cnc2c(Cl)cc(C(=O)NC[C@](O)(c3cc4c(c(-c5cccc(Br)c5F)n3)OC[C@]4(C)C(N)=O)C3CC3)cc2c1] | 655.12 |
| 1092 | 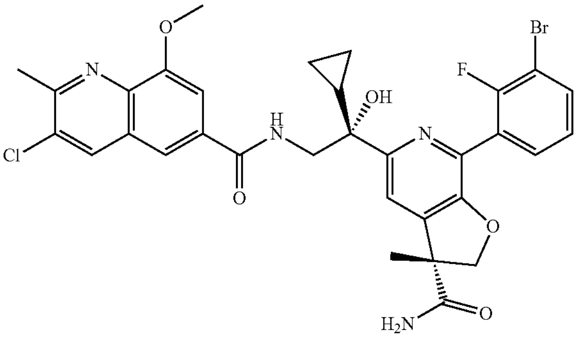 [SMILES: COc1cc(C(=O)NC[C@](O)(c2cc3c(c(-c4cccc(Br)c4F)n2)OC[C@]3(C)C(N)=O)C2CC2)cc2cc(Cl)c(C)nc12] | 685.11 |

TABLE 8-continued
| Example | Structure | MS⁺ m/z |
|---|---|---|
| 1093 | 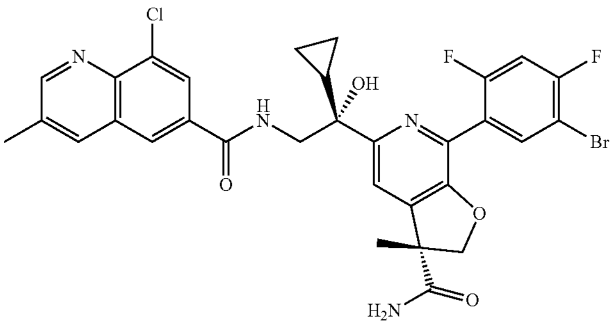 [SMILES: Cc1cnc2c(Cl)cc(C(=O)NC[C@](O)(c3cc4c(c(-c5cc(Br)c(F)cc5F)n3)OC[C@]4(C)C(N)=O)C3CC3)cc2c1] | 673.10 |
| 1094 | 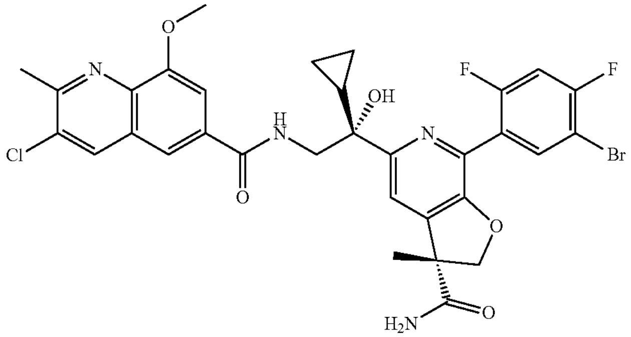 [SMILES: COc1cc(C(=O)NC[C@](O)(c2cc3c(c(-c4cc(Br)c(F)cc4F)n2)OC[C@]3(C)C(N)=O)C2CC2)cc2cc(Cl)c(C)nc12] | 703.18 |
| 1095 | 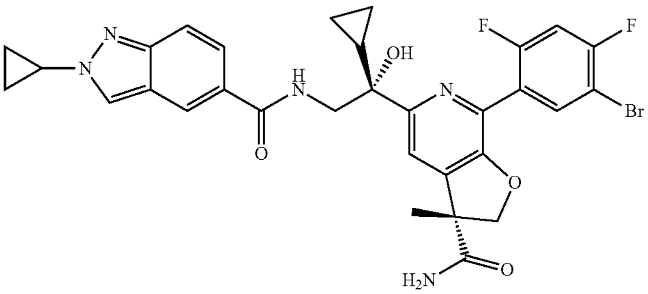 [SMILES: C[C@]1(C(N)=O)COc2c1cc([C@@](O)(CNC(=O)c1ccc3nn(C4CC4)cc3c1)C1CC1)nc2-c1cc(Br)c(F)cc1F] | 654.03 |
| 1096 | 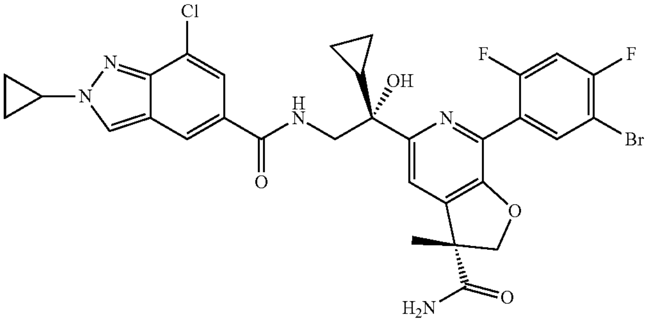 [SMILES: C[C@]1(C(N)=O)COc2c1cc([C@@](O)(CNC(=O)c1cc(Cl)c3nn(C4CC4)cc3c1)C1CC1)nc2-c1cc(Br)c(F)cc1F] | 688.14 |

TABLE 8-continued
| Example | Structure | MS⁺ m/z |
| --- | --- | --- |
| 1097 | 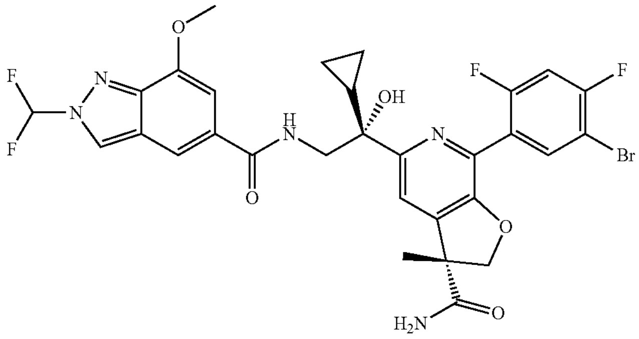 [SMILES: COc1cc(C(=O)NC[C@](O)(c2cc3c(c(-c4cc(Br)c(F)cc4F)n2)OC[C@]3(C)C(N)=O)C2CC2)cc2cn(C(F)F)nc12] | 694.81 |
| 1098 | 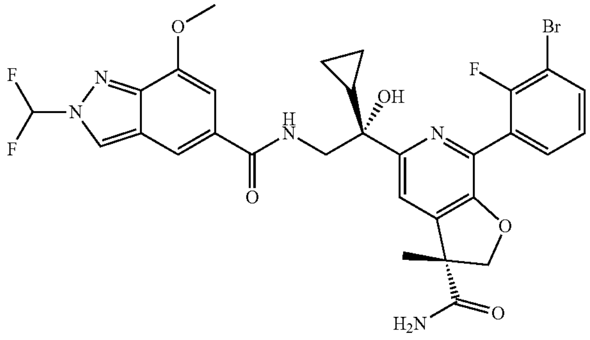 [SMILES: COc1cc(C(=O)NC[C@](O)(c2cc3c(c(-c4cccc(Br)c4F)n2)OC[C@]3(C)C(N)=O)C2CC2)cc2cn(C(F)F)nc12] | 676.09 |
| 1099 | 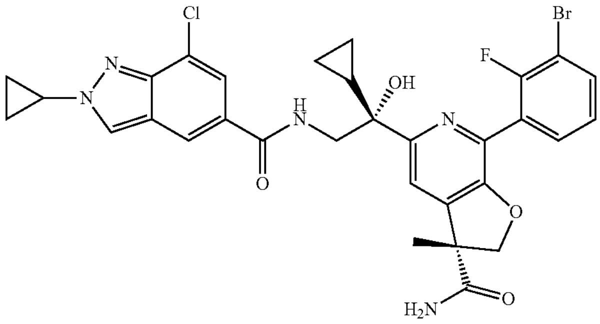 [SMILES: C[C@]1(C(N)=O)COc2c1cc([C@@](O)(CNC(=O)c1cc(Cl)c3nn(C4CC4)cc3c1)C1CC1)nc2-c1cccc(Br)c1F] | 670.12 |
| 1100 | 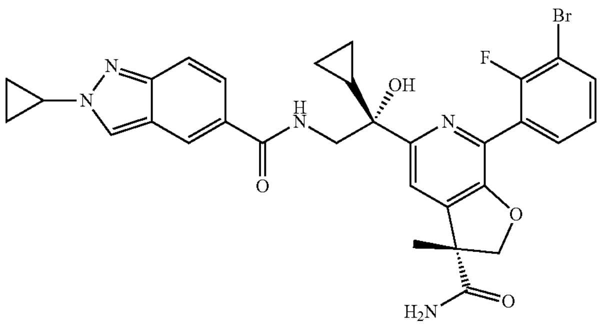 [SMILES: C[C@]1(C(N)=O)COc2c1cc([C@@](O)(CNC(=O)c1ccc3nn(C4CC4)cc3c1)C1CC1)nc2-c1cccc(Br)c1F] | 636.17 |

TABLE 8-continued
| Example | Structure | MS+ m/z |
|---|---|---|
| 1101 | 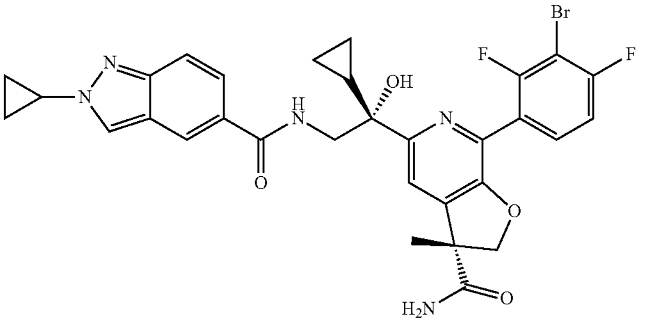 [SMILES: C[C@]1(C(N)=O)COc2c1cc([C@@](O)(CNC(=O)c1ccc3nn(C4CC4)cc3c1)C1CC1)nc2-c1ccc(F)c(Br)c1F] | 654.09 |
| 1102 | 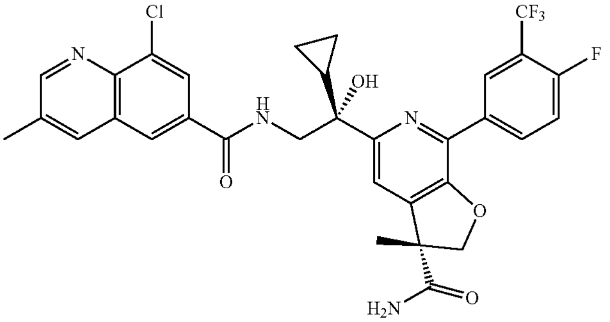 [SMILES: Cc1cnc2c(Cl)cc(C(=O)NC[C@](O)(c3cc4c(c(-c5ccc(F)c(C(F)(F)F)c5)n3)OC[C@]4(C)C(N)=O)C3CC3)cc2c1] | 643.26 |
| 1103 | 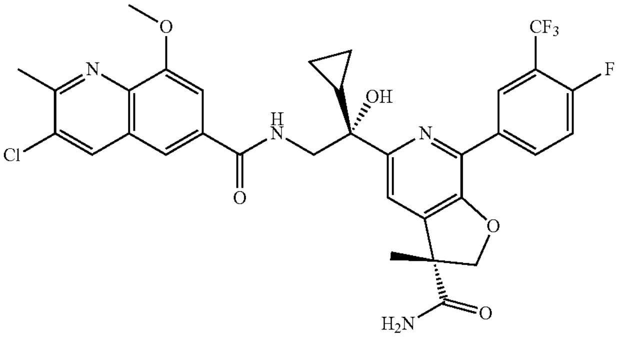 [SMILES: COc1cc(C(=O)NC[C@](O)(c2cc3c(c(-c4ccc(F)c(C(F)(F)F)c4)n2)OC[C@]3(C)C(N)=O)C2CC2)cc2cc(Cl)c(C)nc12] | 673.26 |
| 1104 | 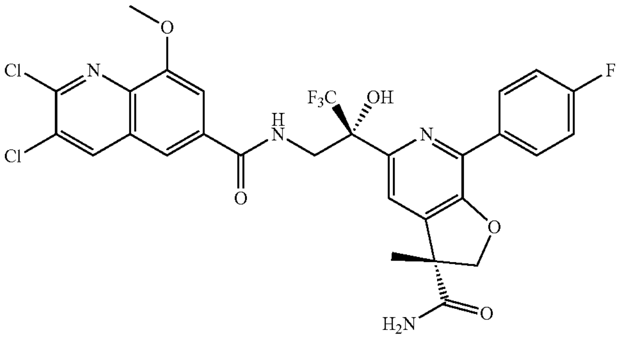 [SMILES: COc1cc(C(=O)NC[C@](O)(c2cc3c(c(-c4ccc(F)cc4)n2)OC[C@]3(C)C(N)=O)C(F)(F)F)cc2cc(Cl)c(Cl)nc12] | 653.31 |

TABLE 8-continued
| Example | Structure | MS+ m/z |
|---|---|---|
| 1105 | 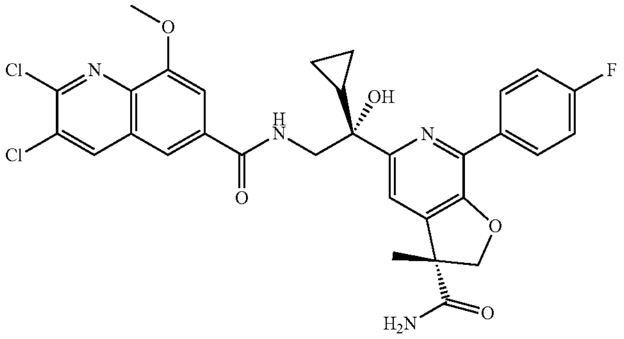 [SMILES: COc1cc(C(=O)NC[C@](O)(c2cc3c(c(-c4ccc(F)cc4)n2)OC[C@]3(C)C(N)=O)C2CC2)cc2cc(Cl)c(Cl)nc12] | 625.1 |
| 1106 | 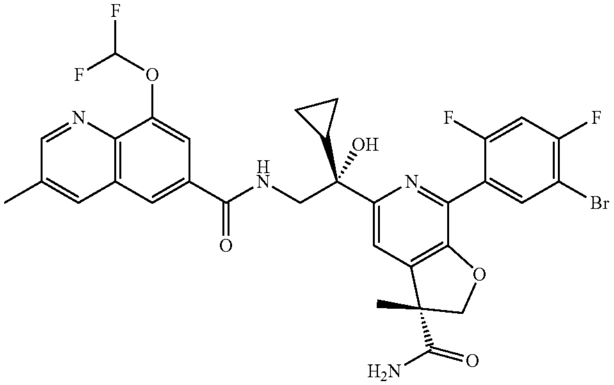 [SMILES: Cc1cnc2c(OC(F)F)cc(C(=O)NC[C@](O)(c3cc4c(c(-c5cc(Br)c(F)cc5F)n3)OC[C@]4(C)C(N)=O)C3CC3)cc2c1] | 702.97 |
| 1107 | 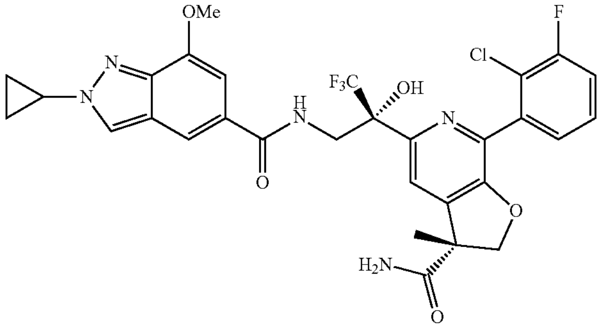 [SMILES: COc1cc(C(=O)NC[C@](O)(c2cc3c(c(-c4cccc(F)c4Cl)n2)OC[C@]3(C)C(N)=O)C(F)(F)F)cc2cn(C3CC3)nc12] | 648.34 |
| 1108 | 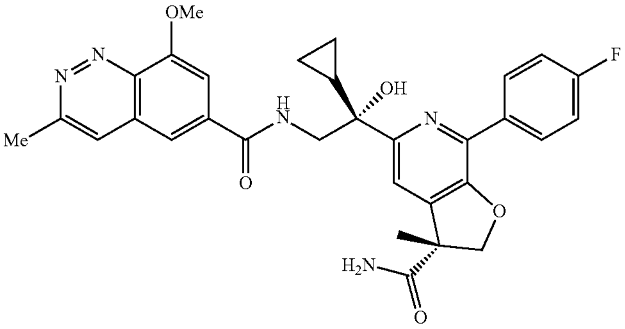 [SMILES: COc1cc(C(=O)NC[C@](O)(c2cc3c(c(-c4ccc(F)cc4)n2)OC[C@]3(C)C(N)=O)C2CC2)cc2cc(C)nnc12] | 572.38 |

TABLE 8-continued
| Example | Structure | MS+ m/z |
| --- | --- | --- |
| 1109 | 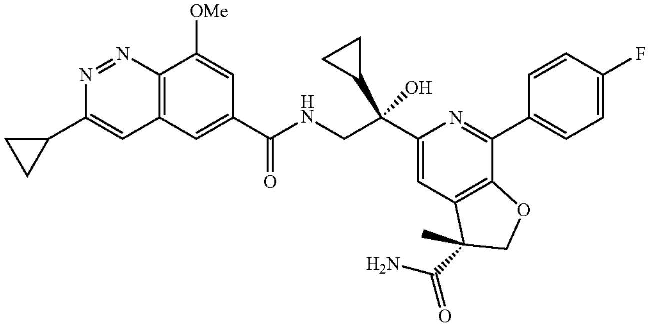 [SMILES: COc1cc(C(=O)NC[C@](O)(c2cc3c(c(-c4ccc(F)cc4)n2)OC[C@]3(C)C(N)=O)C2CC2)cc2cc(C3CC3)nnc12] | 598.38 |
| 1110 | 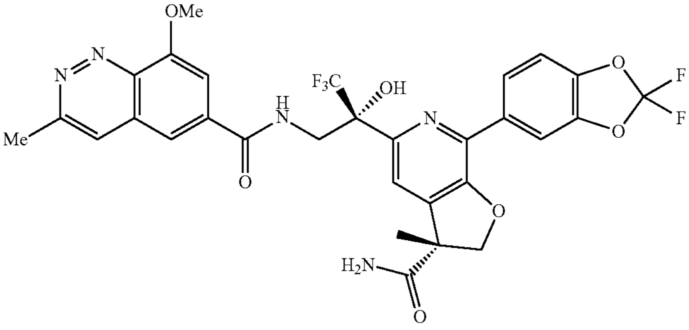 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(C)nnc12] | 662.31 |
| 1111 | 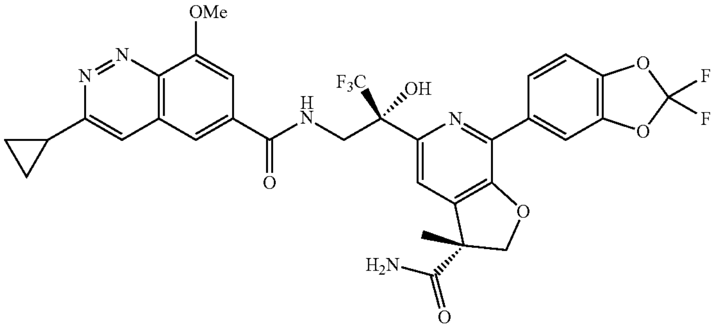 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cc(C3CC3)nnc12] | 688.32 |
| 1112 | 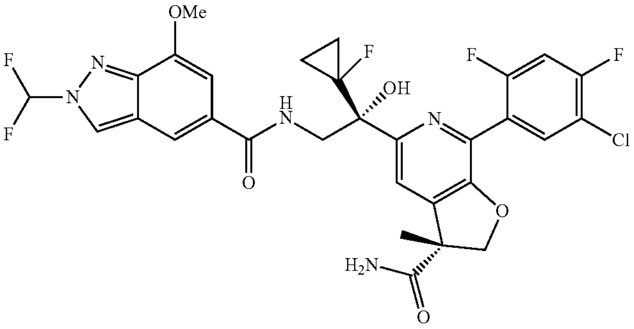 [SMILES: COc1cc(C(=O)NC[C@](O)(c2cc3c(c(-c4cc(Cl)c(F)cc4F)n2)OC[C@]3(C)C(N)=O)C2(F)CC2)cc2cn(C(F)F)nc12] | 666.28 |

TABLE 8-continued
| Example | Structure | MS⁺ m/z |
|---|---|---|
| 1113 | 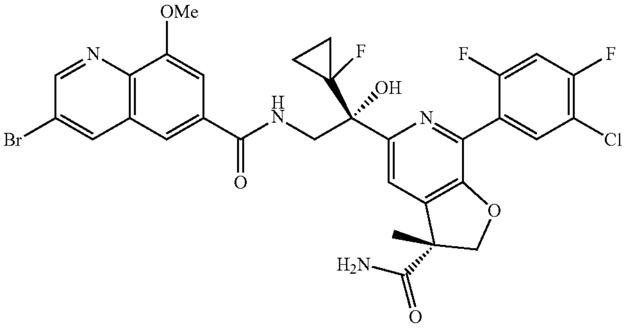 [SMILES: COc1cc(C(=O)NC[C@](O)(c2cc3c(c(-c4cc(Cl)c(F)cc4F)n2)OC[C@]3(C)C(N)=O)C2(F)CC2)cc2cc(Br)cnc12] | 707.08 |
| 1114 | 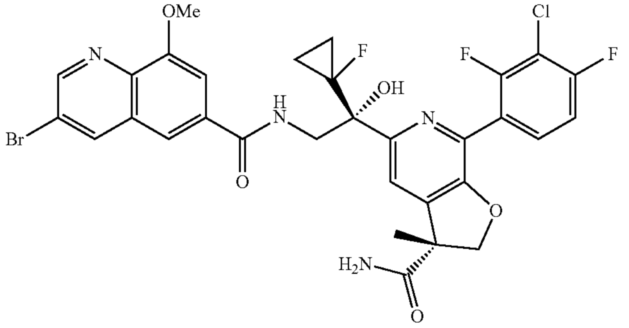 [SMILES: COc1cc(C(=O)NC[C@](O)(c2cc3c(c(-c4ccc(F)c(Cl)c4F)n2)OC[C@]3(C)C(N)=O)C2(F)CC2)cc2cc(Br)cnc12] | 707.08 |
| 1115 | 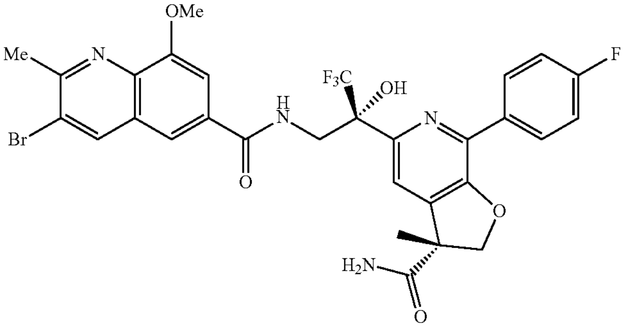 [SMILES: COc1cc(C(=O)NC[C@](O)(c2cc3c(c(-c4ccc(F)cc4)n2)OC[C@]3(C)C(N)=O)C(F)(F)F)cc2cc(Br)c(C)nc12] | 677.12 |
| 1116 | 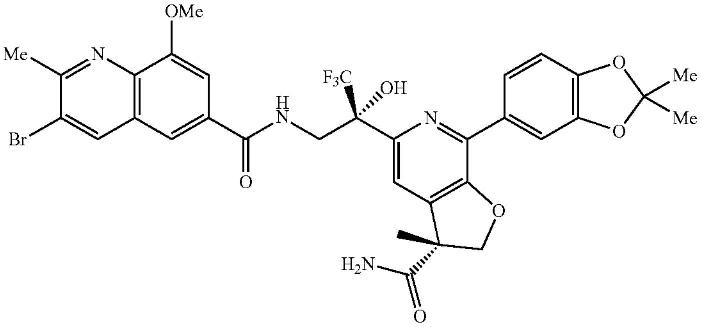 [SMILES: COc1cc(C(=O)NC[C@](O)(c2cc3c(c(-c4ccc5c(c4)OC(C)(C)O5)n2)OC[C@]3(C)C(N)=O)C(F)(F)F)cc2cc(Br)c(C)nc12] | 739.09 |

TABLE 8-continued
| Example | Structure | MS+ m/z |
|---|---|---|
| 1117 | 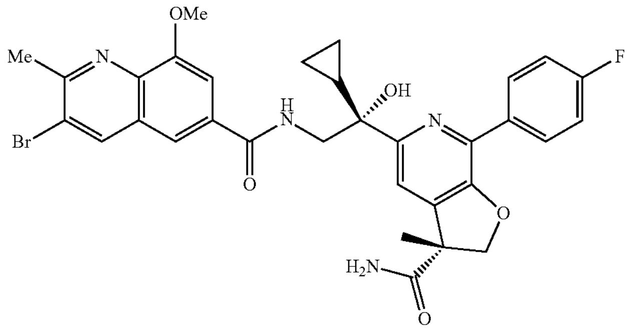 [SMILES: COc1cc(C(=O)NC[C@](O)(c2cc3c(c(-c4ccc(F)cc4)n2)OC[C@]3(C)C(N)=O)C2CC2)cc2cc(Br)c(C)nc12] | 649.18 |
| 1118 | 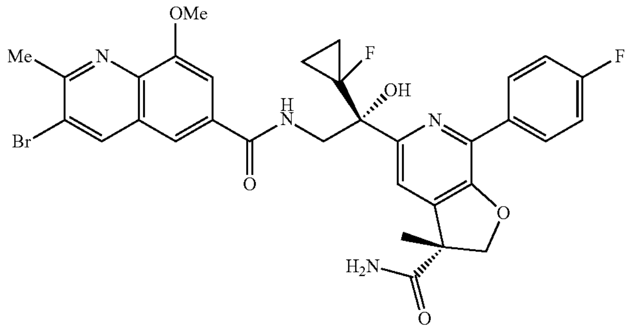 [SMILES: COc1cc(C(=O)NC[C@](O)(c2cc3c(c(-c4ccc(F)cc4)n2)OC[C@]3(C)C(N)=O)C2(F)CC2)cc2cc(Br)c(C)nc12] | 667.21 |
| 1119 | 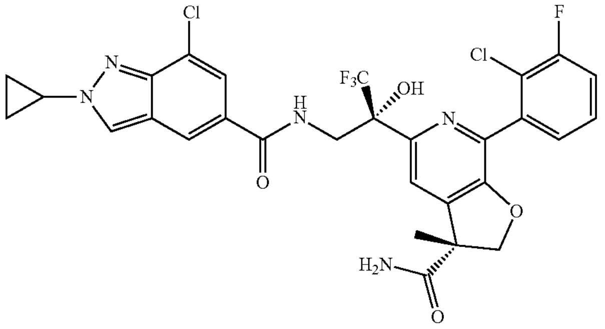 [SMILES: C[C@]1(C(N)=O)COc2c1cc([C@@](O)(CNC(=O)c1cc(Cl)c3nn(C4CC4)cc3c1)C(F)(F)F)nc2-c1cccc(F)c1Cl] | 652.15 |
| 1120 | 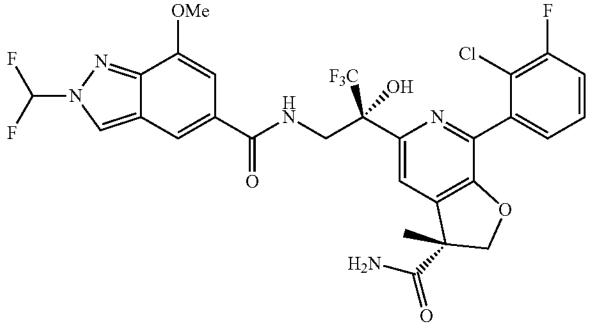 [SMILES: COc1cc(C(=O)NC[C@](O)(c2cc3c(c(-c4cccc(F)c4Cl)n2)OC[C@]3(C)C(N)=O)C(F)(F)F)cc2cn(C(F)F)nc12] | 658.19 |

TABLE 8-continued
| Example | Structure | MS+ m/z |
| --- | --- | --- |
| 1121 | 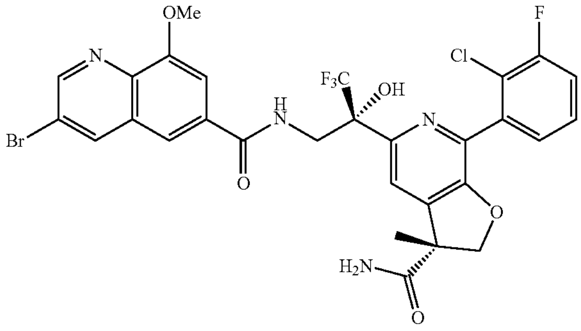 [SMILES: COc1cc(C(=O)NC[C@](O)(c2cc3c(c(-c4cccc(F)c4Cl)n2)OC[C@]3(C)C(N)=O)C(F)(F)F)cc2cc(Br)cnc12] | 699.01 |
| 1122 | 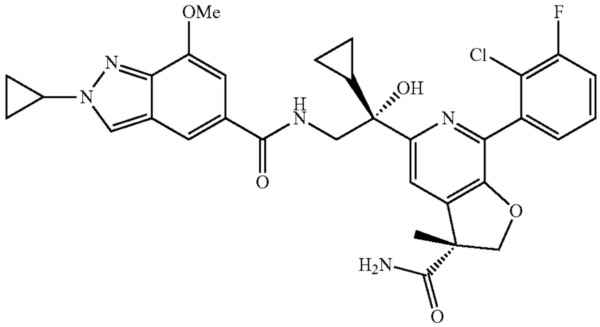 [SMILES: COc1cc(C(=O)NC[C@](O)(c2cc3c(c(-c4cccc(F)c4Cl)n2)OC[C@]3(C)C(N)=O)C2CC2)cc2cn(C3CC3)nc12] | 620.20 |
| 1123 | 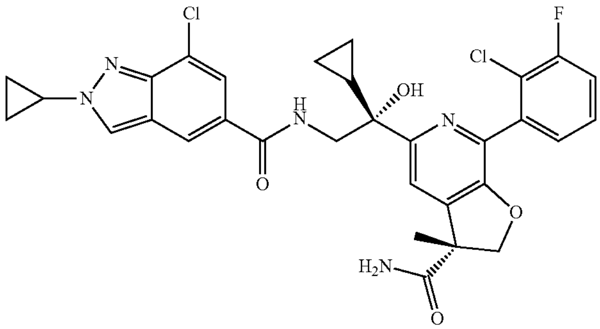 [SMILES: C[C@]1(C(N)=O)COc2c1cc([C@@](O)(CNC(=O)c1cc(Cl)c3nn(C4CC4)cc3c1)C1CC1)nc2-c1cccc(F)c1Cl] | 624.20 |
| 1124 | 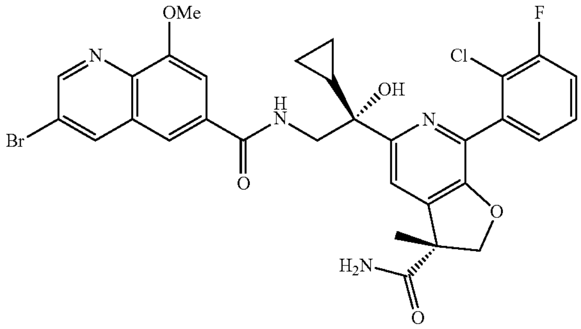 [SMILES: COc1cc(C(=O)NC[C@](O)(c2cc3c(c(-c4cccc(F)c4Cl)n2)OC[C@]3(C)C(N)=O)C2CC2)cc2cc(Br)cnc12] | 671.10 |

TABLE 8-continued
| Example | Structure | MS+ m/z |
|---|---|---|
| 1125 | 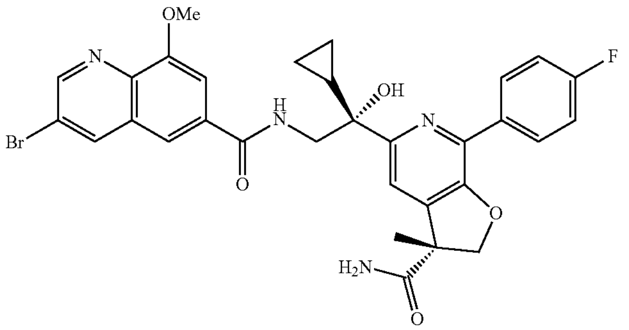 [SMILES: COc1cc(C(=O)NC[C@](O)(c2cc3c(c(-c4ccc(F)cc4)n2)OC[C@]3(C)C(N)=O)C2CC2)cc2cc(Br)cnc12] | 637.08 |
| 1126 | 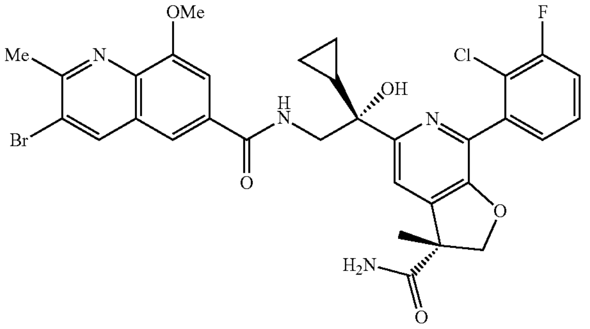 [SMILES: COc1cc(C(=O)NC[C@](O)(c2cc3c(c(-c4cccc(F)c4Cl)n2)OC[C@]3(C)C(N)=O)C2CC2)cc2cc(Br)c(C)nc12] | 684.98 |
| 1127 | 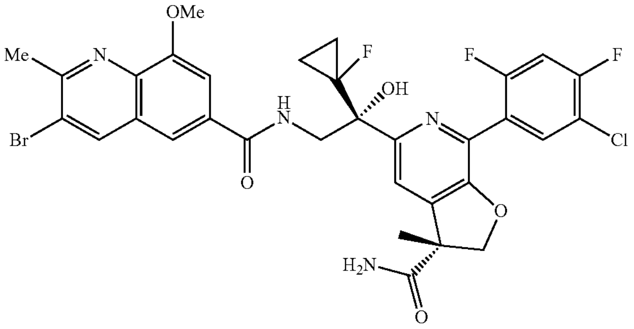 [SMILES: COc1cc(C(=O)NC[C@](O)(c2cc3c(c(-c4cc(Cl)c(F)cc4F)n2)OC[C@]3(C)C(N)=O)C2(F)CC2)cc2cc(Br)c(C)nc12] | 720.94 |
| 1128 | 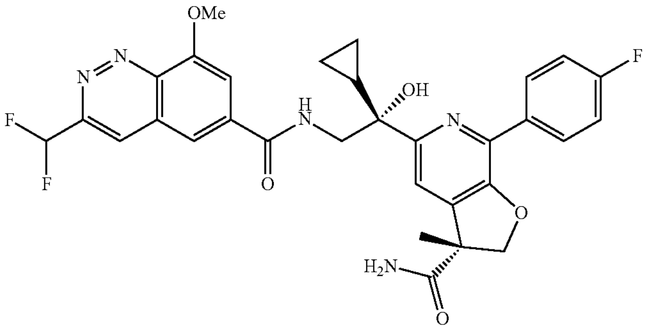 [SMILES: COc1cc(C(=O)NC[C@](O)(c2cc3c(c(-c4ccc(F)cc4)n2)OC[C@]3(C)C(N)=O)C2CC2)cc2cc(C(F)F)nnc12] | 608.20 |

TABLE 8-continued
| Example | Structure | MS⁺ m/z |
|---|---|---|
| 1129 | 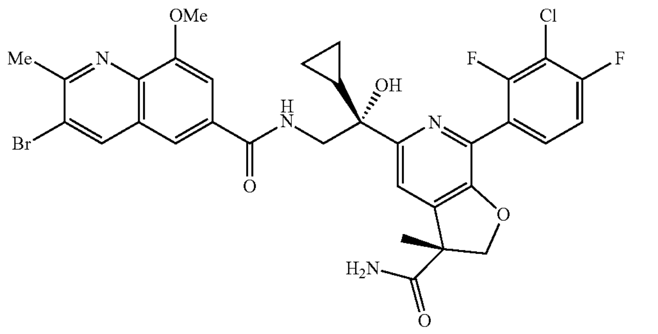 [SMILES: COc1cc(C(=O)NC[C@](O)(c2cc3c(c(-c4ccc(F)c(Cl)c4F)n2)OC[C@]3(C)C(N)=O)C2CC2)cc2cc(Br)c(C)nc12] | 703.20 |
| 1130 | 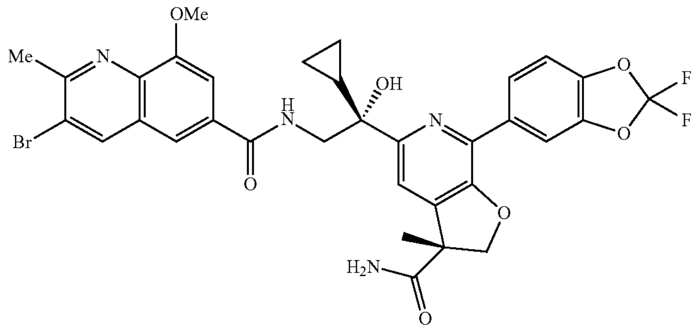 [SMILES: COc1cc(C(=O)NC[C@](O)(c2cc3c(c(-c4ccc5c(c4)OC(F)(F)O5)n2)OC[C@]3(C)C(N)=O)C2CC2)cc2cc(Br)c(C)nc12] | 711.20 |
| 1131 | 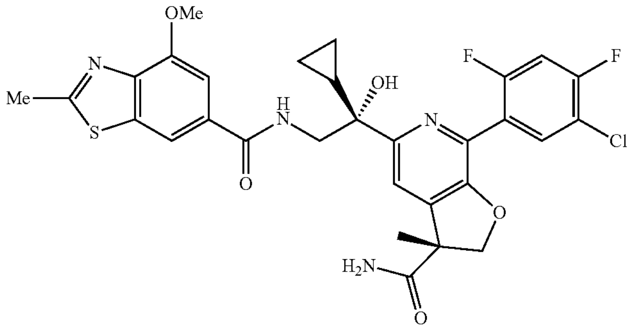 [SMILES: COc1cc(C(=O)NC[C@](O)(c2cc3c(c(-c4cc(Cl)c(F)cc4F)n2)OC[C@]3(C)C(N)=O)C2CC2)cc2sc(C)nc12] | 629.20 |
| 1132 | 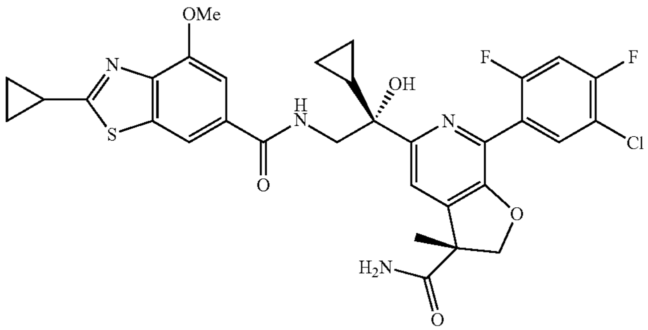 [SMILES: COc1cc(C(=O)NC[C@](O)(c2cc3c(c(-c4cc(Cl)c(F)cc4F)n2)OC[C@]3(C)C(N)=O)C2CC2)cc2sc(C3CC3)nc12] | 655.20 |

TABLE 8-continued
| Example | Structure | MS+ m/z |
|---|---|---|
| 1133 | 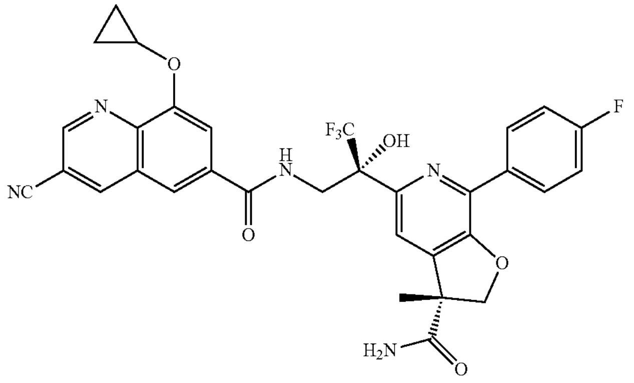 [SMILES: C[C@]1(C(N)=O)COc2c1cc([C@@](O)(CNC(=O)c1cc(OC3CC3)c3ncc(C#N)cc3c1)C(F)(F)F)nc2-c1ccc(F)cc1] | 636.29 |
| 1134 | 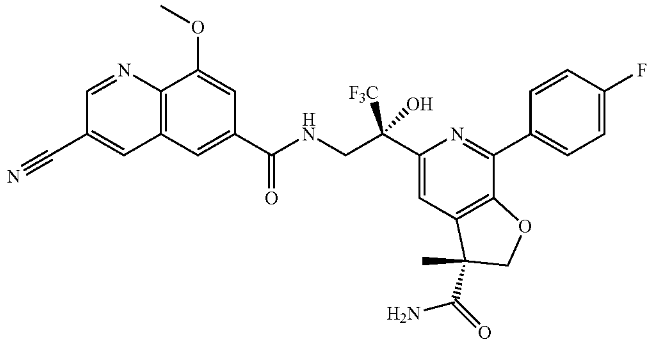 [SMILES: COc1cc(C(=O)NC[C@](O)(c2cc3c(c(-c4ccc(F)cc4)n2)OC[C@]3(C)C(N)=O)C(F)(F)F)cc2cc(C#N)cnc12] | 610.27 |
| 1135 | 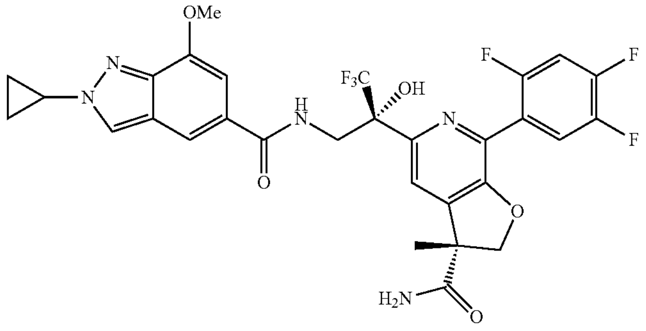 [SMILES: COc1cc(C(=O)NC[C@](O)(c2cc3c(c(-c4cc(F)c(F)cc4F)n2)OC[C@]3(C)C(N)=O)C(F)(F)F)cc2cn(C3CC3)nc12] | 650.26 |
| 1136 | 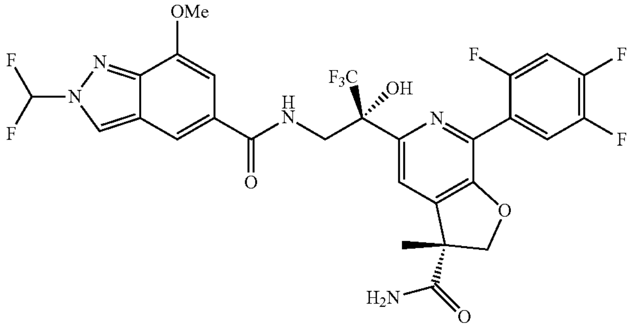 [SMILES: COc1cc(C(=O)NC[C@](O)(c2cc3c(c(-c4cc(F)c(F)cc4F)n2)OC[C@]3(C)C(N)=O)C(F)(F)F)cc2cn(C(F)F)nc12] | 660.20 |

TABLE 8-continued
| Example | Structure | MS⁺ m/z |
|---|---|---|
| 1137 | 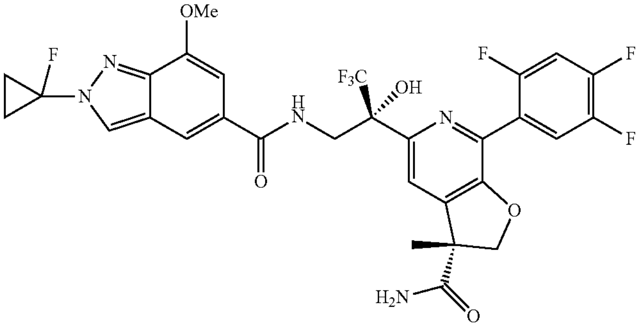 [SMILES: COc1cc(C(=O)NC[C@](O)(c2cc3c(c(-c4cc(F)c(F)cc4F)n2)OC[C@]3(C)C(N)=O)C(F)(F)F)cc2cn(C3(F)CC3)nc12] | 660.20 |
| 1138 | 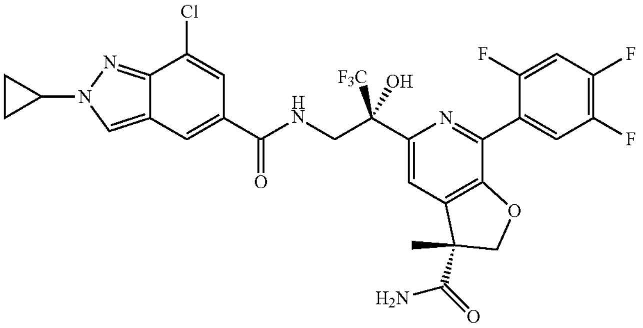 [SMILES: C[C@]1(C(N)=O)COc2c1cc([C@@](O)(CNC(=O)c1cc(Cl)c3nn(C4CC4)cc3c1)C(F)(F)F)nc2-c1cc(F)c(F)cc1F] | 660.20 |
| 1139 | 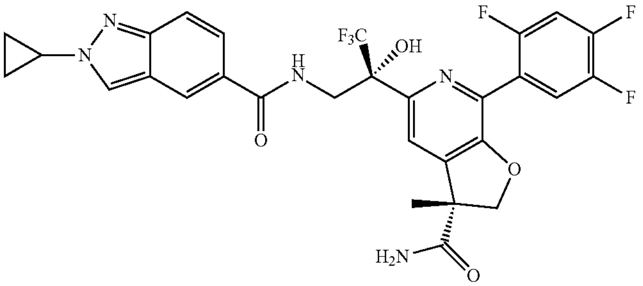 [SMILES: C[C@]1(C(N)=O)COc2c1cc([C@@](O)(CNC(=O)c1ccc3nn(C4CC4)cc3c1)C(F)(F)F)nc2-c1cc(F)c(F)cc1F] | 620.24 |
| 1140 | 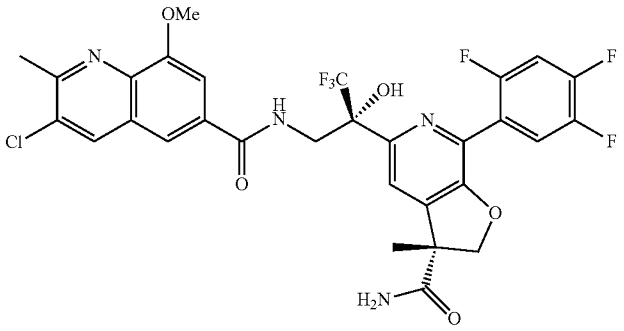 [SMILES: COc1cc(C(=O)NC[C@](O)(c2cc3c(c(-c4cc(F)c(F)cc4F)n2)OC[C@]3(C)C(N)=O)C(F)(F)F)cc2cc(Cl)c(C)nc12] | 669.32 |

TABLE 8-continued
| Example | Structure | MS+ m/z |
|---|---|---|
| 1141 | 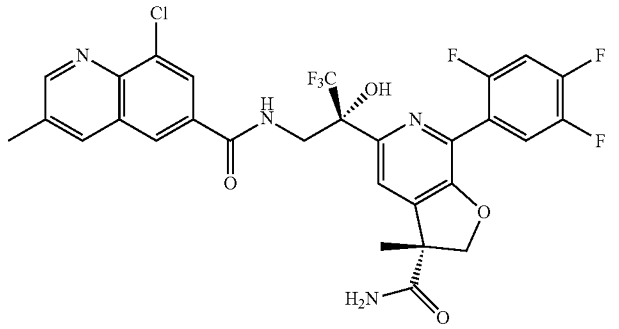 [SMILES: Cc1cnc2c(Cl)cc(C(=O)NC[C@](O)(c3cc4c(c(-c5cc(F)c(F)cc5F)n3)OC[C@]4(C)C(N)=O)C(F)(F)F)cc2c1] | 639.18 |
| 1142 | 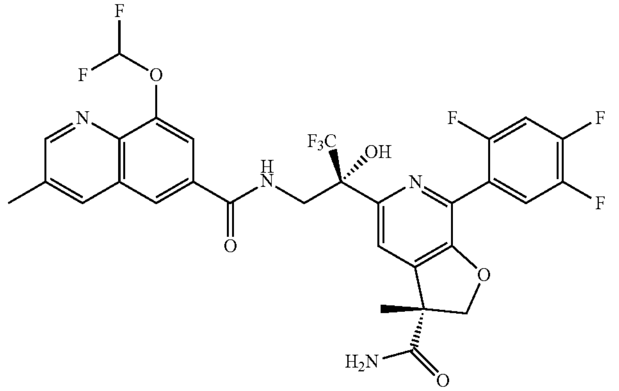 [SMILES: Cc1cnc2c(OC(F)F)cc(C(=O)NC[C@](O)(c3cc4c(c(-c5cc(F)c(F)cc5F)n3)OC[C@]4(C)C(N)=O)C(F)(F)F)cc2c1] | 671.22 |
| 1143 | 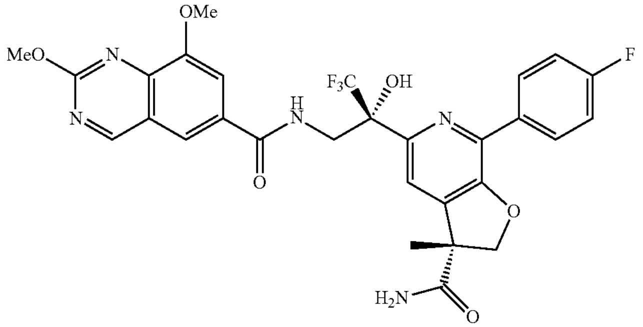 [SMILES: COc1ncc2cc(C(=O)NC[C@](O)(c3cc4c(c(-c5ccc(F)cc5)n3)OC[C@]4(C)C(N)=O)C(F)(F)F)cc(OC)c2n1] | 616.23 |
| 1144 | 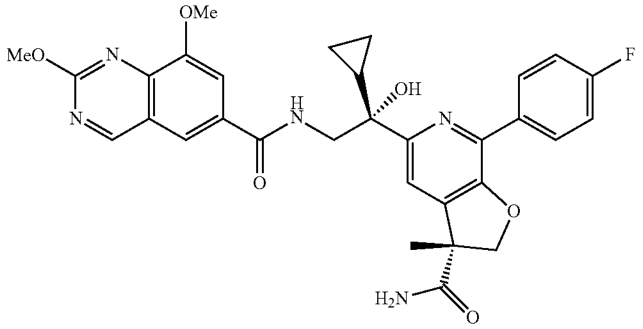 [SMILES: COc1ncc2cc(C(=O)NC[C@](O)(c3cc4c(c(-c5ccc(F)cc5)n3)OC[C@]4(C)C(N)=O)C3CC3)cc(OC)c2n1] | 588.30 |

TABLE 8-continued
| Example | Structure | MS+ m/z |
|---|---|---|
| 1145 | 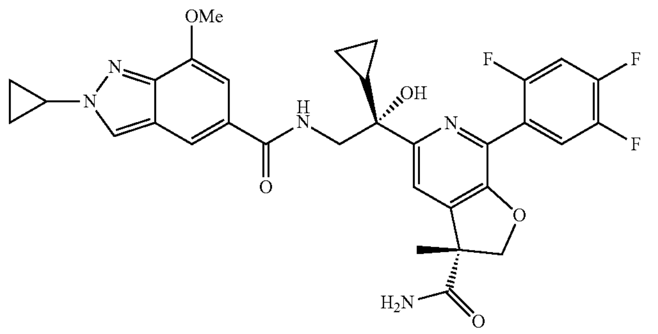 [SMILES: COc1cc(C(=O)NC[C@](O)(c2cc3c(c(-c4cc(F)c(F)cc4F)n2)OC[C@]3(C)C(N)=O)C2CC2)cc2cn(C3CC3)nc12] | 622.31 |
| 1146 | 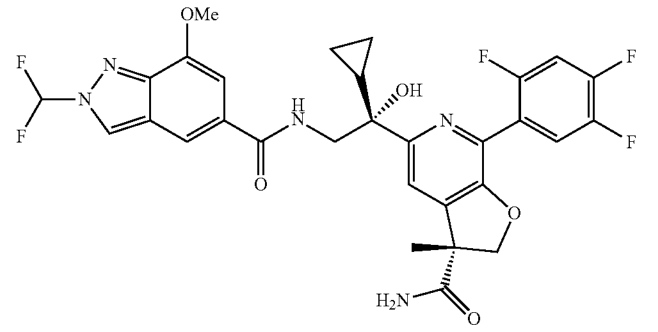 [SMILES: COc1cc(C(=O)NC[C@](O)(c2cc3c(c(-c4cc(F)c(F)cc4F)n2)OC[C@]3(C)C(N)=O)C2CC2)cc2cn(C(F)F)nc12] | 632.28 |
| 1147 | 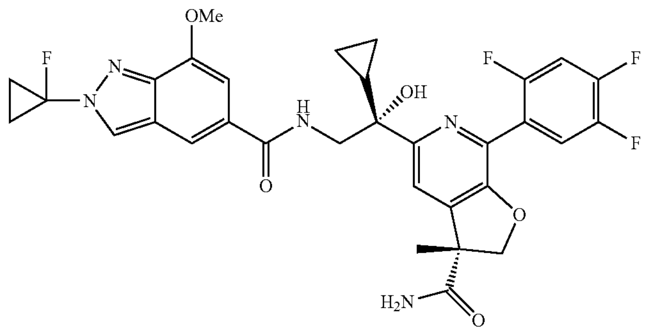 [SMILES: COc1cc(C(=O)NC[C@](O)(c2cc3c(c(-c4cc(F)c(F)cc4F)n2)OC[C@]3(C)C(N)=O)C2CC2)cc2cn(C3(F)CC3)nc12] | 640.30 |
| 1148 | 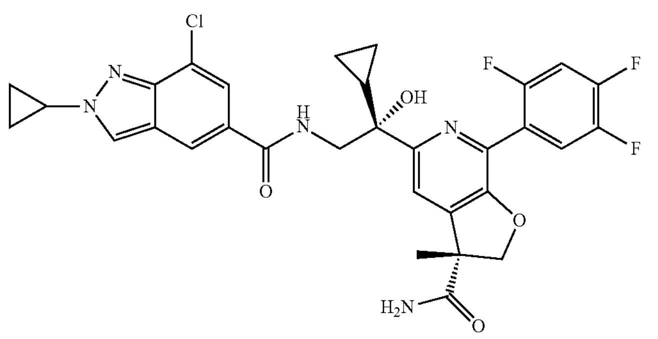 [SMILES: C[C@]1(C(N)=O)COc2c1cc([C@@](O)(CNC(=O)c1cc(Cl)c3nn(C4CC4)cc3c1)C1CC1)nc2-c1cc(F)c(F)cc1F] | 626.26 |

TABLE 8-continued
| Example | Structure | MS+ m/z |
| --- | --- | --- |
| 1149 | 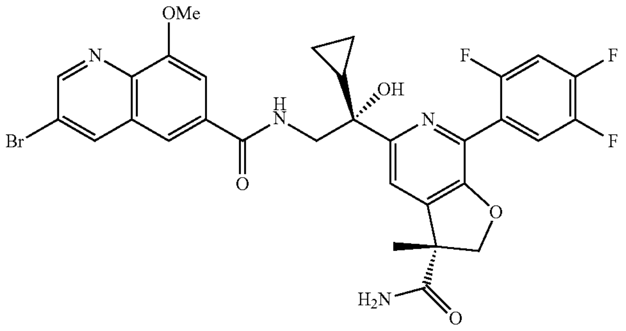 [SMILES: COc1cc(C(=O)NC[C@](O)(c2cc3c(c(-c4cc(F)c(F)cc4F)n2)OC[C@]3(C)C(N)=O)C2CC2)cc2cc(Br)cnc12] | 671.16 |
| 1150 | 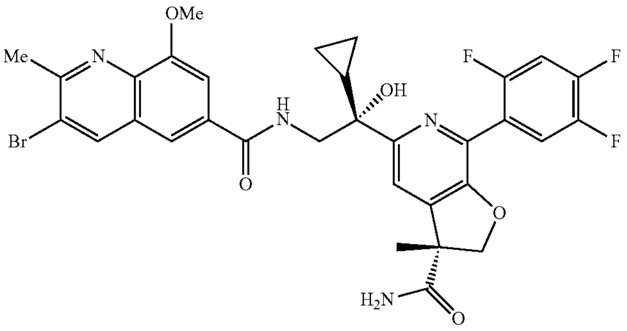 | 685.17 |
| 1151 | 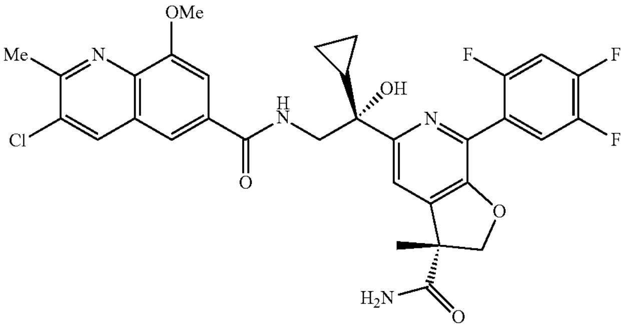 [SMILES: COc1cc(C(=O)NC[C@](O)(c2cc3c(c(-c4cc(F)c(F)cc4F)n2)OC[C@]3(C)C(N)=O)C2CC2)cc2cc(Cl)c(C)nc12] | 641.23 |
| 1152 | 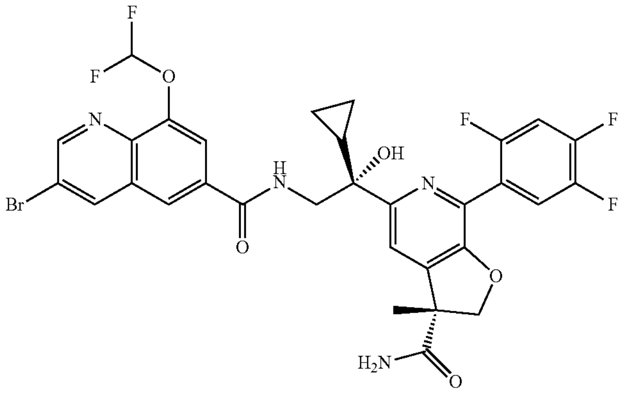 [SMILES: C[C@]1(C(N)=O)COc2c1cc([C@@](O)(CNC(=O)c1cc(OC(F)F)c3ncc(Br)cc3c1)C1CC1)nc2-c1cc(F)c(F)cc1F] | 643.26 |

TABLE 8-continued
| Example | Structure | MS⁺ m/z |
| --- | --- | --- |
| 1153 | 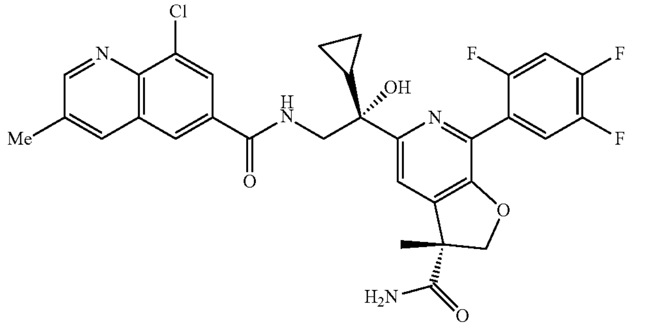 [SMILES: Cc1cnc2c(Cl)cc(C(=O)NC[C@](O)(c3cc4c(c(-c5cc(F)c(F)cc5F)n3)OC[C@]4(C)C(N)=O)C3CC3)cc2c1] | 611.25 |
| 1154 | 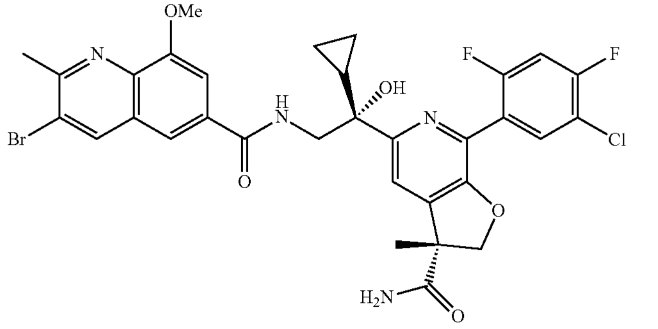 [SMILES: COc1cc(C(=O)NC[C@](O)(c2cc3c(c(-c4cc(Cl)c(F)cc4F)n2)OC[C@]3(C)C(N)=O)C2CC2)cc2cc(Br)c(C)nc12] | 701.16 |
| 1155 | 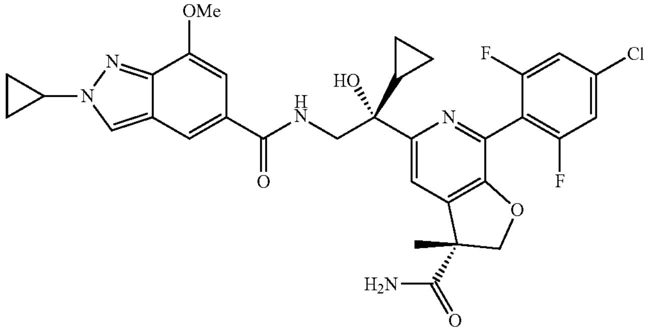 [SMILES: COc1cc(C(=O)NC[C@](O)(c2cc3c(c(-c4c(F)cc(Cl)cc4F)n2)OC[C@]3(C)C(N)=O)C2CC2)cc2cn(C3CC3)nc12] | 638.19 |
| 1156 | 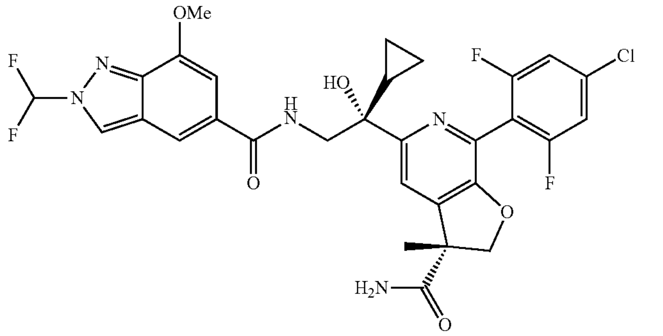 [SMILES: COc1cc(C(=O)NC[C@](O)(c2cc3c(c(-c4c(F)cc(Cl)cc4F)n2)OC[C@]3(C)C(N)=O)C2CC2)cc2cn(C(F)F)nc12] | 648.25 |

TABLE 8-continued
| Example | Structure | MS+ m/z |
| --- | --- | --- |
| 1157 | 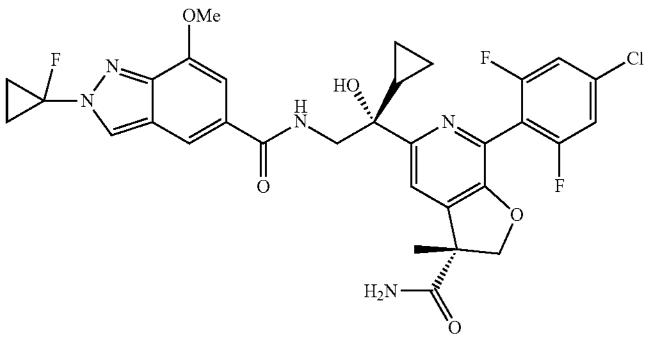 [SMILES: COc1cc(C(=O)NC[C@](O)(c2cc3c(c(-c4c(F)cc(Cl)cc4F)n2)OC[C@]3(C)C(N)=O)C2CC2)cc2cn(C3(F)CC3)nc12] | 656.18 |
| 1158 | 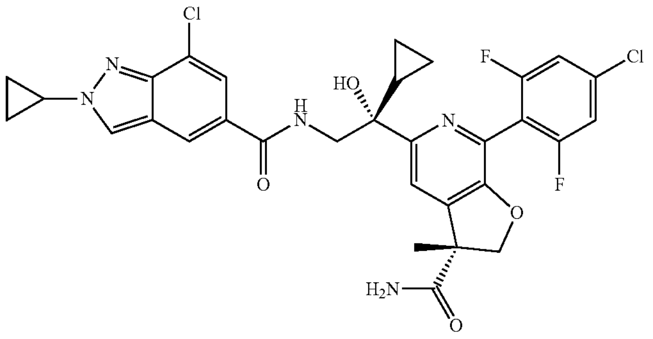 [SMILES: C[C@]1(C(N)=O)COc2c1cc([C@@](O)(CNC(=O)c1cc(Cl)c3nn(C4CC4)cc3c1)C1CC1)nc2-c1c(F)cc(Cl)cc1F] | 642.14 |
| 1159 | 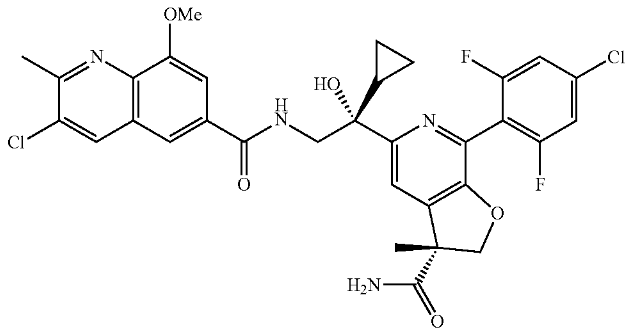 [SMILES: COc1cc(C(=O)NC[C@](O)(c2cc3c(c(-c4c(F)cc(Cl)cc4F)n2)OC[C@]3(C)C(N)=O)C2CC2)cc2cc(Cl)c(C)nc12] | 657.14 |
| 1160 | 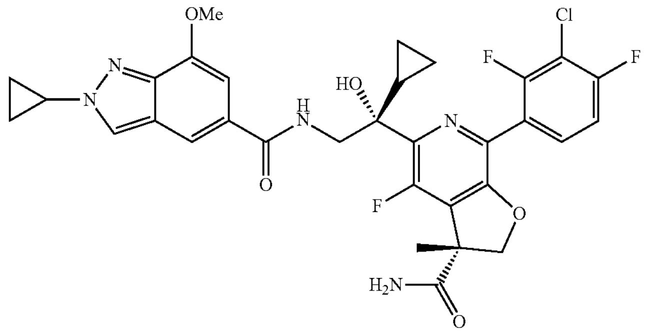 [SMILES: COc1cc(C(=O)NC[C@](O)(c2nc(-c3ccc(F)c(Cl)c3F)c3c(c2F)[C@@](C)(C(N)=O)CO3)C2CC2)cc2cn(C3CC3)nc12] | 656.18 |

TABLE 8-continued
| Example | Structure | MS⁺ m/z |
|---|---|---|
| 1161 | 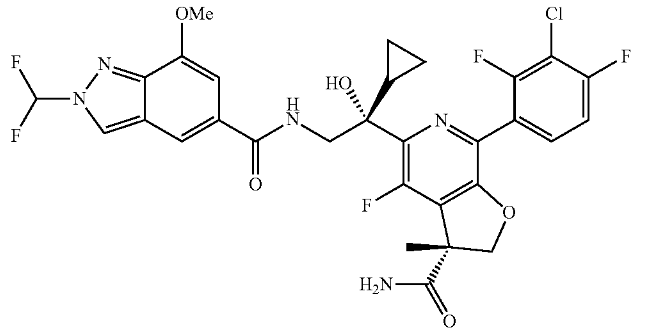 [SMILES: COc1cc(C(=O)NC[C@](O)(c2nc(-c3ccc(F)c(Cl)c3F)c3c(c2F)[C@@](C)(C(N)=O)CO3)C2CC2)cc2cn(C(F)F)nc12] | 666.14 |
| 1162 | 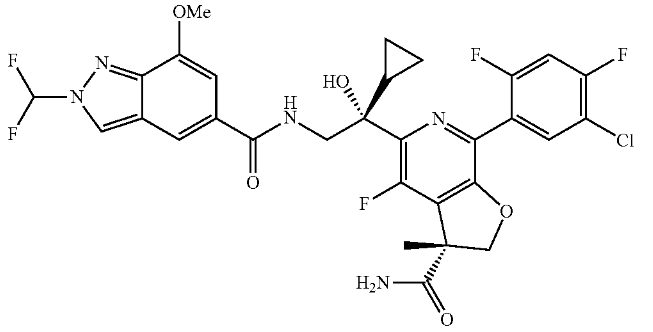 [SMILES: COc1cc(C(=O)NC[C@](O)(c2nc(-c3cc(Cl)c(F)cc3F)c3c(c2F)[C@@](C)(C(N)=O)CO3)C2CC2)cc2cn(C(F)F)nc12] | 666.14 |
| 1163 | 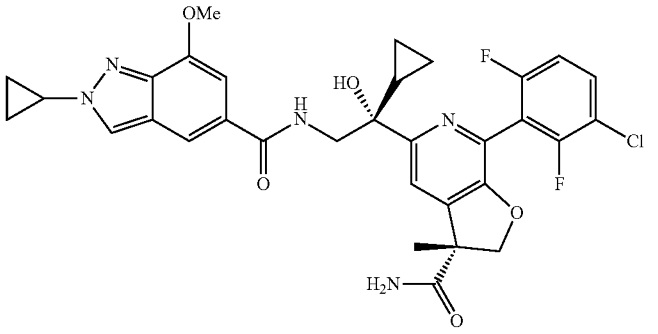 [SMILES: COc1cc(C(=O)NC[C@](O)(c2cc3c(c(-c4c(F)ccc(Cl)c4F)n2)OC[C@]3(C)C(N)=O)C2CC2)cc2cn(C3CC3)nc12] | 638.19 |
| 1164 | 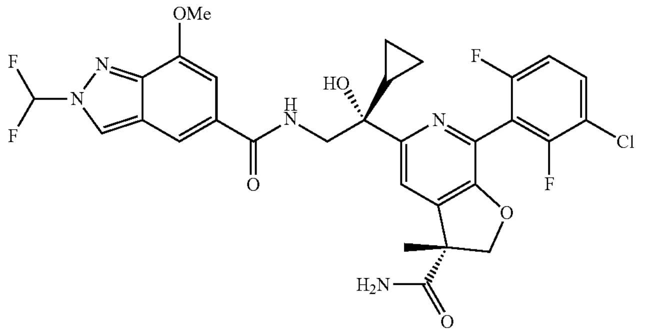 [SMILES: COc1cc(C(=O)NC[C@](O)(c2cc3c(c(-c4c(F)ccc(Cl)c4F)n2)OC[C@]3(C)C(N)=O)C2CC2)cc2cn(C(F)F)nc12] | 648.15 |

TABLE 8-continued
| Example | Structure | MS+ m/z |
|---|---|---|
| 1165 | 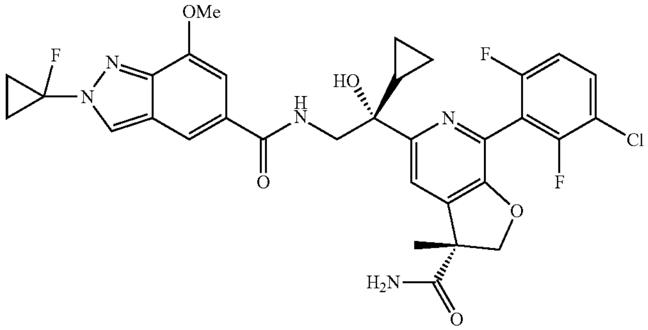 [SMILES: COc1cc(C(=O)NC[C@](O)(c2cc3c(c(-c4c(F)ccc(Cl)c4F)n2)OC[C@]3(C)C(N)=O)C2CC2)cc2cn(C3(F)CC3)nc12] | 656.18 |
| 1166 | 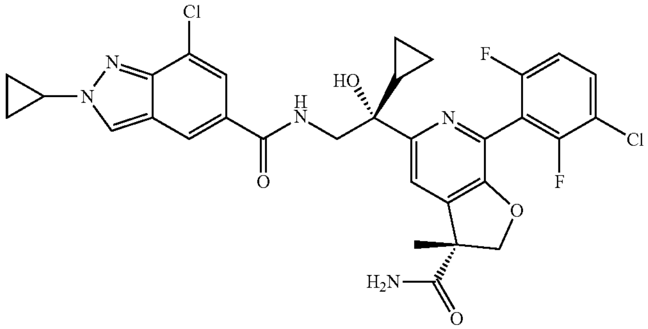 | 642.14 |
| 1167 | 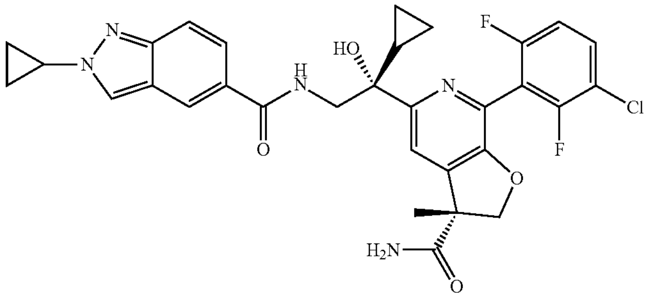 [SMILES: C[C@]1(C(N)=O)COc2c1cc([C@@](O)(CNC(=O)c1ccc3nn(C4CC4)cc3c1)C1CC1)nc2-c1c(F)ccc(Cl)c1F] | 608.18 |
| 1168 | 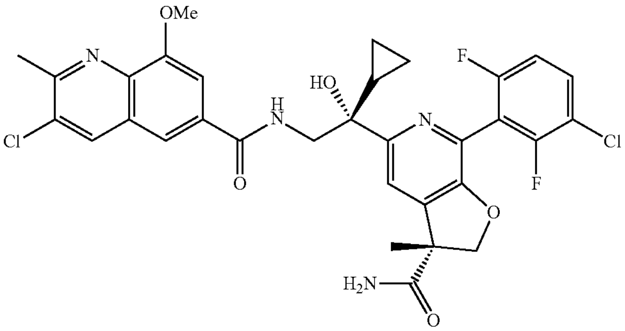 | 657.14 |

TABLE 8-continued
| Example | Structure | MS+ m/z |
|---|---|---|
| 1169 | 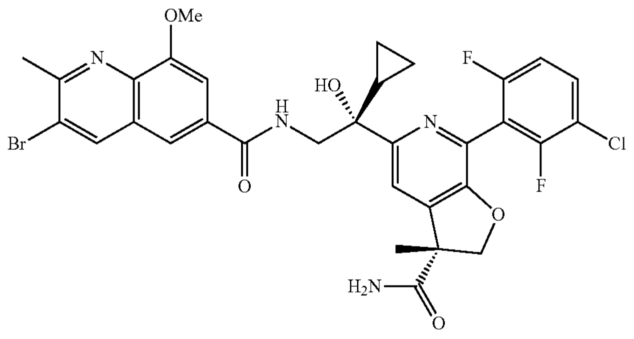 [SMILES: COc1cc(C(=O)NC[C@](O)(c2cc3c(c(-c4c(F)ccc(Cl)c4F)n2)OC[C@]3(C)C(N)=O)C2CC2)cc2cc(Cl)c(C)nc12] | 701.09 |
| 1170 | 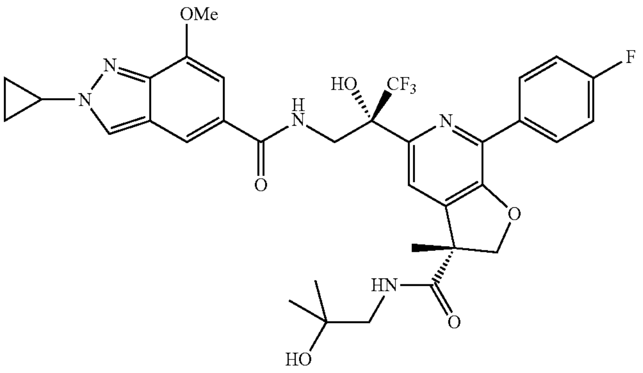 [SMILES: COc1cc(C(=O)NC[C@](O)(c2cc3c(c(-c4ccc(F)cc4)n2)OC[C@]3(C)C(=O)NCC(C)(C)O)C(F)(F)F)cc2cn(C3CC3)nc12] | 686.25 |
| 1171 | 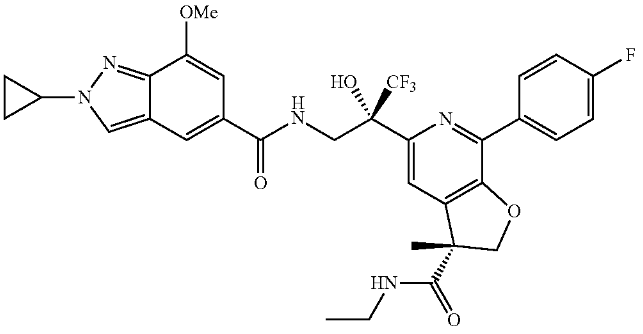 [SMILES: CCNC(=O)[C@@]1(C)COc2c1cc([C@@](O)(CNC(=O)c1cc(OC)c3nn(C4CC4)cc3c1)C(F)(F)F)nc2-c1ccc(F)cc1] | 642.22 |
| 1172 | 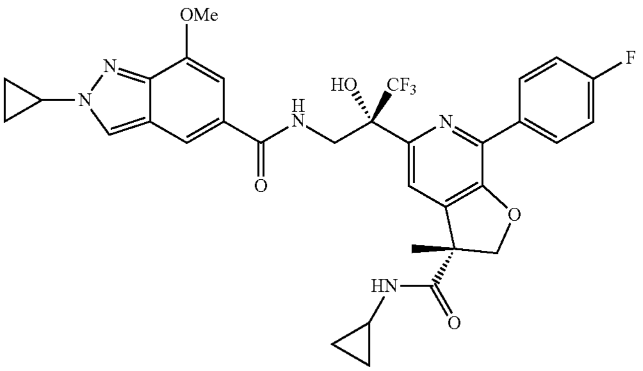 [SMILES: COc1cc(C(=O)NC[C@](O)(c2cc3c(c(-c4ccc(F)cc4)n2)OC[C@]3(C)C(=O)NC2CC2)C(F)(F)F)cc2cn(C3CC3)nc12] | 654.22 |

TABLE 8-continued
| Example | Structure | MS⁺ m/z |
| --- | --- | --- |
| 1173 | 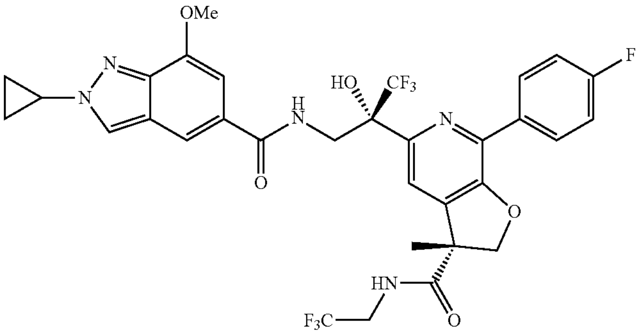 [SMILES: COc1cc(C(=O)NC[C@](O)(c2cc3c(c(-c4ccc(F)cc4)n2)OC[C@]3(C)C(=O)NCC(F)(F)F)C(F)(F)F)cc2cn(C3CC3)nc12] | 696.19 |
| 1174 | 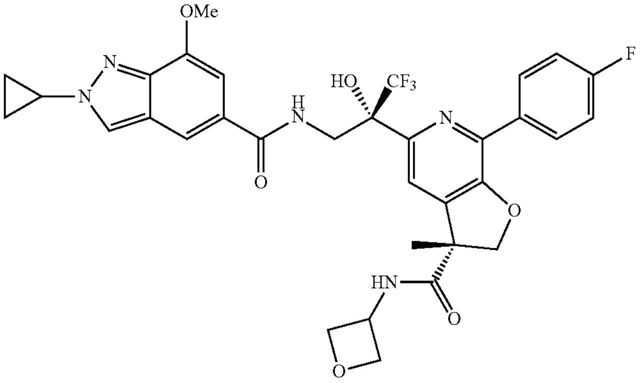 [SMILES: COc1cc(C(=O)NC[C@](O)(c2cc3c(c(-c4ccc(F)cc4)n2)OC[C@]3(C)C(=O)NC2COC2)C(F)(F)F)cc2cn(C3CC3)nc12] | 670.22 |
| 1175 | 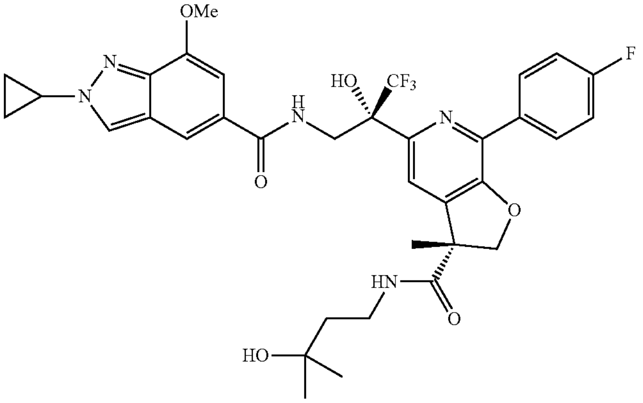 [SMILES: COc1cc(C(=O)NC[C@](O)(c2cc3c(c(-c4ccc(F)cc4)n2)OC[C@]3(C)C(=O)NCCC(C)(C)O)C(F)(F)F)cc2cn(C3CC3)nc12] | 700.26 |
| 1176 | 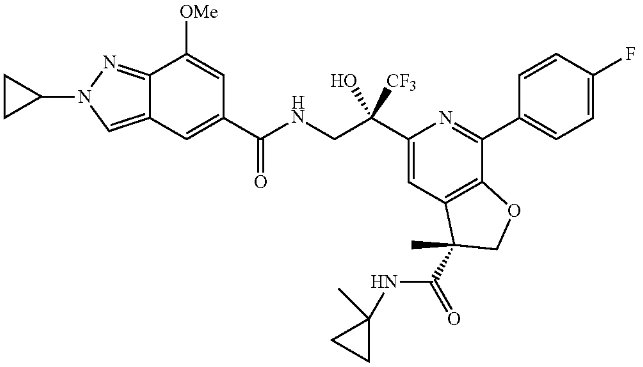 [SMILES: COc1cc(C(=O)NC[C@](O)(c2cc3c(c(-c4ccc(F)cc4)n2)OC[C@]3(C)C(=O)NC2(C)CC2)C(F)(F)F)cc2cn(C3CC3)nc12] | 668.24 |

TABLE 8-continued
| Example | Structure | MS⁺ m/z |
|---|---|---|
| 1177 | 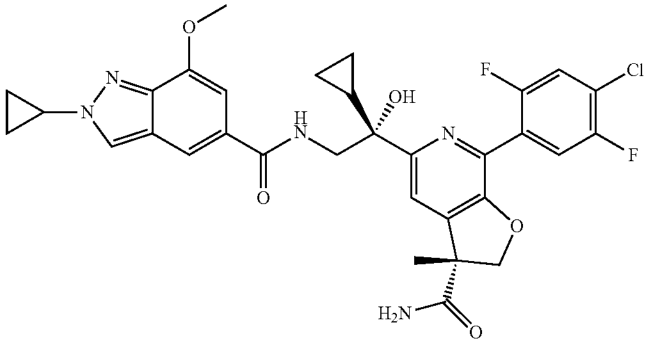 [SMILES: COc1cc(C(=O)NC[C@](O)(c2cc3c(c(-c4cc(F)c(Cl)cc4F)n2)OC[C@]3(C)C(N)=O)C2CC2)cc2cn(C3CC3)nc12] | 638.23 |
| 1178 | 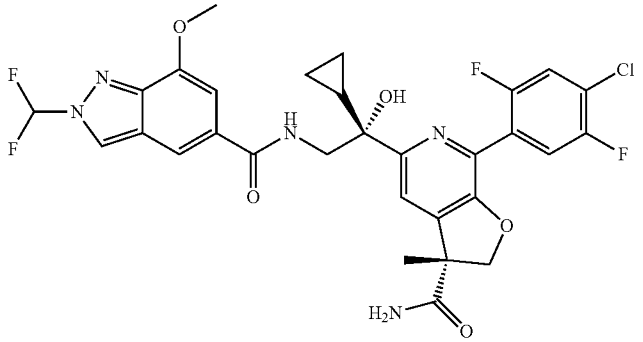 [SMILES: COc1cc(C(=O)NC[C@](O)(c2cc3c(c(-c4cc(F)c(Cl)cc4F)n2)OC[C@]3(C)C(N)=O)C2CC2)cc2cn(C(F)F)nc12] | 648.20 |
| 1179 | 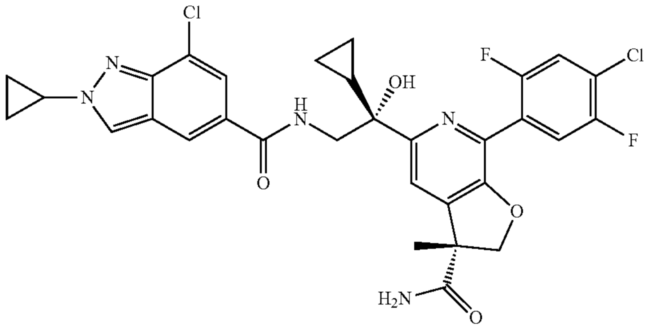 [SMILES: C[C@]1(C(N)=O)COc2c1cc([C@@](O)(CNC(=O)c1cc(Cl)c3nn(C4CC4)cc3c1)C1CC1)nc2-c1cc(F)c(Cl)cc1F] | 642.18 |
| 1180 | 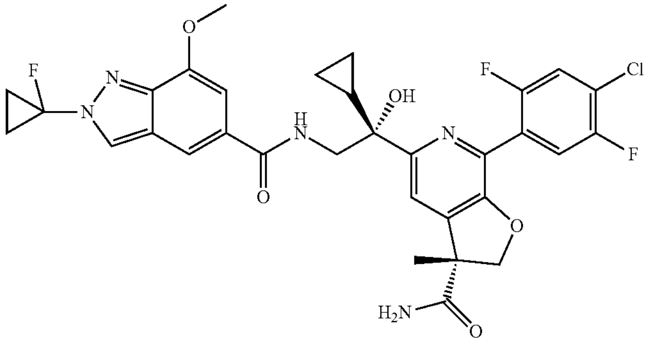 [SMILES: COc1cc(C(=O)NC[C@](O)(c2cc3c(c(-c4cc(F)c(Cl)cc4F)n2)OC[C@]3(C)C(N)=O)C2CC2)cc2cn(C3(F)CC3)nc12] | 656.23 |

TABLE 8-continued
| Example | Structure | MS+ m/z |
|---|---|---|
| 1181 | 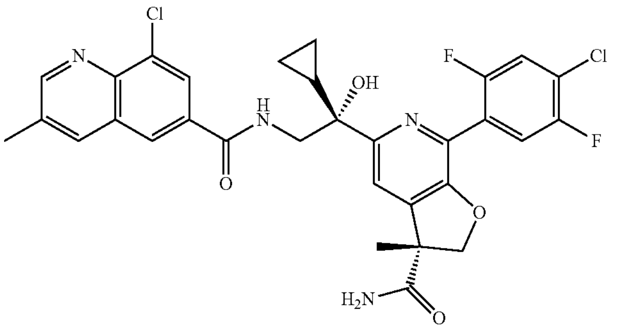 [SMILES: Cc1cnc2c(Cl)cc(C(=O)NC[C@](O)(c3cc4c(c(-c5cc(F)c(Cl)cc5F)n3)OC[C@]4(C)C(N)=O)C3CC3)cc2c1] | 627.12 |
| 1182 | 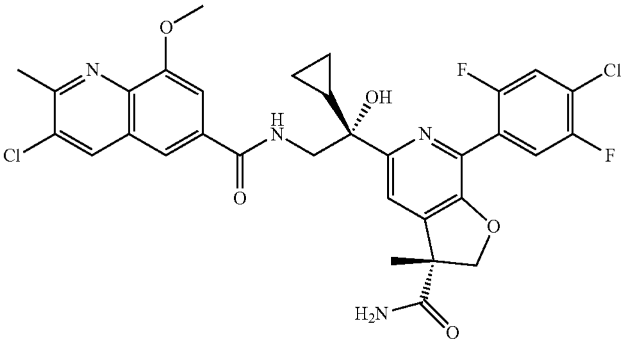 [SMILES: COc1cc(C(=O)NC[C@](O)(c2cc3c(c(-c4cc(F)c(Cl)cc4F)n2)OC[C@]3(C)C(N)=O)C2CC2)cc2cc(Cl)c(C)nc12] | 657.15 |
| 1183 | 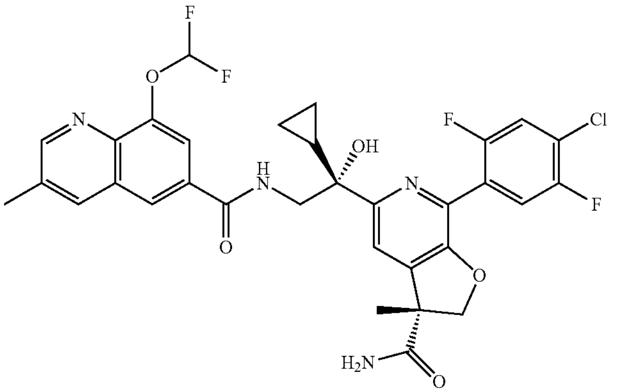 [SMILES: Cc1cnc2c(OC(F)F)cc(C(=O)NC[C@](O)(c3cc4c(c(-c5cc(F)c(Cl)cc5F)n3)OC[C@]4(C)C(N)=O)C3CC3)cc2c1] | 659.19 |
| 1184 | 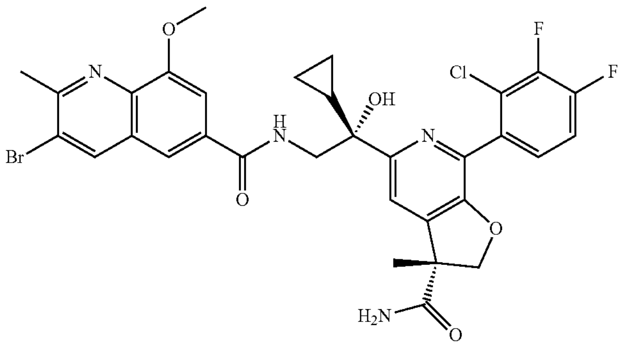 [SMILES: COc1cc(C(=O)NC[C@](O)(c2cc3c(c(-c4ccc(F)c(F)c4Cl)n2)OC[C@]3(C)C(N)=O)C2CC2)cc2cc(Br)c(C)nc12] | 701.08 |

TABLE 8-continued
| Example | Structure | MS+ m/z |
|---|---|---|
| 1185 | 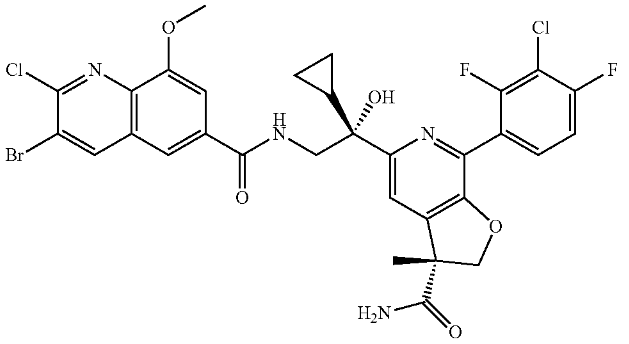 | 721.04 |
| 1186 | 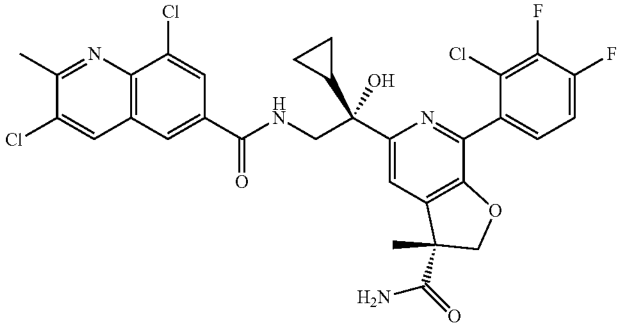 [SMILES: Cc1nc2c(Cl)cc(C(=O)NC[C@](O)(c3cc4c(c(-c5ccc(F)c(F)c5Cl)n3)OC[C@]4(C)C(N)=O)C3CC3)cc2cc1Cl] | 661.27 |
| 1187 | 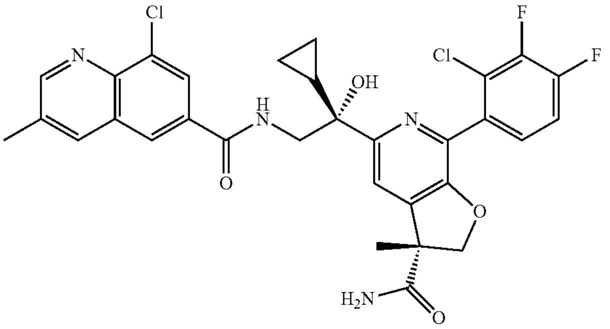 [SMILES: Cc1cnc2c(Cl)cc(C(=O)NC[C@](O)(c3cc4c(c(-c5ccc(F)c(F)c5Cl)n3)OC[C@]4(C)C(N)=O)C3CC3)cc2c1] | 627.23 |
| 1188 | 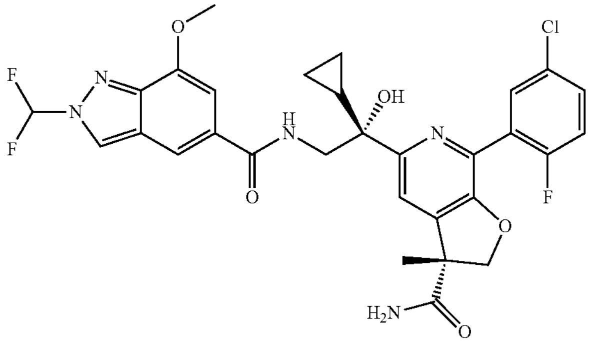 [SMILES: COc1cc(C(=O)NC[C@](O)(c2cc3c(c(-c4cc(Cl)ccc4F)n2)OC[C@]3(C)C(N)=O)C2CC2)cc2cn(C(F)F)nc12] | 630.23 |

TABLE 8-continued
| Example | Structure | MS+ m/z |
|---|---|---|
| 1189 | 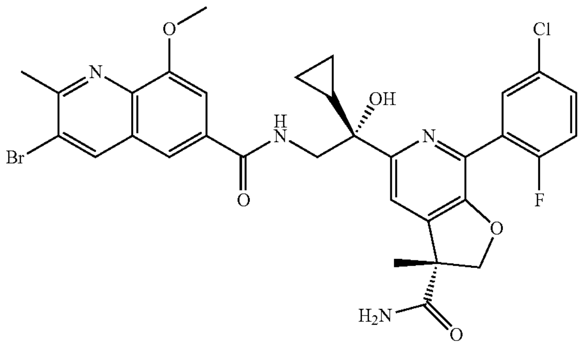 [SMILES: COc1cc(C(=O)NC[C@](O)(c2cc3c(c(-c4cc(Cl)ccc4F)n2)OC[C@]3(C)C(N)=O)C2CC2)cc2cc(Br)c(C)nc12] | 683.06 |
| 1190 | 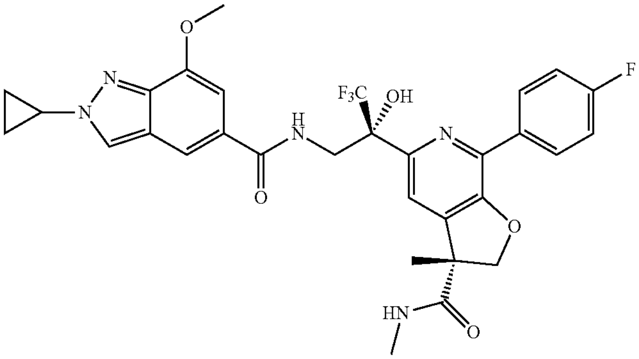 [SMILES: CNC(=O)[C@@]1(C)COc2c1cc([C@@](O)(CNC(=O)c1cc(OC)c3nn(C4CC4)cc3c1)C(F)(F)F)nc2-c1ccc(F)cc1] | 628.23 |
| 1191 | 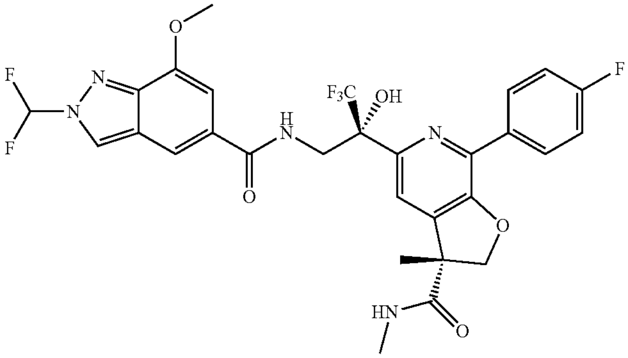 [SMILES: CNC(=O)[C@@]1(C)COc2c1cc([C@@](O)(CNC(=O)c1cc(OC)c3nn(C(F)F)cc3c1)C(F)(F)F)nc2-c1ccc(F)cc1] | 638.23 |
| 1192 | 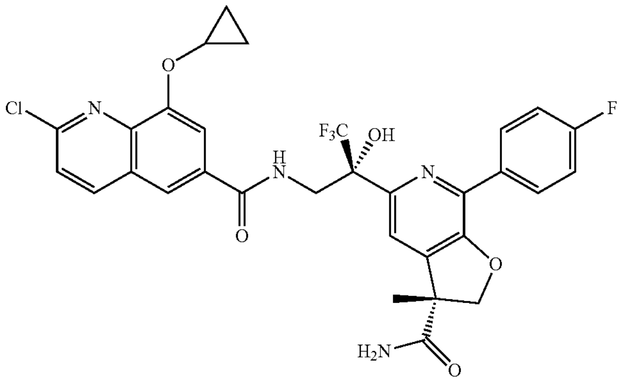 [SMILES: C[C@]1(C(N)=O)COc2c1cc([C@@](O)(CNC(=O)c1cc(OC3CC3)c3nc(Cl)ccc3c1)C(F)(F)F)nc2-c1ccc(F)cc1] | 645.24 |

TABLE 8-continued
| Example | Structure | MS+ m/z |
|---|---|---|
| 1193 | 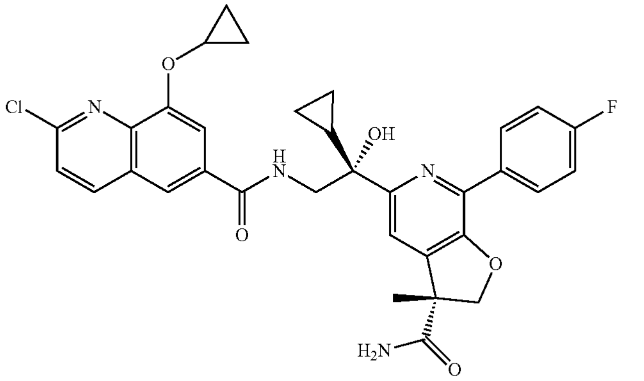 [SMILES: C[C@]1(C(N)=O)COc2c1cc([C@@](O)(CNC(=O)c1cc(OC3CC3)c3nc(Cl)ccc3c1)C1CC1)nc2-c1ccc(F)cc1] | 617.25 |
| 1194 | 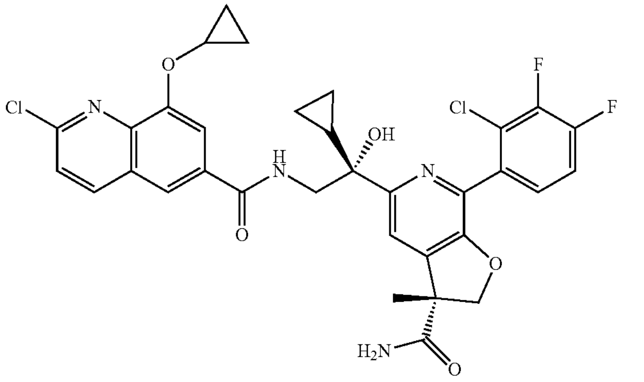 [SMILES: C[C@]1(C(N)=O)COc2c1cc([C@@](O)(CNC(=O)c1cc(OC3CC3)c3nc(Cl)ccc3c1)C1CC1)nc2-c1ccc(F)c(F)c1Cl] | 669.15 |
| 1195 | 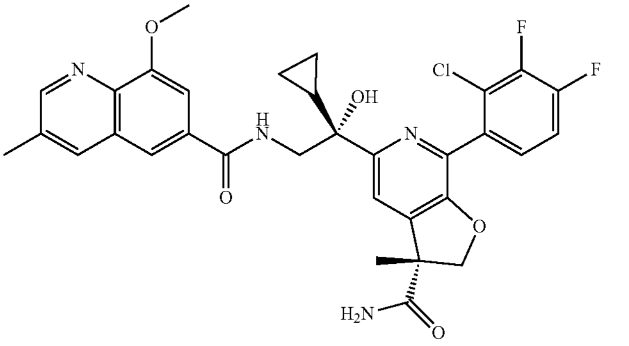 [SMILES: COc1cc(C(=O)NC[C@](O)(c2cc3c(c(-c4ccc(F)c(F)c4Cl)n2)OC[C@]3(C)C(N)=O)C2CC2)cc2cc(C)cnc12] | 623.38 |
| 1196 | 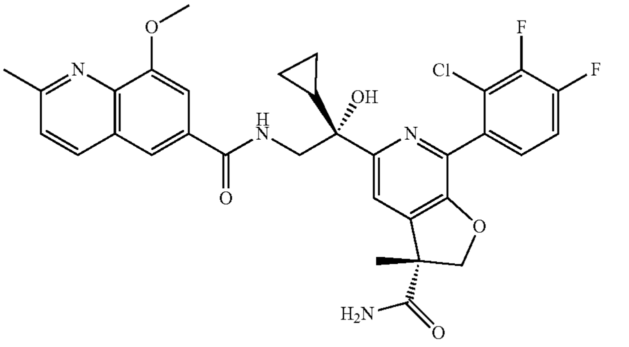 [SMILES: COc1cc(C(=O)NC[C@](O)(c2cc3c(c(-c4ccc(F)c(F)c4Cl)n2)OC[C@]3(C)C(N)=O)C2CC2)cc2ccc(C)nc12] | 623.39 |

TABLE 8-continued
| Example | Structure | MS⁺ m/z |
|---|---|---|
| 1197 | 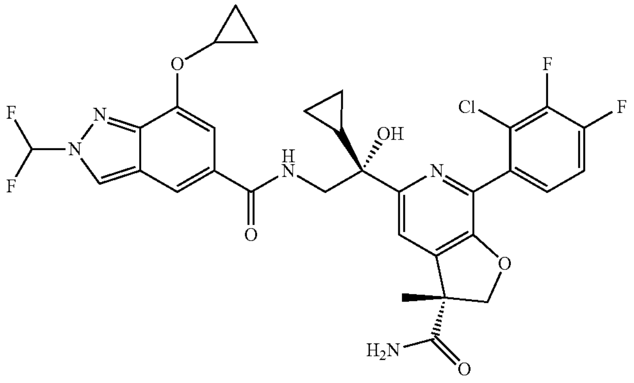 [SMILES: C[C@]1(C(N)=O)COc2c1cc([C@@](O)(CNC(=O)c1cc(OC3CC3)c3nn(C(F)F)cc3c1)C1CC1)nc2-c1ccc(F)c(F)c1Cl] | 674.27 |
| 1198 | 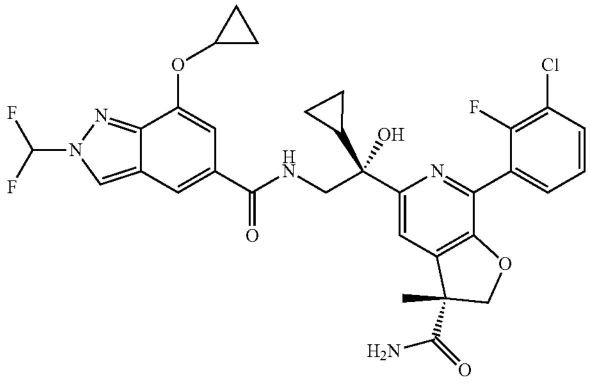 [SMILES: C[C@]1(C(N)=O)COc2c1cc([C@@](O)(CNC(=O)c1cc(OC3CC3)c3nn(C(F)F)cc3c1)C1CC1)nc2-c1cccc(Cl)c1F] | 656.20 |
| 1199 | 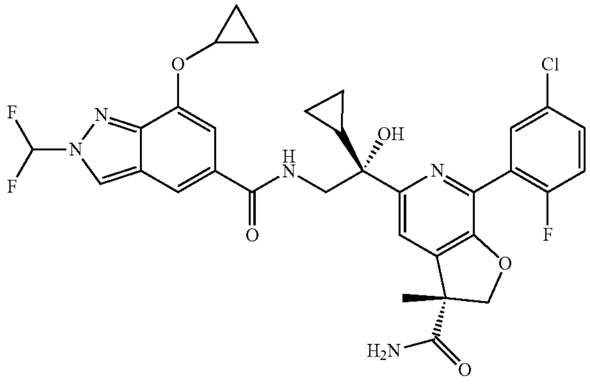 [SMILES: C[C@]1(C(N)=O)COc2c1cc([C@@](O)(CNC(=O)c1cc(OC3CC3)c3nn(C(F)F)cc3c1)C1CC1)nc2-c1cc(Cl)ccc1F] | 656.20 |
| 1200 | 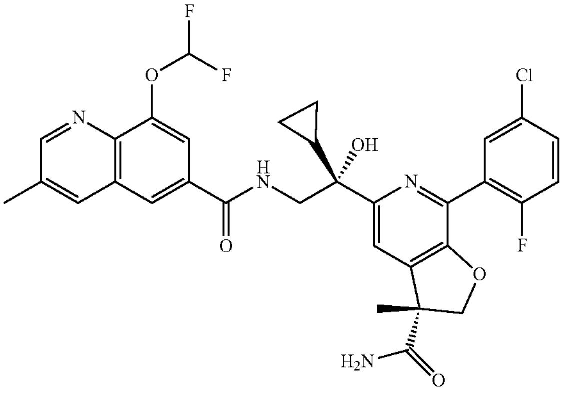 [SMILES: Cc1cnc2c(OC(F)F)cc(C(=O)NC[C@](O)(c3cc4c(c(-c5cc(Cl)ccc5F)n3)OC[C@]4(C)C(N)=O)C3CC3)cc2c1] | 641.19 |

TABLE 8-continued
| Example | Structure | MS+ m/z |
| --- | --- | --- |
| 1201 | 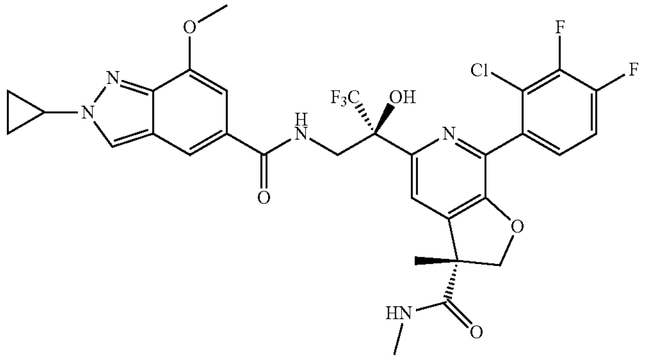 [SMILES: CNC(=O)[C@@]1(C)COc2c1cc([C@](O)(CNC(=O)c1cc(OC)c3nn(C4CC4)cc3c1)C(F)(F)F)nc2-c1ccc(F)c(F)c1Cl] | 680.14 |
| 1202 | 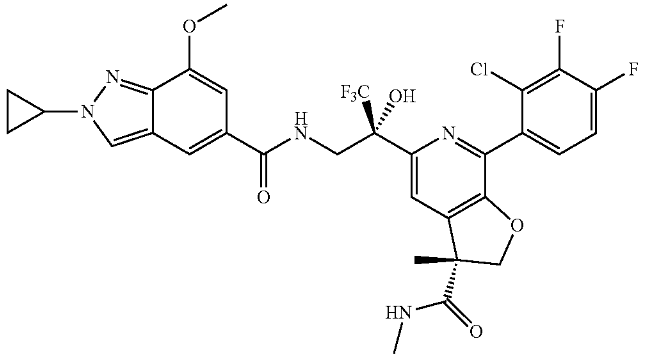 [SMILES: CNC(=O)[C@@]1(C)COc2c1cc([C@@](O)(CNC(=O)c1cc(OC)c3nn(C4CC4)cc3c1)C(F)(F)F)nc2-c1ccc(F)c(F)c1Cl] | 680.14 |
| 1203 | 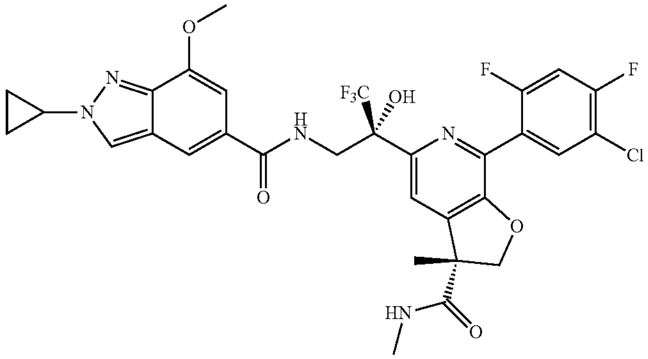 [SMILES: CNC(=O)[C@@]1(C)COc2c1cc([C@@](O)(CNC(=O)c1cc(OC)c3nn(C4CC4)cc3c1)C(F)(F)F)nc2-c1cc(Cl)c(F)cc1F] | 680.16 |
| 1204 | 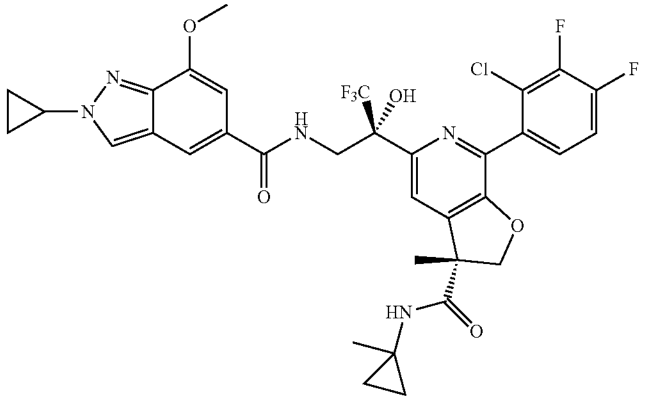 [SMILES: COc1cc(C(=O)NC[C@](O)(c2cc3c(c(-c4ccc(F)c(F)c4Cl)n2)OC[C@]3(C)C(=O)NC2(C)CC2)C(F)(F)F)cc2cn(C3CC3)nc12] | 720.07 |

TABLE 8-continued
| Example | Structure | MS+ m/z |
|---|---|---|
| 1205 | 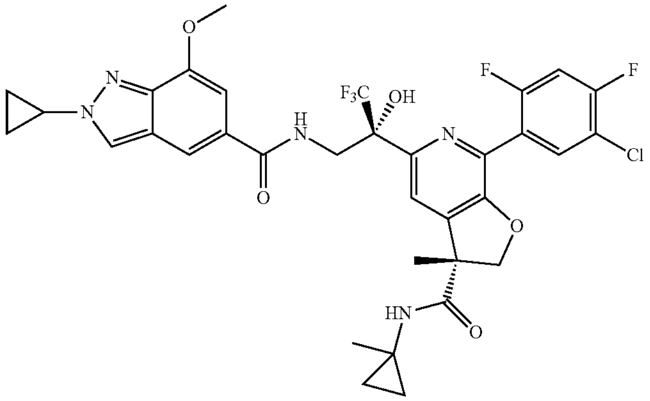 [SMILES: COc1cc(C(=O)NC[C@](O)(c2cc3c(c(-c4cc(Cl)c(F)cc4F)n2)OC[C@]3(C)C(=O)NC2(C)CC2)C(F)(F)F)cc2cn(C3CC3)nc12] | 720.19 |
| 1206 | 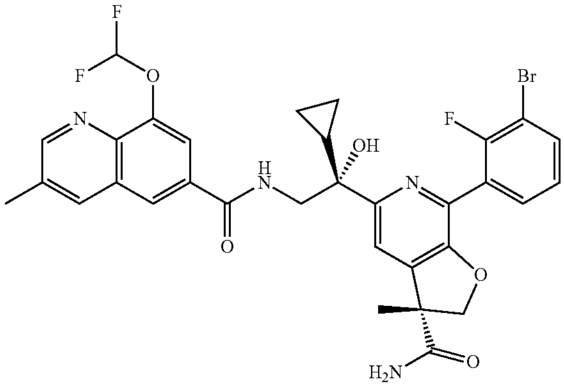 [SMILES: Cc1cnc2c(OC(F)F)cc(C(=O)NC[C@](O)(c3cc4c(c(-c5cccc(Br)c5F)n3)OC[C@]4(C)C(N)=O)C3CC3)cc2c1] | 686.99 |
| 1207 | 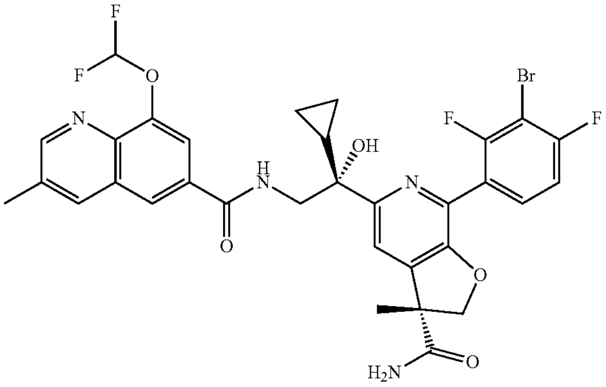 | 704.97 |
| 1208 | 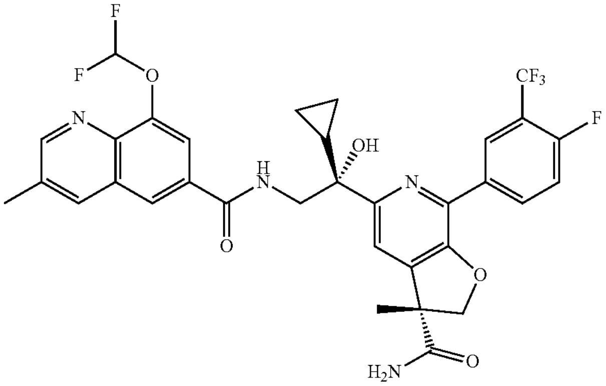 [SMILES: Cc1cnc2c(OC(F)F)cc(C(=O)NC[C@](O)(c3cc4c(c(-c5ccc(F)c(C(F)(F)F)c5)n3)OC[C@]4(C)C(N)=O)C3CC3)cc2c1] | 675.20 |

TABLE 8-continued
| Example | Structure | MS+ m/z |
| --- | --- | --- |
| 1209 | 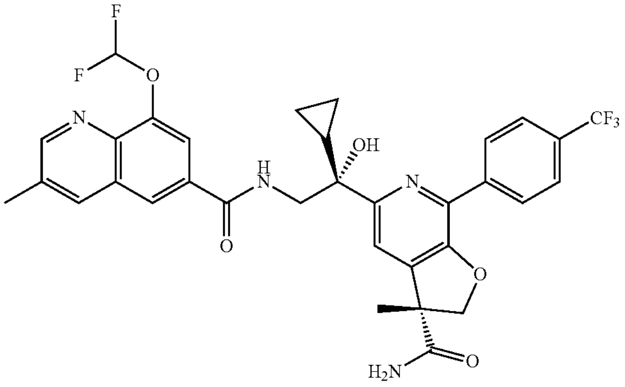 [SMILES: Cc1cnc2c(OC(F)F)cc(C(=O)NC[C@](O)(c3cc4c(c(-c5ccc(C(F)(F)F)cc5)n3)OC[C@]4(C)C(N)=O)C3CC3)cc2c1] | 657.24 |
| 1210 | 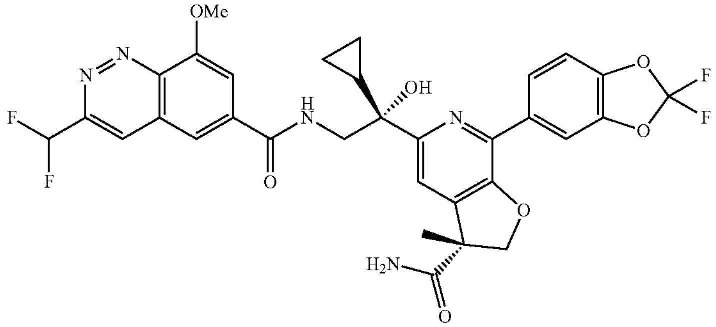 [SMILES: COc1cc(C(=O)NC[C@](O)(c2cc3c(c(-c4ccc5c(c4)OC(F)(F)O5)n2)OC[C@]3(C)C(N)=O)C2CC2)cc2cc(C(F)F)nnc12] | 670.20 |
| 1211 | 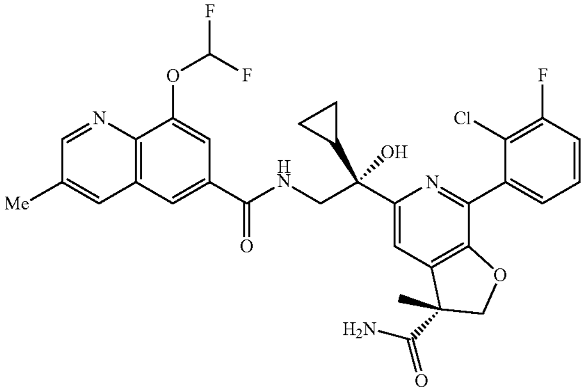 [SMILES: Cc1cnc2c(OC(F)F)cc(C(=O)NC[C@](O)(c3cc4c(c(-c5cccc(F)c5Cl)n3)OC[C@]4(C)C(N)=O)C3CC3)cc2c1] | 641.18 |
| 1212 | 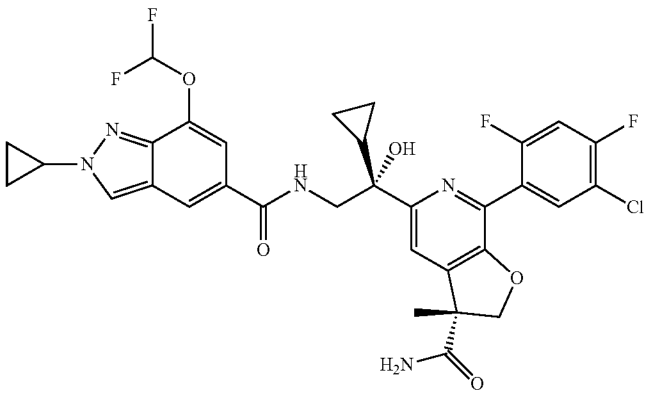 [SMILES: C[C@]1(C(N)=O)COc2c1cc([C@@](O)(CNC(=O)c1cc(OC(F)F)c3nn(C4CC4)cc3c1)C1CC1)nc2-c1cc(Cl)c(F)cc1F] | 674.18 |

TABLE 8-continued
| Example | Structure | MS+ m/z |
|---|---|---|
| 1213 | 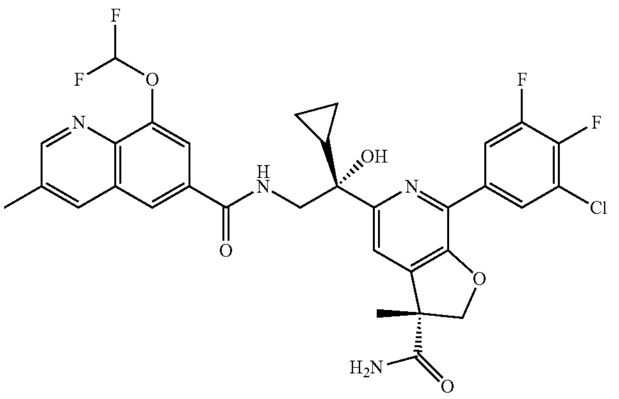 [SMILES: Cc1cnc2c(OC(F)F)cc(C(=O)NC[C@](O)(c3cc4c(c(-c5cc(F)c(F)c(Cl)c5)n3)OC[C@]4(C)C(N)=O)C3CC3)cc2c1] | 659.21 |
| 1214 | 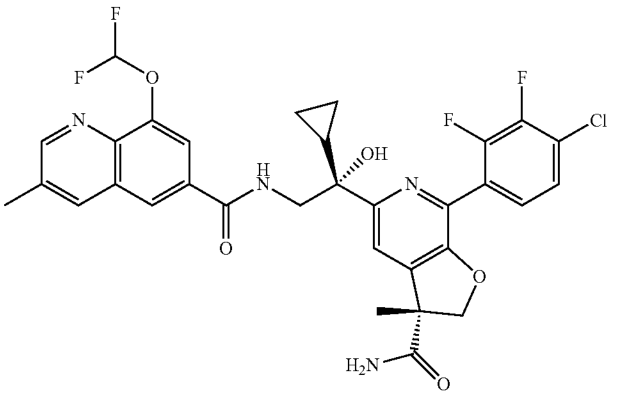 [SMILES: Cc1cnc2c(OC(F)F)cc(C(=O)NC[C@](O)(c3cc4c(c(-c5ccc(Cl)c(F)c5F)n3)OC[C@]4(C)C(N)=O)C3CC3)cc2c1] | 659.18 |
| 1215 | 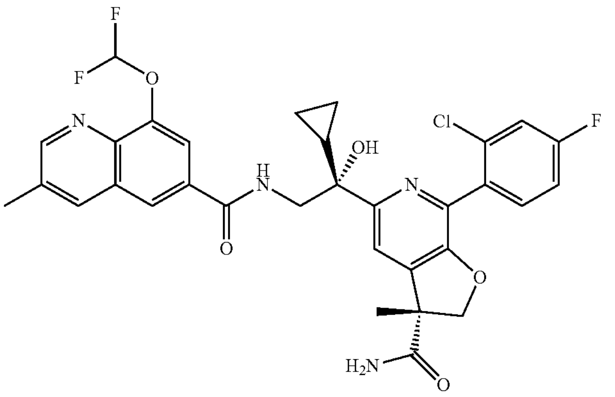 [SMILES: Cc1cnc2c(OC(F)F)cc(C(=O)NC[C@](O)(c3cc4c(c(-c5ccc(F)cc5Cl)n3)OC[C@]4(C)C(N)=O)C3CC3)cc2c1] | 641.20 |
| 1216 | 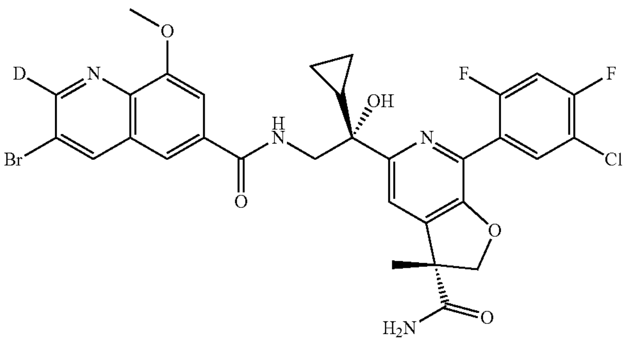 [SMILES: [2H]c1nc2c(OC)cc(C(=O)NC[C@](O)(c3cc4c(c(-c5cc(Cl)c(F)cc5F)n3)OC[C@]4(C)C(N)=O)C3CC3)cc2cc1Br] | 689.94 |

TABLE 8-continued

| Example | Structure | MS+ m/z |
|---|---|---|
| 1217 | 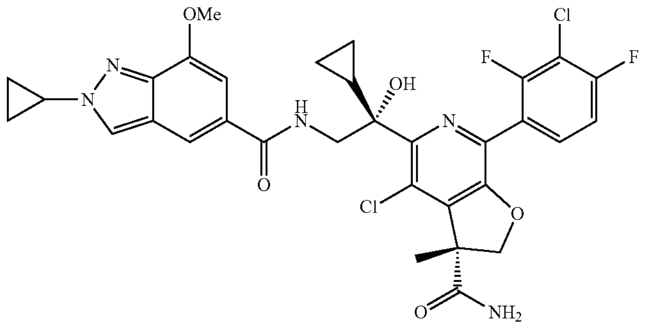 [SMILES: COc1cc(C(=O)NC[C@](O)(c2nc(-c3ccc(F)c(Cl)c3F)c3c(c2Cl)[C@@](C)(C(N)=O)CO3)C2CC2)cc2cn(C3CC3)nc12] | 673.20 |

Intermediate 114

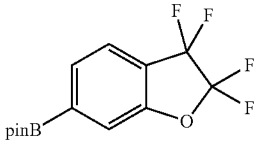

To an oven-dried vial equipped with a stir bar was added 6-bromo-2,2,3,3-tetrafluoro-2,3-dihydrobenzofuran (46 mg, 0.17 mmol), and 1,4-dioxane (0.85 mL). Then, $Pd(dppf)Cl_2$ (13 mg, 0.018 mmol), bis(pinacolato)diboron (65 mg, 0.26 mmol), and potassium acetate (33 mg, 0.34 mmol) were added, and the reaction mixture was sparged with $N_2$ for 5 minutes. The vial was then re-sealed and heated to 90° C. After 3 hours, the reaction mixture was cooled to room temperature and filtered through a pad of silica gel using EtOAc to rinse. The filtrate was concentrated to afford crude boronic ester X as a dark brown oil (50 mg, assuming 100% yield) which was used without further purification.

Intermediate 115

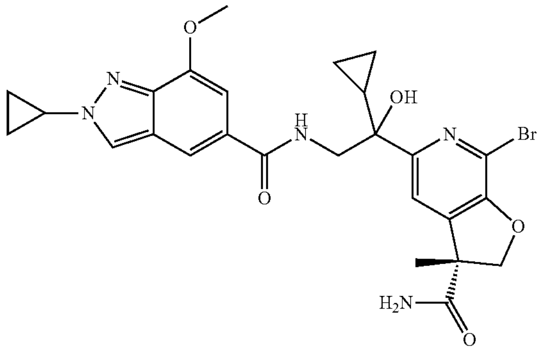 [SMILES: COc1cc(C(=O)NCC(O)(c2cc3c(c(Br)n2)OC[C@]3(C)C(N)=O)C2CC2)cc2cn(C3CC3)nc12]

The following intermediate was prepared in an analogous fashion to Example 890 to afford the desired product as light-yellow solid (1.63 g, 62%) as a mixture of diastereomers. ESI-MS m/z: 572.28 $[M+H]^+$.

The following Table 9 contains examples that were prepared with a similar method to Example 891 using Example 890 and Intermediate 115. If necessary to push conversion, more palladium and boronic acid were added. The majority of compounds were purified and the diastereomers were separated by prep-HPLC ($ACN/H_2O$, 20-90%, 25 min). If reported as a mixture of diastereomers, they were likely not separable by HPLC.

TABLE 9

| Example | Structure | MS+ m/z |
|---|---|---|
| 1218 | 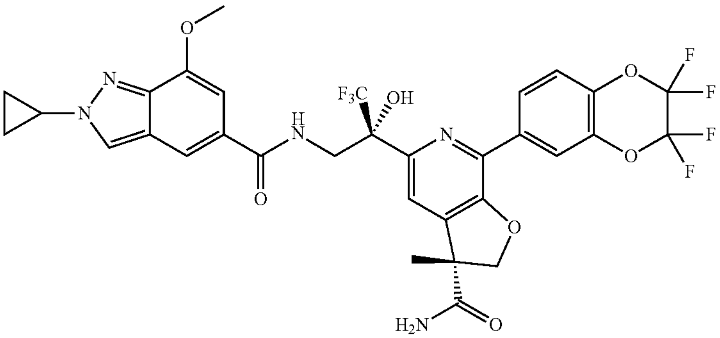 [SMILES: COc1cc(C(=O)NC[C@](O)(c2cc3c(c(-c4ccc5c(c4)OC(F)(F)C(F)(F)O5)n2)OC[C@]3(C)C(N)=O)C(F)(F)F)cc2cn(C3CC3)nc12] | 726.11 |

TABLE 9-continued
| Example | Structure | MS+ m/z |
|---|---|---|
| 1219 | 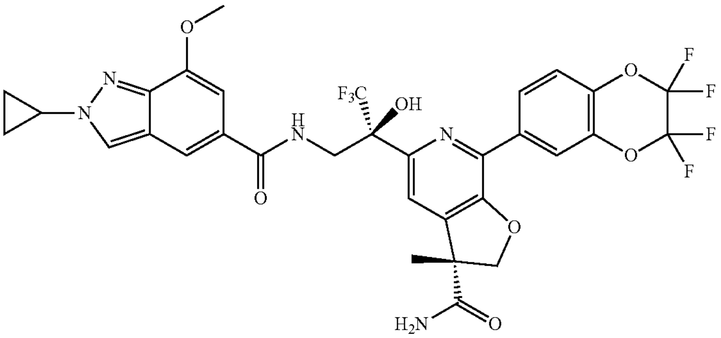 [SMILES: COc1cc(C(=O)NC[C@@](O)(c2cc3c(c(-c4ccc5c(c4)OC(F)(F)C(F)(F)O5)n2)OC[C@]3(C)C(N)=O)C(F)(F)F)cc2cn(C3CC3)nc12] | 726.11 |
| 1220 | 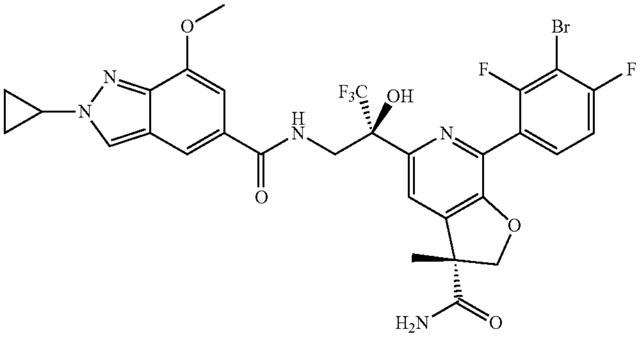 [SMILES: COc1cc(C(=O)NC[C@@](O)(c2cc3c(c(-c4ccc(F)c(Br)c4F)n2)OC[C@]3(C)C(N)=O)C(F)(F)F)cc2cn(C3CC3)nc12] | 712.18 |
| 1221 | 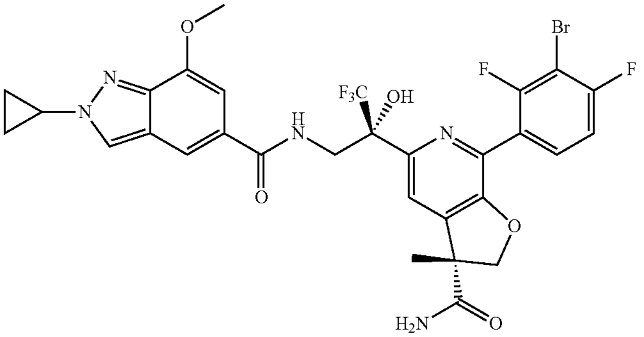 [SMILES: COc1cc(C(=O)NC[C@](O)(c2cc3c(c(-c4ccc(F)c(Br)c4F)n2)OC[C@]3(C)C(N)=O)C(F)(F)F)cc2cn(C3CC3)nc12] | 712.18 |
| 1222 | 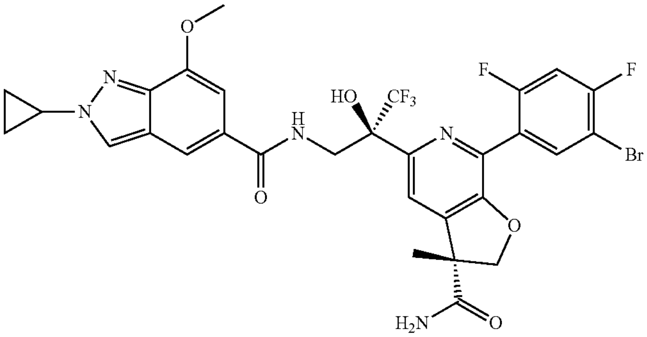 [SMILES: COc1cc(C(=O)NC[C@@](O)(c2cc3c(c(-c4cc(Br)c(F)cc4F)n2)OC[C@]3(C)C(N)=O)C(F)(F)F)cc2cn(C3CC3)nc12] | 712.08 |

TABLE 9-continued
| Example | Structure | MS⁺ m/z |
|---|---|---|
| 1223 | 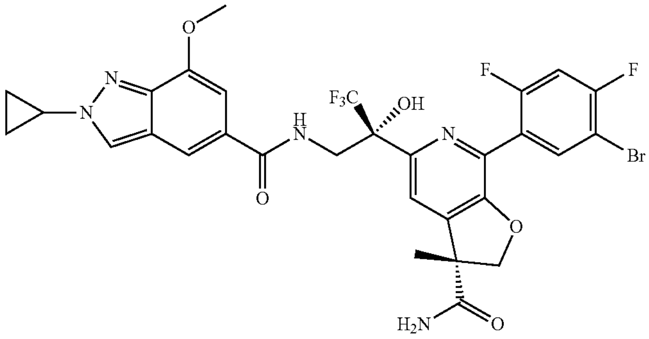 [SMILES: COc1cc(C(=O)NC[C@](O)(c2cc3c(c(-c4cc(Br)c(F)cc4F)n2)OC[C@]3(C)C(N)=O)C(F)(F)F)cc2cn(C3CC3)nc12] | 712.08 |
| 1224 | 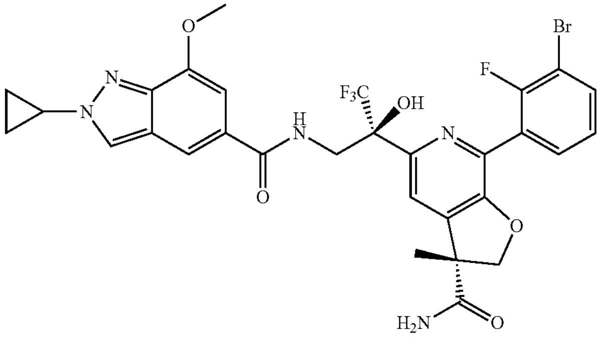 [SMILES: COc1cc(C(=O)NC[C@@](O)(c2cc3c(c(-c4cccc(Br)c4F)n2)OC[C@]3(C)C(N)=O)C(F)(F)F)cc2cn(C3CC3)nc12] | 694.06 |
| 1225 | 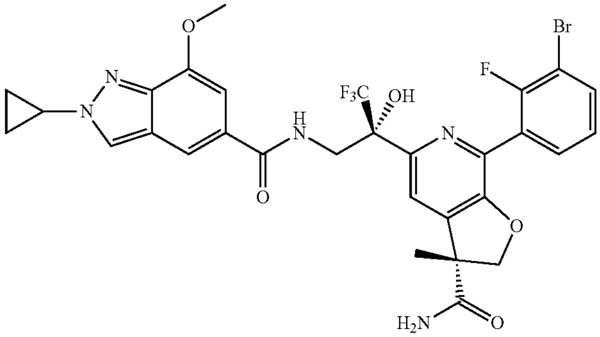 [SMILES: COc1cc(C(=O)NC[C@](O)(c2cc3c(c(-c4cccc(Br)c4F)n2)OC[C@]3(C)C(N)=O)C(F)(F)F)cc2cn(C3CC3)nc12] | 694.06 |
| 1226 | 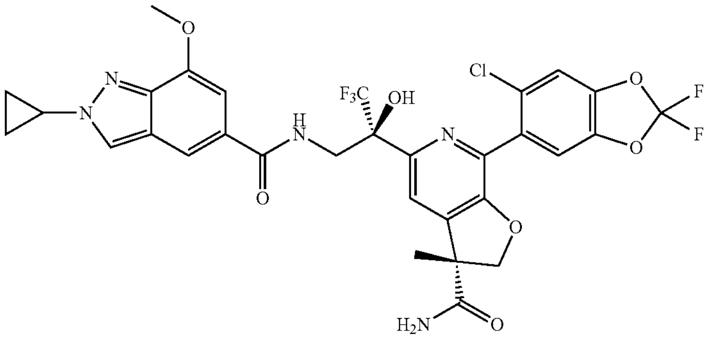 [SMILES: COc1cc(C(=O)NC[C@@](O)(c2cc3c(c(-c4cc5c(cc4Cl)OC(F)(F)O5)n2)OC[C@]3(C)C(N)=O)C(F)(F)F)cc2cn(C3CC3)nc12] | 710.16 |

TABLE 9-continued
| Example | Structure | MS⁺ m/z |
|---|---|---|
| 1227 | 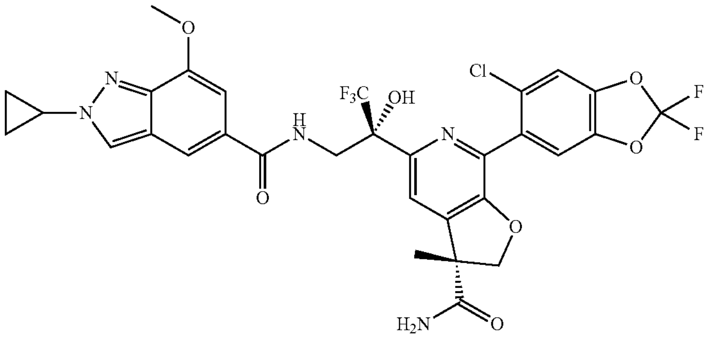 [SMILES: COc1cc(C(=O)NC[C@](O)(c2cc3c(c(-c4cc5c(cc4Cl)OC(F)(F)O5)n2)OC[C@]3(C)C(N)=O)C(F)(F)F)cc2cn(C3CC3)nc12] | 710.17 |
| 1228 | 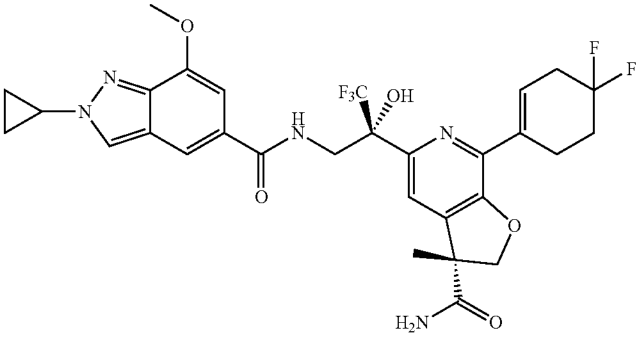 [SMILES: COc1cc(C(=O)NC[C@](O)(c2cc3c(c(C4=CCC(F)(F)CC4)n2)OC[C@]3(C)C(N)=O)C(F)(F)F)cc2cn(C3CC3)nc12] | 636.23 |
| 1229 | 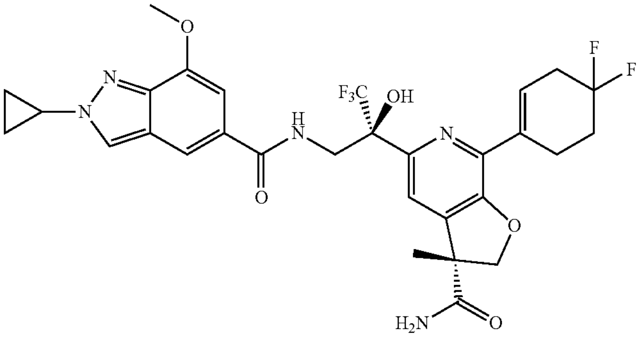 [SMILES: COc1cc(C(=O)NC[C@@](O)(c2cc3c(c(C4=CCC(F)(F)CC4)n2)OC[C@]3(C)C(N)=O)C(F)(F)F)cc2cn(C3CC3)nc12] | 636.27 |
| 1230 | 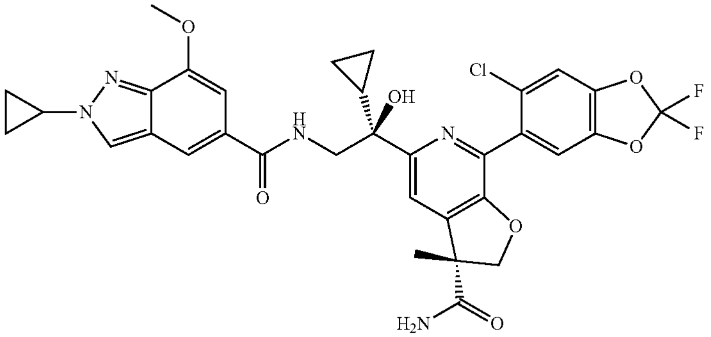 [SMILES: COc1cc(C(=O)NC[C@@](O)(c2cc3c(c(-c4cc5c(cc4Cl)OC(F)(F)O5)n2)OC[C@]3(C)C(N)=O)C2CC2)cc2cn(C3CC3)nc12] | 682.20 |

TABLE 9-continued
| Example | Structure | MS⁺ m/z |
|---|---|---|
| 1231 | 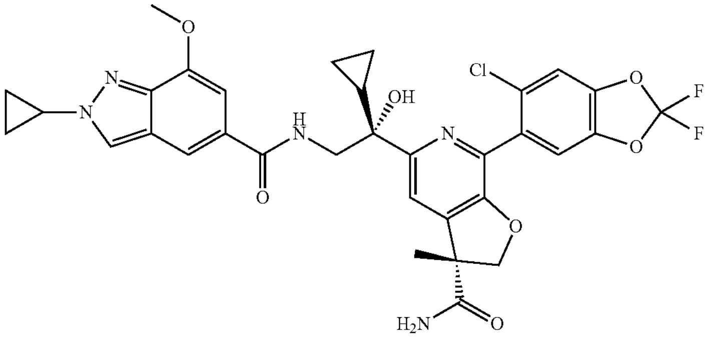 [SMILES: COc1cc(C(=O)NC[C@](O)(c2cc3c(c(-c4cc5c(cc4Cl)OC(F)(F)O5)n2)OC[C@]3(C)C(N)=O)C2CC2)cc2cn(C3CC3)nc12] | 682.23 |
| 1232 | 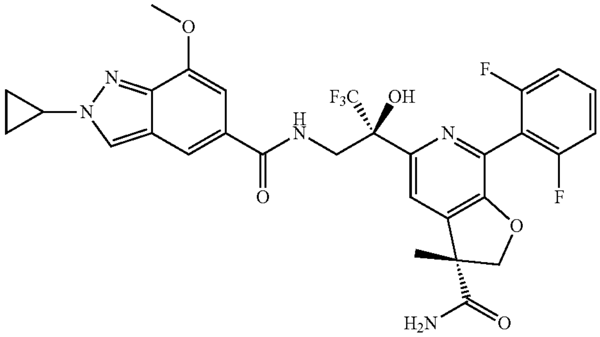 [SMILES: COc1cc(C(=O)NC[C@@](O)(c2cc3c(c(-c4c(F)cccc4F)n2)OC[C@]3(C)C(N)=O)C(F)(F)F)cc2cn(C3CC3)nc12] | 632.27 |
| 1233 | 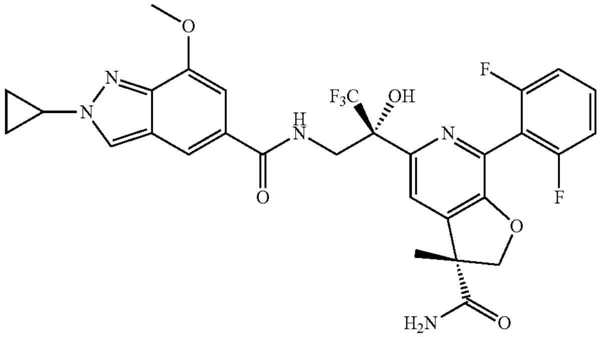 [SMILES: COc1cc(C(=O)NC[C@](O)(c2cc3c(c(-c4c(F)cccc4F)n2)OC[C@]3(C)C(N)=O)C(F)(F)F)cc2cn(C3CC3)nc12] | 632.21 |
| 1234 | 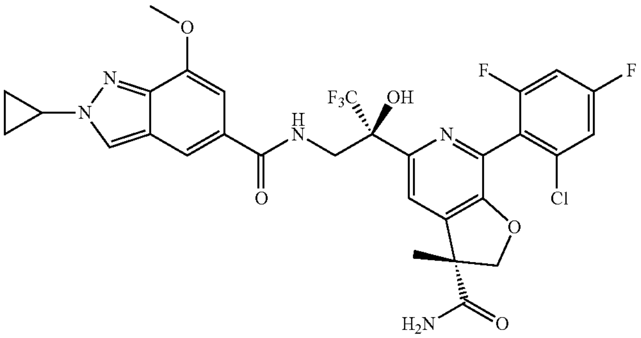 [SMILES: COc1cc(C(=O)NC[C@@](O)(c2cc3c(c(-c4c(F)cc(F)cc4Cl)n2)OC[C@]3(C)C(N)=O)C(F)(F)F)cc2cn(C3CC3)nc12] | 666.14 |

TABLE 9-continued
| Example | Structure | MS⁺ m/z |
|---|---|---|
| 1235 | 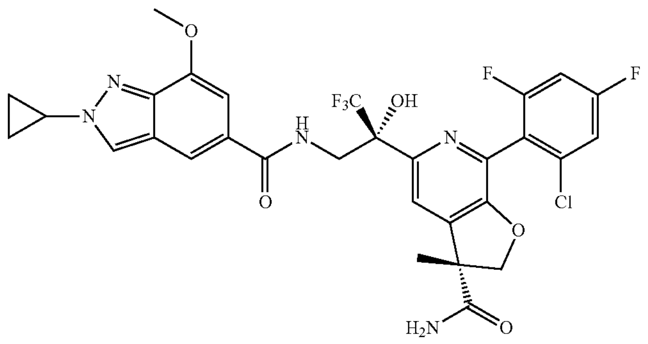 [SMILES: COc1cc(C(=O)NC[C@](O)(c2cc3c(c(-c4c(F)cc(F)cc4Cl)n2)OC[C@]3(C)C(N)=O)C(F)(F)F)cc2cn(C3CC3)nc12] | 666.03 |
| 1236 | 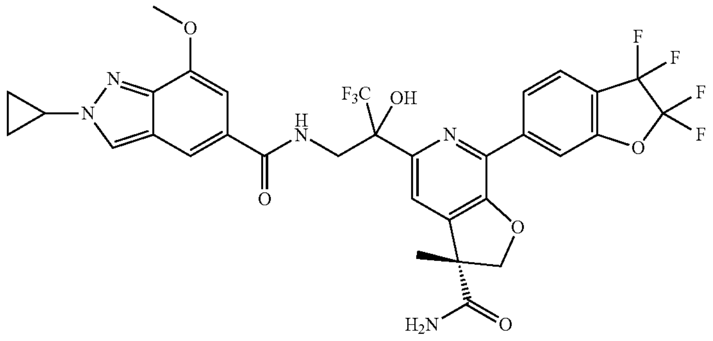 [SMILES: COc1cc(C(=O)NCC(O)(c2cc3c(c(-c4ccc5c(c4)OC(F)(F)C5(F)F)n2)OC[C@]3(C)C(N)=O)C(F)(F)F)cc2cn(C3CC3)nc12] | 710.20 |
| 1237 | 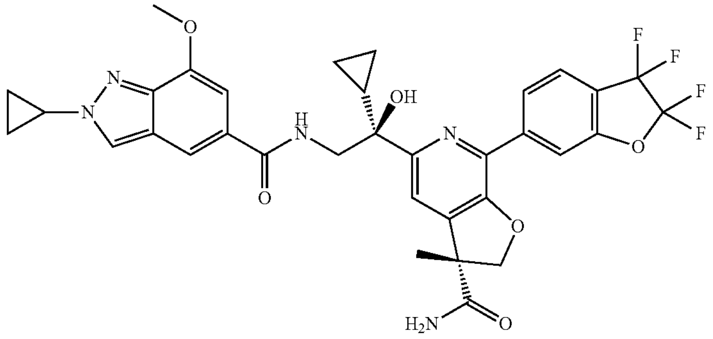 [SMILES: COc1cc(C(=O)NC[C@@](O)(c2cc3c(c(-c4ccc5c(c4)OC(F)(F)C5(F)F)n2)OC[C@]3(C)C(N)=O)C2CC2)cc2cn(C3CC3)nc12] | 682.20 |
| 1238 | 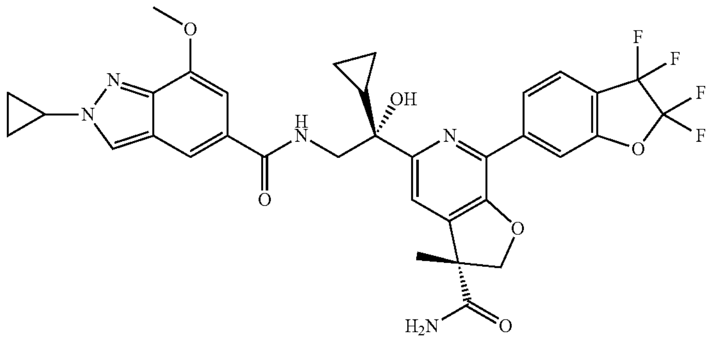 [SMILES: COc1cc(C(=O)NC[C@](O)(c2cc3c(c(-c4ccc5c(c4)OC(F)(F)C5(F)F)n2)OC[C@]3(C)C(N)=O)C2CC2)cc2cn(C3CC3)nc12] | 682.30 |

TABLE 9-continued
| Example | Structure | MS+ m/z |
|---|---|---|
| 1239 | 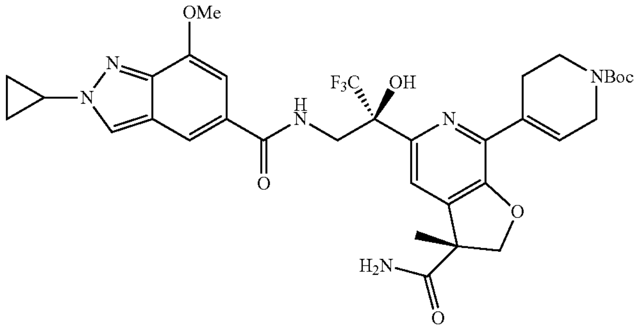 [SMILES: COc1cc(C(=O)NC[C@@](O)(c2cc3c(c(C4=CCN(C(=O)OC(C)(C)C)CC4)n2)OC[C@]3(C)C(N)=O)C(F)(F)F)cc2cn(C3CC3)nc12] | 701.39 |
| 1240 | 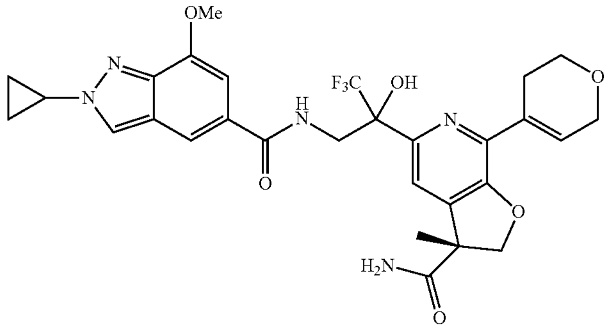 [SMILES: COc1cc(C(=O)NCC(O)(c2cc3c(c(C4=CCOCC4)n2)OC[C@]3(C)C(N)=O)C(F)(F)F)cc2cn(C3CC3)nc12] | 602.20 |
| 1241 | 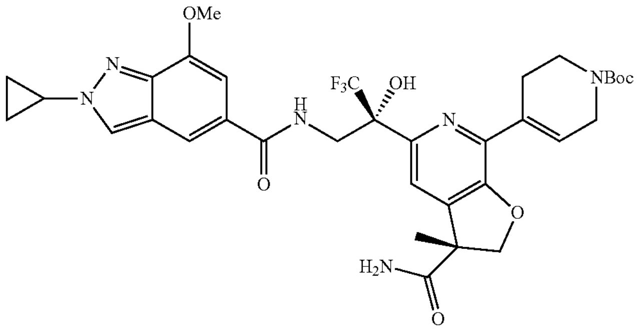 [SMILES: COc1cc(C(=O)NC[C@](O)(c2cc3c(c(C4=CCN(C(=O)OC(C)(C)C)CC4)n2)OC[C@]3(C)C(N)=O)C(F)(F)F)cc2cn(C3CC3)nc12] | 701.40 |
| 1242 | 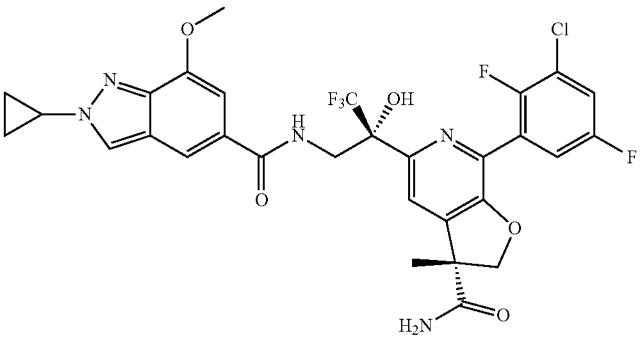 [SMILES: COc1cc(C(=O)NC[C@](O)(c2cc3c(c(-c4cc(F)cc(Cl)c4F)n2)OC[C@]3(C)C(N)=O)C(F)(F)F)cc2cn(C3CC3)nc12] | 666.23 |

TABLE 9-continued
| Example | Structure | MS⁺ m/z |
|---|---|---|
| 1243 | 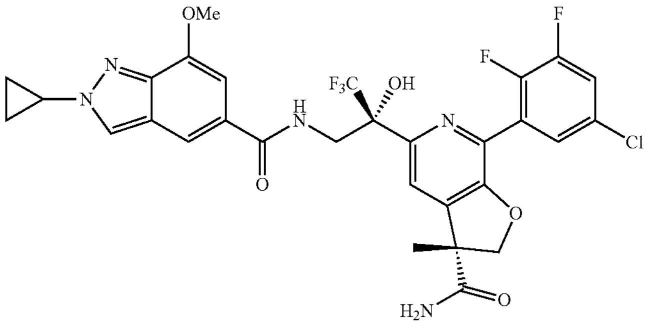 [SMILES: COc1cc(C(=O)NC[C@](O)(c2cc3c(c(-c4cc(Cl)cc(F)c4F)n2)OC[C@]3(C)C(N)=O)C(F)(F)F)cc2cn(C3CC3)nc12] | 666.14 |
| 1244 | 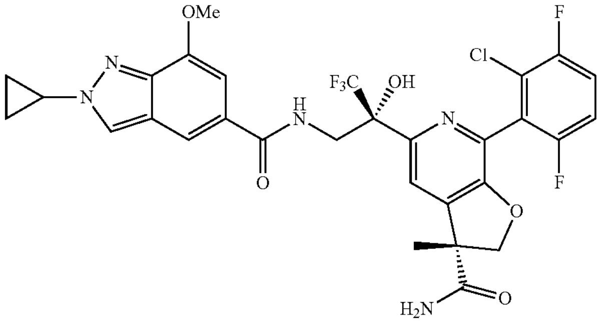 [SMILES: COc1cc(C(=O)NC[C@](O)(c2cc3c(c(-c4c(F)ccc(F)c4Cl)n2)OC[C@]3(C)C(N)=O)C(F)(F)F)cc2cn(C3CC3)nc12] | 666.19 |
| 1245 | 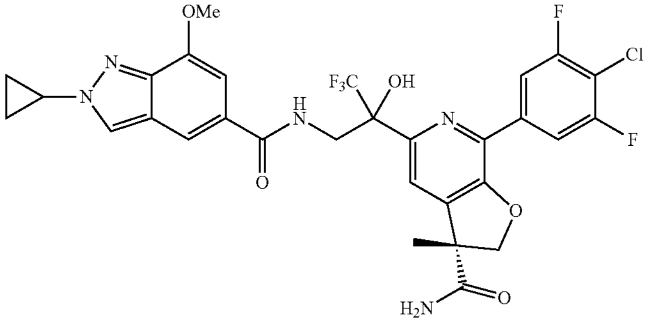 [SMILES: COc1cc(C(=O)NCC(O)(c2cc3c(c(-c4cc(F)c(Cl)c(F)c4)n2)OC[C@]3(C)C(N)=O)C(F)(F)F)cc2cn(C3CC3)nc12] | 666.16 |
| 1246 | 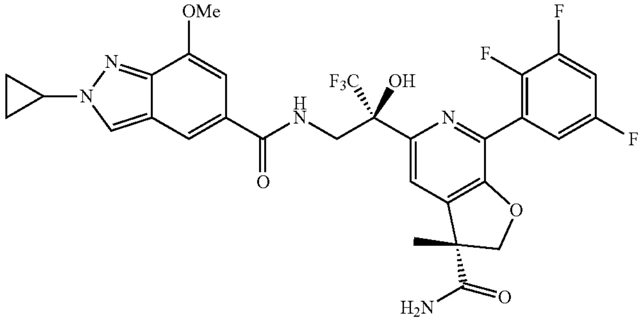 [SMILES: COc1cc(C(=O)NC[C@@](O)(c2cc3c(c(-c4cc(F)cc(F)c4F)n2)OC[C@]3(C)C(N)=O)C(F)(F)F)cc2cn(C3CC3)nc12] | 650.29 |

TABLE 9-continued
| Example | Structure | MS+ m/z |
|---|---|---|
| 1247 | 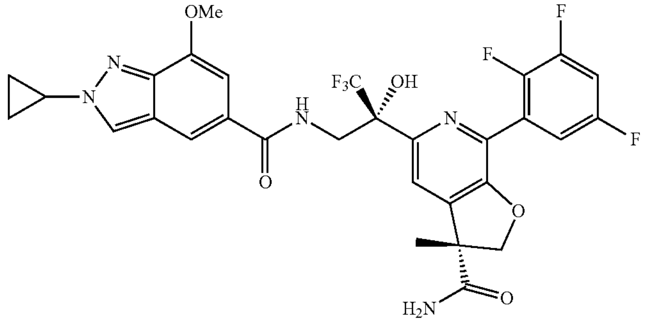 [SMILES: COc1cc(C(=O)NC[C@](O)(c2cc3c(c(-c4cc(F)cc(F)c4F)n2)OC[C@]3(C)C(N)=O)C(F)(F)F)cc2cn(C3CC3)nc12] | 650.29 |
| 1248 | 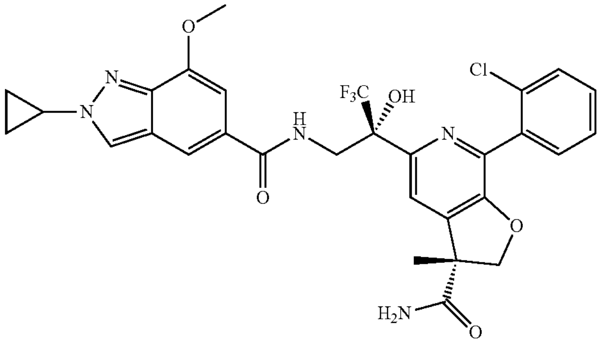 | 630.79 |
| 1249 | 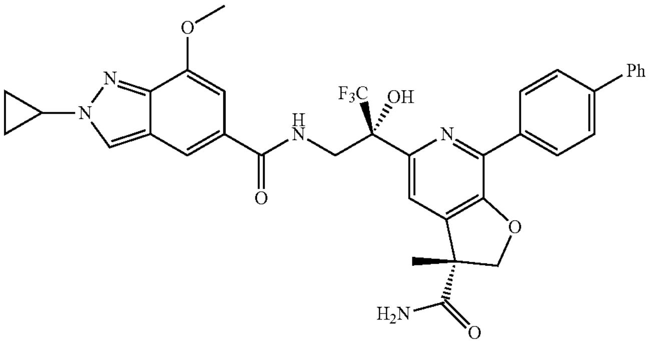 | 673.34 |
| 1250 | 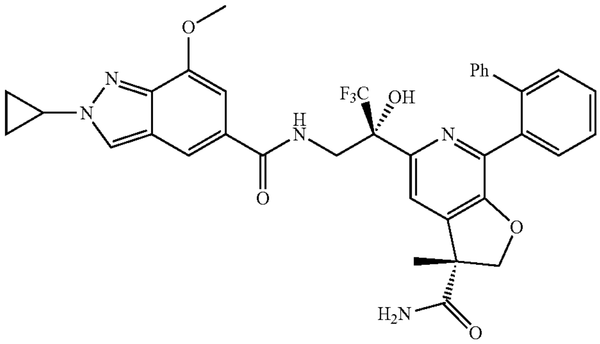 [SMILES: COc1cc(C(=O)NC[C@](O)(c2cc3c(c(-c4ccccc4Cl)n2)OC[C@]3(C)C(N)=O)C(F)(F)F)cc2cn(C3CC3)nc12] | 673.29 |

TABLE 9-continued
| Example | Structure | MS⁺ m/z |
|---|---|---|
| 1251 | 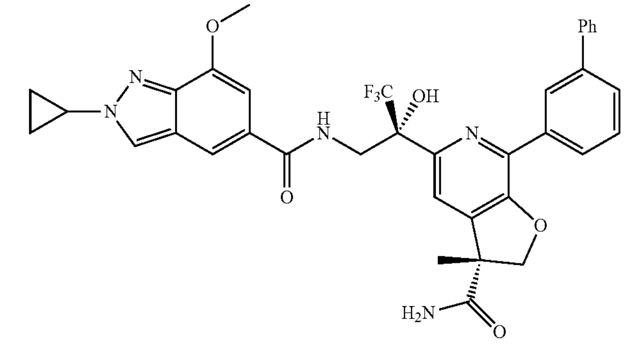 [SMILES: COc1cc(C(=O)NC[C@](O)(c2cc3c(c(-c4cccc(-c5ccccc5)c4)n2)OC[C@]3(C)C(N)=O)C(F)(F)F)cc2cn(C3CC3)nc12] | 672.31 |
| 1252 | 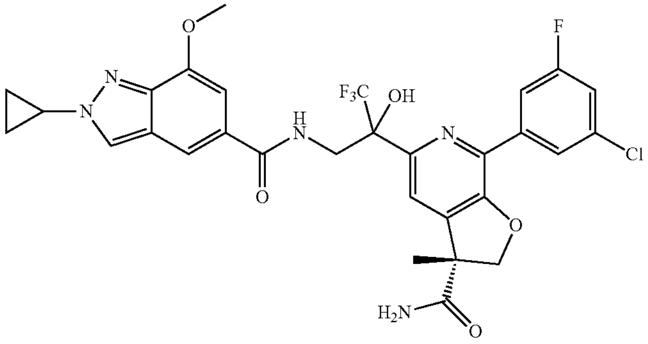 [SMILES: COc1cc(C(=O)NCC(O)(c2cc3c(c(-c4cc(F)cc(Cl)c4)n2)OC[C@]3(C)C(N)=O)C(F)(F)F)cc2cn(C3CC3)nc12] | 649.15 |
| 1253 | 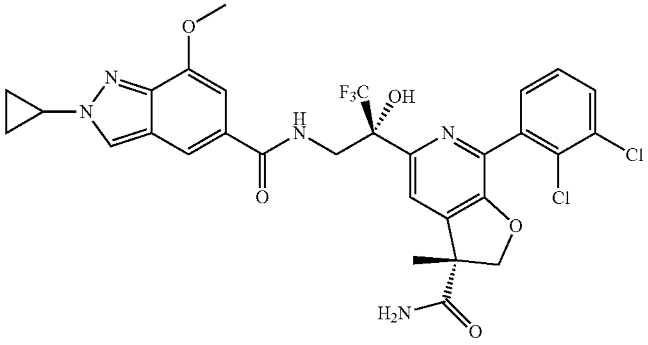 [SMILES: COc1cc(C(=O)NC[C@](O)(c2cc3c(c(-c4cccc(Cl)c4Cl)n2)OC[C@]3(C)C(N)=O)C(F)(F)F)cc2cn(C3CC3)nc12] | 664.15 |
| 1254 | 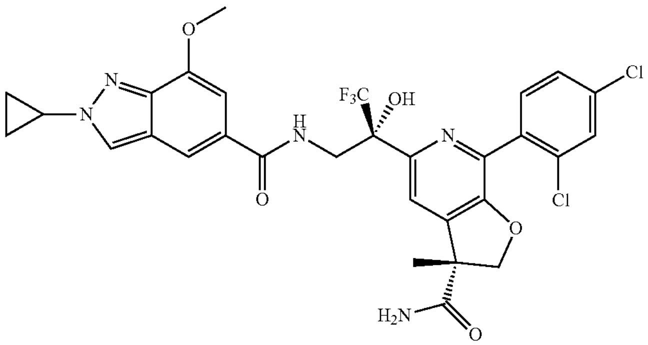 [SMILES: COc1cc(C(=O)NC[C@](O)(c2cc3c(c(-c4ccc(Cl)cc4Cl)n2)OC[C@]3(C)C(N)=O)C(F)(F)F)cc2cn(C3CC3)nc12] | 664.15 |

TABLE 9-continued
| Example | Structure | MS+ m/z |
|---|---|---|
| 1255 | 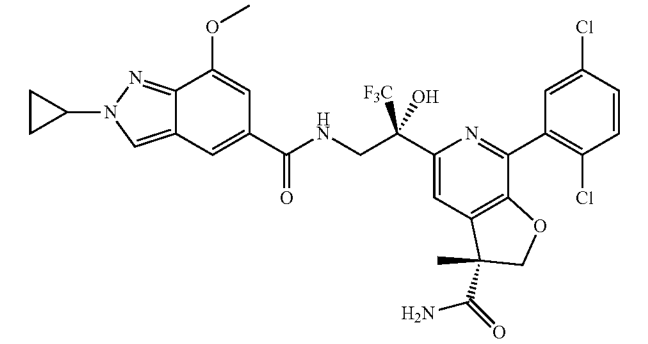 [SMILES: COc1cc(C(=O)NC[C@](O)(c2cc3c(c(-c4cc(Cl)ccc4Cl)n2)OC[C@]3(C)C(N)=O)C(F)(F)F)cc2cn(C3CC3)nc12] | 664.16 |
| 1256 | 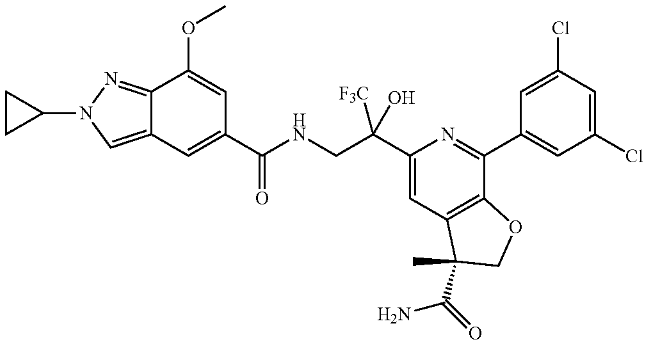 | 664.19 |
| 1257 | 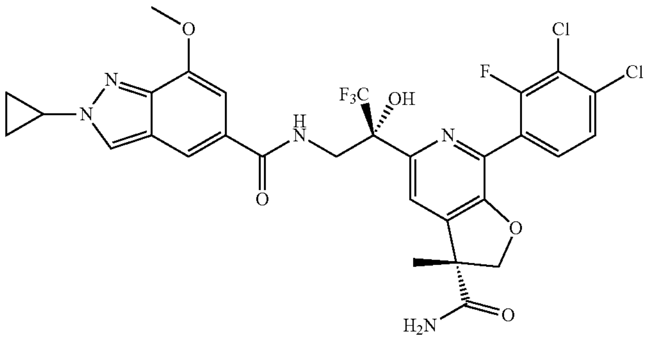 [SMILES: COc1cc(C(=O)NC[C@](O)(c2cc3c(c(-c4ccc(Cl)c(Cl)c4F)n2)OC[C@]3(C)C(N)=O)C(F)(F)F)cc2cn(C3CC3)nc12] | 682.11 |
| 1258 | 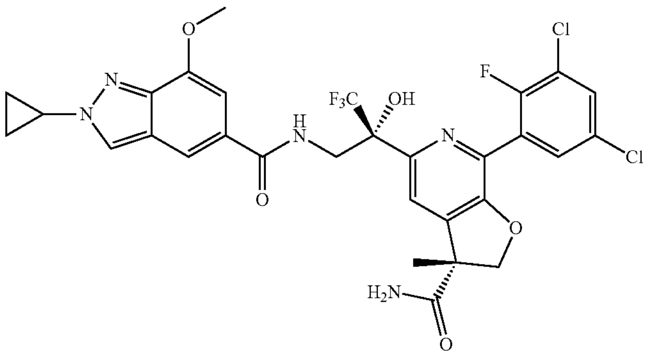 [SMILES: COc1cc(C(=O)NC[C@](O)(c2cc3c(c(-c4cc(Cl)cc(Cl)c4F)n2)OC[C@]3(C)C(N)=O)C(F)(F)F)cc2cn(C3CC3)nc12] | 682.20 |

TABLE 9-continued
| Example | Structure | MS+ m/z |
|---|---|---|
| 1259 | 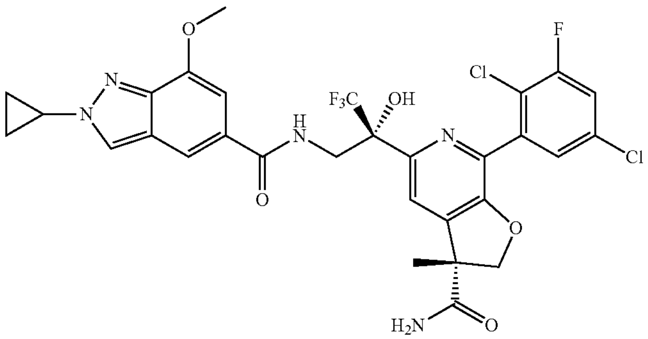 [SMILES: COc1cc(C(=O)NC[C@](O)(c2cc3c(c(-c4cc(Cl)cc(F)c4Cl)n2)OC[C@]3(C)C(N)=O)C(F)(F)F)cc2cn(C3CC3)nc12] | 682.20 |
| 1260 | 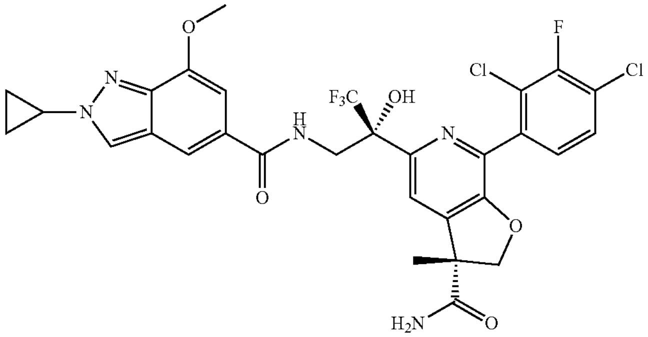 [SMILES: COc1cc(C(=O)NC[C@](O)(c2cc3c(c(-c4ccc(Cl)c(F)c4Cl)n2)OC[C@]3(C)C(N)=O)C(F)(F)F)cc2cn(C3CC3)nc12] | 682.20 |
| 1261 | 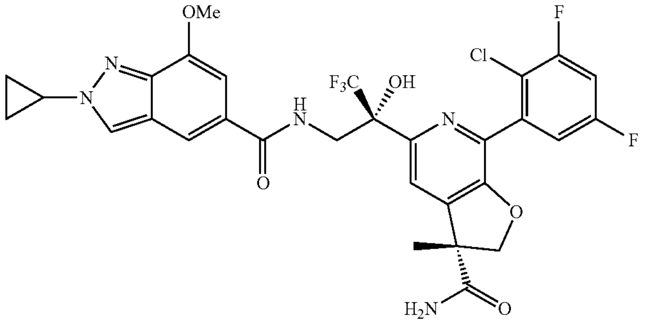 [SMILES: COc1cc(C(=O)NC[C@](O)(c2cc3c(c(-c4cc(F)cc(F)c4Cl)n2)OC[C@]3(C)C(N)=O)C(F)(F)F)cc2cn(C3CC3)nc12] | 666.14 |
| 1262 | 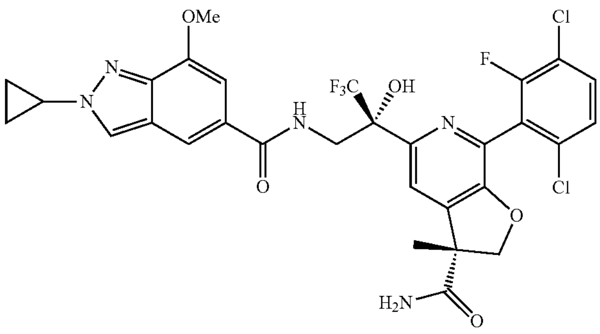 | 682.20 |

TABLE 9-continued
| Example | Structure | MS⁺ m/z |
|---|---|---|
| 1263 | 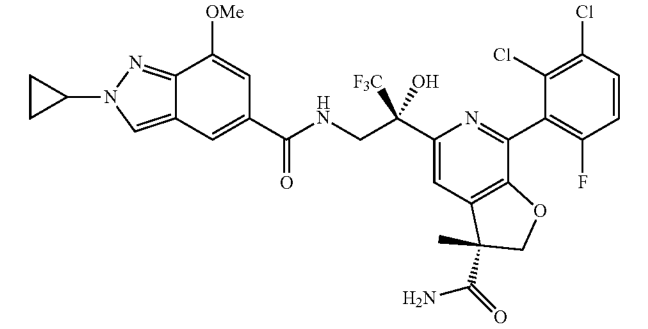 [SMILES: COc1cc(C(=O)NC[C@](O)(c2cc3c(c(-c4c(F)ccc(Cl)c4Cl)n2)OC[C@]3(C)C(N)=O)C(F)(F)F)cc2cn(C3CC3)nc12] | 682.20 |
| 1264 | 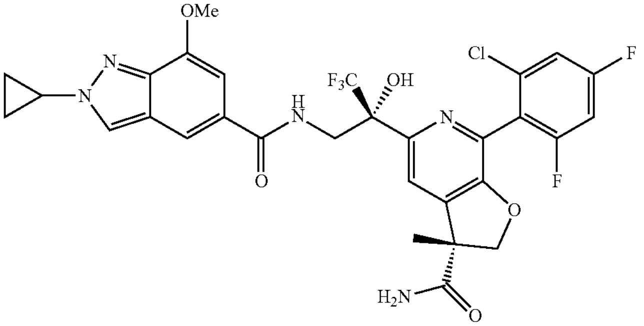 [SMILES: COc1cc(C(=O)NC[C@](O)(c2cc3c(c(-c4c(F)cc(F)cc4Cl)n2)OC[C@]3(C)C(N)=O)C(F)(F)F)cc2cn(C3CC3)nc12] | 682.20 |
| 1265 | 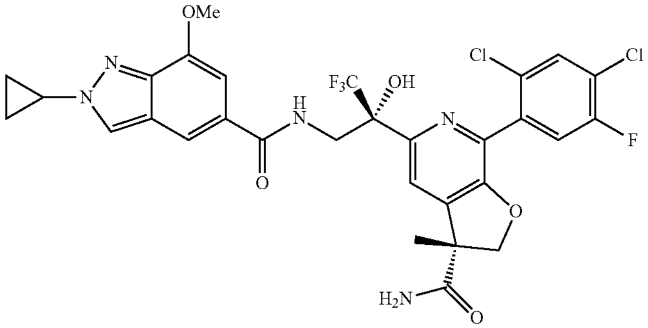 [SMILES: COc1cc(C(=O)NC[C@](O)(c2cc3c(c(-c4cc(F)c(Cl)cc4Cl)n2)OC[C@]3(C)C(N)=O)C(F)(F)F)cc2cn(C3CC3)nc12] | 682.20 |
| 1266 | 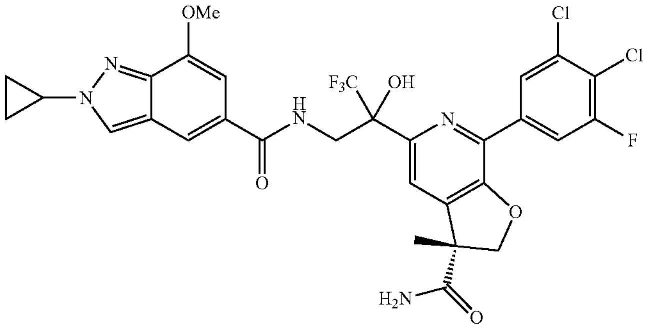 [SMILES: COc1cc(C(=O)NCC(O)(c2cc3c(c(-c4cc(F)c(Cl)c(Cl)c4)n2)OC[C@]3(C)C(N)=O)C(F)(F)F)cc2cn(C3CC3)nc12] | 682.20 |

TABLE 9-continued

| Example | Structure | $MS^+$ m/z |
|---|---|---|
| 1267 | 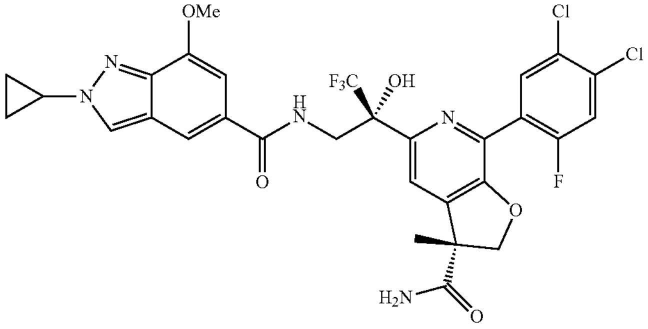 [SMILES: COc1cc(C(=O)NC[C@](O)(c2cc3c(c(-c4cc(Cl)c(Cl)cc4F)n2)OC[C@]3(C)C(N)=O)C(F)(F)F)cc2cn(C3CC3)nc12] | 682.20 |

Example 1268

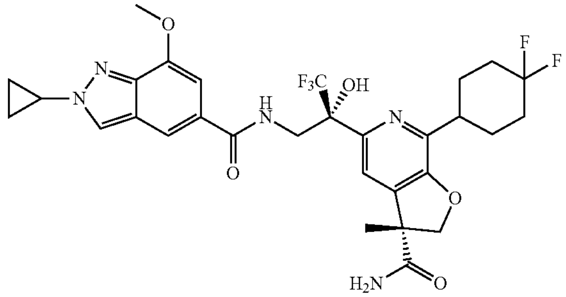 [SMILES: COc1cc(C(=O)NC[C@](O)(c2cc3c(c(C4CCC(F)(F)CC4)n2)OC[C@]3(C)C(N)=O)C(F)(F)F)cc2cn(C3CC3)nc12]

Example 1228 (15 mg, 0.024 mmol) was dissolved in EtOH (0.5 mL) and MeOH (0.5 mL) and palladium on carbon (10% wt., 0.8 mg, 0.00075 mmol) was added. The air in the headspace of the reaction vessel was replaced with $H_2$ from a balloon, and the mixture was allowed to stir under $H_2$ for 24 hours. The reaction mixture was then filtered through a short pad of celite, and the filtrate concentrated to afford the product. (14 mg, 93%). ESI-MS m/z: 638.29 $[M+H]^+$.

Example 1269

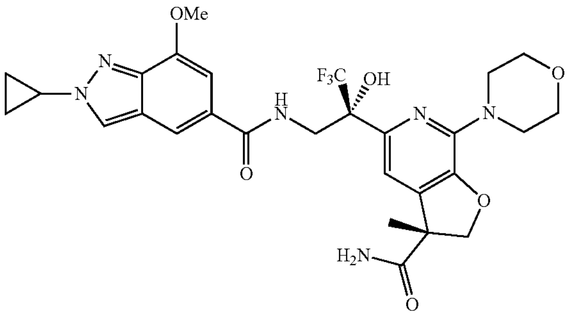 [SMILES: COc1cc(C(=O)NC[C@](O)(c2cc3c(c(N4CCOCC4)n2)OC[C@]3(C)C(N)=O)C(F)(F)F)cc2cn(C3CC3)nc12]

In a vial, Example 890 (30 mg, 0.05 mmol) was dissolved in DMF (1 mL). Morpholine (44 mg, 0.5 mmol) and $K_2CO_3$ (69 mg, 0.5 mmol) were added and the vial was sealed and heated to 100° C. for 24 h. The reaction was cooled to room temperature and diluted with $H_2O$ (1 mL). The aqueous layer was washed with EtOAc and the combined organic layer was dried over $MgSO_4$ and concentrated under reduced pressure. The crude material was purified by prep-HPLC ($ACN/H_2O$, 20-90%, 25 min) to give the title compound (5 mg, 16%). ESI-MS m/z: 605.27 $[M+H]^+$.

Example 1270

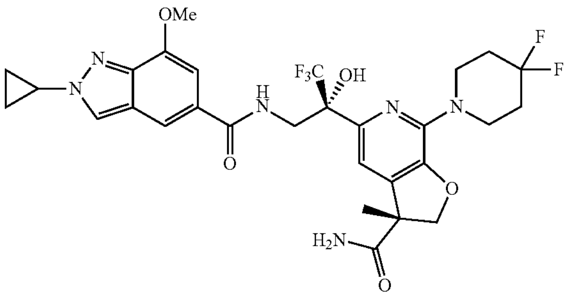 [SMILES: COc1cc(C(=O)NC[C@](O)(c2cc3c(c(N4CCC(F)(F)CC4)n2)OC[C@]3(C)C(N)=O)C(F)(F)F)cc2cn(C3CC3)nc12]

The following example was prepared in an analogous fashion to Example 1269. ESI-MS m/z: 639.20 $[M+H]^+$.

Example 1271

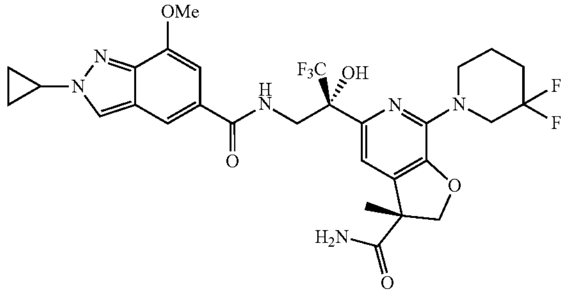 [SMILES: COc1cc(C(=O)NC[C@](O)(c2cc3c(c(N4CCCC(F)(F)C4)n2)OC[C@]3(C)C(N)=O)C(F)(F)F)cc2cn(C3CC3)nc12]

The following example was prepared in an analogous fashion to Example 1269. ESI-MS m/z: 639.20 $[M+H]^+$.

The following Table 10 contains examples that were prepared with the similar method to Example 1 Step c (PyBOP or HATU) and Example 891 using Example 890 and Intermediate 115. The majority of compounds were purified by prep-HPLC ($ACN/H_2O$, 20-90%, 25 min), and some were purified by automated column chromatography (silica gel). The aryl acid and amine coupling partners were prepared according to Intermediates 1-113, or by analogous procedures with slight modifications, and also prepared according to procedures found in U.S. patent application Ser. No. 16/930,622.

TABLE 10
| Example | Structure | MS+ m/z |
|---|---|---|
| 1272 | 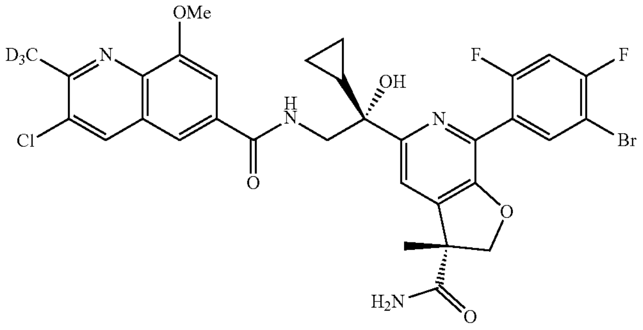 [SMILES: [2H]C([2H])([2H])c1nc2c(OC)cc(C(=O)NC[C@](O)(c3cc4c(c(-c5cc(Br)c(F)cc5F)n3)OC[C@]4(C)C(N)=O)C3CC3)cc2cc1Cl] | 704.04 |
| 1273 | 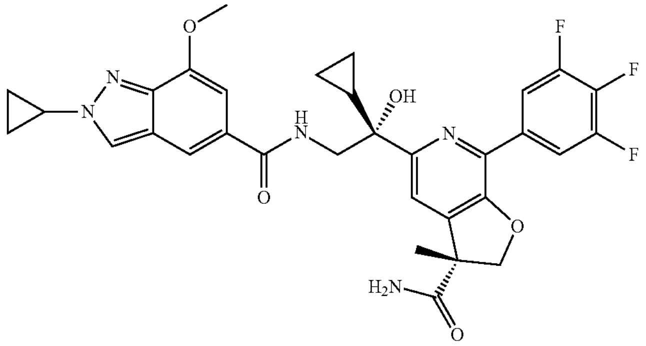 [SMILES: COc1cc(C(=O)NC[C@](O)(c2cc3c(c(-c4cc(F)c(F)c(F)c4)n2)OC[C@]3(C)C(N)=O)C2CC2)cc2cn(C3CC3)nc12] | 622.31 |
| 1274 | 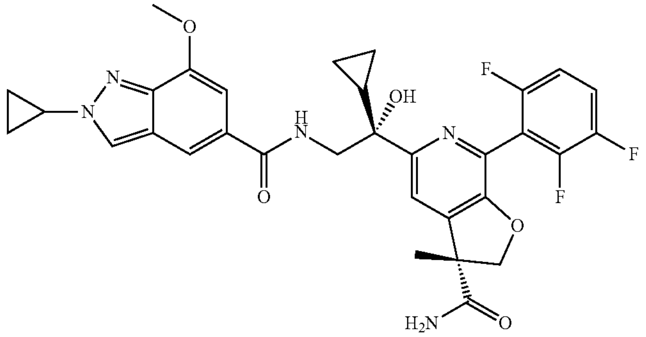 [SMILES: COc1cc(C(=O)NC[C@](O)(c2cc3c(c(-c4c(F)ccc(F)c4F)n2)OC[C@]3(C)C(N)=O)C2CC2)cc2cn(C3CC3)nc12] | 622.29 |
| 1275 | 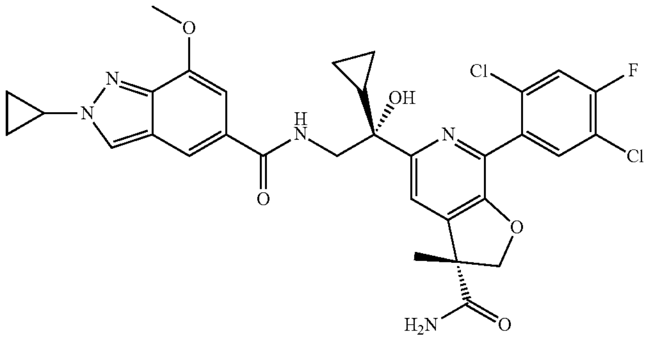 [SMILES: COc1cc(C(=O)NC[C@](O)(c2cc3c(c(-c4cc(Cl)c(F)cc4Cl)n2)OC[C@]3(C)C(N)=O)C2CC2)cc2cn(C3CC3)nc12] | 654.24 |

TABLE 10-continued
| Example | Structure | MS+ m/z |
| --- | --- | --- |
| 1276 | 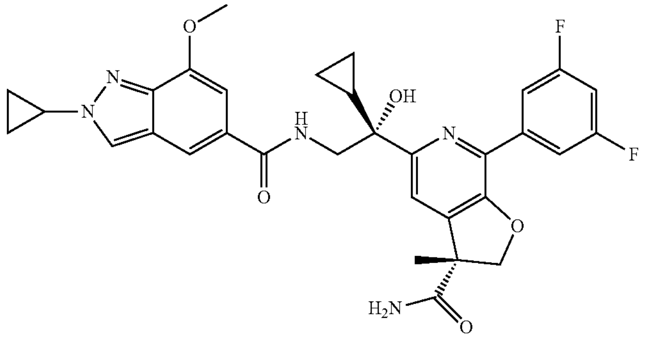 [SMILES: COc1cc(C(=O)NC[C@](O)(c2cc3c(c(-c4cc(F)cc(F)c4)n2)OC[C@]3(C)C(N)=O)C2CC2)cc2cn(C3CC3)nc12] | 604.32 |
| 1277 | 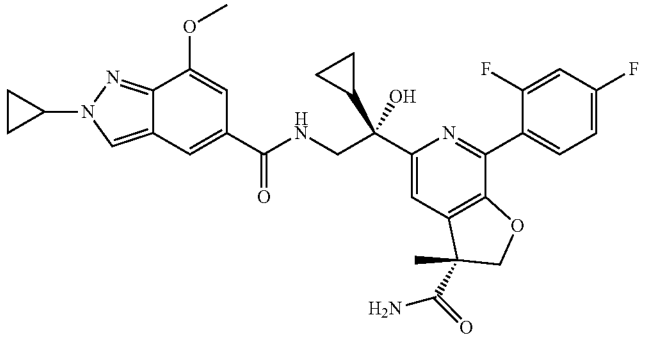 [SMILES: COc1cc(C(=O)NC[C@](O)(c2cc3c(c(-c4ccc(F)cc4F)n2)OC[C@]3(C)C(N)=O)C2CC2)cc2cn(C3CC3)nc12] | 604.32 |
| 1278 | 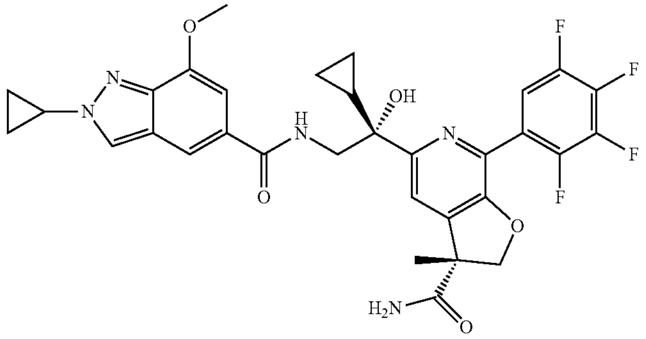 [SMILES: COc1cc(C(=O)NC[C@](O)(c2cc3c(c(-c4cc(F)c(F)c(F)c4F)n2)OC[C@]3(C)C(N)=O)C2CC2)cc2cn(C3CC3)nc12] | 640.29 |
| 1279 | 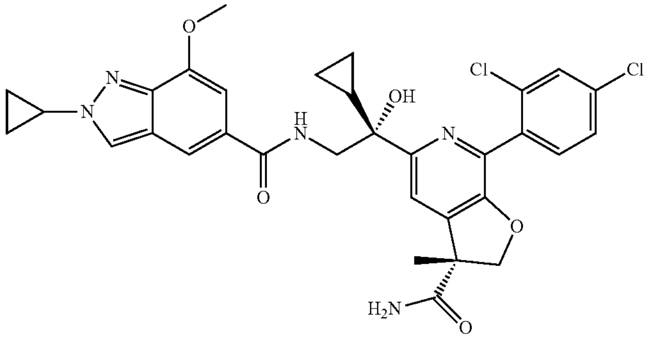 [SMILES: COc1cc(C(=O)NC[C@](O)(c2cc3c(c(-c4ccc(Cl)cc4Cl)n2)OC[C@]3(C)C(N)=O)C2CC2)cc2cn(C3CC3)nc12] | 636.18 |

TABLE 10-continued
| Example | Structure | MS+ m/z |
|---|---|---|
| 1280 | 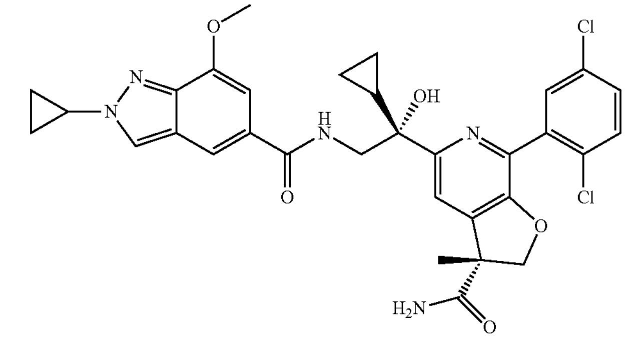 [SMILES: COc1cc(C(=O)NC[C@](O)(c2cc3c(c(-c4cc(Cl)ccc4Cl)n2)OC[C@]3(C)C(N)=O)C2CC2)cc2cn(C3CC3)nc12] | 636.23 |
| 1281 | 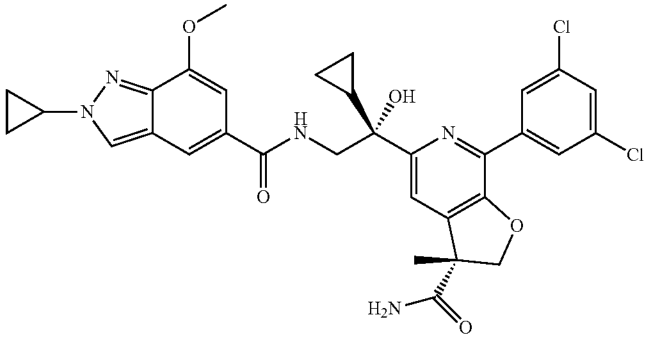 [SMILES: COc1cc(C(=O)NC[C@](O)(c2cc3c(c(-c4cc(Cl)cc(Cl)c4)n2)OC[C@]3(C)C(N)=O)C2CC2)cc2cn(C3CC3)nc12] | 636.24 |
| 1282 | 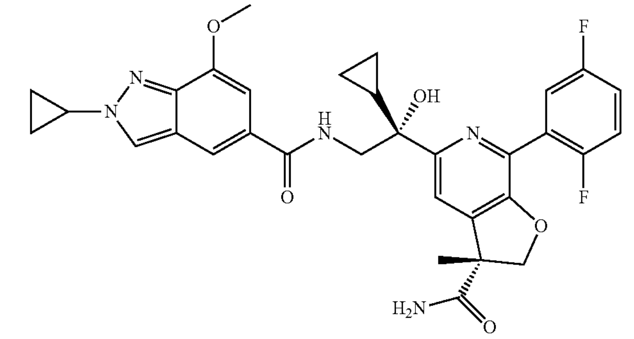 [SMILES: COc1cc(C(=O)NC[C@](O)(c2cc3c(c(-c4cc(F)ccc4F)n2)OC[C@]3(C)C(N)=O)C2CC2)cc2cn(C3CC3)nc12] | 604.23 |
| 1283 | 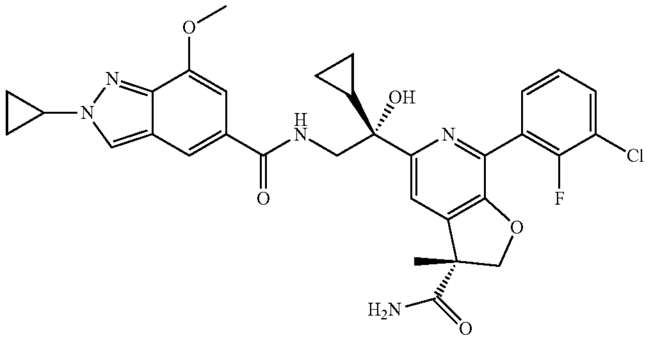 [SMILES: COc1cc(C(=O)NC[C@](O)(c2cc3c(c(-c4cccc(Cl)c4F)n2)OC[C@]3(C)C(N)=O)C2CC2)cc2cn(C3CC3)nc12] | 620.26 |

TABLE 10-continued
| Example | Structure | MS+ m/z |
|---|---|---|
| 1284 | 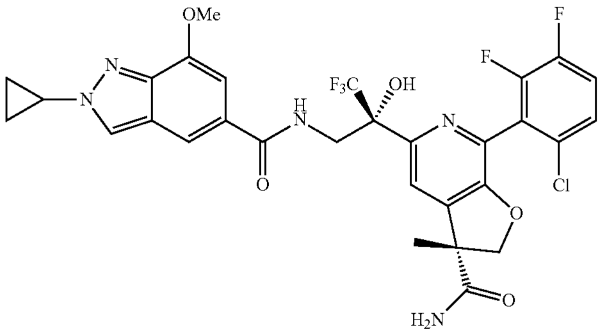 [SMILES: COc1cc(C(=O)NC[C@](O)(c2cc3c(c(-c4c(Cl)ccc(F)c4F)n2)OC[C@]3(C)C(N)=O)C(F)(F)F)cc2cn(C3CC3)nc12] | 666.16 |
| 1285 | 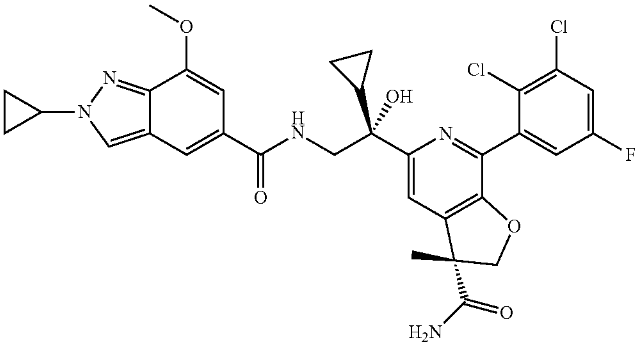 [SMILES: COc1cc(C(=O)NC[C@](O)(c2cc3c(c(-c4cc(F)cc(Cl)c4Cl)n2)OC[C@]3(C)C(N)=O)C2CC2)cc2cn(C3CC3)nc12] | 654.20 |
| 1286 | 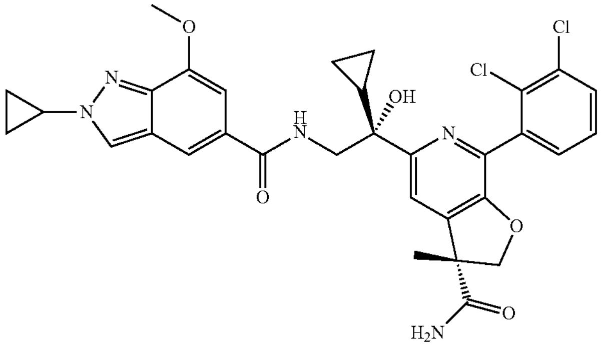 [SMILES: COc1cc(C(=O)NC[C@](O)(c2cc3c(c(-c4cccc(Cl)c4Cl)n2)OC[C@]3(C)C(N)=O)C2CC2)cc2cn(C3CC3)nc12] | 636.18 |
| 1287 | 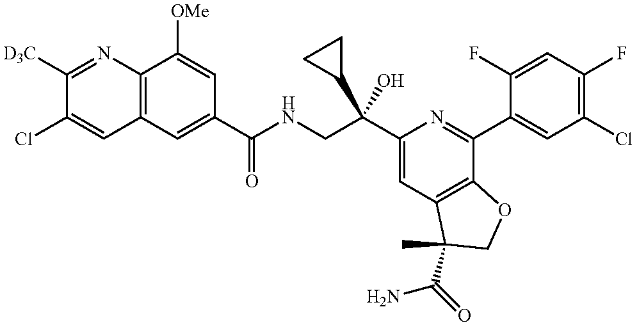 [SMILES: [2H]C([2H])([2H])c1nc2c(OC)cc(C(=O)NC[C@](O)(c3cc4c(c(-c5cc(Cl)c(F)cc5F)n3)OC[C@]4(C)C(N)=O)C3CC3)cc2cc1Cl] | 660.07 |

TABLE 10-continued
| Example | Structure | MS⁺ m/z |
| --- | --- | --- |
| 1288 | 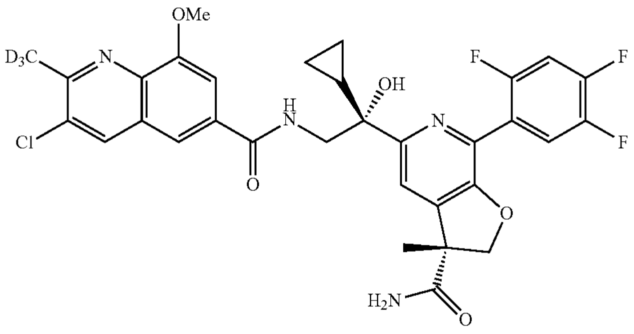 [SMILES: [2H]C([2H])([2H])c1nc2c(OC)cc(C(=O)NC[C@](O)(c3cc4c(c(-c5cc(F)c(F)cc5F)n3)OC[C@]4(C)C(N)=O)C3CC3)cc2cc1Cl] | 644.15 |
| 1289 | 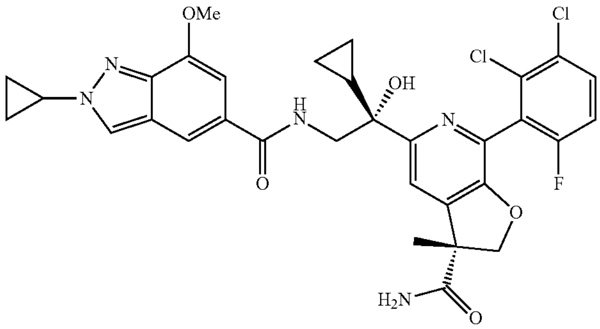 [SMILES: COc1cc(C(=O)NC[C@](O)(c2cc3c(c(-c4c(F)ccc(Cl)c4Cl)n2)OC[C@]3(C)C(N)=O)C2CC2)cc2cn(C3CC3)nc12] | 654.12 |
| 1290 | 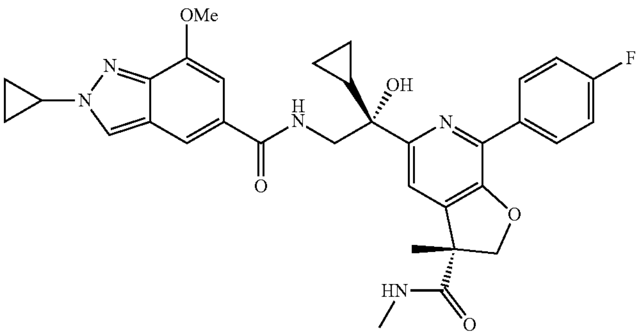 [SMILES: CNC(=O)[C@@]1(C)COc2c1cc([C@@](O)(CNC(=O)c1cc(OC)c3nn(C4CC4)cc3c1)C1CC1)nc2-c1ccc(F)cc1] | 600.29 |
| 1291 | 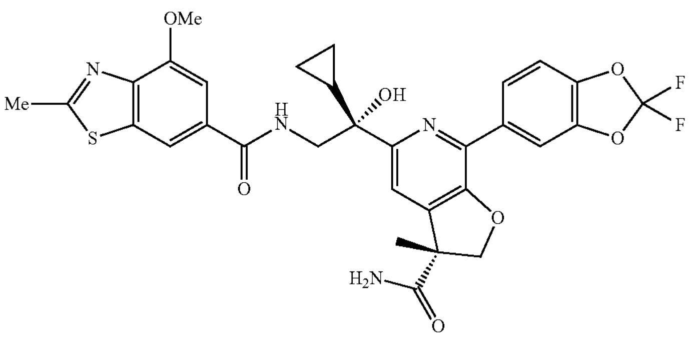 [SMILES: COc1cc(C(=O)NC[C@](O)(c2cc3c(c(-c4ccc5c(c4)OC(F)(F)O5)n2)OC[C@]3(C)C(N)=O)C2CC2)cc2sc(C)nc12] | 639.19 |

TABLE 10-continued
| Example | Structure | MS+ m/z |
|---|---|---|
| 1292 | 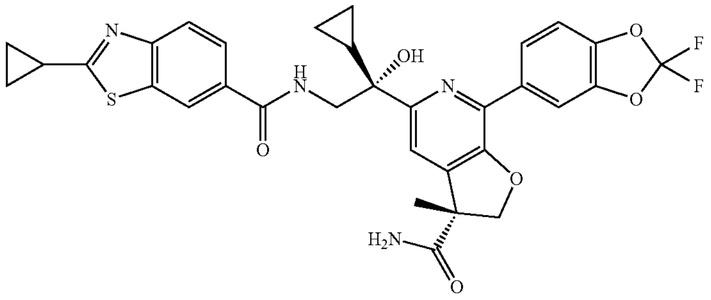 [SMILES: C[C@]1(C(N)=O)COc2c1cc([C@@](O)(CNC(=O)c1ccc3nc(C4CC4)sc3c1)C1CC1)nc2-c1ccc2c(c1)OC(F)(F)O2] | 635.22 |
| 1293 | 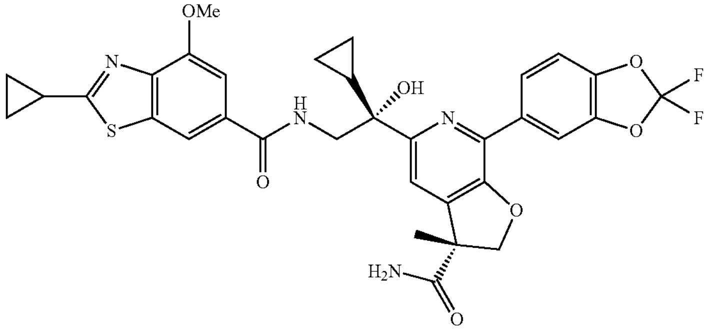 [SMILES: COc1cc(C(=O)NC[C@](O)(c2cc3c(c(-c4ccc5c(c4)OC(F)(F)O5)n2)OC[C@]3(C)C(N)=O)C2CC2)cc2sc(C3CC3)nc12] | 665.20 |
| 1294 | 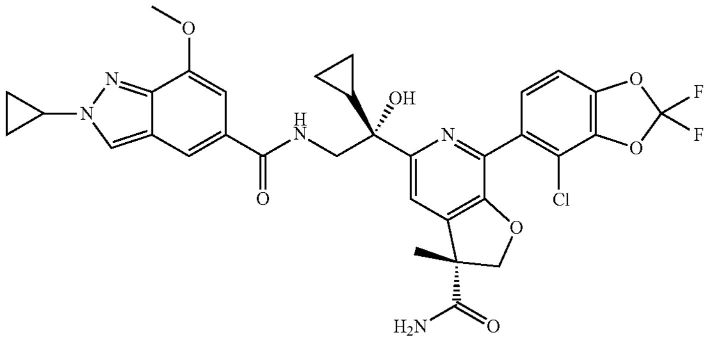 [SMILES: COc1cc(C(=O)NC[C@](O)(c2cc3c(c(-c4ccc5c(c4Cl)OC(F)(F)O5)n2)OC[C@]3(C)C(N)=O)C2CC2)cc2cn(C3CC3)nc12] | 682.30 |
| 1295 | 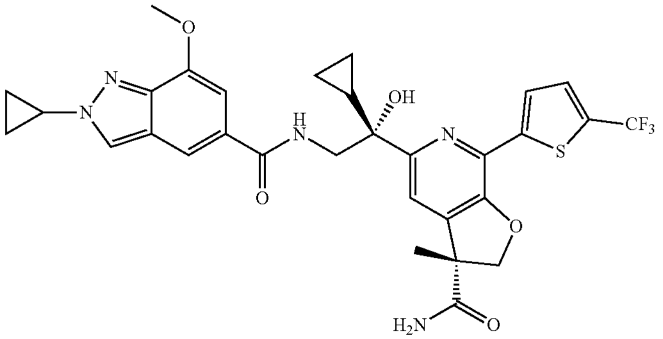 [SMILES: COc1cc(C(=O)NC[C@](O)(c2cc3c(c(-c4ccc(C(F)(F)F)s4)n2)OC[C@]3(C)C(N)=O)C2CC2)cc2cn(C3CC3)nc12] | 642.30 |

TABLE 10-continued
| Example | Structure | MS+ m/z |
|---|---|---|
| 1296 | 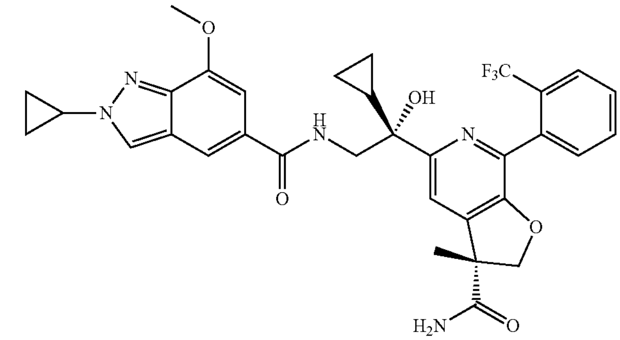 [SMILES: COc1cc(C(=O)NC[C@](O)(c2cc3c(c(-c4ccccc4C(F)(F)F)n2)OC[C@]3(C)C(N)=O)C2CC2)cc2cn(C3CC3)nc12] | 636.35 |
| 1297 | 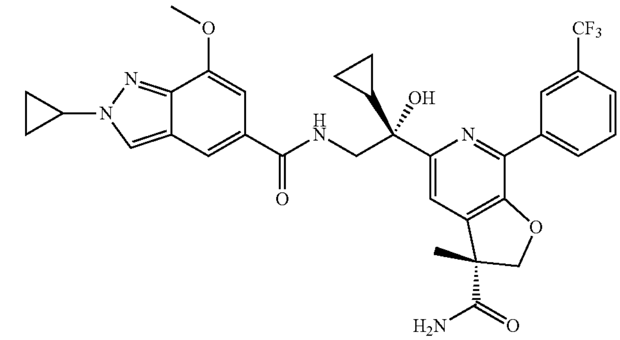 | 636.35 |
| 1298 | 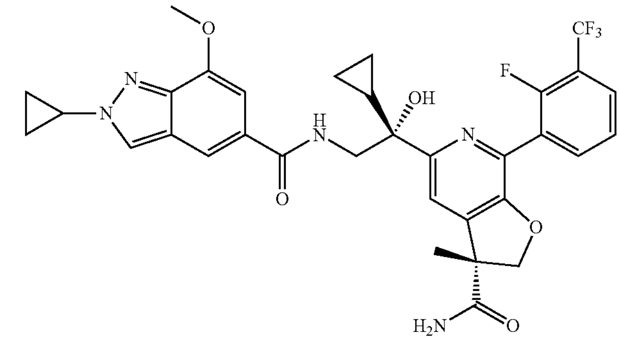 | 654.35 |
| 1299 | 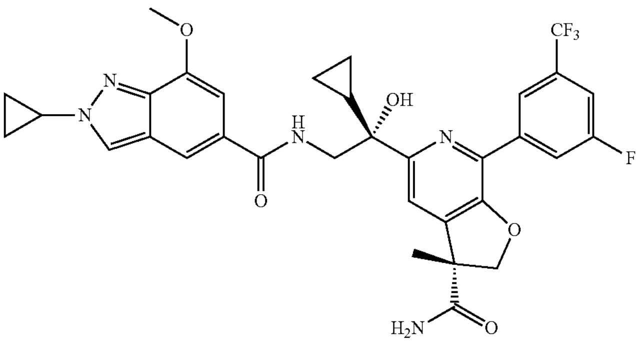 [SMILES: COc1cc(C(=O)NC[C@](O)(c2cc3c(c(-c4cc(F)cc(C(F)(F)F)c4)n2)OC[C@]3(C)C(N)=O)C2CC2)cc2cn(C3CC3)nc12] | 654.35 |

TABLE 10-continued
| Example | Structure | MS⁺ m/z |
|---|---|---|
| 1300 | 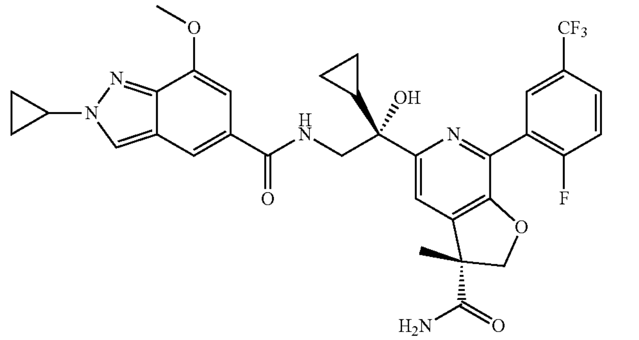 | 654.35 |
| 1301 | 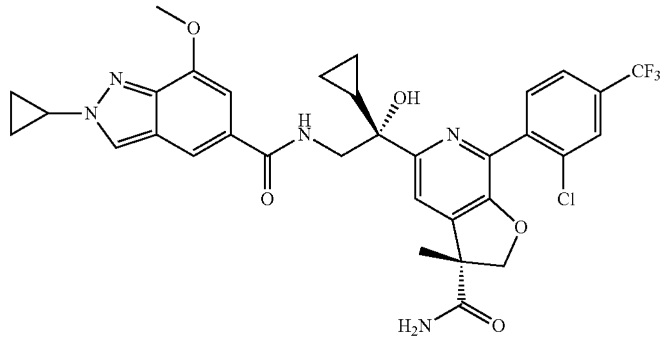 | 670.45 |
| 1302 | 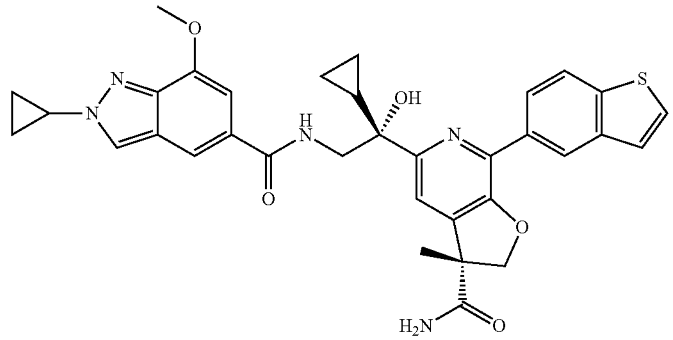 [SMILES: COc1cc(C(=O)NC[C@](O)(c2cc3c(c(-c4ccc5sccc5c4)n2)OC[C@]3(C)C(N)=O)C2CC2)cc2cn(C3CC3)nc12] | 624.35 |
| 1303 | 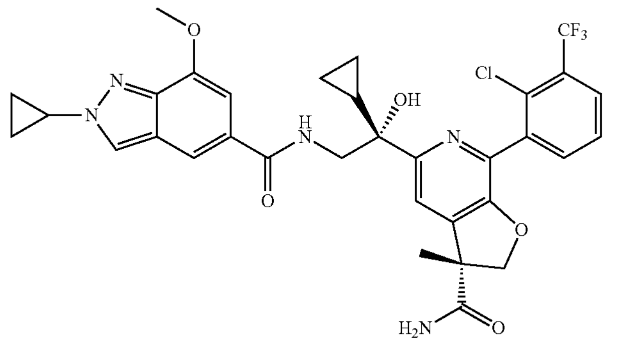 | 670.30 |

TABLE 10-continued
| Example | Structure | MS⁺ m/z |
|---|---|---|
| 1304 | 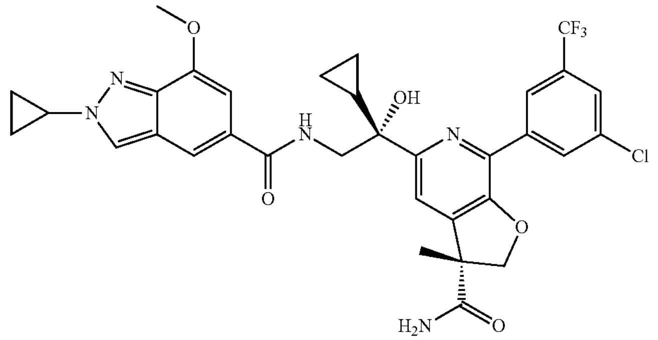 [SMILES: COc1cc(C(=O)NC[C@](O)(c2cc3c(c(-c4cc(Cl)cc(C(F)(F)F)c4)n2)OC[C@]3(C)C(N)=O)C2CC2)cc2cn(C3CC3)nc12] | 670.35 |
| 1305 | 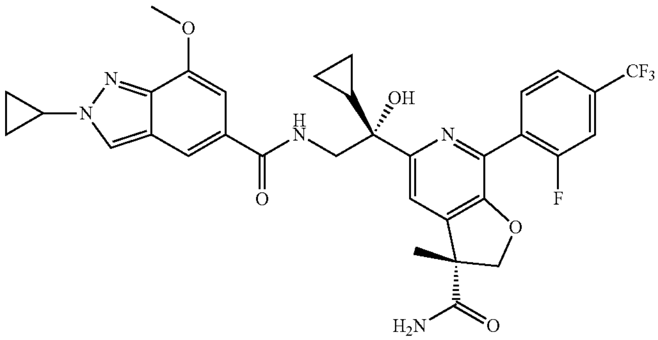 | 654.30 |
| 1306 | 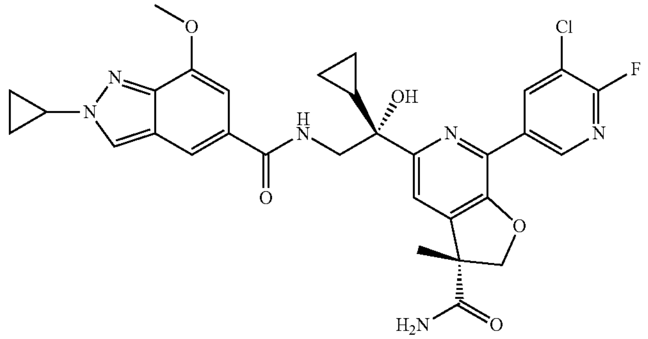 | 621.10 |
| 1307 | 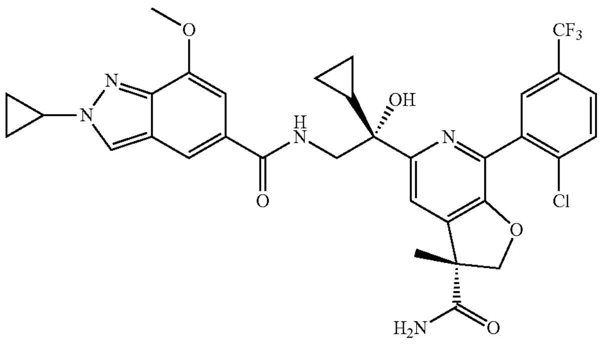 | 670.30 |

TABLE 10-continued
| Example | Structure | MS⁺ m/z |
|---|---|---|
| 1308 | 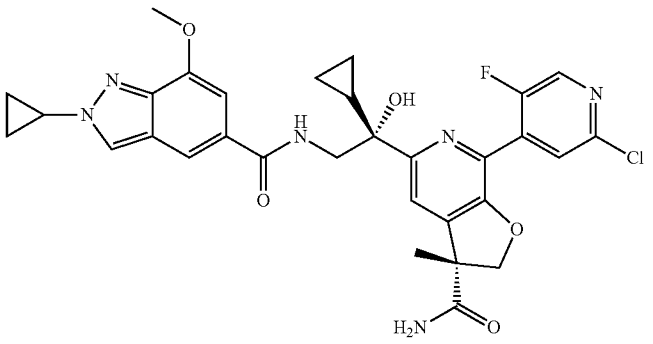 [SMILES: COc1cc(C(=O)NC[C@](O)(c2cc3c(c(-c4cc(Cl)ncc4F)n2)OC[C@]3(C)C(N)=O)C2CC2)cc2cn(C3CC3)nc12] | 621.30 |
| 1309 | 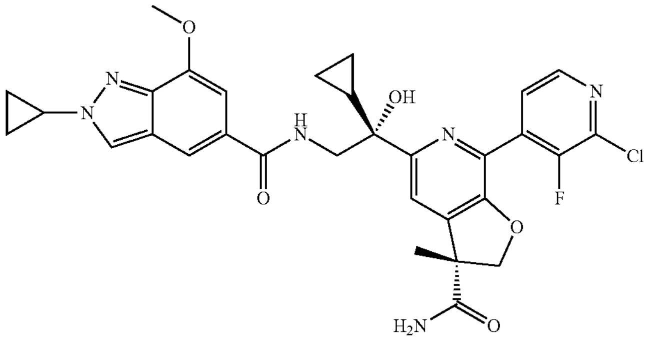 [SMILES: COc1cc(C(=O)NC[C@](O)(c2cc3c(c(-c4ccnc(Cl)c4F)n2)OC[C@]3(C)C(N)=O)C2CC2)cc2cn(C3CC3)nc12] | 621.30 |
| 1310 | 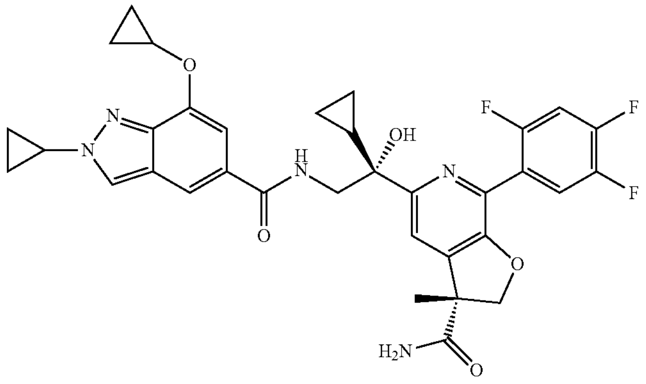 [SMILES: C[C@]1(C(N)=O)COc2c1cc([C@@](O)(CNC(=O)c1cc(OC3CC3)c3nn(C4CC4)cc3c1)C1CC1)nc2-c1cc(F)c(F)cc1F] | 648.32 |
| 1311 | 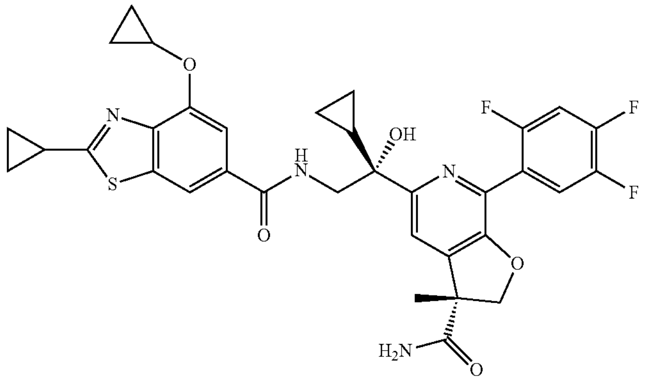 [SMILES: C[C@]1(C(N)=O)COc2c1cc([C@@](O)(CNC(=O)c1cc(OC3CC3)c3nc(C4CC4)sc3c1)C1CC1)nc2-c1cc(F)c(F)cc1F] | 665.27 |

TABLE 10-continued
| Example | Structure | MS⁺ m/z |
|---|---|---|
| 1312 | 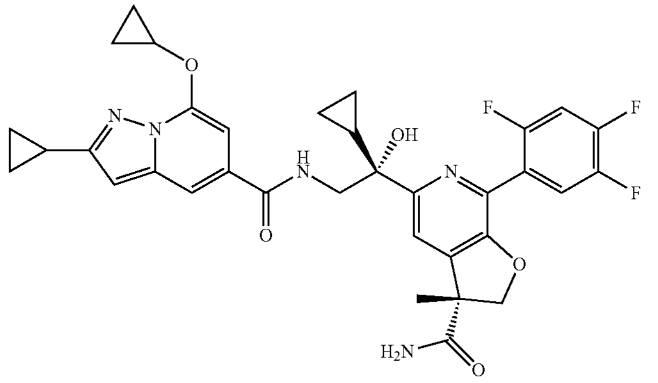 [SMILES: C[C@]1(C(N)=O)COc2c1cc([C@@](O)(CNC(=O)c1cc(OC3CC3)n3nc(C4CC4)cc3c1)C1CC1)nc2-c1cc(F)c(F)cc1F] | 648.31 |
| 1313 | 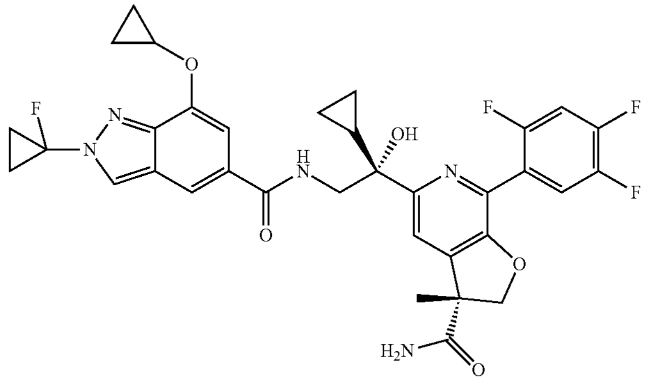 [SMILES: C[C@]1(C(N)=O)COc2c1cc([C@@](O)(CNC(=O)c1cc(OC3CC3)c3nn(C4(F)CC4)cc3c1)C1CC1)nc2-c1cc(F)c(F)cc1F] | 666.31 |
| 1314 | 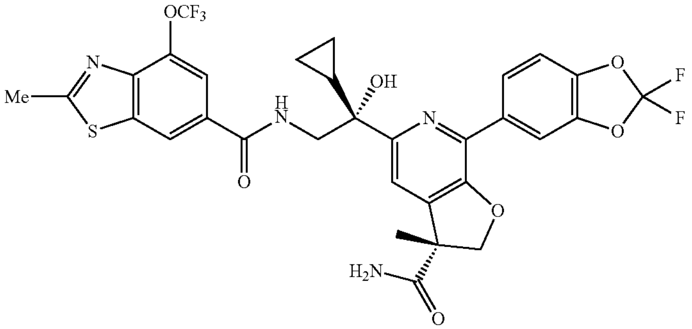 [SMILES: Cc1nc2c(OC(F)(F)F)cc(C(=O)NC[C@](O)(c3cc4c(c(-c5ccc6c(c5)OC(F)(F)O6)n3)OC[C@]4(C)C(N)=O)C3CC3)cc2s1] | 693.19 |
| 1315 | 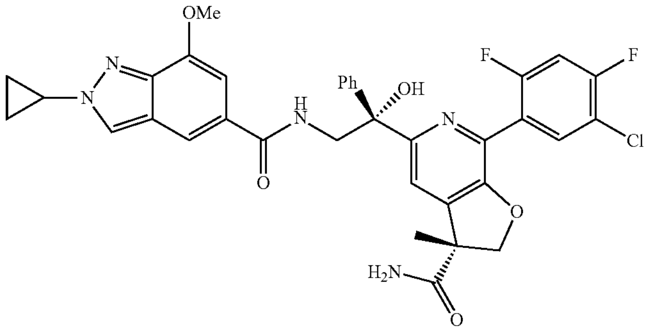 [SMILES: COc1cc(C(=O)NC[C@@](O)(c2ccccc2)c2cc3c(c(-c4cc(Cl)c(F)cc4F)n2)OC[C@]3(C)C(N)=O)cc2cn(C3CC3)nc12] | 674.23 |

TABLE 10-continued
| Example | Structure | MS⁺ m/z |
|---|---|---|
| 1316 | 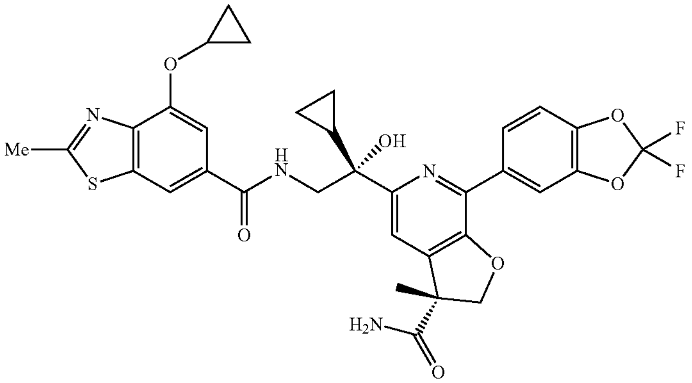 [SMILES: Cc1nc2c(OC3CC3)cc(C(=O)NC[C@](O)(c3cc4c(c(-c5ccc6c(c5)OC(F)(F)O6)n3)OC[C@]4(C)C(N)=O)C3CC3)cc2s1] | 665.26 |
| 1317 | 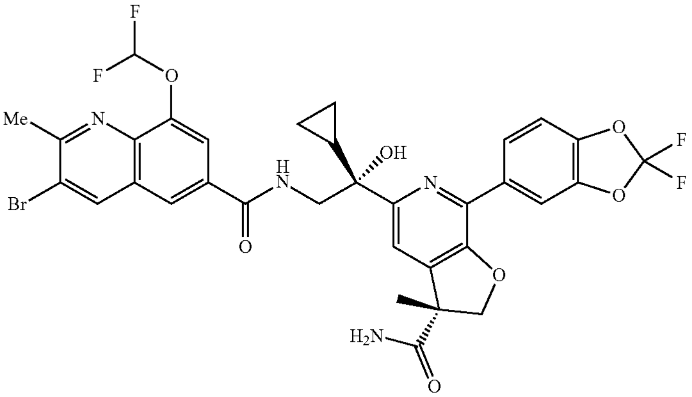 [SMILES: Cc1nc2c(OC(F)F)cc(C(=O)NC[C@](O)(c3cc4c(c(-c5ccc6c(c5)OC(F)(F)O6)n3)OC[C@]4(C)C(N)=O)C3CC3)cc2cc1Br] | 747.18 |
| 1318 | 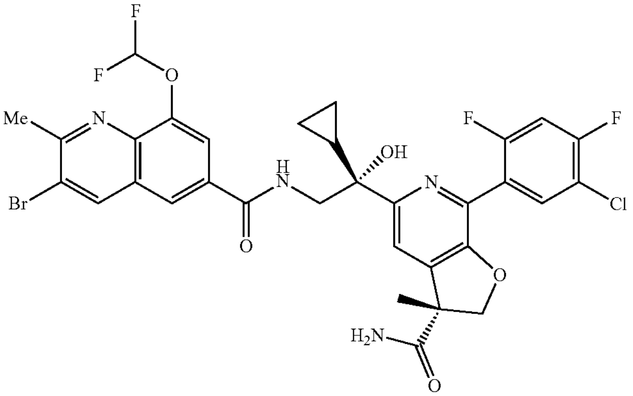 [SMILES: Cc1nc2c(OC(F)F)cc(C(=O)NC[C@](O)(c3cc4c(c(-c5cc(Cl)c(F)cc5F)n3)OC[C@]4(C)C(N)=O)C3CC3)cc2cc1Br] | 737.03 |
| 1319 | 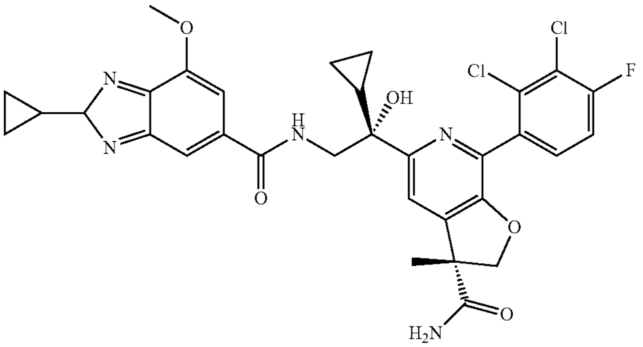 [SMILES: COc1cc(C(=O)NC[C@](O)(c2cc3c(c(-c4ccc(F)c(Cl)c4Cl)n2)OC[C@]3(C)C(N)=O)C2CC2)cc2c1=NC(C1CC1)N=2] | 654.22 |

TABLE 10-continued
| Example | Structure | MS+ m/z |
|---|---|---|
| 1320 | 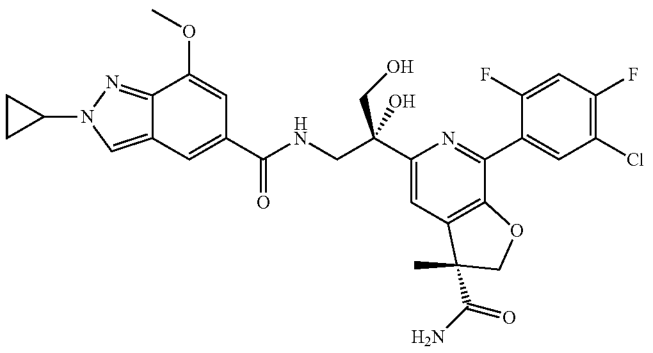 [SMILES: COc1cc(C(=O)NC[C@@](O)(CO)c2cc3c(c(-c4cc(Cl)c(F)cc4F)n2)OC[C@]3(C)C(N)=O)cc2cn(C3CC3)nc12] | 628.20 |
| 1321 | 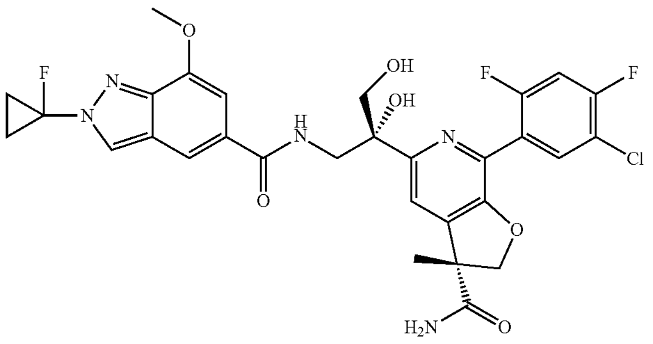 [SMILES: COc1cc(C(=O)NC[C@@](O)(CO)c2cc3c(c(-c4cc(Cl)c(F)cc4F)n2)OC[C@]3(C)C(N)=O)cc2cn(C3(F)CC3)nc12] | 646.18 |
| 1322 | 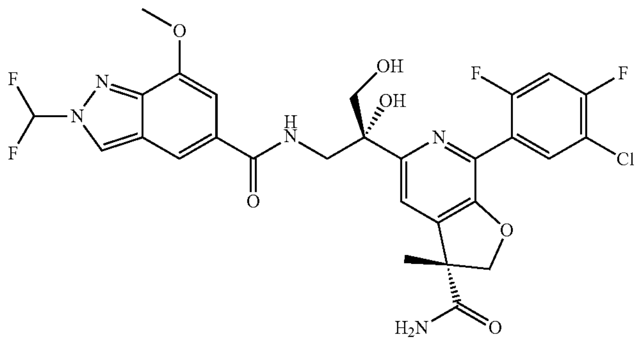 [SMILES: COc1cc(C(=O)NC[C@@](O)(CO)c2cc3c(c(-c4cc(Cl)c(F)cc4F)n2)OC[C@]3(C)C(N)=O)cc2cn(C(F)F)nc12] | 638.24 |
| 1323 | 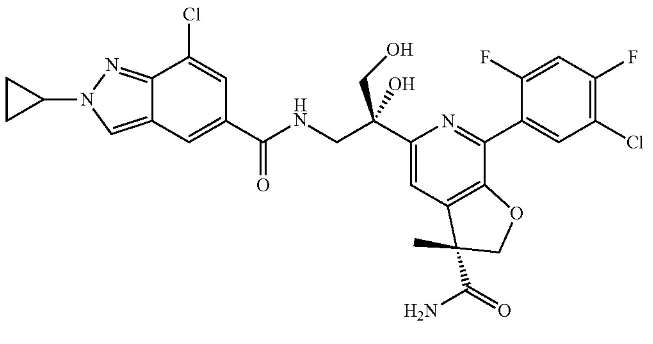 [SMILES: C[C@]1(C(N)=O)COc2c1cc([C@](O)(CO)CNC(=O)c1cc(Cl)c3nn(C4CC4)cc3c1)nc2-c1cc(Cl)c(F)cc1F] | 646.18 |

TABLE 10-continued
| Example | Structure | MS⁺ m/z |
|---|---|---|
| 1324 | 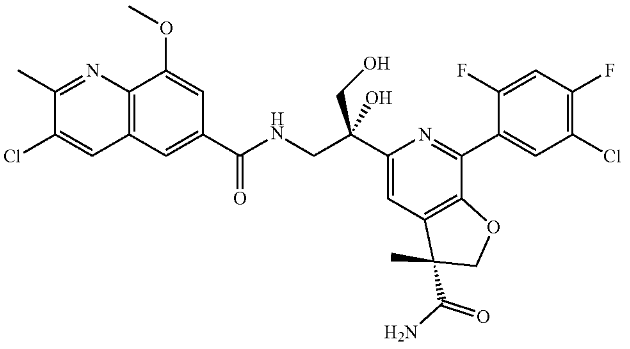 [SMILES: COc1cc(C(=O)NC[C@@](O)(CO)c2cc3c(c(-c4cc(Cl)c(F)cc4F)n2)OC[C@]3(C)C(N)=O)cc2cc(Cl)c(C)nc12] | 647.15 |
| 1325 | 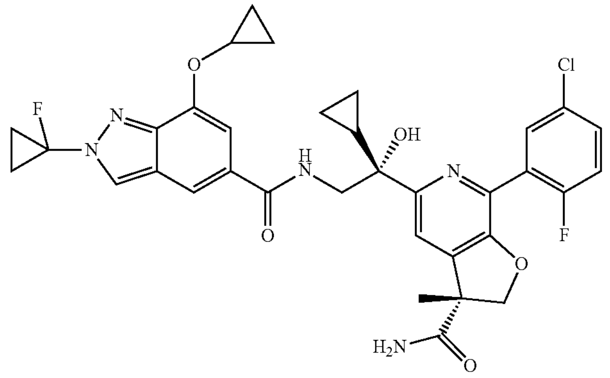 [SMILES: C[C@]1(C(N)=O)COc2c1cc([C@@](O)(CNC(=O)c1cc(OC3CC3)c3nn(C4(F)CC4)cc3c1)C1CC1)nc2-c1cc(Cl)ccc1F] | 664.32 |
| 1326 | 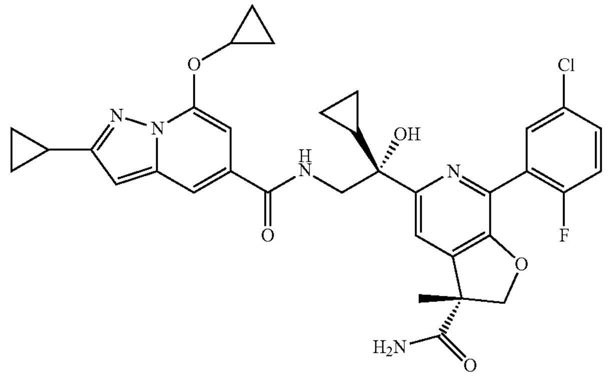 [SMILES: C[C@]1(C(N)=O)COc2c1cc([C@@](O)(CNC(=O)c1cc(OC3CC3)n3nc(C4CC4)cc3c1)C1CC1)nc2-c1cc(Cl)ccc1F] | 646.30 |
| 1327 | 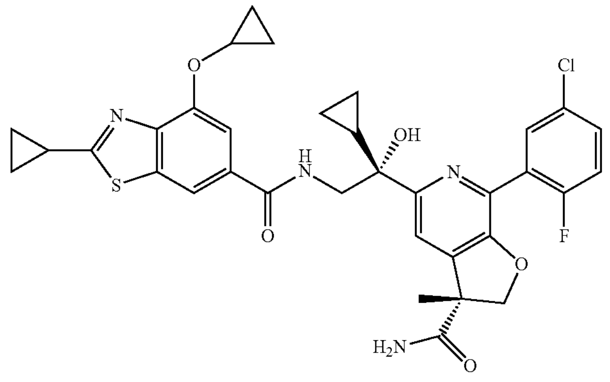 [SMILES: C[C@]1(C(N)=O)COc2c1cc([C@@](O)(CNC(=O)c1cc(OC3CC3)c3nc(C4CC4)sc3c1)C1CC1)nc2-c1cc(Cl)ccc1F] | 663.27 |

TABLE 10-continued
| Example | Structure | MS+ m/z |
|---|---|---|
| 1328 | 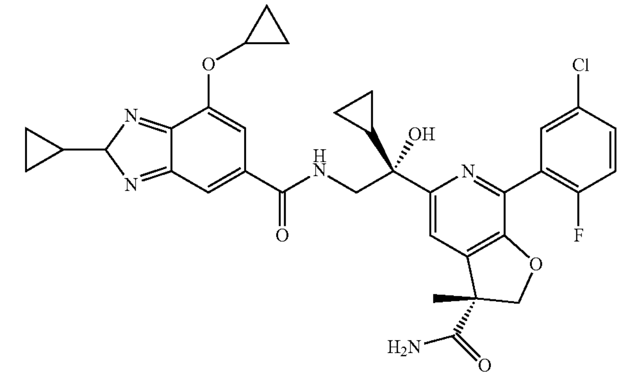 [SMILES: C[C@]1(C(N)=O)COc2c1cc([C@@](O)(CNC(=O)c1cc(OC3CC3)c3c(c1)=NC(C1CC1)N=3)C1CC1)nc2-c1cc(Cl)ccc1F] | 646.31 |
| 1329 | 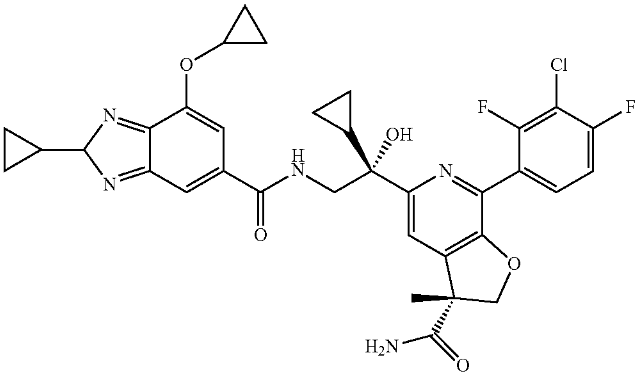 [SMILES: C[C@]1(C(N)=O)COc2c1cc([C@@](O)(CNC(=O)c1cc(OC3CC3)c3c(c1)=NC(C1CC1)N=3)C1CC1)nc2-c1ccc(F)c(Cl)c1F] | 664.27 |
| 1330 | 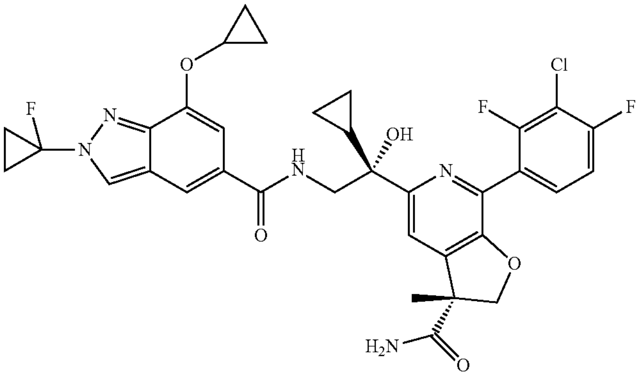 [SMILES: C[C@]1(C(N)=O)COc2c1cc([C@@](O)(CNC(=O)c1cc(OC3CC3)c3nn(C4(F)CC4)cc3c1)C1CC1)nc2-c1ccc(F)c(Cl)c1F] | 682.27 |
| 1331 | 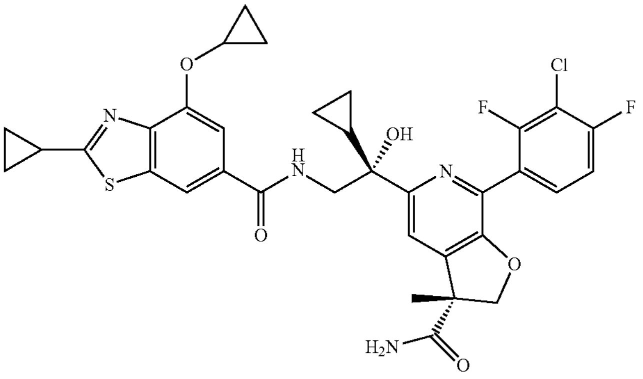 [SMILES: C[C@]1(C(N)=O)COc2c1cc([C@@](O)(CNC(=O)c1cc(OC3CC3)c3nc(C4CC4)sc3c1)C1CC1)nc2-c1ccc(F)c(Cl)c1F] | 681.25 |

TABLE 10-continued
| Example | Structure | MS+ m/z |
| --- | --- | --- |
| 1332 | 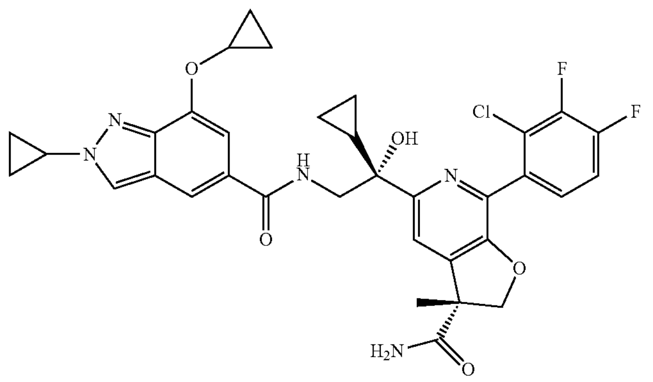 [SMILES: C[C@]1(C(N)=O)COc2c1cc([C@@](O)(CNC(=O)c1cc(OC3CC3)c3nn(C4CC4)cc3c1)C1CC1)nc2-c1ccc(F)c(F)c1Cl] | 664.27 |
| 1333 | 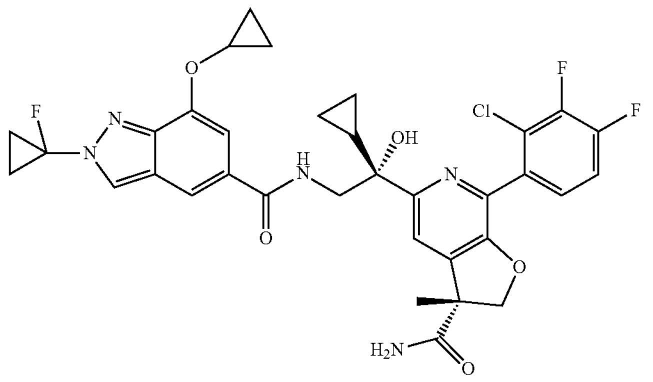 [SMILES: C[C@]1(C(N)=O)COc2c1cc([C@@](O)(CNC(=O)c1cc(OC3CC3)c3nn(C4(F)CC4)cc3c1)C1CC1)nc2-c1ccc(F)c(F)c1Cl] | 682.24 |
| 1334 | 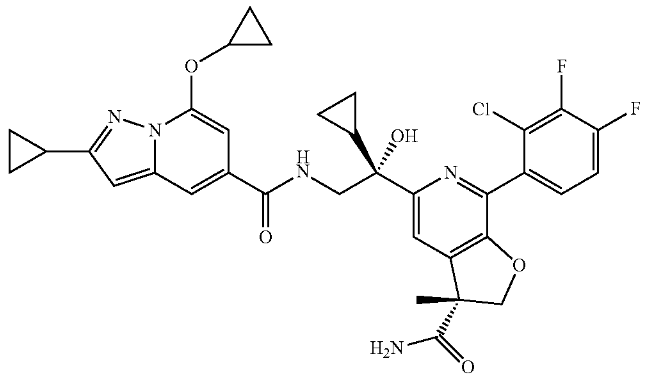 [SMILES: C[C@]1(C(N)=O)COc2c1cc([C@@](O)(CNC(=O)c1cc(OC3CC3)n3nc(C4CC4)cc3c1)C1CC1)nc2-c1ccc(F)c(F)c1Cl] | 664.28 |
| 1335 | 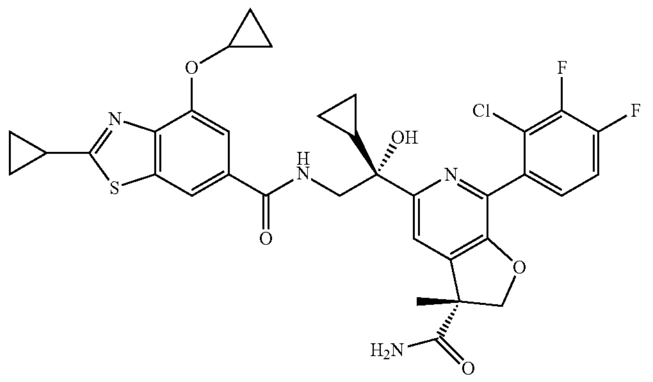 [SMILES: C[C@]1(C(N)=O)COc2c1cc([C@@](O)(CNC(=O)c1cc(OC3CC3)c3nc(C4CC4)sc3c1)C1CC1)nc2-c1ccc(F)c(F)c1Cl] | 681.20 |

The following examples in Table 11 are prepared by using procedures similar to those described above:
| Compound | Structure |
|---|---|
| P1 | 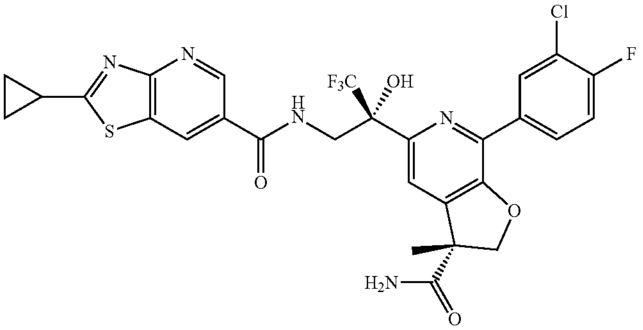 [SMILES: C[C@]1(C(N)=O)COc2c1cc([C@@](O)(CNC(=O)c1cnc3nc(C4CC4)sc3c1)C(F)(F)F)nc2-c1ccc(F)c(Cl)c1] |
| P2 | 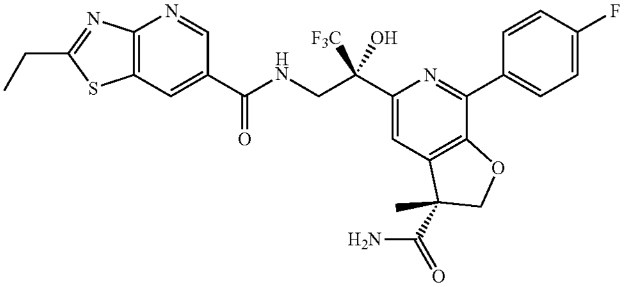 [SMILES: CCc1nc2ncc(C(=O)NC[C@](O)(c3cc4c(c(-c5ccc(F)cc5)n3)OC[C@]4(C)C(N)=O)C(F)(F)F)cc2s1] |
| P3 | 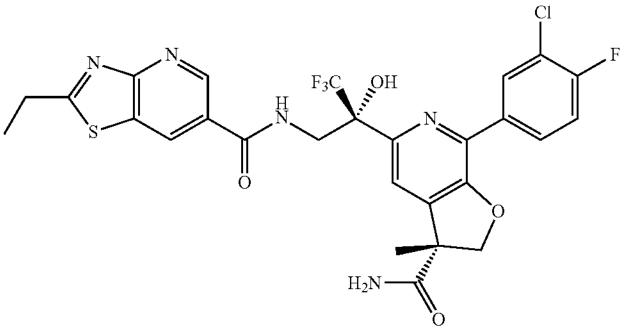 [SMILES: CCc1nc2ncc(C(=O)NC[C@](O)(c3cc4c(c(-c5ccc(F)c(Cl)c5)n3)OC[C@]4(C)C(N)=O)C(F)(F)F)cc2s1] |
| P4 | 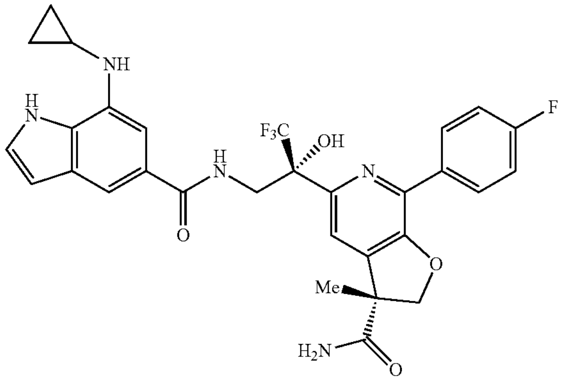 [SMILES: C[C@]1(C(N)=O)COc2c1cc([C@@](O)(CNC(=O)c1cc(NC3CC3)c3[nH]ccc3c1)C(F)(F)F)nc2-c1ccc(F)cc1] |

-continued
| Compound | Structure |
|---|---|
| P5 | 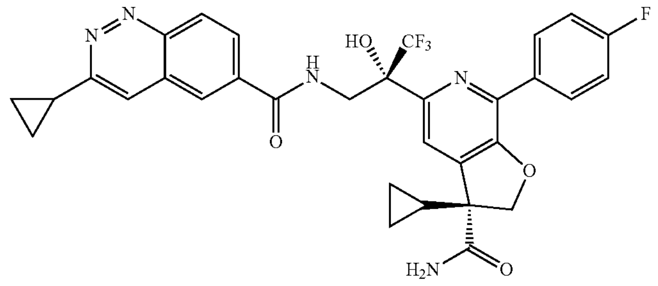 [SMILES: NC(=O)[C@@]1(C2CC2)COc2c1cc([C@@](O)(CNC(=O)c1ccc3nnc(C4CC4)cc3c1)C(F)(F)F)nc2-c1ccc(F)cc1] |
| P6 | 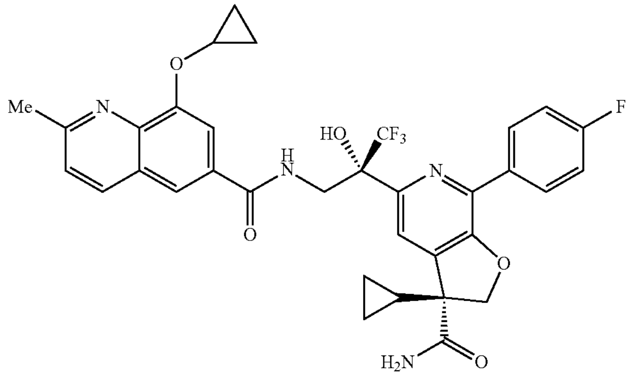 [SMILES: Cc1ccc2cc(C(=O)NC[C@](O)(c3cc4c(c(-c5ccc(F)cc5)n3)OC[C@@]4(C(N)=O)C3CC3)C(F)(F)F)cc(OC3CC3)c2n1] |
| P7 | 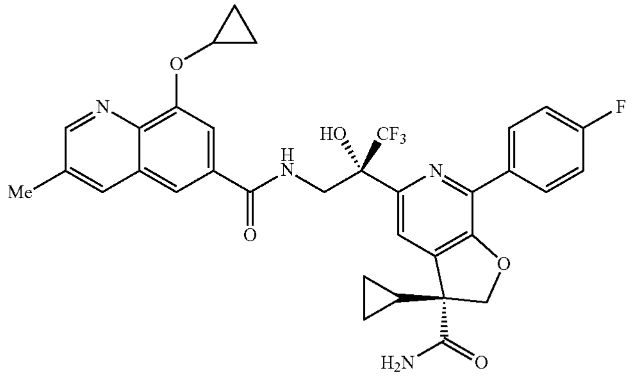 [SMILES: Cc1cnc2c(OC3CC3)cc(C(=O)NC[C@](O)(c3cc4c(c(-c5ccc(F)cc5)n3)OC[C@@]4(C(N)=O)C3CC3)C(F)(F)F)cc2c1] |
| P8 | 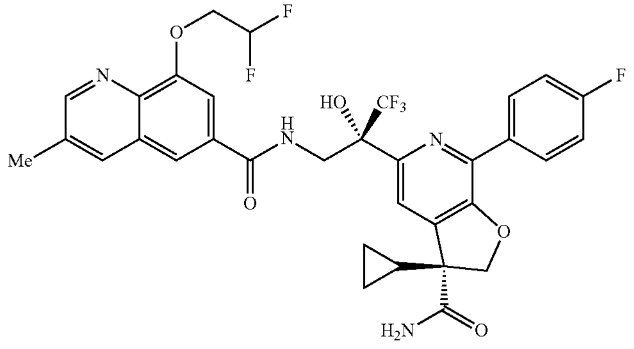 [SMILES: Cc1cnc2c(OCC(F)F)cc(C(=O)NC[C@](O)(c3cc4c(c(-c5ccc(F)cc5)n3)OC[C@@]4(C(N)=O)C3CC3)C(F)(F)F)cc2c1] |

-continued
| Compound | Structure |
|---|---|
| P9 | 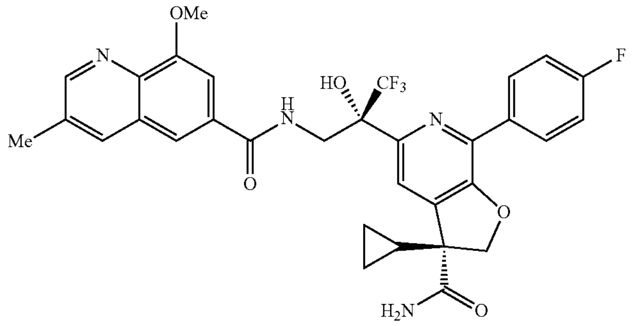 [SMILES: COc1cc(C(=O)NC[C@](O)(c2cc3c(c(-c4ccc(F)cc4)n2)OC[C@@]3(C(N)=O)C2CC2)C(F)(F)F)cc2cc(C)cnc12] |
| P10 | 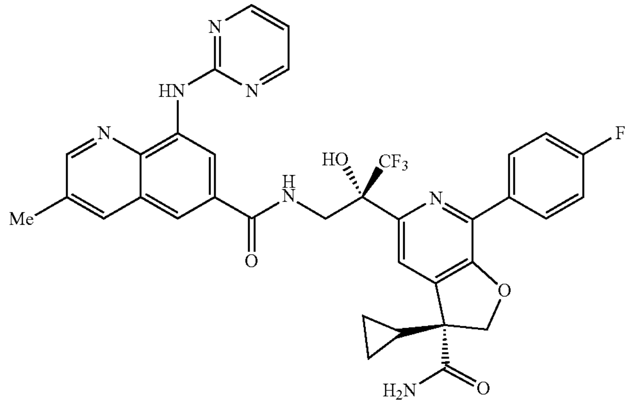 [SMILES: Cc1cnc2c(Nc3ncccn3)cc(C(=O)NC[C@](O)(c3cc4c(c(-c5ccc(F)cc5)n3)OC[C@@]4(C(N)=O)C3CC3)C(F)(F)F)cc2c1] |
| P11 | 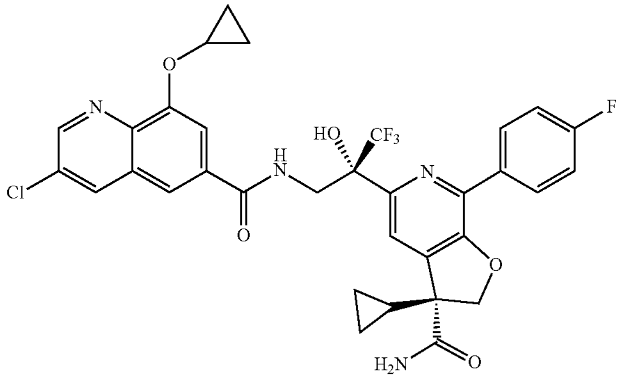 [SMILES: NC(=O)[C@@]1(C2CC2)COc2c1cc([C@@](O)(CNC(=O)c1cc(OC3CC3)c3ncc(Cl)cc3c1)C(F)(F)F)nc2-c1ccc(F)cc1] |
| P12 | 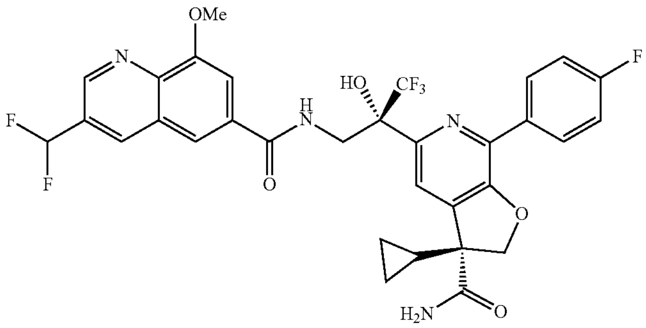 [SMILES: COc1cc(C(=O)NC[C@](O)(c2cc3c(c(-c4ccc(F)cc4)n2)OC[C@@]3(C(N)=O)C2CC2)C(F)(F)F)cc2cc(C(F)F)cnc12] |

-continued
| Compound | Structure |
| --- | --- |
| P13 | 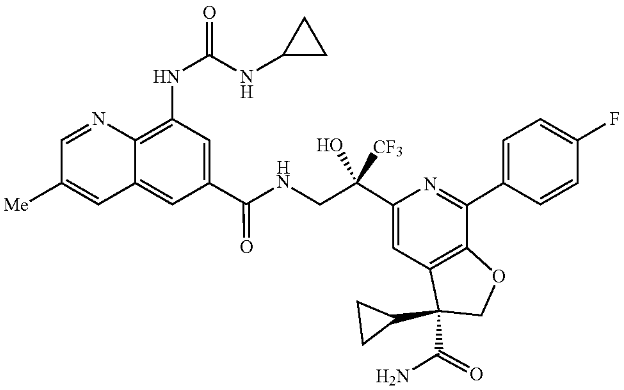 [SMILES: Cc1cnc2c(NC(=O)NC3CC3)cc(C(=O)NC[C@](O)(c3cc4c(c(-c5ccc(F)cc5)n3)OC[C@@]4(C(N)=O)C3CC3)C(F)(F)F)cc2c1] |
| P14 | 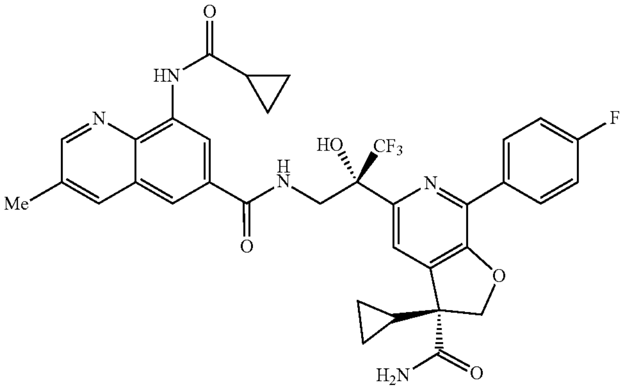 [SMILES: Cc1cnc2c(NC(=O)C3CC3)cc(C(=O)NC[C@](O)(c3cc4c(c(-c5ccc(F)cc5)n3)OC[C@@]4(C(N)=O)C3CC3)C(F)(F)F)cc2c1] |
| P15 | 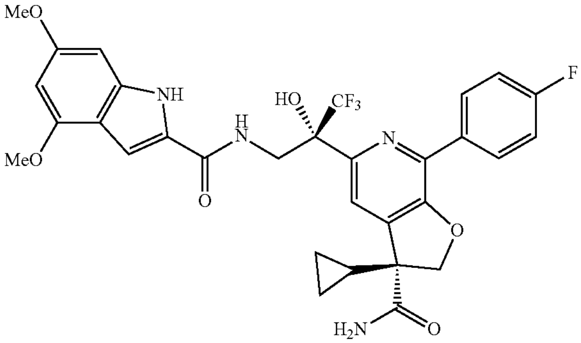 [SMILES: COc1cc(OC)c2cc(C(=O)NC[C@](O)(c3cc4c(c(-c5ccc(F)cc5)n3)OC[C@@]4(C(N)=O)C3CC3)C(F)(F)F)[nH]c2c1] |
| P16 | 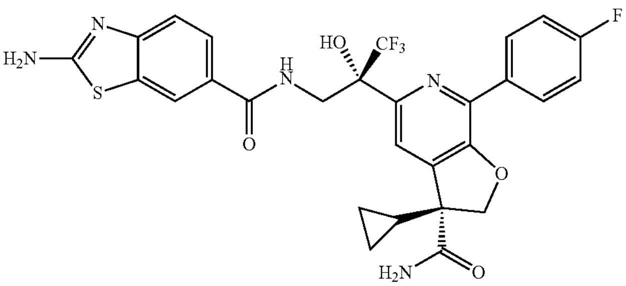 [SMILES: NC(=O)[C@@]1(C2CC2)COc2c1cc([C@@](O)(CNC(=O)c1ccc3nc(N)sc3c1)C(F)(F)F)nc2-c1ccc(F)cc1] |

-continued
| Compound | Structure |
| --- | --- |
| P17 | 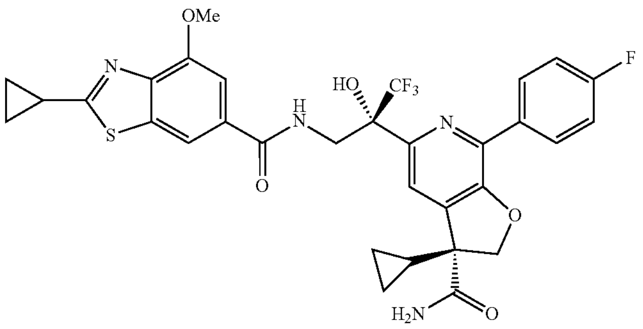 [SMILES: COc1cc(C(=O)NC[C@](O)(c2cc3c(c(-c4ccc(F)cc4)n2)OC[C@@]3(C(N)=O)C2CC2)C(F)(F)F)cc2sc(C3CC3)nc12] |
| P18 | 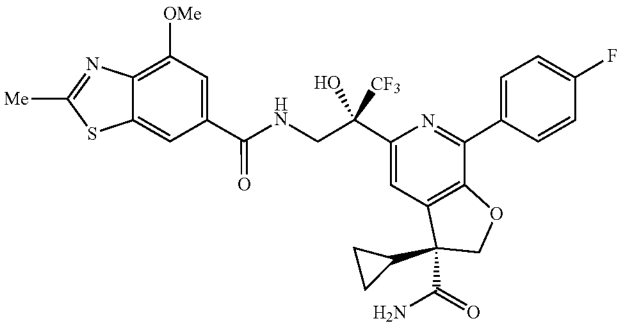 [SMILES: COc1cc(C(=O)NC[C@](O)(c2cc3c(c(-c4ccc(F)cc4)n2)OC[C@@]3(C(N)=O)C2CC2)C(F)(F)F)cc2sc(C)nc12] |
| P19 | 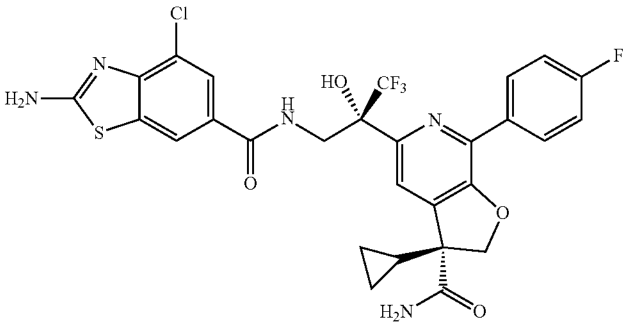 [SMILES: NC(=O)[C@@]1(C2CC2)COc2c1cc([C@@](O)(CNC(=O)c1cc(Cl)c3nc(N)sc3c1)C(F)(F)F)nc2-c1ccc(F)cc1] |
| P20 | 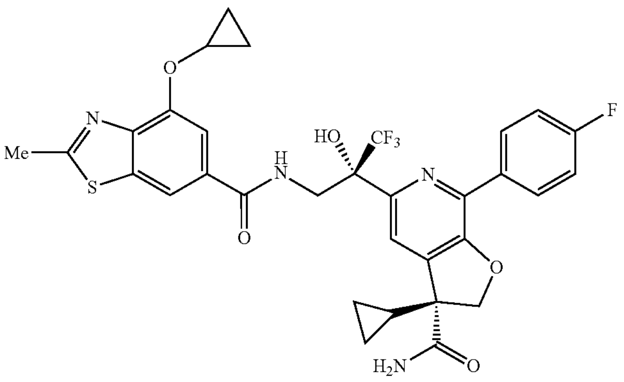 [SMILES: Cc1nc2c(OC3CC3)cc(C(=O)NC[C@](O)(c3cc4c(c(-c5ccc(F)cc5)n3)OC[C@@]4(C(N)=O)C3CC3)C(F)(F)F)cc2s1] |

-continued
| Compound | Structure |
|---|---|
| P21 | 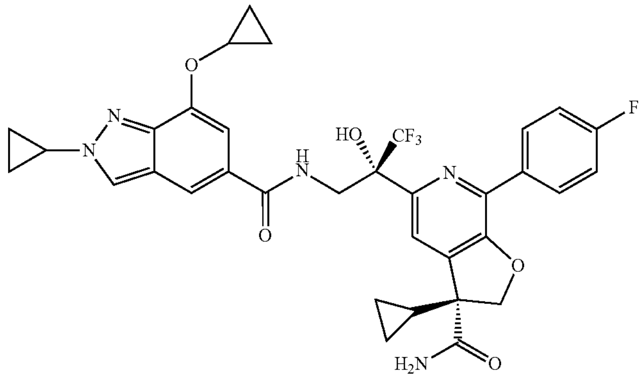 [SMILES: NC(=O)[C@@]1(C2CC2)COc2c1cc([C@@](O)(CNC(=O)c1cc(OC3CC3)c3nn(C4CC4)cc3c1)C(F)(F)F)nc2-c1ccc(F)cc1] |
| P22 | 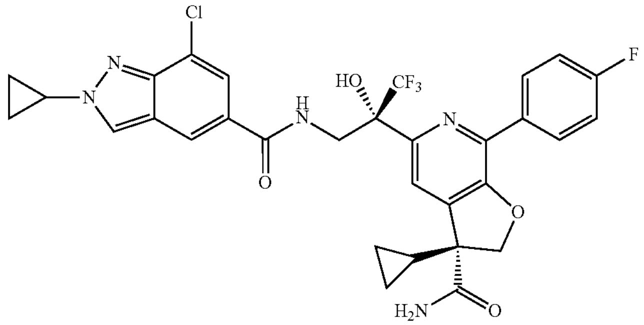 [SMILES: NC(=O)[C@@]1(C2CC2)COc2c1cc([C@@](O)(CNC(=O)c1cc(Cl)c3nn(C4CC4)cc3c1)C(F)(F)F)nc2-c1ccc(F)cc1] |
| P23 | 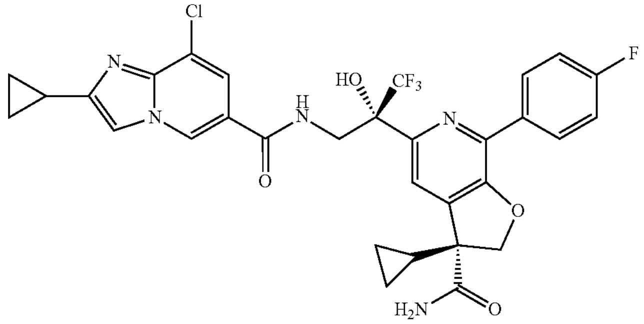 [SMILES: NC(=O)[C@@]1(C2CC2)COc2c1cc([C@@](O)(CNC(=O)c1cc(Cl)c3nc(C4CC4)cn3c1)C(F)(F)F)nc2-c1ccc(F)cc1] |
| P24 | 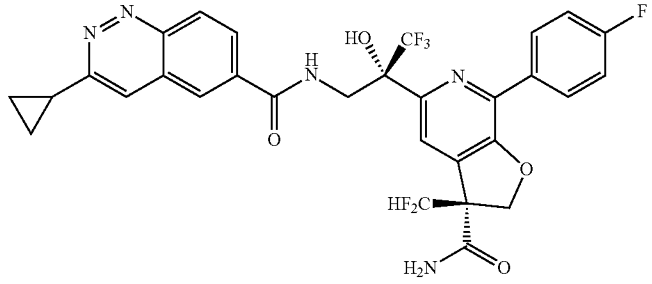 |

-continued
| Compound | Structure |
| --- | --- |
| P25 | 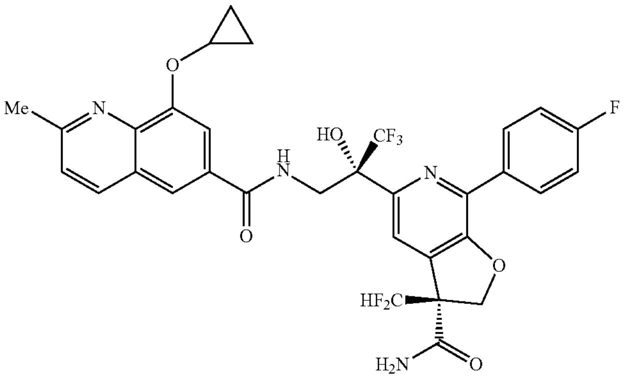 |
| P26 | 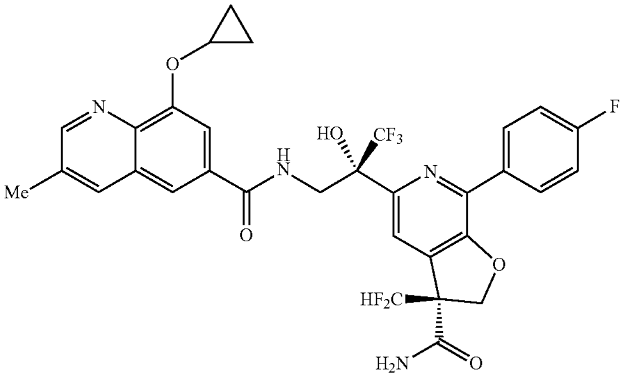 |
| P27 | 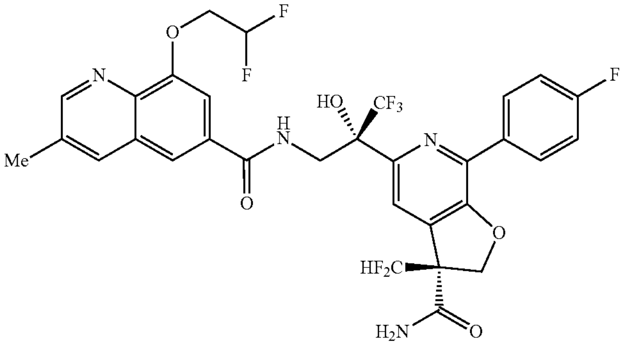 |
| P28 | 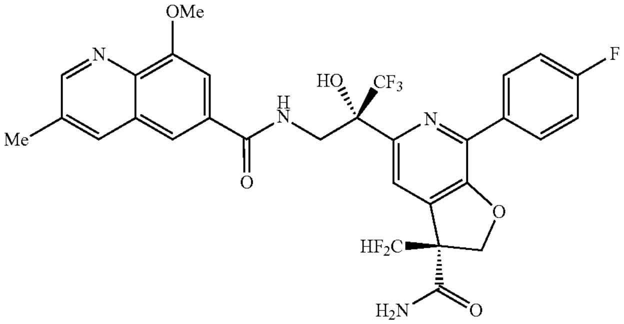 |

-continued
| Compound | Structure |
| --- | --- |
| P29 | 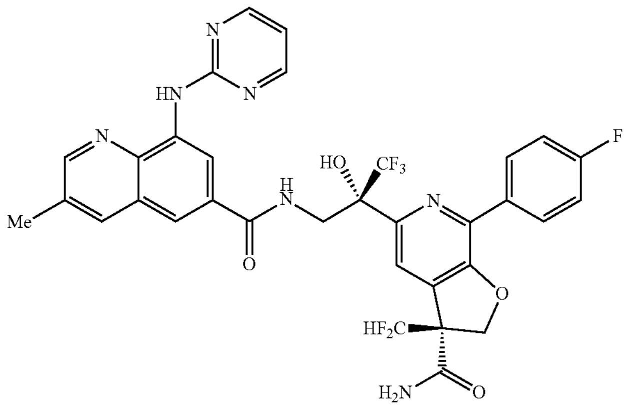 |
| P30 | 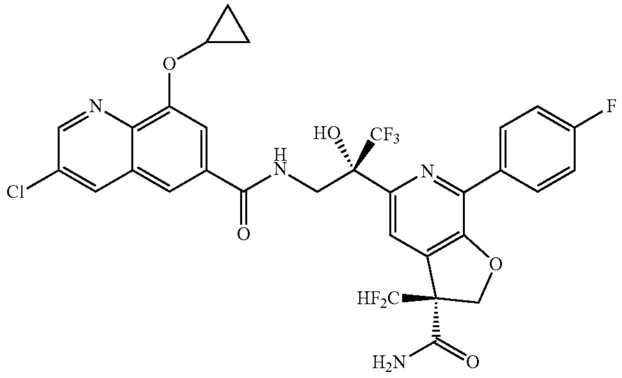 |
| P31 | 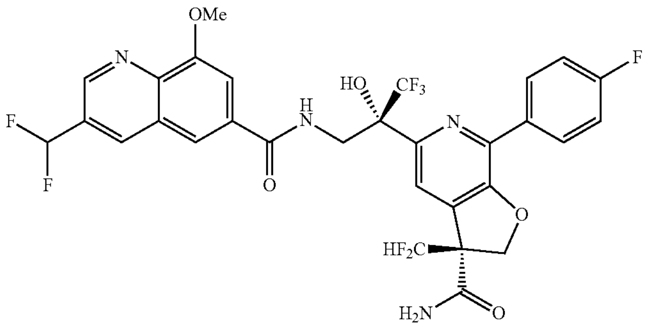 |
| P32 | 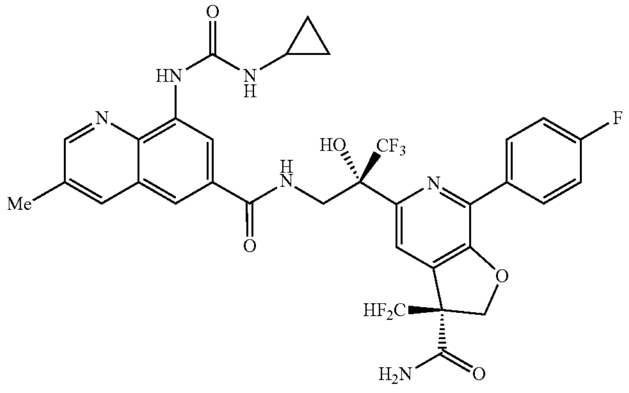 |

-continued
| Compound | Structure |
| --- | --- |
| P33 | 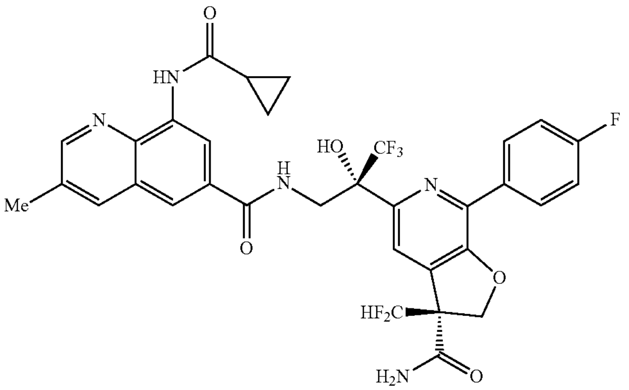 |
| P34 | 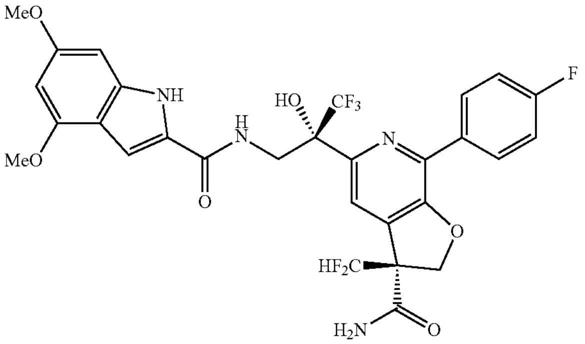 |
| P35 | 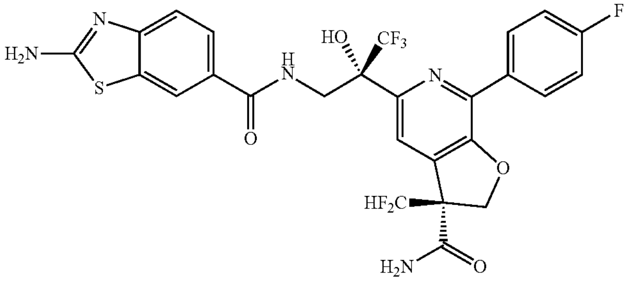 |
| P36 | 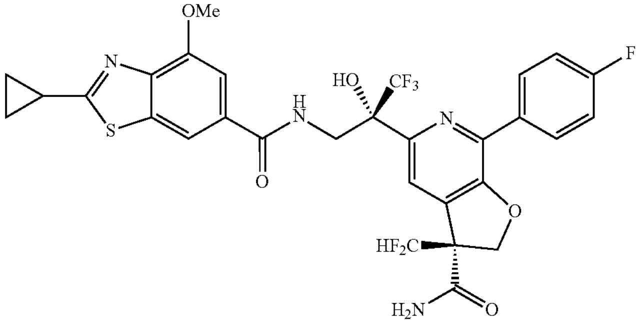 |

-continued
| Compound | Structure |
| --- | --- |
| P37 | 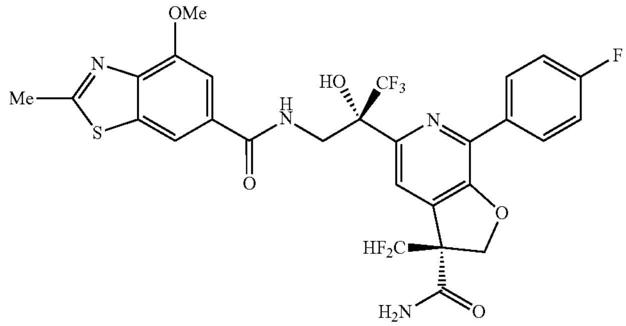 |
| P38 | 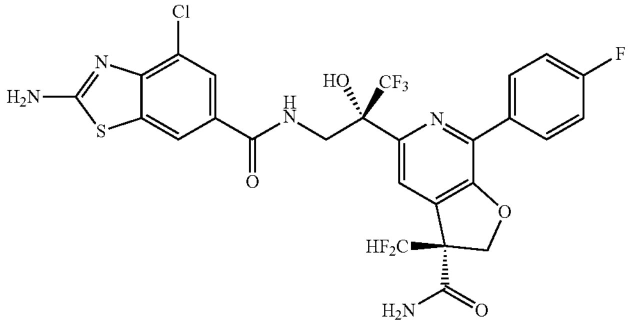 |
| P39 | 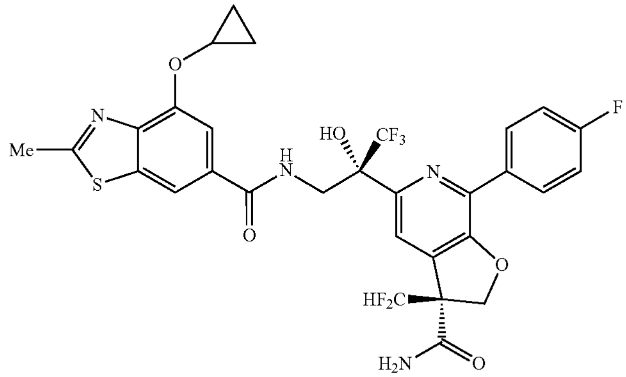 |
| P40 | 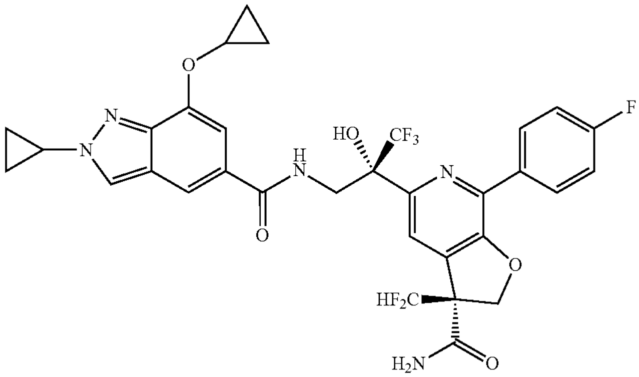 |

-continued
| Compound | Structure |
| --- | --- |
| P41 | 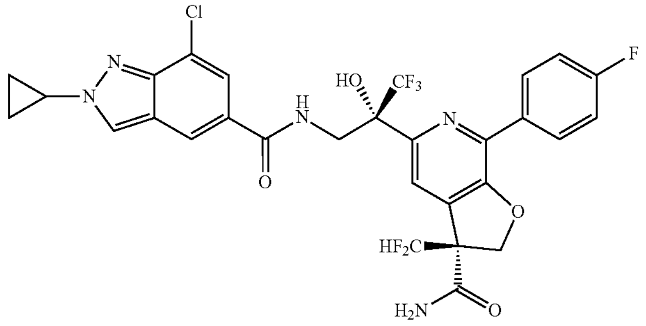 |
| P42 | 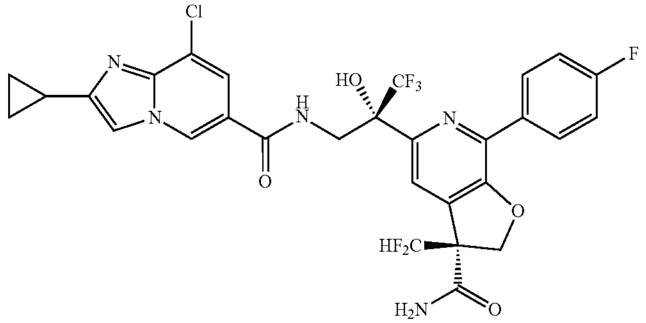 |
| P43 | 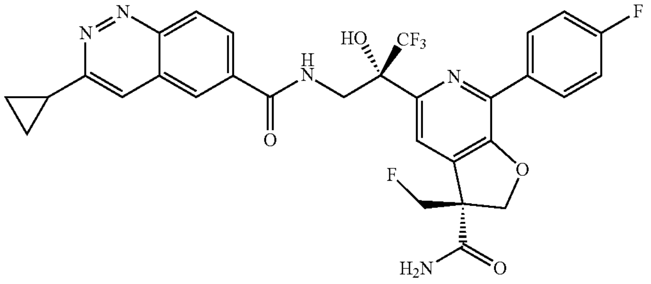 [SMILES: NC(=O)[C@@]1(CF)COc2c1cc([C@@](O)(CNC(=O)c1ccc3nnc(C4CC4)cc3c1)C(F)(F)F)nc2-c1ccc(F)cc1] |
| P44 | 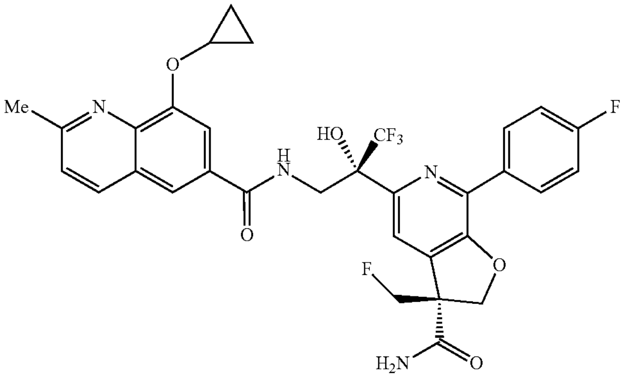 |

-continued
| Compound | Structure |
|---|---|
| P45 | 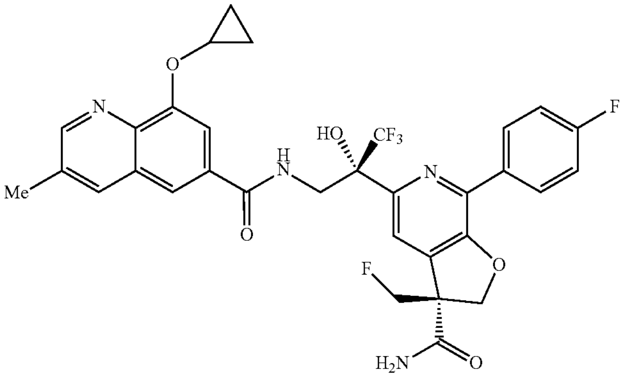 |
| P46 | 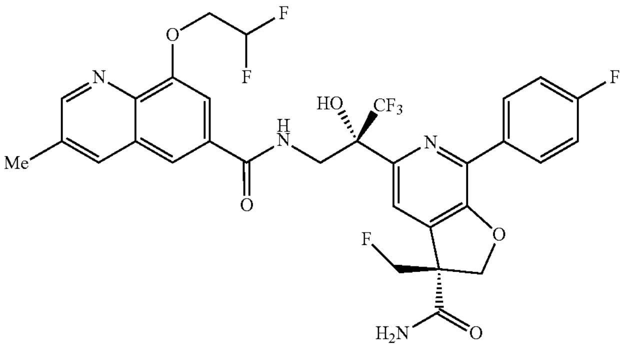 [SMILES: Cc1cnc2c(OCC(F)F)cc(C(=O)NC[C@](O)(c3cc4c(c(-c5ccc(F)cc5)n3)OC[C@]4(CF)C(N)=O)C(F)(F)F)cc2c1] |
| P47 | 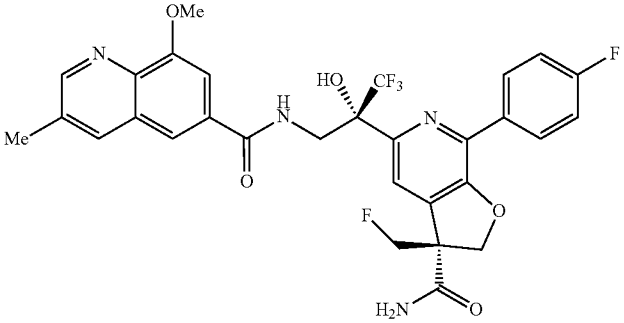 [SMILES: COc1cc(C(=O)NC[C@](O)(c2cc3c(c(-c4ccc(F)cc4)n2)OC[C@]3(CF)C(N)=O)C(F)(F)F)cc2cc(C)cnc12] |
| P48 | 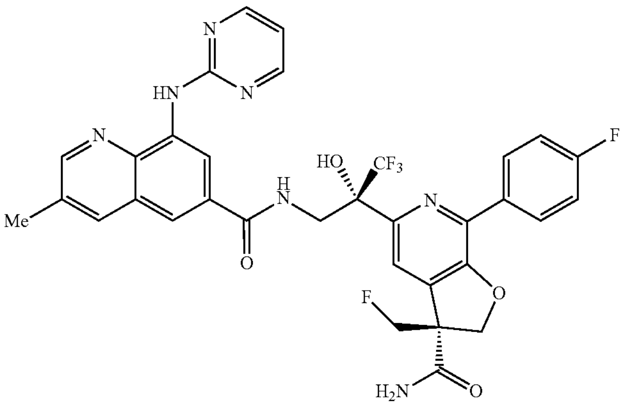 |

-continued
| Compound | Structure |
|---|---|
| P49 | 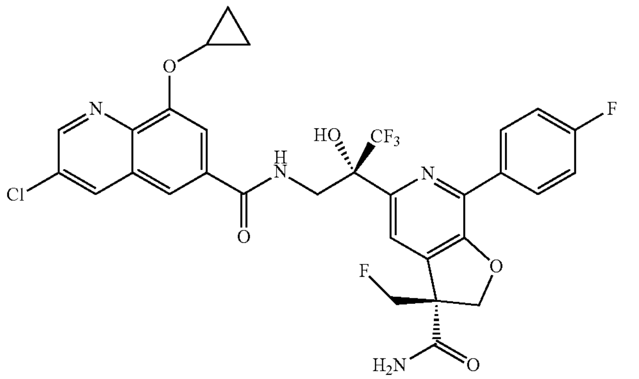 |
| P50 | 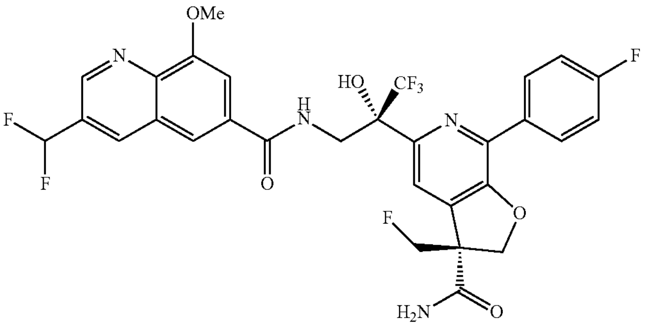 [SMILES: COc1cc(C(=O)NC[C@](O)(c2cc3c(c(-c4ccc(F)cc4)n2)OC[C@]3(CF)C(N)=O)C(F)(F)F)cc2cc(C(F)F)cnc12] |
| P51 | 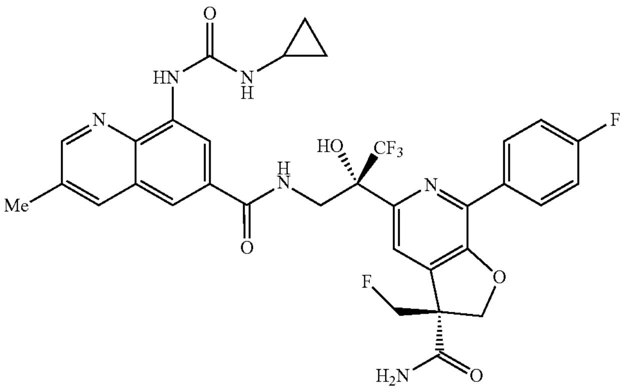 [SMILES: Cc1cnc2c(NC(=O)NC3CC3)cc(C(=O)NC[C@](O)(c3cc4c(c(-c5ccc(F)cc5)n3)OC[C@]4(CF)C(N)=O)C(F)(F)F)cc2c1] |
| P52 | 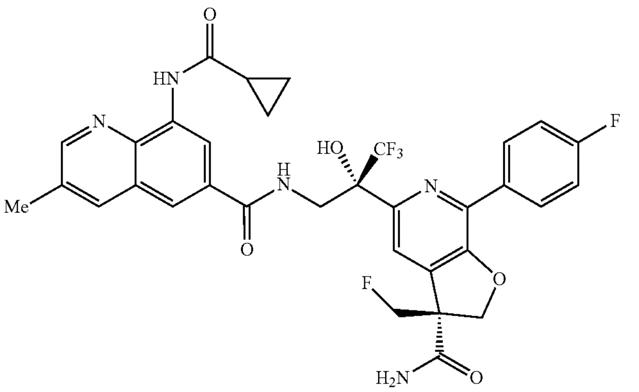 [SMILES: Cc1cnc2c(NC(=O)C3CC3)cc(C(=O)NC[C@](O)(c3cc4c(c(-c5ccc(F)cc5)n3)OC[C@]4(CF)C(N)=O)C(F)(F)F)cc2c1] |

-continued
| Compound | Structure |
|---|---|
| P53 | 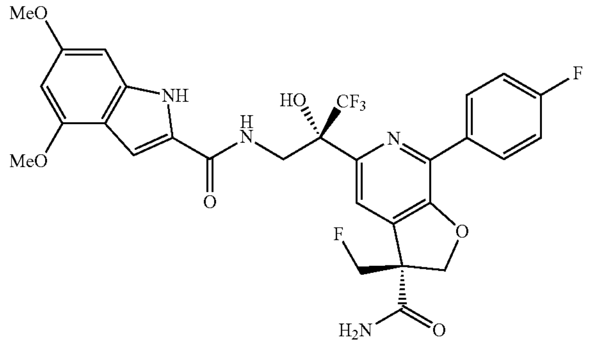 [SMILES: COc1cc(OC)c2cc(C(=O)NC[C@](O)(c3cc4c(c(-c5ccc(F)cc5)n3)OC[C@]4(CF)C(N)=O)C(F)(F)F)[nH]c2c1] |
| P54 | 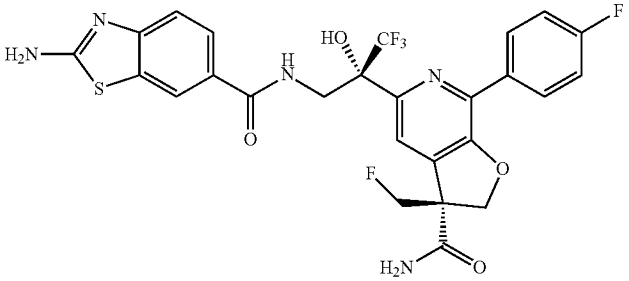 |
| P55 | 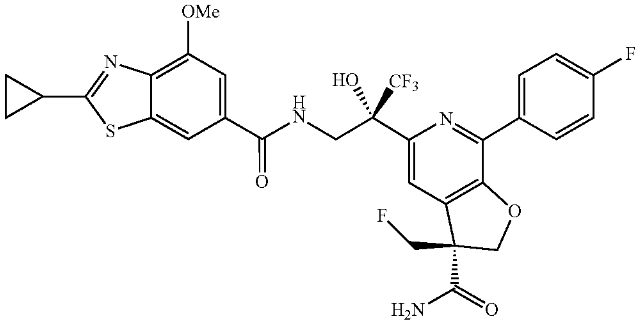 |
| P56 | 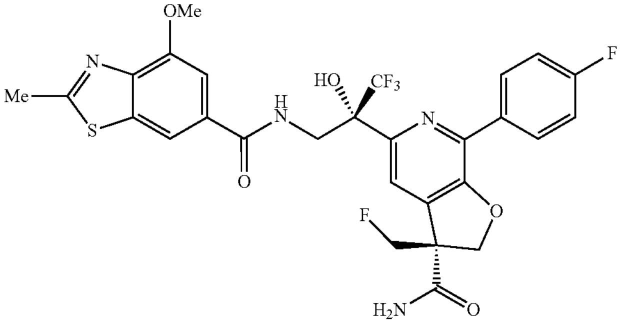 [SMILES: COc1cc(C(=O)NC[C@](O)(c2cc3c(c(-c4ccc(F)cc4)n2)OC[C@]3(CF)C(N)=O)C(F)(F)F)cc2sc(C)nc12] |

-continued
| Compound | Structure |
|---|---|
| P57 | 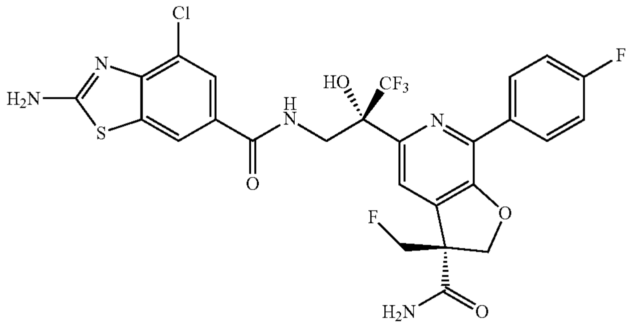 [SMILES: NC(=O)[C@@]1(CF)COc2c1cc([C@@](O)(CNC(=O)c1cc(Cl)c3nc(N)sc3c1)C(F)(F)F)nc2-c1ccc(F)cc1] |
| P58 | 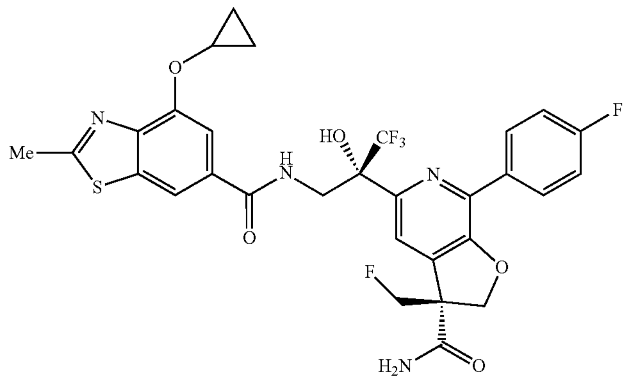 [SMILES: Cc1nc2c(OC3CC3)cc(C(=O)NC[C@](O)(c3cc4c(c(-c5ccc(F)cc5)n3)OC[C@]4(CF)C(N)=O)C(F)(F)F)cc2s1] |
| P59 | 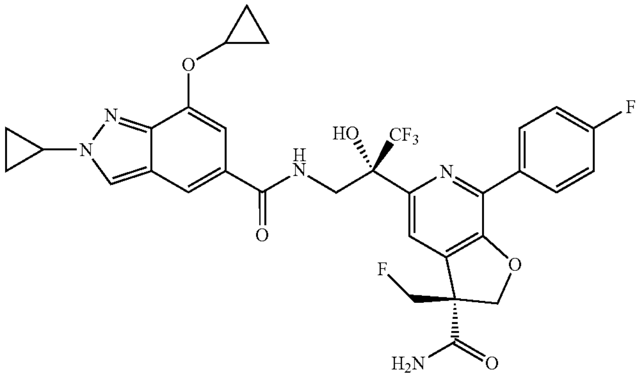 [SMILES: NC(=O)[C@@]1(CF)COc2c1cc([C@@](O)(CNC(=O)c1cc(OC3CC3)c3nn(C4CC4)cc3c1)C(F)(F)F)nc2-c1ccc(F)cc1] |
| P60 | 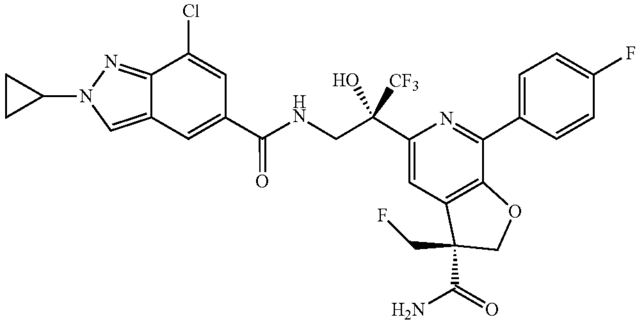 |

-continued
| Compound | Structure |
|---|---|
| P61 | 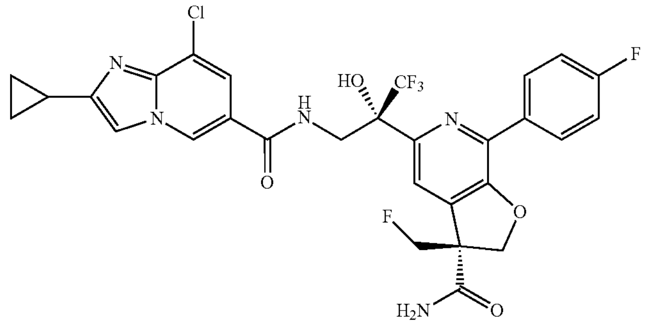 |
| P62 | 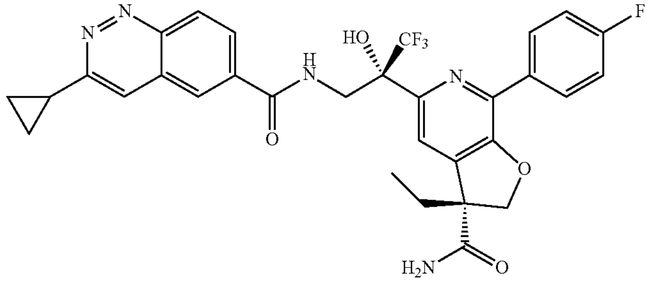 |
| P63 | 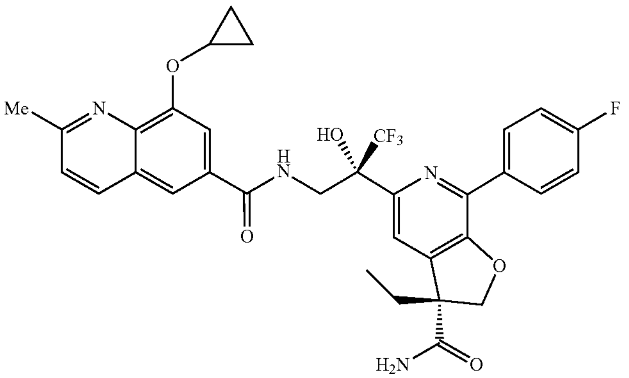 [SMILES: CC[C@]1(C(N)=O)COc2c1cc([C@@](O)(CNC(=O)c1cc(OC3CC3)c3nc(C)ccc3c1)C(F)(F)F)nc2-c1ccc(F)cc1] |
| P64 | 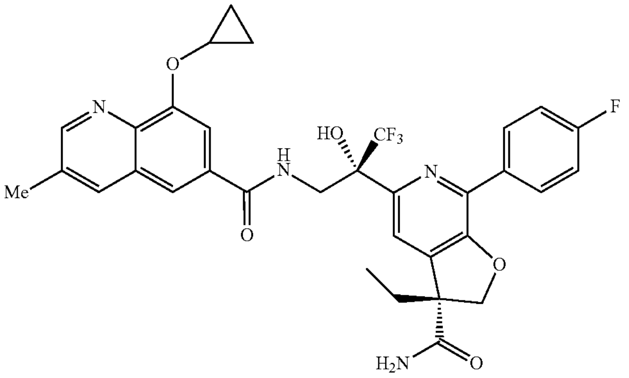 [SMILES: CC[C@]1(C(N)=O)COc2c1cc([C@@](O)(CNC(=O)c1cc(OC3CC3)c3ncc(C)cc3c1)C(F)(F)F)nc2-c1ccc(F)cc1] |

-continued
| Compound | Structure |
|---|---|
| P65 | 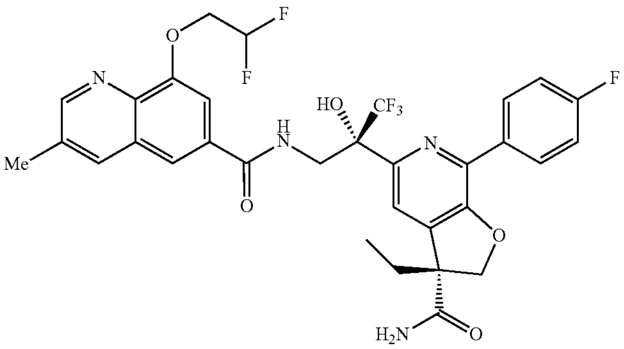 |
| P66 | 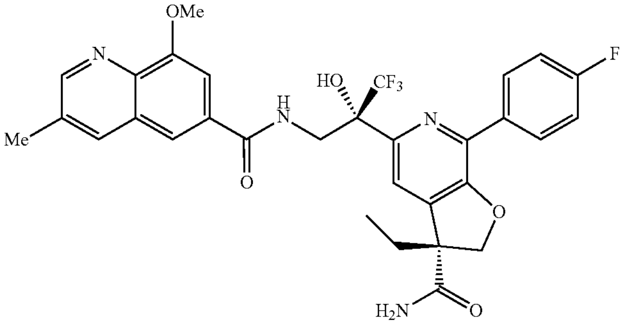 |
| P67 | 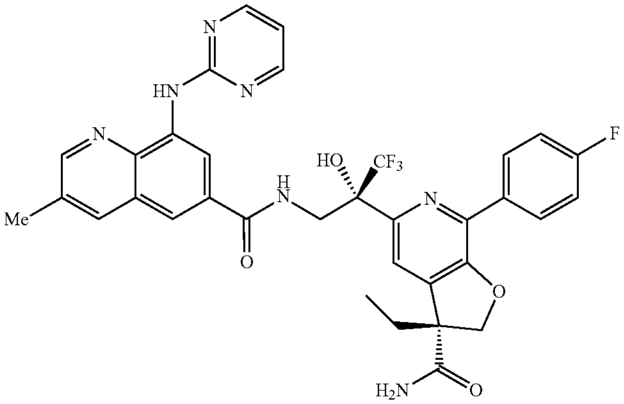 [SMILES: CC[C@]1(C(N)=O)COc2c1cc([C@@](O)(CNC(=O)c1cc(Nc3ncccn3)c3ncc(C)cc3c1)C(F)(F)F)nc2-c1ccc(F)cc1] |
| P68 | 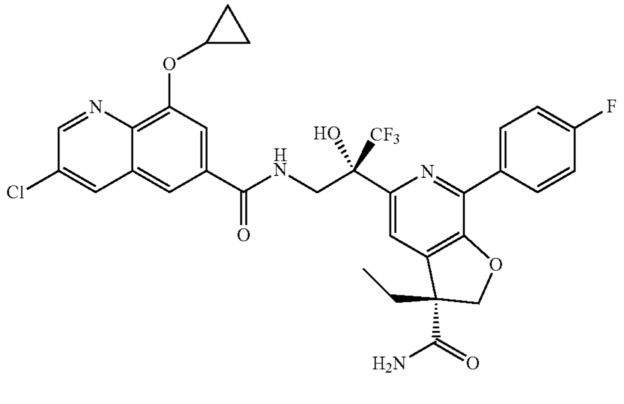 [SMILES: CC[C@]1(C(N)=O)COc2c1cc([C@@](O)(CNC(=O)c1cc(OC3CC3)c3ncc(Cl)cc3c1)C(F)(F)F)nc2-c1ccc(F)cc1] |

-continued
| Compound | Structure |
|---|---|
| P69 | 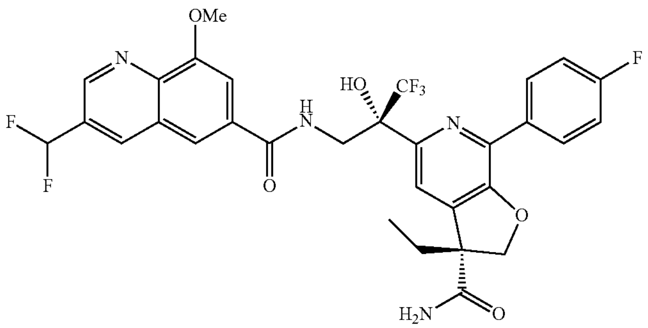 [SMILES: CC[C@]1(C(N)=O)COc2c1cc([C@@](O)(CNC(=O)c1cc(OC)c3ncc(C(F)F)cc3c1)C(F)(F)F)nc2-c1ccc(F)cc1] |
| P70 | 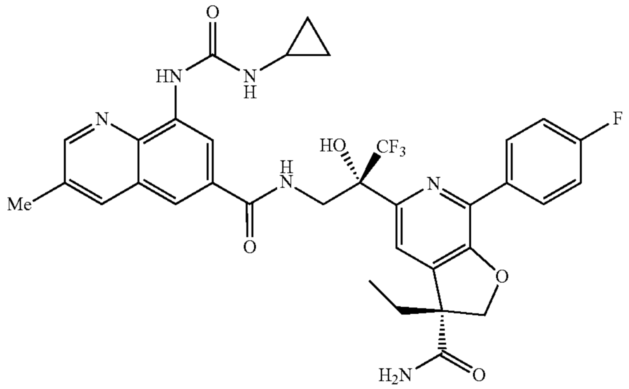 [SMILES: CC[C@]1(C(N)=O)COc2c1cc([C@@](O)(CNC(=O)c1cc(NC(=O)NC3CC3)c3ncc(C)cc3c1)C(F)(F)F)nc2-c1ccc(F)cc1] |
| P71 | 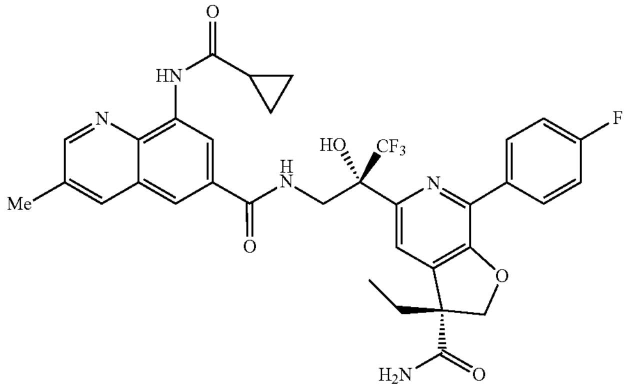 |
| P72 | 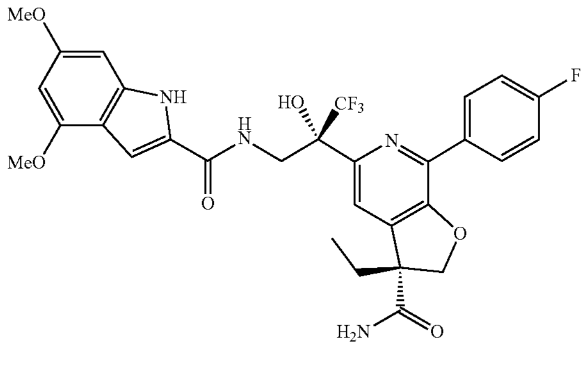 |

-continued
| Compound | Structure |
| --- | --- |
| P73 | 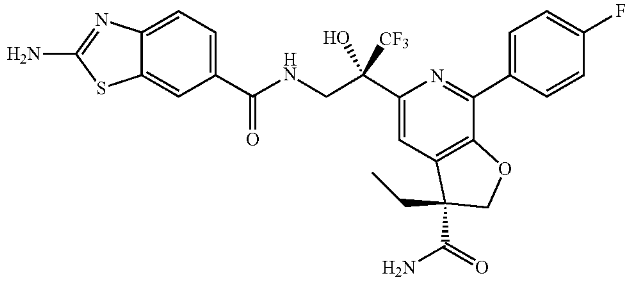 [SMILES: CC[C@]1(C(N)=O)COc2c1cc([C@@](O)(CNC(=O)c1ccc3nc(N)sc3c1)C(F)(F)F)nc2-c1ccc(F)cc1] |
| P74 | 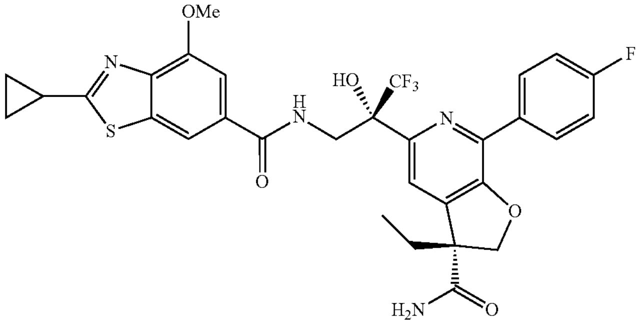 [SMILES: CC[C@]1(C(N)=O)COc2c1cc([C@@](O)(CNC(=O)c1cc(OC)c3nc(C4CC4)sc3c1)C(F)(F)F)nc2-c1ccc(F)cc1] |
| P75 | 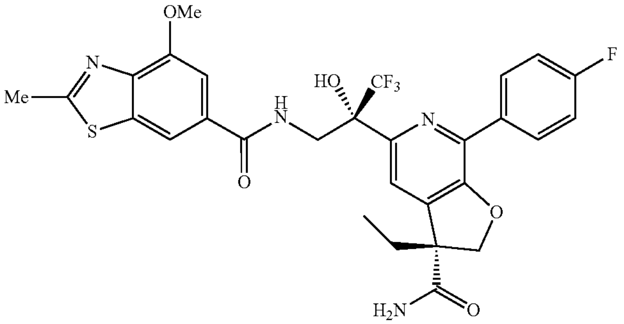 |
| P76 | 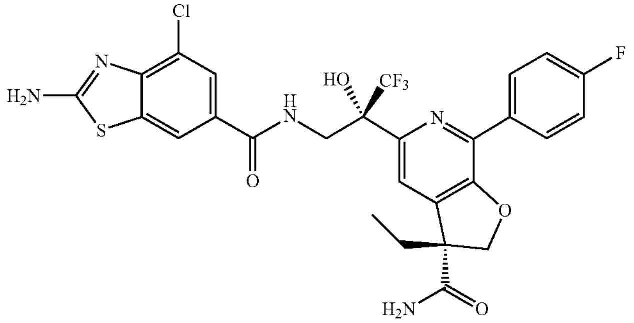 [SMILES: CC[C@]1(C(N)=O)COc2c1cc([C@@](O)(CNC(=O)c1cc(Cl)c3nc(N)sc3c1)C(F)(F)F)nc2-c1ccc(F)cc1] |

-continued
| Compound | Structure |
|---|---|
| P77 | 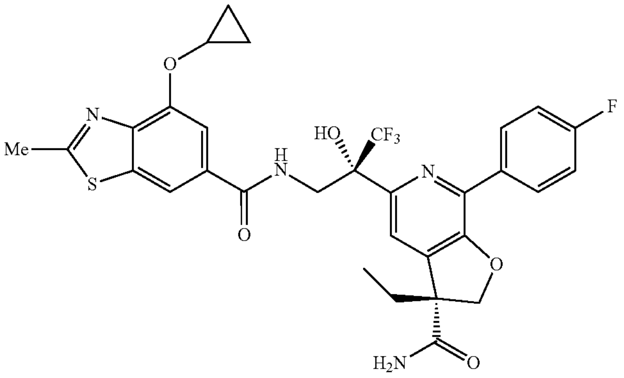 [SMILES: CC[C@]1(C(N)=O)COc2c1cc([C@@](O)(CNC(=O)c1cc(OC3CC3)c3nc(C)sc3c1)C(F)(F)F)nc2-c1ccc(F)cc1] |
| P78 | 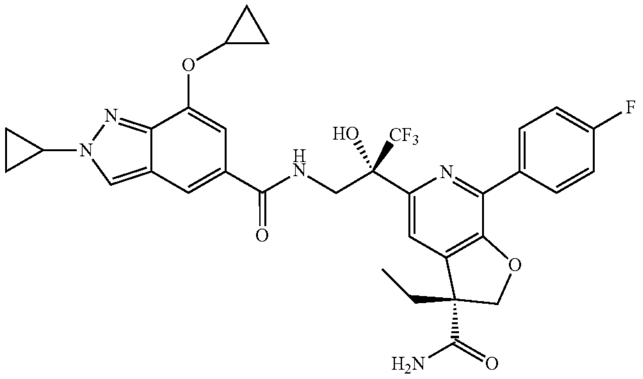 |
| P79 | 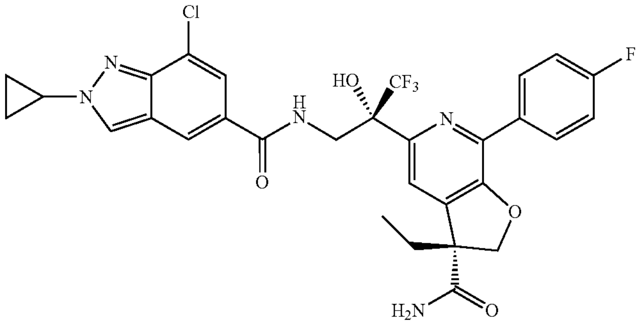 [SMILES: CC[C@]1(C(N)=O)COc2c1cc([C@@](O)(CNC(=O)c1cc(Cl)c3nn(C4CC4)cc3c1)C(F)(F)F)nc2-c1ccc(F)cc1] |
| P80 | 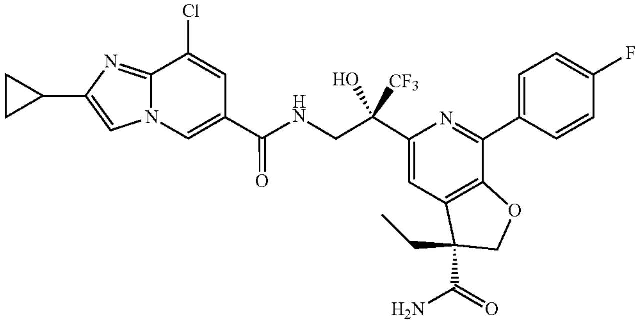 [SMILES: CC[C@]1(C(N)=O)COc2c1cc([C@@](O)(CNC(=O)c1cc(Cl)c3nc(C4CC4)cn3c1)C(F)(F)F)nc2-c1ccc(F)cc1] |

-continued
| Compound | Structure |
| --- | --- |
| P81 | 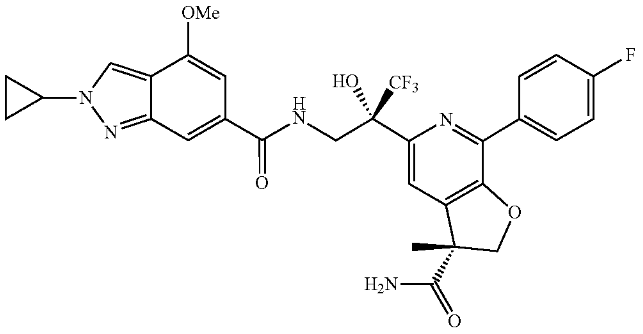 [SMILES: COc1cc(C(=O)NC[C@](O)(c2cc3c(c(-c4ccc(F)cc4)n2)OC[C@]3(C)C(N)=O)C(F)(F)F)cc2nn(C3CC3)cc12] |
| P82 | 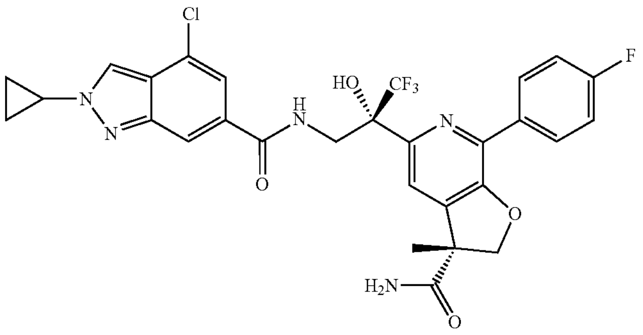 [SMILES: C[C@]1(C(N)=O)COc2c1cc([C@@](O)(CNC(=O)c1cc(Cl)c3cn(C4CC4)nc3c1)C(F)(F)F)nc2-c1ccc(F)cc1] |
| P83 | 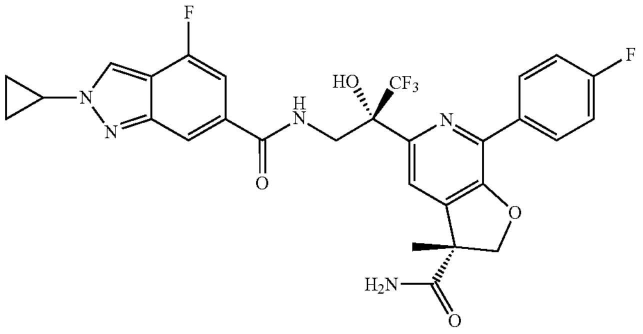 [SMILES: C[C@]1(C(N)=O)COc2c1cc([C@@](O)(CNC(=O)c1cc(F)c3cn(C4CC4)nc3c1)C(F)(F)F)nc2-c1ccc(F)cc1] |
| P84 | 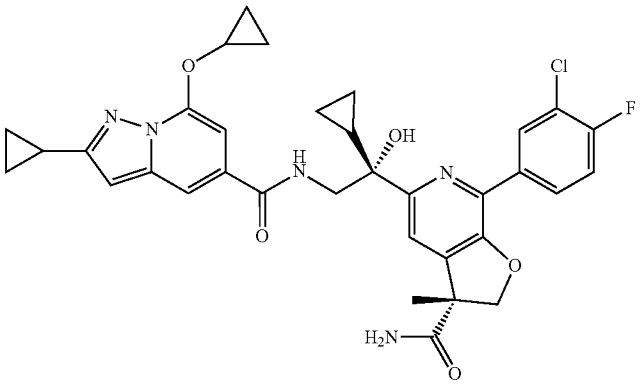 [SMILES: C[C@]1(C(N)=O)COc2c1cc([C@@](O)(CNC(=O)c1cc(OC3CC3)n3nc(C4CC4)cc3c1)C1CC1)nc2-c1ccc(F)c(Cl)c1] |

-continued
| Compound | Structure |
|---|---|
| P85 | 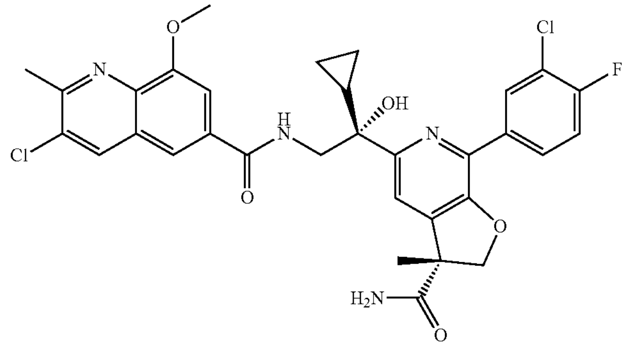 [SMILES: COc1cc(C(=O)NC[C@](O)(c2cc3c(c(-c4ccc(F)c(Cl)c4)n2)OC[C@]3(C)C(N)=O)C2CC2)cc2cc(Cl)c(C)nc12] |
| P86 | 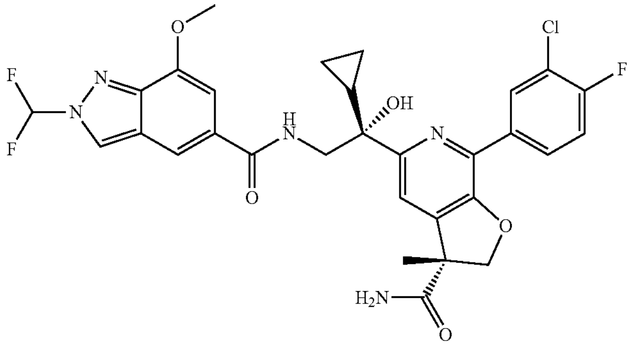 [SMILES: COc1cc(C(=O)NC[C@](O)(c2cc3c(c(-c4ccc(F)c(Cl)c4)n2)OC[C@]3(C)C(N)=O)C2CC2)cc2cn(C(F)F)nc12] |
| P87 | 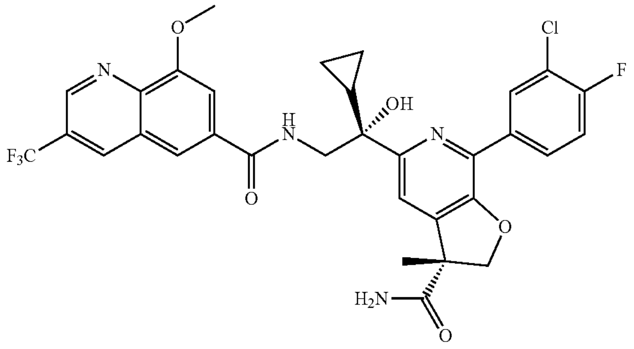 [SMILES: COc1cc(C(=O)NC[C@](O)(c2cc3c(c(-c4ccc(F)c(Cl)c4)n2)OC[C@]3(C)C(N)=O)C2CC2)cc2cc(C(F)(F)F)cnc12] |
| P88 | 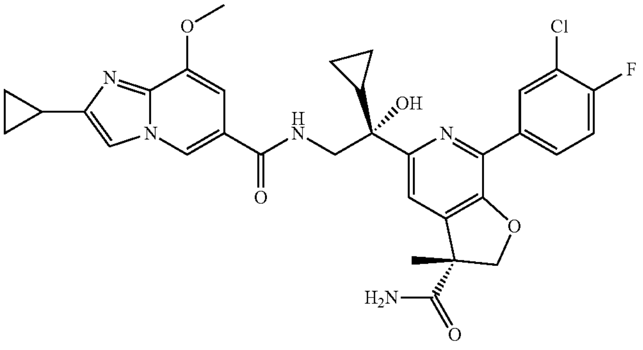 [SMILES: COc1cc(C(=O)NC[C@](O)(c2cc3c(c(-c4ccc(F)c(Cl)c4)n2)OC[C@]3(C)C(N)=O)C2CC2)cn2cc(C3CC3)nc12] |

-continued
| Compound | Structure |
|---|---|
| P89 | 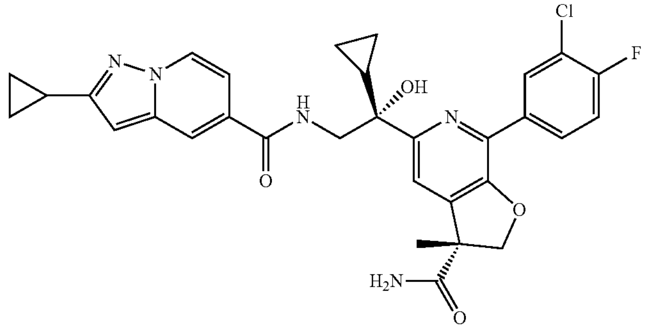 [SMILES: C[C@]1(C(N)=O)COc2c1cc([C@@](O)(CNC(=O)c1ccn3nc(C4CC4)cc3c1)C1CC1)nc2-c1ccc(F)c(Cl)c1] |
| P90 | 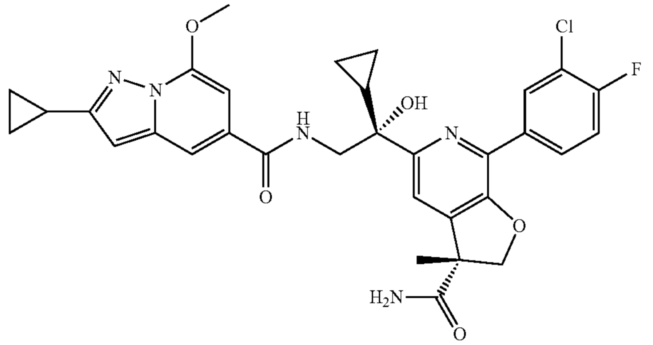 [SMILES: COc1cc(C(=O)NC[C@](O)(c2cc3c(c(-c4ccc(F)c(Cl)c4)n2)OC[C@]3(C)C(N)=O)C2CC2)cc2cc(C3CC3)nn12] |
| P91 | 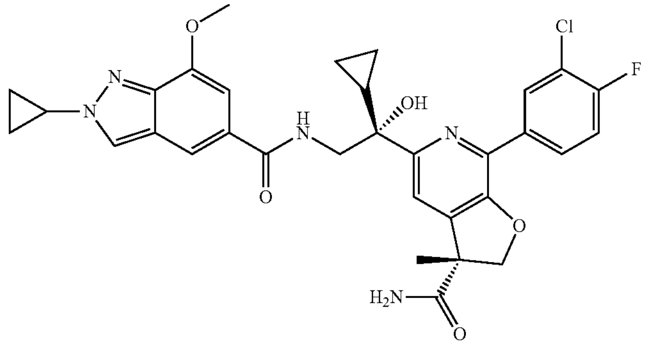 [SMILES: COc1cc(C(=O)NC[C@](O)(c2cc3c(c(-c4ccc(F)c(Cl)c4)n2)OC[C@]3(C)C(N)=O)C2CC2)cc2cn(C3CC3)nc12] |
| P92 | 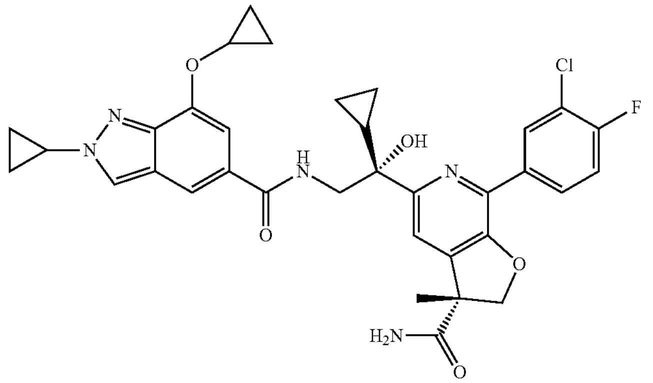 [SMILES: C[C@]1(C(N)=O)COc2c1cc([C@@](O)(CNC(=O)c1cc(OC3CC3)c3nn(C4CC4)cc3c1)C1CC1)nc2-c1ccc(F)c(Cl)c1] |

-continued
| Compound | Structure |
|---|---|
| P93 | 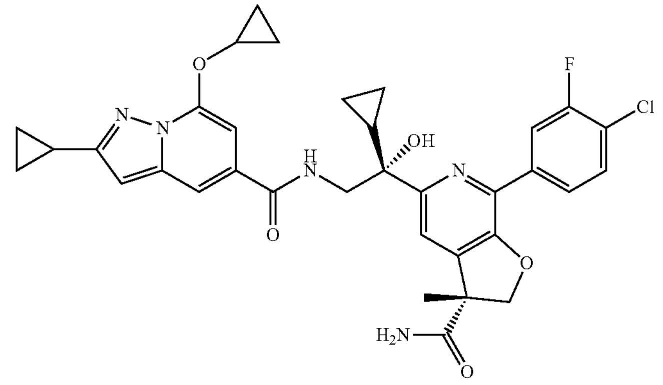 [SMILES: C[C@]1(C(N)=O)COc2c1cc([C@@](O)(CNC(=O)c1cc(OC3CC3)n3nc(C4CC4)cc3c1)C1CC1)nc2-c1ccc(Cl)c(F)c1] |
| P94 | 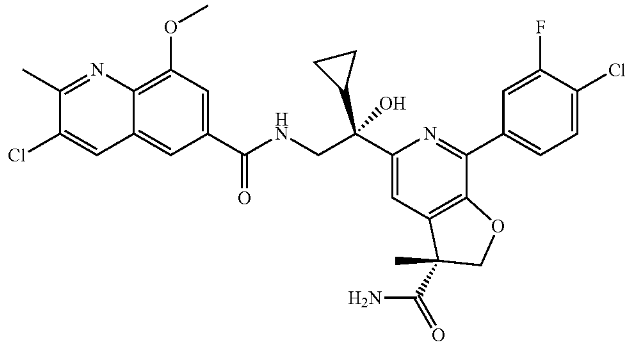 [SMILES: COc1cc(C(=O)NC[C@](O)(c2cc3c(c(-c4ccc(Cl)c(F)c4)n2)OC[C@]3(C)C(N)=O)C2CC2)cc2cc(Cl)c(C)nc12] |
| P95 | 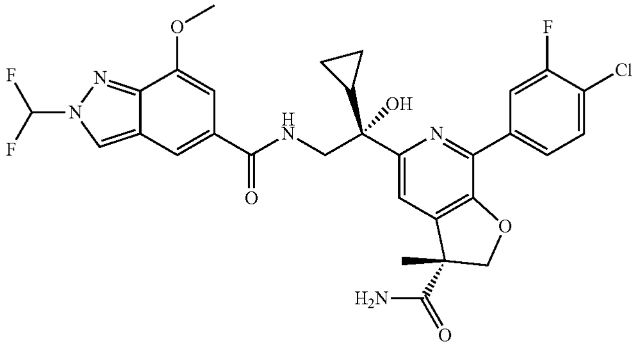 [SMILES: COc1cc(C(=O)NC[C@](O)(c2cc3c(c(-c4ccc(Cl)c(F)c4)n2)OC[C@]3(C)C(N)=O)C2CC2)cc2cn(C(F)F)nc12] |
| P96 | 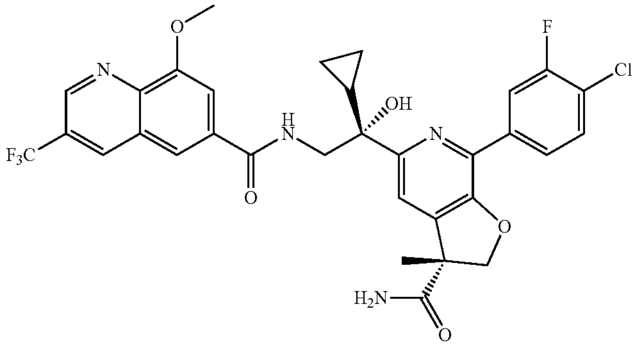 [SMILES: COc1cc(C(=O)NC[C@](O)(c2cc3c(c(-c4ccc(Cl)c(F)c4)n2)OC[C@]3(C)C(N)=O)C2CC2)cc2cc(C(F)(F)F)cnc12] |

-continued
| Compound | Structure |
| --- | --- |
| P97 | 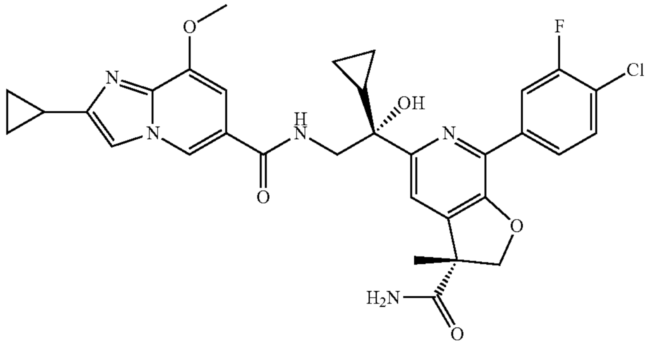 [SMILES: COc1cc(C(=O)NC[C@](O)(c2cc3c(c(-c4ccc(Cl)c(F)c4)n2)OC[C@]3(C)C(N)=O)C2CC2)cn2cc(C3CC3)nc12] |
| P98 | 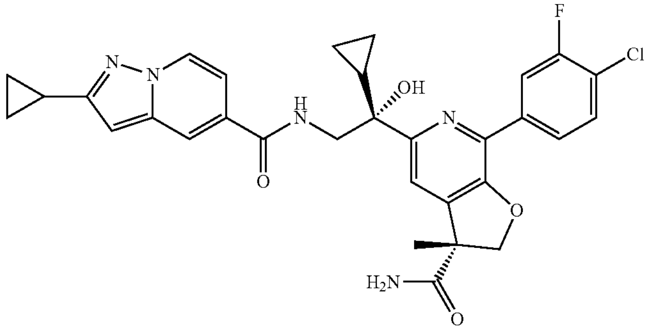 [SMILES: C[C@]1(C(N)=O)COc2c1cc([C@@](O)(CNC(=O)c1ccn3nc(C4CC4)cc3c1)C1CC1)nc2-c1ccc(Cl)c(F)c1] |
| P99 | 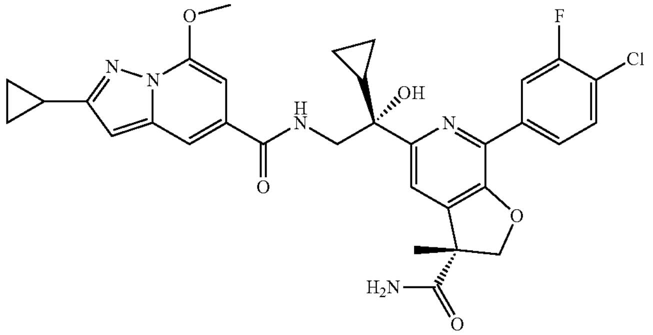 [SMILES: COc1cc(C(=O)NC[C@](O)(c2cc3c(c(-c4ccc(Cl)c(F)c4)n2)OC[C@]3(C)C(N)=O)C2CC2)cc2cc(C3CC3)nn12] |
| P100 | 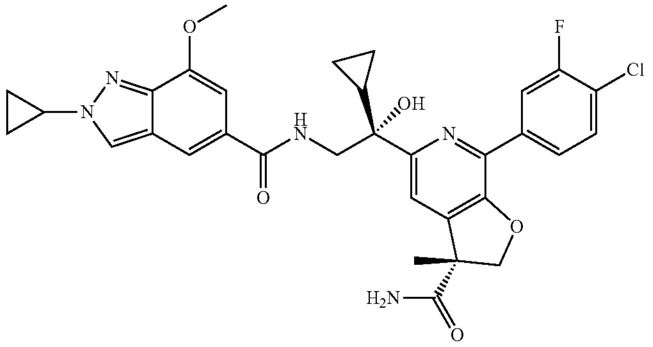 [SMILES: COc1cc(C(=O)NC[C@](O)(c2cc3c(c(-c4ccc(Cl)c(F)c4)n2)OC[C@]3(C)C(N)=O)C2CC2)cc2cn(C3CC3)nc12] |

-continued
| Compound | Structure |
| --- | --- |
| P101 | 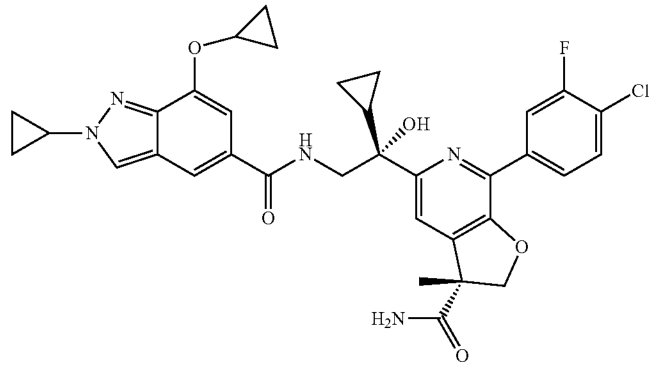 [SMILES: C[C@]1(C(N)=O)COc2c1cc([C@@](O)(CNC(=O)c1cc(OC3CC3)c3nn(C4CC4)cc3c1)C1CC1)nc2-c1ccc(Cl)c(F)c1] |
| P102 | 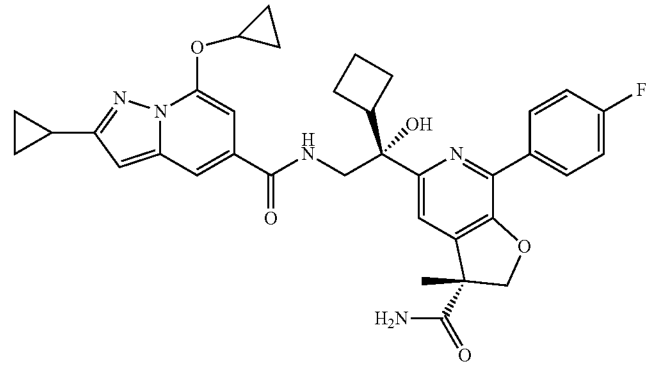 [SMILES: C[C@]1(C(N)=O)COc2c1cc([C@@](O)(CNC(=O)c1cc(OC3CC3)n3nc(C4CC4)cc3c1)C1CCC1)nc2-c1ccc(F)cc1] |
| P103 | 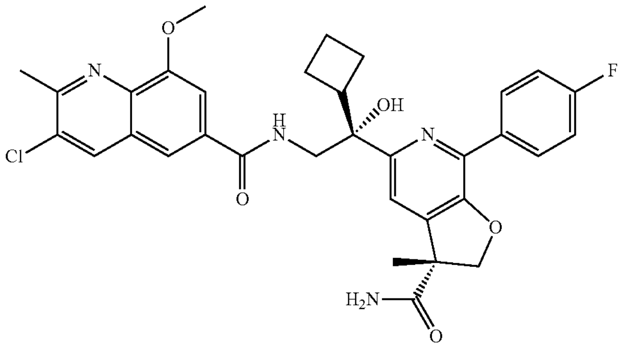 [SMILES: COc1cc(C(=O)NC[C@](O)(c2cc3c(c(-c4ccc(F)cc4)n2)OC[C@]3(C)C(N)=O)C2CCC2)cc2cc(Cl)c(C)nc12] |
| P104 | 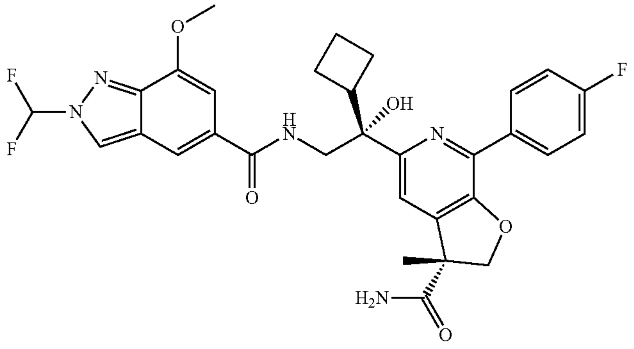 [SMILES: COc1cc(C(=O)NC[C@](O)(c2cc3c(c(-c4ccc(F)cc4)n2)OC[C@]3(C)C(N)=O)C2CCC2)cc2cn(C(F)F)nc12] |

-continued
| Compound | Structure |
|---|---|
| P105 | 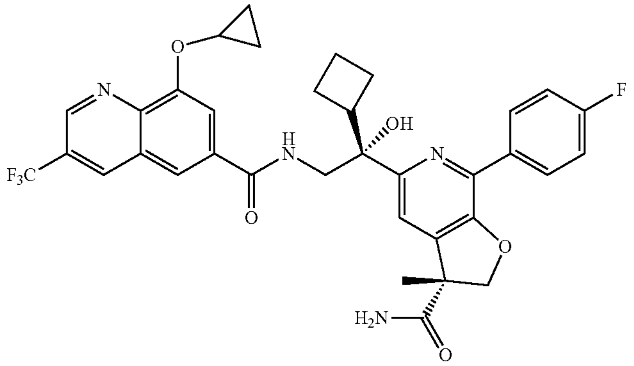 [SMILES: C[C@]1(C(N)=O)COc2c1cc([C@@](O)(CNC(=O)c1cc(OC3CC3)c3ncc(C(F)(F)F)cc3c1)C1CCC1)nc2-c1ccc(F)cc1] |
| P105 | 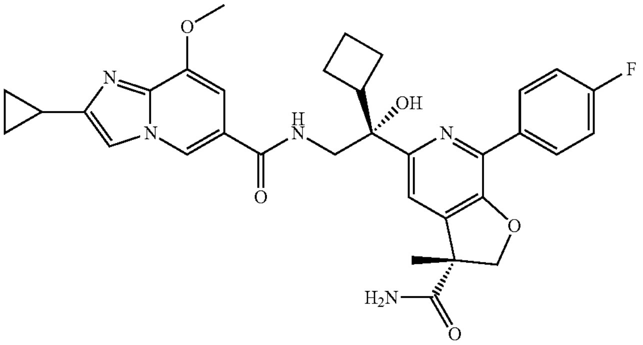 [SMILES: COc1cc(C(=O)NC[C@](O)(c2cc3c(c(-c4ccc(F)cc4)n2)OC[C@]3(C)C(N)=O)C2CCC2)cn2cc(C3CC3)nc12] |
| P106 | 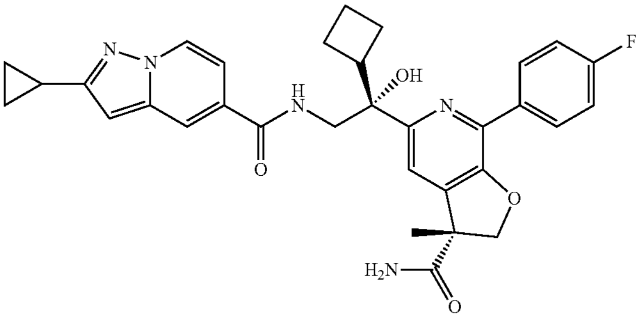 [SMILES: C[C@]1(C(N)=O)COc2c1cc([C@@](O)(CNC(=O)c1ccn3nc(C4CC4)cc3c1)C1CCC1)nc2-c1ccc(F)cc1] |
| P107 | 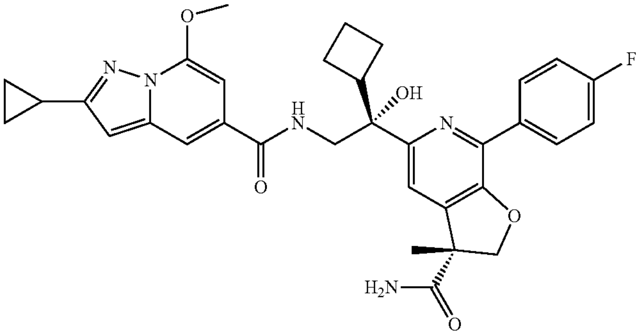 [SMILES: COc1cc(C(=O)NC[C@](O)(c2cc3c(c(-c4ccc(F)cc4)n2)OC[C@]3(C)C(N)=O)C2CCC2)cc2cc(C3CC3)nn12] |

-continued
| Compound | Structure |
|---|---|
| P108 | 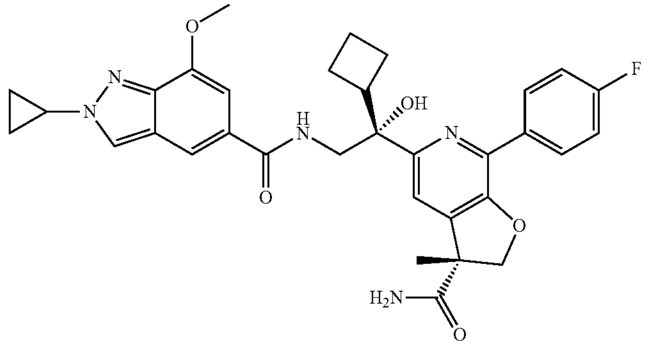 [SMILES: COc1cc(C(=O)NC[C@](O)(c2cc3c(c(-c4ccc(F)cc4)n2)OC[C@]3(C)C(N)=O)C2CCC2)cc2cn(C3CC3)nc12] |
| P109 | 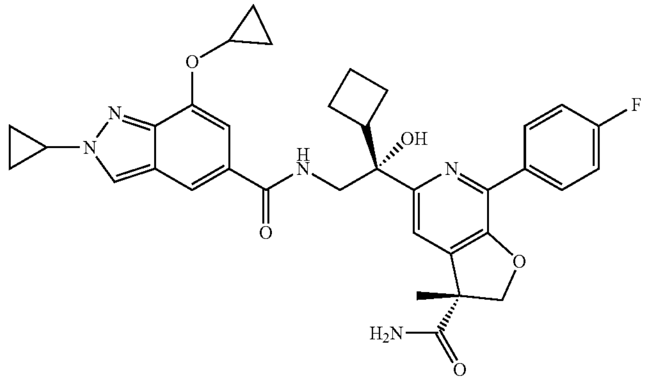 [SMILES: C[C@]1(C(N)=O)COc2c1cc([C@@](O)(CNC(=O)c1cc(OC3CC3)c3nn(C4CC4)cc3c1)C1CCC1)nc2-c1ccc(F)cc1] |
| P110 | 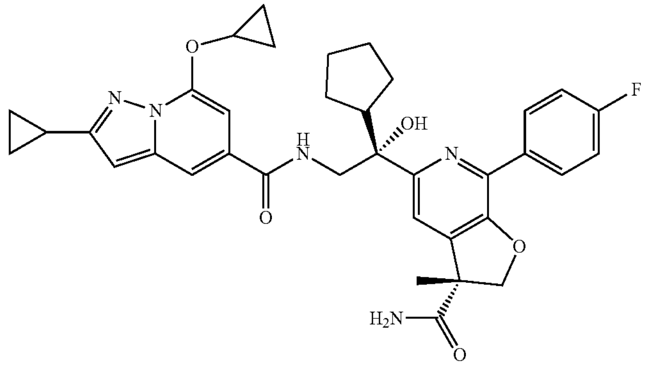 [SMILES: C[C@]1(C(N)=O)COc2c1cc([C@@](O)(CNC(=O)c1cc(OC3CC3)n3nc(C4CC4)cc3c1)C1CCCC1)nc2-c1ccc(F)cc1] |
| P111 | 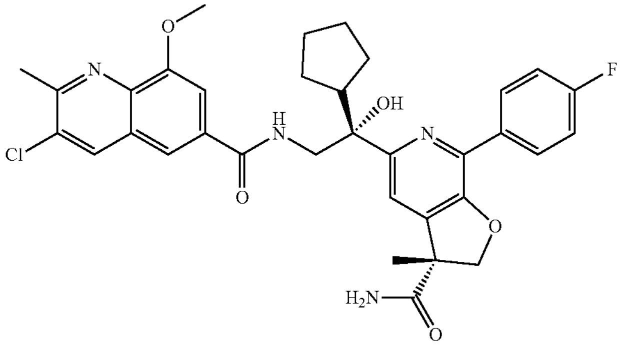 [SMILES: COc1cc(C(=O)NC[C@](O)(c2cc3c(c(-c4ccc(F)cc4)n2)OC[C@]3(C)C(N)=O)C2CCCC2)cc2cc(Cl)c(C)nc12] |

-continued
| Compound | Structure |
| --- | --- |
| P112 | 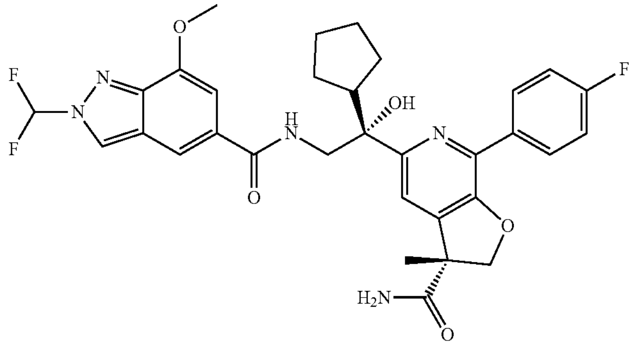 [SMILES: COc1cc(C(=O)NC[C@](O)(c2cc3c(c(-c4ccc(F)cc4)n2)OC[C@]3(C)C(N)=O)C2CCCC2)cc2cn(C(F)F)nc12] |
| P113 | 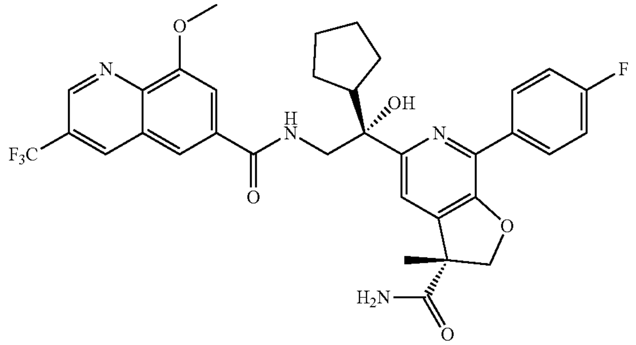 [SMILES: COc1cc(C(=O)NC[C@](O)(c2cc3c(c(-c4ccc(F)cc4)n2)OC[C@]3(C)C(N)=O)C2CCCC2)cc2cc(C(F)(F)F)cnc12] |
| P114 | 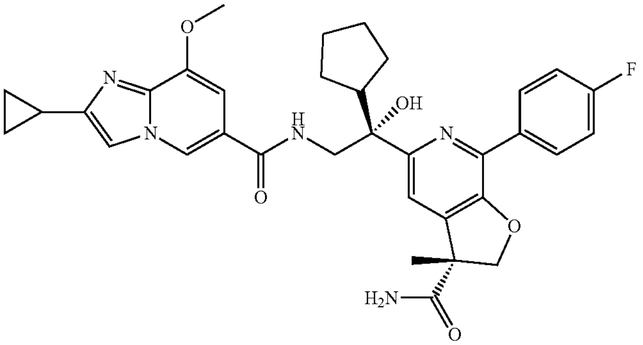 [SMILES: COc1cc(C(=O)NC[C@](O)(c2cc3c(c(-c4ccc(F)cc4)n2)OC[C@]3(C)C(N)=O)C2CCCC2)cn2cc(C3CC3)nc12] |
| P115 | 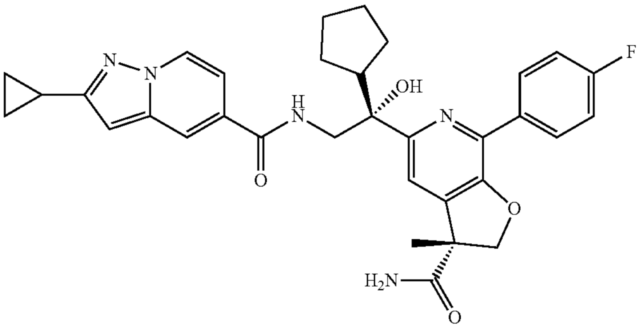 [SMILES: C[C@]1(C(N)=O)COc2c1cc([C@@](O)(CNC(=O)c1ccn3nc(C4CC4)cc3c1)C1CCCC1)nc2-c1ccc(F)cc1] |

-continued
| Compound | Structure |
|---|---|
| P116 | 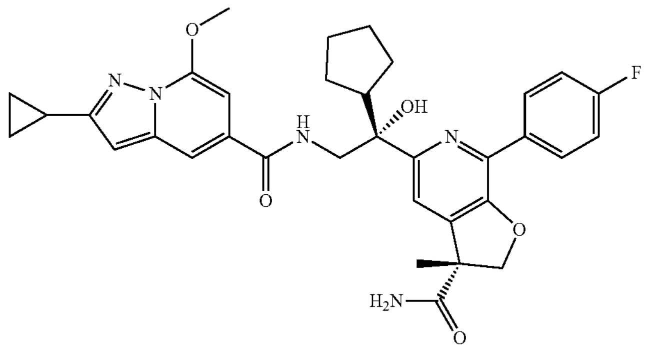 [SMILES: COc1cc(C(=O)NC[C@](O)(c2cc3c(c(-c4ccc(F)cc4)n2)OC[C@]3(C)C(N)=O)C2CCCC2)cc2cc(C3CC3)nn12] |
| P117 | 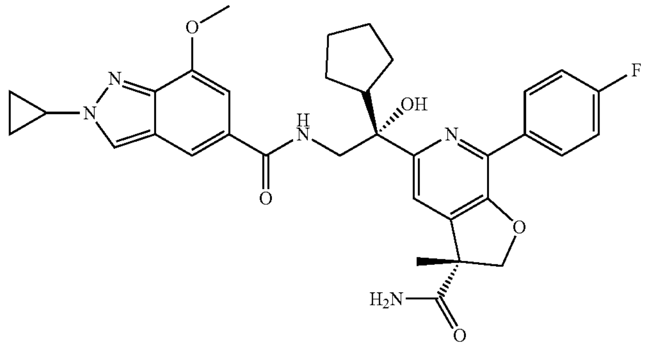 [SMILES: COc1cc(C(=O)NC[C@](O)(c2cc3c(c(-c4ccc(F)cc4)n2)OC[C@]3(C)C(N)=O)C2CCCC2)cc2cn(C3CC3)nc12] |
| P118 | 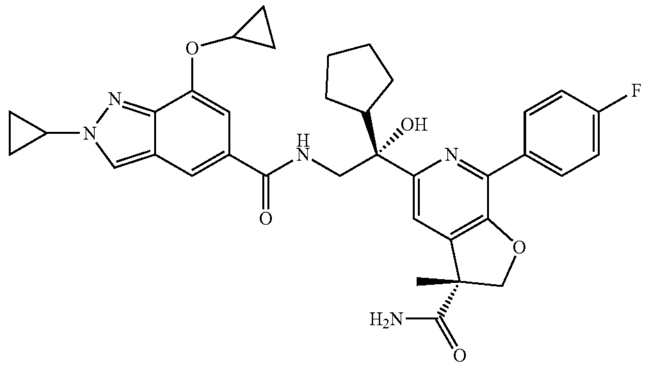 [SMILES: C[C@]1(C(N)=O)COc2c1cc([C@@](O)(CNC(=O)c1cc(OC3CC3)c3nn(C4CC4)cc3c1)C1CCCC1)nc2-c1ccc(F)cc1] |
| P119 | 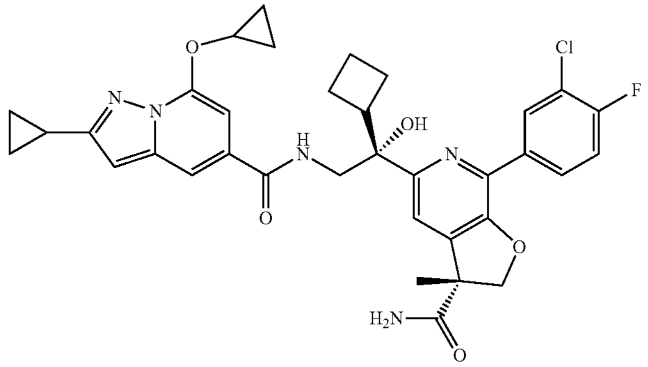 [SMILES: C[C@]1(C(N)=O)COc2c1cc([C@@](O)(CNC(=O)c1cc(OC3CC3)n3nc(C4CC4)cc3c1)C1CCC1)nc2-c1ccc(F)c(Cl)c1] |

-continued
| Compound | Structure |
|---|---|
| P120 | 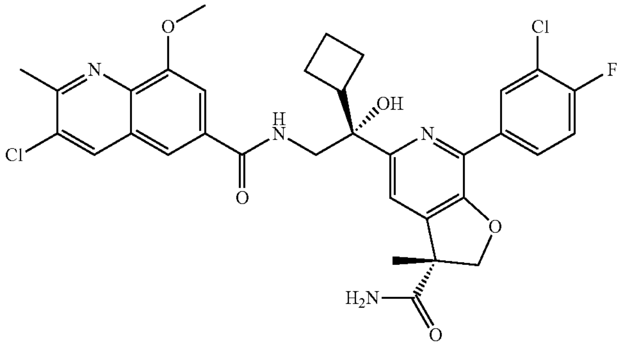 [SMILES: COc1cc(C(=O)NC[C@](O)(c2cc3c(c(-c4ccc(F)c(Cl)c4)n2)OC[C@]3(C)C(N)=O)C2CCC2)cc2cc(Cl)c(C)nc12] |
| P121 | 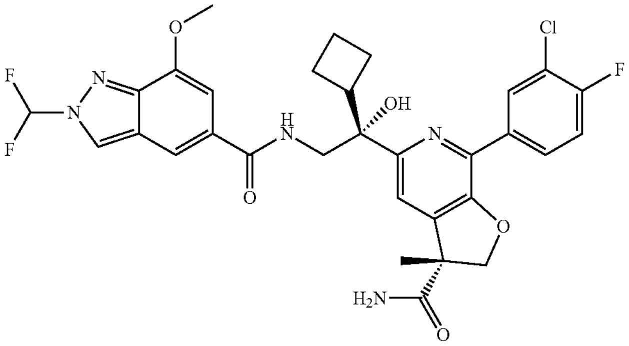 [SMILES: COc1cc(C(=O)NC[C@](O)(c2cc3c(c(-c4ccc(F)c(Cl)c4)n2)OC[C@]3(C)C(N)=O)C2CCC2)cc2cn(C(F)F)nc12] |
| P122 | 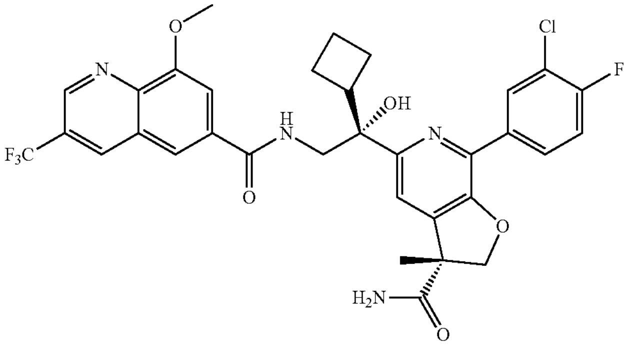 [SMILES: COc1cc(C(=O)NC[C@](O)(c2cc3c(c(-c4ccc(F)c(Cl)c4)n2)OC[C@]3(C)C(N)=O)C2CCC2)cc2cc(C(F)(F)F)cnc12] |
| P123 | 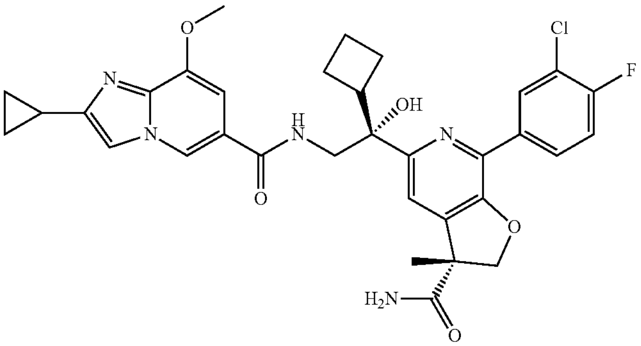 [SMILES: COc1cc(C(=O)NC[C@](O)(c2cc3c(c(-c4ccc(F)c(Cl)c4)n2)OC[C@]3(C)C(N)=O)C2CCC2)cn2cc(C3CC3)nc12] |

-continued
| Compound | Structure |
| --- | --- |
| P124 | 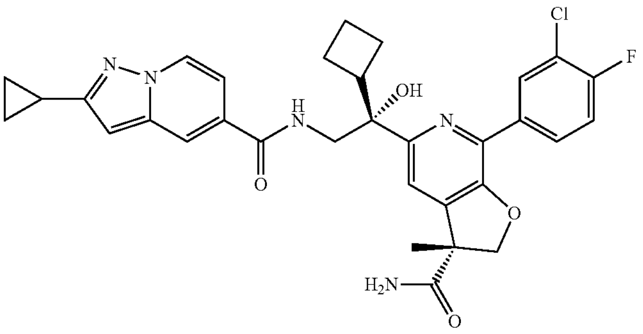 [SMILES: C[C@]1(C(N)=O)COc2c1cc([C@@](O)(CNC(=O)c1ccn3nc(C4CC4)cc3c1)C1CCC1)nc2-c1ccc(F)c(Cl)c1] |
| P125 | 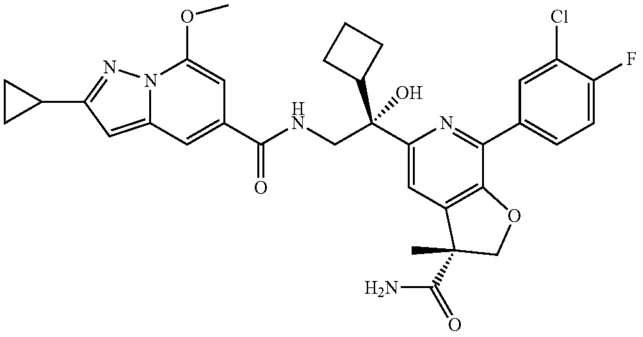 [SMILES: COc1cc(C(=O)NC[C@](O)(c2cc3c(c(-c4ccc(F)c(Cl)c4)n2)OC[C@]3(C)C(N)=O)C2CCC2)cc2cc(C3CC3)nn12] |
| P126 | 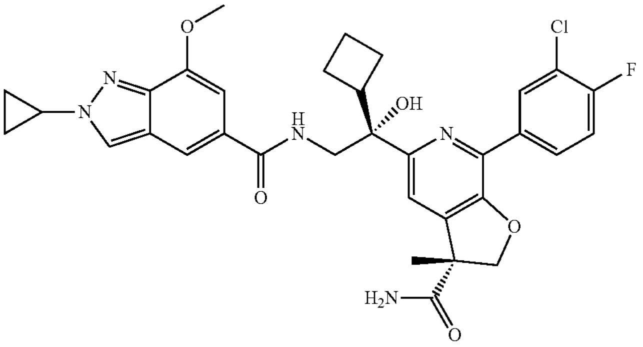 [SMILES: COc1cc(C(=O)NC[C@](O)(c2cc3c(c(-c4ccc(F)c(Cl)c4)n2)OC[C@]3(C)C(N)=O)C2CCC2)cc2cn(C3CC3)nc12] |
| P127 | 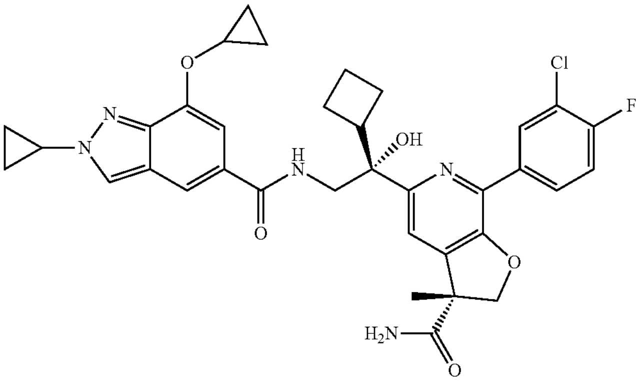 [SMILES: C[C@]1(C(N)=O)COc2c1cc([C@@](O)(CNC(=O)c1cc(OC3CC3)c3nn(C4CC4)cc3c1)C1CCC1)nc2-c1ccc(F)c(Cl)c1] |

-continued
| Compound | Structure |
|---|---|
| P128 | 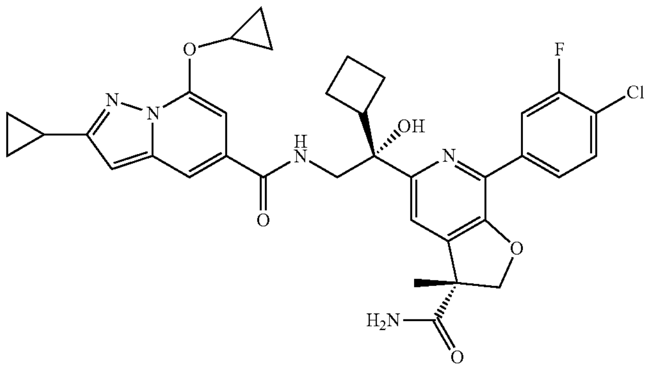 [SMILES: C[C@]1(C(N)=O)COc2c1cc([C@@](O)(CNC(=O)c1cc(OC3CC3)n3nc(C4CC4)cc3c1)C1CCC1)nc2-c1ccc(Cl)c(F)c1] |
| P129 | 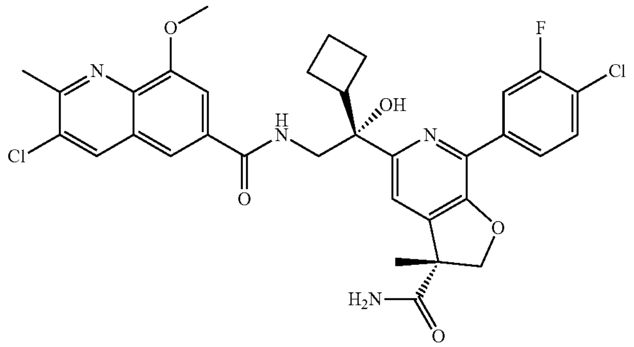 [SMILES: COc1cc(C(=O)NC[C@](O)(c2cc3c(c(-c4ccc(Cl)c(F)c4)n2)OC[C@]3(C)C(N)=O)C2CCC2)cc2cc(Cl)c(C)nc12] |
| P130 | 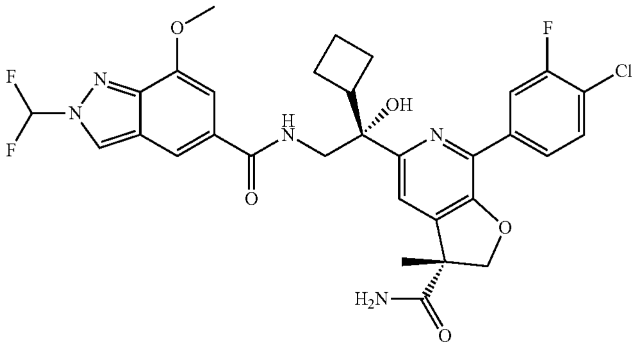 [SMILES: COc1cc(C(=O)NC[C@](O)(c2cc3c(c(-c4ccc(Cl)c(F)c4)n2)OC[C@]3(C)C(N)=O)C2CCC2)cc2cn(C(F)F)nc12] |
| P131 | 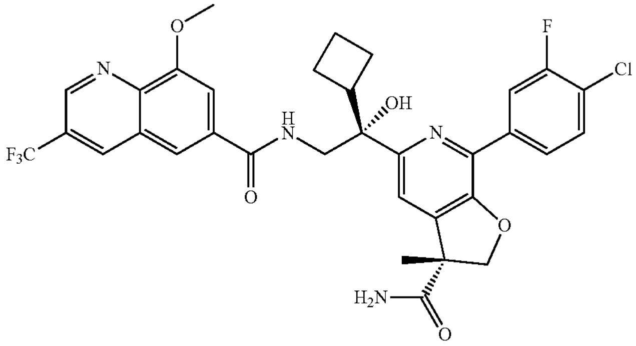 [SMILES: COc1cc(C(=O)NC[C@](O)(c2cc3c(c(-c4ccc(Cl)c(F)c4)n2)OC[C@]3(C)C(N)=O)C2CCC2)cc2cc(C(F)(F)F)cnc12] |

-continued
| Compound | Structure |
|---|---|
| P132 | 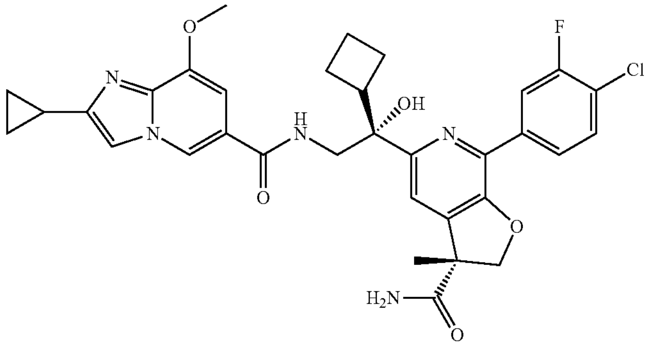 [SMILES: COc1cc(C(=O)NC[C@](O)(c2cc3c(c(-c4ccc(Cl)c(F)c4)n2)OC[C@]3(C)C(N)=O)C2CCC2)cn2cc(C3CC3)nc12] |
| P133 | 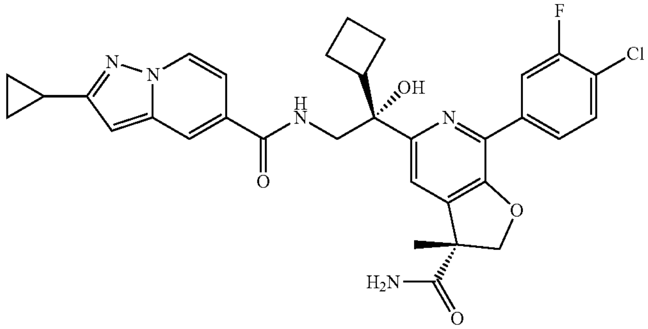 [SMILES: C[C@]1(C(N)=O)COc2c1cc([C@@](O)(CNC(=O)c1ccn3nc(C4CC4)cc3c1)C1CCC1)nc2-c1ccc(Cl)c(F)c1] |
| P134 | 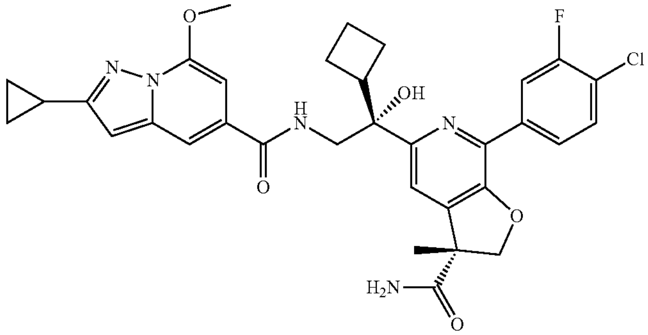 [SMILES: COc1cc(C(=O)NC[C@](O)(c2cc3c(c(-c4ccc(Cl)c(F)c4)n2)OC[C@]3(C)C(N)=O)C2CCC2)cc2cc(C3CC3)nn12] |
| P135 | 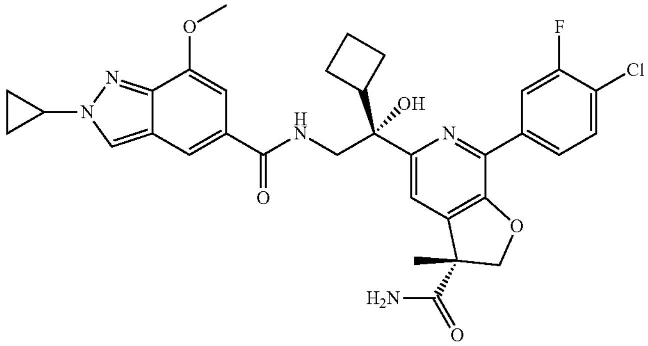 [SMILES: COc1cc(C(=O)NC[C@](O)(c2cc3c(c(-c4ccc(Cl)c(F)c4)n2)OC[C@]3(C)C(N)=O)C2CCC2)cc2cn(C3CC3)nc12] |

-continued
| Compound | Structure |
|---|---|
| P136 | 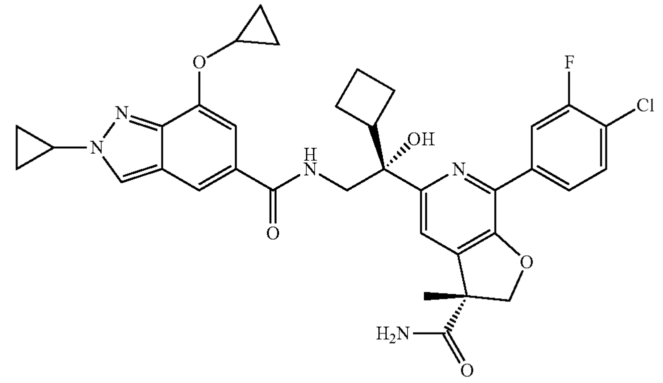 [SMILES: C[C@]1(C(N)=O)COc2c1cc([C@@](O)(CNC(=O)c1cc(OC3CC3)c3nn(C4CC4)cc3c1)C1CCC1)nc2-c1ccc(Cl)c(F)c1] |
| P137 | 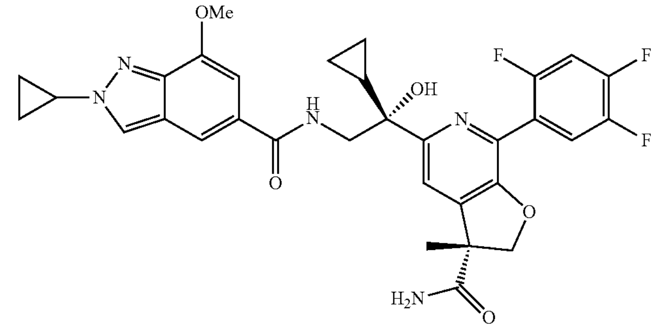 |
| P138 | 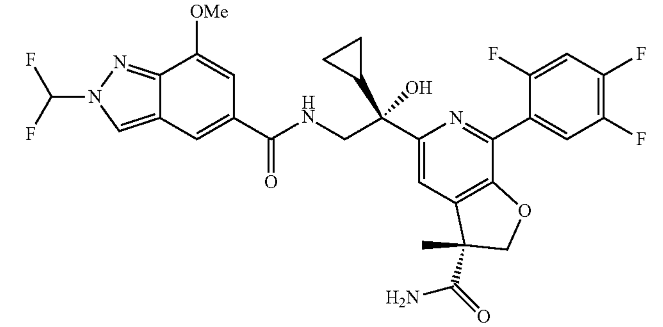 [SMILES: COc1cc(C(=O)NC[C@](O)(c2cc3c(c(-c4cc(F)c(F)cc4F)n2)OC[C@]3(C)C(N)=O)C2CC2)cc2cn(C(F)F)nc12] |
| P139 | 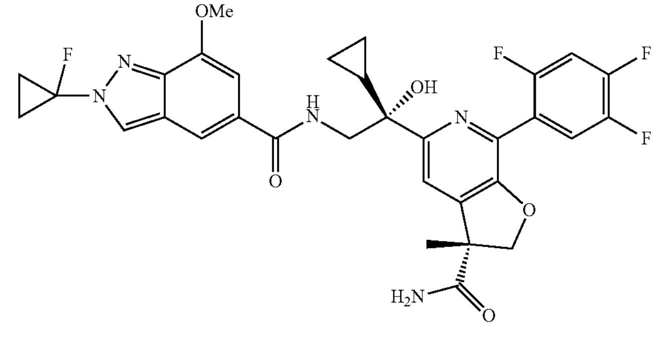 [SMILES: COc1cc(C(=O)NC[C@](O)(c2cc3c(c(-c4cc(F)c(F)cc4F)n2)OC[C@]3(C)C(N)=O)C2CC2)cc2cn(C3(F)CC3)nc12] |

-continued
| Compound | Structure |
|---|---|
| P140 | 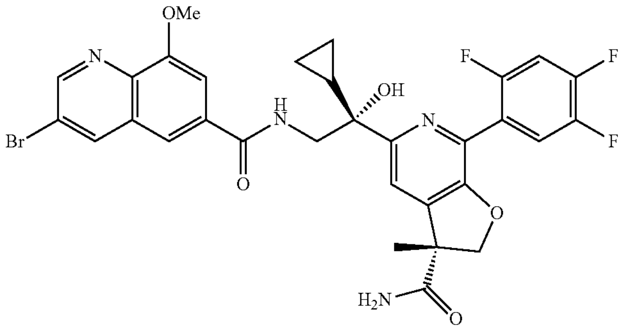 [SMILES: COc1cc(C(=O)NC[C@](O)(c2cc3c(c(-c4cc(F)c(F)cc4F)n2)OC[C@]3(C)C(N)=O)C2CC2)cc2cc(Br)cnc12] |
| P141 | 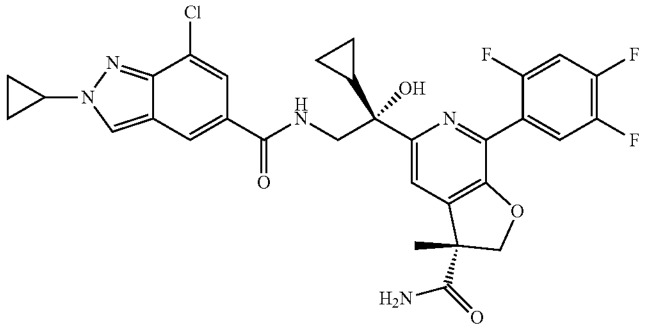 [SMILES: C[C@]1(C(N)=O)COc2c1cc([C@@](O)(CNC(=O)c1cc(Cl)c3nn(C4CC4)cc3c1)C1CC1)nc2-c1cc(F)c(F)cc1F] |
| P142 | 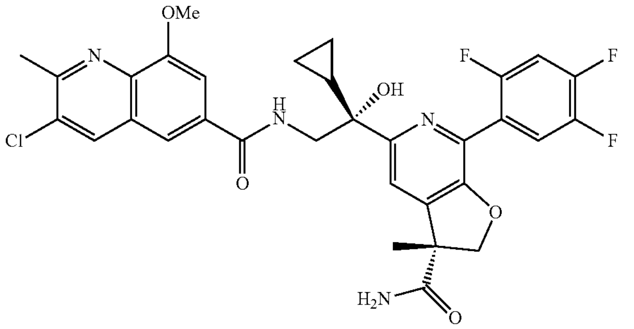 [SMILES: COc1cc(C(=O)NC[C@](O)(c2cc3c(c(-c4cc(F)c(F)cc4F)n2)OC[C@]3(C)C(N)=O)C2CC2)cc2cc(Cl)c(C)nc12] |
| P143 | 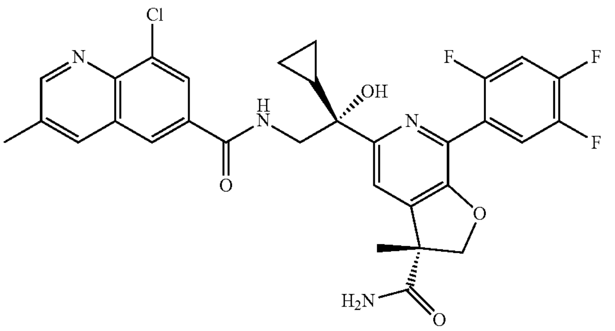 [SMILES: Cc1cnc2c(Cl)cc(C(=O)NC[C@](O)(c3cc4c(c(-c5cc(F)c(F)cc5F)n3)OC[C@]4(C)C(N)=O)C3CC3)cc2c1] |

-continued
| Compound | Structure |
| --- | --- |
| P144 | 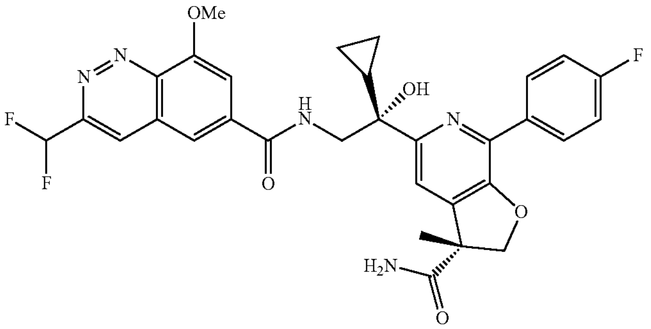 [SMILES: COc1cc(C(=O)NC[C@](O)(c2cc3c(c(-c4ccc(F)cc4)n2)OC[C@]3(C)C(N)=O)C2CC2)cc2cc(C(F)F)nnc12] |
| P145 | 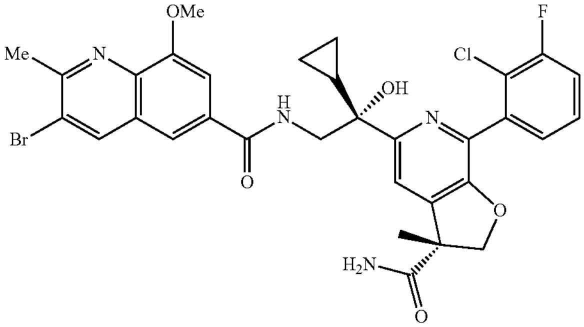 [SMILES: COc1cc(C(=O)NC[C@](O)(c2cc3c(c(-c4cccc(F)c4Cl)n2)OC[C@]3(C)C(N)=O)C2CC2)cc2cc(Br)c(C)nc12] |
| P146 | 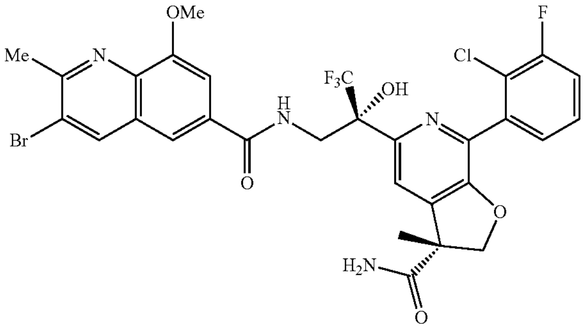 |
| P147 | 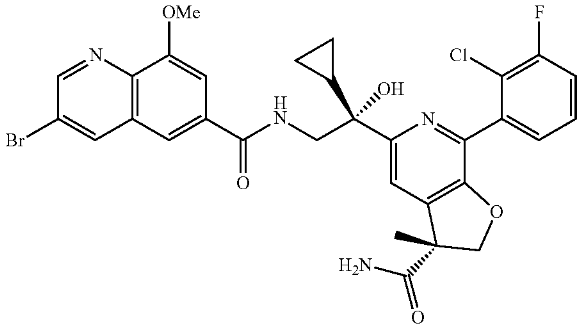 [SMILES: COc1cc(C(=O)NC[C@](O)(c2cc3c(c(-c4cccc(F)c4Cl)n2)OC[C@]3(C)C(N)=O)C2CC2)cc2cc(Br)cnc12] |

-continued
| Compound | Structure |
|---|---|
| P148P | 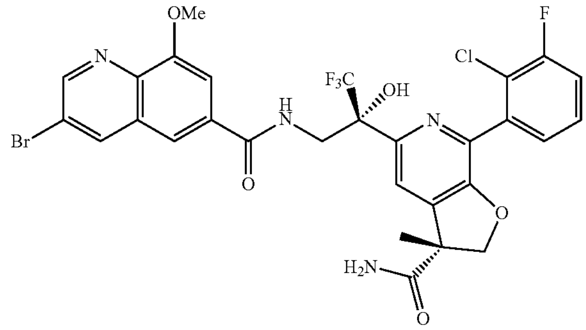 [SMILES: COc1cc(C(=O)NC[C@](O)(c2cc3c(c(-c4cccc(F)c4Cl)n2)OC[C@]3(C)C(N)=O)C(F)(F)F)cc2cc(Br)cnc12] |
| P149 | 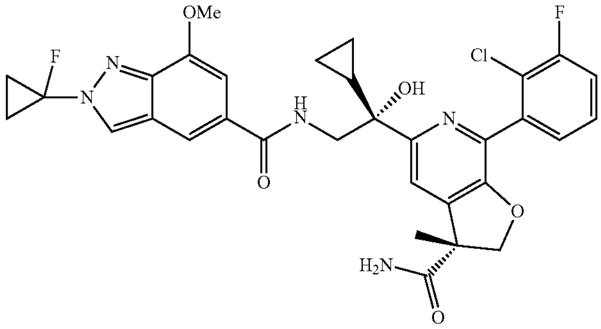 [SMILES: COc1cc(C(=O)NC[C@](O)(c2cc3c(c(-c4cccc(F)c4Cl)n2)OC[C@]3(C)C(N)=O)C2CC2)cc2cn(C3(F)CC3)nc12] |
| P150 | 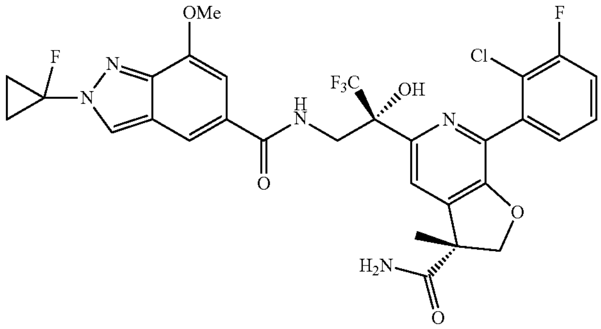 [SMILES: COc1cc(C(=O)NC[C@](O)(c2cc3c(c(-c4cccc(F)c4Cl)n2)OC[C@]3(C)C(N)=O)C(F)(F)F)cc2cn(C3(F)CC3)nc12] |
| P151 | 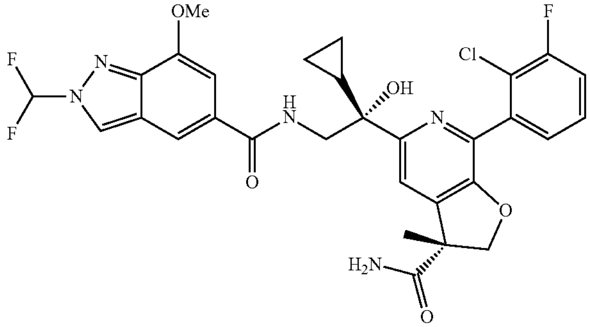 [SMILES: COc1cc(C(=O)NC[C@](O)(c2cc3c(c(-c4cccc(F)c4Cl)n2)OC[C@]3(C)C(N)=O)C2CC2)cc2cn(C(F)F)nc12] |

-continued
| Compound | Structure |
| --- | --- |
| P152 | 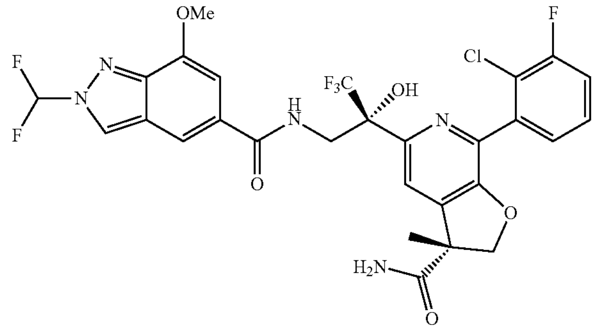 [SMILES: COc1cc(C(=O)NC[C@](O)(c2cc3c(c(-c4cccc(F)c4Cl)n2)OC[C@]3(C)C(N)=O)C(F)(F)F)cc2cn(C(F)F)nc12] |
| P153 | 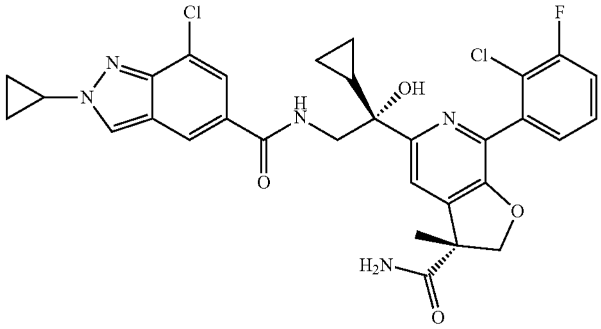 [SMILES: C[C@]1(C(N)=O)COc2c1cc([C@@](O)(CNC(=O)c1cc(Cl)c3nn(C4CC4)cc3c1)C1CC1)nc2-c1cccc(F)c1Cl] |
| P154 | 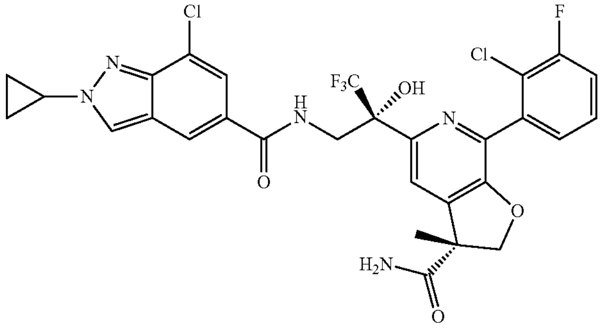 [SMILES: C[C@]1(C(N)=O)COc2c1cc([C@@](O)(CNC(=O)c1cc(Cl)c3nn(C4CC4)cc3c1)C(F)(F)F)nc2-c1cccc(F)c1Cl] |
| P155 | 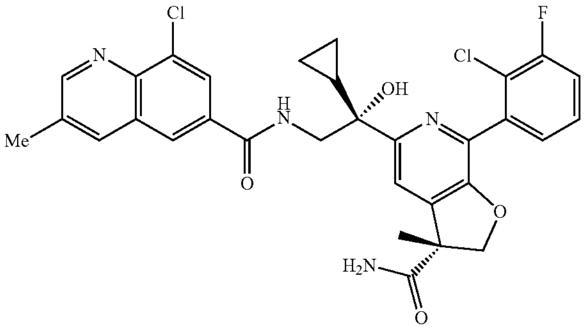 [SMILES: Cc1cnc2c(Cl)cc(C(=O)NC[C@](O)(c3cc4c(c(-c5cccc(F)c5Cl)n3)OC[C@]4(C)C(N)=O)C3CC3)cc2c1] |

-continued
| Compound | Structure |
| --- | --- |
| P156 | 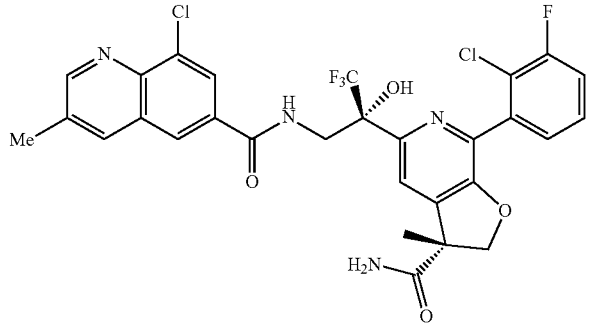 [SMILES: Cc1cnc2c(Cl)cc(C(=O)NC[C@](O)(c3cc4c(c(-c5cccc(F)c5Cl)n3)OC[C@]4(C)C(N)=O)C(F)(F)F)cc2c1] |
| P157 | 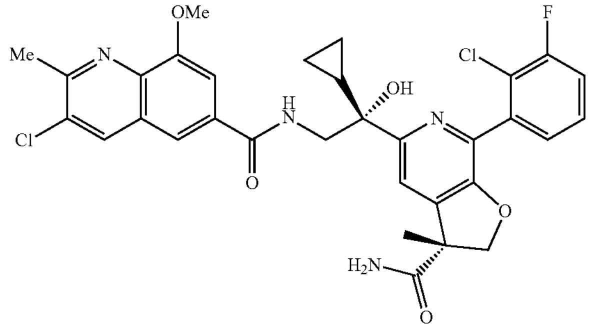 |
| P158 | 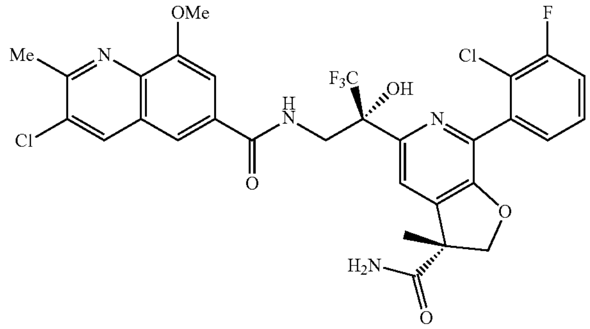 |
| P159 | 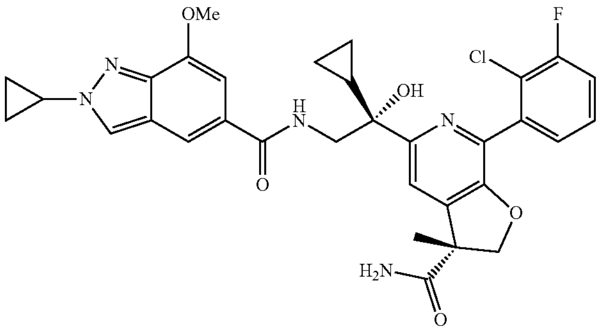 [SMILES: COc1cc(C(=O)NC[C@](O)(c2cc3c(c(-c4cccc(F)c4Cl)n2)OC[C@]3(C)C(N)=O)C2CC2)cc2cn(C3CC3)nc12] |

-continued

| Compound | Structure |
|---|---|
| P160 | 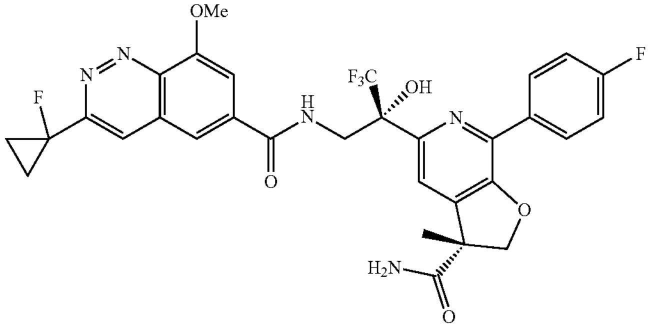 [SMILES: COc1cc(C(=O)NC[C@](O)(c2cc3c(c(-c4ccc(F)cc4)n2)OC[C@]3(C)C(N)=O)C(F)(F)F)cc2cc(C3(F)CC3)nnc12] |
| P161 | 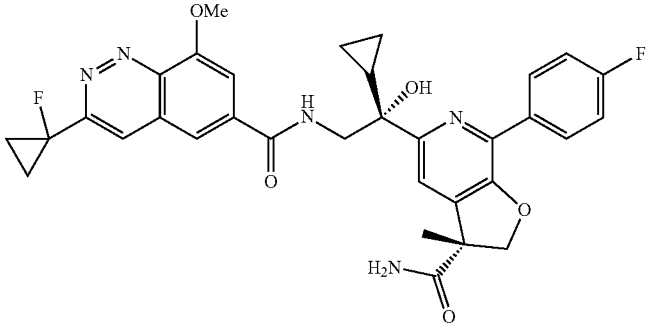 [SMILES: COc1cc(C(=O)NC[C@](O)(c2cc3c(c(-c4ccc(F)cc4)n2)OC[C@]3(C)C(N)=O)C2CC2)cc2cc(C3(F)CC3)nnc12] |
| P162 | 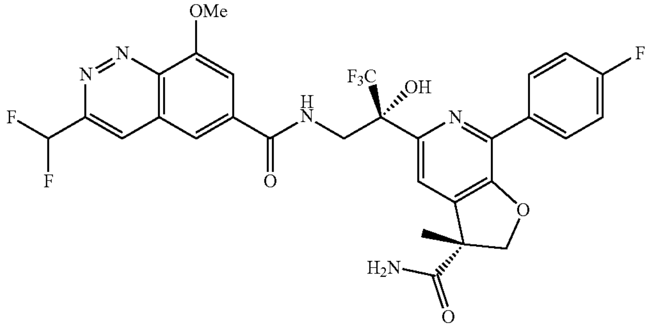 [SMILES: COc1cc(C(=O)NC[C@](O)(c2cc3c(c(-c4ccc(F)cc4)n2)OC[C@]3(C)C(N)=O)C(F)(F)F)cc2cc(C(F)F)nnc12] |
| P163 | 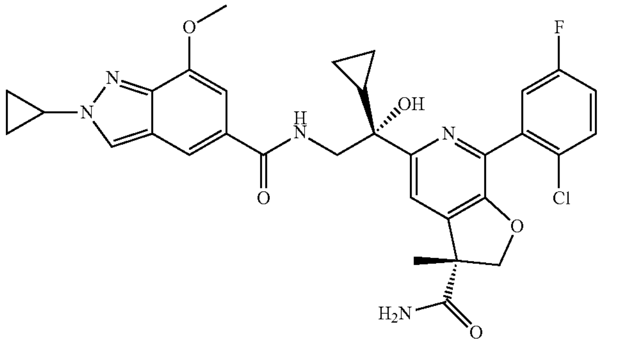 [SMILES: COc1cc(C(=O)NC[C@](O)(c2cc3c(c(-c4cc(F)ccc4Cl)n2)OC[C@]3(C)C(N)=O)C2CC2)cc2cn(C3CC3)nc12] |

Assays

Methods for RSV-A Assay

Hep-2 cells, (originally derived from tumors grown in irradiated-cortisonised weanling rats that had been injected with epidermoid carcinoma tissue from the larynx of a 56 year old male, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days. Viral stock titers were also quantified by a plaque forming unit assay, as described elsewhere.

Following extensive parameter testing, the final assay is run as follows: Hep-2 cells are seeded into the inner 60 wells of a 96-well plate at 8,000 cells per well in a volume of 50 μL using Growth Media (DMEM without phenol red, 1% L-Glut, 1% Penn/Strep, 1% nonessential amino acids, 10% heat-inactivated FBS). 2-fold serial dilutions of control and test compounds are added to the wells in duplicate in a total volume of 25 μL. Viral stock is then added to the wells at a multiplicity of infection (MOI) of 0.1 in a volume of 25 μL, bringing the total volume of each well to 100 μL. The MOI is calculated using the PFU/mL, or $TCID_{50}$ if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 μL of growth media containing an equal quantity of sucrose as those wells receiving the viral stock in order to keep consistent in media and volume conditions. The outer wells of the plate are filled with 125 μL of moat media (DMEM, 1% Penn/Strep) to act as a thermal and evaporative moat around the test wells. Following a 5-day incubation period, the plates are read using ATPlite (50 uL added per well), which quantifies the amount of ATP (a measure of cell health) present in each well. Assay plates are read using the Envision luminometer. These data are used to calculate the $EC_{50}$ each compound (Table 12). $EC_{50}$ ranges are as follows: A<0.2 μM; B>0.2 μM.

TABLE 12

Summary of Activities for RSV-A

| Compound | Human RSV-A ("Long") | Compound | Human RSV-A ("Long") |
|---|---|---|---|
| 3 | A | 4 | A |
| 5 | B | 6 | A |
| 7 | A | 8 | A |
| 9 | A | 10 | A |
| 11 | A | 12 | A |
| 13 | A | 14 | A |
| 15 | A | 16 | A |
| 17 | A | 18 | A |
| 19 | A | 20 | A |
| 21 | A | 22 | A |
| 23 | A | 24 | A |
| 25 | A | 26 | A |
| 27 | A | 28 | A |
| 29 | A | 30 | A |
| 31 | B | 32 | A |
| 33 | B | 34 | A |
| 35 | A | 36 | A |
| 37 | A | 38 | B |
| 39 | B | 40 | A |
| 41 | A | 42 | A |
| 43 | A | 44 | A |
| 45 | A | 46 | A |
| 47 | A | 48 | A |
| 49 | A | 50 | A |
| 51 | A | 52 | A |
| 53 | A | 54 | A |
| 55 | A | 56 | B |
| 57 | A | 58 | A |
| 59 | A | 60 | A |
| 61 | A | 62 | A |
| 63 | A | 64 | A |
| 65 | A | 66 | B |
| 67 | A | 68 | A |
| 69 | A | 70 | A |
| 71 | A | 72 | A |
| 73 | A | 74 | A |

TABLE 12-continued

Summary of Activities for RSV-A

| Compound | Human RSV-A ("Long") | Compound | Human RSV-A ("Long") |
|---|---|---|---|
| 75 | A | 76 | B |
| 77 | A | 78 | A |
| 79 | B | 80 | A |
| 81 | A | 82 | A |
| 83 | A | 84 | A |
| 85 | A | 86 | A |
| 87 | A | 88 | A |
| 89 | A | 90 | A |
| 91 | A | 92 | A |
| 93 | A | 94 | A |
| 95 | A | 96 | A |
| 97 | A | 98 | A |
| 99 | A | 100 | A |
| 101 | A | 102 | A |
| 103 | A | 104 | A |
| 105 | A | 106 | B |
| 107 | B | 108 | A |
| 109 | B | 110 | B |
| 111 | B | 112 | A |
| 113 | A | 114 | A |
| 115 | A | 116 | A |
| 117 | A | 118 | A |
| 119 | A | 120 | A |
| 121 | A | 122 | A |
| 123 | A | 124 | A |
| 125 | B | 126 | B |
| 127 | B | 128 | A |
| 129 | A | 130 | A |
| 131 | A | 132 | A |
| 133 | A | 134 | A |
| 135 | A | 136 | A |
| 137 | A | 138 | A |
| 139 | A | 140 | B |
| 141 | A | 142 | A |
| 143 | A | 144 | B |
| 145 | B | 146 | B |
| 147 | A | 148 | A |
| 149 | A | 150 | B |
| 151 | B | 152 | A |
| 153 | A | 154 | A |
| 155 | A | 156 | A |
| 157 | A | 158 | A |
| 159 | A | 160 | A |
| 161 | A | 162 | B |
| 163 | A | 164 | A |
| 165 | A | 166 | A |
| 167 | A | 168 | A |
| 169 | A | 170 | A |
| 171 | A | 172 | B |
| 173 | A | 174 | A |
| 175 | B | 176 | B |
| 177 | A | 178 | A |
| 179 | A | 180 | B |
| 181 | B | 182 | A |
| 183 | A | 184 | A |
| 185 | B | 186 | B |
| 187 | A | 188 | A |
| 189 | B | 190 | B |
| 191 | A | 192 | B |
| 193 | B | 194 | A |
| 195 | A | 196 | B |
| 197 | A | 198 | B |
| 199 | A | 200 | A |
| 201 | B | 202 | A |
| 203 | A | 204 | A |
| 205 | B | 206 | A |
| 207 | B | 208 | B |
| 209 | B | 210 | A |
| 211 | A | 212 | B |
| 213 | B | 214 | B |
| 215 | A | 216 | A |
| 217 | A | 218 | A |
| 219 | A | 220 | A |
| 221 | A | 222 | A |

TABLE 12-continued

Summary of Activities for RSV-A

| Compound | Human RSV-A ("Long") | Compound | Human RSV-A ("Long") |
|---|---|---|---|
| 223 | A | 224 | A |
| 225 | A | 226 | A |
| 227 | A | 228 | A |
| 229 | A | 232 | A |
| 233 | A | 234 | A |
| 235 | A | 236 | A |
| 237 | A | 238 | B |
| 239 | A | 240 | A |
| 241 | A | 242 | A |
| 243 | B | 244 | B |
| 245 | A | 246 | B |
| 247 | B | 248 | B |
| 249 | B | 250 | B |
| 251 | B | 252 | A |
| 253 | A | 254 | A |
| 255 | A | 256 | A |
| 257 | A | 258 | A |
| 259 | A | 260 | A |
| 261 | A | 262 | B |
| 263 | A | 264 | B |
| 265 | A | 266 | B |
| 267 | A | 268 | A |
| 269 | B | 270 | A |
| 271 | B | 272 | A |
| 273 | B | 274 | A |
| 275 | A | 276 | A |
| 277 | B | 278 | A |
| 279 | B | 280 | A |
| 281 | B | 282 | B |
| 283 | A | 284 | A |
| 285 | A | 286 | A |
| 287 | A | 288 | A |
| 289 | B | 290 | A |
| 291 | B | 292 | A |
| 293 | B | 294 | A |
| 295 | A | 296 | B |
| 297 | A | 298 | B |
| 299 | A | 300 | A |
| 301 | A | 302 | A |
| 303 | A | 304 | A |
| 305 | A | 306 | A |
| 307 | A | 308 | A |
| 309 | A | 310 | B |
| 311 | B | 312 | A |
| 313 | A | 314 | A |
| 315 | A | 316 | A |
| 317 | A | 318 | A |
| 319 | A | 320 | A |
| 321 | A | 322 | A |
| 323 | A | 324 | A |
| 325 | A | 326 | A |
| 327 | A | 328 | A |
| 329 | A | 330 | B |
| 331 | A | 332 | A |
| 333 | B | 334 | B |
| 335 | B | 336 | B |
| 337 | B | 338 | B |
| 339 | B | 340 | A |
| 341 | B | 342 | B |
| 343 | B | 344 | A |
| 345 | B | 346 | B |
| 347 | B | 348 | A |
| 349 | B | 350 | B |
| 351 | B | 352 | B |
| 353 | B | 355 | B |
| 356 | B | 357 | B |
| 358 | B | 359 | B |
| 360 | B | 361 | B |
| 362 | B | 363 | B |
| 364 | B | 365 | B |
| 366 | A | 367 | B |
| 368 | B | 369 | A |
| 370 | A | 371 | B |
| 372 | B | 373 | B |

TABLE 12-continued

Summary of Activities for RSV-A

| Compound | Human RSV-A ("Long") | Compound | Human RSV-A ("Long") |
|---|---|---|---|
| 374 | B | 375 | B |
| 376 | B | 377 | B |
| 378 | B | 379 | B |
| 380 | A | 381 | B |
| 382 | B | 383 | B |
| 384 | B | 385 | B |
| 386 | B | 387 | B |
| 388 | B | 389 | B |
| 390 | B | 391 | B |
| 392 | B | 393 | B |
| 394 | B | 395 | B |
| 396 | B | 397 | B |
| 398 | B | 399 | B |
| 400 | B | 401 | B |
| 402 | B | 403 | B |
| 404 | B | 405 | B |
| 406 | B | 407 | B |
| 408 | B | 409 | B |
| 410 | B | 411 | B |
| 412 | B | 413 | B |
| 414 | B | 415 | B |
| 416 | B | 417 | B |
| 418 | A | 419 | B |
| 420 | B | 421 | B |
| 422 | B | 423 | B |
| 424 | B | 425 | B |
| 426 | B | 427 | B |
| 428 | B | 429 | B |
| 430 | B | 431 | B |
| 432 | B | 433 | B |
| 434 | B | 435 | B |
| 436 | B | 437 | B |
| 438 | B | 439 | B |
| 440 | A | 441 | A |
| 442 | B | 443 | B |
| 444 | A | 445 | B |
| 446 | B | 447 | B |
| 448 | B | 449 | B |
| 450 | B | 451 | B |
| 452 | A | 453 | B |
| 454 | A | 455 | B |
| 456 | B | 457 | B |
| 458 | A | 459 | B |
| 460 | A | 461 | A |
| 462 | A | 463 | A |
| 464 | A | 482 | B |
| 483 | B | 484 | B |
| 485 | B | 486 | A |
| 487 | A | 488 | A |
| 489 | B | 490 | A |
| 491 | A | 492 | A |
| 493 | A | 494 | A |
| 495 | A | 496 | A |
| 497 | A | 498 | A |
| 499 | A | 500 | A |
| 501 | A | 502 | A |
| 503 | A | 504 | A |
| 505 | A | 506 | A |
| 507 | A | 508 | A |
| 509 | A | 510 | A |
| 511 | A | 512 | A |
| 513 | A | 514 | A |
| 515 | A | 516 | A |
| 517 | A | 518 | A |
| 519 | A | 520 | A |
| 521 | A | 522 | A |
| 523 | A | 524 | A |
| 525 | A | 526 | A |
| 527 | A | 528 | A |
| 529 | A | 530 | A |
| 531 | A | 532 | A |
| 533 | A | 534 | A |
| 535 | A | 536 | A |
| 537 | A | 538 | A |

TABLE 12-continued

Summary of Activities for RSV-A

| Compound | Human RSV-A ("Long") | Compound | Human RSV-A ("Long") |
|---|---|---|---|
| 539 | A | 540 | A |
| 541 | A | 542 | A |
| 543 | A | 544 | A |
| 545 | A | 546 | A |
| 547 | A | 548 | A |
| 549 | A | 550 | A |
| 551 | A | 552 | A |
| 553 | A | 554 | A |
| 555 | A | 556 | A |
| 557 | A | 558 | A |
| 559 | A | 560 | A |
| 561 | A | 562 | A |
| 563 | A | 564 | A |
| 565 | A | 566 | A |
| 567 | A | 568 | A |
| 569 | A | 570 | A |
| 571 | A | 572 | A |
| 573 | A | 574 | A |
| 575 | A | 576 | A |
| 577 | A | 578 | A |
| 579 | A | 580 | A |
| 581 | A | 582 | A |
| 583 | A | 584 | A |
| 585 | A | 586 | A |
| 587 | A | 588 | A |
| 589 | A | 590 | A |
| 591 | A | 592 | A |
| 593 | A | 594 | A |
| 595 | A | 596 | A |
| 597 | A | 598 | A |
| 599 | A | 600 | A |
| 601 | A | 602 | A |
| 603 | A | 604 | A |
| 605 | A | 606 | A |
| 607 | A | 608 | A |
| 609 | A | 610 | A |
| 611 | A | 612 | A |
| 613 | A | 614 | A |
| 615 | A | 616 | A |
| 617 | A | 618 | A |
| 619 | A | 620 | A |
| 621 | A | 622 | A |
| 623 | A | 624 | A |
| 625 | A | 626 | A |
| 627 | A | 628 | B |
| 633 | A | 634 | A |
| 635 | B | 636 | A |
| 637 | A | 638 | A |
| 639 | A | 640 | A |
| 641 | A | 642 | A |
| 643 | A | 644 | B |
| 645 | A | 646 | A |
| 647 | A | 648 | A |
| 649 | A | 650 | A |
| 651 | A | 652 | A |
| 653 | A | 654 | A |
| 655 | A | 656 | A |
| 657 | A | 658 | A |
| 659 | A | 660 | A |
| 661 | A | 662 | A |
| 663 | A | 664 | A |
| 665 | A | 666 | A |
| 667 | A | 668 | A |
| 669 | A | 670 | A |
| 671 | A | 672 | A |
| 673 | A | 674 | A |
| 675 | A | | |
| 683 | A | 684 | A |
| 685 | A | 686 | A |
| 687 | A | 688 | A |
| 691 | A | 692 | B |
| 693 | A | 694 | A |
| 695 | A | 696 | A |
| 697 | A | 698 | A |

TABLE 12-continued

Summary of Activities for RSV-A

| Compound | Human RSV-A ("Long") | Compound | Human RSV-A ("Long") |
|---|---|---|---|
| 699 | A | 700 | A |
| 701 | A | 702 | A |
| 703 | A | 704 | A |
| 705 | A | 706 | A |
| 707 | A | 708 | A |
| 709 | A | 710 | A |
| 711 | A | 712 | A |
| 713 | A | 714 | A |
| 715 | A | 716 | A |
| 717 | A | 718 | A |
| 719 | A | 720 | A |
| 721 | A | 722 | A |
| 723 | A | 724 | A |
| 725 | A | 726 | A |
| 727 | A | 728 | A |
| 729 | A | 730 | A |
| 731 | A | 732 | A |
| 733 | A | 734 | A |
| 735 | A | 736 | A |
| 737 | A | 738 | A |
| 739 | A | 740 | A |
| 741 | A | 742 | A |
| 743 | A | 744 | A |
| 745 | A | 746 | A |
| 747 | A | 748 | A |
| 749 | A | 750 | A |
| 751 | A | 752 | A |
| 753 | A | 754 | A |
| 755 | A | 756 | A |
| 757 | A | 758 | A |
| 759 | A | 760 | A |
| 761 | A | 762 | A |
| 763 | A | 764 | A |
| 765 | A | 766 | A |
| 767 | A | 768 | A |
| 773 | A | 774 | A |
| 775 | A | 776 | A |
| 777 | A | 778 | A |
| 779 | A | 780 | A |
| 781 | A | 782 | A |
| 783 | A | 784 | A |
| 785 | A | 786 | A |
| 787 | A | 788 | A |
| 789 | A | 790 | A |
| 791 | A | 792 | A |
| 793 | A | 794 | A |
| 795 | A | 796 | A |
| 797 | A | 798 | A |
| 799 | A | 800 | A |
| 801 | A | 802 | A |
| 805 | B | 806 | B |
| 807 | B | 808 | A |
| 809 | B | 810 | B |
| 811 | A | 812 | B |
| 813 | B | 814 | B |
| 815 | A | 816 | A |
| 817 | A | 818 | A |
| 819 | A | 820 | A |
| 821 | A | 822 | A |
| 823 | A | 824 | A |
| 825 | A | 826 | A |
| 827 | A | 828 | A |
| 829 | A | 830 | A |
| 831 | A | 832 | A |
| 833 | A | 834 | A |
| 835 | A | 836 | A |
| 837 | A | 838 | A |
| 839 | A | 840 | A |
| 841 | A | 842 | A |
| 843 | A | 844 | A |
| 845 | A | 846 | A |
| 847 | A | 848 | A |
| 849 | A | 850 | A |
| 851 | A | 852 | A |

TABLE 12-continued

| Compound | Human RSV-A ("Long") | Compound | Human RSV-A ("Long") |
|---|---|---|---|
| Summary of Activities for RSV-A | | | |
| 853 | A | 854 | B |
| 855 | A | 856 | A |
| 857 | A | 858 | A |
| 859 | A | 860 | A |
| 861 | A | 862 | A |
| 871 | A | 872 | A |
| 873 | A | 874 | B |
| 875 | B | 876 | B |
| 877 | A | 878 | A |
| 879 | B | 880 | B |
| 881 | A | 882 | B |
| 883 | A | 884 | A |
| 885 | A | 886 | A |
| 887 | A | 888 | A |
| 889 | A | 890 | B |
| 891 | A | 892 | B |
| 893 | A | 894 | B |
| 895 | B | 896 | A |
| 897 | B | 898 | A |
| 899 | B | 900 | A |
| 901 | A | 902 | B |
| 903 | A | 904 | B |
| 905 | B | 906 | A |
| 907 | B | 908 | A |
| 909 | A | 910 | B |
| 911 | A | 912 | A |
| 913 | B | 914 | A |
| 915 | A | 916 | A |
| 917 | A | 918 | A |
| 919 | B | 920 | A |
| 921 | B | 922 | A |
| 923 | B | 924 | A |
| 925 | A | 926 | A |
| 927 | A | 928 | A |
| 929 | A | 930 | A |
| 931 | A | 932 | A |
| 933 | A | 934 | A |
| 935 | A | 936 | A |
| 937 | B | 938 | B |
| 939 | A | 940 | A |
| 941 | B | 942 | B |
| 943 | A | 944 | A |
| 945 | A | 946 | A |
| 947 | A | 948 | A |
| 949 | A | 950 | A |
| 951 | A | 952 | A |
| 953 | A | 954 | A |
| 955 | A | 956 | A |
| 961 | A | | |
| 965 | B | 966 | B |
| 967 | B | 968 | B |
| 969 | B | 970 | B |
| 971 | B | 972 | A |
| 973 | B | 974 | A |
| 975 | A | 976 | A |
| 977 | A | 978 | A |
| 979 | A | 980 | A |
| 981 | B | 982 | A |
| 983 | A | 984 | B |
| 985 | A | 986 | A |
| 987 | A | 988 | A |
| 989 | A | 990 | A |
| 991 | A | 992 | A |
| 993 | A | 994 | A |
| 995 | B | 996 | A |
| 997 | A | 998 | A |
| 999 | A | 1000 | A |
| 1001 | A | 1002 | B |
| 1003 | A | 1004 | B |
| 1005 | A | 1006 | B |
| 1007 | A | 1008 | B |
| 1009 | A | 1010 | B |
| 1011 | A | 1012 | B |
| 1013 | A | 1014 | A |

TABLE 12-continued

| Compound | Human RSV-A ("Long") | Compound | Human RSV-A ("Long") |
|---|---|---|---|
| Summary of Activities for RSV-A | | | |
| 1015 | A | 1016 | B |
| 1017 | A | 1018 | B |
| 1019 | A | 1020 | B |
| 1021 | A | 1022 | B |
| 1023 | A | 1024 | B |
| 1025 | A | 1026 | B |
| 1027 | A | 1028 | B |
| 1029 | A | 1030 | A |
| 1031 | A | 1032 | B |
| 1033 | A | 1034 | B |
| 1035 | A | 1036 | B |
| 1037 | A | 1038 | B |
| 1039 | A | 1040 | A |
| 1041 | A | 1042 | A |
| 1043 | A | 1044 | A |
| 1045 | A | 1046 | B |
| 1047 | A | 1048 | B |
| 1049 | A | 1050 | A |
| 1051 | A | 1052 | A |
| 1053 | B | 1054 | A |
| 1055 | B | 1056 | A |
| 1057 | B | 1058 | A |
| 1059 | B | 1060 | A |
| 1061 | B | 1062 | A |
| 1063 | B | 1064 | A |
| 1065 | A | 1066 | B |
| 1067 | A | 1068 | A |
| 1069 | A | 1071 | A |
| 1072 | A | 1073 | A |
| 1074 | A | 1075 | A |
| 1076 | A | 1077 | A |
| 1078 | A | 1079 | A |
| 1080 | A | 1081 | A |
| 1082 | A | 1083 | A |
| 1084 | A | 1085 | A |
| 1086 | A | 1087 | A |
| 1088 | A | 1089 | A |
| 1090 | A | 1091 | A |
| 1092 | A | 1093 | A |
| 1094 | A | 1095 | A |
| 1096 | A | 1097 | A |
| 1098 | A | 1099 | A |
| 1100 | A | 1101 | A |
| 1102 | A | 1103 | A |
| 1104 | B | 1105 | A |
| 1106 | A | 1107 | A |
| 1108 | A | 1109 | A |
| 1110 | A | 1111 | A |
| 1112 | A | 1113 | A |
| 1114 | A | 1115 | A |
| 1116 | A | 1117 | A |
| 1118 | A | 1119 | A |
| 1120 | A | 1121 | A |
| 1122 | A | 1123 | A |
| 1124 | A | 1125 | A |
| 1126 | A | 1127 | A |
| 1128 | A | 1129 | A |
| 1130 | A | 1131 | A |
| 1132 | A | 1133 | A |
| 1134 | A | 1135 | A |
| 1136 | A | 1137 | A |
| 1138 | A | 1139 | A |
| 1140 | A | 1141 | A |
| 1142 | A | 1143 | A |
| 1144 | A | 1145 | A |
| 1146 | A | 1147 | A |
| 1148 | A | 1149 | A |
| 1150 | A | 1151 | A |
| 1152 | A | 1153 | A |
| 1154 | A | 1155 | A |
| 1156 | A | 1157 | A |
| 1158 | A | 1159 | A |
| 1160 | A | 1161 | A |
| 1162 | A | 1163 | A |

TABLE 12-continued

| Summary of Activities for RSV-A | | | |
|---|---|---|---|
| Compound | Human RSV-A ("Long") | Compound | Human RSV-A ("Long") |
| 1164 | A | 1165 | A |
| 1166 | A | 1167 | A |
| 1168 | A | 1169 | A |
| 1170 | A | 1171 | A |
| 1172 | A | 1173 | A |
| 1174 | A | 1175 | A |
| 1176 | A | 1177 | A |
| 1178 | A | 1179 | A |
| 1180 | A | 1181 | A |
| 1182 | A | 1183 | A |
| 1184 | A | 1185 | A |
| 1186 | A | 1187 | A |
| 1188 | A | 1189 | A |
| 1190 | A | 1191 | A |
| 1192 | A | 1193 | A |
| 1194 | A | 1195 | A |
| 1196 | A | 1197 | A |
| 1198 | A | 1199 | A |
| 1200 | A | 1201 | A |
| 1202 | A | 1203 | A |
| 1204 | A | 1205 | A |
| 1206 | A | 1207 | A |
| 1208 | A | 1209 | A |
| 1210 | A | 1211 | A |
| 1212 | A | 1213 | A |
| 1214 | A | 1215 | A |
| 1216 | A | 1217 | B |
| 1218 | A | 1219 | A |
| 1220 | A | 1221 | A |
| 1222 | A | 1223 | A |
| 1224 | A | 1225 | A |
| 1226 | A | 1227 | A |
| 1228 | A | 1229 | B |
| 1230 | B | 1231 | A |
| 1232 | B | 1233 | A |
| 1234 | B | 1235 | A |
| 1236 | B | 1237 | B |
| 1238 | A | 1239 | B |
| 1240 | B | 1241 | B |
| 1242 | A | 1243 | A |
| 1244 | A | 1245 | A |
| 1246 | A | 1247 | A |
| 1248 | A | 1249 | B |
| 1250 | A | 1251 | B |
| 1252 | A | 1253 | A |
| 1254 | A | 1255 | A |
| 1256 | A | 1257 | A |
| 1258 | A | 1259 | A |
| 1260 | A | 1261 | A |
| 1262 | A | 1263 | A |
| 1264 | A | 1265 | A |
| 1266 | A | 1267 | A |
| 1268 | A | 1269 | B |
| 1270 | A | 1271 | A |
| 1272 | A | 1273 | A |
| 1274 | A | 1275 | A |
| 1276 | A | 1277 | A |
| 1278 | A | 1279 | A |
| 1280 | A | 1281 | A |
| 1282 | A | 1283 | A |
| 1284 | A | 1285 | A |
| 1286 | A | 1287 | A |
| 1288 | A | 1289 | A |
| 1290 | A | 1291 | A |
| 1292 | B | 1293 | A |

Methods for HMPV Antiviral Assay

Method-A:

HMPV antiviral activity was evaluated using a recombinant version of HMPV CAN97-83 engineered to contain the coding sequence for enhanced green fluorescence protein (eGFP) in the 3' end of the virus genome (MPV-GFP1, ViraTree). Vero E6 cells (ATCC #CCL-7) were seeded at a density of 12,000 cells/100 μL/well into 96-well cell plates one day prior to the assay. On the day of screening, the cell culture medium was aspirated from the wells and cells were washed twice with serum-free Eagle's Modified Essential Medium (EMEM, ATCC #) containing 1% penicillin-streptomycin (Invitrogen) (SF-EMEM). Cell washes were performed by dispensing 100 μL SF-EMEM per well and immediately aspirating the wash medium from the well. Following the second wash step, serum-free OptiMEM (Invitrogen, Cat No.) (SF-OptiMEM) containing 0.5 μg/mL TPCK-Trypsin (VENDOR) and 1% penicillin-streptomycin was added to the cells at 50 μL/well. Compounds were added into the 96-well plates using a JANUS automated liquid handling system (VENDOR). Compounds were initially diluted 1:50 into an intermediate 96-well plate containing SF-OptiMEM prior to transfer to the assay plate (25 μL/well). Each of the test compounds were tested in duplicate wells at final concentrations starting from 8 μM or 2 μM using ½ stepwise dilutions for a total of 8 points. Virus infection was performed by preparing a working stock of MPV-GFP1 at a multiplicity of infection (MOI) equal to 0.05/25 μL and aliquoting 25 μL of virus inoculum to the compound and positive control wells. SF-OptiMEM was added (25 μL/well) to the appropriate wells to serve as a virus-free negative control for the assay. The final DMSO concentration of all wells is 0.5%. Plates were incubated at 32° C., 5% $CO_2$ for 5 days.

After 5 days incubation, eGFP fluorescence intensity was measured at (X) nM wavelength using a Spectramax i3× plate reader (VENDOR). Percent viral inhibition was calculated using the following equation:

$$y=[100-(X_Q/X_P)]\times 100$$

Where $X_Q$ is the fluorescence intensity measured in a well containing recombinant MPV-GFP1-infected, compound-treated cells and $X_P$ is the average fluorescence intensity measured in the wells containing untreated cells infected with recombinant virus. $EC_{50}$ values were then calculated by non-linear regression using a four parameter curve logistic equation. The curve fit model employed was XLFit Dose Response One Site Model 200:

$$y=(A+(B/(1+((x/C)^D))))$$

Where A is the minimum y value, B is the maximum y value, C is the log $EC_{50}$ value, and D is the slope factor. These data are used to calculate the $EC_{50}$ each compound (Table 13). $EC_{50}$ ranges are as follows: A<0.5 μM; B>0.5 μM.

TABLE 13

| Summary of Activities for HMPV | | | |
|---|---|---|---|
| Compound | HMPV $EC_{50}$ | Compound | HMPV $EC_{50}$ |
| 3 | B | 4 | A |
| 6 | A | 7 | A |
| 8 | A | 9 | A |
| 10 | A | 11 | B |
| 12 | A | 13 | A |
| 14 | A | 16 | A |
| 17 | A | 19 | A |
| 20 | A | 22 | A |
| 23 | A | 24 | A |
| 25 | A | 26 | A |
| 27 | A | 28 | A |
| 29 | A | 30 | A |
| 32 | A | 34 | B |
| 40 | A | 41 | A |

TABLE 13-continued

Summary of Activities for HMPV

| Compound | HMPV $EC_{50}$ | Compound | HMPV $EC_{50}$ |
|---|---|---|---|
| 42 | A | 43 | A |
| 44 | A | 45 | A |
| 47 | A | 48 | A |
| 49 | B | 50 | B |
| 51 | A | 52 | A |
| 53 | A | 54 | B |
| 55 | A | 57 | B |
| 58 | A | 59 | A |
| 60 | A | 62 | B |
| 63 | B | 64 | B |
| 65 | B | 68 | A |
| 70 | A | 72 | A |
| 73 | A | 74 | A |
| 75 | B | 77 | A |
| 78 | B | 80 | A |
| 81 | B | 82 | A |
| 83 | A | 84 | A |
| 85 | A | 86 | A |
| 91 | B | 92 | A |
| 94 | B | 95 | B |
| 96 | A | 97 | B |
| 100 | B | 102 | A |
| 103 | A | 105 | B |
| 108 | B | 112 | B |
| 113 | A | 114 | A |
| 120 | B | 121 | A |
| 124 | A | 128 | A |
| 129 | B | 132 | B |
| 134 | B | 135 | B |
| 136 | B | 137 | B |
| 138 | B | 139 | B |
| 141 | B | 142 | B |
| 143 | A | 147 | A |
| 148 | A | 149 | B |
| 152 | B | 153 | B |
| 154 | B | 155 | B |
| 156 | B | 157 | B |
| 158 | B | 160 | B |
| 161 | B | 165 | B |
| 166 | B | 167 | B |
| 168 | A | 169 | B |
| 170 | A | 174 | B |
| 177 | A | 178 | B |
| 179 | B | 182 | A |
| 183 | B | 184 | B |
| 199 | B | 200 | B |
| 210 | A | 217 | A |
| 218 | A | 219 | A |
| 220 | B | 221 | B |
| 222 | B | 223 | B |
| 224 | B | 226 | B |
| 234 | A | 235 | A |
| 263 | A | 265 | A |
| 267 | A | 268 | B |
| 270 | A | 280 | A |
| 300 | A | 301 | A |
| 305 | A | 306 | A |
| 307 | A | 308 | A |
| 309 | B | 314 | A |
| 315 | A | 321 | A |
| 322 | B | 323 | B |
| 324 | A | 327 | B |
| 329 | A | 441 | B |

Method-B:

In vitro HMPV antiviral activity was evaluated using the clinical isolate TN/1501/A1 and LLC-MK2 cells (ATCC #CCL-7), an immortalized kidney epithelial cell line from *Macaca mulatta.*

Compounds were resuspended in dimethyl sulfoxide (DMSO) at 10 mM and added to a 384-well source plate. The compounds were diluted and transferred onto 384-well assay plates using the Echo-650 automated liquid handling system (Beckman Coulter, Indiana). The test compounds were assessed in duplicate at a top concentration of 10 μM followed by 3-fold serial dilutions to give a total of 10 concentration points. DMSO control wells were also included on the assay plates and were either infected or not, acting as positive and negative controls.

TN/1501/A1 virus infections were performed in-suspension with LLC-MK2 cells. The cells were washed twice with PBS and removed from the cell-culture flask with 0.25% trypsin-EDTA (Thermo Fisher Scientific, MA). The trypsin-EDTA was inactivated by resuspending in 2% fetal bovine serum (FBS) and OptiMEM (ThermoFisher Scientific, MA) containing 1% penicillin-streptomycin. Cells were pelleted by centrifuging for 5 minutes at 800 rpm, the supernatant was removed, and cells were suspended in PBS plus 100 μg/mL $CaCl_2$). This step was performed twice. Cells were then resuspended in serum-free (SF)-OptiMEM containing 4 μg/mL TPCK-Trypsin (Sigma Aldrich, MO), 1% penicillin-streptomycin (ThermoFisher Scientific, MA) and 100 μg/mL $CaCl_2$). Cells were counted and seeded at a density of 5,000 cells/well, 12.5 μL/well.

Virus infections were done at a multiplicity of infection (MOI) of 0.014 with 12.5 μL added per well. SF-OptiMEM, 12.5 μL/well, was added to the appropriate wells to serve as a virus-free negative control for the assay. The final concentration of TPCK-trypsin was 2 μg/mL. Plates were incubated at 37° C., 5% $CO_2$ for 6 days.

After 6 days incubation, 12.5 μL of ATP-Lite (PerkinElmer, MA) was added to each well and the raw luminescence values were determined using the Envision 2104 (Perkin Elmer, MA). The average of the raw luminescence values for the cells and virus only positive control wells was subtracted from all conditions tested and the percent cell health was determined by dividing these values by the average of the cells only negative control wells. $EC_{50}$ values were then calculated by non-linear regression using a four-parameter curve logistic equation. The curve fit model employed was XLFit Dose Response One Site Model 200:

$$y=(A+(B/(1+((x/C)^D)))),$$

where A is the minimum y value, B is the maximum y value, C is the log $EC_{50}$ value, and D is the slope factor. These data are used to calculate the $EC_{50}$ each compound (Table 14). $EC_{50}$ ranges are as follows: A<0.5 μM; B>0.5 μM.

TABLE 14

Summary of Activities for hMPV WT1501

| Compound | HMPV $EC_{50}$ | Compound | HMPV $EC_{50}$ |
|---|---|---|---|
| 486 | B | 487 | B |
| 488 | B | 489 | B |
| 491 | A | 493 | A |
| 494 | A | 495 | A |
| 496 | A | 497 | A |
| 498 | A | 499 | A |
| 500 | A | 501 | B |
| 502 | A | 503 | A |
| 504 | A | 505 | A |
| 506 | A | 507 | A |
| 508 | A | 509 | A |
| 510 | A | 511 | B |
| 512 | B | 513 | A |
| 514 | A | 515 | A |
| 516 | B | 517 | A |
| 518 | A | 519 | B |
| 520 | A | 521 | A |
| 522 | A | 523 | A |
| 524 | A | 525 | A |

TABLE 14-continued

| Summary of Activities for hMPV WT1501 | | | |
|---|---|---|---|
| Compound | HMPV $EC_{50}$ | Compound | HMPV $EC_{50}$ |
| 526 | A | 527 | A |
| 528 | A | 529 | A |
| 530 | A | 531 | A |
| 532 | A | 533 | A |
| 534 | A | 535 | A |
| 536 | A | 537 | A |
| 538 | A | 539 | A |
| 540 | A | 541 | A |
| 542 | A | 543 | A |
| 544 | A | 545 | A |
| 546 | A | 547 | A |
| 548 | A | 549 | A |
| 550 | A | 551 | A |
| 552 | A | 553 | A |
| 554 | A | 555 | A |
| 556 | A | 557 | A |
| 558 | A | 559 | A |
| 560 | A | 561 | A |
| 562 | A | 563 | A |
| 564 | A | 565 | A |
| 566 | A | 567 | A |
| 568 | A | 569 | A |
| 570 | A | 571 | A |
| 572 | A | 573 | A |
| 574 | A | 575 | A |
| 576 | B | 577 | B |
| 578 | B | 579 | B |
| 580 | B | 581 | B |
| 582 | B | 583 | B |
| 585 | B | 586 | B |
| 587 | B | 588 | B |
| 589 | B | 590 | B |
| 591 | A | 592 | A |
| 593 | A | 594 | A |
| 595 | A | 596 | A |
| 597 | B | 598 | A |
| 599 | A | 600 | A |
| 601 | A | 602 | A |
| 603 | B | 604 | A |
| 605 | A | 606 | A |
| 607 | A | 608 | A |
| 609 | A | 610 | A |
| 611 | A | 612 | A |
| 613 | A | 614 | B |
| 615 | A | 616 | A |
| 617 | A | 618 | A |
| 619 | A | 620 | A |
| 621 | A | 622 | A |
| 623 | B | 624 | B |
| 625 | B | 626 | B |
| 627 | B | 628 | B |
| 629 | A | 630 | A |
| 631 | A | 632 | A |
| 633 | A | 636 | A |
| 637 | A | 638 | A |
| 639 | A | 640 | A |
| 641 | A | 642 | B |
| 643 | A | 644 | B |
| 645 | B | 646 | B |
| 647 | B | 648 | B |
| 649 | B | 650 | A |
| 651 | A | 652 | A |
| 653 | B | 654 | A |
| 655 | A | 656 | A |
| 657 | A | 658 | A |
| 659 | A | 660 | A |
| 661 | A | 662 | A |
| 663 | A | 664 | A |
| 665 | A | 666 | A |
| 667 | A | 668 | A |
| 669 | B | 670 | B |
| 671 | B | 672 | B |
| 673 | B | 674 | B |
| 675 | B | 676 | A |
| 677 | B | 678 | A |

TABLE 14-continued

| Summary of Activities for hMPV WT1501 | | | |
|---|---|---|---|
| Compound | HMPV $EC_{50}$ | Compound | HMPV $EC_{50}$ |
| 679 | B | 680 | B |
| 681 | B | 682 | B |
| 683 | A | 684 | A |
| 685 | A | 686 | A |
| 687 | A | 688 | A |
| 689 | A | 690 | A |
| 691 | B | 693 | B |
| 694 | B | 695 | B |
| 696 | B | 697 | A |
| 698 | B | 699 | B |
| 700 | B | 702 | B |
| 703 | A | 704 | A |
| 705 | A | 706 | A |
| 707 | A | 708 | A |
| 709 | B | 710 | A |
| 711 | A | 712 | A |
| 713 | A | 714 | A |
| 715 | A | 716 | A |
| 717 | A | 718 | B |
| 719 | A | 720 | A |
| 721 | B | 722 | A |
| 723 | A | 724 | A |
| 725 | A | 726 | A |
| 727 | A | 728 | A |
| 729 | A | 730 | A |
| 731 | A | 732 | A |
| 733 | A | 734 | A |
| 735 | A | 736 | A |
| 737 | A | 738 | A |
| 739 | A | 740 | A |
| 741 | A | 742 | A |
| 743 | A | 744 | A |
| 745 | A | 746 | A |
| 747 | A | 748 | A |
| 749 | A | 750 | A |
| 751 | A | 752 | A |
| 753 | A | 754 | A |
| 755 | A | 756 | A |
| 757 | A | 758 | A |
| 759 | A | 760 | A |
| 761 | A | 762 | A |
| 763 | A | 764 | A |
| 765 | A | 766 | A |
| 767 | A | 768 | A |
| 769 | A | 770 | A |
| 771 | A | 772 | A |
| 773 | A | 774 | A |
| 775 | A | 776 | A |
| 777 | A | 778 | A |
| 779 | A | 780 | A |
| 781 | A | 782 | A |
| 783 | A | 784 | A |
| 785 | A | 786 | A |
| 787 | A | 788 | A |
| 789 | A | 790 | A |
| 791 | A | 792 | A |
| 793 | A | 794 | A |
| 795 | B | 796 | A |
| 797 | A | 798 | A |
| 799 | A | 800 | A |
| 801 | A | 802 | A |
| 803 | A | 804 | A |
| 811 | A | 815 | A |
| 816 | A | 817 | A |
| 818 | A | 819 | A |
| 820 | A | 821 | B |
| 822 | A | 823 | A |
| 824 | A | 825 | A |
| 826 | A | 827 | A |
| 828 | A | 829 | B |
| 830 | A | 831 | A |
| 832 | B | 833 | B |
| 834 | A | 835 | A |
| 836 | A | 837 | A |
| 838 | A | 839 | A |

TABLE 14-continued

Summary of Activities for hMPV WT1501

| Compound | HMPV $EC_{50}$ | Compound | HMPV $EC_{50}$ |
|---|---|---|---|
| 840 | A | 841 | A |
| 842 | A | 843 | A |
| 844 | A | 845 | A |
| 846 | A | 847 | A |
| 848 | A | 849 | A |
| 850 | B | 851 | A |
| 852 | B | 853 | A |
| 854 | B | 855 | A |
| 856 | A | 857 | A |
| 858 | A | 859 | A |
| 860 | A | 861 | A |
| 862 | A | 863 | B |
| 864 | B | 865 | B |
| 866 | B | 867 | B |
| 868 | B | 869 | A |
| 870 | B | 871 | A |
| 872 | A | 873 | A |
| 874 | B | 876 | B |
| 877 | A | 878 | B |
| 883 | B | 884 | B |
| 885 | A | 886 | A |
| 887 | B | 888 | B |
| 889 | B | 891 | B |
| 893 | A | 896 | B |
| 898 | B | 899 | B |
| 901 | A | 903 | B |
| 908 | A | 909 | B |
| 911 | A | 912 | A |
| 913 | B | 914 | B |
| 915 | A | 916 | A |
| 917 | B | 918 | B |
| 919 | B | 920 | A |
| 921 | B | 922 | A |
| 923 | B | 924 | B |
| 925 | B | 926 | B |
| 927 | B | 928 | B |
| 929 | A | 930 | A |
| 931 | A | 932 | A |
| 933 | B | 934 | B |
| 935 | B | 936 | A |
| 937 | B | 938 | B |
| 939 | B | 940 | B |
| 941 | B | 942 | B |
| 943 | B | 944 | B |
| 945 | B | 946 | A |
| 947 | B | 948 | B |
| 949 | B | 950 | B |
| 951 | A | 952 | A |
| 953 | B | 954 | B |
| 955 | B | 956 | A |
| 957 | A | 958 | A |
| 959 | B | 960 | A |
| 961 | A | 962 | A |
| 963 | A | 964 | A |
| 965 | B | 966 | B |
| 967 | B | 968 | B |
| 969 | B | 970 | B |
| 971 | B | 972 | A |
| 973 | B | 974 | A |
| 975 | A | 976 | B |
| 977 | B | 978 | B |
| 979 | A | 980 | A |
| 981 | B | 982 | B |
| 983 | B | 984 | B |
| 985 | A | 986 | A |
| 987 | A | 988 | A |
| 989 | A | 990 | A |
| 991 | A | 992 | A |
| 993 | A | 994 | A |
| 995 | B | 996 | A |
| 997 | A | 999 | A |
| 1000 | B | 1001 | A |
| 1002 | B | 1003 | A |
| 1004 | B | 1005 | A |
| 1006 | B | 1007 | A |

TABLE 14-continued

Summary of Activities for hMPV WT1501

| Compound | HMPV $EC_{50}$ | Compound | HMPV $EC_{50}$ |
|---|---|---|---|
| 1008 | B | 1009 | A |
| 1010 | B | 1011 | A |
| 1012 | B | 1013 | A |
| 1014 | A | 1015 | A |
| 1016 | B | 1017 | A |
| 1018 | B | 1019 | A |
| 1020 | B | 1021 | A |
| 1022 | B | 1023 | A |
| 1024 | B | 1025 | A |
| 1026 | B | 1027 | A |
| 1028 | B | 1029 | A |
| 1030 | B | 1031 | A |
| 1032 | B | 1033 | A |
| 1034 | B | 1035 | A |
| 1036 | B | 1037 | A |
| 1038 | B | 1039 | A |
| 1040 | B | 1041 | A |
| 1042 | A | 1043 | A |
| 1044 | A | 1045 | A |
| 1046 | B | 1047 | A |
| 1049 | A | 1050 | A |
| 1051 | B | 1052 | A |
| 1053 | B | 1054 | B |
| 1055 | B | 1056 | A |
| 1057 | B | 1058 | A |
| 1059 | B | 1060 | A |
| 1061 | B | 1062 | A |
| 1063 | B | 1064 | A |
| 1065 | A | 1066 | B |
| 1067 | B | 1068 | A |
| 1069 | B | 1072 | A |
| 1074 | A | 1080 | A |
| 1081 | A | 1082 | A |
| 1084 | A | 1085 | A |
| 1087 | A | 1088 | A |
| 1089 | A | 1090 | B |
| 1091 | A | 1092 | A |
| 1093 | A | 1094 | A |
| 1095 | A | 1096 | A |
| 1097 | A | 1098 | A |
| 1099 | A | 1100 | A |
| 1101 | A | 1102 | A |
| 1103 | A | 1104 | B |
| 1105 | B | 1106 | A |
| 1107 | A | 1108 | A |
| 1109 | A | 1110 | A |
| 1111 | A | 1112 | A |
| 1113 | A | 1114 | A |
| 1115 | A | 1116 | A |
| 1117 | A | 1118 | A |
| 1119 | A | 1120 | A |
| 1121 | A | 1122 | A |
| 1123 | A | 1124 | A |
| 1125 | A | 1126 | A |
| 1127 | A | 1128 | B |
| 1133 | B | 1134 | B |
| 1135 | A | 1136 | A |
| 1137 | A | 1138 | A |
| 1139 | A | 1140 | A |
| 1141 | A | 1142 | A |
| 1143 | B | 1144 | B |
| 1145 | A | 1146 | A |
| 1147 | A | 1148 | A |
| 1149 | A | 1150 | A |
| 1151 | A | 1152 | A |
| 1153 | A | 1154 | A |
| 1155 | A | 1156 | A |
| 1157 | A | 1158 | A |
| 1159 | A | 1160 | A |
| 1161 | A | 1162 | A |
| 1163 | A | 1164 | A |
| 1165 | A | 1166 | A |
| 1167 | A | 1168 | A |
| 1169 | A | 1170 | B |
| 1177 | A | 1178 | A |

TABLE 14-continued

Summary of Activities for hMPV WT1501

| Compound | HMPV $EC_{50}$ | Compound | HMPV $EC_{50}$ |
|---|---|---|---|
| 1179 | A | 1180 | A |
| 1181 | A | 1182 | A |
| 1183 | A | 1184 | A |
| 1185 | A | 1186 | A |
| 1187 | A | 1188 | A |
| 1189 | A | 1190 | A |
| 1191 | A | 1192 | B |
| 1193 | B | 1194 | B |
| 1195 | A | 1196 | B |
| 1218 | B | 1219 | B |
| 1220 | B | 1221 | A |
| 1222 | B | 1223 | A |
| 1224 | B | 1225 | A |
| 1226 | B | 1227 | A |
| 1228 | B | 1229 | B |
| 1230 | B | 1231 | A |
| 1232 | B | 1233 | B |
| 1234 | B | 1235 | A |
| 1248 | A | 1249 | B |
| 1250 | B | 1251 | B |
| 1269 | B | | |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (XXV):

(XXV)

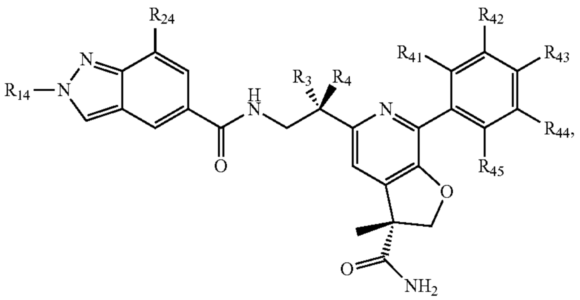

or a pharmaceutically acceptable salt thereof, wherein $R_{14}$ is cyclopropyl or 1-fluorocyclopropyl; $R_{24}$ is hydrogen, Cl, F, or optionally substituted methoxyl; $R_3$ is hydroxy; $R_4$ is cyclopropyl or 1-fluorocyclopropyl; $R_{41}$, $R_{42}$, $R_{43}$, $R_{44}$, and $R_{45}$ are each independently selected from hydrogen, halogen, optionally substituted methyl, optionally substituted methoxy and —CN; alternatively, $R_{42}$ and $R_{43}$, or $R_{41}$ and $R_{42}$ are taken together with the carbon atoms to which they are attached to form a fused 4- to 7-membered carbocyclic ring or heterocyclic ring.

2. The compound of claim 1, wherein $R_{24}$ is methoxy.

3. The compound of claim 2, wherein $R_{14}$ is cyclopropyl.

4. The compound of claim 1, represented by Formula (XXIII-9) or Formula (XXIII-10), (XXIII-9)

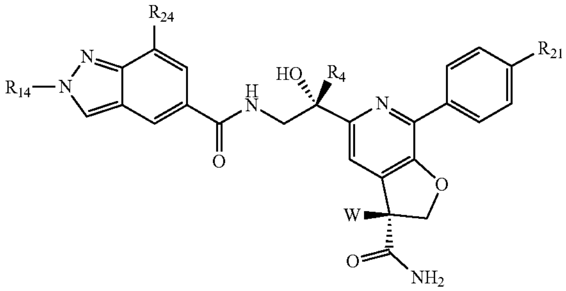

(XXIII-10)

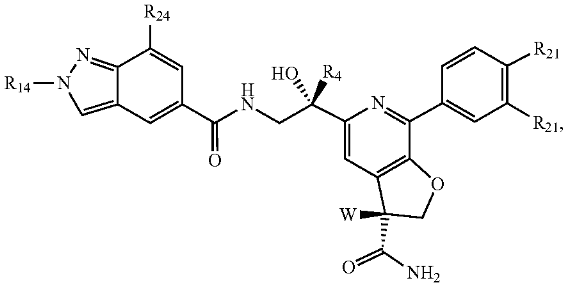

or a pharmaceutically acceptable salt thereof, wherein:

each $R_{21}$ is independently —F, —Cl, —CN, —$CF_3$, —$CH_2F$ or —$CHF_2$;

W is methyl; and $R_4$, $R_{14}$, and $R_{24}$ are as defined in claim 1.

5. A pharmaceutical composition comprising a compound according to claim 1, or a pharmaceutically acceptable salt thereof, and a pharmaceutically acceptable carrier, diluent or excipient.

6. A method of treating or preventing a respiratory syncytial virus (RSV) infection in a subject in need thereof, comprising administering to the subject a therapeutically effective amount of a compound of claim 1 or a pharmaceutically acceptable salt thereof.

7. The method of claim 6, further comprising the step of administering to the subject an additional anti-RSV agent.

8. The method of claim 6, further comprising administering to the subject a steroid anti-inflammatory compound.

9. A method of treating an RSV infection and influenza in a subject in need thereof, comprising administering to the subject a therapeutically effective amount of a compound of claim 1, or a pharmaceutically acceptable salt thereof, and a therapeutically effective amount of an anti-influenza agent.

10. The method of claim 7, wherein the compound and the additional anti-RSV agent are co-formulated.

11. The method of claim 7, wherein the compound and the additional anti-RSV agent are co-administered.

12. A method of treating or preventing a human metapneumovirus (HMPV) infection in a subject in need thereof, comprising administering to the subject a therapeutically effective amount of a compound of claim 1.

13. The method of claim 12, further comprising the step of administering to the subject an additional anti-HMPV agent.

14. The method of claim 13, wherein the compound and the additional anti-HMPV agent are co-formulated.

15. The method of claim 13, wherein the compound and the additional anti-HMPV agent are co-administered.

16. The compound of claim 1, wherein $R_{24}$ is —F, —Cl, or —$OCH_3$; and
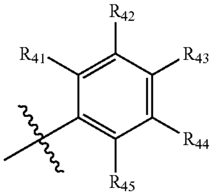
is selected from the groups below:
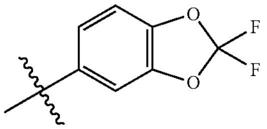
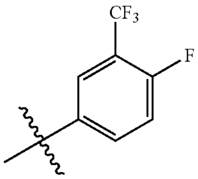
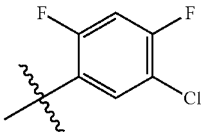
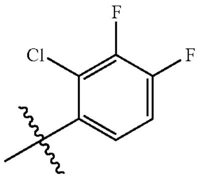
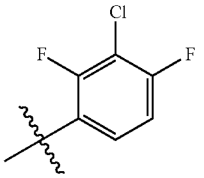
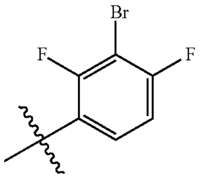
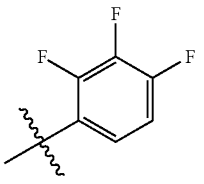
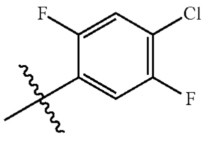
-continued
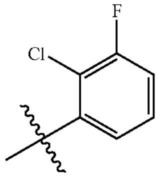
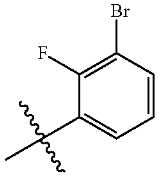
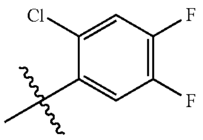
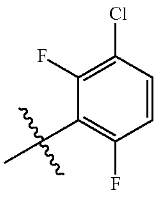
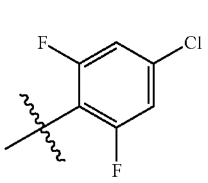
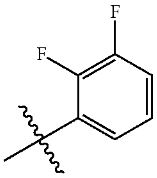
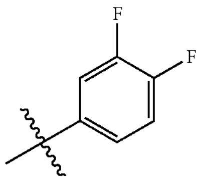
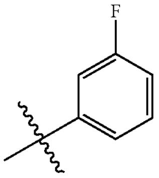
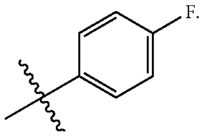
17. A compound selected from the compounds set forth below, or a pharmaceutically acceptable salt thereof:
| | Structure |
|---|---|
| 302 | 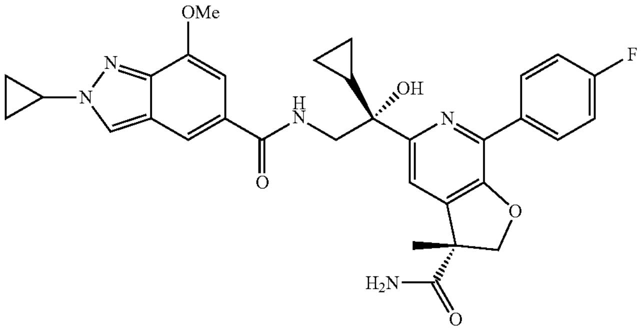 [SMILES: COc1cc(C(=O)NC[C@](O)(c2cc3c(c(-c4ccc(F)cc4)n2)OC[C@]3(C)C(N)=O)C2CC2)cc2cn(C3CC3)nc12] |

-continued
| Structure |
|---|
| 533 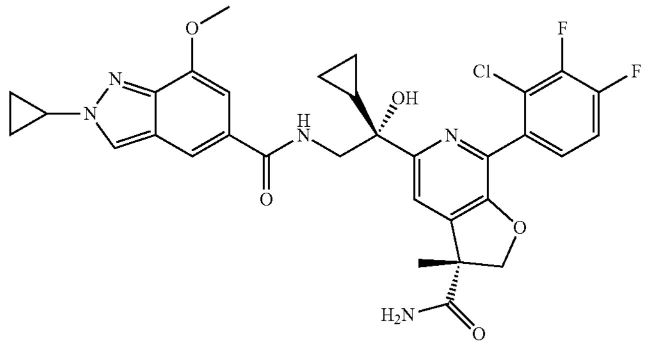 [SMILES: COc1cc(C(=O)NC[C@](O)(c2cc3c(c(-c4ccc(F)c(F)c4Cl)n2)OC[C@]3(C)C(N)=O)C2CC2)cc2cn(C3CC3)nc12] |
| 534 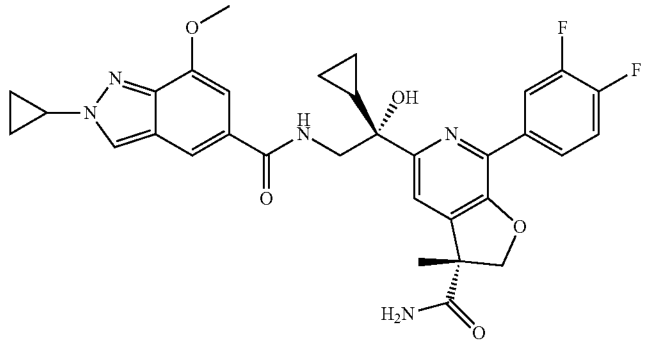 [SMILES: COc1cc(C(=O)NC[C@](O)(c2cc3c(c(-c4ccc(F)c(F)c4)n2)OC[C@]3(C)C(N)=O)C2CC2)cc2cn(C3CC3)nc12] |
| 535 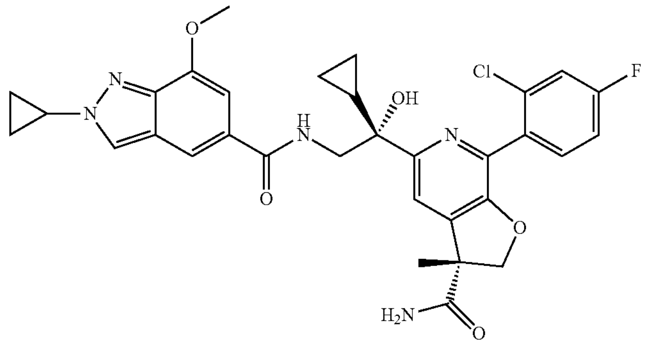 [SMILES: COc1cc(C(=O)NC[C@](O)(c2cc3c(c(-c4ccc(F)cc4Cl)n2)OC[C@]3(C)C(N)=O)C2CC2)cc2cn(C3CC3)nc12] |
| 536 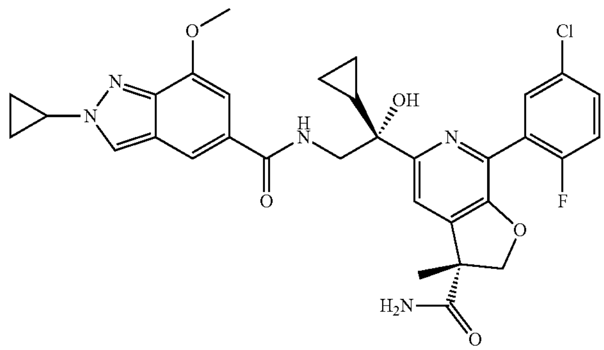 [SMILES: COc1cc(C(=O)NC[C@](O)(c2cc3c(c(-c4cc(Cl)ccc4F)n2)OC[C@]3(C)C(N)=O)C2CC2)cc2cn(C3CC3)nc12] |

-continued
| Structure |
| --- |
| 537 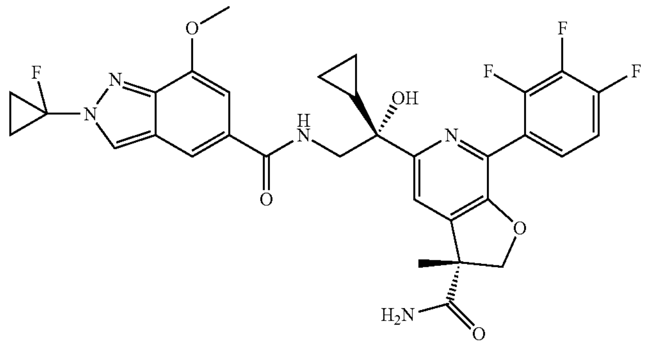 [SMILES: COc1cc(C(=O)NC[C@](O)(c2cc3c(c(-c4ccc(F)c(F)c4F)n2)OC[C@]3(C)C(N)=O)C2CC2)cc2cn(C3(F)CC3)nc12] |
| 545 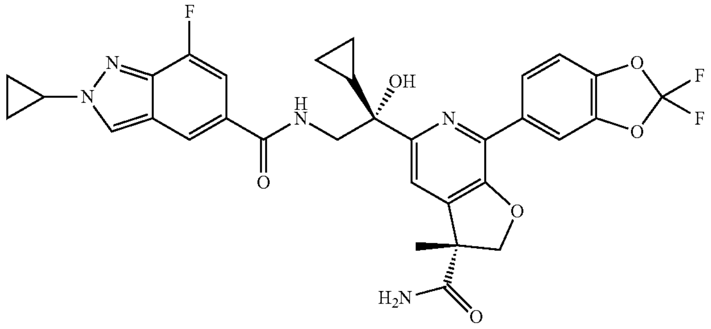 |
| 547 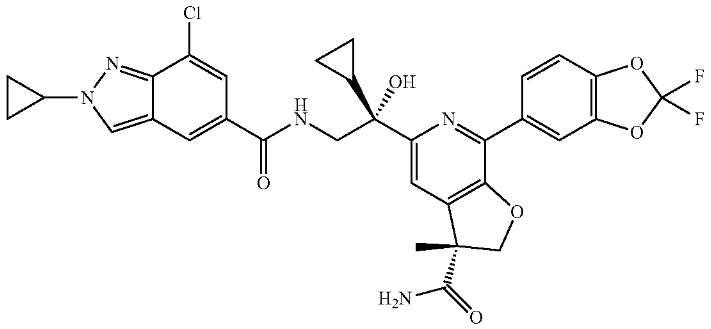 [SMILES: C[C@]1(C(N)=O)COc2c1cc([C@@](O)(CNC(=O)c1cc(F)c3nn(C4CC4)cc3c1)C1CC1)nc2-c1ccc2c(c1)OC(F)(F)O2] |
| 554 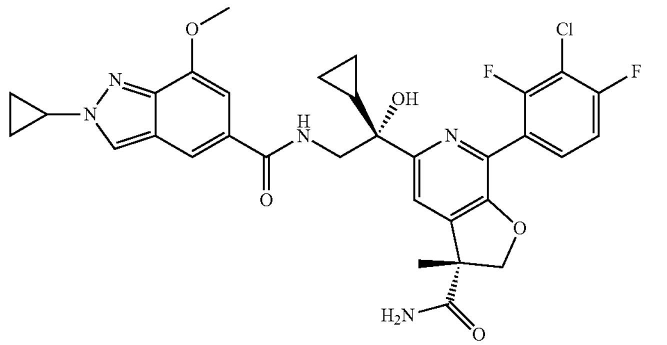 [SMILES: COc1cc(C(=O)NC[C@](O)(c2cc3c(c(-c4ccc(F)c(Cl)c4F)n2)OC[C@]3(C)C(N)=O)C2CC2)cc2cn(C3CC3)nc12] |

-continued
| Structure |
|---|
| 555 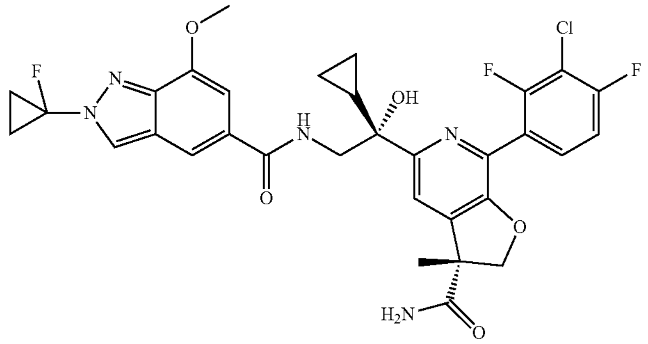 [SMILES: COc1cc(C(=O)NC[C@](O)(c2cc3c(c(-c4ccc(F)c(Cl)c4F)n2)OC[C@]3(C)C(N)=O)C2CC2)cc2cn(C3(F)CC3)nc12] |
| 559 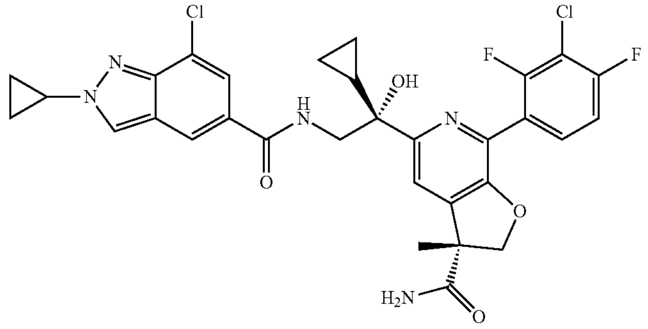 [SMILES: C[C@]1(C(N)=O)COc2c1cc([C@@](O)(CNC(=O)c1cc(Cl)c3nn(C4CC4)cc3c1)C1CC1)nc2-c1ccc(F)c(Cl)c1F] |
| 562 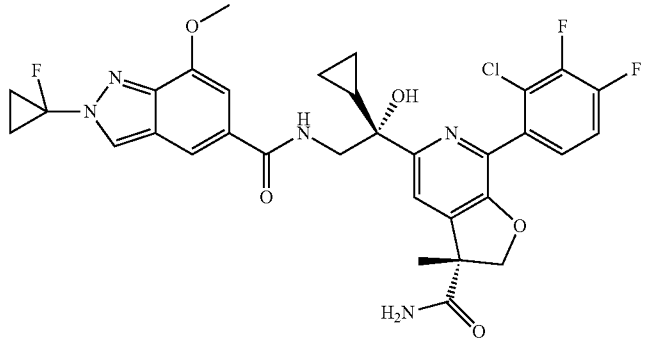 [SMILES: COc1cc(C(=O)NC[C@](O)(c2cc3c(c(-c4ccc(F)c(F)c4Cl)n2)OC[C@]3(C)C(N)=O)C2CC2)cc2cn(C3(F)CC3)nc12] |
| 564 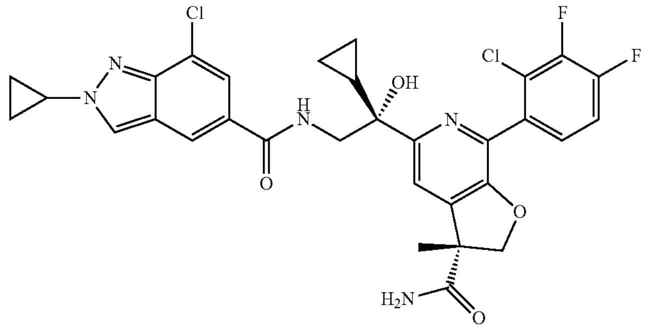 [SMILES: C[C@]1(C(N)=O)COc2c1cc([C@@](O)(CNC(=O)c1cc(Cl)c3nn(C4CC4)cc3c1)C1CC1)nc2-c1ccc(F)c(F)c1Cl] |

-continued
| | Structure |
|---|---|
| 575 | 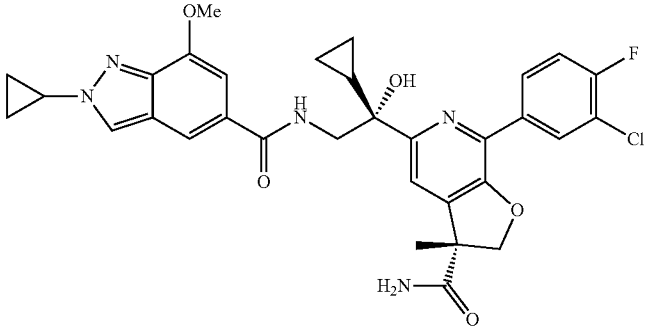 [SMILES: COc1cc(C(=O)NC[C@](O)(c2cc3c(c(-c4ccc(F)c(Cl)c4)n2)OC[C@]3(C)C(N)=O)C2CC2)cc2cn(C3CC3)nc12] |
| 651 | 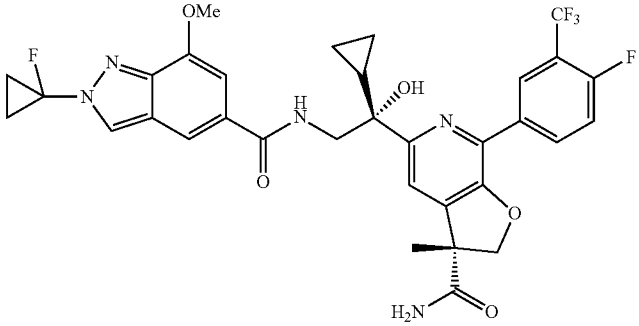 [SMILES: COc1cc(C(=O)NC[C@](O)(c2cc3c(c(-c4ccc(F)c(C(F)(F)F)c4)n2)OC[C@]3(C)C(N)=O)C2CC2)cc2cn(C3(F)CC3)nc12] |
| 652 | 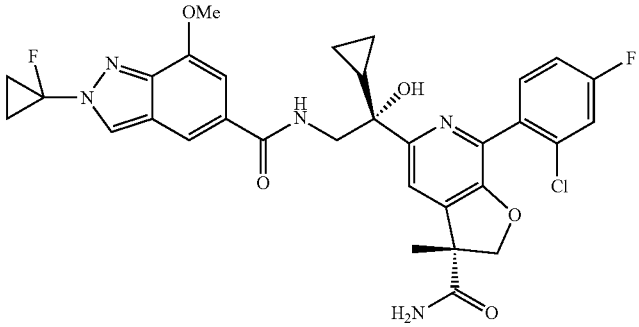 [SMILES: COc1cc(C(=O)NC[C@](O)(c2cc3c(c(-c4ccc(F)cc4Cl)n2)OC[C@]3(C)C(N)=O)C2CC2)cc2cn(C3(F)CC3)nc12] |
| 657 | 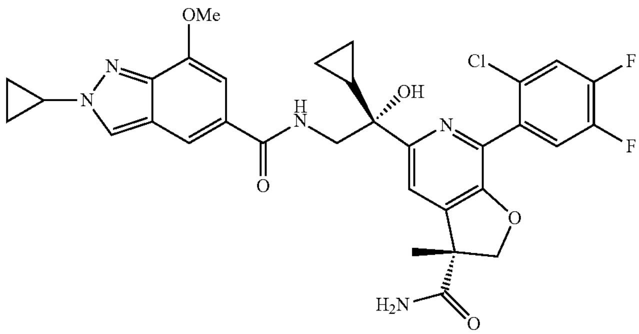 [SMILES: COc1cc(C(=O)NC[C@](O)(c2cc3c(c(-c4cc(F)c(F)cc4Cl)n2)OC[C@]3(C)C(N)=O)C2CC2)cc2cn(C3CC3)nc12] |

-continued
| | Structure |
|---|---|
| 659 | 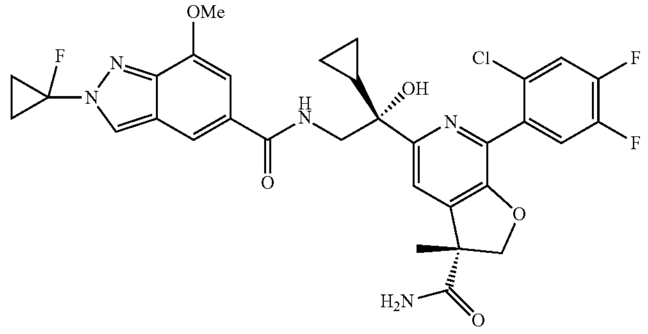 [SMILES: COc1cc(C(=O)NC[C@](O)(c2cc3c(c(-c4cc(F)c(F)cc4Cl)n2)OC[C@]3(C)C(N)=O)C2CC2)cc2cn(C3(F)CC3)nc12] |
| 661 | 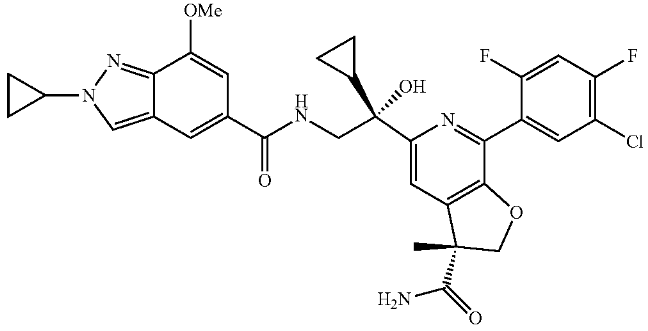 [SMILES: COc1cc(C(=O)NC[C@](O)(c2cc3c(c(-c4cc(Cl)c(F)cc4F)n2)OC[C@]3(C)C(N)=O)C2CC2)cc2cn(C3CC3)nc12] |
| 663 | 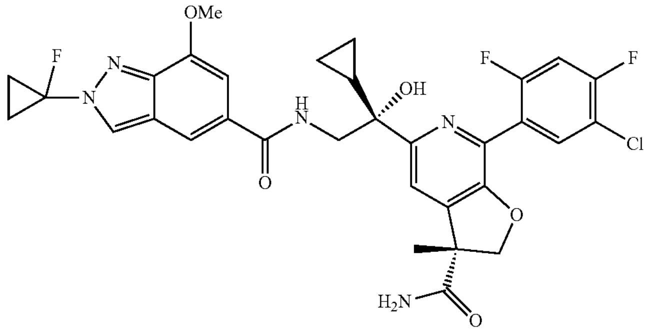 [SMILES: COc1cc(C(=O)NC[C@](O)(c2cc3c(c(-c4cc(Cl)c(F)cc4F)n2)OC[C@]3(C)C(N)=O)C2CC2)cc2cn(C3(F)CC3)nc12] |
| 668 | 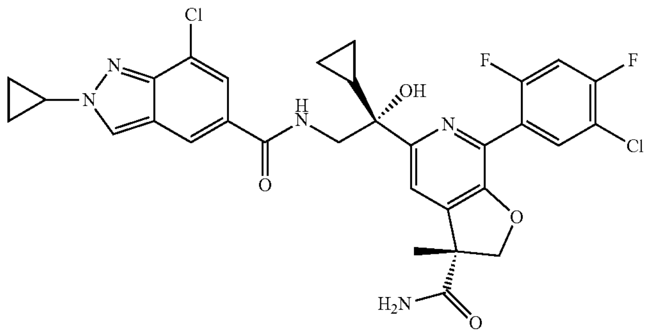 [SMILES: C[C@]1(C(N)=O)COc2c1cc([C@@](O)(CNC(=O)c1cc(Cl)c3nn(C4CC4)cc3c1)C1CC1)nc2-c1cc(Cl)c(F)cc1F] |

-continued
| | Structure |
| --- | --- |
| 676 | 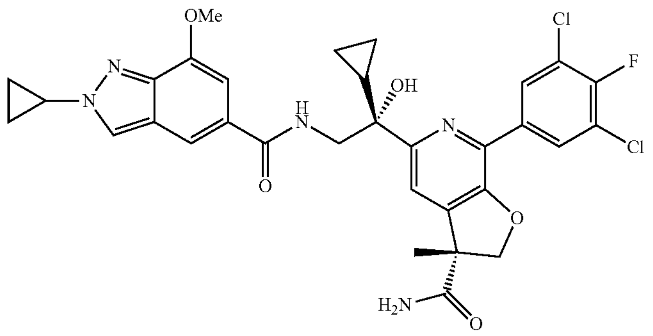 [SMILES: COc1cc(C(=O)NC[C@](O)(c2cc3c(c(-c4cc(Cl)c(F)c(Cl)c4)n2)OC[C@]3(C)C(N)=O)C2CC2)cc2cn(C3CC3)nc12] |
| 678 | 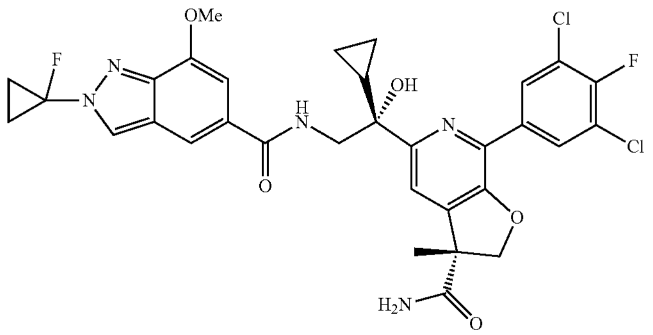 [SMILES: COc1cc(C(=O)NC[C@](O)(c2cc3c(c(-c4cc(Cl)c(F)c(Cl)c4)n2)OC[C@]3(C)C(N)=O)C2CC2)cc2cn(C3(F)CC3)nc12] |
| 680 | 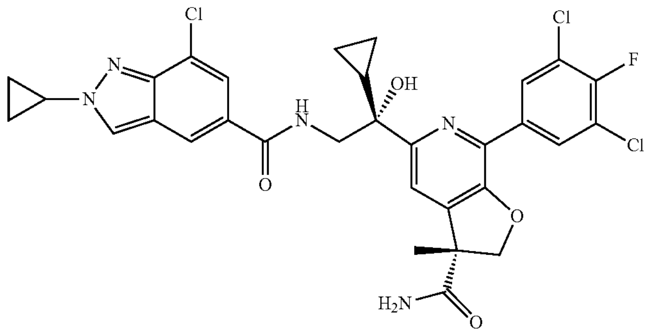 [SMILES: C[C@]1(C(N)=O)COc2c1cc([C@@](O)(CNC(=O)c1cc(Cl)c3nn(C4CC4)cc3c1)C1CC1)nc2-c1cc(Cl)c(F)c(Cl)c1] |
| 683 | 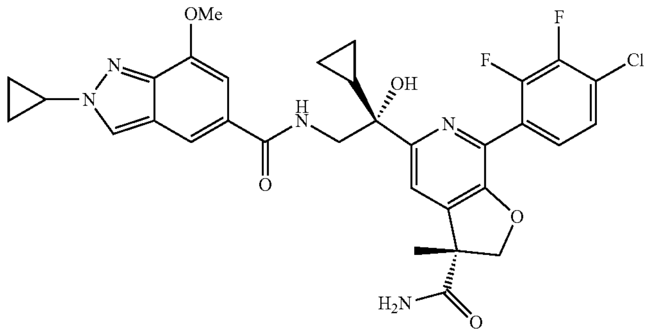 |

-continued
| Structure | |
|---|---|
| 685 | 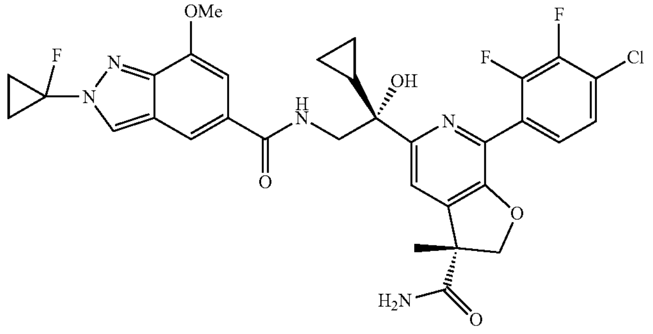 [SMILES: COc1cc(C(=O)NC[C@](O)(c2cc3c(c(-c4ccc(Cl)c(F)c4F)n2)OC[C@]3(C)C(N)=O)C2CC2)cc2cn(C3(F)CC3)nc12] |
| 686 | 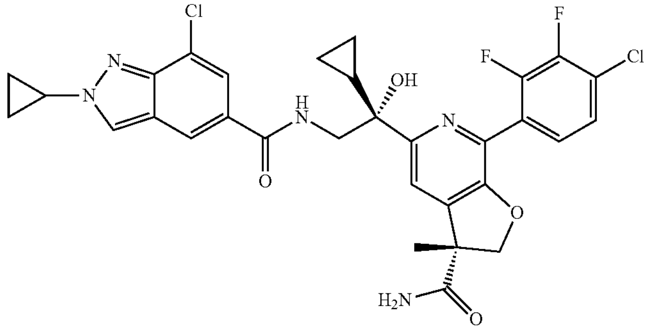 [SMILES: C[C@]1(C(N)=O)COc2c1cc([C@@](O)(CNC(=O)c1cc(Cl)c3nn(C4CC4)cc3c1)C1CC1)nc2-c1ccc(Cl)c(F)c1F] |
| 690 | 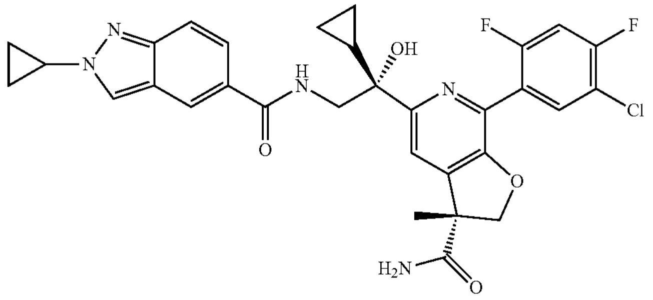 [SMILES: C[C@]1(C(N)=O)COc2c1cc([C@@](O)(CNC(=O)c1ccc3nn(C4CC4)cc3c1)C1CC1)nc2-c1cc(Cl)c(F)cc1F] |
| 705 | 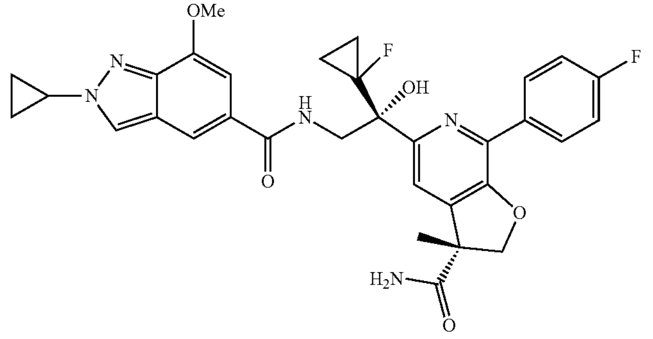 [SMILES: COc1cc(C(=O)NC[C@](O)(c2cc3c(c(-c4ccc(F)cc4)n2)OC[C@]3(C)C(N)=O)C2(F)CC2)cc2cn(C3CC3)nc12] |

-continued
| | Structure |
|---|---|
| 712 | 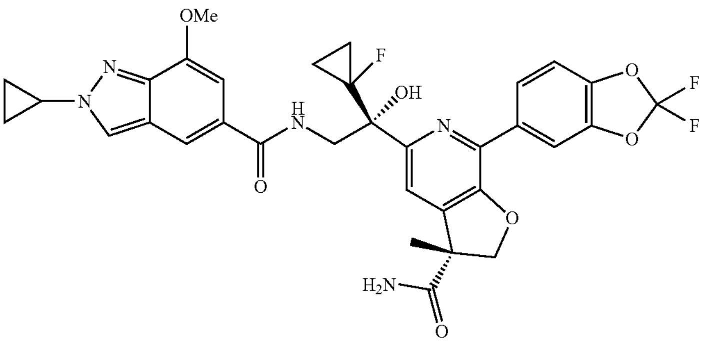 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2cn(C3CC3)nc12] |
| 714 | 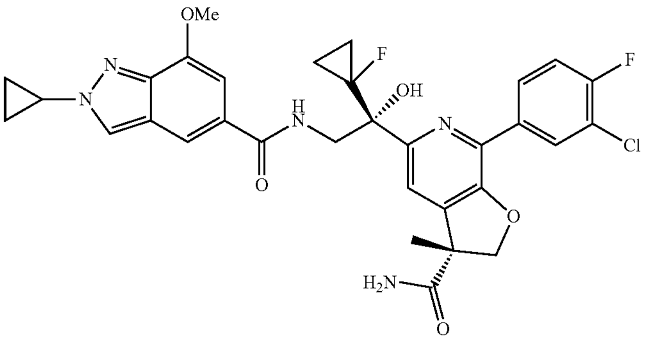 [SMILES: COc1cc(C(=O)NC[C@](O)(c2cc3c(c(-c4ccc(F)c(Cl)c4)n2)OC[C@]3(C)C(N)=O)C2(F)CC2)cc2cn(C3CC3)nc12] |
| 725 | 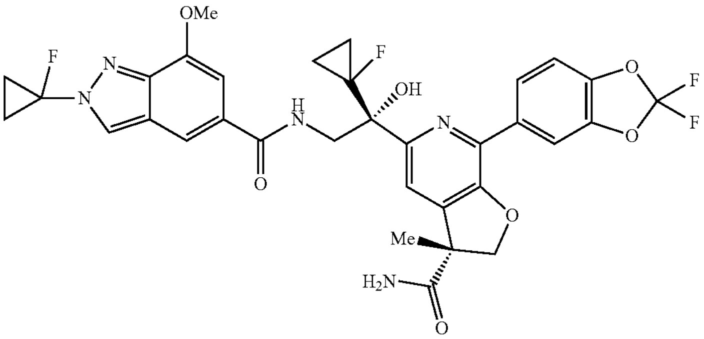 [SMILES: COc1cc(C(=O)NC[C@](O)(c2cc3c(c(-c4ccc5c(c4)OC(F)(F)O5)n2)OC[C@]3(C)C(N)=O)C2(F)CC2)cc2cn(C3(F)CC3)nc12] |
| 729 | 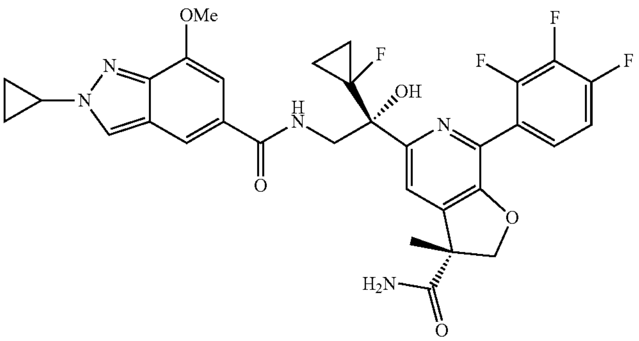 [SMILES: COc1cc(C(=O)NC[C@](O)(c2cc3c(c(-c4ccc(F)c(F)c4F)n2)OC[C@]3(C)C(N)=O)C2(F)CC2)cc2cn(C3CC3)nc12] |

-continued
| | Structure |
|---|---|
| 732 | 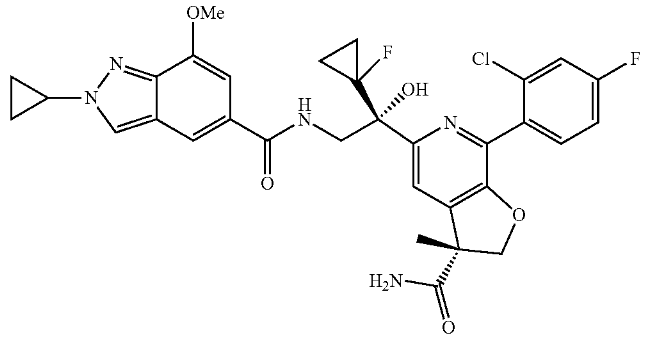 [SMILES: COc1cc(C(=O)NC[C@](O)(c2cc3c(c(-c4ccc(F)cc4Cl)n2)OC[C@]3(C)C(N)=O)C2(F)CC2)cc2cn(C3CC3)nc12] |
| 735 | 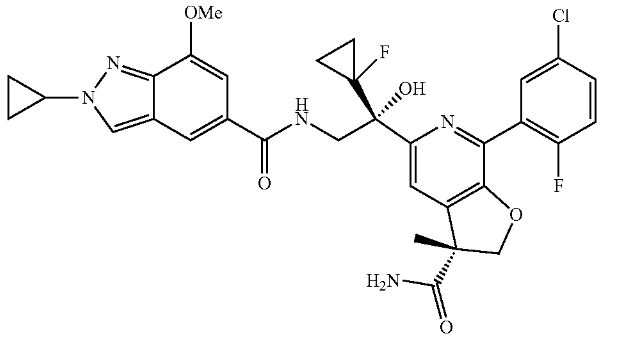 [SMILES: COc1cc(C(=O)NC[C@](O)(c2cc3c(c(-c4cc(Cl)ccc4F)n2)OC[C@]3(C)C(N)=O)C2(F)CC2)cc2cn(C3CC3)nc12] |
| 743 | 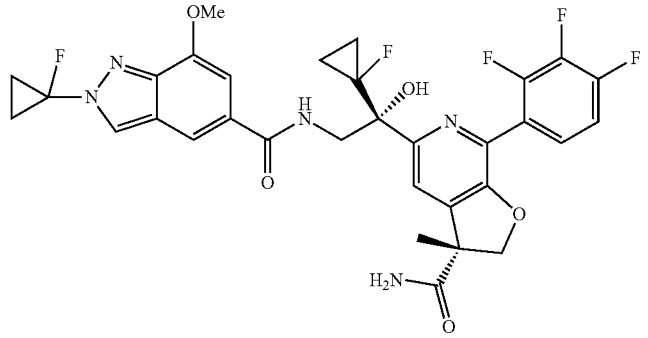 [SMILES: COc1cc(C(=O)NC[C@](O)(c2cc3c(c(-c4ccc(F)c(F)c4F)n2)OC[C@]3(C)C(N)=O)C2(F)CC2)cc2cn(C3(F)CC3)nc12] |
| 745 | 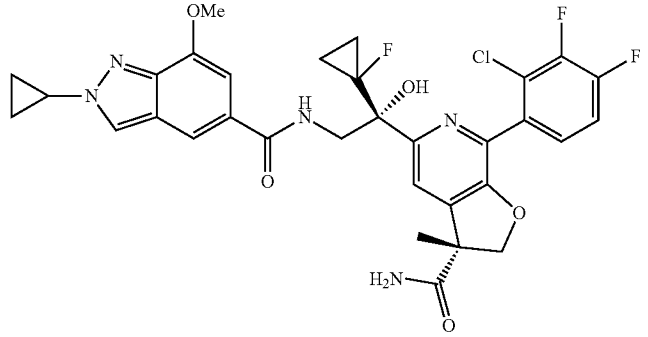 [SMILES: COc1cc(C(=O)NC[C@](O)(c2cc3c(c(-c4ccc(F)c(F)c4Cl)n2)OC[C@]3(C)C(N)=O)C2(F)CC2)cc2cn(C3CC3)nc12] |

-continued
| | Structure |
|---|---|
| 749 | 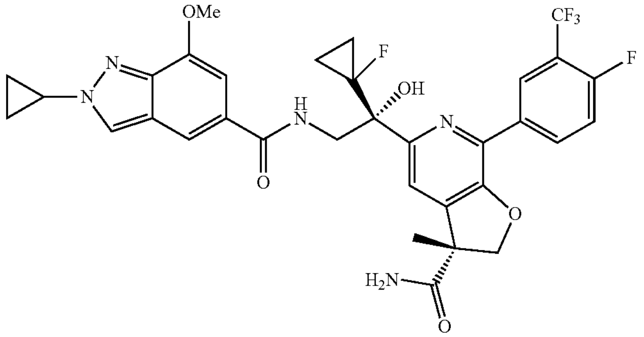 [SMILES: COc1cc(C(=O)NC[C@](O)(c2cc3c(c(-c4ccc(F)c(C(F)(F)F)c4)n2)OC[C@]3(C)C(N)=O)C2(F)CC2)cc2cn(C3CC3)nc12] |
| 752 | 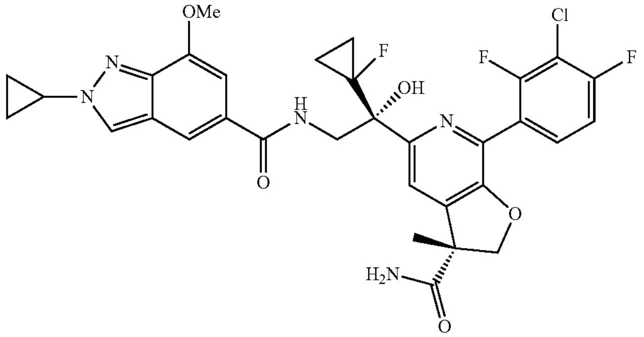 [SMILES: COc1cc(C(=O)NC[C@](O)(c2cc3c(c(-c4ccc(F)c(Cl)c4F)n2)OC[C@]3(C)C(N)=O)C2(F)CC2)cc2cn(C3CC3)nc12] |
| 755 | 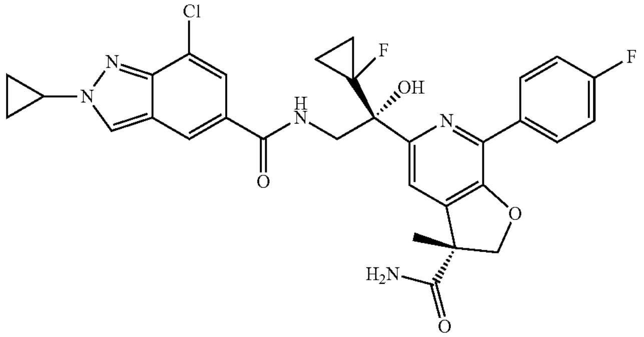 [SMILES: C[C@]1(C(N)=O)COc2c1cc([C@@](O)(CNC(=O)c1cc(Cl)c3nn(C4CC4)cc3c1)C1(F)CC1)nc2-c1ccc(F)cc1] |
| 756 | 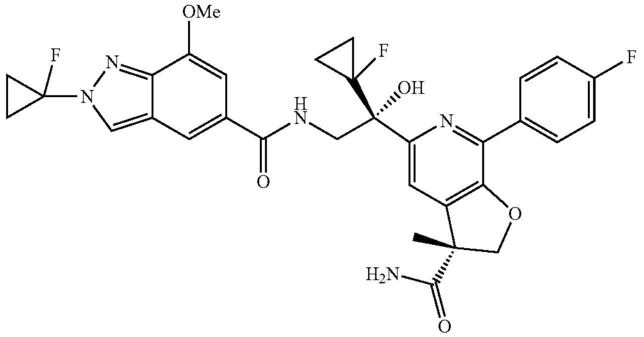 [SMILES: COc1cc(C(=O)NC[C@](O)(c2cc3c(c(-c4ccc(F)cc4)n2)OC[C@]3(C)C(N)=O)C2(F)CC2)cc2cn(C3(F)CC3)nc12] |

-continued
| Structure |
|---|
| 757 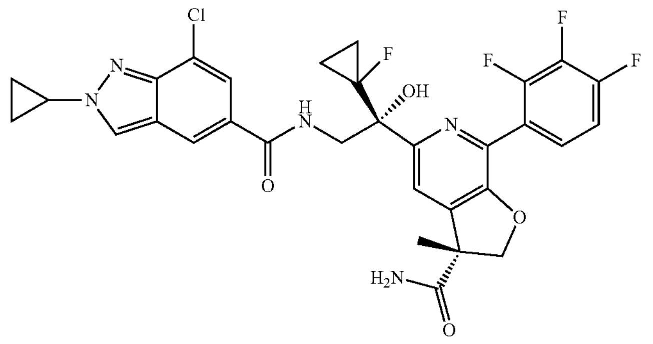 [SMILES: C[C@]1(C(N)=O)COc2c1cc([C@@](O)(CNC(=O)c1cc(Cl)c3nn(C4CC4)cc3c1)C1(F)CC1)nc2-c1ccc(F)c(F)c1F] |
| 758 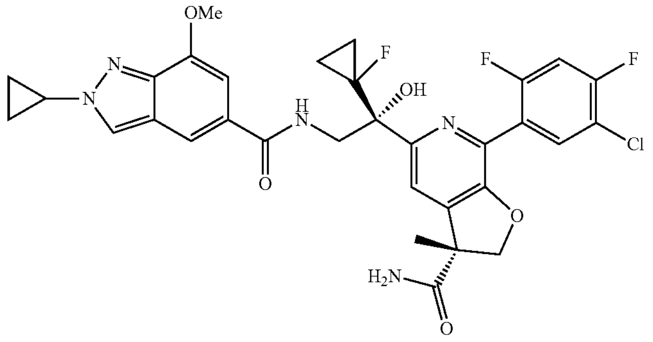 [SMILES: COc1cc(C(=O)NC[C@](O)(c2cc3c(c(-c4cc(Cl)c(F)cc4F)n2)OC[C@]3(C)C(N)=O)C2(F)CC2)cc2cn(C3CC3)nc12] |
| 759 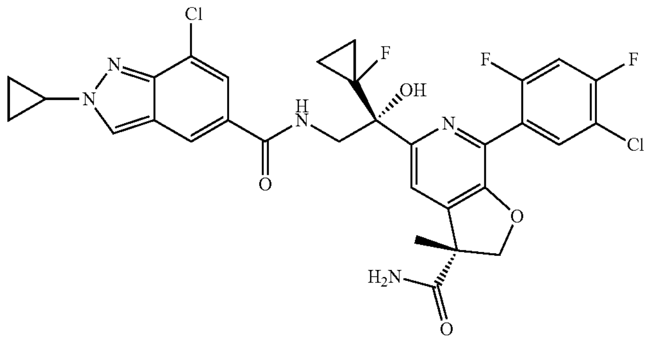 [SMILES: C[C@]1(C(N)=O)COc2c1cc([C@@](O)(CNC(=O)c1cc(Cl)c3nn(C4CC4)cc3c1)C1(F)CC1)nc2-c1cc(Cl)c(F)cc1F] |
| 787 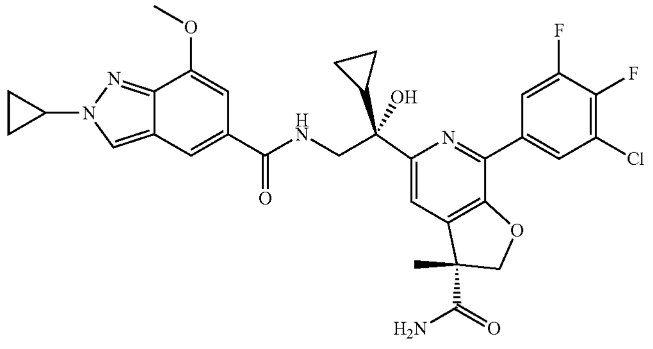 [SMILES: COc1cc(C(=O)NC[C@](O)(c2cc3c(c(-c4cc(F)c(F)c(Cl)c4)n2)OC[C@]3(C)C(N)=O)C2CC2)cc2cn(C3CC3)nc12] |

-continued
| Structure |
|---|
| 790 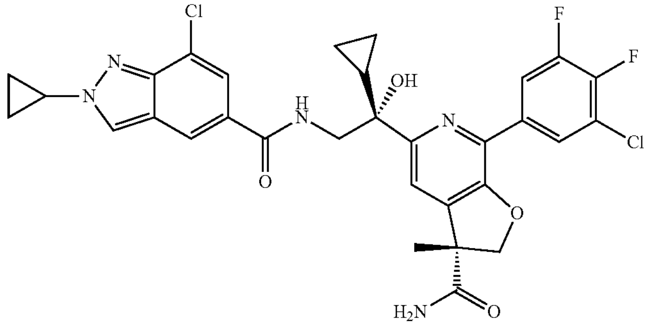 [SMILES: C[C@]1(C(N)=O)COc2c1cc([C@@](O)(CNC(=O)c1cc(Cl)c3nn(C4CC4)cc3c1)C1CC1)nc2-c1cc(F)c(F)c(Cl)c1] |
| 791 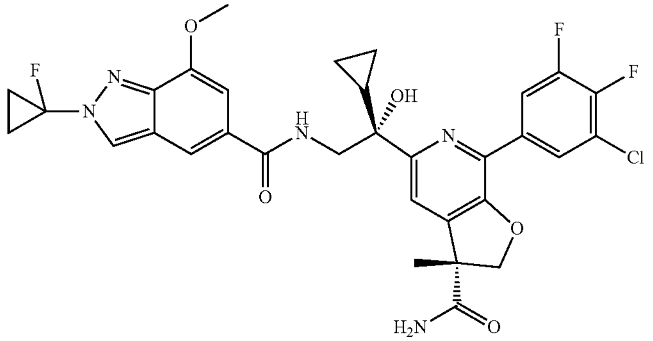 [SMILES: COc1cc(C(=O)NC[C@](O)(c2cc3c(c(-c4cc(F)c(F)c(Cl)c4)n2)OC[C@]3(C)C(N)=O)C2CC2)cc2cn(C3(F)CC3)nc12] |
| 793 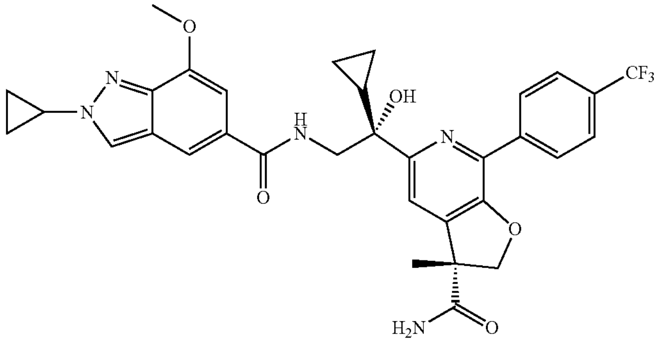 [SMILES: COc1cc(C(=O)NC[C@](O)(c2cc3c(c(-c4ccc(C(F)(F)F)cc4)n2)OC[C@]3(C)C(N)=O)C2CC2)cc2cn(C3CC3)nc12] |
| 794 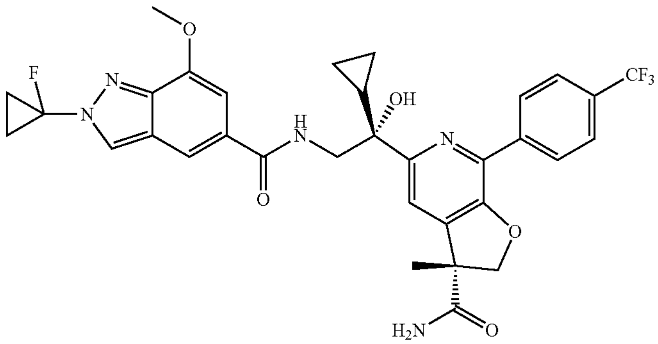 [SMILES: COc1cc(C(=O)NC[C@](O)(c2cc3c(c(-c4ccc(C(F)(F)F)cc4)n2)OC[C@]3(C)C(N)=O)C2CC2)cc2cn(C3(F)CC3)nc12] |

-continued
| | Structure |
|---|---|
| 795 | 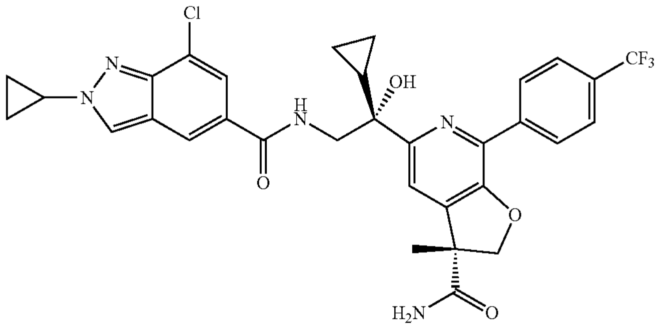 [SMILES: C[C@]1(C(N)=O)COc2c1cc([C@@](O)(CNC(=O)c1cc(Cl)c3nn(C4CC4)cc3c1)C1CC1)nc2-c1ccc(C(F)(F)F)cc1] |
| 799 | 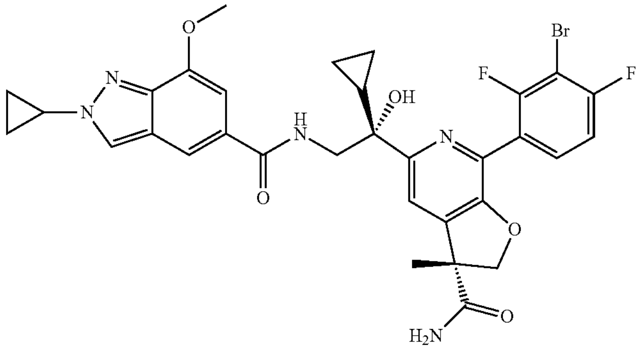 [SMILES: COc1cc(C(=O)NC[C@](O)(c2cc3c(c(-c4ccc(F)c(Br)c4F)n2)OC[C@]3(C)C(N)=O)C2CC2)cc2cn(C3CC3)nc12] |
| 800 | 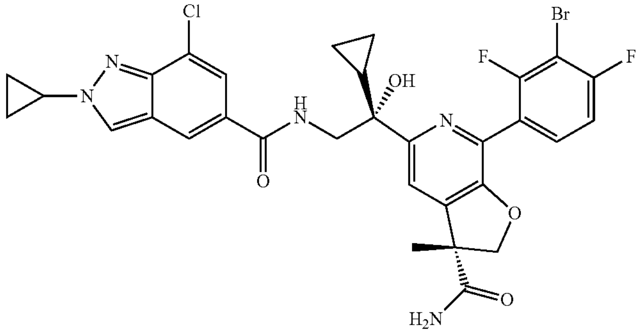 [SMILES: C[C@]1(C(N)=O)COc2c1cc([C@@](O)(CNC(=O)c1cc(Cl)c3nn(C4CC4)cc3c1)C1CC1)nc2-c1ccc(F)c(Br)c1F] |
| 802 | 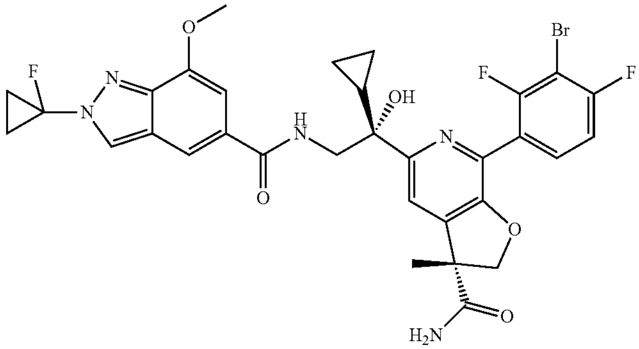 [SMILES: COc1cc(C(=O)NC[C@](O)(c2cc3c(c(-c4ccc(F)c(Br)c4F)n2)OC[C@]3(C)C(N)=O)C2CC2)cc2cn(C3(F)CC3)nc12] |

-continued
| Structure | |
|---|---|
| 815 | 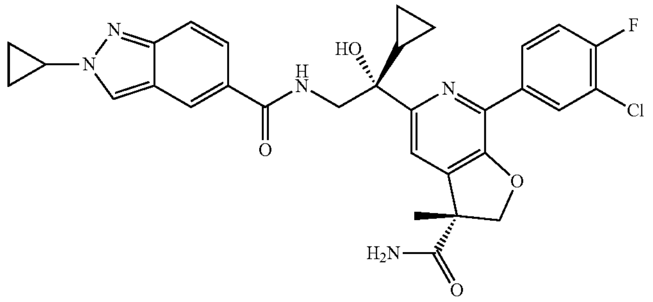 [SMILES: C[C@]1(C(N)=O)COc2c1cc([C@@](O)(CNC(=O)c1ccc3nn(C4CC4)cc3c1)C1CC1)nc2-c1ccc(F)c(Cl)c1] |
| 816 | 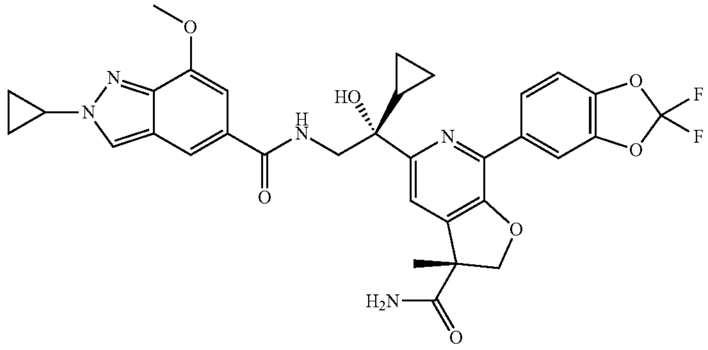 [SMILES: COc1cc(C(=O)NC[C@](O)(c2cc3c(c(-c4ccc5c(c4)OC(F)(F)O5)n2)OC[C@]3(C)C(N)=O)C2CC2)cc2cn(C3CC3)nc12] |
| 831 | 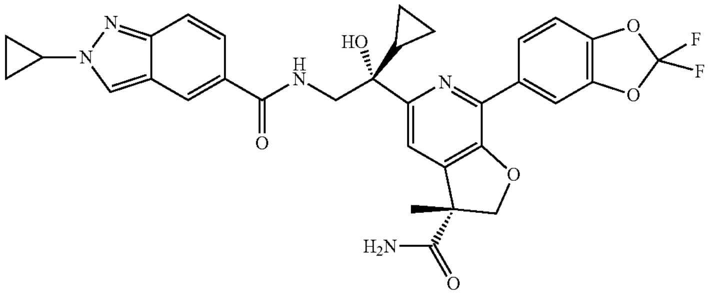 [SMILES: C[C@]1(C(N)=O)COc2c1cc([C@@](O)(CNC(=O)c1ccc3nn(C4CC4)cc3c1)C1CC1)nc2-c1ccc2c(c1)OC(F)(F)O2] |
| 835 | 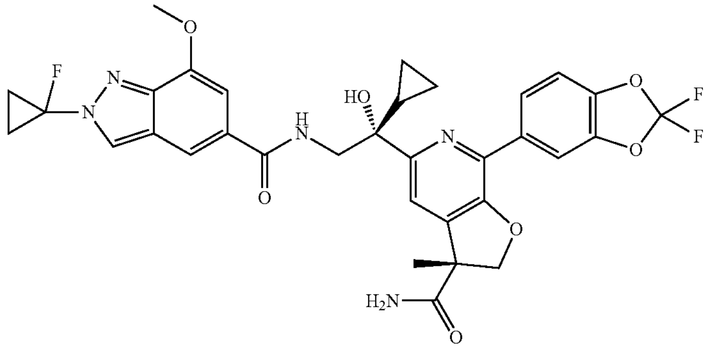 [SMILES: COc1cc(C(=O)NC[C@](O)(c2cc3c(c(-c4ccc5c(c4)OC(F)(F)O5)n2)OC[C@]3(C)C(N)=O)C2CC2)cc2cn(C3(F)CC3)nc12] |

-continued
| Structure |
|---|
| 836 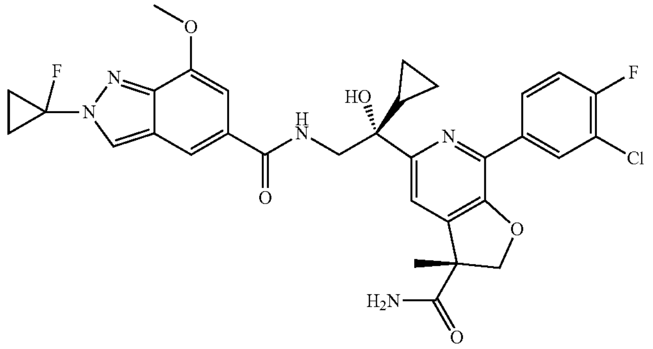 [SMILES: COc1cc(C(=O)NC[C@](O)(c2cc3c(c(-c4ccc(F)c(Cl)c4)n2)OC[C@]3(C)C(N)=O)C2CC2)cc2cn(C3(F)CC3)nc12] |
| 837 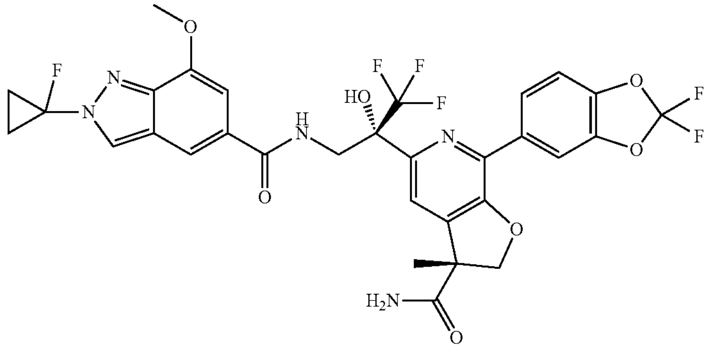 [SMILES: COc1cc(C(=O)NC[C@](O)(c2cc3c(c(-c4ccc5c(c4)OC(F)(F)O5)n2)OC[C@]3(C)C(N)=O)C(F)(F)F)cc2cn(C3(F)CC3)nc12] |
| 838 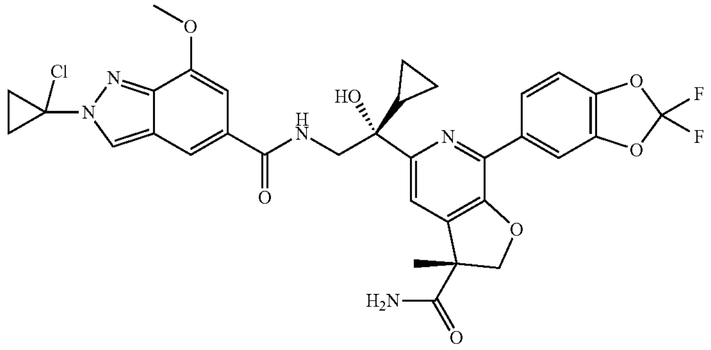 [SMILES: COc1cc(C(=O)NC[C@](O)(c2cc3c(c(-c4ccc5c(c4)OC(F)(F)O5)n2)OC[C@]3(C)C(N)=O)C2CC2)cc2cn(C3(Cl)CC3)nc12] |
| 839 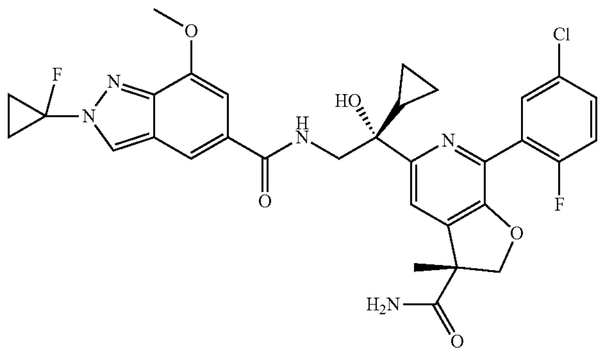 [SMILES: COc1cc(C(=O)NC[C@](O)(c2cc3c(c(-c4cc(Cl)ccc4F)n2)OC[C@]3(C)C(N)=O)C2CC2)cc2cn(C3(F)CC3)nc12] |

-continued
| Structure |
| --- |
| 840 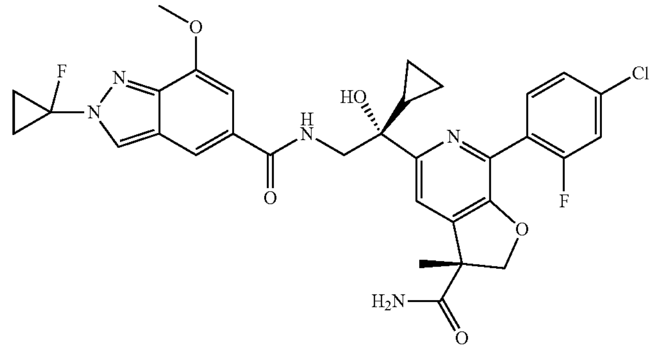 [SMILES: COc1cc(C(=O)NC[C@](O)(c2cc3c(c(-c4ccc(Cl)cc4F)n2)OC[C@]3(C)C(N)=O)C2CC2)cc2cn(C3(F)CC3)nc12] |
| 841 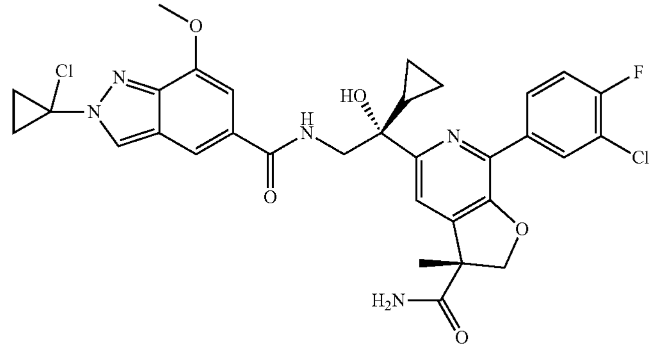 [SMILES: COc1cc(C(=O)NC[C@](O)(c2cc3c(c(-c4ccc(F)c(Cl)c4)n2)OC[C@]3(C)C(N)=O)C2CC2)cc2cn(C3(Cl)CC3)nc12] |
| 842 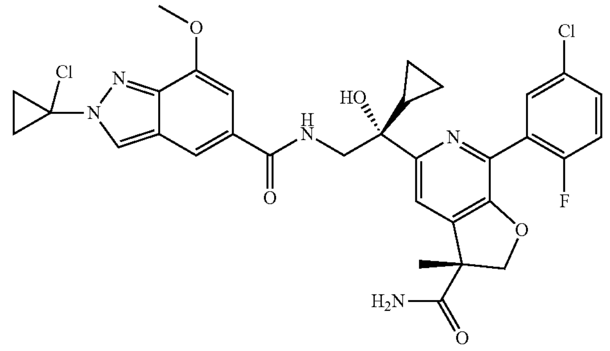 [SMILES: COc1cc(C(=O)NC[C@](O)(c2cc3c(c(-c4cc(Cl)ccc4F)n2)OC[C@]3(C)C(N)=O)C2CC2)cc2cn(C3(Cl)CC3)nc12] |
| 843 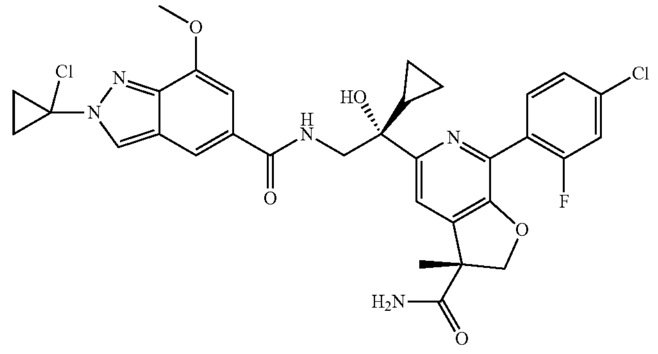 [SMILES: COc1cc(C(=O)NC[C@](O)(c2cc3c(c(-c4ccc(Cl)cc4F)n2)OC[C@]3(C)C(N)=O)C2CC2)cc2cn(C3(Cl)CC3)nc12] |

-continued
| | Structure |
|---|---|
| 844 | 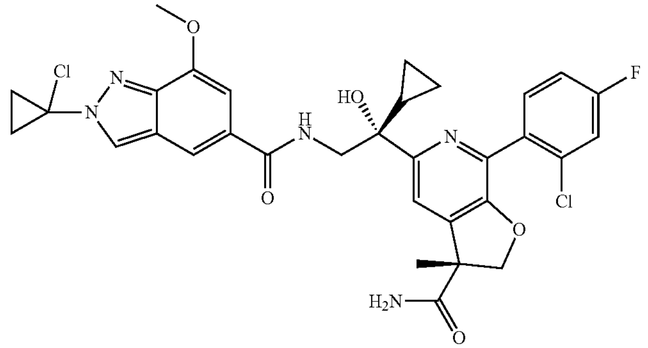 [SMILES: COc1cc(C(=O)NC[C@](O)(c2cc3c(c(-c4ccc(F)cc4Cl)n2)OC[C@]3(C)C(N)=O)C2CC2)cc2cn(C3(Cl)CC3)nc12] |
| 845 | 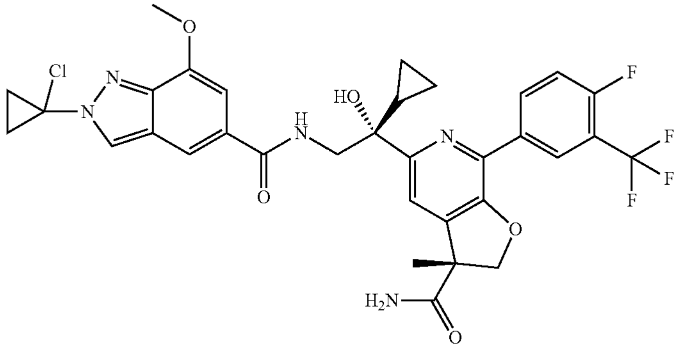 [SMILES: COc1cc(C(=O)NC[C@](O)(c2cc3c(c(-c4ccc(F)c(C(F)(F)F)c4)n2)OC[C@]3(C)C(N)=O)C2CC2)cc2cn(C3(Cl)CC3)nc12] |
| 848 | 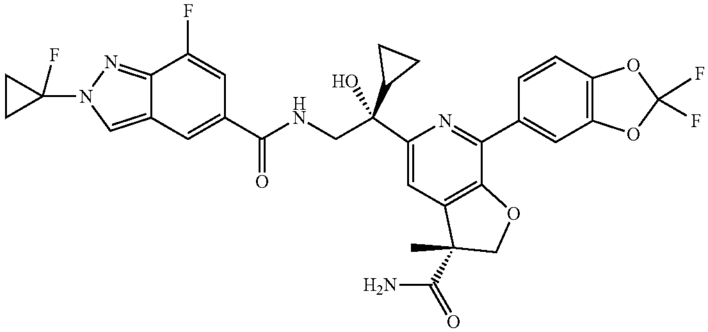 |
| 849 | 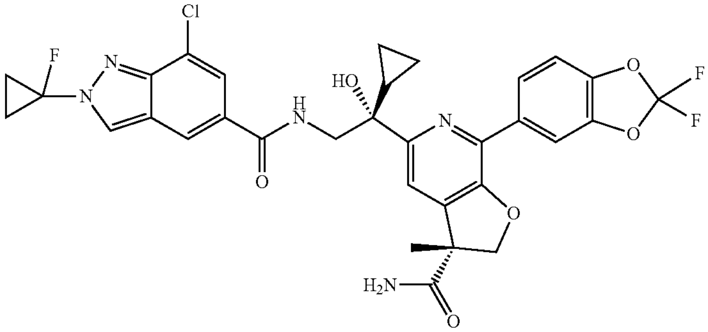 [SMILES: C[C@]1(C(N)=O)COc2c1cc([C@@](O)(CNC(=O)c1cc(F)c3nn(C4(F)CC4)cc3c1)C1CC1)nc2-c1ccc2c(c1)OC(F)(F)O2] |

-continued
| | Structure |
|---|---|
| 871 | 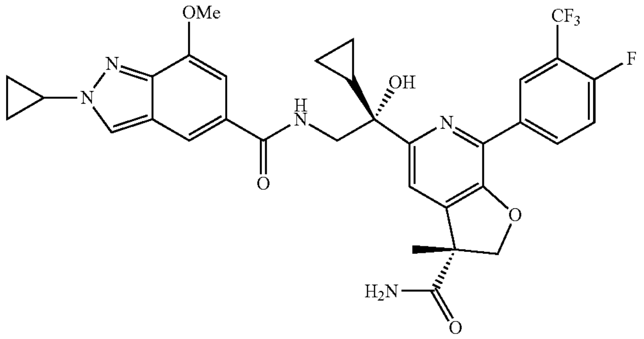 [SMILES: COc1cc(C(=O)NC[C@](O)(c2cc3c(c(-c4ccc(F)c(C(F)(F)F)c4)n2)OC[C@]3(C)C(N)=O)C2CC2)cc2cn(C3CC3)nc12] |
| 872 | 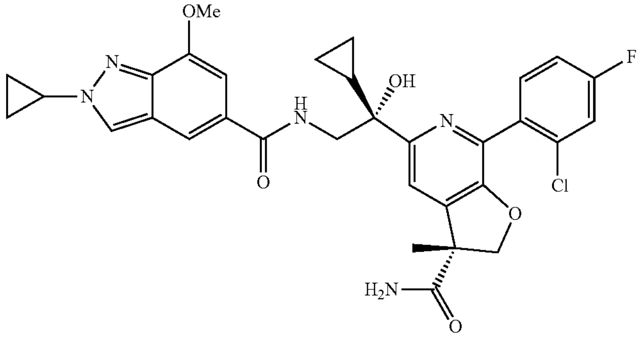 [SMILES: COc1cc(C(=O)NC[C@](O)(c2cc3c(c(-c4ccc(F)cc4Cl)n2)OC[C@]3(C)C(N)=O)C2CC2)cc2cn(C3CC3)nc12] |
| 873 | 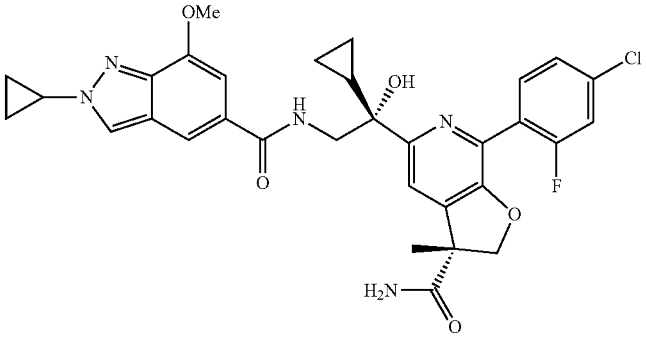 [SMILES: COc1cc(C(=O)NC[C@](O)(c2cc3c(c(-c4ccc(Cl)cc4F)n2)OC[C@]3(C)C(N)=O)C2CC2)cc2cn(C3CC3)nc12] |
| 1085 | 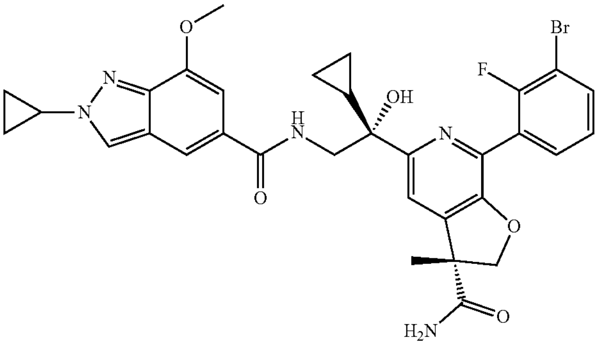 [SMILES: COc1cc(C(=O)NC[C@](O)(c2cc3c(c(-c4cccc(Br)c4F)n2)OC[C@]3(C)C(N)=O)C2CC2)cc2cn(C3CC3)nc12] |

-continued
| | Structure |
|---|---|
| 1087 | 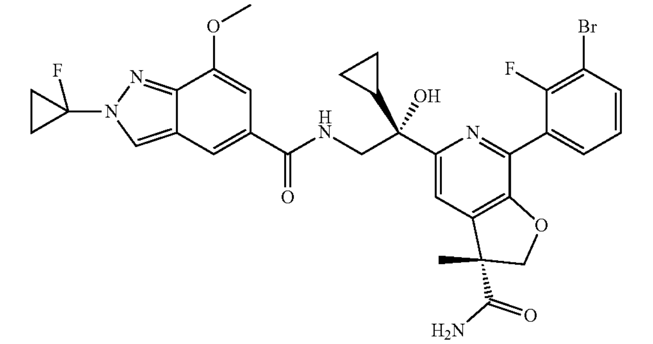 [SMILES: COc1cc(C(=O)NC[C@](O)(c2cc3c(c(-c4cccc(Br)c4F)n2)OC[C@]3(C)C(N)=O)C2CC2)cc2cn(C3(F)CC3)nc12] |
| 1088 | 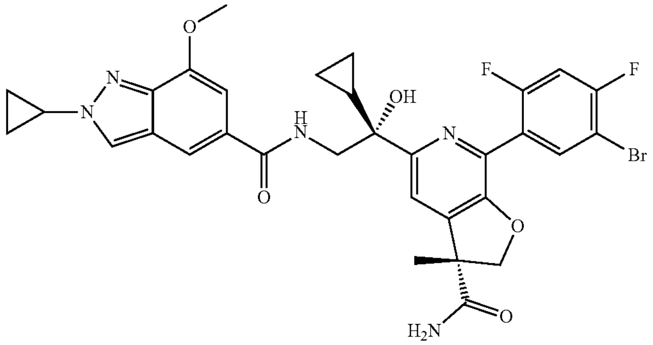 [SMILES: COc1cc(C(=O)NC[C@](O)(c2cc3c(c(-c4cc(Br)c(F)cc4F)n2)OC[C@]3(C)C(N)=O)C2CC2)cc2cn(C3CC3)nc12] |
| 1089 | 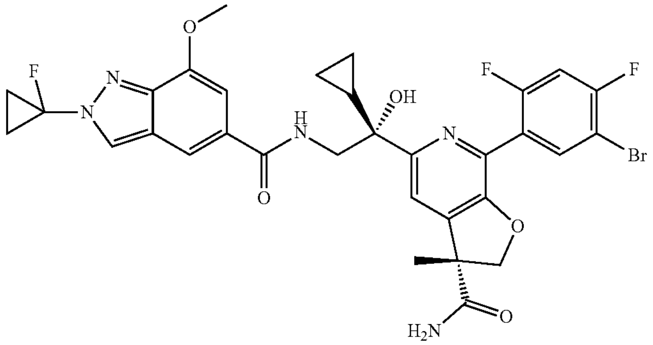 [SMILES: COc1cc(C(=O)NC[C@](O)(c2cc3c(c(-c4cc(Br)c(F)cc4F)n2)OC[C@]3(C)C(N)=O)C2CC2)cc2cn(C3(F)CC3)nc12] |
| 1095 | 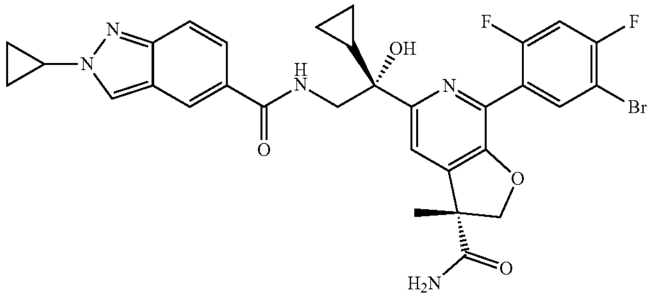 [SMILES: C[C@]1(C(N)=O)COc2c1cc([C@@](O)(CNC(=O)c1ccc3nn(C4CC4)cc3c1)C1CC1)nc2-c1cc(Br)c(F)cc1F] |

-continued
| Structure | |
|---|---|
| 1096 | 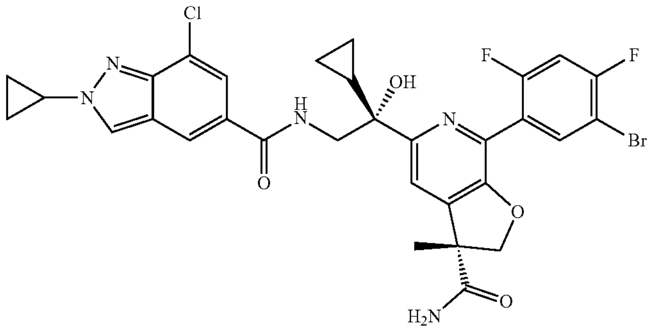 [SMILES: C[C@]1(C(N)=O)COc2c1cc([C@@](O)(CNC(=O)c1cc(Cl)c3nn(C4CC4)cc3c1)C1CC1)nc2-c1cc(Br)c(F)cc1F] |
| 1099 | 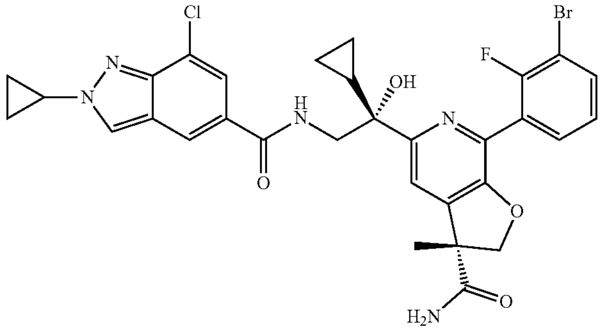 [SMILES: C[C@]1(C(N)=O)COc2c1cc([C@@](O)(CNC(=O)c1cc(Cl)c3nn(C4CC4)cc3c1)C1CC1)nc2-c1cccc(Br)c1F] |
| 1100 | 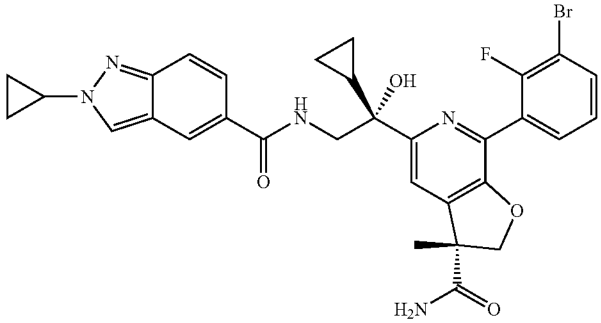 [SMILES: C[C@]1(C(N)=O)COc2c1cc([C@@](O)(CNC(=O)c1ccc3nn(C4CC4)cc3c1)C1CC1)nc2-c1cccc(Br)c1F] |
| 1101 | 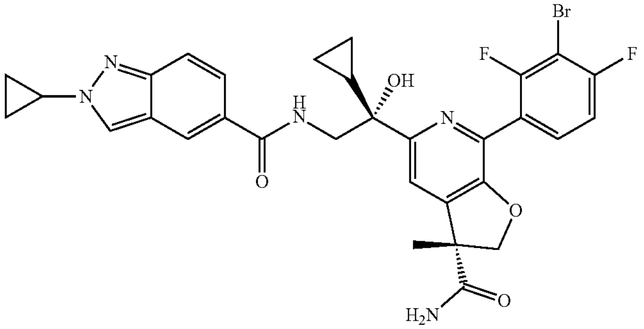 [SMILES: C[C@]1(C(N)=O)COc2c1cc([C@@](O)(CNC(=O)c1ccc3nn(C4CC4)cc3c1)C1CC1)nc2-c1ccc(F)c(Br)c1F] |

-continued
| | Structure |
|---|---|
| 1122 | 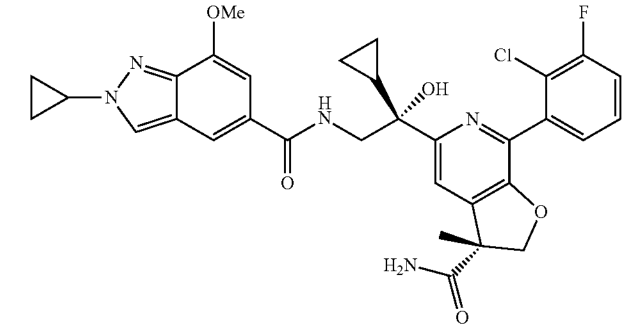 [SMILES: COc1cc(C(=O)NC[C@](O)(c2cc3c(c(-c4cccc(F)c4Cl)n2)OC[C@]3(C)C(N)=O)C2CC2)cc2cn(C3CC3)nc12] |
| 1123 | 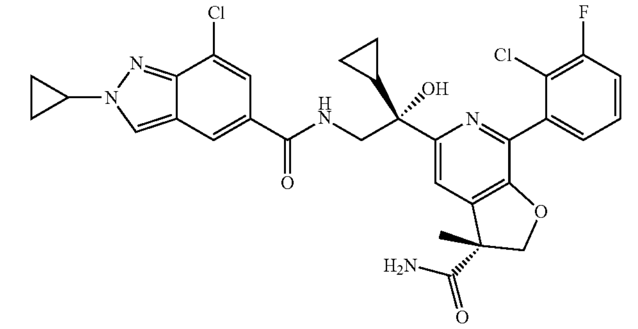 [SMILES: C[C@]1(C(N)=O)COc2c1cc([C@@](O)(CNC(=O)c1cc(Cl)c3nn(C4CC4)cc3c1)C1CC1)nc2-c1cccc(F)c1Cl] |
| 1145 | 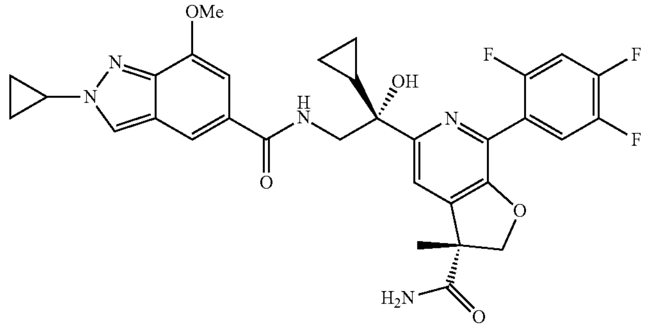 [SMILES: COc1cc(C(=O)NC[C@](O)(c2cc3c(c(-c4cc(F)c(F)cc4F)n2)OC[C@]3(C)C(N)=O)C2CC2)cc2cn(C3CC3)nc12] |
| 1147 | 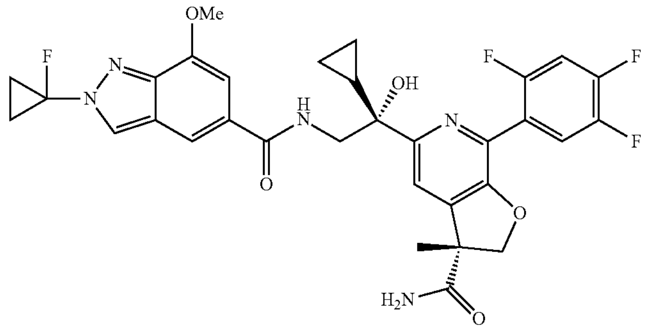 |

-continued
| | Structure |
|---|---|
| 1148 | 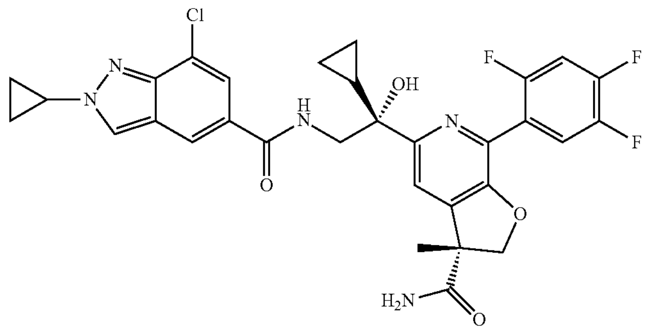 [SMILES: C[C@]1(C(N)=O)COc2c1cc([C@@](O)(CNC(=O)c1cc(Cl)c3nn(C4CC4)cc3c1)C1CC1)nc2-c1cc(F)c(F)cc1F] |
| 1155 | 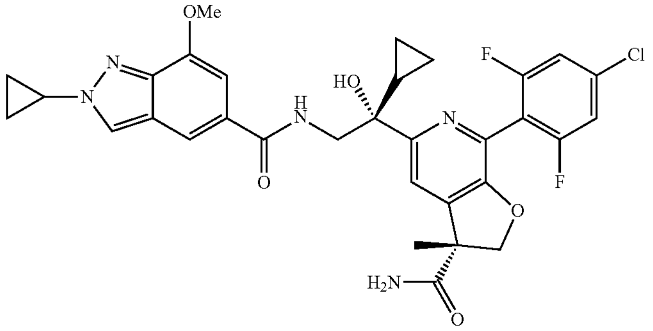 [SMILES: COc1cc(C(=O)NC[C@](O)(c2cc3c(c(-c4c(F)cc(Cl)cc4F)n2)OC[C@]3(C)C(N)=O)C2CC2)cc2cn(C3CC3)nc12] |
| 1157 | 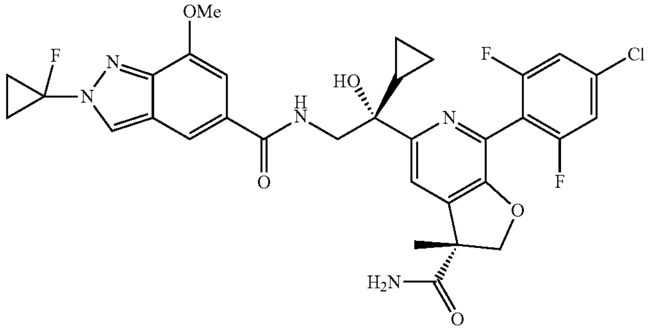 [SMILES: COc1cc(C(=O)NC[C@](O)(c2cc3c(c(-c4c(F)cc(Cl)cc4F)n2)OC[C@]3(C)C(N)=O)C2CC2)cc2cn(C3(F)CC3)nc12] |
| 1158 | 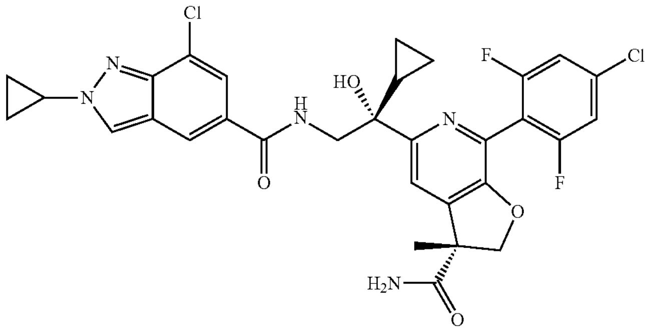 [SMILES: C[C@]1(C(N)=O)COc2c1cc([C@@](O)(CNC(=O)c1cc(Cl)c3nn(C4CC4)cc3c1)C1CC1)nc2-c1c(F)cc(Cl)cc1F] |

-continued
| | Structure |
|---|---|
| 1163 | 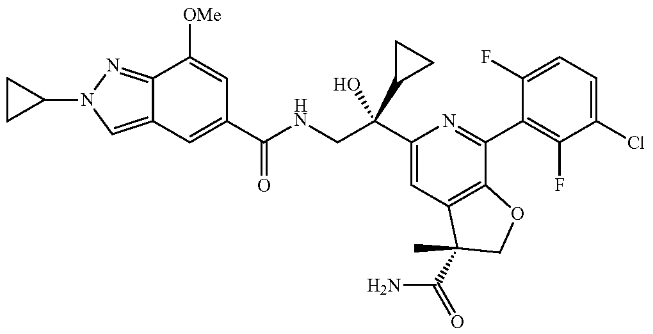 [SMILES: COc1cc(C(=O)NC[C@](O)(c2cc3c(c(-c4c(F)ccc(Cl)c4F)n2)OC[C@]3(C)C(N)=O)C2CC2)cc2cn(C3CC3)nc12] |
| 1165 | 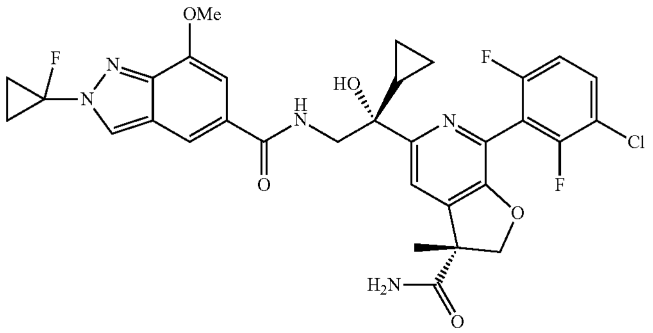 [SMILES: COc1cc(C(=O)NC[C@](O)(c2cc3c(c(-c4c(F)ccc(Cl)c4F)n2)OC[C@]3(C)C(N)=O)C2CC2)cc2cn(C3(F)CC3)nc12] |
| 1166 | 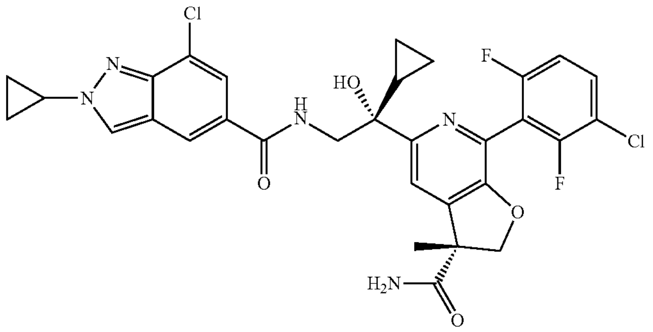 [SMILES: C[C@]1(C(N)=O)COc2c1cc([C@@](O)(CNC(=O)c1cc(Cl)c3nn(C4CC4)cc3c1)C1CC1)nc2-c1c(F)ccc(Cl)c1F] |
| 1167 | 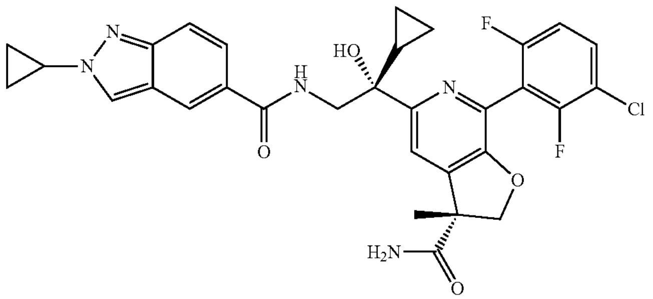 [SMILES: C[C@]1(C(N)=O)COc2c1cc([C@@](O)(CNC(=O)c1ccc3nn(C4CC4)cc3c1)C1CC1)nc2-c1c(F)ccc(Cl)c1F] |

-continued
| Structure |
|---|
| 1177 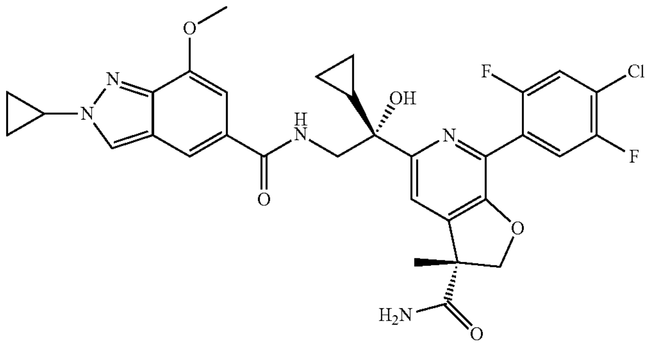 [SMILES: COc1cc(C(=O)NC[C@](O)(c2cc3c(c(-c4cc(F)c(Cl)cc4F)n2)OC[C@]3(C)C(N)=O)C2CC2)cc2cn(C3CC3)nc12] |
| 1179 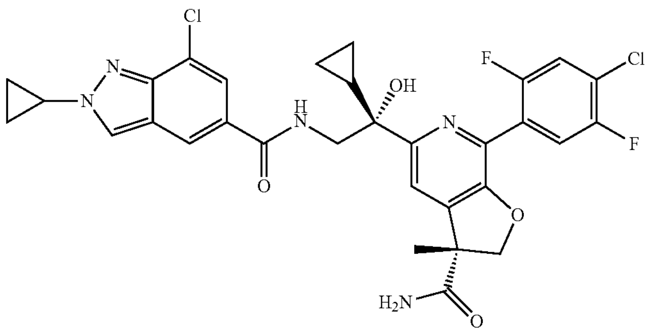 [SMILES: C[C@]1(C(N)=O)COc2c1cc([C@@](O)(CNC(=O)c1cc(Cl)c3nn(C4CC4)cc3c1)C1CC1)nc2-c1cc(F)c(Cl)cc1F] |
| 1180 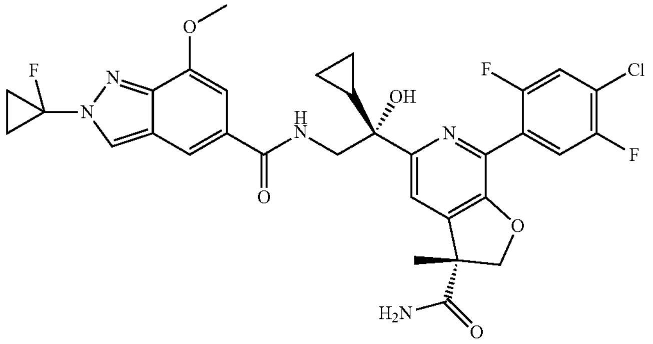 [SMILES: COc1cc(C(=O)NC[C@](O)(c2cc3c(c(-c4cc(F)c(Cl)cc4F)n2)OC[C@]3(C)C(N)=O)C2CC2)cc2cn(C3(F)CC3)nc12] |
| 1212 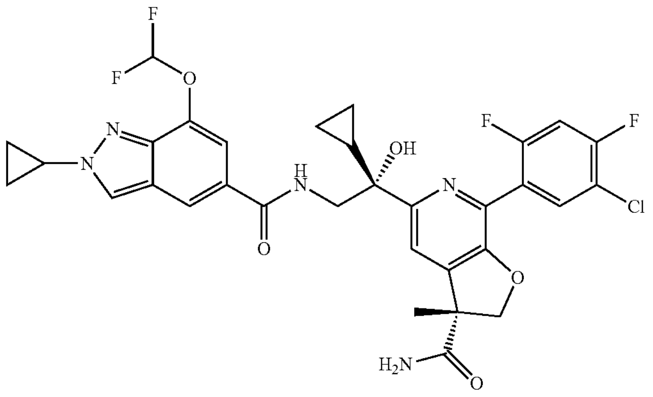 [SMILES: C[C@]1(C(N)=O)COc2c1cc([C@@](O)(CNC(=O)c1cc(OC(F)F)c3nn(C4CC4)cc3c1)C1CC1)nc2-c1cc(Cl)c(F)cc1F] |

-continued
| | Structure |
|---|---|
| 1217 | 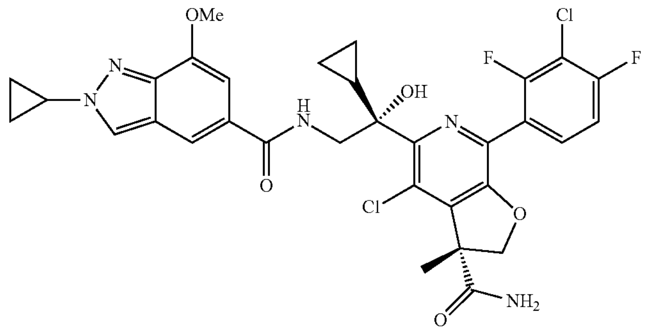 [SMILES: COc1cc(C(=O)NC[C@](O)(c2nc(-c3ccc(F)c(Cl)c3F)c3c(c2Cl)[C@@](C)(C(N)=O)CO3)C2CC2)cc2cn(C3CC3)nc12] |
| 1230 | 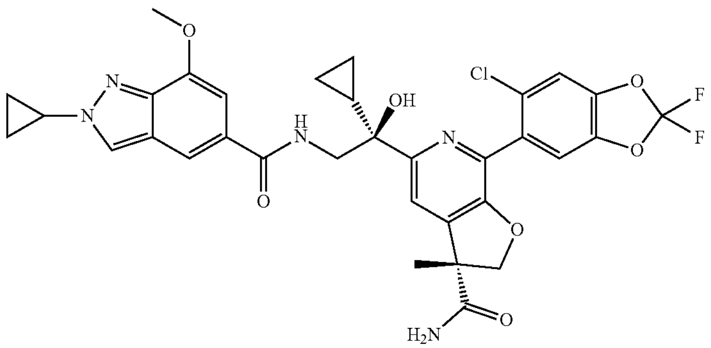 [SMILES: COc1cc(C(=O)NC[C@@](O)(c2cc3c(c(-c4cc5c(cc4Cl)OC(F)(F)O5)n2)OC[C@]3(C)C(N)=O)C2CC2)cc2cn(C3CC3)nc12] |
| 1237 | 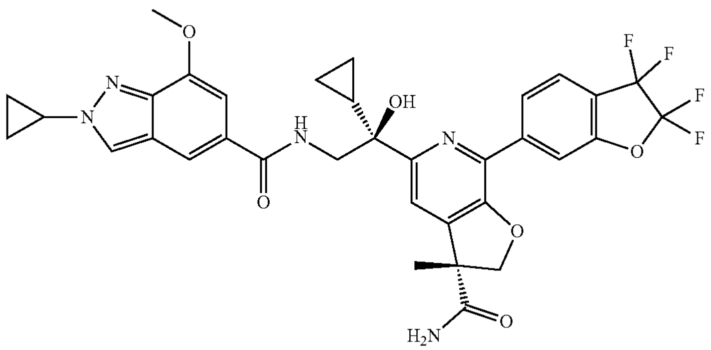 [SMILES: COc1cc(C(=O)NC[C@@](O)(c2cc3c(c(-c4ccc5c(c4)OC(F)(F)C5(F)F)n2)OC[C@]3(C)C(N)=O)C2CC2)cc2cn(C3CC3)nc12] |
| 1238 | 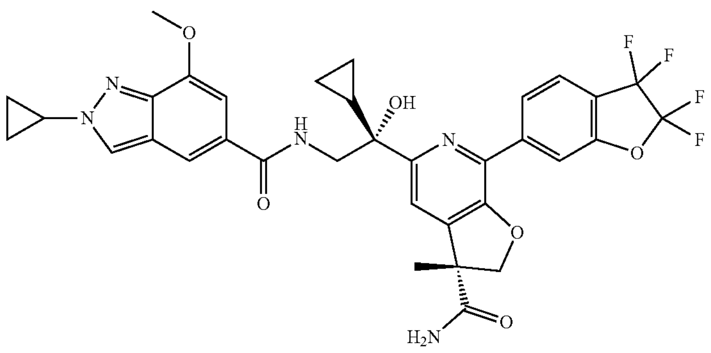 [SMILES: COc1cc(C(=O)NC[C@](O)(c2cc3c(c(-c4ccc5c(c4)OC(F)(F)C5(F)F)n2)OC[C@]3(C)C(N)=O)C2CC2)cc2cn(C3CC3)nc12] |

-continued
| Structure |
| --- |
| 1273 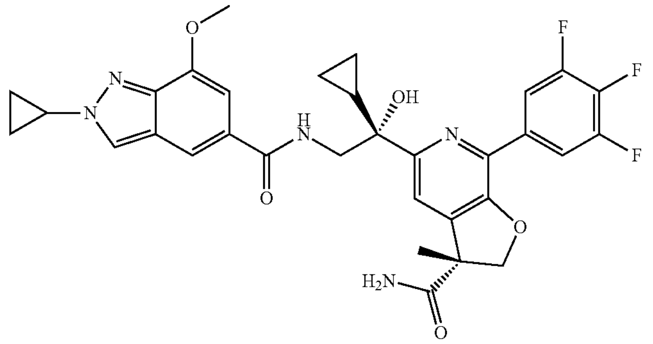 [SMILES: COc1cc(C(=O)NC[C@](O)(c2cc3c(c(-c4cc(F)c(F)c(F)c4)n2)OC[C@]3(C)C(N)=O)C2CC2)cc2cn(C3CC3)nc12] |
| 1274 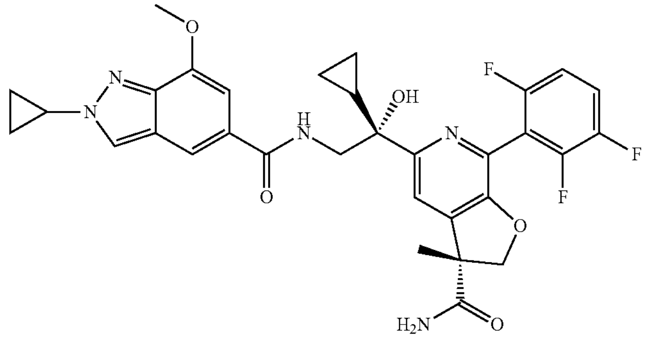 [SMILES: COc1cc(C(=O)NC[C@](O)(c2cc3c(c(-c4c(F)ccc(F)c4F)n2)OC[C@]3(C)C(N)=O)C2CC2)cc2cn(C3CC3)nc12] |
| 1275 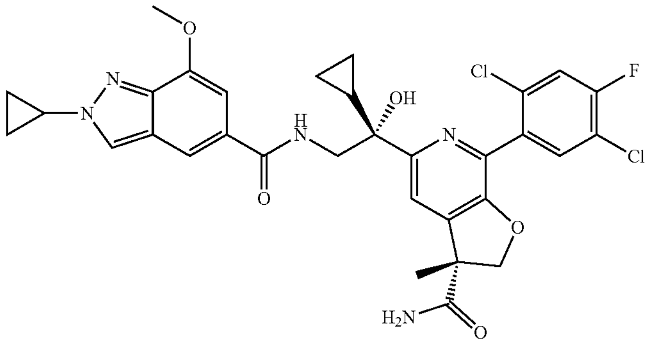 [SMILES: COc1cc(C(=O)NC[C@](O)(c2cc3c(c(-c4cc(Cl)c(F)cc4Cl)n2)OC[C@]3(C)C(N)=O)C2CC2)cc2cn(C3CC3)nc12] |
| 1276 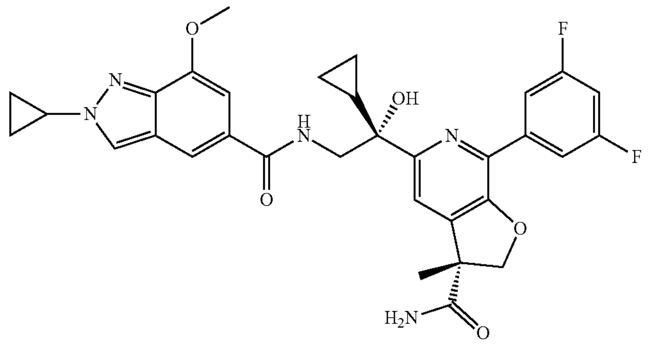 [SMILES: COc1cc(C(=O)NC[C@](O)(c2cc3c(c(-c4cc(F)cc(F)c4)n2)OC[C@]3(C)C(N)=O)C2CC2)cc2cn(C3CC3)nc12] |

-continued
| | Structure |
|---|---|
| 1277 | 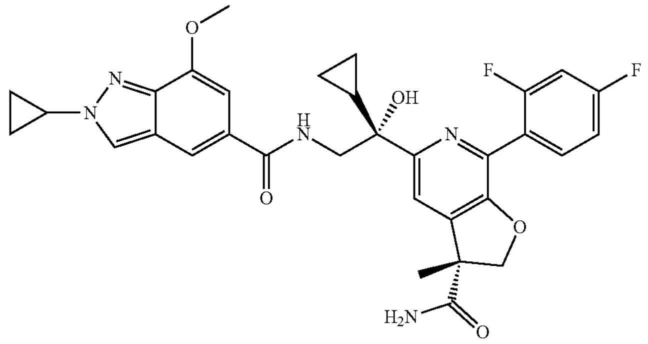 [SMILES: COc1cc(C(=O)NC[C@](O)(c2cc3c(c(-c4ccc(F)cc4F)n2)OC[C@]3(C)C(N)=O)C2CC2)cc2cn(C3CC3)nc12] |
| 1278 | 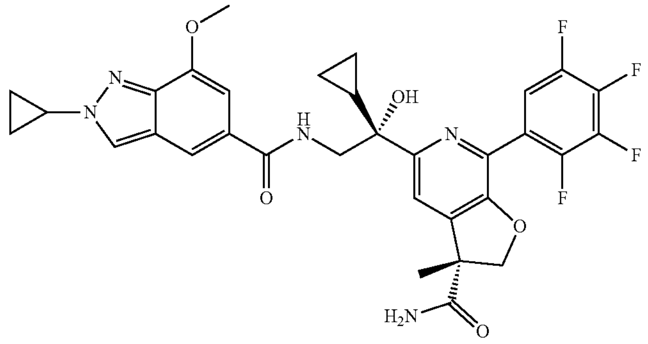 [SMILES: COc1cc(C(=O)NC[C@](O)(c2cc3c(c(-c4cc(F)c(F)c(F)c4F)n2)OC[C@]3(C)C(N)=O)C2CC2)cc2cn(C3CC3)nc12] |
| 1279 | 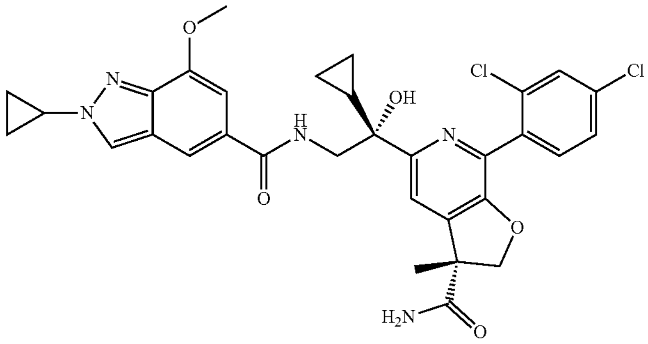 [SMILES: COc1cc(C(=O)NC[C@](O)(c2cc3c(c(-c4ccc(Cl)cc4Cl)n2)OC[C@]3(C)C(N)=O)C2CC2)cc2cn(C3CC3)nc12] |
| 1280 | 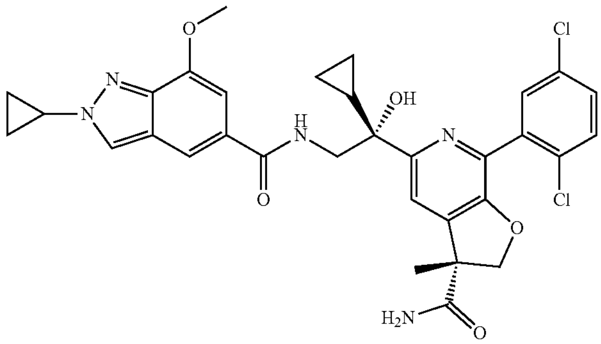 [SMILES: COc1cc(C(=O)NC[C@](O)(c2cc3c(c(-c4cc(Cl)ccc4Cl)n2)OC[C@]3(C)C(N)=O)C2CC2)cc2cn(C3CC3)nc12] |

-continued
| | Structure |
|---|---|
| 1281 | 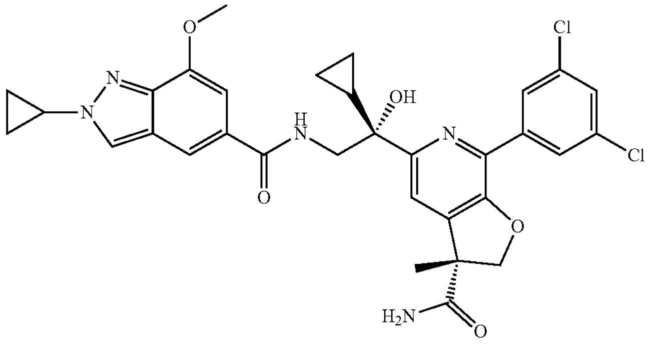 [SMILES: COc1cc(C(=O)NC[C@](O)(c2cc3c(c(-c4cc(Cl)cc(Cl)c4)n2)OC[C@]3(C)C(N)=O)C2CC2)cc2cn(C3CC3)nc12] |
| 1282 | 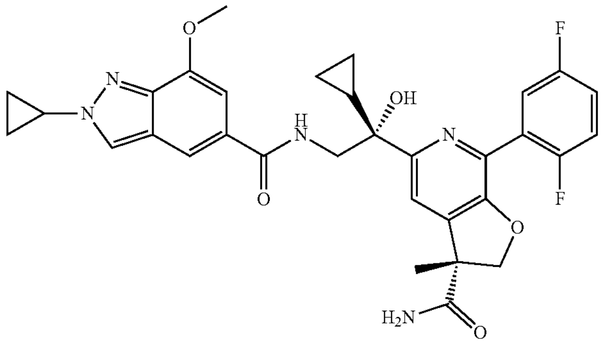 [SMILES: COc1cc(C(=O)NC[C@](O)(c2cc3c(c(-c4cc(F)ccc4F)n2)OC[C@]3(C)C(N)=O)C2CC2)cc2cn(C3CC3)nc12] |
| 1283 | 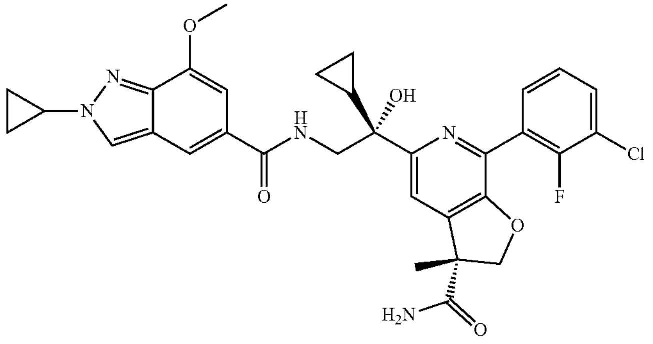 [SMILES: COc1cc(C(=O)NC[C@](O)(c2cc3c(c(-c4cccc(Cl)c4F)n2)OC[C@]3(C)C(N)=O)C2CC2)cc2cn(C3CC3)nc12] |
| 1285 | 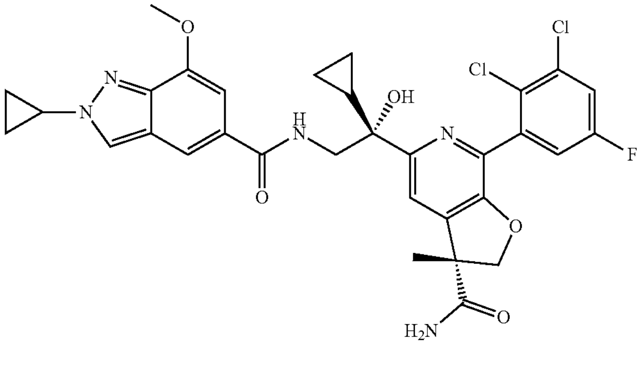 [SMILES: COc1cc(C(=O)NC[C@](O)(c2cc3c(c(-c4cc(F)cc(Cl)c4Cl)n2)OC[C@]3(C)C(N)=O)C2CC2)cc2cn(C3CC3)nc12] |

-continued
| | Structure |
|---|---|
| 1286 | 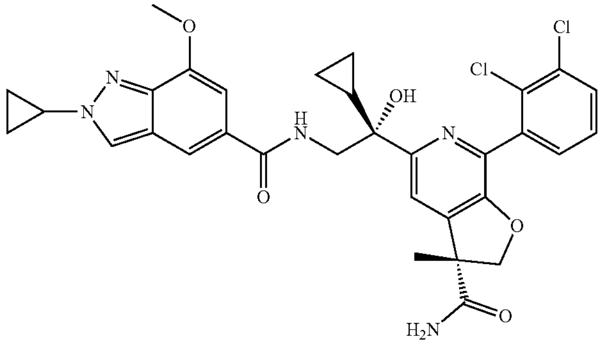 [SMILES: COc1cc(C(=O)NC[C@](O)(c2cc3c(c(-c4cccc(Cl)c4Cl)n2)OC[C@]3(C)C(N)=O)C2CC2)cc2cn(C3CC3)nc12] |
| 1289 | 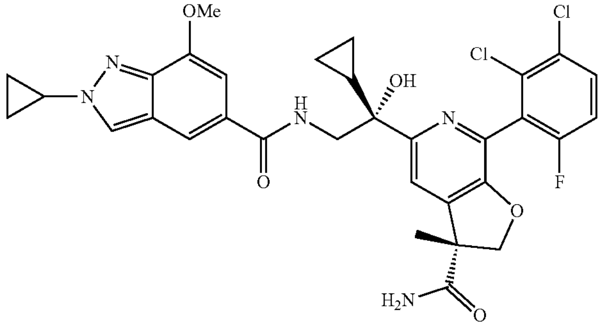 [SMILES: COc1cc(C(=O)NC[C@](O)(c2cc3c(c(-c4c(F)ccc(Cl)c4Cl)n2)OC[C@]3(C)C(N)=O)C2CC2)cc2cn(C3CC3)nc12] |
| 1290 | 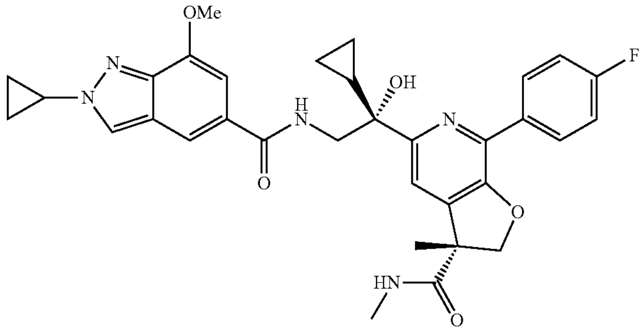 [SMILES: CNC(=O)[C@@]1(C)COc2c1cc([C@@](O)(CNC(=O)c1cc(OC)c3nn(C4CC4)cc3c1)C1CC1)nc2-c1ccc(F)cc1] |
| 1294 | 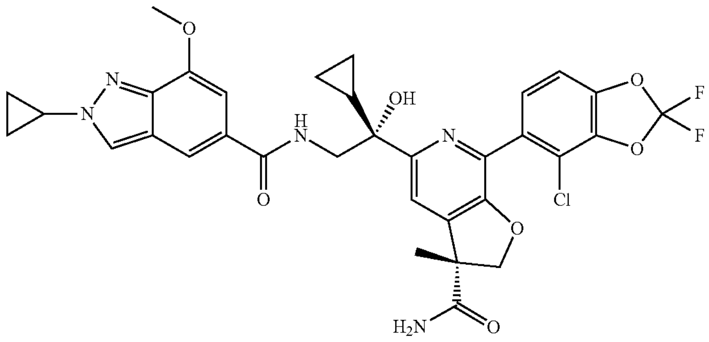 [SMILES: COc1cc(C(=O)NC[C@](O)(c2cc3c(c(-c4ccc5c(c4Cl)OC(F)(F)O5)n2)OC[C@]3(C)C(N)=O)C2CC2)cc2cn(C3CC3)nc12] |

-continued
| | Structure |
|---|---|
| 1296 | 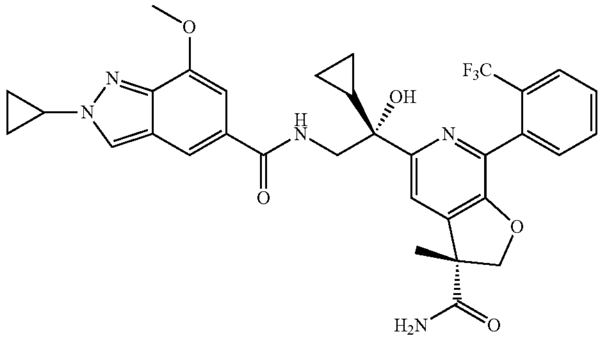 [SMILES: COc1cc(C(=O)NC[C@](O)(c2cc3c(c(-c4ccccc4C(F)(F)F)n2)OC[C@]3(C)C(N)=O)C2CC2)cc2cn(C3CC3)nc12] |
| 1297 | 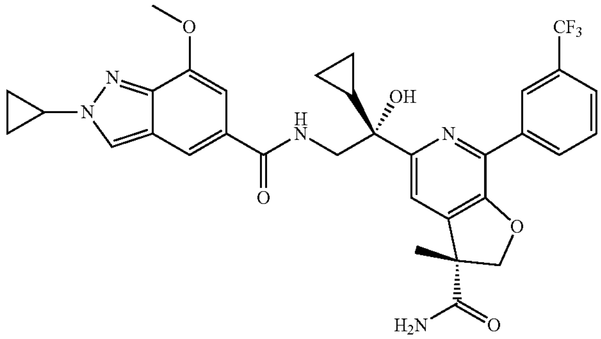 [SMILES: COc1cc(C(=O)NC[C@](O)(c2cc3c(c(-c4cccc(C(F)(F)F)c4)n2)OC[C@]3(C)C(N)=O)C2CC2)cc2cn(C3CC3)nc12] |
| 1298 | 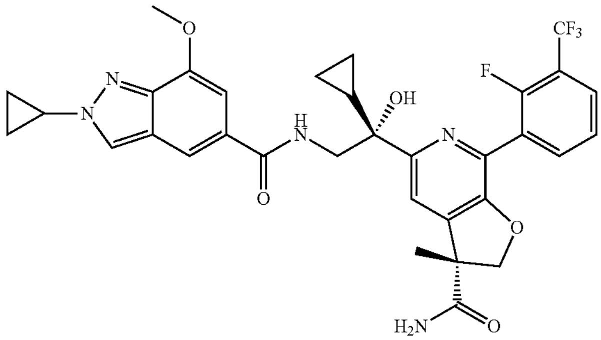 [SMILES: COc1cc(C(=O)NC[C@](O)(c2cc3c(c(-c4cccc(C(F)(F)F)c4F)n2)OC[C@]3(C)C(N)=O)C2CC2)cc2cn(C3CC3)nc12] |
| 1299 | 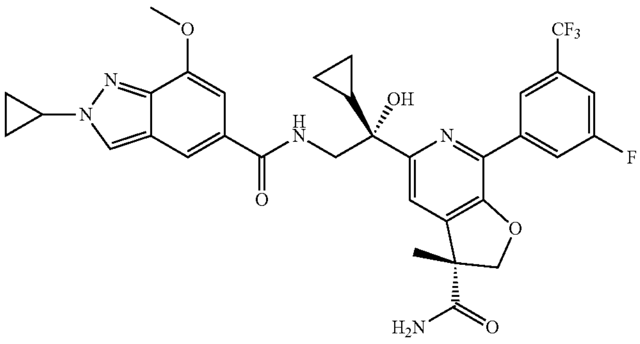 [SMILES: COc1cc(C(=O)NC[C@](O)(c2cc3c(c(-c4cc(F)cc(C(F)(F)F)c4)n2)OC[C@]3(C)C(N)=O)C2CC2)cc2cn(C3CC3)nc12] |

-continued
| | Structure |
|---|---|
| 1300 | 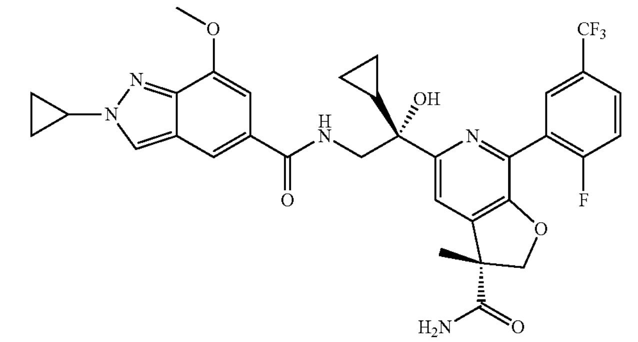 [SMILES: COc1cc(C(=O)NC[C@](O)(c2cc3c(c(-c4cc(C(F)(F)F)ccc4F)n2)OC[C@]3(C)C(N)=O)C2CC2)cc2cn(C3CC3)nc12] |
| 1301 | 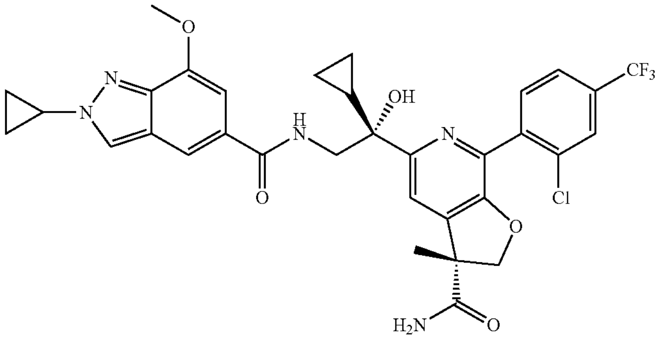 |
| 1303 | 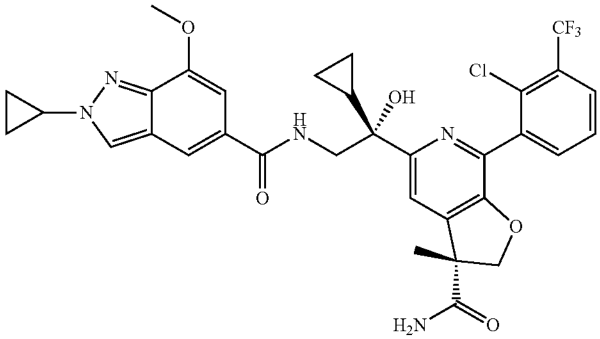 |
| 1304 | 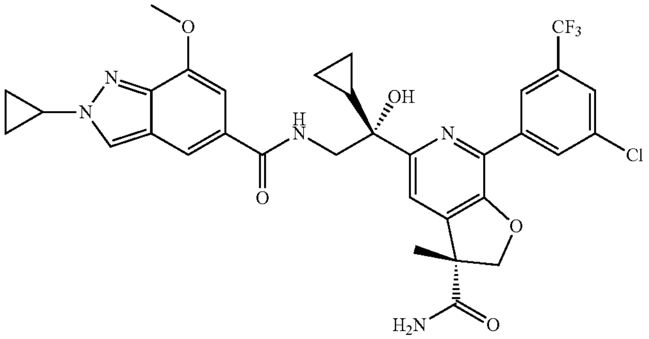 [SMILES: COc1cc(C(=O)NC[C@](O)(c2cc3c(c(-c4cc(Cl)cc(C(F)(F)F)c4)n2)OC[C@]3(C)C(N)=O)C2CC2)cc2cn(C3CC3)nc12] |

-continued
| | Structure |
|---|---|
| 1305 | 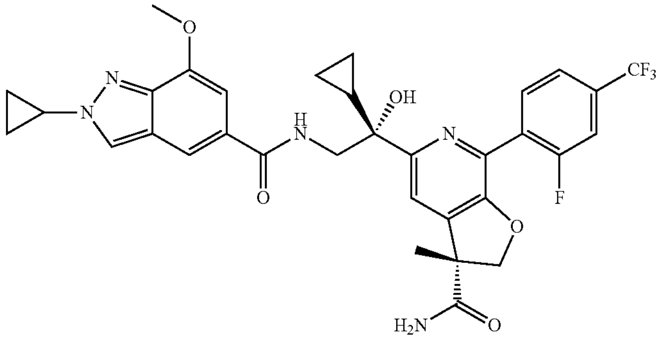 [SMILES: COc1cc(C(=O)NC[C@](O)(c2cc3c(c(-c4ccc(C(F)(F)F)cc4F)n2)OC[C@]3(C)C(N)=O)C2CC2)cc2cn(C3CC3)nc12] |
| 1307 | 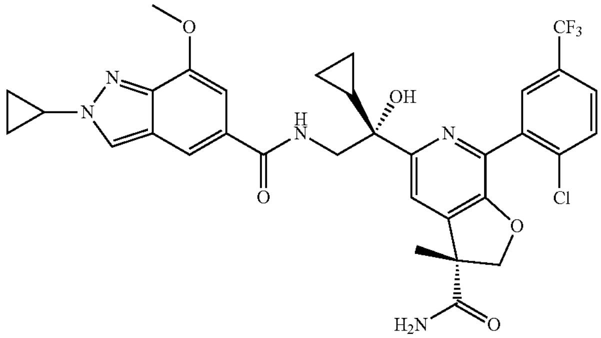 |
| 1319 | 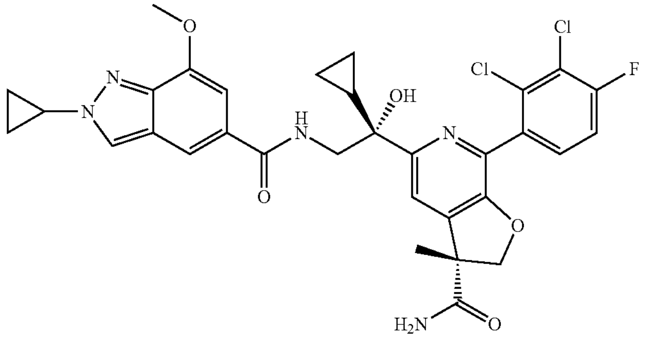 [SMILES: COc1cc(C(=O)NC[C@](O)(c2cc3c(c(-c4ccc(F)c(Cl)c4Cl)n2)OC[C@]3(C)C(N)=O)C2CC2)cc2cn(C3CC3)nc12] |
| P91 | 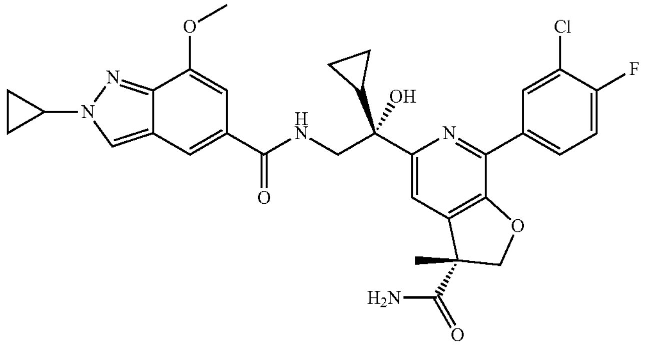 [SMILES: COc1cc(C(=O)NC[C@](O)(c2cc3c(c(-c4ccc(F)c(Cl)c4)n2)OC[C@]3(C)C(N)=O)C2CC2)cc2cn(C3CC3)nc12] |

-continued
| | Structure |
|---|---|
| P100 | 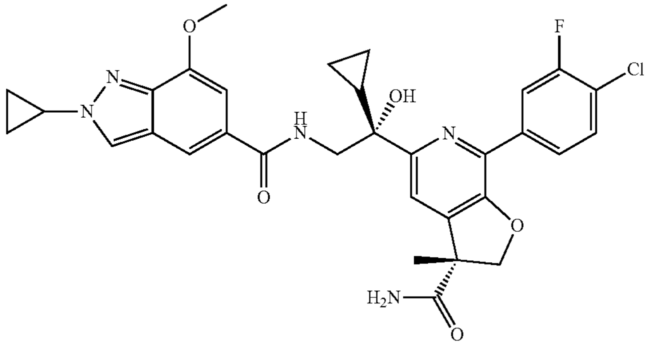 [SMILES: COc1cc(C(=O)NC[C@](O)(c2cc3c(c(-c4ccc(Cl)c(F)c4)n2)OC[C@]3(C)C(N)=O)C2CC2)cc2cn(C3CC3)nc12] |
| P139 | 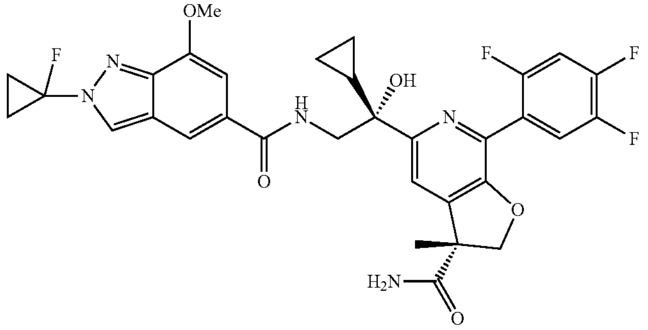 [SMILES: COc1cc(C(=O)NC[C@](O)(c2cc3c(c(-c4cc(F)c(F)cc4F)n2)OC[C@]3(C)C(N)=O)C2CC2)cc2cn(C3(F)CC3)nc12] |
| P141 | 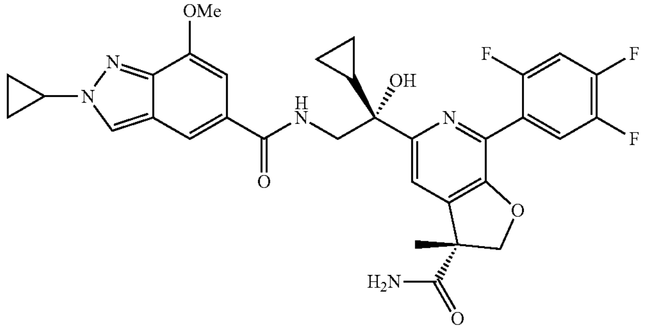 [SMILES: COc1cc(C(=O)NC[C@](O)(c2cc3c(c(-c4cc(F)c(F)cc4F)n2)OC[C@]3(C)C(N)=O)C2CC2)cc2cn(C3CC3)nc12] |
| P149 | 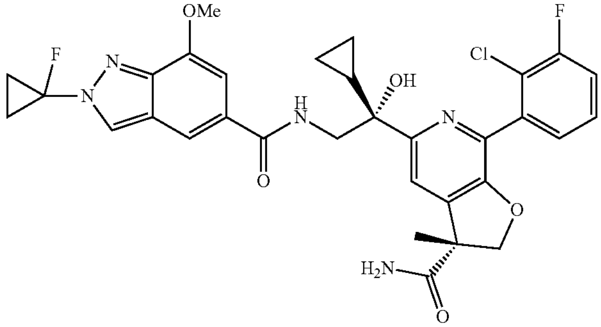 [SMILES: COc1cc(C(=O)NC[C@](O)(c2cc3c(c(-c4cccc(F)c4Cl)n2)OC[C@]3(C)C(N)=O)C2CC2)cc2cn(C3(F)CC3)nc12] |

-continued

| | Structure |
|---|---|
| P153 | 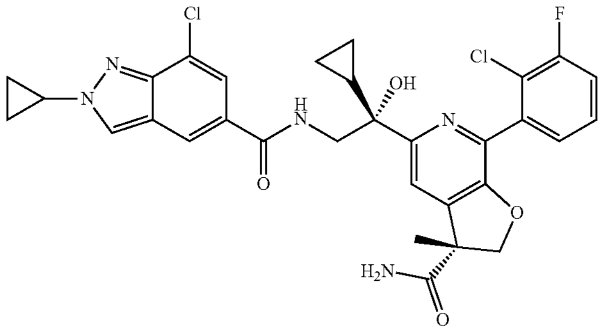 [SMILES: C[C@]1(C(N)=O)COc2c1cc([C@@](O)(CNC(=O)c1cc(Cl)c3nn(C4CC4)cc3c1)C1CC1)nc2-c1cccc(F)c1Cl] |
| P159 | 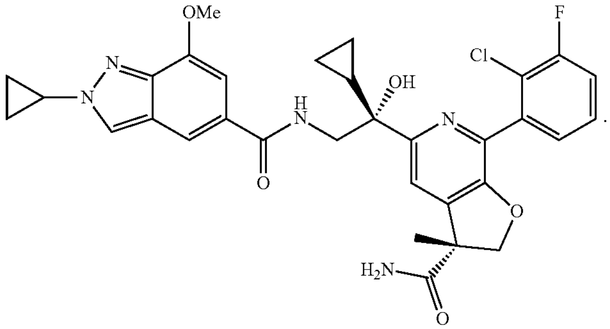 [SMILES: COc1cc(C(=O)NC[C@](O)(c2cc3c(c(-c4cccc(F)c4Cl)n2)OC[C@]3(C)C(N)=O)C2CC2)cc2cn(C3CC3)nc12] |

18. The compound of claim 17, wherein the compound is

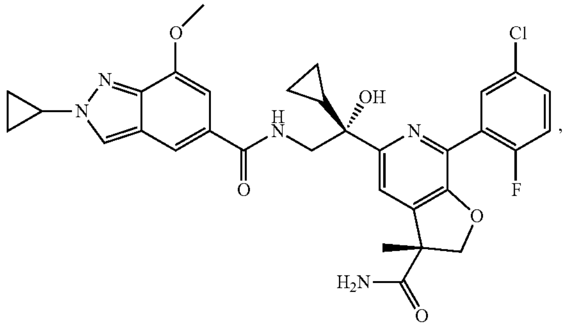 [SMILES: COc1cc(C(=O)NC[C@](O)(c2cc3c(c(-c4cc(Cl)ccc4F)n2)OC[C@]3(C)C(N)=O)C2CC2)cc2cn(C3CC3)nc12]

or a pharmaceutically acceptable salt thereof.

19. The compound of claim 17, wherein the compound is

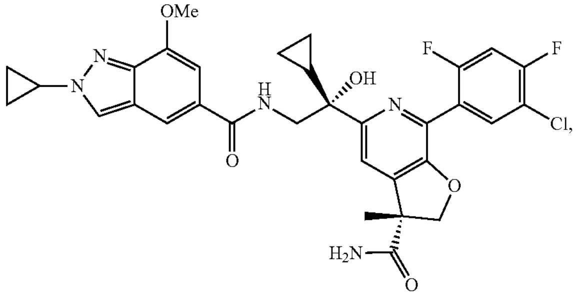 [SMILES: COc1cc(C(=O)NC[C@](O)(c2cc3c(c(-c4cc(Cl)c(F)cc4F)n2)OC[C@]3(C)C(N)=O)C2CC2)cc2cn(C3CC3)nc12]

or a pharmaceutically acceptable salt thereof.

20. The compound of claim 17, wherein the compound is

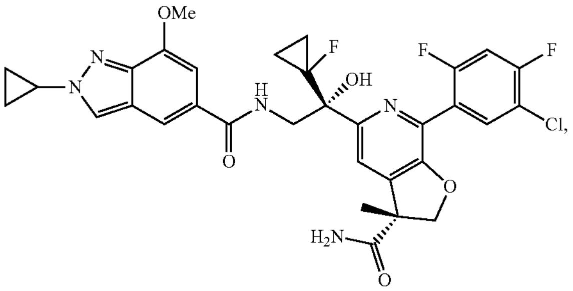 [SMILES: COc1cc(C(=O)NC[C@](O)(c2cc3c(c(-c4cc(Cl)c(F)cc4F)n2)OC[C@]3(C)C(N)=O)C2(F)CC2)cc2cn(C3CC3)nc12]

or a pharmaceutically acceptable salt thereof.

21. The compound of claim 17, wherein the compound is

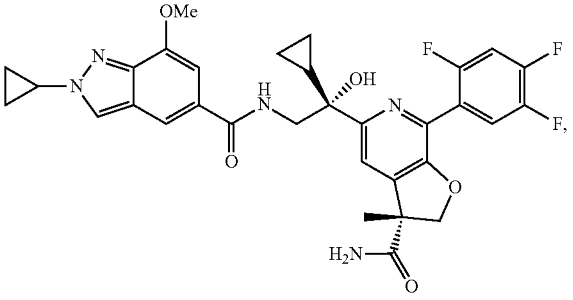 [SMILES: COc1cc(C(=O)NC[C@](O)(c2cc3c(c(-c4cc(F)c(F)cc4F)n2)OC[C@]3(C)C(N)=O)C2CC2)cc2cn(C3CC3)nc12]

or a pharmaceutically acceptable salt thereof.

22. The compound of claim 17, wherein the compound is
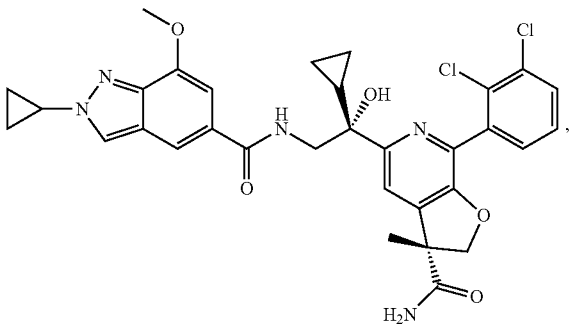 [SMILES: COc1cc(C(=O)NC[C@](O)(c2cc3c(c(-c4cccc(Cl)c4Cl)n2)OC[C@]3(C)C(N)=O)C2CC2)cc2cn(C3CC3)nc12]
or a pharmaceutically acceptable salt thereof.
* * * * *